(12) United States Patent
Crawford et al.

(10) Patent No.: US 8,716,274 B2
(45) Date of Patent: May 6, 2014

(54) HETEROARYL PYRIDONE AND AZA-PYRIDONE COMPOUNDS

(71) Applicant: Genentech, Inc., South San Francisco, CA (US)

(72) Inventors: James John Crawford, San Francisco, CA (US); Daniel Fred Ortwine, San Ramon, CA (US); BinQing Wei, Belmont, CA (US); Wendy B. Young, San Mateo, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/667,133

(22) Filed: Nov. 2, 2012

(65) Prior Publication Data

US 2013/0116235 A1    May 9, 2013

Related U.S. Application Data

(60) Provisional application No. 61/555,393, filed on Nov. 3, 2011.

(51) Int. Cl.
*A61K 31/00* (2006.01)
*C07D 471/00* (2006.01)

(52) U.S. Cl.
USPC ...... 514/210.21; 514/250; 544/344; 544/361; 544/126

(58) Field of Classification Search
USPC .............. 514/210.21, 250; 544/344, 361, 126
See application file for complete search history.

(56) References Cited

U.S. PATENT DOCUMENTS

| 7,683,064 B2 | 3/2010 | Dewdney et al. |
| 7,838,523 B2 | 11/2010 | Blomgren et al. |
| 7,884,108 B2 | 2/2011 | Blomgren et al. |
| 7,902,194 B2 | 3/2011 | Dewdney et al. |
| 7,906,509 B2 | 3/2011 | Kennedy-Smith et al. |
| 7,947,835 B2 | 5/2011 | Brittelli et al. |
| 8,058,446 B2 | 11/2011 | Blomgren et al. |
| 8,124,604 B2 | 2/2012 | Dewdney et al. |
| 2008/0125417 A1 | 5/2008 | Currie et al. |
| 2009/0186898 A1 | 7/2009 | Dewdney et al. |
| 2010/0004231 A1 | 1/2010 | Dewdney et al. |
| 2010/0016301 A1 | 1/2010 | Dewdney et al. |
| 2011/0118233 A1 | 5/2011 | Blomgren et al. |
| 2011/0301145 A1 | 12/2011 | Barbosa et al. |
| 2012/0010191 A1* | 1/2012 | Barbosa et al. ......... 514/210.21 |
| 2012/0040949 A1 | 2/2012 | Berthel et al. |
| 2012/0295885 A1 | 11/2012 | Billedeau et al. |
| 2013/0045965 A1 | 2/2013 | Brotherton-Pleiss et al. |

FOREIGN PATENT DOCUMENTS

| WO | 2012/030990 A1 | 8/2012 |
| WO | 2012/031004 | 8/2012 |

OTHER PUBLICATIONS

Di Paolo et al., "Specific Btk inhibition suppresses B cell- and myeloid cell-mediated arthritis" Nat Chem Biol. 7(1):41-50 ( 2011).
Liu et al., "Antiarthritis effect of a novel Bruton's tyrosine kinase (BTK) inhibitor in rat collagen-induced arthritis and mechanism-based pharmacokinetic/pharmacodynamic modeling: relationships between inhibition of BTK phosphorylation and efficacy" J Pharmacol Exp Ther. 338(1):154-63 ( 2011).

* cited by examiner

*Primary Examiner* — Rei-tsang Shiao
(74) *Attorney, Agent, or Firm* — Alex Andrus; Genentech, Inc.

(57) ABSTRACT

Heteroaryl pyridone and aza-pyridone compounds of Formula I are provided, where one or two of $X^1$, $X^2$, and $X^3$ are N, and including stereoisomers, tautomers, and pharmaceutically acceptable salts thereof, useful for inhibiting Btk kinase, and for treating immune disorders such as inflammation mediated by Btk kinase. Methods of using compounds of Formula I for in vitro, in situ, and in vivo diagnosis, and treatment of such disorders in mammalian cells, or associated pathological conditions, are disclosed.

21 Claims, 19 Drawing Sheets

HETEROARYL PYRIDONE AND AZA-PYRIDONE COMPOUNDS

CROSS REFERENCE TO RELATED APPLICATIONS

This non-provisional application filed under 37 CFR §1.53(b), claims the benefit under 35 USC §119(e) of U.S. Provisional Application Ser. No. 61/555,393 filed on 3 Nov. 2011, which is incorporated by reference in entirety.

FIELD OF THE INVENTION

The invention relates generally to compounds for treating disorders mediated by Bruton's Tyrosine Kinase (Btk) including inflammation, immunological, and cancer, and more specifically to compounds which inhibit Btk activity. The invention also relates to methods of using the compounds for in vitro, in situ, and in vivo diagnosis or treatment of mammalian cells, or associated pathological conditions.

BACKGROUND OF THE INVENTION

Protein kinases, the largest family of human enzymes, encompass well over 500 proteins. Bruton's Tyrosine Kinase (Btk) is a member of the Tec family of tyrosine kinases, and is a regulator of early B-cell development as well as mature B-cell activation, signaling, and survival.

B-cell signaling through the B-cell receptor (BCR) can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mutation of Btk in humans results in X-linked agammaglobulinaemia (XLA). This disease is associated with the impaired maturation of B-cells, diminished immunoglobulin production, compromised T-cell-independent immune responses and marked attenuation of the sustained calcium sign upon BCR stimulation. Evidence for the role of Btk in allergic disorders and/or autoimmune disease and/or inflammatory disease has been established in Btk-deficient mouse models. For example, in standard murine preclinical models of systemic lupus erythematosus (SLE), Btk deficiency has been shown to result in a marked amelioration of disease progression. Moreover, Btk deficient mice can also be resistant to developing collagen-induced arthritis and can be less susceptible to *Staphylococcus*-induced arthritis. A large body of evidence supports the role of B-cells and the humoral immune system in the pathogenesis of autoimmune and/or inflammatory diseases. Protein-based therapeutics (such as Rituxan) developed to deplete B-cells, represent an approach to the treatment of a number of autoimmune and/or inflammatory diseases. Because of Btk's role in B-cell activation, inhibitors of Btk can be useful as inhibitors of B-cell mediated pathogenic activity (such as autoantibody production). Btk is also expressed in osteoclasts, mast cells and monocytes and has been shown to be important for the function of these cells. For example, Btk deficiency in mice is associated with impaired IgE-mediated mast cell activation (marked diminution of TNF-alpha and other inflammatory cytokine release), and Btk deficiency in humans is associated with greatly reduced TNF-alpha production by activated monocytes.

Thus, inhibition of Btk activity can be useful for the treatment of allergic disorders and/or autoimmune and/or inflammatory diseases such as: SLE, rheumatoid arthritis, multiple vasculitides, idiopathic thrombocytopenic purpura (ITP), myasthenia gravis, allergic rhinitis, and asthma (Di Paolo et al (2011) Nature Chem. Biol. 7(1):41-50; Liu et al (2011) Jour. of Pharm. and Exper. Ther. 338(1):154-163). In addition, Btk has been reported to play a role in apoptosis; thus, inhibition of Btk activity can be useful for cancer, as well as the treatment of B-cell lymphoma, leukemia, and other hematological malignancies. Moreover, given the role of Btk in osteoclast function, the inhibition of Btk activity can be useful for the treatment of bone disorders such as osteoporosis. Specific Btk inhibitors have been reported (Liu (2011) Drug Metab. and Disposition 39(10):1840-1849; U.S. Pat. No. 7,884,108, WO 2010/056875; U.S. Pat. No. 7,405,295; U.S. Pat. No. 7,393,848; WO 2006/053121; U.S. Pat. No. 7,947,835; US 2008/0139557; U.S. Pat. No. 7,838,523; US 2008/0125417; US 2011/0118233; PCT/US2011/050034 "PYRIDINONES/PYRAZINONES, METHOD OF MAKING, AND METHOD OF USE THEREOF", filed 31 Aug. 2011; PCT/US2011/050013 "PYRIDAZINONES, METHOD OF MAKING, AND METHOD OF USE THEREOF", filed 31 Aug. 2011; U.S. Ser. No. 13/102,720 "PYRIDONE AND AZA-PYRIDONE COMPOUNDS AND METHODS OF USE", filed 6 May 2011).

SUMMARY OF THE INVENTION

The invention relates generally to Formula I, heteroaryl pyridone and aza-pyridone compounds with Bruton's Tyrosine Kinase (Btk) modulating activity.

Formula I compounds have the structures:

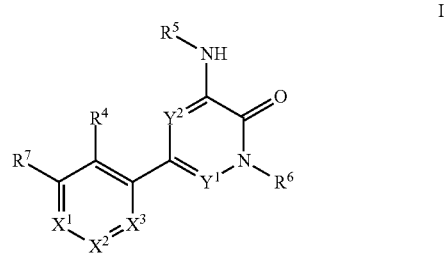

including stereoisomers, tautomers, or pharmaceutically acceptable salts thereof. The various substituents are defined herein below.

One aspect of the invention is a pharmaceutical composition comprised of a Formula I compound and a pharmaceutically acceptable carrier, glidant, diluent, or excipient. The pharmaceutical composition may further comprise a second therapeutic agent.

Another aspect of the invention is a process for making a pharmaceutical composition which comprises combining a Formula I compound with a pharmaceutically acceptable carrier.

The invention includes a method of treating a disease or disorder which method comprises administering a therapeutically effective amount of a Formula I compound to a patient with a disease or disorder selected from immune disorders, cancer, cardiovascular disease, viral infection, inflammation, metabolism/endocrine function disorders and neurological disorders, and mediated by Bruton's tyrosine kinase.

The invention includes a kit for treating a condition mediated by Bruton's tyrosine kinase, comprising: a) a first pharmaceutical composition comprising a Formula I compound; and b) instructions for use.

The invention includes a Formula I compound for use as a medicament, and for use in treating a disease or disorder selected from immune disorders, cancer, cardiovascular disease, viral infection, inflammation, metabolism/endocrine function disorders and neurological disorders, and mediated by Bruton's tyrosine kinase.

The invention includes use of a Formula I compound in the manufacture of a medicament for the treatment of immune disorders, cancer, cardiovascular disease, viral infection, inflammation, metabolism/endocrine function disorders and neurological disorders, and where the medicament mediates Bruton's tyrosine kinase.

The invention includes methods of making a Formula I compound.

BRIEF DESCRIPTION OF THE DRAWINGS

FIG. 1 shows the preparation of 2-(4-(hydroxymethyl)-5-(1-methyl-5-(5-(4-(oxetan-3-yl)piperazin-1-yl)pyridin-2-ylamino)-6-oxo-1,6-dihydropyridin-3-yl)pyridin-3-yl)-3,4,6,7,8,9-hexahydropyrazino[1,2-a]indol-1(2H)-one 101 starting with 2,2,2-Trichloro-1-(4,5,6,7-tetrahydro-1H-indol-2-yl)ethanone 101a.

FIG. 2 shows the preparation of 2-(4-(Hydroxymethyl)-5-(1-methyl-5-(5-(4-methylpiperazin-1-yl)pyridin-2-ylamino)-6-oxo-1,6-dihydropyridin-3-yl)pyridin-3-yl)-3,4,6,7,8,9-hexahydropyrazino[1,2-a]indol-1(2H)-one 102 starting with 1-Methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 102a.

FIG. 3 shows the preparation of 2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 103 starting with 2-Bromo-4-chloronicotinaldehyde 103a.

FIG. 4 shows the preparation of 2-(3-(Hydroxymethyl)-2-(1-methyl-5-(5-(4-(oxetan-3-yl)piperazin-1-yl)pyridin-2-ylamino)-6-oxo-1,6-dihydropyridin-3-yl)pyridin-4-yl)-3,4,6,7,8,9-hexahydropyrazino[1,2-a]indol-1(2H)-one 104 starting with 4-Bromo-2-chloronicotinaldehyde 104a.

FIG. 5 shows the preparation of 4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{6-oxo-8-thia-5-azatricyclo-[7.4.0.0$^{2,7}$]trideca-1(9),2(7)-dien-5-yl}pyridine 105 starting with N-Methoxy-N-methyl-4,5,6,7-tetrahydrobenzo[b]thiophene-2-carboxamide 105a.

FIG. 6 shows the preparation of 4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{4,4-dimethyl-9-oxo-7-thia-10-azatricyclo[6.4.0.0$^{2,6}$]dodeca-1(8),2(6)-dien-10-yl}pyridine-4-carbaldehyde 106 starting with 3,3-Dimethylcyclopentanone 106a.

FIG. 7 shows the preparation of 10-[4-[1-Methyl-5-({5-[4-(oxetan-3-yl)piperazin-1-yl]pyridine-2-yl}amino)-6-oxo-1,6-dihydropyridin-3-yl]-4-(hydroxymethyl)pyridin-3-yl]-4,4-dimethyl-1,10-diazatricyclo[6.4.0.0$^{2,6}$]dodeca-2(6),7-dien-9-one 107 starting with (E)-Ethyl 3-(2-Chloro-4,4-dimethylcyclopent-1-enyl)acrylate 107a.

FIG. 8 shows the preparation of 2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-4,4-dimethyl-1,10-diazatricyclo[6.4.0.0$^{2,6}$]dodeca-2(6),7-dien-9-one 108 starting with 4-Chloro-2-{4,4-dimethyl-9-oxo-1,10-diazatricyclo[6.4.0.0$^{2,6}$]dodeca-2(6),7-dien-10-yl}pyridine-3-carbaldehyde 108a.

FIG. 9 shows the preparation of 2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-4,4-dimethyl-7-thia-10-azatricyclo[6.4.0.0$^{2,6}$]dodeca-1(8),2(6)-dien-9-one 109 starting with 4-Chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a.

FIG. 10 shows the preparation of 2-(3-(Hydroxymethyl)-4-(1-methyl-5-(6-(4-methylpiperazin-1-yl)pyridine-2-ylamino)-6-oxo-1,6-dihydropyridin-3-yl)pyridin-2-yl)-3,4,6,7,8,9-hexahydropyrazino[1,2-a]indol-1(2H)-one 110 starting with 1-Methyl-3-(6-(4-methylpiperazin-1-yl)pyridin-2-ylamino)-5-(4,4,5,5-tetramethyl-1,3,2-dioxaborolan-2-yl)pyridin-2(1H)-one 110a.

FIG. 11 shows the preparation of 2-(3-(Hydroxymethyl)-4-(1-methyl-5-(5-(morpholine-4-carbonyl)pyridin-2-ylamino)-6-oxo-1,6-dihydropyridin-3-yl)pyridin-2-yl)-3,4,6,7,8,9-hexahydropyrazino[1,2-a]indol-1(2H)-one 111 starting with (6-Aminopyridin-3-yl)(morpholino)methanone 111a.

FIG. 12 shows the preparation of 2-(4-(Hydroxymethyl)-5-(1-methyl-5-(5-(4-(oxetan-3-yl)piperazin-1-yl)pyridin-2-ylamino)-6-oxo-1,6-dihydropyridin-3-yl)pyridin-3-yl)-3,4,6,7,8,9-hexahydropyrido[3,4-b]indolizin-1(2H)-one 112 starting with Methyl 5,6,7,8-Tetrahydroindolizine-2-carboxylate 112a.

FIG. 13 shows the preparation of 2-(3-(Hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydropyrazino[1,2-a]indol-1(2H)-one 113 starting with (3-Nitro-1H-pyrazol-5-yl)methanol 113a.

FIG. 14 shows the preparation of (R)-2-(4-(6-(4-(1,4-dimethyl-3-oxopiperazin-2-yl)phenylamino)-4-methyl-5-oxo-4,5-dihydropyrazin-2-yl)-3-(hydroxymethyl)pyridin-2-yl)-3,4,6,7,8,9-hexahydropyrazino[1,2-a]indol-1(2H)-one 114 starting with (R)-5-bromo-3-(4-(1,4-dimethyl-3-oxopiperazin-2-yl)phenylamino)-1-methylpyrazin-2(1H)-one 114a.

FIG. 15 shows the preparation of 2-(3-(Hydroxymethyl)-4-(1-methyl-5-(5-methyl-1H-pyrazol-3-ylamino)-6-oxo-1,6-dihydropyridin-3-yl)pyridin-2-yl)-3,4,6,7,8,9-hexahydropyrazino[1,2-a]indol-1(2H)-one 115 starting with 5-Bromo-1-methyl-3-(5-methyl-1H-pyrazol-3-ylamino)pyridin-2(1H)-one 115a.

FIG. 16 shows the preparation of 4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{6-oxo-8-thia-4,5-diazatricyclo[7.4.0.0$^{2,7}$]trideca-1(9),2(7),3-trien-5-yl}pyridine 116 starting with 3-Bromo-5-{6-oxo-8-thia-4,5-diazatricyclo[7.4.0.0$^{2,7}$]trideca-1(9),2(7),3-trien-5-yl}pyridine-4-carbaldehyde 116a.

FIG. 17 shows the preparation of 2-(3-(hydroxymethyl)-4-(1-methyl-5-(5-(methylsulfonyl)pyridin-2-ylamino)-6-oxo-1,6-dihydropyridin-3-yl)pyridin-2-yl)-3,4,6,7,8,9-hexahydro-pyrazino[1,2-a]indol-1(2H)-one 117 starting with 5-(Methylthio)-2-nitropyridine 117a.

FIG. 18 shows the preparation of 2-(4-(5-(5-Cyclopropyl-1H-pyrazol-3-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 118 starting with tert-Butyl 5-Amino-3-cyclopropyl-1H-pyrazole-1-carboxylate 118a.

Figure 1:
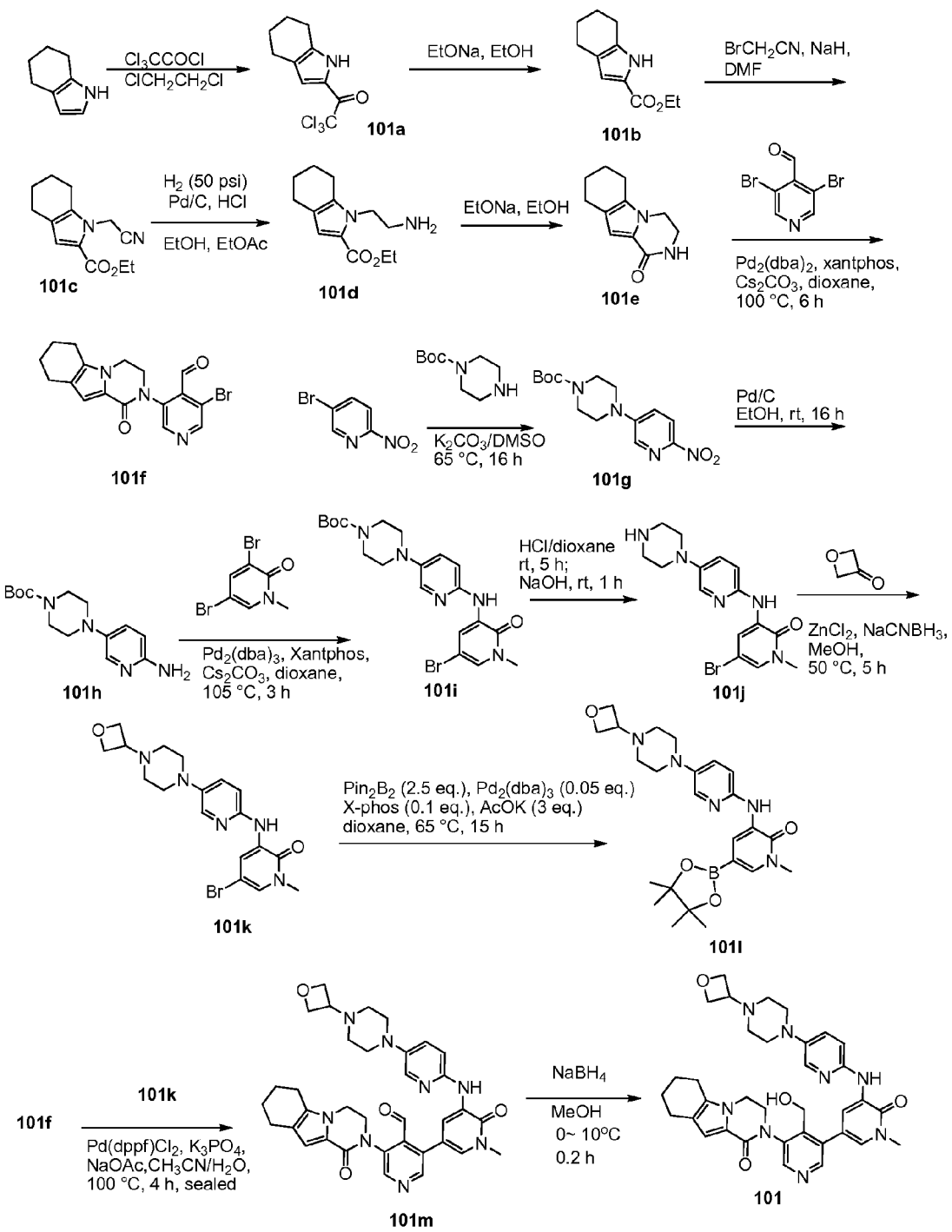
Figure 2:
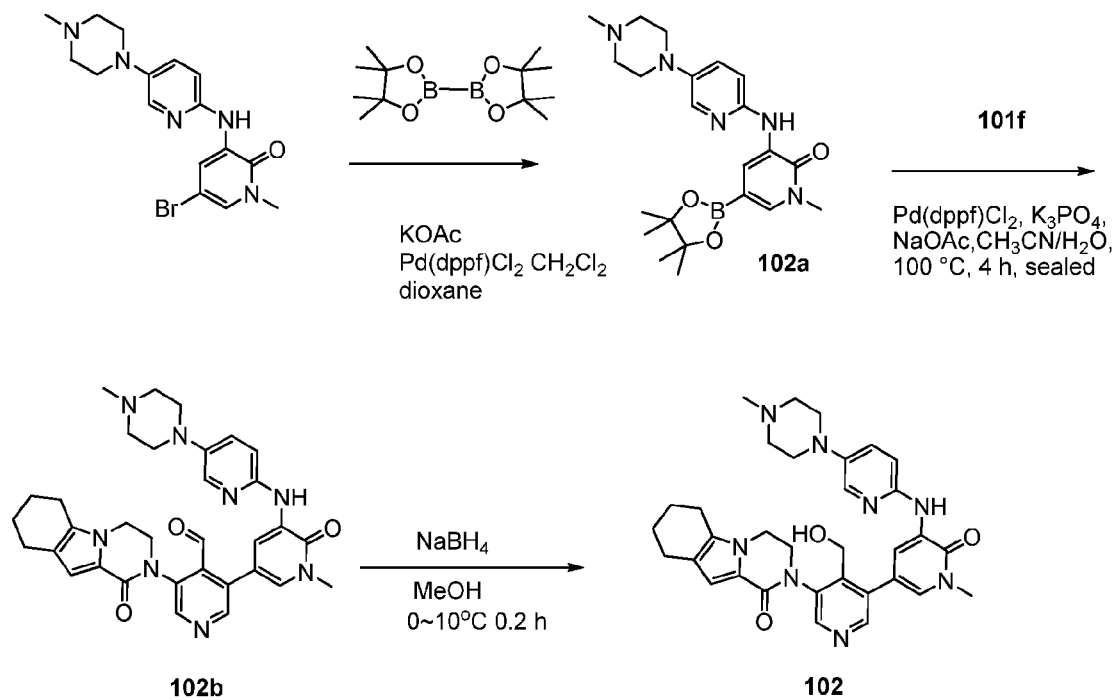
Figure 3:
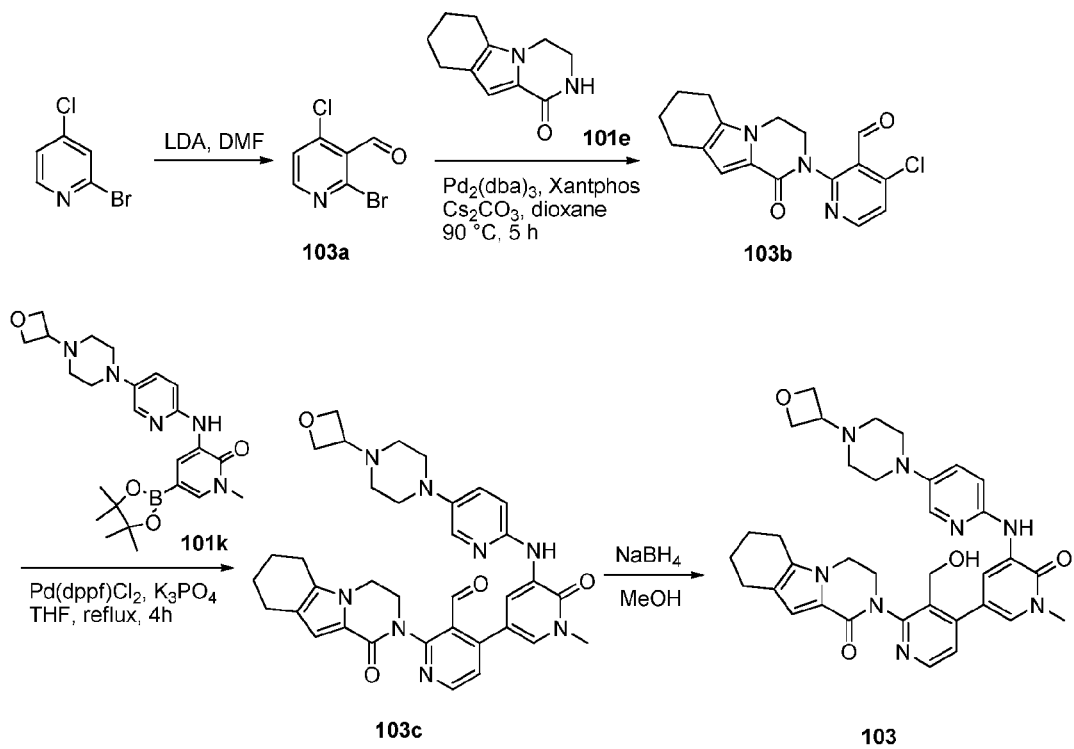
Figure 4:
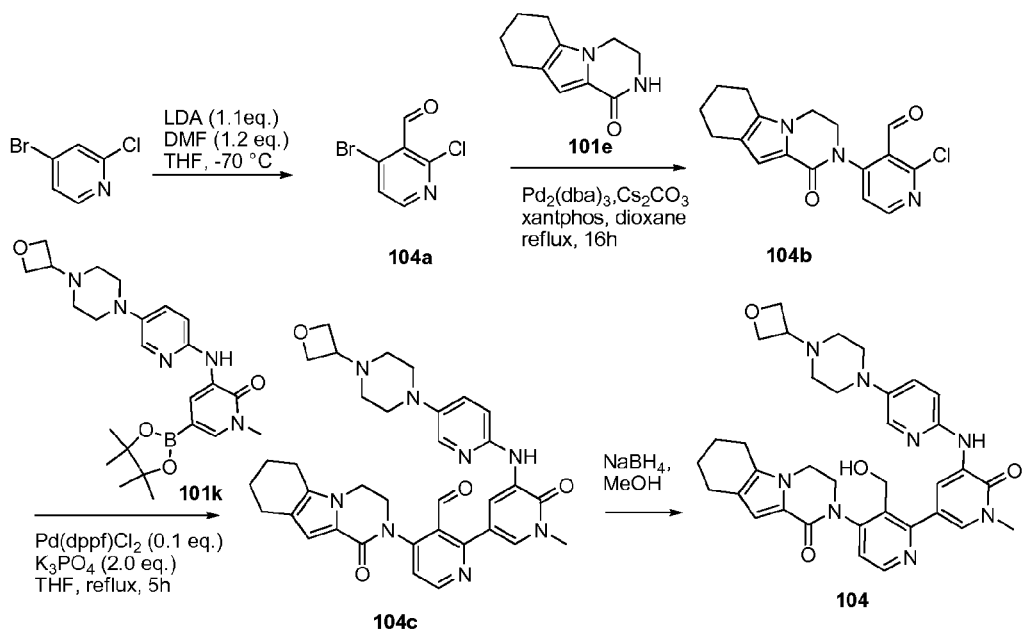
Figure 5:
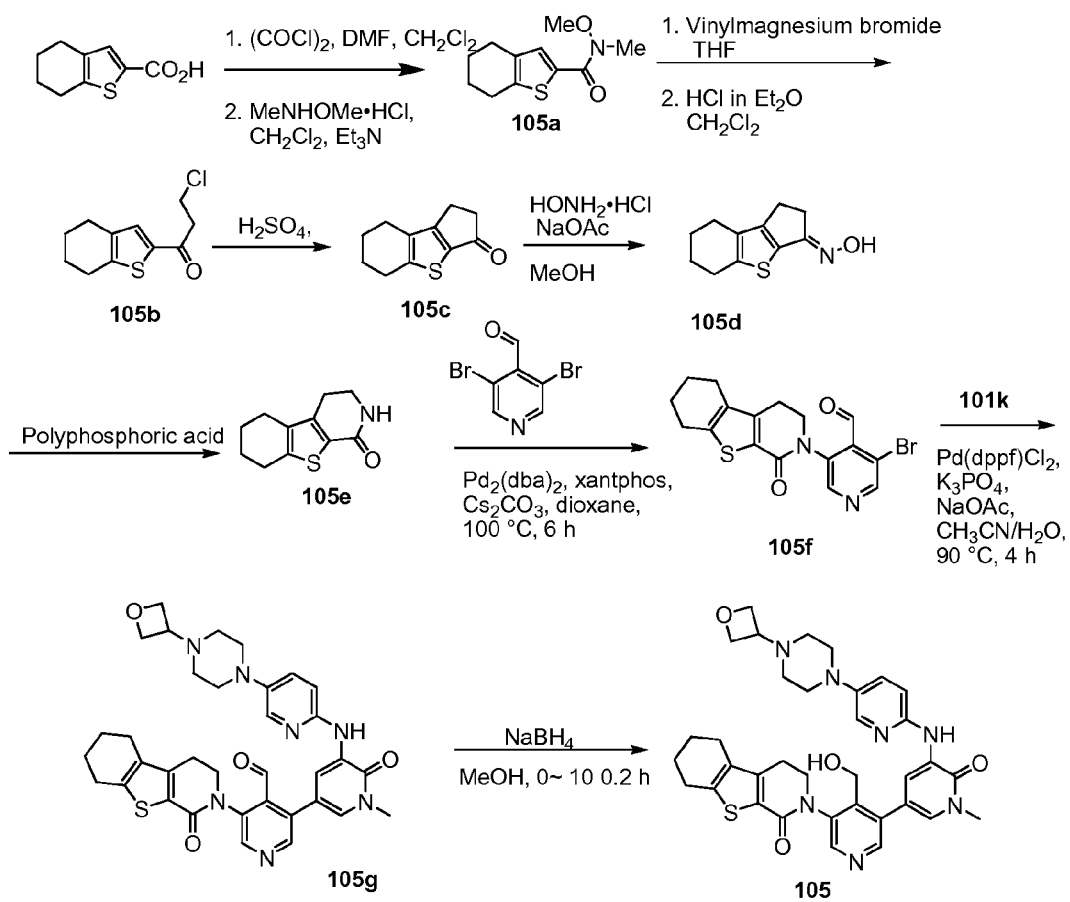
Figure 6:
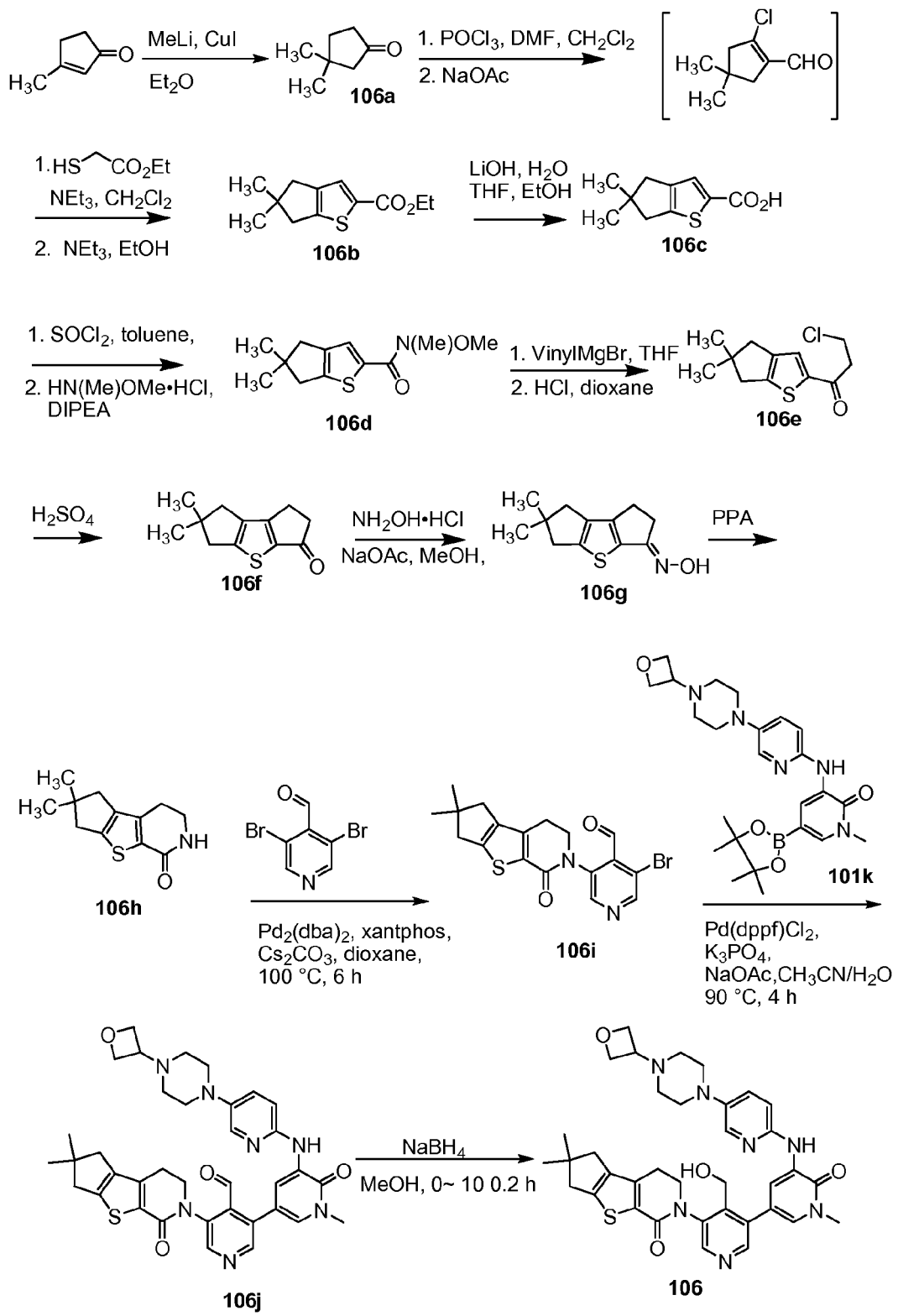
Figure 7:
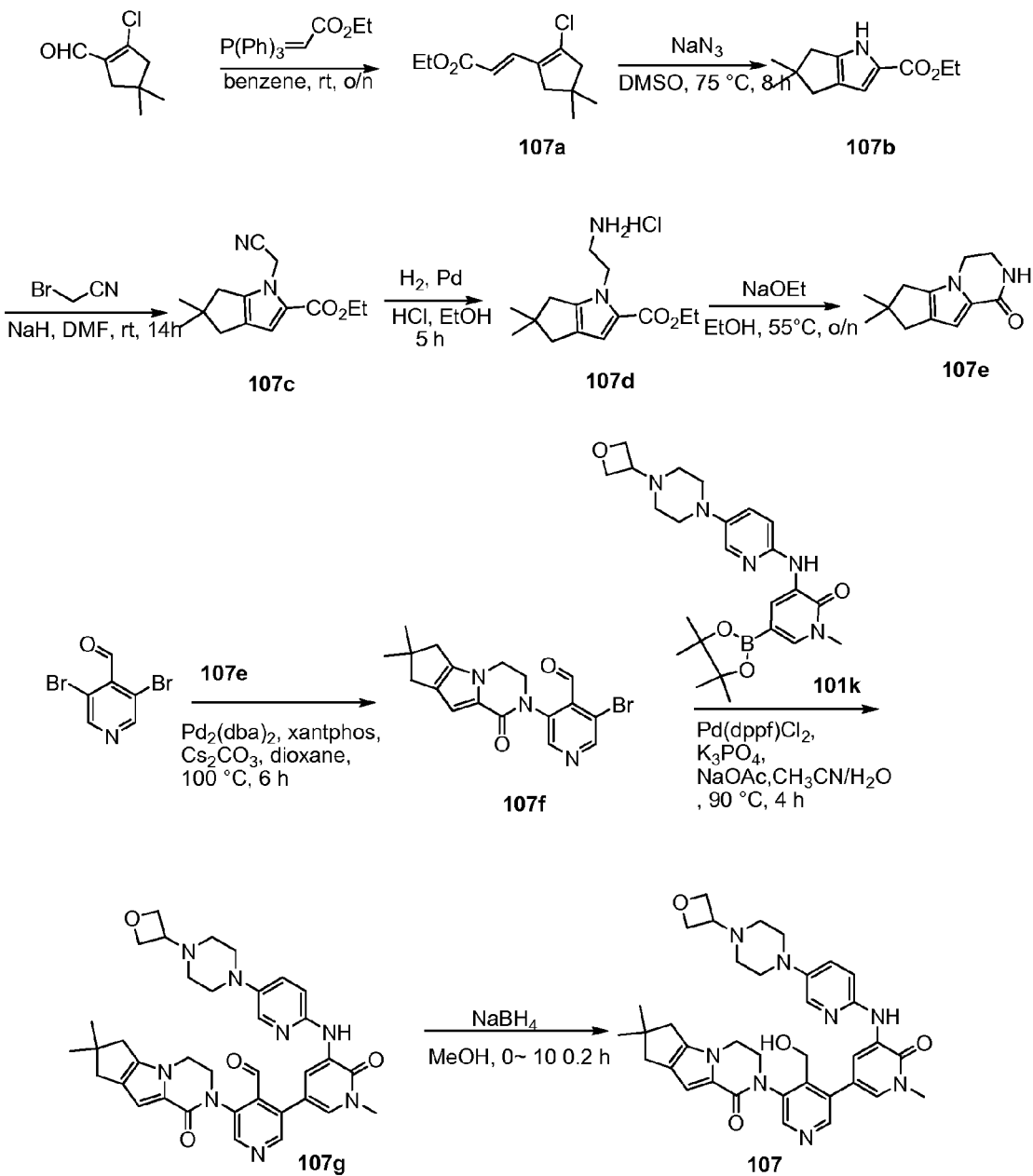
Figure 8:
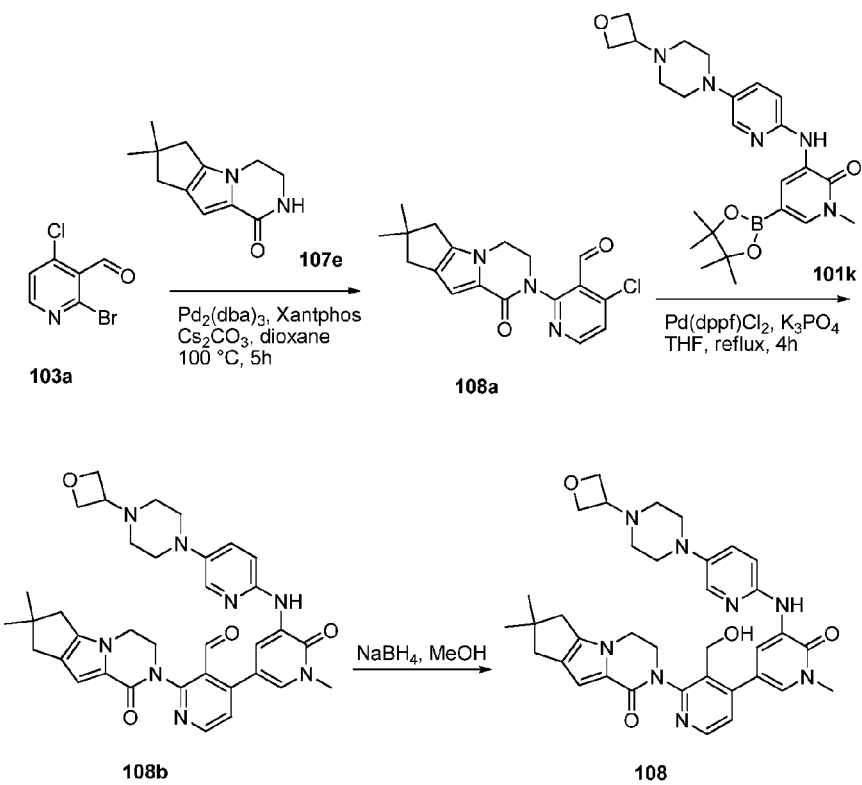
Figure 9:
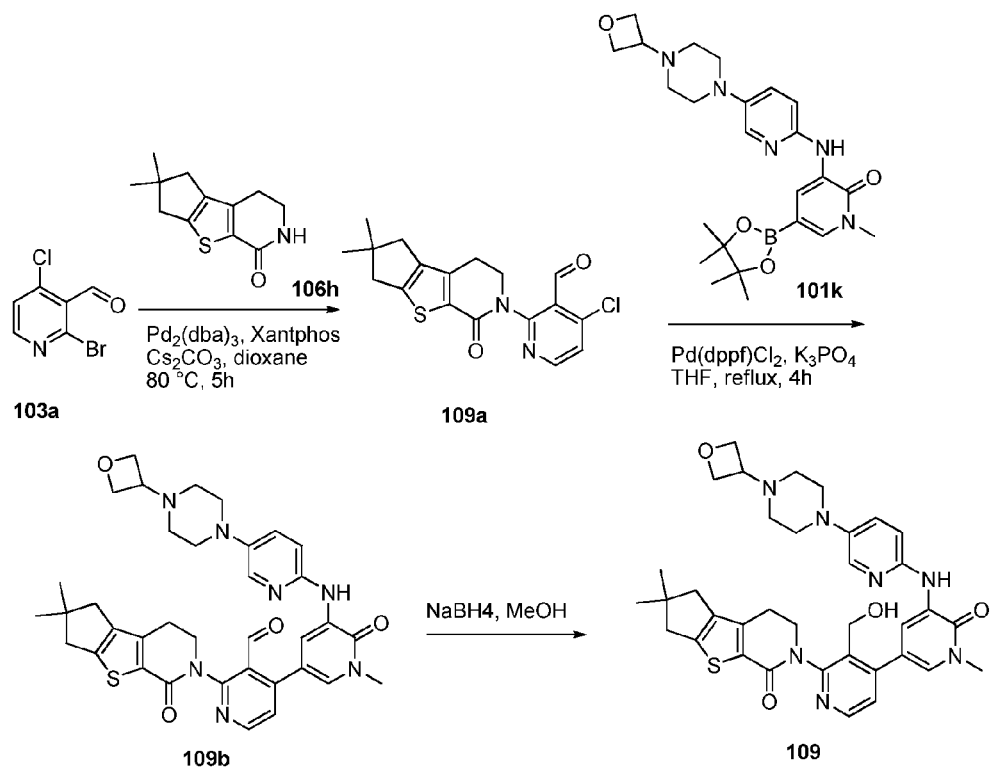
Figure 10:
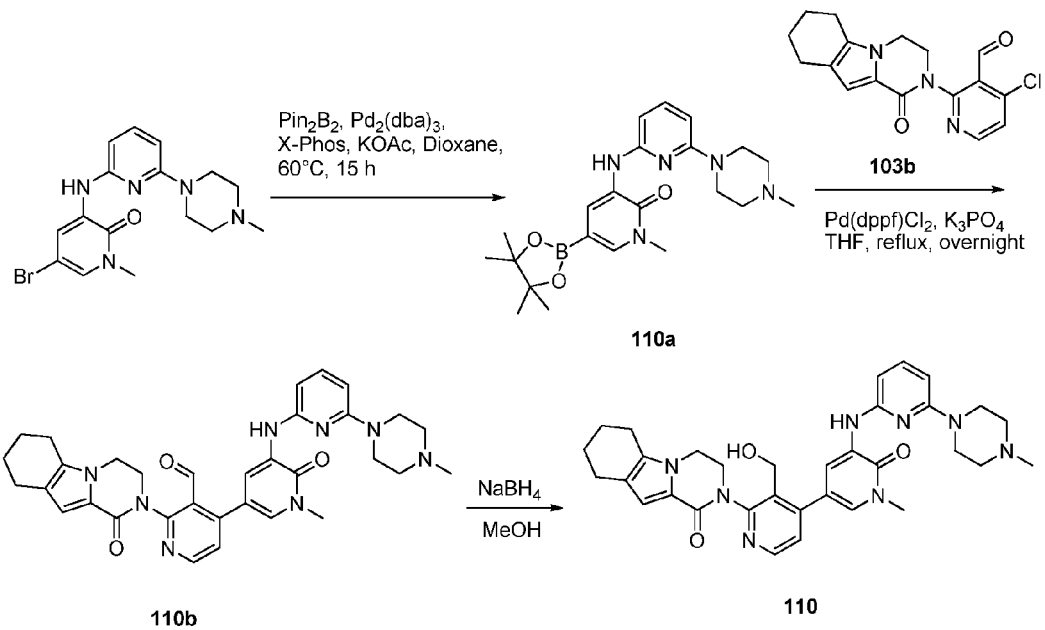
Figure 11:
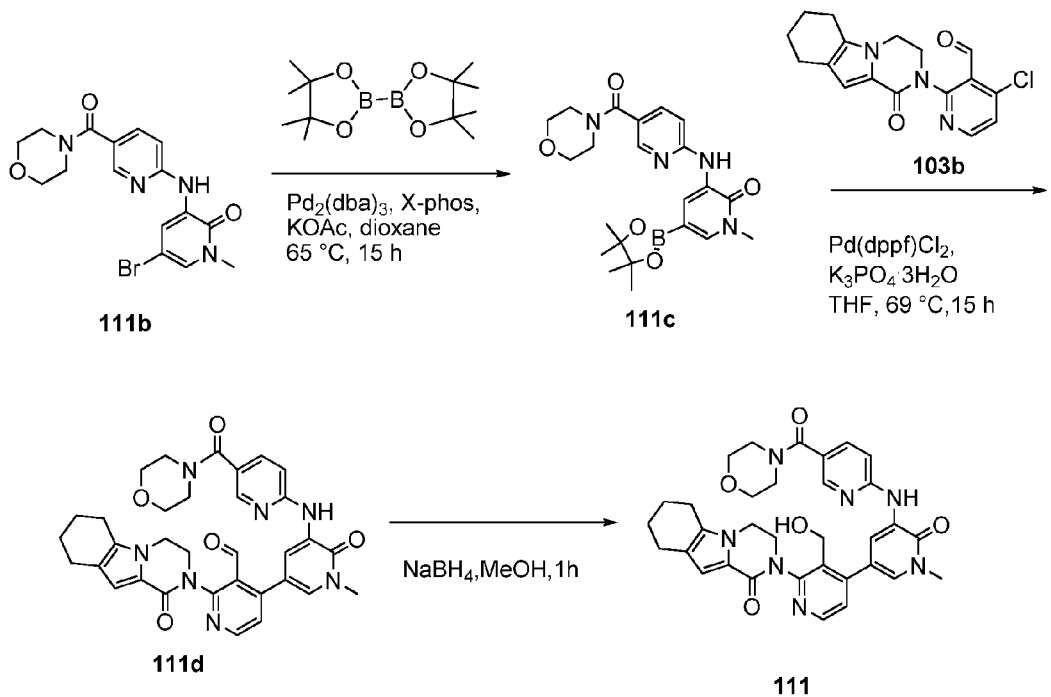
Figure 12:
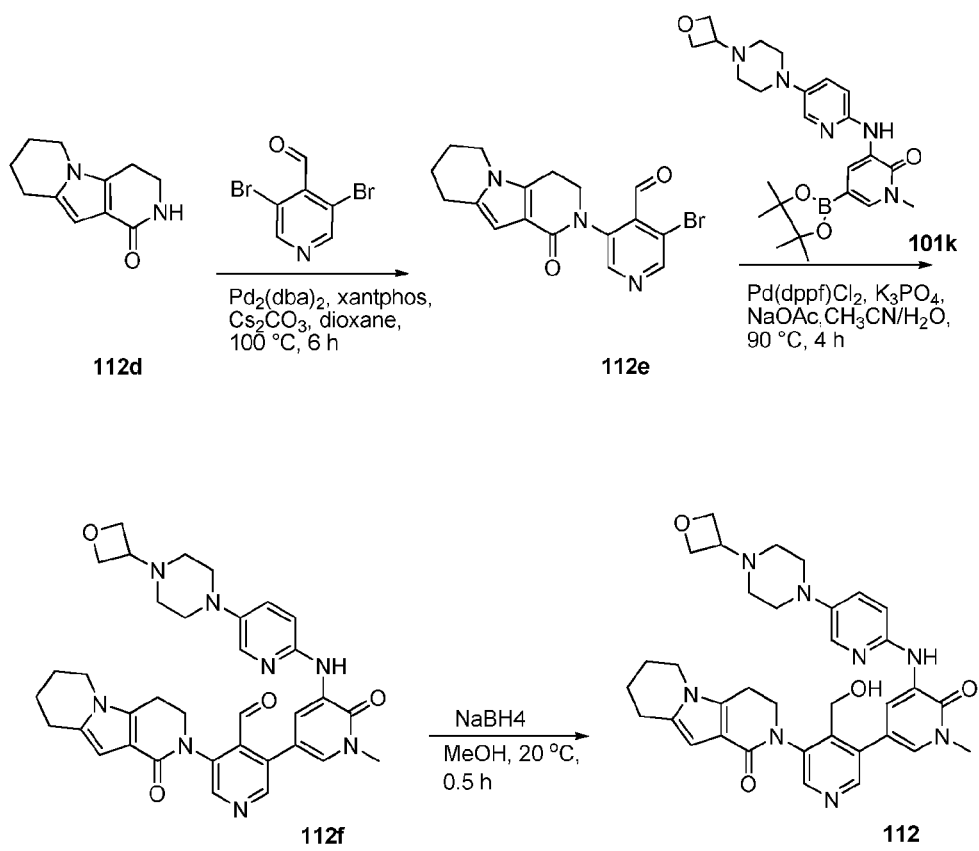
Figure 13:
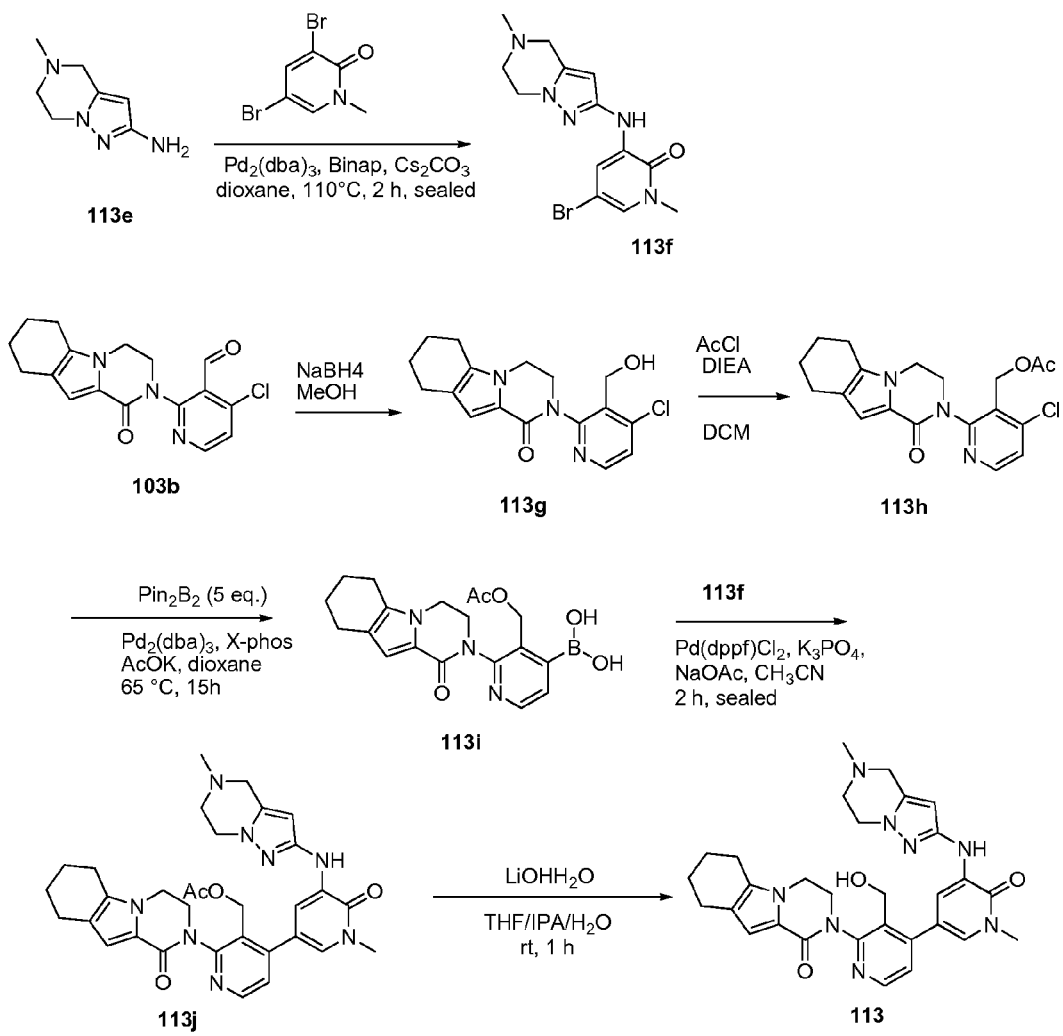
Figure 14:
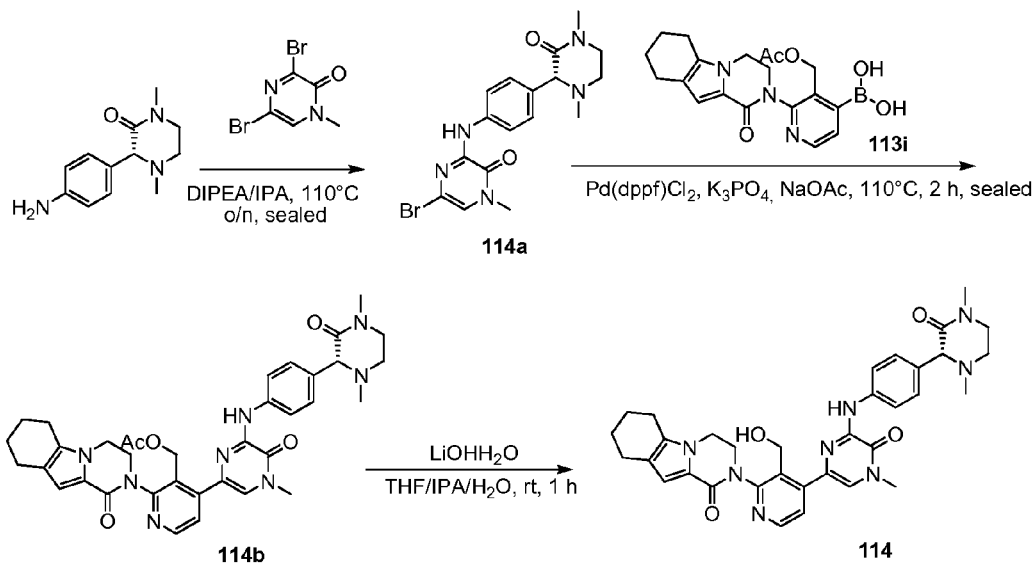
Figure 15:
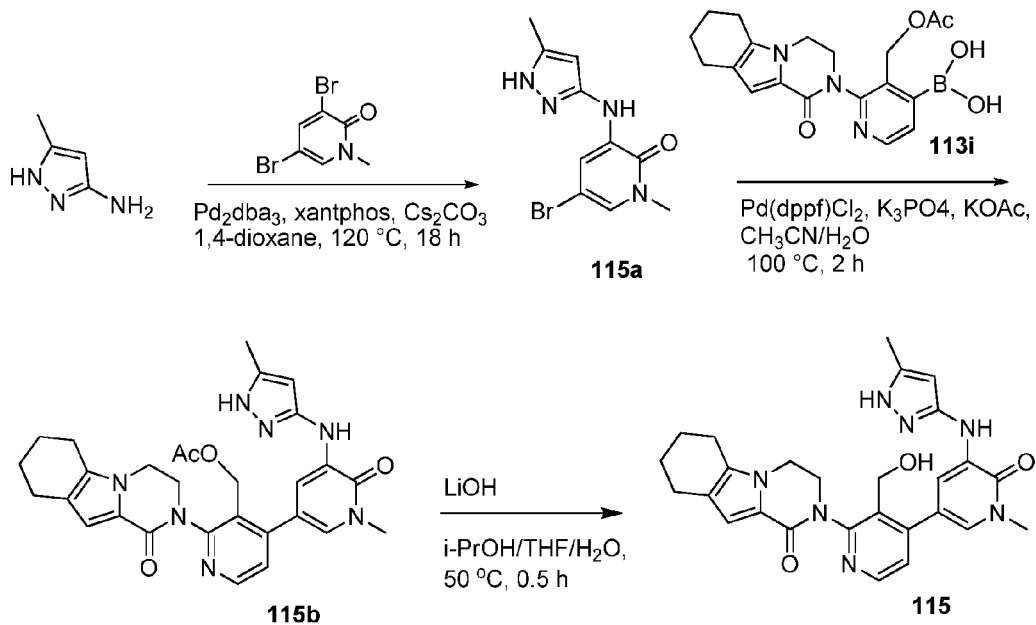
Figure 16:
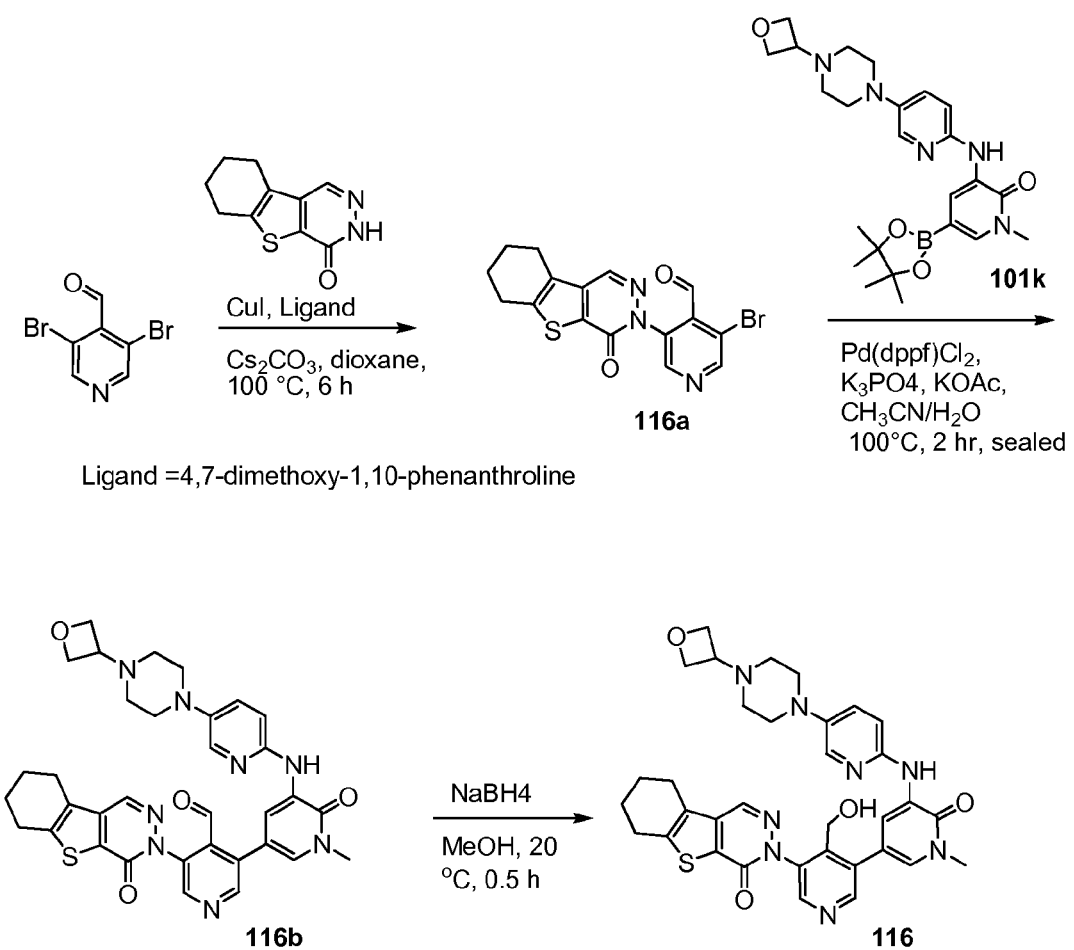
Figure 17:
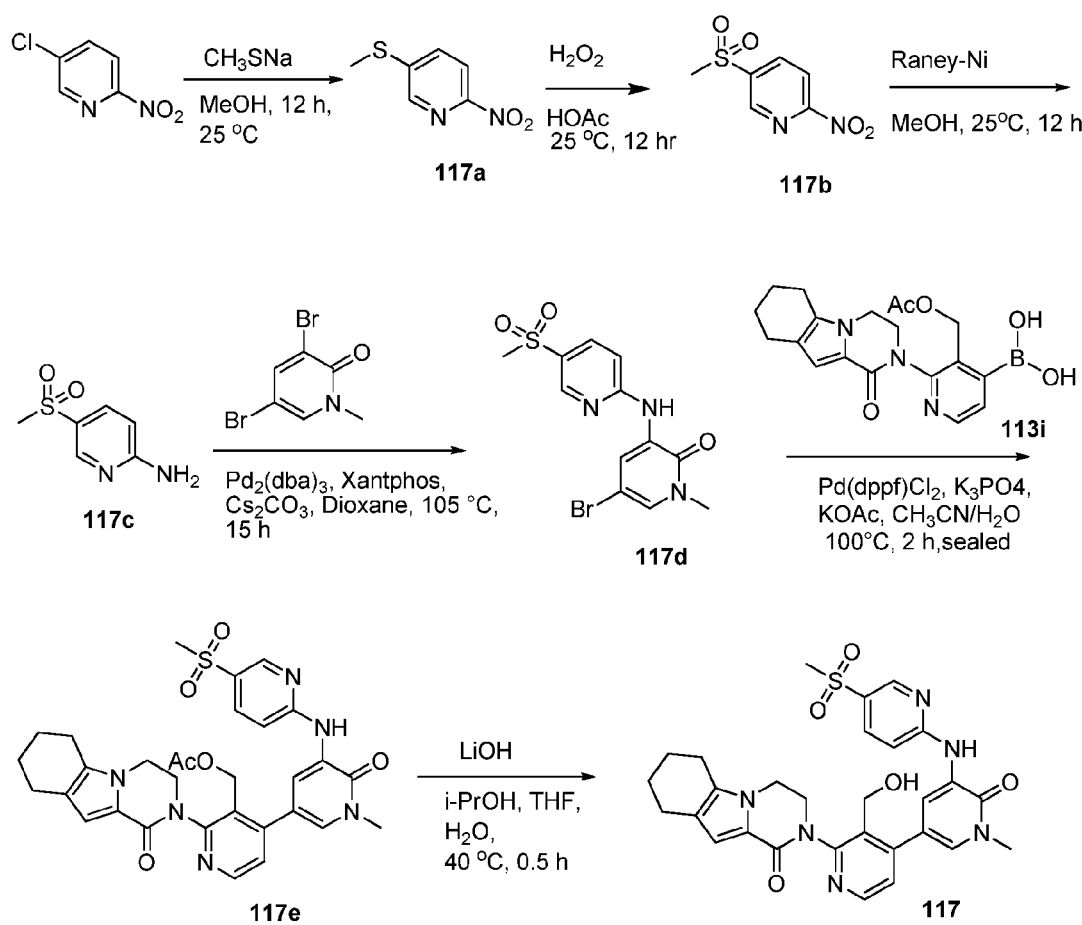
Figure 18:
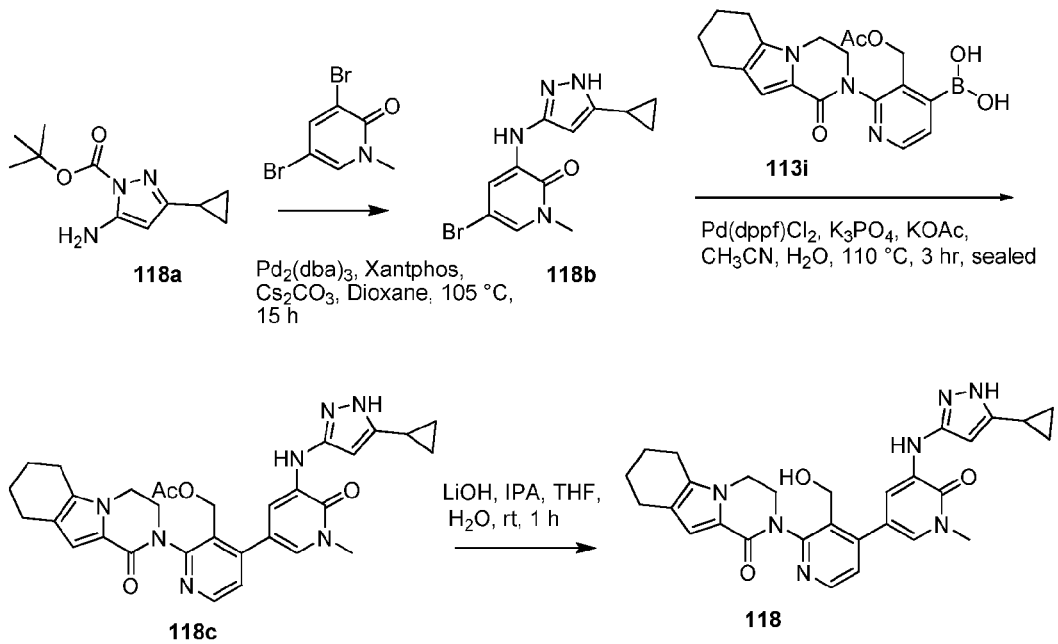
Figure 19:
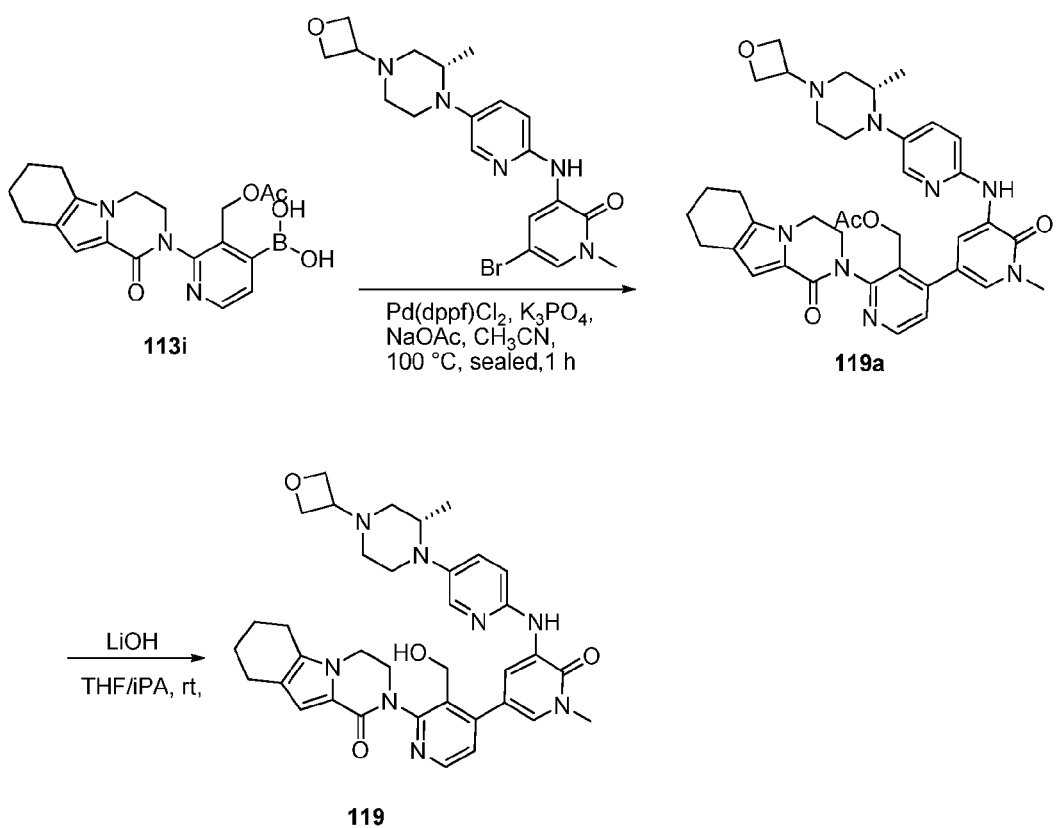
FIG. 19 shows the preparation of (S)-2-(3-(Hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 119 starting with (S)-(4-(1-Methyl-5-(5-(2-methyl-4-(oxetan-3-yl)piperazin-1-yl)pyridin-2-ylamino)-
Figure 20:
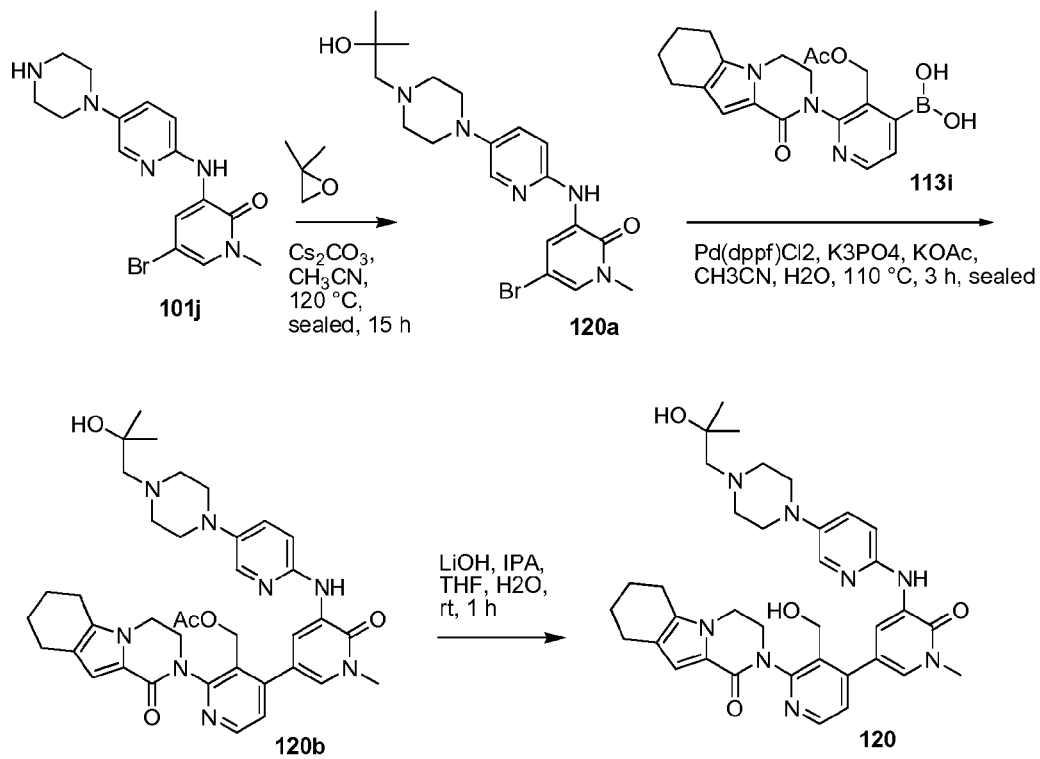
Figure 21:
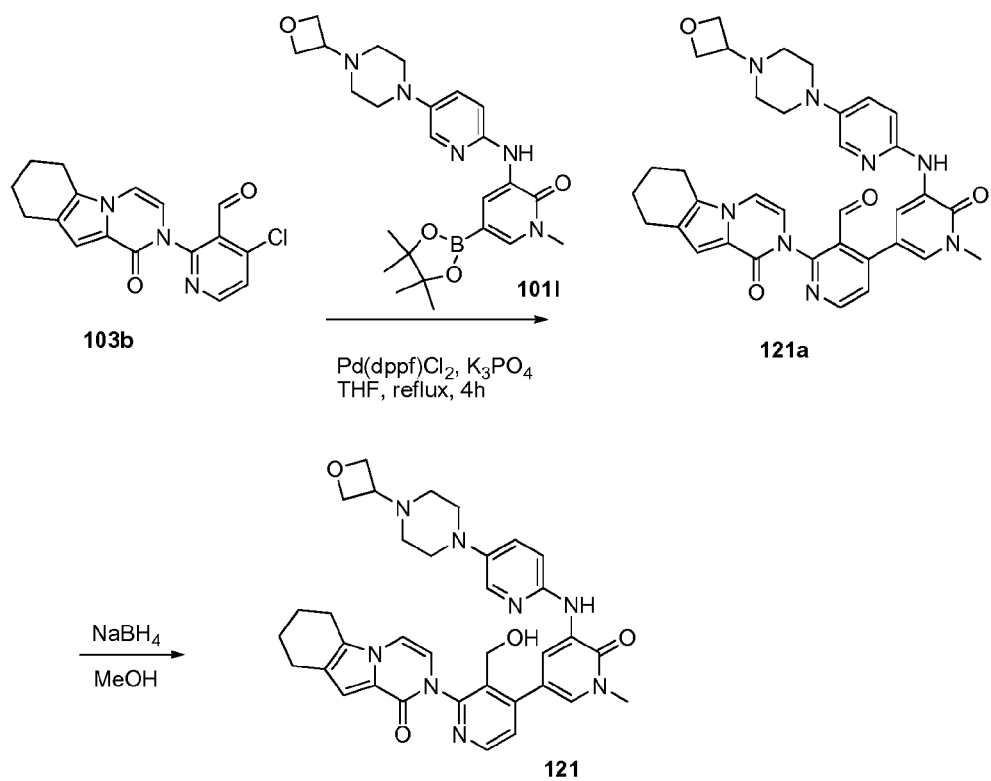
Figure 22:
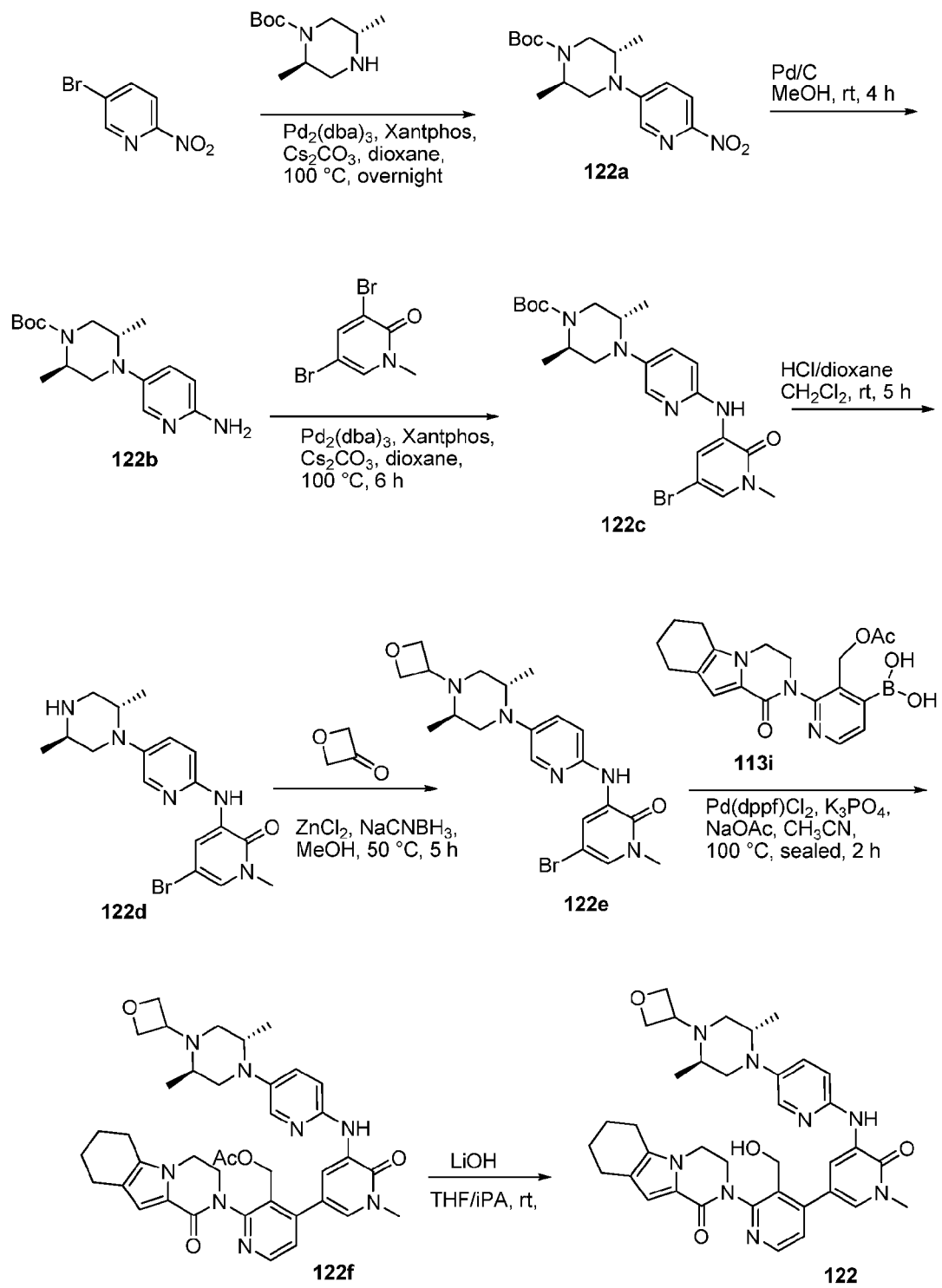
Figure 23:
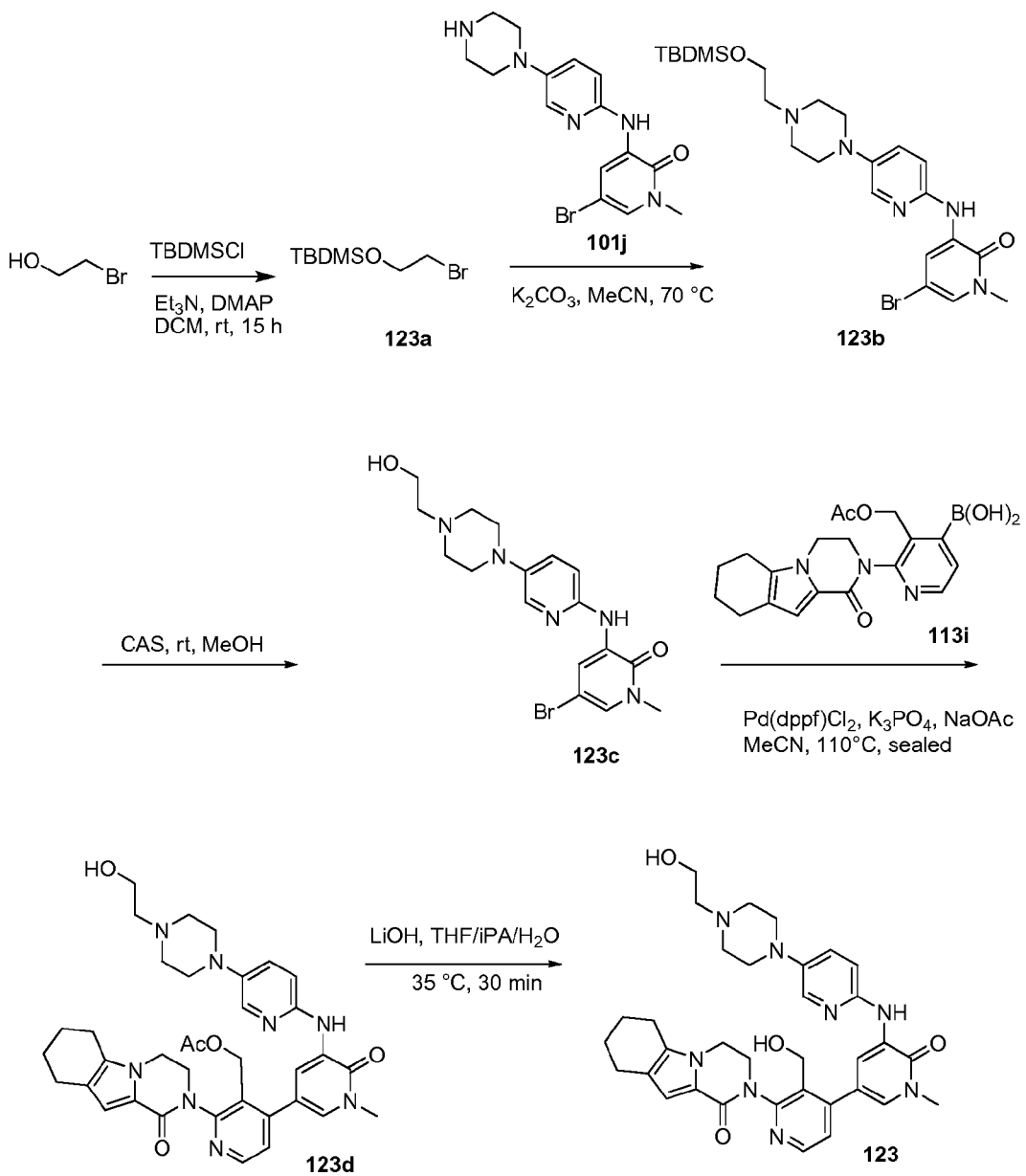
Figure 24:
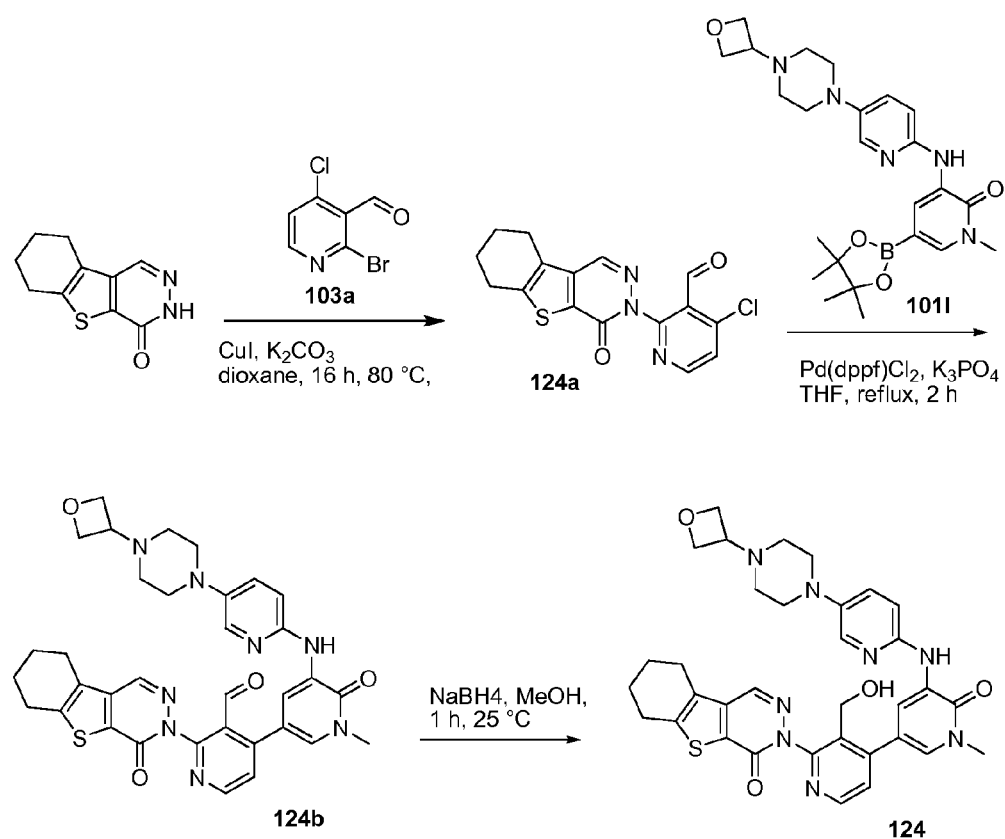
Figure 25:
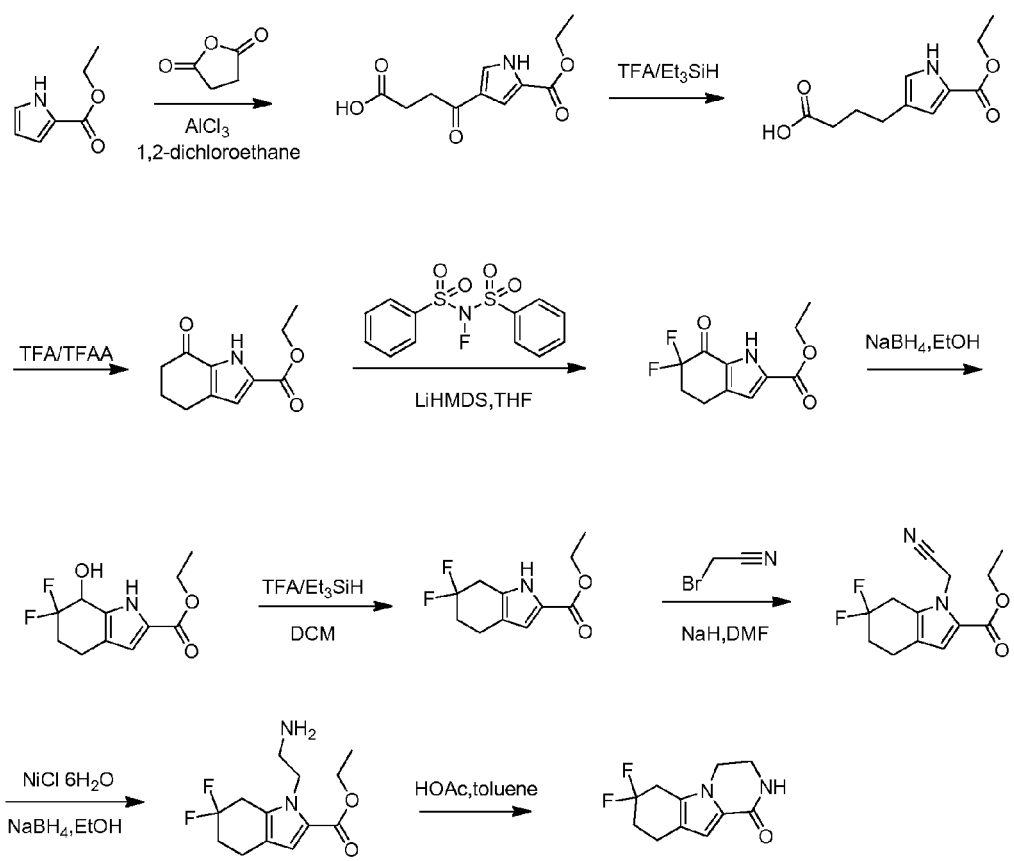

6-oxo-1,6-dihydropyridin-3-yl)-2-(1-oxo-3,4,6,7,8,9-hexahydropyrazino[1,2-a]indol-2(1H)-yl)pyridin-3-yl) methyl acetate 119a FIG. 20 shows the preparation of 2-(4-(5-(5-(4-(2-Hydroxy-2-methylpropyl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 120 starting with 5-Bromo-3-(5-(4-(2-hydroxy-2-methylpropyl)piperazin-1-yl)pyridin-2-ylamino)-1-methylpyridin-2(1H)-one 120a FIG. 21 shows the preparation of 2-(3-(hydroxymethyl)-4-(1-methyl-5-(5-(4-(oxetan-3-yl)piperazin-1-yl)pyridine-2-ylamino)-6-oxo-1,6-dihydropyridin-3-yl)pyridin-2-yl)-6,7,8,9-tetrahydropyrazino[1,2-a]indol-1(2H)-one 121 starting with 4-(1-Methyl-5-(5-(4-(oxetan-3-yl)piperazin-1-yl)pyridin-2-ylamino)-6-oxo-1,6-dihydropyridin-3-yl)-2-(1-oxo-6,7,8,9-tetrahydropyrazino[1,2-a]indol-2(1H)-yl)nicotinaldehyde 121a FIG. 22 shows the preparation of 2-(4-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 122 starting with (2R,5S)-tert-Butyl 2,5-Dimethyl-4-(6-nitropyridin-3-yl)piperazine-1-carboxylate 122a FIG. 23 shows the preparation of 2-(4-(5-(5-(4-(2-Hydroxyethyl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydro-pyrazino[1,2-a]indol-1(2H)-one 123 starting with (2-Bromoethoxy)(tert-butyl)dimethylsilane 123a FIG. 24 shows the preparation of 3-Hydroxymethyl-4-[1-methyl-5-(5-(4-(oxetan-3-yl)piperazin-1-yl)pyridine-2-ylamino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine 124 starting with 4-Chloro-2-{6-oxo-8-thia-4,5-diazatricyclo[7.4.0.0$^{2,7}$]trideca-1(9),2(7),3-trien-5-yl}pyridine-3-carbaldehyde 124a FIG. 25 shows the preparation of 7,7-difluoro-3,4,6,7,8,9-hexahydropyrazino[1,2-a]indol-1(2H)-one, useful for the preparation of 140, starting from ethyl 1H-pyrrole-2-carboxylate.

Figure 26:
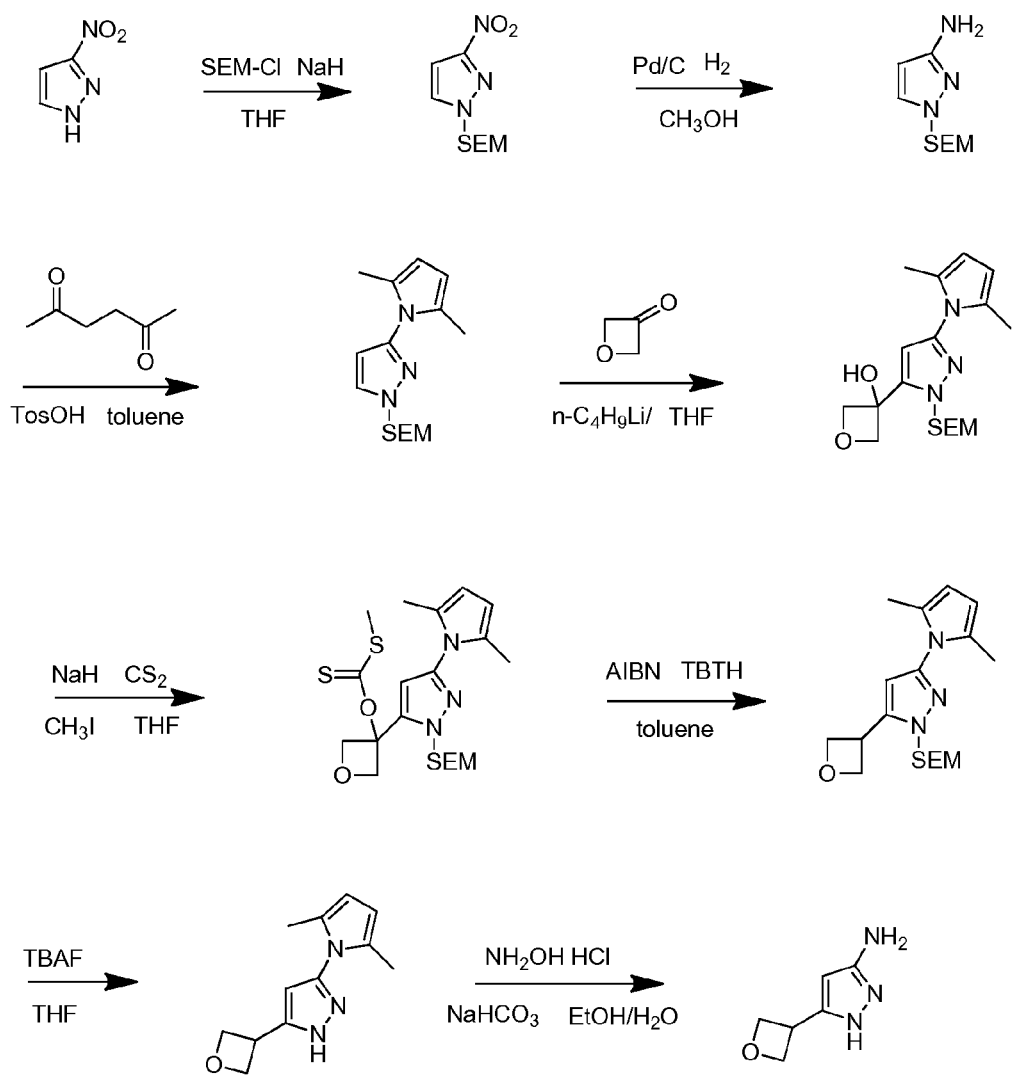

FIG. 26 shows the preparation of 5-(oxetan-3-yl)-1H-pyrazol-3-amine, useful for the preparation of 266, starting from 3-nitro-1H-pyrazole.

DETAILED DESCRIPTION OF EXEMPLARY EMBODIMENTS

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention. The present invention is in no way limited to the methods and materials described. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. The nomenclature used in this Application is based on IUPAC systematic nomenclature, unless indicated otherwise.

DEFINITIONS

When indicating the number of substituents, the term "one or more" refers to the range from one substituent to the highest possible number of substitution, i.e. replacement of one hydrogen up to replacement of all hydrogens by substituents. The term "substituent" denotes an atom or a group of atoms replacing a hydrogen atom on the parent molecule. The term "substituted" denotes that a specified group bears one or more substituents. Where any group may carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents described below. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH^2CH^3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, and the like.

The term "alkylene" as used herein refers to a saturated linear or branched-chain divalent hydrocarbon radical of one to twelve carbon atoms ($C_1$-$C_{12}$), wherein the alkylene radical may be optionally substituted independently with one or more substituents described below. In another embodiment, an alkylene radical is one to eight carbon atoms ($C_1$-$C_8$), or one to six carbon atoms ($C_1$-$C_6$). Examples of alkylene groups include, but are not limited to, methylene (—$CH_2$—), ethylene (—$CH_2CH_2$—), propylene (—$CH_2CH_2CH_2$—), and the like.

The term "alkenyl" refers to linear or branched-chain monovalent hydrocarbon radical of two to eight carbon atoms ($C_2$-$C_8$) with at least one site of unsaturation, i.e., a carbon-carbon, $sp^2$ double bond, wherein the alkenyl radical may be optionally substituted independently with one or more substituents described herein, and includes radicals having "cis" and "trans" orientations, or alternatively, "E" and "Z" orientations. Examples include, but are not limited to, ethylenyl or vinyl (—CH=$CH_2$), allyl (—$CH_2$CH=$CH_2$), and the like.

The term "alkenylene" refers to linear or branched-chain divalent hydrocarbon radical of two to eight carbon atoms ($C_2$-$C_8$) with at least one site of unsaturation, i.e., a carbon-carbon, $sp^2$ double bond, wherein the alkenylene radical may be optionally substituted substituted independently with one or more substituents described herein, and includes radicals having "cis" and "trans" orientations, or alternatively, "E" and "Z" orientations. Examples include, but are not limited to, ethylenylene or vinylene (—CH=CH—), allyl (—$CH_2$CH=CH—), and the like.

The term "alkynyl" refers to a linear or branched monovalent hydrocarbon radical of two to eight carbon atoms ($C_2$-$C_8$) with at least one site of unsaturation, i.e., a carbon-carbon, sp triple bond, wherein the alkynyl radical may be optionally substituted independently with one or more substituents described herein. Examples include, but are not limited to, ethynyl (—C≡CH), propynyl (propargyl, —$CH_2$C≡CH), and the like.

The term "alkynylene" refers to a linear or branched divalent hydrocarbon radical of two to eight carbon atoms ($C_2$-$C_8$) with at least one site of unsaturation, i.e., a carbon-carbon, sp triple bond, wherein the alkynylene radical may be optionally substituted independently with one or more substituents described herein. Examples include, but are not limited to, ethynylene (—C≡C—), propynylene (propargylene, —$CH_2$C≡C—), and the like.

The terms "carbocycle", "carbocyclyl", "carbocyclic ring" and "cycloalkyl" refer to a monovalent non-aromatic, saturated or partially unsaturated ring having 3 to 12 carbon atoms ($C_3$-$C_{12}$) as a monocyclic ring or 7 to 12 carbon atoms as a bicyclic ring. Bicyclic carbocycles having 7 to 12 atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system, or as bridged systems such as bicyclo[2.2.1]heptane, bicyclo[2.2.2]octane and bicyclo[3.2.2]nonane. Spiro moieties are also included within the scope of this definition. Examples of monocyclic carbocycles include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like. Carbocyclyl groups are optionally substituted independently with one or more substituents described herein.

"Aryl" means a monovalent aromatic hydrocarbon radical of 6-20 carbon atoms ($C_6$-$C_{20}$) derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. Aryl groups are optionally substituted independently with one or more substituents described herein.

"Arylene" means a divalent aromatic hydrocarbon radical of 6-20 carbon atoms ($C_6$-$C_{20}$) derived by the removal of two hydrogen atom from a two carbon atoms of a parent aromatic ring system. Some arylene groups are represented in the exemplary structures as "Ar". Arylene includes bicyclic radicals comprising an aromatic ring fused to a saturated, partially unsaturated ring, or aromatic carbocyclic ring. Typical arylene groups include, but are not limited to, radicals derived from benzene (phenylene), substituted benzenes, naphthalene, anthracene, biphenylene, indenylene, indanylene, 1,2-dihydronaphthalene, 1,2,3,4-tetrahydronaphthyl, and the like. Arylene groups are optionally substituted with one or more substituents described herein.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to about 20 ring atoms in which at least one ring atom is a heteroatom selected from nitrogen, oxygen, phosphorus and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo[4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, morpholin-4-yl, piperidin-1-yl, piperazinyl, piperazin-4-yl-2-one, piperazin-4-yl-3-one, pyrrolidin-1-yl, thiomorpholin-4-yl, S-dioxothiomorpholin-4-yl, azocan-1-yl, azetidin-1-yl, octahydropyrido[1,2-a]pyrazin-2-yl, [1,4]diazepan-1-yl, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, azabicyclo[2.2.2]hexanyl, 3H-indolyl quinolizinyl and N-pyridyl ureas. Spiro moieties are also included within the scope of this definition. Examples of a heterocyclic group wherein 2 ring atoms are substituted with oxo (=O) moieties are pyrimidinonyl and 1,1-dioxo-thiomorpholinyl. The heterocycle groups herein are optionally substituted independently with one or more substituents described herein.

The term "heteroaryl" refers to a monovalent aromatic radical of 5-, 6-, or 7-membered rings, and includes fused ring systems (at least one of which is aromatic) of 5-20 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxadiazolyl, oxazolyl, isothiazolyl, pyrrolyl, quinolinyl, isoquinolinyl, tetrahydroisoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. Heteroaryl groups are optionally substituted independently with one or more substituents described herein.

The heterocycle or heteroaryl groups may be carbon (carbon-linked), or nitrogen (nitrogen-linked) bonded where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline.

The terms "treat" and "treatment" refer to therapeutic treatment, wherein the object is to slow down (lessen) an undesired physiological change or disorder, such as the development or spread of arthritis or cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those with the condition or disorder.

The phrase "therapeutically effective amount" means an amount of a compound of the present invention that (i) treats the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

"Inflammatory disorder" as used herein can refer to any disease, disorder, or syndrome in which an excessive or unregulated inflammatory response leads to excessive inflammatory symptoms, host tissue damage, or loss of tissue function. "Inflammatory disorder" also refers to a pathological state mediated by influx of leukocytes and/or neutrophil chemotaxis.

"Inflammation" as used herein refers to a localized, protective response elicited by injury or destruction of tissues, which serves to destroy, dilute, or wall off (sequester) both the injurious agent and the injured tissue. Inflammation is notably associated with influx of leukocytes and/or neutrophil chemotaxis. Inflammation can result from infection with pathogenic organisms and viruses and from noninfectious means such as trauma or reperfusion following myocardial infarction or stroke, immune response to foreign antigen, and autoimmune responses. Accordingly, inflammatory disorders amenable to treatment with Formula I compounds encompass disorders associated with reactions of the specific defense system as well as with reactions of the nonspecific defense system.

"Specific defense system" refers to the component of the immune system that reacts to the presence of specific antigens. Examples of inflammation resulting from a response of the specific defense system include the classical response to foreign antigens, autoimmune diseases, and delayed type hypersensitivity response mediated by T-cells. Chronic inflammatory diseases, the rejection of solid transplanted tissue and organs, e.g., kidney and bone marrow transplants, and graft versus host disease (GVHD), are further examples of inflammatory reactions of the specific defense system.

The term "nonspecific defense system" as used herein refers to inflammatory disorders that are mediated by leukocytes that are incapable of immunological memory (e.g., granulocytes, and macrophages). Examples of inflammation that result, at least in part, from a reaction of the nonspecific defense system include inflammation associated with conditions such as adult (acute) respiratory distress syndrome (ARDS) or multiple organ injury syndromes; reperfusion injury; acute glomerulonephritis; reactive arthritis; dermatoses with acute inflammatory components; acute purulent meningitis or other central nervous system inflammatory disorders such as stroke; thermal injury; inflammatory bowel disease; granulocyte transfusion associated syndromes; and cytokine-induced toxicity.

"Autoimmune disease" as used herein refers to any group of disorders in which tissue injury is associated with humoral or cell-mediated responses to the body's own constituents.

"Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies. "Transplant rejection" as used herein refers to any immune reaction directed against grafted tissue, such as organs or cells (e.g., bone marrow), characterized by a loss of function of the grafted and surrounding tissues, pain, swelling, leukocytosis, and thrombocytopenia. The therapeutic methods of the present invention include methods for the treatment of disorders associated with inflammatory cell activation.

"Inflammatory cell activation" refers to the induction by a stimulus (including, but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including, but not limited to, major histocompatibility antigens or cell adhesion molecules) in inflammatory cells (including but not limited to monocytes, macrophages, T lymphocytes, B lymphocytes, granulocytes (i.e., polymorphonuclear leukocytes such as neutrophils, basophils, and eosinophils), mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory disorder.

The term "NSAID" is an acronym for "non-steroidal anti-inflammatory drug" and is a therapeutic agent with analgesic, antipyretic (lowering an elevated body temperature and relieving pain without impairing consciousness) and, in higher doses, with anti-inflammatory effects (reducing inflammation). The term "non-steroidal" is used to distinguish these drugs from steroids, which (among a broad range of other effects) have a similar eicosanoid-depressing, anti-inflammatory action. As analgesics, NSAIDs are unusual in that they are non-narcotic. NSAIDs include aspirin, ibuprofen, and naproxen. NSAIDs are usually indicated for the treatment of acute or chronic conditions where pain and inflammation are present. NSAIDs are generally indicated for the symptomatic relief of the following conditions: rheumatoid arthritis, osteoarthritis, inflammatory arthropathies (e.g. ankylosing spondylitis, psoriatic arthritis, Reiter's syndrome, acute gout, dysmenorrhoea, metastatic bone pain, headache and migraine, postoperative pain, mild-to-moderate pain due to inflammation and tissue injury, pyrexia, ileus, and renal colic. Most NSAIDs act as non-selective inhibitors of the enzyme cyclooxygenase, inhibiting both the cyclooxygenase-1 (COX-1) and cyclooxygenase-2 (COX-2) isoenzymes. Cyclooxygenase catalyzes the formation of prostaglandins and thromboxane from arachidonic acid (itself derived from the cellular phospholipid bilayer by phospholipase $A_2$). Prostaglandins act (among other things) as messenger molecules in the process of inflammation. COX-2 inhibitors include celecoxib, etoricoxib, lumiracoxib, parecoxib, rofecoxib, rofecoxib, and valdecoxib.

The terms "cancer" refers to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

"Hematological malignancies" (British spelling "Haematological" malignancies) are the types of cancer that affect blood, bone marrow, and lymph nodes. As the three are intimately connected through the immune system, a disease affecting one of the three will often affect the others as well: although lymphoma is a disease of the lymph nodes, it often spreads to the bone marrow, affecting the blood. Hematological malignancies are malignant neoplasms ("cancer"), and they are generally treated by specialists in hematology and/or oncology. In some centers "Hematology/oncology" is a single subspecialty of internal medicine while in others they are considered separate divisions (there are also surgical and radiation oncologists). Not all hematological disorders are malignant ("cancerous"); these other blood conditions may also be managed by a hematologist. Hematological malignancies may derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Leukemias include Acute lymphoblastic leukemia (ALL), Acute myelogenous leukemia (AML), Chronic lymphocytic leukemia (CLL), Chronic myelogenous leukemia (CML), Acute monocytic leukemia (AMOL) and small lymphocytic lymphoma (SLL). Lymphomas include Hodgkin's lymphomas (all four subtypes) and Non-Hodgkin's lymphomas (all subtypes).

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCINO), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB°, SU11248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR®, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, Il), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN®, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g., calicheamicin, calicheamicin gamma1I, calicheamicin omega1 (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARGT™, 2C4, Genentech), trastuzumab (HERCEPTIN®, Genentech), tositumomab (Bexxar, Corixia), and the antibody drug conjugate, gemtuzumab ozogamicin (MYLOTARG®, Wyeth).

Humanized monoclonal antibodies with therapeutic potential as chemotherapeutic agents in combination with the Btk inhibitors of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. Accordingly, the invention includes metabolites of compounds of the invention, including compounds produced by a process comprising contacting a Formula I compound of this invention with a mammal for a period of time sufficient to yield a metabolic product thereof.

The term "package insert" is used to refer to instructions customarily included in commercial packages of therapeutic products, that contain information about the indications, usage, dosage, administration, contraindications and/or warnings concerning the use of such therapeutic products.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity. Enantiomers may be separated from a racemic mixture by a chiral separation method, such as supercritical fluid chromatography (SFC). Assignment of configuration at chiral centers in separated enantiomers may be tentative, and depicted in Table 1 structures for illustrative purposes, while stereochemical determination awaits, such as x-ray crystallographic data.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

The term "pharmaceutically acceptable salts" denotes salts which are not biologically or otherwise undesirable. Pharmaceutically acceptable salts include both acid and base addition salts. The phrase "pharmaceutically acceptable" indicates that the substance or composition must be compatible chemically and/or toxicologically, with the other ingredients comprising a formulation, and/or the mammal being treated therewith.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, malonic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid "mesylate", ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, and polyamine resins A "solvate" refers to an association or complex of one or more solvent molecules and a compound of the invention. Examples of solvents that form solvates include, but are not limited to, water, isopropanol, ethanol, methanol, DMSO, ethylacetate, acetic acid, and ethanolamine.

The term "$EC_{50}$" is the half maximal effective concentration" and denotes the plasma concentration of a particular compound required for obtaining 50% of the maximum of a particular effect in vivo.

The term "Ki" is the inhibition constant and denotes the absolute binding affinity of a particular inhibitor to a receptor. It is measured using competition binding assays and is equal to the concentration where the particular inhibitor would occupy 50% of the receptors if no competing ligand (e.g. a radioligand) was present. Ki values can be converted logarithmically to pKi values (−log Ki), in which higher values indicate exponentially greater potency.

The term "$IC_{50}$" is the half maximal inhibitory concentration and denotes the concentration of a particular compound required for obtaining 50% inhibition of a biological process in vitro. IC$_{50}$ values can be converted logarithmically to pIC$_{50}$ values (−log IC$_{50}$), in which higher values indicate exponentially greater potency. The IC$_{50}$ value is not an absolute value but depends on experimental conditions e.g. concentrations employed, and can be converted to an absolute inhibition constant (Ki) using the Cheng-Prusoff equation (Biochem. Pharmacol. (1973) 22:3099). Other percent inhibition parameters, such as IC$_{70}$, IC$_{90}$, etc., may be calculated.

The terms "compound of this invention," and "compounds of the present invention" and "compounds of Formula I" include compounds of Formulas I and stereoisomers, geometric isomers, tautomers, solvates, metabolites, and pharmaceutically acceptable salts and prodrugs thereof.

Any formula or structure given herein, including Formula I compounds, is also intended to represent hydrates, solvates, and polymorphs of such compounds, and mixtures thereof.

Any formula or structure given herein, including Formula I compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent in the compound of the formula (I). The concentration of such a heavier isotope, specifically deuterium, may be defined by an isotopic enrichment factor. In the compounds of this invention any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this invention any atom specifically designated as a deuterium (D) is meant to represent deuterium.

Heteroaryl Pyridone and Aza-Pyridone Compounds

The present invention provides heteroaryl pyridone and aza-pyridone compounds of Formula I, including Formulas Ia-Ii, and pharmaceutical formulations thereof, which are potentially useful in the treatment of diseases, conditions and/or disorders modulated by Btk kinase:

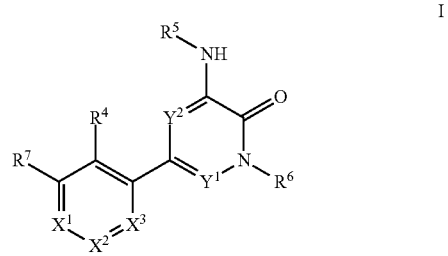

including stereoisomers, tautomers, or pharmaceutically acceptable salts thereof, wherein:

$X^1$ is $CR^1$ or N;
$X^2$ is $CR^2$ or N;
$X^3$ is $CR^3$ or N;
where one or two of $X^1$, $X^2$, and $X^3$ are N;
$R^1$, $R^2$ and $R^3$ are independently selected from H, F, Cl, —NH$_2$, —NHCH$_3$, —N(CH$_3$)$_2$, —OH, —OCH$_3$, —OCH$_2$CH$_3$, —OCH$_2$CH$_2$OH, and C$_1$-C$_3$ alkyl;
$R^4$ is selected from H, F, Cl, CN, —CH$_2$OH, —CH(CH$_3$)OH, —C(CH$_3$)$_2$OH, —CH(CF$_3$)OH, —CHF, —CHF, —CH$_2$CHF$_2$, —CF$_3$, —C(O)NH$_2$, —C(O)NHCH$_3$, —C(O)N(CH$_3$)$_2$, —NH$_2$, —NHCH$_3$, —N(CH$_3$)$_2$, —NHC(O)CH$_3$, —OH, —OCH$_3$, —OCH$_2$CH$_3$, —OCH$_2$CH$_2$OH, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;
$R^5$ is optionally substituted C$_6$-C$_{20}$ aryl, C$_3$-C$_{12}$ carbocyclyl, C$_2$-C$_{20}$ heterocyclyl, C$_1$-C$_{20}$ heteroaryl, —(C$_6$-C$_{20}$ aryl)-(C$_2$-C$_{20}$ heterocyclyl), —(C$_1$-C$_{20}$ heteroaryl)-(C$_2$-C$_{20}$ heterocyclyl), —(C$_1$-C$_{20}$ heteroaryl)-(C$_2$-C$_{20}$ heterocyclyl)-(C$_2$-C$_{20}$ heterocyclyl), —(C$_1$-C$_{20}$ heteroaryl)-(C$_2$-C$_{20}$ heterocyclyl)-(C$_1$-C$_6$ alkyl), —(C$_1$-C$_{20}$ heteroaryl)-(C$_1$-C$_6$ alkyl), —(C$_2$-C$_{20}$ heterocyclyl)-(C$_1$-C$_6$ alkyl), —(C$_2$-C$_{20}$ heterocyclyl)-(C$_3$-C$_{12}$ carbocyclyl), —(C$_1$-C$_{20}$ heteroaryl)-(C$_3$-C$_{12}$ carbocyclyl), or —(C$_1$-C$_{20}$ heteroaryl)-C(=O)—(C$_2$-C$_{20}$ heterocyclyl);
$R^6$ is H, F, —CH$_3$, —CH$_2$CH$_3$, —CH$_2$CH$_2$OH, —NH$_2$, or —OH;
$R^7$ is selected from the structures:

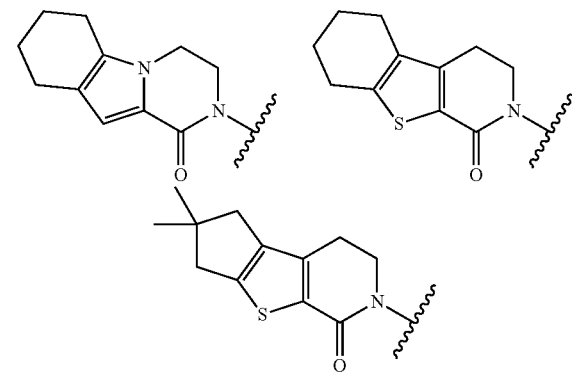

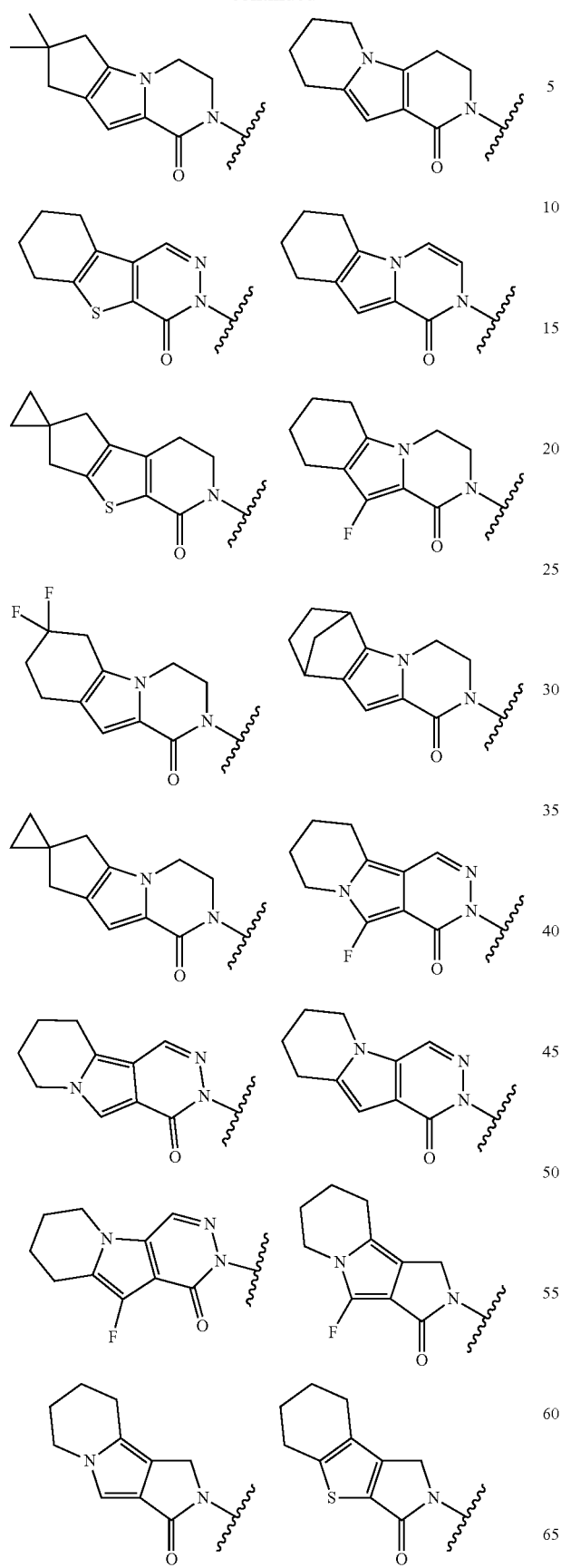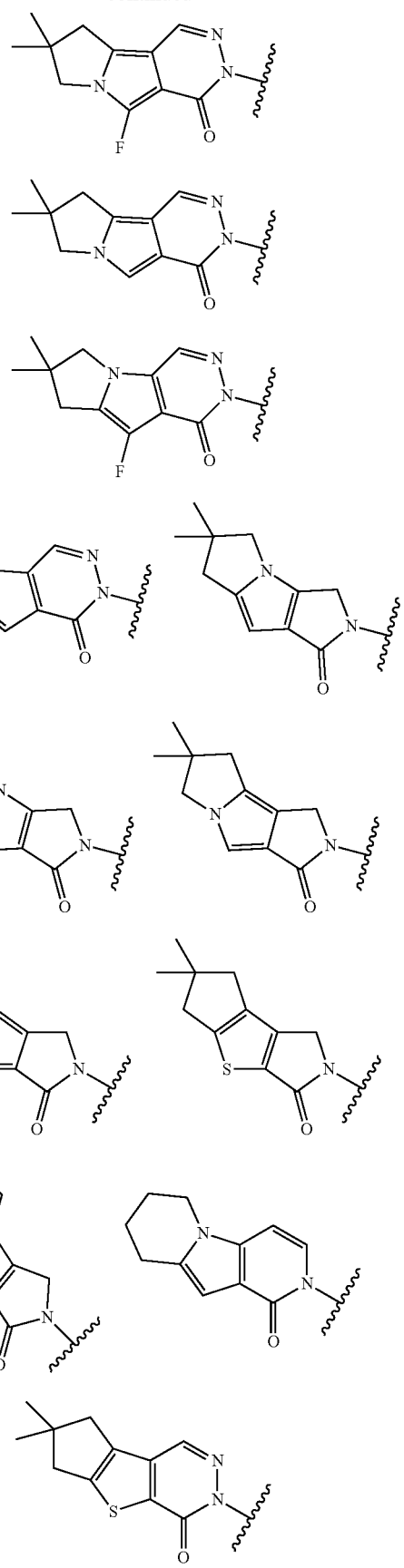

-continued

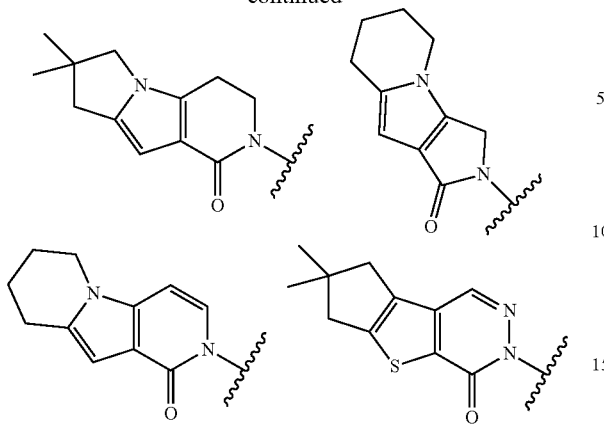

where the wavy line indicates the site of attachment; and $Y^1$ and $Y^2$ are independently selected from CH and N, where $Y^1$ and $Y^2$ are not each N;

where alkyl, carbocyclyl, heterocyclyl, aryl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, and morpholino.

Exemplary embodiments of Formula I compounds include compounds of Formulas Ia-c:

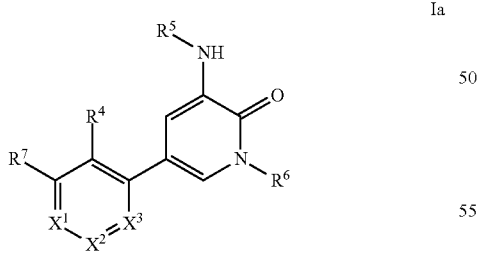

Ia

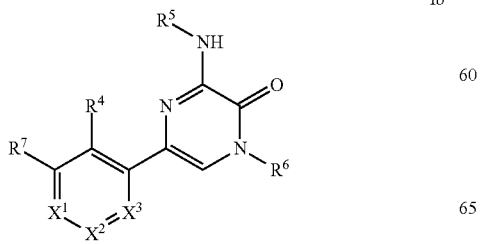

Ib

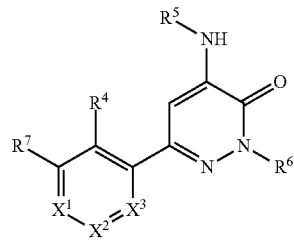

Ic

Exemplary embodiments of Formula I compounds also include compounds of Formulas Id-i:

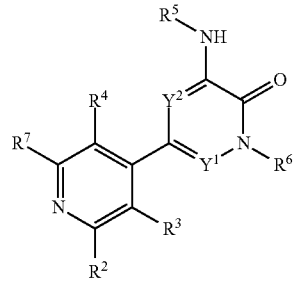

Id

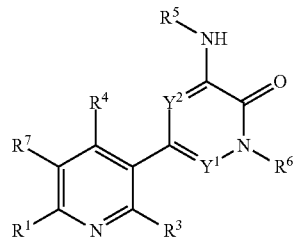

Ie

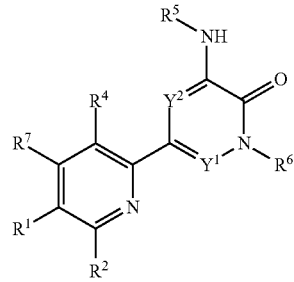

If

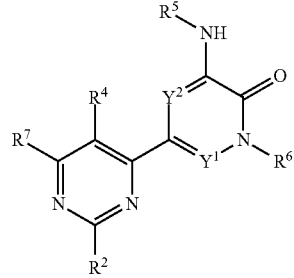

Ig

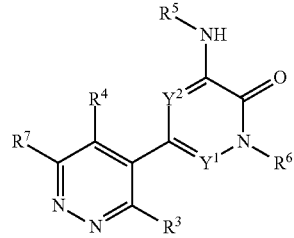

Ih

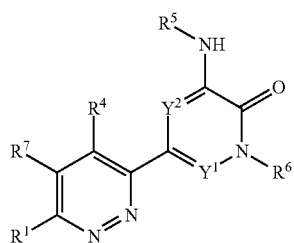
                                                                    Ii Exemplary embodiments of Formula I compounds include wherein $X^1$ is N, $X^1$ is N, $X^1$ is N, $X^1$ and $X^3$ are N, $X^1$ and $X^2$ are N, or $X^2$ and $X^3$ are N, as shown in Formulas Ic-Ii.

Exemplary embodiments of Formula I compounds include wherein $R^5$ is optionally substituted $C_1$-$C_{20}$ heteroaryl selected from pyrazolyl, pyridinyl, pyrimidinyl, 5-methyl-4,5,6,7-tetrahydropyrazolo[1,5-a]pyrazin-2-yl, 5-acetyl-4,5,6,7-tetrahydropyrazolo[1,5-a]pyrazin-2-yl, 6,7-dihydro-4H-pyrazolo[5,1-c][1,4]oxazin-2-yl, and 1-methyl-5-(5-(4-methylpiperazin-1-yl)pyridin-2-yl.

Exemplary embodiments of Formula I compounds include wherein $R^5$ is —($C_1$-$C_{20}$ heteroaryl)-($C_2$-$C_{20}$ heterocyclyl) where heteroaryl is optionally substituted pyridinyl and heterocyclyl is optionally substituted piperazinyl.

Exemplary embodiments of Formula I compounds include wherein $R^5$ is phenyl, optionally substituted with one or more groups selected from F, Cl, —$CH_3$, —$S(O)_2CH_3$, cyclopropyl, azetidinyl, oxetanyl, and morpholino.

Exemplary embodiments of Formula I compounds include wherein $R^5$ is selected from the structures:

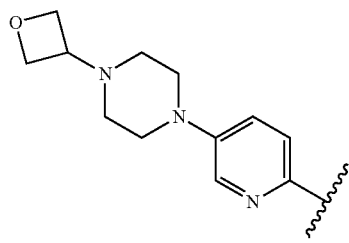

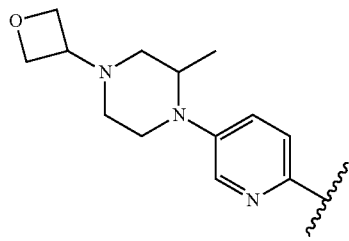

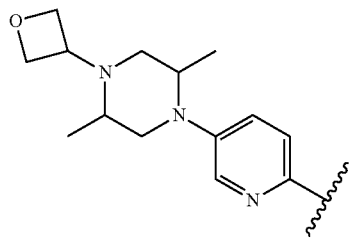

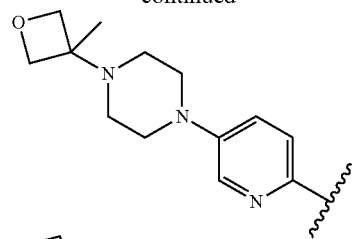

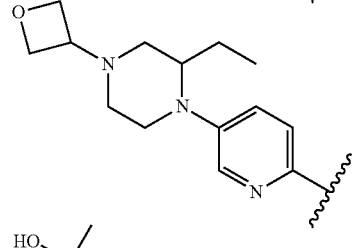

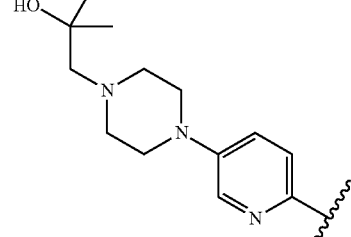

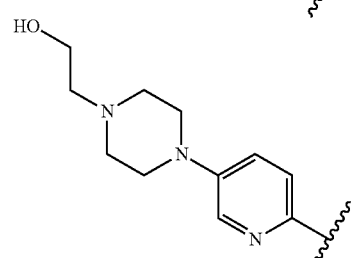

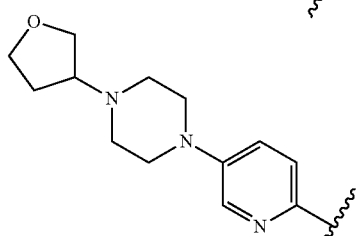

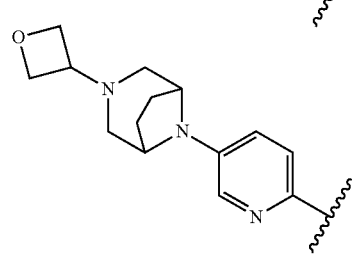

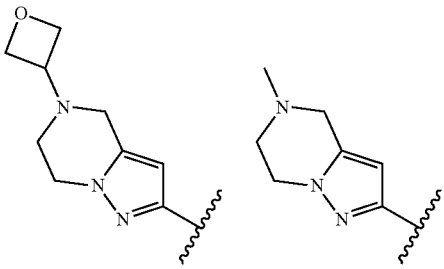

-continued
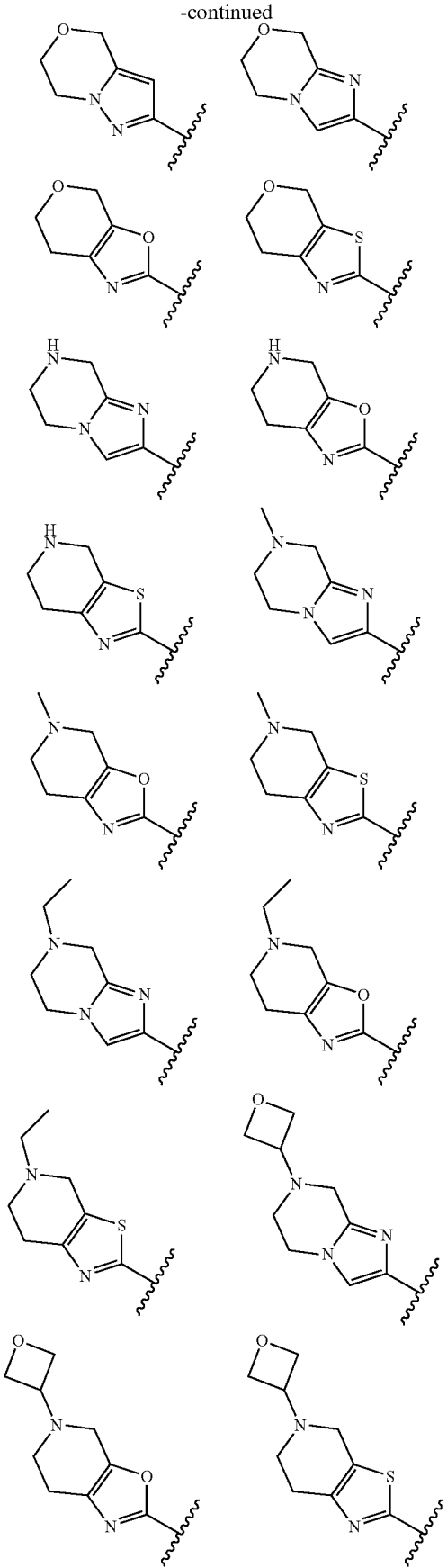
-continued
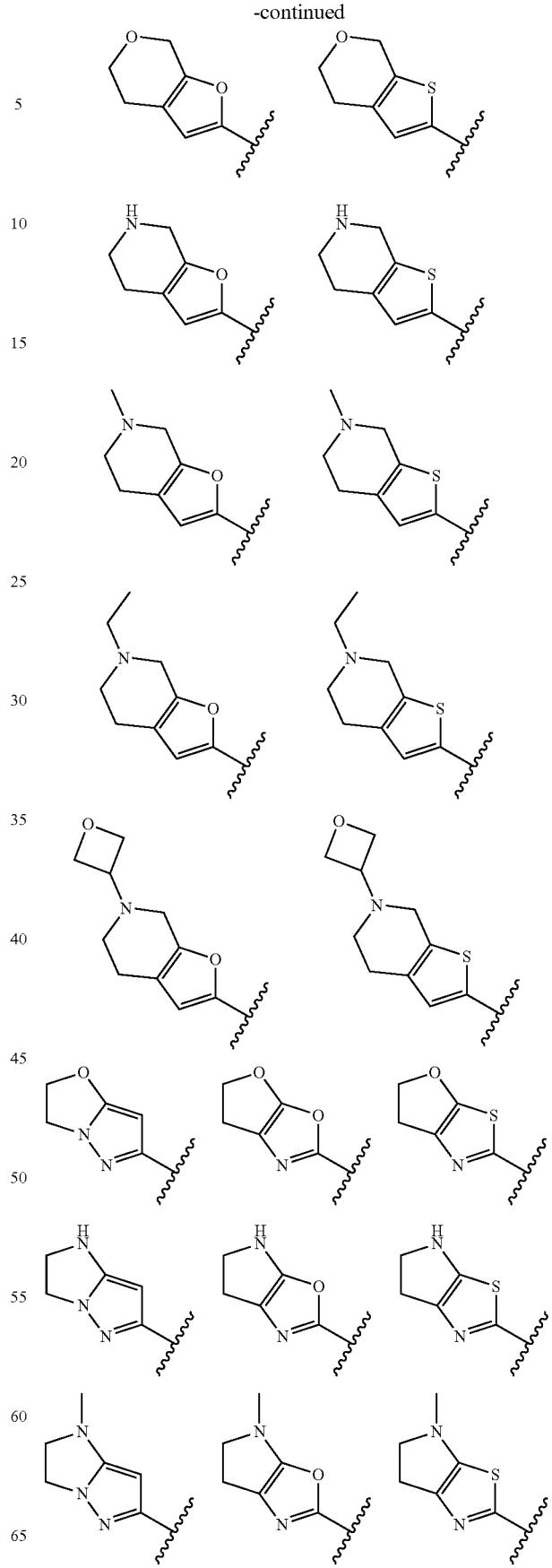

27
-continued
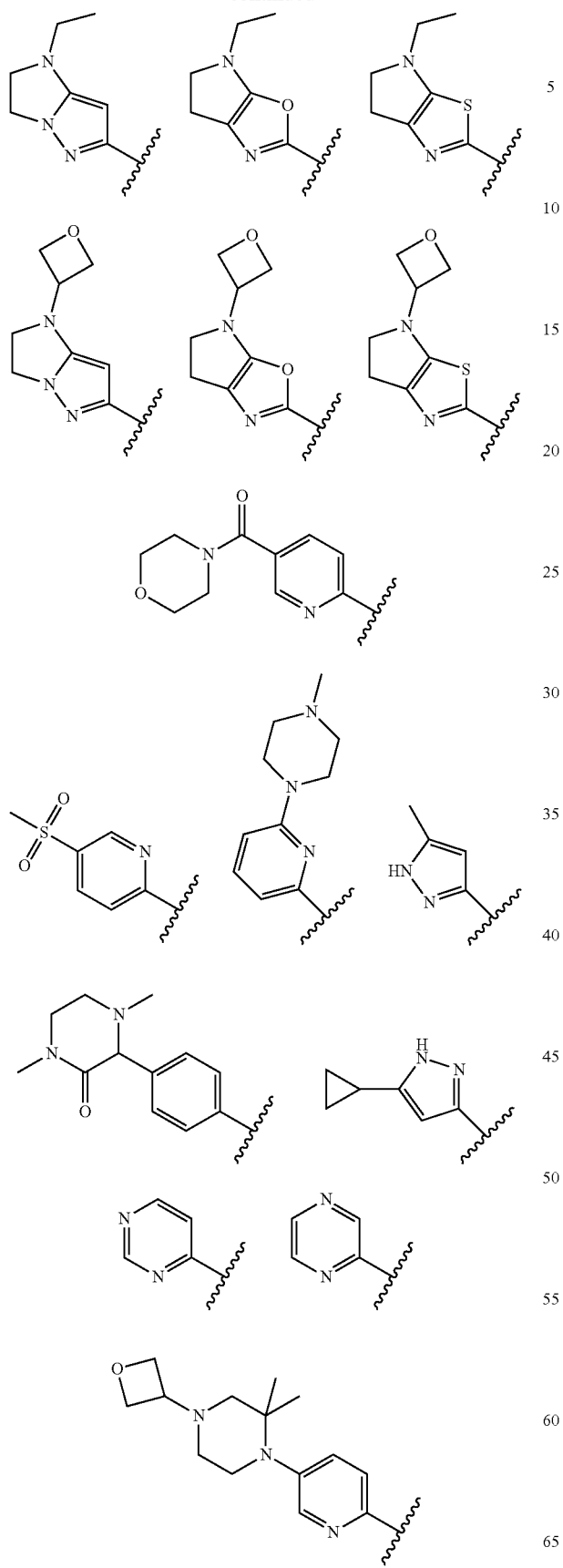
28
-continued
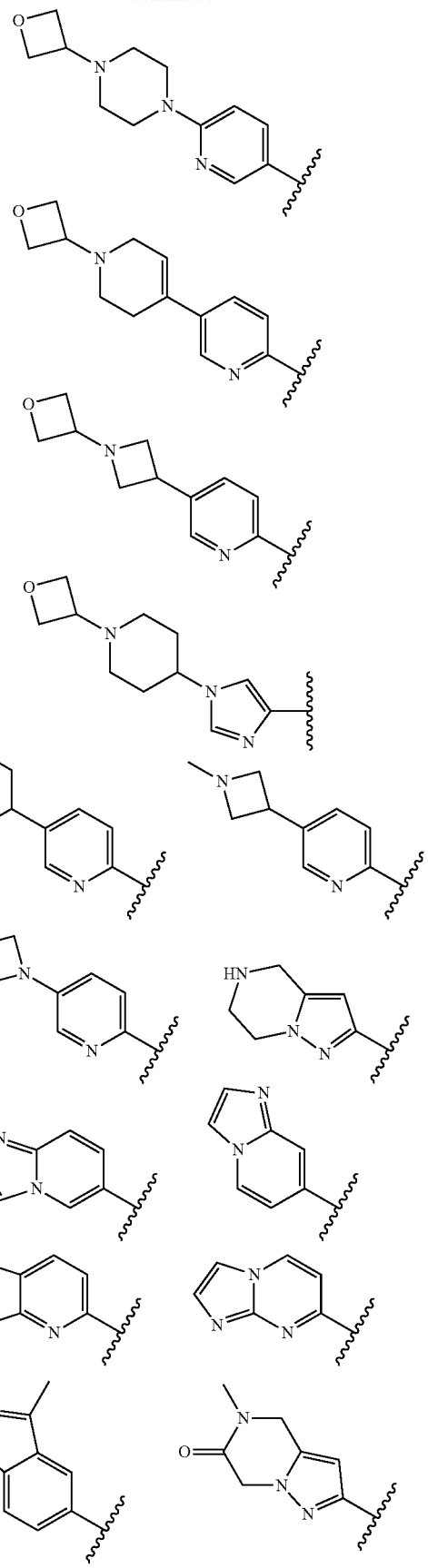

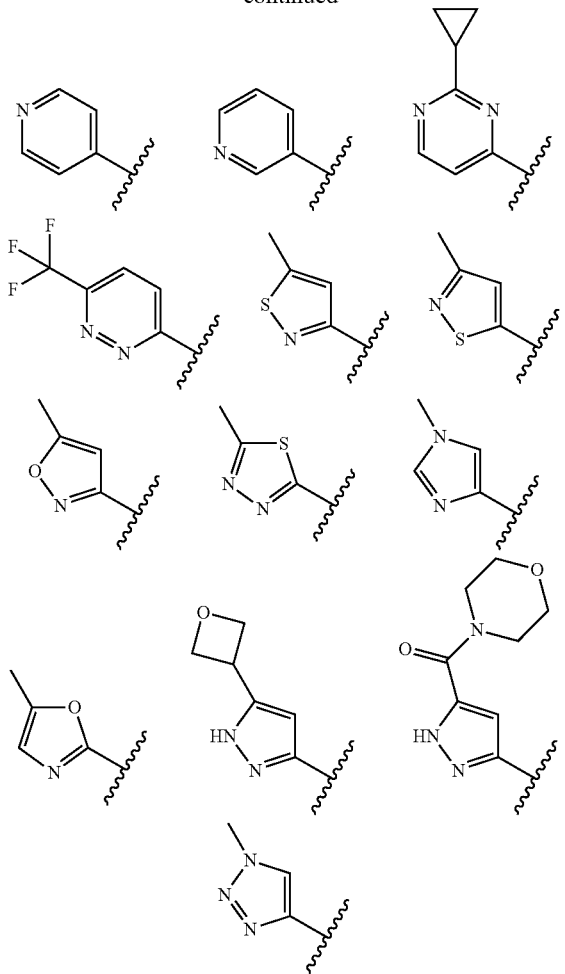

where the wavy line indicates the site of attachment.

Exemplary embodiments of Formula I compounds include wherein $R^5$ is:

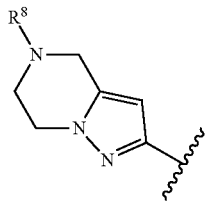

where $R^8$ is selected from H, —$CH_3$, —$CH_2OCH_3$, —$CH_2CH_3$, —$CH(CH_3)_2$, —$CH_2CH_2OH$, —$CH_2CH_2OCH_3$, —$CH_2F$, —$CHF_2$, —$CF_3$, —$CH_2CF_3$, —$CH_2CHF_2$, —$CH(CH_3)CN$, —$C(CH_3)_2CN$, —$CH_2CN$, —$C(O)CH_3$, —$C(O)CH_2CH_3$, —$C(O)CH(CH_3)_2$, —$NH_2$, —$NHCH_3$, —$N(CH_3)_2$, —OH, —$OCH_3$, —$OCH_2CH_3$, —$OCH_2CH_2OH$, cyclopropyl, and oxetanyl.

Exemplary embodiments of Formula I compounds include wherein $R^6$ is $CH_3$.

Exemplary embodiments of Formula I compounds include wherein $Y^1$ is CH and $Y^2$ is N, $Y^1$ is N and $Y^2$ is CH, $Y^1$ and $Y^2$ are each CH, or $Y^1$ and $Y^2$ are each CH and $R^6$ is $CH_3$.

Exemplary embodiments of Formula I compounds include the compounds in Tables 1 and 2.

The Formula I compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention.

In addition, the present invention embraces all diastereomers, including cis-trans (geometric) and conformational isomers. For example, if a Formula I compound incorporates a double bond or a fused ring, the cis- and trans-forms, as well as mixtures thereof, are embraced within the scope of the invention.

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The compounds of the present invention may exist in unsolvated as well as solvated forms with pharmaceutically acceptable solvents such as water, ethanol, and the like, and it is intended that the invention embrace both solvated and unsolvated forms.

The compounds of the present invention may also exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Biological Evaluation

The relative efficacies of Formula I compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "$IC_{50}$". Determination of $IC_{50}$ values can be accomplished using conventional techniques known in the art. In general, an $IC_{50}$ can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the $IC_{50}$ value. Analogously, other inhibitory concentrations can be defined through appropriate determinations of activity. For example, in some settings it can be desirable to establish a 90% inhibitory concentration, i.e., $IC_{90}$, etc.

Formula I compounds were tested by a standard biochemical Btk Kinase Assay (Example 901).

A general procedure for a standard cellular Btk Kinase Assay that can be used to test Formula I compounds is a Ramos Cell Btk Assay (Example 902).

A standard cellular B-cell proliferation assay can be used to test Formula I compounds with B-cells purified from spleen of Balb/c mice (Example 903).

A standard T cell proliferation assay can be used to test Formula I compounds with T-cells purified from spleen of Balb/c mice (Example 904).

A CD86 Inhibition assay can be conducted on Formula I compounds for the inhibition of B cell activity using total mouse splenocytes purified from spleens of 8-16 week old Balb/c mice (Example 905).

A B-ALL Cell Survival Assay can be conducted on Formula I compounds to measure the number of viable B-ALL cells in culture (Example 906).

A CD69 Whole Blood Assay can be conducted on Formula I compounds to determine the ability of compounds to inhibit the production of CD69 by B lymphocytes in human whole blood activated by crosslinking surface IgM with goat F(ab')2 anti-human IgM (Example 907). CD69 is a type II C-type lectin involved in lymphocyte migration and cytokine secretion. CD69 expression represents one of the earliest available indicators of leukocyte activation and its rapid induction occurs through transcriptional activation (Vazquez et al (2009) Jour. of Immunology Published Oct. 19, 2009, doi: 10.4049/jimmunol.0900839). Concentration-dependent inhibition of antigen receptor stimulation by selective Btk inhibitors induces cell surface expression of the lymphocyte activation marker CD69 (Honigberg et al (2010) Proc. Natl. Acad. Sci. 107(29):13075-13080). Thus, CD69 inhibition by selective Btk inhibitors may be correlated with therapeutic efficacy of certain B-cell disorders. The CD69 Hu Blood FACS IC70 values are displayed for exemplary Formula I compounds in Tables 1 and 2.

The cytotoxic or cytostatic activity of Formula I exemplary compounds can be measured by: establishing a proliferating mammalian tumor cell line in a cell culture medium, adding a Formula I compound, culturing the cells for a period from about 6 hours to about 5 days; and measuring cell viability (Example 908). Cell-based in vitro assays are used to measure viability, i.e. proliferation ($IC_{50}$), cytotoxicity ($EC_{50}$), and induction of apoptosis (caspase activation) and may be useful in predicting clinical efficacy against hematological malignancies and solid tumors.

The in vitro potency of the combinations of Formula I compounds with chemotherapeutic agents can be measured by the cell proliferation assay of Example 908; the CellTiter-Glo® Luminescent Cell Viability Assay, commercially available from Promega Corp., Madison, Wis. This homogeneous assay method is based on the recombinant expression of Coleoptera luciferase (U.S. Pat. No. 5,583,024; U.S. Pat. No. 5,674,713; U.S. Pat. No. 5,700,670) and determines the number of viable cells in culture based on quantitation of the ATP present, an indicator of metabolically active cells (Crouch et al (1993) J. Immunol. Meth. 160:81-88; U.S. Pat. No. 6,602, 677). The CellTiter-Glo® Assay was conducted in 96 or 384 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

The anti-proliferative efficacy of Formula I exemplary compounds and combinations with chemotherapeutic agents are measured by the CellTiter-Glo® Assay (Example 908) against certain hematological tumor cell lines. $EC_{50}$ values are established for the tested compounds and combinations.

Exemplary Formula I compounds in Tables 1 and 2 were made, characterized, and tested for inhibition of Btk according to the methods of this invention, and have the following structures and corresponding names (ChemDraw Ultra, Version 9.0.1, and ChemBioDraw, Version 11.0, CambridgeSoft Corp., Cambridge Mass.). Where more than one name is associated with a Formula I compound or intermediate, the chemical structure shall define the compound.

TABLE 1

| No. | Structure | IUPAC_Name | Mol Weight | CD69 Hu Blood FACS IC70 (μM) |
|---|---|---|---|---|
| 101 | 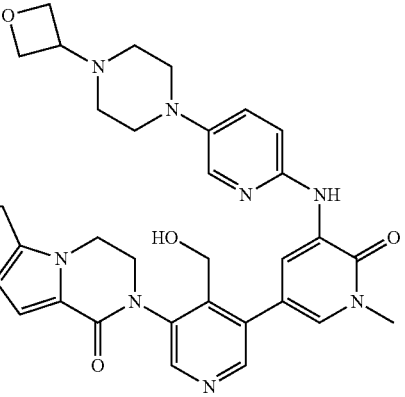 | 2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-3,4,6,7,8,9-hexahydro-2H-pyrazino[1,2-a]indol-1-one | 636.74 | 0.132 |

TABLE 1-continued

| No. | Structure | IUPAC_Name | Mol Weight | CD69 Hu Blood FACS IC70 (μM) |
|---|---|---|---|---|
| 102 | 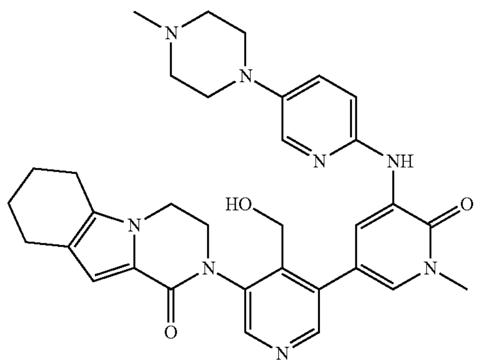 [SMILES: CN1CCN(c2ccc(Nc3cc(-c4cncc(N5CCn6c(cc7c6CCCC7)C5=O)c4CO)cn(C)c3=O)nc2)CC1] | 2-{4-Hydroxymethyl-1'-methyl-5'-[5-(4-methyl-piperazin-1-yl)-pyridin-2-ylamino]-6'-oxo-1',6'-dihydro-[3,3']bipyridinyl-5-yl}-3,4,6,7,8,9-hexahydro-2H-pyrazino[1,2-a]indol-1-one | 594.71 | 0.132 |
| 103 | 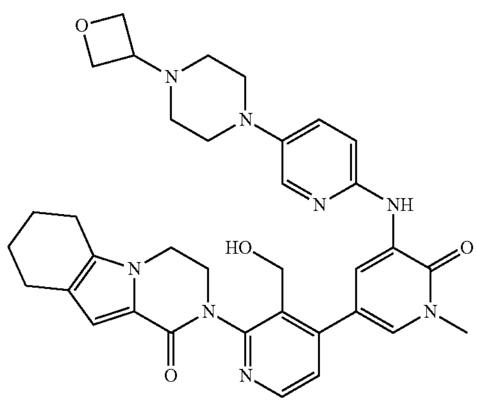 [SMILES: Cn1cc(-c2ccnc(N3CCn4c(cc5c4CCCC5)C3=O)c2CO)cc(Nc2ccc(N3CCN(C4COC4)CC3)cn2)c1=O] | 2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one | 636.74 | 0.0776 |
| 104 | 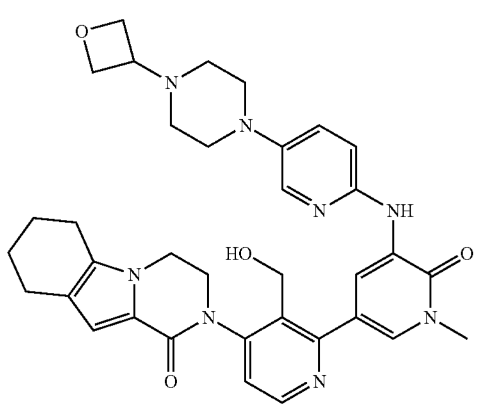 [SMILES: Cn1cc(-c2nccc(N3CCn4c(cc5c4CCCC5)C3=O)c2CO)cc(Nc2ccc(N3CCN(C4COC4)CC3)cn2)c1=O] | 2-(3-(Hydroxymethyl)-2-(1-methyl-5-(5-(4-(oxetan-3-yl)piperazin-1-yl)pyridin-2-ylamino)-6-oxo-1,6-dihydropyridin-3-yl)pyridin-4-yl)-3,4,6,7,8,9-hexahydropyrazino[1,2-a]indol-1(2H)-one | 636.74 | 0.793 |

TABLE 1-continued

| No. | Structure | IUPAC_Name | Mol Weight | CD69 Hu Blood FACS IC70 (μM) |
|---|---|---|---|---|
| 105 | 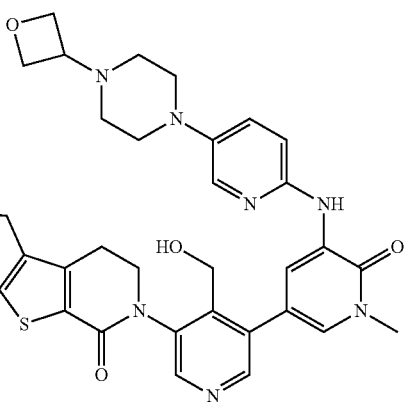 | 2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-3,4,5,6,7,8-hexahydro-2H-benzo[4,5]thieno[2,3-c]pyridin-1-one | 653.79 | 0.0654 |
| 106 | 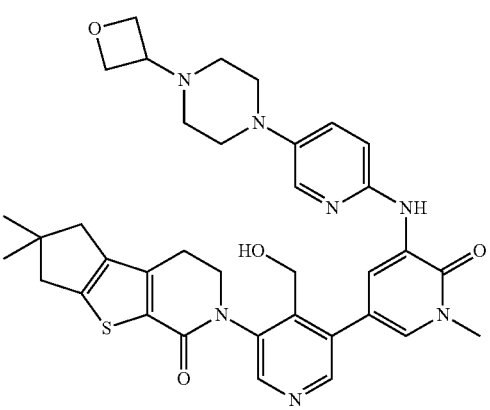 [SMILES: Cn1cc(-c2cncc(N3CCc4c(sc5c4CC(C)(C)C5)C3=O)c2CO)cc(Nc2ccc(N3CCN(C4COC4)CC3)cn2)c1=O] | 6-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-2,2-dimethyl-2,3,5,6-tetrahydro-1H,4H-8-thia-6-aza-cyclopenta[a]inden-7-one | 667.82 | 0.0576 |
| 107 | 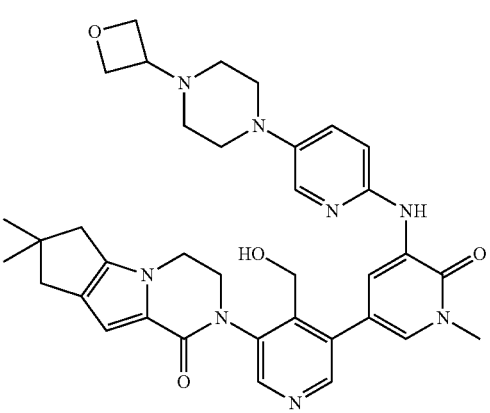 [SMILES: Cn1cc(-c2cncc(N3CCn4c(cc5c4CC(C)(C)C5)C3=O)c2CO)cc(Nc2ccc(N3CCN(C4COC4)CC3)cn2)c1=O] | 2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-7,7-dimethyl-3,4,7,8-tetrahydro-2H,6H-cyclopenta[4,5]pyrrolo[1,2-a]pyrazin-1-one | 650.77 | 0.0216 |

TABLE 1-continued

| No. | Structure | IUPAC_Name | Mol Weight | CD69 Hu Blood FACS IC70 (μM) |
|---|---|---|---|---|
| 108 | 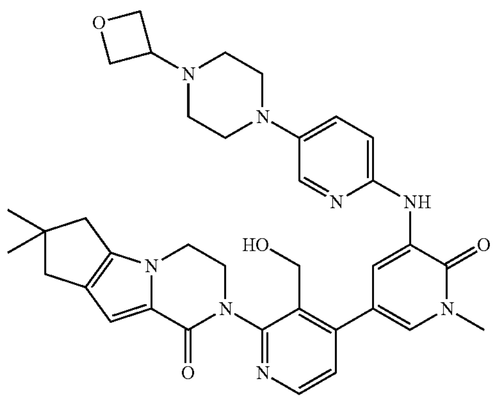 [SMILES: Cn1cc(-c2ccnc(N3CCn4c(cc5c4CC(C)(C)C5)C3=O)c2CO)cc(Nc2ccc(N3CCN(C4COC4)CC3)cn2)c1=O] | 2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one | 650.77 | 0.0319 |
| 109 | 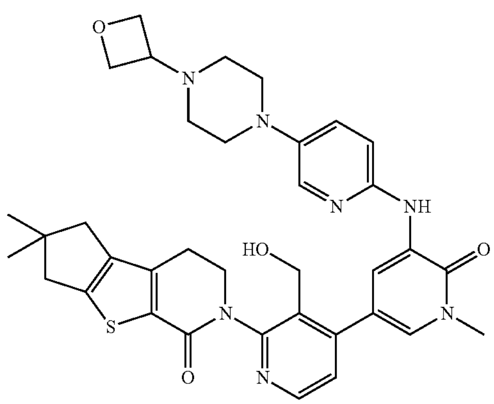 [SMILES: Cn1cc(-c2ccnc(N3CCc4c(sc5c4CC(C)(C)C5)C3=O)c2CO)cc(Nc2ccc(N3CCN(C4COC4)CC3)cn2)c1=O] | 6-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-2,2-dimethyl-2,3,5,6-tetrahydro-1H,4H-8-thia-6-aza-cyclopenta[a]inden-7-one | 667.82 | 0.0501 |
| 110 | 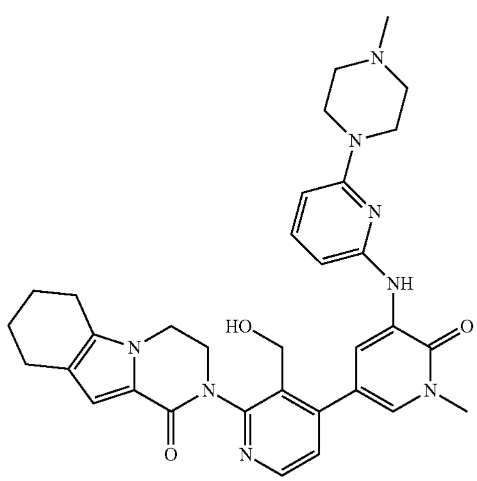 [SMILES: CN1CCN(c2cccc(Nc3cc(-c4ccnc(N5CCn6c(cc7c6CCCC7)C5=O)c4CO)cn(C)c3=O)n2)CC1] | 2-{3'-Hydroxymethyl-1-methyl-5-[6-(4-methyl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 594.71 | 2.7 |

TABLE 1-continued

| No. | Structure | IUPAC_Name | Mol Weight | CD69 Hu Blood FACS IC70 (μM) |
|---|---|---|---|---|
| 111 | 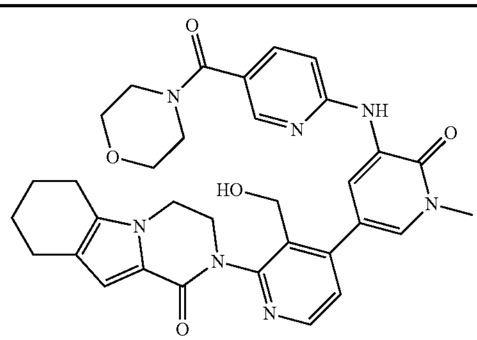 | 2-{3'-Hydroxymethyl-1-methyl-5-[5-(morpholine-4-carbonyl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 609.68 | 0.131 |
| 112 | 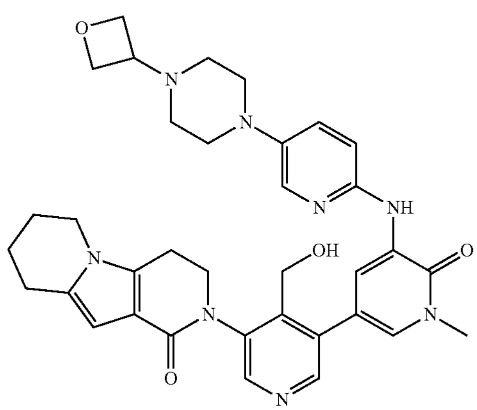 [SMILES: Cn1cc(-c2cncc(N3CCc4c(cc5n4CCCC5)C3=O)c2CO)cc(Nc2ccc(N3CCN(C4COC4)CC3)cn2)c1=O] | 2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-2,3,5,6,7,8-hexahydro-4H-2,4b-diaza-fluoren-1-one | 636.74 | 0.492 |
| 113 | 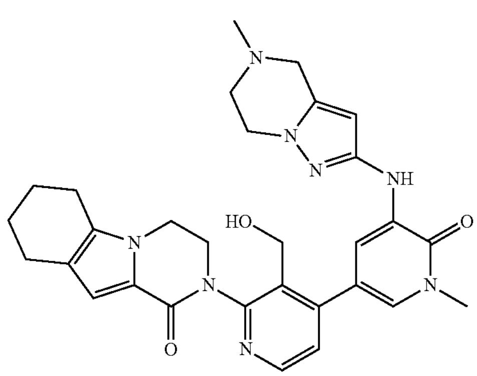 [SMILES: CN1CCn2nc(Nc3cc(-c4ccnc(N5CCn6c(cc7c6CCCC7)C5=O)c4CO)cn(C)c3=O)cc2C1] | 2-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one | 554.64 | 0.0625 |
| 114 | 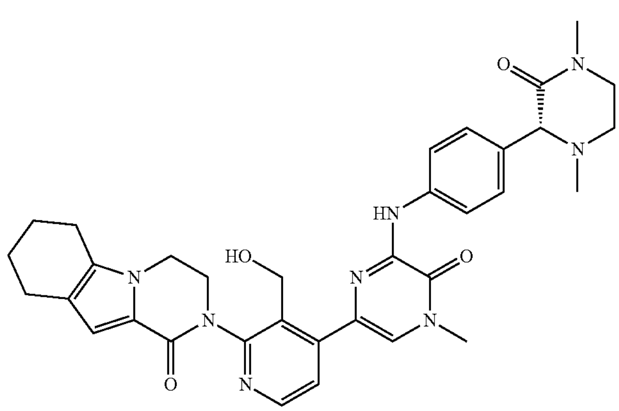 [SMILES: CN1CCN(C)[C@H](c2ccc(Nc3nc(-c4ccnc(N5CCn6c(cc7c6CCCC7)C5=O)c4CO)cn(C)c3=O)cc2)C1=O] | 2-(4-{6-[4-((R)-1,4-Dimethyl-3-oxo-piperazin-2-yl)-phenylamino]-4-methyl-5-oxo-4,5-dihydro-pyrazin-2-yl}-3-hydroxymethyl-pyridin-2-yl)-3,4,6,7,8,9-hexahydro-2H-pyrazino[1,2-a]indol-1-one | 622.72 | 0.0802 |

TABLE 1-continued

| No. | Structure | IUPAC_Name | Mol Weight | CD69 Hu Blood FACS IC70 (μM) |
|---|---|---|---|---|
| 115 | 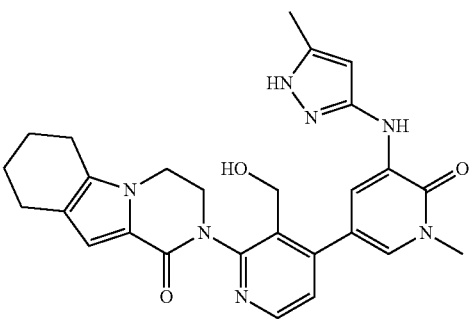 [SMILES: Cc1cc(Nc2cc(-c3ccnc(N4CCn5c(cc6c5CCCC6)C4=O)c3CO)cn(C)c2=O)n[nH]1] | 2-[3'-Hydroxymethyl-1-methyl-5-(5-methyl-1H-pyrazol-3-ylamino)-6-oxo-1,6-dihydro-[3,4']bipyridinyl-2'-yl]-3,4,6,7,8,9-hexahydro-2H-pyrazino[1,2-a]indol-1-one | 499.56 | 0.286 |
| 116 | 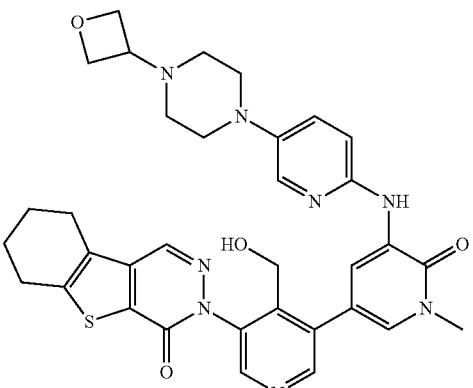 | 3-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-6,7,8,9-tetrahydro-3H-benzo[4,5]thieno[2,3-d]pyridazin-4-one | 652.77 | 0.377 |
| 117 | 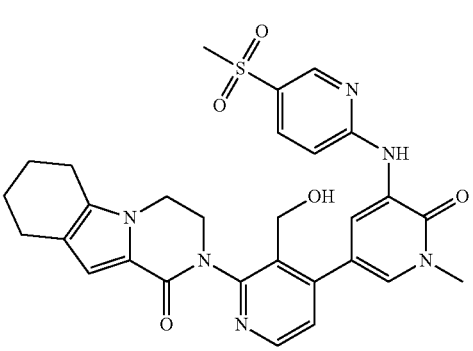 [SMILES: Cn1cc(-c2ccnc(N3CCn4c(cc5c4CCCC5)C3=O)c2CO)cc(Nc2ccc(S(C)(=O)=O)cn2)c1=O] | 2-[3'-Hydroxymethyl-5-(5-methane sulfonyl-pyridin-2-ylamino)-1-methyl-6-oxo-1,6-dihydro-[3,4']bipyridinyl-2'-yl]-3,4,6,7,8,9-hexahydro-2H-pyrazino[1,2-a]indol-1-one | 574.65 | 0.396 |
| 118 | 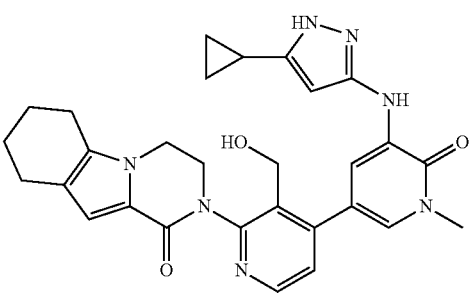 [SMILES: Cn1cc(-c2ccnc(N3CCn4c(cc5c4CCCC5)C3=O)c2CO)cc(Nc2cc(C3CC3)[nH]n2)c1=O] | 2-[5-(5-Cyclopropyl-1H-pyrazol-3-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one | 525.60 | 0.608 |

TABLE 1-continued

| No. | Structure | IUPAC_Name | Mol Weight | CD69 Hu Blood FACS IC70 (μM) |
|---|---|---|---|---|
| 119 | 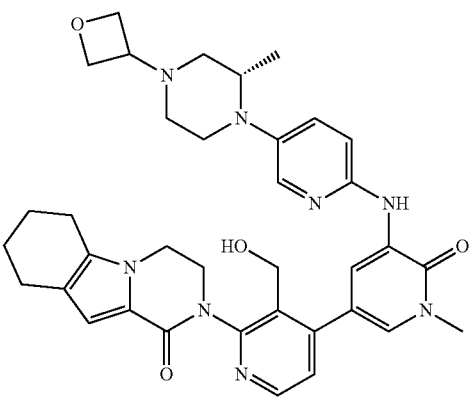 [SMILES: C[C@H]1CN(C2COC2)CCN1c1ccc(Nc2cc(-c3ccnc(N4CCn5c(cc6c5CCCC6)C4=O)c3CO)cn(C)c2=O)nc1] | 2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 650.77 | 0.0356 |
| 120 | 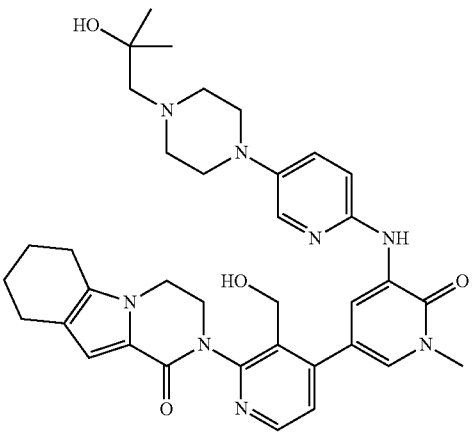 [SMILES: Cn1cc(-c2ccnc(N3CCn4c(cc5c4CCCC5)C3=O)c2CO)cc(Nc2ccc(N3CCN(CC(C)(C)O)CC3)cn2)c1=O] | 2-(3'-Hydroxymethyl-5-{5-[4-(2-hydroxy-2-methyl-propyl)-piperazin-1-yl]-pyridin-2-ylamino}-1-methyl-6-oxo-1,6-dihydro-[3,4']bipyridinyl-2'-yl)-3,4,6,7,8,9-hexahydro-2H-pyrazino[1,2-a]indol-1-one | 652.79 | 0.283 |
| 121 | 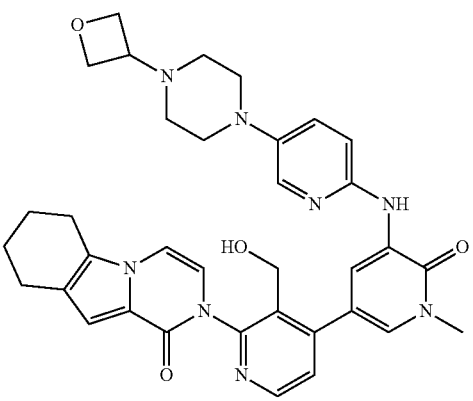 [SMILES: Cn1cc(-c2ccnc(-n3ccn4c5c(cc4c3=O)CCCC5)c2CO)cc(Nc2ccc(N3CCN(C4COC4)CC3)cn2)c1=O] | 2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-6,7,8,9-tetrahydro-2H-pyrazino[1,2-a]indol-1-one | 634.73 | 0.0323 |

TABLE 1-continued

| No. | Structure | IUPAC_Name | Mol Weight | CD69 Hu Blood FACS IC70 (μM) |
|---|---|---|---|---|
| 122 | 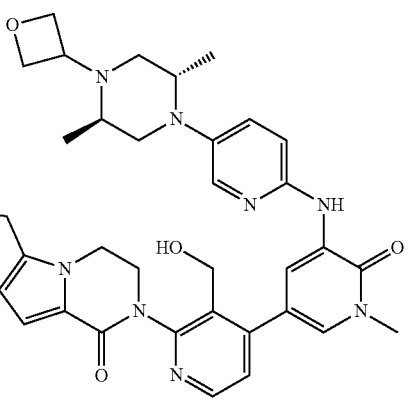 | 2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-3,4,6,7,8,9-hexahydro-2H-pyrazino[1,2-a]indol-1-one | 664.80 | 0.0127 |
| 123 | 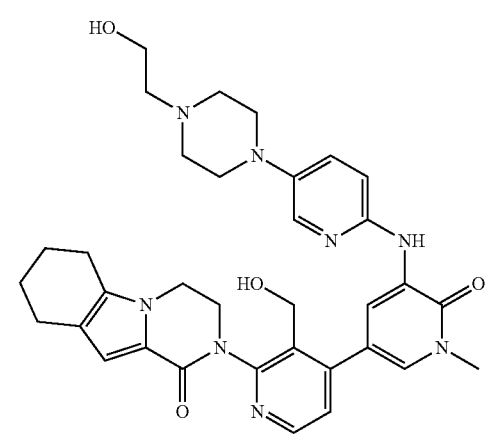 [SMILES: Cn1cc(-c2ccnc(N3CCn4c(cc5c4CCCC5)C3=O)c2CO)cc(Nc2ccc(N3CCN(CCO)CC3)cn2)c1=O] | 2-(5-{5-[4-(2-Hydroxy-ethyl)-piperazin-1-yl]-pyridin-2-ylamino}-3'-hydroxymethyl-1-methyl-6-oxo-1,6-dihydro-[3,4']bipyridinyl-2'-yl)-3,4,6,7,8,9-hexahydro-2H-pyrazino[1,2-a]indol-1-one | 624.73 | 0.0331 |
| 124 | 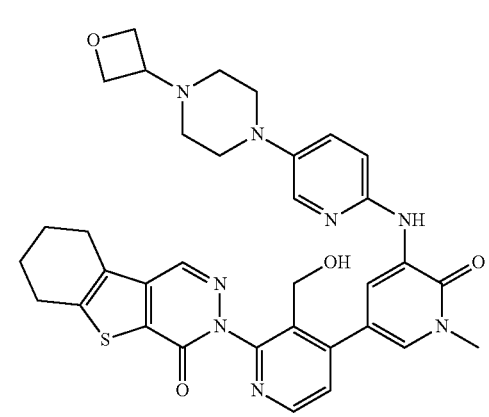 [SMILES: Cn1cc(-c2ccnc(-n3ncc4c5c(sc4c3=O)CCCC5)c2CO)cc(Nc2ccc(N3CCN(C4COC4)CC3)cn2)c1=O] | 3-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-6,7,8,9-tetrahydro-3H-benzo[4,5]thieno[2,3-d]pyridazin-4-one | 652.77 | 0.0362 |

TABLE 1-continued

| No. | Structure | IUPAC_Name | Mol Weight | CD69 Hu Blood FACS IC70 (μM) |
|---|---|---|---|---|
| 125 | 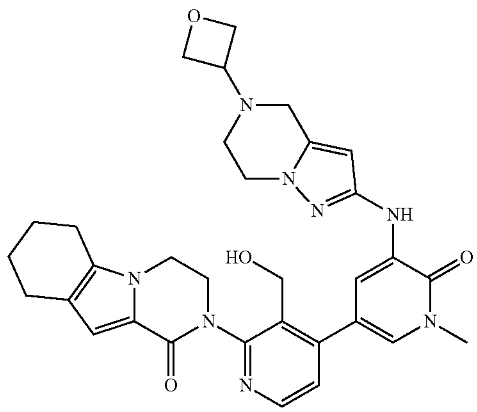 [SMILES: Cn1cc(-c2ccnc(N3CCn4c(cc5c4CCCC5)C3=O)c2CO)cc(Nc2cc3n(n2)CCN(C2COC2)C3)c1=O] | 2-[3'-Hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one | 596.68 | 0.0873 |
| 126 | 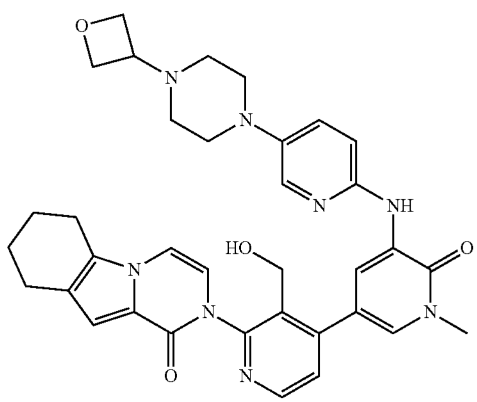 [SMILES: Cn1cc(-c2ccnc(-n3ccn4c5c(cc4c3=O)CCCC5)c2CO)cc(Nc2ccc(N3CCN(C4COC4)CC3)cn2)c1=O] | 2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-6,7,8,9-tetrahydro-2H-pyrazino[1,2-a]indol-1-one | 634.73 | 0.138 |
| 127 | 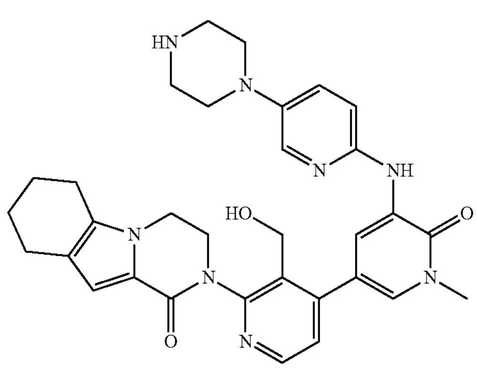 [SMILES: Cn1cc(-c2ccnc(N3CCn4c(cc5c4CCCC5)C3=O)c2CO)cc(Nc2ccc(N3CCNCC3)cn2)c1=O] | 2-[3'-Hydroxymethyl-1-methyl-6-oxo-5-(5-piperazin-1-yl-pyridin-2-ylamino)-1,6-dihydro-[3,4']bipyridinyl-2'-yl]-3,4,6,7,8,9-hexahydro-2H-pyrazino[1,2-a]indol-1-one | 580.68 | 0.141 |

TABLE 1-continued

| No. | Structure | IUPAC_Name | Mol Weight | CD69 Hu Blood FACS IC70 (μM) |
|---|---|---|---|---|
| 128 | 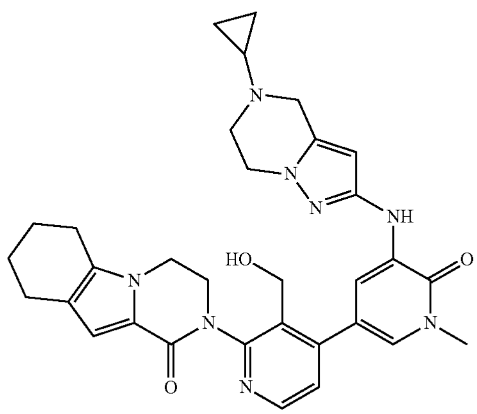 [SMILES: Cn1cc(-c2ccnc(N3CCn4c(cc5c4CCCC5)C3=O)c2CO)cc(Nc2cc3n(n2)CCN(C2CC2)C3)c1=O] | 2-[5-(5-Cyclopropyl-4,5,6,7-tetrahydro-pyrazolo[1,5-a]pyrazin-2-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one | 580.68 | 0.0918 |
| 129 | 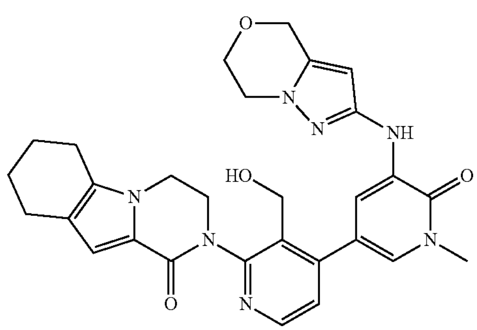 [SMILES: Cn1cc(-c2ccnc(N3CCn4c(cc5c4CCCC5)C3=O)c2CO)cc(Nc2cc3n(n2)CCOC3)c1=O] | 2-[5-(6,7-Dihydro-4H-pyrazolo[5,1-c][1,4]oxazin-2-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one | 541.60 | 0.0917 |
| 130 | 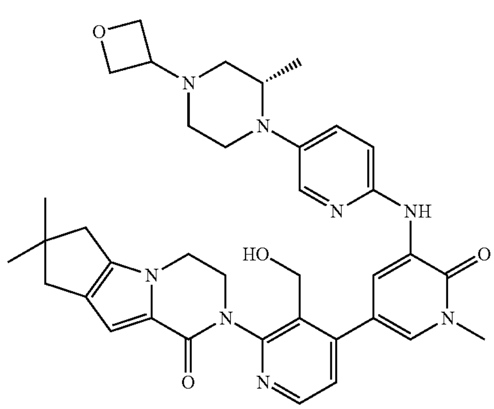 [SMILES: C[C@H]1CN(C2COC2)CCN1c1ccc(Nc2cc(-c3ccnc(N4CCn5c(cc6c5CC(C)(C)C6)C4=O)c3CO)cn(C)c2=O)nc1] | 2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one | 664.80 | 0.012 |

TABLE 1-continued

| No. | Structure | IUPAC_Name | Mol Weight | CD69 Hu Blood FACS IC70 (μM) |
|---|---|---|---|---|
| 131 | 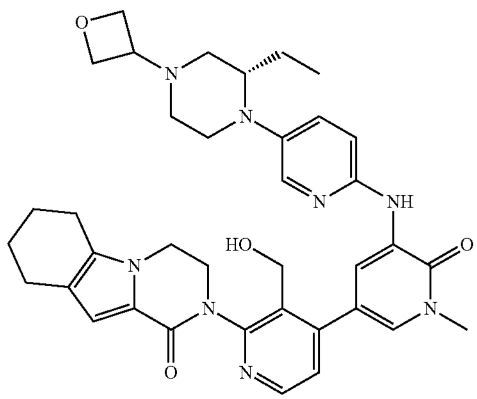 [SMILES: CC[C@H]1CN(C2COC2)CCN1c1ccc(Nc2cc(-c3ccnc(N4CCn5c(cc6c5CCCC6)C4=O)c3CO)cn(C)c2=O)nc1] | 2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-3,4,6,7,8,9-hexahydro-2H-pyrazino[1,2-a]indol-1-one | 664.80 | 0.0155 |
| 132 | 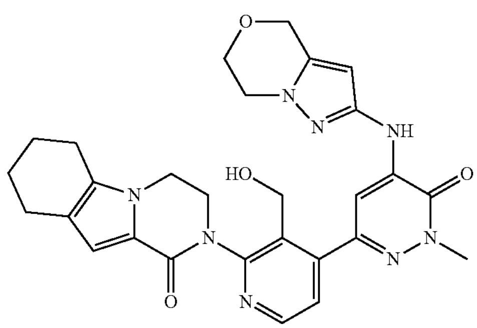 [SMILES: Cn1nc(-c2ccnc(N3CCn4c(cc5c4CCCC5)C3=O)c2CO)cc(Nc2cc3n(n2)CCOC3)c1=O] | 2-{4-[5-(6,7-Dihydro-4H-pyrazolo[5,1-c][1,4]oxazin-2-ylamino)-1-methyl-6-oxo-1,6-dihydro-pyridazin-3-yl]-3-hydroxymethyl-pyridin-2-yl}-3,4,6,7,8,9-hexahydro-2H-pyrazino[1,2-a]indol-1-one | 542.59 | 0.263 |
| 133 | 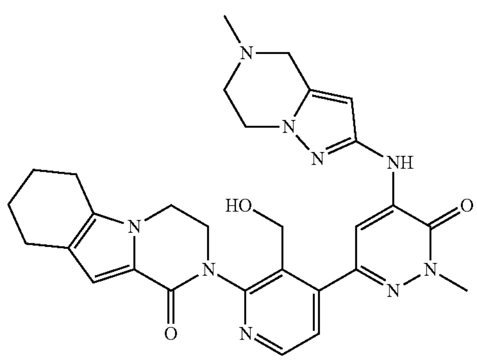 [SMILES: CN1CCn2nc(Nc3cc(-c4ccnc(N5CCn6c(cc7c6CCCC7)C5=O)c4CO)nn(C)c3=O)cc2C1] | 2-{3-Hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-3,4,6,7,8,9-hexahydro-2H-pyrazino[1,2-a]indol-1-one | 555.63 | 0.227 |
| 134 | 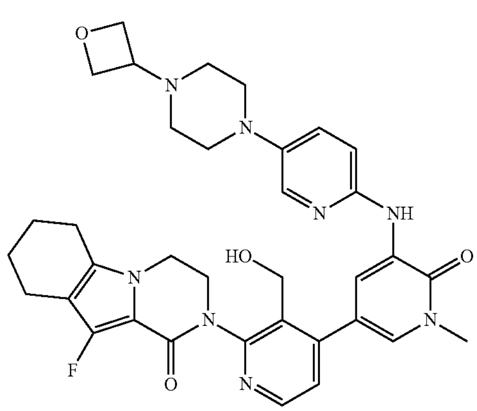 [SMILES: Cn1cc(-c2ccnc(N3CCn4c5c(c(F)c4C3=O)CCCC5)c2CO)cc(Nc2ccc(N3CCN(C4COC4)CC3)cn2)c1=O] | 10-Fluoro-2-{3'-hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 654.73 | 0.0944 |

TABLE 1-continued

| No. | Structure | IUPAC_Name | Mol Weight | CD69 Hu Blood FACS IC70 (μM) |
|---|---|---|---|---|
| 135 | 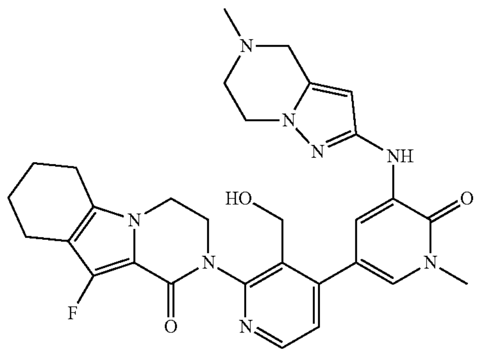 [SMILES: CN1CCn2nc(Nc3cc(-c4ccnc(N5CCn6c7c(c(F)c6C5=O)CCCC7)c4CO)cn(C)c3=O)cc2C1] | 10-Fluoro-2-[3'-hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one | 572.63 | 0.107 |
| 136 | 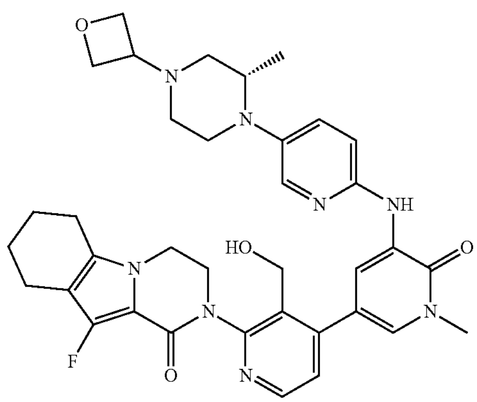 [SMILES: C[C@H]1CN(C2COC2)CCN1c1ccc(Nc2cc(-c3ccnc(N4CCn5c6c(c(F)c5C4=O)CCCC6)c3CO)cn(C)c2=O)nc1] | 10-Fluoro-2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 668.76 | 0.030 |
| 137 | 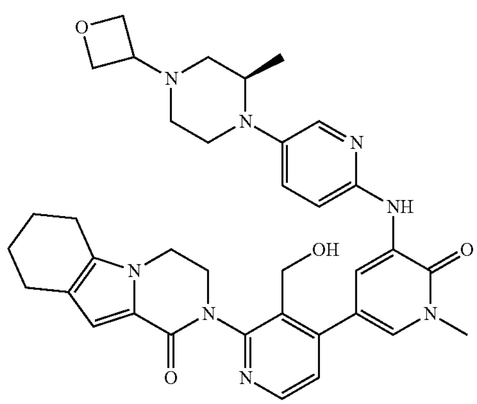 [SMILES: C[C@@H]1CN(C2COC2)CCN1c1ccc(Nc2cc(-c3ccnc(N4CCn5c(cc6c5CCCC6)C4=O)c3CO)cn(C)c2=O)nc1] | 2-{3'-Hydroxymethyl-1-methyl-5-[5-((R)-2-methyl-4-oxetan-3-yl-piperazin-1-yl)-pyridin-2-ylamino)-6-oxo-1,6-dihydro-[3,4']bipyridinyl-2'-yl}-3,4,6,7,8,9-hexahydro-2H-pyrazino[1,2-a]indol-1-one | 650.77 | 0.0646 |
| 138 | 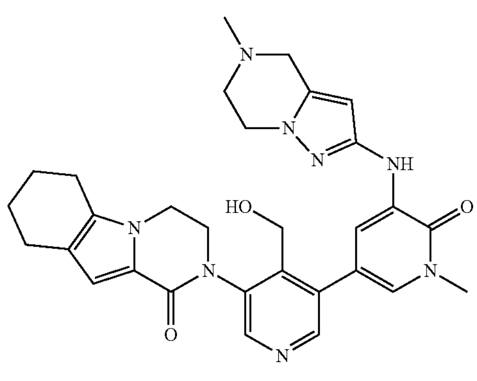 [SMILES: CN1CCn2nc(Nc3cc(-c4cncc(N5CCn6c(cc7c6CCCC7)C5=O)c4CO)cn(C)c3=O)cc2C1] | 2-[4-Hydroxymethyl-1'-methyl-5'-(5-methyl-4,5,6,7-tetrahydro-pyrazolo[1,5-a]pyrazin-2-ylamino)-6'-oxo-1',6'-dihydro-[3,3']bipyridinyl-5-yl]-3,4,6,7,8,9-hexahydro-2H-pyrazino[1,2-a]indol-1-one | 554.64 | 0.353 |

TABLE 1-continued

| No. | Structure | IUPAC_Name | Mol Weight | CD69 Hu Blood FACS IC70 (μM) |
|---|---|---|---|---|
| 139 | 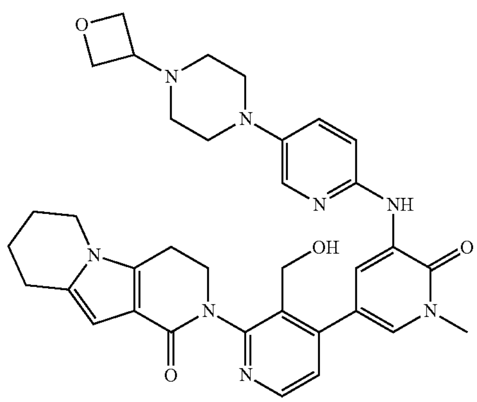 [SMILES: Cn1cc(-c2ccnc(N3CCc4c(cc5n4CCCC5)C3=O)c2CO)cc(Nc2ccc(N3CCN(C4COC4)CC3)cn2)c1=O] | 2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-2,3,5,6,7,8-hexahydro-4H-2,4b-diaza-fluoren-1-one | 636.74 | 0.326 |
| 140 | 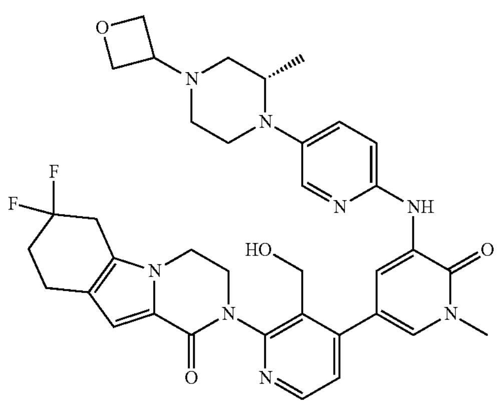 [SMILES: C[C@H]1CN(C2COC2)CCN1c1ccc(Nc2cc(-c3ccnc(N4CCn5c(cc6c5CC(F)(F)CC6)C4=O)c3CO)cn(C)c2=O)nc1] | 7,7-Difluoro-2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 686.75 | 0.308 |
| 141 | 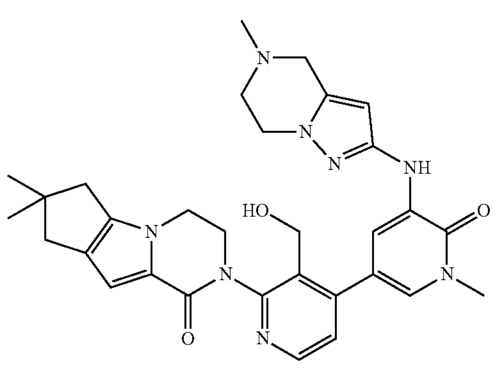 [SMILES: CN1CCn2nc(Nc3cc(-c4ccnc(N5CCn6c(cc7c6CC(C)(C)C7)C5=O)c4CO)cn(C)c3=O)cc2C1] | 2-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 568.67 | 0.0266 |
| 142 | 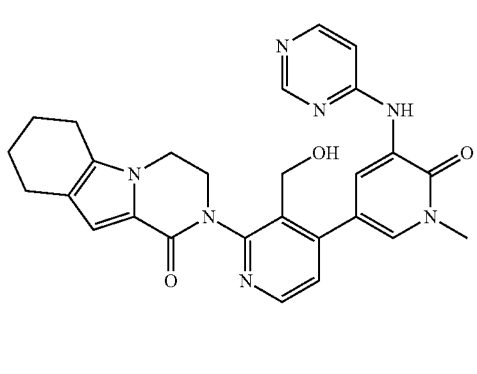 [SMILES: Cn1cc(-c2ccnc(N3CCn4c(cc5c4CCCC5)C3=O)c2CO)cc(Nc2ccncn2)c1=O] | 2-[3'-Hydroxymethyl-1-methyl-6-oxo-5-(pyrimidin-4-ylamino)-1,6-dihydro-[3,4']bipyridinyl-2'-yl] 3,4,6,7,8,9-hexahydro-2H-pyrazino[1,2-a]indol-1-one | 497.55 | 2.1 |

TABLE 1-continued

| No. | Structure | IUPAC_Name | Mol Weight | CD69 Hu Blood FACS IC70 (μM) |
|---|---|---|---|---|
| 143 | 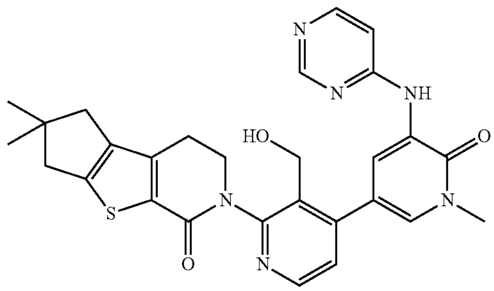 [SMILES: Cn1cc(-c2ccnc(N3CCc4c(sc5c4CC(C)(C)C5)C3=O)c2CO)cc(Nc2ccncn2)c1=O] | 6-[3'-Hydroxymethyl-1-methyl-6-oxo-5-(pyrimidin-4-ylamino)-1,6-dihydro[3,4']bipyridinyl-2'-yl]-2,2-dimethyl-2,3,5,6-tetrahydro-1H,4H-8-thia-6-aza-cyclopenta[a]inden-7-one | 528.63 | 0.0309 |
| 144 | 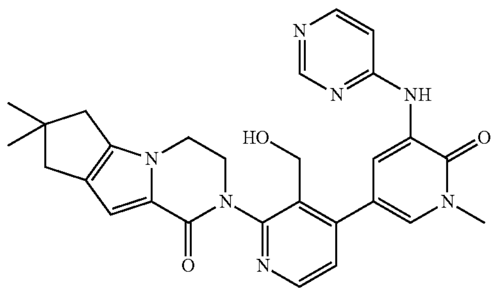 [SMILES: Cn1cc(-c2ccnc(N3CCn4c(cc5c4CC(C)(C)C5)C3=O)c2CO)cc(Nc2ccncn2)c1=O] | 2-[3'-Hydroxymethyl-1-methyl-6-oxo-5-(pyrimidin-4-ylamino)-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 511.58 | 0.106 |
| 145 | 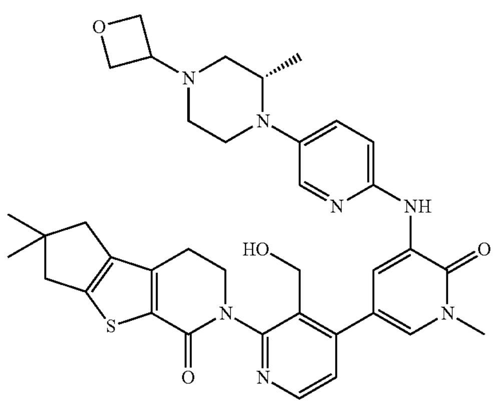 [SMILES: C[C@H]1CN(C2COC2)CCN1c1ccc(Nc2cc(-c3ccnc(N4CCc5c(sc6c5CC(C)(C)C6)C4=O)c3CO)cn(C)c2=O)nc1] | 6-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,2-dimethyl-2,3,5,6-tetrahydro-1H,4H-8-thia-6-aza-cyclopenta[a]inden-7-one | 681.85 | 0.0147 |
| 146 | 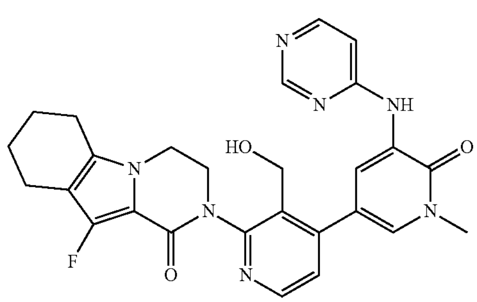 [SMILES: Cn1cc(-c2ccnc(N3CCn4c5c(c(F)c4C3=O)CCCC5)c2CO)cc(Nc2ccncn2)c1=O] | 10-Fluoro-2-[3'-hydroxymethyl-1-methyl-6-oxo-5-(pyrimidin-4-ylamino)-1,6-dihydro-[3,4']bipyridinyl-2'-yl]-3,4,6,7,8,9-hexahydro-2H-pyrazino[1,2-a]indol-1-one | 515.54 | 0.0856 |

TABLE 1-continued

| No. | Structure | IUPAC_Name | Mol Weight | CD69 Hu Blood FACS IC70 (μM) |
|---|---|---|---|---|
| 147 | 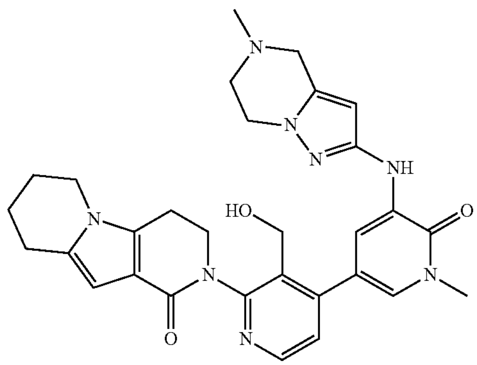 [SMILES: CN1CCn2nc(Nc3cc(-c4ccnc(N5CCc6c(cc7n6CCCC7)C5=O)c4CO)cn(C)c3=O)cc2C1] | 2-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-2,3,5,6,7,8-hexahydro-4H-2,4b-diaza-fluoren-1-one | 554.64 | 0.32 |
| 148 | 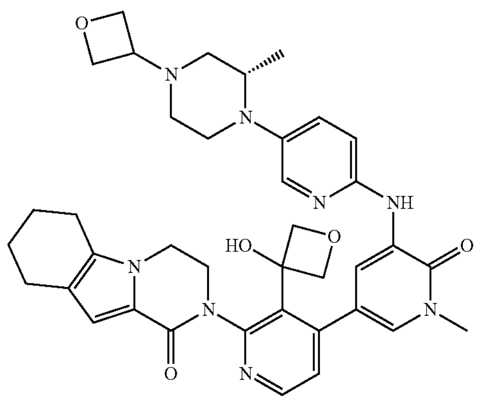 [SMILES: C[C@H]1CN(C2COC2)CCN1c1ccc(Nc2cc(-c3ccnc(N4CCn5c(cc6c5CCCC6)C4=O)c3C3(O)COC3)cn(C)c2=O)nc1] | 2-{3'-(3-Hydroxy-oxetan-3-yl)-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 692.81 | 5 |
| 149 | 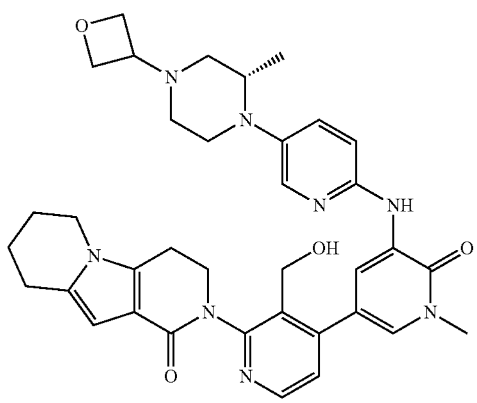 [SMILES: C[C@H]1CN(C2COC2)CCN1c1ccc(Nc2cc(-c3ccnc(N4CCc5c(cc6n5CCCC6)C4=O)c3CO)cn(C)c2=O)nc1] | 2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,3,5,6,7,8-hexahydro-4H-2,4b-diaza-fluoren-1-one | 650.77 | 0.0454 |
| 150 | 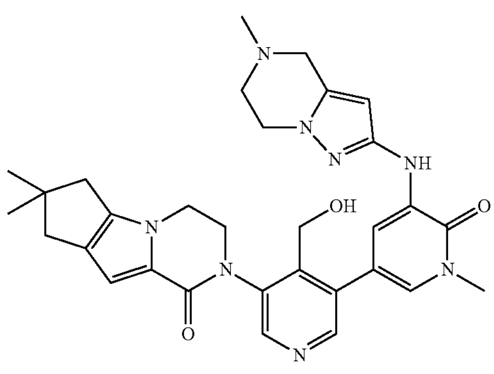 [SMILES: CN1CCn2nc(Nc3cc(-c4cncc(N5CCn6c(cc7c6CC(C)(C)C7)C5=O)c4CO)cn(C)c3=O)cc2C1] | 2-[4-Hydroxymethyl-1'-methyl-5'-(5-methyl-4,5,6,7-tetrahydro-pyrazolo[1,5-a]pyrazin-2-ylamino)-6'-oxo-1',6'-dihydro-[3,3']bipyridinyl-5-yl]-7,7-dimethyl-3,4,7,8-tetrahydro-2H,6H-cyclopenta[4,5]pyrrolo[1,2-a]pyrazin-1-one | 568.67 | 0.0316 |

TABLE 1-continued

| No. | Structure | IUPAC_Name | Mol Weight | CD69 Hu Blood FACS IC70 (µM) |
|---|---|---|---|---|
| 151 | 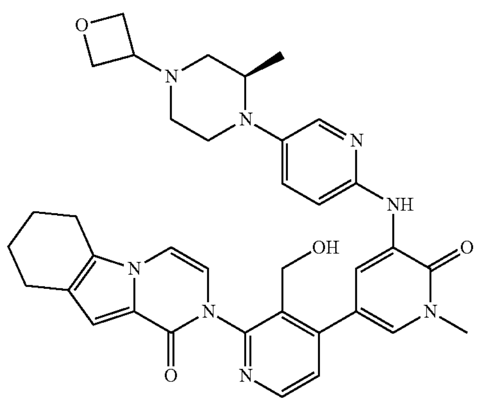 [SMILES: C[C@@H]1CN(C2COC2)CCN1c1ccc(Nc2cc(-c3ccnc(-n4ccn5c6c(cc5c4=O)CCCC6)c3CO)cn(C)c2=O)nc1] | 2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-2H-pyrazino[1,2-a]indol-1-one | 648.75 | 0.0455 |
| 152 | 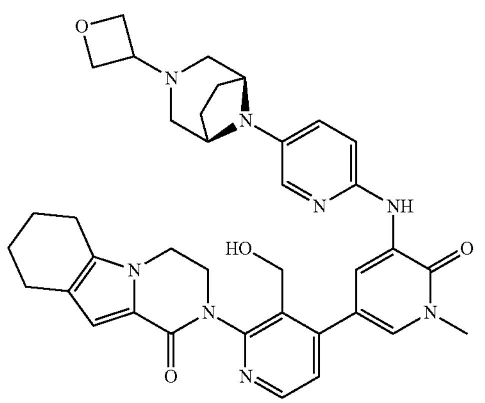 [SMILES: Cn1cc(-c2ccnc(N3CCn4c(cc5c4CCCC5)C3=O)c2CO)cc(Nc2ccc(N3[C@@H]4CC[C@H]3CN(C3COC3)C4)cn2)c1=O] | 2-{3'-Hydroxymethyl-1-methyl-5-[5-((1S,5R)-3-oxetan-3-yl-3,8-diaza-bicyclo[3.2.1]oct-8-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one | 662.78 | 0.188 |
| 153 | 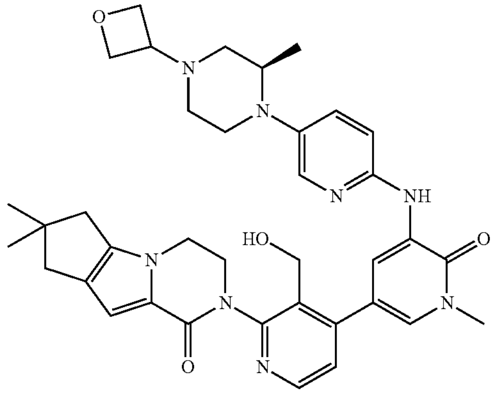 [SMILES: C[C@@H]1CN(C2COC2)CCN1c1ccc(Nc2cc(-c3ccnc(N4CCn5c(cc6c5CC(C)(C)C6)C4=O)c3CO)cn(C)c2=O)nc1] | 2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one | 664.80 | 0.0238 |

TABLE 1-continued

| No. | Structure | IUPAC_Name | Mol Weight | CD69 Hu Blood FACS IC70 (µM) |
|---|---|---|---|---|
| 154 | 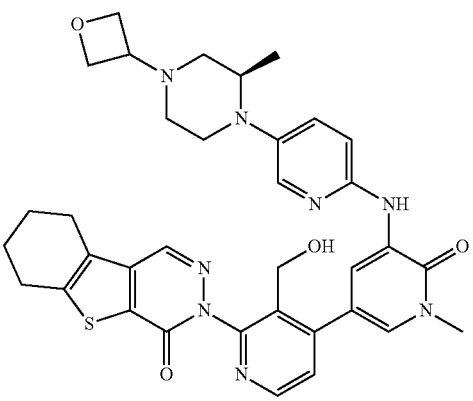 [SMILES: C[C@@H]1CN(C2COC2)CCN1c1ccc(Nc2cc(-c3ccnc(-n4ncc5c6c(sc5c4=O)CCCC6)c3CO)cn(C)c2=O)nc1] | 3-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-3H-benzo[4,5]thieno[2,3-d]pyridazin-4-one | 666.79 | 0.0374 |
| 155 | 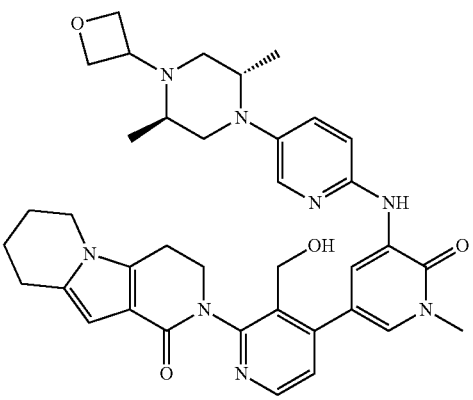 [SMILES: C[C@@H]1CN(c2ccc(Nc3cc(-c4ccnc(N5CCc6c(cc7n6CCCC7)C5=O)c4CO)cn(C)c3=O)nc2)[C@@H](C)CN1C1COC1] | 2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl} 2,3,5,6,7,8-hexahydro-4H-2,4b-diaza-fluoren-1-one | 664.80 | 0.0454 |
| 156 | 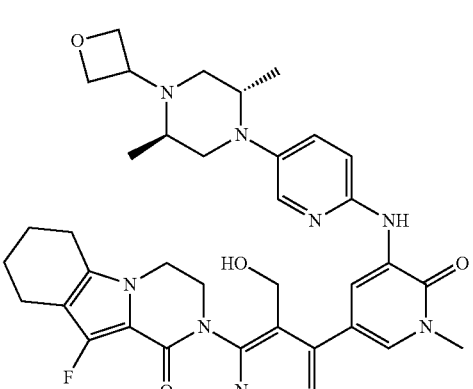 | 2-{5-[5-(2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-10-fluoro-3,4,6,7,8,9-hexahydro-2H-pyrazino[1,2-a]indol-1-one | 682.79 | 0.0145 |

TABLE 1-continued

| No. | Structure | IUPAC_Name | Mol Weight | CD69 Hu Blood FACS IC70 (μM) |
|---|---|---|---|---|
| 157 | 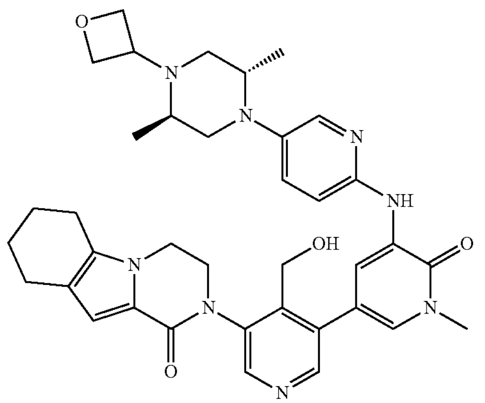 [SMILES: C[C@@H]1CN(c2ccc(Nc3cc(-c4cncc(N5CCn6c(cc7c6CCCC7)C5=O)c4CO)cn(C)c3=O)nc2)[C@@H](C)CN1C1COC1] | 2-{5'-[5-((2S,5R)-2,5-Dimethyl-4-oxetan-3-yl-piperazin-1-yl)-pyridin-2-ylamino]-4-hydroxymethyl-1'-methyl-6'-oxo-1',6'-dihydro-[3,3']bipyridinyl-5-yl}-3,4,6,7,8,9-hexahydro-2H-pyrazino[1,2-a]indol-1-one | 664.80 | 0.0298 |
| 158 | 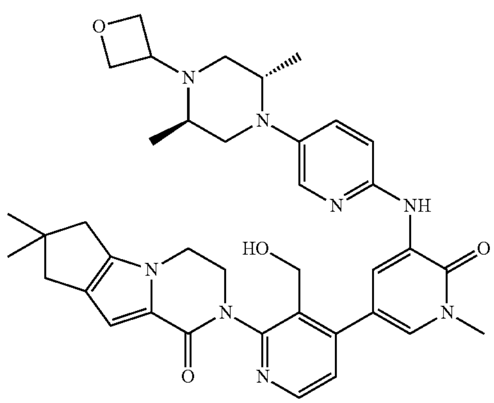 [SMILES: C[C@@H]1CN(c2ccc(Nc3cc(-c4ccnc(N5CCn6c(cc7c6CC(C)(C)C7)C5=O)c4CO)cn(C)c3=O)nc2)[C@@H](C)CN1C1COC1] | 2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one | 678.82 | 0.020 |
| 159 | 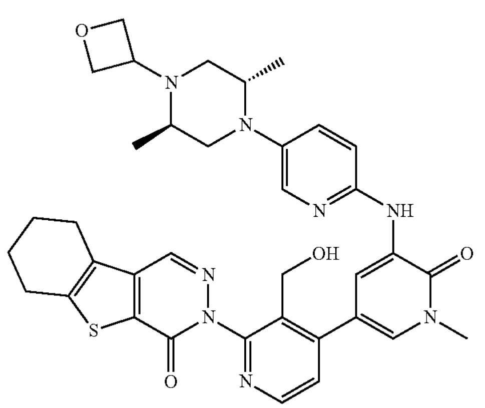 [SMILES: C[C@@H]1CN(c2ccc(Nc3cc(-c4ccnc(-n5ncc6c7c(sc6c5=O)CCCC7)c4CO)cn(C)c3=O)nc2)[C@@H](C)CN1C1COC1] | 3-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one | 680.82 | 0.082 |

TABLE 1-continued

| No. | Structure | IUPAC_Name | Mol Weight | CD69 Hu Blood FACS IC70 (µM) |
|---|---|---|---|---|
| 160 | 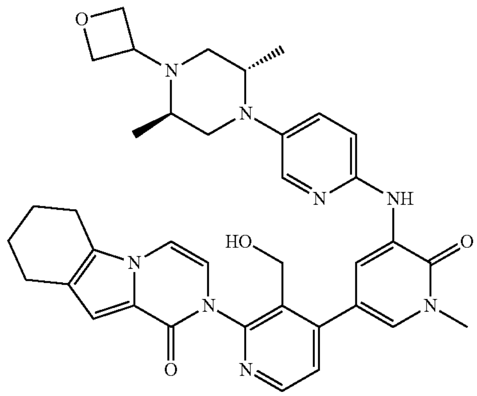 [SMILES: C[C@@H]1CN(c2ccc(Nc3cc(-c4ccnc(-n5ccn6c7c(cc6c5=O)CCCC7)c4CO)cn(C)c3=O)nc2)[C@@H](C)CN1C1COC1] | 2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one | 662.78 | 0.0547 |
| 161 | 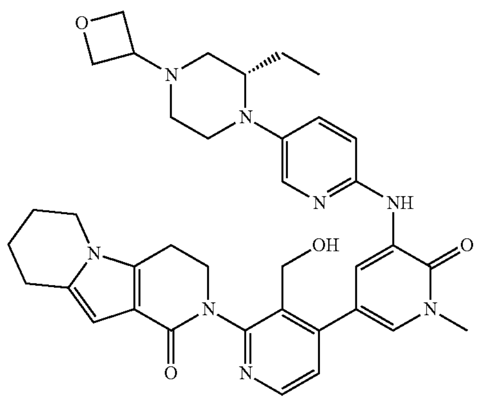 [SMILES: CC[C@H]1CN(C2COC2)CCN1c1ccc(Nc2cc(-c3ccnc(N4CCc5c(cc6n5CCCC6)C4=O)c3CO)cn(C)c2=O)nc1] | 2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-2,3,5,6,7,8-hexahydro-4H-2,4b-diaza-fluoren-1-one | 664.80 | 0.064 |
| 162 | 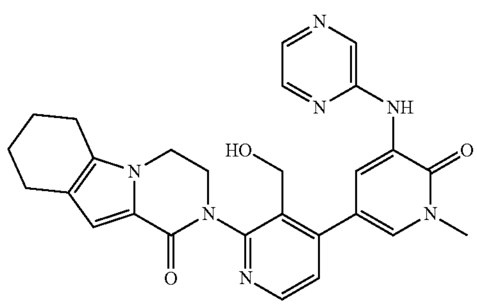 [SMILES: Cn1cc(-c2ccnc(N3CCn4c(cc5c4CCCC5)C3=O)c2CO)cc(Nc2cnccn2)c1=O] | 2-[3'-Hydroxymethyl-1-methyl-6-oxo-5-(pyrazin-2-ylamino)-1,6-dihydro-[3,4']bipyridinyl-2'-yl]-3,4,6,7,8,9-hexahydro-2H-pyrazino[1,2-a]indol-1-one | 497.55 | 0.434 |
| 163 | 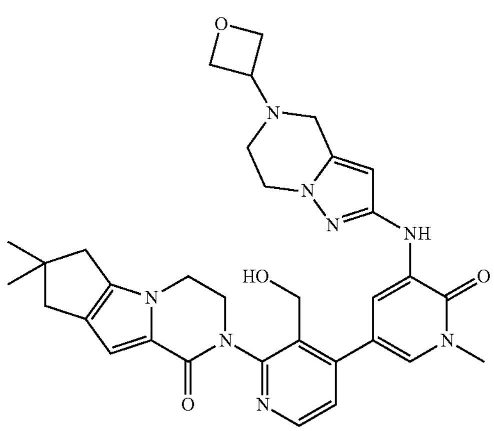 [SMILES: Cn1cc(-c2ccnc(N3CCn4c(cc5c4CC(C)(C)C5)C3=O)c2CO)cc(Nc2cc3n(n2)CCN(C2COC2)C3)c1=O] | 2-[3'-Hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 610.71 | 0.0228 |

TABLE 1-continued

| No. | Structure | IUPAC_Name | Mol Weight | CD69 Hu Blood FACS IC70 (μM) |
|---|---|---|---|---|
| 164 | 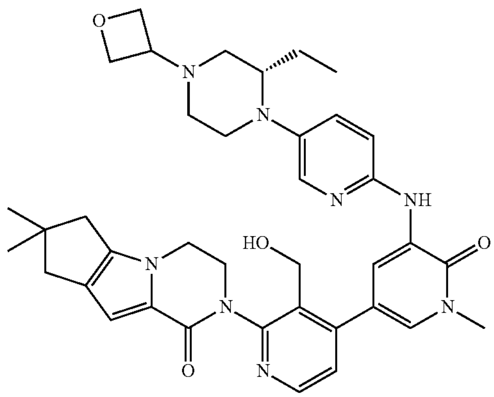 [SMILES: CC[C@H]1CN(C2COC2)CCN1c1ccc(Nc2cc(-c3ccnc(N4CCn5c(cc6c5CC(C)(C)C6)C4=O)c3CO)cn(C)c2=O)nc1] | 2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one | 678.82 | 0.029 |
| 165 | 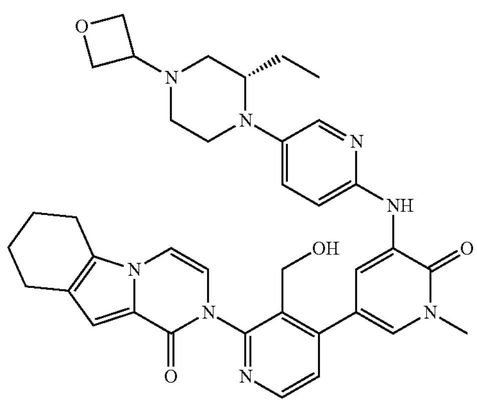 [SMILES: CC[C@H]1CN(C2COC2)CCN1c1ccc(Nc2cc(-c3ccnc(-n4ccn5c6c(cc5c4=O)CCCC6)c3CO)cn(C)c2=O)nc1] | 2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one | 662.78 | 0.0417 |
| 166 | 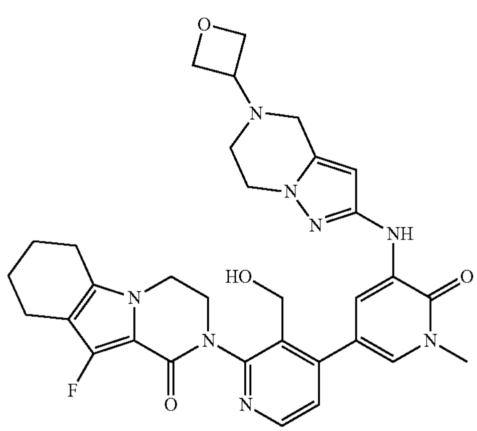 [SMILES: Cn1cc(-c2ccnc(N3CCn4c5c(c(F)c4C3=O)CCCC5)c2CO)cc(Nc2cc3n(n2)CCN(C2COC2)C3)c1=O] | 10-Fluoro-2-[3'-hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one | 614.67 | 0.155 |

TABLE 1-continued

| No. | Structure | IUPAC_Name | Mol Weight | CD69 Hu Blood FACS IC70 (µM) |
|---|---|---|---|---|
| 167 | 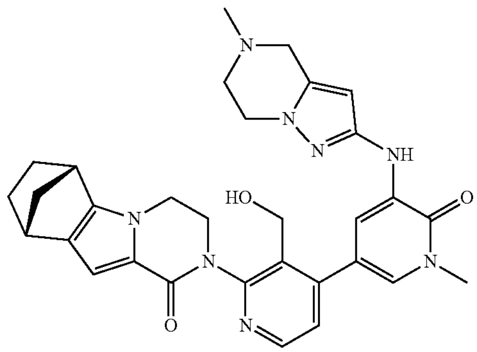 [SMILES: CN1CCn2nc(Nc3cc(-c4ccnc(N5CCn6c(cc7c6[C@H]6CC[C@@H]7C6)C5=O)c4CO)cn(C)c3=O)cc2C1] | 2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one | 566.65 | 0.119 |
| 168 | 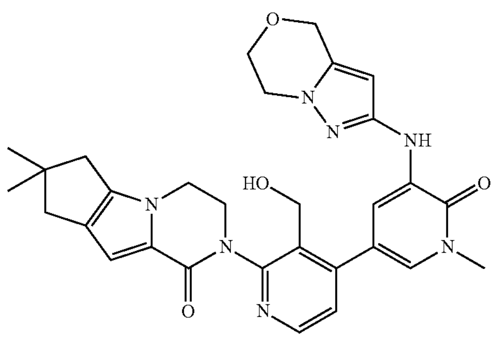 [SMILES: Cn1cc(-c2ccnc(N3CCn4c(cc5c4CC(C)(C)C5)C3=O)c2CO)cc(Nc2cc3n(n2)CCOC3)c1=O] | 2-[5-(6,7-Dihydro-4H-pyrazolo[5,1-c][1,4]oxazin-2-ylamino)-3'-hydroxymethyl-1-methyl-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 555.63 | 0.0635 |
| 169 | 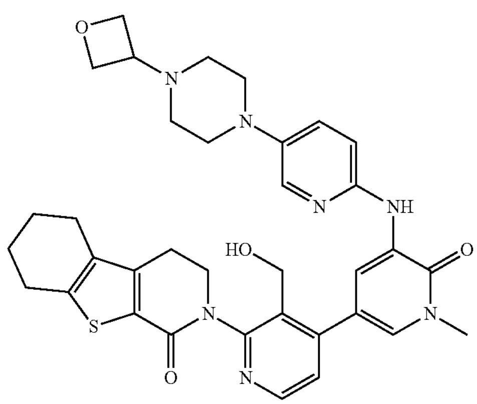 [SMILES: Cn1cc(-c2ccnc(N3CCc4c(sc5c4CCCC5)C3=O)c2CO)cc(Nc2ccc(N3CCN(C4COC4)CC3)cn2)c1=O] | 2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-3,4,5,6,7,8-hexahydro-2H-benzo[4,5]thieno[2,3-c]pyridin-1-one | 653.79 | 0.206 |
| 170 | 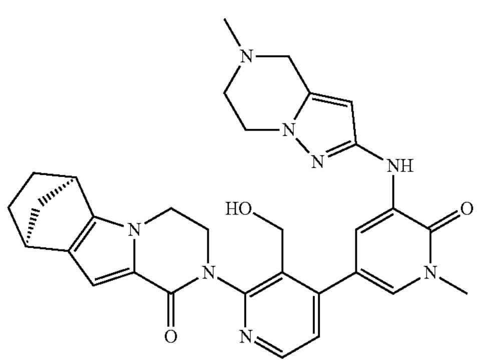 [SMILES: CN1CCn2nc(Nc3cc(-c4ccnc(N5CCn6c(cc7c6[C@@H]6CC[C@H]7C6)C5=O)c4CO)cn(C)c3=O)cc2C1] | 2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one | 566.65 | 0.335 |

TABLE 1-continued

| No. | Structure | IUPAC_Name | Mol Weight | CD69 Hu Blood FACS IC70 (µM) |
|---|---|---|---|---|
| 171 | 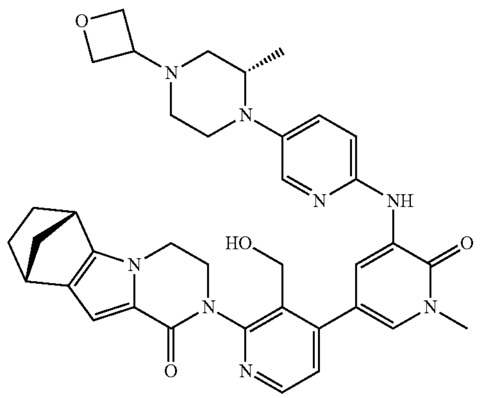 [SMILES: C[C@H]1CN(C2COC2)CCN1c1ccc(Nc2cc(-c3ccnc(N4CCn5c(cc6c5[C@H]5CC[C@@H]6C5)C4=O)c3CO)cn(C)c2=O)nc1] | (1S,11R)-6-[3-(Hydroxymethyl)-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridin-2-yl]-3,6-diazatetracyclo[9.2.1.0$^{2,10}$.0$^{3,8}$]tetradeca-2(10),8-dien-7-one | 662.78 | 0.036 |
| 172 | 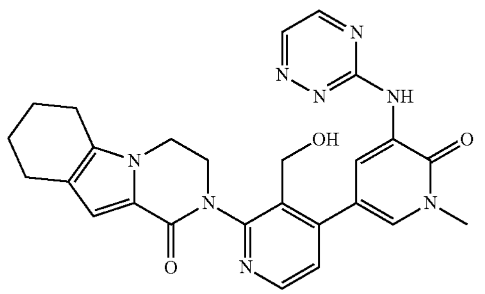 [SMILES: Cn1cc(-c2ccnc(N3CCn4c(cc5c4CCCC5)C3=O)c2CO)cc(Nc2nccnn2)c1=O] | 2-(4-(5-(1,2,4-triazin-3-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one | 498.54 | 5 |
| 173 | 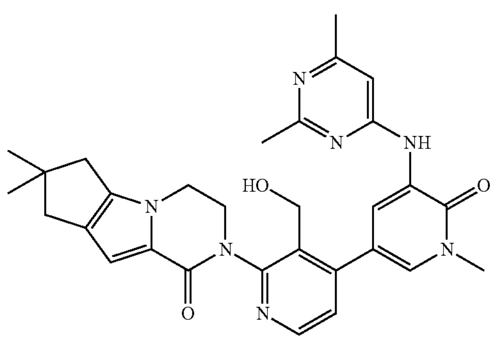 [SMILES: Cc1cc(Nc2cc(-c3ccnc(N4CCn5c(cc6c5CC(C)(C)C6)C4=O)c3CO)cn(C)c2=O)nc(C)n1] | 2-[5-(2,6-Dimethyl-pyrimidin-4-ylamino)-3'-hydroxymethyl-1-methyl-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 539.63 | 1 |
| 174 | 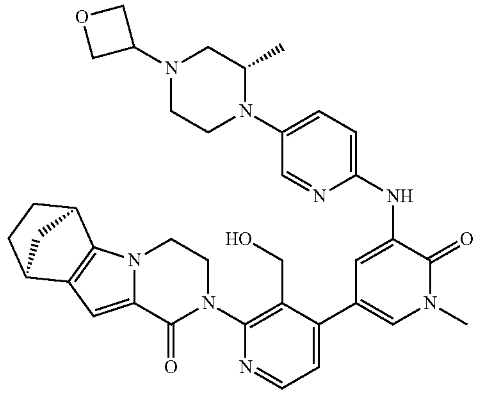 [SMILES: C[C@H]1CN(C2COC2)CCN1c1ccc(Nc2cc(-c3ccnc(N4CCn5c(cc6c5[C@@H]5CC[C@H]6C5)C4=O)c3CO)cn(C)c2=O)nc1] | (1R,11S)-6-[3-(Hydroxymethyl)-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridin-2-yl]-3,6-diazatetracyclo[9.2.1.0$^{2,10}$.0$^{3,8}$]tetradeca-2(10),8-dien-7-one | 662.78 | 0.101 |

TABLE 1-continued

| No. | Structure | IUPAC_Name | Mol Weight | CD69 Hu Blood FACS IC70 (μM) |
|---|---|---|---|---|
| 175 | 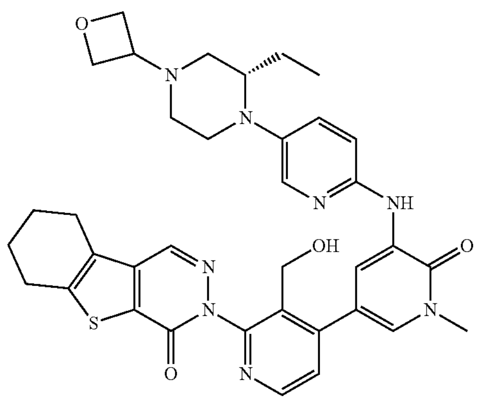 [SMILES: CC[C@H]1CN(C2COC2)CCN1c1ccc(Nc2cc(-c3ccnc(-n4ncc5c6c(sc5c4=O)CCCC6)c3CO)cn(C)c2=O)nc1] | 3-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one | 680.82 | 0.0466 |
| 176 | 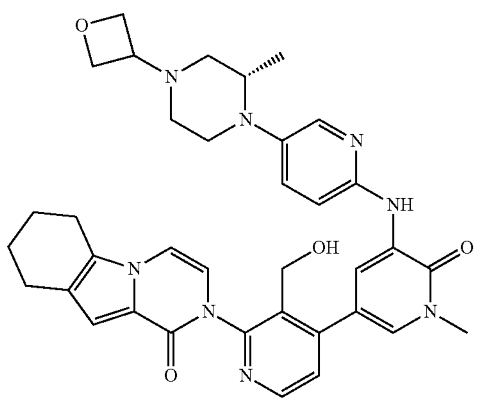 [SMILES: C[C@H]1CN(C2COC2)CCN1c1ccc(Nc2cc(-c3ccnc(-n4ccn5c6c(cc5c4=O)CCCC6)c3CO)cn(C)c2=O)nc1] | (S)-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-6,7,8,9-tetrahydropyrazino[1,2-a]indol-1(2H)-one | 648.75 | 0.0375 |
| 177 | 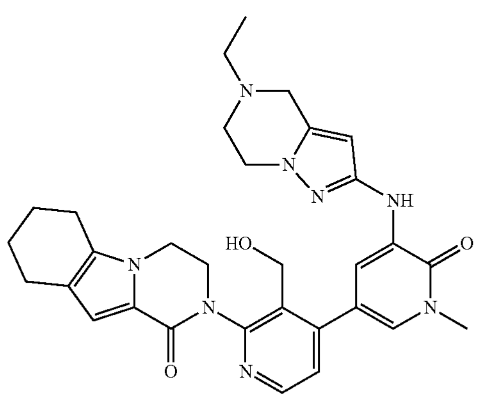 [SMILES: CCN1CCn2nc(Nc3cc(-c4ccnc(N5CCn6c(cc7c6CCCC7)C5=O)c4CO)cn(C)c3=O)cc2C1] | 2-(4-(5-(5-ethyl-4,5,6,7-tetrahydropyrazolo[1,5-a]pyrazin-2-ylamino)-1-methyl-6-oxo-1,6-dihydropyridin-3-yl)-3-(hydroxymethyl)pyridin-2-yl) 3,4,6,7,8,9-hexahydropyrazino[1,2-a]indol-1(2H)-one | 568.67 | 0.107 |
| 178 | 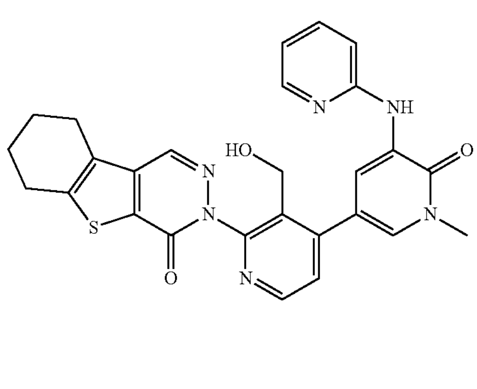 [SMILES: Cn1cc(-c2ccnc(-n3ncc4c5c(sc4c3=O)CCCC5)c2CO)cc(Nc2ccccn2)c1=O] | 3-[3'-Hydroxymethyl-1-methyl-6-oxo-5-(pyridin-2-ylamino)-1,6-dihydro-[3,4']bipyridinyl-2'-yl]-6,7,8,9-tetrahydro-3H-benzo[4,5]thieno[2,3-d]pyridazin-4-one | 512.58 | 1.1 |

TABLE 1-continued

| No. | Structure | IUPAC_Name | Mol Weight | CD69 Hu Blood FACS IC70 (μM) |
|---|---|---|---|---|
| 179 | 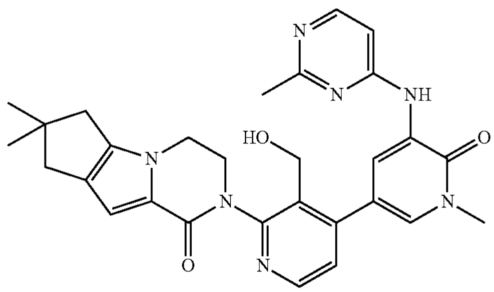 [SMILES: Cc1nccc(Nc2cc(-c3ccnc(N4CCn5c(cc6c5CC(C)(C)C6)C4=O)c3CO)cn(C)c2=O)n1] | 2-[3'-Hydroxymethyl-1-methyl-5-(2-methyl-pyrimidin-4-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 525.60 | 0.209 |
| 180 | 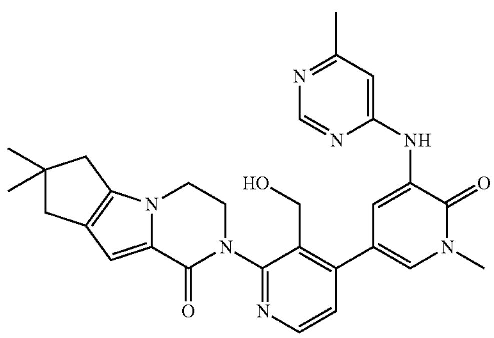 [SMILES: Cc1cc(Nc2cc(-c3ccnc(N4CCn5c(cc6c5CC(C)(C)C6)C4=O)c3CO)cn(C)c2=O)ncn1] | 2-[3'-Hydroxymethyl-1-methyl-5-(6-methyl-pyrimidin-4-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 525.60 | 0.245 |
| 181 | 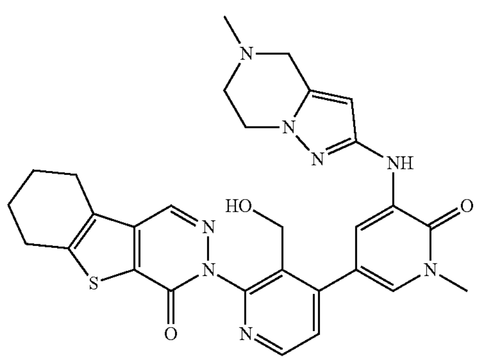 [SMILES: CN1CCn2nc(Nc3cc(-c4ccnc(-n5ncc6c7c(sc6c5=O)CCCC7)c4CO)cn(C)c3=O)cc2C1] | 3-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-6,7,8,9-tetrahydro-3H-benzo[4,5]thieno[2,3-d]pyridazin-4-one | 570.67 | 0.144 |
| 182 | 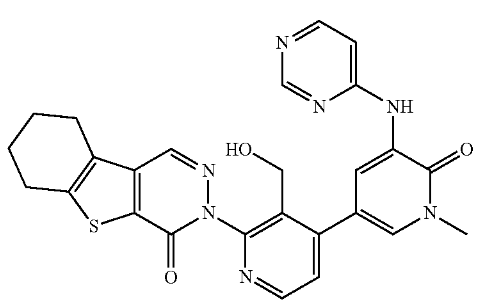 [SMILES: Cn1cc(-c2ccnc(-n3ncc4c5c(sc4c3=O)CCCC5)c2CO)cc(Nc2ccncn2)c1=O] | 3-[3'-Hydroxymethyl-1-methyl-6-oxo-5-(pyrimidin-4-ylamino)-1,6-dihydro-[3,4']bipyridinyl-2'-yl]-6,7,8,9-tetrahydro-3H-benzo[4,5]thieno[2,3-d]pyridazin-4-one | 513.57 | 0.813 |

TABLE 1-continued

| No. | Structure | IUPAC_Name | Mol Weight | CD69 Hu Blood FACS IC70 (μM) |
|---|---|---|---|---|
| 183 | 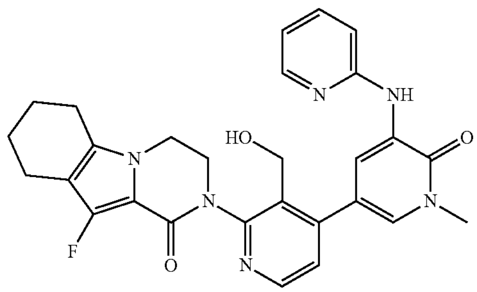 [SMILES: Cn1cc(-c2ccnc(N3CCn4c5c(c(F)c4C3=O)CCCC5)c2CO)cc(Nc2ccccn2)c1=O] | 10-fluoro-2-(3-(hydroxymethyl)-4-(1-methyl-6-oxo-5-(pyridin-2-ylamino)-1,6-dihydropyridin-3-yl)pyridin-2-yl)-3,4,6,7,8,9-hexahydropyrazino[1,2-a]indol-1(2H)-one | 514.55 | 0.906 |
| 184 | 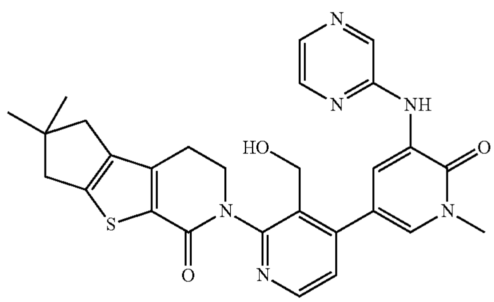 [SMILES: Cn1cc(-c2ccnc(N3CCc4c(sc5c4CC(C)(C)C5)C3=O)c2CO)cc(Nc2cnccn2)c1=O] | 6-[3'-Hydroxymethyl-1-methyl-6-oxo-5-(pyrazin-2-ylamino)-1,6-dihydro-[3,4']bipyridinyl-2'-yl]-2,2-dimethyl-2,3,5,6-tetrahydro-1H,4H-8-thia-6-aza-cyclopenta[a]inden-7-one | 528.63 | 0.601 |
| 185 | 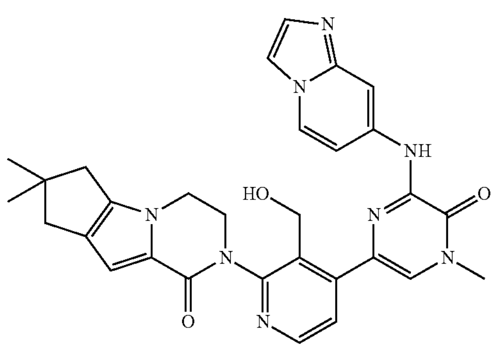 [SMILES: Cn1cc(-c2ccnc(N3CCn4c(cc5c4CC(C)(C)C5)C3=O)c2CO)nc(Nc2ccn3ccnc3c2)c1=O] | 2-{3-Hydroxymethyl-4-[6-(imidazo[1,2-a]pyridin-7-ylamino)-4-methyl-5-oxo-4,5-dihydro-pyrazin-2-yl]-pyridin-2-yl}-7,7-dimethyl-3,4,7,8-tetrahydro-2H,6H-cyclopenta[4,5]pyrrolo[1,2-a]pyrazin-1-one | 550.61 | 1.3 |
| 186 | 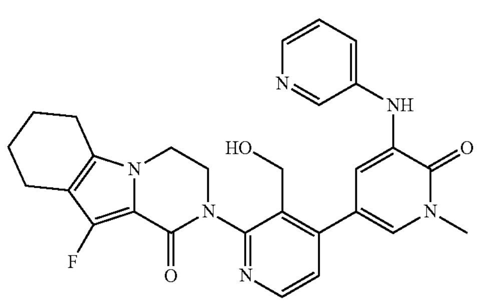 [SMILES: Cn1cc(-c2ccnc(N3CCn4c5c(c(F)c4C3=O)CCCC5)c2CO)cc(Nc2cccnc2)c1=O] | 10-fluoro-2-(3-(hydroxymethyl)-4-(4-methyl-5-oxo-6-(pyridin-3-ylamino)-4,5-dihydropyrazin-2-yl)pyridin-2-yl)-3,4,6,7,8,9-hexahydropyrazino[1,2-a]indol-1(2H)-one | 515.54 | 1.6 |

TABLE 1-continued

| No. | Structure | IUPAC_Name | Mol Weight | CD69 Hu Blood FACS IC70 (µM) |
|---|---|---|---|---|
| 187 | 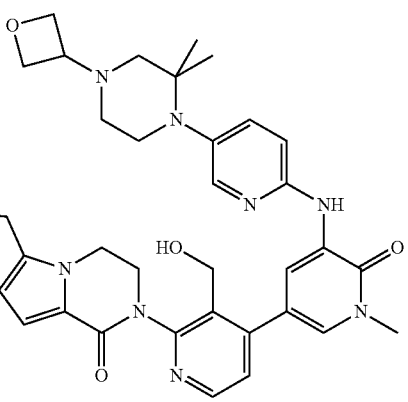 | 2-(4-(5-(5-(2,2-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one | 664.80 | 0.0451 |
| 188 | 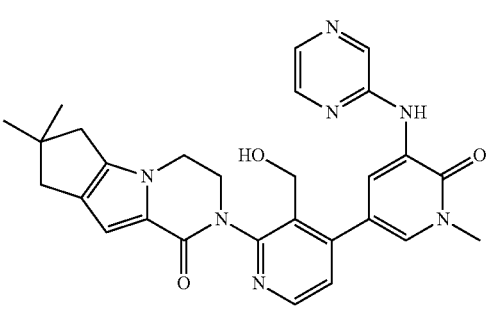 [SMILES: Cn1cc(-c2ccnc(N3CCn4c(cc5c4CC(C)(C)C5)C3=O)c2CO)cc(Nc2cnccn2)c1=O] | 2-[3'-Hydroxymethyl-1-methyl-6-oxo-5-(pyrazin-2-ylamino)-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one | 511.57 | 0.601 |
| 189 | 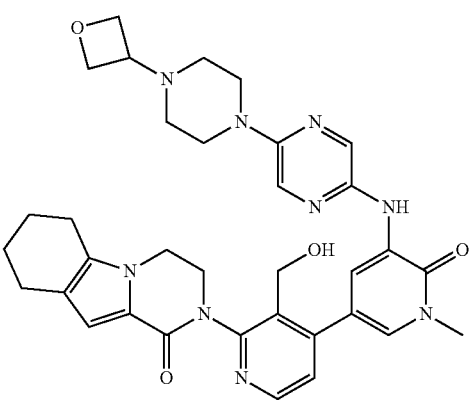 [SMILES: Cn1cc(-c2ccnc(N3CCn4c(cc5c4CCCC5)C3=O)c2CO)cc(Nc2cnc(N3CCN(C4COC4)CC3)cn2)c1=O] | 2-(3-(hydroxymethyl)-4-(1-methyl-5-(5-(4-(oxetan-3-yl)piperazin-1-yl)pyrazin-2-ylamino)-6-oxo-1,6-dihydropyridin-3-yl)pyridin-2-yl)-3,4,6,7,8,9-hexahydropyrazino[1,2-a]indol-1(2H)-one | 637.73 | 0.652 |

TABLE 2

| No. | Structure | IUPAC Name | CD69 Hu Blood FACS (IC70) |
|---|---|---|---|
| 190 | 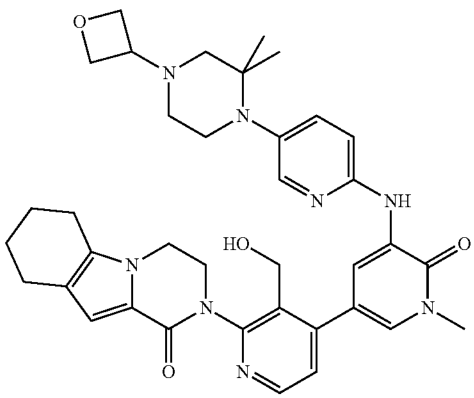 [SMILES: Cn1cc(-c2ccnc(N3CCn4c(cc5c4CCCC5)C3=O)c2CO)cc(Nc2ccc(N3CCN(C4COC4)CC3(C)C)cn2)c1=O] | 2-[4-[5-[[5-[2,2-dimethyl-4-(oxetan-3-yl)piperazin-1-yl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one | 0.0704 |
| 191 | 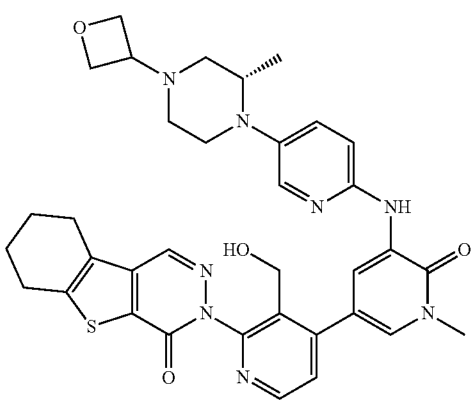 [SMILES: C[C@H]1CN(C2COC2)CCN1c1ccc(Nc2cc(-c3ccnc(-n4ncc5c6c(sc5c4=O)CCCC6)c3CO)cn(C)c2=O)nc1] | 3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydrobenzothiopheno[2,3-d]pyridazin-4-one | 0.0435 |
| 192 | 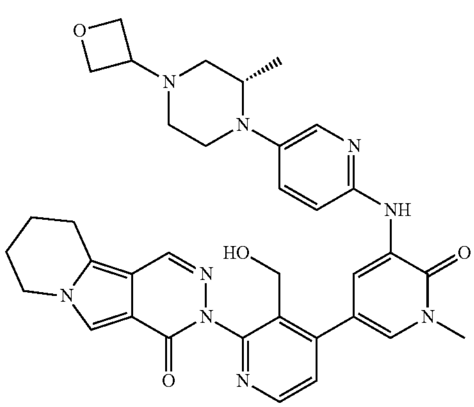 [SMILES: C[C@H]1CN(C2COC2)CCN1c1ccc(Nc2cc(-c3ccnc(-n4ncc5c6n(cc5c4=O)CCCC6)c3CO)cn(C)c2=O)nc1] | 3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one | 1.1 |

TABLE 2-continued

| No. | Structure | IUPAC Name | CD69 Hu Blood FACS (IC70) |
|---|---|---|---|
| 193 | 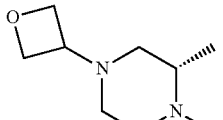 | 2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydropyridazino[4,5-b]indolizin-1-one | 0.0995 |
| 194 | 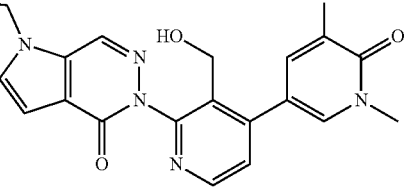 | 3-[3-(hydroxymethyl)-4-[1-methyl-6-oxo-5-(pyrazin-2-ylamino)-3-pyridyl]-2-pyridyl]-6,7,8,9-tetrahydrobenzothiopheno[2,3-d]pyridazin-4-one | 1.2 |
| 195 | 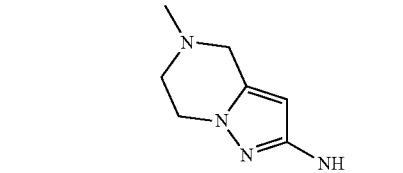 | 2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyrazino[1,2-a]indol-1-one | 0.101 |
| 196 | 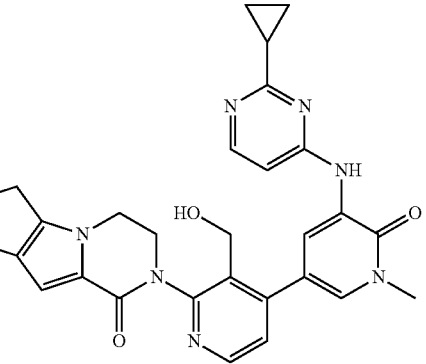 | 3-[4-[5-[(2-cyclopropylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.325 |

TABLE 2-continued

| No. | Structure | IUPAC Name | CD69 Hu Blood FACS (IC70) |
|---|---|---|---|
| 197 | 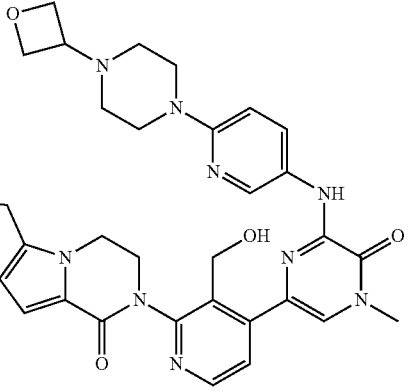 | 2-[3-(hydroxymethyl)-4-[4-methyl-6-[[6-[4-(oxetan-3-yl)piperazin-1-yl]-3-pyridyl]amino]-5-oxo-pyrazin-2-yl]-2-pyridyl]-3,4,6,7,8,9-hexahydropyrazino[1,2-a]indol-1-one | 2.3 |
| 198 | 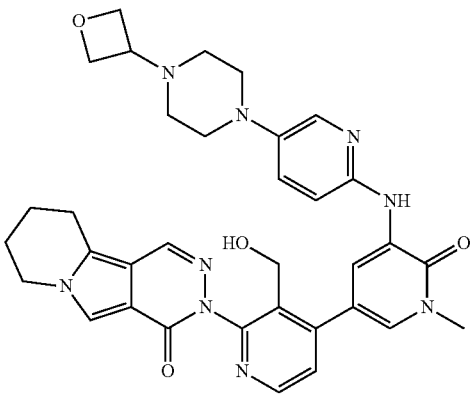 [SMILES: Cn1cc(-c2ccnc(-n3ncc4c5n(cc4c3=O)CCCC5)c2CO)cc(Nc2ccc(N3CCN(C4COC4)CC3)cn2)c1=O] | 3-[3-(hydroxymethyl)-4-[1-methyl-5-[[5-[4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one | 6 |
| 199 | 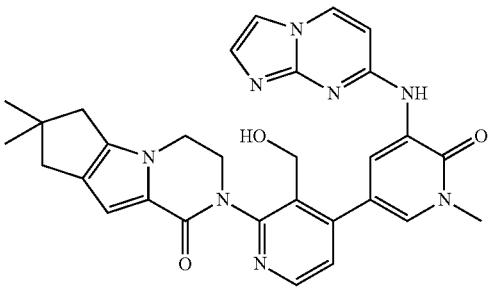 [SMILES: Cn1cc(-c2ccnc(N3CCn4c(cc5c4CC(C)(C)C5)C3=O)c2CO)cc(Nc2ccn3ccnc3n2)c1=O] | 3-[3-(hydroxymethyl)-4-[5-(imidazo[1,2-a]pyrimidin-7-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.934 |
| 200 | 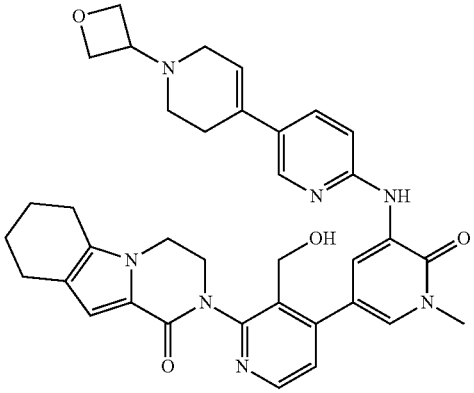 [SMILES: Cn1cc(-c2ccnc(N3CCn4c(cc5c4CCCC5)C3=O)c2CO)cc(Nc2ccc(C3=CCN(C4COC4)CC3)cn2)c1=O] | 2-[3-(hydroxymethyl)-4-[1-methyl-5-[[5-[1-(oxetan-3-yl)-3,6-dihydro-2H-pyridin-4-yl]-2-pyridyl]amino]-6-oxo-3-pyridyl]-2-pyridyl]-3,4,6,7,8,9-hexahydropyrazino[1,2-a]indol-1-one | 0.636 |

TABLE 2-continued

| No. | Structure | IUPAC Name | CD69 Hu Blood FACS (IC70) |
|---|---|---|---|
| 201 | 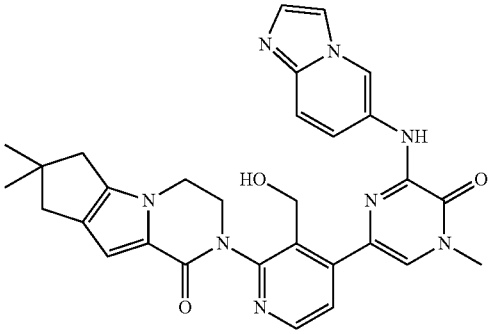 [SMILES: Cn1cc(-c2ccnc(N3CCn4c(cc5c4CC(C)(C)C5)C3=O)c2CO)nc(Nc2ccc3nccn3c2)c1=O] | 3-[3-(hydroxymethyl)-4-[6-(imidazo[1,2-a]pyridin-6-ylamino)-4-methyl-5-oxo-pyrazin-2-yl]-2-pyridyl]-7,7-dimethyl-1,2,6,8-tetrahydrocyclopenta[3,4]pyrrolo[3,5-b]pyrazin-4-one | 3.3 |
| 202 | 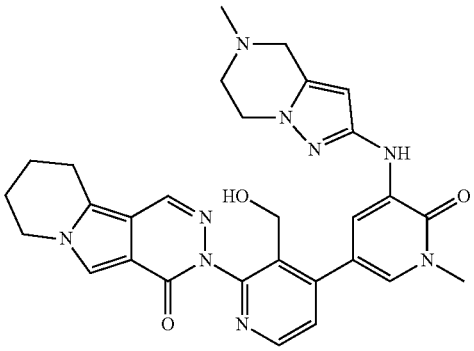 [SMILES: CN1CCn2nc(Nc3cc(-c4ccnc(-n5ncc6c7n(cc6c5=O)CCCC7)c4CO)cn(C)c3=O)cc2C1] | 3-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-7,8,9,10-tetrahydropyridazino[4,5-a]indolizin-4-one | 7.3 |
| 203 | 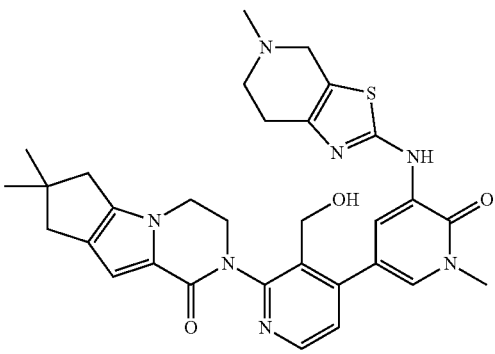 [SMILES: CN1CCc2nc(Nc3cc(-c4ccnc(N5CCn6c(cc7c6CC(C)(C)C7)C5=O)c4CO)cn(C)c3=O)sc2C1] | 3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0605 |
| 204 | 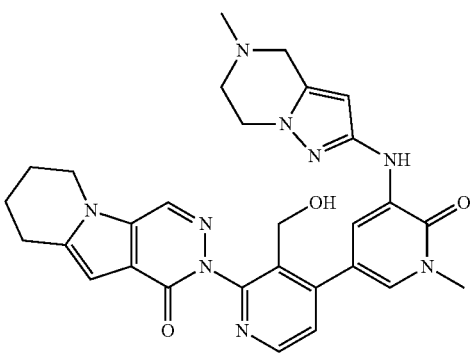 [SMILES: CN1CCn2nc(Nc3cc(-c4ccnc(-n5ncc6c(cc7n6CCCC7)c5=O)c4CO)cn(C)c3=O)cc2C1] | 2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyridazino[4,5-b]indolizin-1-one | 0.436 |

TABLE 2-continued

| No. | Structure | IUPAC Name | CD69 Hu Blood FACS (IC70) |
|-----|-----------|------------|---------------------------|
| 205 | 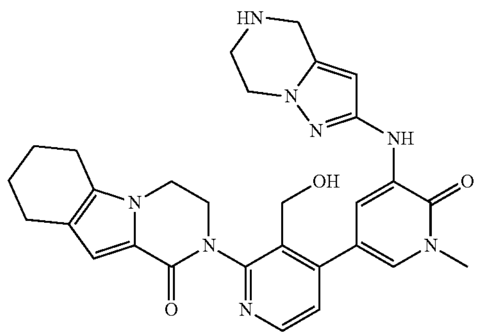 [SMILES: Cn1cc(-c2ccnc(N3CCn4c(cc5c4CCCC5)C3=O)c2CO)cc(Nc2cc3n(n2)CCNC3)c1=O] | 2-[3-(hydroxymethyl)-4-[1-methyl-6-oxo-5-(4,5,6,7-tetrahydropyrazolo[1,5-a]pyrazin-2-ylamino)-3-pyridyl]-2-pyridyl]-3,4,6,7,8,9-hexahydropyrazino[1,2-a]indol-1-one | 0.114 |
| 206 | 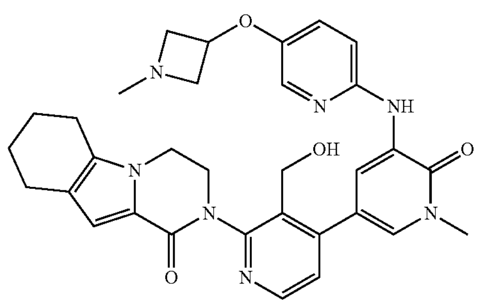 [SMILES: CN1CC(Oc2ccc(Nc3cc(-c4ccnc(N5CCn6c(cc7c6CCCC7)C5=O)c4CO)cn(C)c3=O)nc2)C1] | 2-[3-(hydroxymethyl)-4-[1-methyl-5-[[5-(1-methylazetidin-3-yl)oxy-2-pyridyl]amino]-6-oxo-3-pyridyl]-2-pyridyl]-3,4,6,7,8,9-hexahydropyrazino[1,2-a]indol-1-one | 0.15 |
| 207 | 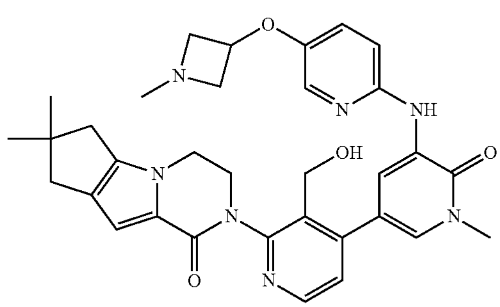 [SMILES: CN1CC(Oc2ccc(Nc3cc(-c4ccnc(N5CCn6c(cc7c6CC(C)(C)C7)C5=O)c4CO)cn(C)c3=O)nc2)C1] | 3-[3-(hydroxymethyl)-4-[1-methyl-5-[[5-(1-methylazetidin-3-yl)oxy-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0414 |
| 208 | 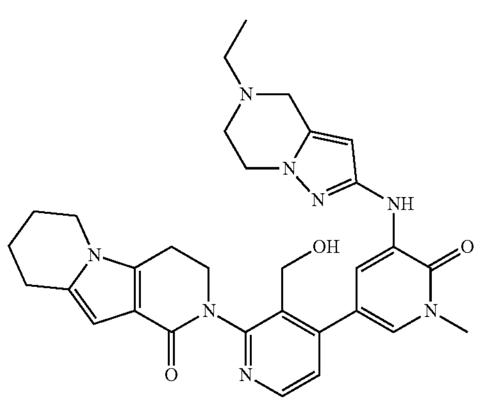 [SMILES: CCN1CCn2nc(Nc3cc(-c4ccnc(N5CCc6c(cc7n6CCCC7)C5=O)c4CO)cn(C)c3=O)cc2C1] | 2-[4-[5-[(5-ethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrido[3,4-b]indolizin-1-one | 0.58 |

TABLE 2-continued

| No. | Structure | IUPAC Name | CD69 Hu Blood FACS (IC70) |
|---|---|---|---|
| 209 | 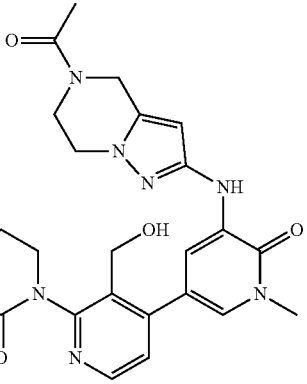 | 2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one | 0.116 |
| 210 | 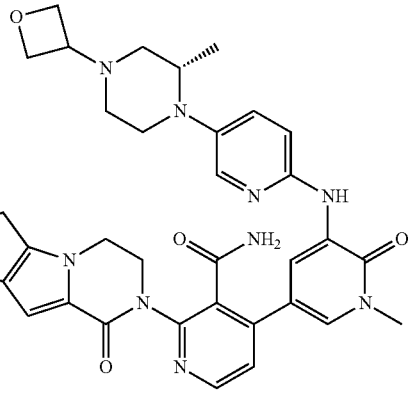 | 2-(7,7-dimethyl-4-oxo-1,2,6,8-tetrahydrocyclopenta[3,4]pyrrolo[3,5-b]pyrazin-3-yl)-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide | 0.914 |
| 211 | 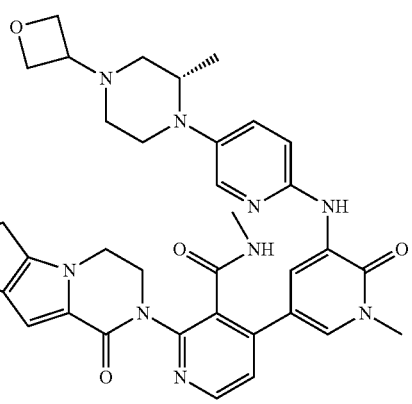 | 2-(7,7-dimethyl-4-oxo-1,2,6,8-tetrahydrocyclopenta[3,4]pyrrolo[3,5-b]pyrazin-3-yl)-N-methyl-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide | 2.1 |

TABLE 2-continued

| No. | Structure | IUPAC Name | CD69 Hu Blood FACS (IC70) |
|---|---|---|---|
| 212 | 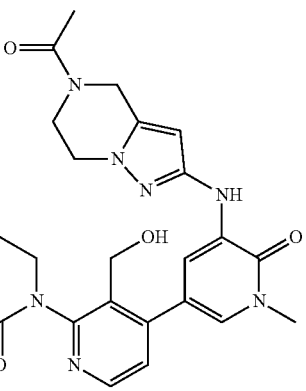 | 3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.0152 |
| 213 | 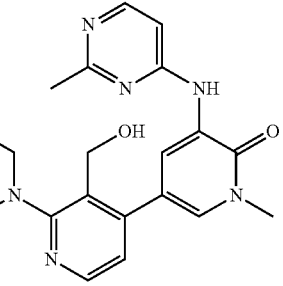 | 10-fluoro-2-[3-(hydroxymethyl)-4-[1-methyl-5-[(2-methylpyrimidin-4-yl)amino]-6-oxo-3-pyridyl]-2-pyridyl]-3,4,6,7,8,9-hexahydropyrazino[1,2-a]indol-1-one | 0.62 |
| 214 | 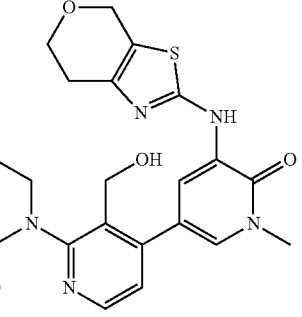 | 3-[4-[5-(6,7-dihydro-4H-pyrano[4,3-d]thiazol-2-ylamino)-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.124 |
| 215 | 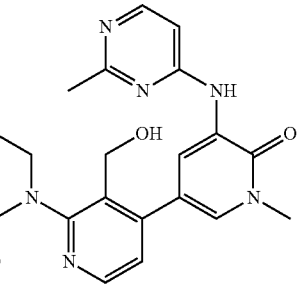 | 3-[4-(hydroxymethyl)-5-[1-methyl-5-[(2-methylpyrimidin-4-yl)amino]-6-oxo-3-pyridyl]-3-pyridyl]-7,7-dimethyl-1,2,6,8-tetrahydrocyclopenta[3,4]pyrrolo[3,5-b]pyrazin-4-one | 0.457 |

TABLE 2-continued

| No. | Structure | IUPAC Name | CD69 Hu Blood FACS (IC70) |
|---|---|---|---|
| 216 | 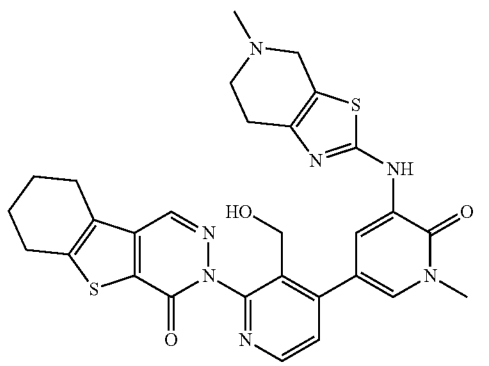 [SMILES: CN1CCc2nc(Nc3cc(-c4ccnc(-n5ncc6c7c(sc6c5=O)CCCC7)c4CO)cn(C)c3=O)sc2C1] | 3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-6,7,8,9-tetrahydrobenzothiopheno[2,3-d]pyridazin-4-one | 0.357 |
| 217 | 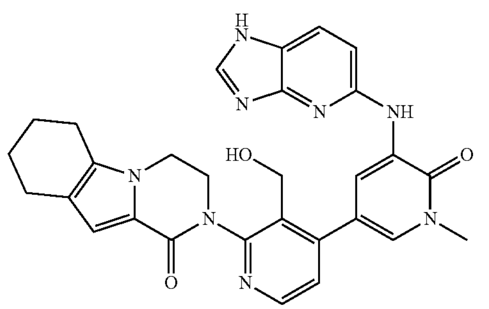 [SMILES: Cn1cc(-c2ccnc(N3CCn4c(cc5c4CCCC5)C3=O)c2CO)cc(Nc2ccc3[nH]cnc3n2)c1=O] | 2-[3-(hydroxymethyl)-4-[5-(1H-imidazo[4,5-b]pyridin-5-ylamino)-1-methyl-6-oxo-3-pyridyl]-2-pyridyl]-3,4,6,7,8,9-hexahydropyrazino[1,2-a]indol-1-one | 2.9 |
| 218 | 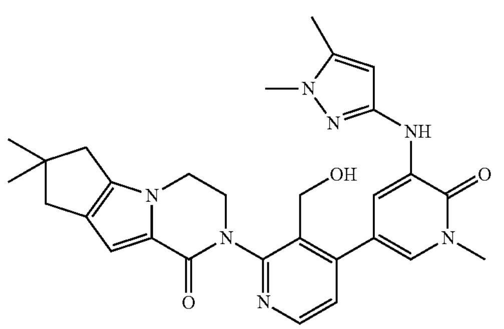 [SMILES: Cc1cc(Nc2cc(-c3ccnc(N4CCn5c(cc6c5CC(C)(C)C6)C4=O)c3CO)cn(C)c2=O)nn1C] | 3-[4-[5-[(1,5-dimethylpyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.0741 |
| 219 | 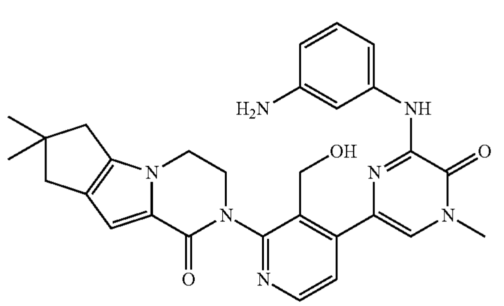 [SMILES: Cn1cc(-c2ccnc(N3CCn4c(cc5c4CC(C)(C)C5)C3=O)c2CO)nc(Nc2cccc(N)c2)c1=O] | 3-[4-[6-(3-aminoanilino)-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one | 0.204 |

TABLE 2-continued

| No. | Structure | IUPAC Name | CD69 Hu Blood FACS (IC70) |
|---|---|---|---|
| 220 | 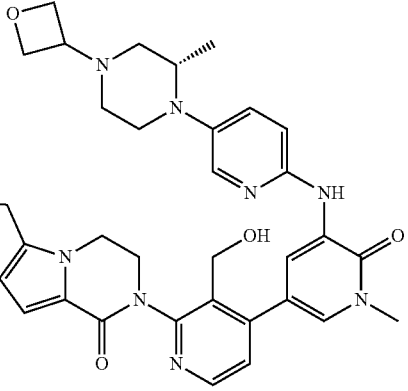 | 5-[2-(3,4,6,7,8,9-hexahydro-1H-pyrazino[1,2-a]indol-2-yl)-3-(hydroxymethyl)-4-pyridyl]-1-methyl-3-[[5-[(2S)-2-methyl-4-(oxetan-3-yl)piperazin-1-yl]-2-pyridyl]amino]pyridin-2-one | 1.6 |
| 221 | 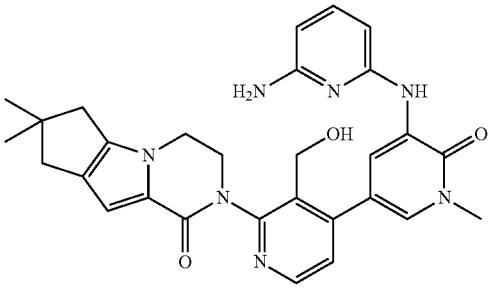 [SMILES: Cn1cc(-c2ccnc(N3CCn4c(cc5c4CC(C)(C)C5)C3=O)c2CO)cc(Nc2cccc(N)n2)c1=O] | 3-[4-[5-[(6-amino-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.121 |
| 222 | 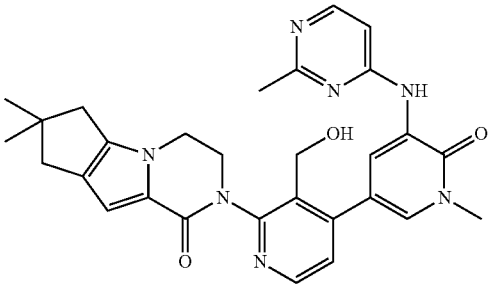 | 3-[3-(hydroxymethyl)-4-[5-[(2-methylpyrimidin-4-yl)amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one | 0.178 |
| 223 | 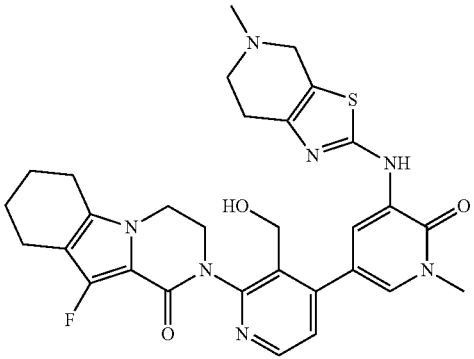 [SMILES: CN1CCc2nc(Nc3cc(-c4ccnc(N5CCn6c7c(c(F)c6C5=O)CCCC7)c4CO)cn(C)c3=O)sc2C1] | 10-fluoro-2-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-3,4,6,7,8,9-hexahydropyrazino[1,2-a]indol-1-one | 0.43 |

TABLE 2-continued

| No. | Structure | IUPAC Name | CD69 Hu Blood FACS (IC70) |
|---|---|---|---|
| 224 | 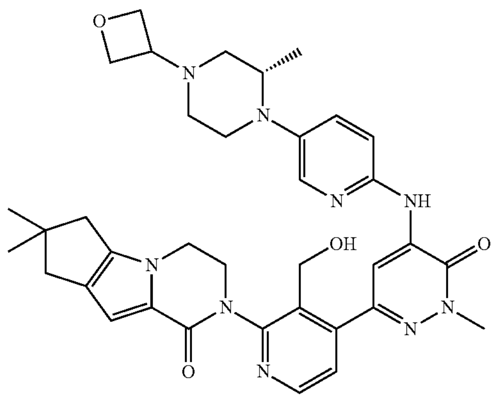 [SMILES: C[C@H]1CN(C2COC2)CCN1c1ccc(Nc2cc(-c3ccnc(N4CCn5c(cc6c5CC(C)(C)C6)C4=O)c3CO)nn(C)c2=O)nc1] | 3-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one | 0.0307 |
| 225 | 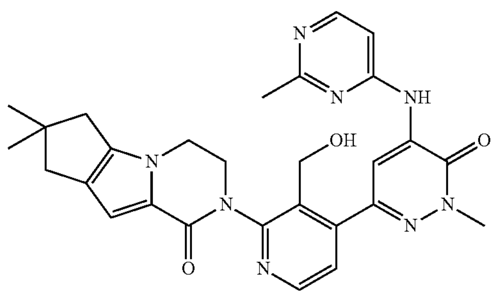 [SMILES: Cc1nccc(Nc2cc(-c3ccnc(N4CCn5c(cc6c5CC(C)(C)C6)C4=O)c3CO)nn(C)c2=O)n1] | 3-[3-(hydroxymethyl)-4-[1-methyl-5-[(2-methylpyrimidin-4-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one | 0.766 |
| 226 | 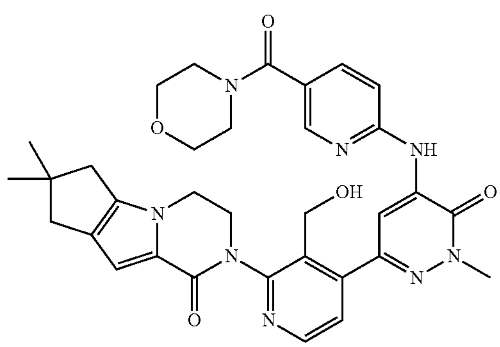 [SMILES: Cn1nc(-c2ccnc(N3CCn4c(cc5c4CC(C)(C)C5)C3=O)c2CO)cc(Nc2ccc(C(=O)N3CCOCC3)cn2)c1=O] | 3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one | 0.117 |
| 227 | 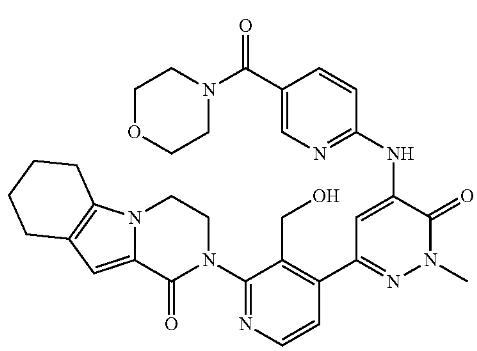 [SMILES: Cn1nc(-c2ccnc(N3CCn4c(cc5c4CCCC5)C3=O)c2CO)cc(Nc2ccc(C(=O)N3CCOCC3)cn2)c1=O] | 2-[3-(hydroxymethyl)-4-[1-methyl-5-[[5-(morpholine-4-carbonyl)-2-pyridyl]amino]-6-oxo-pyridazin-3-yl]-2-pyridyl]-3,4,6,7,8,9-hexahydropyrazino[1,2-a]indol-1-one | 0.73 |

TABLE 2-continued

| No. | Structure | IUPAC Name | CD69 Hu Blood FACS (IC70) |
|---|---|---|---|
| 228 | 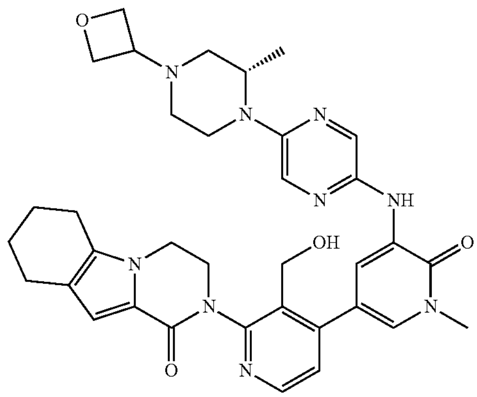 [SMILES: C[C@H]1CN(C2COC2)CCN1c1cnc(Nc2cc(-c3ccnc(N4CCn5c(cc6c5CCCC6)C4=O)c3CO)cn(C)c2=O)cn1] | 2-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-3,4,6,7,8,9-hexahydropyrazino[1,2-a]indol-1-one | 0.369 |
| 229 | 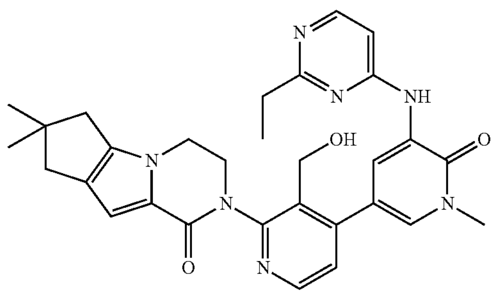 [SMILES: CCc1nccc(Nc2cc(-c3ccnc(N4CCn5c(cc6c5CC(C)(C)C6)C4=O)c3CO)cn(C)c2=O)n1] | 3-[4-[5-[(2-ethylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.583 |
| 230 | 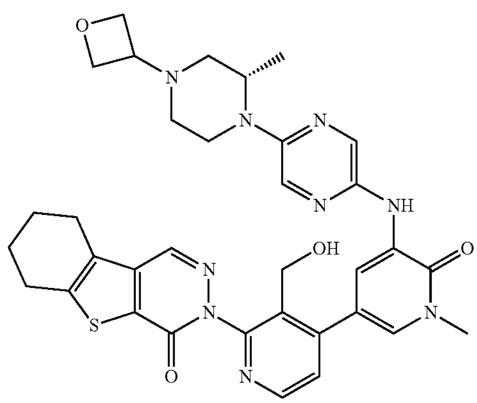 [SMILES: C[C@H]1CN(C2COC2)CCN1c1cnc(Nc2cc(-c3ccnc(-n4ncc5c6c(sc5c4=O)CCCC6)c3CO)cn(C)c2=O)cn1] | 3-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-6,7,8,9-tetrahydrobenzothiopheno[2,3-d]pyridazin-4-one | 0.179 |
| 231 | 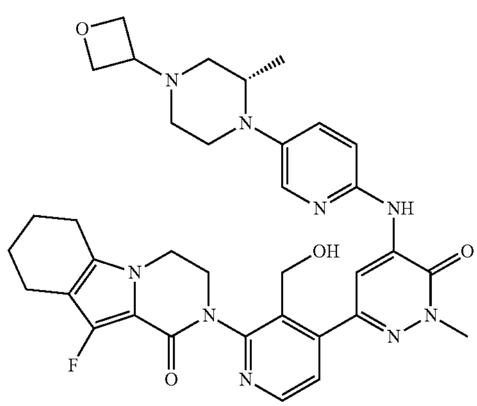 [SMILES: C[C@H]1CN(C2COC2)CCN1c1ccc(Nc2cc(-c3ccnc(N4CCn5c6c(c(F)c5C4=O)CCCC6)c3CO)nn(C)c2=O)nc1] | 10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-3,4,6,7,8,9-hexahydropyrazino[1,2-a]indol-1-one | 0.0624 |

TABLE 2-continued

| No. | Structure | IUPAC Name | CD69 Hu Blood FACS (IC70) |
|---|---|---|---|
| 232 | 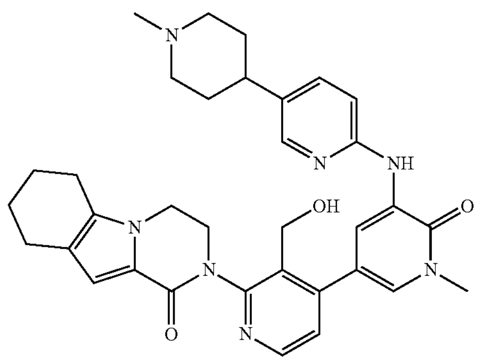 [SMILES: CN1CCC(c2ccc(Nc3cc(-c4ccnc(N5CCn6c(cc7c6CCCC7)C5=O)c4CO)cn(C)c3=O)nc2)CC1] | 2-[3-(hydroxymethyl)-4-[1-methyl-5-[[5-(1-methyl-4-piperidyl)-2-pyridyl]amino]-6-oxo-3-pyridyl]-2-pyridyl]-3,4,6,7,8,9-hexahydropyrazino[1,2-a]indol-1-one | 0.0518 |
| 233 | 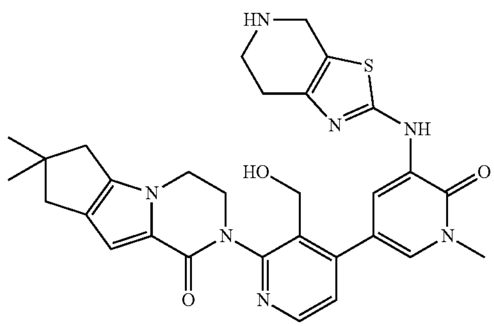 [SMILES: Cn1cc(-c2ccnc(N3CCn4c(cc5c4CC(C)(C)C5)C3=O)c2CO)cc(Nc2nc3c(s2)CNCC3)c1=O] | 3-[3-(hydroxymethyl)-4-[1-methyl-6-oxo-5-(4,5,6,7-tetrahydrothiazolo[5,4-c]pyridin-2-ylamino)-3-pyridyl]-2-pyridyl]-7,7-dimethyl-1,2,6,8-tetrahydrocyclopenta[3,4]pyrrolo[3,5-b]pyrazin-4-one | 0.0657 |
| 234 | 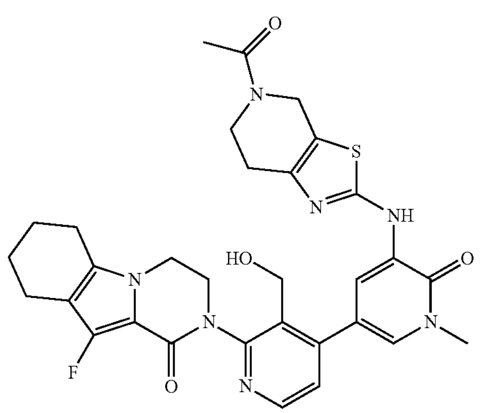 [SMILES: CC(=O)N1CCc2nc(Nc3cc(-c4ccnc(N5CCn6c7c(c(F)c6C5=O)CCCC7)c4CO)cn(C)c3=O)sc2C1] | 2-[4-[5-[(5-acetyl-6,7-dihydro-4H-thiazolo[5,4-c]pyridin-2-yl)amino]-1-methyl-6-oxo-3-pyridyl]-3-(hydroxymethyl)-2-pyridyl]-10-fluoro-3,4,6,7,8,9-hexahydropyrazino[1,2-a]indol-1-one | 0.183 |
| 235 | 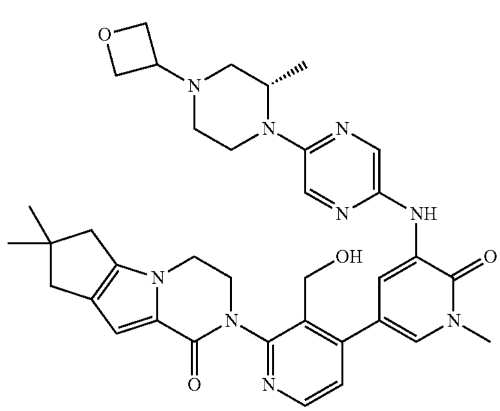 [SMILES: C[C@H]1CN(C2COC2)CCN1c1cnc(Nc2cc(-c3ccnc(N4CCn5c(cc6c5CC(C)(C)C6)C4=O)c3CO)cn(C)c2=O)cn1] | 3-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.112 |

TABLE 2-continued

| No. | Structure | IUPAC Name | CD69 Hu Blood FACS (IC70) |
|---|---|---|---|
| 236 | 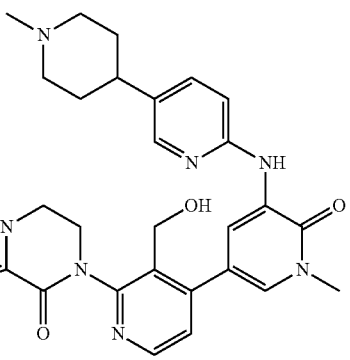 | 3-[3-(hydroxymethyl)-4-[1-methyl-5-[[5-(1-methyl-4-piperidyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0336 |
| 237 | 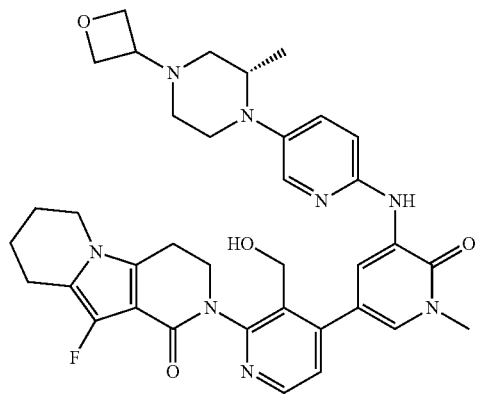 [SMILES: C[C@H]1CN(C2COC2)CCN1c1ccc(Nc2cc(-c3ccnc(N4CCc5c(c(F)c6n5CCCC6)C4=O)c3CO)cn(C)c2=O)nc1] | 10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-3,4,6,7,8,9-hexahydropyrido[3,4-b]indolizin-1-one | 0.0461 |
| 238 | 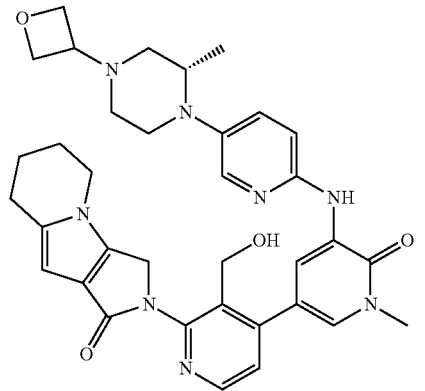 [SMILES: C[C@H]1CN(C2COC2)CCN1c1ccc(Nc2cc(-c3ccnc(N4Cc5c(cc6n5CCCC6)C4=O)c3CO)cn(C)c2=O)nc1] | 2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-5,6,7,8-tetrahydro-1H-pyrrolo[3,4-b]indolizin-3-one | 5 |
| 239 | 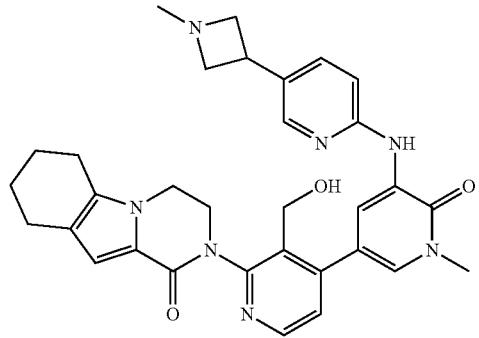 [SMILES: CN1CC(c2ccc(Nc3cc(-c4ccnc(N5CCn6c(cc7c6CCCC7)C5=O)c4CO)cn(C)c3=O)nc2)C1] | 2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrazino[1,2-a]indol-1-one | 0.153 |

TABLE 2-continued

| No. | Structure | IUPAC Name | CD69 Hu Blood FACS (IC70) |
|---|---|---|---|
| 240 | 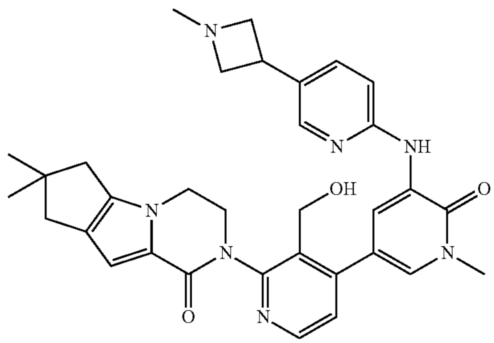 [SMILES: CN1CC(c2ccc(Nc3cc(-c4ccnc(N5CCn6c(cc7c6CC(C)(C)C7)C5=O)c4CO)cn(C)c3=O)nc2)C1] | 3-[3-(hydroxymethyl)-4-[1-methyl-5-[[5-(1-methylazetidin-3-yl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0229 |
| 241 | 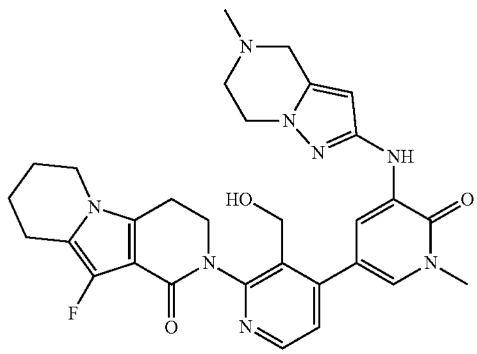 [SMILES: CN1CCn2nc(Nc3cc(-c4ccnc(N5CCc6c(c(F)c7n6CCCC7)C5=O)c4CO)cn(C)c3=O)cc2C1] | 10-fluoro-2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-3,4,6,7,8,9-hexahydropyrido[3,4-b]indolizin-1-one | 0.19 |
| 242 | 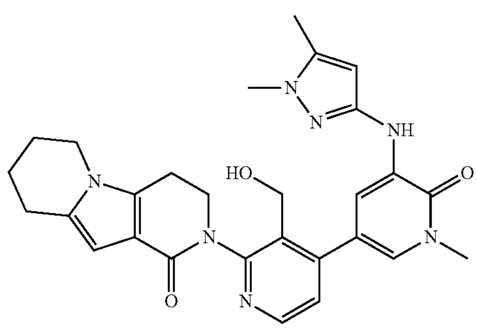 [SMILES: Cc1cc(Nc2cc(-c3ccnc(N4CCc5c(cc6n5CCCC6)C4=O)c3CO)cn(C)c2=O)nn1C] | 2-[4-[5-[(1,5-dimethylpyrazol-3-yl)amino]-1-methyl-6-oxo-3-pyridyl]-3-(hydroxymethyl)-2-pyridyl]-3,4,6,7,8,9-hexahydropyrido[3,4-b]indolizin-1-one | 1.2 |
| 243 | 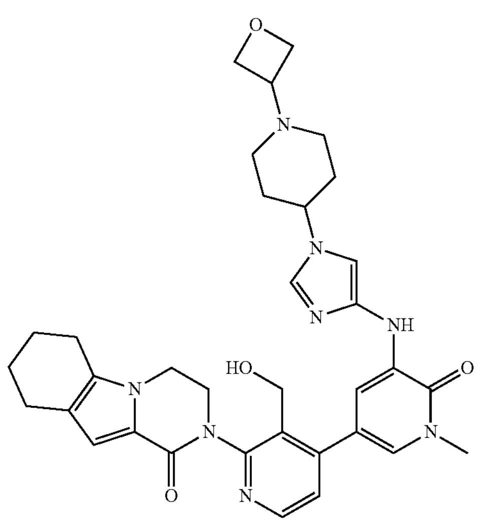 [SMILES: Cn1cc(-c2ccnc(N3CCn4c(cc5c4CCCC5)C3=O)c2CO)cc(Nc2cn(C3CCN(C4COC4)CC3)cn2)c1=O] | 2-[3-(hydroxymethyl)-4-[1-methyl-5-[[1-[1-(oxetan-3-yl)-4-piperidyl]imidazol-4-yl]amino]-6-oxo-3-pyridyl]-2-pyridyl]-3,4,6,7,8,9-hexahydropyrazino[1,2-a]indol-1-one | 2.8 |

TABLE 2-continued

| No. | Structure | IUPAC Name | CD69 Hu Blood FACS (IC70) |
|---|---|---|---|
| 244 | 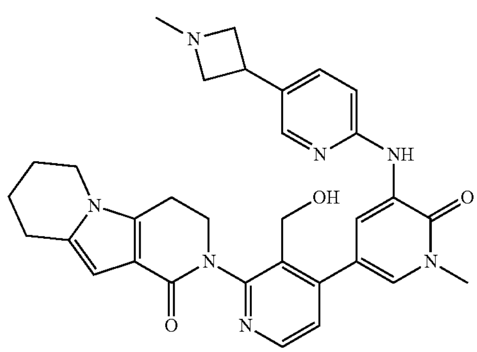 [SMILES: CN1CC(c2ccc(Nc3cc(-c4ccnc(N5CCc6c(cc7n6CCCC7)C5=O)c4CO)cn(C)c3=O)nc2)C1] | 2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrido[3,4-b]indolizin-1-one | 0.138 |
| 245 | 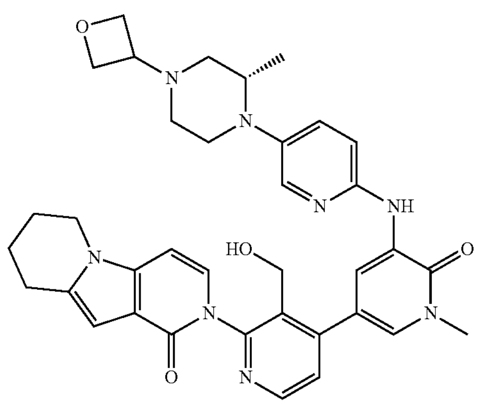 [SMILES: C[C@H]1CN(C2COC2)CCN1c1ccc(Nc2cc(-c3ccnc(-n4ccc5c(cc6n5CCCC6)c4=O)c3CO)cn(C)c2=O)nc1] | 2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydropyrido[3,4-b]indolizin-1-one | 0.065 |
| 246 | 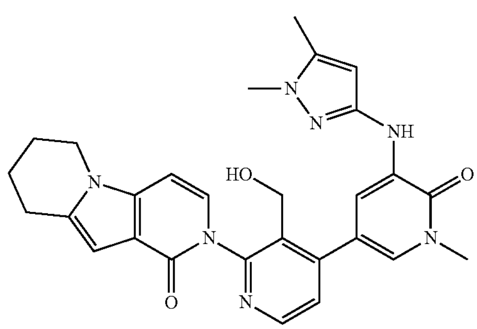 [SMILES: Cc1cc(Nc2cc(-c3ccnc(-n4ccc5c(cc6n5CCCC6)c4=O)c3CO)cn(C)c2=O)nn1C] | 2-[4-[5-[(1,5-dimethylpyrazol-3-yl)amino]-1-methyl-6-oxo-3-pyridyl]-3-(hydroxymethyl)-2-pyridyl]-6,7,8,9-tetrahydropyrido[3,4-b]indolizin-1-one | 1.7 |
| 247 | 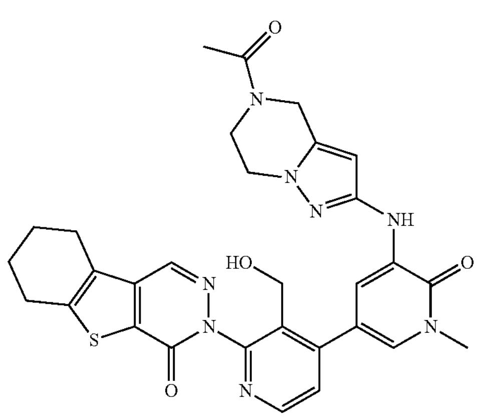 [SMILES: CC(=O)N1CCn2nc(Nc3cc(-c4ccnc(-n5ncc6c7c(sc6c5=O)CCCC7)c4CO)cn(C)c3=O)cc2C1] | 3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-6,7,8,9-tetrahydrobenzothiopheno[2,3-d]pyridazin-4-one | 0.145 |

TABLE 2-continued

| No. | Structure | IUPAC Name | CD69 Hu Blood FACS (IC70) |
|---|---|---|---|
| 248 | 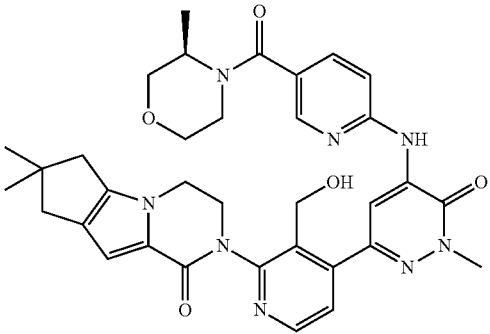 [SMILES: C[C@@H]1COCCN1C(=O)c1ccc(Nc2cc(-c3ccnc(N4CCn5c(cc6c5CC(C)(C)C6)C4=O)c3CO)nn(C)c2=O)nc1] | 3-[3-(hydroxymethyl)-4-[1-methyl-5-[[5-[(3R)-3-methylmorpholine-4-carbonyl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one | 0.0703 |
| 249 | 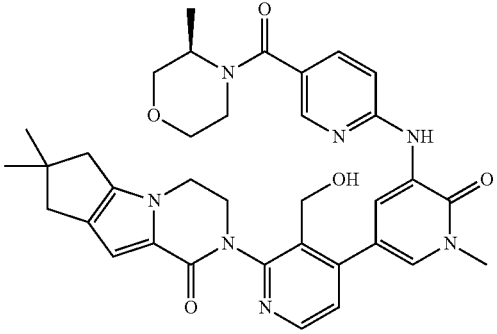 [SMILES: C[C@@H]1COCCN1C(=O)c1ccc(Nc2cc(-c3ccnc(N4CCn5c(cc6c5CC(C)(C)C6)C4=O)c3CO)cn(C)c2=O)nc1] | 3-[3-(hydroxymethyl)-4-[1-methyl-5-[[5-[(3R)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0177 |
| 250 | 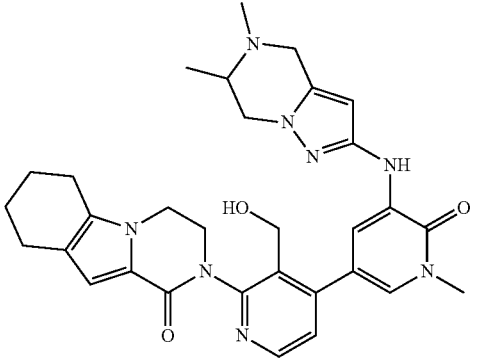 [SMILES: CC1Cn2nc(Nc3cc(-c4ccnc(N5CCn6c(cc7c6CCCC7)C5=O)c4CO)cn(C)c3=O)cc2CN1C] | 2-[4-[5-[(5,6-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one | 0.171 |
| 251 | | | |
| 252 | 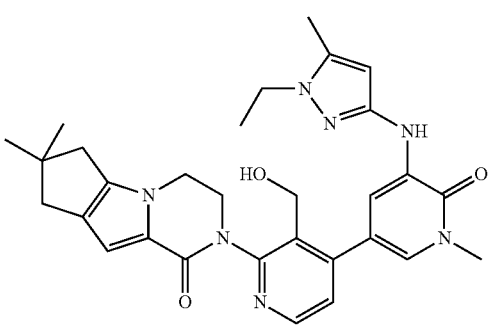 [SMILES: CCn1nc(Nc2cc(-c3ccnc(N4CCn5c(cc6c5CC(C)(C)C6)C4=O)c3CO)cn(C)c2=O)cc1C] | 3-[4-[5-[(1-ethyl-5-methyl-pyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.252 |

TABLE 2-continued

| No. | Structure | IUPAC Name | CD69 Hu Blood FACS (IC70) |
|---|---|---|---|
| 253 | 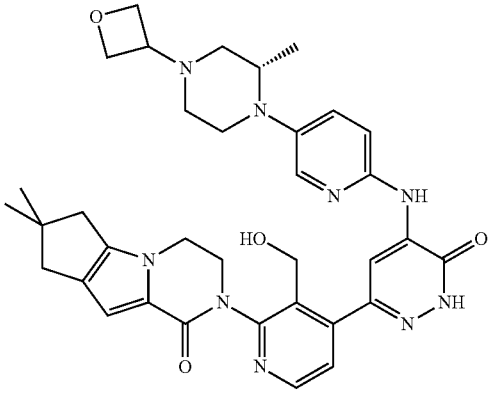 [SMILES: C[C@H]1CN(C2COC2)CCN1c1ccc(Nc2cc(-c3ccnc(N4CCn5c(cc6c5CC(C)(C)C6)C4=O)c3CO)n[nH]c2=O)nc1] | 3-[3-(hydroxymethyl)-4-[5-[[5-[(2S)-2-methyl-4-(oxetan-3-yl)piperazin-1-yl]-2-pyridyl]amino]-6-oxo-1H-pyridazin-3-yl]-2-pyridyl]-7,7-dimethyl-1,2,6,8-tetrahydrocyclopenta[3,4]pyrrolo[3,5-b]pyrazin-4-one | 0.0164 |
| 254 | 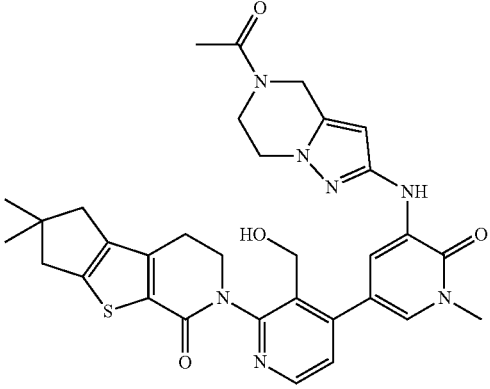 [SMILES: CC(=O)N1CCn2nc(Nc3cc(-c4ccnc(N5CCc6c(sc7c6CC(C)(C)C7)C5=O)c4CO)cn(C)c3=O)cc2C1] | 3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]thieno[1,3-c]pyridin-4-one | 0.0373 |
| 255 | 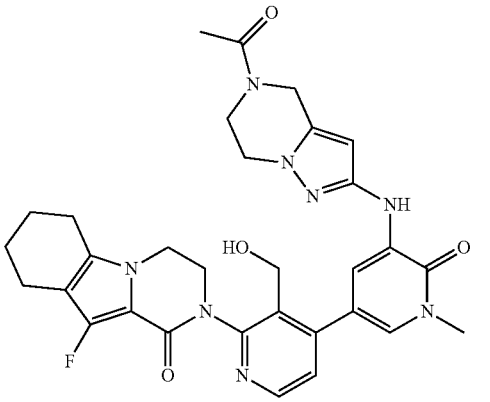 [SMILES: CC(=O)N1CCn2nc(Nc3cc(-c4ccnc(N5CCn6c7c(c(F)c6C5=O)CCCC7)c4CO)cn(C)c3=O)cc2C1] | 2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-10-fluoro-3,4,6,7,8,9-hexahydropyrazino[1,2-a]indol-1-one | 0.094 |

TABLE 2-continued

| No. | Structure | IUPAC Name | CD69 Hu Blood FACS (IC70) |
|---|---|---|---|
| 256 | 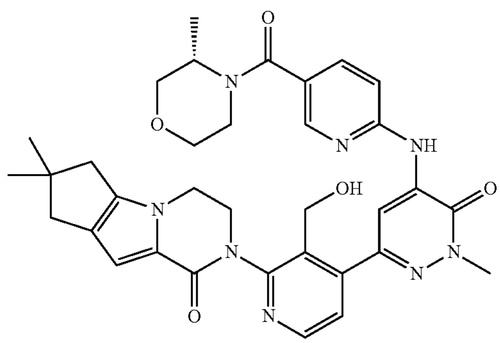 [SMILES: C[C@H]1COCCN1C(=O)c1ccc(Nc2cc(-c3ccnc(N4CCn5c(cc6c5CC(C)(C)C6)C4=O)c3CO)nn(C)c2=O)nc1] | 3-[3-(hydroxymethyl)-4-[1-methyl-5-[[5-[(3S)-3-methylmorpholine-4-carbonyl]-2-pyridyl]amino]-6-oxo-ripydazin-3-yl]-2-pyridyl]-7,7-dimethyl-1,2,6,8-tetrahydrocyclopenta[3,4]pyrrolo[3,5-b]pyrazin-4-one | 0.08 |
| 257 | 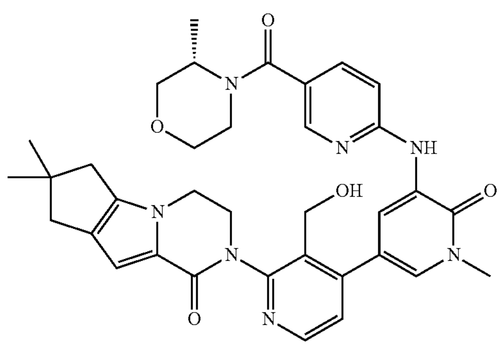 [SMILES: C[C@H]1COCCN1C(=O)c1ccc(Nc2cc(-c3ccnc(N4CCn5c(cc6c5CC(C)(C)C6)C4=O)c3CO)cn(C)c2=O)nc1] | 3-[3-(hydroxymethyl)-4-[1-methyl-5-[[5-[(3S)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0216 |
| 258 | 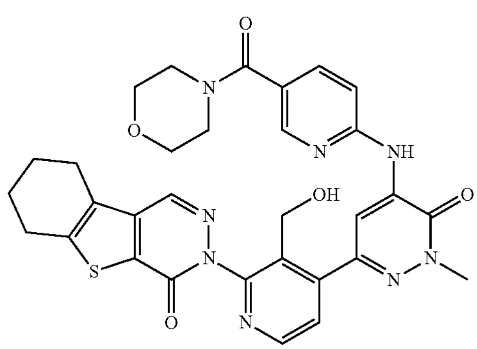 [SMILES: Cn1nc(-c2ccnc(-n3ncc4c5c(sc4c3=O)CCCC5)c2CO)cc(Nc2ccc(C(=O)N3CCOCC3)cn2)c1=O] | 3-[3-(hydroxymethyl)-4-[1-methyl-5-[[5-(morpholine-4-carbonyl)-2-pyridyl]amino]-6-oxo-pyridazin-3-yl]-2-pyridyl]-6,7,8,9-tetrahydrobenzothiopheno[2,3-d]pyridazin-4-one | 0.646 |
| 259 | 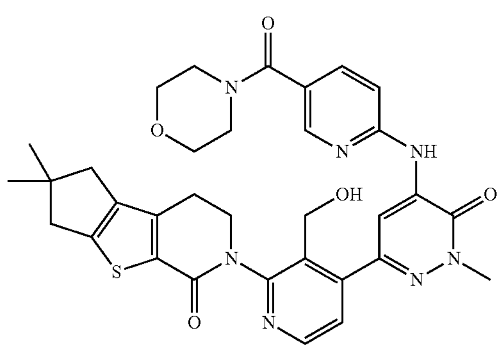 [SMILES: Cn1nc(-c2ccnc(N3CCc4c(sc5c4CC(C)(C)C5)C3=O)c2CO)cc(Nc2ccc(C(=O)N3CCOCC3)cn2)c1=O] | 3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]thieno[1,3-c]pyridin-4-one | 0.301 |

TABLE 2-continued

| No. | Structure | IUPAC Name | CD69 Hu Blood FACS (IC70) |
|---|---|---|---|
| 260 | 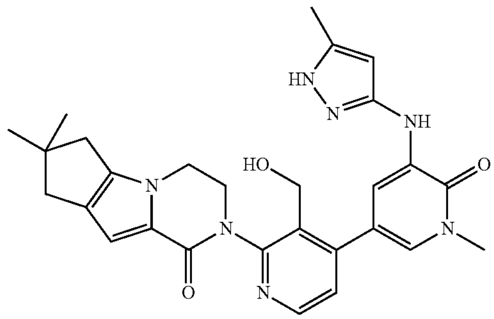 [SMILES: Cc1cc(Nc2cc(-c3ccnc(N4CCn5c(cc6c5CC(C)(C)C6)C4=O)c3CO)cn(C)c2=O)n[nH]1] | 3-[3-(hydroxymethyl)-4-[1-methyl-5-[(5-methyl-1H-pyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0606 |
| 261 | 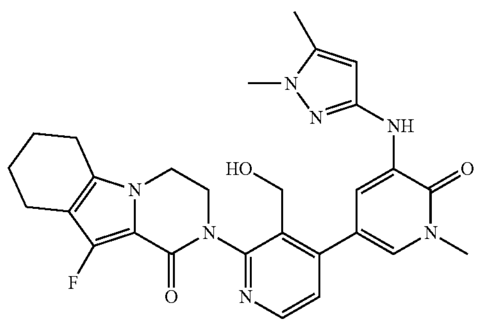 [SMILES: Cc1cc(Nc2cc(-c3ccnc(N4CCn5c6c(c(F)c5C4=O)CCCC6)c3CO)cn(C)c2=O)nn1C] | 2-[4-[5-[(1,5-dimethylpyrazol-3-yl)amino]-1-methyl-6-oxo-3-pyridyl]-3-(hydroxymethyl)-2-pyridyl]-10-fluoro-3,4,6,7,8,9-hexahydropyrido[3,4-b]indolizin-1-one | 2.9 |
| 262 | 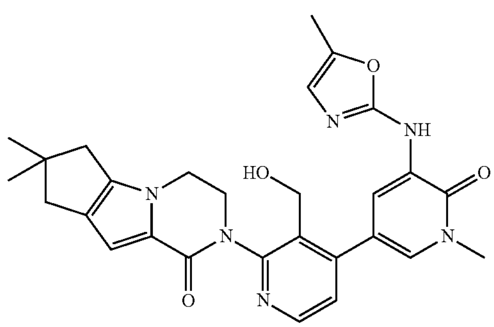 [SMILES: Cc1cnc(Nc2cc(-c3ccnc(N4CCn5c(cc6c5CC(C)(C)C6)C4=O)c3CO)cn(C)c2=O)o1] | 3-[3-(hydroxymethyl)-4-[1-methyl-5-[(5-methyloxazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.577 |
| 263 | 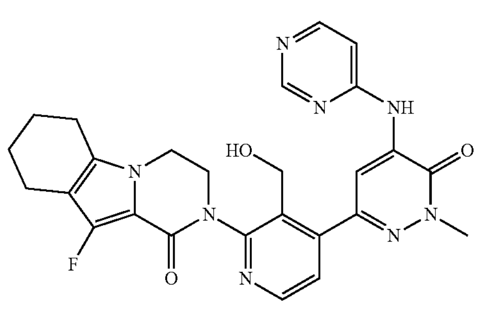 | 10-fluoro-2-[3-(hydroxymethyl)-4-[1-methyl-6-oxo-5-(pyrimidin-4-ylamino)pyridazin-3-yl]-2-pyridyl]-3,4,6,7,8,9-hexahydropyrazino[1,2-a]indol-1-one | 2.2 |

TABLE 2-continued

| No. | Structure | IUPAC Name | CD69 Hu Blood FACS (IC70) |
|---|---|---|---|
| 264 | 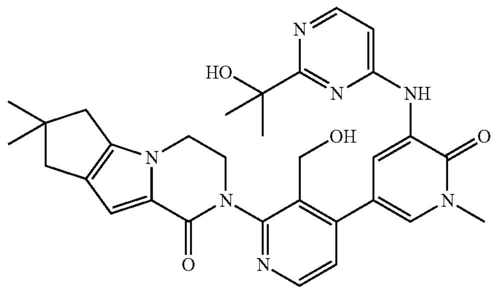 [SMILES: Cn1cc(-c2ccnc(N3CCn4c(cc5c4CC(C)(C)C5)C3=O)c2CO)cc(Nc2ccnc(C(C)(C)O)n2)c1=O] | 3-[3-(hydroxymethyl)-4-[5-[[2-(1-hydroxy-1-methyl-ethyl)pyrimidin-4-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.653 |
| 265 | 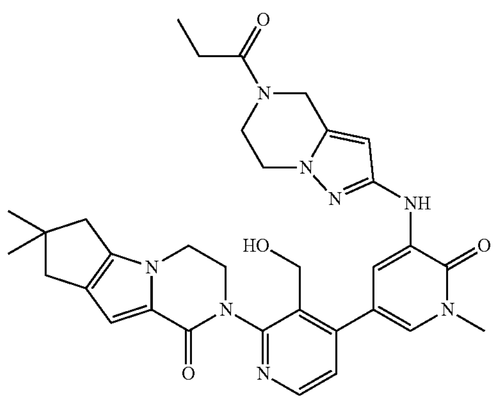 [SMILES: CCC(=O)N1CCn2nc(Nc3cc(-c4ccnc(N5CCn6c(cc7c6CC(C)(C)C7)C5=O)c4CO)cn(C)c3=O)cc2C1] | 3-[3-(hydroxymethyl)-4-[1-methyl-6-oxo-5-[(5-propanoyl-6,7-dihydro-4H-pyrazolo[1,5-a]pyrazin-2-yl)amino]-3-pyridyl]-2-pyridyl]-7,7-dimethyl-1,2,6,8-tetrahydrocyclopenta[3,4]pyrrolo[3,5-b]pyrazin-4-one | 0.0091 |
| 266 | 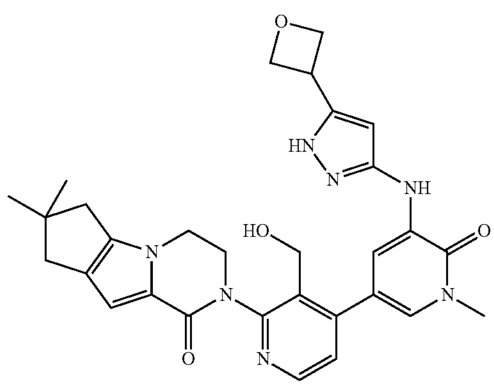 [SMILES: Cn1cc(-c2ccnc(N3CCn4c(cc5c4CC(C)(C)C5)C3=O)c2CO)cc(Nc2cc(C3COC3)[nH]n2)c1=O] | 3-[3-(hydroxymethyl)-4-[1-methyl-5-[[5-(oxetan-3-yl)-1H-pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0293 |
| 267 | 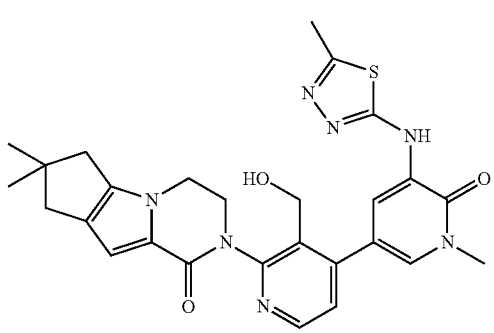 [SMILES: Cc1nnc(Nc2cc(-c3ccnc(N4CCn5c(cc6c5CC(C)(C)C6)C4=O)c3CO)cn(C)c2=O)s1] | 3-[3-(hydroxymethyl)-4-[1-methyl-5-[(5-methyl-1,3,4-thiadiazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.225 |

TABLE 2-continued

| No. | Structure | IUPAC Name | CD69 Hu Blood FACS (IC70) |
|---|---|---|---|
| 268 | 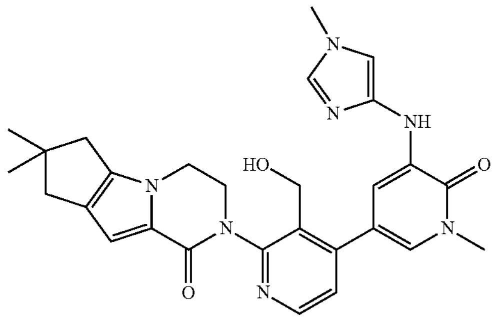 [SMILES: Cn1cnc(Nc2cc(-c3ccnc(N4CCn5c(cc6c5CC(C)(C)C6)C4=O)c3CO)cn(C)c2=O)c1] | 3-[3-(hydroxymethyl)-4-[1-methyl-5-[(1-methylimidazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.212 |
| 269 | 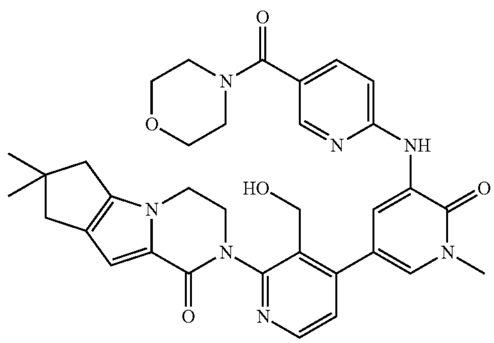 [SMILES: Cn1cc(-c2ccnc(N3CCn4c(cc5c4CC(C)(C)C5)C3=O)c2CO)cc(Nc2ccc(C(=O)N3CCOCC3)cn2)c1=O] | 3-[3-(hydroxymethyl)-4-[1-methyl-5-[[5-(morpholine-4-carbonyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0251 |
| 270 | 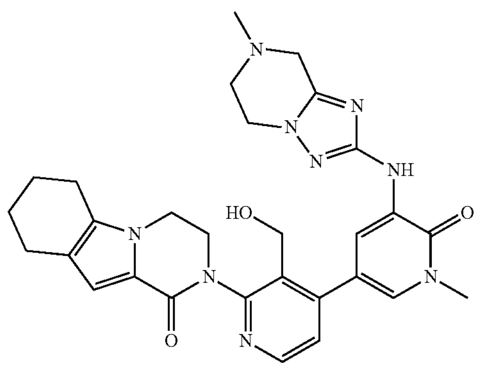 [SMILES: CN1CCn2nc(Nc3cc(-c4ccnc(N5CCn6c(cc7c6CCCC7)C5=O)c4CO)cn(C)c3=O)nc2C1] | 2-[3-(hydroxymethyl)-4-[1-methyl-5-[(7-methyl-6,8-dihydro-5H-[1,2,4]triazolo[1,5-a]pyrazin-2-yl)amino]-6-oxo-3-pyridyl]-2-pyridyl]-3,4,6,7,8,9-hexahydropyrazino[1,2-a]indol-1-one | 5.9 |
| 271 | 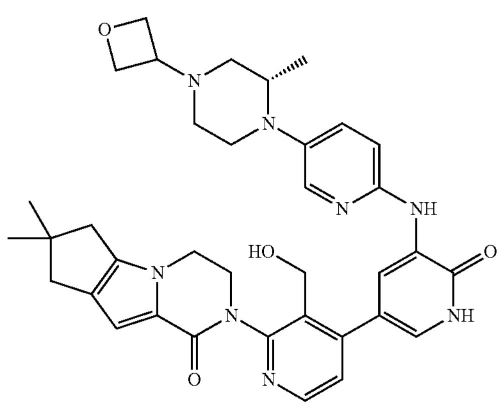 [SMILES: C[C@H]1CN(C2COC2)CCN1c1ccc(Nc2cc(-c3ccnc(N4CCn5c(cc6c5CC(C)(C)C6)C4=O)c3CO)c[nH]c2=O)nc1] | 3-[3-(hydroxymethyl)-4-[5-[[5-[(2S)-2-methyl-4-(oxetan-3-yl)piperazin-1-yl]-2-pyridyl]amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one | 0.0245 |

TABLE 2-continued

| No. | Structure | IUPAC Name | CD69 Hu Blood FACS (IC70) |
|---|---|---|---|
| 272 | 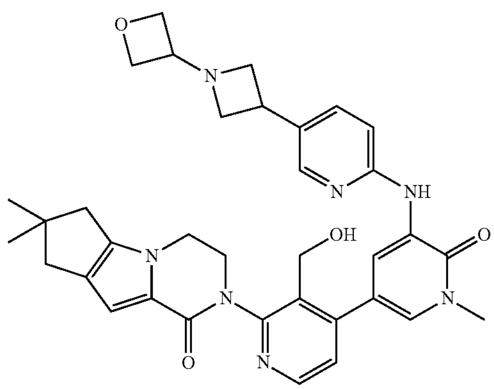 [SMILES: Cn1cc(-c2ccnc(N3CCn4c(cc5c4CC(C)(C)C5)C3=O)c2CO)cc(Nc2ccc(C3CN(C4COC4)C3)cn2)c1=O] | 3-[3-(hydroxymethyl)-4-[1-methyl-5-[[5-[1-(oxetan-3-yl)azetidin-3-yl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.034 |
| 273 | 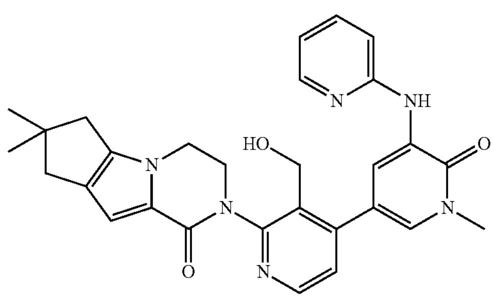 [SMILES: Cn1cc(-c2ccnc(N3CCn4c(cc5c4CC(C)(C)C5)C3=O)c2CO)cc(Nc2ccccn2)c1=O] | 3-[3-(hydroxymethyl)-4-[1-methyl-6-oxo-5-(2-pyridylamino)-3-pyridyl]-2-pyridyl]-7,7-dimethyl-1,2,6,8-tetrahydrocyclopenta[3,4]pyrrolo[3,5-b]pyrazin-4-one | 0.299 |
| 274 | 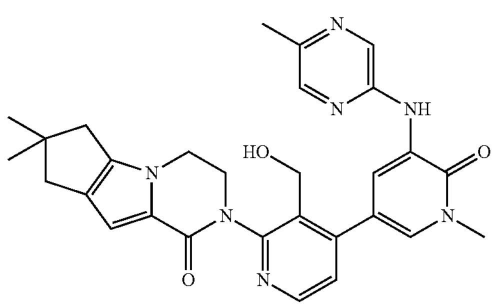 [SMILES: Cc1cnc(Nc2cc(-c3ccnc(N4CCn5c(cc6c5CC(C)(C)C6)C4=O)c3CO)cn(C)c2=O)cn1] | 3-[3-(hydroxymethyl)-4-[1-methyl-5-[(5-methylpyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.466 |
| 275 | 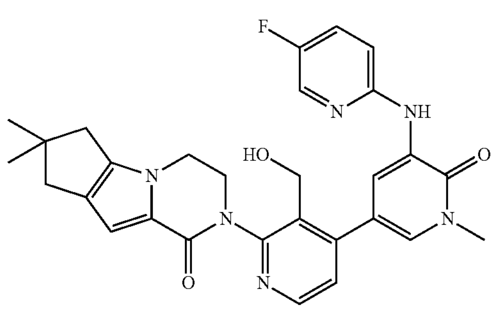 [SMILES: Cn1cc(-c2ccnc(N3CCn4c(cc5c4CC(C)(C)C5)C3=O)c2CO)cc(Nc2ccc(F)cn2)c1=O] | 3-[4-[5-[(5-fluoro-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.423 |

TABLE 2-continued

| No. | Structure | IUPAC Name | CD69 Hu Blood FACS (IC70) |
|---|---|---|---|
| 276 | 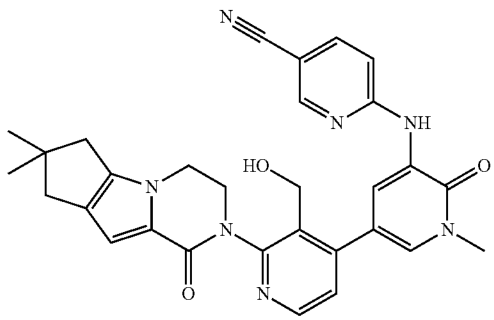 [SMILES: Cn1cc(-c2ccnc(N3CCn4c(cc5c4CC(C)(C)C5)C3=O)c2CO)cc(Nc2ccc(C#N)cn2)c1=O] | 6-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyridine-3-carbonitrile | 0.358 |
| 277 | 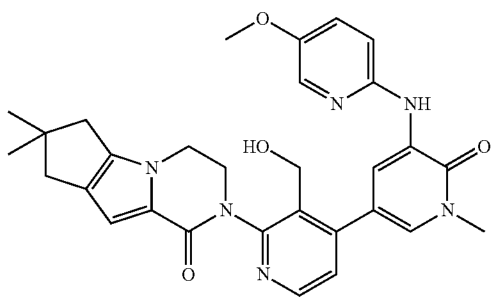 | 3-[3-(hydroxymethyl)-4-[5-[(5-methoxy-2-pyridyl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.339 |
| 278 | 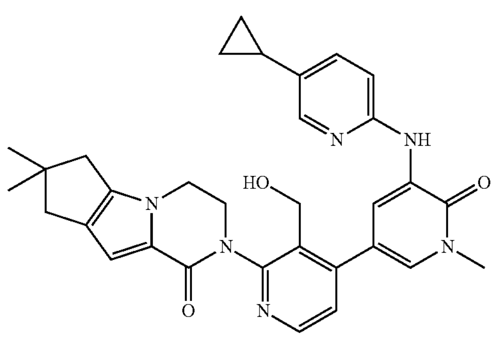 [SMILES: Cn1cc(-c2ccnc(N3CCn4c(cc5c4CC(C)(C)C5)C3=O)c2CO)cc(Nc2ccc(C3CC3)cn2)c1=O] | 3-[4-[5-[(5-cyclopropyl-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 3.2 |
| 279 | 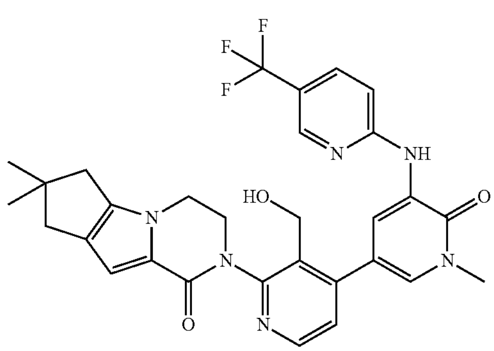 [SMILES: Cn1cc(-c2ccnc(N3CCn4c(cc5c4CC(C)(C)C5)C3=O)c2CO)cc(Nc2ccc(C(F)(F)F)cn2)c1=O] | 3-[3-(hydroxymethyl)-4-[1-methyl-6-oxo-5-[[5-(trifluoromethyl)-2-pyridyl]amino]-3-pyridyl]-2-pyridyl]-7,7-dimethyl-1,2,6,8-tetrahydrocyclopenta[3,4]pyrrolo[3,5-b]pyrazin-4-one | 2.1 |

TABLE 2-continued

| No. | Structure | IUPAC Name | CD69 Hu Blood FACS (IC70) |
|---|---|---|---|
| 280 | 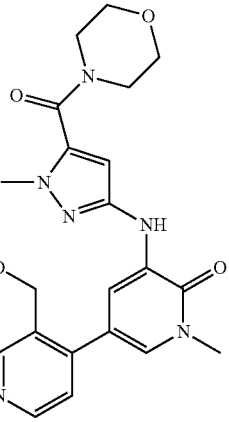 | 3-[3-(hydroxymethyl)-4-[1-methyl-5-[[1-methyl-5-(morpholine-4-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0141 |
| 281 | 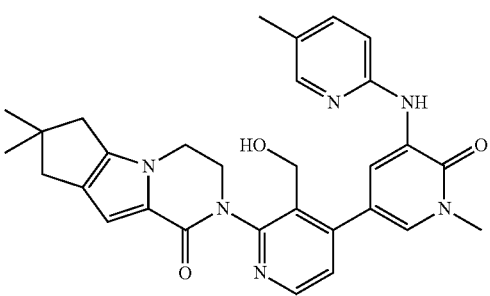 [SMILES: Cc1ccc(Nc2cc(-c3ccnc(N4CCn5c(cc6c5CC(C)(C)C6)C4=O)c3CO)cn(C)c2=O)nc1] | 3-[3-(hydroxymethyl)-4-[1-methyl-5-[(5-methyl-2-pyridyl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.718 |
| 282 | 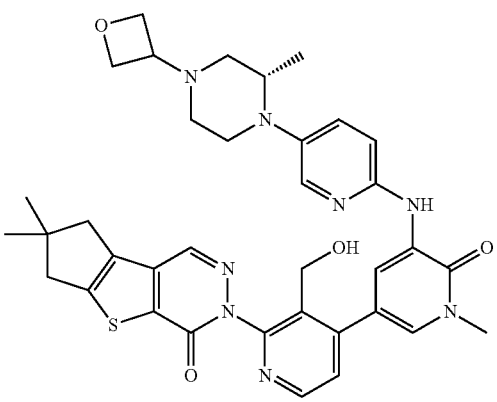 [SMILES: C[C@H]1CN(C2COC2)CCN1c1ccc(Nc2cc(-c3ccnc(-n4ncc5c6c(sc5c4=O)CC(C)(C)C6)c3CO)cn(C)c2=O)nc1] | 3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,7-dimethyl-6,8-dihydrocyclopenta[3,4]thieno[1,3-d]pyridazin-4-one | 0.0174 |
| 283 | 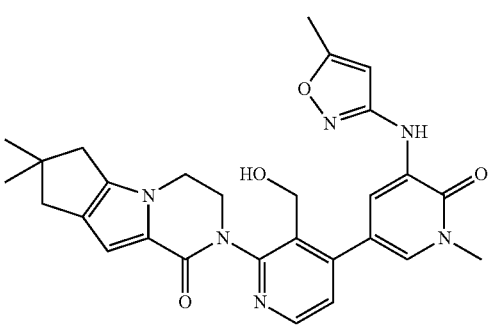 [SMILES: Cc1cc(Nc2cc(-c3ccnc(N4CCn5c(cc6c5CC(C)(C)C6)C4=O)c3CO)cn(C)c2=O)no1] | 3-[3-(hydroxymethyl)-4-[1-methyl-5-[(5-methylisoxazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.143 |

TABLE 2-continued

| No. | Structure | IUPAC Name | CD69 Hu Blood FACS (IC70) |
|---|---|---|---|
| 284 | 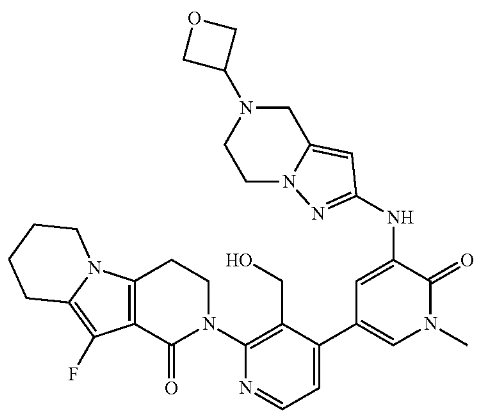 [SMILES: Cn1cc(-c2ccnc(N3CCc4c(c(F)c5n4CCCC5)C3=O)c2CO)cc(Nc2cc3n(n2)CCN(C2COC2)C3)c1=O] | 10-fluoro-2-[3-(hydroxymethyl)-4-[1-methyl-5-[[5-(oxetan-3-yl)-6,7-dihydro-4H-pyrazolo[1,5-a]pyrazin-2-yl]amino]-6-oxo-3-pyridyl]-2-pyridyl]-3,4,6,7,8,9-hexahydropyrido[3,4-b]indolizin-1-one | 0.131 |
| 285 | 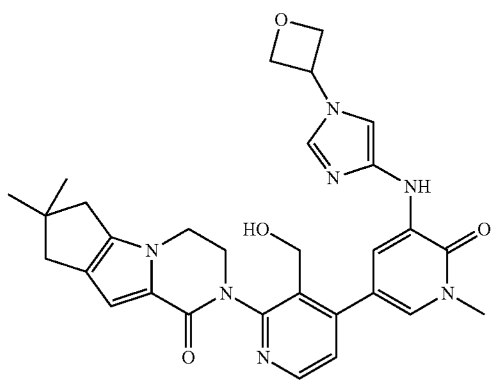 [SMILES: Cn1cc(-c2ccnc(N3CCn4c(cc5c4CC(C)(C)C5)C3=O)c2CO)cc(Nc2cn(C3COC3)cn2)c1=O] | 3-[3-(hydroxymethyl)-4-[1-methyl-5-[[1-(oxetan-3-yl)imidazol-4-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.175 |
| 286 | 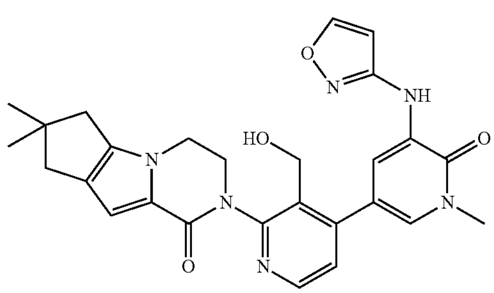 [SMILES: Cn1cc(-c2ccnc(N3CCn4c(cc5c4CC(C)(C)C5)C3=O)c2CO)cc(Nc2ccon2)c1=O] | 3-[3-(hydroxymethyl)-4-[5-(isoxazol-3-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.167 |
| 287 | 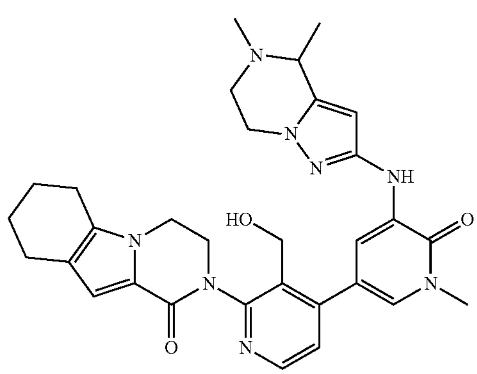 [SMILES: CC1c2cc(Nc3cc(-c4ccnc(N5CCn6c(cc7c6CCCC7)C5=O)c4CO)cn(C)c3=O)nn2CCN1C] | 2-[4-[5-[(4,5-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one | 0.127 |

TABLE 2-continued

| No. | Structure | IUPAC Name | CD69 Hu Blood FACS (IC70) |
|---|---|---|---|
| 288 | 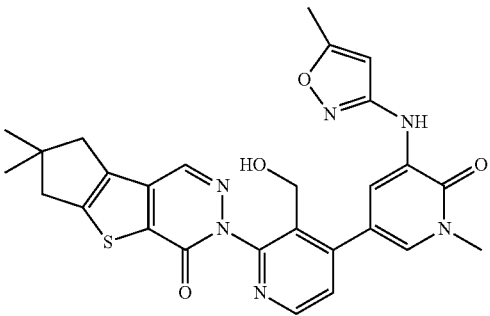 [SMILES: Cc1cc(Nc2cc(-c3ccnc(-n4ncc5c6c(sc5c4=O)CC(C)(C)C6)c3CO)cn(C)c2=O)no1] | 3-[3-(hydroxymethyl)-4-[1-methyl-5-[(5-methylisoxazol-3-yl)amino]-6-oxo-3-pyridyl]-2-pyridyl]-7,7-dimethyl-6,8-dihydrocyclopenta[3,4]thieno[1,3-d]pyridazin-4-one | 0.229 |
| 289 | 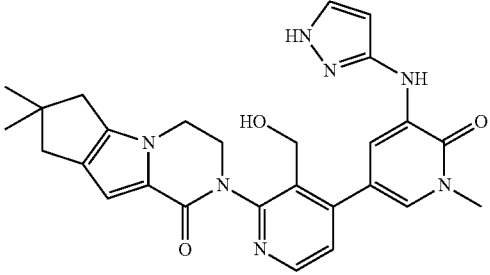 [SMILES: Cn1cc(-c2ccnc(N3CCn4c(cc5c4CC(C)(C)C5)C3=O)c2CO)cc(Nc2cc[nH]n2)c1=O] | 3-[3-(hydroxymethyl)-4-[1-methyl-6-oxo-5-(1H-pyrazol-3-ylamino)-3-pyridyl]-2-pyridyl]-7,7-dimethyl-1,2,6,8-tetrahydrocyclopenta[3,4]pyrrolo[3,5-b]pyrazin-4-one | 0.214 |
| 290 | 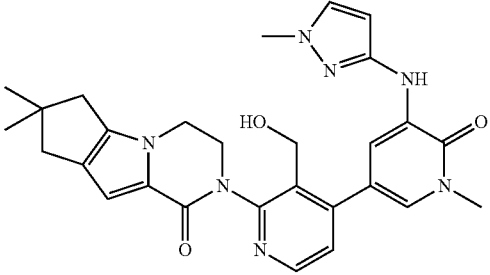 [SMILES: Cn1ccc(Nc2cc(-c3ccnc(N4CCn5c(cc6c5CC(C)(C)C6)C4=O)c3CO)cn(C)c2=O)n1] | 3-[3-(hydroxymethyl)-4-[1-methyl-5-[(1-methylpyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.113 |
| 291 | 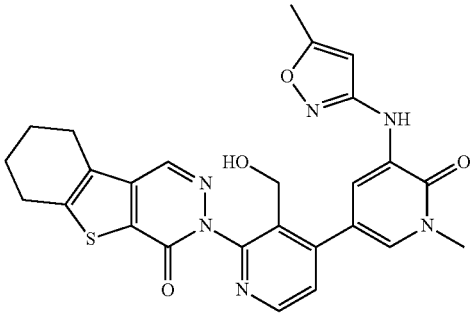 [SMILES: Cc1cc(Nc2cc(-c3ccnc(-n4ncc5c6c(sc5c4=O)CCCC6)c3CO)cn(C)c2=O)no1] | 3-[3-(hydroxymethyl)-4-[1-methyl-5-[(5-methylisoxazol-3-yl)amino]-6-oxo-3-pyridyl]-2-pyridyl]-6,7,8,9-tetrahydrobenzothiopheno[2,3-d]pyridazin-4-one | 0.843 |

TABLE 2-continued

| No. | Structure | IUPAC Name | CD69 Hu Blood FACS (IC70) |
|---|---|---|---|
| 292 | 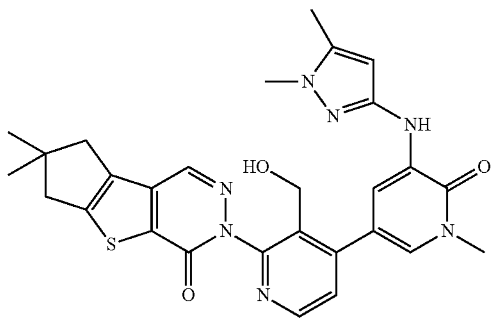 [SMILES: Cc1cc(Nc2cc(-c3ccnc(-n4ncc5c6c(sc5c4=O)CC(C)(C)C6)c3CO)cn(C)c2=O)nn1C] | 3-[4-[5-[(1,5-dimethylpyrazol-3-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one | 0.118 |
| 293 | 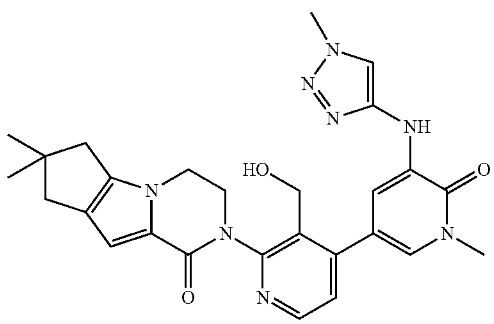 [SMILES: Cn1cc(Nc2cc(-c3ccnc(N4CCn5c(cc6c5CC(C)(C)C6)C4=O)c3CO)cn(C)c2=O)nn1] | 3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0691 |
| 294 | 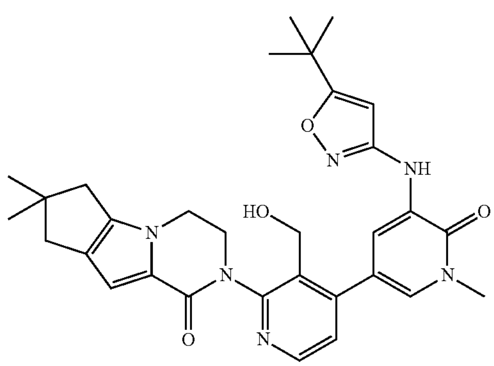 [SMILES: Cn1cc(-c2ccnc(N3CCn4c(cc5c4CC(C)(C)C5)C3=O)c2CO)cc(Nc2cc(C(C)(C)C)on2)c1=O] | 3-[4-[5-[(5-tert-butylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.276 |
| 295 | 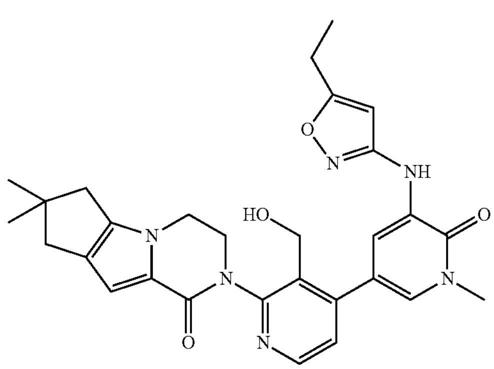 [SMILES: CCc1cc(Nc2cc(-c3ccnc(N4CCn5c(cc6c5CC(C)(C)C6)C4=O)c3CO)cn(C)c2=O)no1] | 3-[4-[5-[(5-ethylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.134 |

TABLE 2-continued

| No. | Structure | IUPAC Name | CD69 Hu Blood FACS (IC70) |
|---|---|---|---|
| 296 | 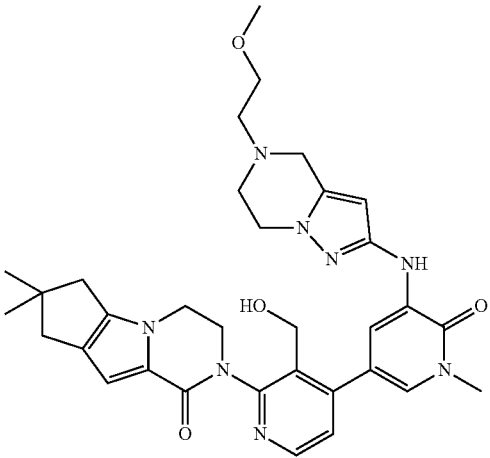 [SMILES: COCCN1CCn2nc(Nc3cc(-c4ccnc(N5CCn6c(cc7c6CC(C)(C)C7)C5=O)c4CO)cn(C)c3=O)cc2C1] | 3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]pyrrolopyrazin-4-one | 0.0193 |
| 297 | 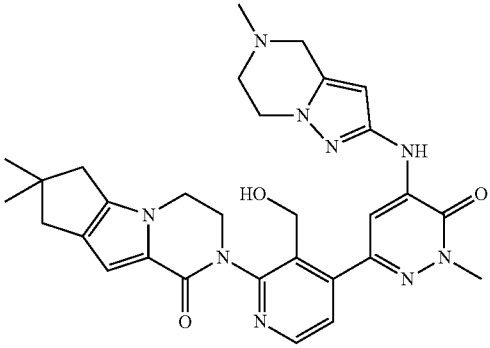 [SMILES: CN1CCn2nc(Nc3cc(-c4ccnc(N5CCn6c(cc7c6CC(C)(C)C7)C5=O)c4CO)nn(C)c3=O)cc2C1] | 3-[3-(hydroxymethyl)-4-[1-methyl-5-[(5-methyl-6,7-dihydro-4H-pyrazolo[1,5-a]pyrazin-2-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one | 0.14 |
| 298 | 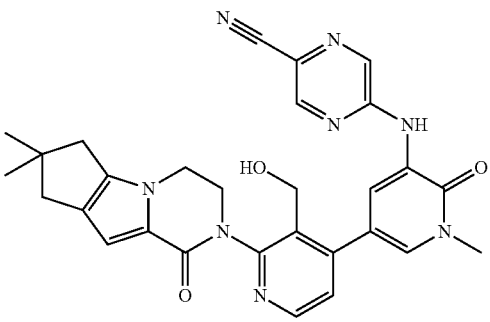 [SMILES: Cn1cc(-c2ccnc(N3CCn4c(cc5c4CC(C)(C)C5)C3=O)c2CO)cc(Nc2cnc(C#N)cn2)c1=O] | 5-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyrazine-2-carbonitrile | 0.869 |

TABLE 2-continued

| No. | Structure | IUPAC Name | CD69 Hu Blood FACS (IC70) |
|---|---|---|---|
| 299 | 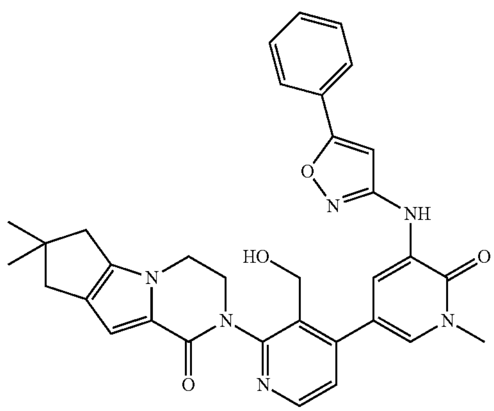 [SMILES: Cn1cc(-c2ccnc(N3CCn4c(cc5c4CC(C)(C)C5)C3=O)c2CO)cc(Nc2cc(-c3ccccc3)on2)c1=O] | 3-[3-(hydroxymethyl)-4-[1-methyl-6-oxo-5-[(5-phenylisoxazol-3-yl)amino]-3-pyridyl]-2-pyridyl]-7,7-dimethyl-1,2,6,8-tetrahydrocyclopenta[3,4]pyrrolo[3,5-b]pyrazin-4-one | 2.1 |
| 300 | 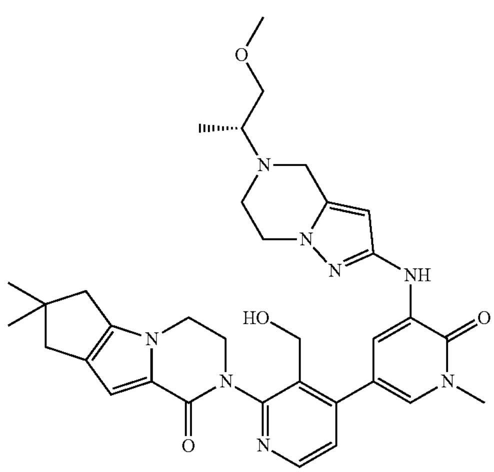 [SMILES: COC[C@@H](C)N1CCn2nc(Nc3cc(-c4ccnc(N5CCn6c(cc7c6CC(C)(C)C7)C5=O)c4CO)cn(C)c3=O)cc2C1] | (R)-2-(3'-(hydroxymethyl)-5-((5-(1-methoxypropan-2-yl)-4,5,6,7-tetrahydropyrazolo[1,5-a]pyrazin-2-yl)amino)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one | 0.024 |
| 301 | 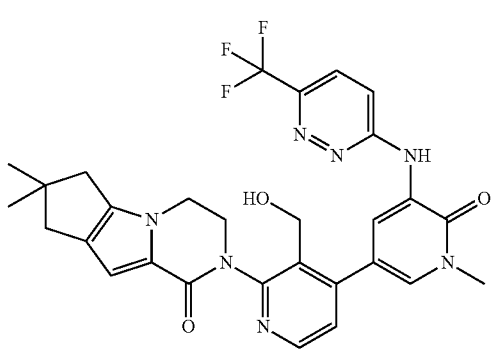 [SMILES: Cn1cc(-c2ccnc(N3CCn4c(cc5c4CC(C)(C)C5)C3=O)c2CO)cc(Nc2ccc(C(F)(F)F)nn2)c1=O] | 3-[3-(hydroxymethyl)-4-[1-methyl-6-oxo-5-[[6-(trifluoromethyl)pyridazin-3-yl]amino]-3-pyridyl]-2-pyridyl]-7,7-dimethyl-1,2,6,8-tetrahydrocyclopenta[3,4]pyrrolo[3,5-b]pyrazin-4-one | 1.3 |

TABLE 2-continued

| No. | Structure | IUPAC Name | CD69 Hu Blood FACS (IC70) |
|---|---|---|---|
| 302 | 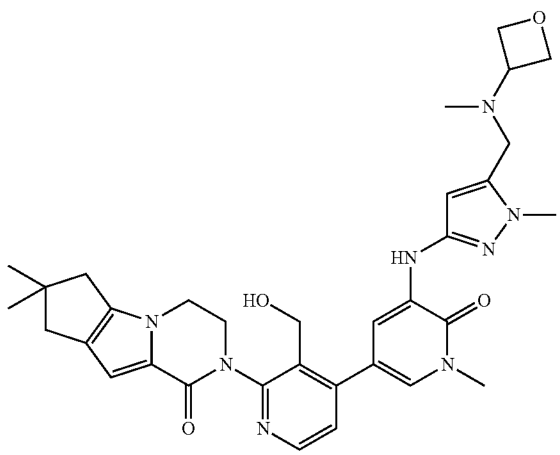 | 3-[3-(hydroxymethyl)-4-[1-methyl-5-[[1-methyl-5-[[methyl(oxetan-3-yl)amino]methyl]pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0228 |
| 303 | 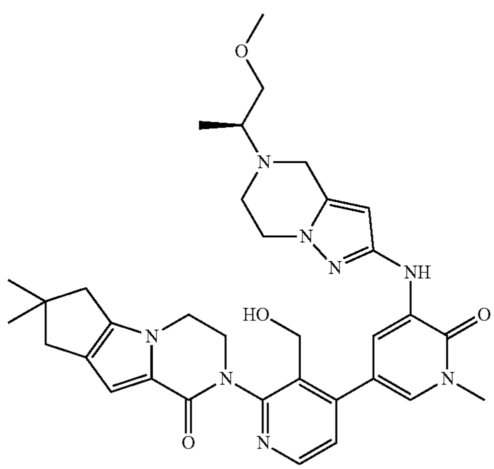 [SMILES: COC[C@H](C)N1CCn2nc(Nc3cc(-c4ccnc(N5CCn6c(cc7c6CC(C)(C)C7)C5=O)c4CO)cn(C)c3=O)cc2C1] | (S)-2-(3'-(hydroxymethyl)-5-((5-(1-methoxypropan-2-yl)-4,5,6,7-tetrahydropyrazolo[1,5-a]pyrazin-2-yl)amino)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one | 0.0179 |
| 304 | 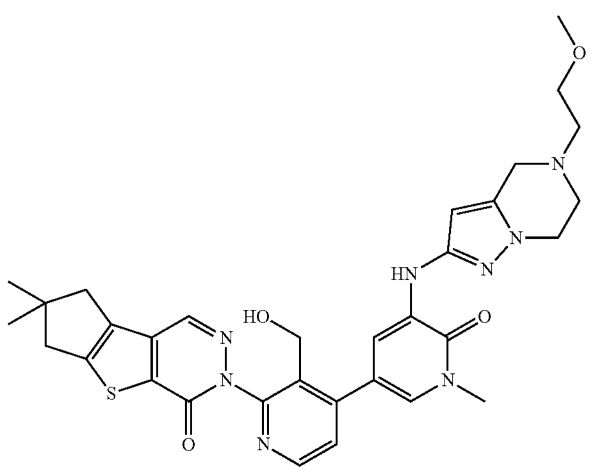 [SMILES: COCCN1CCn2nc(Nc3cc(-c4ccnc(-n5ncc6c7c(sc6c5=O)CC(C)(C)C7)c4CO)cn(C)c3=O)cc2C1] | 3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-6,8-dihydrocyclopenta[3,4]thieno[1,3-d]pyridazin-4-one | 0.04 |

TABLE 2-continued

| No. | Structure | IUPAC Name | CD69 Hu Blood FACS (IC70) |
|---|---|---|---|
| 305 | 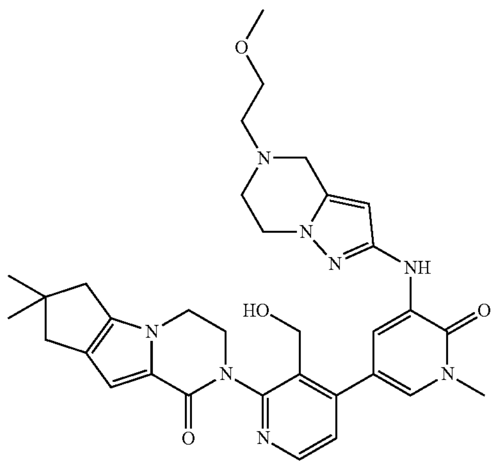 [SMILES: COCCN1CCn2nc(Nc3cc(-c4ccnc(N5CCn6c(cc7c6CC(C)(C)C7)C5=O)c4CO)cn(C)c3=O)cc2C1] | 3-[3-(hydroxymethyl)-4-[5-[[5-(2-methoxyethyl)-6,7-dihydro-4H-pyrazolo[1,5-a]pyrazin-2-yl]amino]-1-methyl-6-oxo-pyridazin-3-yl]-2-pyridyl]-7,7-dimethyl-1,2,6,8-tetrahydrocyclopenta[3,4]pyrrolo[3,5-b]pyrazin-4-one | 0.0832 |
| 306 | 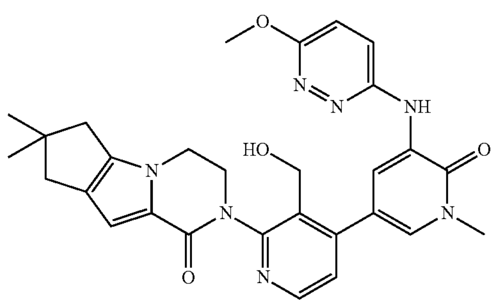 [SMILES: COc1ccc(Nc2cc(-c3ccnc(N4CCn5c(cc6c5CC(C)(C)C6)C4=O)c3CO)cn(C)c2=O)nn1] | 3-[3-(hydroxymethyl)-4-[5-[(6-methoxypyridazin-3-yl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.602 |
| 307 | 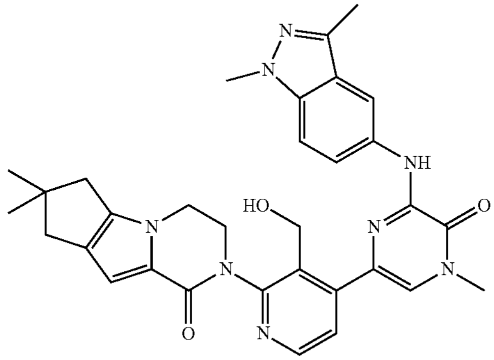 [SMILES: Cc1nn(C)c2ccc(Nc3nc(-c4ccnc(N5CCn6c(cc7c6CC(C)(C)C7)C5=O)c4CO)cn(C)c3=O)cc12] | 3-[4-[6-[(1,3-dimethylindazol-5-yl)amino]-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one | |

TABLE 2-continued

| No. | Structure | IUPAC Name | CD69 Hu Blood FACS (IC70) |
|---|---|---|---|
| 308 | 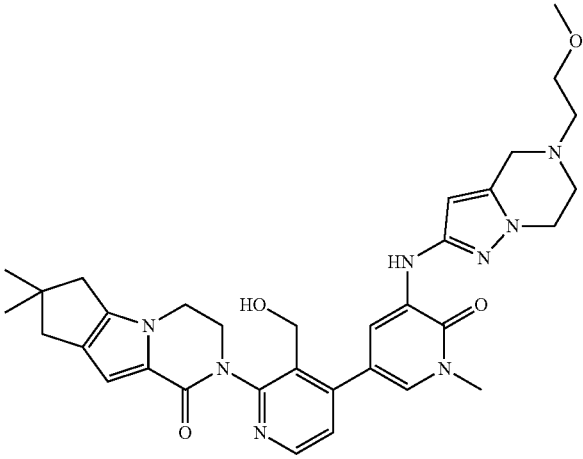 [SMILES: COCCN1CCn2nc(Nc3cc(-c4ccnc(N5CCn6c(cc7c6CC(C)(C)C7)C5=O)c4CO)cn(C)c3=O)cc2C1] | 3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]thieno[1,3-c]pyridin-4-one | 0.0546 |
| 309 | 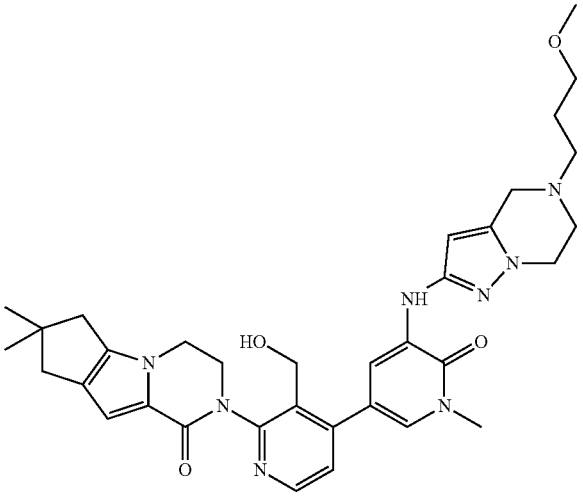 | 3-[3-(hydroxymethyl)-4-[5-[[5-(3-methoxypropyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.0398 |
| 310 | 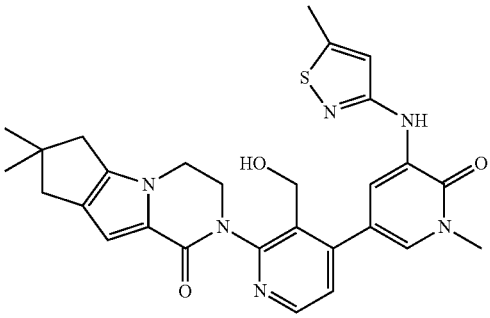 | 3-[3-(hydroxymethyl)-4-[1-methyl-5-[(5-methylisothiazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.119 |

TABLE 2-continued

| No. | Structure | IUPAC Name | CD69 Hu Blood FACS (IC70) |
|---|---|---|---|
| 311 | 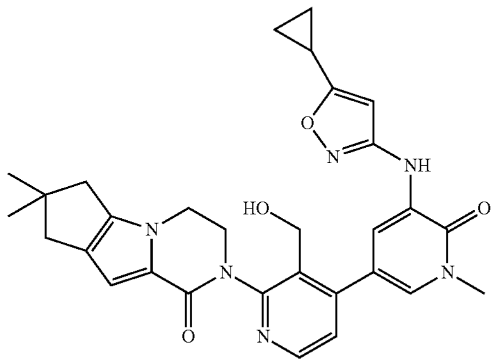 [SMILES: Cn1cc(-c2ccnc(N3CCn4c(cc5c4CC(C)(C)C5)C3=O)c2CO)cc(Nc2cc(C3CC3)on2)c1=O] | 3-[4-[5-[(5-cyclopropylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.158 |
| 312 | 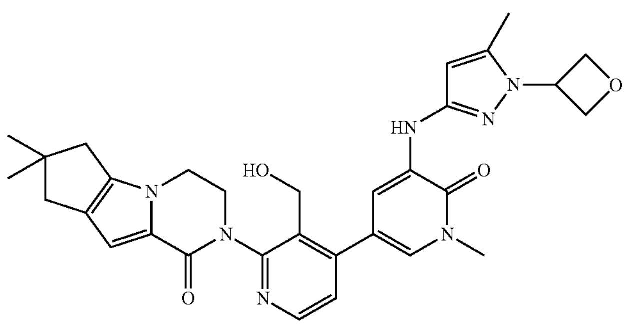 [SMILES: Cc1cc(Nc2cc(-c3ccnc(N4CCn5c(cc6c5CC(C)(C)C6)C4=O)c3CO)cn(C)c2=O)nn1C1COC1] | 3-[3-(hydroxymethyl)-4-[1-methyl-5-[[5-methyl-1-(oxetan-3-yl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 5.6 |
| 313 | 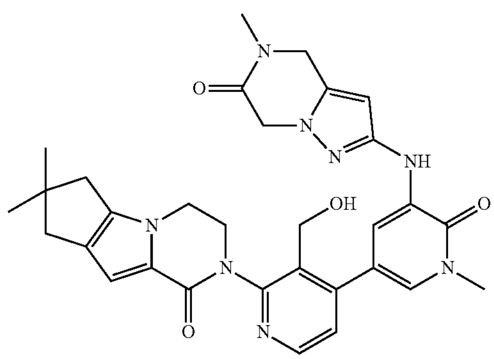 [SMILES: CN1Cc2cc(Nc3cc(-c4ccnc(N5CCn6c(cc7c6CC(C)(C)C7)C5=O)c4CO)cn(C)c3=O)nn2CC1=O] | 3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one | 0.0191 |
| 314 | 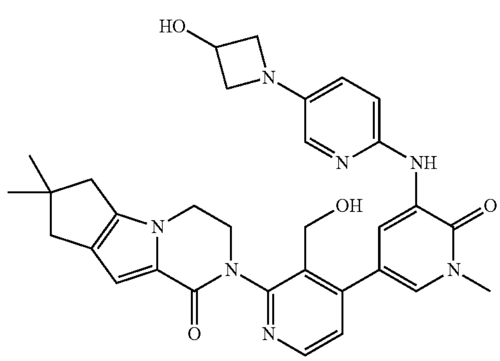 [SMILES: Cn1cc(-c2ccnc(N3CCn4c(cc5c4CC(C)(C)C5)C3=O)c2CO)cc(Nc2ccc(N3CC(O)C3)cn2)c1=O] | 3-[4-[5-[[5-(3-hydroxyazetidin-1-yl)-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.0446 |

TABLE 2-continued

| No. | Structure | IUPAC Name | CD69 Hu Blood FACS (IC70) |
|---|---|---|---|
| 315 | 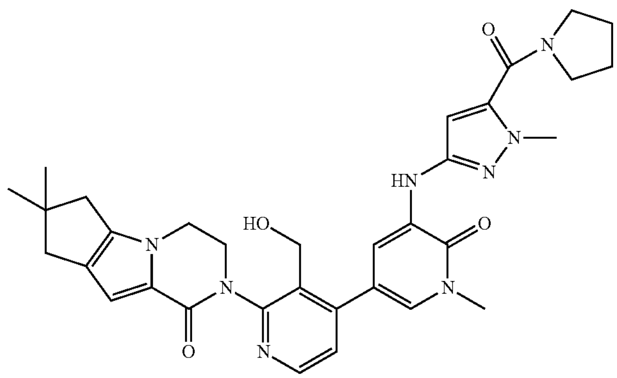 [SMILES: Cn1nc(Nc2cc(-c3ccnc(N4CCn5c(cc6c5CC(C)(C)C6)C4=O)c3CO)cn(C)c2=O)cc1C(=O)N1CCCC1] | 3-[3-(hydroxymethyl)-4-[1-methyl-5-[[1-methyl-5-(pyrrolidine-1-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one | 0.015 |
| 316 | 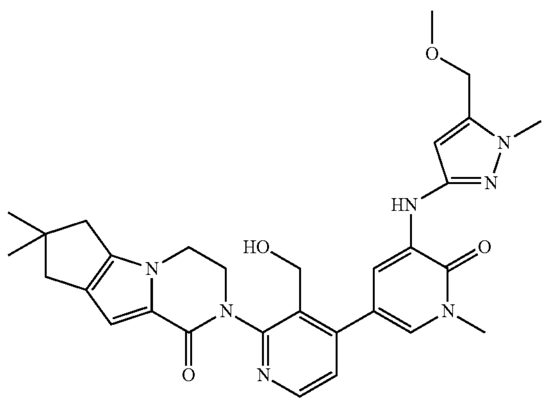 | 3-[3-(hydroxymethyl)-4-[5-[[5-(methoxymethyl)-1-methyl-pyrazol-3-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.0202 |
| 317 | 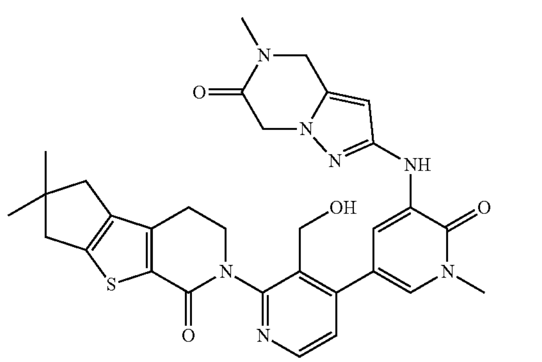 [SMILES: CN1Cc2cc(Nc3cc(-c4ccnc(N5CCc6c(sc7c6CC(C)(C)C7)C5=O)c4CO)cn(C)c3=O)nn2CC1=O] | 3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]thieno[1,3-c]pyridin-4-one | 0.0586 |
| 318 | 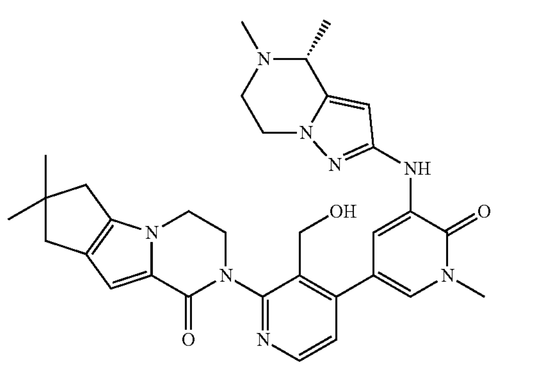 [SMILES: C[C@@H]1c2cc(Nc3cc(-c4ccnc(N5CCn6c(cc7c6CC(C)(C)C7)C5=O)c4CO)cn(C)c3=O)nn2CCN1C] | (R)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one | 0.108 |

TABLE 2-continued

| No. | Structure | IUPAC Name | CD69 Hu Blood FACS (IC70) |
|---|---|---|---|
| 319 | 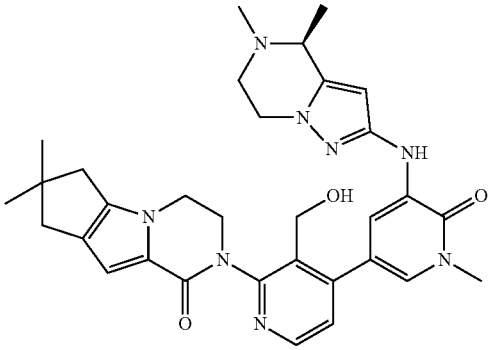 [SMILES: C[C@H]1c2cc(Nc3cc(-c4ccnc(N5CCn6c(cc7c6CC(C)(C)C7)C5=O)c4CO)cn(C)c3=O)nn2CCN1C] | (S)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one | 0.0167 |
| 320 | 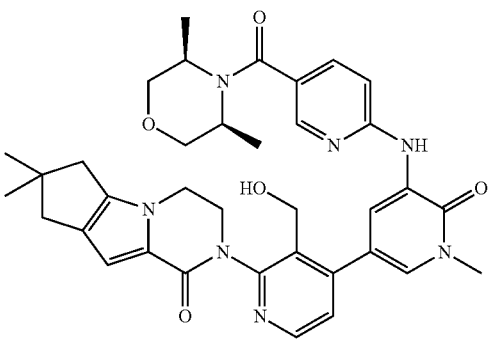 [SMILES: C[C@@H]1COC[C@H](C)N1C(=O)c1ccc(Nc2cc(-c3ccnc(N4CCn5c(cc6c5CC(C)(C)C6)C4=O)c3CO)cn(C)c2=O)nc1] | 3-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.0468 |
| 321 | 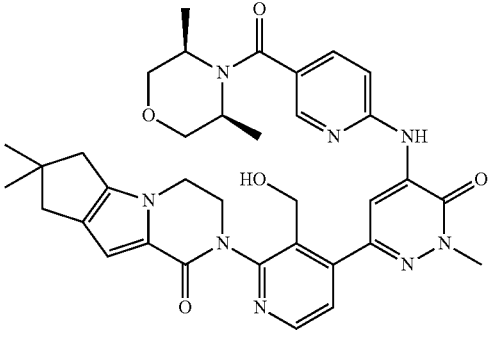 | 3-[4-[5-[[5-[(3S,5R)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1,2,6,8-tetrahydrocyclopenta[3,4]pyrrolo[3,5-b]pyrazin-4-one | 0.112 |
| 322 | 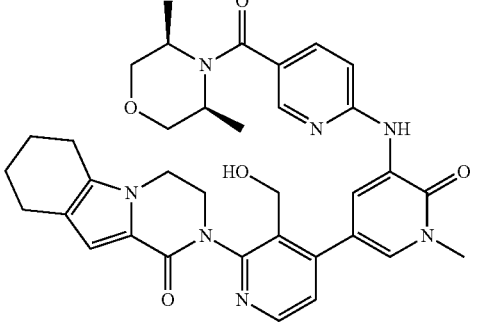 | 2-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one | 0.0796 |

TABLE 2-continued

| No. | Structure | IUPAC Name | CD69 Hu Blood FACS (IC70) |
|---|---|---|---|
| 323 | 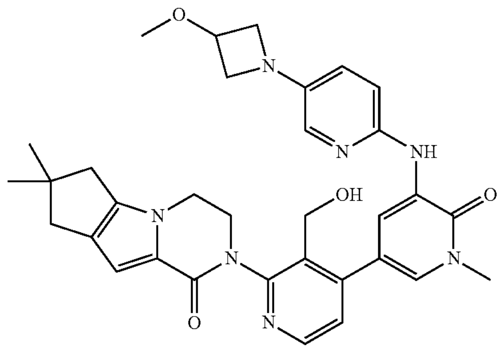 [SMILES: COC1CN(c2ccc(Nc3cc(-c4ccnc(N5CCn6c(cc7c6CC(C)(C)C7)C5=O)c4CO)cn(C)c3=O)nc2)C1] | 3-[3-(hydroxymethyl)-4-[5-[[5-(3-methoxyazetidin-1-yl)-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.279 |
| 324 | 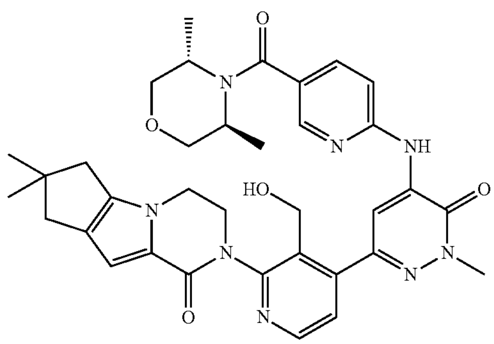 [SMILES: C[C@H]1COC[C@H](C)N1C(=O)c1ccc(Nc2cc(-c3ccnc(N4CCn5c(cc6c5CC(C)(C)C6)C4=O)c3CO)nn(C)c2=O)nc1] | 3-[4-[5-[[5-[(3S,5S)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1,2,6,8-tetrahydrocyclopenta[3,4]pyrrolo[3,5-b]pyrazin-4-one | 0.0858 |
| 325 | 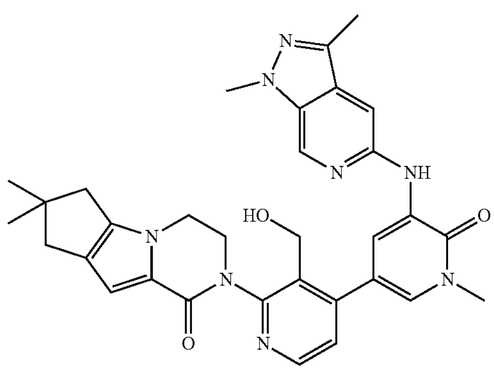 [SMILES: Cc1nn(C)c2cnc(Nc3cc(-c4ccnc(N5CCn6c(cc7c6CC(C)(C)C7)C5=O)c4CO)cn(C)c3=O)cc12] | 3-[4-[5-[(1,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 1.4 |
| 326 | 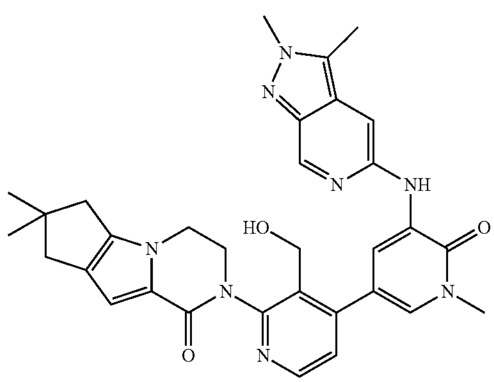 [SMILES: Cc1c2cc(Nc3cc(-c4ccnc(N5CCn6c(cc7c6CC(C)(C)C7)C5=O)c4CO)cn(C)c3=O)ncc2nn1C] | 3-[4-[5-[(2,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 1.4 |

TABLE 2-continued

| No. | Structure | IUPAC Name | CD69 Hu Blood FACS (IC70) |
|---|---|---|---|
| 327 | 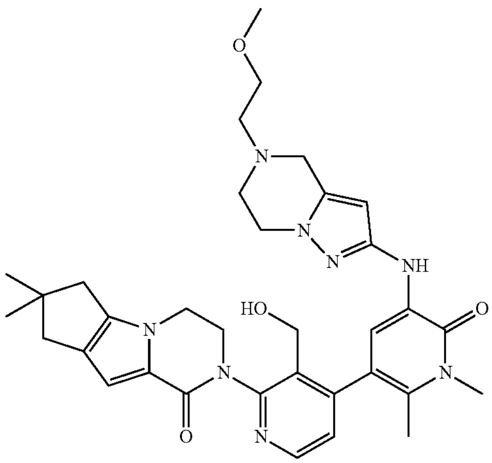 [SMILES: COCCN1CCn2nc(Nc3cc(-c4ccnc(N5CCn6c(cc7c6CC(C)(C)C7)C5=O)c4CO)c(C)n(C)c3=O)cc2C1] | 3-[3-(hydroxymethyl)-4-[5-[[5-(2-methoxyethyl)-6,7-dihydro-4H-pyrazolo[1,5-a]pyrazin-2-yl]amino]-1,2-dimethyl-6-oxo-3-pyridyl]-2-pyridyl]-7,7-dimethyl-1,2,6,8-tetrahydrocyclopenta[3,4]pyrrolo[3,5-b]pyrazin-4-one | 2.2 |
| 328 | 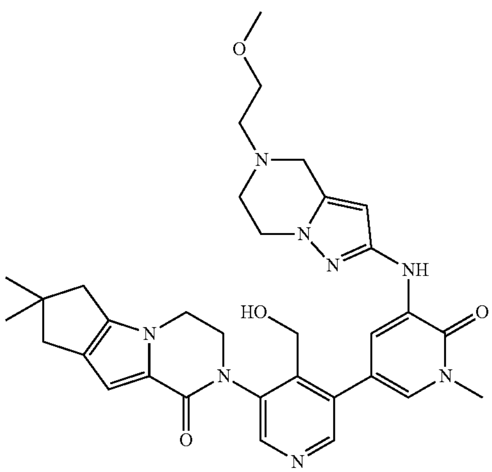 [SMILES: COCCN1CCn2nc(Nc3cc(-c4cncc(N5CCn6c(cc7c6CC(C)(C)C7)C5=O)c4CO)cn(C)c3=O)cc2C1] | 3-[4-(hydroxymethyl)-5-[5-[[5-(2-methoxyethyl)-6,7-dihydro-4H-pyrazolo[1,5-a]pyrazin-2-yl]amino]-1-methyl-6-oxo-3-pyridyl]-3-pyridyl]-7,7-dimethyl-1,2,6,8-tetrahydrocyclopenta[3,4]pyrrolo[3,5-b]pyrazin-4-one | 0.0124 |
| 329 | 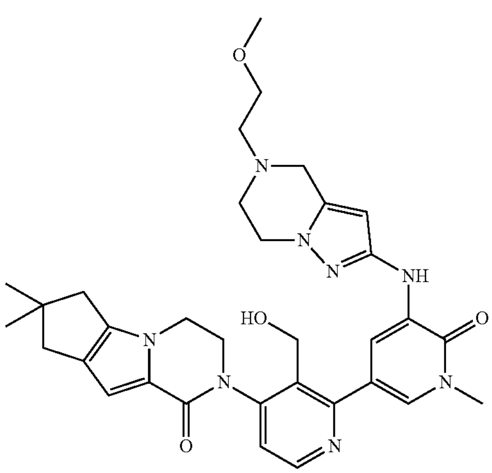 [SMILES: COCCN1CCn2nc(Nc3cc(-c4nccc(N5CCn6c(cc7c6CC(C)(C)C7)C5=O)c4CO)cn(C)c3=O)cc2C1] | 3-[3-(hydroxymethyl)-2-[5-[[5-(2-methoxyethyl)-6,7-dihydro-4H-pyrazolo[1,5-a]pyrazin-2-yl]amino]-1-methyl-6-oxo-3-pyridyl]-4-pyridyl]-7,7-dimethyl-1,2,6,8-tetrahydrocyclopenta[3,4]pyrrolo[3,5-b]pyrazin-4-one | 0.11 |

TABLE 2-continued

| No. | Structure | IUPAC Name | CD69 Hu Blood FACS (IC70) |
|---|---|---|---|
| 330 | 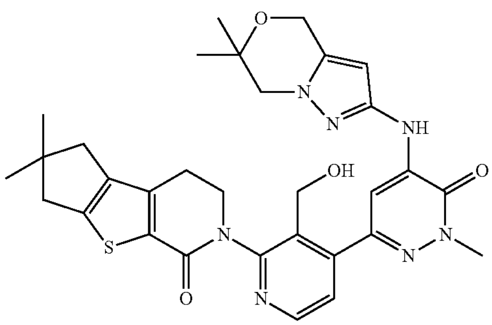 [SMILES: Cn1nc(-c2ccnc(N3CCc4c(sc5c4CC(C)(C)C5)C3=O)c2CO)cc(Nc2cc3n(n2)CC(C)(C)OC3)c1=O] | 3-[4-[5-[(6,6-dimethyl-4,7-dihydropyrazolo[5,1-c][1,4]oxazin-2-yl)amino]-1-methyl-6-oxo-pyridazin-3-yl]-3-(hydroxymethyl)-2-pyridyl]-7,7-dimethyl-1,2,6,8-tetrahydrocyclopenta[3,4]thieno[1,3-c]pyridin-4-one | 0.235 |
| 331 | 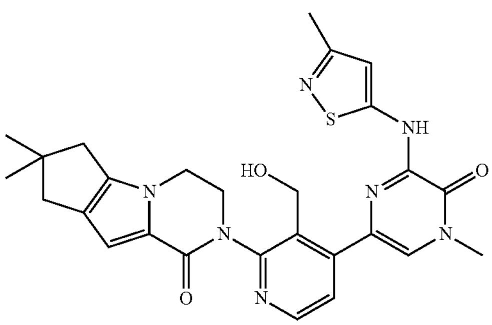 [SMILES: Cc1cc(Nc2nc(-c3ccnc(N4CCn5c(cc6c5CC(C)(C)C6)C4=O)c3CO)cn(C)c2=O)sn1] | 3-[3-(hydroxymethyl)-4-[4-methyl-6-[(3-methylisothiazol-5-yl)amino]-5-oxo-pyrazin-2-yl]-2-pyridyl]-7,7-dimethyl-1,2,6,8-tetrahydrocyclopenta[3,4]pyrrolo[3,5-b]pyrazin-4-one | |
| 332 | 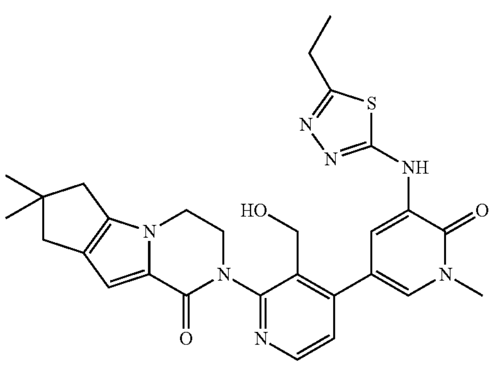 [SMILES: CCc1nnc(Nc2cc(-c3ccnc(N4CCn5c(cc6c5CC(C)(C)C6)C4=O)c3CO)cn(C)c2=O)s1] | 3-[4-[5-[(5-ethyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.0919 |
| 333 | 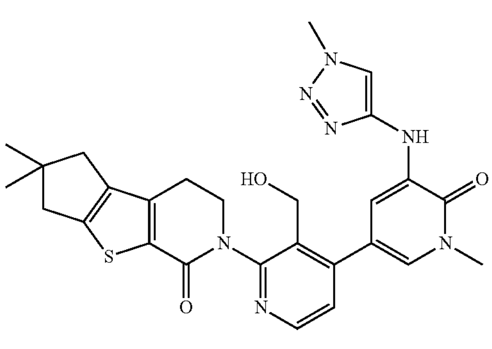 [SMILES: Cn1cc(Nc2cc(-c3ccnc(N4CCc5c(sc6c5CC(C)(C)C6)C4=O)c3CO)cn(C)c2=O)nn1] | 3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]thieno[1,3-c]pyridin-4-one | 0.209 |

TABLE 2-continued

| No. | Structure | IUPAC Name | CD69 Hu Blood FACS (IC70) |
|---|---|---|---|
| 334 | 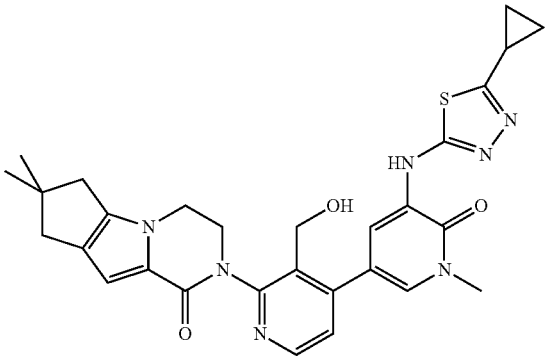 [SMILES: Cn1cc(-c2ccnc(N3CCn4c(cc5c4CC(C)(C)C5)C3=O)c2CO)cc(Nc2nnc(C3CC3)s2)c1=O] | 3-[4-[5-[(5-cyclopropyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.193 |
| 335 | 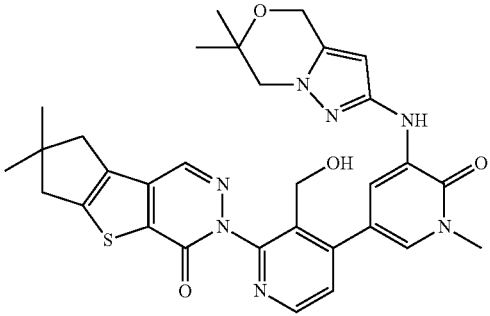 [SMILES: Cn1cc(-c2ccnc(-n3ncc4c5c(sc4c3=O)CC(C)(C)C5)c2CO)cc(Nc2cc3n(n2)CC(C)(C)OC3)c1=O] | 3-[4-[5-[(6,6-dimethyl-4,7-dihydropyrazolo[5,1-c][1,4]oxazin-2-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one | 0.0528 |
| 336 | 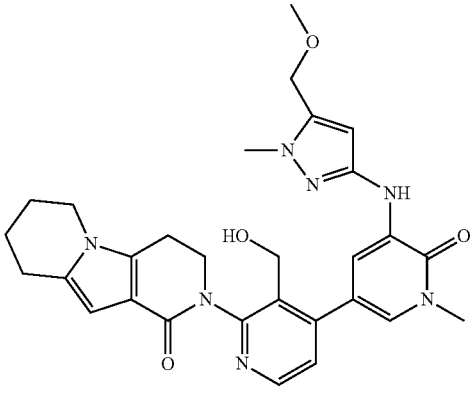 [SMILES: COCc1cc(Nc2cc(-c3ccnc(N4CCc5c(cc6n5CCCC6)C4=O)c3CO)cn(C)c2=O)nn1C] | 2-[3-(hydroxymethyl)-4-[5-[[5-(methoxymethyl)-1-methyl-pyrazol-3-yl]amino]-1-methyl-6-oxo-3-pyridyl]-2-pyridyl]-3,4,6,7,8,9-hexahydropyrido[3,4-b]indolizin-1-one | 0.33 |
| 337 | 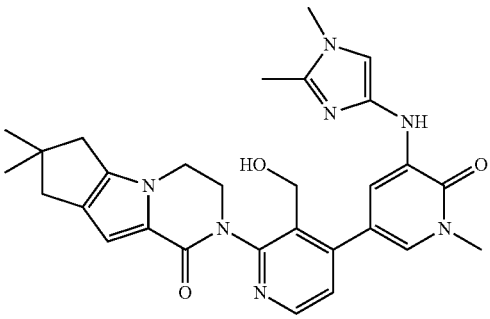 [SMILES: Cc1nc(Nc2cc(-c3ccnc(N4CCn5c(cc6c5CC(C)(C)C6)C4=O)c3CO)cn(C)c2=O)cn1C] | 3-[4-[5-[(1,2-dimethylimidazol-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one | 0.613 |

TABLE 2-continued

| No. | Structure | IUPAC Name | CD69 Hu Blood FACS (IC70) |
|---|---|---|---|
| 338 | 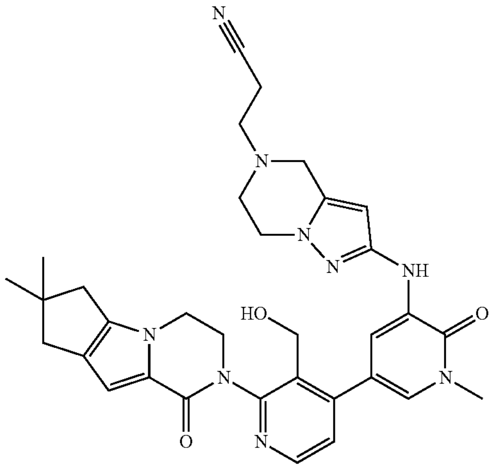 [SMILES: Cn1cc(-c2ccnc(N3CCn4c(cc5c4CC(C)(C)C5)C3=O)c2CO)cc(Nc2cc3n(n2)CCN(CCC#N)C3)c1=O] | 3-[2-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]-6,7-dihydro-4H-pyrazolo[1,5-a]pyrazin-5-yl]propanenitrile | 0.0178 |
| 339 | 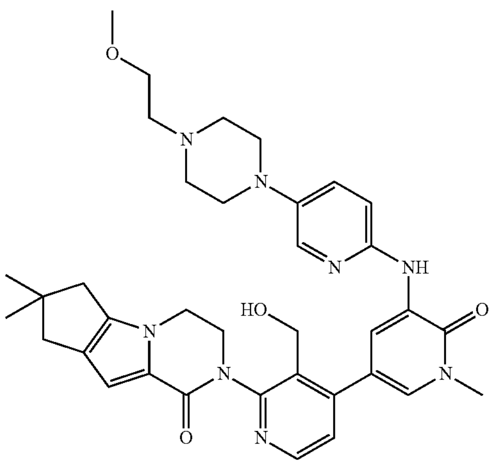 [SMILES: COCCN1CCN(c2ccc(Nc3cc(-c4ccnc(N5CCn6c(cc7c6CC(C)(C)C7)C5=O)c4CO)cn(C)c3=O)nc2)CC1] | 3-[3-(hydroxymethyl)-4-[5-[[5-[4-(2-methoxyethyl)piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.0535 |
| 340 | 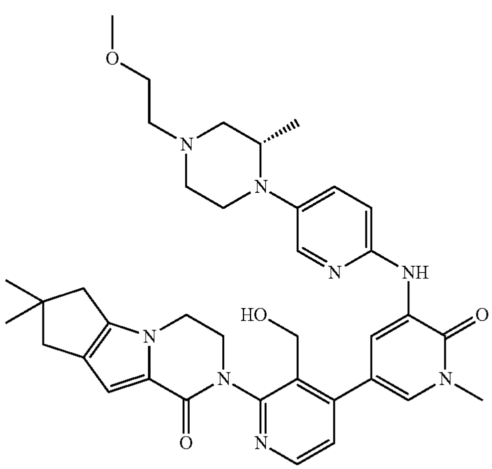 [SMILES: COCCN1CCN(c2ccc(Nc3cc(-c4ccnc(N5CCn6c(cc7c6CC(C)(C)C7)C5=O)c4CO)cn(C)c3=O)nc2)[C@@H](C)C1] | 3-[3-(hydroxymethyl)-4-[5-[[5-[(2S)-4-(2-methoxyethyl)-2-methyl-piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one | 0.0207 |

Administration of Formula I Compounds

The compounds of the invention may be administered by any route appropriate to the condition to be treated. Suitable routes include oral, parenteral (including subcutaneous, intramuscular, intravenous, intraarterial, intradermal, intrathecal and epidural), transdermal, rectal, nasal, topical (including buccal and sublingual), vaginal, intraperitoneal, intrapulmonary and intranasal. For local immunosuppressive treatment, the compounds may be administered by intralesional administration, including perfusing or otherwise contacting the graft with the inhibitor before transplantation. It will be appreciated that the preferred route may vary with for example the condition of the recipient. Where the compound is administered orally, it may be formulated as a pill, capsule, tablet, etc. with a pharmaceutically acceptable carrier or excipient. Where the compound is administered parenterally, it may be formulated with a pharmaceutically acceptable parenteral vehicle and in a unit dosage injectable form, as detailed below.

A dose to treat human patients may range from about 10 mg to about 1000 mg of Formula I compound. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

Methods of Treatment with Formula I Compounds

Formula I compounds of the present invention are useful for treating a human or animal patient suffering from a disease or disorder arising from abnormal cell growth, function or behavior associated with Btk kinase such as an immune disorder, cardiovascular disease, viral infection, inflammation, a metabolism/endocrine disorder or a neurological disorder, may thus be treated by a method comprising the administration thereto of a compound of the present invention as defined above. A human or animal patient suffering from cancer may also be treated by a method comprising the administration thereto of a compound of the present invention as defined above. The condition of the patient may thereby be improved or ameliorated.

Formula I compounds may be useful for in vitro, in situ, and in vivo diagnosis or treatment of mammalian cells, organisms, or associated pathological conditions, such as systemic and local inflammation, immune-inflammatory diseases such as rheumatoid arthritis, immune suppression, organ transplant rejection, allergies, ulcerative colitis, Crohn's disease, dermatitis, asthma, systemic lupus erythematosus, Sjögren's Syndrome, multiple sclerosis, scleroderma/systemic sclerosis, idiopathic thrombocytopenic purpura (ITP), anti-neutrophil cytoplasmic antibodies (ANCA) vasculitis, chronic obstructive pulmonary disease (COPD), psoriasis, and for general joint protective effects.

Methods of the invention also include treating such diseases as arthritic diseases, such as rheumatoid arthritis, monoarticular arthritis, osteoarthritis, gouty arthritis, spondylitis; Behcet disease; sepsis, septic shock, endotoxic shock, gram negative sepsis, gram positive sepsis, and toxic shock syndrome; multiple organ injury syndrome secondary to septicemia, trauma, or hemorrhage; ophthalmic disorders such as allergic conjunctivitis, vernal conjunctivitis, uveitis, and thyroid-associated ophthalmopathy; eosinophilic granuloma; pulmonary or respiratory disorders such as asthma, chronic bronchitis, allergic rhinitis, ARDS, chronic pulmonary inflammatory disease (e.g., chronic obstructive pulmonary disease), silicosis, pulmonary sarcoidosis, pleurisy, alveolitis, vasculitis, emphysema, pneumonia, bronchiectasis, and pulmonary oxygen toxicity; reperfusion injury of the myocardium, brain, or extremities; fibrosis such as cystic fibrosis; keloid formation or scar tissue formation; atherosclerosis; autoimmune diseases, such as systemic lupus erythematosus (SLE), autoimmune thyroiditis, multiple sclerosis, some forms of diabetes, and Reynaud's syndrome; and transplant rejection disorders such as GVHD and allograft rejection; chronic glomerulonephritis; inflammatory bowel diseases such as chronic inflammatory bowel disease (CIBD), Crohn's disease, ulcerative colitis, and necrotizing enterocolitis; inflammatory dermatoses such as contact dermatitis, atopic dermatitis, psoriasis, or urticaria; fever and myalgias due to infection; central or peripheral nervous system inflammatory disorders such as meningitis, encephalitis, and brain or spinal cord injury due to minor trauma; Sjogren's syndrome; diseases involving leukocyte diapedesis; alcoholic hepatitis; bacterial pneumonia; antigen-antibody complex mediated diseases; hypovolemic shock; Type I diabetes mellitus; acute and delayed hypersensitivity; disease states due to leukocyte dyscrasia and metastasis; thermal injury; granulocyte transfusion-associated syndromes; and cytokine-induced toxicity.

Methods of the invention also include treating cancer selected from breast, ovary, cervix, prostate, testis, genitourinary tract, esophagus, larynx, glioblastoma, neuroblastoma, stomach, skin, keratoacanthoma, lung, epidermoid carcinoma, large cell carcinoma, non-small cell lung carcinoma (NSCLC), small cell carcinoma, lung adenocarcinoma, bone, colon, adenoma, pancreas, adenocarcinoma, thyroid, follicular carcinoma, undifferentiated carcinoma, papillary carcinoma, seminoma, melanoma, sarcoma, bladder carcinoma, liver carcinoma and biliary passages, kidney carcinoma, pancreatic, myeloid disorders, lymphoma, hairy cells, buccal cavity, naso-pharyngeal, pharynx, lip, tongue, mouth, small intestine, colon-rectum, large intestine, rectum, brain and central nervous system, Hodgkin's, leukemia, bronchus, thyroid, liver and intrahepatic bile duct, hepatocellular, gastric, glioma/glioblastoma, endometrial, melanoma, kidney and renal pelvis, urinary bladder, uterine corpus, uterine cervix, multiple myeloma, acute myelogenous leukemia, chronic myelogenous leukemia, lymphocytic leukemia, chronic lymphoid leukemia (CLL), myeloid leukemia, oral cavity and pharynx, non-Hodgkin lymphoma, melanoma, and villous colon adenoma.

The methods of the invention can have utility in treating subjects who are or can be subject to reperfusion injury, i.e., injury resulting from situations in which a tissue or organ experiences a period of ischemia followed by reperfusion. The term "ischemia" refers to localized tissue anemia due to obstruction of the inflow of arterial blood. Transient ischemia followed by reperfusion characteristically results in neutrophil activation and transmigration through the endothelium of the blood vessels in the affected area. Accumulation of activated neutrophils in turn results in generation of reactive oxygen metabolites, which damage components of the involved tissue or organ. This phenomenon of "reperfusion injury" is commonly associated with conditions such as vascular stroke (including global and focal ischemia), hemorrhagic shock, myocardial ischemia or infarction, organ transplantation, and cerebral vasospasm. To illustrate, reperfusion injury occurs at the termination of cardiac bypass procedures or during cardiac arrest when the heart, once prevented from receiving blood, begins to reperfuse. It is expected that inhibition of Btk activity may result in reduced amounts of reperfusion injury in such situations.

Pharmaceutical Formulations

In order to use a compound of this invention for the therapeutic treatment of mammals including humans, it is normally formulated in accordance with standard pharmaceutical practice as a pharmaceutical composition. According to this aspect of the invention there is provided a pharmaceutical composition comprising a compound of this invention in association with a pharmaceutically acceptable diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent) is dissolved in a suitable solvent in the presence of one or more of the excipients described above. The compound of the present invention is typically formulated into pharmaceutical dosage forms to provide an easily controllable dosage of the drug and to enable patient compliance with the prescribed regimen.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

Pharmaceutical formulations of the compounds of the present invention may be prepared for various routes and types of administration. For example, a compound of Formula I having the desired degree of purity may optionally be mixed with pharmaceutically acceptable diluents, carriers, excipients or stabilizers (Remington's Pharmaceutical Sciences (1980) 16th edition, Osol, A. Ed.), in the form of a lyophilized formulation, milled powder, or an aqueous solution. Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The compound ordinarily can be stored as a solid composition, a lyophilized formulation or as an aqueous solution.

The pharmaceutical compositions of the invention will be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the compound to be administered will be governed by such considerations, and is the minimum amount necessary to ameliorate, or treat the hyperproliferative disorder.

As a general proposition, the initial pharmaceutically effective amount of the inhibitor administered parenterally per dose will be in the range of about 0.01-100 mg/kg, namely about 0.1 to 20 mg/kg of patient body weight per day, with the typical initial range of compound used being 0.3 to 15 mg/kg/day.

Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations of compounds of Formula I may be prepared. Suitable examples of sustained-release preparations include semipermeable matrices of solid hydrophobic polymers containing a compound of Formula I, which matrices are in the form of shaped articles, e.g., films, or microcapsules. Examples of sustained-release matrices include polyesters, hydrogels (for example, poly(2-hydroxyethyl-methacrylate), or poly(vinyl alcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate) and poly-D-(−)-3-hydroxybutyric acid.

The formulations include those suitable for the administration routes detailed herein. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of a compound of Formula I suitable for oral administration may be prepared as discrete units such as pills, capsules, cachets or tablets each containing a predetermined amount of a compound of Formula I. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom. Tablets, troches, lozenges, aqueous or oil suspensions, dispersible powders or granules, emulsions, hard or soft capsules, e.g., gelatin capsules, syrups or elixirs may be prepared for oral use. Formulations of compounds of Formula I intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

For treatment of the eye or other external tissues, e.g., mouth and skin, the formulations are preferably applied as a topical ointment or cream containing the active ingredient(s) in an amount of, for example, 0.075 to 20% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of the emulsions of this invention may be constituted from known ingredients in a known manner. While the phase may comprise merely an emulsifier, it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulsifiers and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate.

Aqueous suspensions of Formula I compounds contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of compounds of Formula I may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butanediol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of about 0.5 to 20% w/w, for example about 0.5 to 10% w/w, for example about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

Formulations suitable for intrapulmonary or nasal administration have a particle size for example in the range of 0.1 to 500 microns (including particle sizes in a range between 0.1 and 500 microns in increments microns such as 0.5, 1, 30 microns, 35 microns, etc.), which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents such as compounds heretofore used in the treatment or prophylaxis disorders as described below.

Formulations suitable for vaginal administration may be presented as pessaries, tampons, creams, gels, pastes, foams or spray formulations containing in addition to the active ingredient such carriers as are known in the art to be appropriate.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Combination Therapy

The compounds of Formula I may be employed alone or in combination with other therapeutic agents for the treatment of a disease or disorder described herein, such as inflammation or a hyperproliferative disorder (e.g., cancer). In certain embodiments, a compound of Formula I is combined in a pharmaceutical combination formulation, or dosing regimen as combination therapy, with an additional, second therapeutic compound that has anti-inflammatory or anti-hyperproliferative properties or that is useful for treating an inflammation, immune-response disorder, or hyperproliferative disorder (e.g., cancer). The additional therapeutic may be an anti-inflammatory agent, an immunomodulatory agent, chemotherapeutic agent, an apoptosis-enhancer, a neurotropic factor, an agent for treating cardiovascular disease, an agent for treating liver disease, an anti-viral agent, an agent for treating blood disorders, an agent for treating diabetes, and an agent for treating immunodeficiency disorders. The second therapeutic agent may be an NSAID anti-inflammatory agent. The second therapeutic agent may be a chemotherapeutic agent. The second compound of the pharmaceutical combination formulation or dosing regimen preferably has complementary activities to the compound of Formula I such that they do not adversely affect each other. Such compounds are suitably present in combination in amounts that are effective for the purpose intended. In one embodiment, a composition of this invention comprises a compound of Formula I, or a stereoisomer, tautomer, solvate, metabolite, or pharmaceutically acceptable salt or prodrug thereof, in combination with a therapeutic agent such as an NSAID.

The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein preferably there is a time period while both (or all) active agents simultaneously exert their biological activities.

Suitable dosages for any of the above coadministered agents are those presently used and may be lowered due to the combined action (synergy) of the newly identified agent and other therapeutic agents or treatments.

The combination therapy may provide "synergy" and prove "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g., by different injections in separate syringes, separate pills or capsules, or separate infusions. In general, during alternation therapy, an effective dosage of each active ingredient is administered sequentially, i.e., serially, whereas in combination therapy, effective dosages of two or more active ingredients are administered together.

In a particular embodiment of therapy, a compound of Formula I, or a stereoisomer, tautomer, solvate, metabolite, or pharmaceutically acceptable salt or prodrug thereof, may be combined with other therapeutic, hormonal or antibody agents such as those described herein, as well as combined with surgical therapy and radiotherapy. Combination therapies according to the present invention thus comprise the administration of at least one compound of Formula I, or a stereoisomer, tautomer, solvate, metabolite, or pharmaceutically acceptable salt or prodrug thereof, and the use of at least one other cancer treatment method. The amounts of the compound(s) of Formula I and the other pharmaceutically active therapeutic agent(s) and the relative timings of administration will be selected in order to achieve the desired combined therapeutic effect.

Metabolites of Compounds of Formula I

Also falling within the scope of this invention are the in vivo metabolic products of Formula I described herein. Such products may result for example from the oxidation, reduction, hydrolysis, amidation, deamidation, esterification, deesterification, enzymatic cleavage, and the like, of the administered compound. Accordingly, the invention includes metabolites of compounds of Formula I, including compounds produced by a process comprising contacting a compound of this invention with a mammal for a period of time sufficient to yield a metabolic product thereof.

Metabolite products typically are identified by preparing a radiolabelled (e.g., $^{14}$C or $^3$H) isotope of a compound of the invention, administering it parenterally in a detectable dose (e.g., greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolite products, so long as they are not otherwise found in vivo, are useful in diagnostic assays for therapeutic dosing of the compounds of the invention.

Articles of Manufacture

In another embodiment of the invention, an article of manufacture, or "kit", containing materials useful for the treatment of the diseases and disorders described above is provided. In one embodiment, the kit comprises a container comprising a compound of Formula I, or a stereoisomer, tautomer, solvate, metabolite, or pharmaceutically acceptable salt or prodrug thereof. The kit may further comprise a label or package insert on or associated with the container. The term "package insert" is used to refer to instructions customarily included in commercial packages of therapeutic products, that contain information about the indications, usage, dosage, administration, contraindications and/or warnings concerning the use of such therapeutic products. Suitable containers include, for example, bottles, vials, syringes, blister pack, etc. The container may be formed from a variety of materials such as glass or plastic. The container may hold a compound of Formula I or a formulation thereof which is effective for treating the condition and may have a sterile access port (for example, the container may be an intravenous solution bag or a vial having a stopper pierceable by a hypodermic injection needle). At least one active agent in the composition is a compound of Formula I. The label or package insert indicates that the composition is used for treating the condition of choice, such as cancer. In addition, the label or package insert may indicate that the patient to be treated is one having a disorder such as a hyperproliferative disorder, neurodegeneration, cardiac hypertrophy, pain, migraine or a neurotraumatic disease or event. In one embodiment, the label or package inserts indicates that the composition comprising a compound of Formula I can be used to treat a disorder resulting from abnormal cell growth. The label or package insert may also indicate that the composition can be used to treat other disorders. Alternatively, or additionally, the article of manufacture may further comprise a second container comprising a pharmaceutically acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The kit may further comprise directions for the administration of the compound of Formula I and, if present, the second pharmaceutical formulation. For example, if the kit comprises a first composition comprising a compound of Formula I and a second pharmaceutical formulation, the kit may further comprise directions for the simultaneous, sequential or separate administration of the first and second pharmaceutical compositions to a patient in need thereof.

In another embodiment, the kits are suitable for the delivery of solid oral forms of a compound of Formula I, such as tablets or capsules. Such a kit preferably includes a number of unit dosages. Such kits can include a card having the dosages oriented in the order of their intended use. An example of such a kit is a "blister pack". Blister packs are well known in the packaging industry and are widely used for packaging pharmaceutical unit dosage forms. If desired, a memory aid can be provided, for example in the form of numbers, letters, or other markings or with a calendar insert, designating the days in the treatment schedule in which the dosages can be administered.

According to one embodiment, a kit may comprise (a) a first container with a compound of Formula I contained therein; and optionally (b) a second container with a second pharmaceutical formulation contained therein, wherein the second pharmaceutical formulation comprises a second compound with anti-hyperproliferative activity. Alternatively, or additionally, the kit may further comprise a third container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

In certain other embodiments wherein the kit comprises a composition of Formula I and a second therapeutic agent, the kit may comprise a container for containing the separate compositions such as a divided bottle or a divided foil packet, however, the separate compositions may also be contained within a single, undivided container. Typically, the kit comprises directions for the administration of the separate components. The kit form is particularly advantageous when the separate components are preferably administered in different dosage forms (e.g., oral and parenteral), are administered at different dosage intervals, or when titration of the individual components of the combination is desired by the prescribing physician.

Preparation of Formula I Compounds

Compounds of Formula I may be synthesized by synthetic routes that include processes analogous to those well-known in the chemical arts, particularly in light of the description contained herein, and those for other heterocycles described in: Comprehensive Heterocyclic Chemistry II, Editors Katritzky and Rees, Elsevier, 1997, e.g. Volume 3; Liebigs Annalen der Chemie, (9):1910-16, (1985); Helvetica Chimica Acta, 41:1052-60, (1958); Arzneimittel-Forschung, 40(12):1328-31, (1990), each of which are expressly incorporated by reference. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1-23, Wiley, N.Y. (1967-2006 ed.), or *Beilsteins Handbuch der organischen Chemie*, 4, Aufl. ed. Springer-Verlag, Berlin, including supplements (also available via the Beilstein online database).

Synthetic chemistry transformations and protecting group methodologies (protection and deprotection) useful in synthesizing Formula I compounds and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3$^{rd}$ Ed., John Wiley and Sons (1999); and L. Paquette, ed., Encyclopedia of Reagents for Organic Synthesis, John Wiley and Sons (1995) and subsequent editions thereof.

Compounds of Formula I may be prepared singly or as compound libraries comprising at least 2, for example 5 to 1,000 compounds, or 10 to 100 compounds. Libraries of compounds of Formula I may be prepared by a combinatorial 'split and mix' approach or by multiple parallel syntheses using either solution phase or solid phase chemistry, by procedures known to those skilled in the art. Thus according to a further aspect of the invention there is provided a compound library comprising at least 2 compounds, or pharmaceutically acceptable salts thereof.

The Figures and Examples provide exemplary methods for preparing Formula I compounds. Those skilled in the art will appreciate that other synthetic routes may be used to synthesize the Formula I compounds. Although specific starting materials and reagents are depicted and discussed in the Figures and Examples, other starting materials and reagents can be easily substituted to provide a variety of derivatives and/or reaction conditions. In addition, many of the exemplary compounds prepared by the described methods can be further modified in light of this disclosure using conventional chemistry well known to those skilled in the art.

In preparing compounds of Formulas I, protection of remote functionality (e.g., primary or secondary amine) of intermediates may be necessary. The need for such protection will vary depending on the nature of the remote functionality and the conditions of the preparation methods. Suitable amino-protecting groups include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, Protective Groups in Organic Synthesis, John Wiley & Sons, New York, 1991.

Experimental procedures, intermediates and reagents useful for useful for the preparation of Formula I compounds may be found in U.S. Ser. No. 13/102,720, "PYRIDONE AND AZA-PYRIDONE COMPOUNDS AND METHODS OF USE", filed 6 May 2011, which is incorporated by reference in its entirety.

FIGS. 1-24 describe the synthesis of exemplary embodiments of Formula I compounds 101-124, more fully described in Examples 101-124, and may be useful for the preparation of other Formula I compounds.

General Preparative Procedures

General Procedure: Suzuki Coupling

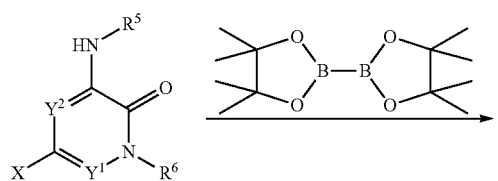

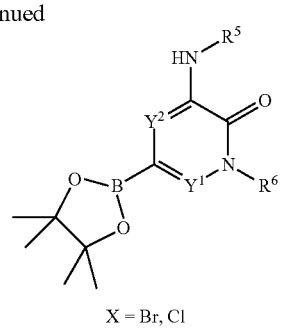

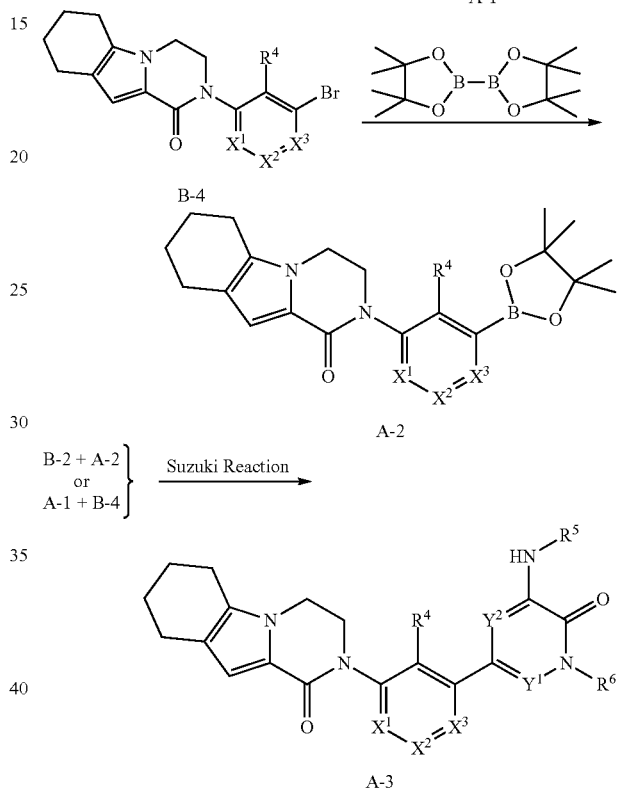

The Suzuki-type coupling reaction is useful to form carbon-carbon bonds to attach the rings of Formula I compounds and intermediates such as A-3 (Suzuki (1991) Pure Appl. Chem. 63:419-422; Miyaura and Suzuki (1979) Chem. Reviews 95(7):2457-2483; Suzuki (1999) J. Organometal. Chem. 576:147-168). Suzuki coupling is a palladium mediated cross coupling reaction of a heteroarylhalide, such as B-2 or B-4, with a boronic acid such as A-1 or A-2. For example, B-2 may be combined with about 1.5 equivalents of 4,4,4',4', 5,5,5',5'-octamethyl-2,2'-bi(1,3,2-dioxaborolane), and dissolved in about 3 equivalents of sodium carbonate as a 1 molar solution in water and an equal volume of acetonitrile. A catalytic amount, or more, of a low valent palladium reagent, such as bis(triphenylphosphine)palladium(II) dichloride, is added. In some cases potassium acetate is used in place of sodium carbonate to adjust the pH of the aqueous layer. The reaction is then heated to about 140-150° C. under pressure in a microwave reactor (Biotage AB, Uppsala, Sweden) for 10 to 30 minutes. The contents are extracted with ethyl acetate, or another organic solvent. After evaporation of the organic layer the boron ester A-1 may be purified on silica or by reverse phase HPLC. Substituents are as defined, or protected forms or precursors thereof. Likewise, bromide intermediate B-4 can be boronylated to give A-2.

Suzuki coupling of B-2 and A-2, or of A-1 and B-4, gives Formula I compound or intermediate A-3. Boronic ester (or acid) (1.5 eq) A-1 or A-2, and a palladium catalyst such as bis(triphenylphosphine)palladium(II) chloride (0.05 eq) is added to a mixture of halo intermediate (1 eq) B-2 or B-4 in acetonitrile and 1 M of sodium carbonate aqueous solution (equal volume as acetonitrile). The reaction mixture is heated to about 150° C. in a microwave for about 15 min. LC/MS indicates when the reaction is complete. Water is added to the mixture, and the precipitated product is filtered and purified by HPLC to yield the product A-3. Substituents $R^{1'}$, $R^{2'}$, $R^{4'}$ may be $R^1$, $R^2$, $R^4$ as defined, or protected forms or precursors thereof.

A variety of palladium catalysts can be used during the Suzuki coupling step. Various low valent, Pd(II) and Pd(0) catalysts may be used in the Suzuki coupling reaction, including $PdCl2(PPh_3)_2$, $Pd(t-Bu)_3$, $PdCl_2$ dppf $CH_2Cl_2$, $Pd(PPh_3)_4$, $Pd(OAc)/PPh_3$, $Cl_2Pd[(Pet_3)]_2$, $Pd(DIPHOS)_2$, $Cl_2Pd(Bipy)$, $[PdCl(Ph_2PCH_2PPh_2)]_2$, $Cl_2Pd[P(o-tol)_3]_2$, $Pd_2(dba)_3/P(o-tol)_3$, $Pd_2(dba)/P(furyl)_3$, $Cl_2Pd[P(furyl)_3]_2$, $Cl_2Pd(PMePh_2)_2$, $Cl_2Pd[P(4-F-Ph)_3]_2$, $Cl_2Pd[P(C_6F_6)_3]_2$, $Cl_2Pd[P(2-COOH-Ph)(Ph)_2]_2$, $Cl_2Pd[P(4-COOH-Ph)(Ph)_2]_2$, and encapsulated catalysts Pd EnCat™ 30, Pd EnCat™ TPP30, and Pd(II)EnCat™ BINAP30 (US 2004/0254066).

General Procedure: Buchwald Reaction

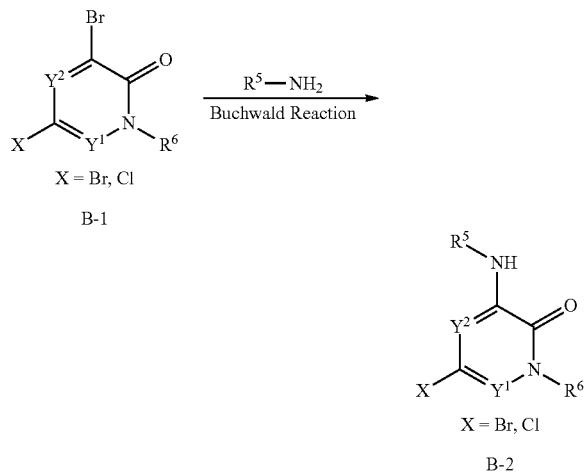

The Buchwald reaction is useful to aminate 6-bromo intermediates B-1 (Wolf and Buchwald (2004) Org. Synth Coll. Vol. 10:423; Paul et al (1994) Jour. Amer. Chem. Soc. 116: 5969-5970). To a solution of halo intermediate B-1 in DMF is added the appropriate amine $R^5$—$NH_2$ (200 mol %), $Cs_2CO_3$ (50 mol %), $Pd_2(dba)_3$ (5 mol %), and 4,5-bis(diphenylphosphino)-9,9-dimethylxanthene (Xantphos, CAS Reg. No. 161265-03-8, 10 mol %). The reaction is heated to about 110° C. under pressure in a microwave reactor (Biotage AB, Uppsala, Sweden) for about 30 min. The resulting solution is concentrated in vacuo to give B-2. Other palladium catalysts and phosphine ligands may be useful.

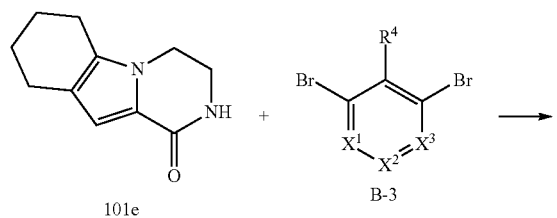

N-Heteroaryl amide intermediates B-4 can also be prepared under Buchwald conditions with cyclic amide intermediates ($R^7$) such as 3,4,6,7,8,9-hexahydropyrazino[1,2-a]indol-1(2H)-one 101e and heteroaryl dibromides B-3.

Methods of Separation

In the methods of preparing Formula I compounds, it may be advantageous to separate reaction products from one another and/or from starting materials. The desired products of each step or series of steps is separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed (SMB) and preparative thin or thick layer chromatography, as well as techniques of small scale thin layer and flash chromatography.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like. Selection of appropriate methods of separation depends on the nature of the materials involved, such as, boiling point and molecular weight in distillation and sublimation, presence or absence of polar functional groups in chromatography, stability of materials in acidic and basic media in multiphase extraction, and the like.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

A single stereoisomer, e.g., an enantiomer, substantially free of its stereoisomer may be obtained by resolution of the racemic mixture using a method such as formation of diastereomers using optically active resolving agents (Eliel, E. and Wilen, S. "Stereochemistry of Organic Compounds," John Wiley & Sons, Inc., New York, 1994; Lochmuller, C. H., (1975) J. Chromatogr., 113(3):283-302). Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions. See: "Drug Stereochemistry, Analytical Methods and Pharmacology," Irving W. Wainer, Ed., Marcel Dekker, Inc., New York (1993).

Under method (1), diastereomeric salts can be formed by reaction of enantiomerically pure chiral bases such as brucine, quinine, ephedrine, strychnine, α-methyl-β-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts.

Alternatively, by method (2), the substrate to be resolved is reacted with one enantiomer of a chiral compound to form a diastereomeric pair (E. and Wilen, S. "Stereochemistry of Organic Compounds", John Wiley & Sons, Inc., 1994, p. 322). Diastereomeric compounds can be formed by reacting asymmetric compounds with enantiomerically pure chiral derivatizing reagents, such as menthyl derivatives, followed by separation of the diastereomers and hydrolysis to yield the pure or enriched enantiomer. A method of determining optical purity involves making chiral esters, such as a menthyl ester, e.g., (−) menthyl chloroformate in the presence of base, or Mosher ester, α-methoxy-α-(trifluoromethyl)phenyl acetate (Jacob III. J. Org. Chem. (1982) 47:4165), of the racemic mixture, and analyzing the $^1$H NMR spectrum for the presence of the two atropisomeric enantiomers or diastereomers. Stable diastereomers of atropisomeric compounds can be separated and isolated by normal- and reverse-phase chromatography following methods for separation of atropisomeric naphthyl-isoquinolines (WO 96/15111). By method (3), a racemic mixture of two enantiomers can be separated by chromatography using a chiral stationary phase ("Chiral Liquid Chromatography" (1989) W. J. Lough, Ed., Chapman and Hall, New York; Okamoto, J. Chromatogr., (1990) 513:375-378). Enriched or purified enantiomers can be distinguished by methods used to distinguish other chiral molecules with asymmetric carbon atoms, such as optical rotation and circular dichroism.

EXAMPLES

Example 101a 2,2,2-Trichloro-1-(4,5,6,7-tetrahydro-1H-indol-2-yl)ethanone 101a

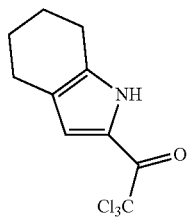

101a

A 100-mL single-neck round-bottomed flask equipped with a magnetic stirrer, condenser and nitrogen inlet was purged with nitrogen and charged with 4,5,6,7-tetrahydro-1H-indole (3.00 g, 24.8 mmol), trichloroacetyl chloride (13.5 g, 74.4 mmol) and 1,2-dichloroethane (50 mL). The solution was stirred at 85° C. for 2 h. After that time, the reaction mixture was concentrated under reduced pressure to afford a 100% yield (6.50 g) of 2,2,2-trichloro-1-(4,5,6,7-tetrahydro-1H-indol-2-yl)ethanone 101a as a black semi-solid: $^1$H NMR (500 MHz, DMSO-$d_6$) δ 11.94 (s, 1H), 7.05 (s, 1H), 2.62 (t, 2H, J=6.0 Hz), 2.47 (t, 2H, J=6.0 Hz), 1.80 (m, 2H), 1.65 (m, 2H); MS (ESI+) m/z 266.0 (M+H)

Example 101b

Ethyl 4,5,6,7-Tetrahydro-1H-indole-2-carboxylate 101b

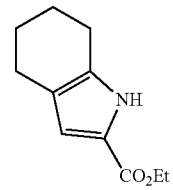

101b

A 100-mL single-neck round-bottomed flask equipped with a magnetic stirrer and nitrogen inlet was purged with nitrogen and charged with 101a (6.50 g, 24.8 mmol), sodium ethoxide (17.0 mg, 0.25 mmol) and ethanol (40 mL). The solution was stirred at room temperature for 1 h. After that time, the reaction mixture was concentrated under reduced pressure. The residue was purified by column chromatography to afford a 100% yield (4.80 g) of ethyl 4,5,6,7-tetrahydro-1H-indole-2-carboxylate 101b as a brown solid: mp 70-72° C.; $^1$H NMR (300 MHz, CDCl$_3$) δ 9.08 (s, 1H), 6.75 (s, 1H), 4.25 (q, 2H, J=7.2 Hz), 2.65 (t, 2H, J=6.0 Hz), 2.56 (t, 2H, J=6.0 Hz), 1.85 (m, 4H), 1.28 (t, 3H, J=7.2 Hz); MS (ESI+) m/z 194.1 (M+H)

Example 101c

Ethyl 1-(Cyanomethyl)-4,5,6,7-tetrahydro-1H-indole-2-carboxylate 101c

101c

A 125-mL single-neck round-bottomed flask equipped with a magnetic stirrer and nitrogen inlet was purged with nitrogen and charged with 101b (5.76 g, 29.8 mmol) and DMF (50 mL). The solution was cooled to 0° C. using an ice bath. NaH (60% dispersion in mineral oil, 1.43 g, 35.8 mmol) was added. The resulting mixture was stirred at room temperature for 1 h. After that time, bromoacetonitrile (1.43 g, 35.8 mmol) was added. The mixture was stirred at room temperature for 14 h. After that time, the reaction mixture was concentrated under reduced pressure and the residue was partitioned between ethyl acetate (150 mL) and water (450 mL). The organic layer was separated, and the aqueous layer was extracted with ethyl acetate (3×150 mL). The combined organic layers were washed with brine, dried over sodium sulfate and concentrated under reduced pressure. The residue was purified by column chromatography to afford a 55% yield (3.80 g) of ethyl 1-(cyanomethyl)-4,5,6,7-tetrahydro-1H-indole-2-carboxylate 101c as a yellow semi-solid: $^1$H NMR (300 MHz, CDCl$_3$) δ 6.66 (s, 1H), 5.29 (s, 2H), 4.28 (q, 2H, J=7.2 Hz), 2.62 (t, 2H, J=6.3 Hz), 2.49 (t, 2H, J=6.3 Hz), 1.92 (m, 2H), 1.75 (m, 2H), 1.33 (t, 3H, J=7.2 Hz); MS (ESI+) m/z 233.1 (M+H)

Example 101d

Ethyl 1-(2-Aminoethyl)-4,5,6,7-tetrahydro-1H-indole-2-carboxylate 101d

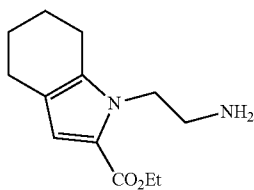

A 200-mL Parr reactor bottle was purged with nitrogen and charged with 10% palladium on carbon (50% wet, 1.28 g dry weight), 101c (3.00 g, 12.9 mmol), 12% hydrochloric acid (6.5 mL, 25 mmol), ethyl acetate (60 mL) and ethanol (40 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. diatomaceous earth filter agent (CELITE®, Imerys Minerals California, Inc.) CELITE® 521 (4.0 g) was added, and the mixture was filtered through a pad of CELITE® 521. The filter cake was washed with ethanol (2×20 mL), and the combined filtrates were concentrated to dryness under reduced pressure. The residue was partitioned between ethyl acetate (150 mL) and 10% aqueous potassium carbonate (100 mL). The organic layer was separated, and the aqueous layer was extracted with ethyl acetate (3×75 mL). The combined organic layers were dried over sodium sulfate and concentrated under reduced pressure. The residue was triturated with ethanol (5 mL) to afford a 71% yield (1.71 g) of ethyl 1-(2-aminoethyl)-4,5,6,7-tetrahydro-1H-indole-2-carboxylate 101d as a white solid: mp 102-104° C.; $^1$H NMR (500 MHz, DMSO-d$_6$) δ 6.61 (s, 1H), 6.22 (br, 2H), 4.15 (m, 4H), 2.77 (m, 2H), 2.59 (t, 2H, J=6.5 Hz), 2.42 (t, 2H, J=6.5 Hz), 1.70 (m, 2H), 1.62 (m, 2H), 1.23 (t, 3H, J=7.0 Hz); MS (APCI+) m/z 237.2 (M+H)

Example 101e 3,4,6,7,8,9-Hexahydropyrazino[1,2-a]indol-1(2H)-one 101e

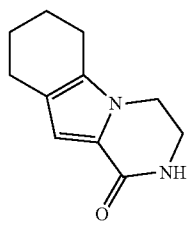

A 100-mL single-neck round-bottomed flask equipped with a magnetic stirrer and nitrogen inlet was purged with nitrogen and charged with 101d (1.80 g, 7.63 mmol), sodium ethoxide (1.55 g, 22.8 mmol) and ethanol (50 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 42% yield (605 mg) of 3,4,6,7,8,9-hexahydropyrazino[1,2-a]indol-1(2H)-one 101e as a white solid: mp 207-209° C.; $^1$H NMR (500 MHz, DMSO-d$_6$) δ 7.41 (s, 1H), 6.36 (s, 1H), 3.84 (t, 2H, J=6.0 Hz), 3.42 (m, 2H), 2.51 (t, 2H, J=6.0 Hz), 2.42 (t, 2H, J=6.0 Hz), 1.76 (m, 2H), 1.65 (m, 2H); (APCI+) m/z 191.3 (M+H)

Example 101f

3-Bromo-5-(1-oxo-3,4,6,7,8,9-hexahydropyrazino[1,2-a]indol-2(1H)-yl)isonicotinaldehyde 101f

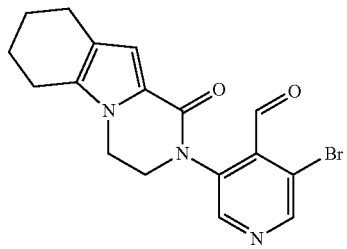 [SMILES: O=Cc1c(Br)cncc1N1CCn2c(cc3c2CCCC3)C1=O]

A 50-mL single-neck round-bottomed flask equipped with a magnetic stirrer and a reflux condenser was charged with 101e (300 mg, 1.57 mmol), 3,5-dibromoisonicotinaldehyde (2) (517 mg, 1.96 mmol), 4,5-bis(diphenylphosphino)-9,9-dimethylxanthene (XantPhos, 120 mg, 0.2 mmol), tris(dibenzylideneacetone)dipalladium(0) (180 mg, 0.2 mmol), Cs$_2$CO$_3$ (650 mg, 2 mmol), and 1,4-dioxane (8 mL). After three cycles of vacuum/argon flush, the mixture was heated at 100° C. for 6 h. It was then cooled to room temperature and filtered. The filtrate was concentrated under reduced pressure and the resulting residue was purified by flash column chromatography eluting with DCM/MeOH (from 40:1 to 20:1) to afford 101f as a pale yellow solid (350 mg, 40%). MS: [M+H]$^+$ 374.

Example 101g tert-Butyl 4-(6-Nitropyridin-3-yl)piperazine-1-carboxylate 101g

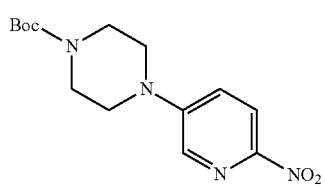

Into a solution of 5-bromo-2-nitropyridine (30 g, 148 mmol) in DMSO (1 L) were added K$_2$CO$_3$ (40 g, 296 mmol) and tert-butyl piperazine-1-carboxylate (28 g, 148 mmol). The mixture was stirred at 65° C. overnight. After cooling down, it was poured into water (2 L). The solid precipitated was collected and dried under vacuum. It was then further purified by flash column eluting with 20:1 petroleum ether/ ethyl acetate and then with methylene chloride to give 101g as a yellow solid (17 g, 37%). MS: [M+H]+ 309.

Example 101h tert-Butyl 4-(6-Aminopyridin-3-yl)piperazine-1-carboxylate 101h

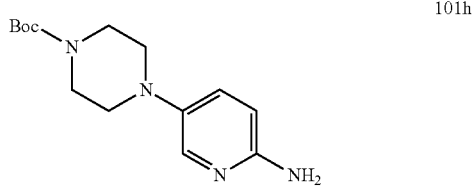 [SMILES: CC(C)(C)OC(=O)N1CCN(c2ccc(N)nc2)CC1]

A 500-mL bottle was purged with nitrogen and charged with tert-butyl 4-(6-nitropyridin-3-yl)piperazine-1-carboxylate 101g (3.1 g, 10 mmol), 10% palladium on carbon (50% wet, 1.0 g) and ethanol (100 mL). It was evacuated, charged with hydrogen gas, and stirred for 16 h at room temperature. The hydrogen was then evacuated and nitrogen was charged into the bottle. The catalyst was removed by filtration through a pad of CELITE® and the filtrate concentrated under reduced pressure to afford 101h (2.7 g, 97%). MS: [M+H]+ 279

Example 101i tert-Butyl 4-(6-(5-bromo-1-methyl-2-oxo-1,2-dihydropyridin-3-ylamino)pyridine-3-yl)piperazine-1-carboxylate 101i

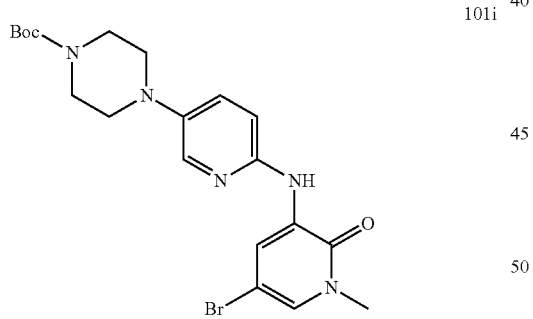

A 100-mL single-neck round-bottomed flask equipped with a magnetic stirrer and reflux condenser was charged with 1,4-dioxane (50 mL), 101h (1.3 g, 4.7 mmol), 3,5-dibromo-1-methylpyridin-2(1H)-one (1.24 g, 4.7 mmol), and cesium carbonate (3.8 g, 12 mmol). After bubbling nitrogen through the resulting mixture for 30 minutes, XantPhos (272 mg, 0.47 mmol) and tris(dibenzylideneacetone)dipalladium(0) (430 mg, 0.47 mmol) were added, and the reaction mixture was heated at reflux for 3 h. After this time the reaction was cooled to room temperature, partitioned between ethyl acetate (100 mL) and water (100 mL), and filtered. The aqueous layer was separated and extracted with ethyl acetate (50 mL×2). The organic layers were combined, washed with brine (50 mL), and dried over sodium sulfate. The drying agent was removed by filtration and the filtrate was concentrated under reduced pressure. The residue was purified on flash column eluting with 50:1 methylene chloride/methanol to afford 101i (1.3 g, 59%). MS: [M+H]+ 464.

Example 101j

5-Bromo-1-methyl-3-(5-(piperazin-1-yl)pyridin-2-ylamino)pyridin-2(1H)-one 101j

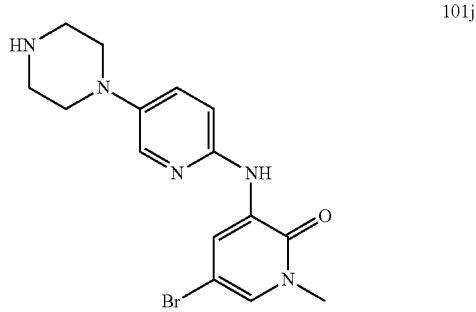 [SMILES: Cn1cc(Br)cc(Nc2ccc(N3CCNCC3)cn2)c1=O]

A mixture of 101i (3.6 g, 7.8 mmol) and 4.0 M HCl/dioxane (10 mL) was stirred for 5 h at room temperature. It was then concentrated at reduced pressure. The residue was basified with aqueous 1.0M NaOH and extracted with methylene chloride. The combined organic layers were washed with water and concentrated under reduced pressure to give 101j (2.46 g, 87%). MS: [M+H]+ 364.

Example 101k

5-Bromo-1-methyl-3-(5-(4-(oxetan-3-yl)piperazin-1-yl)pyridin-2-ylamino)pyridin-2(1H)-one 101k

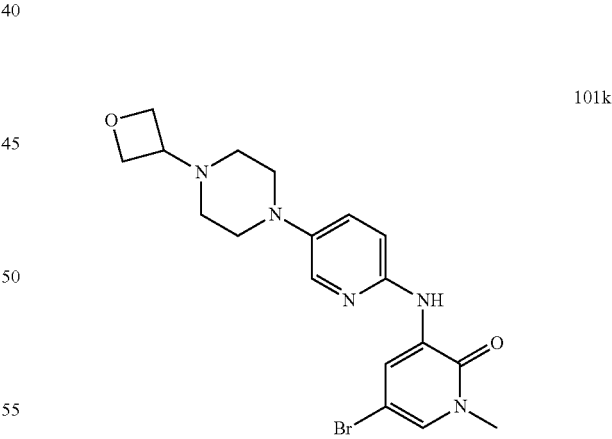

A mixture of 101j (2.75 g, 7.5 mmol), oxetan-3-one (1.6 g, 22.7 mmol), NaBH$_3$CN (4.75 g, 22.5 mmol), and zinc chloride (3 g, 22.7 mmol) in methanol (125 mL) was stirred for hours at 50° C. The mixture was added to water and extracted with methylene chloride for three times. The organic layers were concentrated under reduced pressure. The residue was purified by column chromatography eluting with 25:1 methylene chloride/methanol to give 101k (1.92 g, 61%). MS:

[M+H]⁺ 420. ¹H NMR (500 MHz, DMSO) δ 8.58 (d, J=2.5, 1H), 8.55 (s, 1H), 7.94 (d, J=3, 1H), 7.54 (d, J=2.5, 1H), 7.39 (dd, J=3, 1H), 7.25 (d, J=4, 1H), 4.56 (t, J=6.5, 2H), 4.46 (t, J=6.5, 2H), 3.50 (s, 3H), 3.43 (m, 1H), 3.01 (m, 4H), 2.40 (m, 4H).

Example 101l

1-Methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101l A 500-mL single-neck round-bottomed flask equipped with a magnetic stirrer and a reflux condenser was charged with 101k (10.5 g, 25 mmol), Pin₂B₂ (15.6 g, 2.5 eq., 62 mmol), Pd₂(dba)₃ (1.14 g, 0.05 eq., 1.25 mmol), X-phos (1.16 g, 0.1 eq., 2.5 mmol), AcOK (7.35 g, 3 eq., 75 mmol) and dioxane (150 mL). After three cycles of vacuum/argon flush, the mixture was heated to 65° C. for 14 h. It was then cooled to room temperature and filtered. The filtrate was concentrated under reduced pressure and the resulting residue was washed by PE/EA=3/1 (80 mL) to afford 101l as a yellow solid (10.5 g, 94%). MS: [M+H]⁺ 468.

Example 101m 3-(1-methyl-5-(5-(4-(oxetan-3-yl)piperazin-1-yl)pyridin-2-ylamino)-6-oxo-1,6-dihydropyridin-3-yl)-5-(1-oxo-3,4,6,7,8,9-hexahydropyrazino[1,2-a]indol-2(1H)-yl)isonicotinaldehyde 101m A sealed tube was charged with 101f (200 mg, 0.53 mmol), 101l (250 mg, 0.53 mmol), PdCl₂(dppf) (42 mg, 0.05 mmol), K₃PO₄ (210 mg, 1.0 mmol), and NaOAc (85 mg, 1.0 mmol) in acetonitrile/H₂O (8 mL/1 mL). After three cycles of vacuum/argon flush, the mixture was heated at 100° C. in a sealed tube for 4 h. It was then filtered and the filtrate was evaporated in vacuo. The residue was purified on reverse phase Combi-flash eluting with 20:1 DCM/MeOH to afford 101m (135 mg, 40%). LCMS: [M+H]⁺ 635.

Example 101

2-(4-(hydroxymethyl)-5-(1-methyl-5-(5-(4-(oxetan-3-yl)piperazin-1-yl)pyridin-2-ylamino)-6-oxo-1,6-dihydropyridin-3-yl)pyridin-3-yl)-3,4,6,7,8,9-hexahydropyrazino[1,2-a]indol-1(2H)-one 101

A mixture of 101m (135 mg, 0.21 mmol) and NaBH₄ (20 mg, 0.5 mmol) in MeOH (5 mL) was stirred at 0° C. for 0.5 h. The mixture was quenched with water and the residue was extracted with EtOAc (5 mL×2). The combined EtOAc extract was concentrated under reduced pressure and the residue was purified with reverse-phase prep-HPLC to afford 101 (55 mg, 40%). LCMS: [M+H]⁺ 637. ¹H NMR (500 MHz, DMSO) δ 8.58 (s, 1H), 8.55 (s, 1H), 8.49 (s, 1H), 8.41 (s, 1H), 7.86 (d, J=3.0, 1H), 7.38-7.37 (m, 2H), 7.25-7.23 (m, 1H), 6.54 (s, 1H), 5.16 (t, J=3.0, 1H), 4.56-4.40 (m, 6H), 4.19-4.12 (m, 3H), 3.95 (t, J=3.0, 1H), 3.60 (s, 3H), 3.43-3.41 (m, 1H), 3.06 (s, 4H), 2.57-2.61 (m, 2H), 2.45-2.48 (m, 6H), 1.78-1.80 (m, 2H), 1.69-1.70 (m, 2H)

Example 102a

1-Methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 102a

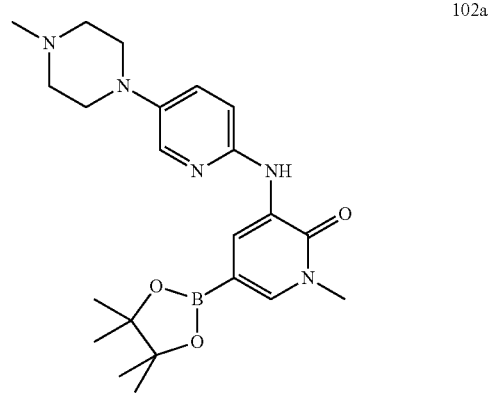 [SMILES: CN1CCN(c2ccc(Nc3cc(B4OC(C)(C)C(C)(C)O4)cn(C)c3=O)nc2)CC1]

A 1-L single-neck round-bottomed flask equipped with a magnetic stirrer and thermoregulator was purged with nitrogen and charged with 5-bromo-1-methyl-3-[5-(4-methylpiperazin-1-yl)-pyridin-2-ylamino]-1H-pyridin-2-one prepared according to US 2009/0318448, (10.0 g, 0.027 mol), bis (pinacolato)diboron (8.06 g, 0.032 mol), potassium acetate (10.4 g, 0.11 mol) and 1,4-dioxane (200 mL). After a stream of nitrogen was passed through the resulting suspension for 30 min., Pd(dppf)Cl₂·CH₂Cl₂ (582 mg, 0.795 mmol) was added. The resulting reaction mixture was stirred at reflux for 3 h. Then, it was cooled to room temperature, partitioned between water (400 mL) and ethyl acetate (600 mL) and filtered through a pad of CELITE®. The organic phase was extracted, dried over sodium sulfate, filtered and concentrated. The residue was triturated with a mixture of diethyl ether (50 mL) and hexanes (250 mL), and the suspension was filtered. The filter cake was dried under vacuum at room temperature to afford a 27% yield (3.04 g) of 1-methyl-3-[5-(4-methyl-piperazin-1-yl)-pyridin-2-ylamino]-5-(4,4,5,5-tetramethyl-[1,3,2]dioxaborolan-2-yl)-1H-pyridin-2-one 102a as a brown solid.

Example 102b 3-(1-Methyl-5-(5-(4-methylpiperazin-1-yl)pyridin-2-ylamino)-6-oxo-1,6-dihydropyridin-3-yl)-5-(1-oxo-3,4,6,7,8,9-hexahydropyrazino[1,2-a]indol-2(1H)-yl)isonicotinaldehyde 102b A sealed tube was charged with 3-bromo-5-(1-oxo-3,4,6,7,8,9-hexahydropyrazino[1,2-a]indol-2(1H)-yl)isonicotinaldehyde 101f (200 mg, 0.53 mmol), 1-methyl-3-(5-(4-methylpiperazin-1-yl)pyridin-2-ylamino)-5-(4,4,5,5-tetramethyl-1,3,2-dioxaborolan-2-yl)pyridine-2(1H)-one 102a (225 mg, 0.53 mmol), PdCl₂(dppf) (42 mg, 0.05 mmol), K₃PO₄ (210 mg, 1 mmol), and NaOAc (85 mg, 1 mmol) in acetonitrile/H2O (8 mL/1 mL). After three cycles of vacuum/argon flush, the mixture was heated at 100° C. for 4 h. It was then filtered and the filtrate was evaporated in vacuo. The residue was purified on flash column eluting with 20:1 DCM/MeOH to afford 102b (135 mg, 43%). LCMS: [M+H]⁺ 593.

Example 102

2-(4-(Hydroxymethyl)-5-(1-methyl-5-(5-(4-methylpiperazin-1-yl)pyridin-2-ylamino)-6-oxo-1,6-dihydropyridin-3-yl)pyridin-3-yl)-3,4,6,7,8,9-hexahydropyrazino[1,2-a]indol-1(2H)-one 102

A mixture of 3-(1-methyl-5-(5-(4-methylpiperazin-1-yl)pyridin-2-ylamino)-6-oxo-1,6-dihydropyridin-3-yl)-5-(1-oxo-3,4,6,7,8,9-hexahydropyrazino[1,2-a]indol-2(1H)-yl) isonicotinaldehyde 102b (135 mg, 0.22 mmol) and NaBH$_4$ (20 mg, 0.5 mmol) in MeOH (5 mL) was stirred at 0° C. for 0.5 h. The mixture was quenched with water and the residue was extracted with EtOAc (5 mL×2). The combined EtOAc extract was concentrated under reduced pressure and the residue was purified with reverse-phase prep-HPLC to afford 102 (18 mg, 20%). LCMS: [M+H]$^+$ 595. $^1$H NMR (500 MHz, DMSO) δ 8.59 (s, 1H), 8.55 (s, 1H), 8.49 (s, 1H), 8.45 (s, 1H), 7.87 (s, 1H), 7.37-7.38 (m, 2H), 7.23-7.25 (m, 1H), 6.54 (s, 1H), 5.16 (t, J=3.0, 1H), 4.40 (s, 2H), 4.14-4.18 (m, 3H), 3.93-3.95 (m, 1H), 3.60 (s, 3H), 3.09 (s, 4H), 2.60-2.61 (m, 6H), 2.48-2.34 (m, 5H), 1.78-1.79 (m, 2H), 1.69-1.70 (m, 2H)

Example 103a

2-Bromo-4-chloronicotinaldehyde 103a

To a solution of 2-bromo-4-chloropyridine (1.6 g, 8.0 mmol) in anhydrous tetrahydrofuran (40 mL) cooled at –70° C. was added the solution of lithium diisopropyl-amide (5.0 mL, 10.0 mmol, 2.0 M) over a period of 5 minutes and stirred at –70° C. for another 1 h. Anhydrous DMF (1.3 g) was introduced over a period of 3 minutes and the mixture was stirred for another 30 minutes. It was then quenched with saturated NH$_4$Cl (30 mL) and extracted with ethyl acetate (20 mL×3). The combined organic layer was dried over anhydrous Mg$_2$SO$_4$, filtered, and evaporated under reduced pressure. The residue was purified by silica-gel column chromatography eluting with petroleum ether/ethyl acetate (20:1) to afford 103a as a yellow solid (900 mg, 48%). $^1$H NMR (500 MHz, DMSO) δ 10.21 (s, 1H), 8.52 (d, J=5.5 Hz, 1H), 7.79 (d, J=5.0 Hz, 1H).

Example 103b

4-Chloro-2-(1-oxo-3,4,6,7,8,9-hexahydropyrazino[1,2-a]indol-2(1H)-yl)nicotinaldehyde 103b A 100-mL single-neck round-bottomed flask equipped with a magnetic stirrer and a reflux condenser was charged with 103a (800 mg, 3.5 mmol), 3,4,6,7,8,9-hexahydropyrazino[1,2-a]indol-1(2H)-one 101e (665 mg, 3.5 mmol), tris(dibenzylideneacetone)dipalladium(0) (320 mg, 0.35 mmol), XantPhos (400 mg, 0.7 mmol), Cs$_2$CO$_3$ (2.3 g, 7.0 mmol), and 1,4-dioxane (20 mL). After three cycles of vacuum/argon flush, the mixture was heated at 90° C. for 5 h. It was then cooled to room temperature and filtered. The filtrate was concentrated under reduced pressure and the resulting residue was purified by silica-gel column chromatography eluting with dichloromethane/methanol (80:1) to afford 103b as a yellow solid (1.2 g, 50%). MS: [M+H]$^+$ 330.

Example 103c 4-(1-Methyl-5-(5-(4-(oxetan-3-yl)piperazin-1-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)nicotinaldehyde 103c A 100-mL single-neck round-bottomed flask equipped with a magnetic stirrer and a reflux condenser was charged with 103b (600 mg, 1.0 mmol), 1-methyl-3-(5-(4-(oxetan-3-yl)piperazin-1-yl)pyridin-2-ylamino)-5-(4,4,5,5-tetramethyl-1,3,2-dioxa-borolan-2-yl)pyridin-2(1H)-one 101l (468 mg, 1.0 mmol), Pd(dppf)Cl$_2$ (81 mg, 0.1 mmol), K$_3$PO$_4$.3H$_2$O (678 mg, 3.0 mmol), and tetrahydrofuran (20 mL). After three cycles of vacuum/argon flush, the mixture was heated at reflux for 4 h. It was then cooled to room temperature and filtered. The filtrate was concentrated under reduced pressure and the resulting residue was purified by silica-gel column chromatography eluting with dichloromethane/methanol (40:1) to afford 103c as yellow solid (510 mg, 73%). MS: [M+H]$^+$ 635.

Example 103

2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 103

To the solution of 103c (500 mg, 0.8 mmol) in methanol (50 mL) was added sodium borohydride (91 mg, 2.4 mmol) at 0° C. and stirred for another 30 minutes. Then the reaction mixture was quenched with water (3 mL) and concentrated. The residue was purified with reverse-phase prep-HPLC to afford 103 (224 mg, 45%). LCMS: [M+H]$^+$ 637. $^1$H NMR (500 MHz, DMSO) δ 8.61 (d, J=3.0, 1H), 8.48 (d, J=6.0, 1H), 7.92 (d, J=3.5, 1H), 7.81 (d, J=3.0, 1H), 7.78 (s, 1H), 7.38 (d, J=6.0, 1H), 7.24-7.27 (m, 1H), 6.88 (s, 1H), 6.81 (d, J=11.5, 1H), 5.01-5.04, (m, 1H), 4.60-4.71 (m, 5H), 4.32-4.49 (m, 2H), 3.83-4.15 (m, 3H), 3.70 (s, 3H), 3.53-3.59 (m, 1H), 3.13-3.16 (m, 4H), 2.55-2.61 (m, 4H), 2.49-2.52 (m, 4H), 1.78-1.90 (m, 4H)

Example 104a

4-Bromo-2-chloronicotinaldehyde 104a

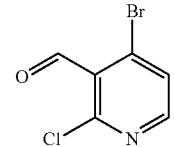

To a solution of 4-bromo-2-chloropyridine (12.0 g, 60.0 mmol) in anhydrous tetrahydrofuran (300 mL) cooled at –70° C. was added the solution of lithium diisopropylamide (30.0 mL, 60.0 mmol, 2.0 M) over a period of 30 minutes and stirred for another at –70° C. 2 h. Anhydrous DMF (12.0 g) was introduced over a period of 10 minutes and stirred for another 30 minutes. It was then quenched with saturated NaHCO$_3$ (200 mL), extracted with ethyl acetate (100 mL×3). The combined organic layer was dried over anhydrous Mg$_2$SO$_4$, filtered, and evaporated under reduced pressure. The residue was purified by silica-gel column chromatography eluting with petroleum ether/ethyl acetate (20:1) to afford 104a as a yellow solid (4.0 g, 29%). $^1$H NMR (500 MHz, DMSO) δ 10.23 (s, 1H), 8.44 (d, J=5.5 Hz, 1H), 7.94 (d, J=5.5 Hz, 1H).

Example 104b

2-Chloro-4-(1-oxo-3,4,6,7,8,9-hexahydropyrazino[1,2-a]indol-2(1H)-yl)nicotinaldehyde 104b

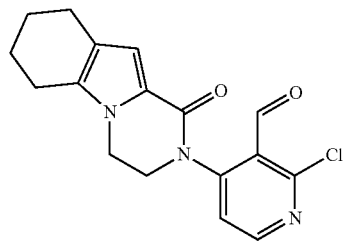 [SMILES: O=Cc1c(N2CCn3c(cc4c3CCCC4)C2=O)ccnc1Cl]

A 100-mL single-neck round-bottomed flask equipped with a magnetic stirrer and a reflux condenser was charged with 104a (1.1 g, 5.0 mmol), 3,4,6,7,8,9-hexahydropyrazino[1,2-a]indol-1(2H)-one 101e (477 mg, 2.5 mmol), tris(dibenzylideneacetone)dipalladium(0) (230 mg, 0.25 mmol), XantPhos (430 mg, 0.75 mmol), $Cs_2CO_3$ (1.6 g, 5.0 mmol), and 1,4-dioxane (50 mL). After three cycles of vacuum/argon flush, the mixture was heated at 65° C. for 2 h. It was then cooled to room temperature and filtered. The filtrate was concentrated under reduced pressure and the resulting residue was purified by silica-gel column chromatography eluting with dichloromethane/methanol (40:1) to afford 104b as a yellow solid (1.1 g, 80%). MS: $[M+H]^+$ 330.

Example 104c 2-(1-Methyl-5-(5-(4-(oxetan-3-yl)piperazin-1-yl)pyridin-2-ylamino)-6-oxo-1,6-dihydropyridin-3-yl)-4-(1-oxo-3,4,6,7,8,9-hexahydropyrazino[1,2-a]indol-2(1H)-yl)nicotinaldehyde 104c A 100-mL single-neck round-bottomed flask equipped with a magnetic stirrer and a reflux condenser was charged with 104b (658 mg, 1.0 mmol), 1-methyl-3-(5-(4-(oxetan-3-yl)piperazin-1-yl)pyridin-2-ylamino)-5-(4,4,5,5-tetramethyl-1,3,2-dioxa-borolan-2-yl)pyridin-2(1H)-one 101l (622 mg, 2.0 mmol), Pd (dppf) $Cl_2$ (65 mg, 0.08 mmol), $K_3PO_4 \cdot 3H_2O$ (361 mg, 1.6 mmol), and tetrahydrofuran (40 mL). After three cycles of vacuum/argon flush, the mixture was heated at reflux for 4 h. It was then cooled to room temperature and filtered. The filtrate was concentrated under reduced pressure and the resulting residue was purified by silica-gel column chromatography eluting with dichloromethane/methanol (40:1) to afford 104c as a yellow solid (400 mg, 63%). MS: $[M+H]^+$ 635.

Example 104

2-(3-(Hydroxymethyl)-2-(1-methyl-5-(5-(4-(oxetan-3-yl)piperazin-1-yl)pyridin-2-ylamino)-6-oxo-1,6-dihydropyridin-3-yl)pyridin-4-yl)-3,4,6,7,8,9-hexahydropyrazino[1,2-a]indol-1(2H)-one 104

To the solution of 104c (360 mg, 0.6 mmol) in methanol (50 mL) was added sodium borohydride (70 mg, 1.8 mmol) at 0° C. and stirred for another 30 minutes. Then the reaction mixture was quenched with water (2 mL) and concentrated. The residue was purified with reverse-phase prep-HPLC to afford 104 (63 mg, 16%) as an off-white solid. LCMS: $[M+H]^+$ 637. $^1$H NMR (500 MHz, DMSO) δ 8.70 (d, J=3.0, 1H), 8.65 (d, J=5.5, 1H), 8.34 (s, 1H), 7.85 (d, J=3.0, 1H), 7.60 (d, J=2.5, 1H), 7.36-7.37 (m, 2H), 7.22-7.23 (m, 1H), 6.56 (s, 1H), 5.12 (t, J=5.5, 1H), 4.55-4.56 (m, 2H), 4.43-4.45 (m, 4H), 4.14-4.16 (m, 3H), 3.93-3.95 (m, 1H), 3.60 (s, 3H), 3.43-3.44 (m, 1H), 3.05-3.08 (m, 4H), 2.61-2.63 (m, 2H), 2.46-2.47 (m, 2H), 2.36-2.39 (m, 4H), 1.68-1.78 (m, 4H).

Example 105a

N-Methoxy-N-methyl-4,5,6,7-tetrahydrobenzo[b]thiophene-2-carboxamide 105a

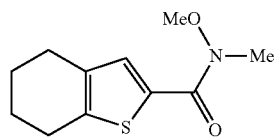

A 250-mL single-neck round-bottomed flask equipped with a magnetic stirrer was purged with nitrogen, charged with 4,5,6,7-tetrahydrobenzo[b]thiophene-2-carboxylic acid (3.00 g, 16.5 mmol), methylene chloride (80 mL), and DMF (60 mg, 0.825 mmol) and cooled to 0° C. To the resulting solution, oxalyl chloride (2.31 g, 18.2 mmol) was added dropwise. After this addition was complete, the reaction was warmed to room temperature and stirred for 2 h. After this time, the reaction was concentrated to dryness under reduced pressure. The resulting white solid was dissolved in methylene chloride (80 mL) and the solution cooled to 0° C. Triethylamine (5.00 g, 49.5 mmol) and N,O-dimethylhydroxylamine (1.61 g, 16.5 mmol) were then added. After the addition was complete, the cooling bath was removed, and the reaction mixture was stirred at room temperature for 16 h. After this time, the reaction mixture was partitioned between water (100 mL) and ethyl acetate (200 mL). The layers were separated, and the aqueous phase was extracted with ethyl acetate (100 mL). The combined organic extracts were washed with water (100 mL), followed by brine (100 mL) and dried over sodium sulfate. The drying agent was removed by filtration, and the solvent was evaporated under reduced pressure. The resulting residue was purified by flash chromatography to afford an 88% yield of 105a (3.29 gm) as a white solid: mp 36-37° C.; $^1$H NMR (500 MHz, CDCl$_3$) δ 7.79 (s, 1H), 3.76 (s, 3H), 3.34 (s, 3H), 2.78 (t, 2H, J=6.0 Hz), 2.62 (t, 2H, J=6.0 Hz), 1.82 (m, 4H); MS (APCI+) m/z 226.3 (M+H)

Example 105b

3-Chloro-1-(4,5,6,7-tetrahydrobenzo[b]thiophen-2-yl)propan-1-one 105b

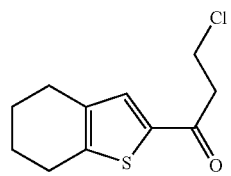

A 100-mL single-necked round-bottomed flask equipped with a magnetic stirrer was purged with nitrogen and charged with 105a (2.70 g, 12.0 mmol) and anhydrous THF (45 mL), and the solution was cooled to −10° C. with acetone/ice bath.

A 1.0 M solution of vinylmagnesium bromide in THF (13.2 mL, 13.2 mmol) was added dropwise, and the resulting reaction mixture was stirred at 0° C. for 4 h. After this time, the reaction mixture was partitioned between ethyl acetate (100 mL) and 2 M aqueous hydrochloric acid (40 mL). The layers were separated, and the aqueous phase was extracted with ethyl acetate (40 mL). The combined organic extracts were washed with water (100 mL), followed by brine (100 mL), dried over sodium sulfate, filtered and concentrated under reduced pressure. The resulting residue was dissolved in methylene chloride (30 mL), and a 2 M solution of hydrogen chloride in diethyl ether (15 mL) was added. After stirring at room temperature for 1 h, the solvents were removed under reduced pressure. Purification of the resulting residue by column chromatography afforded a 29% yield (804 mg) of 105b as an off-white solid: mp 57-58° C.; $^1$H NMR (500 MHz, CDCl$_3$) δ 7.41 (s, 1H), 3.89 (t, 2H, J=7.0 Hz), 3.30 (t, 2H, J=7.0 Hz), 2.81 (t, 2H, J=6.0 Hz), 2.64 (t, 2H, J=6.0 Hz), 1.83 (m, 4H); MS (ECI+) m/z 229.1 (M+H)

Example 105c 5,6,7,8-Tetrahydro-1H-benzo[b]cyclopenta[d]thiophen-3(2H)-one 105c

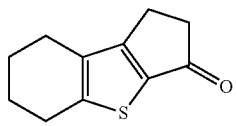

105c

A 50-mL single-necked round-bottomed flask equipped with a magnetic stirrer was charged with 105b (800 mg, 3.51 mmol) and 98% sulfuric acid (8 mL). After stirring at 95° C. for 16 h, the reaction mixture was poured into ice (50 g), and the resulting suspension was extracted with ethyl acetate (3×50 mL). The organic extracts were combined, dried over sodium sulfate, filtered and concentrated under reduced pressure. The resulting residue was purified by flash chromatography to afford 105c in 47% yield (320 mg) as an off-white solid: mp 75-76° C.; $^1$H NMR (500 MHz, CDCl$_3$) δ 2.89 (m, 2H), 2.87-2.83 (m, 4H), 2.56 (t, 2H, J=6.5 Hz), 1.84 (m, 4H)

Example 105d 5,6,7,8-Tetrahydro-1H-benzo[b]cyclopenta[d]thiophen-3(2H)-one oxime 105d

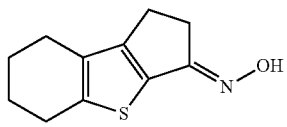

105d

A 100-mL single-neck round-bottomed flask equipped with a mechanical stirrer and nitrogen inlet was charged with hydroxylamine hydrochloride (573 mg, 8.25 mmol) and methanol (10 mL). The mixture was cooled to 0° C. using an ice bath. Sodium acetate (677 mg, 8.25 mmol) was added. The mixture was stirred at 0° C. for 30 min. After this time, 105c (319 mg, 1.65 mmol) was added, and the reaction was stirred at room temperature for 16 h. After this time, the mixture was concentrated, and the resulting residue was triturated with water (10 mL). The resulting solid was collected and dried in a vacuum oven at 45° C. to afford an 84% yield (287 mg) of 105d as an off-white solid: mp 173-174° C.; $^1$H NMR (500 MHz, DMSO-d$_6$) δ 10.38 (s, 1H), 2.97 (m, 2H), 2.77-2.73 (m, 4H), 2.47 (m, 2H), 1.75 (m, 4H); MS (APCI+) m/z 208.3 (M+H)

Example 105e 3,4,5,6,7,8-Hexahydrobenzothieno[2,3-c]pyridin-1(2H)-one 105e

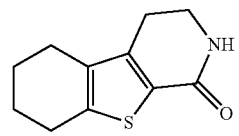

105e

A 50-mL single-neck round-bottomed flask equipped with a reflux condenser, magnetic stirrer and nitrogen inlet was charged with 105d (285 mg, 1.38 mmol) and polyphosphoric acid (15 g). After stirring at 80° C. for 16 h, the reaction mixture was cooled to room temperature, and water (30 mL) was added. The resulting mixture was stirred for 30 min and filtered. The filter cake was washed with water (20 mL) and dried in a vacuum oven at 45° C. to afford a 75% yield (215 mg) of 105e as an off-white solid: mp 203° C. dec; $^1$H NMR (500 MHz, CDCl$_3$) δ 5.62 (s, 1H), 3.59 (t, 2H, J=7.0 Hz), 2.81 (t, 2H, J=6.0 Hz), 2.72 (t, 2H, J=7.0 Hz), 2.48 (t, 2H, J=6.0 Hz), 1.84 (m, 4H). MS (APCI+) m/z 208.3 (M+H)

Example 105f

3-Bromo-5-{6-oxo-8-thia-5-azatricyclo[7.4.0.0$^{2,7}$]trideca-1(9),2(7)-dien-5-yl}pyridine-4-carbaldehyde 105f

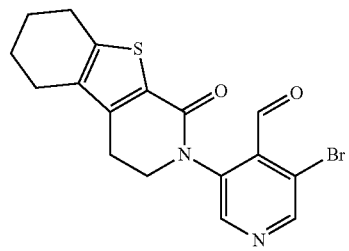 [SMILES: O=Cc1c(Br)cncc1N1CCc2c(sc3c2CCCC3)C1=O]

To a 100-mL single-neck round-bottomed flask equipped with a magnetic stirrer and reflux condenser was charged with 1,4-dioxane (15 mL), 3,5-dibromoisonicotin-aldehyde (400 mg, 1.5 mmol), 8-thia-5-azatricyclo[7.4.0.0$^{2,7}$]trideca-1(9),2(7)-dien-6-one 105e (146 mg, 0.76 mmol), and cesium carbonate (176 mg, 1.5 mmol). Xantphos (40 mg, 0.08 mmol) and Pd$_2$(dba)$_3$ (70 mg, 0.08 mmol) were added, and the reaction mixture was heated at 100° C. for 5 h. After this time the reaction was cooled to room temperature and filtered. The filtrate was concentrated under reduced pressure and the residue was purified on flash column eluting with DCM:MeOH (20:1) to afford 105f (200 mg, 70%). MS: [M+H]+ 377.

Example 105g

3-[1-Methyl-5-({5-[4-(oxetan-3-yl)piperazin-1-yl]pyridine-2-yl}amino)-6-oxo-1,6-dihydropyridin-3-yl]-5-{6-oxo-8-thia-5-azatricyclo[7.4.0.0²,⁷]trideca-1(9),2(7)-dien-5-yl}pyridine-4-carbaldehyde 105g

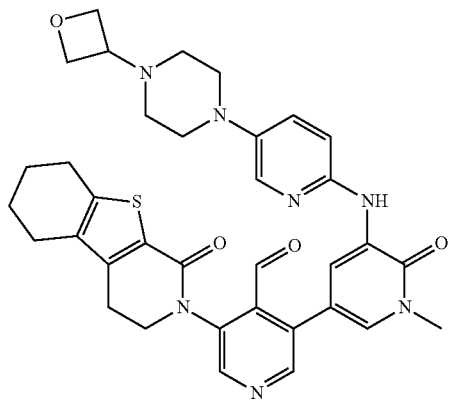 [SMILES: Cn1cc(-c2cncc(N3CCc4c(sc5c4CCCC5)C3=O)c2C=O)cc(Nc2ccc(N3CCN(C4COC4)CC3)cn2)c1=O]

A sealed tube was charged with 105f (200 mg, 0.53 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 10I1 (240 mg, 0.51 mmol), PdCl₂(dppf) (42 mg, 0.05 mmol), K₃PO₄ (230 mg, 1 mmol), and NaOAc (80 mg, 1 mmol) in CH₃CN (5 mL) and H₂O (1.5 mL). The system was evacuated and refilled with N₂. The reaction mixture was heated at 100° C. for 2 h. It was then cooled to room temperature and filtered. The filtrate was concentrated under reduced pressure and the resulting residue was purified by flash column chromatography eluting with 10:1 of DCM/MeOH to afford 105g in 40% yield (138 mg) as a pale yellow solid. MS: [M+H]+ 638.

Example 105

4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{6-oxo-8-thia-5-azatricyclo-[7.4.0.0²,⁷]trideca-1(9),2(7)-dien-5-yl}pyridine 105

To a solution of 3-[1-methyl-5-({5-[4-(oxetan-3-yl)piperazin-1-yl]pyridine-2-yl}amino)-6-oxo-1,6-dihydropyridin-3-yl]-5-{6-oxo-8-thia-5-azatricyclo[7.4.0.0²,⁷]trideca-1(9),2(7)-dien-5-yl}pyridine-4-carbaldehyde 105g (130 mg, 0.20 mmol) in methanol (5 mL) at 0° C. was added sodium borohydride (22 mg, 0.6 mmol) and stirred for 30 minutes. Then the reaction mixture was quenched with water (1.0 mL) and concentrated. The residue was purified by reverse-phase prep-HPLC to afford 105 (90 mg, 65%). LCMS: [M+H]+: 654. ¹H NMR (500 MHz, DMSO) δ 8.58 (d, J=2.0, 1H), 8.56 (s, 1H), 8.49 (s, 1H), 8.41 (s, 1H), 7.86 (s, 1H), 7.36 (m, 2H), 7.24-7.22 (m, 1H), 5.14 (t, J=3.0, 1H), 4.56-4.42 (m, 6H), 4.08-3.90 (m, 2H), 3.60 (s, 3H), 3.43 (d, J=3.5, 1H), 3.07 (s, 4H), 2.89-2.79 (m, 4H), 2.55-2.53 (m, 2H), 2.39-2.37 (m, 4H), 1.80-1.81 (m, 4H)

Example 106a 3,3-Dimethylcyclopentanone 106a

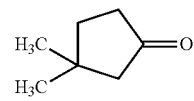

A 1-L three-neck round-bottomed flask equipped with a magnetic stirrer, addition funnel and nitrogen inlet was purged with nitrogen and charged with ether (200 mL) and copper (I) iodide (54.46 g, 0.286 mol). The mixture was cooled to 0° C., methyllithium (1.6 M in ether, 357.5 mL, 0.572 mol) was added dropwise to the reaction mixture over 1.5 h and stirred at 0° C. for additional 2 h. After this time a solution of 3-methylcyclo-pent-2-enone (25 g, 0.260 mol) in ether (150 mL) was added dropwise over 1.5 h. The reaction mixture was then stirred at 0° C. for 2 h and poured into sodium sulfate deca-hydrate (300 g). The resulting mixture was stirred for 30 min. After this time the mixture was filtered and washed with ether (1000 mL). The filtrate was concentrated and distilled under reduced pressure to afford a 70% yield (20.5 g) of 3,3-dimethylcyclo-pentanone 106a as a colorless liquid: by 50-55° C. (at 10 mmHg); ¹H NMR (300 MHz, CDCl₃) δ 2.31 (t, 2H, J=7.8 Hz), 2.05 (s, 2H), 1.79 (t, 2H, J=7.8 Hz); MS (ESI+) m/z 113.3 (M+H)

Example 106b

Ethyl 5,5-Dimethyl-5,6-dihydro-4H-cyclopenta[b]thiophene-2-carboxylate 106b

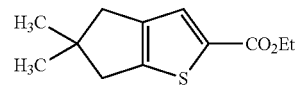

A 500-mL three-neck round-bottomed flask equipped with a magnetic stirrer, reflux condenser, addition funnel and nitrogen inlet was purged with nitrogen and charged with DMF (9.49 g, 0.100 mol) and methylene chloride (100 mL). The reaction mixture was cooled to 0° C. and phosphorus oxychloride (14.1 g, 0.920 mol) was added dropwise to the reaction over 30 min. Once this addition was complete, the reaction was warmed to room temperature and stirred for 1 h. After this time a solution of 106a (11.2 g, 0.100 mol) in methylene chloride (100 mL) was added dropwise over 1 h. The reaction was then stirred at reflux for 18 h. The reaction mixture was cooled to room temperature and poured into a mixture of crushed ice (400 mL) and sodium acetate (100 g, 1.22 mol). The resulting mixture was stirred for 45 min. After this time the aqueous layer was separated and extracted with methylene chloride (2×500 mL). The combined organic layers were then washed with water (2×200 mL), followed by brine (200 mL) and dried over sodium sulfate. The drying agent was then removed by filtration, and the filtrate was concentrated to afford crude product 2-chloro-4,4-dimethylcyclopent-1-enecarbaldehyde which was placed in a 500-mL three-neck round bottomed flask equipped with a mechanical stirrer, reflux condenser and nitrogen inlet. Methylene chloride (200 mL), ethyl 2-mercaptoacetate (11.0 g, 0.092 mol) and triethylamine (30 g, 0.207 mol) were then added. The reaction mixture was then stirred at reflux for 6 h. After this time the reaction was cooled to room temperature and concentrated to a thick orange residue. Ethanol (200 mL) and triethylamine (30.0 g, 0.207 mol) were added and the reaction was heated at reflux for 12 h. The reaction was then cooled to room temperature and concentrated under reduced pressure and the resulting residue was diluted with ether (600 mL). The resulting mixture was washed with 1 M hydrochloric acid (150 mL), brine (100 mL), dried over sodium sulfate, filtered and concentrated under reduced pressure. The resulting residue was purified by flash chromatography to afford 106b in 34% yield (7.70 g) as a colorless liquid: $^1$H NMR (300 MHz, CDCl$_3$) δ 7.48 (s, 1H), 4.33 (q, 2H, J=7.2 Hz), 2.72 (s, 2H), 2.56 (s, 2H), 1.38 (t, 3H, J=1.8 Hz), 1.17 (s, 6H); MS (ESI+) m/z 225.1

Example 106c 5,5-Dimethyl-5,6-dihydro-4H-cyclopenta[b]thiophene-2-carboxylic acid 106c

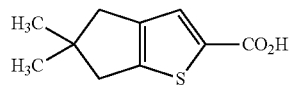

106c

In a 250-mL single-neck round-bottomed flask equipped with a magnetic stirrer and reflux condenser, 106b (4.00 g, 17.8 mmol) was dissolved in ethanol (50 mL). THF (50 mL), water (50 mL) and lithium hydroxide (854 mg, 35.6 mmol) were added, and the mixture was stirred at 60° C. for 4 h. After this time the reaction was cooled to room temperature and acidified with 2M hydrochloric acid to pH 1.5, and then extracted with ethyl acetate (2×200 mL). The organic layers were combined, washed with water (2×100 mL), followed by brine (100 ml) and dried over sodium sulfate. The drying agent was then separated by filtration. After evaporating the resulting filtrate, 106c was obtained in 91% yield (3.2 g) as a white solid: mp 170-172° C.; $^1$H NMR (300 MHz, CDCl$_3$) δ 12.77 (s, 1H), 7.46 (s, 1H), 2.71 (s, 2H), 2.53 (s, 2H), 1.20 (s, 6H); MS (ESI−) m/z 195.0

Example 106d 5,5-Dimethyl-5,6-dihydro-4H-cyclopenta[b]thiophene-2-carboxylic acid 106d

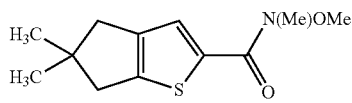

106d

A 100-mL single-neck round-bottomed flask equipped with a magnetic stirrer, reflux condenser and a bubbler placed on the condenser was charged with 106c (2.30 g, 11.6 mmol), toluene (25 mL), thionyl chloride (4.09 g, 34.9 mmol) and DMF (1 drop). The mixture was heated at reflux for 1 h and then evaporated under reduced pressure on a rotary evaporator at 45° C. The resulting acid chloride was diluted with methylene chloride (20 mL).

In a separate 250-mL three-neck round-bottomed flask equipped with a magnetic stirrer N,O-dimethylhydroxylamine hydrochloride (2.26 g, 23.2 mmol) and N,N-diisopropylethylamine (2.97 g, 23.0 mmol) were dissolved in anhydrous methylene chloride (20 mL) under nitrogen, and the solution was cooled to 0° C. in an ice/water bath. The solution of the acid chloride was added, and the reaction mixture was stirred at room temperature for 18 h. The reaction mixture was extracted with water (100 mL), 10% aqueous citric acid (50 mL) and a 1:1 mixture of saturated aqueous sodium bicarbonate and water (100 mL). The organic layer was dried over sodium sulfate and evaporated under reduced pressure on a rotary evaporator to afford a 93% yield (2.60 g) of 106d as a light yellow solid: $^1$H NMR (300 MHz, CDCl$_3$) δ 7.66 (s, 1H), 3.77 (s, 3H), 3.35 (s, 3H), 2.74 (s, 2H), 2.58 (s, 2H), 1.23 (s, 6H)

Example 106e

3-Chloro-1-(5,5-dimethyl-5,6-dihydro-4H-cyclopenta[b]thiophen-2-yl)propan-1-one 106e

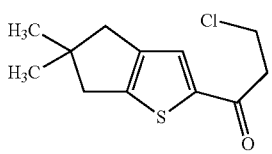

106e

A 100-mL single-neck round-bottomed flask equipped with a magnetic stirrer was purged with nitrogen and charged with 106d (2.41 g, 10.0 mmol) and anhydrous THF (20 mL). The solution was cooled to −70° C., and 1 M vinylmagnesium bromide in THF (11 mL, 11.0 mmol) was added with the reaction temperature maintained below −60° C. The reaction mixture was stirred at −13 to −7° C. for 2 h and then warmed to room temperature over 30 min. The reaction was again cooled to −70° C., and a 2 M solution of hydrogen chloride in ether (22.5 ml, 45 mmol) was added. The reaction was then stored in a freezer at −10° C. overnight. After this time the mixture was evaporated under reduced pressure on a rotary evaporator, and the resulting residue partitioned between water (100 mL) and ether (100 mL). The ether extract was dried over sodium sulfate and evaporated under reduced pressure on a rotary evaporator to afford crude 106e (2.86 g, 118%) as a brown oil with approximately 75% purity (by NMR): $^1$H NMR (300 MHz, CDCl$_3$) δ 7.45 (s, 1H), 3.89 (t, 2H, J=6.9 Hz), 3.30 (t, 2H, J=6.9 Hz), 2.75 (s, 2H), 2.59 (s, 2H), 1.24 (s, 6H)

Example 106f 6,6-Dimethyl-1,2,6,7-tetrahydrodicyclopenta[b,d]thiophen-3(5H)-one 106f

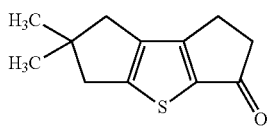

106f

A 100-mL single-neck round-bottomed flask equipped with a magnetic stirrer was charged with crude 106e (2.86 g, 10.0 mmol presuming quantitative yield) and 98% sulfuric acid. The reaction mixture was heated in a 90° C. oil bath overnight. The reaction mixture was placed into an ice/acetone bath, and a cold (5° C.) solution of dipotassium hydrogen phosphate (105 g, 0.603 mol) in water (300 mL) was added in one portion. The resulting mixture was shaken with ethyl acetate (300 mL) and filtered. The filter cake was washed with ethyl acetate (100 mL). The ethyl acetate layer of the filtrate was separated, dried over sodium sulfate and evaporated under reduced pressure on a rotary evaporator. the resulting residue was purified by flash column chromatography (silica, 80:20 hexanes/ethyl acetate) to afford 106f in 37% yield over two steps (683 mg) as an amorphous brown solid: mp 60-62° C.; $^1$H NMR (500 MHz, CDCl$_3$) δ 2.92-2.87 (m, 4H), 2.79 (s, 2H), 2.53 (s, 2H), 1.26 (s, 6H); LCMS (ESI+) m/z 207.0 (M+H)

Example 106g 6,6-Dimethyl-1,2,6,7-tetrahydrodicyclopenta[b,d]thiophen-3(5H)-one 106g

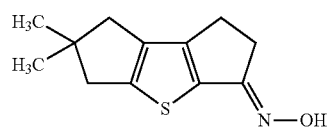

A 250-mL single-neck round-bottomed flask equipped with a magnetic stirrer and nitrogen inlet was charged with hydroxylamine hydrochloride (688 mg, 9.90 mmol), sodium acetate (812 mg, 9.90 mmol) and methanol (10 mL), and the mixture at room temperature for 30 min. After this time, a solution of 106f (680 mg, 3.30 mmol) was added dropwise at room temperature, and the reaction was stirred at room temperature for 14 h under nitrogen atmosphere. Since the reaction was not complete, hydroxylamine hydrochloride (1.15 g, 16.5 mmol) and sodium acetate (1.35 g, 16.5 mmol) were added, and the stirring was continued at room temperature for 58 h. After this time, the mixture was diluted with methylene chloride (150 mL) and water (100 mL), and the layers were separated. The organic layer was washed with brine (50 mL) and dried over sodium sulfate. The drying agent was removed by filtration and the filtrate was concentrated to afford crude 106g in quantitative yield (730 mg) as a yellow semi-solid which was used in the next step without purification: mp 122-124° C.; $^1$H NMR for major isomer (500 MHz, CDCl$_3$) δ 3.13-3.11 (m, 2H), 2.85-2.83 (m, 2H), 2.77 (s, 2H), 2.49 (s, 2H), 1.24 (s, 6H); MS (ESI+) m/z 222.0 (M+H)

Example 106h 6,6-Dimethyl-3,4,6,7-tetrahydro-5H-cyclopenta[4,5]thieno[2,3-c]pyridine-1(2H)-one 106h

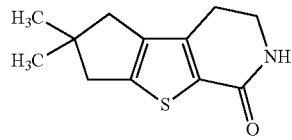

A 100-mL three-neck round-bottomed flask equipped with a reflux condenser, mechanical stirrer and nitrogen inlet was charged with 106g (700 mg, 3.16 mmol) and polyphosphoric acid (25 g). The reaction mixture was stirred at 80° C. for 13 h under nitrogen atmosphere. After this time, the mixture was cooled to 0° C. and water (50 mL) was added dropwise carefully maintaining the internal temperature between 10-45° C. The mixture was diluted with 90:10 methylene chloride/methanol (100 mL) and the layers were separated. The aqueous layer was extracted with 90:10 methylene chloride/methanol (50 mL), and the combined organic layers were washed with saturated aqueous sodium bicarbonate (50 mL), brine (150 mL) and dried over sodium sulfate. The drying agent was removed by filtration. The filtrate was concentrated under reduced pressure, and the resulting residue was purified by flash column chromatography (silica, 95:5 methylene chloride/methanol) to afford 6,6-dimethyl-3,4,6,7-tetrahydro-5H-cyclopenta[4,5]thieno[2,3-c]pyridine-1(2H)-one 106h in 90% yield (630 mg) as an amorphous off-white solid: mp 205-207° C.; $^1$H NMR (500 MHz, CDCl$_3$) δ 5.51 (s, 1H), 3.60-3.56 (m, 2H), 2.76-2.73 (m, 4H), 2.49 (s, 2H), 1.26 (s, 6H); MS (ESI+) m/z 222.0 (M+H)

Example 106i

3-Bromo-5-{4,4-dimethyl-9-oxo-7-thia-10-azatricyclo[6.4.0.0$^{2,6}$]dodeca-1(8), 2(6)-dien-10-yl}pyridine-4-carbaldehyde 106i

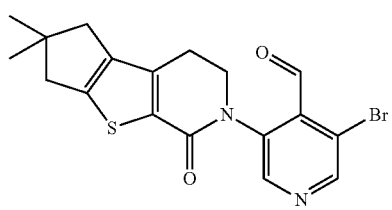

To a 100-mL single-neck round-bottomed flask equipped with a magnetic stirrer and reflux condenser was charged with 1,4-dioxane (15 mL), 3,5-dibromoisonicotin-aldehyde (400 mg, 1.5 mmol), 4,4-dimethyl-7-thia-10-azatricyclo[6.4.0.0$^{2,6}$]dodeca-1(8),2(6)-dien-9-one (106h) (170 mg, 0.76 mmol), and cesium carbonate (176 mg, 1.5 mmol). Xantphos (40 mg, 0.08 mmol) and Pd$_2$(dba)$_3$ (70 mg, 0.08 mmol) were added, and the reaction mixture was heated at 100° C. for 5 h. After this time the reaction was cooled to room temperature and filtered. The filtrate was concentrated under reduced pressure and the residue was purified on flash column eluting with DCM:MeOH (20:1) to afford 106i (200 mg, 65%). MS: [M+H]$^+$ 405.

Example 106j

3-[1-Methyl-5-({5-[4-(oxetan-3-yl)piperazin-1-yl]pyridine-2-yl}amino)-6-oxo-1,6-dihydropyridin-3-yl]-5-{4,4-dimethyl-9-oxo-7-thia-10-azatricyclo[6.4.0.0$^{2,6}$]dodeca-1(8), 2(6)-dien-10-yl}pyridine-4-carbaldehyde 106j

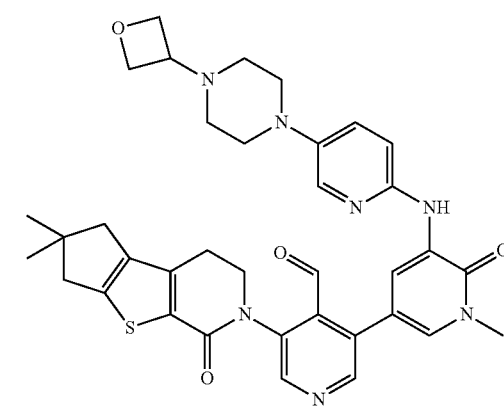

A sealed tube was charged with 106i (200 mg, 0.50 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 10ll (240 mg, 0.51 mmol), PdCl$_2$(dppf) (42 mg, 0.05 mmol), K$_3$PO$_4$ (230 mg, 1 mmol), and NaOAc (80 mg, 1 mmol) in CH₃CN (5 mL) and H₂O (1.5 mL). The system was evacuated and refilled with N₂. The reaction mixture was heated at 100° C. for 2 h. It was then cooled to room temperature and filtered. The filtrate was concentrated under reduced pressure and the resulting residue was purified by flash column chromatography eluting with 10:1 DCM/MeOH to afford 106j (130 mg, 40%) as a pale yellow solid. MS: [M+H]⁺ 666.

Example 106

4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{4,4-dimethyl-9-oxo-7-thia-10-azatricyclo[6.4.0.0$^{2,6}$]dodeca-1(8), 2(6)-dien-10-yl}pyridine-4-carbaldehyde 106

To a solution of 106j (130 mg, 0.20 mmol) in methanol (5 mL) at 0° C. was added sodium borohydride (22 mg, 0.6 mmol) and stirred for 30 minutes. Then the reaction mixture was quenched with water (1.0 mL) and concentrated. The residue was purified by reverse-phase prep-HPLC to afford 106 (60 mg, 45%) as a yellow solid. LCMS: [M+H]⁺ 668. ¹H NMR (500 MHz, DMSO) δ 8.58 (d, J=2.0, 1H), 8.56 (s, 1H), 8.49 (s, 1H), 8.41 (s, 1H), 7.87 (d, J=2.5, 1H), 7.38-7.36 (m, 2H), 7.24-7.22 (m, 1H), 5.15 (t, J=5.0, 1H), 4.56-4.42 (m, 6H), 4.08-4.04 (m, 2H), 3.60 (s, 3H), 3.43-3.42 (m, 1H), 3.07-2.94 (m, 6H), 2.55-2.53 (m, 4H), 2.39-2.38 (m, 4H), 1.23 (s, 6H)

Example 107a (E)-Ethyl 3-(2-Chloro-4,4-dimethylcyclopent-1-enyl)acrylate 107a

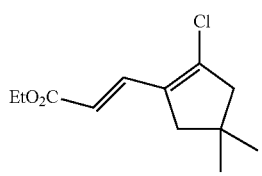

107a

The following two procedures were adapted from *Organic Preparations and Procedures Int.*, 29(4):471-498. A 500-mL single neck round bottomed flask equipped with a magnetic stirrer and nitrogen inlet was charged with 2-chloro-4,4-dimethylcyclopent-1-enecarbaldehyde (38 g, 240 mmol) in benzene (240 mL). To the solution was added ethoxycarbonylmethylene triphenylphosphorane (84 g, 240 mmol). The mixture was stirred for 14 h. After that time, the solvent was evaporated and the residue was triturated with hexanes (2 L) to extract the product away from the PPh₃ by-products. The organic layer was dried over sodium sulfate and concentrated in vacuo. The residue was purified by column chromatography using a 100% hexane-1:1 hexane/ethyl acetate gradient to afford a 37% yield (20 g) of (E)-ethyl 3-(2-chloro-4,4-dimethylcyclopent-1-enyl)acrylate 107a.

Example 107b

Ethyl 5,5-Dimethyl-1,4,5,6-tetrahydrocyclopenta[b]pyrrole-2-carboxylate 107b

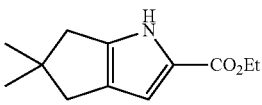

107b

A 250-mL single neck round bottomed flask equipped with a magnetic stirrer and nitrogen inlet was charged with 107a (17 g, 74 mmol) in DMSO (100 mL). To the solution was added sodium azide (9.6 g, 150 mmol). The mixture was then heated to 75° C. and stirred for 8 h. After cooling to rt (room temperature), H₂O (100 mL) and CH₂Cl₂ (200 mL) were added and the organic layer was separated. The aqueous layer was extracted with CH₂Cl₂ (50 mL). The combined organic layers were washed with brine, dried over sodium sulfate and concentrated in vacuo. The residue was purified by column chromatography using a 100% hexane-1:1 hexane/ethyl acetate gradient to afford a 37% yield (5.7 g) of 107b.

Example 107c

Ethyl 1-(Cyanomethyl)-5,5-dimethyl-1,4,5,6-tetrahydrocyclopenta[b]pyrrole-2-carboxylate 107c

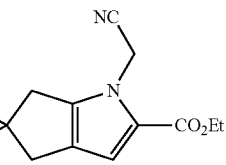

107c

A 250-mL single neck round bottomed flask equipped with a magnetic stirrer and nitrogen inlet was charged with 107b (6.2 g, 30 mmol) in DMF (57 mL). To the solution was added NaH (80% dispersion in mineral oil, 1.26 g, 42.1 mmol). The resulting mixture was stirred at rt for 90 min. After that time, bromoacetonitrile (2.94 mL, 42 mmol) was added. The mixture was stirred for 14 h. After that time, water (100 mL) and ethyl acetate (200 mL) were added and the organic layer was separated. The aqueous layer was extracted with ethyl acetate (2×50 mL). The combined organic layers were washed with brine, dried over sodium sulfate and concentrated in vacuo. The residue was purified by column chromatography to afford a 95% yield (7 g) of 107c.

Example 107d

Ethyl 1-(2-Aminoethyl)-5,5-dimethyl-1,4,5,6-tetrahydrocyclopenta[b]pyrrole-2-carboxylate hydrochloride 107d

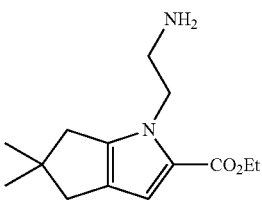

107d

A 500-mL Parr reactor bottle was purged with nitrogen and charged with 10% palladium on carbon (50% wet, 2.0 g dry weight), 107c (4.5 g, 18 mmol), 12% hydrochloric acid (9.2 mL, 37 mmol), ethyl acetate (80 mL) and ethanol (52 mL). The bottle was attached to a Parr hydrogenator, evacuated, charged with hydrogen gas to a pressure of 50 psi and shaken for 6 h. After this time, the hydrogen was evacuated, and nitrogen was charged into the bottle. CELITE® 521 (10.0 g) was added, and the mixture was filtered through a pad of CELITE® 521. The filter cake was washed with ethanol (2×50 mL), and the combined filtrates were concentrated to dryness under reduced pressure. The crude residue ethyl 1-(2-aminoethyl)-5,5-dimethyl-1,4,5,6-tetrahydrocyclopenta[b]pyrrole-2-carboxylate hydrochloride 107d was carried onto the next step without further purification.

Example 107e 4,4-Dimethyl-1,10-diazatricyclo[6.4.0.0$^{2,6}$]dodeca-2(6),7-dien-9-one 107e

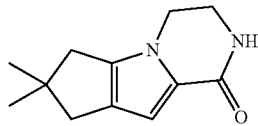

A 100-mL single-neck round-bottomed flask equipped with a magnetic stirrer and nitrogen inlet was purged with nitrogen and charged with crude 1-(2-aminoethyl)-5,5-dimethyl-1,4,5,6-tetrahydrocyclopenta[b]pyrrole-2-carboxylate hydrochloride 107d (~18 mmol), sodium ethoxide (6.2 g, 92 mmol) and ethanol (120 mL). The mixture was stirred at 55° C. over night. After that time, the reaction mixture was concentrated under reduced pressure and the residue was partitioned between ethyl acetate (200 mL) and water (100 mL). The solution was filtered. The solid was washed with ethyl acetate (15 mL) to give 850 mg of desired product 107e. The organic layer was separated, and the aqueous layer was extracted with ethyl acetate (2×100 mL). The combined organic layers were dried over sodium sulfate and concentrated under reduced pressure to near dryness. The solution was filtered and the solid (1.44 g) was washed with ethyl acetate (15 mL). The combined solids were dried under vacuum a afford 61% yield (2.3 g) of 107e.

Example 107f

3-Bromo-5-{4,4-dimethyl-9-oxo-1,10-diazatricyclo[6.4.0.0$^{2,6}$]dodeca-2(6),7-dien-10-yl}pyridine-4-carbaldehyde 107f A 100-mL single-neck round-bottomed flask equipped with a magnetic stirrer and reflux condenser was charged with 1,4-dioxane (15 mL), 3,5-dibromoisonicotinaldehyde (400 mg, 1.5 mmol), 107e (155 mg, 0.76 mmol), and cesium carbonate (176 mg, 1.5 mmol). Xantphos (40 mg, 0.08 mmol) and Pd$_2$(dba)$_3$ (70 mg, 0.08 mmol) were added, and the reaction mixture was heated at 100° C. for 5 h. After this time the reaction was cooled to room temperature and filtered. The filtrate was concentrated under reduced pressure. The residue was purified on flash column eluting with DCM:MeOH (20:1) to afford 107f (200 mg, 70%). MS: [M+H]$^+$ 388.

Example 107g

5-[1-Methyl-5-({5-[4-(oxetan-3-yl)piperazin-1-yl]pyridine-2-yl}amino)-6-oxo-1,6-dihydropyridin-3-yl]-3-{4,4-dimethyl-9-oxo-1,10-diazatricyclo[6.4.0.0$^{2,6}$]-dodeca-2(6),7-dien-10-yl}pyridine-4-carbaldehyde 107g A sealed tube was charged with 107f (200 mg, 0.51 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 1011 (240 mg, 0.51 mmol), PdCl$_2$(dppf) (42 mg, 0.05 mmol), K$_3$PO$_4$ (230 mg, 1 mmol), and NaOAc (80 mg, 1 mmol) in CH$_3$CN (5 mL) and H$_2$O (1.5 mL). The system was evacuated and refilled with N$_2$. The reaction mixture was heated at 100° C. for 2 h. It was then cooled to room temperature and filtered. The filtrate was concentrated under reduced pressure and the resulting residue was purified by flash column chromatography eluting with 10:1 of DCM/MeOH to afford 107g in 35% yield (120 mg) as a brown solid. MS: [M+H]$^+$ 649.

Example 107

10-[4-[1-Methyl-5-({5-[4-(oxetan-3-yl)piperazin-1-yl]pyridine-2-yl}amino)-6-oxo-1,6-dihydropyridin-3-yl]-4-(hydroxymethyl)pyridin-3-yl]-4,4-dimethyl-1,10-diazatricyclo[6.4.0.0$^{2,6}$]dodeca-2(6),7-dien-9-one 107

To a solution of 107g (120 mg, 0.18 mmol) in methanol (5 mL) at 0° C. was added sodium borohydride (22 mg, 0.6 mmol) and the mixture was stirred for 30 minutes. Then the reaction mixture was quenched with water (1.0 mL) and concentrated. The residue was purified by reverse-phase prep-HPLC to afford 107 (72 mg, 60%). LCMS: [M+H]$^+$: 651. $^1$H NMR (500 MHz, CDCl$_3$) δ 8.65 (s, 1H), 8.59 (s, 1H), 8.49 (s, 1H), 7.86 (d, J=1.5, 1H), 7.36 (m, 2H), 7.22 (d, J=2.4, 2H), 6.52 (s, 1H), 5.16 (t, J=3.0, 1H), 4.56-4.44 (m, 6H), 4.21-4.12 (m, 3H), 3.92 (m, 1H), 3.60 (s, 3H), 3.43-3.42 (m, 1H), 3.06 (s, 4H), 2.57-2.38 (m, 8H), 1.21 (s, 6H)

Example 108a

4-Chloro-2-{4,4-dimethyl-9-oxo-1,10-diazatricyclo[6.4.0.0$^{2,6}$]dodeca-2(6),7-dien-10-yl}pyridine-3-carbaldehyde 108a A 100-mL single-neck round-bottomed flask equipped with a magnetic stirrer and a reflux condenser was charged with 2-bromo-4-chloronicotinaldehyde 103a (3.0 g, 13.6 mmol), 4,4-dimethyl-1,10-diazatricyclo[6.4.0.0$^{2,6}$]dodeca-2(6),7-dien-9-one 107e (1.84 g, 9.0 mmol), tris(dibenzylideneacetone)dipalladium(0) (826 mg, 0.9 mmol), XantPhos (1.04 mg, 1.8 mmol), Cs$_2$CO$_3$ (5.8 g, 18.0 mmol), and 1,4-dioxane (40 mL). After three cycles of vacuum/argon flush, the mixture was heated at 90° C. for 5 h. It was then cooled to room temperature and filtered. The filtrate was concentrated under reduced pressure and the resulting residue was recrystallized from ethyl acetate to afford 108a as a yellow solid (730 mg, purity: 99%; yield: 31.7%). MS: [M+H]$^+$ 344.0.

Example 108b 4-(1-Methyl-5-(5-(4-(oxetan-3-yl)piperazin-1-yl)pyridin-2-ylamino)-6-oxo-1,6-dihydropyridin-3-yl)-2-{4,4-dimethyl-9-oxo-1,10-diazatricyclo[6.4.0.0$^{2,6}$]-dodeca-2(6),7-dien-10-yl}nicotinaldehyde 108b A 100-mL single-neck round-bottomed flask equipped with a magnetic stirrer and a reflux condenser was charged with 4-chloro-2-{4,4-dimethyl-9-oxo-1,10-diaza-tricyclo[6.4.0.0²,⁶]dodeca-2(6),7-dien-10-yl}pyridine-3-carbaldehyde 108a (350 mg, 1.02 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101I (476 mg, 1.02 mmol), Pd(dppf)Cl$_2$ (83 mg, 0.10 mmol), K$_3$PO$_4$ (526 mg, 3.06 mmol), and tetrahydrofuran (20 mL). After three cycles of vacuum/argon flush, the mixture was heated at reflux for 4 h. It was then cooled to room temperature and filtered. The filtrate was concentrated under reduced pressure and the resulting residue was purified by silica-gel column chromatography eluting with dichloromethane/methanol (40:1) to afford 108b as white solid (400 mg, 61%). MS: [M+H]$^+$649.4.

Example 108

2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-4,4-dimethyl-1,10-diazatricyclo[6.4.0.0²,⁶]dodeca-2(6),7-dien-9-one 108

To a solution of 4-(1-methyl-5-(5-(4-(oxetan-3-yl)piperazin-1-yl)pyridin-2-ylamino)-6-oxo-1,6-dihydropyridin-3-yl)-2-{4,4-dimethyl-9-oxo-1,10-diazatricyclo-[6.4.0.0²,⁶]dodeca-2(6),7-dien-10-yl}nicotinaldehyde 108b (400 mg, 0.62 mmol) in methanol (30 mL) at 0° C. was added sodium borohydride (70 mg, 1.86 mmol) and stirred for 30 minutes. Then the reaction mixture was quenched with water (1.0 mL) and concentrated. The residue was purified by reverse-phase prep-HPLC to afford 108 (170 mg, 42%). LCMS: [M+H]$^+$ 651.4. $^1$H NMR (500 MHz, CDCl$_3$) δ 8.63 (d, J=2.0, 1H), 8.48 (d, J=5.0, 1H), 7.92 (d, J=2.5, 1H), 7.82 (d, J=2.5, 1H), 7.78 (s, 1H), 7.36 (d, J=5.0, 1H), 7.27-7.25 (m, 1H), 6.84 (s, 1H), 6.81 (d, J=9.5, 1H), 5.05 (t, J=6.5, 1H), 4.72-4.64 (m, 5H), 4.51-4.48 (m, 1H), 4.34-4.32 (m, 1H), 4.15 (d, J=4.5, 2H), 3.87-3.84 (m, 1H), 3.71 (s, 3H), 3.59-3.54 (m, 1H), 3.16-3.14 (m, 4H), 2.58-2.50 (m, 8H), 1.27 (s, 6H)

Example 109a

4-Chloro-2-{4,4-dimethyl-9-oxo-7-thia-10-azatricyclo[6.4.0.0²,⁶]dodeca-1(8),2(6)-dien-10-yl}pyridine-3-carbaldehyde 109a A 100-mL single-neck round-bottomed flask equipped with a magnetic stirrer and a reflux condenser was charged with 2-bromo-4-chloronicotinaldehyde 103a (660 mg, 3.0 mmol), 4,4-dimethyl-7-thia-10-azatricyclo[6.4.0.0²,⁶]dodeca-1(8),2(6)-dien-9-one 106h (665 mg, 3.0 mmol), tris(dibenzylideneacetone)dipalladium(0) (270 mg, 0.3 mmol), XantPhos (340 mg, 0.6 mmol), Cs$_2$CO$_3$ (2.0 g, 6.0 mmol), and 1,4-dioxane (20 mL). After three cycles of vacuum/argon flush, the mixture was heated at 90° C. for 5 h. It was then cooled to room temperature and filtered. The filtrate was concentrated under reduced pressure and the resulting residue was purified by silica-gel column chromatography eluting with dichloromethane to afford 109a as yellow solid (105 mg, 14%). MS: [M+H]$^+$ 361.

Example 109b 4-(1-Methyl-5-(5-(4-(oxetan-3-yl)piperazin-1-yl)pyridin-2-ylamino)-6-oxo-1,6-dihydropyridin-3-yl)-2-{4,4-dimethyl-9-oxo-7-thia-10-azatricyclo[6.4.0.0²,⁶]-dodeca-1(8),2(6)-dien-10-yl}nicotinaldehyde 109b A 100-mL single-neck round-bottomed flask equipped with a magnetic stirrer and a reflux condenser was charged with 109a (75 mg, 0.2 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101I (94 mg, 0.2 mmol), Pd(dppf)Cl$_2$ (17 mg, 0.02 mmol), K$_3$PO$_4$.3H$_2$O (140 mg, 0.6 mmol), and tetrahydrofuran (10 mL). After three cycles of vacuum/argon flush, the mixture was heated at reflux for 4 h. It was then cooled to room temperature and filtered. The filtrate was concentrated under reduced pressure and the resulting residue was purified by silica-gel column chromatography eluting with dichloromethane/methanol (40:1) to 109b as yellow solid (60 mg, 47%). MS: [M+H]$^+$ 666.

Example 109

2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-4,4-dimethyl-7-thia-10-azatricyclo[6.4.0.0²,⁶]dodeca-1(8),2(6)-dien-9-one 109

To a solution of 109b (60 mg, 0.1 mmol) in methanol (5 mL) at 0° C. was added sodium borohydride (11 mg, 0.3 mmol) and the mixture was stirred for 30 minutes. Then the reaction mixture was quenched with water (0.3 mL) and concentrated. The residue was purified with reverse-phase prep-HPLC to afford 109 (14 mg, 24%) as a brown solid. LCMS: [M+H]$^+$ 668. $^1$H NMR (500 MHz, DMSO) δ 8.60 (d, J=2.5, 1H), 8.48 (d, J=5.0, 1H), 8.42 (s, 1H), 7.85 (d, J=3.0, 1H), 7.44 (d, J=2.0, 1H), 7.34-7.38 (m, 2H), 7.23 (d, J=9.0, 1H), 4.94 (t, J=5.0, 1H), 4.55 (t, J=7.0, 2H), 4.39-4.46 (m, 4H), 4.14-4.19 (m, 1H), 3.79-3.83 (m, 1H), 3.59 (s, 3H), 3.42-3.44 (m, 1H), 3.00-3.07 (m, 5H), 2.85-2.90 (m, 1H), 2.76 (s, 2H), 2.52-2.59 (m, 2H), 2.36-2.39 (m, 4H), 1.21 (d, J=6.5, 6H)

Example 110a

1-Methyl-3-(6-(4-methylpiperazin-1-yl)pyridin-2-ylamino)-5-(4,4,5,5-tetramethyl-1,3,2-dioxaborolan-2-yl)pyridin-2(1H)-one 110a A 250-mL single-neck round-bottomed flask equipped with a magnetic stirrer and a condenser was charged with 5-bromo-1-methyl-3-(6-(4-methylpiperazin-1-yl)pyridin-2-ylamino)pyridin-2(1H)-one (0.45 g, 1.08 mmol), (PinB)$_2$ (1.37 g, 5.4 mmol), Pd$_2$(dba)$_3$ (49 mg, 0.054 mmol), X-Phos (52 mg 0.11 mmol), KOAc (318 mg, 3.24 mmol), 1,4-dioxane 20 mL). After three cycles of vacuum/argon flush, the reaction mixture was heated at 60° C. for 15 h. It was then cooled to room temperature and filtered. The filtrate was concentrated under reduced pressure to afford crude 110a, which was used directly in the next reaction. MS: [M+H]$^+$ 426.

Example 110b 4-(1-Methyl-5-(6-(4-methylpiperazin-1-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)nicotinaldehyde 110b A 100-mL single-neck round-bottomed flask equipped with a magnetic stirrer and a reflux condenser was charged with 4-chloro-2-(1-oxo-3,4,6,7,8,9-hexahydropyrazino-[1,2-a]indol-2(1H)-yl)nicotinaldehyde 103b (377 mg, 1.15 mmol), 110a (320 mg, 0.78 mmol), Pd(dppf)Cl$_2$ (130 mg, 0.16 mmol), K$_3$PO$_4$.3H$_2$O (52.9 mg, 0.23 mmol), and tetrahydrofuran (20 mL). After three cycles of vacuum/argon flush, the mixture was heated at reflux overnight, cooled to room temperature and filtered. The filtrate was concentrated under reduced pressure and the resulting residue was purified by silica-gel column chromatography eluting with dichloromethane/methanol (40:1) to afford 110b as yellow solid (351 mg, 76%). MS: [M+H]$^+$ 593.

Example 110

2-(3-(Hydroxymethyl)-4-(1-methyl-5-(6-(4-methylpiperazin-1-yl)pyridine-2-ylamino)-6-oxo-1,6-dihydropyridin-3-yl)pyridin-2-yl)-3,4,6,7,8,9-hexahydropyrazino[1,2-a]indol-1(2H)-one 110

To the solution of 110b (60 mg, 0.1 mmol) in methanol (50 mL) was added sodium borohydride (11.5 mg, 0.3 mmol) at 0° C. and the mixture was stirred for another 30 minutes. Then the reaction mixture was quenched with water (3 mL) and concentrated. The residue was purified with reverse-phase prep-HPLC to afford 110 (26.2 mg, 49%). LCMS: [M+H]$^+$ 595. $^1$H NMR (500 MHz, CDCl$_3$) δ 8.69 (d, J=1.5, 1H), 8.46 (d, J=5.0, 1H), 7.97 (s, 1H), 7.80 (s, 1H), 7.41-7.37 (m, 1H), 7.34 (d, J=1.5, 1H), 6.89 (s, 1H), 6.22 (d, J=8.0, 1H), 6.15 (d, J=8.5, 1H), 5.10 (t, J=6.5, 1H), 4.66-4.64 (m, 1H), 4.51-4.30 (m, 2H), 4.15-4.12 (m, 2H), 3.93-3.89 (m, 1H), 3.71 (s, 3H), 3.58-3.48 (m, 4H), 2.61-2.56 (m, 7H), 2.47-2.39 (m, 3H), 1.91-1.87 (m, 2H), 1.79-1.78 (d, J=5.0, 3H)

Example 111a (6-Aminopyridin-3-yl)(morpholino)methanone 111a

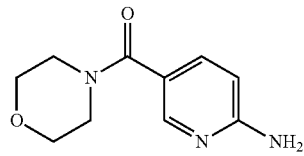

111a

To a solution of morpholine (9.00 g, 103 mmol) in EtOH (400 mL) was added EDCI (10.0 g, 52.2 mmol), HOBt (7.00 g 51.8 mmol), and 6-aminonicotinic acid (6.00 g, 43.4 mmol). After stirring for 18 h, the resulting suspension was filtered. The solid was triturated with a mixture of MeOH (100 mL) and methylene chloride (100 mL) to afford 111a as a white solid (2.7 g, 30%). LCMS: (M+H)$^+$ 208

Example 111b

5-Bromo-1-methyl-3-(5-(morpholine-4-carbonyl)pyridin-2-ylamino)pyridine-2(1H)-one 111b

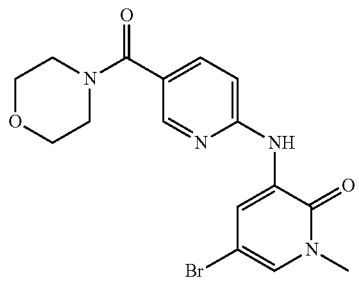

111b

Following the procedure described for synthesis of 101i, intermediate 111a and 3,5-dibromo-1-methylpyridin-2(1H)-one were reacted to give 111b in 21% yield. LCMS: (M+H)$^+$ 394. $^1$H NMR (500 MHz, MeOD) δ 8.84 (d, J=2.5, 1H), 8.42 (d, J=2, 1H), 7.72 (m, 1H), 7.42 (d, J=2, 1H), 7.11 (d, J=8.5, 1H), 3.72 (m, 8H), 3.63 (s, 3H).

Example 111c

1-Methyl-3-(5-(morpholine-4-carbonyl)pyridin-2-ylamino)-5-(4,4,5,5-tetramethyl-1,3,2-dioxaborolan-2-yl)pyridin-2(1H)-one 111c A 250-mL single-neck round-bottomed flask equipped with a magnetic stirrer and a condenser was charged with 111b (1.0 g, 0.25 mmol), X-phos (120 mg, 0.025 mmol), Pd$_2$(dba)$_3$ (110 g, 0.0125 mmol), KOAc (750 mg, 0.75 mmol), 4,4,4',4',5,5,5',5'-octamethyl-2,2'-bi(1,3,2-dioxaborolane) (3.2 g, 1.25 mmol) and 1,4-dioxane (50 mL). After three cycles of vacuum/argon flush, the reaction mixture was heated at 100° C. for 15 h. It was then cooled to room temperature and filtered. The filtrate was concentrated under reduced pressure and the resulting residue was purified by flash column chromatography eluting with 5:1 petroleum ether/ethyl acetate to afford 111c as a yellow solid (700 mg, 63%). MS: [M+H]$^+$ 441.

Example 111d 4-(1-Methyl-5-(5-(morpholine-4-carbonyl)pyridin-2-ylamino)-6-oxo-1,6-dihydropyridin-3-yl)-2-(1-oxo-3,4,6,7,8,9-hexahydropyrazino[1,2-a]indol-2(1H)-yl)nicotinaldehyde 111d A 250-mL single-neck round-bottomed flask equipped with a magnetic stirrer and a condenser was charged with 111c (450 mg, 1.26 mmol), 4-chloro-2-(1-oxo-3,4,6,7,8,9-hexahydropyrazino[1,2-a]indol-2(1H)-yl)nicotinaldehyde 103b (413 mg, 1.26 mmol), Pd(dppf)Cl$_2$ (102 mg, 0.126 mmol), K$_3$PO$_4$.3H$_2$O (85 mg, 0.352 mmol), and THF (10 mL). After three cycles of vacuum/argon flush, the reaction mixture was heated at 100° C. for 15 h. It was then cooled to room temperature and filtered. The filtrate was concentrated under reduced pressure and the resulting residue was purified by flash column chromatography eluting with 7:1 petroleum ether/ethyl acetate to afford 111d as a yellow solid (700 mg, 63%). MS: [M+H]$^+$ 608.

Example 111

2-(3-(Hydroxymethyl)-4-(1-methyl-5-(5-(morpholine-4-carbonyl)pyridin-2-ylamino)-6-oxo-1,6-dihydropyridin-3-yl)pyridin-2-yl)-3,4,6,7,8,9-hexahydropyrazino[1,2-a]indol-1(2H)-one 111

A mixture of 111d (60 mg, 0.05 mmol), NaBH$_4$ (6.4 mg, 0.1 mmol) and MeOH (5 mL) was stirred at 0° C. for 30 mins. The mixture was evaporated in vacuo and the residue was extracted with EtOAc (10 mL×2). The combined EtOAc extract was concentrated under reduced pressure and the residue was purified with reverse-phase prep-HPLC to give 111 (27 mg, 44%). LCMS: [M+H]$^+$ 610. $^1$H NMR (500 MHz, DMSO) δ 9.00 (s, 1H), 8.78 (d, J=2.0, 1H), 8.49 (d, J=5, 1H), 8.26 (d, J=2.0, 1H), 7.65-7.67 (m, 2H), 7.60 (d, J=2.5, 1H), 6.58 (s, 1H), 4.96 (t, J=5, 1H), 4.40-4.46 (m, 2H), 4.11-4.24 (m, 3H), 3.86-3.88 (m, 1H), 3.56-3.62 (m, 8H), 3.50 (s, 4H), 2.62-2.63 (m, 2H), 2.46-2.47 (m, 2H), 1.67-1.80 (m, 4H)

Example 112a

Methyl 5,6,7,8-Tetrahydroindolizine-2-carboxylate 112a

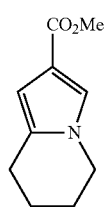

112a

A 500-mL round-bottomed flask equipped with a magnetic stirrer and nitrogen inlet was purged with nitrogen and charged with 5,6,7,8-tetrahydroindolizine-2-carboxylic acid (30.4 g, 184 mmol), DMF (1.00 g, 13.6 mmol) and methylene chloride (300 mL). The solution was cooled to 0° C. using an ice bath. Oxalyl chloride (28.0 g, 221 mmol) was added dropwise, and the reaction mixture was warmed to room temperature over 30 min and stirred for 5 h. After this time, the resulting solution was concentrated to afford a brown solid. This solid was dissolved in anhydrous methanol (400 mL), and the solution was cooled to 0° C. Triethylamine (57 g, 552 mmol) was added to the reaction mixture, and it was stirred for a further 2 h at room temperature. After this time, the reaction mixture was concentrated to dryness under reduced pressure. The residue was diluted with methylene chloride (300 mL) and washed with water (200 mL) and saturated aqueous sodium bicarbonate (200 mL). The organic layer was dried over sodium sulfate, filtered and concentrated under reduced pressure. The resulting residue was titrated with hexane (200 mL) to afford 112a in 58% yield (19.1 g) as a white solid: mp 72-74° C.; $^1$H NMR (300 MHz, DMSO-$d_6$) δ 7.13 (s, 1H), 6.23 (s, 1H), 3.93 (t, 2H, J=6.0 Hz), 3.77 (s, 3H), 2.75 (t, 2H, J=6.0 Hz), 1.93 (m, 2H), 1.80 (m, 2H); (APCI+) m/z 180.1 (M+H)

Example 112b

Methyl 3-(Cyanomethyl)-5,6,7,8-tetrahydroindoliz-ine-2-carboxylate 112b

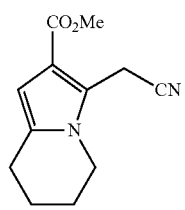

112b

A 500-mL three-neck round-bottomed flask equipped with an addition funnel, thermometer and charged with 112a (6.70 g, 37.4 mmol), Iodoacetonitrile (12.5 g, 74.9 mmol), iron (II) sulfate heptahydrate (5.20 g, 18.7 mmol) and dimethyl sulfoxide (250 mL). Hydrogen peroxide (35%, 18.2 g, 187 mmol) was added dropwise to the mixture in 1 h through a syringe pump at room temperature using a water bath. Iron (II) sulfate heptahydrate (2 to 3 equivalent) was added to the reaction mixture in portions to keep the temperature between 25° C. to 35° C., until the color of the reaction mixture is deep red. If TLC shows the reaction not completed, then more hydrogen peroxide (2-3 equivalent) and more iron (II) sulfate heptahydrate (1-2 equivalent) are added in the same manner until the reaction is completed. After that time, the reaction mixture was partitioned between saturated sodium bicarbonate solution (200 mL) and ethyl acetate (400 mL). The organic layer was separated, and the aqueous layer was extracted with ethyl acetate (2×100 mL). The combined organic layers were washed with saturated Sodium thiosulfate solution (50 mL), dried over sodium sulfate and concentrated under reduced pressure. The residue was purified by column chromatography to afford a 78% yield (6.40 g) of 112b as a yellow oil: $^1$H NMR (500 MHz, CDCl$_3$) δ 6.23 (s, 1H), 4.23 (s, 2H), 3.94 (t, 2H, J=6.5 Hz), 3.81 (s, 3H), 2.74 (t, 2H, J=6.5 Hz), 2.00 (m, 2H), 1.83 (m, 2H); (APCI+) m/z 219.3 (M+H)

Example 112c

Methyl 3-(2-Aminoethyl)-5,6,7,8-tetrahydroindoliz-ine-2-carboxylate Hydrogen Chloride Salt 112c

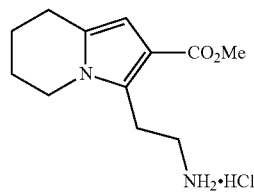

112c

Methyl 3-(Cyanomethyl)-5,6,7,8-tetrahydroindolizine-2-carboxylate 112b was hydrogenated with platinum oxide catalyst under 50 psi of hydrogen in ethanol and ethyl acetate in the presence of hydrogen chloride overnight at room temperature to give 112c (380 mg, 1.74 mmol) which was used directly in the next step.

Example 112d 3,4,6,7,8,9-Hexahydropyrido[3,4-b]indolizin-1(2H)-one 112d

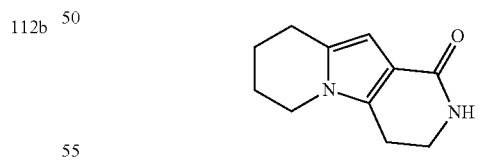

112d

A 100-mL single-neck round-bottomed flask equipped with a magnetic stirrer and nitrogen inlet was purged with nitrogen and charged with methyl 3-(2-aminoethyl)-5,6,7,8-tetrahydroindolizine-2-carboxylate hydrogen chloride salt 112c (prepared above, estimated 1.74 mmol, presuming quantitative yield), sodium ethoxide (354 mg, 5.22 mmol) and ethanol (20 mL). The mixture was stirred at 55° C. for 5 h. After that time, the reaction mixture was concentrated under reduced pressure and the residue was partitioned between ethyl acetate (200 mL) and water (100 mL). The organic layer was separated, and the aqueous layer was extracted with ethyl acetate (2×100 mL). The combined organic layers were washed with brine, dried over sodium sulfate and concentrated under reduced pressure. The residue was purified by column chromatography to afford a 67% yield (220 mg) of 112d as a white solid: mp 195-197° C.; $^1$H NMR (500 MHz, DMSO-d$_6$) δ 6.76 (s, 1H), 5.89 (s, 1H), 3.78 (t, 2H, J=6.5 Hz), 3.35 (m, 2H), 2.66 (m, 4H), 1.87 (m, 2H), 1.72 (m, 2H); (APCI+) m/z 191.3 (M+H)

Example 112e

3-Bromo-5-(1-oxo-3,4,6,7,8,9-hexahydropyrido[3,4-b]indolizin-2(1H)-yl)isonicotinaldehyde 112e A 100-mL single-neck round-bottomed flask equipped with a magnetic stirrer and reflux condenser was charged with 1,4-dioxane (15 mL), 3,5-dibromoisonicotinaldehyde (400 mg, 1.5 mmol), 112d (142 mg, 0.76 mmol) and cesium carbonate (176 mg, 1.5 mmol). Xantphos (40 mg, 0.08 mmol) and Pd$_2$(dba)$_3$ (70 mg, 0.08 mmol) were added, and the reaction mixture was heated at 100° C. for 5 h. After this time the reaction was cooled to room temperature and filtered. The filtrate was concentrated under reduced pressure and the residue was purified on flash column eluting with DCM:MeOH (20:1) to afford 112e (200 mg, 70%). MS: [M+H]

Example 112f 3-(1-Methyl-5-(5-(4-(oxetan-3-yl)piperazin-1-yl)pyridin-2-ylamino)-6-oxo-1,6-dihydropyridin-3-yl)-5-(1-oxo-3,4,6,7,8,9-hexahydropyrido[3,4-b]indolizin-2(1H)-yl)isonicotinaldehyde 112f A sealed tube was charged with 112e (200 mg, 0.53 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridine-2(1H)-one 1011 (240 mg, 0.51 mmol), PdCl$_2$(dppf) (42 mg, 0.05 mmol), K$_3$PO$_4$ (230 mg, 1 mmol), and NaOAc (80 mg, 1 mmol) in CH$_3$CN (5 mL) and H$_2$O (1.5 mL). The system was evacuated and refilled with N$_2$. The reaction mixture was heated at 100° C. for 2 h. It was then cooled to room temperature and filtered. The filtrate was concentrated under reduced pressure and the resulting residue was purified by flash column chromatography eluting with 10:1 of DCM/MeOH to afford 112f (138 mg, 40%) as a pale yellow solid. MS: [M+H]$^+$ 635.

Example 112

2-(4-(Hydroxymethyl)-5-(1-methyl-5-(5-(4-(oxetan-3-yl)piperazin-1-yl)pyridin-2-ylamino)-6-oxo-1,6-dihydropyridin-3-yl)pyridin-3-yl)-3,4,6,7,8,9-hexahydropyrido[3,4-b]indolizin-1(2H)-one 112

A mixture of 112f (130 mg, 0.20 mmol) and NaBH4 (20 mg, 0.5 mmol) in MeOH (5 mL) was stirred at 0° C. for 0.5 h. The mixture was quenched with water and extracted with EtOAc (5 mL×2). The combined EtOAc extract was concentrated under reduced pressure and the residue was purified with reverse-phase prep-HPLC to afford 112 (48 mg, 34%). LCMS: [M+H]$^+$: 637. $^1$H NMR (500 MHz, DMSO) δ 8.58 (s, 1H), 8.48 (s, 1H), 8.45 (s, 1H), 8.39 (s, 1H), 7.86 (d, J=2.4, 1H), 7.37-7.36 (m, 2H), 7.23-7.21 (m, 1H), 6.02 (s, 1H), 5.02 (s, 1H), 4.54 (t, J=6.5, 2H), 4.45 (t, J=5.5, 2H), 4.36-4.35 (m, 2H), 4.00-3.79 (m, 4H), 3.59 (s, 3H), 3.43-3.41 (m, 1H), 3.07-2.96 (m, 6H), 2.70 (t, J=6.0, 2H), 2.39-2.38 (m, 4H), 1.92-1.90 (m, 2H), 1.75-1.73 (m, 2H).

Example 113a (3-Nitro-1H-pyrazol-5-yl)methanol 113a

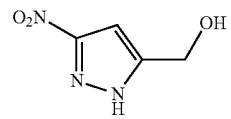

113a

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford (3-nitro-1H-pyrazol-5-yl)methanol 113a in a 94% yield (24.0 g) as a light yellow solid: $^1$H NMR (300 MHz, DMSO-d$_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H)

Example 113b (1-(2-Bromoethyl)-3-nitro-1H-pyrazol-5-yl)methanol 113b

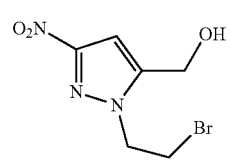

113b

A 1-L three-necked round-bottomed flask equipped with a mechanical stirrer and thermoregulator was purged with nitrogen and charged with 113a (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The

Example 113c 1-(2-Bromoethyl)-5-(bromomethyl)-3-nitro-1H-pyrazole 113c

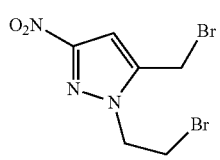

A 500-mL three-necked round-bottomed flask equipped with a magnetic stirrer, nitrogen inlet and reflux condenser was purged with nitrogen and charged with 113b (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexanes (approximately 20 mL) was added and the solution became cloudy. The mixture was heated until a solid precipitate formed, methylene chloride (9 mL) was added and the solution became clear. The solution in was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole (19.7 g). The combined filtrates were evaporated and the procedure was performed again to afford an additional 9.70 g of 1-(2-bromoethyl)-5-(bromo-methyl)-3-nitro-1H-pyrazole. The solids were combined and dried under high vacuum for 18 h to afford a 57% yield (26.0 g) of 1-(2-bromoethyl)-5-(bromomethyl)-3-nitro-1H-pyrazole 113c as white crystals: mp 95-97° C.; $^1$H NMR (300 MHz, CDCl$_3$) δ 6.93 (s, 1H), 4.63 (t, 2H, J=6.0 Hz), 4.54 (s, 2H), 3.86 (t, 2H, J=6.0 Hz).

Example 113d

5-Methyl-2-nitro-4,5,6,7-tetrahydropyrazolo[1,5-a]pyrazine 113d

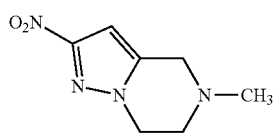

A 1-L single-neck round-bottomed flask equipped with a magnetic stirrer and nitrogen inlet was charged with THF (350 mL), 113c (10.0 g, 32.2 mmol), 2M methylamine solution in THF (113 mL, 225 mmol) and stirred at room temperature for 72 h. After this time the reaction was concentrated to dryness under reduced pressure, and the resulting solid was stirred with a mixture of ethyl acetate (75 mL) and 10% aqueous potassium carbonate (75 mL). The aqueous layer was separated and extracted with ethyl acetate (2×75 mL). The combined organic extracts were washed with 10% aqueous potassium carbonate (75 mL), followed by brine (50 mL) and dried over sodium sulfate. The drying agent was removed by filtration, and the filtrate concentrated under reduced pressure to afford 113d in 97% yield (5.70 g) as a yellow solid: $^1$H NMR (300 MHz, CDCl$_3$) δ 6.62 (s, 1H), 4.28 (t, 2H, J=5.4 Hz), 3.67 (s, 2H), 2.95 (t, 2H, J=5.4 Hz), 2.52 (s, 3H); MS (ESI+) m/z 183.0 (M+H)

Example 113e

5-Methyl-4,5,6,7-tetrahydropyrazolo[1,5-a]pyrazin-2-amine 113e

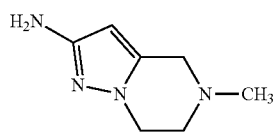

A 500-mL Parr reactor bottle was purged with nitrogen and charged with 10% palladium on carbon (50% wet, 800 mg dry weight) and a solution of 113d (4.00 g, 2.20 mmol) in ethanol (160 mL). The bottle was attached to Parr hydrogenator, evacuated, charged with hydrogen gas to a pressure of 45 psi and shaken for 2 h. After this time, the hydrogen was evacuated, and nitrogen was charged into the bottle. CELITE® 521 (1.0 g) was added, and the mixture was filtered through a pad of CELITE® 521. The filter cake was washed with ethanol (2×75 mL), and the combined filtrates were concentrated to dryness under reduced pressure to afford a 99% yield of 113e (3.31 g) as an orange solid: $^1$H NMR (300 MHz, CDCl$_3$) δ 5.34 (s, 1H), 3.98 (t, 2H, J=5.4 Hz), 3.52 (s, 3H), 2.84 (t, 2H, J=5.7 Hz), 2.45 (s, 3H); MS (ESI+) m/z 153.1 (M+H)

Example 113f

5-Bromo-1-methyl-3-(5-methyl-4,5,6,7-tetrahydro-pyrazolo[1,5-a]pyrazin-2-ylamino)pyridin-2(1H)-one 113f

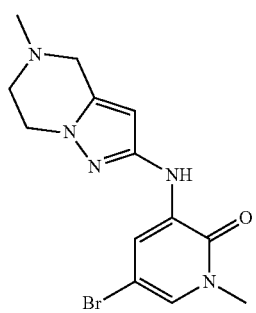

A sealed tube equipped with a magnetic stirrer was charged with 113e (1.02 g, 6.7 mmol), 3,5-dibromo-1-methylpyridin-2(1H)-one (2.15 g, 8.1 mmol), Pd$_2$(dba)$_3$ (610 mg, 0.67 mmol), 2,2-bis(diphenylphosphino)-1,1-binaphthyl (775 mg, 1.34 mmol), cesium carbonate (4.37 g, 13.6 mmol), and 1,4-dioxane (30 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (15:1, V/V) to afford 113f (380 mg, 14%) as a white solid. LCMS: [M+H]$^+$ 338

Example 113g 2-(4-chloro-3-(hydroxymethyl)pyridin-2-yl)-3,4,6,7,8,9-hexahydropyrazino[1,2-a]indol-1(2H)-one 113g

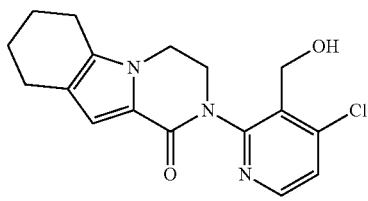

To a solution of 4-chloro-2-(1-oxo-3,4,6,7,8,9-hexahydropyrazino[1,2-a]indol-2(1H)-yl)nicotinaldehyde 103b (1.0 g, 3.0 mmol) in methanol (50 mL) was added sodium borohydride (380 mg, 9.0 mmol) at 10° C. and the mixture was stirred for another 30 minutes. Then the reaction mixture was quenched with water (1 mL) and concentrated. The residue was dissolved in dichloromethane (50 mL) and washed with water (10 mL). The organic phase was dried over anhydrous Na$_2$SO$_4$, filtered, and evaporated under reduced pressure to afford 113g as a yellow solid (900 mg, 90%). MS: [M+H]$^+$ 332.

Example 113h (4-Chloro-2-(1-oxo-3,4,6,7,8,9-hexahydropyrazino[1,2-a]indol-2(1H)-yl)pyridine-3-yl)methyl acetate 113h

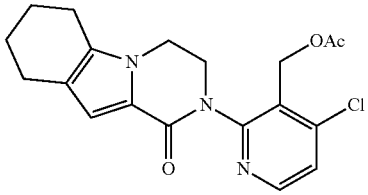

To a mixture of 113g (900 mg, 2.7 mol) and triethylamine (900 mg, 9.0 mol) in dichloromethane (5 mL) was added dropwise acetyl chloride (600 mg, 6.0 mol) while stirring at room temperature and stirred for another 1 h. The reaction mixture was concentrated and purified by silica-gel column chromatography eluting with dichloromethane to afford 113h as white solid (950 mg, 94%). MS: [M+H]$^+$ 374.

Example 113i (2-(1-Oxo-3,4,6,7,8,9-hexahydropyrazino[1,2-a]indol-2(1H)-yl)-4-(4,4,5,5-tetramethyl-1,3,2-dioxaborolan-2-yl)pyridin-3-yl)methyl acetate 113i

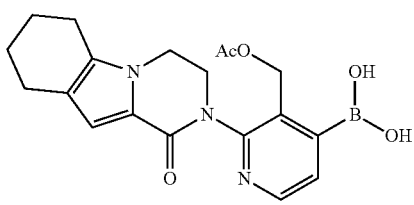

A 100-mL single-neck round-bottomed flask equipped with a magnetic stirrer and a reflux condenser was charged with 113h (950 mg, 2.5 mmol), Pin$_2$B$_2$ (1.6 g, 2.0 eq., 5 mmol), Pd$_2$(dba)$_3$ (230 mg, 0.1 eq., 0.25 mmol), X-phos (232 mg, 0.2 eq., 0.5 mmol), AcOK (735 mg, 3 eq., 7.5 mmol) and dioxane (20 mL). After three cycles of vacuum/argon flush, the mixture was heated to 65° C. for 14 h. It was then cooled to room temperature and filtered. The filtrate was concentrated under reduced pressure and the resulting residue was washed by PE/EA=3/1 (10 mL) to afford 113i as yellow solid (950 mg, 87%). MS: [M+H]$^+$ 383.

Example 113j (4-(1-Methyl-5-(5-methyl-4,5,6,7-tetrahydropyrazolo[1,5-a]pyrazin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 113j

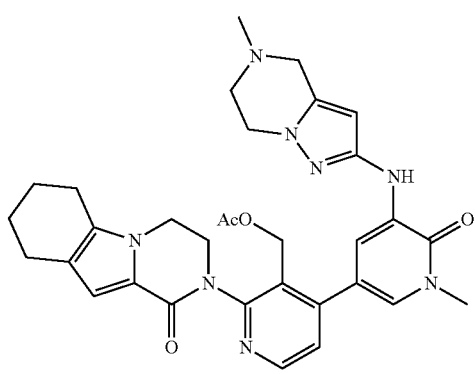

113j

A sealed tube equipped with a magnetic stirrer was charged with 113f (190 mg, 0.56 mmol), 113i (215 mg, 0.56 mmol), Pd (dppf)Cl$_2$ (47 mg, 0.056 mmol), 1.0 M NaOAc (93 mg, 1.12 mmol, 2.0 equiv), 1.0 M K$_3$PO$_4$ (240 mg, 1.12 mmol, 2.0 equiv), and acetonitrile (3 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (10:1, V/V) to afford 113j (300 mg, 94%) as a brown solid. LCMS: [M+H]$^+$ 597

Example 113

2-(3-(Hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydropyrazino[1,2-a]indol-1(2H)-one 113

A mixture of 113j (300 mg, 0.50 mmol) and LiOH.H$_2$O (120 mg, 2.50 mmol) in $^i$PrOH/THF (1:1, 3 mL) and H$_2$O (1 mL) was stirred at 30° C. for 2 h. The mixture was evaporated in vacuo and the residue was extracted with EtOAc (10 mL×2). The combined EtOAc extract was concentrated under reduced pressure and the residue was purified with reverse-phase prep-HPLC to afford 113 (91 mg, 32%) as a white solid. LCMS: [M+H]$^+$ 555. $^1$H NMR (500 MHz, CDCl$_3$) δ 8.47 (d, J=5.0, 1H), 7.95 (d, J=5.0, 1H), 7.72 (d, J=2.0, 1H), 7.42 (s, 1H), 7.35 (d, J=5.0, 1H), 6.89 (s, 1H), 5.69 (s, 1H), 5.01-5.02 (m, 1H), 4.61-4.62 (m, 1H), 4.48-4.49 (m, 1H), 4.32-4.33 (m, 1H), 4.15-4.07 (m, 4H), 3.86-3.87 (m, 1H), 3.69 (s, 3H), 3.60-3.59 (m, 2H), 2.88 (t, J=6.0, 2H), 2.61-2.56 (m, 4H), 2.47 (s, 3H), 1.89-1.90 (m, 2H), 1.78-1.79 (m, 2H)

Example 114a (R)-5-bromo-3-(4-(1,4-dimethyl-3-oxopiperazin-2-yl)phenylamino)-1-methylpyrazin-2(1H)-one 114a

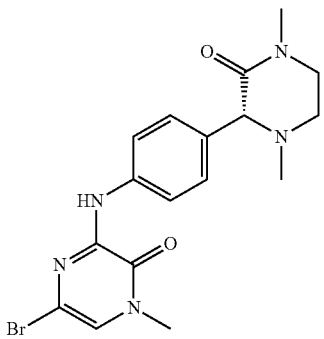

114a

A sealed tube equipped with a magnetic stirrer was charged with (R)-3-(4-aminophenyl)-1,4-dimethylpiperazin-2-one (1.08 g, 5 mmol), 3,5-dibromo-1-methylpyridin-2(1H)-one (1.47 g, 5.5 mmol), diisopropylethylamine (1.94 g, 15 mmol), and $^i$PrOH (20 mL). After three cycles of vacuum/argon flush, the mixture was heated at 110° C. overnight. After cooling down to room temperature, water (20 mL) was added to, and the mixture was extracted with ethyl acetate (50 mL×2). The organic layer was separated, combined, dried over anhydrous sodium sulfate, and concentrated. The resulting residue was purified by silica gel column chromatography eluting with dichloromethane/methanol (10:1, UV) to afford 114a (1.8 g, 90%) as a red solid. LCMS: [M+H]$^+$ 406

Example 114b (R)-(4-(6-(4-(1,4-dimethyl-3-oxopiperazin-2-yl)phenylamino)-4-methyl-5-oxo-4,5-dihydropyrazin-2-yl)-2-(1-oxo-3,4,6,7,8,9-hexahydropyrazino[1,2-a]indol-2(1H)-yl)pyridin-3-yl)methyl acetate 114b

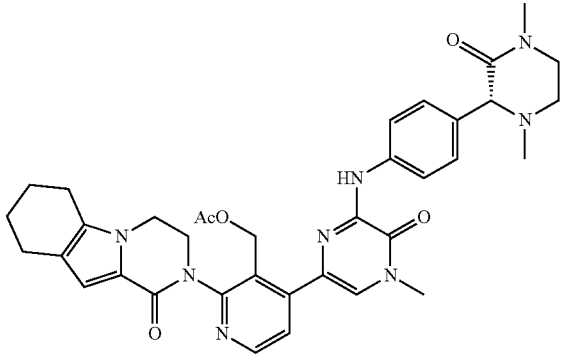

114b

A sealed tube equipped with a magnetic stirrer was charged with 114a (228 mg, 0.56 mmol), 3-(acetoxymethyl)-2-(1-oxo-3,4,6,7,8,9-hexahydropyrazino[1,2-a]indol-2(1H)-yl)pyridin-4-ylboronic acid 113i (215 mg, 0.56 mmol), Pd (dppf)Cl$_2$ (47 mg, 0.056 mmol), 1.0 M NaOAc (93 mg, 1.12 mmol, 2.0 equiv), 1.0 M K₃PO₄ (240 mg, 1.12 mmol, 2.0 equiv), and acetonitrile (3 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (10:1, V/V) to 114b (360 mg, 96%) as a brown solid. LCMS: [M+H]⁺ 665.

Example 114

(R)-2-(4-(6-(4-(1,4-dimethyl-3-oxopiperazin-2-yl)phenylamino)-4-methyl-5-oxo-4,5-dihydropyrazin-2-yl)-3-(hydroxymethyl)pyridin-2-yl)-3,4,6,7,8,9-hexahydropyrazino[1,2-a]indol-1(2H)-one 114

A mixture of 114b (360 mg, 0.54 mmol) and LiOH.H₂O (138 mg, 2.76 mmol) in ⁱPrOH/THF (1:1, 3 mL) and H₂O (1 mL) was stirred at 30° C. for 2 h. The mixture was evaporated in vacuo and the residue was extracted with EtOAc (10 mL×2). The combined EtOAc extract was concentrated under reduced pressure and the residue was purified with reverse-phase prep-HPLC to afford 114 (72 mg, 21%) as a white solid. LCMS: [M+H]⁺ 623. ¹H NMR (500 MHz, CDCl₃) δ 8.53 (d, J=4.5, 1H), 8.31 (s, 1H), 8.10 (s, 1H), 7.83-7.78 (m, 3H), 7.36 (d, J=8.0, 2H), 6.89 (s, 1H), 5.12-5.14 (m, 1H), 4.68-4.70 (m, 1H), 4.49-4.53 (m, 1H), 4.38-4.43 (m, 1H), 4.15-4.06 (m, 2H), 3.89-3.90 (m, 1H), 3.72-3.73 (m, 2H), 3.65 (s, 3H), 3.21-3.22 (m, 1H), 3.01-3.03 (m, 4H), 2.71-2.56 (m, 5H), 2.20 (s, 3H), 1.90-1.92 (m, 2H), 1.79-1.80 (m, 2H)

Example 115a

5-Bromo-1-methyl-3-(5-methyl-1H-pyrazol-3-ylamino)pyridin-2(1H)-one 115a

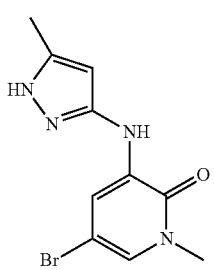

115a

A 100-mL single-neck round-bottomed flask equipped with a magnetic stirrer and reflux condenser was charged with 1,4-dioxane (15 mL), 5-methyl-1H-pyrazol-3-amine (1 g, 10 mmol) (1), 3,5-dibromo-1-methylpyridin-2(1H)-one (4 g, 15 mmol) (2), and cesium carbonate (6.4 g, 20 mmol). Xantphos (400 mg, 0.8 mmol) and Pd₂(dba)₃ (700 mg, 0.8 mmol) were added, and the reaction mixture was heated at 100° C. for 5 h. After this time the reaction was cooled to room temperature and filtered. The filtrate was concentrated under reduced pressure and the residue was purified on flash column eluting with DCM:MeOH (20:1) to afford 115a (1.0 g, 35%). MS: [M+H]⁺ 283.

Example 115b 4-(1-Methyl-5-(5-methyl-1H-pyrazol-3-ylamino)-6-oxo-1,6-dihydropyridin-3-yl)-2-(1-oxo-3,4,6,7,8,9-hexahydropyrazino[1,2-a]indol-2(1H)-yl)nicotinaldehyde 115b

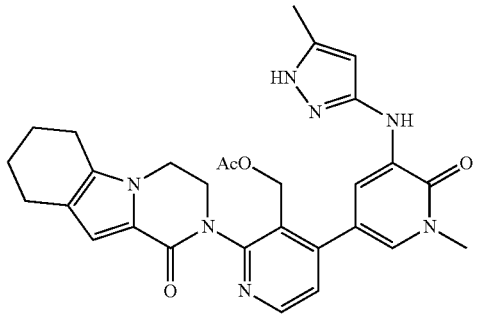

115b

A sealed tube was charged with 115a (280 mg, 1 mmol), 3-(acetoxymethyl)-2-(1-oxo-3,4,6,7,8,9-hexahydropyrazino[1,2-a]indol-2(1H)-yl)pyridin-4-ylboronic acid 113i (420 mg, 1.1 mmol), PdCl₂(dppf) (41 mg, 0.056 mmol), K₃PO₄ (100 mg), and NaOAc (50 mg) in CH₃CN (10 mL) and H₂O (3 mL). The system was evacuated and refilled with N₂. The reaction mixture was heated at 100° C. for 2 h. It was then cooled to room temperature and filtered. The filtrate was concentrated under reduced pressure and the resulting residue was purified by flash column chromatography eluting with 10:1 of DCM/MeOH to afford 115b in 35% yield (190 mg) as a pale yellow solid. MS: [M+H]⁺ 542.

Example 115

2-(3-(Hydroxymethyl)-4-(1-methyl-5-(5-methyl-1H-pyrazol-3-ylamino)-6-oxo-1,6-dihydropyridin-3-yl)pyridin-2-yl)-3,4,6,7,8,9-hexahydropyrazino[1,2-a]indol-1(2H)-one 115

A 100-mL single-neck round-bottomed flask was charged with 115b (190 mg, 0.35 mol) in THF/iPA/H₂O (5 mL/5 mL/2 mL) and LiOH (85 mg, 3.5 mmol) while stirring. This mixture was stirred at 50° C. for 0.5 h. Then 20 mL H₂O was added and the mixture was extracted with EA (30 mL×3). The combined organic layer was dried over Na₂SO₄ and concentrated to give a yellow solid, which was further purified by reverse-phase prep-HPLC to afford 115 as a white solid (48 mg, 30% yield). LCMS: [M+H]⁺ 500. ¹H NMR (500 MHz, CDCl3) δ 8.44 (d, J=6.0, 1H), 7.95 (s, 1H), 7.69 (s, 1H), 7.44 (s, 1H), 7.30 (d, J=6.0, 2H), 6.87 (s, 1H), 5.74 (s, 1H), 4.59-3.86 (m, 7H), 3.69 (s, 3H), 2.57-2.56 (m, 4H), 2.25 (s, 3H) 1.88-1.77 (m, 4H)

Example 116a

3-Bromo-5-{6-oxo-8-thia-4,5-diazatricyclo[7.4.0.0²,⁷]trideca-1(9),2(7),3-trien-5-yl}pyridine-4-carbaldehyde 116a

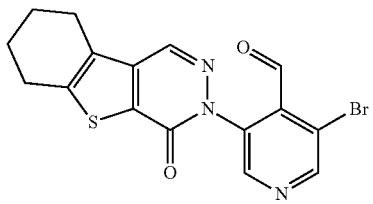

To a 100-mL single-neck round-bottomed flask equipped with a magnetic stirrer and reflux condenser was charged with 1,4-dioxane (15 mL), 3,5-dibromoisonicotinaldehyde (200 mg, 0.76 mmol), 8-thia-4,5-diazatricyclo[7.4.0.0²,⁷]trideca-1(9),2(7),3-trien-6-one 191d (160 mg, 0.76 mmol), and cesium carbonate (176 mg, 1.5 mmol). Cuprous iodide CuI (100 mg, 0.76 mmol) and 4,7-dimethoxy-1,10-phenanthroline (127 mg, 0.52 mmol) were added, and the reaction mixture was heated at 100° C. for 5 h. After this time the reaction was cooled to room temperature and filtered. The filtrate was concentrated under reduced pressure and the residue was purified on flash column eluting with EtOAC/PE (1:2) to afford 116a (80 mg, 30%). MS: [M+H]⁺ 390.

Example 116b

3-[1-Methyl-5-({5-[4-(oxetan-3-yl)piperazin-1-yl]pyridine-2-yl}amino)-6-oxo-1,6-dihydropyridin-3-yl]-5-{6-oxo-8-thia-4,5-diazatricyclo[7.4.0.0²,⁷]trideca-1(9),2(7),3-trien-5-yl}pyridine-4-carbaldehyde 116b

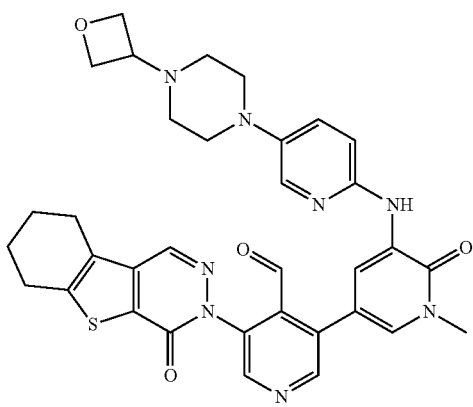

A sealed tube was charged with 116a (80 mg, 0.20 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 1011 (96 mg, 0.20 mmol), PdCl₂(dppf) (18 mg, 0.02 mmol), K₃PO₄ (30 mg), and NaOAc (20 mg) in CH₃CN (5 mL) and H₂O (1 mL). The system was evacuated and refilled with N₂. The reaction mixture was heated at 100° C. for 2 h. It was then cooled to room temperature and filtered. The filtrate was concentrated under reduced pressure and the resulting residue was purified by flash column chromatography eluting with 10:1 of DCM/MeOH to afford 116b in 35% yield (46 mg). MS: [M+H]⁺ 651.

Example 116

4-Hydroxymethyl-3-[1-methyl-5-({5-[4-(oxetan-3-yl)piperazin-1-yl]pyridine-2-yl}amino)-6-oxo-1,6-dihydropyridin-3-yl]-5-{6-oxo-8-thia-4,5-diazatricyclo[7.4.0.0²,⁷]trideca-1(9),2(7),3-trien-5-yl}pyridine 116

To a solution of 116b (46 mg, 0.07 mmol) at 0° C. in methanol (4 mL) was added sodium borohydride (20 mg, 0.7 mmol) and stirred for 30 minutes. Then the reaction mixture was quenched with water (1.0 mL) and concentrated. The residue was purified by reverse-phase prep-HPLC to afford 116 (12 mg, 28%) as a yellow solid. LCMS: [M+H]⁺ 653. ¹H NMR (500 MHz, DMSO) δ 8.60 (s, 1H), 8.59 (s, 1H), 8.56 (d, J=2.0, 1H), 8.50 (s, 1H), 8.44 (s, 1H), 7.87 (d, J=3.0, 1H), 7.38-7.36 (m, 2H), 7.24-7.22 (m, 1H), 4.90 (m, 1H), 4.56-4.53 (m, 2H), 4.46-4.44 (m, 4H), 3.59 (s, 3H), 3.44-3.42 (m, 1H), 3.06 (t, J=4.5, 4H), 2.94-2.93 (m, 2H), 2.85-2.84 (m, 2H), 2.38 (t, J=4.0, 4H), 1.89-1.84 (m, 4H)

Example 117a 5-(Methylthio)-2-nitropyridine 117a

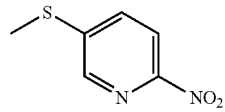

To a mixture of 5-chloro-2-nitropyridine (3 g, 18 mmol) in MeOH (20 mL), sodium methanethiolate (1.4 g, 20 mmol) was added at 0° C. and the mixture stirred at 20° C. for 2 hours. The resulting suspension was filtered and washed with water, and dried in vacuum to afford crude 117a as a yellow solid (2 g, 66%) without purification for next step. MS: [M+H]⁺ 171.

Example 117b 5-(Methylsulfonyl)-2-nitropyridine 117b

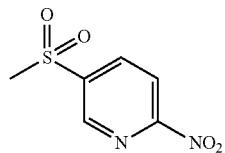

To a mixture of 117a (260 mg, 0.5 mmol) in acetic acid (15 mL) was added H₂O₂ (aq. 30%) (7.5 mL) and the reaction mixture was stirred overnight at 25° C. The reaction solution was poured into water and extracted with EtOAC and concentrated to a pale yellow liquid, purified by silica gel with (EtOAC/PE: 1:3) to give 117b (2 g, 86%). MS: [M+H]+ 203.

Example 117c 5-(Methylsulfonyl)pyridin-2-amine 117c

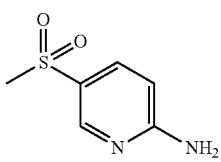

A mixture of 117b (2 g, 10 mmol), MeOH (10 mL), Pd/C (120 mg) in methanol (8 mL) was stirred fat 25° C. under $H_2$ (50 Psi) overnight. The Pd/C was removed by filtration and the filtrate was concentrated under reduced pressure to give 117c (1.7 g, 98%). MS: [M+H]+ 173.

Example 117d

5-Bromo-1-methyl-3-(5-(methylsulfonyl)pyridin-2-ylamino)pyridin-2(1H)-one 117d

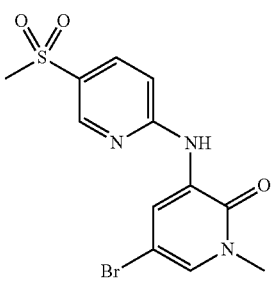

A 250-mL single-neck round-bottomed flask equipped with a magnetic stirrer and reflux condenser was charged with 1,4-dioxane (15 mL), 117c (1.7 g, 10 mmol), 3,5-dibromo-1-methylpyridin-2(1H)-one (5.2 g, 20 mmol) and cesium carbonate (6.4 g, 20 mmol). Xantphos (300 mg, 0.8 mmol) and $Pd_2(dba)_3$ (500 mg, 0.8 mmol) were added, and the reaction mixture was heated at 100° C. for 5 h (hours). After this time the reaction was cooled to room temperature. The mixture was removed by filtration and the filtrate was concentrated under reduced pressure. The residue was purified on flash column eluting with DCM:MeOH (20:1) to afford 117d (1 g, 30%). MS: [M+H]+ 358.

Example 117e (4-(1-Methyl-5-(5-(methylsulfonyl)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridine-3-yl)methyl acetate 117e

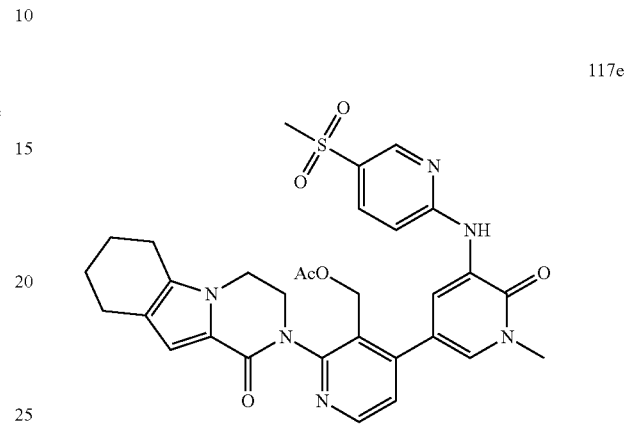

A sealed tube was charged with 117d (100 mg, 0.28 mmol), 3-(acetoxymethyl)-2-(1-oxo-3,4,6,7,8,9-hexahydropyrazino[1,2-a]indol-2(1H)-yl)pyridin-4-ylboronic acid 113i (115 mg, 0.3 mmol), $PdCl_2(dppf)$ (25 mg, 0.03 mmol), $K_3PO_4$ (126 mg, 0.6 mmol), and NaOAc (60 mg, 0.6 mmol) in MeCN (8 mL) and $H_2O$ (1 mL). The system was evacuated and refilled with $N_2$. The reaction mixture was heated at 100° C. for 2 h. It was then cooled to room temperature and filtered. The filtrate was concentrated under reduced pressure and the resulting residue was purified by silica gel flash column eluting with DCM:MeOH (20:1) to afford 117e (100 mg, 40%). MS: [M+H]+ 617.

Example 117

2-(3-(hydroxymethyl)-4-(1-methyl-5-(5-(methylsulfonyl)pyridin-2-ylamino)-6-oxo-1,6-dihydropyridin-3-yl)pyridin-2-yl)-3,4,6,7,8,9-hexahydro-pyrazino[1,2-a]indol-1(2H)-one 117

A 100-mL single-neck round-bottomed flask compound was charged with 117e (100 mg, 0.2 mol) in THF/iPA/$H_2O$ (5 mL/5 mL/2 mL) and LiOH (50 mg, 2 mmol) while stirring. This mixture was stirred at 50° C. for 0.5 h. Then 20 mL $H_2O$ was added and the mixture was extracted with EA (30 mL×3). The combined organic layer was dried over $Na_2SO_4$ and concentrated to give a yellow solid, which was further purified by reverse-phase prep-HPLC to afford 117 as a white solid (72 mg, 90% yield). MS: [M+H]+ 575. $^1$H NMR (500 MHz, CDCl3) δ 9.39 (s, 1H), 8.84 (d, J=2.0, 1H), 8.60 (d, J=2.5, 1H), 8.50 (d, J=2.5, 1H), 7.98 (dd, J=2.5, 4.0, 1H), 7.69 (d, J=2.4, 1H), 7.49-7.47 (d, J=9.0, 1H), 7.38-7.37 (m, 1H), 6.58 (s, 1H), 4.99 (t, J=4.5, 1H), 4.47-4.39 (m, 2H), 4.26-4.11 (m, 3H), 3.88-3.86 (m, 1H), 3.62 (s, 3H), 3.19 (s, 3H), 2.66-2.54 (m, 2H), 2.48-2.46 (m, 2H), 1.79-1.66 (m, 4H)

Example 118a tert-Butyl 5-Amino-3-cyclopropyl-1H-pyrazole-1-carboxylate 118a

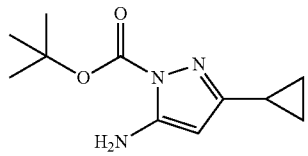

118a

To a mixture of 3-cyclopropyl-1H-pyrazole-5-amine (0.25 g, 2 mmol) and K$_2$CO$_3$ (0.828 g, 6 mmol) in THF (5 mL) was added (Boc)$_2$O (0.436 g, 2 mmol) in THF (5 mL). The reaction mixture was stirred at room temperature for 15 h. It was then filtered and concentrated. The residue was purified by flash column eluting with 6:1 petroleum ether/ethyl acetate to afford 118a as a white solid (240 mg, 54%). LCMS: (M-Boc)$^+$ 124.

Example 118b

5-Bromo-3-(3-cyclopropyl-1H-pyrazol-5-ylamino)-1-methylpyridin-2(1H)-one 118b

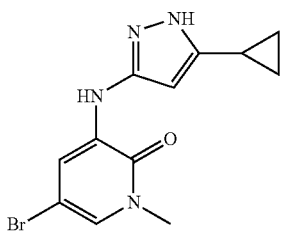

118b

A 100-mL single-neck round-bottomed flask equipped with a magnetic stirrer and reflux condenser was charged with 1,4-dioxane (15 mL), 118a (455 mg, 1.95 mmol), 3,5-dibromo-1-methylpyridin-2(1H)-one (0.40 g, 1.5 mmol), and cesium carbonate (1.22 g, 3.75 mmol). After bubbling nitrogen through the resulting mixture for 30 minutes, XantPhos (87 mg, 0.15 mmol) and tris(dibenzylideneacetone)dipalladium(0) (70 mg, 0.075 mmol) were added, and the reaction mixture was heated at reflux for 15 h. After this time the reaction was cooled to room temperature, partitioned between ethyl acetate (30 mL) and water (30 mL). The aqueous layer was separated and extracted with ethyl acetate (50 mL×2). The organic layers were combined, washed with brine (50 mL) and dried over sodium sulfate. The drying agent was removed by filtration and the filtrate was concentrated under reduced pressure. The residue was purified on flash column eluting with 50:1 DCM/MeOH to afford 118b as a yellow solid (320 mg, 50%). LCMS: (M+H)$^+$ 309. $^1$H NMR (500 MHz, DMSO) δ 11.85 (s, 1H), 8.23 (s, 1H), 8.02 (d, J=2.5, 1H), 7.35 (d, J=2.5, 1H), 5.77 (d, J=2, 1H), 3.46 (s, 3H), 1.83 (m, 1H), 0.90 (m, 2H), 0.64 (m, 2H)

Example 118c (4-(5-(5-Cyclopropyl-1H-pyrazol-3-ylamino)-1-methyl-6-oxo-1,6-dihydropyridin-3-yl)-2-(1-oxo-3,4,6,7,8,9-hexahydropyrazino[1,2-a]indol-2(1H)-yl)pyridine-3-yl)methyl acetate 118c

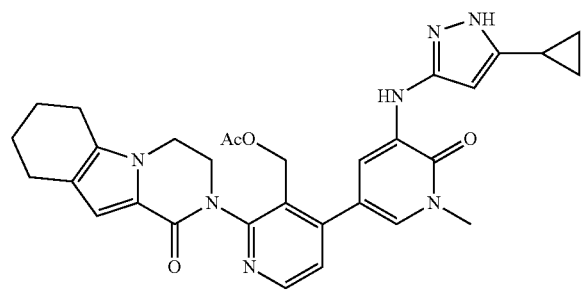

118c

A sealed tube equipped with a magnetic stirrer was charged with 118b (310 mg, 1 mmol), 3-(acetoxymethyl)-2-(1-oxo-3,4,6,7,8,9-hexahydropyrazino[1,2-a]indol-2(1H)-yl)pyridine-4-ylboronic acid 113i (385 mg, 1 mmol), Pd(dppf)Cl$_2$ (80 mg, 0.1 mmol), K$_3$PO$_4$ (424 mg, 2 mmol), NaOAc (165 mg, 2 mmol), CH$_3$CN (15 mL), and water (1 mL). After three cycles of vacuum/argon flush, the mixture was heated at 110° C. for 3 h. It was evaporated in vacuo. The residue was purified by silica gel column chromatography eluting with dichloromethane/methanol (50:1, V/V) to afford 118c (400 mg, 68%) as a yellow solid. LCMS: [M+H]$^+$ 569

Example 118

2-(4-(5-(5-Cyclopropyl-1H-pyrazol-3-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 118

A mixture of 118c (350 mg, 0.62 mmol) and LiOH.H$_2$O (260 mg, 6.2 mmol) in $^i$PrOH/THF (1:1, 3 mL) and H$_2$O (1 mL) was stirred at 30° C. for 1 h. The mixture was evaporated in vacuo and the residue was extracted with EtOAc (10 mL×2). The combined EtOAc extract was concentrated under reduced pressure and the residue was purified by reverse-phase prep-HPLC to afford 118 (200 mg, 54%) as a white solid. LCMS: [M+H]$^+$ 526. $^1$H NMR (500 MHz, DMSO) δ 11.83 (s, 1H), 8.48 (d, J=5, 1H), 8.05 (d, J=2, 1H), 8.03 (s, 1H), 7.38 (d, J=2, 1H), 7.31 (d, J=5, 1H), 6.58 (s, 1H), 5.81 (d, J=2, 1H), 4.95 (t, J=5, 1H), 4.49-4.51 (m, 1H), 4.38-4.40 (m, 1H), 4.19-4.21 (m, 3H), 3.85-3.87 (m, 1H), 3.58 (s, 3H), 2.61-2.62 (m, 1H), 2.56-2.57 (m, 1H), 2.48-2.49 (m, 2H), 1.81-1.82 (m, 3H), 1.70-1.71 (m, 2H), 0.88-0.89 (m, 2H), 0.63-0.64 (m, 2H)

Example 119a (S)-(4-(1-Methyl-5-(5-(2-methyl-4-(oxetan-3-yl)piperazin-1-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 119a

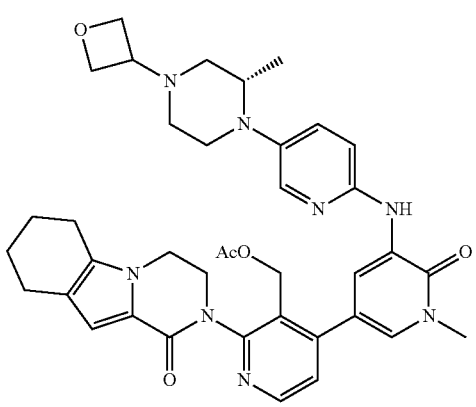

Following the procedures as described for 118c, (2-(1-oxo-3,4,6,7,8,9-hexahydropyrazino[1,2-a]indol-2(1H)-yl)-4-(4,4,5,5-tetramethyl-1,3,2-dioxaborolan-2-yl)pyridin-3-yl)methyl acetate 113i (250 mg) and (S)-5-bromo-1-methyl-3-(3-methyl-5-(4-(oxetan-3-yl)piperazin-1-yl)pyridin-2-ylamino)pyridin-2(1H)-one 130e (233 mg) were reacted to give 119a as a yellow solid (230 mg, 62%). LCMS: [M+H]+ 693

Example 119

(S)-2-(3-(Hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 119

Following the procedures as described for 118, acetate hydrolysis of 119a with LiOH.H₂O in ⁱPrOH/THF (1:1) and H₂O, gave 119 as a white solid (184 mg, 85%). LCMS: [M+H]+ 651. ¹H NMR (500 MHz, CDCl3) δ 8.65 (d, J=2.5, 1H), 8.50 (d, J=5.0, 1H), 7.99 (s, 1H), 7.87 (s, 1H), 7.84 (d, J=2.0, 1H), 7.35 (d, J=5.0, 1H), 7.33 (d, J=7.0, 1H), 6.90 (s, 1H), 6.83 (d, J=9.0, 1H), 5.04-5.06 (m, 1H), 4.62-4.73 (m, 5H), 4.51 (s, 1H), 4.32 (s, 1H), 4.16 (s, 1H), 4.11 (s, 1H), 3.89 (s, 1H), 3.72 (s, 3H), 3.57 (t, J=6.0, 1H), 3.48 (s, 1H), 3.07-3.12 (m, 2H), 2.53-2.63 (m, 7H), 2.24 (m, 1H), 1.88-1.93 (m, 2H), 1.80 (s, 2H), 0.99 (d, J=6.5, 3H).

Example 120a

5-Bromo-3-(5-(4-(2-hydroxy-2-methylpropyl)piperazin-1-yl)pyridin-2-ylamino)-1-methylpyridin-2(1H)-one 120a

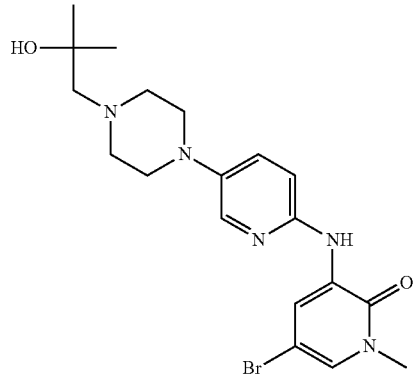

A sealed tube equipped with a magnetic stirrer was charged with 5-bromo-1-methyl-3-(5-(piperazin-1-yl)pyridin-2-ylamino)pyridin-2(1H)-one 101j (500 mg, 1.37 mmol), 2,2-dimethyloxirane (990 mg, 13.7 mmol), Cs₂CO₃ (1.3 g, 4.11 mmol), and CH₃CN (15 mL). After three cycles of vacuum/argon flush, the mixture was heated at 110° C. for 15 h. It was then filtered and the filtrate was evaporated in vacuum. Crude 120a thus obtained was used in the next step without further purification (460 mg, 77%). LCMS: [M+H]+ 437.

Example 120b (4-(5-(5-(4-(2-Hydroxy-2-methylpropyl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 120b

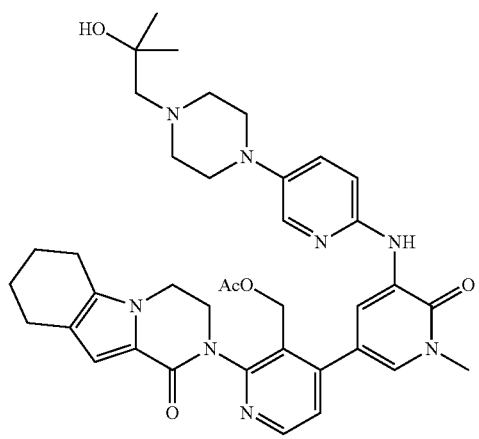

Following the procedures as described for preparation of 118c, reaction of 120a (435 mg, 1.0 mmol) and 3-(acetoxymethyl)-2-(1-oxo-3,4,6,7,8,9-hexahydropyrazino[1,2-a]indol- 2(1H)-yl)pyridin-4-ylboronic acid 113i (383 mg, 1 mmol) gave 120b (437 mg, 63%). LCMS: [M+H]⁺ 696.

Example 120

2-(4-(5-(5-(4-(2-Hydroxy-2-methylpropyl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 120

Following the procedures as described for the preparation of 118, acetate hydrolysis of 120b (70 mg, 0.1 mmol) with LiOH.H$_2$O in $^i$PrOH/THF (1:1) and H$_2$O, gave 120 (27 mg, 42%) as a gray solid. LCMS: [M+H]⁺ 653. $^1$H NMR (500 MHz, DMSO-d6) δ 8.61 (d, J=3, 1H), 8.50 (d, J=5, 1H), 8.41 (s, 1H), 7.83 (d, J=3, 1H), 7.46 (d, J=2, 1H), 7.36 (m, 2H), 7.24 (d, J=9, 1H), 6.58 (s, 1H), 4.95 (m, 1H), 4.44 (m, 2H), 4.24 (m, 2H), 4.13 (m, 2H), 3.87-3.88 (m, 1H), 3.60 (s, 3H), 3.03-3.05 (m, 4H), 2.64-2.66 (m, 5H), 2.61-2.63 (m, 1H), 2.49-2.51 (m, 2H), 2.24 (s, 2H), 1.70-1.71 (m, 4H), 1.10 (s, 6H).

Example 121a 4-(1-Methyl-5-(5-(4-(oxetan-3-yl)piperazin-1-yl)pyridin-2-ylamino)-6-oxo-1,6-dihydropyridin-3-yl)-2-(1-oxo-6,7,8,9-tetrahydropyrazino[1,2-a]indol-2(1H)-yl)nicotinaldehyde 121a A flask was charged with 4-chloro-2-(1-oxo-6,7,8,9-tetrahydropyrazino[1,2-a]indol-2(1H)-yl)nicotinaldehyde 103b (88 mg, 0.27 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101l (125 mg, 0.27 mmol), PdCl$_2$(dppf) (18 mg, 0.02 mmol), K$_3$PO$_4$ (30 mg), in THF (5 mL) and H$_2$O (1 mL). The system was evacuated and refilled with N$_2$. The reaction mixture was refluxed for 4 h, and then cooled to room temperature. It was then filtered and the filtrate was concentrated under reduced pressure. The resulting residue was purified by flash column chromatography eluting with 10:1 of DCM/MeOH to afford 121a (90 mg, 56%) as a yellow solid. MS: [M+H]⁺ 633.

Example 121

2-(3-(hydroxymethyl)-4-(1-methyl-5-(5-(4-(oxetan-3-yl)piperazin-1-yl)pyridine-2-ylamino)-6-oxo-1,6-dihydropyridin-3-yl)pyridin-2-yl)-6,7,8,9-tetrahydropyrazino[1,2-a]indol-1(2H)-one 121

At 0° C., to a suspension of 121a (76 mg, 0.12 mmol) in methanol (4 mL) was added sodium borohydride (20 mg, 0.7 mmol) and stirred for 30 minutes. Then the reaction mixture was quenched with water (1.0 mL) and concentrated. The residue was purified by reverse-phase prep-HPLC to afford 121 (56 mg, 74%). LCMS: [M+H]⁺ 635. $^1$H NMR (500 MHz, DMSO) δ 8.66 (d, J=2.0, 1H), 8.57 (d, J=5.0, 1H), 7.93 (d, J=3.0, 1H), 7.85 (d, J=2.5, 1H), 7.80 (s, 1H), 7.50 (d, J=5.0, 1H), 7.24-7.27 (m, 1H), 7.06 (s, 1H), 6.97 (d, J=6.0, 1H), 6.81 (d, J=8.0, 1H), 6.67 (d, J=6.0, 1H), 5.08 (d, J=11.5, 1H), 4.67-4.72 (m, 4H), 4.51 (d, J=12.0, 1H), 4.35 (t, J=12.0, 1H), 3.72 (s, 3H), 3.57-3.59 (m, 1H), 3.16-3.17 (m, 4H), 2.70-2.74 (m, 4H), 2.52-2.53 (m, 4H), 1.94-1.95 (m, 2H), 1.84-1.86 (m, 2H).

Example 122a (2R,5S)-tert-Butyl 2,5-Dimethyl-4-(6-nitropyridin-3-yl)piperazine-1-carboxylate 122a

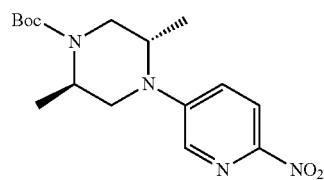

Following the procedures as described for compound 101g, (2R,5S)-tert-butyl-2,5-dimethylpiperazine-1-carboxylate (1.5 g, 6.0 mmol), and 5-bromo-2-nitropyridine (1212 mg, 6.0 mmol) were reacted to give 122a as a yellow solid (1500 mg, 75%). LCMS: [M+H]⁺ 337

Example 122b (2R,5S)-tert-Butyl 4-(6-Aminopyridin-3-yl)-2,5-dimethylpiperazine-1-carboxylate 122b

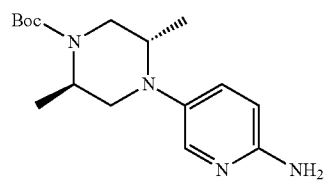

Following the procedures as described for compound 101h, reaction of 122a (1.5 g, 4.46 mmol) afforded 122b as a yellow solid (1130 mg, 83%). LCMS: [M+H]⁺ 307

Example 122c (2R,5S)-tert Butyl 4-(6-(5-Bromo-1-methyl-2-oxo-1,2-dihydropyridin-3-ylamino)pyridin-3-yl)-2,5-dimethylpiperazine-1-carboxylate 122c

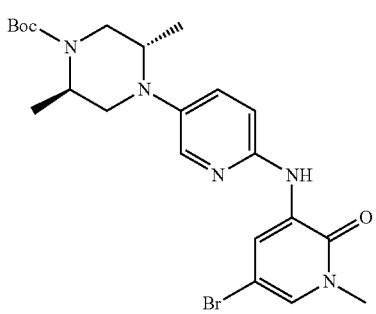

Following the procedures as described for compound 101i, reaction of 122b (766 mg, 2.50 mmol) and 3,5-dibromo-1-methylpyridin-2(1H)-one (668 mg, 2.50 mmol) afforded 122c as a yellow solid (978 mg, 79%). LCMS: [M+H]⁺ 492

Example 122d (2R,5S)-tert-Butyl 4-(6-(5-Bromo-1-methyl-2-oxo-1,2-dihydropyridin-3-ylamino)pyridin-3-yl)-2,5-dimethylpiperazine-1-carboxylate 122d

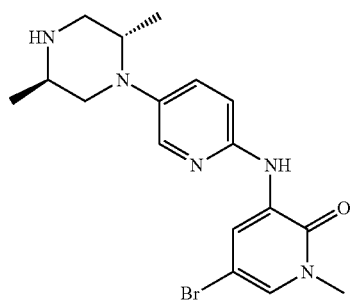

Following the procedures as described for compound 101j, reaction of 122c (978 mg, 1.99 mmol) gave 122d as a yellow solid (700 mg, 90%). LCMS: [M+H]$^+$ 392

Example 122e

5-Bromo-3-(5-((2S,5R)-2,5-dimethyl-4-(oxetan-3-yl)piperazin-1-yl)pyridin-2-ylamino)-1-methylpyridin-2(1H)-one 122e

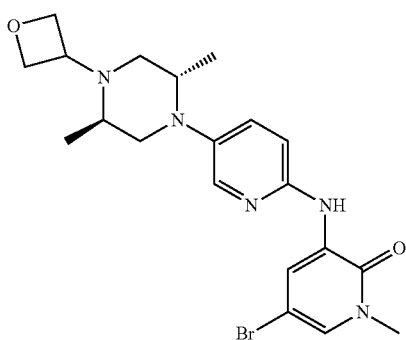

Following the procedures as described for compound 101k, reaction of 122d (700 mg, 1.79 mmol), afforded 122e as a yellow solid (723 mg, 91%). LCMS: [M+H]$^+$ 448

Example 122f (4-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 122f

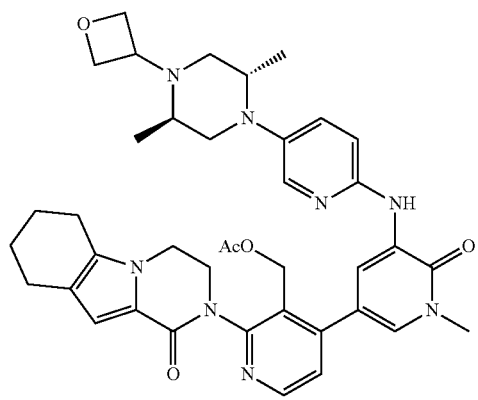

Following the procedures as described for compound 113j, reaction of 122e (723 mg, 1.62 mmol) and 3-(acetoxymethyl)-2-(1-oxo-3,4,6,7,8,9-hexahydropyrazino[1,2-a]indol-2(1H)-yl)pyridin-4-ylboronic acid 113i (613 mg, 1.62 mmol) afforded 122f as a yellow solid (464 mg, 41%). LCMS: [M+H]$^+$ 707

Example 122

2-(4-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 122

Following the procedures as described for compound 113, hydrolysis of 122f (464 mg, 0.66 mmol) with lithium hydroxide afforded 122 as a white solid (83 mg, 20%). LCMS: [M+H]$^+$ 665. $^1$H NMR (500 MHz, CDCl$_3$) δ 8.69 (d, J=2.5, 1H), 8.51 (d, J=5.0, 1H), 8.03 (d, J=2.5, 1H), 7.88 (s, 1H), 7.86 (d, J=2.5, 1H), 7.38 (d, J=5.0, 2H), 6.90 (s, 1H), 6.82 (d, J=9.0, 1H), 5.07 (s, 1H), 4.77-4.72 (m, 2H), 4.68-4.61 (m, 3H), 4.52 (s, 1H), 4.33 (s, 1H), 4.17-4.11 (m, 2H), 3.88 (s, 1H), 3.76 (s, 1H), 3.73 (s, 3H), 3.19 (s, 1H), 2.93-2.90 (m, 1H), 2.73 (s, 2H), 2.63-2.57 (m, 4H), 2.48 (s, 1H), 1.99-1.90 (m, 3H), 1.80 (s, 2H), 0.91 (t, J=5.5, 6H)

Example 123a (2-Bromoethoxy)(tert-butyl)dimethylsilane 123a

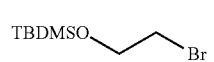

To a solution of 2-bromoethanol (5.0 g, 40.3 mmol) in DCM (20 mL) was added tert-butyldimethylsilyl chloride (9.1 g, 60.5 mmol) followed by the additions of triethylamine (8.14 g, 80.6 mmol) and 4-dimethylaminopyridine (49.2 mg, 0.4 mmol). The mixture was stirred at room temperature for 15 h and concentrated in vacuo. The residue was partitioned between 1N HCl and ethyl acetate. The aqueous portion was extracted with ethyl acetate. The combined organic portion was washed with brine, dried over sodium sulfate, filtered and concentrated in vacuo to afford yellow oil, which was purified by column chromatography eluting with PE:EA (50:1) to afford 123a as colorless oil (6.0 g, 62.4%). LCMS: (M+H)$^+$ 241.

Example 123b

5-Bromo-3-(5-(4-(2-(tert-butyldimethylsilyloxy)ethyl)piperazin-1-yl)pyridine-2-ylamino)-1-methylpyridin-2(1H)-one 123b

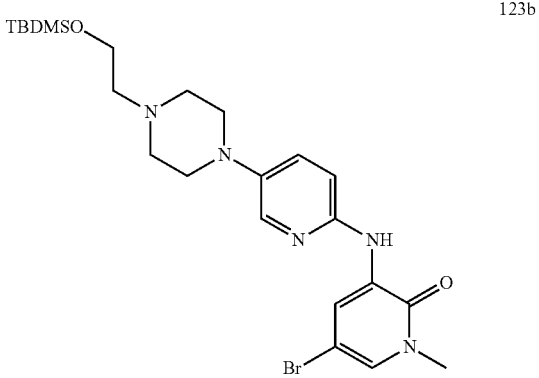 [SMILES: Cn1cc(Br)cc(Nc2ccc(N3CCN(CCO[Si](C)(C)C(C)(C)C)CC3)cn2)c1=O]

To a suspension of 123a (231 mg, 0.96 mmol) in MeCN (40 mL) at 70° C. was added 5-bromo-1-methyl-3-(5-(piperazin-1-yl)pyridin-2-ylamino)pyridin-2(1H)-one 101j (350 mg, 0.96 mmol). The reaction mixture was stirred for 3 days. It was then filtered and the filtrate was concentrated under reduced pressure. The resulting residue was purified by silica-gel column chromatography eluting with dichloromethane/methanol (30:1) to afford 123b as yellow solid (452 mg, 90%). MS: [M+H]$^+$ 524.7.

Example 123c

5-Bromo-3-(5-(4-(2-hydroxyethyl)piperazin-1-yl)pyridin-2-ylamino)-1-methylpyridin-2(1H)-one 123c

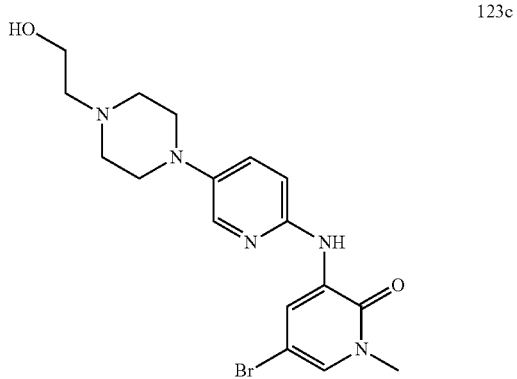 [SMILES: Cn1cc(Br)cc(Nc2ccc(N3CCN(CCO)CC3)cn2)c1=O]

To a suspension of 123b (300 mg, 0.57 mmol) at room temperature in MeOH (20 mL) was added L(−)-camphorsulfonic acid (199 mg, 0.86 mmol). The reaction mixture was stirred overnight. Water (20 mL) was added and the mixture was extracted with ethyl acetate (50 mL×2). The combined organic layer was dried over anhydrous sodium sulfate and concentrated to afford 123c (325 mg, 95%) as a yellow solid. MS: [M+H]$^+$ 408.7.

Example 123d (4-(5-(5-(4-(2-Hydroxyethyl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 123d

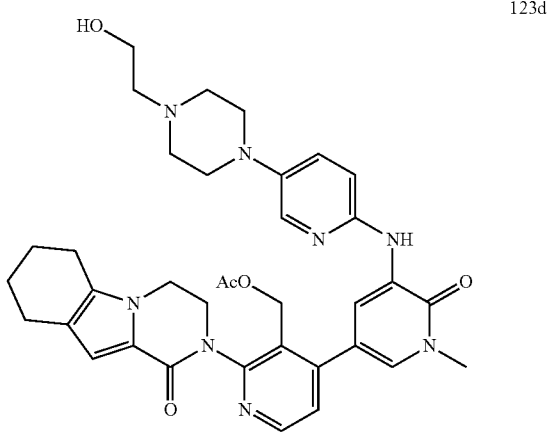 [SMILES: CC(=O)OCc1c(-c2cc(Nc3ccc(N4CCN(CCO)CC4)cn3)c(=O)n(C)c2)ccnc1N1CCn2c(cc3c2CCCC3)C1=O]

A sealed tube was charged with 123c (200 mg, 0.49 mmol), 3-(acetoxymethyl)-2-(1-oxo-3,4,6,7,8,9-hexahydropyrazino[1,2-a]indol-2(1H)-yl)pyridin-4-ylboronic acid (113i) (188 mg, 0.49 mmol), Pd(dppf)Cl$_2$ (40 mg, 0.049 mmol), K$_3$PO$_4$ (208 mg, 0.98 mmol), NaOAc (133 mg, 0.98 mmol), H$_2$O (3 mL), and MeCN (50 mL). The mixture was heated at 110° for 3 h. The solvent was evaporated in vacuo and the residue was purified by silica gel chromatography eluting with 30:1 DCM/MeOH to 123d (187 mg, 57%). MS: [M+H]$^+$ 667.7.

Example 123

2-(4-(5-(5-(4-(2-Hydroxyethyl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydro-pyrazino[1,2-a]indol-1(2H)-one 123

A mixture of 123d (187 mg, 0.28 mmol) and LiOH (235 mg, 5.6 mmol) in iPrOH/THF (1:1, 3.5 mL) and H$_2$O (0.5 mL) was stirred at 35° C. for 0.5 h. It was then evaporated in vacuo and the residue was extracted with EtOAc (5 mL×2). The combined EtOAc extract was concentrated under reduced pressure and the residue was purified by reverse-phase prep-HPLC to afford 123 (40 mg, 31%) as a yellow solid. MS: [M+H]$^+$ 625.4. $^1$H NMR (500 MHz, CDCl$_3$) δ 8.63 (d, J=2.5, 1H), 8.49 (d, J=5.0, 1H), 7.92 (d, J=2.5, 1H), 7.82 (d, J=2.0, 1H), 7.78 (s, 1H), 7.36 (d, J=5.5, 1H), 7.27-7.25 (m, 1H), 6.89 (s, 1H), 6.81 (d, J=9.5, 1H), 5.04-5.02 (m, 1H), 4.62 (d, J=10, 1H), 4.50-4.47 (m, 1H), 4.34-4.29 (m, 1H), 4.12-4.09 (m, 2H), 3.89-3.85 (m, 1H), 3.71-3.67 (m, 5H), 3.15-3.12 (m, 4H), 2.74-2.54 (m, 10H), 1.92-1.87 (m, 2H), 1.79-1.78 (m, 3H)

Example 124a

4-Chloro-2-{6-oxo-8-thia-4,5-diazatricyclo[7.4.0.0$^{2,7}$]trideca-1(9),2(7),3-trien-5-yl}pyridine-3-carbaldehyde 124a To a suspension of 2-bromo-4-chloronicotinaldehyde 103a (641 mg, 2.9 mmol) and 8-thia-4,5-diazatricyclo[7.4.0.0$^{2,7}$]trideca-1(9),2(7),3-trien-6-one 191d (400 mg, 1.94 mmol) in dioxane (20 mL) was added K$_2$CO$_3$ (536 mg, 3.88 mmol), CuI (369 mg, 1.94 mmol), and 4,7-dimethoxy-1,10-phenanthroline (471 mg, 1.96 mmol). After bubbling nitrogen through the resulting solution for 30 min, the mixture was stirred at 80° C. for 16 h. It was allowed to cool to room temperature and added into H$_2$O (100 mL). The aqueous layer was separated and extracted with ethyl acetate (2×200 mL). The combined organic layer was washed with brine (100 mL) and dried over sodium sulfate. The drying agent was removed by filtration and the filtrate was concentrated under reduced pressure. The residue was purified on flash column eluting with PE:EA (5:1) to afford 124a (230 mg, 34%). LCMS: [M+H]$^+$ 346

Example 124b

4-[1-Methyl-5-(5-(4-(oxetan-3-yl)piperazin-1-yl)pyridin-2-ylamino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine-3-carbaldehyde 124b A round bottom flask was charged with 124a, 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 1011 (271 mg, 0.58 mmol), PdCl$_2$(dppf) (50 mg, 0.06 mmol), K$_3$PO$_4$.3H$_2$O (323 mg, 1.16 mmol), THF (15 mL), and H$_2$O (5 mL). After three cycles of vacuum/argon flush, the mixture was heated at 70° C. for 2 h. It was then filtered and the filtrate was evaporated in vacuo. The residue was purified on flash column chromatography eluting with 1:3 petroleum/ethyl acetate to afford 124b as a yellow solid (200 mg, 53%). LCMS: [M+H]+ 651

Example 124

3-Hydroxymethyl-4-[1-methyl-5-(5-(4-(oxetan-3-yl)piperazin-1-yl)pyridine-2-ylamino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine 124

A mixture of 4-[1-methyl-5-(5-(4-(oxetan-3-yl)piperazin-1-yl)pyridin-2-ylamino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine-3-carbaldehyde 124b (200 mg, 0.31 mmol), NaBH$_4$ (35 mg, 0.92 mmol) and CH$_3$OH (10 mL) was stirred at 25° C. for 1 h. The mixture was then extracted with CH$_2$Cl$_2$ (10 mL×2). The combined CH$_2$Cl$_2$ extract was concentrated under reduced pressure. The residue was purified with reverse-phase prep-HPLC to afford 124 (100 mg, 50%) as a yellow solid. LCMS: [M+H]+ 653. $^1$H NMR (500 MHz, DMSO) δ 8.64 (d, J=2.0 Hz, 1H), 8.57 (d, J=5.0 Hz, 1H), 8.46-8.48 (m, 2H), 7.88 (d, J=3.0 Hz, 1H), 7.54 (d, J=5.0 Hz, 1H), 7.48 (d, J=2.5 Hz, 1H), 7.37-7.39 (m, 1H), 7.24 (d, J=9.0 Hz, 1H), 4.85-4.87 (m, 1H), 4.55-4.57 (m, 2H), 4.45-4.47 (m, 2H), 3.67-4.39 (m, 2H), 3.60 (s, 3H), 3.42-3.45 (m, 1H), 3.06-3.08 (m, 4H), 2.95 (s, 2H), 2.87 (s, 2H), 2.38-2.40 (m, 4H), 1.87-1.89 (m, 4H).

Example 125a (3-Nitro-1H-pyrazol-5-yl)methanol 125a

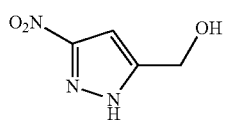

A 3-L three-neck round-bottomed flask equipped with a mechanical stirrer, addition funnel and nitrogen inlet was purged with nitrogen and charged with 3-nitropyrazole-5-carboxylic acid (28.0 g, 178 mmol) and THF (420 mL) and cooled to −5° C. using an ice/acetone bath. Borane-THF complex solution (1.0 M, 535 mL, 535 mmol) was added at a rate that maintained the internal reaction temperature below 5° C. After the addition was complete the cooling bath was removed and the reaction was stirred at room temperature for 18 h. After this time the reaction was cooled to −5° C. using an ice/acetone bath, water (70 mL) and 4N hydrochloric acid (70 mL) was added and the reaction was stirred at reflux for 1 h in order to destroy the borane complex with pyrazole. The reaction was cooled to room temperature and concentrated under reduced pressure to a volume of approximately 30 mL. Ethyl acetate (175 mL) was added and the mixture stirred for 15 min. The aqueous layer was separated and extracted with ethyl acetate (4×200 mL). The combined organic layers were washed with saturated aqueous sodium bicarbonate (2×50 mL), brine (50 mL) and dried over sodium sulfate, the drying agent was removed by filtration, and the filtrate concentrated under reduced pressure to afford 125a in a 94% yield (24.0 g) as a light yellow solid: $^1$H NMR (300 MHz, DMSO-d$_6$) δ 13.90 (br s, 1H), 6.87 (s, 1H), 5.58 (t, 1H, J=5.4 Hz), 4.53 (d, 2H, J=5.1 Hz); MS (ESI+) m/z 144.0 (M+H)

Example 125b (1-(2-Bromoethyl)-3-nitro-1H-pyrazol-5-yl)methanol 125b

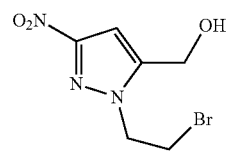

A 1-L three-necked round-bottomed flask equipped with a mechanical stirrer and thermoregulator was purged with nitrogen and charged with 125a (25.0 g, 175 mmol), DMF (250 mL), and cesium carbonate (70.0 g, 215 mmol) was heated at 104° C. for 5 min. The reaction mixture was then cooled to 0° C. using an ice/acetone bath and dibromoethane (329 g, 1.75 mol) was added portionwise (no exotherm). The reaction was stirred at 0° C. for 1 then at room temperature for 4 h. After this time a solution of KH$_2$PO4 (40 g) in water (400 mL) was added slowly. The reaction mixture stirred at room temperature for 30 min. Ethyl acetate (450 mL) was added and the aqueous layer was separated and extracted with ethyl acetate (2×100 mL). The combined organic layers were washed with water (200 mL), brine (200 mL), dried over sodium sulfate, and the drying agent was removed by filtration. The filtrate was concentrated under reduced pressure to afford an 86% yield (37.5 g) of crude 125b as an orange oil: $^1$H NMR (300 MHz, CDCl$_3$) δ 6.85 (s, 1H), 4.82 (d, 2H, J=5.4 Hz), 4.66 (t, 2H, J=6.3 Hz), 3.83 (t, 2H, J=6.3 Hz); MS (ESI+) m/z 249.9 (M+H).

Example 125c 1-(2-Bromoethyl)-5-(bromomethyl)-3-nitro-1H-pyrazole 125c

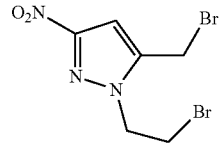

A 500-mL three-necked round-bottomed flask equipped with a magnetic stirrer, nitrogen inlet and reflux condenser was purged with nitrogen and charged with 125b (37.0 g, 148 mmol) and chloroform (160 mL). The reaction was cooled to −5° C. using an ice/acetone bath and phosphorous tribromide (40.0 g, 148 mmol) was added portionwise. The cooling bath was removed and the reaction stirred at reflux for 2 h. After this time, the reaction was cooled to −5° C. and saturated aqueous sodium bicarbonate (250 mL) was added until a pH of 8.5 was reached. The mixture was extracted with ethyl acetate (3×150 mL) and the combined organic layers were washed with saturated aqueous sodium carbonate (2×50 mL), brine (75 mL), dried over sodium sulfate and the drying agent was removed by filtration. The filtrate was concentrated under reduced pressure to afford a yellow residue that was dissolved with gentle heating in methylene chloride (60 mL). Hexanes (approximately 20 mL) was added and the solution became cloudy. The mixture was heated until a solid precipitate formed, methylene chloride (9 mL) was added and the solution became clear. The solution was left to cool to room temperature and after 4 h the resulting crystals were collected by vacuum filtration. The filter cake was washed with a ice cold 1:2 mixture of methylene chloride:hexanes (2×20 mL) to afford 1-(2-bromoethyl)-5-(bromomethyl)-3-nitro-1H-pyrazole (19.7 g). The combined filtrates were evaporated and the procedure was performed again to afford an additional 9.70 g of 1-(2-bromoethyl)-5-(bromo-methyl)-3-nitro-1H-pyrazole. The solids were combined and dried under high vacuum for 18 h to afford a 57% yield (26.0 g) of 125c as white crystals: mp 95-97° C.; $^1$H NMR (300 MHz, CDCl$_3$) δ 6.93 (s, 1H), 4.63 (t, 2H, J=6.0 Hz), 4.54 (s, 2H), 3.86 (t, 2H, J=6.0 Hz).

Example 125d 2-nitro-4,5,6,7-tetrahydropyrazolo[1,5-a]pyrazine 125d

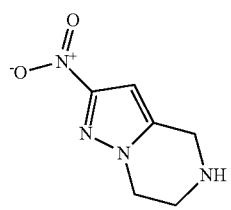

A sealed tube equipped with a magnetic stirrer was charged with 125c (4 g, 12.9 mmol) 0.5M ammonia solution in dioxane (200 mL). The resulting mixture was carefully heated to 50° C. overnight. After this time, the reaction mixture was concentrated under reduced pressure, and to the residue was added H$_2$O (50 mL) and EtOAc (50 mL). The aqueous layer was separated and extracted with EtOAc (2×50 mL). The combined organic extracts were washed with brine (100 mL) and dried over sodium sulfate. The resulting solution was concentrated under reduced pressure to afford a 100% yield (2.1 g) of crude 125d.

Example 125e 1-(2-nitro-6,7-dihydropyrazolo[1,5-a]pyrazin-5(4H)-yl)ethanone 125e

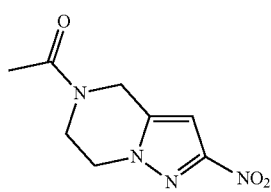

A 200 mL round bottom flask was charged with 125d (2.1 g, 12.9 mmol), triethylamine (5.5 mL, 38.7 mmol), acetyl chloride (1.1 mL, 15.5 mmol) and CH$_2$Cl$_2$ (100 mL). The mixture stirred at room temperature over night. After this time, the reaction mixture was concentrated under reduced pressure, and to the residue was added H$_2$O (50 mL) and EtOAc (50 mL). The aqueous layer was separated and extracted with EtOAc (2×50 mL). The combined organic extracts were washed with brine (100 mL). The combined aqueous extracts were back extracted with 9:1 CH$_2$Cl$_2$:MeOH (2×50 mL). The combined organics were dried over sodium sulfate. The resulting residue was purified by column chromatography eluting with a gradient of CH$_2$Cl$_2$—9:1 CH$_2$Cl$_2$:MeOH to afford a 84% yield (2.3 g) of 125e.

Example 125f 1-(2-amino-6,7-dihydropyrazolo[1,5-a]pyrazin-5 (4H)-yl)ethanone 125f

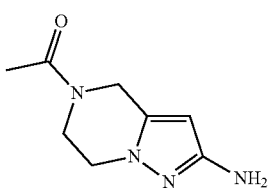

A 500-mL Parr hydrogenation bottle was charged with 125e (2.3 g, 10.9 mmol), 10% palladium on carbon (50% wet, 570 mg dry weight) and ethanol (100 mL). The bottle was evacuated, charged with hydrogen gas to a pressure of 50 psi and shaken for 2 h on a Parr hydrogenation apparatus. The catalyst was removed by filtration through a pad of CELITE® 521 washing with 1:1 CH$_2$Cl$_2$:MeOH (500 mL). The resulting solution was concentrated under reduced pressure to afford a 95% yield (1.9 g) of crude 125f.

Example 125g 3-(5-acetyl-4,5,6,7-tetrahydropyrazolo[1,5-a]pyrazin-2-ylamino)-5-bromo-1-methylpyridin-2(1H)-one 125g

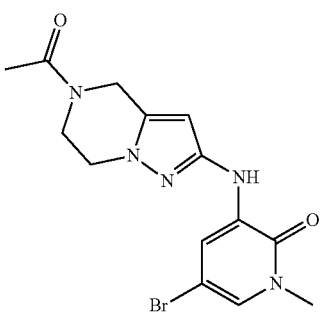

A sealed tube was equipped with a magnetic stirrer and charged with 125f (860 mg, 4.8 mmol), 3,5-dibromo-1-methylpyridin-2(1H)-one (1.8 g, 6.7 mmol), and cesium carbonate (3.4 g, 10.5 mmol) in 1,4-dioxane (67 mL). After bubbling nitrogen through the solution for 30 min, Xantphos (330 mg, 0.6 mmol) and tris(dibenzylideneacetone)dipalladium(0)

(300 mg, 0.3 mmol) were added, and the reaction mixture was heated to 100° C. for 16 h. After this time, H₂O (50 mL) and EtOAc (50 mL) were added. The aqueous layer was separated and extracted with EtOAc (2×50 mL). The combined organic extracts were washed with brine (100 mL) and dried over sodium sulfate. The resulting residue was purified by column chromatography eluting with a gradient of CH₂Cl₂ —60:35:5 CH₂Cl₂:Et₂O:MeOH to afford a 41% yield of 125g (720 mg).

Experiment 125h

5-Bromo-1-methyl-3-(4,5,6,7-tetrahydropyrazolo[1,5-a]pyrazin-2-ylamino)pyridin-2(1H)-one 125h

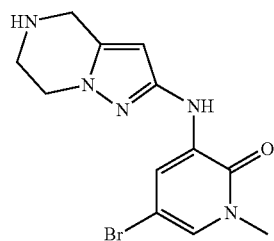

A 50 mL round bottom flask with a magnetic stirrer and reflux condenser was charged with 125g (250 mg, 0.7 mmol), aqueous NaOH (5N, 6 mL), ethanol (6 mL). The mixture stirred at reflux for 30 min. After this time, ethyl acetate (5 mL) and water (5 mL) were added. The separated aqueous layer was extracted with ethyl acetate (2×5 mL). The combined organics were washed with brine (10 mL), dried over sodium sulfate, filtered and concentrated under reduced pressure to afford a 91% yield (200 mg) of crude 125h.

Example 125i

5-Bromo-1-methyl-3-(5-(oxetan-3-yl)-4,5,6,7-tetrahydropyrazolo[1,5-a]pyrazin-2-ylamino)pyridin-2(1H)-one 125i

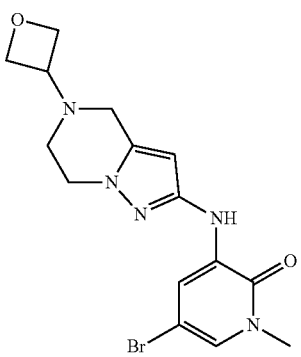

Compound 125i was synthesized using the same procedure as 101k, where 5-bromo-1-methyl-3-(4,5,6,7-tetrahydropyrazolo[1,5-a]pyrazin-2-ylamino)pyridin-2(1H)-one (125h) (250 mg, 0.78 mmol), and oxetan-3-one (600 mg, 8.3 mmol) in methanol (8 mL) were mixed. Sodium cyanoborohydride (148 mg, 3 mmol) and zinc chloride (165 mg, 1.5 mmol) in methanol (8 mL) was added, and the reaction was heated at 48° C. for 12 hours. Work-up and flash column chromatography (silica, 60:35:5 methylene chloride/diethyl ether/methanol) afford a 34% yield (100 mg) of 5-bromo-1-methyl-3-(5-(oxetan-3-yl)-4,5,6,7-tetrahydropyrazolo[1,5-a]pyrazin-2-ylamino)pyridin-2(1H)-one (125i) as a light green solid: MS (ESI+) m/z 382.1 (M+H).

Example 125j (4-(1-Methyl-5-(5-(oxetan-3-yl)-4,5,6,7-tetrahydropyrazolo[1,5-a]pyrazin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 125j

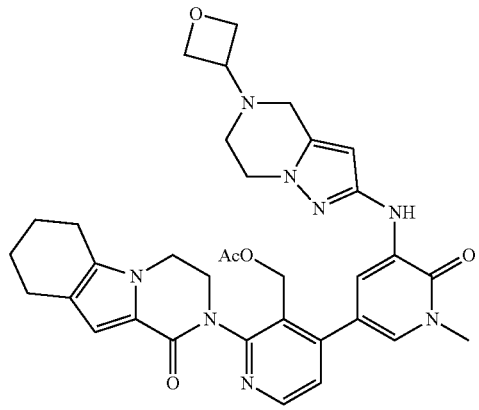

Following the procedures as described for compound 113j, 3-(acetoxymethyl)-2-(1-oxo-3,4,6,7,8,9-hexahydropyrazino[1,2-a]indol-2(1H)-yl)pyridin-4-ylboronic acid 113i (200 mg, 0.52 mmol) and 125i (198 mg, 0.52 mmol) were reacted to give 125j as a yellow solid (200 mg, 60%). LCMS: [M+H]⁺ 639

Example 125

2-(3-(Hydroxymethyl)-4-(1-methyl-5-(5-(oxetan-3-yl)-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydropyrazino[1,2-a]indol-1(2H)-one 125

Following the procedures as described in Example 123, 125j (200 mg 0.31 mmol) was hydrolyzed by lithium hydroxide to give 125 as a white solid (116 mg, 62%). LCMS: [M+H]⁺ 597. ¹H NMR (500 MHz, CDCl3) δ 8.48 (d, J=5.0, 1H), 7.95 (d, J=2.0, 1H), 7.69 (d, J=2.0, 1H), 7.43 (s, 1H), 7.34 (d, J=5.5, 1H), 6.89 (s, 1H), 5.73 (s, 1H), 5.02 (t, J=6.5, 1H), 4.75 (t, J=6.5, 2H), 4.67 (t, J=6.5, 2H), 4.61-4.63 (m, 1H), 4.50 (s, 1H), 4.31-4.35 (m, 1H), 4.10-4.16 (m, 4H), 3.86-3.88 (m, 1H), 3.74-3.79 (m, 1H), 3.70 (s, 3H), 3.56 (d, J=4.5, 2H), 2.82 (t, J=4.5, 2H), 2.50-2.62 (m, 4H), 1.88-1.92 (m, 2H), 1.78-1.82 (m, 2H)

Example 126a

3-Bromo-5-(1-oxo-6,7,8,9-tetrahydropyrazino[1,2-a]indol-2(1H)-yl)isonicotinaldehyde 126a

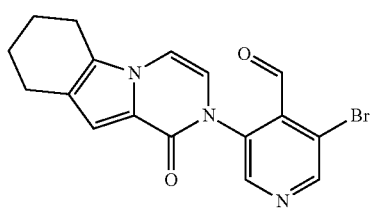

A 100-mL single-neck round-bottomed flask equipped with a magnetic stirrer and reflux condenser was charged with 1,4-dioxane (15 mL), 3,5-dibromoisonicotinaldehyde (604 mg, 2.28 mmol), 6,7,8,9-tetrahydropyrazino[1,2-a]indol-1(2H)-one (142 mg, 0.76 mmol) and cesium carbonate (485 mg, 1.5 mmol). CuI (143 mg, 0.76 mmol) and 4,7-dimethoxy-1,10-phenanthroline (127 mg, 0.52 mmol) were added, and the reaction mixture was heated at 100° C. for 5 h. After this time, the reaction was cooled to room temperature. It was then filtered and the filtrate was concentrated under reduced pressure. The residue was purified on flash column eluting with EtOAC/PE (1:2) to afford 126a (100 mg, 35%) as a yellow solid. MS: [M+H]$^+$ 372.

Example 126b 3-(1-Methyl-5-(5-(4-(oxetan-3-yl)piperazin-1-yl)pyridin-2-ylamino)-6-oxo-1,6-dihydropyridin-3-yl)-5-(1-oxo-6,7,8,9-tetrahydropyrazino[1,2-a]indol-2(1H)-yl)isonicotinaldehyde 126b

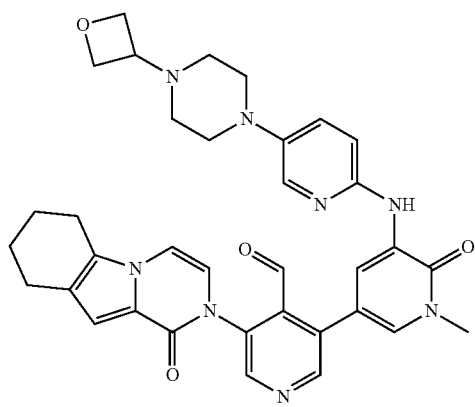

A sealed tube was charged with 126a (100 mg, 0.27 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101l (125 mg, 0.27 mmol), PdCl$_2$(dppf) (18 mg, 0.02 mmol), K$_3$PO$_4$ (30 mg), and NaOAc (20 mg) in CH$_3$CN (5 mL) and H$_2$O (1 mL). The system was evacuated and refilled with N$_2$. The reaction mixture was heated at 100° C. for 2 h, and then cooled to room temperature. It was then filtered and the filtrate was concentrated under reduced pressure. The resulting residue was purified by flash column chromatography eluting with 10:1 of DCM/MeOH to afford 126b (80 mg, 48%) as a yellow solid. MS: [M+H]$^+$ 633.

Example 126

2-(4-(Hydroxymethyl)-5-(1-methyl-5-(5-(4-(oxetan-3-yl)piperazin-1-yl)pyridin-2-ylamino)-6-oxo-1,6-dihydropyridin-3-yl)pyridin-3-yl)-6,7,8,9-tetrahydropyrazino[1,2-a]indol-1(2H)-one 126

To a suspension of 126b (76 mg, 0.12 mmol) at 0° C. in methanol (4 mL) was added sodium borohydride (20 mg, 0.7 mmol) and the mixture was stirred for 30 minutes. Then the reaction mixture was quenched with water (1.0 mL) and concentrated. The residue was purified by reverse-phase prep-HPLC to afford 126 (28 mg, 37%). LCMS: [M+H]$^+$ 635. $^1$H NMR (500 MHz, DMSO) δ 8.61 (d, J=2.5, 1H), 8.59 (s, 1H), 8.50 (s, 1H), 8.43 (s, 1H), 7.86 (d, J=3.0, 1H), 7.38-7.36 (m, 2H), 7.27-7.22 (m, 2H), 6.82-6.78 (m, 2H), 5.18-5.11 (m, 1H), 4.55 (t, J=6.0, 2H), 4.45 (t, J=6.0, 2H), 4.41-4.29 (m, 2H), 3.60 (s, 3H), 3.44-3.42 (m, 1H), 3.06 (t, J=4.5, 4H), 2.75-2.73 (m, 2H), 2.62-2.60 (m, 2H), 2.38 (t, J=4.5, 4H), 1.86-1.75 (m, 4H).

Example 127a (4-(1-Methyl-6-oxo-5-(5-(piperazin-1-yl)pyridin-2-ylamino)-1,6-dihydropyridin-3-yl)-2-(1-oxo-3,4,6,7,8,9-hexahydropyrazino[1,2-a]indol-2(1H)-yl)pyridin-3-yl)methyl Acetate 127a

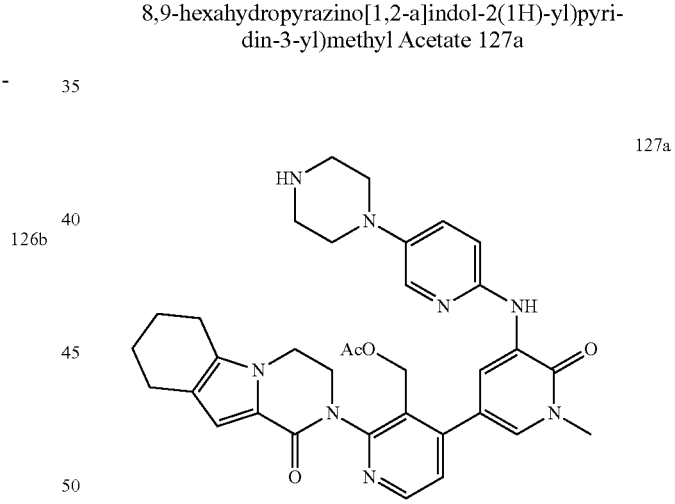

A 100-mL single-neck round-bottomed flask equipped with magnetic stirrer and reflux condenser was charged with 5-bromo-1-methyl-3-(5-(piperazin-1-yl)pyridin-2-ylamino)pyridin-2(1H)-one 101j (200 mg, 0.55 mmol), 3-(acetoxymethyl)-2-(1-oxo-3,4,6,7,8,9-hexahydropyrazino[1,2-a]indol-2(1H)-yl)pyridin-4-ylboronic acid 113i (210 mg, 0.55 mmol), Pd(dppf)Cl$_2$ (45 mg, 0.055 mmol), K$_3$PO$_4$ (284 mg, 1.65 mmol), and tetrahydrofuran (20 mL). After three cycles of vacuum/argon flush, the mixture was heated at reflux for 5 h. It was then cooled to room temperature and filtered. The filtrate was concentrated under reduced pressure and the resulting residue was purified by silica-gel column chromatography eluting with dichloromethane/methanol (33:1) to afford 127a as a brown solid (200 mg, 58.3%). MS: [M+H]$^+$ 623.7.

Example 127

2-(3-(Hydroxymethyl)-4-(1-methyl-6-oxo-5-(5-(piperazin-1-yl)pyridin-2-ylamino)-1,6-dihydropyridin-3-yl)pyridin-2-yl)-3,4,6,7,8,9-hexahydropyrazino[1,2-a]indol-1(2H)-one 127

A mixture of 127a (190 mg, 0.31 mmol) and LiOH (571 mg, 13.6 mmol) in ⁱPrOH/THF (1:1, 3.5 mL) and H₂O (0.5 mL) was stirred at 35° C. for 0.5 h. It was then evaporated in vacuo and the residue was extracted with EtOAc (5 mL×2). The combined EtOAc extract was concentrated under reduced pressure and the residue was purified by reverse-phase prep-HPLC to afford 127 (50 mg, 26.9%). MS: [M+H]⁺ 581.3. ¹H NMR (500 MHz, CDCl₃) δ 8.63 (d, J=2.0, 1H), 8.49 (d, J=5.0, 1H), 7.91 (d, J=3.5, 1H), 7.82 (d, J=2.0, 1H), 7.77 (s, 1H), 7.37 (d, J=5.0, 1H), 7.20-7.25 (m, 1H), 6.89 (s, 1H), 6.81 (d, J=9.0, 1H), 5.04-5.02 (m, 1H), 4.64-4.61 (m, 1H), 4.50 (d, J=5.0, 1H), 4.34-4.31 (m, 1H), 4.18-4.08 (m, 2H), 3.89-3.86 (m, 1H), 3.71 (s, 3H), 3.05-3.06 (m, 8H), 2.62-2.56 (m, 4H), 1.92-1.88 (m, 2H), 1.81-1.78 (m, 3H)

Example 128a

5-Cyclopropyl-2-nitro-4,5,6,7-tetrahydropyrazolo[1,5-a]pyrazine 128a

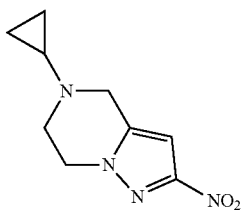

A mixture of 1-(2-bromoethyl)-5-(bromomethyl)-3-nitro-1H-pyrazole 113c (4 g, 12.9 mmol) and cyclopropanamine (7.35 g, 129 mmol) in THF (40 mL) was stirred at 30° C. overnight. After the completion of the reaction, the mixture was filtered and the solid was washed with THF (100 mL). The filtrate was concentrated under reduced pressure to give 128a (2.68 g, 99%). MS: [M+H]⁺ 209.

Example 128b

5-Cyclopropyl-4,5,6,7-tetrahydropyrazolo[1,5-a]pyrazin-2-amine 128b

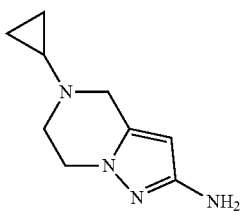

A mixture of 128a (2.68 g, 12.9 mmol), Fe (3.6 g, 64.4 mmol) and NH₄Cl (4.1 g, 77.4 mmol) in ethanol (30 mL) and water (5 mL) was heated at reflux for 2 h. After the completion of the reaction, the mixture was filtered and the solid was washed with ethanol (150 mL). The filtrate was evaporated in vacuo and the residue was extracted with methanol/methylene chloride (1/7). The combined extracts were dried over Na₂SO₄ and evaporated. The residue was purified on reverse phase Combi-flash to give 128b (1.8 g, 75%). MS: [M+H]⁺ 179.

Example 128c

5-Bromo-3-(5-cyclopropyl-4,5,6,7-tetrahydropyrazolo[1,5-a]pyrazin-2-ylamino)-1-methylpyridin-2(1H)-one 128c

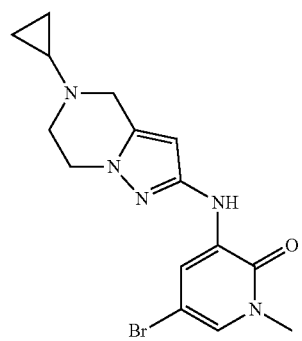

A mixture of 128b (1.39 g, 7.8 mmol), XantPhos (450 mg, 0.78 mmol), Pd₂dba₃ (476 mg, 0.52 mmol), 3,5-dibromo-1-methylpyridin-2(1H)-one (1.72 g, 6.5 mmol) and Cs₂CO₃ (6.3 mg. 19.5 mmol) in 1,4-dioxane (30 mL) was heated at reflux for 1 h. After the completion of the reaction the mixture was filtered off and the solid was washed with methanol (60 mL). The filtrate was evaporated in vacuo and the residue was purified on reverse phase Combi-flash to give 128c (0.84 g, 30%). MS: [M+H]⁺ 364.

Example 128d (4-(5-(5-Cyclopropyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 128d

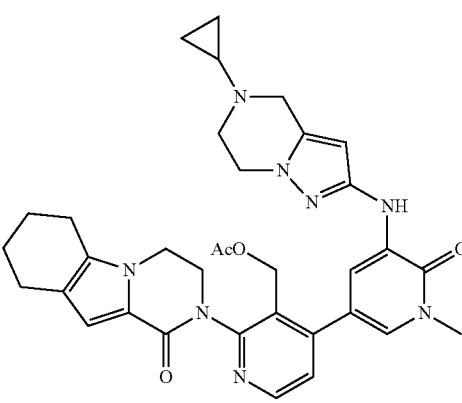

Following the procedures as described in Example 113j, reaction of 128c (230 mg, 0.6 mmol) and 3-(acetoxymethyl)-2-(1-oxo-3,4,6,7,8,9-hexahydropyrazino[1,2-a]indol-2(1H)-

Example 128

2-(4-(5-(5-Cyclopropyl-4,5,6,7-tetrahydropyrazolo[1,5-a]pyrazin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 128

Following the procedures as described in Example 113, 128d (331 mg, 0.53 mmol) was hydrolyzed with lithium hydroxide afforded 128 as a white solid (54 mg, 20%). LCMS: [M+H]+ 581. $^1$H NMR (500 MHz, CDCl$_3$) δ 8.48 (d, J=5.0, 1H), 7.93 (d, J=2.0, 1H), 7.72 (d, J=2.0, 1H), 7.40 (s, 1H), 7.34 (d, J=5.0, 1H), 6.90 (s, 1H), 5.70 (s, 1H), 5.03-5.02 (m, 1H), 4.64-4.62 (m, 1H), 4.52 (s, 1H), 4.32 (s, 1H), 4.16-4.03 (m, 4H), 3.89-3.87 (m, 1H), 3.80 (s, 2H), 3.70 (s, 3H), 3.12-3.10 (m, 2H), 2.61-2.57 (m, 4H), 1.90 (d, J=5.5, 3H), 1.79 (s, 2H), 0.56 (d, J=6.0, 2H), 0.53 (s, 2H)

Example 129a

2-Nitro-6,7-dihydro-4H-pyrazolo[5,1-c][1,4]oxazine 129a

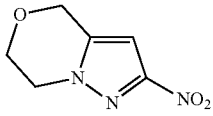

A 250-mL single-neck round-bottomed flask equipped with a magnetic stirrer and reflux condenser was charged with 1-(2-bromoethyl)-5-(bromomethyl)-3-nitro-1H-pyrazole 113c (3.00 g, 9.59 mmol) and 4M aqueous hydrobromic acid (120 mL), and the resulting mixture was heated at reflux for 24 h. After this time, the reaction mixture was concentrated under reduced pressure to approximately 6 mL volume, and the residue was stirred in 2M aqueous sodium hydroxide (40 mL) for 2 h. After this time methylene chloride was added (40 mL) and the mixture was stirred for 15 min. The aqueous layer was separated and extracted with methylene chloride (2×50 mL). The combined organic extracts were washed with brine (100 mL) and dried over sodium sulfate. The drying agent was removed by filtration and the filtrate concentrated under reduced pressure to afford a 62% yield (1.01 g) of 129a as a white solid: mp 110-112° C.; $^1$H NMR (300 MHz, CDCl$_3$) δ 6.68 (s, 1H), 4.87 (s, 2H), 4.28 (t, 2H, J=5.4 Hz), 4.20 (t, 2H, J=5.1 Hz); MS (ESI+) m/z 170.0 (M+H).

Example 129b 6,7-Dihydro-4H-pyrazolo[5,1-c][1,4]oxazin-2-amine 129b

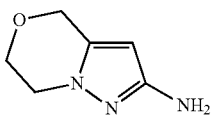

A 500-mL Parr hydrogenation bottle was purged with nitrogen and charged with 129a (1.01 g, 5.92 mmol), 10% palladium on carbon (50% wet, 125 mg dry weight) and ethanol (50 mL). The bottle was evacuated, charged with hydrogen gas to a pressure of 25 psi and shaken for 2 h on a Parr hydrogenation apparatus. The hydrogen was then evacuated and nitrogen charged to the bottle. The catalyst was removed by filtration through a pad of CELITE® 521 and the filtrate concentrated under reduced pressure. The resulting residue was purified by column chromatography using 400 cc of silica gel and eluting with 3% methanol in methylene chloride. The fractions containing 129b were collected to afford, after concentrating under reduced pressure, a 73% yield (601 mg) of 129b as a yellow solid: mp 74-76° C. $^1$H NMR (300 MHz, CDCl$_3$) δ 5.37 (s, 1H), 4.72 (s, 2H), 4.07 (t, 2H, J=5.1 Hz), 3.98 (t, 2H, J=5.1 Hz), 3.57 (br s, 2H); MS (ESI+) m/z 140.4 (M+H).

Example 129c

5-Bromo-3-(6,7-dihydro-4H-pyrazolo[5,1-c][1,4]oxazin-2-ylamino)-1-methylpyridin-2(1H)-one 129c

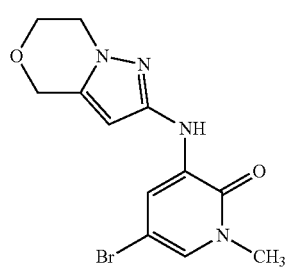

A 50-mL three-neck round-bottomed flask equipped with a magnetic stirrer, reflux condenser and nitrogen inlet was charged with 1,4-dioxane (20 mL), 129b (600 mg, 4.31 mmol), 3,5-dibromo-1-methylpyridine-2(1H)-one (1.44 g, 5.40 mmol) and cesium carbonate (3.08 g, 9.48 mmol). After bubbling nitrogen through the resulting solution for 30 min, Xantphos (300 mg, 0.52 mmol) and tris(dibenzylideneacetone)dipalladium(0) (320 mg, 0.35 mmol) were added, and the reaction mixture was heated at reflux for 2 h. After this time the reaction was cooled to room temperature, partitioned between ethyl acetate (75 mL) and water (75 mL) and filtered. The aqueous layer was separated and extracted with ethyl acetate (2×25 mL). The organic layers were combined and washed with brine (50 mL) and dried over sodium sulfate. The drying agent was removed by filtration and the filtrate concentrated under reduced pressure. The resulting residue was purified by column chromatography using 500 cc of silica gel and eluting with 1% methanol in methylene chloride. The fractions containing 129c were collected to afford, after concentrating under reduced pressure, a 31% yield (433 mg) of 129c as a green solid: mp 195-197° C.; $^1$H NMR (300 MHz, CDCl$_3$) δ 7.92 (d, 1H, J=2.4 Hz), 7.44 (s, 1H), 6.90 (d, 1H, J=2.4 Hz), 5.65 (s, 1H), 4.80 (s, 2H), 4.13 (s, 2H), 3.61 (s, 5H); MS (ESI+) m/z 324.9 (M+H).

Example 129d (4-(5-(6,7-Dihydro-4H-pyrazolo[5,1-c][1,4]oxazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 129d

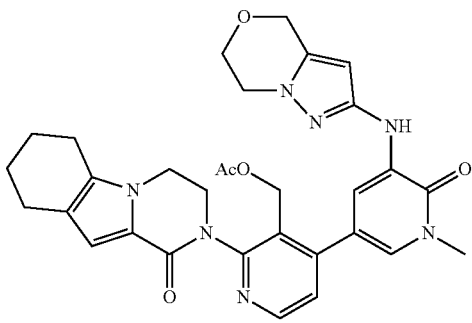

129d

Following the procedures as described in Example 113j, reaction of 3-(acetoxymethyl)-2-(1-oxo-3,4,6,7,8,9-hexahydropyrazino[1,2-a]indol-2(1H)-yl)pyridin-4-ylboronic acid 113i (200 mg, 0.52 mmol) and 129c (170 mg, 0.52 mmol) gave 129d as a yellow solid (185 mg, 61%). LCMS: [M+H]+ 584

Example 129

2-(4-(5-(6,7-Dihydro-4H-pyrazolo[5,1-c][1,4]oxazin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 129

Following the procedures as described in Example 113, 129d (180 mg 0.31 mmol) was hydrolyzed with lithium hydroxide to give 129 as a white solid (100 mg, 62%). LCMS: [M+H]+ 542. $^1$H NMR (500 MHz, CDCl$_3$) δ 8.48 (d, J=5.0, 1H), 7.98 (d, J=2.0, 1H), 7.71 (d, J=2.0, 1H), 7.46 (s, 1H), 7.35 (d, J=5.0, 1H), 6.89 (s, 1H), 5.72 (s, 1H), 5.03 (d, J=6.5, 1H), 4.79 (s, 2H), 4.61-4.64 (m, 1H), 4.50 (s, 1H), 4.31-4.35 (m, 1H), 4.06-4.16 (m, 6H), 3.86 (s, 1H), 3.71 (s, 3H), 2.56-2.62 (m, 4H), 1.88-1.92 (m, 2H), 1.80 (m, 2H)

Example 130a (3S)-tert-Butyl 3-methyl-4-(6-nitropyridin-3-yl)piperazine-1-carboxylate 130a

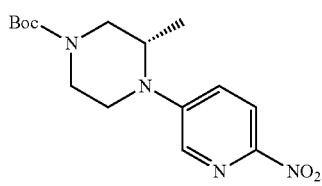

130a

Following the procedures as described for compound 101g, reaction of 5-bromo-2-nitropyridine (10.5 g, 50 mmol), and (3S)-tert-butyl-3-methylpiperazine-1-carboxylate (10.0 g, 50 mmol) afforded 130a as a yellow solid (8.05 g, 50%). LCMS: [M+H]+ 323

Example 130b (3S)-tert-butyl-4-(6-aminopyridin-3-yl)-3-methylpiperazine-1-carboxylate 130b

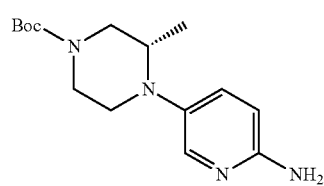

130b

Following the procedures as described for compound 101h, hydrogenation of 130a (5.8 g) afforded 130b as a brown solid (4.9 g, 96%). LCMS: [M+H]+ 293

Example 130c (3S)-tert-Butyl-4-(6-(5-bromo-1-methyl-2-oxo-1,2-dihydropyridin-3-ylamino)pyridine-3-yl)-3-methylpiperazine-1-carboxylate 130c

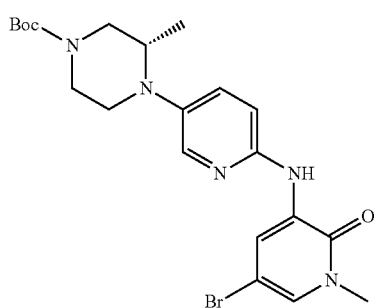

130c

Following the procedures as described for compound 101i, reaction of 130b (4.0 g) and 3,5-dibromo-1-methylpyridin-2(1H)-one (5.5 g) afforded 130c as a yellow solid (5.4 g, 83%). LCMS: [M+H]+ 478

Example 130d (3S)-5-Bromo-1-methyl-3-(5-(2-methylpiperazin-1-yl)pyridin-2-ylamino)pyridine-2(1H)-one 130d

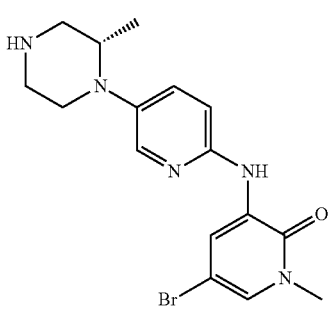

130d

Following the procedures as described for compound 101j, acidic hydrolysis of the Boc group of 130c (3.1 g) afforded 130d as a yellow solid (2.3 g, 95%). LCMS: [M+H]+ 380.

Example 130e (3S)-5-Bromo-1-methyl-3-(5-(2-methyl-4-(oxetan-3-yl)piperazin-1-yl)pyridine-2-ylamino)pyridin-2(1H)-one 130e

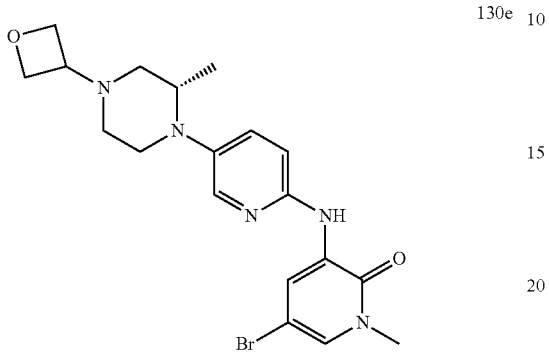

Following the procedures as described for compound 101k, reductive amination of 130d (2.35 g) with oxetan-3-one (0.4 mL) afforded 130e as a yellow solid (2.6 g, 98%). LCMS: [M+H]$^+$ 434.

Example 130f (3S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 130f

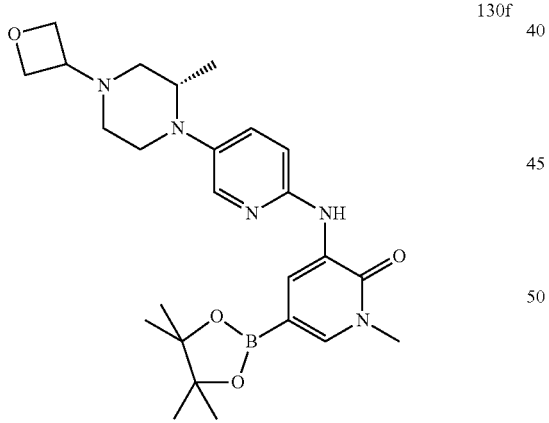

A 100 mL single-neck round-bottomed flask equipped with a magnetic stirrer and a reflux condenser was charged with 130e (1.0 g, 1.0 eq., 2.3 mmol), Pin$_2$B$_2$ (1.46 g, 2.50 eq., 5.75 mmol), Pd$_2$(dba)$_3$ (105 mg, 0.05 eq., 0.125 mmol), X-Phos (93 mg, 0.1 eq., 0.23 mmol), AcOK (676 mg, 3.0 eq., 6.9 mmol), and dioxane (50 mL). After three cycles of vacuum/argon flush, the mixture was heated at 90° C. for 4 hrs, then cooled to room temperature and filtered. The filtrate was concentrated under reduced pressure and the resulting residue was washed with 3:1 PE/EA (80 mL) to afford 130f as yellow solid (1.0 g, 90%). MS: [M+H]$^+$ 482.

Example 130g (3S)-4-[1-methyl-5-({5-[2-methyl 4-(oxetan-3-yl)piperazin-1-yl]pyridine-2-yl}amino)-6-oxo-1,6-dihydropyridin-3-yl]-2-{4,4-dimethyl-9-oxo-1,10-diazatricyclo[6.4.0.0$^{2,6}$]dodeca-2(6),7-dien-10-yl}pyridine-3-carbaldehyde 130g

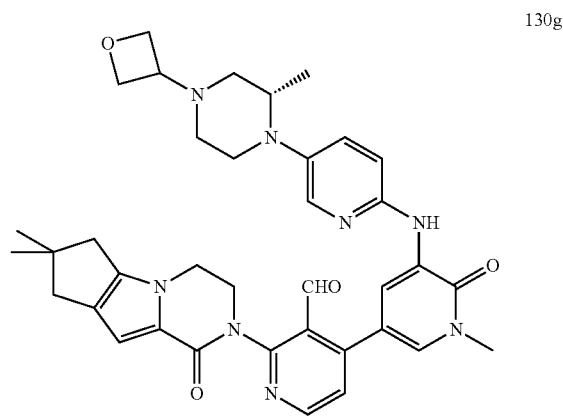

A 50 mL single-neck round-bottomed flask equipped with a magnetic stirrer and a reflux condenser was charged with 130f (420 mg, 1.0 eq., 0.44 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (200 mg, 2 eq., 0.88 mmol):

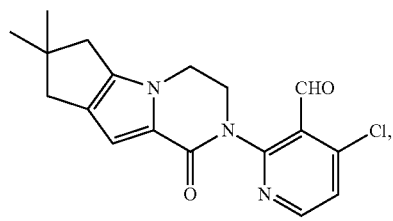 [SMILES: CC1(C)Cc2cc3n(c2C1)CCN(c1nccc(Cl)c1C=O)C3=O]

PdCl$_2$(dppf) (36 mg, 0.1 eq., 0.044 mmol), K$_3$PO$_4$ (279 mg, 3 eq., 1.32 mmol), and THF (20 mL). After three cycles of vacuum/argon flush, the mixture was heated at reflux for 5 h. It was then cooled to room temperature and filtered. The filtrate was concentrated under reduced pressure and the resulting residue was washed with 3:1 PE/EA (80 mL) to afford 130g (90 mg, 31%) as a yellow solid. MS: [M+H]$^+$ 663.

Example 130

(3S)-10-[4-[1-methyl-5-({5-[2-methyl 4-(oxetan-3-yl)piperazin-1-yl]pyridine-2-yl}amino)-6-oxo-1,6-dihydropyridin-3-yl]-3-(hydroxymethyl)pyridin-2-yl]-4,4-dimethyl-1,10-diazatricyclo[6.4.0.0$^{2,6}$]dodeca-2(6),7-dien-9-one 130

A 50 mL single-neck round-bottomed flask equipped with a magnetic stirrer and was charged with 130g (90 mg, 1 eq., 0.11 mmol), LiOH (7.9 mg, 3 eq., 0.33 mmol), i-PrOH (3 mL), THF (3 mL) and H$_2$O (2 mL). The mixture was stirred at 30° C. for 2 h. It was then filtered and concentrated. The residue was purified by reverse-phase prep-HPLC to afford 130 (40 mg, 44%) as a yellow solid. LCMS: [M+H]$^+$ 665.4. $^1$H NMR (500 MHz, CDCl$_3$) δ 8.65 (d, J=2.0, 1H), 8.48 (d, J=5.0, 1H), 7.96 (d, J=2.0, 1H), 7.84-7.83 (m, 2H), 7.36 (d, J=5.0, 1H), 7.31 (dd, J=3.0, 9.0, 1H), 6.84 (s, 1H), 6.81 (d, J=9.0, 1H), 5.08-5.05 (m, 1H), 4.71-4.61 (m, 5H), 4.51-4.29 (m, 2H), 4.16-4.15 (m, 2H), 3.87-3.85 (m, 1H), 3.72 (s, 3H), 3.55-3.45 (m, 2H), 3.06-3.08 (m, 2H), 2.59-2.47 (m, 7H), 2.22-2.17 (m, 1H), 1.27 (s, 6H), 0.98 (d, J=6.5, 3H).

Example 131a (S)-(4-(5-(5-(2-ethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 131a

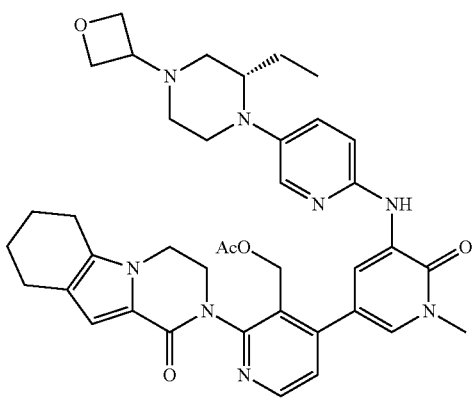

A sealed tube equipped with a magnetic stirrer was charged with (S)-5-bromo-3-(5-(2-ethyl-4-(oxetan-3-yl)piperazin-1-yl)pyridin-2-ylamino)-1-methylpyridin-2(1H)-one 161e (269 mg, 0.60 mmol):

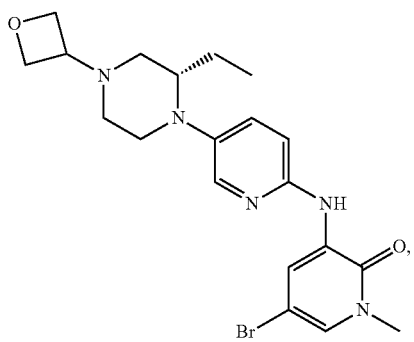 [SMILES: CC[C@H]1CN(C2COC2)CCN1c1ccc(Nc2cc(Br)cn(C)c2=O)nc1]

113i (230 mg, 0.60 mmol), Pd(dppf)Cl$_2$ (25 mg, 0.03 mmol), NaOAc (98 mg, 1.2 mmol), K$_3$PO$_4$ (254 mg, 1.2 mmol), and acetonitrile (4 mL). After three cycles of vacuum/argon flush, the mixture was heated at 100° C. for 1 h. It was then filtered and the filtrate was evaporated in vacuo. The residue was purified by silica gel column chromatography eluting with dichloromethane/methanol (25:1, UV) to afford 131a (150 mg, 40%) as a brown solid. LCMS: [M+H]$^+$ 707

Example 131

(S)-2-(4-(5-(5-(2-ethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 131

A mixture of 131a (150 mg, 0.21 mmol) and LiOH (50 mg, 2.1 mmol) in $^i$PrOH/THF (1:1, 4 mL) and H$_2$O (1 mL) was stirred at 30° C. for 1 h. The mixture was evaporated in vacuo and the residue was extracted with EtOAc (10 mL×2). The combined EtOAc extract was concentrated under reduced pressure and the residue was purified by reverse-phase prep-HPLC to afford 131 (26 mg, 25%) as a white solid. LCMS: [M+H]$^+$ 665. $^1$H NMR (500 MHz, CDCl$_3$) δ 8.64 (d, J=2.0, 1H), 8.50 (d, J=5.0, 1H), 7.93 (d, J=2.5, 1H), 7.83 (d, J=1.5, 2H), 7.38 (d, J=5.0, 1H), 7.27 (d, J=5.0, 1H), 6.90 (s, 1H), 6.83 (d, J=8.5, 1H), 4.73-4.64 (m, 5H), 4.50 (s, 1H), 4.33-4.31 (m, 1H), 4.20-4.16 (m, 2H), 3.88-3.86 (m, 1H), 3.73 (s, 3H), 3.53-3.51 (m, 1H), 3.33 (s, 1H), 3.13 (t, J=5.0, 2H), 2.61-2.56 (m, 4H), 2.45 (d, J=4.0, 2H), 2.37 (s, 1H), 1.91-1.79 (m, 7H), 1.39-1.40 (m, 1H), 0.83 (t, J=7.0, 3H).

Example 132a

6-Chloro-4-(6,7-dihydro-4H-pyrazolo[5,1-c][1,4]oxazin-2-ylamino)-2-methylpyridazin-3(2H)-one 132a

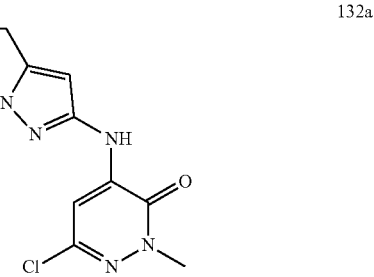

A mixture of 6,7-dihydro-4H-pyrazolo[5,1-c][1,4]oxazin-2-amine 129b (0.8 g, 5.76 mmol), xantophos (360 mg, 0.623 mmol), Pd$_2$dba$_3$ (384 mg, 0.42 mmol), 4-bromo-6-chloro-2-methylpyridazin-3(2H)-one (1.28 g, 5.76 mmol) and Cs$_2$CO$_3$ (5.05 g, 17.3 mmol) in 1,4-dioxane (40 mL) was heated at reflux for 2 h. After the completion of the reaction, the mixture was filtered off, and washed with MeOH (60 mL). The filtrate was evaporated in vacuo. The residue was purified on reverse phase Combi-flash to give 132a (1.3 g, 81%). MS: [M+H]$^+$ 282.

Example 132b (4-(5-(6,7-Dihydro-4H-pyrazolo[5,1-c][1,4]oxazin-2-ylamino)-1-methyl-6-oxo-1,6-dihydropyridazin-3-yl)-2-(1-oxo-3,4,6,7,8,9-hexahydropyrazino[1,2-a]indol-2(1H)-yl)pyridin-3-yl)methyl Acetate 132b

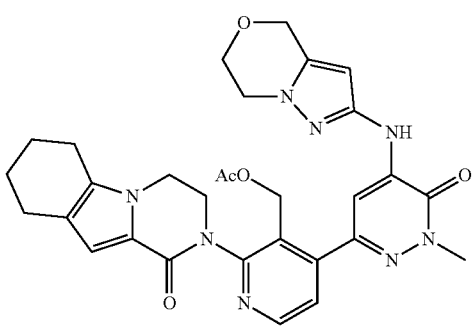

Following the procedures as described for compound 131a, reaction of 3-(acetoxymethyl)-2-(1-oxo-3,4,6,7,8,9-hexahydropyrazino[1,2-a]indol-2(1H)-yl)pyridin-4-ylboronic acid 113i (200 mg, 0.52 mmol) and 132a (146 mg, 0.52 mmol) afforded 132b as a yellow solid (100 mg, 53%). LCMS: [M+H]+ 585

Example 132

2-(4-(5-(6,7-Dihydro-4H-pyrazolo[5,1-c][1,4]oxazin-2-ylamino)-1-methyl-6-oxo-1,6-dihydropyridazin-3-yl)-3-(hydroxymethyl)pyridin-2-yl)-3,4,6,7,8,9-hexahydropyrazino[1,2-a]indol-1(2H)-one 132

Following the procedures as described for compound 131, hydrolysis of 132b (100 mg 0.171 mmol) with lithium hydroxide afforded 132 as a white solid (60 mg, 65%). LCMS: [M+H]+ 543. $^1$H NMR (500 MHz, CDCl$_3$) δ 8.55 (d, J=5.0, 1H), 8.01 (s, 1H), 7.94 (s, 1H), 7.43 (d, J=5.5, 1H), 6.87 (s, 1H), 5.97 (s, 1H), 4.80 (s, 2H), 4.58 (s, 3H), 4.47 (s, 1H), 4.15-1.14 (m, 2H), 4.11 (s, 4H), 3.90 (s, 4H), 2.61-2.60 (m, 2H), 2.57 (t, J=6.5, 2H), 1.89-1.91 (m, 2H), 1.79-1.80 (m, 2H)

Example 133a

6-Chloro-2-methyl-4-(5-methyl-4,5,6,7-tetrahydropyrazolo[1,5-a]pyrazin-2-ylamino)pyridazin-3(2H)-one 133a

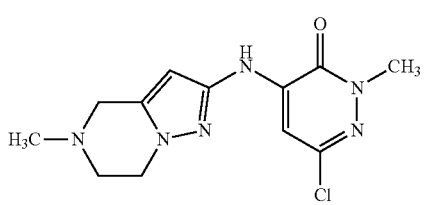

A 250-mL three-neck round-bottomed flask equipped with a reflux condenser, magnetic stirrer and nitrogen inlet was charged with 4-bromo-6-chloro-2-methylpyridazin-3(2H)-one (1.90 g, 8.53 mmol):

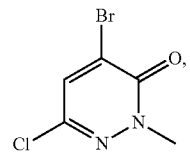

113e (1.18 g, 7.75 mmol) and 1,4-dioxane (40 mL). The flask was purged with nitrogen and cooled to 0° C. A 1 M solution of lithium hexamethyldisilazide in THF (39 mL, 39.0 mmol) was added. After bubbling nitrogen through the resulting suspension for 30 min, Xantphos (381 mg, 0.659 mmol) and tris(dibenzylidene-acetone)dipalladium(0) (355 mg, 0.388 mmol) were added, and the reaction mixture was heated at reflux for 2 h. After this time, the mixture was cooled to room temperature and diluted with water (10 mL). The pH of the solution was adjusted to 7.6 with 2 N hydrochloric acid. The organic layer was separated, and the aqueous layer was extracted with ethyl acetate (3×40 mL). The combined organic layers were dried over sodium sulfate and concentrated under reduced pressure. The residue was purified by column chromatography on silica to afford a 76% yield (1.74 g) of 133a as an off-white solid: mp 184-186° C.; $^1$H NMR (300 MHz, DMSO-d$_6$) δ 9.62 (s, 1H), 7.72 (s, 1H), 6.00 (s, 1H), 4.04 (t, 2H, J=5.1 Hz), 3.65 (s, 3H), 3.53 (s, 2H), 2.82 (t, 2H, J=5.1 Hz), 2.37 (s, 3H); MS (ESI+) m/z 295.1 (M+H).

Example 133b (4-(1-Methyl-5-(5-methyl-4,5,6,7-tetrahydropyrazolo[1,5-a]pyrazin-2-ylamino)-6-oxo-1,6-dihydropyridazin-3-yl)-2-(1-oxo-3,4,6,7,8,9-hexahydropyrazino[1,2-a]indol-2(1H)-yl)pyridin-3-yl)methyl Acetate 133b

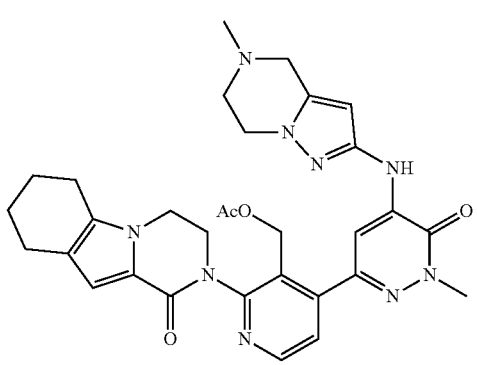

Following the procedures as described for compound 131a and starting with 3-(acetoxymethyl)-2-(1-oxo-3,4,6,7,8,9-hexahydropyrazino[1,2-a]indol-2(1H)-yl)pyridin-4-ylboronic acid 113i (200 mg, 0.52 mmol) and 132a (153 mg, 0.52 mmol) afforded 132b as a yellow solid (170 mg, 55%). LCMS: [M+H]+ 598

Example 133

2-(3-(Hydroxymethyl)-4-(1-methyl-5-(5-methyl-4,5,6,7-tetrahydropyrazolo[1,5-a]pyrazin-2-ylamino)-6-oxo-1,6-dihydropyridazin-3-yl)pyridin-2-yl)-3,4,6,7,8,9-hexahydropyrazino[1,2-a]indol-1(2H)-one 133

Hydrolysis of 133b (160 mg 0.267 mmol) with lithium hydroxide afforded 133 as a white solid (94 mg, 63%).

LCMS: [M+H]⁺ 556. ¹H NMR (500 MHz, CDCl₃) δ 8.55 (d, J=5.0, 1H), 7.98 (s, 1H), 7.89 (s, 1H), 7.43 (d, J=5.0, 1H), 6.87 (s, 1H), 5.94 (s, 1H), 4.57 (s, 3H), 4.47 (s, 1H), 4.11-4.15 (m, 4H), 3.89 (s, 3H), 3.87 (s, 1H), 3.61 (d, J=4.0, 2H), 2.90 (s, 2H), 2.61 (d, J=4.0, 2H), 2.57 (t, J=6.0, 2H), 2.49 (s, 3H), 1.89-1.91 (m, 2H), 1.79-0.80 (m, 2H)

Example 134a

10-Bromo-1H,2H,3H,4H,6H,7H,8H,9H-pyrazino[1,2-a]indol-1-one 134a

Into a 250-mL 3-necked round-bottom flask was placed a solution of 1H,2H,3H,4H,6H,7H,8H,9H-pyrazino[1,2-a]indol-1-one 101e (9.5 g, 49.94 mmol, 1.00 equiv) in N,N-dimethylformamide (100 mL), followed by the addition of N-bromosuccinimide (9.8 g, 55.06 mmol, 1.10 equiv) in several batches at 0° C. The resulting solution was stirred at room temperature for 2 h and diluted with 500 mL of water. The precipitate was filtered and dried in a vacuum oven to afford 9.5 g (71%) of 119a as a light brown solid.

Example 134b

10-Fluoro-1H,2H,3H,4H,6H,7H,8H,9H-pyrazino[1,2-a]indol-1-one 134b

Into a 2-L 4-necked round-bottom flask purged and maintained with an inert atmosphere of nitrogen was placed a solution of 134a (40 g, 148.62 mmol, 1.00 equiv) in tetrahydrofuran (200 mL), followed by the addition of n-BuLi (2.4 M) (218 mL, 3.50 equiv) dropwise with stirring at −78° C. The resulting solution was stirred at −40° C. for 3 h. To this was added a solution of N-fluorobenzenesulfonimide (98.7 g, 313.33 mmol, 2.10 equiv) in tetrahydrofuran (200 mL) dropwise with stirring at −78° C. The resulting solution was stirred at room temperature for 3 h, quenched by the addition of 200 mL of water and extracted with 3×500 mL of ethyl acetate. The combined organic layers were dried over anhydrous sodium sulfate and concentrated under vacuum. The crude product (30 g) was purified by Prep-HPLC with the following conditions (mobile phase, A: 0.05% trifluoroacetic acid/water; B: CH₃CN; gradient: 10% B-25% B) to afford 5.05 g (16%) of 134b as a white solid. MS: [M+H]⁺ 209. 1H NMR (300 MHz, CDCl₃) δ 6.16 (br, 1H), 3.90-3.86 (m, 2H), 3.65-3.62 (m, 2H), 2.53-2.47 (m, 4H), 1.88-1.80 (m, 2H), 1.77-1.72 (m, 2H).

Example 134c

4-Chloro-2-(10-fluoro-1-oxo-3,4,6,7,8,9-hexahydropyrazino[1,2-a]indol-2(1H)-yl)nicotinaldehyde 134c

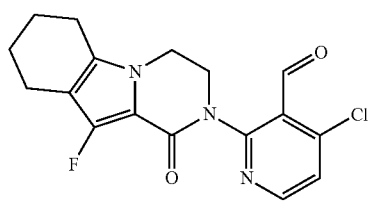

134c

A 100-mL single-neck round-bottomed flask equipped with a magnetic stirrer and reflux condenser was charged with 1,4-dioxane (60 mL), 134b (500 mg, 2.4 mmol):

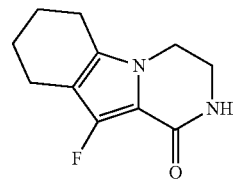 [SMILES: O=C1NCCn2c3c(c(F)c21)CCCC3]

2-bromo-4-chloronicotinaldehyde 103a (1.60 g, 7.2 mmol), and potassium acetate (471 mg, 4.8 mmol). After bubbling nitrogen through the resulting mixture for 30 minutes, Xantphos (140 mg, 0.24 mmol) and tris(dibenzylideneacetone)dipalladium(0) (220 mg, 0.24 mmol) were added, and the reaction mixture was heated at 80° C. for 10 h. After this time the reaction was cooled to room temperature, partitioned between ethyl acetate (40 mL) and water (40 mL), and filtered. The aqueous layer was separated and extracted with ethyl acetate (50 mL×3). The combined organic layer was washed with brine (30 mL) and dried over sodium sulfate. The drying agent was removed by filtration and the filtrate was concentrated under reduced pressure. The residue was purified on flash column eluting with 3:1 PE/EA to afford 134c (678 mg, 81%) as yellow solid. MS: [M+H]⁺ 348. ¹H NMR (500 MHz, DMSO-d6) δ 9.87 (s, 1H), 8.60 (d, J=5.5, 1H), 7.56 (d, J=5.5, 1H), 4.23-4.25 (m, 2H), 4.13-4.15 (m, 2H), 2.59 (t, J=6.0, 2H), 2.41 (t, J=6.0, 2H), 1.75-1.80 (m, 2H), 1.66-1.70 (m, 2H)

Example 134d 2-(10-Fluoro-1-oxo-3,4,6,7,8,9-hexahydropyrazino[1,2-a]indol-2(1H)-yl)-4-(1-methyl-5-(5-(4-(oxetan-3-yl)piperazin-1-yl)pyridin-2-ylamino)-6-oxo-1,6-dihydropyridin-3-yl)nicotinaldehyde 134d

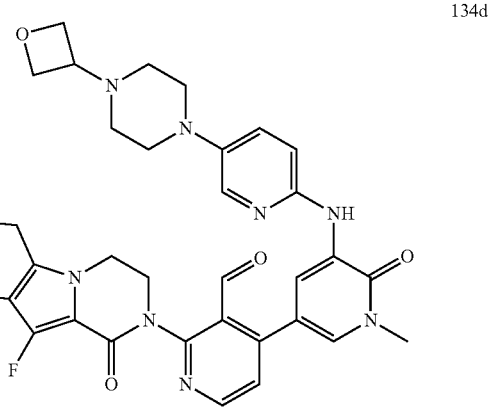

134d

A mixture of 134c (300 mg, 0.86 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 101l (403 mg, 0.86 mmol), CH₃COONa (142 mg, 1.72 mmol), K₃PO₄ (460 mg, 1.72 mmol), PdCl₂(dppf) (71 mg, 0.086 mmol) in CH₃CN (25 mL) and H₂O (1 mL) was heated at 100° C. for 3 hours. After reaction it was evaporated the residue was purified by silical-gel column eluting with methylene chloride/methanol (30:1) to afford 134d (312 mg, yield 55%) as a brown solid. MS: (M+H)⁺ 653.

Example 134

10-Fluoro-2-(3-(hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 134

To a solution of 134d (200 mg, 0.30 mmol) in MeOH (20 mL) was added NaBH₄ (40 mg, 0.9 mmol). The mixture was stirred at 20° C. for 2 h. After reaction it was evaporated and the residue was purified by reverse-phase prep-HPLC to afford 134 (108 mg, yield 54%) as a yellow solid. MS: (M+H)⁺ 655. ¹H NMR (500 MHz, DMSO-d6) δ 8.61 (d, J=2.0, 1H), 8.49 (d, J=5.0, 1H), 8.43 (s, 1H), 7.85 (d, J=2.5, 1H), 7.45 (d, J=1.5, 1H), 7.37-7.39 (m, 1H), 7.35 (d, J=5.0, 1H), 7.24 (d, J=9.0, 1H), 4.99 (s, 1H), 4.56 (t, J=6.5, 2H), 4.40-4.47 (m, 4H), 4.18-4.22 (m, 2H), 4.05-4.09 (m, 1H), 3.84-3.96 (m, 1H), 3.60 (s, 3H), 3.41-3.46 (m, 1H), 3.07 (s, 4H), 2.54-2.61 (m, 2H), 2.39-2.42 (m, 6H), 1.78 (s, 2H), 1.69 (s, 2H)

Example 135a

1-Methyl-3-(5-methyl-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 135a

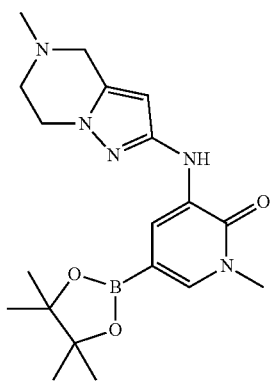

135a

A 100-mL single-neck round-bottomed flask equipped with a magnetic stirrer and a condenser was charged with compound 113h (1.0 g, 3 mmol), Pin₂B₂ (3.8 g, 15 mmol), Pd(dppf)Cl₂ (137 mg, 0.15 mmol), X-phos (143 mg, 0.3 mmol), KOAc (88 mg, 9 mmol), and 1,4-dioxane (50 mL). After three cycles of vacuum/argon flush, the reaction mixture was heated at 60° C. for 15 h. It was then cooled to room temperature and filtered. The filtrate was concentrated under reduced pressure and the resulting residue was washed with petroleum ether to afford 135a as a yellow solid (0.87 g, 75%). MS: [M+H]⁺ 386

Example 135b 2-(10-Fluoro-1-oxo-3,4,6,7,8,9-hexahydropyrazino[1,2-a]indol-2(1H)-yl)-4-(1-methyl-5-(5-methyl-4,5,6,7-tetrahydropyrazolo[1,5-a]pyrazin-2-ylamino)-6-oxo-1,6-dihydropyridin-3-yl)nicotinaldehyde 135b

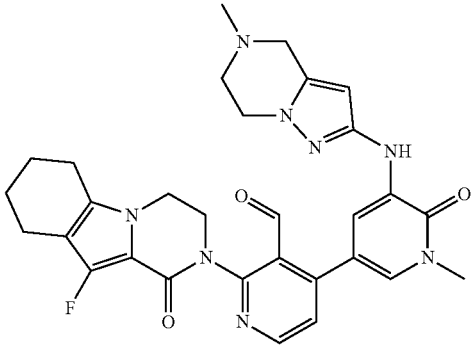

135b

A suspension of 135a (385 mg, 1 mmol), 4-chloro-2-(10-fluoro-1-oxo-3,4,6,7,8,9-hexahydropyrazino[1,2-a]indol-2(1H)-yl)nicotinaldehyde 134c (347 mg, 1 mmol), K₃PO₄ (424 mg, 2 mmol), NaOAc (164 g, 2 mmol) and 1,1'-bis(diphenylphosphino)ferrocenedichloropalladium(II) (41 mg, 0.05 mmol) in CH₃CN (50 ml) was heated at 100° C. under an N₂ balloon for 4 h. Analysis of reaction mixture by LCMS showed completed conversion to the desired product. The reaction mixture was cooled to room temperature and diluted with DCM (50 ml) and water (80 mL). The aqueous layer was separated and extracted with DCM (3×50 mL). The combined organic layer was dried over Na₂SO₄, filtered, and concentrated. The dark residue was purified by silica gel column chromatography eluting with DCM/MeOH (from 80/1 to 30/1) to afford 135b (285 g, 50%) as yellow solid. MS: [M+H]⁺ 571

Example 135

10-Fluoro-2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydropyrazino[1,2-a]indol-1(2H)-one 135

To a solution of 135b (280 g, 0.49 mmol) in MeOH (50 mL) was added NaBH₄ (56 g, 1.47 mmol) at room temperature. After the reaction was stirred for 3 h, LCMS indicated the reaction was completed. Then the mixture was poured into H₂O (50 mL) and extracted with DCM (50 mL×3). The combined organic layer was washed with brine (50 mL), dried over Na₂SO₄, filtered, and concentrated. The residue was purified by reverse-phase prep-HPLC to afford 135 (187 mg, 67%) as a white solid. MS: [M+H]⁺ 572. ¹H NMR (500 MHz, CDCl₃) δ 8.47 (d, J=5.5, 1H), 7.95 (d, J=2.0, 1H), 7.70 (d, J=2.0, 1H), 7.42 (s, 1H), 7.35 (d, J=5.5, 1H), 5.70 (s, 1H), 4.96 (t, J=7.0, 1H), 4.62 (s, 1H), 4.45 (s, 1H), 4.33 (s, 1H), 4.07-4.12 (m, 4H), 3.84 (s, 1H), 3.70 (s, 3H), 3.60 (s, 2H), 2.88 (t, J=5.5, 2H), 2.61 (s, 2H), 2.57 (s, 2H), 2.48 (s, 3H), 1.86-1.90 (m, 2H), 1.77 (s, 2H)

Example 136a (S)-2-(10-Fluoro-1-oxo-3,4,6,7,8,9-hexahydropy-razino[1,2-a]indol-2(1H)-yl)-4-(1-methyl-5-(5-(2-methyl-4-(oxetan-3-yl)piperazin-1-yl)pyridin-2-ylamino)-6-oxo-1,6-dihydropyridin-3-yl)nicotinaldehyde 136a

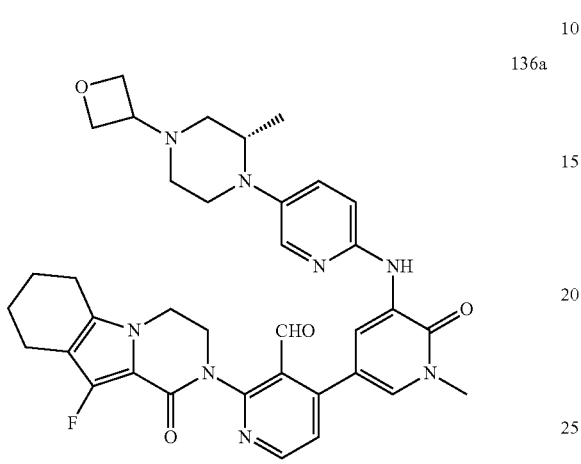

136a

A 50 mL single-neck round-bottomed flask equipped with a magnetic stirrer and a reflux condenser was charged with (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 130f (225 mg, 1.5 eq., 0.47 mmol), 4-chloro-2-(10-fluoro-1-oxo-3,4,6,7,8,9-hexahydropyrazino[1,2-a]indol-2(1H)-yl)nicotinaldehyde 134c (150 mg, 1 eq., 0.43 mmol):

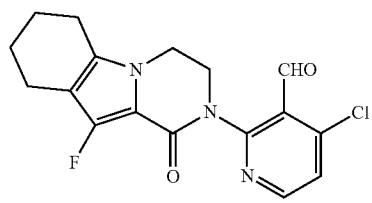 [SMILES: O=Cc1c(Cl)ccnc1N1CCn2c3c(c(F)c2C1=O)CCCC3]

PdCl$_2$(dppf) (35 mg, 0.1 eq., 0.043 mmol), K$_3$PO$_4$ (273 mg, 3 eq., 1.29 mmol), and THF (20 mL). After three cycles of vacuum/argon flush, the mixture was heated at reflux for 5 h. It was then cooled to room temperature and filtered. The filtrate was concentrated under reduced pressure and the resulting residue was purified by column chromatography with DCM/EtOH (40:1) to afford 136a as yellow solid (100 mg, 34%). MS: [M+H]$^+$ 667.3.

Example 136

(S)-10-Fluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 136

A 25 mL single-neck round-bottomed flask equipped with a magnetic stirrer was charged with 136a (100 mg, 1.0 eq., 0.15 mmol), NaBH$_4$ (17 mg, 3.0 eq., 0.45 mmol), and MeOH (10 mL). The mixture was stirred at room temperature for 1 h. The residue was purified by reverse-phase prep-HPLC to afford 136 (64 mg, 64%). LCMS: [M+H]$^+$ 669.3. $^1$H NMR (500 MHz, CDCl$_3$) δ 8.64 (d, J=2.0, 1H), 8.48 (d, J=5.0, 1H), 7.96 (d, J=2.5, 1H), 7.83-7.82 (m, 2H), 7.36 (d, J=5.0, 1H), 7.30 (dd, J=2.5, 9.0, 1H), 6.81 (d, J=8.5, 1H), 4.99-4.96 (m, 1H), 4.71-4.61 (m, 5H), 4.45-3.83 (m, 5H), 3.71 (s, 3H), 3.54-3.45 (m, 2H), 3.08-3.06 (m, 2H), 2.56-2.47 (m, 7H), 2.21-2.17 (m, 1H), 1.89-1.76 (m, 4H), 0.98 (d, J=6.5, 3H)

Example 137a (R)-(4-(1-Methyl-5-(5-(2-methyl-4-(oxetan-3-yl)piperazin-1-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 137a

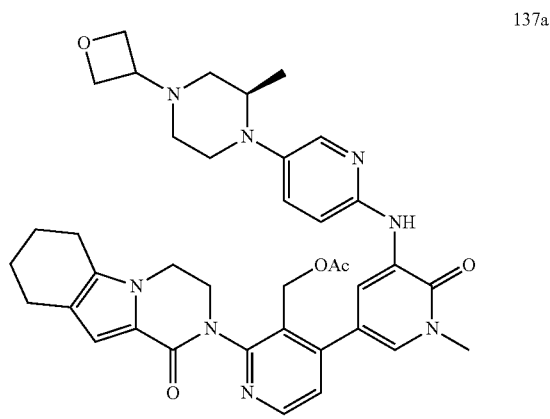 [SMILES: CC(=O)OCc1c(-c2cc(Nc3ccc(N4CCN(C5COC5)C[C@H]4C)cn3)c(=O)n(C)c2)ccnc1N1CCn2c(cc3c2CCCC3)C1=O]

137a

A mixture of (R)-5-bromo-1-methyl-3-(5-(2-methyl-4-(oxetan-3-yl)piperazin-1-yl)pyridin-2-ylamino)pyridin-2(1H)-one 151f, the enantiomer of 130f (283 mg, 0.65 mmol):

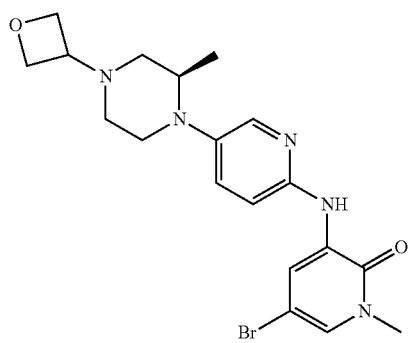 [SMILES: C[C@@H]1CN(C2COC2)CCN1c1ccc(Nc2cc(Br)cn(C)c2=O)nc1]

3-(acetoxymethyl)-2-(1-oxo-3,4,6,7,8,9-hexahydropyrazino[1,2-a]indol-2(1H)-yl)pyridin-4-ylboronic acid 113i (250 mg, 0.65 mmol), PdCl$_2$(dppf) (53 mg, 0.065 mmol), NaOAc (107 mg, 1.3 mmol), K$_3$PO$_4$ (347 mg, 1.3 mmol) in acetonitrile (30 mL) was heated at 100° C. for 3 h. The solvent was evaporated in vacuo and the residue was purified by flash column chromatography eluting with 30:1 DCM/MeOH to afford 137a (216 mg, 48%) as a brown solid. LCMS: [M+H]$^+$ 693.4

Example 137

(R)-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexa-hydropyrazino[1,2-a]indol-1(2H)-one 137

To a solution of 137a (200 mg, 0.29 mmol) in propan-2-ol (8 mL), tetrahydrofuran (8 mL), and water (2.0 mL) was added LiOH (690 mg, 29 mmol). The mixture was stirred at 30° C. for 2 h. It was then evaporated and the residue was purified by reverse-phase prep-HPLC to afford 137 (143 mg, 76%) as a white solid. LCMS: (M+H)+ 651.4. $^1$H NMR (500 MHz, DMSO-d6) δ 8.63 (d, J=2.0, 1H), 8.49 (d, J=5.0, 1H), 8.45 (s, 1H), 7.84 (d, J=2.5, 1H), 7.47 (d, J=2.0, 1H), 7.37-7.39 (m, 1H), 7.35 (d, J=5.5, 1H), 7.25 (d, J=9.5, 1H), 6.58 (s, 1H), 4.95 (t, J=4.0, 1H), 4.54-4.58 (m, 2H), 4.40-4.49 (m, 4H), 4.11-4.26 (m, 3H), 3.86-3.88 (m, 1H), 3.68 (s, 1H), 3.61 (s, 3H), 3.37-3.42 (m, 1H), 3.08-3.11 (m, 1H), 2.95 (t, J=9.0, 1H), 2.62-2.67 (m, 1H), 2.54-2.59 (m, 2H), 2.48 (t, J=6.0, 2H), 2.30-2.36 (m, 2H), 2.19 (t, J=8.0, 1H), 1.81 (s, 2H), 1.68-1.72 (m, 2H), 0.93 (d, J=6.0, 3H)

Example 138a 3-(1-Methyl-5-(5-methyl-4,5,6,7-tetrahydropyrazolo[1,5-a]pyrazin-2-ylamino)-6-oxo-1,6-dihydropyridin-3-yl)-5-(1-oxo-3,4,6,7,8,9-hexahydropyrazino[1,2-a]indol-2(1H)-yl)isonicotinaldehyde 138a

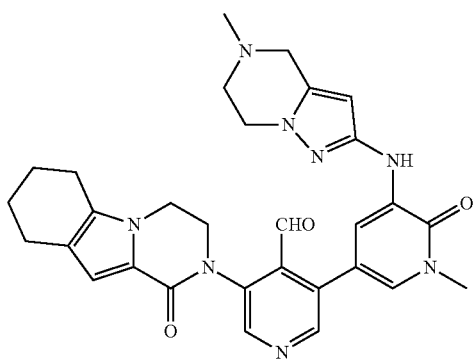

A 100-mL single-neck round-bottomed flask was charged with 3-bromo-5-(1-oxo-3,4,6,7,8,9-hexahydropyrazino[1,2-a]indol-2(1H)-yl)isonicotinaldehyde 101f (298 mg, 0.7 mmol), 1-methyl-3-(5-methyl-4,5,6,7-tetrahydropyrazolo[1,5-a]pyrazin-2-ylamino)-5-(4,4,5,5-tetra-methyl-1,3,2-dioxaborolan-2-yl)pyridin-2(1H)-one 135a (325 mg, 0.84 mmol), PdCl$_2$(dppf) (30 mg, 0.035 mmol), K$_3$PO$_4$ (300 mg, 1.4 mmol), and NaOAc.3H$_2$O (200 mg, 1.4 mmol) in CH$_3$CN (70 mL). The system was evacuated and refilled with Argon. The reaction mixture was heated at 100° C. for 2 h. It was then cooled to room temperature and filtered. The filtrate was concentrated under reduced pressure and the resulting residue was purified by flash column chromatography eluting with 25:1 DCM/MeOH to afford 138a (220 mg, 55%) as a pale yellow solid. MS: [M+H]+ 553.3.

Example 138

2-(4-(Hydroxymethyl)-5-(1-methyl-5-(5-methyl-4,5,6,7-tetrahydropyrazolo[1,5-a]pyrazin-2-ylamino)-6-oxo-1,6-dihydropyridin-3-yl)pyridin-3-yl)-3,4,6,7,8,9-hexahydropyrazino[1,2-a]indol-1(2H)-one 138

A mixture of 138a (200 mg, 0.36 mmol) and NaBH4 (50 mg, 1.2 mmol) in MeOH (60 mL) was stirred at room temperature for 2 h. The mixture was quenched with water and extracted with EtOAc (10 mL×3). The combined EtOAc extract was concentrated under reduced pressure and the residue was purified with reverse-phase prep-HPLC to afford 138 (162 mg, 85%). LCMS: [M+H]+: 555.3. $^1$H NMR (500 MHz, CDCl$_3$) δ 8.64 (s, 1H), 8.49 (s, 1H), 7.97 (d, J=2.5, 1H), 7.42 (s, 1H), 7.33 (d, J=2, 1H), 6.88 (s, 1H), 5.68 (s, 1H), 4.65-4.63 (m, 1H), 4.57-4.55 (m, 1H), 4.37 (t, J=11, 1H), 4.20-4.16 (m, 3H), 4.07-3.98 (m, 3H), 3.70 (s, 3H), 3.59 (s, 2H), 2.87 (t, J=5.5, 2H), 2.61-2.56 (m, 4H), 2.48 (s, 3H), 1.92-1.90 (m, 2H), 1.80-1.79 (m, 2H)

Example 139a

4-Chloro-2-(1-oxo-3,4,6,7,8,9-hexahydropyrido[3,4-b]indolizin-2(1H)-yl)nicotinaldehyde 139a

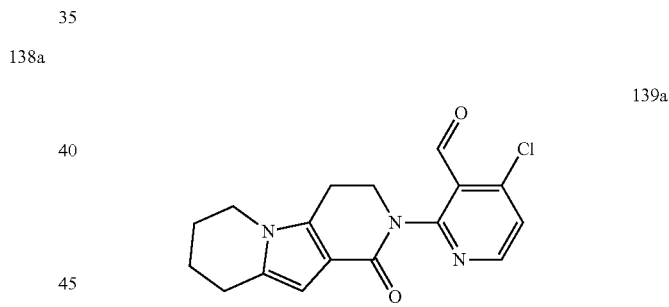

A 250-mL single-neck round-bottomed flask equipped with a magnetic stirrer and reflux condenser was charged with 1,4-dioxane (50 mL), 2-bromo-4-chloronicotin-aldehyde 103a (1.4 g, 6.4 mmol), 3,4,6,7,8,9-hexahydropyrido[3,4-b]indolizin-1(2H)-one 112d (0.6 g, 3.2 mmol), Pd$_2$(dba)$_3$ (293 mg, 0.32 mmol), XantPhos (370 mg, 0.64 mmol), and potassium carbonate (627 mg, 6.4 mmol). After three cycles of vacuum/argon flush, the mixture was heated at 80° C. overnight. After this time the reaction was cooled to room temperature. It was then filtered and the filtrate was evaporated in vacuo. The residue was purified by silica gel column chromatography eluting with DCM/CH$_3$OH (20:1, UV) to afford 139a (528 mg, 50%) as a yellow solid. MS: [M+H]+ 330. $^1$H NMR (500 MHz, CDCl$_3$) δ 10.09 (s, 1H), 8.37 (d, J=5.5, 1H), 7.16 (d, J=5.5, 1H), 6.25 (s, 1H), 4.29-4.32 (m, 2H), 3.83-3.86 (m, 2H), 2.96-2.99 (m, 2H), 2.75-2.78 (m, 2H), 2.00-2.07 (m, 2H), 1.82-1.85 (m, 2H)

Example 139b 4-(1-Methyl-5-(5-(4-(oxetan-3-yl)piperazin-1-yl)pyridin-2-ylamino)-6-oxo-1,6-dihydropyridin-3-yl)-2-(1-oxo-3,4,6,7,8,9-hexahydropyrido[3,4-b]indolizin-2(1H)-yl)nicotinaldehyde 139b

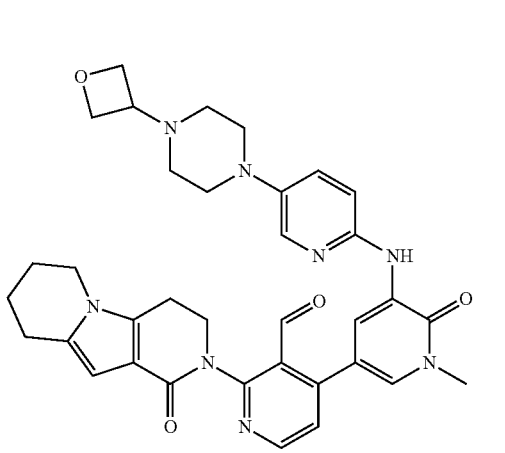

A round-bottomed flask was charged with 139a (100 mg, 0.30 mmol), 1-methyl-3-(5-(4-(oxetan-3-yl)piperazin-1-yl)pyridin-2-ylamino)-5-(4,4,5,5-tetramethyl-1,3,2-dioxaborolan-2-yl)pyridin-2(1H)-one 1011 (140 mg, 0.30 mmol), PdCl$_2$ (dppf) (25 mg, 0.03 mmol), K$_3$PO$_4$·3H$_2$O (160 mg, 0.60 mmol), NaOAc (59 mg, 0.60 mmol), acetonitrile (10 mL), and H$_2$O (5 mL). After three cycles of vacuum/argon flush, the mixture was heated at 100° C. for 3 h. It was then filtered and the filtrate was evaporated in vacuo. The residue was purified on flash column chromatography eluting with 1:3 petroleum/ethyl acetate to afford 139b as a yellow solid (95 mg, 50%). LCMS: [M+H]$^+$ 635

Example 139

2-(3-(Hydroxymethyl)-4-(1-methyl-5-(5-(4-(oxetan-3-yl)piperazin-1-yl)pyridine-2-ylamino)-6-oxo-1,6-dihydropyridin-3-yl)pyridin-2-yl)-3,4,6,7,8,9-hexahydropyrido[3,4-b]indolizin-1(2H)-one 139

A mixture of 139b (95 mg, 0.15 mmol), NaBH$_4$ (17 mg, 0.45), and CH$_3$OH (10 mL) was stirred at 25° C. for 1 h. The mixture was extracted with CH$_2$Cl$_2$ (10 mL×2). The combined CH$_2$Cl$_2$ extract was concentrated under reduced pressure. The residue was purified with reverse-phase prep-HPLC to afford 139 (60 mg, 63%). LCMS: [M+H]$^+$ 637. $^1$H NMR (500 MHz, DMSO-d6) δ 8.63 (d, J=2.0, 1H), 8.47 (d, J=5.5, 1H), 8.42 (s, 1H), 7.85 (d, J=2.5, 1H), 7.49 (d, J=2.0, 1H), 7.37-7.39 (m, 1H), 7.30 (d, J=5.0, 1H), 7.24 (d, J=9.0, 1H), 6.05 (s, 1H), 4.47-4.57 (m, 2H), 4.41-4.47 (m, 2H), 4.39-4.41 (m, 1H), 4.33-4.35 (m, 1H), 4.11-4.16 (m, 1H), 3.93-3.96 (m, 1H), 3.76-3.82 (m, 2H), 3.59 (s, 3H), 3.41-3.45 (m, 2H), 3.06-3.08 (m, 4H), 2.98-3.01 (m, 1H), 2.92-2.95 (m, 1H), 2.71-2.72 (m, 2H), 2.36-2.39 (m, 4H), 1.91-1.93 (m, 2H), 1.72-1.78 (m, 2H)

Example 140a (S)-2-(7,7-Difluoro-1-oxo-3,4,6,7,8,9-hexahydropyrazino[1,2-a]indol-2(1H)-yl)-4-(1-methyl-5-(5-(2-methyl-4-(oxetan-3-yl)piperazin-1-yl)pyridin-2-ylamino)-6-oxo-1,6-dihydropyridin-3-yl)nicotinaldehyde 140a

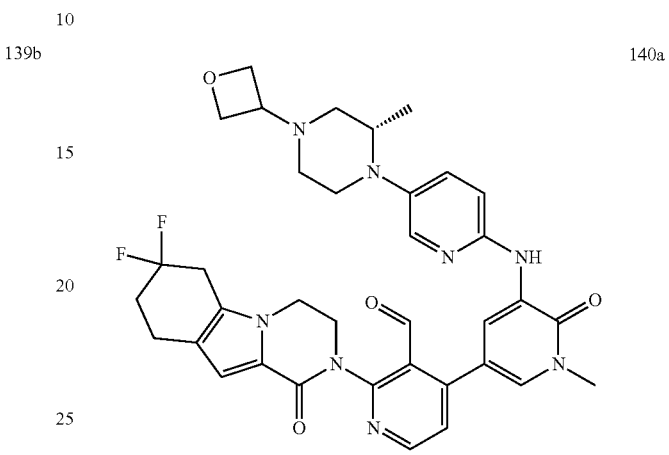

Following the procedures as described in Example 130g, reaction of (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 130f and 4-chloro-2-(7,7-difluoro-1-oxo-3,4,6,7,8,9-hexahydropyrazino[1,2-a]indol-2(1H)-yl)nicotin-aldehyde (170 mg):

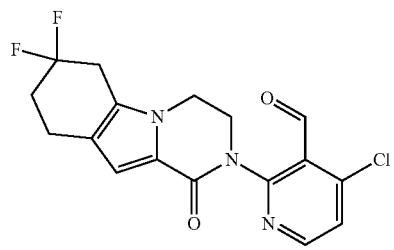 [SMILES: O=Cc1c(Cl)ccnc1N1CCn2c(cc3c2CC(F)(F)CC3)C1=O]

afforded 140a was as a yellow solid (200 mg, 60%). LCMS: [M+H]$^+$ 684.3. 4-Chloro-2-(7,7-difluoro-1-oxo-3,4,6,7,8,9-hexahydropyrazino[1,2-a]indol-2(1H)-yl)nicotin-aldehyde was prepared from 7,7-difluoro-3,4,6,7,8,9-hexahydropyrazino[1,2-a]indol-1(2H)-one according to the reaction scheme in FIG. 25.

Example 140

(S)-7,7-Difluoro-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 140

Following the procedures as described in Example 130, sodium borohydride reduction of 140a (200 mg) afforded 140 as a yellow solid (104 mg, 51%). LCMS: [M+H]$^+$ 686.3. $^1$H NMR (500 MHz, DMSO) δ 8.62 (d, J=2.0, 1H), 8.46-8.49 (m, 2H), 7.83 (d, J=3.0, 1H), 7.45 (d, J=2.5, 1H), 7.35-7.38 (m, 2H), 7.25 (d, J=9.5, 1H), 6.64 (s, 1H), 4.95-4.97 (m, 1H), 4.54-4.57 (m, 2H), 4.38-4.48 (m, 4H), 4.15-4.27 (m, 3H), 3.87-3.90 (m, 1H), 3.67 (s, 1H), 3.59 (s, 3H), 3.26-3.39 (m, 3H), 3.08-3.10 (m, 1H), 2.92-2.96 (m, 1H), 2.63-2.67 (m, 2H), 2.52-2.55 (m, 1H), 2.30-2.36 (m, 2H), 2.18-2.24 (m, 3H), 0.93 (d, J=6.0, 3H)

Example 141a

4-Chloro-2-{4,4-dimethyl-9-oxo-1,10-diazatricyclo[6.4.0.0$^{2,6}$]dodeca-2(6),7-dien-10-yl}pyridine-3-carbaldehyde 141a

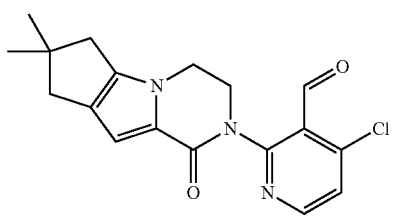

A 100-mL single-neck round-bottomed flask equipped with a magnetic stirrer and a reflux condenser was charged with 2-bromo-4-chloronicotinaldehyde 103a (3.0 g, 13.6 mmol), 4,4-dimethyl-1,10-diazatricyclo[6.4.0.0$^{2,6}$]dodeca-2(6),7-dien-9-one 107e (1.84 g, 9.0 mmol), tris(dibenzylideneacetone)dipalladium(0) (826 mg, 0.9 mmol), XantPhos (1.04 mg, 1.8 mmol), Cs$_2$CO$_3$ (5.8 g, 18.0 mmol), and 1,4-dioxane (40 mL). After three cycles of vacuum/argon flush, the mixture was heated at 90° C. for 5 h. It was then cooled to room temperature and filtered. The filtrate was concentrated under reduced pressure and the resulting residue was recrystallized from ethyl acetate to afford 141a as yellow solid (730 mg, 31.7%). MS: [M+H]$^+$ 344.0.

Example 141b

2-{4,4-Dimethyl-9-oxo-1,10-diazatricyclo[6.4.0.0$^{2,6}$]dodeca-2(6),7-dien-10-yl}-4-[1-methyl-5-({5-methyl-4H,5H,6H,7H-pyrazolo[1,5-a]pyrazin-2-yl}amino)-6-oxo-1,6-dihydropyridin-3-yl]pyridine-3-carbaldehyde 141b

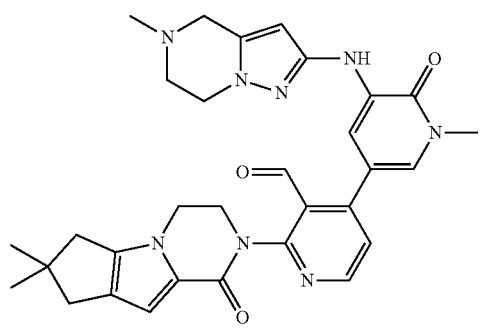

A 100-mL single-neck round-bottomed flask equipped with a magnetic stirrer and a reflux condenser was charged with 141a (130 mg, 0.38 mmol), 1-methyl-3-(5-methyl-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 135a (146 mg, 0.38 mmol), Pd(dppf)Cl$_2$ (31 mg, 0.038 mmol), K$_3$CO$_3$ (105 mg, 0.76 mmol), and DMF (20 mL). After three cycles of vacuum/argon flush, the mixture was heated at 110° C. for 2 h. It was then cooled to room temperature and filtered. The filtrate was concentrated under reduced pressure and the resulting residue was purified by silica-gel column chromatography eluting with dichloromethane/methanol (30:1) to afford 141b as brown solid (160 mg, 74.6%). MS: [M+H]$^+$ 567.3.

Example 141

2-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 141

To a solution of 141b (150 mg, 0.26 mmol) at room temperature in methanol (10 mL) was added sodium borohydride (29 mg, 0.78 mmol) and the resulting mixture was stirred for 30 minutes. It was quenched with water (1.0 mL) and concentrated. The residue was purified by reverse-phase prep-HPLC to afford 141 (35 mg, 23.2%). LCMS: [M+H]$^+$ 569.3. $^1$H NMR (500 MHz, CDCl$_3$) δ 8.46 (d, J=5.0, 1H), 7.94 (d, J=2.5, 1H), 7.72 (d, J=2.0, 1H), 7.41 (s, 1H), 7.33 (d, J=5.5, 1H), 6.83 (s, 1H), 5.68 (s, 1H), 5.03-5.00 (m, 1H), 4.64-4.61 (m, 1H), 4.51-4.48 (m, 1H), 4.32-4.27 (m, 1H), 4.21-4.09 (m, 4H), 3.91-3.82 (m, 1H), 3.69 (s, 3H), 3.62-3.58 (m, 2H), 2.87 (t, J=2.5, 2H), 2.57 (d, J=4.0, 2H), 2.54 (s, 2H), 2.51 (s, 3H), 1.27 (s, 6H)

Example 142a

5-Bromo-1-methyl-3-(pyrimidin-4-ylamino)pyridin-2(1H)-one 142a

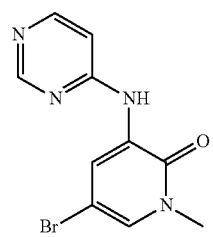

A 100-mL single-neck round-bottomed flask equipped with a magnetic stirrer and nitrogen inlet was charged with 3,5-dibromo-1-methylpyridin-2(1H)-one (2.00 g, 21.0 mmol), 2-aminopyrimidine (5.61 g, 21.0 mmol), cesium carbonate (13.7 g, 42.1 mmol), DMF (5 mL) and 1,4-dioxane (70 mL). After bubbling nitrogen through the resulting suspension for 30 min, Xantphos (1.10 g, 1.89 mmol) and tris(dibenzylideneacetone)dipalladium(0) (963 mg, 1.05 mmol) were added. A reflux condenser was attached to the flask, and the reaction mixture was heated at 100° C. for 4 h. After this time, the mixture was cooled to room temperature and diluted with 90:10 methylene chloride/methanol (150 mL) and water (100 mL), and the layers were separated. The aqueous layer was extracted with 90:10 methylene chloride/methanol (50 mL), and the combined organic layers were washed with brine and dried over sodium sulfate. The drying agent was removed by filtration. The filtrate was concentrated under reduced pressure, and the resulting residue was purified by flash column chromatography (silica, 90:10 methylene chloride/methanol) to afford 142a in 58% yield (3.42 g) as an amorphous light green solid: mp 217-219° C.; $^1$H NMR (500 MHz, CDCl$_3$) δ 9.29 (s, 1H), 8.77 (s, 1H), 8.72 (d, J=2.5 Hz, 1H), 8.36 (d, J=6.0 Hz, 1H), 7.69 (d, J=2.5 Hz, 1H), 7.37 (dd, J=5.5, 1.0 Hz, 1H), 3.53 (s, 3H); LCMS (ESI+) m/z 281.0 (M+H).

Example 142b (4-(1-Methyl-6-oxo-5-(pyrimidin-4-ylamino)-1,6-dihydropyridin-3-yl)-2-(1-oxo-3,4,6,7,8,9-hexahydropyrazino[1,2-a]indol-2(1H)-yl)pyridin-3-yl)methyl Acetate 142b

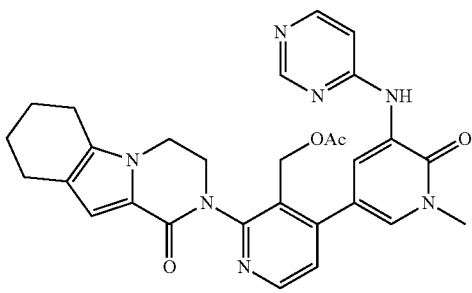

142b

A sealed tube equipped with a magnetic stirrer was charged with 142a (154.5 mg, 0.55 mmol), (2-(1-oxo-3,4,6,7,8,9-hexahydropyrazino[1,2-a]indol-2(1H)-yl)-4-(4,4,5,5-tetramethyl-1,3,2-dioxaborolan-2-yl)pyridin-3-yl)methyl acetate 113i (252.5 mg, 0.55 mmol), Pd(dppf)Cl$_2$ (25.9 mg, 0.03135 mmol), NaOAc (108 mg, 1.1 mmol), K$_3$PO$_4$·3H$_2$O (293 mg, 1.1 mmol), acetonitrile (6 mL), and water (0.5 mL). After three cycles of vacuum/argon flush, the mixture was heated at 110° C. for 2 h. It was then filtered and the filtrate was evaporated in vacuo. The residue was purified by silica gel column chromatography eluting with dichloromethane/methanol (15:1, UV) to afford 142b (117 mg, 30%) as a brown solid. LCMS: [M+H]$^+$ 540.2

Example 142

2-[3'-Hydroxymethyl-1-methyl-6-oxo-5-(pyrimidin-4-ylamino)-1,6-dihydro-[3,4']bipyridinyl-2'-yl]-3,4,6,7,8,9-hexahydro-2H-pyrazino[1,2-a]indol-1-one 142

A mixture of 142b (121.6 mg, 0.225 mmol) and LiOH (100 mg, 4.2 mmol) in $^i$PrOH/THF (1:1, 4 mL) and H$_2$O (1 mL) was stirred at 35° C. for 0.5 h. The mixture was evaporated in vacuo and the residue was extracted with EtOAc (20 mL×3). The combined EtOAc extract was concentrated under reduced pressure and the residue was purified by reverse-phase prep-HPLC to afford 142 (54 mg, 48.2%) as a pale yellow solid. LCMS: [M+H]$^+$ 498.1. $^1$H NMR (500 MHz, DMSO-d6) δ 9.23 (s, 1H), 8.76 (d, J=2.5, 1H), 8.65 (s, 1H), 8.50 (d, J=5.0, 1H), 8.31 (d, J=6.0, 1H), 7.69 (d, J=2.5, 1H), 7.37 (d, J=5.0, 1H), 7.31-7.33 (m, 1H), 6.58 (s, 1H), 4.97 (t, J=4.5, 1H), 4.39-4.43 (m, 2H), 4.10-4.24 (m, 3H), 3.87 (d, J=12.0, 1H), 3.61 (s, 3H), 2.57-2.64 (m, 2H), 2.47 (d, J=6, 2H), 1.79 (d, J=4.0, 2H), 1.69 (d, J=6.0, 2H)

Example 143a

1-Methyl-3-(pyrimidin-4-ylamino)-5-(4,4,5,5-tetramethyl-1,3,2-dioxaborolan-2-yl)pyridin-2(1H)-one 143a

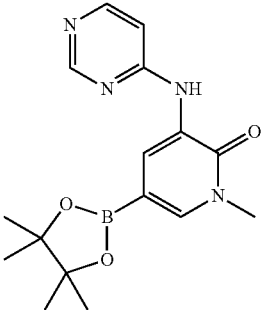

143a

A 250-mL single-neck round-bottomed flask equipped with a magnetic stirrer and a condenser was charged with 5-bromo-1-methyl-3-(pyrimidin-4-ylamino)pyridin-2(1H)-one 142a (4.0 g, 14 mmol), X-phos (400 mg, 0.7 mmol), Pd2(dba)3 (635 mg, 0.7 mmol), KOAc (7.3 mg, 28 mmol), 4,4,4',4',5,5,5',5'-octamethyl-2,2'-bi(1,3,2-dioxaborolane) (10.6 g, 42 mmol), and 1,4-dioxane (100 mL). After three cycles of vacuum/argon flush, the reaction mixture was heated at 60° C. for 8 h. It was then cooled to room temperature and filtered. The filtrate was concentrated under reduced pressure and the resulting residue was purified by flash column chromatography eluting with 5:1 petroleum ether/ethyl acetate to afford 143a as a pale yellow solid (3.8 mg, 82%). MS: [M+H]$^+$ 329.5.

Example 143b 4-(1-Methyl-5-(pyrimidin-4-ylamino)-6-oxo-1,6-dihydropyridin-3-yl)-2-{4,4-dimethyl-9-oxo-7-thia-10-azatricyclo[6.4.0.0$^{2,6}$]dodeca-1(8),2(6)-dien-10-yl}nicotinaldehyde 143b

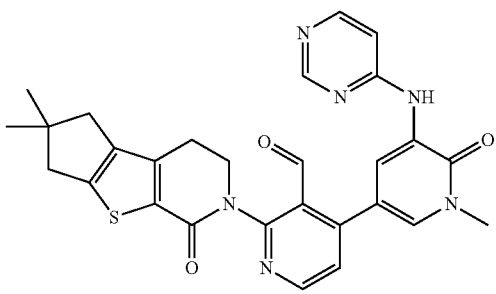

143b

A 250-mL single-neck round-bottomed flask equipped with a magnetic stirrer and a condenser was charged with 143a (150 mg, 0.46 mmol), 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (164 mg, 0.46 mmol):

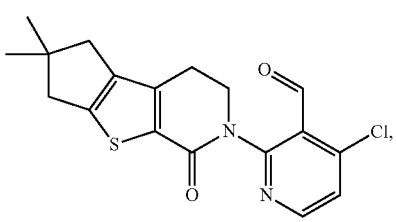 [SMILES: CC1(C)Cc2sc3c(c2C1)CCN(c1nccc(Cl)c1C=O)C3=O]

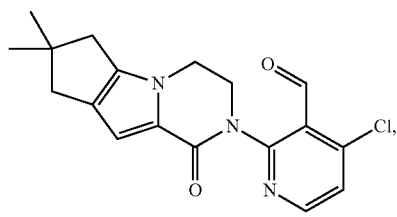 [SMILES: CC1(C)Cc2cc3n(c2C1)CCN(c1nccc(Cl)c1C=O)C3=O]

Pd(dppf)Cl2 (16 mg, 0.02 mmol), K3PO4.3H2O (223 mg, 0.92 mmol) in CH$_3$CN (5 mL) and H$_2$O (1 mL). After three cycles of vacuum/argon flush, the reaction mixture was heated at 100° C. for 3 h. It was then cooled to room temperature and filtered. The filtrate was concentrated under reduced pressure and the resulting residue was purified by flash column chromatography eluting with 20:1 of DCM/MeOH to afford 143b as a yellow solid (110 mg, 48%). MS: [M+H]$^+$ 527.

Example 143

6-[3'-Hydroxymethyl-1-methyl-6-oxo-5-(pyrimidin-4-ylamino)-1,6-dihydro-[3,4']bipyridinyl-2'-yl]-2,2-dimethyl-2,3,5,6-tetrahydro-1H,4H-8-thia-6-aza-cyclopenta[a]inden-7-one 143

A mixture of 143b (110 mg, 0.2 mmol), NaBH4 (30 mg, 0.8 mmol), and MeOH (5 mL) was stirred at 25° C. for 30 mins. The mixture was evaporated in vacuo and the residue was extracted with EtOAc (10 mL×2). The combined EtOAc extract was concentrated under reduced pressure and the residue was purified with reverse-phase prep-HPLC to afford 143 (48 mg, 44%). LCMS: [M+H]$^+$ 529. 1H NMR (500 MHz, DMSO) δ 9.23 (s, 1H), 8.76 (d, J=2.5, 1H), 8.65 (s, 1H), 8.51-8.49 (m, 1H), 8.31 (m, 1H), 7.67 (d, J=3.0, 1H), 7.38-7.37 (m, 1H), 7.33-7.31 (m, 1H), 5.02-5.01 (m, 1H), 4.43 (d, J=2.5, 2H), 4.18-4.15 (m, 1H), 3.83-3.81 (m, 1H), 3.61-3.59 (m, 3H), 3.03-2.99 (m, 1H), 2.91-2.89 (m, 1H), 2.76 (s, 2H), 2.60-2.53 (m, 2H), 1.23-1.22 (m, 6H)

Example 144a 4-(1-Methyl-5-(pyrimidin-4-ylamino)-6-oxo-1,6-dihydropyridin-3-yl)-2-{4,4-dimethyl-9-oxo-1,10-diazatricyclo[6.4.0.0$^{2,6}$]dodeca-2(6),7-dien-10-yl}nicotinaldehyde 144a

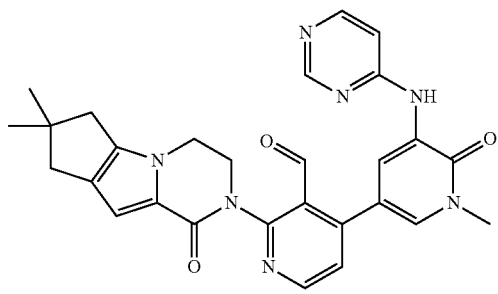

144a

A 250-mL single-neck round-bottomed flask equipped with a magnetic stirrer and a condenser was charged with 1-methyl-3-(pyrimidin-4-ylamino)-5-(4,4,5,5-tetramethyl-1,3,2-dioxaborolan-2-yl)pyridin-2(1H)-one 143a (150 mg, 0.46 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (157 mg, 0.46 mmol):

Pd(dppf)C12 (16 mg, 0.02 mmol), K$_3$PO$_4$.3H$_2$O (223 mg, 0.92 mmol) in CH$_3$CN (5 mL) and H$_2$O (1 mL). After three cycles of vacuum/argon flush, the reaction mixture was heated at 100° C. for 3 h. It was then cooled to room temperature and filtered. The filtrate was concentrated under reduced pressure and the resulting residue was purified by flash column chromatography eluting with 20:1 of DCM/MeOH to afford 144a as a yellow solid (98 mg, 48%). MS: [M+H]$^+$ 510.

Example 144

2-[3'-Hydroxymethyl-1-methyl-6-oxo-5-(pyrimidin-4-ylamino)-1,6-dihydro-[3,4']bipyridinyl-2'-yl]-7,7-dimethyl-3,4,7,8-tetrahydro-2H,6H-cyclopenta-[4,5]pyrrolo[1,2-a]pyrazin-1-one 144

A mixture of 144a (98 mg, 0.19 mmol), NaBH$_4$ (30 mg, 0.8 mmol) and MeOH (5 mL) was stirred at 25° C. for 30 mins. The mixture was evaporated in vacuo and the residue was extracted with EtOAc (10 mL×2). The combined EtOAc extract was concentrated under reduced pressure and the residue was purified with reverse-phase prep-HPLC to give 144 (25 mg, 42%). LCMS: [M+H]$^+$ 512. 1H NMR (500 MHz, DMSO) δ 9.18 (s, 1H), 8.76-8.74 (m, 1H), 8.64 (s, 1H), 8.50-8.47 (m, 1H), 8.31-8.30 (m, 1H), 7.68-7.69 (m, 1H), 7.37-7.36 (m, 1H), 7.33-7.31 (m, 1H), 6.56 (s, 1H), 5.07-5.04 (m, 1H), 4.44-4.41 (m, 2H), 4.23-4.18 (m, 3H), 3.86-3.84 (m, 1H), 3.61 (s, 3H), 2.61-2.56 (m, 2H), 2.42 (s, 2H), 1.21-1.20 (m, 6H)

Example 145a (S)-4-(1-methyl-5-(5-(2-methyl-4-(oxetan-3-yl)piperazin-1-yl)pyridin-2-ylamino)-6-oxo-1,6-dihydropyridin-3-yl)-2-{4,4-dimethyl-9-oxo-7-thia-10-azatricyclo[6.4.0.0$^{2,6}$]dodeca-1(8),2(6)-dien-10-yl}nicotinaldehyde 145a

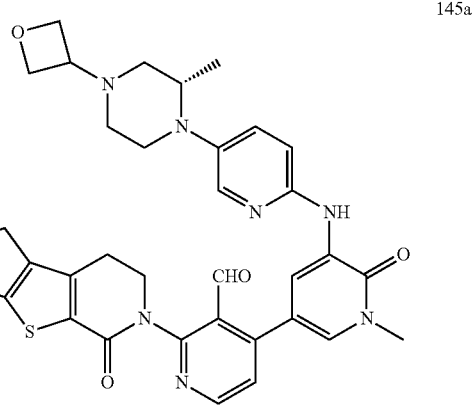

145a

A 50 mL single-neck round-bottomed flask equipped with a magnetic stirrer and a reflux condenser was charged with (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 130f (160 mg, 1 eq., 0.33 mmol), 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (120 mg, 1 eq., 0.33 mmol):

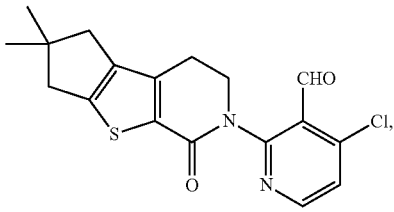 [SMILES: CC1(C)Cc2sc3c(c2C1)CCN(c1nccc(Cl)c1C=O)C3=O]

PdCl$_2$(dppf) (27 mg, 0.1 eq., 0.033 mmol), K$_3$PO$_4$ (140 mg, 2 eq., 0.66 mmol), NaOAc (54 mg, 2 eq., 0.66 mmol), and CH$_3$CN (20 mL). After three cycles of vacuum/argon flash, the mixture was heated at 100° C. for 2 h. It was then cooled to room temperature and filtered. The filtrate was concentrated under reduced pressure and the resulting residue was purified by column chromatography eluting with DCM/EtOH (40/1) to afford 145a as yellow solid (97 mg, 43%). MS: [M+H]$^+$ 680.3.

Example 145

6-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,2-dimethyl-2,3,5,6-tetrahydro-1H,4H-8-thia-6-azacyclopenta[a]inden-7-one 145

A 25 mL single-neck round-bottomed flask equipped with a magnetic stirrer was charged with 145a (97 mg, 1.0 eq., 0.14 mmol), NaBH$_4$ (16 mg, 3.0 eq., 0.42 mmol), and MeOH (10 mL). The mixture was stirred at room temperature for 1 h. The residue was purified by reverse-phase prep-HPLC to afford 145 (61 mg, 63%). LCMS: [M+H]$^+$ 682.3. $^1$H NMR (500 MHz, CDCl$_3$) δ 8.65 (d, J=2.5, 1H), 8.50 (d, J=5.0, 1H), 7.97 (d, J=2.5, 1H), 7.84 (s, 1H), 7.80 (d, J=2.5, 1H), 7.37 (d, J=5.0, 1H), 7.30 (dd, J=3.0, 9.0, 1H), 6.81 (d, J=9.0, 1H), 4.82-4.79 (m, 1H), 4.71-4.61 (m, 5H), 4.45-4.31 (m, 2H), 3.85-3.80 (m, 1H), 3.71 (s, 3H), 3.54-3.46 (m, 2H), 3.07 (d, J=5.0, 2H), 2.98-2.93 (m, 2H), 2.79 (s, 2H), 2.60-2.46 (m, 5H), 2.21-2.18 (m, 1H), 1.28 (s, 6H), 0.98 (d, J=6.0, 3H)

Example 146a

4-Chloro-2-(10-fluoro-1-oxo-3,4,6,7,8,9-hexahydropyrazino[1,2-a]indol-2(1H)-yl)nicotinaldehyde 146a

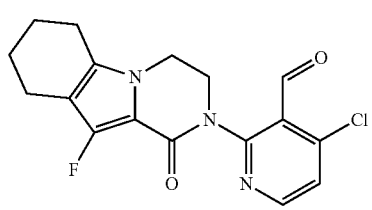

To a solution of 2-bromo-4-chloronicotinaldehyde 103a (1600 mg, 7.27 mmol), 10-fluoro-3,4,6,7,8,9-hexahydropyrazino[1,2-a]indol-1(2H)-one (500 mg, 2.40 mmol):

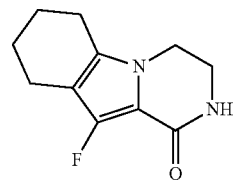 [SMILES: O=C1NCCn2c3c(c(F)c21)CCCC3]

in dioxane (50 mL) was added KOAc (471 mg, 4.82 mmol), Pd$_2$(dba)$_3$ (220 mg, 0.24 mmol), and 4,5-bis(diphenylphosphino)-9,9-dimethyl-xanthene (140 mg, 0.24 mmol). After bubbling argon through the resulting solution for 30 min, the mixture was stirred at 80° C. for 10 h. It was allowed to cool to room temperature and H$_2$O (100 mL) was added. The aqueous layer was separated and extracted with ethyl acetate (2×200 mL). The combined organic layer was washed with brine (100 mL) and dried over sodium sulfate. The drying agent was removed by filtration and the filtrate was concentrated under reduced pressure. The residue was purified on flash column eluting with PE/EA (3:1) to afford 146a as a yellow solid (420 mg, 49%). LCMS: [M+H]$^+$ 348

Example 146b 2-(10-Fluoro-1-oxo-3,4,6,7,8,9-hexahydropyrazino[1,2-a]indol-2(1H)-yl)-4-(1-methyl-6-oxo-5-(pyrimidin-4-ylamino)-1,6-dihydropyridin-3-yl)nicotinaldehyde 146b A round-bottomed flask was charged with 146a (200 mg, 0.58 mmol), 1-methyl-3-(pyrimidin-4-ylamino)-5-(4,4,5,5-tetramethyl-1,3,2-dioxaborolan-2-yl)pyridin-2(1H)-one 143a (227 mg, 0.69 mmol), PdCl$_2$(dppf) (47 mg, 0.06 mmol), K$_3$PO$_4$ (244 mg, 1.15 mmol), NaOAc (94 mg, 1.15 mmol), acetonitrile (30 mL), and H$_2$O (3 mL). After three cycles of vacuum/argon flush, the mixture was heated at 100° C. for 3 h. It was then filtered and the filtrate was evaporated in vacuo. The residue was purified on flash column chromatography eluting with 1:20 methanol/dichloro-methane to afford 146b as a red solid (79 mg, 27%). LCMS: [M+H]$^+$ 514

Example 146

10-Fluoro-2-(3-(hydroxymethyl)-4-(1-methyl-6-oxo-5-(pyrimidin-4-ylamino)-1,6-dihydropyridin-3-yl)pyridin-2-yl)-3,4,6,7,8,9-hexahydropyrazino[1,2-a]indol-1(2H)-one 146

A mixture of 146b (79 mg, 0.15 mmol), NaBH$_4$ (22 mg, 0.60), and CH$_3$OH (10 mL) was stirred at 25° C. for 1 h. The mixture was extracted with CH$_2$Cl$_2$ (10 mL×2). The combined CH$_2$Cl$_2$ extract was concentrated under reduced pressure. The residue was purified with reverse-phase prep-HPLC to afford 146 (39 mg, 49%). LCMS: [M+H]+ 516. 1H NMR (500 MHz, CDCl3) δ 8.83 (d, J=2.0, 1H), 8.78 (s, 1H), 8.52 (d, J=5.0, 1H), 8.35 (d, J=5.5, 1 H), 8.12 (s, 1H), 8.03 (d, J=2.0, 1H), 7.36 (d, J=5.0, 1H), 6.76-6.77 (m, 1H), 5.07 (s, 1H), 4.65 (d, J=9.5, 1H), 4.48 (d, J=9.5, 1H), 4.29 (d, J=1.5, 1H), 4.02-4.13 (m, 2H), 3.79 (d, J=6.5, 1H), 3.73 (s, 3H), 2.52-2.58 (m, 4H), 1.85-1.90 (m, 2H), 1.77 (d, J=5.0, 2H)

Example 147a

4-Chloro-2-(1-oxo-3,4,6,7,8,9-hexahydropyrido[3,4-b]indolizin-2(1H)-yl)nicotinaldehyde 147a

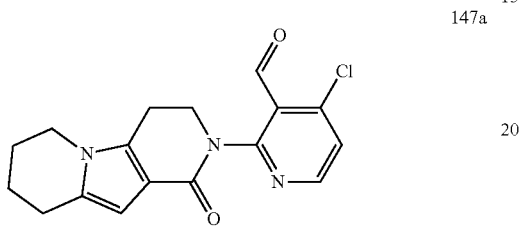

147a

A 250-mL single-neck round-bottomed flask equipped with a magnetic stirrer and reflux condenser was charged with 1,4-dioxane (50 mL), 2-bromo-4-chloronicotin-aldehyde 103a (1.4 g, 6.4 mmol), 3,4,6,7,8,9-hexahydropyrido[3,4-b]indolizin-1(2H)-one 112d (0.6 g, 3.2 mmol), Pd2(dba)3 (293 mg, 0.32 mmol), XantPhos (370 mg, 0.64 mmol), and potassium acetate (627 mg, 6.4 mmol). After three cycles of vacuum/argon flush, the mixture was heated at 80° C. overnight. After this time the reaction was cooled to room temperature. It was then filtered and the filtrate was evaporated in vacuo. The residue was purified by silica gel column chromatography eluting with CH2Cl2/CH3OH (20:1, UV) to afford 147a (528 mg, 50%) as a yellow solid. MS: [M+H]+ 330. 1H NMR (500 MHz, CDCl3) δ 10.09 (s, 1H), 8.37 (d, J=5.5, 1H), 7.16 (d, J=5.5, 1H), 6.25 (s, 1H), 4.29-4.32 (m, 2H), 3.83-3.86 (m, 2H), 2.96-2.99 (m, 2H), 2.77-2.78 (m, 2H), 2.00-2.07 (m, 2H), 1.83-1.85 (m, 2H)

Example 147b 2-(3-Formyl-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydropyrido[3,4-b]indolizin-1(2H)-one 147b

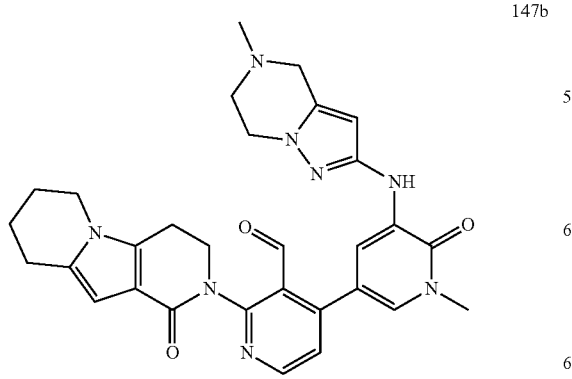

147b

A round-bottomed flask was charged with 4-chloro-2-(1-oxo-3,4,6,7,8,9-hexahydropyrido[3,4-b]indolizin-2(1H)-yl)nicotinaldehyde 147a (100 mg, 0.30 mmol), 1-methyl-3-(5-methyl-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 135a (116 mg, 0.30 mmol), PdCl2(dppf) (25 mg, 0.03 mmol), K3PO4.3H2O (160 mg, 0.60 mmol), NaOAc (59 mg, 0.60 mmol), acetonitrile (10 mL), and H2O (5 mL). After three cycles of vacuum/argon flush, the mixture was heated at 100° C. for 3 h. It was then filtered and the filtrate was evaporated in vacuo. The residue was purified on flash column chromatography eluting with 1:3 petroleum/ethyl acetate to afford 147b as a yellow solid (100 mg, 60%). LCMS: [M+H]+ 553

Example 147

2-(3-(Hydroxymethyl)-4-(1-methyl-5-(5-methyl-4,5,6,7-tetrahydro-pyrazolo[1,5-a]pyrazin-2-ylamino)-6-oxo-1,6-dihydropyridin-3-yl)pyridin-2-yl)-3,4,6,7,8,9-hexahydropyrido[3,4-b]indolizin-1(2H)-one 147

A mixture of 147b (100 mg, 0.18 mmol), NaBH4 (21 mg, 0.54), and CH3OH (10 mL) was stirred at 25° C. for 1 h. The mixture was extracted with CH2Cl2 (10 mL×2). The combined CH2Cl2 extract was concentrated under reduced pressure. The residue was purified with reverse-phase prep-HPLC to afford 147 (60 mg, 60%). LCMS: [M+H]+ 555. 1H NMR (500 MHz, DMSO) δ 8.45 (d, J=5.0, 1H), 8.19 (s, 1H), 8.06 (d, J=5.0, 1H), 7.41 (d, J=2.0, 1H), 7.29 (d, J=5.0, 1H), 6.04 (s, 1H), 5.88 (s, 1H), 4.92 (s, 1H), 4.33-4.42 (m, 2H), 4.11-4.16 (m, 1H), 3.91-3.96 (m, 3H), 3.77-3.82 (m, 2H), 3.57 (s, 3H), 3.45-3.48 (m, 2H), 2.91-3.01 (m, 2H), 2.71-2.79 (m, 4H), 2.35 (s, 3H), 1.90-1.92 (m, 2H), 1.71-1.79 (m, 2H)

Example 148a 3-(2-Bromo-4-chloropyridin-3-yl)oxetan-3-ol 148a

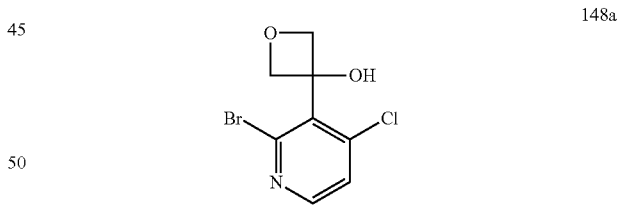

148a

To a solution of 2-bromo-4-chloropyridine (14 g, 70 mmol) in dry THF (200 mL) was added LDA (42.0 mL, 84.0 mmol, 2.0 M) dropwise at −70° C. After stirring for 0.5 h at this temperature, a solution of oxetan-3-one (6.6 g, 90 mmol) in dry THF (40 mL) was added slowly and the reaction mixture was stirred at 0° C. for an additional 1 h. Saturated aqueous NH4Cl (50 mL) and EA (200 mL) were added. The mixture was partitioned between water and ethyl acetate. The aqueous layer was extracted with ethyl acetate. The combined organic layer was washed with water and brine. After drying over anhydrous magnesium sulfate, the solvent was evaporated and the crude material was purified by SGC eluting with DCM to afford 148a as a yellow solid (8.8 g, 45%). MS: [M+H]+ 266.0.

Example 148b 2-(4-Chloro-3-(3-hydroxyoxetan-3-yl)pyridin-2-yl)-3,4,6,7,8,9-hexahydropyrazino[1,2-a]indol-1(2H)-one 148b

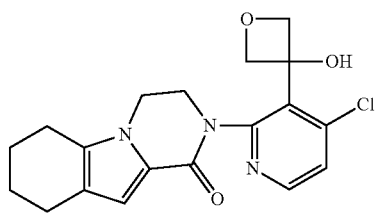

A 100 mL single-neck round-bottomed flask equipped with a magnetic stirrer was charged with 3,4,6,7,8,9-hexahydropyrazino[1,2-a]indol-1(2H)-one 101e (190 mg, 1.0 mmol), 148a (795 mg, 3.0 mmol), CuI (95 mg, 0.5 mmol), DMEDA (88 mg, 1.0 mmol), KOAc (294 mg, 3.0 mmol), and 1,4-dioxane (50 ml). The system was evacuated and then refilled with N$_2$. A reflux condenser was attached to the flask, and the reaction mixture was heated at 85° C. for 15 h. Then, the mixture was cooled to room temperature and filtered. The filtrate was concentrated under reduced pressure and the resulting residue was purified by flash column chromatography eluting with 2:1 petroleum ether/ethyl acetate to afford 148b as a yellow solid (156 mg, 42%). MS: [M+H]$^+$ 374.2.

Example 148

(S)-2-(3-(3-Hydroxyoxetan-3-yl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one 148

A 100-mL single-neck round-bottomed flask was charged with 148b (100 mg, 0.3 mmol), (S)-1-methyl-3-(5-(2-methyl-4-(oxetan-3-yl)piperazin-1-yl)pyridine-2-ylamino)-5-(4,4,5,5-tetramethyl-1,3,2-dioxaborolan-2-yl)pyridin-2(1H)-one 130f (173 mg, 0.36 mmol), Pd(dppf)Cl$_2$ (15 mg, 0.015 mmol), K$_3$PO$_4$ (130 mg, 0.6 mmol), and NaOAc.3H$_2$O (90 mg, 0.6 mmol) in CH$_3$CN (30 mL). The system was evacuated and refilled with N$_2$. The reaction mixture was heated at 100° C. for 2 h. It was then cooled to room temperature and filtered. The filtrate was concentrated under reduced pressure and the resulting residue was purified by flash column chromatography eluting with 25:1 DCM/MeOH to afford 148 (30 mg, 20%) as a pale yellow solid. MS: [M+H]$^+$ 693.3. $^1$H NMR (500 MHz, CDCl$_3$) δ 8.69 (d, J=2, 1H), 8.50 (d, J=5, 1H), 8.01 (d, J=2.5, 1H), 7.85 (s, 1H), 7.67 (s, 1H), 7.38-7.32 (m, 2H), 6.89 (s, 1H), 6.83 (d, J=8.5, 1H), 6.67 (s, 1H), 4.93 (d, J=6, 1H), 4.71-4.63 (m, 6H), 4.46 (d, J=7.5, 1H), 4.24-4.18 (m, 2H), 4.10-4.05 (m, 1H), 3.90 (d, J=12.5, 1H), 3.70 (s, 3H), 3.55-3.46 (m, 2H), 3.10 (t, J=4.5, 2H), 2.63-2.48 (m, 7H), 2.22 (t, J=7.5, 1H), 1.92-1.88 (m, 2H), 1.82-1.77 (m, 2H), 1.02-1.00 (m, 3H)

Example 149a (S)-4-(1-Methyl-5-(5-(2-methyl-4-(oxetan-3-yl)piperazin-1-yl)pyridin-2-ylamino)-6-oxo-1,6-dihydropyridin-3-yl)-2-(1-oxo-3,4,6,7,8,9-hexahydropyrido[3,4-b]indolizin-2(1H)-yl)nicotinaldehyde 149a

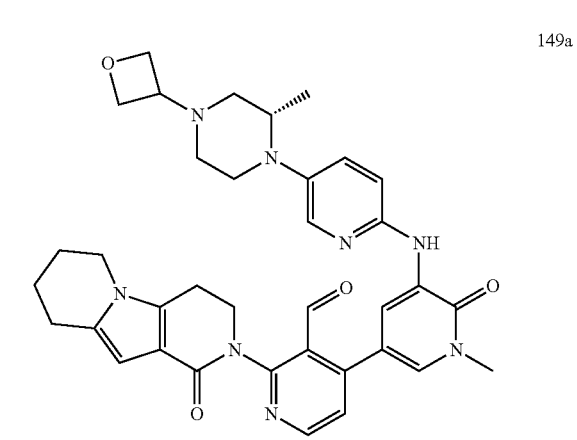 [SMILES: C[C@H]1CN(C2COC2)CCN1c1ccc(Nc2cc(-c3ccnc(N4CCc5c(cc6n5CCCC6)C4=O)c3C=O)cn(C)c2=O)nc1]

A 100-mL round-bottomed flask equipped with a reflux condenser was charged with 4-chloro-2-(1-oxo-3,4,6,7,8,9-hexahydropyrido[3,4-b]indolizin-2(1H)-yl)nicotinaldehyde 139a (100 mg, 0.30 mmol), (S)-1-methyl-3-(5-(2-methyl-4-(oxetan-3-yl)-piperazin-1-yl)pyridin-2-ylamino)-5-(4,4,5,5-tetramethyl-1,3,2-dioxaborolan-2-yl)pyridin-2(1H)-one 191j (146 mg, 0.30 mmol), PdCl$_2$(dppf) (25 mg, 0.030 mmol), K$_3$PO$_4$.trihydrate (160 mg, 0.60 mmol), sodium acetate (49 mg, 0.60 mmol), acetonitrile (20 mL), and water (3 mL). After three cycles of vacuum/argon flush, the mixture was heated at 100° C. for 3 h. It was then filtered and the filtrate was evaporated under reduced pressure. The residue was purified by silica-gel column chromatography eluting with 1:3 petroleum/ethyl acetate to afford 149a as a yellow solid (97 mg, 50%). MS-ESI: [M+H]$^+$ 649

Example 149

2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,3,5,6,7,8-hexahydro-4H-2,4-b-diaza-fluoren-1-one 149

A mixture of 149a (97 mg, 0.15 mmol), NaBH$_4$ (17 mg, 0.45), and methanol (10 mL) was stirred at 25° C. for 1 h. The reaction mixture was then quenched with water (10 mL) and concentrated under reduced pressure. The residue was extracted with dichloromethane (2×10 mL). The combined dichloromethane extract was concentrated under reduced pressure and the residue was purified with reverse-phase prep-HPLC to afford 149 (62 mg, 63%). MS-ESI: [M+H]$^+$ 651.3. $^1$H NMR (500 MHz, DMSO-d$_6$) δ 8.63 (s, 1H), 8.46 (d, J=5.0 Hz, 1H), 8.43 (s, 1H), 7.83 (d, J=3.0 Hz, 1H), 7.48 (d, J=2.0 Hz, 1H), 7.38-7.36 (m, 1H), 7.31 (J=5.0 Hz, 1H), 7.25-7.23 (m, 1H), 6.04 (s, 1H), 4.57-4.55 (m, 2H), 4.48-4.46 (m, 1H), 4.42-4.38 (m, 2H), 4.35-4.33 (m, 1H), 4.15-4.12 (m, 1H), 3.96-3.94 (m, 1H), 3.82-3.78 (m, 2H), 3.69-3.67 (m, 1H), 3.59 (s, 3H), 3.41-3.38 (m, 2H), 3.18-3.15 (m, 2H), 3.00-2.95 (m, 3H), 2.73-2.71 (m, 2H), 2.30-2.28 (m, 2H), 2.20-2.16 (m, 1H), 1.93-1.89 (m, 3H), 1.77-1.75 (m, 1H), 0.93 (d, J=6.5 Hz, 3H).

Example 150a

3-{4,4-Dimethyl-9-oxo-1,10-diazatricyclo[6.4.0.0$^{2,6}$]dodeca-2(6),7-dien-10-yl}-5-[1-methyl-5-({5-methyl-4H,5H,6H,7H-pyrazolo[1,5-a]pyrazin-2-yl}amino)-6-oxo-1,6-dihydropyridin-3-yl]pyridine-4-carbaldehyde 150a

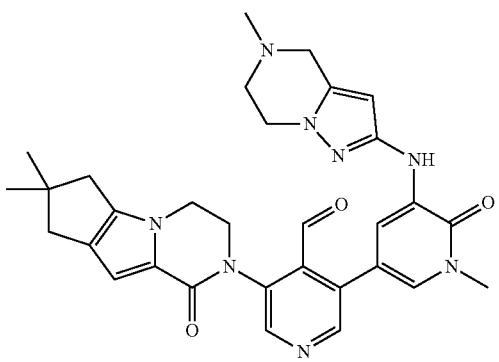

A 25-mL single-neck round-bottomed flask equipped with a magnetic stirrer and a reflux condenser was charged with 3-bromo-5-{4,4-dimethyl-9-oxo-1,10-diazatricyclo[6.4.0.0$^{2,6}$]dodeca-2(6),7-dien-10-yl}pyridine-4-carbaldehyde 107f (233 mg, 0.60 mmol), 1-methyl-3-({5-methyl-4H,5H,6H,7H-pyrazolo[1,5-a]pyrazin-2-yl}amino)-5-(4,4,5,5-tetramethyl-1,3,2-dioxaborolan-2-yl)-1,2-dihydropyridin-2-one 135a (231 mg, 0.60 mmol), Pd(dppf)Cl$_2$ (49 mg, 0.060 mmol), potassium acetate (118 mg, 1.2 mmol), K$_3$PO$_4$·trihydrate (320 mg, 1.2 mmol), acetonitrile (12 mL), and water (5 drops). After three cycles of vacuum/argon flush, the mixture was heated at 110° C. for 2 h. It was then filtered and the filtrate was evaporated under reduced pressure. The residue was purified by silica-gel column chromatography eluting with 30:1 dichloromethane/methanol to afford 150a (168 mg, 49%) as a solid. MS-ESI: [M+H]$^+$ 567

Example 150

2-[4-Hydroxymethyl-1'-methyl-5'-(5-methyl-4,5,6,7-tetrahydro-pyrazolo[1,5-a]pyrazin-2-ylamino)-6'-oxo-1',6'-dihydro-[3,3]bipyridinyl-5-yl]-7,7-dimethyl-3,4,7,8-tetrahydro-2H,6H-cyclopenta[4,5]pyrrolo[1,2-a]pyrazin-1-one 150

To a solution of 150a (170 mg, 0.30 mmol) in methanol (10 mL) was added sodium borohydride (68 mg, 1.8 mmol) at 0° C. The mixture was stirred at room temperature for 30 minutes. Then the reaction mixture was quenched with water (2 mL) and concentrated. The residue was purified with reverse-phase prep-HPLC to afford 150 (42 mg, 25%) as a pale yellow solid. MS-ESI: [M+H]$^+$ 569. $^1$H NMR (500 MHz, CDCl$_3$) δ 8.63 (s, 1H), 8.48 (s, 1H), 7.95 (d, J=2.0 Hz, 1H), 7.40 (s, 1H), 7.32 (d, J=2.5 Hz, 1H), 6.82 (s, 1H), 5.67 (s, 1H), 4.63-4.55 (m, 2H), 4.37-4.35 (m, 1H), 4.22-4.18 (m, 3H), 4.05-3.97 (m, 3H), 3.69 (s, 3H), 3.59-3.57 (m, 2H), 2.86 (t, J=6.0 Hz, 2H), 2.56 (s, 2H), 2.50 (s, 2H), 2.46 (s, 3H), 1.26 (s, 6H).

Example 151a (R)-tert-Butyl 3-Methyl-4-(6-nitropyridin-3-yl)piperazine-1-carboxylate 151a

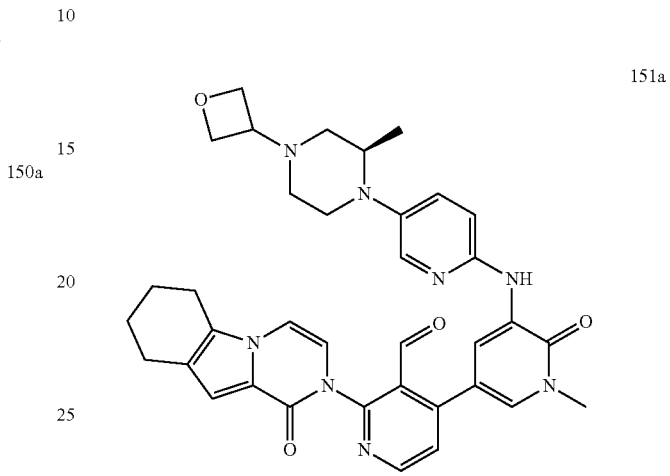

A 250-mL single-neck round-bottomed flask equipped with a magnetic stirrer and a reflux condenser was charged with 1,4-dioxane (60 mL), 5-bromo-2-nitropyridine (2.0 g, 10.0 mmol), (R)-tert-butyl 3-methylpiperazine-1-carboxylate (2.0 g, 10.0 mmol), and cesium carbonate (6.5 g, 20 mmol). After bubbling nitrogen through the resulting mixture for 10 minutes, tris(dibenzylideneacetone)dipalladium(0) (915 mg, 1.0 mmol) and XantPhos (579 mg, 1.0 mmol) were added. The system was subjected to three cycles of vacuum/argon flush and heated at 100° C. for 15 h. After this time the reaction was cooled to room temperature and filtered. The filtrate was partitioned between ethyl acetate (100 mL) and water (100 mL). The aqueous layer was separated and extracted with ethyl acetate (3×50 mL). The combined organic layer was washed with brine (100 mL) and dried over sodium sulfate. The drying agent was removed by filtration and the filtrate was concentrated under reduced pressure. The residue was purified by silica-gel column chromatography eluting with 30:1 dichloromethane/methanol to afford 151a (1.6 g, 44%) as yellow solid. MS-ESI: [M+H]$^+$ 323. $^1$H NMR (500 MHz, DMSO-d$_6$) δ 8.21 (d, J=3.5 Hz, 1H), 8.18 (d, J=9.0 Hz, 1H), 7.45-7.43 (m, 1H), 4.34-4.33 (m, 1H), 3.92-3.99 (m, 1H), 3.80 (d, J=12.5 Hz, 2H), 3.06-3.23 (m, 3H), 1.43 (s, 9H), 1.09 (d, J=6.5 Hz, 3H).

Example 151b (R)-tert-Butyl 4-(6-Aminopyridin-3-yl)-3-methylpiperazine-1-carboxylate 151b A 250-mL flask was purged with nitrogen and charged with 151a (1.5 g, 4.6 mmol), 10% palladium on carbon (50% wet, 200 mg), and methanol (70 mL). It was evacuated, charged with hydrogen gas, and stirred at room temperature for 10 h. The hydrogen was then evacuated and nitrogen was charged into the flask. The catalyst was removed by filtration through a pad of CELITE® and the filtrate was concentrated under reduced pressure to afford 151b (1.1 g, 81%) as brown solid. MS-ESI: [M+H]+ 293

Example 151c (R)-tert-Butyl 4-(6-(5-Bromo-1-methyl-2-oxo-1,2-dihydropyridin-3-ylamino)pyridin-3-yl)-3-methylpiperazine-1-carboxylate 151c A 100-mL single-neck round-bottomed flask equipped with a magnetic stirrer and a reflux condenser was charged with 1,4-dioxane (40 mL), 151b (1.0 g, 3.4 mmol), 3,5-dibromo-1-methylpyridin-2(1H)-one (2.7 g, 10.2 mmol), and cesium carbonate (2.2 g, 6.8 mmol). After bubbling nitrogen through the resulting mixture for 10 minutes, XantPhos (198 mg, 0.34 mmol) and tris(dibenzylideneacetone)dipalladium (0) (313 mg, 0.34 mmol) were added. The reaction mixture was subjected to three cycles of vacuum/argon flush and heated at 100° C. for 5 h. After this time the reaction was cooled to room temperature and filtered. The filtrate was partitioned between ethyl acetate (50 mL) and water (50 mL). The aqueous layer was separated and extracted with ethyl acetate (3×30 mL). The combined organic layer was washed with brine (50 mL) and dried over sodium sulfate. The drying agent was removed by filtration and the filtrate was concentrated under reduced pressure. The residue was purified by silica-gel column chromatography eluting with 30:1 dichloromethane/methanol to afford 151c as yellow solid (1.1 g, 63%). MS-ESI: [M+H]+ 478.

Example 151d (R)-5-Bromo-1-methyl-3-(5-(2-methylpiperazin-1-yl)pyridin-2-ylamino)pyridin-2(1H)-one 151d To a mixture of 151c (600 mg, 1.26 mmol) in methanol (20 mL) was added HCl/dioxane (4M, 4 mL). The reaction mixture was stirred at room temperature for 4 h. It was then concentrated under reduced pressure. The residue was basified with aqueous 1M NaOH and extracted with dichloromethane (3×30 mL). The combined organic layer was washed with brine and concentrated under reduced pressure to afford 151d (450 mg, 95%) as yellow solid. MS-ESI: [M+H]+ 378.

Example 151e (R)-5-Bromo-1-methyl-3-(542-methyl-4-(oxetan-3-yl)piperazin-1-yl)pyridin-2-ylamino)pyridin-2(1H)-one 151f A mixture of 151d (40.0 g, 106 mmol), oxetan-3-one (11.4 g, 159 mmol), NaBH₃CN (10.0 g, 159 mmol), and zinc chloride (21.3 g, 159 mmol) in methanol (700 mL) was stirred at 50° C. for 5 hours. water (50 mL) was added to the mixture and concentrated under reduced pressure. The residue was extracted with dichloromethane (3×200 mL) and the combined organic layer was concentrated under reduced pressure. The residue was purified by silica-gel column chromatography eluting with 40:1 dichloromethane/methanol to afford 151e (35 g, 73%). MS: [M+H]+ 434.

Example 151f (R)-1-Methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 151f

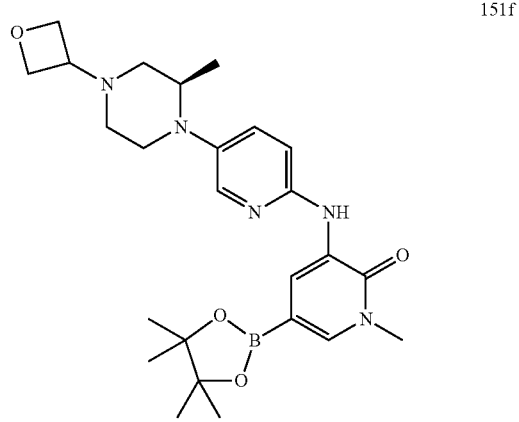 [SMILES: C[C@@H]1CN(C2COC2)CCN1c1ccc(Nc2cc(B3OC(C)(C)C(C)(C)O3)cn(C)c2=O)nc1]

151f

To a solution of 151e (2.0 g, 4.60 mmol), 4,4,4',4',5,5,5',5'-octamethyl-2,2'-bi(1,3,2-dioxaborolane) (3.50 g, 13.80 mmol) in dioxane (50 mL) was added PdCl₂(dppf) (377.10 mg, 0.46 mmol) and potassium acetate (2.70 g, 27.80 mmol). The mixture was stirred at 10° C. for 12 h under argon atmosphere. After reaction the mixture was filtered and the filtrate was evaporated under reduced pressure. The residue was purified by silica-gel column chromatography eluting with 15:1 methylene chloride/methanol to afford 151f (1.10 g, 49%) as a brown solid. MS: [M+H]+ 482.3

Example 151g (R)-4-(1-Methyl-5-(5-(2-methyl-4-(oxetan-3-yl)piperazin-1-yl)pyridin-2-ylamino)-6-oxo-1,6-dihydropyridin-3-yl)-2-(1-oxo-6,7,8,9-tetrahydropyrazino[1,2-a]indol-2(1H)-yl)nicotinaldehyde 151g A 100-mL round-bottomed flask equipped with a reflux condenser was charged with 4-chloro-2-(1-oxo-6,7,8,9-tetrahydropyrazino[1,2-a]indol-2(1H)-yl)nicotinaldehyde 103b (150 mg, 0.45 mmol), 151f (331 mg, 0.69 mmol), PdCl₂(dppf) (37 mg, 0.045 mmol), K₃PO₄ (190 mg, 0.90 mmol), sodium acetate (74 mg, 0.90 mmol), acetonitrile (15 mL), and water (1.5 mL). After three cycles of vacuum/argon flush, the mixture was heated at 100° C. for 3 h. It was then filtered and the filtrate was evaporated under reduced pressure. The residue was purified with silica-gel column chromatography eluting with 1:20 methanol/dichloromethane to afford 151g as a red solid (89 mg, 30%). MS-ESI: [M+H]+ 647

Example 151

2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-2H-pyrazino[1,2-a]indol-1-one 151

A mixture of 151g (89 mg, 0.14 mmol), NaBH₄ (22 mg, 0.60), and methanol (10 mL) was stirred at 25° C. for 1 h. The mixture was quenched with water (8 mL) and concentrated under reduced pressure. The residue was extracted with dichloromethane (2×10 mL). The combined dichloromethane extract was concentrated under reduced pressure and the residue was purified with reverse-phase prep-HPLC to afford 151 (35 mg, 39%). MS-ESI: [M+H]+649. ¹H NMR (500 MHz, CDCl₃) δ 8.65 (d, J=2.0 Hz, 1H), 8.55 (d, J=5.0 Hz, 1H), 8.46 (s, 1H), 7.83 (d, J=2.5 Hz, 1H), 7.50-7.48 (m, 2H), 7.38-7.36 (m, 1H), 7.26-7.24 (m, 2H), 6.83-6.80 (m, 2H), 4.98 (bs, 1H), 4.57-4.54 (m, 2H), 4.48-4.33 (m, 4H), 3.67-3.66 (m, 1H), 3.60 (s, 3H), 3.39-3.38 (m, 2H), 3.09-3.08 (m, 1H), 2.96-2.94 (m, 1H), 2.76-2.74 (m, 2H), 2.64-2.62 (m, 2H), 2.36-2.31 (m, 2H), 2.20-2.17 (t, J=7.5 Hz, 1H), 1.88-1.86 (m, 2H), 1.75-1.74 (m, 2H), 0.93 (d, J=6.5 Hz, 3H).

Example 152a tert-Butyl 8-(6-Nitropyridin-3-yl)-3,8-diazabicyclo[3.2.1]octane-3-carboxylate 152a

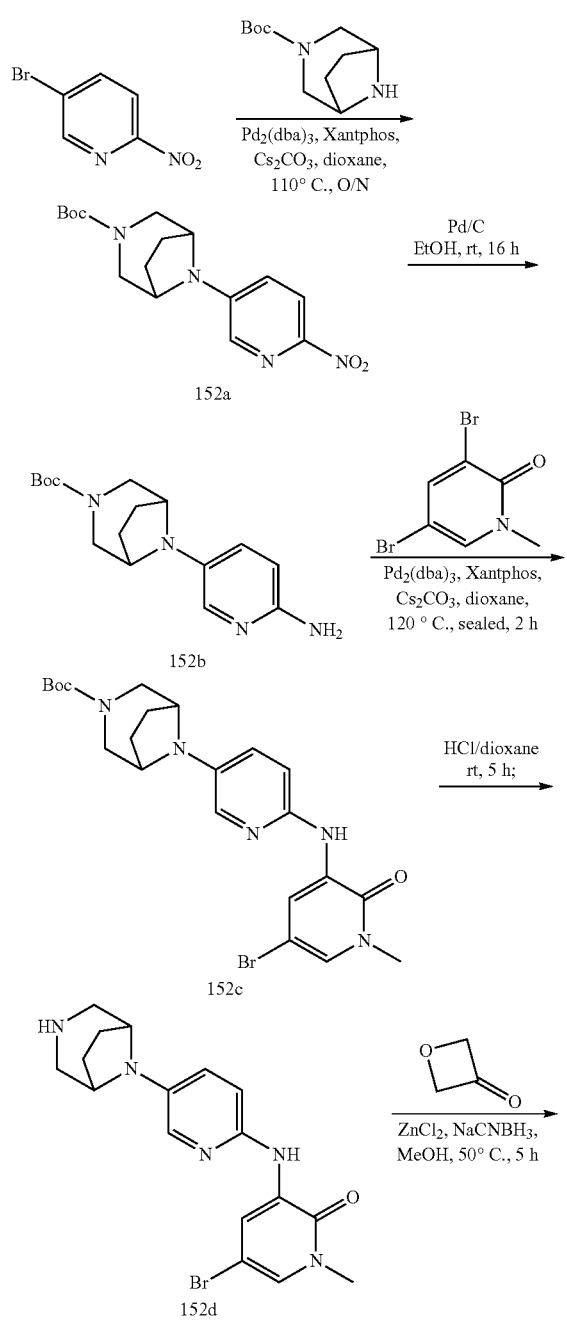

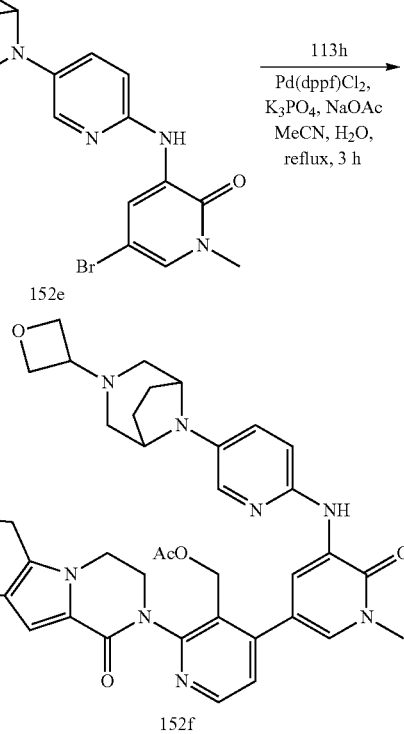

A 250-mL single-neck round-bottomed flask equipped with a magnetic stirrer and a reflux condenser was charged with 1,4-dioxane (100 mL), 5-bromo-2-nitropyridine (2.5 g, 12.4 mmol), tert-butyl 3,8-diazabicyclo[3.2.1]octane-3-carboxylate (869 g, 4.1 mmol), Pd₂(dba)₃ (193 mg, 0.21 mmol), XantPhos (237 mg, 0.41 mmol), and cesium carbonate (2.7 g, 8.2 mmol). After three cycles of vacuum/argon flush, the mixture was stirred at 110° C. overnight. The reaction was cooled to room temperature. It was then filtered and the filtrate was evaporated in vacuo. The residue was purified by silica-gel column chromatography eluting with 3:1 petroleum ether/ethyl acetate to afford 152a (2.63 g, 66.8%) as a yellow solid. MS-ESI: [M+H]⁺ 335.2.

Example 152b tert-Butyl 8-(6-Aminopyridin-3-yl)-3,8-diazabicyclo[3.2.1]octane-3-carboxylate 152b A 100-mL single-neck round-bottomed flask was purged with nitrogen and charged with 152a (2.5 g, 7.5 mmol), 10% palladium on carbon (50% wet, 250 mg) and methanol (40 mL). The mixture was evacuated, charged with hydrogen gas, and stirred at room temperature for 16 h. The hydrogen was then evacuated and nitrogen was charged into the flask. The catalyst was removed by filtration through a pad of CELITE® and the filtrate was concentrated under reduced pressure to afford 152b (1.51 g, 66%) as a colorless oil. MS-ESI: [M+H]⁺ 305.3

Example 152c tert-Butyl 8-(6-(5-Bromo-1-methyl-2-oxo-1,2-dihydropyridin-3-ylamino)pyridin-3-yl)-3,8-diazabicyclo[3.2.1]octane-3-carboxylate 152c A sealed tube equipped with a magnetic stirrer was charged with 152b (1.3 g, 4.3 mmol), 3,5-dibromo-1-methylpyridin-2(1H)-one (1.2 g, 4.3 mmol), tris(dibenzylideneacetone)dipalladium(0) (394 mg, 0.43 mmol), XantPhos (497 mg, 0.86 mmol), Cs$_2$CO$_3$ (2.8 g, 8.6 mmol), and 1,4-dioxane (15 mL). After three cycles of vacuum/argon flush, the mixture was stirred at 120° C. for 2 h. The filtrate was concentrated under reduced pressure and the resulting residue was purified by silica-gel column chromatography eluting with 50:1 dichloromethane/methanol to afford 152c as a yellow solid (900 mg, 43%). MS-ESI: [M+H]$^+$ 490.3.

Example 152d 3-(5-(3,8-Diazabicyclo[3.2.1]octan-8-yl)pyridin-2-ylamino)-5-bromo-1-methyl-pyridin-2(1H)-one 152d A mixture of 152c (900 mg, 1.84 mmol) and 4.0M HCl/dioxane (60 mL) was stirred at room temperature for 5 h. It was then concentrated under reduced pressure to afford crude 152d as a yellow solid (700 mg, 98%), which was used in the next step without further purification. MS-ESI: [M+H]$^+$ 390.3.

Example 152e

5-Bromo-1-methyl-3-(5-(3-(oxetan-3-yl)-3,8-diazabicyclo[3.2.1]octan-8-yl)pyridin-2-ylamino)pyridine-2(1H)-one 152e A mixture of 152d (676 mg, 1.7 mmol), oxetan-3-one (251 mg, 3.5 mmol), NaBH$_3$CN (274 mg, 4.4 mmol), and zinc chloride (592 mg, 4.4 mmol) in methanol (30 mL) was stirred at 50° C. for 5 hours. water was added and the mixture was concentrated under reduced pressure. The residue was extracted with dichloromethane three times. The combined extract was concentrated under reduced pressure to afford crude 152e as a yellow solid (650 mg, 84%), which was used in the next step without further purification. MS-ESI: [M+H]$^+$ 446.2.

Example 152f (4-(1-Methyl-5-(5-(3-(oxetan-3-yl)-3,8-diazabicyclo[3.2.1]octan-8-yl)pyridine-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 152f A 50-mL single-neck round-bottomed flask equipped with a magnetic stirrer and a reflux condenser was charged with 152e (300 mg, 0.67 mmol), 3-(acetoxymethyl)-2-(1-oxo-3,4,6,7,8,9-hexahydropyrazino[1,2-a]indol-2(1H)-yl)pyridin-4-ylboronic acid 113h (257 mg, 0.67 mmol), Pd(dppf)Cl$_2$ (55 mg, 0.067 mmol), K$_3$PO$_4$ (284 mg, 1.34 mmol), sodium acetate (110 mg, 1.34 mmol), water (6 drops), and acetonitrile (20 mL). After three cycles of vacuum/argon flush, the mixture was stirred at reflux for 3 h. It was then cooled to room temperature and filtered. The filtrate was concentrated under reduced pressure and the resulting residue was purified by silica-gel column chromatography eluting with 30:1 dichloromethane/methanol to afford 152f as a brown solid (200 mg, 42%). MS-ESI: [M+H]$^+$705.4.

Example 152

2-{3'-Hydroxymethyl-1-methyl-5-[5-((1S,5R)-3-oxetan-3-yl-3,8-diaza-bicyclo[3.2.1]oct-8-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one 152

A mixture of 152f (180 mg, 0.26 mmol) and lithium hydroxide (215 mg, 5.1 mmol) in i-propanol/THF (1:1, 4 mL) and water (1 mL) was stirred at 35° C. for 1 h. The mixture was evaporated in vacuo and the residue was diluted with water and ethyl acetate. The water phase was separated and extracted with ethyl acetate (2×10 mL). The combined ethyl acetate extract was concentrated under reduced pressure and the residue was purified by reverse-phase prep-HPLC to afford 152 (12 mg, 71%) as a yellow solid. MS-ESI: [M+H]$^+$ 663.3. $^1$H NMR (500 MHz, DMSO-d$_6$) δ 8.55 (d, J=2.5 Hz, 1H), 8.48 (d, J=5.0 Hz, 1H), 8.32 (s, 1H), 7.80 (d, J=2.5 Hz, 1H), 7.43 (d, J=2.0 Hz, 1H), 7.33 (d, J=5.0 Hz, 1H), 7.25-7.23 (m, 1H), 7.20 (d, J=9.0 Hz, 1H), 6.57 (s, 1H), 4.96-4.94 (m, 1H), 4.48-4.43 (m, 3H), 4.39-4.37 (m, 3H), 4.25-4.19 (m, 5H), 3.85 (d, J=11.5 Hz, 1H), 3.59 (s, 3H), 2.66-2.54 (m, 4H), 2.40-2.36 (m, 3H), 2.17 (d, J=10.5 Hz, 2H), 1.94-1.65 (m, 8H).

Example 153a

2-{4,4-Dimethyl-9-oxo-1,10-diazatricyclo[6.4.0.0$^{2,6}$]dodeca-2(6),7-dien-10-yl}-4-[1-methyl-5-({5-[(2R)-2-methyl-4-(oxetan-3-yl)piperazin-1-yl]pyridin-2-yl}amino)-6-oxo-1,6-dihydropyridin-3-yl]pyridine-3-carbaldehyde 153a

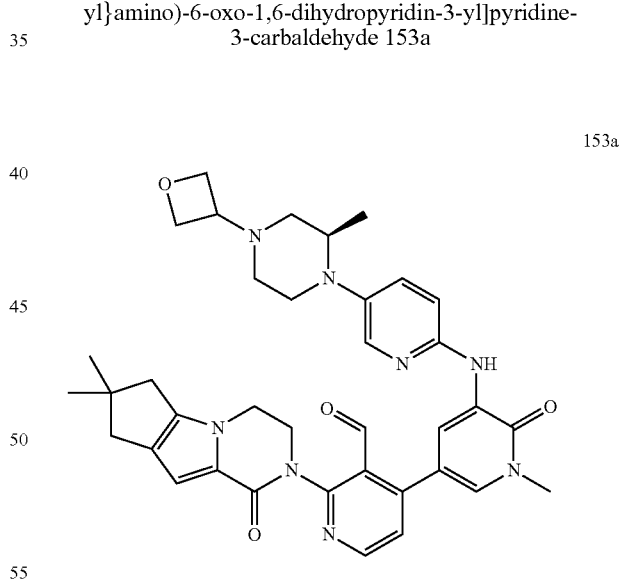

153a

A 50-mL round-bottomed flask equipped with a reflux condenser was charged with 4-chloro-2-{4,4-dimethyl-9-oxo-1,10-diazatricyclo[6.4.0.0$^{2,6}$]dodeca-2(6),7-dien-10-yl}pyri-dine-3-carbaldehyde 108a (105 mg, 0.30 mmol), 1-methyl-3-({5-[(2R)-2-methyl-4-(oxetan-3-yl)piperazin-1-yl]pyridin-2-yl}amino)-5-(tetra-methyl-1,3,2-dioxaborolan-2-yl)-1,2-dihydropyridin-2-one 151g (216 mg, 0.45 mmol), PdCl$_2$(dppf) (25 mg, 0.030 mmol), K$_3$PO$_4$ (126 mg, 0.60 mmol), sodium acetate (49 mg, 0.60 mmol), acetonitrile (15 mL), and water (1.5 mL). After three cycles of vacuum/argon flush, the mixture was heated at 80° C. for 2 h. It was then filtered and the filtrate was evaporated under reduced pressure. The residue was purified by silica-gel column chromatography eluting with 1:20 methanol/dichloromethane to afford 153a as a red solid (82 mg, 41%). MS-ESI: [M+H]+ 663

Example 153

2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one 153

A mixture of 153a (82 mg, 0.12 mmol), NaBH$_4$ (22 mg, 0.60), and methanol (10 mL) was stirred at 25° C. for 1 h. It was then quenched with water (5 mL) and concentrated under reduced pressure. The residue was extracted with dichloromethane (2×10 mL). The combined dichloromethane extract was concentrated under reduced pressure and the residue was purified with reverse-phase prep-HPLC to afford 153 (22 mg, 28%). MS-ESI: [M+H]+665. $^1$H NMR (500 MHz, CDCl$_3$) δ 8.65 (d, J=2.0 Hz, 1H), 8.48 (d, J=5.0 Hz, 1H), 7.96 (s, 1H), 7.84 (s, 1H), 7.83 (s, 1H), 7.36 (d, J=5.0 Hz, 1H), 7.32-7.26 (m, 1H), 6.84-6.80 (m, 2H), 5.30 (s, 1H), 4.71-4.32 (m, 7H), 4.15 (d, J=5.0 Hz, 2H), 3.85 (t, J=8.0 Hz, 1H), 3.71 (s, 3H), 3.57-3.43 (m, 2H), 3.08-3.06 (m, 2H), 2.57-2.48 (m, 7H), 2.22-2.20 (m, 1H), 1.27 (s, 6H), 0.98 (d, J=6.5 Hz, 3H).

Example 154a

4-[1-Methyl-5-({5-[(2R)-2-methyl-4-(oxetan-3-yl)piperazin-1-yl]pyridin-2-yl}amino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine-3-carbaldehyde 154a

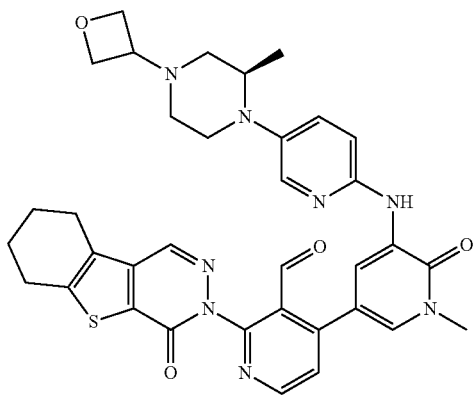

154a

A 100-mL round-bottomed flask equipped with a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (84 mg, 0.24 mmol), (R)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 151g (173 mg, 0.36 mmol), PdCl$_2$(dppf) (20 mg, 0.024 mmol), K$_3$PO$_4$ (100 mg, 0.48 mmol), sodium acetate (40 mg, 0.48 mmol), acetonitrile (20 mL), and water (2 mL). After three cycles of vacuum/argon flush, the mixture was heated at 100° C. for 3 h. It was then filtered and the filtrate was evaporated under reduced pressure. The residue was purified by silica-gel column chromatography eluting with 1:20 methanol/dichloromethane to afford 154a as a red solid (112 mg, 70%). MS-ESI: [M+H]+ 665

Example 154

3-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-3H-benzo[4,5]thieno[2,3-d]pyridazin-4-one 154

A mixture of 154a (150 mg, 0.23 mmol), NaBH$_4$ (35 mg, 0.92), and methanol (10 mL) was stirred at room temperature for 1 h. The mixture was then quenched with water (8 mL) and concentrated under reduced pressure. The residue was extracted with dichloromethane (2×10 mL). The combined dichloromethane extract was concentrated under reduced pressure and the residue was purified with reverse-phase prep-HPLC to afford 154 (29 mg, 19%). MS-ESI: [M+H]+ 667. $^1$H NMR (500 MHz, DMSO-d$_6$) δ 8.64 (d, J=2.5 Hz, 1H), 8.56 (d, J=5.0 Hz, 1H), 8.49-8.47 (m, 2H), 7.85 (d, J=3.0 Hz, 1H), 7.53 (d, J=5.0 Hz, 1H), 7.48 (d, J=2.5 Hz, 1H), 7.38-7.36 (m, 1H), 7.24 (d, J=8.5 Hz, 1H), 4.85 (t, J=9.5 Hz, 1H), 4.57-4.54 (m, 2H), 4.43-4.36 (m, 4H), 3.69-3.68 (m, 1H), 3.60 (s, 3H), 3.40-3.36 (m, 1H), 3.11-3.07 (m, 1H), 2.97-2.86 (m, 6H), 2.33-2.31 (m, 2H), 2.16 (t, J=8.5 Hz, 1H), 1.89-1.86 (m, 4H), 0.92 (d, J=6.5 Hz, 3H).

Example 155a 3-(5-((2S,5R)-2,5-Dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 155a A 100-mL single-neck round-bottomed flask equipped with a magnetic stirrer and a reflux condenser was charged with 5-bromo-3-(5-((2S,5R)-2,5-dimethyl-4-(oxetan-3-yl)piperazin-1-yl)pyridin-2-ylamino)-1-methylpyridin-2(1H)-one 122e (3.0 g, 6.70 mmol), Pin$_2$B$_2$ (8442 mg, 33.5 mmol), Pd$_2$(dba)$_3$ (311 mg, 0.34 mmol), X-phos (319 mg, 0.67 mmol), potassium acetate (1970 mg, 20.1 mmol), and dioxane (50 mL). After three cycles of vacuum/argon flush, the mixture was heated at 60° C. for 16 h. It was then cooled to room temperature and filtered. The filtrate was concentrated under reduced pressure. The resulting residue was washed with 8:1 petroleum ether/ethyl acetate (80 mL) to afford 155a as a yellow solid (3 g, 90%). MS: [M+H]+ 496.4.

Example 155b 4-(5-(5-(2,5-Dimethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrido[3,4-b]indolizin-2(1H)-yl)nicotinaldehyde 155b

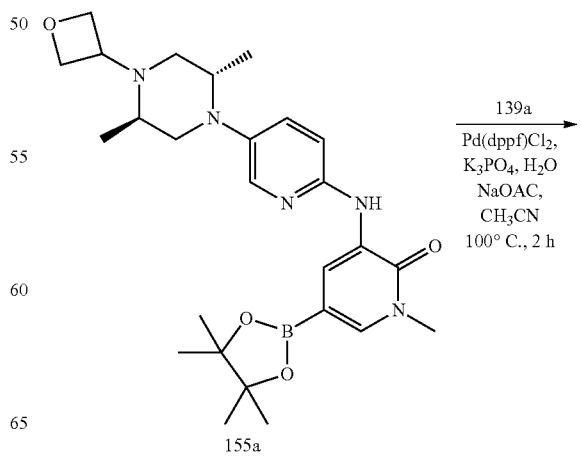

155a

-continued

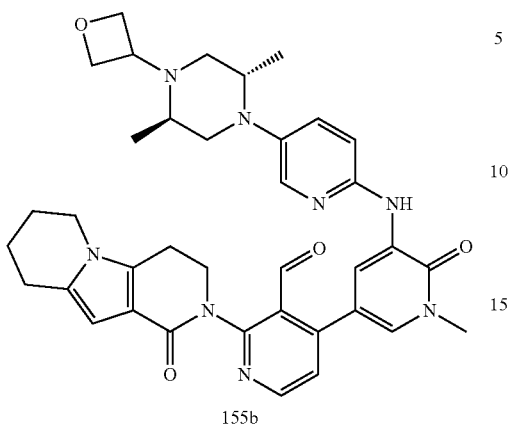

155b

A 50-mL single-neck round-bottomed flask equipped with a magnetic stirrer and a reflux condenser was charged with 4-chloro-2-(1-oxo-3,4,6,7,8,9-hexahydropyrido[3,4-b]indolizin-2(1H)-yl)nicotinaldehyde 139a (133 mg, 0.40 mmol), 155a (198 mg, 0.40 mmol), Pd(dppf)Cl$_2$ (17 mg, 0.020 mmol), K$_3$PO$_4$ (254 mg, 1.2 mmol), sodium acetate (98 mg, 1.2 mmol), water (5 drops), and acetonitrile (10 mL). After three cycles of vacuum/argon flush, the mixture was heated at reflux for 3 h. It was then cooled to room temperature and filtered. The filtrate was concentrated under reduced pressure and the resulting residue was purified by silica-gel column chromatography eluting with 30:1 dichloromethane/methanol to afford 155b as white solid (80 mg, 30%). MS-ESI: [M+H]$^+$ 663.3.

Example 155

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-2,3,5,6,7,8-hexahydro-4H-2,4b-diaza-fluoren-1-one 155

To a solution of 155b (80 mg, 0.12 mmol) at 0° C. in methanol (5 mL) was added sodium borohydride (12 mg, 0.36 mmol). The reaction mixture was stirred for 30 minutes. It was then quenched with water (1 mL) and concentrated under reduced pressure. The residue was purified by reverse-phase prep-HPLC to afford 155 (32 mg, 40%). MS-ESI: [M+H]$^+$ 665.3. $^1$H NMR (500 MHz, CDCl$_3$) δ 8.68 (d, J=2.0 Hz, 1H), 8.50 (d, J=5.0 Hz, 1H), 8.04 (d, J=2.5 Hz, 1H), 7.88 (s, 1H), 7.86 (d, J=2.5 Hz, 1H), 7.37-7.33 (m, 2H), 6.82 (d, J=9.0 Hz, 1H), 6.32 (s, 1H), 5.02 (d, J=13.0 Hz, 1H), 4.78-4.71 (m, 2H), 4.67-4.61 (m, 3H), 4.44-4.39 (m, 1H), 4.31-4.29 (m, 1H), 3.96-3.91 (m, 1H), 3.86-3.80 (m, 2H), 3.78-3.75 (m, 1H), 3.72 (s, 3H), 3.21-3.19 (m, 1H), 3.01-2.93 (m, 3H), 2.85-2.83 (m, 2H), 2.72 (d, J=10.0 Hz, 2H), 2.49-2.47 (m, 1H), 2.05-2.03 (m, 2H), 1.98-1.97

Example 156a 4-(5-(5-(((2S,5R)-2,5-Dimethyl-4-(oxetan-3-yl)piperazin-1-yl)pyridin-2-ylamino)-1-methyl-6-oxo-1,6-dihydropyridin-3-yl)-2-(10-fluoro-1-oxo-3,4,6,7,8,9-hexahydropyrazino[1,2-a]indol-2(1H)-yl)nicotinaldehyde 156a

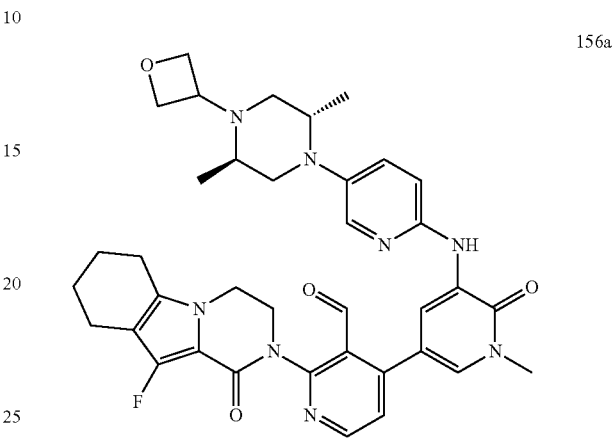

156a

A 50-mL single-neck round-bottomed flask equipped with a magnetic stirrer and a reflux condenser was charged with 3-(5-(((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 155a (171 mg, 0.35 mmol), 4-chloro-2-(10-fluoro-1-oxo-3,4,6,7,8,9-hexahydropyrazino[1,2-a]indol-2(1H)-yl)nicotinaldehyde 134c (120 mg, 0.35 mmol), K$_3$PO$_4$ (146 mg, 0.69 mmol), PdCl$_2$(dppf) (28 mg, 0.035 mmol), sodium acetate (56 mg, 0.69 mmol), water (5 drops) and acetonitrile (20 mL). After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 40/1 dichloromethane/methanol to afford 156a as a yellow solid (60 mg, 25%). MS-ESI: [M+H]$^+$ 681.3

Example 156

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-10-fluoro-3,4,6,7,8,9-hexahydro-2H-pyrazino[1,2-a]indol-1-one 156

A 50-mL round-bottomed flask equipped with a magnetic stirrer was charged with 156a (60 mg, 0.088 mmol), NaBH$_4$ (17 mg, 0.44 mmol), and methanol (10 mL). The mixture was stirred at room temperature for 1 h. It was then quenched with water and concentrated under reduced pressure. The residue was purified by reverse-phase prep-HPLC to afford 156 (15 mg, 25%). MS-ESI: [M+H]$^+$ 683.5. $^1$H NMR (500 MHz, CDCl$_3$) δ 8.67 (d, J=2.5 Hz, 1H), 8.48 (d, J=5.0 Hz, 1H), 8.02 (d, J=2.5 Hz, 1H), 7.87 (s, 1H), 7.84 (d, J=2.0 Hz, 1H), 7.37-7.35 (m, 2H), 6.81 (d, J=9.0 Hz, 1H), 4.99-4.59 (m, 6H), 4.45-4.32 (m, 2H), 4.12-4.03 (m, 2H), 3.85-3.73 (m, 2H), 3.71 (s, 3H), 3.19-3.16 (m, 1H), 2.91-2.89 (m, 1H), 2.75-2.69 (m, 2H), 2.57-2.47 (m, 5H), 1.97-1.76 (m, 5H), 0.89-0.87 (m, overlap, 6H).

Example 157

2-{5'-[5-((2S,5R)-2,5-Dimethyl-4-oxetan-3-yl-piperazin-1-yl)-pyridin-2-ylamino]-4-hydroxymethyl-1'-methyl-6'-oxo-1',6'-dihydro-[3,3]bipyridinyl-5-yl}-3,4,6,7,8,9-hexahydro-2H-pyrazino[1,2-a]indol-1-one 157

A 25-mL single-neck round-bottomed flask equipped with a magnetic stirrer and a reflux condenser was charged with 3-bromo-5-(1-oxo-3,4,6,7,8,9-hexahydropyrazino[1,2a]indol-2(1H)-yl)isonicotinaldehyde 101f (200 mg, 0.54 mmol), 3-(5-((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 155a (267 mg, 0.54 mmol), Pd(dppf)Cl$_2$ (44 mg, 0.054 mmol), K$_3$PO$_4$ (229 mg, 1.08 mmol), sodium acetate (89 mg, 1.08 mmol), water (0.2 mL) and acetonitrile (10 mL). After three cycles of vacuum/argon flush, the mixture was heated at reflux for 2 h. It was then cooled to room temperature and filtered. The filtrate was concentrated under reduced pressure and the residue was purified by reverse-phase prep-HPLC to afford 157 (35.5 mg, 11%) as a yellow solid. MS-ESI: [M+H]$^+$ 665.4. $^1$H NMR (500 MHz, CDCl$_3$) δ 8.65-8.63 (m, 2H), 8.50 (s, 1H), 7.80 (s, 1H), 7.87 (s, 1H), 7.48-7.47 (m, 1H), 7.36 (d, J=7.5 Hz, 1H), 6.88 (s, 1H), 6.81 (d, J=9.0 Hz, 1H), 4.75-4.54 (m, overlap, 6H), 4.37-4.13 (m, overlap, 4H), 4.00-3.95 (m, 1H), 3.74-3.73 (m, 1H), 3.72 (s, 3H), 3.19-3.15 (m, 1H), 2.91-2.90 (m, 1H), 2.74-2.44 (m, overlap, 7H), 1.92-1.88 (m, 2H), 1.81-1.79 (m, 2H), 0.90-0.89 (m, 6H).

Example 158a

4-[5-({5-[(2S,5R)-2,5-Dimethyl-4-(oxetan-3-yl)piperazin-1-yl]pyridin-2-yl}amino)-1-methyl-6-oxo-1,6-dihydropyridin-3-yl]-2-{4,4-dimethyl-9-oxo-1,10-diazatri-cyclo[6.4.0.0$^{2,6}$]dodeca-2(6),7-dien-10-yl}pyridine-3-carbaldehyde 158a

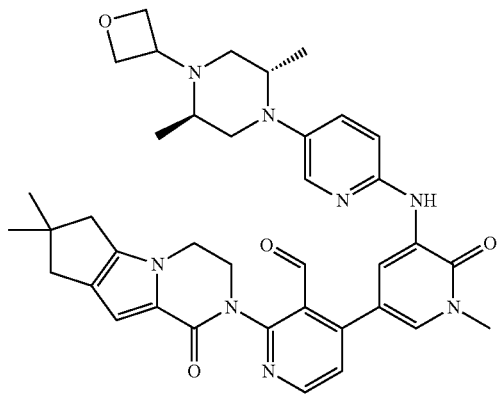

A 100-mL single-neck round-bottomed flask equipped with a reflux condenser was charged with (4-chloro-2-{4,4-dimethyl-9-oxo-1,10-diazatricyclo[6.4.0.0$^{2,6}$]dodeca-2(6),7-dien-10-yl}pyridine-3-carbaldehyde) 108a (280 mg, 0.80 mmol), 3-(5-((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 155a (480 mg, 0.96 mmol), Pd(dppf)Cl$_2$ (33 mg, 0.040 mmol), K$_3$PO$_4$ (339 mg, 1.6 mmol), sodium acetate.trihydrate (218 mg, 1.6 mmol), and acetonitrile (100 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 25:1 of dichloromethane/methanol to afford 158a (300 mg, 54%) as a yellow brown solid. MS-ESI: [M+H]$^+$ 677.3.

Example 158

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one 158

A mixture of 158a (200 mg, 0.30 mmol) and NaBH$_4$ (36 mg, 0.90 mmol) in methanol (30 mL) was stirred at 30° C. for 1 h. The mixture was quenched with water (5 mL) and extracted with ethyl acetate (3×10 mL). The combined ethyl acetate extract was concentrated under reduced pressure and the residue was purified by reverse-phase prep-HPLC to afford 158 (110 mg, 55%) as a white solid. MS-ESI: [M+H]$^+$ 679.4. $^1$H NMR (500 MHz, CDCl$_3$) δ 8.68 (d, J=2.0 Hz, 1H), 8.50 (d, J=5.0 Hz, 1H), 8.03 (d, J=2.5 Hz, 1H), 7.88 (s, 1H), 7.87 (d, J=2.0 Hz, 1H), 7.37-7.36 (m, 2H), 6.85 (s, 1H), 6.81 (d, J=3.5 Hz, 1H), 5.07 (t, J=7.0 Hz, 1H), 4.77-4.71 (m, 2H), 4.67-4.61 (m, 3H), 4.53-4.51 (m, 1H), 4.34-4.32 (m, 1H), 4.16 (d, J=5.5 Hz, 2H), 3.88-3.86 (m, 1H), 3.76 (t, J=7.5 Hz, 1H), 3.72 (s, 3H), 3.20-3.17 (m, 1H), 2.92 (dd, J=3.0, 11.5 Hz, 1H), 2.76-2.70 (m, 2H), 2.58 (d, J=6.0 Hz, 2H), 2.52 (s, 2H), 2.49-2.46 (m, 1H), 1.97-1.93 (m, 1H), 1.28 (s, 6H), 0.92-0.89 (m, 6H).

Example 159a

4-[5-({5-[2,5-Dimethyl-4-(oxetan-3-yl)piperazin-1-yl]pyridin-2-yl}amino)-1-methyl-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine-3-carbaldehyde 159a

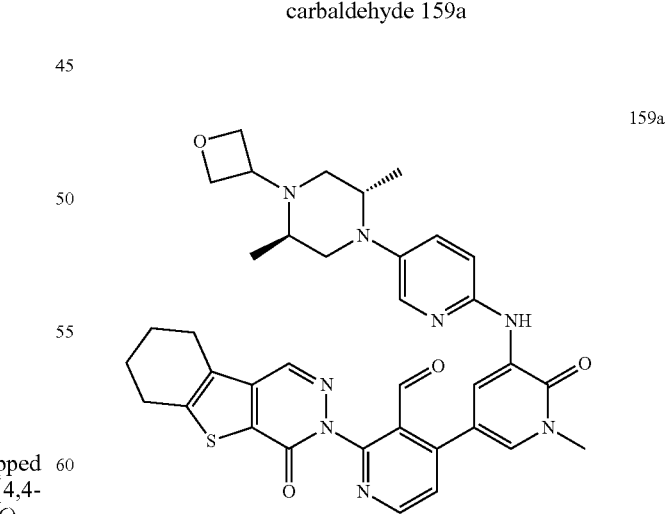

A 100-mL round-bottomed flask equipped with a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (200 mg, 0.58 mmol), 3-({5-[(2S,5R)-2,5-dimethyl-4-(oxetan-3-yl)piperazin-1-yl]pyridin-2-yl}amino)-1-methyl-5-(4,4,5,5-tetramethyl-1,3,2-dioxaborolan-2-yl)-1,2-dihydropyridin-2-one 155a (1.0 g, 2.0 mmol), PdCl$_2$(dppf) (47 mg, 0.060 mmol), K$_3$PO$_4$ (280 mg, 1.2 mmol), sodium acetate (95 mg, 1.2 mmol), acetonitrile (15 mL), and water (1.5 mL). After three cycles of vacuum/argon flush, the mixture was heated at 100° C. for 3 h. It was then filtered and the filtrate was evaporated under reduced pressure. The residue was purified with silica-gel column chromatography eluting with 1:20 methanol/dichloromethane to afford 159a as a red solid (150 mg, 38%). MS-ESI: [M+H]$^+$ 679

Example 159

3-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one 159

A mixture of 159a (130 mg, 0.19 mmol), NaBH$_4$ (22 mg, 0.60), and methanol (10 mL) was stirred at 25° C. for 1 h. The mixture was then quenched with water (8 mL) and concentrated under reduced pressure. The residue was extracted with dichloromethane (2×10 mL). The combined dichloromethane extract was concentrated under reduced pressure and the residue was purified with reverse-phase prep-HPLC to afford 159 (28 mg, 22%). MS-ESI: [M+H]$^+$ 681. $^1$H NMR (500 MHz, CDCl$_3$) δ 8.71 (d, J=2.5 Hz, 1H), 8.65 (d, J=5.0 Hz, 1H), 8.30 (s, 1H), 8.04 (s, 1H), 7.87 (s, 1H), 7.70 (d, J=2.0 Hz, 1H), 7.55 (d, J=5.0 Hz, 1H), 7.37 (d, J=9.0 Hz, 1H), 6.81 (d, J=9.0 Hz, 1H), 4.67-4.61 (m, 2H), 4.71-4.64 (m, 2H), 4.44-4.42 (m, 2H), 4.34-4.33 (m, 1H), 3.83-3.76 (m, 1H), 3.72 (s, 3H), 3.20-3.16 (m, 1H), 2.99-2.84 (m, 6H), 2.79-2.71 (m, 2H), 2.50-2.48 (m, 1H), 2.02-1.98 (m, 4H), 0.91 (d, J=6.0 Hz, 6H).

Example 160a 4-(5-(5-((2S,5R)-2,5-Dimethyl-4-(oxetan-3-yl)piperazin-1-yl)pyridin-2-ylamino)-1-methyl-6-oxo-1,6-dihydropyridin-3-yl)-2-(1-oxo-6,7,8,9-tetrahydropyrazino[1,2-a]indol-2(1H)-yl)nicotinaldehyde 160a

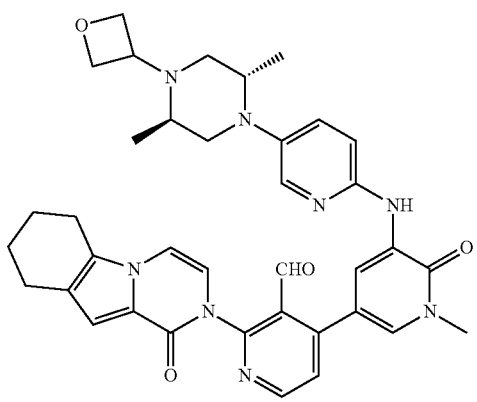

160a

A 50-mL single-neck round-bottomed flask equipped with a magnetic stirrer and a reflux condenser was charged with 4-chloro-2-(1-oxo-6,7,8,9-tetrahydropyrazino[1,2-a]indol-2(1H)-yl)nicotinaldehyde 103b (150 mg, 1.0 eq., 0.46 mmol), 3-(5-((2S,5R)-2,5-dimethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 155a (228 mg, 0.46 mmol), K$_3$PO$_4$ (195 mg, 0.92 mmol), PdCl$_2$(dppf) (37 mg, 0.046 mmol), sodium acetate (75 mg, 0.92 mmol), water (8 drops), and acetonitrile (20 mL). After three cycles of vacuum/argon flush, the mixture was heated at 80° C. for 2 h. It was then cooled to room temperature and filtered. The filtrate was concentrated under reduced pressure and the resulting residue was purified by silica-gel column chromatography eluting with 40:1 dichloromethane/ethanol to afford 160a as yellow solid (80 mg, 26%). MS-ESI: [M+H]$^+$ 661.4.

Example 160

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one 160

A 50-mL single-neck round-bottomed flask equipped with a magnetic stirrer was charged with 160a (80 mg, 0.12 mmol), NaBH$_4$ (23 mg, 0.60 mmol), and methanol (10 mL). The mixture was stirred at room temperature for 1 h. It was quenched with water (1 mL) and filtered. The filtrate was concentrated under reduced pressure and the residue was purified by reverse-phase prep-HPLC to afford 160 (44 mg, 55%). MS-ESI: [M+H]$^+$ 663.3. $^1$H NMR (500 MHz, CDCl$_3$) δ 8.72-8.70 (m, 1H), 8.57 (d, J=5.0 Hz, 1H), 8.03 (d, J=2.5 Hz, 1H), 7.89-7.87 (m, 2H), 7.50 (d, J=5.0 Hz, 1H), 7.37-7.35 (m, 1H), 7.06 (s, 1H), 6.97 (d, J=6.0 Hz, 1H), 6.81 (d, J=9.0 Hz, 1H), 6.68 (d, J=6.0 Hz, 1H), 5.10-5.08 (m, 1H), 4.76-4.32 (m, 6H), 3.76-3.72 (m, 4H), 3.20-3.17 (m, 1H), 2.93-2.90 (m, 1H), 2.76-2.69 (m, 6H), 2.49-2.46 (m, 1H), 1.97-1.94 (m, 3H), 1.87-1.84 (m, 2H), 0.89 (t, J=6.5 Hz, 6H).

Example 161a (S)-tert-Butyl 3-Ethyl-4-(6-nitropyridin-3-yl)piperazine-1-carboxylate 161a

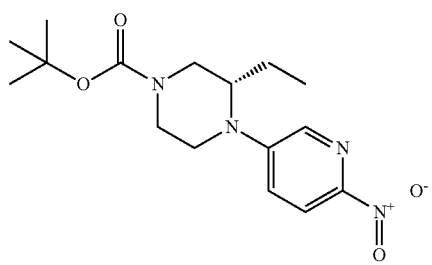

A 250-mL single-neck round-bottomed flask equipped with a magnetic stirrer and a reflux condenser was charged with 1,4-dioxane (50 mL), 5-bromo-2-nitropyridine (2.02 g, 10 mmol), (S)-tert-butyl 3-ethylpiperazine-1-carboxylate (2.14 g, 10.0 mmol), Pd$_2$(dba)$_3$ (458 mg, 0.50 mmol), Xant-Phos (576 mg, 1.0 mmol), and cesium carbonate (6.52 g, 20 mmol). After three cycles of vacuum/argon flush, the mixture was heated at 100° C. overnight. After this time the reaction was cooled to room temperature. It was then filtered and the filtrate was evaporated under reduced pressure. The residue was purified by silica-gel column chromatography eluting with 3:1 petroleum ether/ethyl acetate to afford 161a (700 mg, 22%) as a yellow solid. MS: [M+H]$^+$ 336

Example 161b (S)-tert-Butyl 4-(6-Aminopyridin-3-yl)-3-ethylpiperazine-1-carboxylate 161b A 100-mL single-neck round-bottomed flask was purged with nitrogen and charged with 161a (0.7 g, 2.08 mmol), 10% palladium on carbon (50% wet, 208 mg), and methanol (40 mL). The mixture was evacuated, charged with hydrogen gas, and stirred at room temperature for 6 h. The hydrogen was then evacuated and nitrogen was charged into the flask. The catalyst was removed by filtration through a pad of CELITE® and the filtrate was concentrated under reduced pressure to afford 161b (568 mg, 89%). MS: [M+H]$^+$ 306

Example 161c (S)-tert-Butyl 4-(6-(5-Bromo-1-methyl-2-oxo-1,2-dihydropyridin-3-ylamino)pyridin-3-yl)-3-ethylpiperazine-1-carboxylate 161c A 100-mL single-neck round-bottomed flask equipped with a magnetic stirrer and a reflux condenser was charged with 1,4-dioxane (50 mL), 161b (568 mg, 1.86 mmol), 3,5-dibromo-1-methylpyridin-2(1H)-one (498 mg, 1.86 mmol), Pd$_2$(dba)$_3$ (85 mg, 0.093 mmol), XantPhos (107 mg, 0.186 mmol), and cesium carbonate (1.198 g, 3.72 mmol). After three cycles of vacuum/argon flush, the mixture was heated at 100° C. for 6 h. It was then filtered and the filtrate was evaporated under reduced pressure. The residue was purified by silica-gel column chromatography eluting with 100:1 dichloromethane/methanol to afford 161c (502 mg, 55%) as a yellow solid. MS: [M+H]$^+$ 492.

Example 161d (S)-5-Bromo-3-(5-(2-ethylpiperazin-1-yl)pyridin-2-ylamino)-1-methylpyridin-2(1H)-one 161d A mixture of 161c (502 mg, 1.02 mmol), dichloromethane (2 mL), and 4.0 M HCl/dioxane (4 mL) was stirred at room temperature for 5 h. It was then concentrated under reduced pressure to afford crude 161d as a yellow solid (263 mg, 66%), which was used in the next step without further purification. MS: [M+H]$^+$ 392.

Example 161e (S)-5-Bromo-3-(5-(2-ethyl-4-(oxetan-3-yl)piperazin-1-yl)pyridin-2-ylamino)-1-methylpyridin-2(1H)-one 161e A mixture of 161d (263 mg, 0.67 mmol), oxetan-3-one (96 mg, 1.34 mmol), NaBH$_3$CN 104 mg, 1.68 mmol), and zinc chloride (227 mg, 1.68 mmol) in methanol (10 mL) was stirred at 50° C. for 5 hours. Water (10 mL) was then added to the reaction. The resulting mixture was concentrated under reduced pressure. The residue was extracted with dichloromethane three times. The combined organic layer was concentrated under reduced pressure and the residue was purified by silica-gel column chromatography eluting with 50:1 dichloromethane/methanol to afford 161e (203 mg, 68%). MS: [M+H]$^+$ 448.

Example 161f (S)-3-(5-(2-Ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 161f A 100-mL single-neck round-bottomed flask equipped with a magnetic stirrer and a reflux condenser was charged with 161e (3219 mg, 7.20 mmol), Pin$_2$B$_2$ (9072 mg, 36.0 mmol), Pd$_2$(dba)$_3$ (329 mg, 0.36 mmol), X-phos (302 mg, 0.72 mmol), potassium acetate (2117 mg, 21.6 mmol), and dioxane (50 mL). After three cycles of vacuum/argon flush, the mixture was heated at 60° C. for 16 h. It was then cooled to room temperature and filtered. The filtrate was concentrated under reduced pressure and the resulting residue was washed with 8:1 petroleum ether/ethyl acetate (80 mL) to afford 161f as yellow solid (3.0 g, 84%). MS: [M+H]$^+$ 496.4.

Example 161g 4-(5-(5-(2-Ethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrido[3,4-b]indolizin-2(1H)-yl)nicotinaldehyde 161g

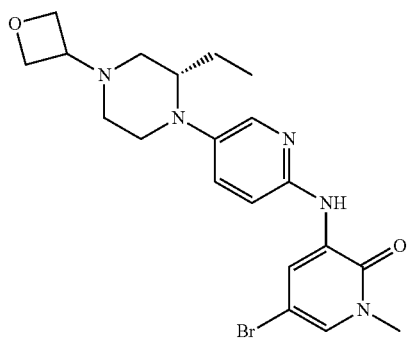 [SMILES: CC[C@H]1CN(C2COC2)CCN1c1ccc(Nc2cc(Br)cn(C)c2=O)nc1]

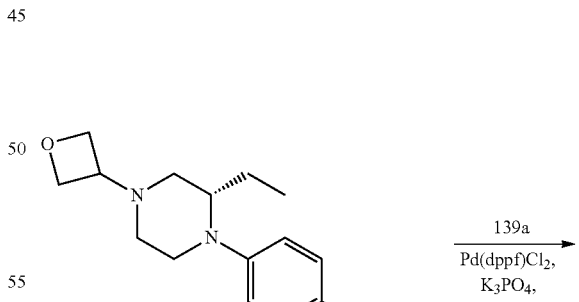

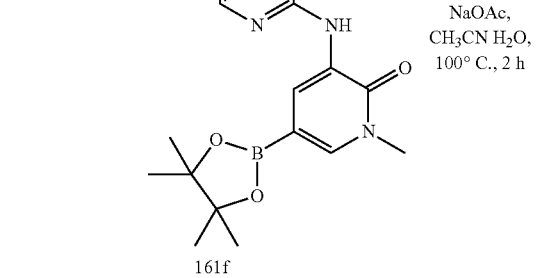

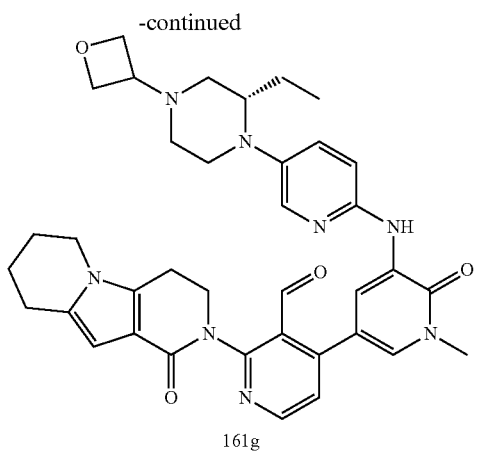

161g

A 50-mL round-bottomed flask equipped with a reflux condenser was charged with 161f (200 mg, 0.40 mmol), 4-chloro-2-(1-oxo-3,4,6,7,8,9-hexahydropyrido[3,4-b]indolizin-2(1H)-yl)nicotinaldehyde 139a (132 mg, 0.40 mmol), K₃PO₄ 3 water (213 mg, 0.80 mmol), sodium acetate (66 mg, 0.80 mmol), 1,1'-bis(diphenylphosphino)ferrocenedichloropalladium(II) (16 mg, 0.020 mmol), and acetonitrile (20 mL). After three cycles of vacuum/N₂ flush, the mixture was heated at 100° C. under N₂ protection for 2 h. Analysis of the reaction mixture by LCMS showed complete conversion to the desired product. The reaction mixture was cooled to room temperature and filtered. The filtrate was concentrated under reduced pressure. The residue was diluted with dichloromethane (50 mL) and water (50 mL). The aqueous layer was separated and extracted with dichloromethane (3×20 mL). The combined organic layer was dried over Na₂SO₄, filtered, and concentrated under reduced pressure. The dark residue was purified by silica-gel column chromatography eluting with dichloromethane/methanol (80/1 to 30/1) to afford 161g (150 mg, 57%) as yellow solid. MS-ESI: [M+H]+ 663

Example 161

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-2,3,5,6,7,8-hexahydro-4H-2,4-b-diaza-fluoren-1-one 161

To a solution of 161g (120 mg, 0.18 mmol) in methanol (20 mL) was added NaBH₄ (21 mg, 0.54 mmol) at room temperature. After the reaction was stirred for 1 h, LCMS indicated the reaction was complete. Then the mixture was poured into water (20 mL) and concentrated under reduced pressure. The residue was extracted with dichloromethane (3×40 mL). The combined organic layer was washed with brine (20 mL), dried over Na₂SO₄, filtered, and concentrated. The residue solid was purified by prep-HPLC to afford 161 (97 mg, 81%) as white solid. MS-ESI: [M+H]+ 665. ¹H NMR (500 MHz, CDCl₃) δ 8.63 (s, 1H), 8.50 (d, J=5.0 Hz, 1H), 7.93 (s, 1H), 7.84-7.82 (m, 2H), 7.35 (d, J=4.5 Hz, 1H), 7.28 (s, 1H), 6.82 (d, J=9.0 Hz, 1H), 6.32 (s, 1H), 5.01-4.99 (m, 1H), 4.73-4.64 (m, 5H), 4.45-4.40 (m, 1H), 4.30 (t, J=12.0 Hz, 1H), 3.94-3.91 (m, 1H), 3.85-3.83 (m, 2H), 3.72 (s, 3H), 3.55-3.53 (m, 1H), 3.34-3.32 (m, 1H), 3.14-3.12 (m, 2H), 3.04-2.92 (m, 2H), 2.84-2.82 (m, 2H), 2.59-2.57 (m, 1H), 2.46-2.44 (m, 2H), 2.38-2.36 (m, 1H), 2.06-2.01 (m, 2H), 1.90-1.86 (m, 2H), 1.68-1.66 (m, 1H), 1.43-1.39 (m, 1H), 0.82 (t, J=7.5 Hz, 3H).

Example 162a

5-Bromo-1-methyl-3-(pyrazin-2-ylamino)pyridin-2(1H)-one 162a

A 100-mL single-neck round-bottomed flask equipped with a magnetic stirrer and a reflux condenser was charged with pyrazin-2-amine (500 mg, 5.3 mmol), 3,5-dibromo-1-methylpyridin-2(1H)-one (1335 mg, 5.3 mmol), Pd₂(dba)₃ (229 mg, 0.25 mmol), XantPhos (289 mg, 0.50 mmol), cesium carbonate (3.26 g, 10 mmol) and 1,4-dioxane (50 mL). After three cycles of vacuum/argon flush, the mixture was stirred at 100° C. for 2 h. It was then filtered and the filtrate was evaporated in vacuo. The residue was purified by silica-gel column chromatography eluting with 50:1 dichloromethane/methanol to afford 162a (420 mg, 30%) as a yellow solid. MS-ESI: [M+H]+ 281.0.

Example 162b (4-(1-Methyl-6-oxo-5-(pyrazin-2-ylamino)-1,6-dihydropyridin-3-yl)-2-(1-oxo-3,4,6,7,8,9-hexahydropyrazino[1,2-a]indol-2(1H)-yl)pyridin-3-yl)methyl acetate 162b

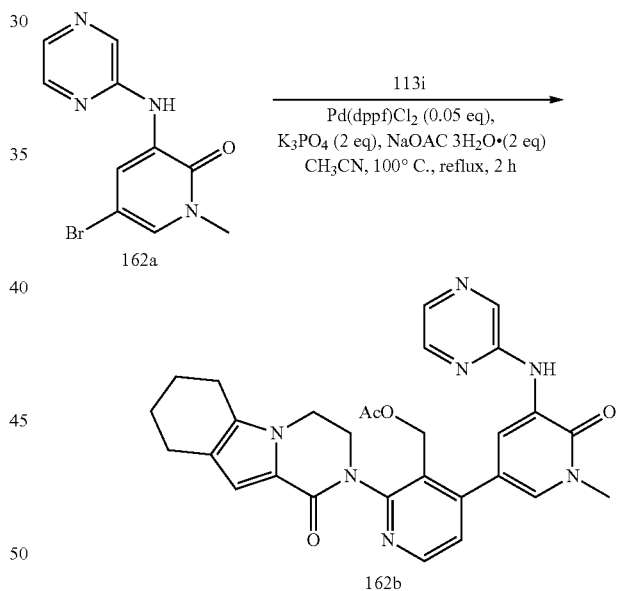

A 100-mL single-neck round-bottomed flask equipped with a reflux condenser was charged with 162a (170 mg, 0.61 mmol), 3-(acetoxymethyl)-2-(1-oxo-3,4,6,7,8,9-hexahydropyrazino[1,2-a]indol-2(1H)-yl)pyridin-4-ylboronic acid 113i (280 mg, 0.72 mmol), Pd(dppf)Cl₂ (30 mg, 0.037 mmol), K₃PO₄·trihydrate (270 mg, 1.2 mmol), sodium acetate (180 mg, 1.2 mmol), acetonitrile (20 mL), and water (0.5 mL). The system was evacuated and refilled with N₂. The reaction mixture was stirred at 100° C. for 2 h. It was then cooled to room temperature and filtered. The filtrate was concentrated under reduced pressure and the resulting residue was purified by silica-gel column chromatography eluting with 25:1 of dichloromethane/methanol to afford 162b (130 mg, 40%) as a yellow brown solid. MS-ESI: [M+H]+ 540.3

Example 162

2-[3'-Hydroxymethyl-1-methyl-6-oxo-5-(pyrazin-2-ylamino)-1,6-dihydro-[3,4']bipyridinyl-2'-yl]-3,4,6,7,8,9-hexahydro-2H-pyrazino[1,2-a]indol-1-one 162

A mixture of 162b (110 mg, 0.20 mmol) and lithium hydroxide (84 mg, 2.0 mmol) in i-propanol/THF (1:1, 4 mL) and water (1 mL) was stirred at 30° C. for 1 h. The mixture was evaporated in vacuo and the residue was diluted with water and ethyl acetate. The water phase was separated and extracted with ethyl acetate (2×10 mL). The combined ethyl acetate extract was concentrated under reduced pressure and the residue was purified by reverse-phase prep-HPLC to afford 162 (85 mg, 85%) as pale yellow solid. MS-ESI: [M+H]$^+$ 498.3. $^1$H NMR (500 MHz, CHCl$_3$) δ 8.73 (d, J=2.5 Hz, 1H), 8.54 (d, J=5 Hz, 1H), 8.29 (s, 1H), 8.15-8.14 (m, 2H), 8.01 (d, J=2.5 Hz, 1H), 8.00 (d, J=2.0 Hz, 1H), 7.37 (d, J=5 Hz, 1H), 6.91 (s, 1H), 4.66-4.65 (m, 1H), 4.52-4.51 (m, 1H), 4.32-4.31 (m, 1H), 4.18-4.17 (m, 1H), 4.14-4.12 (m, 1H), 3.90-3.88 (m, 1H), 3.75 (s, 3H), 2.62-2.57 (m, 4H), 1.92-1.88 (m, 3H), 1.80-1.79 (m, 2H).

Example 163a

1-Methyl-5-(5-(oxetan-3-yl)-4,5,6,7-tetrahydropyrazolo[1,5-a]pyrazin-2-ylamino)-6-oxo-1,6-dihydropyridin-3-ylboronic acid 163a A 100-mL round bottomed flask equipped with a magnetic stirrer was charged with 5-bromo-1-methyl-3-(5-(oxetan-3-yl)-4,5,6,7-tetrahydropyrazolo[1,5-a]pyrazin-2-ylamino)pyridin-2(1H)-one 125i (1.0 g, 2.64 mmol), 4,4,4',4',5,5,5',5'-octamethyl-2,2'-bi(1,3,2-dioxaborolane) (2.0 g, 7.92 mmol), PdCl$_2$(dppf) (190 mg, 0.26 mmol), potassium acetate (776 mg, 7.92 mmol), and dioxane (40 mL). After bubbling argon into the mixture for 30 minutes, a reflux condenser was attached to the flask and mixture was stirred at 100° C. for 6 h under an argon atmosphere. The resulting mixture was filtered and the filtrate was evaporated under reduced pressure. The residue was purified by reverse-phase Combiflash eluting with 0.3% NH$_4$HCO$_3$ water/CH$_3$CN to afford 163a as a white solid (300 mg, 33%). MS: [M+H]$^+$ 346.

Example 163b

2-{4,4-Dimethyl-9-oxo-1,10-diazatricyclo[6.4.0.0$^{2,6}$]dodeca-2(6),7-dien-10-yl}-4-(1-methyl-5-{[5-(oxetan-3-yl)-4H,5H,6H,7H-pyrazolo[1,5-a]pyrazin-2-yl]amino}-6-oxo-1,6-dihydropyridin-3-yl)pyridine-3-carbaldehyde 163b

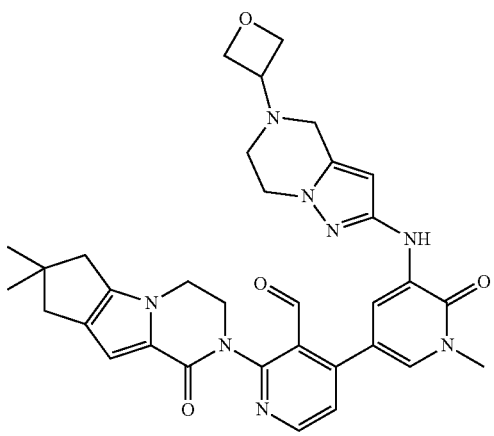

A 100-mL single-neck round-bottomed flask equipped with a reflux condenser was charged with (4-chloro-2-{4,4-dimethyl-9-oxo-1,10-diazatricyclo[6.4.0.0$^{2,6}$]dodeca-2(6),7-dien-10-yl}pyridine-3-carbaldehyde) 108a (280 mg, 0.81 mmol), 163a (440 mg, 0.96 mmol), Pd(dppf)Cl$_2$ (40 mg, 0.049 mmol), K$_3$PO$_4$ (360 mg, 1.6 mmol), sodium acetate trihydrate (240 mg, 1.6 mmol), water (6 drops), and acetonitrile (20 mL). The system was evacuated and refilled with N$_2$. The reaction mixture was stirred at 100° C. for 2 h. It was then cooled to room temperature and filtered. The filtrate was concentrated under reduced pressure and the resulting residue was purified by silica-gel column chromatography eluting with 25:1 dichloromethane/methanol to afford 163b (150 mg, 31%) as a yellow brown solid. MS-ESI: [M+H]$^+$ 609.3

Example 163

2-[3'-Hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 163

A mixture of 163b (80 mg, 0.12 mmol) and NaBH$_4$ (15 mg, 0.36 mmol) in methanol (5 mL) was stirred at 30° C. for 2 h. The mixture was quenched with water and concentrated under reduced pressure. The residue was extracted with ethyl acetate (3×10 mL). The combined ethyl acetate extract was concentrated under reduced pressure and the residue was purified by reverse-phase prep-HPLC to afford 163 (30 mg, 50%) as dark red solid. MS-ESI: [M+H]$^+$ 611.4. $^1$H NMR (500 MHz, CHCl$_3$) δ 8.48 (d, J=5.5 Hz, 1H), 7.96 (d, J=2.5 Hz, 1H), 7.70 (d, J=2, 1H), 7.43 (s, 1H), 7.34 (d, J=5 Hz, 1H), 6.8 (s, 1H), 5.70 (s, 1H), 5.03 (t, J=6, 1H), 4.77-4.73 (m, 3H), 4.68 (t, J=6.5 Hz, 2H), 4.51-4.50 (m, 1H), 4.34-4.33 (m, 1H), 4.23-4.16 (m, 2H), 4.09 (t, J=5.5 Hz, 2H), 3.86-3.85 (m, 1H), 3.79-3.74 (m, 1H), 3.71 (s, 3H), 3.56 (d, J=4, 2H), 2.83 (t, J=5.5 Hz, 2H), 2.58 (d, J=5.5 Hz, 2H), 2.52 (s, 2H), 1.28 (s, 6H).

Example 164a

2-{4,4-Dimethyl-9-oxo-1,10-diazatricyclo[6.4.0.0$^{2,6}$]dodeca-2(6),7-dien-10-yl}-4-[5-({5-[(2S)-2-ethyl-4-(oxetan-3-yl)piperazin-1-yl]pyridin-2-yl}amino)-1-methyl-6-oxo-1,6-dihydropyridin-3-yl]pyridine-3-carbaldehyde 164a

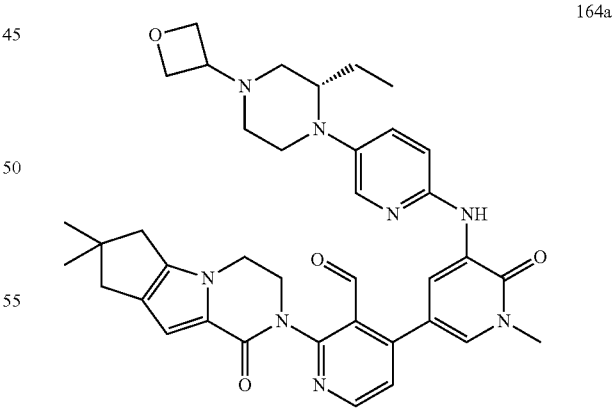

A 100-mL single-neck round-bottomed flask equipped with a reflux condenser was charged with (4-chloro-2-{4,4-dimethyl-9-oxo-1,10-diazatricyclo[6.4.0.0$^{2,6}$]dodeca-2(6),7-dien-10-yl}pyridine-3-carbaldehyde) 108a (280 mg, 0.8 mmol), (S)-3-(5-(2-ethyl-4-(oxetan-3-yl)piperazin-1-yl)pyridin-2-ylamino)-1-methyl-5-(4,4,5,5-tetra-methyl-1,3,2-dioxaborolan-2-yl)pyridin-2(1H)-one 161f (500 mg, 0.96 mmol), Pd(dppf)Cl$_2$ (33 mg, 0.040 mmol), K$_3$PO$_4$ (360 mg, 1.6 mmol), sodium acetate trihydrate (240 mg, 1.6 mmol), and acetonitrile (100 mL). The system was evacuated and refilled with $N_2$. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 164a (320 mg, 60%) as a yellow brown solid. MS-ESI: [M+H]$^+$ 677.3.

Example 164

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one 164

A mixture of 164a (200 mg, 0.30 mmol) and $NaBH_4$ (36 mg, 0.90 mmol) in methanol (30 mL) was stirred at 30° C. for 2 h. The mixture was quenched with water and concentrated under reduced pressure. The residue was extracted with ethyl acetate (3×10 mL). The combined ethyl acetate extract was concentrated under reduced pressure and the residue was purified by reverse-phase prep-HPLC to afford 164 (140 mg, 72%) as light green solid. MS-ESI: [M+H]$^+$ 679.3. $^1$H NMR (500 MHz, CDCl$_3$) δ 8.63 (d, J=2.5 Hz, 1H), 8.49 (d, J=5.0 Hz, 1H), 7.93 (d, J=2.5 Hz, 1H), 7.83 (s, 1H), 7.82 (s, 1H), 7.37 (d, J=5.0 Hz, 1H), 7.27 (s, 1H), 6.85 (s, 1H), 6.82 (d, J=9.0 Hz, 1H), 5.06 (s, 1H), 4.71-4.61 (m, 5H), 4.52-4.50 (m, 1H), 4.34-4.32 (m, 1H), 4.16 (d, J=4.5 Hz, 2H), 3.87-3.85 (m, 1H), 3.72 (s, 3H), 3.55-3.50 (m, 1H), 3.33-3.30 (m, 1H), 3.12 (t, J=5.0 Hz, 2H), 2.58-2.55 (m, 3H), 2.52 (s, 2H), 2.44 (d, J=3.5 Hz, 2H), 2.35 (t, J=5.5 Hz, 1H), 1.68-1.64 (m, 1H), 1.42-1.37 (m, 1H), 1.28 (s, 6H), 0.82 (t, J=7.5 Hz, 3H).

Example 165a (S)-4-(5-(5-(2-Ethyl-4-(oxetan-3-yl)piperazin-1-yl)pyridin-2-ylamino)-1-methyl-6-oxo-1,6-dihydropyridin-3-yl)-2-(1-oxo-6,7,8,9-tetrahydropyrazino[1,2-a]indol-2(1H)-yl)nicotinaldehyde 165a

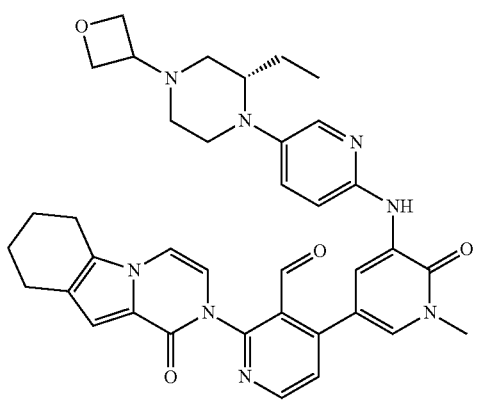

A 50-mL flask equipped with a reflux condenser was charged with 4-chloro-2-(1-oxo-6,7,8,9-tetrahydropyrazino[1,2-a]indol-2(1H)-yl)nicotinaldehyde 103b (164 mg, 0.50 mmol), (S)-3-(5-(2-ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 161f (347 mg, 0.70 mmol), potassium acetate (137 mg, 1.4 mmol), 1,1'-bis(diphenylphosphino)ferrocenedichloropalladium(II) (29 mg, 0.035 mmol), water (5 drops), and acetonitrile (20 mL). After three cycles of vacuum/argon flush, the mixture was heated at 100° C. under argon atmosphere for 3 h. The reaction mixture was cooled to room temperature and filtered. The filtrate was concentrated under reduced pressure. The residue was diluted with dichloromethane (50 mL) and water (50 mL). The aqueous layer was separated and extracted with dichloromethane (3×20 mL). The combined organic layer was dried over $Na_2SO_4$, filtered, and concentrated under reduced pressure. The dark residue was purified by silica-gel column chromatography eluting with dichloromethane/methanol (80/1 to 25/1) to afford 165a (151 mg, 46%) as yellow solid. MS-ESI: [M+H]$^+$ 661

Example 165

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one 165

To a solution of 165a (100 mg, 0.15 mmol) in methanol (10 mL) was added $NaBH_4$ (34 mg, 0.90 mmol) at room temperature. After the reaction was stirred for 1 h, LCMS indicated the reaction was complete. Then the mixture was quenched with water (8 mL) and concentrated under reduced pressure. The residue was extracted with dichloromethane (3×10 mL). The combined organic layer was washed with brine (30 mL), dried over $Na_2SO_4$, filtered, and concentrated under reduced pressure. The residue was purified by reverse-phase prep-HPLC to afford 165 (35 mg, 35%) as light yellow solid. MS-ESI: [M+H]$^+$ 663. $^1$H NMR (500 MHz, DMSO-d$_6$) δ 8.64 (s, 1H), 8.57 (d, J=5.0 Hz, 1H), 8.44 (s, 1H), 7.82 (d, J=2.0 Hz, 1H), 7.51-7.48 (m, 2H), 7.35 (dd, J=2.0 Hz, 9.0 Hz, 1H), 7.27-7.23 (m, 2H), 6.83-6.81 (m, 2H), 4.97 (bs, 1H), 4.59-4.55 (m, 2H), 4.49-4.32 (m, 4H), 3.61 (s, 3H), 3.51-3.47 (m, 1H), 3.42-3.37 (m, 1H), 3.17-3.16 (m, 1H), 3.01-2.98 (m, 1H), 2.76-2.74 (m, 2H), 2.63-2.61 (m, 3H), 2.55-2.54 (m, 1H), 2.19-2.16 (m, 1H), 2.12-2.07 (m, 1H), 1.90-1.85 (m, 2H), 1.77-1.66 (m, 3H), 1.27-1.25 (m, 1H), 0.79 (t, J=7.0 Hz, 3H).

Example 166a 2-(10-Fluoro-1-oxo-3,4,6,7,8,9-hexahydropyrazino[1,2-a]indol-2(1H)-yl)-4-(1-methyl-5-(5-(oxetan-3-yl)-4,5,6,7-tetrahydropyrazolo[1,5-a]pyrazin-2-ylamino)-6-oxo-1,6-dihydropyridin-3-yl)nicotinaldehyde 166a

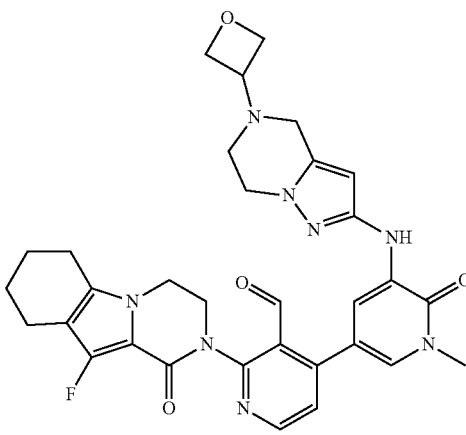

A 100-mL single-neck round-bottomed flask equipped with a magnetic stirrer and reflux condenser was charged with 1-methyl-3-(5-(oxetan-3-yl)-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 163a (354 mg, 0.83 mmol), 4-chloro-2-(10-fluoro-1-oxo-3,4,6,7,8,9-hexahydropyrazino[1,2-a]indol-2(1H)-yl)nicotinaldehyde 134c (289 mg, 0.83 mmol), PdCl₂(dppf) (68 mg, 0.08 mmol), K₃PO₄ (352 mg, 1.66 mmol), sodium acetate (136 mg, 1.66 mmol), acetonitrile (50 mL), and water (3 mL). The system was evacuated and refilled with N₂. The reaction mixture was heated at 100° C. for 2 h. It was then cooled to room temperature and filtered. The filtrate was concentrated under reduced pressure and the resulting residue was purified by silica-gel column chromatography eluting with 30:1 dichloromethane/methanol to afford 166a (305 mg, 60%) as a brown solid. MS-ESI: [M+H]⁺: 613.6.

Example 166

10-Fluoro-2-[3'-hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one 166

To a suspension of 166a (250 mg, 0.41 mmol) in methanol (20 mL) was added sodium borohydride (47 mg, 1.23 mmol) at 0° C. The mixture was stirred for 30 minutes. It was then quenched with water (2 mL) and concentrated under reduced pressure. The residue was purified by reverse-phase prep-HPLC to afford 166 (20 mg, 6.6%). MS-ESI: [M+H]⁺ 615.6. ¹H NMR (500 MHz, CDCl₃) δ 8.46 (d, J=5.0 Hz, 1H), 7.94 (d, J=3.0 Hz, 1H), 7.66 (d, J=2.0 Hz, 1H), 7.43 (s, 1H), 7.34 (d, J=5.0 Hz, 1H), 5.75 (s, 1H), 4.95 (t, J=6.5 Hz, 1H), 4.76-4.74 (m, 2H), 4.69-4.65-4.67 (m, 3H), 4.46-4.44 (m, 1H), 4.35-4.33 (m, 1H), 4.10-4.08 (m, 4H), 3.38-3.35 (m, 2H), 3.69 (s, 3H), 3.58-3.56 (m, 2H), 2.84-2.82 (m, 2H), 2.58-2.53 (m, 4H), 1.89-1.84 (m, 2H), 1.77-1.76 (m, 2H).

Example 167a

3-Chlorobicyclo[2.2.1]hept-2-ene-2-carbaldehyde 167a

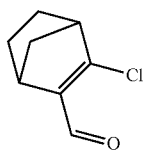

A 250-mL three-neck round-bottomed flask equipped with a magnetic stirrer and a reflux condenser was purged with nitrogen and charged with anhydrous 1,2-dichloroethane (24 mL) and anhydrous DMF (9.12 g, 125 mmol). The reaction mixture was cooled to 0° C. and phosphorus oxychloride (15.3 g, 100 mmol) was added over a period of 5 minutes while maintaining the reaction temperature between 0 and 10° C. The cooling bath was removed and the reaction was stirred at room temperature for 30 minutes. A solution of bicyclo[2.2.1]heptan-2-one (5.50 g, 50.0 mmol) in 1,2-dichloroethane (10 mL) was added and the resulting mixture was heated at 80° C. overnight. After this time, the reaction was poured into a solution of potassium monohydrogen phosphate (43.5 g, 250 mmol) in water (200 mL) and stirred for 15 minutes. The organic layer was separated and concentrated under reduced pressure. The residue was dissolved in methylene chloride (300 mL) and washed with water (2×50 mL). The methylene chloride layer was dried over sodium sulfate, filtered, and concentrated under reduced pressure. The residue was purified by silica-gel column chromatography eluting with 1:100 ethyl acetate/petroleum ether to afford 167a as a yellow oil (2.2 g, 28%). MS: [M+H]⁺ 157. ¹H NMR (500 MHz, CDCl₃) δ 9.80 (s, 1H), 3.42-3.41 (m, 1H), 3.08-3.07 (m, 1H), 1.95-1.77 (m, 2H), 1.68-1.66 (m, 1H), 1.41-1.17 (m, 3H).

Example 167b (E)-Ethyl 3-(3-Chlorobicyclo[2.2.1]hept-2-en-2-yl)acrylate 167b

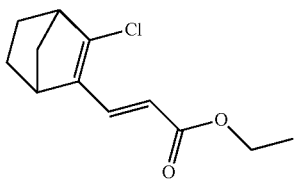

To a solution of 167a (9.0 g, 57.7 mmol) in methylene chloride (250 mL) was added ethyl 2-(triphenyl-λ⁵-phosphanylidene)acetate (20 g, 57.7 mmol). The mixture was stirred at room temperature overnight. It was then evaporated under reduced pressure. The residue was purified by silica-gel column chromatography eluting with 1:100 ethyl acetate/petroleum ether to afford 167b as a yellow oil (6.0 g, 46%). MS: [M+H]⁺ 227.

Example 167c

Ethyl 3-Azatricyclo[5.2.1.0²,⁶]deca-2(6),4-diene-4-carboxylate 167c

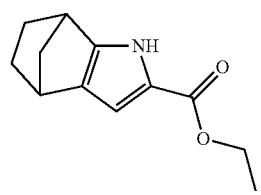

To a solution of 167b (5.0 g, 22 mmol) in DMSO (30 mL) was added NaN₃ (2.2 g, 33 mmol). The mixture was heated at 105° C. for 6 hours. Water (13 mL) was added to the reaction mixture after cooling down to room temperature and the resulting mixture was extracted with methylene chloride (3×50 mL). The combined organic phase was dried over Na₂SO₄ and evaporated under reduced pressure to dryness. The residue was purified by silica-gel column chromatography eluting with 20:1 methylene chloride/methanol to afford 167c as a brown solid (2.7 g, 60%). MS: [M+H]⁺ 206. ¹H NMR (500 MHz, CDCl₃) δ 11.51 (s, 1H), 6.45 (s, 1H), 4.16 (q, J=6.5 Hz, 2H), 3.26-3.24 (m, 2H), 1.82-1.79 (m, 2H), 1.74-1.72 (m, 2H), 1.24 (t, J=6.5 Hz, 3H), 0.91-0.89 (m, 2H).

Example 167d

Ethyl 3-(Cyanomethyl)-3-azatricyclo[5.2.1.0²,⁶]deca-2(6),4-diene-4-carboxylate 167d

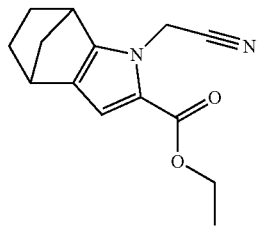 [SMILES: CCOC(=O)c1cc2c(n1CC#N)C1CCC2C1]

Into a solution of 167c (3.0 g, 14.6 mmol) in anhydrous DMF (30 mL) was added NaH (880 mg, 22 mmol). The mixture was stirred at room temperature for 30 minutes. 2-Bromoacetonitrile (3.5 g, 29.3 mmol) was added and the resulting mixture was heated at 65° C. for 1 hour. It was then stirred at room temperature overnight. After reaction water (30 mL) was added and the resulting mixture was extracted with ethyl acetate (200 mL×3). The combined organic phase was evaporated under reduced pressure to dryness. The residue was purified by silica-gel column chromatography eluting with 20:1 methylene chloride/methanol to afford 167d as a brown solid (2.6 g, 72%). MS: [M+H]⁺ 245.

Example 167e

Ethyl 3-(2-Aminoethyl)-3-azatricyclo[5.2.1.0²,⁶]deca-2(6),4-diene-4-carboxylate 167e

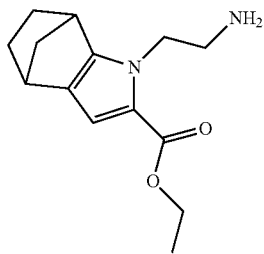 [SMILES: CCOC(=O)c1cc2c(n1CCN)C1CCC2C1]

A suspension of 167d (4.0 g, 16 mmol) and Raney Ni (400 mg) in methanol (60 mL) was hydrogenated in a Parr apparatus at 50 psi overnight. The mixture was filtered through a pad of CELITE® and the filtrate was concentrated under reduced pressure. The residue was purified by silica-gel column chromatography eluting with 20:1 methylene chloride/methanol to afford 167e as a yellow solid (2.0 g, 50%). MS: [M+H]⁺ 249.

Example 167f 3,6-Diazatetracyclo[9.2.1.0²,¹⁰.0³,⁸]tetradeca-2(10),8-dien-7-one 167f

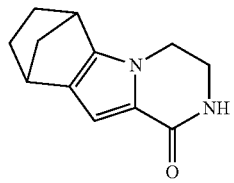 [SMILES: O=C1NCCn2c1cc1c2C2CCC1C2]

Into a solution of 167e (1.8 g, 7.2 mmol) in ethanol (40 mL) was added sodium methoxide (2.5 g, 36 mmol). The mixture was heated at 65° C. for 12 hours. It was then cooled to room temperature. The solvent was evaporated to dryness under reduced pressure. The residue was purified by silica-gel column chromatography eluting with 20:1 methylene chloride/methanol to afford the racemate as a brown solid (800 mg, 53%), chiral resolution of which afforded 167f and 170a. MS: [M+H]⁺ 203.

Example 167g

4-Chloro-2-[(1S,11R)-7-oxo-3,6-diazatetracyclo[9.2.1.0²,¹⁰.0³,⁸]tetradeca-2(10),8-dien-6-yl]pyridine-3-carbaldehyde 167g A 100-mL single-neck round-bottomed flask equipped with a magnetic stirrer and a reflux condenser was charged with 1,4-dioxane (30 mL), 167f (400 mg, 2.0 mmol), 2-bromo-4-chloronicotinaldehyde (1.30 g, 6.0 mmol), and potassium acetate (390 mg, 4.0 mmol). After bubbling nitrogen through the resulting mixture for 30 minutes, Xantphos (110 mg, 0.20 mmol) and tris(dibenzylideneacetone)dipalladium(0) (180 mg, 0.20 mmol) were added and the reaction mixture was heated at 80° C. for 10 h. It was then cooled to room temperature and filtered. The filtrate was partitioned between ethyl acetate (50 mL) and water (30 mL). The aqueous layer was separated and extracted with ethyl acetate (3×30 mL). The combined organic layer was washed with brine (20 mL) and dried over sodium sulfate. The drying agent was removed by filtration and the filtrate was concentrated under reduced pressure. The residue was purified with silica-gel column chromatography eluting with 2:1 petroleum ether/ethyl acetate to afford 167g (391 mg, 57%) as yellow solid. MS-ESI: [M+H]⁺ 342.2

Example 167h

4-[1-Methyl-5-({5-methyl-4H,5H,6H,7H-pyrazolo[1,5-a]pyrazin-2-yl}amino)-6-oxo-1,6-dihydropyridin-3-yl]-2-[(1S,11R)-7-oxo-3,6-diazatetracyclo[9.2.1.0²,¹⁰.0³,⁸]tetradeca-2(10),8-dien-6-yl]pyridine-3-carbaldehyde 167h

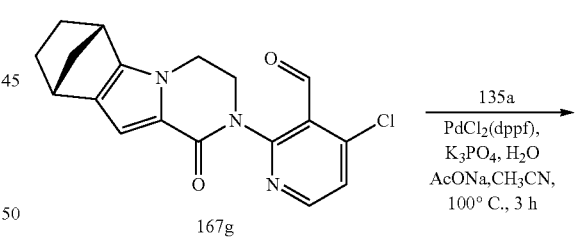

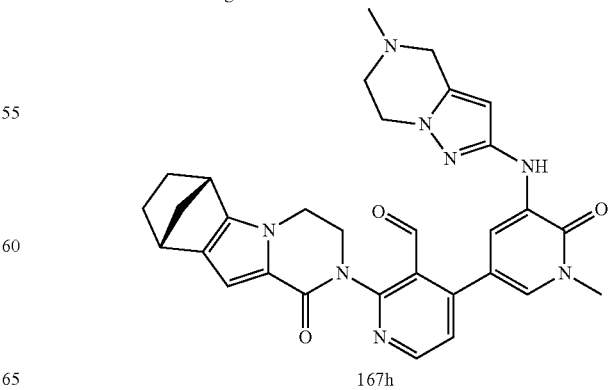

A 100-mL round-bottomed flask equipped with a reflux condenser was charged with 167g (150 mg, 0.44 mmol), 1-methyl-3-(5-methyl-4,5,6,7-tetrahydropyrazolo[1,5-a]pyrazin-2-ylamino)-5-(4,4,5,5-tetra-methyl-1,3,2-dioxaborolan-2-yl)pyridin-2(1H)-one 135a (169 mg, 0.44 mmol), sodium acetate (72 mg, 0.88 mmol), K$_3$PO$_4$ (234 mg, 0.88 mmol), PdCl$_2$(dppf) (36 mg, 0.044 mmol), acetonitrile (20 mL), and water (1 mL). After bubbling nitrogen through the mixture for 30 minutes, it was heated at 100° C. under N$_2$ for 3 hours. The reaction mixture was cooled to room temperature and filtered. The filtrate was concentrated under reduced pressure and the residue was purified by silica-gel column chromatography eluting with 25:1 dichloromethane/methanol to afford 167h (132 mg, 53%) as a brown solid. MS-ESI: [M+H]$^+$ 565.3

Example 167

2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one 167

A solution of 167h (120 mg, 0.21 mmol) in methanol (20 mL) was added NaBH$_4$ (24 mg, 0.63 mmol). The mixture was stirred at 20° C. for 2 h. The reaction was quenched with water and concentrated under reduced pressure. The residue was purified by reverse-phase prep-HPLC to afford 167 (98 mg, 83%) as a yellow solid. MS-ESI: [M+H]$^+$ 567.3. $^1$H NMR (500 MHz, DMSO-d$_6$) δ 8.48 (d, J=5.0 Hz, 1H), 8.19 (s, 1H), 8.05 (d, J=2.5 Hz, 1H), 7.40 (s, 1H), 7.32 (d, J=5.0 Hz, 1H), 6.53 (d, J=5.5 Hz, 1H), 5.89 (s, 1H), 4.98 (t, J=5.0 Hz, 1H), 4.48-4.30 (m, 3H), 4.27-4.22 (m, 2H), 3.92-3.91 (m, 2H), 3.86-3.84 (m, 1H), 3.60 (s, 3H), 3.52-3.33 (m, 3H), 3.29 (ps, 1H), 2.79-2.77 (m, 2H), 2.35 (s, 3H), 1.87-1.76 (m, 3H), 1.60-1.59 (m, 1H), 1.09-0.91 (m, 2H).

Example 168a 3-(6,7-Dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 168a A 250-mL round bottomed flask equipped with a magnetic stirrer and a reflux condenser was charged with the mixture of 5-bromo-3-(6,7-dihydro-4H-pyrazolo[5,1-c][1,4]oxazin-2-ylamino)-1-methylpyridin-2(1H)-one 129c (1.3 g, 4.0 mmol), bis(pinacolato)diboron (2.03 g, 8.0 mmol), PdCl$_2$(dppf) (439 mg, 0.60 mmol), potassium acetate (784 mg, 8.0 mmol), and 1,4-dioxane (60 mL). After bubbling nitrogen through the mixture for 30 minutes, it was heated at reflux for 15 h. The mixture was cooled to room temperature upon completion of the reaction and filtered. The solid was washed with ethyl acetate (100 mL). The combined filtrate was evaporated under reduced pressure and the residue was purified by silica-gel column chromatography eluting with 30:1 dichloromethane/methanol to afford 168a (446 mg, 30%). MS: [M+H]$^+$ 373.

Example 168b 4-(1-Methyl-5-(6,7-dihydro-4H-pyrazolo[5,1-c][1,4]oxazin-2-ylamino)-6-oxo-1,6-dihydropyridin-3-yl)-2-(4,4-dimethyl-9-oxo-1,10-diazatricyclo[6.4.0.0$^{2,6}$]dodeca-2(6),7-dien-10-yl)nicotinaldehyde 168b

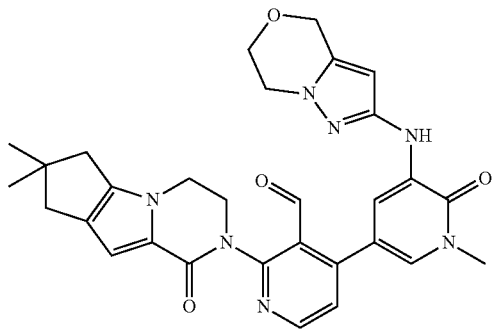

168b

A 50-mL single-neck round-bottomed flask equipped with a magnetic stirrer and a reflux condenser was charged with 4-chloro-2-{4,4-dimethyl-9-oxo-1,10-diazatricyclo[6.4.0.02,6]dodeca-2(6),7-dien-10-yl}pyridine-3-carbaldehyde 108a (200 mg, 0.58 mmol), 168a (433 mg, 1.16 mmol), PdCl$_2$(dppf) (48 mg, 0.052 mmol), K$_3$PO$_4$ (246 mg, 1.16 mmol), sodium acetate (96 mg, 1.16 mmol), acetonitrile (10 mL), and water (0.5 mL). The system was evacuated and refilled with N$_2$. The reaction mixture was stirred at 100° C. for 2 h. It was then cooled to room temperature and filtered. The filtrate was concentrated under reduced pressure and the resulting residue was purified by silica-gel column chromatography eluting with 30:1 dichloromethane/methanol to afford 168b (250 mg, 78%) as a yellow solid. MS-ESI: [M+H]$^+$ 554.6.

Example 168

2-[5-(6,7-Dihydro-4H-pyrazolo[5,1-c][1,4]oxazin-2-ylamino)-3'-hydroxymethyl-1-methyl-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 168

To a suspension of 168b (200 mg, 0.36 mmol) at 0° C. in methanol (10 mL) was added sodium borohydride (42 mg, 1.1 mmol). The reaction mixture was stirred for 30 minutes and quenched with water (2 mL). It was then concentrated under reduced pressure and the residue was purified by reverse-phase prep-HPLC to afford 168 (53 mg, 21%) as a yellow solid. MS-ESI: [M+H]$^+$ 556.6. $^1$H NMR (400 MHz, CDCl$_3$) δ 8.46 (d, J=5.2 Hz, 1H), 7.97 (d, J=2.4 Hz, 1H), 7.71 (d, J=2.0 Hz, 1H), 7.45 (s, 1H), 7.33 (d, J=5.2 Hz, 1H), 6.83 (s, 1H), 5.71 (s, 1H), 5.04-5.01 (m, 1H), 4.78 (s, 2H), 4.64-4.62 (m, 1H), 4.49 (d, J=2.8 Hz, 1H), 4.32-4.28 (m, 1H), 4.14 (d, J=4.4 Hz, 2H), 4.09-4.08 (m, 4H), 3.87-3.83 (m, 1H), 3.70 (s, 3H), 2.56 (d, J=2.8 Hz, 2H), 2.50 (s, 2H), 1.26 (s, 6H).

Example 169a

4-Chloro-2-{6-oxo-8-thia-5-azatricyclo[7.4.0.0$^{2,7}$]trideca-1(9),2(7)-dien-5-yl}pyridine-3-carbaldehyde 169a

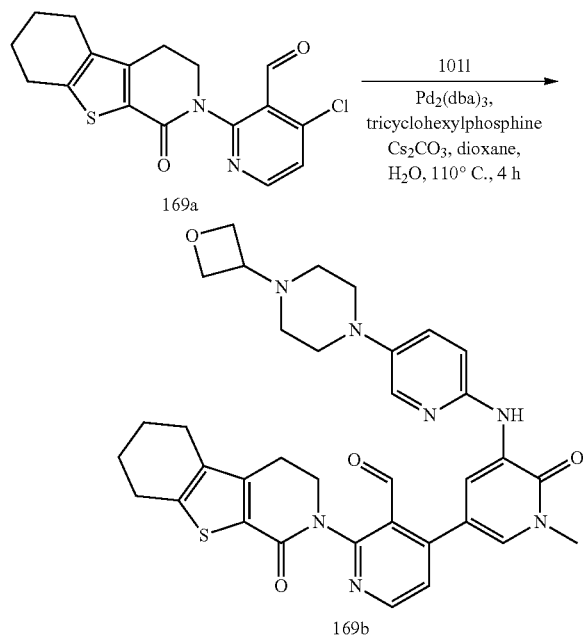

A 100-mL single-neck round-bottomed flask equipped with a reflux condenser was charged with 2-bromo-4-chloronicotinaldehyde 103a (1276 mg, 5.80 mmol), 8-thia-5-azatricyclo[7.4.0.0$^{2,7}$]trideca-1(9),2(7)-dien-6-one 105e (600 mg, 2.90 mmol), CuI (551 mg, 2.90 mmol), K$_2$CO$_3$ (800 mg, 5.80 mmol), 4,7-dimethoxy-1,10-phenanthroline (696 mg, 2.90 mmol), and dioxane (20 mL). After bubbling nitrogen through the resulting solution for 10 min, the mixture was stirred at 95° C. for 16 h. It was then cooled to room temperature and filtered. To the residue was added water (20 mL). The aqueous layer was separated and extracted with ethyl acetate (3×20 mL). The combined organic layer was washed with brine (50 mL) and dried over sodium sulfate. The drying agent was removed by filtration and the filtrate was concentrated under reduced pressure. The residue was purified by silica-gel column chromatography eluting with 10:1 petroleum ether/ethyl acetate to afford 169a (171 mg, 17%). LCMS-ESI: [M+H]$^+$ 347

Example 169b

4-[1-Methyl-5-({5-[4-(oxetan-3-yl)piperazin-1-yl]pyridin-2-yl}amino)-6-oxo-1,6-dihydropyridin-3-yl]-2-{6-oxo-8-thia-5-azatricyclo[7.4.0.0$^{2,7}$]trideca-1(9),2(7)-dien-5-yl}pyridine-3-carbaldehyde 169b A 50-mL single-neck round-bottomed flask equipped with a reflux condenser was charged with 169a (150 mg, 0.43 mmol), 3-(5-(2-ethyl-4-(oxetan-3-yl)piperazin-1-yl)pyridine-2-ylamino)-1-methyl-5-(4,4,5,5-tetramethyl-1,3,2-dioxaborolan-2-yl)pyridin-2(1H)-one 101l (200 mg, 0.43 mmol), Pd$_2$(dba)$_3$ (37 mg, 0.040 mmol), tricyclohexylphosphine (120 mg, 0.43 mmol), Cs$_2$CO$_3$ (281 mg, 0.86 mmol), dioxane (10 mL), and water (0.1 mL). After three cycles of vacuum/argon flush, the mixture was heated at 110° C. for 4 h. It was then filtered and the filtrate was evaporated under reduced pressure. The residue was purified by silica-gel column chromatography eluting with 1:3 petroleum/ethyl acetate to afford 169b as a yellow solid (45 mg, 16%). LCMS-ESI: [M+H]$^+$ 652

Example 169

2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-3,4,5,6,7,8-hexahydro-2H-benzo[4,5]thieno[2,3-c]pyridin-1-one 169

A mixture of 169b (45 mg, 0.070 mmol), NaBH$_4$ (8 mg, 0.21) and methanol (5 mL) was stirred at room temperature for 1 h. The reaction mixture was quenched with water (5 mL) and concentrated under reduced pressure. The residue was extracted with dichloromethane (2×10 mL). The combined dichloromethane extract was concentrated under reduced pressure. The residue was purified with reverse-phase prep-HPLC to afford 169 (14 mg, 30%). LCMS-ESI: [M+H]$^+$ 654. $^1$H NMR (500 MHz, DMSO-d$_6$) δ 8.62 (s, 1H), 8.50 (d, J=2.0 Hz, 1H), 8.43 (s, 1H), 7.86 (d, J=4.5 Hz, 1H), 7.45 (d, J=2.5 Hz, 1H), 7.39-7.34 (m, 2H), 7.25-7.22 (m, 1H), 4.95-4.93 (m, 1H), 4.57-4.55 (m, 2H), 4.47-4.41 (m, 4H), 4.19-4.17 (m, 1H), 3.82-3.80 (m, 1H), 3.60 (s, 3H), 3.45-3.43 (m, 1H), 3.32-3.30 (m, 1H), 3.09-3.07 (m, 4H), 3.01-2.90 (m, 1H), 2.89-2.88 (m, 1H), 2.80-2.79 (m, 2H), 2.51-2.50 (m, 1H), 2.40-2.38 (m, 4H), 1.83-1.80 (m, 4H).

Example 170b

4-Chloro-2-[(1R,11S)-7-oxo-3,6-diazatetracyclo[9.2.1.0$^{2,10}$.0$^{3,8}$]tetradeca-2(10),8-dien-6-yl]pyridine-3-carbaldehyde 170b A 100-mL single-neck round-bottomed flask equipped with a magnetic stirrer and a reflux condenser was charged with 1,4-dioxane (30 mL), (1S,11R)-3,6-diazatetracyclo[9.2.1.0$^{2,10}$.0$^{3,8}$]tetradeca-2(10),8-dien-7-one 170a (400 mg, 2.0 mmol), 2-bromo-4-chloronicotinaldehyde 103a (1.30 g, 6.0 mmol), and potassium acetate (390 mg, 4.0 mmol). After bubbling nitrogen through the resulting mixture for 30 minutes, Xantphos (110 mg, 0.20 mmol) and tris(dibenzylideneacetone)dipalladium(0) (180 mg, 0.20 mmol) were added, and the reaction mixture was heated at 80° C. for 10 h. After this time the reaction was cooled to room temperature and filtered. The filtrate was partitioned between ethyl acetate (50 mL) and water (30 mL). The aqueous layer was separated and extracted with ethyl acetate (3×30 mL). The combined organic layer was washed with brine (20 mL) and dried over sodium sulfate. The drying agent was removed by filtration and the filtrate was concentrated under reduced pressure. The residue was purified by silica-gel column chromatography eluting with 2:1 petroleum ether/ethyl acetate to afford 170b (405 mg, 59%) as a yellow solid. MS-ESI: [M+H]$^+$ 342.2

Example 170c

4-[1-Methyl-5-({5-methyl-4H,5H,6H,7H-pyrazolo[1,5-a]pyrazin-2-yl}amino)-6-oxo-1,6-dihydropyridin-3-yl]-2-[(1R,11S)-7-oxo-3,6-diazatetracyclo[9.2.1.0$^{2,10}$.0$^{3,8}$]tetradeca-2(10),8-dien-6-yl]pyridine-3-carbaldehyde 170c

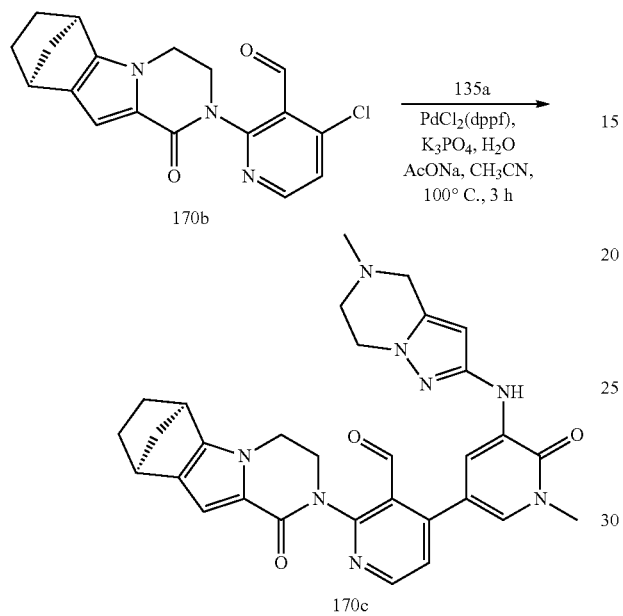

A 100-mL round-bottomed flask equipped with a reflux condenser was charged with 170b (150 mg, 0.44 mmol), 1-methyl-3-(5-methyl-4,5,6,7-tetrahydropyrazolo[1,5-a]pyrazin-2-ylamino)-5-(4,4,5,5-tetra-methyl-1,3,2-dioxaborolan-2-yl)pyridin-2(1H)-one 135a (169 mg, 0.44 mmol), sodium acetate (72 mg, 0.88 mmol), K$_3$PO$_4$ (234 mg, 0.88 mmol), Pd (dppf) Cl$_2$ (36 mg, 0.044 mmol), acetonitrile (20 mL), and water (1 mL). After bubbling nitrogen through the reaction mixture for 30 minutes, it was heated at 100° C. for 3 hours. The reaction mixture was evaporated under reduced pressure and the residue was purified by silica-gel column chromatography eluting with 25:1 dichloromethane/methanol to afford 170c (146 mg, 52%) as a brown solid. MS-ESI: [M+H]$^+$ 565.3

Example 170

2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one 170

A solution of 170c (122 mg, 0.22 mmol) in methanol (20 mL) was added NaBH$_4$ (24 mg, 0.64 mmol). The mixture was stirred at 20° C. for 2 h. The reaction was evaporated under reduced pressure and the residue was purified by reverse-phase prep-HPLC to afford the title compound (98 mg, 75%) as a white solid. MS-ESI: [M+H]$^+$ 567.3. $^1$H NMR (500 MHz, DMSO-d$_6$) δ 8.48 (d, J=5.0 Hz, 1H), 8.19 (s, 1H), 8.05 (d, J=2.5 Hz, 1H), 7.40 (s, 1H), 7.32 (d, J=5.0 Hz, 1H), 6.53 (s, 1H), 5.89 (s, 1H), 4.98 (t, J=5.0 Hz, 1H), 4.48-4.30 (m, 3H), 4.27-4.22 (m, 2H), 3.92-3.91 (m, 2H), 3.86-3.84 (m, 1H), 3.59 (s, 3H), 3.49-3.47 (m, 3H), 3.30-3.28 (m, 1H), 2.79-2.77 (m, 2H), 2.35 (s, 3H), 1.87-1.76 (m, 3H), 1.61-1.59 (m, 1H), 1.09-0.88 (m, 2H).

Example 171a

4-[1-Methyl-5-({5-[(2S)-2-methyl-4-(oxetan-3-yl)piperazin-1-yl]pyridin-2-yl}amino)-6-oxo-1,6-dihydropyridin-3-yl]-2-[(1S,11R)-7-oxo-3,6-diazatetracyclo[9.2.1.0$^{2,10}$.0$^{3,8}$]tetradeca-2(10),8-dien-6-yl]pyridine-3-carbaldehyde 171a

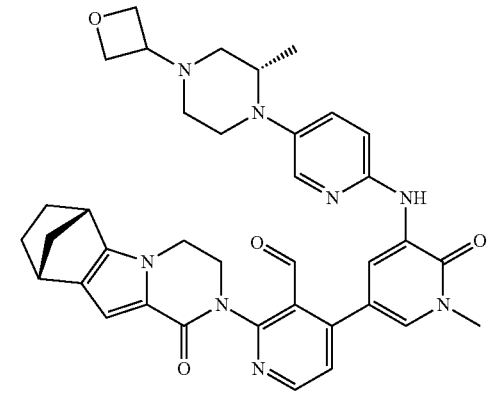

A 50-mL single-neck round-bottomed flask equipped with a magnetic stirrer and a reflux condenser was charged with acetonitrile (30 mL), 4-chloro-2-[(1S,11R)-7-oxo-3,6-diazatetracyclo[9.2.1.0$^{2,10}$.0$^{3,8}$]tetradeca-2(10),8-dien-6-yl]pyridine-3-carbaldehyde 167g (170 mg, 0.50 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 130f (336 mg, 0.70 mmol), water (3 mL), and potassium acetate (147 mg, 1.5 mmol). After bubbling argon through the suspension for 30 minutes, 1,1'-bis(diphenylphosphino)ferrocenedichloropalladium(II) (408 mg, 0.05 mmol) was added. The system was subjected to three cycles of vacuum/argon flush and heated at 80° C. for 3 h. It was then cooled to room temperature and filtered. The solid was washed with dichloromethane (2×100 ml). The combined filtrate was concentrated under reduced pressure and the residue was purified by silica-gel column chromatography eluting with dichloromethane/methanol (50:1 to 30:1) to afford 171a (95 mg, 29%) as a light yellow solid. MS-ESI: [M+H]$^+$ 661.3

Example 171

(S)-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one 171

To a solution of 171a (90 mg, 0.136 mmol) in methanol (10 mL) was added NaBH$_4$ (26 mg, 0.7 mmol) at room temperature. After the reaction was stirred for 1 h, LCMS indicated the reaction was complete. It was quenched with water (30 mL) and concentrated under reduced pressure. The residue was extracted with dichloromethane (3×30 mL). The combined organic layer was washed with brine (30 mL), dried over Na$_2$SO$_4$, filtered, and concentrated under reduced pressure. The residue solid was purified by reverse-phase prep-HPLC to afford 171 (35 mg, 31.5%) as light yellow solid. MS-ESI: [M+H]$^+$ 663.3. $^1$H NMR (500 MHz, DMSO-d$_6$) δ 8.62 (s, 1H), 8.48 (d, J=5.0 Hz, 1H), 8.44 (s, 1H), 7.83 (d, J=2.5 Hz, 1H), 7.47 (s, 1H), 7.38 (dd, J=2.5, 9.0 Hz 1H), 7.34 (d, J=5.0 Hz, 1H), 7.24 (d, J=9.5 Hz, 1H), 6.51 (s, 1H), 4.97 (t, J=4.5 Hz, 1H), 4.58-4.54 (m, 2H), 4.50-4.37 (m, 4H), 4.30-4.24 (m, 2H), 3.86-3.84 (m, 1H), 3.69-3.67 (m, 1H), 3.60 (s, 3H), 3.47 (s, 1H), 3.42-3.37 (m, 1H), 3.30 (s, 2H), 3.10-3.07 (m, 1H), 2.95-2.92 (m, 1H), 2.36-2.29 (m, 3H), 2.21-2.16 (m, 1H), 1.88-1.754 (m, 3H), 1.60-1.58 (m, 1H), 1.08-1.05 (m, 1H), 0.98-0.96 (m, 1H), 0.93 (d, J=6.0 Hz, 3H).

Example 172a 3-(1,2,4-Triazin-3-ylamino)-5-bromo-1-methylpyridin-2(1H)-one 172a

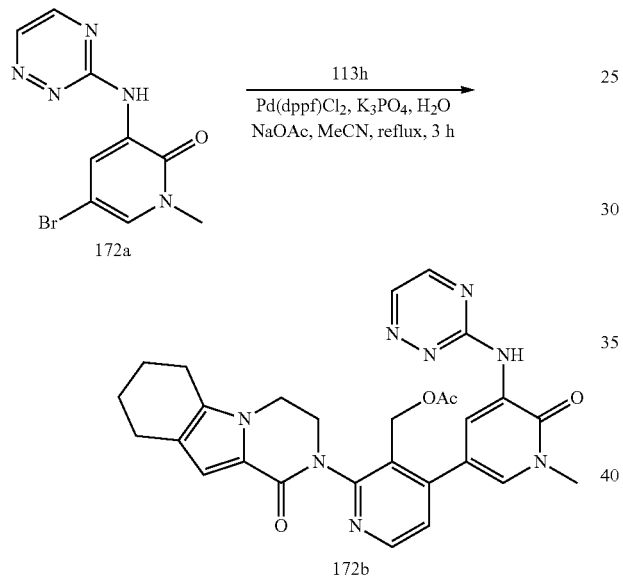

A 500-mL single-neck round-bottomed flask equipped with a magnetic stirrer and a reflux condenser was charged with 1,4-dioxane (100 mL), 1,2,4-triazin-3-amine (1.5 g, 15.6 mmol), 3,5-dibromo-1-methylpyridin-2(1H)-one (4.2 g, 15.6 mmol), Pd$_2$(dba)$_3$ (458 mg, 1.56 mmol), XantPhos (1.8 g, 3.12 mmol), and cesium carbonate (10 g, 31.2 mmol). After three cycles of vacuum/argon flush, the mixture was stirred at 90° C. for 2.5 h. After this time the reaction was filtered and the filtrate was evaporated in vacuo. The resulting residue was recrystallized from ethyl acetate to afford 172a as a yellow solid (1.76 g, 40%). MS-ESI: [M+H]$^+$ 282.

Example 172b (4-(5-(1,2,4-Triazin-3-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 172b A 100-mL single-neck round-bottomed flask equipped with a magnetic stirrer and a reflux condenser was charged with 172a (200 mg, 0.71 mmol), 3-(acetoxymethyl)-2-(1-oxo-3,4,6,7,8,9-hexahydropyrazino[1,2-a]indol-2(1H)-yl)pyridin-4-ylboronic acid 113i (272 mg, 0.71 mmol), Pd(dppf)Cl$_2$ (58 mg, 0.071 mmol), sodium acetate (193 mg, 1.42 mmol), K$_3$PO$_4$ (321 mg, 1.42 mmol), water (0.5 mL) and acetonitrile (10 mL). After three cycles of vacuum/argon flush, the mixture was stirred at 100° C. for 3 h. After this time the reaction was filtered and the filtrate was evaporated in vacuo. The resulting residue was recrystallized from ethyl acetate to afford 172b as yellow solid (380 mg, 99%). MS-ESI: [M+H]$^+$ 541.2

Example 172

2-(4-(5-(1,2,4-triazin-3-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one A mixture of 172b (350 mg, 0.65 mmol) and lithium hydroxide (273 mg, 6.5 mmol) in i-propanol/THF (1:1, 5 mL) and water (0.5 mL) was stirred at 36° C. for 0.5 h. It was then cooled to room temperature and filtered. The filtrate was concentrated under reduced pressure and the resulting residue was washed by reverse-phase prep-HPLC to afford 172 (90 mg, 28%). MS-ESI: [M+H]$^+$ 499.2. $^1$H NMR (500 MHz, CDCl$_3$) δ 8.77 (d, J=2.5 Hz, 1H), 8.72 (d, J=2.0 Hz, 1H), 8.67 (s, 1H), 8.50 (d, J=5.0 Hz, 1H), 8.34 (d, J=2.0 Hz, 1H), 8.05 (d, J=2.5 Hz, 1H), 7.35 (d, J=5.0 Hz, 1H), 6.89 (s, 1H), 5.10 (t, J=6.5 Hz, 1H), 4.65-4.51 (m, 2H), 4.31-4.27 (m, 1H), 4.16-4.08 (m, 2H), 3.90-3.87 (m, 1H), 3.75 (s, 3H), 2.62-2.56 (m, 4H), 1.92-1.87 (m, 2H), 1.79-1.78 (m, 2H).

Example 173a

5-Bromo-3-(2,6-dimethylpyrimidin-4-ylamino)-1-methylpyridin-2(1H)-one 173a

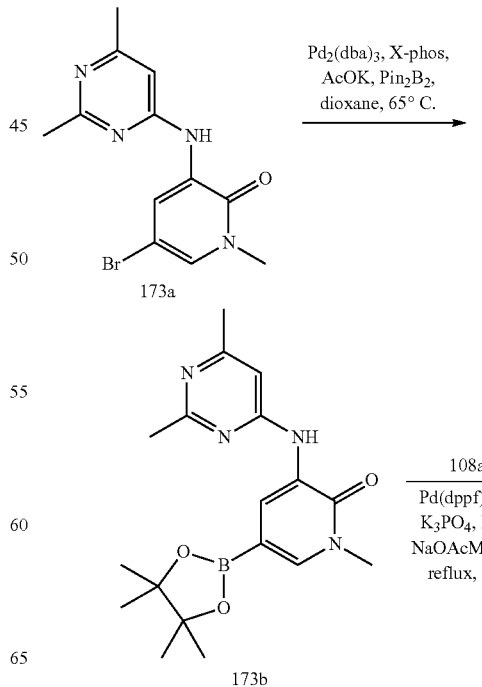

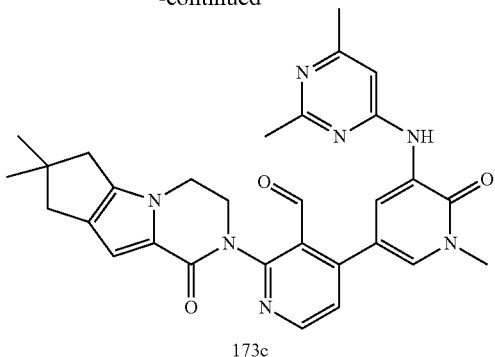

173c

A 250-mL single-neck round-bottomed flask equipped with a magnetic stirrer and a reflux condenser was charged with 1,4-dioxane (150 mL), 2,6-dimethylpyrimidin-4-amine (2.5 g, 20.3 mmol), 3,5-dibromo-1-methylpyridin-2(1H)-one (5.4 g, 20.3 mmol), Pd$_2$(dba)$_3$ (1.86 mg, 2.03 mmol), Xant-Phos (2.3 g, 4.06 mmol), and cesium carbonate (13.2 g, 40.6 mmol). After three cycles of vacuum/argon flush, the mixture was heated at 90° C. for 2.5 h. After this time the reaction was filtered and the filtrate was evaporated in vacuo. The resulting residue was recrystallized from ethyl acetate to afford 173a as a yellow solid (4.4 g, 40%). MS-ESI: [M+H]$^+$ 309.0.

Example 173b 3-(2,6-Dimethylpyrimidin-4-ylamino)-1-methyl-5-(4,4,5,5-tetramethyl-1,3,2-dioxaborolan-2-yl)pyridin-2(1H)-one 173b A 250-mL single-neck round-bottomed flask equipped with a magnetic stirrer and a reflux condenser was charged with 173a (1.5 g, 4.9 mmol), Pin$_2$B$_2$ (6.2 g, 24.5 mmol), Pd$_2$(dba)$_3$ (449 mg, 0.49 mmol), X-phos (467 mg, 0.98 mmol), potassium acetate (1.4 g, 14.7 mmol), and dioxane (60 mL). After three cycles of vacuum/argon flush, the mixture was heated at 65° C. for 16 h. The reaction was filtered and the filtrate was evaporated in vacuo. The resulting residue was recrystallized from ethyl acetate to afford 173b as a light gray solid (1.2 g, 72%). MS-ESI: [M+H]$^+$ 357.2.

Example 173c

2-{4,4-Dimethyl-9-oxo-1,10-diazatricyclo[6.4.0.0$^{2,6}$]dodeca-2(6),7-dien-10-yl}-4-{5-[(2,6-dimethylpyrimidin-4-yl)amino]-1-methyl-6-oxo-1,6-dihydropyridin-3-yl}pyridine-3-carbaldehyde 173c A 100-mL round-bottomed flask equipped with a magnetic stirrer and a reflux condenser was charged with 173b (250 mg, 0.70 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (240 mg, 0.70 mmol), Pd(dppf)Cl$_2$ (57 mg, 0.071 mmol), sodium acetate (19 mg, 1.4 mmol), K$_3$PO$_4$ (316 mg, 1.4 mmol), water (0.5 mL), and acetonitrile (15 mL). After three cycles of vacuum/argon flush, the mixture was heated at 100° C. for 3 h. After this time the reaction was filtered and the filtrate was evaporated in vacuo. The resulting residue was recrystallized from ethyl acetate to afford 173c as a brown solid (300 mg, 80%). MS-ESI: [M+H]$^+$ 538.3.

Example 173

2-[5-(2,6-Dimethyl-pyrimidin-4-ylamino)-3'-hydroxymethyl-1-methyl-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 173

At 0° C., to a solution of 173c (290 mg, 0.54 mmol) in methanol (5 mL) was added sodium borohydride (62 mg, 1.62 mmol). The reaction mixture was stirred at room temperature for 20 minutes and quenched with water (1 mL). It was then concentrated under reduced pressure and the residue was purified by reverse-phase prep-HPLC to afford 173 as white solid (50 mg, 17%). MS-ESI: [M+H]$^+$ 540.3. $^1$H NMR (500 MHz, CDCl$_3$) δ 8.90 (d, J=2.5 Hz, 1H), 8.51 (d, J=5.0 Hz, 1H), 8.01 (d, J=2.0 Hz, 1H), 8.00 (s, 1H), 7.35 (d, J=5.5 Hz, 1H), 6.85 (s, 1H), 6.45 (s, 1H), 5.16-5.13 (m, 1H), 4.67-4.52 (m, 2H), 4.33-4.29 (m, 1H), 4.16 (d, J=5.0 Hz, 2H), 3.90-3.86 (m, 1H), 3.72 (s, 3H), 2.58-2.56 (m, overlap, 5H), 2.51 (s, 2H), 2.40 (s, 3H), 2.02 (s, 6H).

Example 174a

4-[1-Methyl-5-({5-[(2S)-2-methyl-4-(oxetan-3-yl)piperazin-1-yl]pyridin-2-yl}amino)-6-oxo-1,6-dihydropyridin-3-yl]-2-[(1R,11S)-7-oxo-3,6-diazatetracyclo[9.2.1.0$^{2,10}$.0$^{3,8}$]tetradeca-2(10),8-dien-6-yl]pyridine-3-carbaldehyde 174a

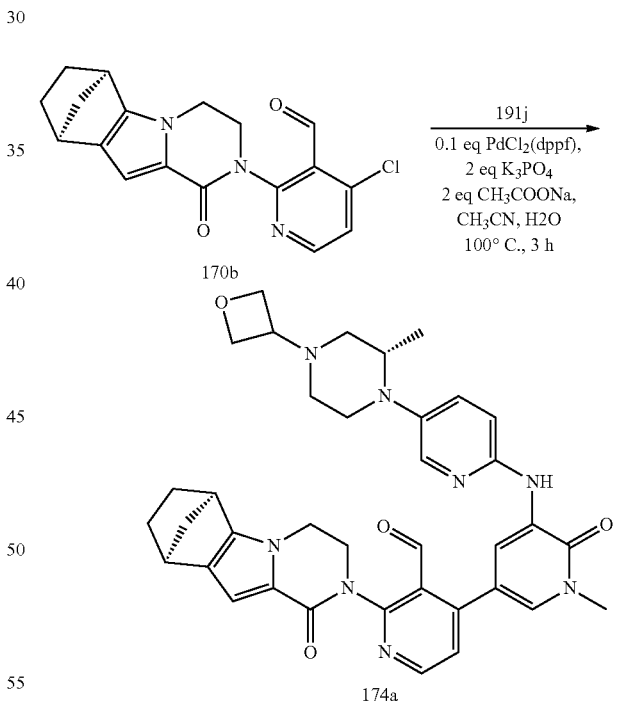

174a

A round-bottomed flask was charged with 4-chloro-2-[(1R,11S)-7-oxo-3,6-diazatetracyclo[9.2.1.0$^{2,10}$.0$^{3,8}$]tetradeca-2(10),8-dien-6-yl]pyridine-3-carbaldehyde 170b (200 mg, 0.59 mmol), 1-methyl-3-({5-[(2S)-2-methyl-4-(oxetan-3-yl)piperazin-1-yl]pyridin-2-yl}amino)-5-(4,4,5,5-tetramethyl-1,3,2-dioxaborolan-2-yl)-1,2-dihydropyridin-2-one 191j (400 mg, 0.88 mmol), PdCl$_2$(dppf) (50 mg, 0.06 mmol), K$_3$PO$_4$3 water (300 mg, 1.20 mmol), sodium acetate (100 mg, 1.20 mmol), acetonitrile (15 mL), and water (1.5 mL). After three cycles of vacuum/argon flush, the mixture was heated at 100° C. for 3 h. It was then filtered and the filtrate was evaporated under reduced pressure. The residue was purified with silica-gel column chromatography eluting with 1:20 methanol/dichloromethane to afford 174a as a red solid (170 mg, 44%). MS-ESI: [M+H]+ 661.3

Example 174

(1R,11S)-6-[3-(Hydroxymethyl)-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridin-2-yl]-3,6-diazatetracyclo[9.2.1.0$^{2,10}$.0$^{3,8}$]tetradeca-2(10),8-dien-7-one 174

A mixture of 174a (150 mg, 0.23 mmol), NaBH$_4$ (34 mg, 0.90), and methanol (10 mL) was stirred at room temperature for 1 h. The mixture was quenched with water (30 ml) and concentrated under reduced pressure. The residue was extracted with dichloromethane (2×10 mL). The combined dichloromethane extract was concentrated under reduced pressure and the residue was purified with reverse-phase prep-HPLC to afford 174 (42 mg, 28%). MS-ESI: [M+H]+ 663.3. $^1$H NMR (500 MHz, CDCl$_3$) δ 8.65 (d, J=3.0 Hz, 1H), 8.48 (d, J=6.0 Hz, 1H), 7.96 (d, J=2.5 Hz, 1H), 7.85-7.84 (m, 2H), 7.36 (d, J=6.5 Hz, 1H), 7.32 (dd, J=3.5, 11.0 Hz, 1H), 6.82-6.80 (m, 2H), 5.16-5.06 (m, 1H), 4.72-4.61 (m, 5H), 4.08-4.05 (m, 1H), 4.32-4.21 (m, 3H), 3.88-3.85 (m, 1H), 3.71 (s, 3H), 3.54-3.50 (m, 2H), 3.38-3.37 (m, 2H), 3.08-3.06 (m, 2H), 2.57-2.54 (m, 1H), 2.48-2.45 (m, 2H), 2.21-2.17 (m, 1H), 1.93-1.91 (m, 3H), 1.66-1.64 (m, 1H), 1.14-1.08 (m, 2H), 0.98 (d, J=8.0 Hz, 3H).

Example 175a

4-Chloro-2-{6-oxo-8-thia-4,5-diazatricyclo[7.4.0.0$^{2,7}$]trideca-1(9),2(7),3-trien-5-yl}pyridine-3-carbaldehyde 175a

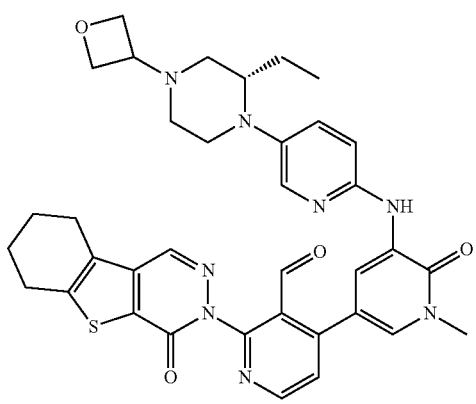

175a

A 250-mL single-neck round-bottomed flask equipped with a magnetic stirrer and a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (150 mg, 0.43 mmol), 3-(5-(2-ethyl-4-(oxetan-3-yl)piperazin-1-yl)pyridin-2-ylamino)-1-methyl-5-(4,4,5,5-tetramethyl-1,3,2-dioxaborolan-2-yl)pyridin-2(1H)-one 161f (215 mg, 0.43 mmol), PdCl$_2$(dppf) (33 mg, 0.040 mmol), K$_3$PO$_4$ trihydrate (202 mg, 0.86 mmol), sodium acetate (71 mg, 0.86 mmol), acetonitrile (10 mL), and water (2 mL). After three cycles of vacuum/argon flush, the mixture was heated at 100° C. for 3 h. It was then filtered and the filtrate was evaporated under reduced pressure. The residue was purified by silica-gel column chromatography eluting with 1:3 petroleum/ethyl acetate to afford 175a as a yellow solid (108 mg, 37%). MS-ESI: [M+H]+ 679

Example 175

3-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one 175

A mixture of 175a (200 mg, 0.16 mmol), NaBH$_4$ (18 mg, 0.48), and methanol (8 mL) was stirred at 25° C. for 1 h. Then the reaction mixture was quenched with water (10 mL) and evaporated under reduced pressure. The residue was extracted with dichloromethane (2×10 mL). The combined dichloromethane extract was concentrated under reduced pressure and the residue was purified with reverse-phase prep-HPLC to afford 175 (55 mg, 50%). MS-ESI: [M+H]+ 681. $^1$H NMR (500 MHz, DMSO-d$_6$) 8.61 (d, J=2.0 Hz, 1H), 8.57-8.56 (m, 1H), 8.47 (s, 1H), 8.43 (s, 1H), 7.83 (d, J=3.0 Hz, 1H), 7.54-7.53 (m, 1H), 7.47 (d, J=2.0 Hz, 1H), 7.35-7.32 (m, 1H), 7.24-7.22 (m, 1H), 4.85-4.83 (m, 1H), 4.59-4.55 (m, 2H), 4.47-4.44 (m, 1H), 4.40-4.36 (m, 2H), 3.60 (s, 3H), 3.51-3.49 (m, 1H), 3.40-3.38 (m, 1H), 3.17-3.14 (m, 1H), 3.00-2.95 (m, 3H), 2.87-2.85 (m, 2H), 2.66-2.60 (m, 1H), 2.55-2.53 (m, 1H), 2.18-2.15 (m, 1H), 2.10-2.06 (m, 1H), 1.89-1.86 (m, 4H), 1.68-1.64 (m, 1H), 1.28-1.25 (m, 2H), 0.79 (t, J=9.5 Hz, 3H).

Example 176a (S)-4-(1-Methyl-5-(5-(2-methyl-4-(oxetan-3-yl)piperazin-1-yl)pyridin-2-ylamino)-6-oxo-1,6-dihydropyridin-3-yl)-2-(1-oxo-6,7,8,9-tetrahydropyrazino[1,2-a]indol-2(1H)-yl)nicotinaldehyde 176a

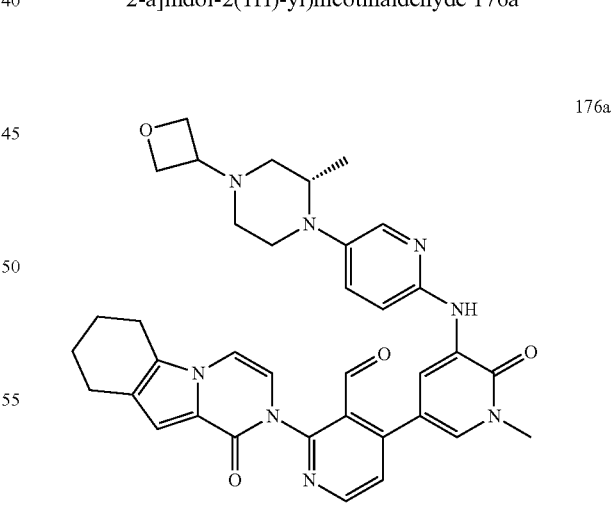

176a

A round-bottomed flask was charged with 4-chloro-2-(1-oxo-6,7,8,9-tetrahydropyrazino[1,2-a]indol-2(1H)-yl)nicotinaldehyde 121a (180 mg, 0.55 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (397 mg, 0.82 mmol), PdCl$_2$(dppf) (45 mg, 0.06 mmol), K$_3$PO$_4$ trihydrate (286 mg, 1.10 mmol), sodium acetate (90 mg, 1.10 mmol), acetonitrile (15 mL), and water (1.5 mL). After three cycles of vacuum/argon flush, the mixture was heated at 100° C. for 3 h. It was then filtered and the filtrate was evaporated under reduced pressure. The residue was purified by silica-gel column chromatography eluting with 1:20 methanol/dichloromethane to afford 176a as a red solid (228 mg, 64%). MS-ESI: [M+H]$^+$ 647.3

Example 176

(S)-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-6,7,8,9-tetrahydropyrazino[1,2-a]indol-1(2H)-one 176

A mixture of 176a (200 mg, 0.31 mmol), NaBH$_4$ (47 mg, 1.20), and methanol (10 mL) was stirred at room temperature for 1 h. The reaction mixture was then quenched with water (10 mL) and concentrated under reduced pressure. The residue was extracted with dichloromethane (2×10 mL). The combined dichloromethane extract was concentrated under reduced pressure and the residue was purified with reverse-phase prep-HPLC to afford 176 (42 mg, 28%). MS-ESI: [M+H]$^+$ 649.3. $^1$H NMR (500 MHz, DMSO-d$_6$) δ 8.66 (d, J=2.5 Hz, 1H), 8.56 (d, J=5.5 Hz, 1H), 8.47 (s, 1H), 7.84 (d, J=2.5 Hz, 1H), 7.50-7.48 (m, 2H), 7.39-7.36 (m, 1H), 7.26-7.24 (m, 2H), 6.83-6.80 (m, 2H), 4.57-4.54 (m, 2H), 4.48-4.40 (m, 3H), 4.35-4.33 (m, 1H), 3.69-3.67 (m, 1H), 3.60 (s, 3H), 3.41-3.38 (m, 2H), 3.11-3.08 (m, 1H), 2.97-2.93 (m, 1H), 2.76-2.74 (m, 2H), 2.62-2.60 (m, 2H), 2.52-2.51 (m, 1H), 2.35-2.32 (m, 2H), 2.19-2.17 (m, 1H), 1.90-1.87 (m, 2H), 1.77-1.75 (m, 2H), 0.94 (d, J=6.5 Hz, 3H).

Example 177a (4-(5-(5-Ethyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 177a A 50-mL single-neck round-bottomed flask equipped with a magnetic stirrer and a reflux condenser was charged with 5-bromo-3-(5-ethyl-4,5,6,7-tetrahydropyrazolo[1,5-a]pyrazin-2-ylamino)-1-methylpyridin-2(1H)-one 208c (300 mg, 0.85 mmol), 3-(acetoxymethyl)-2-(1-oxo-3,4,6,7,8,9-hexahydropyrazino[1,2-a]indol-2(1H)-yl)pyridin-4-ylboronic acid 113i (1.21 g, 3.16 mmol), PdCl$_2$(dppf) (35 mg, 0.043 mmol), K$_3$PO$_4$ (361 mg, 1.70 mmol), sodium acetate (140 mg, 1.70 mmol), acetonitrile (10 mL), and water (0.5 mL). The system was evacuated and refilled with N$_2$. The reaction mixture was stirred at 100° C. for 2 h. It was then cooled to room temperature and filtered. The filtrate was concentrated under reduced pressure and the resulting residue was purified by silica-gel column chromatography eluting with 30:1 dichloromethane/methanol to afford 177a (365 mg, 60%) as a brown oil. MS-ESI: [M+H]$^+$ 611

Example 177

2-(4-(5-(5-ethyl-4,5,6,7-tetrahydropyrazolo[1,5-a]pyrazin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 177

To a solution of 177a (300 mg, 0.49 mmol) in propan-2-ol (4 mL), tetrahydrofuran (4 mL), and water (1 mL) was added lithium hydroxide (35 mg, 1.47 mmol). The mixture was stirred at room temperature for 0.5 h. It was evaporated and the residue was purified by reverse-phase prep-HPLC to afford 177 (79 mg, 28%) as a white solid. MS-ESI: [M+H]$^+$ 569. $^1$H NMR (500 MHz, CDCl$_3$) δ 8.46 (d, J=5.5 Hz, 1H), 7.92 (d, J=2.0 Hz, 1H), 7.70 (d, J=2.0 Hz, 1H), 7.39 (s, 1H), 7.33 (d, J=5.5 Hz, 1H), 6.88 (s, 1H), 5.69 (s, 1H), 4.99-4.97 (m, 1H), 4.61-4.60 (m, 1H), 4.48-4.46 (m, 1H), 4.33-4.31 (m, 1H), 4.14-4.06 (m, 4H), 3.87-3.85 (m, 1H), 3.69 (s, 3H), 3.62 (d, J=5.5 Hz, 2H), 2.91 (d, J=5.0 Hz, 2H), 2.63-2.55 (m, 6H), 1.91-1.87 (m, 2H), 1.79-1.78 (m, 2H), 1.17 (t, J=7.5 Hz, 3H).

Example 178a

5-Bromo-1-methyl-3-(pyridin-2-ylamino)pyridin-2(1H)-one 178a

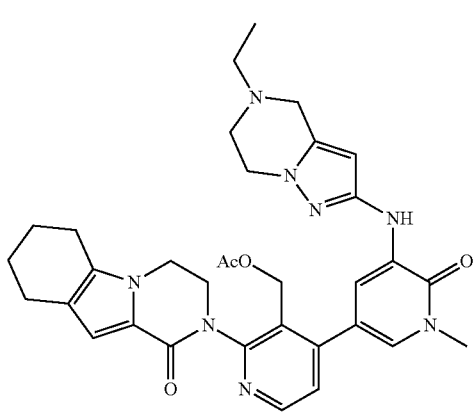

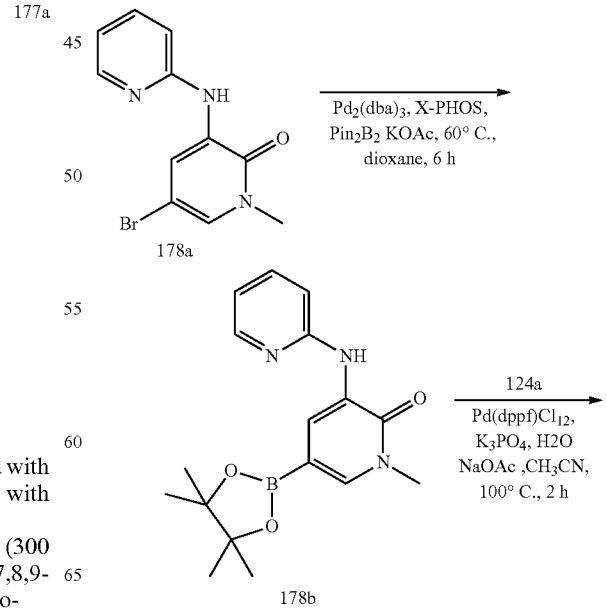

-continued

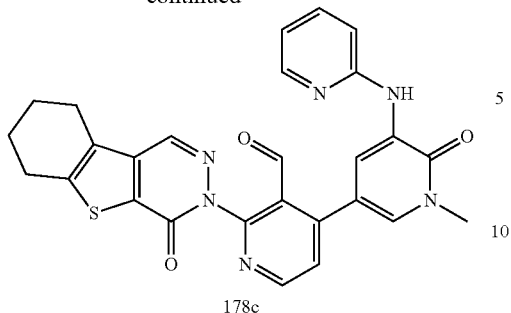

178c

A 250-mL single-neck round-bottomed flask equipped with a magnetic stirrer and a reflux condenser was charged with 1,4-dioxane (60 mL), 5-bromo-2-nitropyridine (8.0 g, 31.8 mmol), pyridin-2-amine (1.0 g, 10.6 mmol), and cesium carbonate (7.0 g, 21.2 mmol). After bubbling nitrogen through the resulting mixture for 30 minutes, XantPhos (616 mg, 1.0 mmol) and tris(dibenzylideneacetone)dipalladium (0) (973 mg, 1.0 mmol) were added. The reaction mixture was subjected to three cycles of vacuum/argon flush and heated at 100° C. for 12 h. After this time the reaction was cooled to room temperature and filtered. The filtrate was partitioned between ethyl acetate (100 mL) and water (100 mL). The aqueous layer was separated and extracted with ethyl acetate (3×150 mL). The combined organic layer was washed with brine (50 mL) and dried over sodium sulfate. The drying agent was removed by filtration and the filtrate was concentrated under reduced pressure. The residue was purified on silica-gel column eluting with 30:1 dichloromethane/methanol to afford 178a (1.5 g, 51%) as yellow solid. MS: [M+H]+ 280

Example 178b

1-Methyl-3-(pyridin-2-ylamino)-5-(4,4,5,5-tetramethyl-1,3,2-dioxaborolan-2-yl)pyridin-2(1H)-one 178b A 100-mL single-neck round-bottomed flask equipped with a magnetic stirrer and a reflux condenser was charged with 178a (1.06 g, 3.8 mmol), Pin$_2$B$_2$ (4.8 g, 19.0 mmol), Pd$_2$(dba)$_3$ (348 mg, 0.38 mmol), X-Phos (350 mg, 0.76 mmol), potassium acetate (1.12 g, 11.40 mmol), and dioxane (30 mL). After three cycles of vacuum/argon flush, the mixture was heated at 60° C. for 6 h. It was then cooled to room temperature and filtered. The filtrate was concentrated under reduced pressure and the resulting residue was purified by silica-gel column chromatography eluting with 3:1 petroleum ether/ethyl acetate to afford 178b as yellow solid (1.2 g, 96%). MS-ESI: [M+H]+ 328.2

Example 178c

4-{1-Methyl-6-oxo-5-[(pyridin-2-yl)amino]pyridin-3-yl}-2-{6-oxo-8-thia-4,5-diazatricyclo[7.4.0.0$^{2,7}$]trideca-1(9),2(7),3-trien-5-yl}pyridine-3-carbaldehyde 178c A 50-mL single-neck round-bottomed flask equipped with a magnetic stirrer and a reflux condenser was charged with 178b (131 mg, 0.40 mmol), 4-chloro-2-{6-oxo-8-thia-4,5-diazatricyclo[7.4.0.0$^{2,7}$]trideca-1(9),2(7),3-trien-5-yl}pyridine-3-carbaldehyde 124a (138 mg, 0.40 mmol), Pd(dppf)Cl$_2$ (33 mg, 0.040 mmol), K$_3$PO$_4$ (170 mg, 0.80 mmol), sodium acetate (66 mg, 0.80 mmol), water (6 drops), and acetonitrile (10 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 178c as a yellow solid (180 mg, 88%). MS-ESI: [M+H]+ 511.2

Example 178

3-[3'-Hydroxymethyl-1-methyl-6-oxo-5-(pyridin-2-ylamino)-1,6-dihydro-[3,4']bipyridinyl-2'-yl]-6,7,8,9-tetrahydro-3H-benzo[4,5]thieno[2,3-d]pyridazin-4-one 178

To a solution of 178c (179 mg, 0.35 mmol) in methanol (6 mL) was added sodium borohydride (39 mg, 1.05 mmol) at 0° C. The reaction mixture was stirred for 30 minutes and quenched with water (1.0 mL). It was then concentrated under reduced pressure and the residue was purified by reverse-phase prep-HPLC to afford 178 (100 mg, 56%). MS-ESI: [M+H]+ 513.3. $^1$H NMR (500 MHz, CDCl$_3$) δ 8.81 (s, 1H), 8.68 (d, J=5.0 Hz, 1H), 8.32 (s, 1H), 8.27 (d, J=4.0 Hz, 1H), 7.94 (bs, 1H), 7.76 (d, J=1.5 Hz, 1H), 7.58-7.56 (m, 2H), 6.85-6.80 (m, 2H), 4.47-4.45 (m, 2H), 4.38-4.36 (m, 1H), 3.74 (s, 3H), 3.01-2.99 (m, 2H), 2.89-2.87 (m, 2H), 2.02-1.99 (m, 4H).

Example 179a 4-(1-Methyl-5-(2-methylpyrimidin-4-ylamino)-6-oxo-1,6-dihydropyridin-3-yl)-2-(4,4-dimethyl-9-oxo-1,10-diazatricyclo[6.4.0.0$^{2,6}$]dodeca-2(6),7-dien-10-yl)nicotinaldehyde 179a

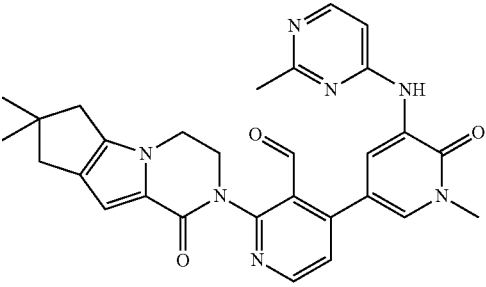

179a

A 50-mL round-bottomed flask equipped with a reflux condenser was charged with 1-methyl-3-(2-methylpyrimidin-4-ylamino)-5-(4,4,5,5-tetramethyl-1,3,2-dioxaborolan-2-yl)pyridin-2(1H)-one 213b (510 mg, 1.5 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (343 mg, 1.0 mmol), K$_3$PO$_4$ (424 mg, 2.0 mmol), sodium acetate (272 mg, 2.0 mmol), 1,1'-bis(diphenylphosphino)ferrocenedichloropalladium(II) (40 mg, 0.044 mmol), acetonitrile (20 mL), and water (0.5 mL). After bubbling nitrogen through the mixture for 30 minutes, it was was heated at 100° C. under N$_2$ protection for 2 h. Analysis of the reaction mixture by LCMS showed complete conversion to the desired product. The reaction mixture was cooled to room temperature and filtered. The filtrate was concentrated under reduced pressure. The residue was diluted with dichloromethane (30 mL) and water (30 mL). The aqueous layer was separated and extracted with dichloromethane (3×20 mL). The combined organic layer was dried over Na$_2$SO$_4$, filtered, and concentrated under reduced pressure. The dark residue was purified by silica-gel column chromatography eluting with dichloromethane/methanol (80/1 to 30/1) to afford 179a (300 mg, 57%) as a yellow solid. MS-ESI: [M+H]+ 524

Example 179

2-[3'-Hydroxymethyl-1-methyl-5-(2-methyl-pyrimidin-4-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 179

To a solution of 179a (262 mg, 0.50 mmol) in methanol/dichloromethane (10/10 mL) was added NaBH$_4$ (57 mg, 1.5 mmol) at room temperature. After the reaction was stirred for 1 h, LCMS indicated the reaction was complete. Then the mixture was concentrated under reduced pressure. The residue was diluted with water (5 mL) and dichloromethane (20 mL). The water phase was separated and extracted with dichloromethane (3×10 mL). The combined organic layer was washed with brine (30 mL), dried over Na$_2$SO$_4$, filtered, and concentrated under reduced pressure. The residue solid was purified by reverse-phase prep-HPLC to afford 179 (180 mg, 69%) as white solid. MS-ESI: [M+H]+ 526. $^1$H NMR (500 MHz, CDCl$_3$) δ 8.93 (d, J=2.0 Hz, 1H), 8.53 (d, J=5.5 Hz, 1H), 8.28 (d, J=5.5 Hz, 1H), 8.07 (s, 1H), 8.03 (d, J=2.0 Hz, 1H), 7.36 (s, 1H), 6.86 (s, 1H), 6.60 (d, J=6.0 Hz, 1H), 5.18-5.16 (m, 1H), 4.70-4.67 (m, 1H), 4.55-4.53 (m, 1H), 4.33-4.31 (m, 1H), 4.18-4.16 (m, 2H), 3.91-3.90 (m, 1H), 3.74 (s, 3H), 2.60 (s, 3H), 2.58 (d, J=5.5 Hz, 2H), 2.52 (s, 2H), 1.28 (s, 6H).

Example 180a

5-Bromo-1-methyl-3-(6-methylpyrimidin-4-ylamino)pyridin-2(1H)-one 180a

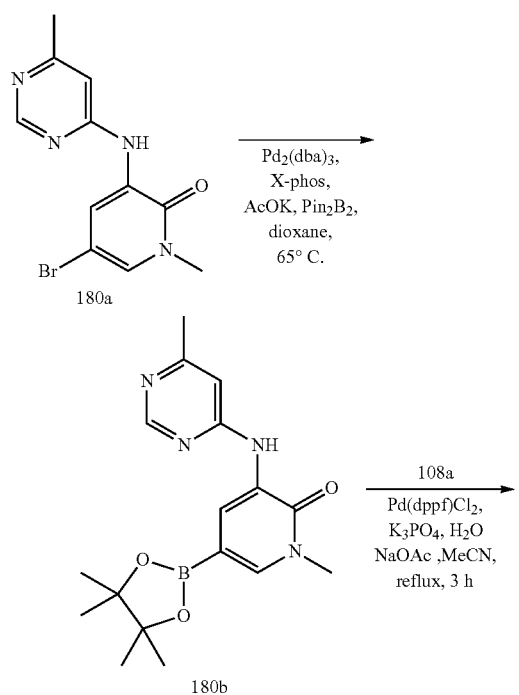

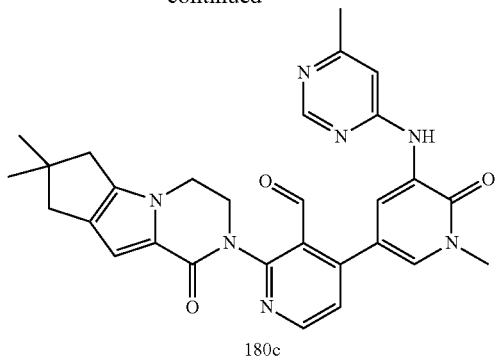

A 100-mL single-neck round-bottomed flask equipped with a magnetic stirrer and a reflux condenser was charged with 6-methylpyrimidin-4-amine (800 mg, 2.6 mmol), 3,5-dibromo-1-methylpyridin-2(1H)-one (694 mg, 2.6 mmol), tris(dibenzylideneacetone)dipalladium(0) (238 mg, 0.26 mmol), XantPhos (300 mg, 0.52 mmol), Cs$_2$CO$_3$ (1.7 g, 5.2 mmol), and 1,4-dioxane (30 mL). After three cycles of vacuum/argon flush, the mixture was heated at 90° C. for 2.5 h. The mixture was cooled to room temperature and filtered. The filtrate was concentrated under reduced pressure and the resulting residue was purified by silica-gel column chromatography eluting with 50:1 dichloromethane/methanol to afford 180a as a yellow solid (800 mg, 36%). MS-ESI: [M+H]+ 295.1

Example 180b

1-Methyl-3-(6-methylpyrimidin-4-ylamino)-5-(4,4,5,5-tetramethyl-1,3,2-dioxaborolan-2-yl)pyridin-2(1H)-one 180b A 100-mL single-neck round-bottomed flask equipped with a magnetic stirrer and a reflux condenser was charged with 180a (1.0 g, 3.4 mmol), Pin$_2$B$_2$ (4.3 g, 17 mmol), Pd$_2$(dba)$_3$ (312 mg, 0.34 mmol), X-phos (324 mg, 0.68 mmol), potassium acetate (666 mg, 6.8 mmol), and dioxane (40 mL). After three cycles of vacuum/argon flush, the mixture was heated at 65° C. for 14 h. It was then cooled to room temperature and filtered. The filtrate was concentrated under reduced pressure and the resulting residue was washed with 3:1 petroleum ether/ethyl acetate (80 mL) to afford 180b as a yellow solid (600 mg, 50%). MS-ESI: [M+H]+ 343.2.

Example 180c

2-{4,4-Dimethyl-9-oxo-1,10-diazatricyclo[6.4.0.0$^{2,6}$]dodeca-2(6),7-dien-10-yl}-4-{1-methyl-5-[(6-methylpyrimidin-4-yl)amino]-6-oxo-1,6-dihydropyridin-3-yl}pyridine-3-carbaldehyde 180c A 50-mL single-neck round-bottomed flask equipped with a magnetic stirrer and a reflux condenser was charged with 180b (239 mg, 0.70 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (239 mg 0.70 mmol), Pd(dppf)Cl$_2$ (57 mg, 0.070 mmol), sodium acetate (115 mg, 1.4 mmol), K$_3$PO$_4$ (320 mg, 1.4 mmol), water (5 mL), and acetonitrile (15 mL). After three cycles of vacuum/argon flush, the mixture was heated at 100° C. for 3 h. After this time the reaction was filtered and the filtrate was concentrated under reduced pressure. The resulting residue was purified by silica-gel column chromatography eluting with 40:1 dichloromethane/methanol to afford 180c as a yellow solid (170 mg, 47%). MS-ESI: [M+H]+ 524.2.

Example 180

2-[3'-Hydroxymethyl-1-methyl-5-(6-methyl-pyrimidin-4-ylamino)-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 180

At 0° C., to a solution of 180c with water (1 mL). It was then concentrated under reduced pressure and the residue was purified by reverse-phase prep-HPLC to afford 180 (47 mg, 32%). MS-ESI: [M+H]+ 526.2. $^1$H NMR (500 MHz, CDCl$_3$) δ 8.82 (d, J=2.5 Hz, 1H), 8.68 (s, 1H), 8.51 (d, J=2.5 Hz, 1H), 8.02-8.00 (m, 2H), 7.35 (d, J=5.0 Hz, 1H), 6.84 (s, 1H), 6.62 (s, 1H), 5.13 (t, J=6.5 Hz, 1H), 4.67-4.52 (m, 2H), 4.29-4.15 (m, 3H), 3.88-3.86 (m, 1H), 3.72 (s, 3H), 2.57 (d, J=5.5 Hz, 2H), 2.51 (s, 2H), 2.43 (s, 3H), 1.28 (s, 6H).

Example 181a

4-[1-Methyl-5-({5-methyl-4H,5H,6H,7H-pyrazolo[1,5-a]pyrazin-2-yl}amino)-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridine-3-carbaldehyde 181a

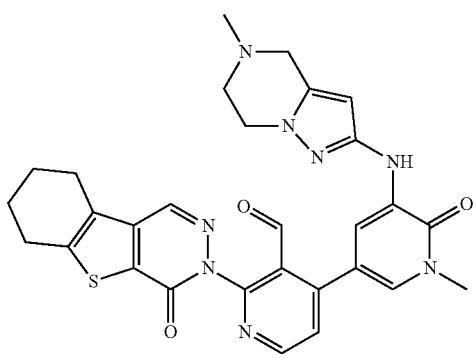

A 100-mL single-neck round-bottomed flask equipped with a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (210 mg, 0.60 mmol), 1-methyl-3-(5-methyl-4,5,6,7-tetrahydropyrazolo[1,5-a]pyrazin-2-ylamino)-5-(4,4,5,5-tetra-methyl-1,3,2-dioxaborolan-2-yl)pyridin-2(1H)-one 135a (346 mg, 0.90 mmol), Pd(dppf)Cl$_2$ (30 mg, 0.030 mmol), K$_3$PO$_4$ (270 mg, 1.2 mmol), sodium acetate trihydrate (180 mg, 1.2 mmol), water (6 drops), and acetonitrile (40 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 181a (300 mg, 88%) as a yellow brown solid. MS-ESI: [M+H]+ 569.3.

Example 181

3-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-6,7,8,9-tetrahydro-3H-benzo[4,5]thieno[2,3-d]pyridazin-4-one 181

A mixture of 181a (300 mg, 0.50 mmol) and NaBH$_4$ (60 mg, 1.5 mmol) in methanol (20 mL) was stirred at 30° C. for 1 h. The mixture was quenched with water and concentrated under reduced pressure. The residue was extracted with ethyl acetate (3×10 mL). The combined ethyl acetate extract was concentrated under reduced pressure and the residue was purified by reverse-phase prep-HPLC to afford 181 (100 mg, 35%). MS-ESI: [M+H]+ 571.2. $^1$H NMR (500 MHz, CHCl$_3$) δ 8.64 (d, J=5.0 Hz, 1H), 8.30 (s, 1H), 8.00 (d, J=2.0 Hz, 1H), 7.57 (d, J=2.0 Hz, 1H), 7.53 (d, J=5.0 Hz, 1H), 7.43 (s, 1H), 5.70 (s, 1H), 4.45-4.43 (m, 2H), 4.32 (bs, 1H), 4.11-4.09 (m, 2H), 3.71 (s, 3H), 3.63 (s, 2H), 2.99-2.97 (m, 2H), 2.93-2.91 (m, 2H), 2.88-2.86 (m, 2H), 2.50 (s, 3H), 2.00-1.98 (m, 4H).

Example 182a

4-{1-Methyl-6-oxo-5-[(pyrimidin-4-yl)amino]-1,6-dihydropyridin-3-yl}-2-{6-oxo-8-thia-4,5-diazatricyclo[7.4.0.0$^{2,7}$]trideca-1(9),2(7),3-trien-5-yl}pyridine-3-carbaldehyde 182a

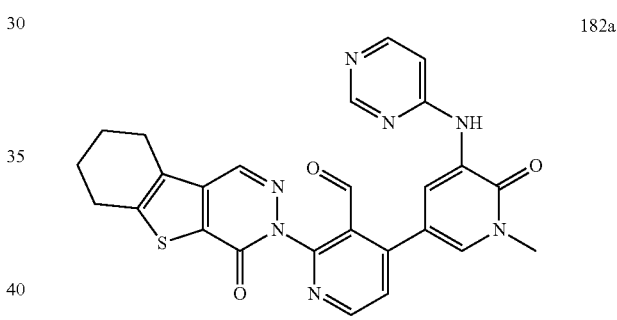

A 50-mL single-neck round-bottomed flask equipped with a magnetic stirrer and a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (345 mg, 1.0 mmol), 1-methyl-3-(pyrimidin-4-ylamino)-5-(4,4,5,5-tetramethyl-1,3,2-dioxaborolan-2-yl)pyridin-2 (1H)-one 143a (328 mg, 1.0 mmol), Pd(dppf)Cl$_2$ (82 mg, 0.10 mmol), sodium acetate (162 mg, 2.0 mmol), K$_3$PO$_4$ (424 mg, 2.0 mmol), and acetonitrile/water (20/1 mL). After three cycles of vacuum/argon flush, the mixture was heated at 100° C. for 3 h. It was then cooled to room temperature and filtered. The filtrate was concentrated under reduced pressure and the resulting residue was purified by silica-gel column chromatography eluting with 40:1 dichloromethane/methanol to afford 182a as a yellow solid (156 mg, 30%). MS-ESI: [M+H]+ 512.1.

Example 182

3-[3'-Hydroxymethyl-1-methyl-6-oxo-5-(pyrimidin-4-ylamino)-1,6-dihydro-[3,4']bipyridinyl-2'-yl]-6,7,8,9-tetrahydro-3H-benzo[4,5]thieno[2,3-d]pyridazin-4-one 182

At room temperature, to a solution of 182a (140 mg, 0.27 mmol) in methanol (5 mL) was added sodium borohydride (31 mg, 0.82 mmol). The reaction mixture was stirred for 20 minutes and quenched with water (1 mL). It was then concentrated under reduced pressure and the resulting residue was purified by silica-gel column chromatography eluting with 60:1 dichloromethane/methanol to afford 182 as a white solid (60 mg, 43%). MS-ESI: [M+H]⁺ 514.2. ¹H NMR (500 MHz, CDCl₃) δ 8.89 (d, J=2.5 Hz, 1H), 8.82 (s, 1H), 8.70 (d, J=5.5 Hz, 1H), 8.36 (d, J=6.5 Hz, 1H), 8.31 (s, 1H), 8.20 (s, 1H), 7.89 (d, J=2.0 Hz, 1H), 7.55 (d, J=5.0 Hz, 1H), 6.80 (d, J=9.5 Hz, 1H), 4.44-4.42 (m, 3H), 3.75 (s, 3H), 2.99-2.98 (m, 2H), 2.88-2.87 (m, 2H), 2.03-1.98 (m, 4H).

Example 183a 2-(10-Fluoro-1-oxo-3,4,6,7,8,9-hexahydropyrazino[1,2-a]indol-2(1H)-yl)-4-(1-methyl-6-oxo-5-(pyridin-2-ylamino)-1,6-dihydropyridin-3-yl)nicotinaldehyde 183a

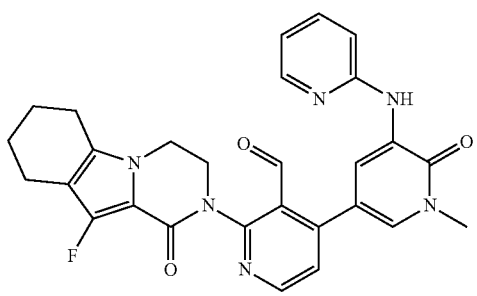

183a

A 100-mL flask equipped with a reflux condensor was charged with 4-chloro-2-(10-fluoro-1-oxo-3,4,6,7,8,9-hexahydropyrazino[1,2-a]indol-2(1H)-yl)nicotinaldehyde 134c (297 mg, 0.57 mmol), 1-methyl-3-(pyridin-2-ylamino)-5-(4,4,5,5-tetramethyl-1,3,2-dioxaborolan-2-yl)pyridin-2(1H)-one 178b (186 mg, 0.57 mmol), sodium acetate (90 mg, 1.1 mmol), K₃PO₄ (234 mg, 1.1 mmol), PdCl₂(dppf) (50 mg, 0.057 mmol), acetonitrile (25 mL), and water (1 mL). After bubbling nitrogen through the mixture for 30 minutes, it was heated at 100° C. under nitrogen atmosphere for 3 hours. It was then cooled to room temperature and filtered. The filtrate was concentrated under reduced pressure and the residue was purified by silica-gel column chromatography eluting with 20:1 methylene chloride/methanol to afford 183a (178 mg, 61%) as a brown solid. MS-ESI: [M+H]⁺ 513.3.

Example 183

10-fluoro-2-(3-(hydroxymethyl)-4-(1-methyl-6-oxo-5-(pyridin-2-ylamino)-1,6-dihydropyridin-3-yl)pyridin-2-yl)-3,4,6,7,8,9-hexahydropyrazino[1,2-a]indol-1(2H)-one 183

A mixture of 183a (160 mg, 0.31 mmol) and NaBH₄ (59 mg, 1.55 mmol) in methanol (20 mL) was stirred at 20° C. for 2 h. The reaction was then quenched with water and evaporated under reduced pressure. The residue was purified by reverse-phase prep-HPLC to afford 183 (42 mg, 26%) as an off-white solid. MS-ESI: [M+H]⁺ 515.3. ¹H NMR (500 MHz, DMSO-d₆) δ 8.74 (d, J=2.5 Hz, 1H), 8.65 (s, 1H), 8.50 (d, J=5.0 Hz, 1H), 8.18-8.17 (m, 1H), 7.61-7.58 (m, 1H), 7.53 (d, J=2.0 Hz, 1H), 7.36 (d, J=5.0 Hz, 1H), 7.31 (d, J=8.5 Hz, 1H), 6.81-6.79 (m, 1H), 4.95 (t, J=5.0 Hz, 1H), 4.49-4.40 (m, 2H), 4.22-4.14 (m, 2H), 4.10-4.05 (m, 1H), 3.87-3.85 (m, 1H), 3.62 (s, 3H), 2.64-2.60 (m, 1H), 2.57-2.53 (m, 1H), 2.43-2.41 (m, 2H), 1.81-1.75 (m, 2H), 1.71-1.67 (m, 2H).

Example 184a

1-Methyl-3-(pyrazin-2-ylamino)-5-(4,4,5,5-tetramethyl-1,3,2-dioxaborolan-2-yl)pyridin-2(1H)-one 184a

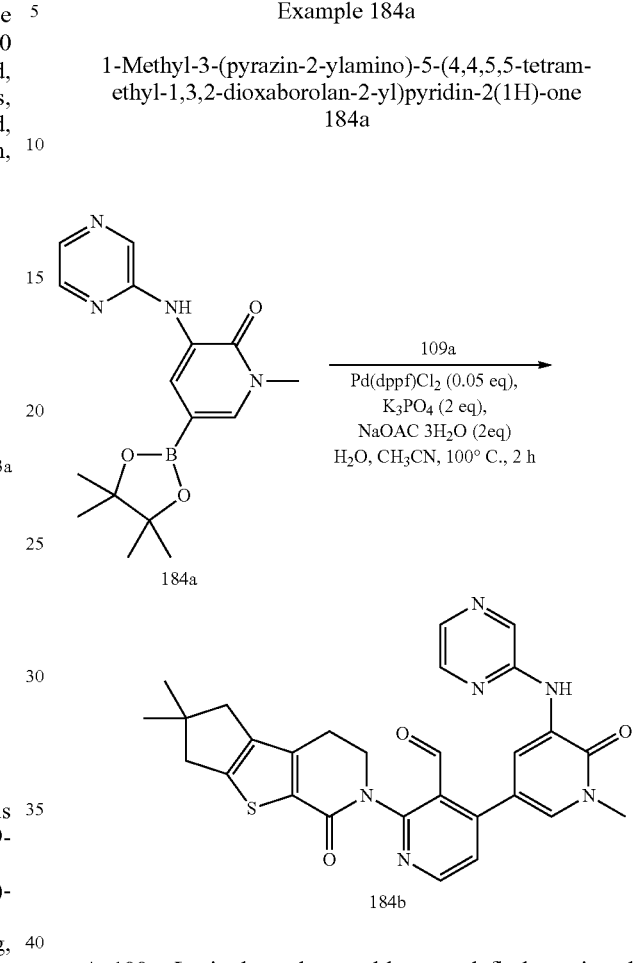

A 100-mL single-neck round-bottomed flask equipped with a magnetic stirrer and a reflux condenser was charged with 5-bromo-1-methyl-3-(pyrazin-2-ylamino)pyridin-2(1H)-one 162a (600 mg, 2.1 mmol), Pin₂B₂ (2540 mg, 10 mmol), Pd₂(dba)₃ (100 mg, 0.11 mmol), X-phos (100 mg, 0.25 mmol), potassium acetate (600 mg, 6.1 mmol), and dioxane (30 mL). After three cycles of vacuum/argon flush, the mixture was heated at 65° C. for 15 h. It was then cooled to room temperature and filtered. The filtrate was concentrated under reduced pressure and the resulting residue was washed by petroleum ether to afford 184a as a yellow solid (700 mg, 90%). MS-ESI: [M+H]⁺ 329.4

Example 184b

2-{4,4-Dimethyl-9-oxo-7-thia-10-azatricyclo[6.4.0.0²,⁶]dodeca-1(8),2(6)-dien-10-yl}-4-{1-methyl-6-oxo-5-[(pyrazin-2-yl)amino]-1,6-dihydropyridin-3-yl}pyridine-3-carbaldehyde 184b A 25-mL single-neck round-bottomed flask equipped with a reflux condenser was charged with 4-chloro-2-{4,4-dimethyl-9-oxo-7-thia-10-azatricyclo[6.4.0.0²,⁶]dodeca-1(8),2(6)-dien-10-yl}pyridine-3-carbaldehyde 109a (100 mg, 0.30 mmol), 184a (170 mg, 0.60 mmol), Pd(dppf)Cl₂ (12 mg, 0.015 mmol), K₃PO₄ (130 mg, 0.60 mmol), sodium acetate trihydrate (85 mg, 0.60 mmol), acetonitrile (10 mL), and water (6 drops). The system was evacuated and refilled with N₂. The reaction mixture was stirred at 100° C. for 2 h. It was then cooled to room temperature and filtered. The filtrate was concentrated under reduced pressure and the resulting residue was purified by silica-gel column chromatography eluting with 25:1 of dichloromethane/methanol to afford 184b (80 mg, 54%) as a yellow brown solid. MS-ESI: [M+H]⁺ 527.2.

Example 184

6-[3'-Hydroxymethyl-1-methyl-6-oxo-5-(pyrazin-2-ylamino)-1,6-dihydro-[3,4']bipyridinyl-2'-yl]-2,2-dimethyl-2,3,5,6-tetrahydro-1H,4H-8-thia-6-aza-cyclopenta[a]inden-7-one 184

A mixture of 184b (80 mg, 0.15 mmol) and NaBH₄ (18 mg, 0.45 mmol) in methanol (5 mL) was stirred at 30° C. for 2 h. The mixture was quenched with water and concentrated under reduced pressure. The residue was extracted with ethyl acetate (3×10 mL). The combined ethyl acetate extract was concentrated under reduced pressure and the residue was purified by reverse-phase prep-HPLC to afford 184 (24 mg, 35%) as a white solid. MS-ESI: [M+H]⁺ 529.3. ¹H NMR (500 MHz, CHCl₃) δ 8.73 (d, J=2.0 Hz, 1H), 8.54 (d, J=5.0 Hz, 1H), 8.29 (s, 1H), 8.14 (d, J=8.0 Hz, 2H), 8.02 (s, 1H), 7.96 (d, J=2.5 Hz, 1H), 7.37 (d, J=5.5 Hz, 1H), 4.86-4.83 (m, 1H), 4.71-4.68 (m, 1H), 4.46-4.41 (m, 1H), 4.32 (t, J=11.0 Hz, 1H), 3.85-3.81 (m, 1H), 3.74 (s, 3H), 2.99-2.94 (m, 2H), 2.81 (s, 2H), 2.61-2.51 (m, 2H), 1.30 (s, 6H).

Example 185a

5-Bromo-3-(imidazo[1,2-a]pyridin-7-ylamino)-1-methylpyrazin-2(1H)-one 185a

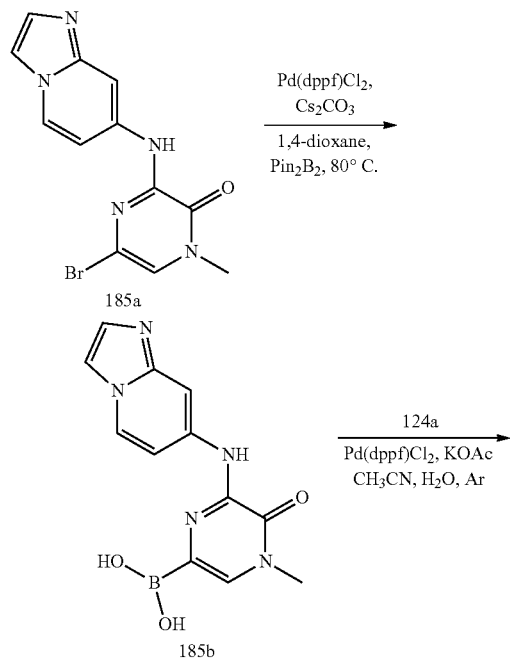

Example 185b 6-(Imidazo[1,2-a]pyridin-7-ylamino)-4-methyl-5-oxo-4,5-dihydropyrazin-2-ylboronic Acid 185b

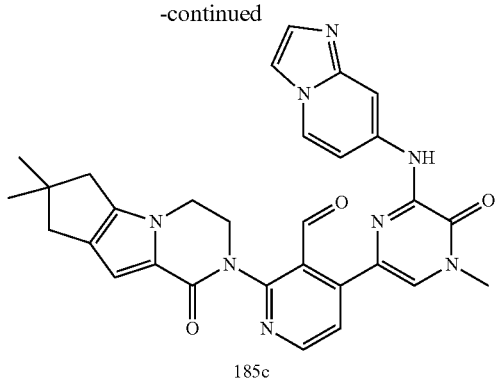

A 100-mL round-bottomed flask equipped with a reflux condenser was charged with imidazo[1,2-a]pyridin-7-amine (665 mg, 5.0 mmol), Cs₂CO₃ (3.26 g, 10 mmol), 3,5-dibromo-1-methylpyrazin-2(1H)-one (1.86 g, 7.0 mmol), Xantphos (289 mg, 0.50 mmol), Pd₂(dba)₃ (458 mg, 0.50 mmol), and 1,4-dioxane (30 mL). After bubbling nitrogen through the mixture for 30 minutes, it was heated at 100° C. under nitrogen atmosphere for 16 h. Analysis of the reaction mixture by LCMS showed little starting material remained. The reaction mixture was cooled to room temperature and filtered. The filtrate was diluted with dichloromethane (60 mL) and water (50 mL). The aqueous layer was separated and extracted with dichloromethane (3×20 mL). The combined organic layers was dried over Na₂SO₄, filtered, and concentrated under reduced pressure. The dark residue was purified by silica-gel column chromatography eluting with dichloromethane/methanol (60/1 to 30/1) to afford 185a (700 mg, 44%) as a light yellow solid. MS-ESI: [M+H]⁺ 320

A 100-mL round-bottomed flask equipped with a reflux condenser was charged with 185a (638 mg, 1.99 mmol), 4,4,4',4',5,5,5',5'-octamethyl-2,2'-bi(1,3,2-dioxaborolane) (Pin₂B₂, 2.54 mg, 10 mmol), 1,1'-bis(diphenylphosphino)ferrocenedichloropalladium(II) (163 mg, 0.18 mmol), Cs₂CO₃ (1.3 g, 3.98 mmol), and 1,4-dioxane (20 mL). After bubbling nitrogen through the mixture for 30 minutes, it was heated at 80° C. under nitrogen atmosphere for 3 h. The reaction mixture was cooled to room temperature and filtered. The filtrate was diluted with petroleum ether (150 mL) and ethyl acetate (15 mL). The resulting suspension was stirred at room temperature for 30 minutes. The solid was collected by filtration and further purified by silica-gel column chromatography eluting with dichloromethane/methanol (60/1 to 15/1) to afford 185b (400 mg, 70%) as an off-white solid. MS-ESI: [M+H]⁺ 286

Example 185c

2-{4,4-Dimethyl-9-oxo-1,10-diazatricyclo[6.4.0.0²,⁶]dodeca-2(6),7-dien-10-yl}-4-(6-{imidazo[1,2-a]pyridin-7-ylamino}-4-methyl-5-oxopyrazin-2-yl)pyridine-3-carbaldehyde 185c A 100-mL round-bottomed flask equipped with a magnetic stirrer and a reflux condenser was charged with 185b (400 mg, 1.40 mmol), 4-chloro-2-{4,4-dimethyl-9-oxo-1,10-diazatricyclo[6.4.0.0²,⁶]dodeca-2(6),7-dien-10-yl}pyridine-3-carbaldehyde 108a (192 mg, 0.56 mmol), potassium acetate (220 mg, 2.24 mmol), acetonitrile (20 mL), and water (0.5 mL). After bubbling nitrogen through the suspension for 30 minutes, 1,1'-bis(diphenylphosphino)Ferrocenedichloropalladium(II) (49 mg, 0.054 mmol) was added. The system was subjected to three cycles of vacuum/argon flush and heated at 80° C. for 3 h. It was then cooled to room temperature and filtered. The solid was washed with dichloromethane (2×20 mL). The combined filtrate was concentrated under reduced pressure and the residue was purified by silica-gel column chromatography eluting with dichloromethane/methanol (40:1 to 10:1) to afford 185c (90 mg, 29%) as a light yellow solid. MS-ESI: [M+H]⁺ 549

Example 185

2-{3-Hydroxymethyl-4-[6-(imidazo[1,2-a]pyridin-7-ylamino)-4-methyl-5-oxo-4,5-dihydro-pyrazin-2-yl]-pyridin-2-yl}-7,7-dimethyl-3,4,7,8-tetrahydro-2H,6H-cyclopenta[4,5]pyrrolo[1,2-a]pyrazin-1-one 185

To a solution of 185c (80 mg, 0.146 mmol) in methanol (5 mL) was added NaBH₄ (34 mg, 0.90 mmol) at room temperature. After the reaction was stirred for 1 h, LCMS indicated the reaction was complete. The reaction mixture was quenched with water (3 mL) and concentrated under reduced pressure. The residue was extracted with dichloromethane (3×10 mL). The combined organic layer was washed with brine (30 mL), dried over Na₂SO₄, filtered, and concentrated under reduced pressure. The residue was purified by reverse-phase prep-HPLC to afford 185 (49 mg, 61%) as light yellow solid. MS-ESI: [M+H]⁺ 551. ¹H NMR (500 MHz, DMSO-d₆) δ 9.67 (s, 1H), 8.57 (d, J=10.5 Hz, 1H), 8.51 (s, 1H), 8.41 (d, J=7.0 Hz, 1H), 7.77 (s, 1H), 7.75 (s, 1H), 7.63 (s, 1H), 7.46 (d, J=6.0 Hz, 1H), 7.42 (s, 1H), 6.59 (s, 1H), 5.04-5.02 (m, 1H), 4.67-4.64 (m, 1H), 4.519-4.481 (m, 1H), 4.31-4.20 (m, 3H), 3.88 (d, J=7.0 Hz, 1H), 3.58 (s, 3H), 2.63-2.55 (m, 2H), 2.44-2.42 (m, 2H), 1.23 (s, 6H).

Example 186a

5-Bromo-1-methyl-3-(pyridin-3-ylamino)pyrazin-2(1H)-one 186a

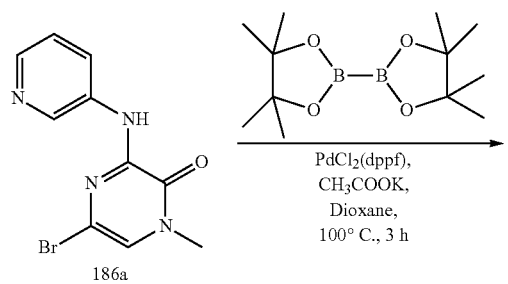

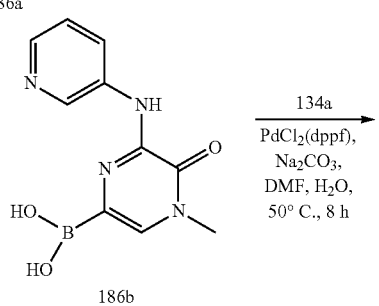

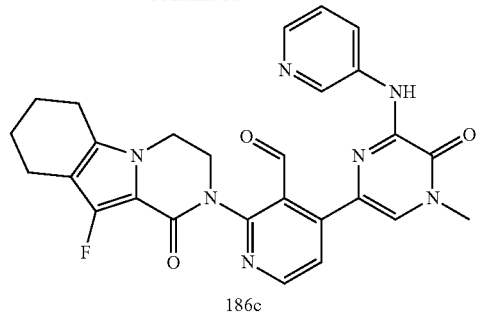

A 100-mL single-neck round-bottomed flask equipped with a magnetic stirrer and a reflux condenser was charged with pyridin-3-amine (940 mg, 10 mmol), 3,5-dibromo-1-methylpyrazin-2(1H)-one (5.4 g, 20 mmol), i-propanol (50 mL), and di-1-propylethylamine (10 mL). The mixture was heated at reflux for 5 h. After the completion of the reaction, it was cooled to room temperature. The solvent was removed under reduced pressure. The crude was purified by silica-gel column chromatography eluting with 30:1 dichloromethane/methanol to afford 186a (1.4 g, 50%) as a yellow solid. MS-ESI: [M+H]⁺ 281.6.

Example 186b

4-Methyl-5-oxo-6-(pyridin-3-ylamino)-4,5-dihydro-pyrazin-2-ylboronic acid 186b

A 250-mL round-bottomed flask equipped with a reflux condenser was charged with 186a (800 mg, 2.86 mmol), 4,4,4',4',5,5,5',5'-octamethyl-2,2'-bi(1,3,2-dioxaborolane) (2.18 g, 8.57 mmol), Pd (dppf) Cl₂ (204 mg, 0.28 mmol), potassium acetate (560 mg, 5.71 mmol), and dioxane (60 mL). After bubbling nitrogen through the mixture for 30 minutes, it was stirred at 100° C. for 3 h under nitrogen. The mixture was cooled to room temperature and filtered. The filtrate was evaporated under reduce pressure. The residue solid was washed with petroleum ether (2×30 mL) to afford 186b (406 mg, 58%) as a brown solid. MS-ESI: [M+H]⁺ 247.3.

Example 186c 2-(10-Fluoro-1-oxo-3,4,6,7,8,9-hexahydropyrazino[1,2-a]indol-2(1H)-yl)-4-(4-methyl-5-oxo-6-(pyridin-3-ylamino)-4,5-dihydropyrazin-2-yl)nicotinaldehyde 186c A 50-mL round-bottomed flask equipped with a reflux condenser was charged with 186b (127 mg, 0.52 mmol), 4-chloro-2-(10-fluoro-1-oxo-3,4,6,7,8,9-hexahydropyrazino[1,2-a]indol-2(1H)-yl)nicotinaldehyde 134c (180 mg, 0.52 mmol), Na₂CO₃ (110 mg, 1.04 mmol), PdCl₂(dppf) (38 mg, 0.052 mmol), DMF (12 mL), and water (1 mL). After bubbling nitrogen through the mixture for 30 minutes, it was heated at 50° C. for 8 hours under nitrogen. The reaction was then cooled to room temperature and concentrated under reduce pressure. The residue was purified by silica-gel column chromatography eluting with 30:1 methylene chloride/methanol to afford 186c (132 mg, 49%) as a brown solid. MS-ESI: [M+H]⁺ 514.3.

Example 186

10-fluoro-2-(3-(hydroxymethyl)-4-(4-methyl-5-oxo-6-(pyridin-3-ylamino)-4,5-dihydropyrazin-2-yl)pyridin-2-yl)-3,4,6,7,8,9-hexahydropyrazino[1,2-a]indol-1(2H)-one 186

To a solution of 186c (118 mg, 0.23 mmol) in methanol (15 mL) was added NaBH4 (27 mg, 0.70 mmol). The mixture was stirred at 20° C. for 2 h. The reaction was quenched with water and evaporated under reduced pressure. The residue was purified by reverse-phase prep-HPLC to afford 186 (33 mg, 28%) as a white solid. MS-ESI: [M+H]$^+$ 516.3. $^1$H NMR (500 MHz, DMSO-d$_6$) δ 9.78 (s, 1H), 8.54 (d, J=5.0 Hz, 1H), 8.39-8.37 (m, 2H), 8.06-8.04 (m, 2H), 7.76 (s, 1H), 7.59 (d, J=5.5 Hz, 1H), 4.97 (t, J=5.0 Hz, 1H), 4.68-4.65 (m, 1H), 4.51-4.47 (m, 1H), 4.25-4.19 (m, 2H), 4.10-4.05 (m, 1H), 3.91-3.88 (m, 1H), 3.58 (s, 3H), 2.66-2.60 (m, 1H), 2.57-2.53 (m, 1H), 2.44-2.42 (m, 2H), 1.82-1.75 (m, 2H), 1.71-1.67 (m, 2H).

Example 187a (4-(5-(5-(2,2-Dimethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 187a

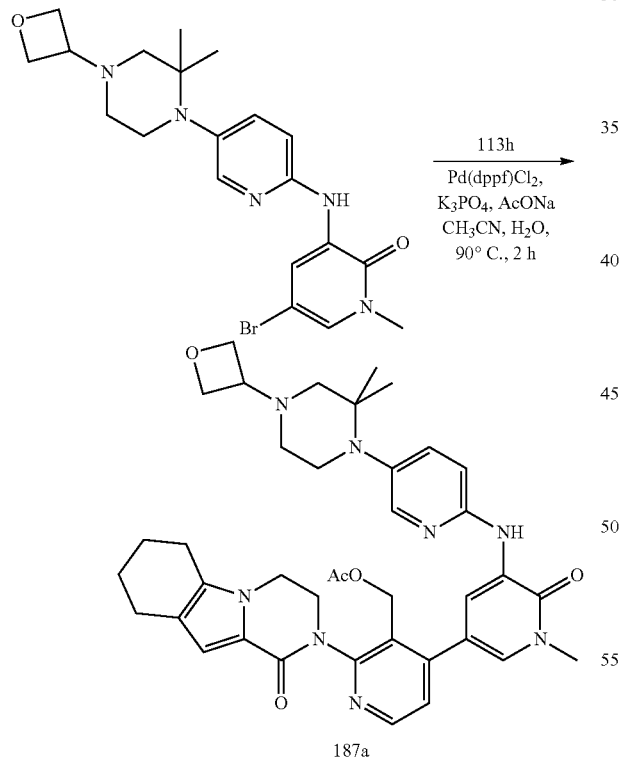

A 50-mL single-neck round-bottomed flask equipped with a magnetic stirrer and a reflux condenser was charged with 5-bromo-3-(5-(2,2-dimethyl-4-(oxetan-3-yl)piperazin-1-yl)pyridin-2-ylamino)-1-methylpyridin-2(1H)-one 190e (200 mg, 1.0 eq., 0.45 mmol), (2-(1-oxo-3,4,6,7,8,9-hexahydropyrazino[1,2-a]indol-2(1H)-yl)-4-(4,4,5,5-tetramethyl-1,3,2-dioxaborolan-2-yl)pyridin-3-yl)methyl acetate 113i (345 mg, 2 eq., 0.90 mmol), PdCl$_2$(dppf) (36 mg, 0.1 eq., 0.045 mmol), K$_3$PO$_4$ (191 mg, 2 eq., 0.90 mmol), sodium acetate (74 mg, 2.0 eq., 0.90 mmol), acetonitrile (15 mL), and water (0.1 mL). After three cycles of vacuum/argon flush, the mixture was stirred at 90° C. for 2 h. It was then cooled to room temperature and filtered. The filtrate was concentrated under reduced pressure and the resulting residue was purified by silica-gel column chromatography eluting with 50:1 dichloromethane/ethanol to afford 187a (100 mg, 31%) as yellow solid. MS-ESI: [M+H]$^+$ 707.4.

Example 187

2-(4-(5-(5-(2,2-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one 187

A 50-mL single-neck round-bottomed flask equipped with a magnetic stirrer was charged with 187a (100 mg, 1 eq., 0.14 mmol), lithium hydroxide (54 mg, 10 eq., 1.4 mmol), i-propanol (3 mL), THF (3 mL) and water (2 mL). The mixture was stirred at 30° C. for 1 h. It was then filtered and the filtrate was concentrated under reduced pressure. The residue was purified by reverse-phase prep-HPLC to afford 187 as a white solid (43 mg, 46%). MS-ESI: [M+H]$^+$ 665.3. $^1$H NMR (500 MHz, DMSO-d$_6$) δ 8.69 (d, J=2.0 Hz, 1H), 8.60 (s, 1H), 8.48 (d, J=5.0 Hz, 1H), 7.93 (d, J=2.0 Hz, 1H), 7.51 (d, J=1.5 Hz, 1H), 7.42-7.40 (m, 1H), 7.35 (d, J=5.0 Hz, 1H), 7.24 (d, J=8.5 Hz, 1H), 6.58 (s, 1H), 4.98 (brs, 1H), 4.54 (t, J=6.0 Hz, 2H), 4.46-4.38 (m, 4H), 4.25-3.85 (m, 4H), 3.60 (s, 3H), 3.38-3.35 (m, 1H), 3.03-2.54 (m, 4H), 2.47 (t, J=6.0 Hz, 2H), 2.32-2.12 (m, 4H), 1.79-1.67 (m, 4H), 0.97 (s, 6H).

Example 188a (2-{4,4-Dimethyl-9-oxo-1,10-diazatricyclo[6.4.0.0$^{2,6}$]dodeca-2(6),7-dien-10-yl}-4-{1-methyl-6-oxo-5-[(pyrazin-2-yl)amino]-1,6-dihydropyridin-3-yl}pyridin-3-yl)methyl Acetate 188a

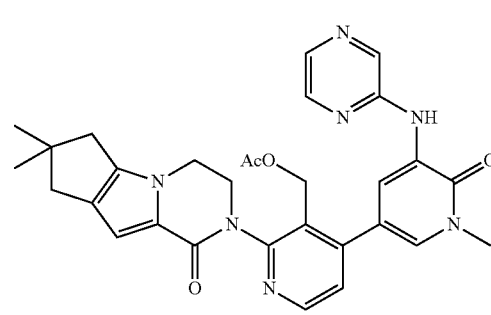

A 50-mL single-neck round-bottomed flask equipped with a reflux condenser was charged with 5-bromo-1-methyl-3-(pyrazin-2-ylamino)pyridin-2(1H)-one 162a (210 mg, 0.70 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (560 mg, 1.4 mmol), Pd(dppf)Cl$_2$ (70 mg, 0.035 mmol), K$_3$PO$_4$ (320 mg, 1.4 mmol), sodium acetate trihydrate (210 mg, 1.4 mmol), acetonitrile (10 mL), and water (6 drops). The system was evacuated and refilled with N$_2$. The reaction mixture was stirred at 100° C. for 2 h. It was then cooled to room temperature and filtered. The filtrate was concentrated under reduced pressure and the resulting residue was purified by silica-gel column chromatography eluting with 25:1 of dichloromethane/methanol to afford 188a (150 mg, 40%) as a yellow brown solid. MS-ESI: [M+H]$^+$ 554.2.

Example 188

2-[3'-Hydroxymethyl-1-methyl-6-oxo-5-(pyrazin-2-ylamino)-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one 188

A mixture of 188a (150 mg, 0.27 mmol) and lithium hydroxide (103 mg, 2.7 mmol) in i-propanol/THF (5:3, 8 mL) and water (2 mL) was stirred at 30° C. for 1 h. The mixture was evaporated in vacuo and the residue was extracted with ethyl acetate (2×20 mL). The combined ethyl acetate extract was concentrated under reduced pressure and the residue was purified by reverse-phase prep-HPLC to afford 188 (40 mg, 35%) as a white solid. MS-ESI: [M+H]$^+$ 512.3. $^1$H NMR (500 MHz, CHCl$_3$) δ 8.73 (d, J=2.0 Hz, 1H), 8.53 (d, J=5.0 Hz, 1H), 8.29 (s, 1H), 8.15-8.13 (m, overlap, 2H), 8.02-8.00 (m, 2H), 7.38 (d, J=5.0 Hz, 1H), 6.86 (s, 1H), 5.12 (s, 1H), 4.68-4.51 (m, 2H), 4.33-4.29 (m, 1H), 4.18 (t, J=5.5 Hz, 2H), 3.91-3.86 (m, 1H), 3.75 (s, 3H), 2.60-2.58 (m, 2H), 2.53 (s, 2H), 1.28 (s, 6H).

Example 189a tert-Butyl 4-(Pyrazin-2-yl)piperazine-1-carboxylate 189a

A 500-mL single-neck round-bottomed flask equipped with a magnetic stirrer and a reflux condenser was charged with DMSO (250 mL), tert-butyl piperazine-1-carboxylate (15.8 g, 85.0 mmol), 2-chloropyrazine (9.7 g, 85.0 mmol), and Cs$_2$CO$_3$ (55.3 g, 170 mmol). The mixture was heated at 60° C. for 3 days. After this time the reaction was cooled to room temperature. It was then filtered and the filtrate was evaporated under reduced pressure. The residue was purified by silica-gel column chromatography eluting with 5:1 petroleum ether/ethyl acetate to afford 189a (13.3 g, 60%) as a yellow solid. MS: [M+H]$^+$ 265.3

Example 189b tert-Butyl 4-(5-Bromopyrazin-2-yl)piperazine-1-carboxylate 189b

A 500-mL single-neck round-bottomed flask equipped with a magnetic stirrer and a reflux condenser was charged with acetonitrile (150 mL), 189a (3.0 g, 8.8 mmol), and N-bromosuccinimide (1.56 g, 8.8 mmol). The mixture was stirred at room temperature overnight. It was then concentrated under reduced pressure and the resulting residue was purified by silica-gel column chromatography eluting with 10:1 petroleum ether/ethyl acetate to afford 189b as a yellow solid (2.85 g, 73.4%). MS: [M+H]$^+$ 343.3. $^1$H NMR (500 MHz, (CD$_3$)$_2$CO) δ 8.03 (s, 1H), 7.94 (s, 1H), 3.48-3.46 (m, 4H), 3.42-3.40 (m, 4H), 1.33 (s, 9H).

Example 189c tert-Butyl 4-(5-(Diphenylmethyleneamino)pyrazin-2-yl)piperazine-1-carboxylate 189c A 250-mL single-neck round-bottomed flask equipped with a magnetic stirrer and a reflux condenser was charged with 189b (3.3 g, 9.6 mmol), diphenylmethanimine (1.74 g, 9.6 mmol), palladium diacetate (440 mg, 0.48 mmol), (R)-(+)-2,2'-bis(diphenylphosphino)-1,1'-binaphthyl (598 mg, 0.96 mmol), Cs$_2$CO$_3$ (6.2 g, 19.2 mmol), and 1,4-dioxane (80 mL). After three cycles of vacuum/argon flush, the mixture was heated at 115° C. for 64 h. It was then cooled to room temperature and filtered. The filtrate was concentrated under reduced pressure and the resulting residue was purified by silica-gel column chromatography eluting with 5:1 petroleum ether/ethyl acetate to afford 189c as a yellow solid (3.2 g, 75%). MS: [M+H]$^+$ 444.2.

Example 189d tert-Butyl 4-(5-Aminopyrazin-2-yl)piperazine-1-carboxylate 189d

To a solution of 189c (2.5 g, 5.6 mmol) in methanol (25 mL) was added sodium acetate (0.56 g, 6.8 mmol) and hydroxylamine hydrochloride (0.7 g, 10 mmol). The reaction mixture was stirred for 0.5 h. It was then concentrated under reduced pressure and the residue was purified by column chromatography eluting with 15:1 dichloromethane/methanol to afford 189d (1.3 g, 71%). MS: [M+H]$^+$ 280.3.

Example 189e tert-Butyl 4-(5-(5-Bromo-1-methyl-2-oxo-1,2-dihydropyridin-3-ylamino)pyrazin-2-yl)piperazine-1-carboxylate 189e A mixture of 189d (1.1 g, 3.94 mmol), 3,5-dibromo-1-methylpyridin-2(1H)-one (1.1 g, 3.94 mmol), palladium diacetate (45 mg, 0.20 mmol), (R)-(+)-2,2'-bis(diphenylphosphino)-1,1'-binaphthyl (245 mg, 0.39 mmol), and Cs$_2$CO$_3$ (2.6 g, 7.9 mmol) in 1,4-dioxane (150 mL) was heated at 120° C. for 2 hours. It was then cooled to room temperature and concentrated under reduced pressure. The residue was purified by column chromatography eluting with 30:1 dichloromethane/methanol to afford 189e (900 mg, 54%). MS: [M+H]$^+$ 465.1.

Example 189f

5-Bromo-1-methyl-3-(5-(piperazin-1-yl)pyrazin-2-ylamino)pyridin-2(1H)-one 189f

A mixture of 189e (1.0 g, 2.2 mmol) and 4.0 M HCl/dioxane (60 mL) was stirred at room temperature for 5 h. It was then concentrated under reduced pressure to afford crude 189f as a yellow solid (760 mg, 98%), which was used in the next step without further purification. MS: [M+H]$^+$ 395.1.

Example 189g

5-Bromo-1-methyl-3-(5-(4-(oxetan-3-yl)piperazin-1-yl)pyrazin-2-ylamino)pyridine-2(1H)-one 189g

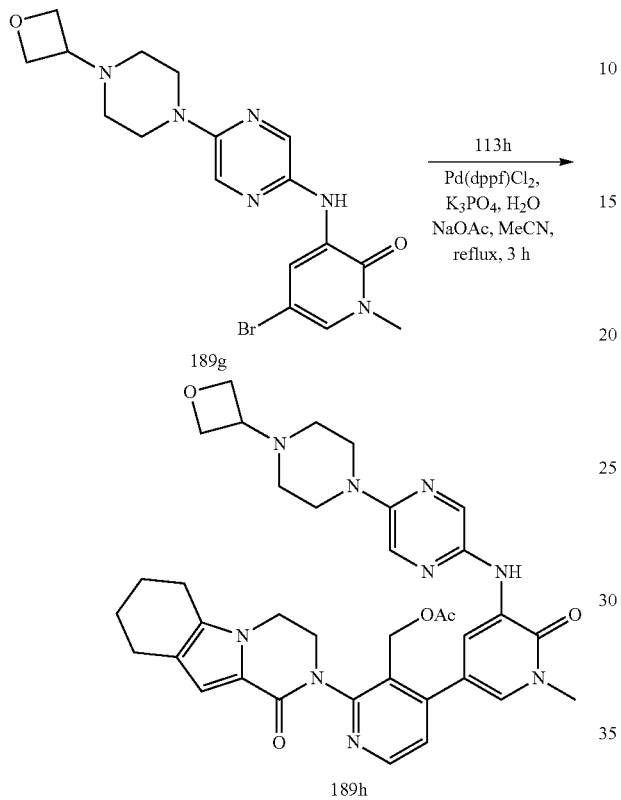

A mixture of 189f (740 mg, 2.0 mmol), oxetan-3-one (288 mg, 4.0 mmol), NaBH₃CN (315 mg, 5.0 mmol), and zinc chloride (680 mg, 5.0 mmol) in methanol (60 mL) was stirred at 50° C. for 5 hours. It was then quenched with water and concentrated under reduced pressure. The residue was extracted with dichloromethane three times. The combined extract was concentrated under reduced pressure to afford crude 189g as a yellow solid (660 mg, 78%), which was used in the next step without further purification. MS: [M+H]⁺ 423.1.

Example 189h (4-(1-Methyl-5-(5-(4-(oxetan-3-yl)piperazin-1-yl) pyrazin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 189h A 50-mL round-bottomed flask equipped with a reflux condenser was charged with 189g (180 mg, 0.43 mmol), 3-(acetoxymethyl)-2-(1-oxo-3,4,6,7,8,9-hexahydropyrazino[1,2-a]indol-2(1H)-yl)pyridin-4-ylboronic acid 113i (165 mg, 0.43 mmol), Pd(dppf)Cl₂ (35 mg, 0.043 mmol), sodium acetate (71 mg, 0.86 mmol), K₃PO₄ (194 mg, 0.86 mmol), acetonitrile (10 mL), and water (0.5 mL). After three cycles of vacuum/argon flush, the mixture was heated at 100° C. for 3 h. After this time the reaction was filtered and the filtrate was concentrated under reduced pressure. The resulting residue was purified by silica-gel column chromatography eluting with 40:1 dichloromethane/methanol to afford 189h as a yellow solid (100 mg, 34%). MS-ESI: [M+H]⁺ 680.3.

Example 189

2-(3-(hydroxymethyl)-4-(1-methyl-5-(5-(4-(oxetan-3-yl)piperazin-1-yl)pyrazin-2-ylamino)-6-oxo-1,6-dihydropyridin-3-yl)pyridin-2-yl)-3,4,6,7,8,9-hexahydropyrazino[1,2-a]indol-1(2H)-one 189

At room temperature, to a solution of 189h (90 mg, 0.13 mmol) in i-propanol/THF (1:1, 5 mL) and water (0.5 mL) was added lithium hydroxide (126 mg, 2.9 mmol). The reaction mixture was stirred at 35° C. for 0.5 h. It was then cooled to room temperature and filtered. The filtrate was concentrated under reduced pressure and the resulting residue was purified with by reverse-phase prep-HPLC to afford 189 (60 mg, 71%) as yellow solid. MS-ESI: [M+H]⁺ 638.3. ¹H NMR (500 MHz, CDCl₃) δ 8.48 (d, J=5.0 Hz, 1H), 8.43 (d, J=2.0 Hz, 1H), 7.98 (s, 1H), 7.82 (d, J=1.5 Hz, 1H), 7.80 (s, 1H), 7.78 (s, 1H), 7.33 (d, J=5.0 Hz, 1H), 6.89 (s, 1H), 5.04-5.01 (m, 1H), 4.72-4.50 (m, 6H), 4.32-4.30 (m, 1H), 4.15-4.09 (m, 2H), 3.88-3.86 (m, 1H), 3.72 (s, 3H), 3.57-3.49 (m, 5H), 2.61-2.43 (m, 8H), 1.92-1.78 (m, 4H).

Example 190a tert-Butyl 3,3-Dimethyl-4-(6-nitropyridin-3-yl)piperazine-1-carboxylate 190a

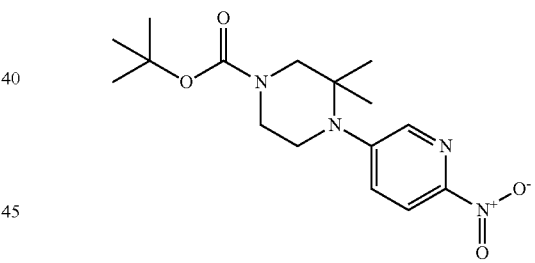

A 100-mL single-neck round-bottomed flask equipped with a magnetic stirrer and a reflux condenser was charged with 5-bromo-2-nitropyridine (5.6 g, 28.0 mmol), tert-butyl 3,3-dimethyl-4-piperazine-1-carboxylate (3.0 g, 14.0 mmol), cesium carbonate (9.1 g, 28 mmol), and 1,4-dioxane (50 mL). After bubbling nitrogen through the resulting solution for 30 min, Binap (870 mg, 1.4 mmol) and tris(dibenzylideneacetone)-dipalladium(0) (1.2 g, 1.4 mmol) were added. The reaction mixture was subjected to three cycles of vacuum/argon flush and stirred at 120° C. for 24 h. After this time the reaction was cooled to room temperature, filtered and the filtrate was partitioned between ethyl acetate (200 mL) and water (50 mL). The aqueous layer was separated and extracted with ethyl acetate (3×50 mL). The combined organic layers were washed with brine (50 mL) and dried over sodium sulfate. The drying agent was removed by filtration and the filtrate was concentrated under reduced pressure. The residue was purified by silica-gel column chromatography eluting with 5:1 petroleum ether/ethyl acetate to afford 190a (1.27 g, 27%). LCMS: [M+H]+ 337.2.

Example 190b tert-Butyl 4-(6-Aminopyridin-3-yl)-3,3-dimethylpiperazine-1-carboxylate 190b A 50-mL round-bottomed flask was purged with nitrogen and charged with tert-butyl 3,3-dimethyl-4-(6-nitropyridin-3-yl)piperazine-1-carboxylate 190a (1100 mg, 3.2 mmol), 10% palladium on carbon (10% wet, 110 mg), and methanol (20 mL). It was then evacuated, charged with hydrogen gas, and stirred at room temperature for 5 h. The hydrogen was evacuated and nitrogen was charged into the flask. The catalyst was removed by filtration through a pad of diatomaceous earth filter agent (CELITE®, Imerys Minerals California, Inc.) and the filtrate was concentrated under reduced pressure to afford 190b (950 mg, 94%). LCMS: [M+H]+ 307.3

Example 190c tert-Butyl 4-(6-(5-Bromo-1-methyl-2-oxo-1,2-dihydropyridin-3-ylamino)pyridin-3-yl)-3,3-dimethylpiperazine-1-carboxylate 190c A 100-mL single-neck round-bottomed flask equipped with a magnetic stirrer and a reflux condenser was charged with tert-butyl 4-(6-aminopyridin-3-yl)-3,3-dimethylpiperazine-1-carboxylate 190b (950 mg, 3.1 mmol), 3,5-dibromo-1-methylpyridin-2(1H)-one (1240 mg, 4.6 mmol), 1,4-dioxane (30 mL), and cesium carbonate (2015 mg, 6.2 mmol). After bubbling nitrogen through the resulting solution for 5 min, Xantphos (179 mg, 0.31 mmol) and tris(dibenzylideneacetone)dipalladium(0) (283 mg, 0.31 mmol) were added. The reaction mixture was subjected to three cycles of vacuum/argon flush and heated at reflux for 10 h. After this time the reaction was cooled to room temperature and filtered. The filtrate was partitioned between ethyl acetate (50 mL) and water (10 mL). The aqueous layer was separated and extracted with ethyl acetate (3×20 mL). The combined organic layer was washed with brine (30 mL) and dried over sodium sulfate. The drying agent was removed by filtration and the filtrate was concentrated under reduced pressure. The residue was purified by silica-gel column chromatography eluting with 4:1 petroleum ether/ethyl acetate to afford 190c (1.21 g, 79%). LCMS: [M+H]+ 492.1.

Example 190d

5-Bromo-3-(5-(2,2-dimethylpiperazin-1-yl)pyridin-2-ylamino)-1-methylpyridin-2(1H)-one 190d To a solution of tert-butyl 4-(6-(5-bromo-1-methyl-2-oxo-1,2-dihydropyridin-3-ylamino)pyridin-3-yl)-3,3-dimethylpiperazine-1-carboxylate 190c (1.19 g, 1.9 mmol) in dichloromethane (20 mL) was added 3M HCl in diethyl ether (15 mL). The reaction mixture was stirred at room temperature for 4 h. It was then concentrated under reduced pressure to afford 190d (900 mg, 95%). LCMS: [M+H]+ 392.1.

Example 190e

5-Bromo-3-(5-(2,2-dimethyl-4-(oxetan-3-yl)piperazin-1-yl)pyridin-2-ylamino)-1-methylpyridin-2(1H)-one 190e A mixture of 5-bromo-3-(5-(2,2-dimethylpiperazin-1-yl)pyridin-2-ylamino)-1-methyl-pyridin-2(1H)-one 190d (900 mg, 2.3 mmol), oxetan-3-one (497 mg, 6.9 mmol), NaBH₃CN (435 mg, 6.9 mmol), and zinc chloride (311 mg, 2.3 mmol) in methanol (30 mL) was stirred at 50° C. for 4 hours. It was then concentrated under reduced pressure. Water (10 mL) was added to the residue and the mixture was extracted with chloroform (3×50 mL). The combined organic layer was concentrated under reduced pressure. The residue was purified by silica-gel column-chromatography eluting with 50:1 dichloromethane/methanol to afford 190e (800 mg, 78%). LCMS: [M+H]+ 448.1. ¹H NMR (500 MHz, CDCl₃) δ 8.65 (d, J=2.0 Hz, 1H), 8.11 (d, J=2.5 Hz, 1H), 7.85 (s, 1H), 7.37-7.34 (m, 1H), 6.96 (d, J=2.5 Hz, 1H), 6.72 (d, J=8.5 Hz, 1H), 4.69-4.61 (m, 4H), 3.60 (s, 3H), 3.50-3.14 (m, 3H), 2.43-2.17 (m, 4H), 1.06 (s, 6H).

Example 190f 2-(4-Chloro-3-(hydroxymethyl)pyridin-2-yl)-3,4,6,7,8,9-hexahydropyrazino[1,2-a]indol-1(2H)-one 190f

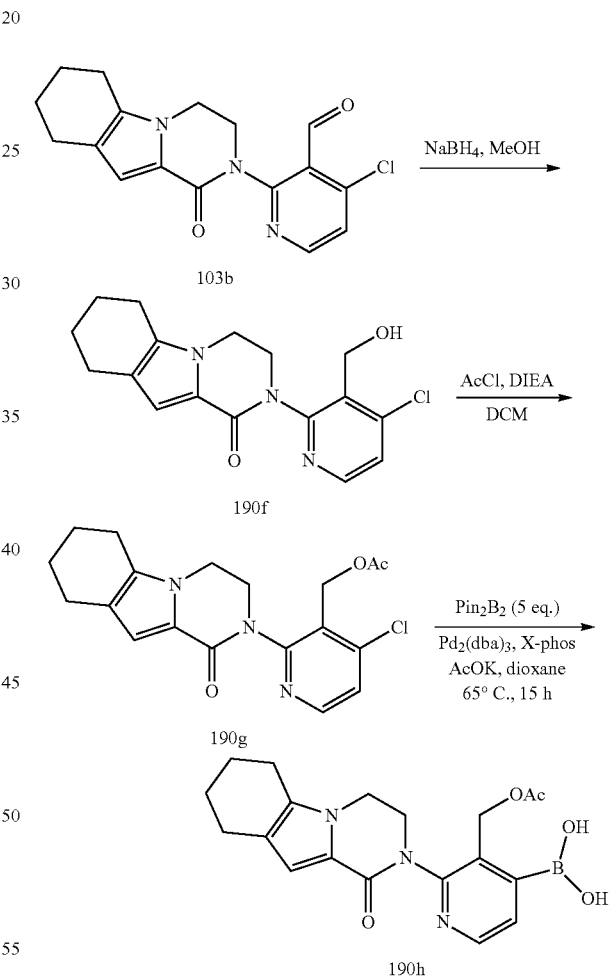

To a solution of 4-chloro-2-(1-oxo-3,4,6,7,8,9-hexahydropyrazino[1,2-a]indol-2(1H)-yl)-nicotinaldehyde 103b (1.0 g, 3.0 mmol) in methanol (30 mL) was added sodium borohydride (380 mg, 9.0 mmol) at 10° C. The reaction mixture was stirred for 30 minutes and quenched with water (10 mL). It was then concentrated under reduced pressure and the residue was dissolved in dichloromethane (50 mL). The mixture was washed with water (10 mL), dried over anhydrous Na₂SO₄, filtered, and evaporated under reduced pressure to afford 190f as a yellow solid (900 mg, 90%). MS-ESI: [M+H]+ 332.

Example 190g (4-Chloro-2-(1-oxo-3,4,6,7,8,9-hexahydropyrazino
[1,2-a]indol-2(1H)-yl)pyridine-3-yl)methyl Acetate
190g To a mixture of 2-(4-chloro-3-(hydroxymethyl)pyridin-2-yl)-3,4,6,7,8,9-hexahydropyrazino[1,2-a]indol-1(2H)-one 190f (900 mg, 2.7 mol) and triethylamine (900 mg, 9.0 mol) in dichloromethane (25 mL) was added dropwise acetyl chloride (600 mg, 6.0 mol) while stirring at room temperature. The reaction mixture was stirred for 1 h and concentrated under reduced pressure. The residue was purified by silica-gel column chromatography eluting with dichloromethane to afford 190g as white solid (950 mg, 94%). MS-ESI: [M+H]$^+$ 374.

Example 190h (4-Chloro-2-(1-oxo-3,4,6,7,8,9-hexahydropyrazino
[1,2-a]indol-2(1H)-yl)pyridin-3-yl)methyl Acetate
190h A 100-mL single-neck round-bottomed flask equipped with a magnetic stirrer and a reflux condenser was charged with (4-chloro-2-(1-oxo-3,4,6,7,8,9-hexahydro-pyrazino[1,2-a]indol-2(1H)-yl)pyridin-3-yl)methyl acetate 190g (950 mg, 2.5 mmol), Pin$_2$B$_2$(4,4,4',4',5,5,5',5'-octamethyl-2,2'-bi(1,3,2-dioxaborolane) (1.6 g, 2.0 eq., 5 mmol), Pd$_2$(dba)$_3$ (230 mg, 0.1 eq., 0.25 mmol), X-phos (232 mg, 0.2 eq., 0.50 mmol), potassium acetate (735 mg, 3 eq., 7.5 mmol), and dioxane (20 mL). After three cycles of vacuum/argon flush, the mixture was heated at 65° C. for 15 h. It was then cooled to room temperature and filtered. The filtrate was concentrated under reduced pressure and the resulting residue was washed with 3:1 petroleum ether/ethyl acetate to afford 190h as yellow solid (950 mg, 87%). MS-ESI: [M+H]$^+$ 383.

Example 190i (4-(5-(5-(2,2-Dimethyl-4-(oxetan-3-yl)piperazin-1-yl)pyridin-2-ylamino)-1-methyl-6-oxo-1,6-dihydro-pyridin-3-yl)-2-(1-oxo-3,4,6,7,8,9-hexahydropy-razino[1,2-a]indol-2(1H)-yl)pyridin-3-yl)methyl
Acetate 190i

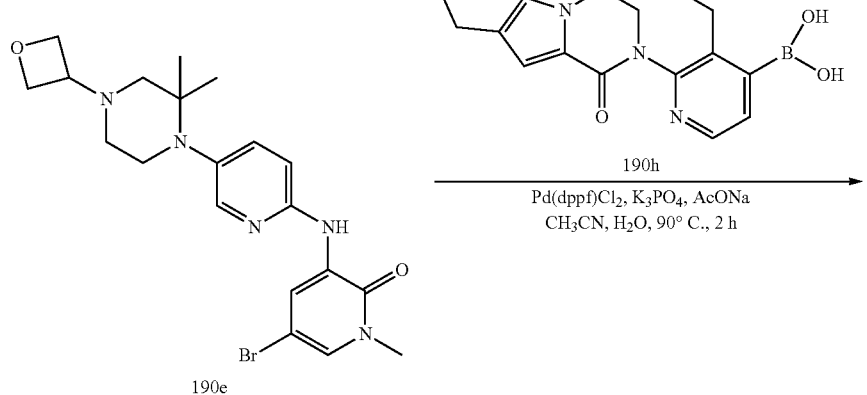

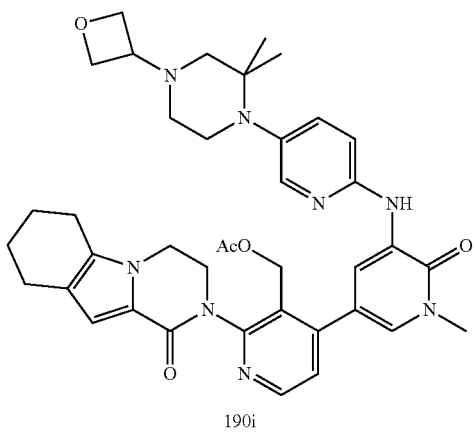

A 50-mL single-neck round-bottomed flask equipped with a magnetic stirrer and a reflux condenser was charged with 5-bromo-3-(5-(2,2-dimethyl-4-(oxetan-3-yl)piperazin-1-yl)pyridin-2-ylamino)-1-methylpyridin-2(1H)-one 190e (200 mg, 1.0 eq., 0.45 mmol), (2-(1-oxo-3,4,6,7,8,9-hexahydropyrazino[1,2-a]indol-2(1H)-yl)-4-(4,4,5,5-tetramethyl-1,3,2-dioxaborolan-2-yl)pyridin-3-yl)methyl acetate 190h (345 mg, 2 eq., 0.90 mmol), PdCl$_2$(dppf) (36 mg, 0.1 eq., 0.045 mmol), K$_3$PO$_4$ (191 mg, 2 eq., 0.90 mmol), sodium acetate (74 mg, 2.0 eq., 0.90 mmol), acetonitrile (15 mL), and water (0.1 mL). After three cycles of vacuum/argon flush, the mixture was stirred at 90° C. for 2 h. It was then cooled to room temperature and filtered. The filtrate was concentrated under reduced pressure and the resulting residue was purified by silica-gel column chromatography eluting with 50:1 dichloromethane/ethanol to afford 190i (100 mg, 31%) as yellow solid. MS-ESI: [M+H]$^+$707.4.

Example 190

2-[4-[5-[[5-[2,2-dimethyl-4-(oxetan-3-yl)piperazin-1-yl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one 190

A 50-mL single-neck round-bottomed flask equipped with a magnetic stirrer was charged with (4-(5-(5-(2,2-dimethyl-4-(oxetan-3-yl)piperazin-1-yl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 190i (100 mg, 1 eq., 0.14 mmol), lithium hydroxide (54 mg, 10 eq., 1.4 mmol), i-propanol (3 mL), THF (3 mL) and water (2 mL). The mixture was stirred at 30° C. for 1 h. It was then filtered and the filtrate was concentrated under reduced pressure. The residue was purified by reverse-phase prep-HPLC to afford 190 as a white solid (43 mg, 46%). MS-ESI: [M+H]$^+$ 665.3. $^1$H NMR (500 MHz, DMSO-d$_6$) δ 8.69 (d, J=2.0 Hz, 1H), 8.60 (s, 1H), 8.48 (d, J=5.0 Hz, 1H), 7.93 (d, J=2.0 Hz, 1H), 7.51 (d, J=1.5 Hz, 1H), 7.42-7.40 (m, 1H), 7.35 (d, J=5.0 Hz, 1H), 7.24 (d, J=8.5 Hz, 1H), 6.58 (s, 1H), 4.98 (brs, 1H), 4.54 (t, J=6.0 Hz, 2H), 4.46-4.38 (m, 4H), 4.25-3.85 (m, 4H), 3.60 (s, 3H), 3.38-3.35 (m, 1H), 3.03-2.54 (m, 4H), 2.47 (t, J=6.0 Hz, 2H), 2.32-2.12 (m, 4H), 1.79-1.67 (m, 4H), 0.97 (s, 6H)

Example 191a

N-tert-Butyl-4,5,6,7-tetrahydrobenzo[b]thiophene-2-carboxamide 191a

A mixture of 4,5,6,7-tetrahydrobenzo[b]thiophene-2-carboxylic acid (500 g, 2.75 mol, 1.0 equiv) and thionyl chloride (655 g, 5.5 mol, 2.0 equiv) was heated under reflux for 3 h. Excess thionyl chloride was removed by distillation under reduced pressure. The residue was taken up in dichloromethane (1.0 L) and a solution of tert-butylamine (402 g, 5.5 mol, 2.0 equiv) in dichloromethane (500 mL) was added with stirring while the temperature of the mixture being kept below 10° C. The resulting solution was stirred at 25° C. for 16 h. Most of the solvent was removed under reduced pressure. The residue was chilled in an ice-bath and 2M KOH solution was introduced slowly to adjust the pH to 11 with stirring. The suspension was filtered and the solid collected, washed three times with water, and dried in vacuum to afford 191a as a white solid (580 g, 80%, over two steps). MS: [M+H]$^+$ 238. $^1$H NMR (500 MHz, CDCl$_3$) δ 7.02 (s, 1H), 5.77 (s, 1H), 2.65 (t, J=6.0 Hz, 1H), 2.47 (t, J=6.0 Hz, 1H), 1.74-1.70 (m, 4H), 1.35 (s, 9H).

Example 191c

N-tert-Butyl-3-(diazenylmethyl)-4,5,6,7-tetrahydrobenzo-[b]thiophene-2-carboxamide 191c A solution of 191a (100 g, 0.42 mol, 1.0 equiv) in THF (500 mL) was slowly added to n-butyl lithium (672 mL, 2.5M in THF, 1.68 mol, 4.0 equiv) at −78° C. under argon protection. The mixture was stirred for 2 h. N,N-Dimethylformamide (306 g, 4.2 mol, 10.0 equiv) was added to the mixture while the temperature being sustained at −78° C. After another 2.0 h, the reaction mixture was quenched by addition of methanol (500 mL) at −78° C. It was stirred for 0.50 h at room temperature to afford 191b in situ. Then 80% aqueous hydrazine hydrate (131 g, 2.1 mol) was added and the mixture was refluxed at 65° C. overnight. The organic solvent was removed under reduced pressure. The residue was filtered and the resulting yellow solid was washed with water. The solid was dried in vacuum to afford 191c, which was used for the next step without further purification. MS: [M+H]$^+$ 280.

Example 191d

8-Thia-4,5-diazatricyclo[7.4.0.0$^{2,7}$]trideca-(9),2(7),3-trien-6-one 191d

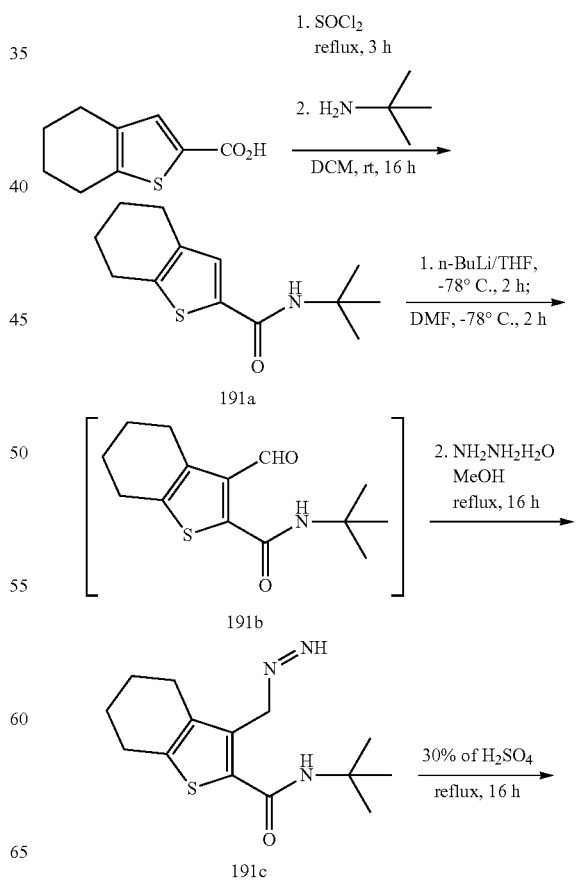

-continued

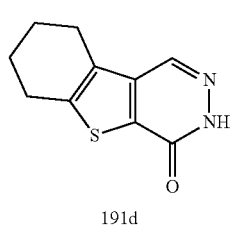

191d

A mixture of N-tert-butyl-3-(diazenylmethyl)-4,5,6,7-tetrahydrobenzo[b]thiophene-2-carboxamide 191c (40 g, 144 mmol) in $H_2SO_4$ (30% aqueous, 3 L) was refluxed at 105° C. for 24 h. It was then filtered and the filtrate was extracted with dichloromethane (3×1 L). The combined extract was dried over $Na_2SO_4$ and evaporated under reduced pressure. The residue was purified by silica-gel column chromatography eluting with 100:1 dichloromethane/methanol to afford 191d as a white solid (9.0 g, 31%). MS: $[M+H]^+$ 207. $^1H$ NMR (500 MHz, $CDCl_3$) δ 8.15 (s, 1H), 2.96-2.94 (m, 2H), 2.86-2.84 (m, 2H), 1.96-1.94 (m, 4H).

Example 191e (3S)-tert-Butyl 3-Methyl-4-(6-nitropyridin-3-yl)piperazine-1-carboxylate 191e Following the procedure described for compound 101g and starting with (3S)-tert-butyl 3-methylpiperazine-1-carboxylate (10.0 g, 50 mmol) and 5-bromo-2-nitropyridine (10.5 g, 50 mmol) afforded 191e as a yellow solid (8.05 g, 50%). MS-ESI: $[M+H]^+$ 323

Example 191f (3S)-tert-Butyl 4-(6-Aminopyridin-3-yl)-3-methylpiperazine-1-carboxylate 191f Following the procedure described for compound 101h and starting with (3S)-tert-butyl 3-methyl-4-(6-nitropyridin-3-yl)piperazine-1-carboxylate 191e (5.8 g, 18 mmol) afforded 191f as a brown solid (4.9 g, 93%). MS-ESI: $[M+H]^+$ 293

Example 191g (3S)-tert-Butyl 4-(6-(5-Bromo-1-methyl-2-oxo-1,2-dihydropyridin-3-ylamino) pyridine-3-yl)-3-methylpiperazine-1-carboxylate 191g Following the procedure described for compound 101i and starting with (3S)-tert-butyl-3-methyl-4-(6-nitropyridin-3-yl)piperazine-1-carboxylate 191f (4.0 g, 13.7 mmol) and 3,5-dibromo-1-methylpyridin-2(1H)-one (5.5 g, 20.6 mmol) afforded 191g as a yellow solid (5.4 g, 83%). MS-ESI: $[M+H]^+$ 478

Example 191h (3S)-5-Bromo-1-methyl-3-(5-(2-methylpiperazin-1-yl)pyridin-2-ylamino)pyridine-2(1H)-one 191h

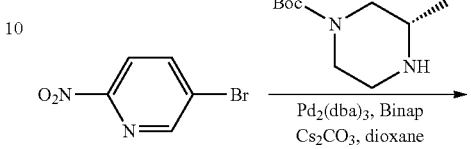

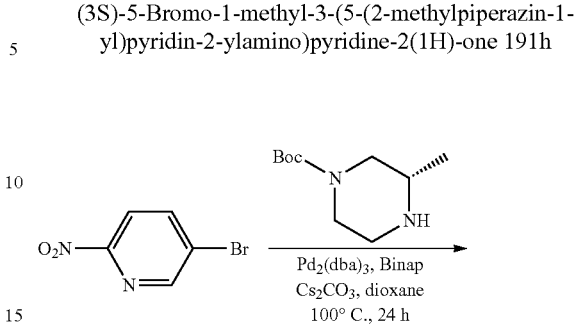

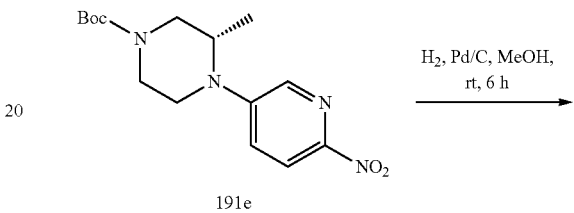

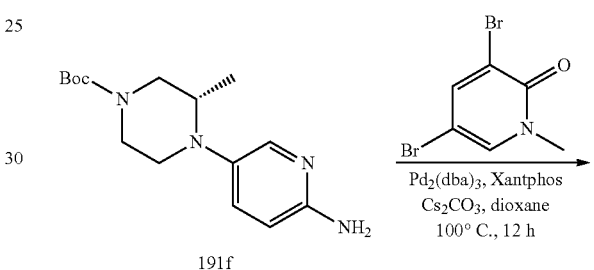

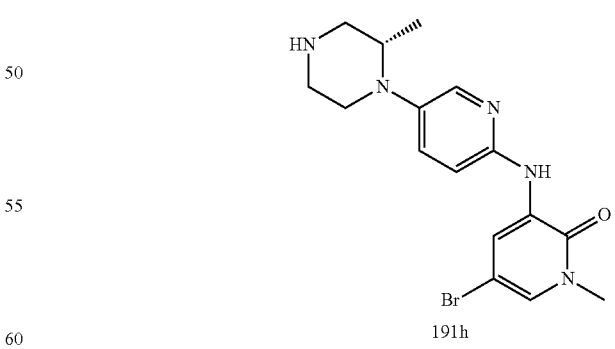

Following the procedure described for compound 101j and starting with (3S)-tert-butyl 4-(6-(5-bromo-1-methyl-2-oxo-1,2-dihydropyridin-3-ylamino)pyridine-3-yl)-3-methyl-piperazine-1-carboxylate 191g (3.1 g, 6.5 mmol) afforded 191h as a yellow solid (2.3 g, 94%). MS-ESI: $[M+H]^+$ 378.

Example 191i (S)-5-Bromo-1-methyl-3-(5-(2-methyl-4-(oxetan-3-yl)piperazin-1-yl)pyridin-2-ylamino)pyridin-2(1H)-one 191i A mixture of (S)-5-bromo-1-methyl-3-(5-(2-methylpiperazin-1-yl)pyridin-2-ylamino)pyridin-2(1H)-one 191h (40.0 g, 106 mmol), oxetan-3-one (11.4 g, 159 mmol), NaBH$_3$CN (10.0 g, 159 mmol), and zinc chloride (21.3 g, 159 mmol) in methanol (700 mL) was stirred at 50° C. for 5 hours. The mixture was added to water (100 mL) and concentrated under reduced pressure. The residue was extracted with dichloromethane (200 mL×3). The combined organic layer was concentrated under reduced pressure and the residue was purified by silica-gel column chromatography eluting with 40:1 dichloromethane/methanol to afford 191i (35 g, 73%). MS: [M+H]$^+$ 434.

Example 191j (3S)-1-Methyl-3-(5-(2-methyl-4-(oxetan-3-yl)piperazin-1-yl)-pyridin-2-ylamino)-5-(4,4,5,5-tetramethyl-1,3,2-dioxaborolan-2-yl)pyridin-2(1H)-one 191j

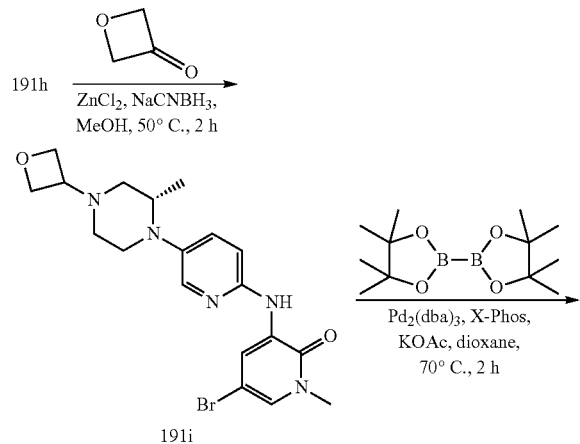

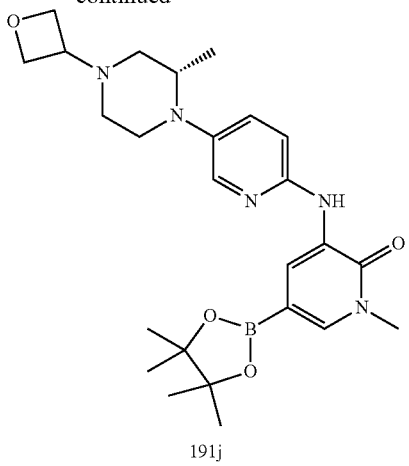

A 100-mL single-neck round-bottomed flask equipped with a magnetic stirrer and a reflux condenser was charged with (S)-tert-butyl-4-(6-(5-bromo-1-methyl-2-oxo-1,2-dihydropyridin-3-ylamino)pyridine-3-yl)-3-methylpiperazine-1-carboxylate 191i (1.0 g, 1.0 eq., 2.3 mmol), Pin$_2$B$_2$ (1.46 g, 2.50 eq., 5.75 mmol), Pd$_2$(dba)$_3$ (105 mg, 0.05 eq., 0.125 mmol), X-Phos (93 mg, 0.1 eq., 0.23 mmol), potassium acetate (676 mg, 3.0 eq., 6.9 mmol), and dioxane (50 mL). After three cycles of vacuum/argon flush, the mixture was heated at 90° C. for 4 h. It was then cooled to room temperature and filtered. The filtrate was concentrated under reduced pressure and the resulting residue was washed with 3:1 petroleum ether/ethyl acetate (80 mL) to afford 191j as yellow solid (1.0 g, 90%). MS: [M+H]$^+$ 482.

Example 191k

4-[1-Methyl-5-({5-[(2S)-2-methyl-4-(oxetan-3-yl)piperazin-1-yl]pyridin-2-yl}amino)-6-oxo-1,6-dihydropyridin-3-yl]-2-{6-oxo-8-thia-4,5-diaza-tricyclo[7.4.0.0$^{2,7}$]tri-deca-1(9),2(7),3-trien-5-yl}pyridine-3-carbaldehyde 191k

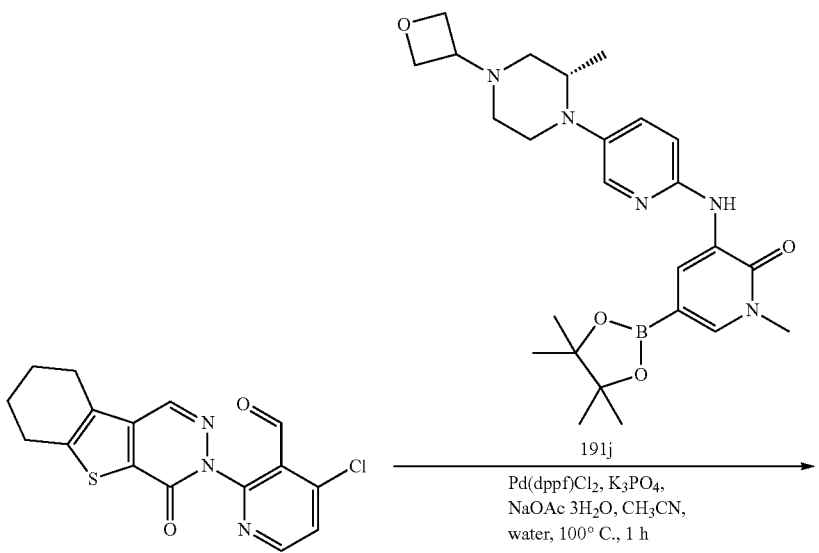

-continued

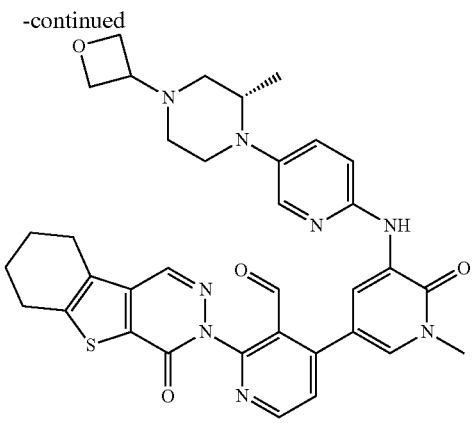

191k

A 50-mL round-bottomed flask equipped with a reflux condenser was charged with (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (168 mg, 0.35 mmol), 4-chloro-2-{6-oxo-8-thia-4,5-diazatricyclo[7.4.0.0$^{2,7}$]trideca-1(9),2(7),3-trien-5-yl}pyridine-3-carbaldehyde 124a (121 mg, 0.35 mmol), K$_3$PO$_4$ (148 mg, 0.70 mmol), 1,1'-bis(diphenylphosphino)ferrocenedichloropalladium(II) (13 mg, 0.0175 mmol), sodium acetate trihydrate (95 mg, 0.70 mmol), water (6 drops), and acetonitrile (10 mL). After bubbling nitrogen through the mixture for 30 minutes, it was heated at 100° C. under N$_2$ protection for 1 h. Analysis of reaction mixture by LCMS showed completed conversion to the desired product. The reaction mixture was cooled to room temperature and filtered. The filtrate was concentrated under reduced pressure. The residue was diluted with dichloromethane (30 mL) and water (30 mL). The aqueous layer was separated and extracted with dichloromethane (3×20 mL). The combined organic layer was dried over Na$_2$SO$_4$, filtered, and concentrated under reduced pressure. The dark residue was purified by silica-gel column chromatography eluting with dichloromethane/methanol (80/1 to 30/1) to afford 191k (118 mg, 51%) as yellow solid. MS-ESI: [M+H]$^+$ 665

Example 191

5-[3-(Hydroxymethyl)-4-[1-methyl-5-({5-[(2S)-2-methyl-4-(oxetan-3-yl)pipera-zin-1-yl]pyridin-2-yl}amino)-6-oxo-1,6-dihydropyridin-3-yl]pyridin-2-yl]-8-thia-4,5-diazatricyclo[7.4.0.0$^{2,7}$]trideca-1(9),2(7),3-trien-6-one 191

To a solution of 4-[1-methyl-5-({5-[(2S)-2-methyl-4-(oxetan-3-yl)piperazin-1-yl]pyridin-2-yl}amino)-6-oxo-1,6-dihydropyridin-3-yl]-2-{6-oxo-8-thia-4,5-diazatricyclo-[7.4.0.0$^{2,7}$]trideca-1(9),2(7),3-trien-5-yl}pyridine-3-carbaldehyde 191k (118 mg, 0.18 mmol) in methanol/dichloromethane (10/10 mL) was added NaBH$_4$ (21 mg, 0.54 mmol) at room temperature. After the reaction was stirred for 1 h, LCMS indicated the reaction was completed. Then the mixture was poured into water (20 mL) and concentrated under reduced pressure. The residue was extracted with dichloromethane (20 mL×3). The combined organic layer was washed with brine (30 mL), dried over Na$_2$SO$_4$, filtered, and concentrated under reduced pressure. The residue solid was purified by reverse-phase prep-HPLC to afford 191 (71 mg, 60%) as white solid. MS-ESI: [M+H]$^+$ 667. $^1$H NMR (500 MHz, DMSO-d$_6$) δ 8.64 (d, J=2.5 Hz, 1H), 8.58 (d, J=5.0 Hz, 1H), 8.48-8.46 (m, 2H), 7.86 (d, J=3.0 Hz, 1H), 7.54 (d, J=5.5 Hz, 1H), 7.48 (d, J=2.0 Hz, 1H), 7.37 (dd, J=3.0, 9.0 Hz, 1H), 7.25 (d, J=9.5 Hz, 1H), 4.86-4.85 (m, 1H), 4.58-4.55 (m, 2H), 4.48-4.46 (m, 2H), 4.42-4.40 (m, 2H), 3.65-3.64 (m, 1H), 3.61 (s, 3H), 3.41-3.99 (m, 1H), 3.05-3.04 (m, 1H), 2.97-2.95 (m, 3H), 2.87-2.86 (m, 2H), 2.52-2.51 (m, 1H), 2.34-2.32 (m, 2H), 2.21-2.20 (m, 1H), 1.89-1.87 (m, 4H), 0.94 (d, J=6.0 Hz, 3H).

Example 192a

Methyl 1-Formyl-5,6,7,8-tetrahydroindolizine-2-carboxylate 192a

A 100-mL round-bottomed flask equipped with a magnetic stirrer was purged with nitrogen and charged with anhydrous dichloroethane (10 mL) and anhydrous DMF (0.7 mL, 9.0 mmol). The reaction mixture was cooled to 0° C. and phosphorus oxychloride (0.7 mL, 7.3 mmol) was added over a period of 2 min, while maintaining the reaction temperature between 0° C. and 10° C. The cooling bath was removed and the reaction was stirred at room temperature for 1 hour. A solution of methyl 5,6,7,8-tetrahydroindolizine-2-carboxylate 112a (1.0 g, 5.6 mmol) in acetonitrile (10 mL) was added and the mixture was stirred at room temperature for additional 3 hours. After this time, the solvent was concentrated under reduced pressure and the oily residue was taken up with saturated aqueous NaHCO$_3$ (20 mL). The aqueous layer was extracted with ethyl acetate (3×70 mL). The combined organic layer was washed with water (20 mL), dried over Na$_2$SO$_4$ and evaporated under reduced pressure. The residue was purified by silica-gel column chromatography eluting with 1:1 ethyl acetate/petroleum ether to afford 192a as a white solid (406 mg, 33%). MS: (M+H)$^+$ 208.3. $^1$H NMR (500 MHz, DMSO) δ 10.29 (s, 1H), 7.43 (s, 1H), 3.99 (t, J=6.0 Hz, 2H), 3.76 (s, 3H), 2.95 (t, J=6.5 Hz, 2H), 1.90-1.85 (m, 2H), 1.78-1.74 (m, 2H).

Example 192b 7,8,9,10-Tetrahydropyridazino[4,5-a]indolizin-4(3H)-one 192b

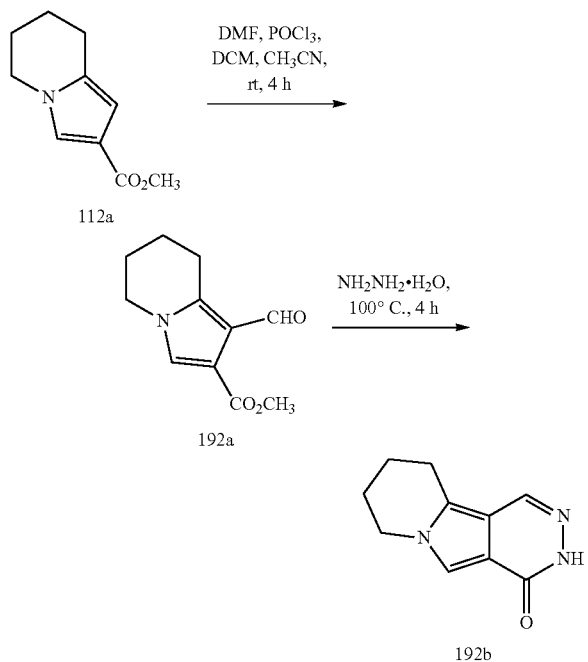

A 100 mL single-neck round-bottomed flask was charged with hydrazinium hydroxide (20 mL), methyl 1-formyl-5,6,7,8-tetrahydroindolizine-2-carboxylate 192a (2.5 g, 12.0 mmol). The reaction mixture was heated at 100° C. for 4 hours. After this time the reaction was cooled to room temperature and filtered to afford 192b as a yellow solid (1.9 g, 83%). MS: (M+H)$^+$ 190.3. $^1$H NMR (500 MHz, DMSO) δ 11.44 (s, 1H), 8.03 (s, 1H), 7.42 (s, 1H), 4.18 (t, J=6.0 Hz, 2H), 2.96 (t, J=6.5 Hz, 2H), 1.98-1.93 (m, 2H), 1.87-1.82 (m, 2H).

Example 192c

4-Chloro-2-(4-oxo-7,8,9,10-tetrahydropyridazino[4,5-a]indolizin-3(4H)-yl)nicotinaldehyde 192c A 100-mL single-neck round-bottomed flask equipped with a magnetic stirrer and a reflux condenser was charged with 1,4-dioxane (50 mL), potassium carbonate (1.5 g, 10.6 mmol), 7,8,9,10-tetrahydropyridazino[4,5-a]indolizin-4(3H)-one 192b (1.0 g, 5.3 mmol), and 2-bromo-4-chloronicotinaldehyde (3.5 g, 15.9 mmol). After bubbling nitrogen through the resulting mixture for 30 minutes, copper(I) bromide (75.0 mg, 0.53 mmol) and sarcosine (47.0 mg, 0.53 mmol) were added, and the reaction mixture was heated at 95° C. for 12 h. After this time the reaction was cooled to room temperature and filtered. The filtrate was partitioned between methylene chloride (60 mL) and water (40 mL). The aqueous layer was separated and extracted with methylene chloride (3×70 mL). The combined organic layer was washed with brine (30 mL) and dried over sodium sulfate. The drying agent was removed by filtration and the filtrate was concentrated under reduced pressure. The residue was purified by silica-gel column chromatography eluting with 10:1 ethyl acetate/petroleum ether to afford 192c as a brown solid (521 mg, 30%). MS-ESI: [M+H]$^+$ 329.2.

Example 192d (S)-4-(1-Methyl-5-(5-(2-methyl-4-(oxetan-3-yl)piperazin-1-yl)pyridin-2-ylamino)-6-oxo-1,6-dihydropyridin-3-yl)-2-(4-oxo-7,8,9,10-tetrahydropyridazino[4,5-a]indolizin-3(4H)-yl)nicotinaldehyde 192d

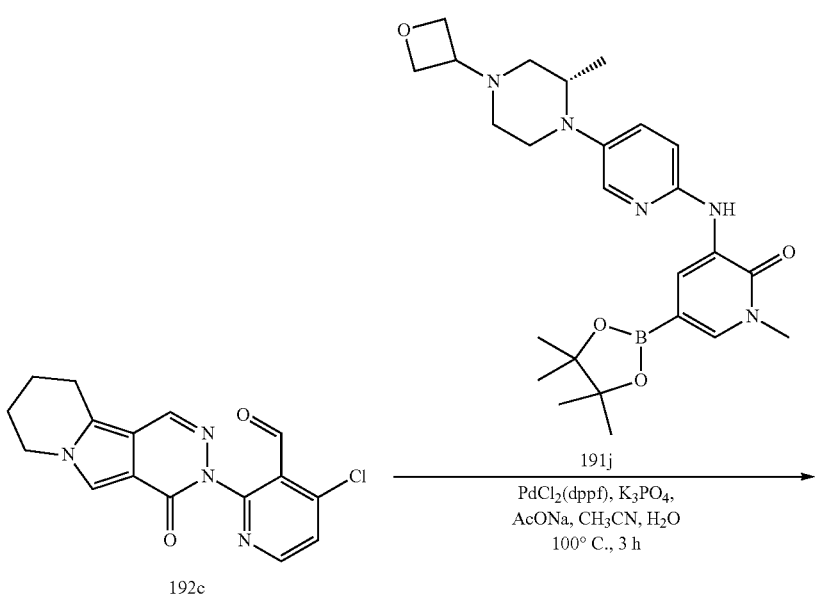

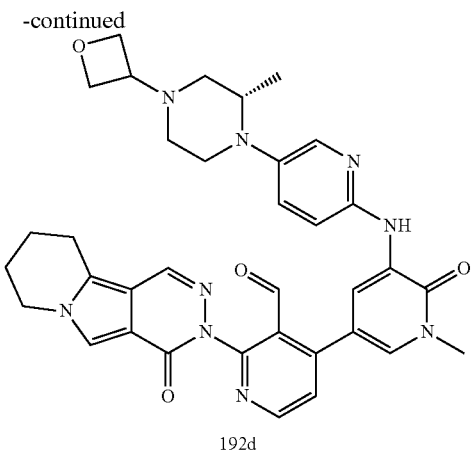

192d

A 100-mL round-bottomed flask equipped with a reflux condenser was charged with 4-chloro-2-(4-oxo-7,8,9,10-tetrahydropyridazino[4,5-a]indolizin-3(4H)-yl)nicotinaldehyde 192c (196 mg, 0.60 mmol), (S)-1-methyl-3-(5-(2-methyl-4-(oxetan-3-yl)-piperazin-1-yl)pyridin-2-ylamino)-5-(4,4,5,5-tetramethyl-1,3,2-dioxaborolan-2-yl)pyridin-2(1H)-one 191j (290 mg, 0.60 mmol), sodium acetate (100 mg, 1.2 mmol), K$_3$PO$_4$ (320 mg, 1.2 mmol), PdCl$_2$(dppf) (50 mg, 0.060 mmol), acetonitrile (25 mL), and water (1 mL). After bubbling nitrogen through the mixture for 30 minutes, it was heated at 100° C. for 3 hours under N$_2$ protection. The reaction mixture was cooled to room temperature and evaporated under reduced pressure. The residue was purified by silica-gel column chromatography eluting with 20:1 methylene chloride/methanol to afford 192d 173 mg, 44%) as a brown solid. MS-ESI: [M+H]$^+$ 648.4.

Example 192

3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one 192

To a solution of 192d (160 mg, 0.25 mmol) in MeOH (20 mL) was added NaBH$_4$ (28 mg, 0.75 mmol). The mixture was stirred at 20° C. for 2 h and evaporated under reduced pressure. The residue was purified by reverse-phase prep-HPLC to afford 192 (97 mg, 60%) as a yellow solid. MS-ESI: [M+H]$^+$ 650.4. $^1$H NMR (500 MHz, DMSO-d$_6$) δ 8.65 (d, J=2.5 Hz, 1H), 8.54 (d, J=4.5 Hz, 1H), 8.45 (s, 1H), 8.25 (s, 1H), 7.86 (d, J=2.5 Hz, 1H), 7.62 (s, 1H), 7.51 (d, J=2.5 Hz, 1H), 7.47 (d, J=5.0 Hz, 1H), 7.38-7.36 (m, 1H), 7.25 (d, J=9.5 Hz, 1H), 4.66 (s, 1H), 4.57-4.54 (m, 2H), 4.48-4.46 (m, 1H), 4.43-4.41 (m, 1H), 4.33 (s, 2H), 4.25-4.21 (m, 2H), 3.69-3.66 (m, 1H), 3.60 (s, 3H), 3.42-3.37 (m, 1H), 3.11-3.07 (m, 1H), 3.06-3.04 (m, 2H), 2.97-2.92 (m, 1H), 2.55-2.53 (m, 1H), 2.35-2.29 (m, 2H), 2.19-2.17 (m, 1H), 2.04-1.96 (m, 2H), 1.93-1.85 (m, 2H), 0.93 (d, J=6.5 Hz, 3H).

Example 193a

Methyl 2-(Hydroxy(pyridin-2-yl)methyl)acrylate 193a

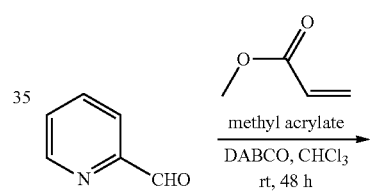

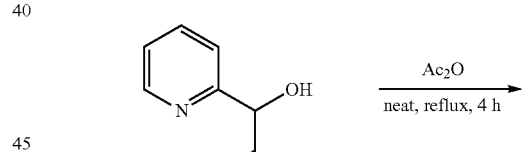

193a

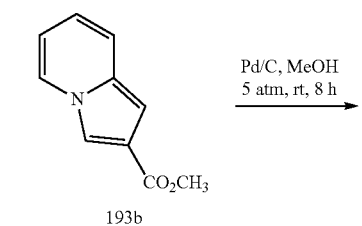

193b

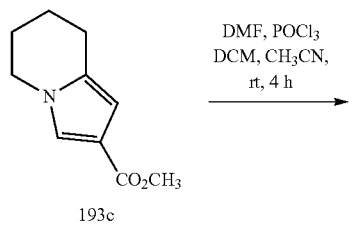

193c

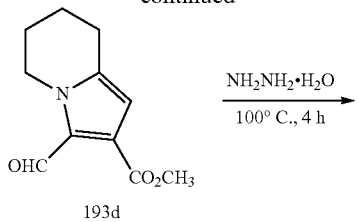

193d

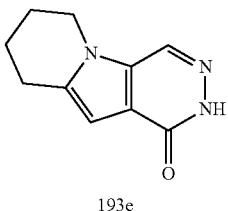

193e

A 250-mL single-neck round-bottomed flask was charged with chloroform (100 mL), picolinaldehyde (10.7 g, 0.10 mol), methyl acrylate (8.60 g, 0.10 mol), and 1,4-diaza-bicyclo[2.2.2]octane (0.560 g, 5.00 mmol). The reaction mixture stirred at room temperature for 48 h. After this time the reaction was concentrated under reduced pressure and the residue was purified by silica-gel column chromatography eluting with 3:1 petroleum ether/ethyl acetate to afford 193a as dark yellow oil (11.6 g, 60%). MS-ESI: $(M+H)^+$ 194.2. $^1$H NMR (500 MHz, CDCl$_3$) δ 8.54 (d, J=5.0 Hz, 1H), 7.69-7.66 (m, 1H), 7.42 (d, J=8.0 Hz, 1H), 7.22-7.20 (m, 1H), 6.36 (s, 1H), 5.97 (s, 1H), 5.62 (s, 1H), 4.85 (s, 1H), 3.74 (s, 3H).

Example 193b

Methyl Indolizine-2-carboxylate 193b

A 250-mL single-neck round-bottomed flask equipped with a magnetic stirrer and a reflux condenser was charged with acetic anhydride (80 mL) and 193a (6.68 g, 34.6 mmol). The reaction mixture was heated at reflux under nitrogen for 4 h. After this time the reaction was cooled to room temperature, poured onto the mixture of ice (100 g) and aqueous saturated sodium bicarbonate (200 mL), and stirred for 1 h. The resulting solution was neutralized with saturated aqueous sodium bicarbonate and extracted with methylene chloride (3×200 mL). The combined organic extract was dried over sodium sulfate and concentrated under reduced pressure. The residue was purified by silica-gel column chromatography eluting with 10:1 petroleum ether/ethyl acetate (10:1) to afford 193b as a white solid (2.1 g, 35%). MS-ESI: $(M+H)^+$ 176.2. $^1$H NMR (500 MHz, CDCl$_3$) δ 7.86-7.84 (m, 1H), 7.79 (d, J=1.0 Hz, 1H), 7.36-7.34 (m, 1H), 6.82 (s, 1H), 6.70-6.66 (m, 1H), 6.55-6.51 (m, 1H), 3.88 (s, 3H).

Example 193c

Methyl 5,6,7,8-Tetrahydroindolizine-2-carboxylate 193c

A 250-mL round-bottomed flask was purged with nitrogen and charged with 193b (2.0 g, 11.4 mmol), 10% palladium on carbon (50% wet, 200 mg), and methanol (50 mL). It was evacuated, charged with hydrogen gas, and stirred under 5 atm hydrogen at room temperature for 8 h. The hydrogen was then evacuated and nitrogen was charged into the flask. The catalyst was removed by filtration through a pad of CELITE® and the filtrate concentrated under reduced pressure to afford 193c as a white solid (1.1 g, 81%). MS-ESI: $[M+H]^+$ 180.3. $^1$H NMR (500 MHz, DMSO-d$_6$) δ 7.25 (d, J=2.0 Hz, 1H), 6.09 (s, 1H), 3.93 (t, J=6.0 Hz, 2H), 3.66 (s, 3H), 2.67 (t, J=6.0 Hz, 2H), 1.87-1.83 (m, 2H), 1.75-1.70 (m, 2H).

Example 193d

Methyl 3-Formyl-5,6,7,8-tetrahydroindolizine-2-carboxylate 193d

A 100-mL round-bottomed flask equipped with a magnetic stirrer was purged with nitrogen and charged with anhydrous dichloroethane (20 mL) and anhydrous DMF (0.70 mL, 9.0 mmol). To the mixture at 0° C. was added phosphorus oxychloride (0.70 mL, 7.3 mmol) over a period of 2 min, while maintaining the reaction temperature between 0° C. and 10° C. The cooling bath was removed and the reaction was stirred at room temperature for 1 hour. A solution of 193c (1.0 g, 5.6 mmol) in acetonitrile (10 mL) was added and the reaction mixture was stirred at room temperature for 3 hours. After this time, it was concentrated under reduced pressure. The oily residue was taken up with saturated aqueous NaHCO$_3$ (20 mL) and extracted with ethyl acetate (3×50 mL). The combined organic layer was washed with water (50 mL), dried over Na$_2$SO$_4$, and evaporated under reduced pressure. The residue was purified by silica-gel column chromatography eluting with 1:5 ethyl acetate/petroleum ether to afford 193d as a white solid (703 mg, 58%). MS-ESI: $(M+H)^+$ 208.3. $^1$H NMR (500 MHz, DMSO-d$_6$) δ 10.14 (s, 1H), 6.40 (s, 1H), 4.27 (t, J=6.0 Hz, 2H), 3.78 (s, 3H), 2.78 (t, J=6.0 Hz, 2H), 1.94-1.85 (m, 2H), 1.78-1.69 (m, 2H).

Example 193e 6,7,8,9-Tetrahydropyridazino[4,5-b]indolizin-1(2H)-one 193e

A 100-mL single-neck round-bottomed flask equipped with a reflux condenser was charged with 193d (600 mg, 2.9 mmol) and hydrazine hydrate (20 mL). The reaction mixture was heated at 100° C. for 4 hours. After this time the reaction was cooled to room temperature and filtered to afford 193e as a yellow solid (413 mg, 75%). MS-ESI: $(M+H)^+$ 190.1. $^1$H NMR (500 MHz, DMSO-d$_6$) δ 12.17 (s, 1H), 8.24 (s, 1H), 6.33 (s, 1H), 4.16 (t, J=6.0 Hz, 2H), 2.88 (t, J=6.5 Hz, 2H), 2.00-1.96 (m, 2H), 1.84-1.79 (m, 2H).

Example 193f

4-Chloro-2-(1-oxo-6,7,8,9-tetrahydropyridazino[4,5-b]indolizin-2(1H)-yl)nicotinaldehyde 193f A 100-mL single-neck round-bottomed flask equipped with a reflux condenser was charged with 1,4-dioxane (40 mL), 193e (800 mg, 3.6 mmol), 2-bromo-4-chloronicotinaldehyde (2.8 g, 12.6 mmol), and potassium carbonate (1.2 g, 8.4 mmol). After bubbling nitrogen through the resulting mixture for 30 minutes, copper(I) iodide (800 mg, 4.2 mmol) and 4,7-dimethoxy-1,10-phenanthroline (1.0 g, 4.2 mmol) were added, and the reaction mixture was heated at 90° C. for 12 h. After this time the reaction was cooled to room temperature and filtered. The filtrate was partitioned between methylene chloride (60 mL) and water (40 mL). The aqueous layer was separated and extracted with methylene chloride (3×40 mL). The combined organic layer was washed with brine (30 mL) and dried over sodium sulfate. The drying agent was removed by filtration and the filtrate was concentrated under reduced pressure. The residue was purified by silica-gel column chromatography eluting with 1:1 ethyl acetate/petroleum ether to afford 193f as a brown solid (513 mg, yield 37%). MS-ESI: [M+H]$^+$ 329.1.

Example 193g (S)-4-(1-Methyl-5-(5-(2-methyl-4-(oxetan-3-yl)piperazin-1-yl)-pyridin-2-yl-amino)-6-oxo-1,6-dihydropyridin-3-yl)-2-(1-oxo-6,7,8,9 tetrahydro-pyridazino[4,5-b]indolizin-2(1H)-yl)nicotinaldehyde 193g

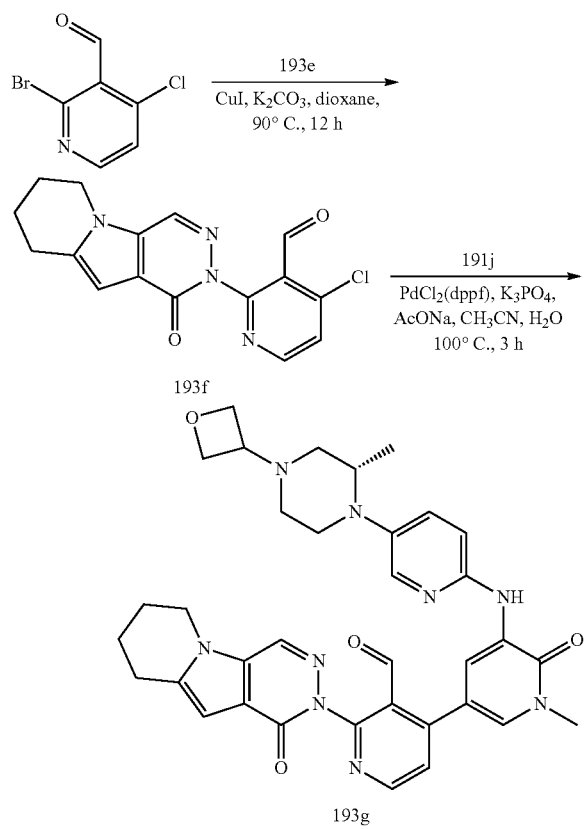

A 100-mL round-bottomed flask equipped with a reflux condenser was charged with 193f (200 mg, 0.61 mmol), 191j (293 mg, 0.60 mmol), sodium acetate (98 mg, 1.2 mmol), K$_3$PO$_4$ (254 mg, 1.2 mmol), PdCl$_2$(dppf) (50 mg, 0.060 mmol), acetonitrile (25 mL), and water (1 mL). After bubbling nitrogen through the mixture for 30 minutes, it was heated at 100° C. for 3 hours. The mixture was cooled to room temperature and filtered. The filtrate was concentrated under reduced pressure and the residue was purified by silica-gel column chromatography eluting with 25:1 methylene chloride/methanol to afford 193g (206 mg, 53%) as a brown solid. MS-ESI: [M+H]$^+$ 648.3.

Example 193

2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydropyridazino[4,5-b]indolizin-1-one 193

To a solution of 193g (180 mg, 0.28 mmol) in methanol (20 mL) was added NaBH4 (32 mg, 0.84 mmol). The mixture was stirred at 20° C. for 2 h and quenched with water. It was then evaporated under reduced pressure and the residue was purified by reverse-phase prep-HPLC to afford 193 (140 mg, 78%) as an off-white solid. MS-ESI: [M+H]$^+$ 650.4. $^1$H NMR (500 MHz, DMSO-d$_6$) δ 8.67 (d, J=2.0 Hz, 1H), 8.55 (d, J=5.5 Hz, 1H), 8.47 (s, 1H), 8.48 (s, 1H), 7.85 (d, J=2.5 Hz, 1H), 7.52-7.50 (m, 2H), 7.38-7.36 (m, 1H), 7.25 (d, J=8.5 Hz, 1H), 6.49 (s, 1H), 4.72 (t, J=5.0 Hz, 1H), 4.57-4.54 (m, 2H), 4.47 (t, J=6.0 Hz, 1H), 4.41 (t, J=6.0 Hz, 1H), 4.33-4.29 (m, 2H), 4.28-4.25 (m, 2H), 3.71-3.65 (m, 1H), 3.60 (s, 3H), 3.41-3.77 (m, 1H), 3.10-3.08 (m, 1H), 2.98-2.90 (m, 3H), 2.57-2.52 (m, 1H), 2.35-2.30 (m, 2H), 2.18-2.16 (m, 1H), 2.06-2.0 (m, 2H), 1.89-1.82 (m, 2H), 0.93 (d, J=6.0 Hz, 3H).

Example 194a

1-Methyl-3-(pyrazin-2-ylamino)-5-(4,4,5,5-tetramethyl-1,3,2-dioxaborolan-2-yl)pyridin-2(1H)-one 194a A 250-mL single-neck round-bottomed flask equipped with a magnetic stirrer and a reflux condenser was charged with 5-bromo-1-methyl-3-(pyrazin-2-ylamino)pyridin-2(1H)-one 142a (600 mg, 2.0 mmol), Pin$_2$B$_2$ (2.54 g, 10 mmol), Pd$_2$(dba)$_3$ (100 mg, 0.10 mmol), X-phos (100 mg, 0.20 mmol), potassium acetate (600 mg, 6.0 mmol), and dioxane (80 mL). After three cycles of vacuum/argon flush, the mixture was heated at 65° C. for 16 h. It was then cooled to room temperature and filtered. The filtrate was concentrated under reduced pressure and the resulting residue was washed with petroleum ether to afford 194a as a yellow solid (crude product) (1.0 g, LCMS purity: 70%). MS-ESI: [M+H]$^+$ 329.4.

Example 194b

4-{1-Methyl-6-oxo-5-[(pyrazin-2-yl)amino]-1,6-dihydropyridin-3-yl}-2-{6-oxo-8-thia-4,5-diazatricyclo[7.4.0.0$^{2,7}$]trideca-1(9),2(7),3-trien-5-yl}pyridine-3-carbaldehyde 194b

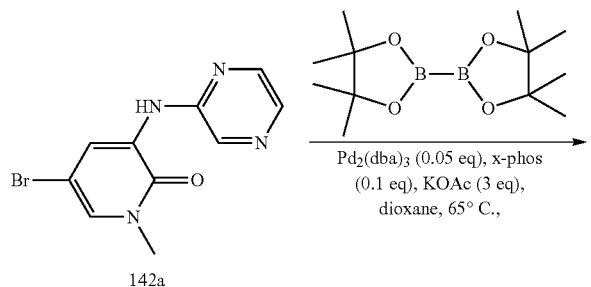

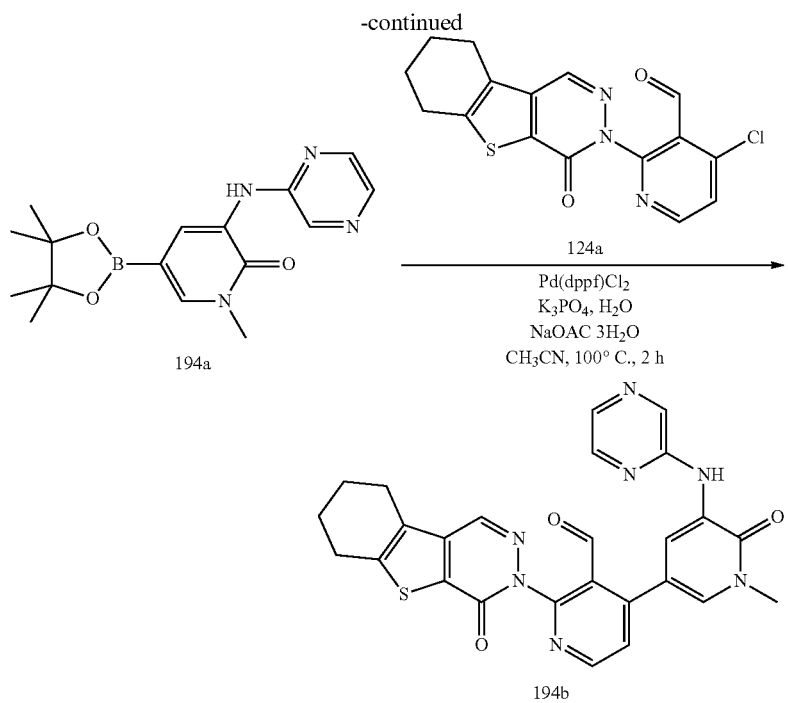

A 100-mL single-neck round-bottomed flask equipped with a reflux condenser was charged with 4-chloro-2-{6-oxo-8-thia-4,5-diazatricyclo[7.4.0.0$^{2,7}$]trideca-1(9),2(7),3-trien-5-yl}pyridine-3-carbaldehyde 124a (345 mg, 1.0 mmol), 194a (659 mg, 2.0 mmol), Pd(dppf)Cl$_2$ (50 mg, 0.050 mmol), K$_3$PO$_4$ (450 mg, 2.0 mmol), sodium acetate trihydrate (300 mg, 2.0 mmol), water (6 drops) and, acetonitrile (40 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 194b (250 mg, 49%) as a yellow brown solid. MS-ESI: [M+H]$^+$ 512.3.

Example 194

3-[3-(hydroxymethyl)-4-[1-methyl-6-oxo-5-(pyrazin-2-ylamino)-3-pyridyl]-2-pyridyl]-6,7,8,9-tetrahydrobenzothiopheno[2,3-d]pyridazin-4-one 194

A mixture of 194b (200 mg, 0.4 mmol) and NaBH$_4$ (48 mg, 1.2 mmol) in methanol (20 mL) was stirred at 30° C. for 2 h. The mixture was quenched with water (5 mL) and concentrated under reduced pressure. The residue was extracted with ethyl acetate (3×10 mL). The combined with ethyl acetate extract was concentrated under reduced pressure and the residue was purified by reverse-phase prep-HPLC to afford 194 (60 mg, 30%) as a white solid. MS-ESI: [M+H]$^+$ 514.2. $^1$H NMR (500 MHz, CDCl$_3$) δ 8.78 (d, J=2.0 Hz, 1H), 8.69 (d, J=5.0 Hz, 1H), 8.31 (s, 1H), 8.29 (s, 1H), 8.17 (s, 1H), 8.13 (s, 1H), 8.04 (d, J=2.5 Hz, 1H), 7.83 (d, J=2.5 Hz, 1H), 7.56 (d, J=5 Hz, 1H), 4.44-4.37 (m, 3H), 3.76 (s, 3H), 3.01-2.99 (m, 2H), 2.88-2.86 (m, 2H), 2.01-1.96 (m, 4H).

Example 195a

Ethyl 4,5,6,7-Tetrahydro-1H-indole-2-carboxylate 195a

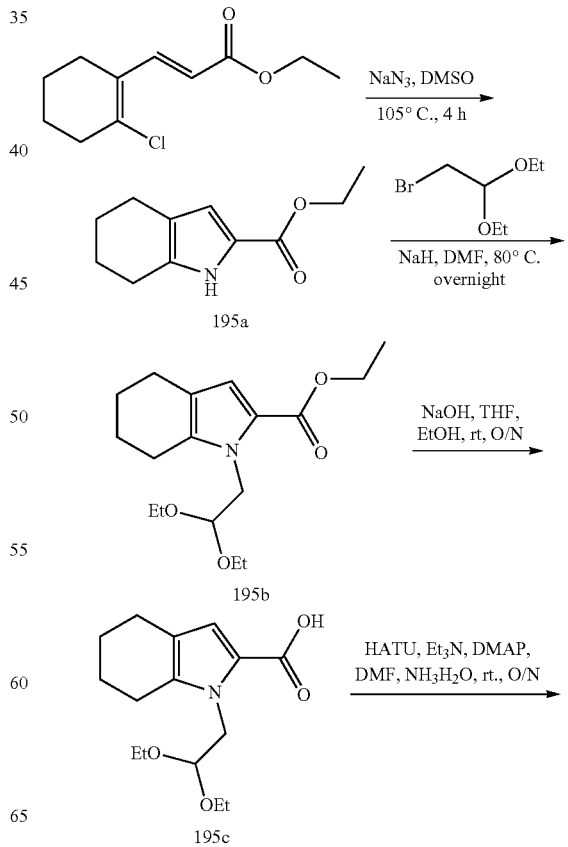

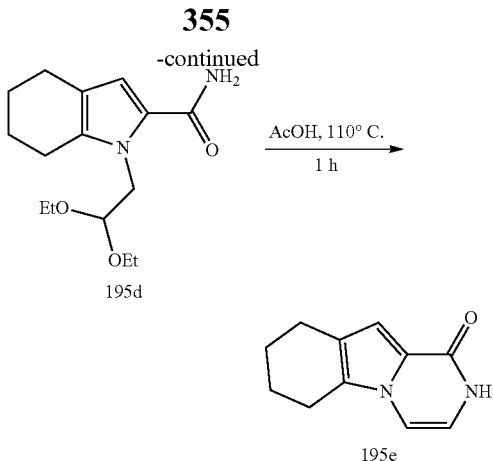

To a mixture of ethyl 3-(2-chlorocyclohex-1-enyl)acrylate (21.4 g, 100 mmol) in DMSO (100 mL) was added sodium azide (9.75 g, 150 mmol). The reaction mixture was heated at 105° C. for 4 h. After cooling to room temperature, the mixture was poured into ice water. The resulting precipitate was collected by filtration to afford 195a (18.0 g, 93.3%). MS-ESI: [M+H]$^+$ 194.

Example 195b

Ethyl 1-(2,2-Diethoxyethyl)-4,5,6,7-tetrahydro-1H-indole-2-carboxylate 195b

To a suspension of NaH (1.44 g, 60.2 mmol) in N,N-dimethylformamide (DMF) (30 mL) was slowly added 195a (5.80 g, 30.1 mmol) at 0° C. The resulting mixture was stirred at room temperature for 0.5 h, followed by the addition of 2-bromo-1,1-diethoxyethane (11.9 g, 60.2 mmol). The reaction was heated at 70° C. for 30 h and quenched with water (100 mL). The mixture was then extracted with ethyl acetate (3×100 mL). The combined organic phase was concentrated under reduced pressure and the residue was purified with silica-gel column chromatography eluting with 40:1 petroleum ether/ethyl acetate to 195b (4.7 g, 51%). MS-ESI: [M-EtOH+H]$^+$ 264. $^1$H NMR (500 MHz, DMSO-d$_6$) δ 6.65 (s, 1H), 4.59 (t, J=5.0 Hz, 1H), 4.17-4.16 (m, 4H), 3.59-3.57 (m, 2H), 3.27-3.26 (m, 2H), 2.61 (t, J=6.0 Hz, 2H), 2.51 (t, J=6.0 Hz, 2H), 1.73-1.71 (m, 2H), 1.63-1.61 (m, 2H), 1.25 (t, J=7.0 Hz, 3H), 1.02 (t, J=7.0 Hz, 6H).

Example 195c 1-(2,2-Diethoxyethyl)-4,5,6,7-tetrahydro-1H-indole-2-carboxylic Acid 195c To a mixture of 195b (4.7 g, 15.2 mmol) in a mixed solvent of ethanol (20 mL), tetrahydrofuran (20 mL), and water (30 mL) was added sodium hydroxide (3.0 g, 75.0 mmol). The reaction was heated at 75° C. for two days and concentrated under reduced pressure. The residue was suspended in water and neutralized with diluted aqueous citric acid solution. The mixture was extracted with ethyl acetate (3×100 mL) and the combined organic phase was concentrated under reduced pressure to afford 195c (3.32 g, 78%). MS-ESI: [M-EtOH+H]$^+$ 236.

Example 195d 1-(2,2-Diethoxyethyl)-4,5,6,7-tetrahydro-1H-indole-2-carboxamide 195d To a mixture of 195c (2.8 g, 10.0 mmol) in N,N-dimethylformamide (30 mL) was added O-(7-azabenzotriazol-1-yl)-N,N,N',N'-tetramethyluronium hexafluorophosphate (HATU) (5.7 g, 15.0 mmol), Et$_3$N (1.5 g, 15.0 mmol), and DMAP (128 mg, 1.0 mmol). The reaction mixture was stirred at room temperature for overnight. Saturated ammonium hydroxide (30 mL) was added and the resulting mixture was further stirred for 2 h. It was then diluted with water (100 mL) and extracted with ethyl acetate (3×100 mL). The combined organic phase was concentrated under reduced pressure and the residue was purified by silica-gel column chromatography eluting with petroleum ether/ethyl acetate (6:1 to 3:1) to afford 195d (2.7 g, 96%). MS-ESI: [M-EtOH+H]$^+$ 235. $^1$H NMR (500 MHz, DMSO) δ 7.35 (bs, 1H), 6.70 (bs, 1H), 6.60 (s, 1H), 4.60 (t, J=5.5 Hz, 1H), 4.18 (d, J=4.0 Hz, 2H), 3.57-3.56 (m, 2H), 3.25 (m, 2H), 2.57 (t, J=6.0 Hz, 2H), 2.40 (t, J=6.0 Hz, 2H), 1.71 (t, J=5.0 Hz, 2H), 1.64 (t, J=5.0 Hz, 2H), 1.01 (t, J=7.0 Hz, 6H).

Example 195e 6,7,8,9-Tetrahydropyrazino[1,2-a]indol-1(2H)-one 195e

A mixture of 195d (2.7 g, 9.6 mmol) and acetic acid (10 mL) was heated at 110° C. for 2 h. The mixture was cooled to room temperature and neutralized with aqueous sodium carbonate solution and extracted with ethyl acetate (3×30 mL). The combined organic phase was concentrated under reduced pressure to afford 195e as a yellow solid (1.6 g, 88%). MS-ESI: [M+H]$^+$ 189.3. $^1$H NMR (500 MHz, DMSO-d$_6$) δ 10.28 (s, 1H), 7.02 (d, J=5.5 Hz, 1H), 6.63 (s, 1H), 6.52 (pt, J=5.5 Hz, 1H), 2.66 (t, J=6.0 Hz, 2H), 2.57 (t, J=6.0 Hz, 2H), 1.83-1.82 (m, 2H), 1.73-1.72 (m, 2H).

Example 195f

4-Chloro-2-(1-oxo-6,7,8,9-tetrahydropyrazino[1,2-a]indol-2(1H)-yl)nicotinaldehyde 195f

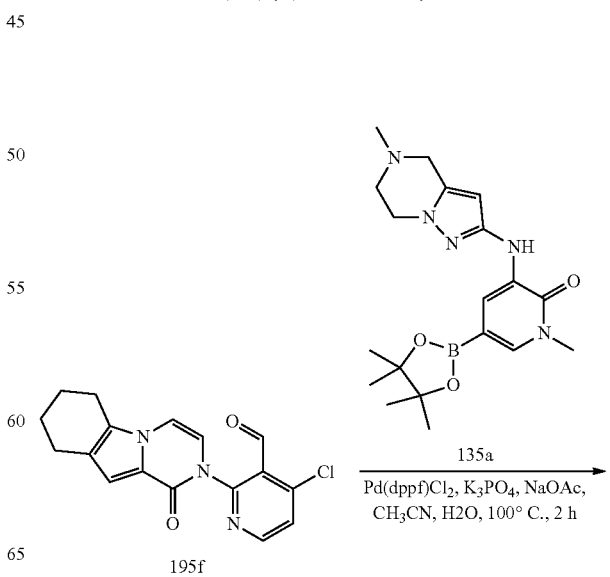

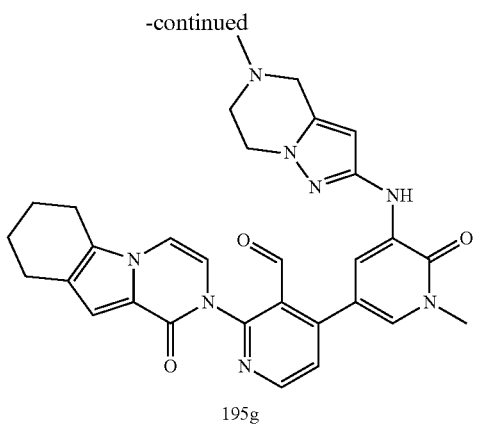

195g

A 100-mL single-neck round-bottomed flask equipped with a magnetic stirrer and a reflux condenser was charged with 1,4-dioxane (15 mL), 2-bromo-4-chloronicotinaldehyde 103a (503 mg, 2.28 mmol), 195e (142 mg, 0.76 mmol), cesium carbonate (490 mg, 1.5 mmol), CuI (143 mg, 0.76 mmol), and 4,7-dimethoxy-1,10-phenanthroline (127 mg, 0.52 mmol). After three cycles of vacuum/argon flush, the mixture was heated at 80° C. for 10 hrs. It was then cooled to room temperature and filtered. The filtrate was washed with brine and concentrated under reduced pressure. The resulting residue was purified with silica-gel column chromatography eluting with 1:4 ethyl acetate/petroleum ether to afford 195f (160 mg, 65%) as a yellow solid. MS-ESI: [M+H]$^+$ 328.

Example 195g 2-(3-(Formyl)-4-(1-methyl-5-(5-methyl-4,5,6,7-tet-rahydropyrazolo[1,5-a]pyrazin-2-ylamino)-6-oxo-1,6-dihydropyridin-3-yl)pyridin-2-yl)-6,7,8,9-tetrahy-dro-pyrazino[1,2-a]indol-1(2H)-one 195g A 50-mL single-neck round-bottomed flask equipped with a reflux condenser was charged with 195f (130 mg, 0.40 mmol), 1-methyl-3-(5-methyl-4,5,6,7-tetrahydropyrazolo[1,5-a]pyrazin-2-ylamino)-5-(4,4,5,5-tetra-methyl-1,3,2-dioxaborolan-2-yl)pyridin-2(1H)-one 135a (154 mg, 0.40 mmol), Pd(dppf)Cl$_2$ (29 mg, 0.040 mmol), K$_3$PO$_4$ (170 mg, 0.80 mmol), sodium acetate (66 mg, 0.80 mmol), water (6 drops), and acetonitrile (10 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 195g as yellow solid (120 mg, 54%). MS-ESI: [M+H]$^+$ 551.2

Example 195

2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyrazino[1,2-a]indol-1-one 195

To a solution of 195g (120 mg, 0.22 mmol) in methanol (5 mL) at 0° C. was added sodium borohydride (25 mg, 0.66 mmol). The reaction mixture was stirred for 30 minutes. It was then quenched with water (1.0 mL) and concentrated under reduced pressure. The residue was purified by reverse-phase prep-HPLC to afford 195 (70 mg, 58%). MS-ESI: [M+H]$^+$ 553.3. $^1$H NMR (500 MHz, CDCl$_3$) δ 8.56 (d, J=5.0 Hz, 1H), 7.99 (d, J=2.0 Hz, 1H), 7.75 (d, J=2.0 Hz, 1H), 7.49 (d, J=4.5 Hz, 1H), 7.43 (s, 1H), 7.07 (s, 1H), 6.97 (d, J=6.0 Hz, 1H), 6.67 (d, J=6.0 Hz, 1H), 5.70 (s, 1H), 5.08-5.06 (m, 1H), 4.51-4.49 (m, 1H), 4.36-4.34 (m, 1H), 4.14-4.05 (m, 2H), 3.72 (s, 3H), 3.62-3.60 (m, 2H), 2.91-2.89 (m, 2H), 2.75-2.70 (m, 4H), 2.49 (s, 3H), 1.97-1.95 (m, 2H), 1.86-1.84 (m, 2H).

Example 196a 2-cyclopropylpyrimidin-4-amine 196a

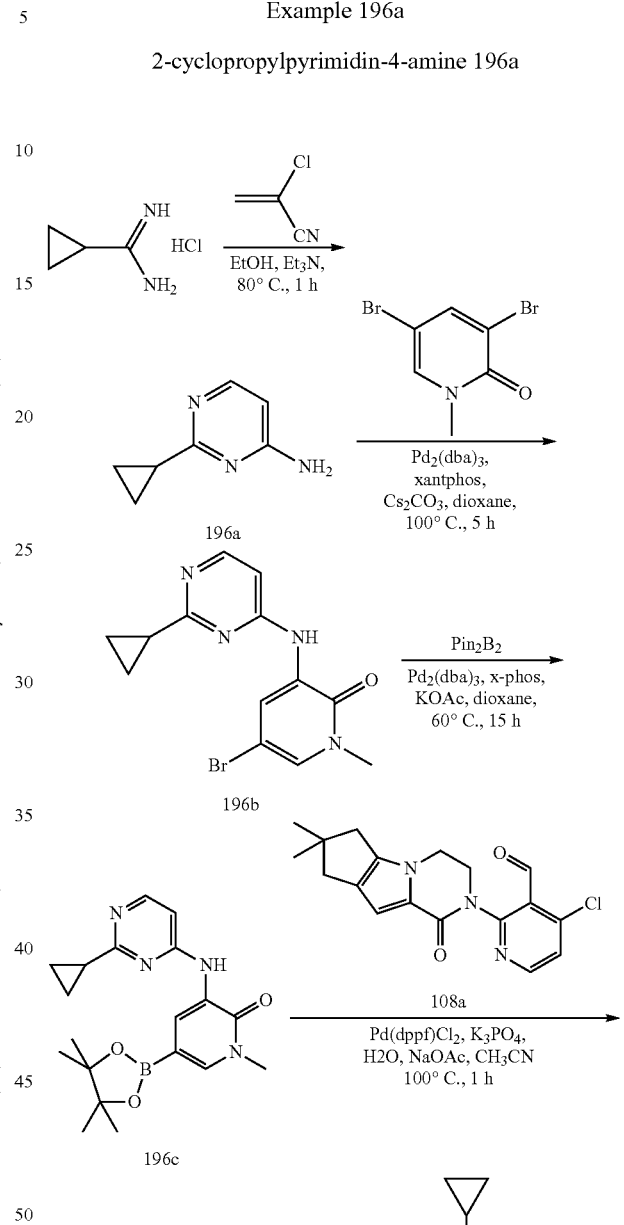

Cyclopropylcarbamidine hydrochloride (1.0 g, 8.3 mmol) was dissolved in ethanol (25 mL) and triethylamine (1.26 g, 12.5 mmol), followed by the addition of 2-chloroacrylo-nitrile (870 mg, 10 mmol). The resulting orange-yellow solution was refluxed for 1 h. The mixture was cooled to room temperature and filtered. The filtrate was concentrated in vacuo and the residue was purified by reverse-phase Combi-flash to afford 196a (300 mg, 27%) as a light brown solid. MS-ESI: [M+H]+ 136

Example 196b

5-Bromo-3-(2-cyclopropylpyrimidin-4-ylamino)-1-methylpyridin-2(1H)-one 196b

A 100-mL single-neck round-bottomed flask equipped with a magnetic stirrer and a reflux condenser was charged with 196a (300 mg, 2.22 mmol), 3,5-dibromo-1-methylpyridin-2(1H)-one (593 mg, 2.22 mmol), and cesium carbonate (1.45 g, 4.44 mmol). After bubbling nitrogen through the suspension for 30 minutes, Xantphos (127 mg, 0.22 mmol) and tris(dibenzyl-ideneacetone)dipalladium(0) (100 mg, 0.11 mmol) were added. The system was subject to three cycles of vacuum/argon flush and heated at reflux for 5 h. It was then cooled to room temperature and filtered. The solid was washed with dichloromethane (2×50 mL). The combined filtrate was concentrated under reduced pressure and the residue was washed with acetonitrile (5 mL) to afford 196b (420 mg, 59%) as a yellow solid. MS-ESI: [M+H]+321

Example 196c 3-(2-Cyclopropylpyrimidin-4-ylamino)-1-methyl-5-(4,4,5,5-tetramethyl-1,3,2-dioxaborolan-2-yl)pyridin-2(1H)-one 196c A 100-mL single-neck round-bottomed flask equipped with a magnetic stirrer and a condenser was charged with 196b (380 mg, 1.2 mmol), Pin$_2$B$_2$ (1.5 g, 5.9 mmol), Pd$_2$(dba)$_3$ (55 mg, 0.060 mmol), X-phos (57 mg, 0.060 mmol), potassium acetate (350 mg, 3.6 mmol), and 1,4-dioxane (20 mL). The reaction mixture was subjected to three cycles of vacuum/argon flush and was heated at 60° C. for 15 h. It was then cooled to room temperature and filtered. The filtrate was concentrated under reduced pressure and the resulting residue was washed with petroleum ether to afford 196c (410 mg, 94%) as yellow solid, which was used directly for next step without further purification. MS-ESI: [M+H]+ 369

Example 196d

4-{5-[(2-Cyclopropylpyridin-4-yl)amino]-1-methyl-6-oxo-1,6-dihydropyridin-3-yl}-2-{4,4-dimethyl-9-oxo-1,10-diazatricyclo[6.4.0.0$^{2,6}$]dodeca-2(6),7-dien-10-yl}pyridine-3-carbaldehyde 196d A 50-mL round-bottomed flask equipped with a reflux condenser was charged with 196c (258 mg, 0.70 mmol), 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (240 mg, 0.70 mmol), K$_3$PO$_4$ (297 mg, 1.4 mmol), sodium acetate (190 mg, 1.4 mmol), 1,1'-bis(diphenylphosphino)ferrocenedichloropalladium(II) (29 mg, 0.035 mmol), acetonitrile (10 mL), and water (0.5 mL). After bubbling nitrogen through the mixture for 30 minutes, it was heated at 100° C. under N$_2$ protection for 1 h. Analysis of reaction by LCMS showed completed conversion to the desired product. The mixture was cooled to room temperature and diluted with dichloromethane (20 mL) and water (20 mL). The aqueous layer was separated and extracted with dichloromethane (3×20 mL). The combined organic layer was dried over Na$_2$SO$_4$, filtered, and concentrated under reduced pressure. The dark residue was purified by silica-gel column chromatography eluting with dichloromethane/methanol (80/1 to 30/1) to afford 196d (220 mg, 57%) as yellow solid. MS-ESI: [M+H]+ 549

Example 196

3-[4-[5-[(2-cyclopropylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 196

To a solution of 196d (200 mg, 0.36 mmol) in methanol/dichloromethane (5/5 mL) was added NaBH$_4$ (42 mg, 1.1 mmol) at room temperature. After the reaction was stirred for 1 h, LCMS indicated the reaction was completed. The mixture was concentrated under reduced pressure and water (10 mL) was added to the residue. It was then extracted with dichloromethane (20 mL×3). The combined organic layer was washed with brine (30 mL), dried over Na$_2$SO$_4$, filtered, and concentrated under reduced pressure. The residue was purified by prep-HPLC to afford 196 (135 mg, 68%) as a white solid. MS-ESI: [M+H]+ 551. $^1$H NMR (500 MHz, CDCl$_3$) δ 8.84 (d, J=2.5 Hz, 1H), 8.53 (d, J=5.0 Hz, 1H), 8.22 (d, J=6.0 Hz, 1H), 8.13 (d, J=1.5 Hz, 1H), 8.01 (s, 1H), 7.38 (d, J=5.0 Hz, 1H), 6.86 (s, 1H), 6.52 (d, J=6.0 Hz, 1H), 5.22-5.19 (m, 1H), 4.72-4.69 (m, 1H), 4.56-4.54 (m, 1H), 4.31 (t, J=11.0 Hz, 1H), 4.17 (d, J=5.0 Hz, 2H), 3.94-3.91 (m, 1H), 3.74 (s, 3H), 2.58 (d, J=5.5 Hz, 2H), 2.53 (s, 2H), 2.18-2.13 (m, 1H), 1.29 (s, 6H), 1.16-1.13 (m, 1H), 1.06-0.95 (m, 3H).

Example 197a tert-Butyl 4-(5-Nitropyridin-2-yl)piperazine-1-carboxylate 197a

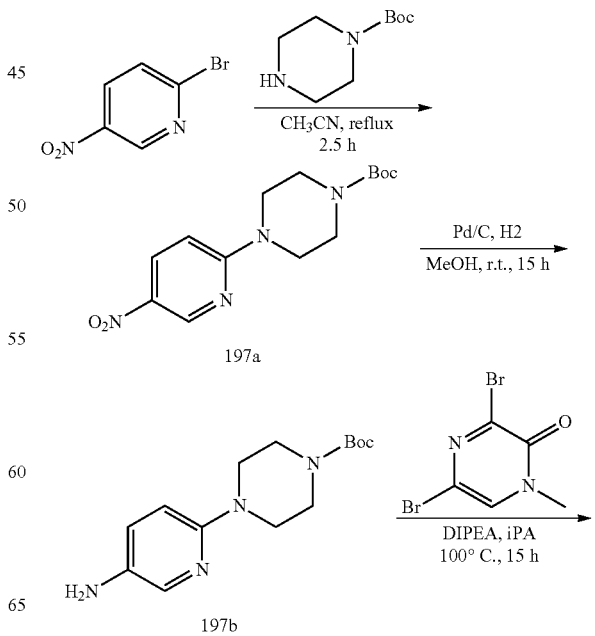

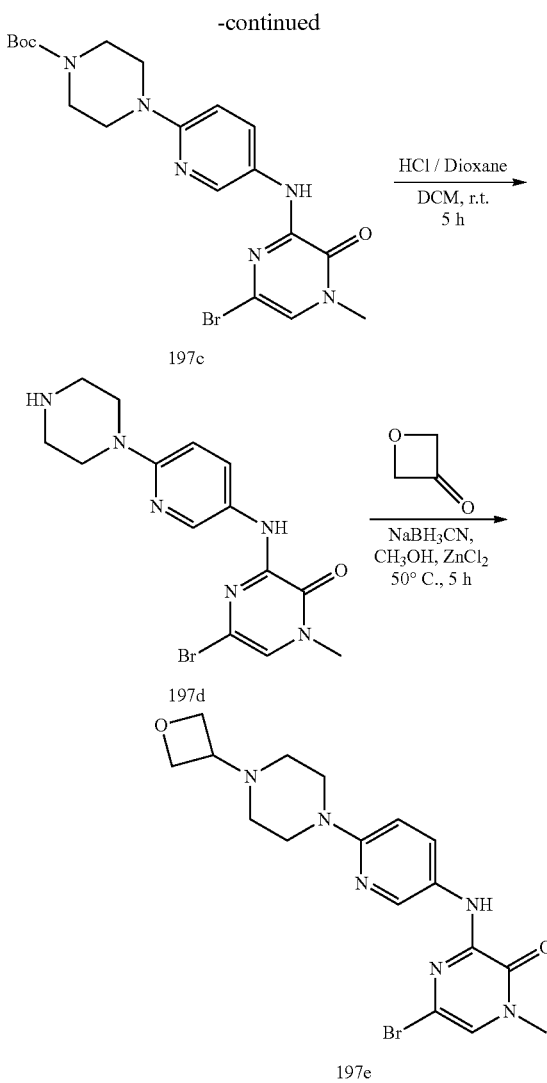

A mixture of 2-bromo-5-nitropyridine (5.0 g, 24.6 mmol), tert-butyl piperazine-1-carboxylate (13.8 g, 74.2 mmol), acetonitrile (150 mL) was stirred at reflux for 2.5 h. After the reaction was completed, the solvent was removed under reduced pressure to afford 197a as a yellow solid (4.1 g, 54%). MS-ESI: [M+H]$^+$ 309.

Example 197b tert-Butyl 4-(5-Aminopyridin-2-yl)piperazine-1-carboxylate 197b

A 250-mL round-bottomed flask was purged with nitrogen and charged with 197a (4.0 g, 13.0 mmol), 10% palladium on carbon (10% wet, 500 mg), and methanol (130 mL). The flask was evacuated, charged with hydrogen gas, and stirred at room temperature for 15 h. Hydrogen was then evacuated and nitrogen was charged to the flask. The catalyst was removed by filtration through a pad of CELITE® and the filtrate was concentrated under reduced pressure to afford 197b (3.3 g, 91%). MS-ESI: [M+H]$^+$ 279

Example 197c tert-Butyl 4-(5-(6-Bromo-4-methyl-3-oxo-3,4-dihydropyrazin-2-ylamino)pyridin-2-yl)piperazine-1-carboxylate 197c A mixture of 197b (500 mg, 1.8 mmol), 3,5-dibromo-1-methylpyrazin-2(1H)-one (530 mg, 2.0 mmol), N-ethyl-N-isopropylpropan-2-amine (1.5 mL, 0.90 mmol), and propan-2-ol (20 mL) was stirred at 100° C. for 15 h. After the reaction was completed, the solvent was removed under reduced pressure to afford 197c as a brown solid (375 mg, 45%). MS-ESI: [M+H]$^+$ 465.

Example 197d

5-Bromo-1-methyl-3-(6-(piperazin-1-yl)pyridin-3-ylamino)-pyrazin-2(1H)-one 197d

To a solution of 197c (500 mg, 1.08 mmol) in dichloromethane (10 mL) was added 4.0 M HCl/dioxane (10 mL). The reaction mixture was stirred at room temperature for 5 h. It was then concentrated under reduced pressure to afford 197d (358 mg, 91%). MS-ESI: [M+H]$^+$ 365.

Example 197e

5-Bromo-1-methyl-3-(6-(4-(oxetan-3-yl)piperazin-1-yl)pyridin-3-ylamino)pyrazin-2(1H)-one 197e A mixture of 197d (0.75 g, 2.1 mmol), oxetan-3-one (0.24 mL, 4.2 mmol), NaBH$_3$CN (0.32 g, 5.1 mmol), and zinc chloride/diethyl ether (5.1 mL, 5.1 mmol) in methanol (30 mL) was stirred at 50° C. for 5 hours. The solid was removed by filtration and the filtrate was concentrated under reduced pressure. The residue was purified by silica-gel column chromatography eluting with 10:1 dichloromethane/methanol to afford 197e (550 mg, 64%). MS-ESI: [M+H]$^+$ 421.

Example 197f (4-(4-Methyl-6-(6-(4-(oxetan-3-yl)piperazin-1-yl)pyridin-3-ylamino)-5-oxo-4,5-dihydropyrazin-2-yl)-2-(1-oxo-3,4,6,7,8,9-hexahydropyrazino[1,2-a]indol-2(1H)-yl)pyridin-3-yl)methyl Acetate 197f

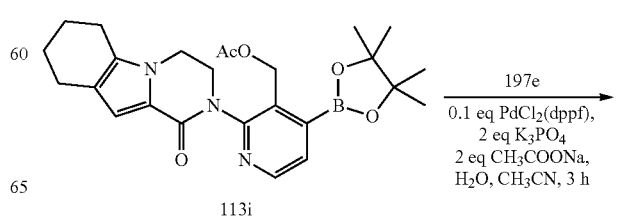

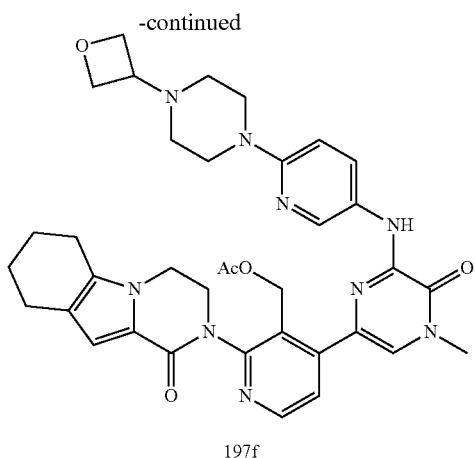

197f

A round-bottomed flask equipped with a reflux condenser was charged with 197e (200 mg, 0.48 mmol), 3-(acetoxymethyl)-2-(1-oxo-3,4,6,7,8,9-hexahydropyrazino[1,2-a]indol-2(1H)-yl)pyridin-4-ylboronic acid 113i (364 mg, 0.95 mmol), PdCl$_2$(dppf) (40 mg, 0.049 mmol), K$_3$PO$_4$ 3H$_2$O (250 mg, 0.95 mmol), sodium acetate (80 mg, 0.95 mmol), acetonitrile (10 mL), and water (0.5 mL). After three cycles of vacuum/argon flush, the mixture was heated at 80° C. for 3 h. It was then filtered and the filtrate was evaporated in vacuo. The residue was purified by silica-gel column chromatography eluting with 1:20 methanol/dichloromethane to afford 197f as a red solid (230 mg, 70%). MS-ESI: [M+H]$^+$ 680

Example 197

2-[3-(hydroxymethyl)-4-[4-methyl-6-[[6-[4-(oxetan-3-yl)piperazin-1-yl]-3-pyridyl]amino]-5-oxo-pyrazin-2-yl]-2-pyridyl]-3,4,6,7,8,9-hexahydropyrazino[1,2-a]indol-1-one 197

A mixture of 197f (200 mg, 0.30 mmol) and lithium hydroxide (70 mg, 3.0 mmol) in THF (9 mL), i-propanol (6 mL), and water (1 mL) was stirred at room temperature for 0.5 h. The mixture was concentrated under reduced pressure and diluted with water (4 mL). It was then extracted with dichloromethane (2×10 mL) and the combined dichloromethane extract was concentrated under reduced pressure. The residue was purified with reverse-phase prep-HPLC to afford 197 (59 mg, 30%) as yellow solid. MS-ESI: [M+H]$^+$ 638. $^1$H NMR (500 MHz, DMSO-d$_6$) δ 9.30 (s, 1H), 8.70 (d, J=2.5 Hz, 1H), 8.49 (d, J=5.5 Hz, 1H), 8.14-8.11 (m, 1H), 7.59 (s, 1H), 7.55 (d, J=5.0 Hz, 1H), 6.82 (d, J=9.5 Hz, 1H), 6.58 (s, 1H), 4.93 (t, J=5.5 Hz, 1H), 4.60-4.54 (m, 3H), 4.48-4.42 (m, 3H), 4.26-4.08 (m, 3H), 3.86 (d, J=12.0 Hz, 1H), 3.54 (s, 3H), 3.44-3.40 (m, overlap, 5H), 2.66-2.53 (m, 2H), 2.46-2.47 (m, 2H), 2.35-2.33 (m, 4H), 1.80-1.68 (m, 4H).

Example 198a 4-(1-Methyl-5-(5-(4-(oxetan-3-yl)piperazin-1-yl)pyridin-2-ylamino)-6-oxo-1,6-dihydropyridin-3-yl)-2-(4-oxo-7,8,9,10-tetrahydropyridazino[4,5-a]indolizin-3(4H)-yl)nicotinaldehyde 198a

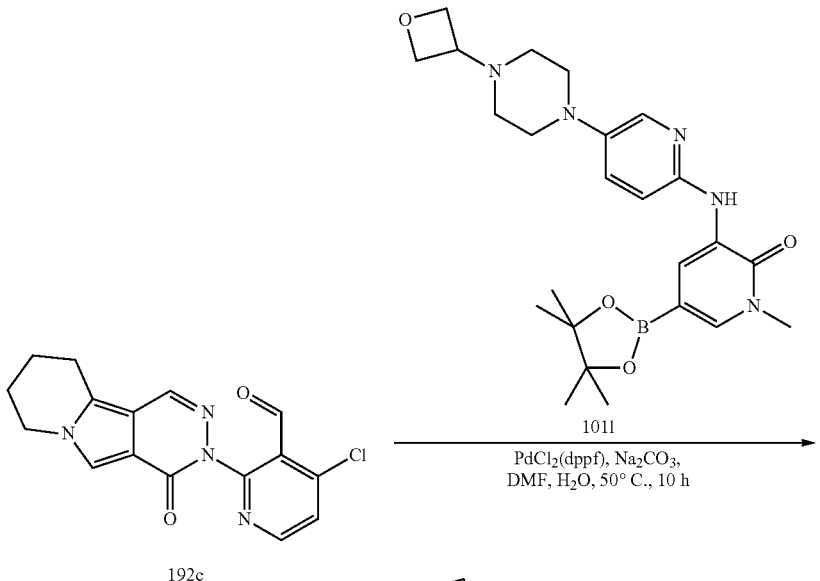

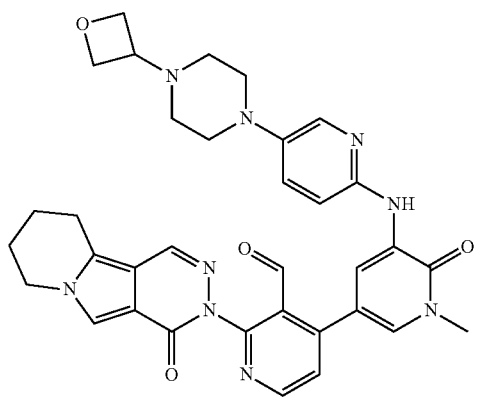

198a

A 50-mL round bottomed flask equipped with a reflux condenser was charged with 4-chloro-2-(4-oxo-7,8,9,10-tetrahydropyridazino[4,5-a]indolizin-3(4H)-yl)nicotinaldehyde 192c (118 mg, 0.36 mmol), 1-methyl-3-(5-(4-(oxetan-3-yl)piperazin-1-yl)pyridin-2-yl-amino)-5-(4,4,5,5-tetramethyl-1,3,2-dioxaborolan-2-yl)pyridin-2(1H)-one 101l (171 mg, 0.36 mmol), Na$_2$CO$_3$ (78 mg, 0.72 mmol), Pd(dppf)Cl$_2$ (30 mg, 0.036 mmol), DMF (10 mL), and water (1 mL). After bubbling nitrogen through the mixture for 30 minutes, it was heated at 50° C. for 10 hours under N$_2$ protection. It was then cooled to room temperature and evaporated under reduced pressure. The residue was purified by silica-gel column chromatography eluting with 20:1 dichloromethane/methanol to afford 198a (93 mg, 40%) as a brown solid. MS-ESI: [M+H]$^+$ 634.3.

Example 198

3-[3-(hydroxymethyl)-4-[1-methyl-5-[[5-[4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one 198

To a solution of 198a (80 mg, 0.13 mmol) in methanol (4 mL) was added NaBH4 (14 mg, 0.39 mmol). The mixture was stirred at 20° C. for 2 h. It was then evaporated under reduced pressure and the residue was purified by reverse-phase prep-HPLC to afford 198 (38 mg, 43%) as an off-white solid. MS-ESI: [M+H]$^+$ 636.4. $^1$H NMR (500 MHz, DMSO-d$_6$) δ 8.65 (d, J=2.0 Hz, 1H), 8.54 (d, J=5.0 Hz, 1H), 8.44 (s, 1H), 8.25 (s, 1H), 7.88 (d, J=2.5 Hz, 1H), 7.62 (s, 1H), 7.50 (d, J=2.0 Hz, 1H), 7.46 (d, J=4.5 Hz, 1H), 7.39-7.36 (m, 1H), 7.25-7.23 (m, 1H), 4.67 (bs, 1H), 4.55 (t, J=6.5 Hz, 2H), 4.46 (t, J=6.0 Hz, 2H), 4.33-4.31 (m, 2H), 4.26-4.20 (m, 2H), 3.59 (s, 3H), 3.46-3.41 (m, 1H), 3.09-3.03 (m, 6H), 2.39-2.37 (m, 4H), 2.04-1.96 (m, 2H), 1.93-1.86 (m, 2H).

Example 199a

Imidazo[1,2-a]pyrimidin-7-amine 199a

To the solution of pyrimidine-2,4-diamine (3.0 g, 0.027 mol) in ethanol (90 mL) and aqueous NaHCO$_3$ (2M, 20 mL) was added 2-chloroacetaldehyde (4.3 g, 0.055 mol). The mixture was stirred at 70° C. overnight. TLC showed the starting material disappeared. The solvent was removed under reduced pressure and the residue was extracted with ethyl acetate (3×30 mL). The combined organic layer was concentrated under reduced pressure and the residue was purified by silica-gel column chromatography eluting with 1:5 petroleum ether/ethyl acetate to afford 199a as a white solid (2.2 g, 60%). MS: [M+H]$^+$ 135.1.

Example 199b

5-Bromo-3-(imidazo[1,2-a]pyrimidin-7-ylamino)-1-methylpyridin-2(1H)-one 199b

A 250-mL round-bottomed flask equipped with a magnetic stirrer and a reflux condenser was charged with 199a (2.2 g, 16.4 mmol), 3,5-dibromo-1-methylpyridin-2(1H)-one (8.77 g, 32.8 mmol), Pd$_2$dba$_3$ (1.5 g, 1.64 mmol), Xantphos (1.88 g, 3.28 mmol), Cs$_2$CO$_3$ (10.7 g. 32.8 mmol), and 1,4-dioxane (150 mL). The system was evacuated and then refilled with N$_2$. It was then heated at reflux for 3 h. After the completion of the reaction, the mixture was filtered off and the solid was washed with methanol (60 mL). The combined filtrate was evaporated under reduced pressure and the residue was purified by silica-gel column chromatography eluting with 20:1 dichloromethane/methanol to afford 199b as a light green solid (1.63 g, 31%). MS: [M+H]$^+$ 320.1

Example 199c

10-[4-chloro-3-(hydroxymethyl)pyridin-2-yl]-4,4-dimethyl-1,10-diazatricyclo[6.4.0.0$^{2,6}$]dodeca-2(6),7-dien-9-one 199c

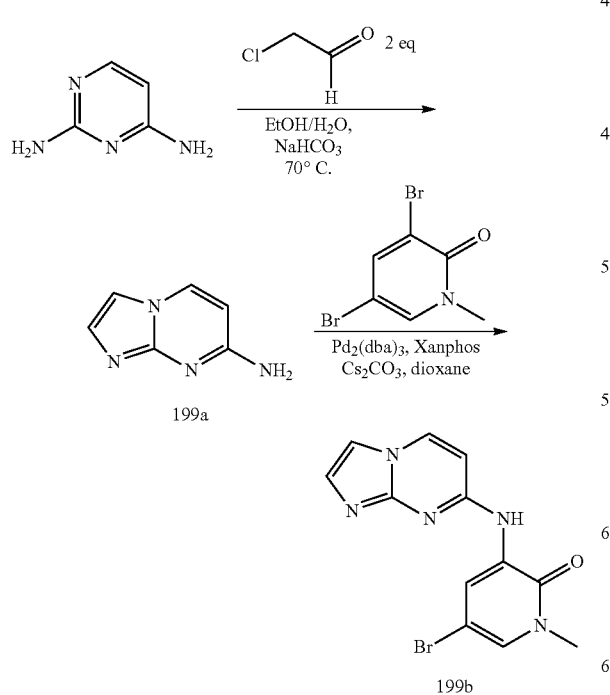

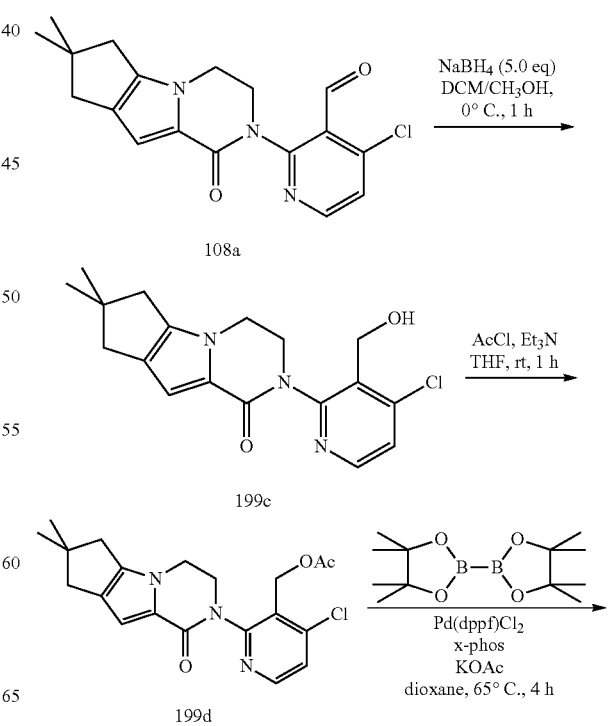

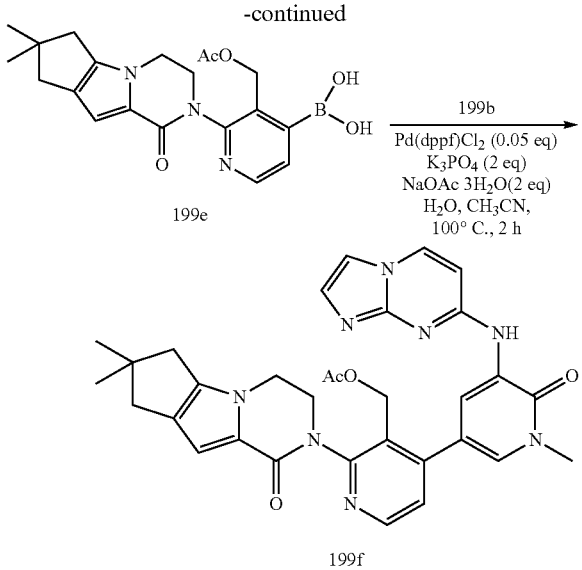

A 250-mL single-neck round-bottomed flask equipped with a magnetic stirrer was charged with 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (9.0 g, 26.1 mmol, 1.0 eq.), methanol (50 mL), dichloromethane (30 mL), and NaBH$_4$ (5.95 g, 156.6 mmol, 5.0 eq.) at 0° C. The reaction mixture was stirred for 1 h. After the reaction was completed, the reaction was quenched with water and concentrated under reduced pressure. The residue was extracted with dichloromethane. The combined organic layer was dried over Na$_2$SO$_4$ and concentrated under reduced pressure. The residue was purified by silica-gel column chromatography eluting with 1:4 ethyl acetate/petroleum ether to afford 199c as a white solid (7.0 g, 77%). MS-ESI: [M+H]$^+$ 345.9.

Example 199d (4-Chloro-2-{4,4-dimethyl-9-oxo-1,10-diazatricyclo-[6.4.0.0$^{2,6}$]dodeca-2(6),7-dien-10-yl}pyridin-3-yl)methyl Acetate 199d A 250-mL single-neck round-bottomed flask equipped with a magnetic stirrer was charged with 199c (7.0 g, 20.2 mmol, 1.0 eq.), triethylamine (4.08 g, 40.4 mmol, 2.0 eq.), and THF (50 mL). To the mixture was added the solution of acetyl chloride (2.36 g, 30.3 mmol, 1.5 eq.) in THF (20 mL) dropwise. The reaction mixture was stirred at room temperature for one hour. After the reaction was completed, it was quenched with ice water and evaporated under reduced pressure. The residue was extracted with dichloromethane. The combined organic layer was dried over Na$_2$SO$_4$ and concentrated under reduced pressure. The resulting residue was washed with 1:8 ethyl acetate/petroleum to afford 199d as a white solid (5.9 g, 76%). MS-ESI: [M+H]$^+$ 388.3.

Example 199e

{3-[(Acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic Acid 199e A 250-mL single-neck round-bottomed flask equipped with a magnetic stirrer and a reflux condenser was charged with 199d (4.5 g, 1.0 eq., 11.6 mmol), Pin$_2$B$_2$ (7.38 g, 2.5 eq., 29.0 mmol), PdCl$_2$(dppf) (473 mg, 0.05 eq., 0.58 mmol), x-phos (470 mg, 0.1 eq., 1.16 mmol), potassium acetate (3.41 g, 3.0 eq., 34.8 mmol), and dioxane (100 mL). After three cycles of vacuum/argon flush, the mixture was heated at 65° C. for 4 h. It was then cooled to room temperature and filtered. The filtrate was concentrated under reduced pressure to afford crude 199e as a brown-red liquid (4.0 g, purity: 65%). MS-ESI: [M+H]$^+$ 398.3.

Example 199f (2-{4,4-Dimethyl-9-oxo-1,10-diazatricyclo[6.4.0.0$^{2,6}$]dodeca-2(6),7-dien-10-yl}-4-[5-({imidazo[1,2-a]pyrimidin-7-yl}amino)-1-methyl-6-oxo-1,6-dihydropyridin-3-yl]pyridin-3-yl)methyl Acetate 199f A 100-mL single-neck round-bottomed flask equipped with a reflux condenser was charged with 199b (500 mg, 1.5 mmol), {3-[(acetyloxy)methyl]-2-{4,4-dimethyl-9-oxo-1,10-diazatri-cyclo[6.4.0.0$^{2,6}$]dodeca-2(6),7-dien-10-yl}pyridin-4-yl}boronic acid 199e (1200 mg, 3.0 mmol), Pd(dppf)Cl$_2$ (65 mg, 0.075 mmol), K$_3$PO$_4$ (650 mg, 3.0 mmol), sodium acetate trihydrate (420 mg, 3.0 mmol), water (6 drops), and acetonitrile (20 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 199f (240 mg, 40%) as a yellow-brown solid. MS-ESI: [M+H]$^+$ 593.4.

Example 199

3-[3-(hydroxymethyl)-4-[5-(imidazo[1,2-a]pyrimidin-7-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one 199

A mixture of 199f (180 mg, 0.30 mmol) and lithium hydroxide (130 mg, 3.0 mmol) in i-propanol/THF (5:3, 8 mL) and water (2 mL) was stirred at 30° C. for 1 h. The mixture was evaporated in vacuo and the residue was diluted with water (3 mL). It was then extracted with ethyl acetate (2×10 mL). The combined ethyl acetate extract was concentrated under reduced pressure and the residue was purified by prep-HPLC to afford 199 (40 mg, 30%) as white solid. MS-ESI: [M+H]$^+$ 551.3. $^1$H NMR (500 MHz, CHCl$_3$) δ 9.09 (d, J=1.5 Hz, 1H), 8.51 (d, J=5.0 Hz, 1H), 8.23 (s, 1H), 8.13 (d, J=7.0 Hz, 1H), 7.93 (d, J=2.0 Hz, 1H), 7.45 (s, 1H), 7.38 (d, J=5.0 Hz, 1H), 7.27 (s, 1H), 6.84 (s, 1H), 6.47 (d, J=7.5 Hz, 1H), 5.10 (s, 1H), 4.67-4.50 (m, 2H), 4.32-4.18 (m, 3H), 3.93-3.88 (m, 1H), 3.74 (s, 3H), 2.60-2.58 (m, 2H), 2.52 (s, 2H), 1.28 (s, 6H).

Example 200a tert-Butyl 4-(6-Nitropyridin-3-yl)-5,6-dihydropyridine-1(2H)-carboxylate 200a

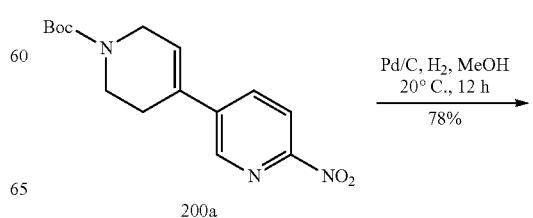

-continued

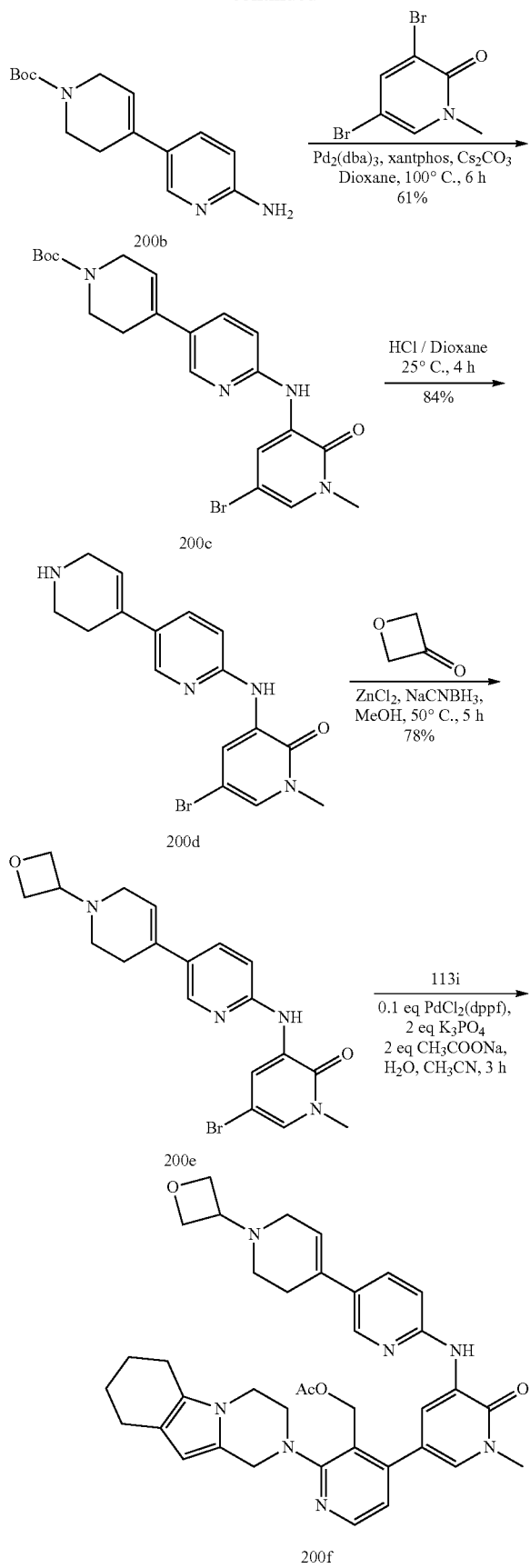

A mixture of 5-bromo-2-nitropyridine (2.0 g, 9.7 mmol), tert-butyl 4-(4,4,5,5-tetramethyl-1,3,2-dioxaborolan-2-yl)-5,6-dihydropyridine-1(2H)-carboxylate (3.0 g, 9.7 mmol), Pd(dppf)Cl$_2$ (792 mg, 0.97 mmol), K$_3$PO$_4$.3H$_2$O (5.2 g, 19.4 mmol), and sodium acetate (1.59 g, 19.4 mmol) in acetonitrile (100 mL) and water (5 mL) was evacuated and then refilled with N$_2$. The reaction mixture was heated at 80° C. for 6 h. It was then cooled to room temperature and filtered. The filtrate was concentrated under reduced pressure and the resulting residue was purified by silica-gel column chromatography eluting with 1:5 ethyl acetate/petroleum ether to afford 200a as a yellow solid (2.2 g, 74%).

Example 200b tert-Butyl 4-(6-Aminopyridin-3-yl)piperidine-1-carboxylate 200b

A 500-mL round-bottomed flask was purged with nitrogen and charged with 200a (2.5 g, 8.2 mmol), 10% palladium on carbon (50% wet, 300 mg), and methanol (80 mL). The flask was evacuated, charged with hydrogen gas, and stirred at room temperature under hydrogen atmosphere for 12 h. The hydrogen was then evacuated and nitrogen was charged to the flask. The catalyst was removed by filtration through a pad of CELITE® and the filtrate was concentrated under reduced pressure to afford 200b (1.8 g, 78%) as a white solid. MS-ESI: [M+H]$^+$ 278.1

Example 200c tert-Butyl 4-(6-(5-Bromo-1-methyl-2-oxo-1,2-dihydropyridin-3-ylamino)pyridin-3-yl)-5,6-dihydropyridine-1(2H)-carboxylate 200c A 100-mL single-neck round-bottomed flask equipped with a magnetic stirrer and a reflux condenser was charged 200b (2.0 g, 7.2 mmol), 3,5-dibromo-1-methylpyridin-2(1H)-one (1.9 g, 7.2 mmol), cesium carbonate (4.7 g, 14.4 mmol), and 1,4-dioxane (50 mL). After bubbling nitrogen through the resulting mixture for 30 min, Xantphos (418 mg, 0.72 mmol) and tris(dibenzylideneacetone)dipalladium(0) (661 mg, 0.72 mmol) were added. The reaction mixture was subject to three cycles of vacuum/argon flush and heated at 100° C. for 6 h. After this time the reaction was cooled to room temperature and filtered. The filtrate was partitioned between ethyl acetate (120 mL) and water (60 mL). The aqueous layer was separated and extracted with ethyl acetate (3×80 mL). The combined organic layer was washed with brine (30 mL) and dried over sodium sulfate. The drying agent was removed by filtration and the filtrate was concentrated under reduced pressure. The residue was purified by silica-gel column chromatography eluting with 1:4 ethyl acetate/petroleum ether to afford 200c (2.0 g, 61%) as a yellow solid. MS-ESI: [M+H]$^+$ 463.2

Example 200d

5-Bromo-1-methyl-3-(5-(1,2,3,6-tetrahydropyridin-4-yl)pyridin-2-ylamino)pyridin-2(1H)-one 200d A mixture of 200c (1.0 g, 2.3 mmol) and 4 M HCl/dioxane (10 mL) was stirred at room temperature for 4 h. The mixture was concentrated under reduced pressure. The residue was basified with aqueous sodium hydroxide and extracted with dichloromethane. The combined organic layer was washed

Example 200e

5-Bromo-1-methyl-3-(5-(1-(oxetan-3-yl)-1,2,3,6-tetrahydropyridin-4-yl)pyridin-2-ylamino)pyridin-2(1H)-one 200e A mixture of 200d (500 mg, 1.4 mmol), oxetan-3-one (298 mg, 4.2 mmol), NaBH$_3$CN (261 mg, 4.2 mmol), and 1 mol/L zinc chloride in ethoxyethane (4 mL, 4.2 mmol) in methanol (20 mL) was stirred at 50° C. for 5 hours. Water (20 mL) was added to the reaction and the resulting mixture was extracted with dichloromethane (3×50 mL). The combined organic layer was concentrated under reduced pressure and the residue was purified by silica-gel column chromatography eluting with 10:1 methylene chloride/methanol to afford 200e (450 mg, 78%) as a yellow solid. MS-ESI: [M+H]$^+$ 419.1

Example 200f (4-(1-Methyl-5-(5-(1-(oxetan-3-yl)-1,2,3,6-tetrahydropyridin-4-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 200f A round-bottomed flask equipped with a reflux condenser was charged with 200e (300 mg, 0.72 mmol), 3-(acetoxymethyl)-2-(1-oxo-3,4,6,7,8,9-hexahydropyrazino[1,2-a]indol-2(1H)-yl)pyridin-4-ylboronic acid 113i (414 mg, 1.08 mmol), PdCl$_2$(dppf) (57 mg, 0.070 mmol), K$_3$PO$_4$·3H$_2$O (560 mg, 2.16 mmol), sodium acetate (177 mg, 2.16 mmol), acetonitrile (10 mL), and water (0.5 mL). After three cycles of vacuum/argon flush, the mixture was heated at 80° C. for 3 h. It was then filtered and the filtrate was evaporated in vacuo. The residue was purified with silica-gel column chromatography eluting with 1:20 methanol/dichloromethane to afford 200f as a red solid (324 mg, 68%). MS-ESI: [M+H]$^+$ 676.2

Example 200

2-[3-(hydroxymethyl)-4-[1-methyl-5-[[5-[1-(oxetan-3-yl)-3,6-dihydro-2H-pyridin-4-yl]-2-pyridyl]amino]-6-oxo-3-pyridyl]-2-pyridyl]-3,4,6,7,8,9-hexahydropyrazino[1,2-a]indol-1-one 200

A mixture of 200f (260 mg, 0.39 mmol) and lithium hydroxide (92.4 mg, 3.85 mmol) in THF (9 mL), isopropanol (6 mL), and water (1 mL) was stirred at room temperature for 0.5 h. The mixture was extracted concentrated under reduced pressure and diluted with water (4 mL). It was then extracted with dichloromethane (2×10 mL) and the combined C dichloromethane extract was concentrated under reduced pressure. The residue was purified with reverse-phase prep-HPLC to afford 200 (53.1 mg, 20%) as yellow solid. MS-ESI: [M+H]$^+$ 634.2. $^1$H NMR (500 MHz, DMSO-d$_6$) δ 8.76 (d, J=1.5 Hz, 1H), 8.74 (s, 1H), 8.49 (d, J=5.5 Hz, 1H), 8.24 (d, J=2.0 Hz, 1H), 7.73-7.71 (m, 1H), 7.54 (d, J=2.5 Hz, 1H), 7.36 (d, J=5.0 Hz, 1H), 7.30 (d, J=8.5 Hz, 1H), 6.58 (s, 1H), 6.11 (s, 1H), 4.97 (s, 1H), 4.57 (t, J=6.5 Hz, 2H), 4.38-4.49 (m, 4H), 4.08-4.26 (m, 3H), 3.86 (d, J=12.0 Hz, 1H), 3.61 (s, 3H), 3.54-3.45 (m, 1H), 2.95 (s, 2H), 2.68-2.54 (m, 2H), 2.48-2.46 (m, overlap, 6H),1.83-1.75 (m, 2H), 1.73-1.65 (m, 2H).

Example 201a

5-Bromo-3-(imidazo[1,2-a]pyridin-7-ylamino)-1-methylpyrazin-2(1H)-one 201a

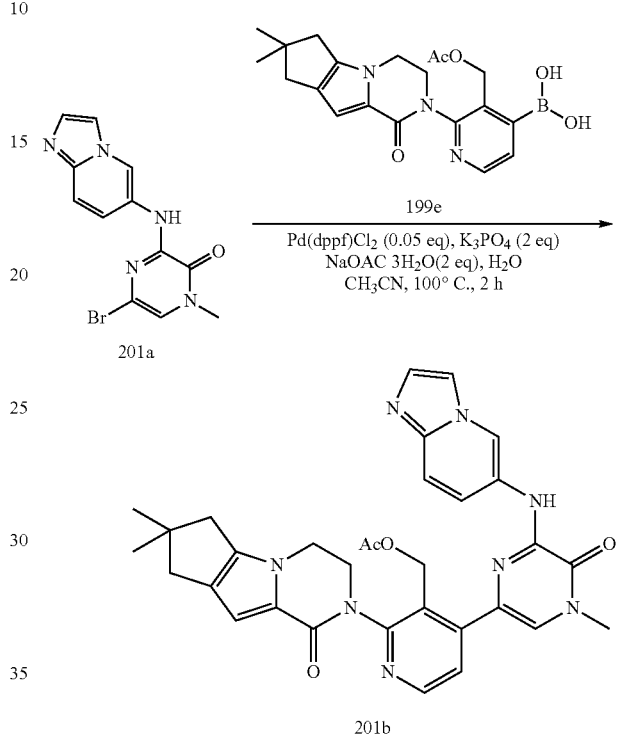

A 100-mL round-bottomed flask equipped with a reflux condenser was charged with imidazo[1,2-a]pyridin-7-amine (665 mg, 5.0 mmol), Cs$_2$CO$_3$ (3.26 g, 10 mmol), 3,5-dibromo-1-methylpyrazin-2(1H)-one (1.86 g, 7.0 mmol), Xantphos (289 mg, 0.50 mmol), Pd$_2$(dba)$_3$ (458 mg, 0.50 mmol), and 1,4-dioxane (30 mL). After bubbling nitrogen through the mixture for 30 minutes, it was heated at 100° C. under nitrogen atmosphere for 16 h. Analysis of the reaction mixture by LCMS showed little starting material remained. The reaction mixture was cooled to room temperature and filtered. The filtrate was diluted with dichloromethane (60 mL) and water (50 mL). The aqueous layer was separated and extracted with dichloromethane (3×20 mL). The combined organic layers was dried over Na$_2$SO$_4$, filtered, and concentrated under reduced pressure. The dark residue was purified by silica-gel column chromatography eluting with dichloromethane/methanol (60/1 to 30/1) to afford 201a (700 mg, 44%) as light yellow solid. MS-ESI: [M+H]$^+$ 320

Example 201b (2-{4,4-Dimethyl-9-oxo-1,10-diazatricyclo[6.4.0.0$^{2,6}$]dodeca-2(6),7-dien-10-yl}-4-[6-({imidazo[1,2-a]pyridin-6-yl}amino)-4-methyl-5-oxo-4,5-dihydropyrazin-2-yl]pyridin-3-yl)methyl Acetate 201b A 25-mL single-neck round-bottomed flask equipped with a reflux condenser was charged with 201a (64 mg, 0.20 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (160 mg, 0.40 mmol), Pd(dppf)Cl$_2$ (10 mg, 0.012 mmol), K$_3$PO$_4$ (100 mg, 0.39 mmol), NaOAc.3H$_2$O (60 mg, 0.44 mmol), water (6 drops), and acetonitrile (5 mL). The system was evacuated and refilled with N$_2$. The reaction mixture was stirred at 100° C. for 2 h. It was then cooled to room temperature and filtered. The filtrate was concentrated under reduced pressure and the resulting residue was purified by silica-gel column chromatography eluting with 20:1 dichloromethane/methanol to afford 201b (40 mg, 34%) as a yellow brown solid. MS-ESI: [M+H]$^+$ 593.2.

Example 201

3-[3-(hydroxymethyl)-4-[6-(imidazo[1,2-a]pyridin-6-ylamino)-4-methyl-5-oxo-pyrazin-2-yl]-2-pyridyl]-7,7-dimethyl-1,2,6,8-tetrahydrocyclopenta[3,4]pyrrolo[3,5-b]pyrazin-4-one 201

A mixture of 201b (40 mg, 0.067 mmol) and lithium hydroxide (25 mg, 0.60 mmol) in i-propanol/THF (3:2, 5 mL) and water (1 mL) was stirred at 30° C. for 1 h. The mixture was evaporated in vacuo and the residue was extracted with ethyl acetate (2×10 mL). The combined ethyl acetate extract was concentrated under reduced pressure and the residue was purified by reverse-phase prep-HPLC to afford 201 (10 mg, 30%) as a white solid. MS-ESI: [M+H]$^+$ 551.3. $^1$H NMR (500 MHz, CHCl$_3$) δ 9.58 (s, 1H), 8.58 (d, J=5.0 Hz, 1H), 8.18 (s, 1H), 8.12 (s, 1H), 7.73 (d, J=5.0 Hz, 1H), 7.63-7.61 (m, 2H), 7.55 (s, 1H), 7.13-7.11 (m, 1H), 6.87 (s, 1H), 5.19-5.17 (m, 1H), 4.77-4.75 (m, 1H), 4.57-4.42 (m, 2H), 4.20-4.17 (m, 2H), 3.92-3.90 (m, 1H), 3.70 (s, 3H), 2.60-2.53 (m, 4H), 1.29 (s, 6H).

Example 202a 4-(1-Methyl-5-(5-methyl-4,5,6,7-tetrahydropyrazolo[1,5-a]pyrazin-2-ylamino)-6-oxo-1,6-dihydropyridin-3-yl)-2-(4-oxo-7,8,9,10-tetrahydropyridazino[4,5-a]indolizin-3(4H)-yl)nicotinaldehyde 202a

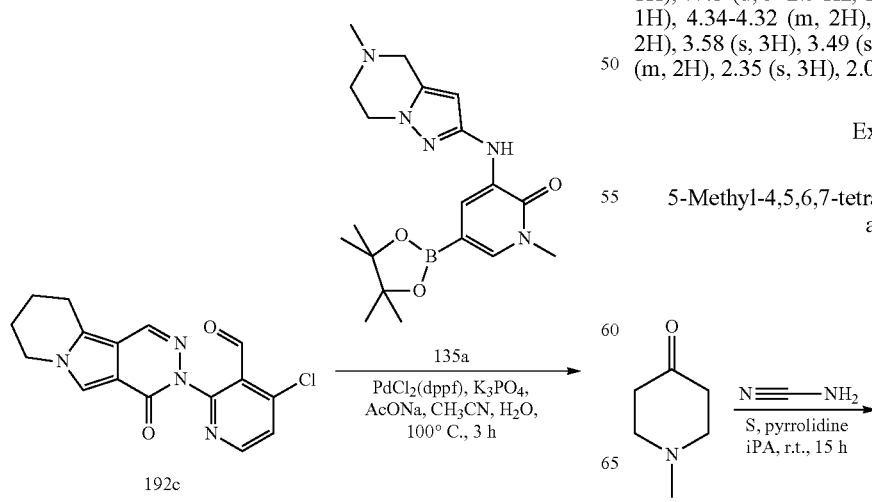

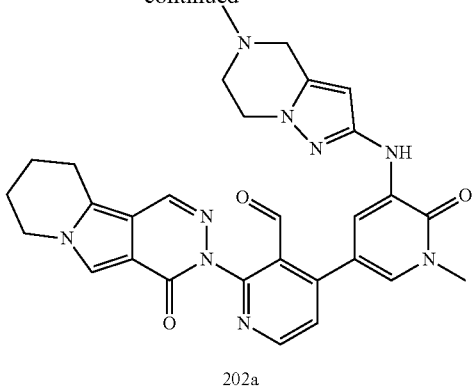

202a

A 100-mL round-bottomed flask equipped with a reflux condenser was charged with 4-chloro-2-(4-oxo-7,8,9,10-tetrahydropyridazino[4,5-a]indolizin-3(4H)-yl)nicotinaldehyde 192c (200 mg, 0.60 mmol), 1-methyl-3-(5-methyl-4,5,6,7-tetrahydropyra-zolo[1,5-a]pyrazin-2-ylamino)-5-(4,4,5,5-tetramethyl-1,3,2-dioxaborolan-2-yl)pyridin-2(1H)-one 135a (230 mg, 0.60 mmol), sodium acetate (100 mg, 1.2 mmol), K$_3$PO$_4$ (320 mg, 1.2 mmol), PdCl$_2$(dppf) (50 mg, 0.060 mmol), acetonitrile (25 mL), and water (1 mL). After bubbling nitrogen through the mixture for 30 minutes, it was heated at 100° C. for 3 hours under N$_2$ protection. The reaction was cooled to room temperature and evaporated under reduced pressure. The residue was purified by silica-gel column chromatography eluting with 25:1 methylene chloride/methanol to afford 202a (205 mg, 62%) as a brown solid. MS-ESI: [M+H]$^+$ 552.3.

Example 202

3-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-7,8,9,10-tetrahydropyridazino[4,5-a]indolizin-4-one 202

To a solution of 202a (180 mg, 0.33 mmol) in methanol (25 mL) was added NaBH$_4$ (37 mg, 0.99 mmol). The mixture was stirred at 20° C. for 2 h and quenched with water. It was then evaporated under reduced pressure and the residue was purified by reverse-phase prep-HPLC to afford 202 (120 mg, 66%) as a white solid. MS-ESI: [M+H]$^+$ 554.3. $^1$H NMR (500 MHz, DMSO-d$_6$) δ 8.53 (d, J=5.0 Hz, 1H), 8.25 (s, 1H), 8.19 (s, 1H), 8.07 (d, J=2.0 Hz, 1H), 7.61 (s, 1H), 7.45 (d, J=5.0 Hz, 1H), 7.43 (d, J=2.5 Hz, 1H), 5.89 (s, 1H), 4.65 (t, J=5.0 Hz, 1H), 4.34-4.32 (m, 2H), 4.26-4.20 (m, 2H), 3.93-3.91 (m, 2H), 3.58 (s, 3H), 3.49 (s, 2H), 3.06-3.04 (m, 2H), 2.79-2.77 (m, 2H), 2.35 (s, 3H), 2.04-1.96 (m, 2H), 1.93-1.86 (m, 2H).

Example 203a

5-Methyl-4,5,6,7-tetrahydrothiazolo[5,4-c]pyridin-2-amine 203a

-continued

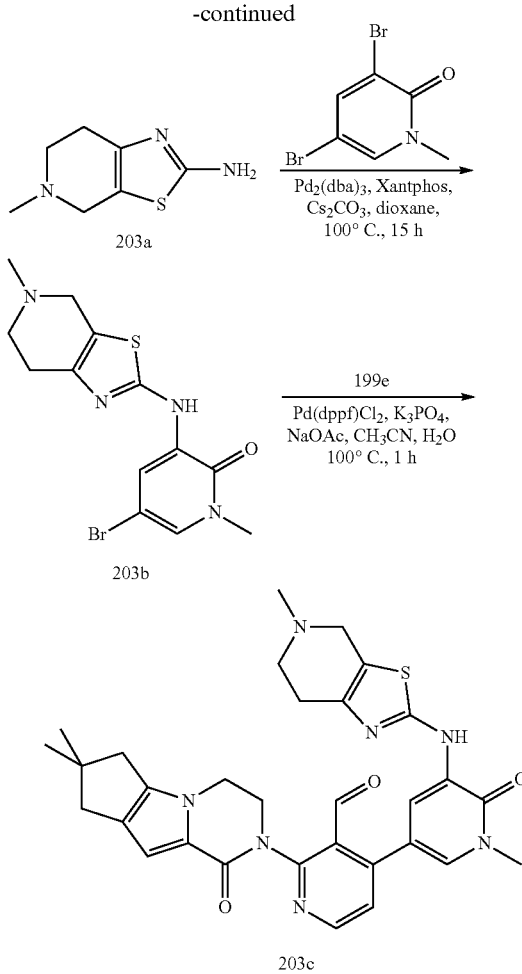

Example 203c

10-[3-(Acetoxymethyl)-4-[1-methyl-5-({5-methyl-4H,5H,6H,7H-[1,3]thiazolo[5,4-c]pyridin-2-yl}amino)-6-oxo-1,6-dihydropyridin-3-yl]pyridin-2-yl]-4,4-dimethyl-1,10-diazatricyclo[6.4.0.0$^{2,6}$]dodeca-2(6),7-dien-9-one 203c A 50-mL round-bottomed flask equipped with a reflux condenser was charged with 203b (178 mg, 0.50 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (200 mg, 0.50 mmol), K$_3$PO$_4$ (212 mg, 1.0 mmol), sodium acetate (82 mg, 1.0 mmol), 1,1'-bis(diphenylphosphino)ferrocene-dichloropalladium(II) (21 mg, 0.025 mmol), acetonitrile (10 mL), and water (0.5 mL). After bubbling nitrogen through the mixture for 30 minutes, it was heated at 100° C. under N$_2$ protection for 1 h. Analysis of reaction mixture by LCMS showed complete conversion to the desired product. The reaction mixture was cooled to room temperature and filtered. The filtrate was concentrated under reduced pressure and the residue was diluted with dichloromethane (20 mL) and water (10 mL). The aqueous layer was separated and extracted with dichloromethane (2×20 mL). The combined organic layer was dried over Na$_2$SO$_4$, filtered, and concentrated under reduced pressure. The dark residue was purified by silica-gel column chromatography eluting with dichloromethane/methanol (80/1 to 30/1) to afford 203c (135 mg, 43%) as yellow solid. MS-ESI: [M+H]$^+$ 584

A solution of 1-methyl-4-piperidone (11.3 g, 100 mmol) in 2-propanol (80 mL) was heated to 50° C. To the solution were sequentially added a solution of cyanamide (4.2 g, 100 mmol) in 2-propanol (25 mL) and sulfur powder (3.2 g, 100 mmol). After a catalytic amount of pyrrolidine (1.3 mL) was added, the resultant mixture was stirred at 50° C. for 2 hours. The reaction mixture was allowed to cool to room temperature and stirred overnight. It was then cooled to or below 10° C. in an ice-water bath and stirred for 1 hour at the same temperature. The precipitated crystals were collected by filtration and washed with 2-propanol (20 mL). The wet crystals were dried in vacuum to afford 203a (10 g, 59%). MS: [M+H]$^+$ 170. $^1$H NMR (500 MHz, DMSO-d$_6$) δ 6.70 (s, 2H), 3.31 (s, 2H), 2.61 (t, J=5.5 Hz, 2H), 2.45 (m, 2H), 2.33 (s, 3H).

Example 203b

5-Bromo-1-methyl-3-(5-methyl-4,5,6,7-tetrahydrothiazolo[5,4-c]pyridin-2-ylamino)pyridin-2(1H)-one 203b Following the procedures described for 191g and starting with 203a (4.0 g, 23.5 mmol) and 3,5-dibromo-1-methylpyridin-2(1H)-one (3.0 g, 17.8 mmol) afforded 203b as yellow solid (2.8 g, 44%). MS: [M+H]$^+$ 357.

Example 203

3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 203

To a solution of 203c (140 g, 0.22 mmol) in THF/i-propanol/water (5/2/2 mL) was added LiOH (54 mg, 2.2 mmol) at room temperature. After the reaction was stirred for 1 h, LCMS indicated the reaction was completed. Then the mixture was concentrated under reduced pressure and diluted with water (3 mL). It was then extracted with dichloromethane (3×10 mL). The combined organic layer was washed with brine (30 mL), dried over Na$_2$SO$_4$, filtered, and concentrated under reduced pressure. The residue was purified by prep-HPLC to afford 203 (85 mg, 66%) as white solid. MS-ESI: [M+H]$^+$ 586. $^1$H NMR (500 MHz, CDCl$_3$) δ 8.50 (d, J=5.5 Hz, 1H), 8.37 (d, J=2.0 Hz, 1H), 8.32 (s, 1H), 7.95 (d, J=2.0 Hz, 1H), 7.34 (d, J=5.0 Hz, 1H), 6.85 (s, 1H), 5.11-5.09 (m, 1H), 4.67-4.64 (m, 1H), 4.52 (bs, 1H), 4.30-4.28 (m, 1H), 4.16 (d, J=4.5 Hz, 2H), 3.89-3.86 (m, 1H), 3.72 (s, 3H), 3.60 (s, 2H), 2.84-2.81 (m, 4H), 2.58 (d, J=5.0 Hz, 2H), 2.53 (s, 3H), 2.52 (s, 2H), 1.28 (s, 6H).

Example 204a 4-(1-Methyl-5-(5-methyl-4,5,6,7-tetrahydropyrazolo[1,5-a]pyrazin-2-ylamino)-6-oxo-1,6-dihydropyridin-3-yl)-2-(1-oxo-6,7,8,9-tetrahydropyridazino[4,5-b]indolizin-2(1H)-yl)nicotinaldehyde 204a

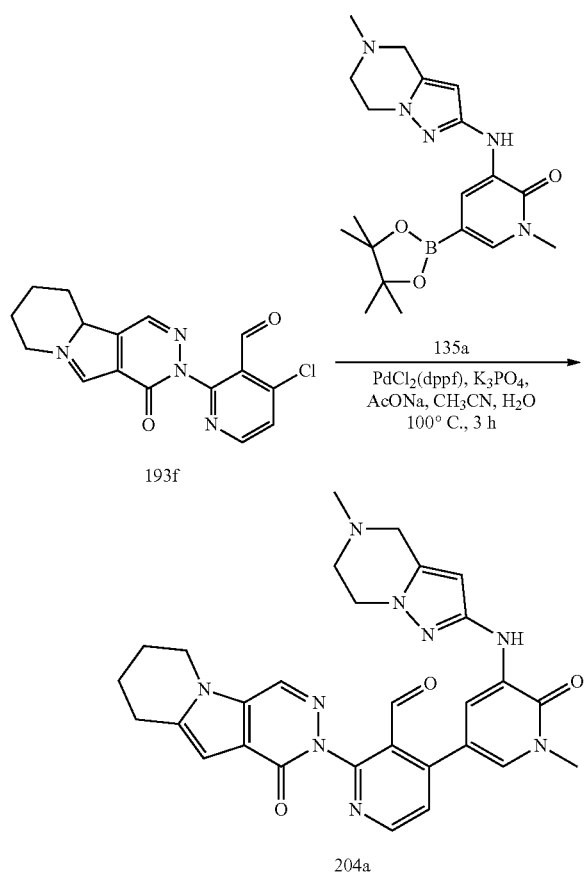

A 100-mL round-bottomed flask equipped with a reflux condenser was charged with 4-chloro-2-(1-oxo-6,7,8,9-tetrahydropyridazino[4,5-b]indolizin-2(1H)-yl)nicotinaldehyde 193f (200 mg, 0.60 mmol), 1-methyl-3-(5-methyl-4,5,6,7-tetrahydropyrazolo-[1,5-a]pyrazin-2-ylamino)-5-(4,4,5,5-tetramethyl-1,3,2-dioxaborolan-2-yl)pyridin-2(1H)-one 135a (230 mg, 0.60 mmol), sodium acetate (100 mg, 1.2 mmol), $K_3PO_4$ (320 mg, 1.2 mmol), $PdCl_2$(dppf) (50 mg, 0.060 mmol), acetonitrile (25 mL), and water (1 mL). After bubbling nitrogen through the resulting mixture for 30 minutes, the mixture was heated at 100° C. for 3 hours. The reaction mixture was cooled to room temperature and concentrated under reduced pressure. The residue was purified by silica-gel column chromatography eluting with 20:1 methylene chloride/methanol to afford 204a (185 mg, 55%) as a brown solid. MS-ESI: $[M+H]^+$ 552.3.

Example 204

2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyridazino[4,5-b]indolizin-1-one 204

To a solution of 204a (160 mg, 0.29 mmol) in methanol (20 mL) was added $NaBH_4$ (33.0 mg, 0.87 mmol). The mixture was stirred at 20° C. for 2 h and quenched with water. It was then evaporated under reduced pressure and the residue was purified by reverse-phase prep-HPLC to afford 204 (120 mg, 75%) as a white solid. MS-ESI: $[M+H]^+$ 554.3. $^1$H NMR (500 MHz, DMSO-$d_6$) δ 8.55 (d, J=5.0 Hz, 1H), 8.46 (s, 1H), 8.23 (s, 1H), 8.09 (d, J=2.5 Hz, 1H), 7.49 (d, J=5.0 Hz, 1H), 7.40 (d, J=2.0 Hz, 1H), 6.49 (s, 1H), 5.89 (s, 1H), 4.73 (bs, 1H), 4.30 (s, 2H), 4.27-4.25 (m, 2H), 3.93-3.91 (m, 2H), 3.58 (s, 3H), 3.49 (s, 2H), 2.95-2.93 (m, 2H), 2.78-2.76 (m, 2H), 2.34 (s, 3H), 2.04-1.99 (m, 2H), 1.88-1.83 (m, 2H).

Example 205a

2-Nitro-4,5,6,7-tetrahydropyrazolo[1,5-a]pyrazine 205a

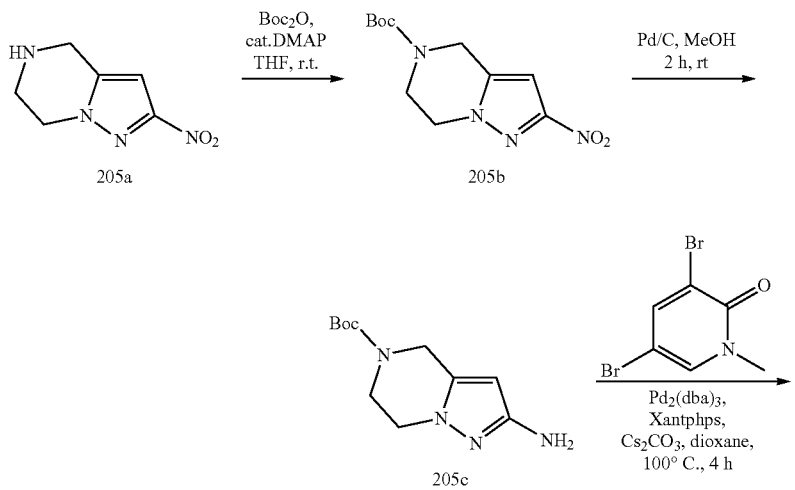

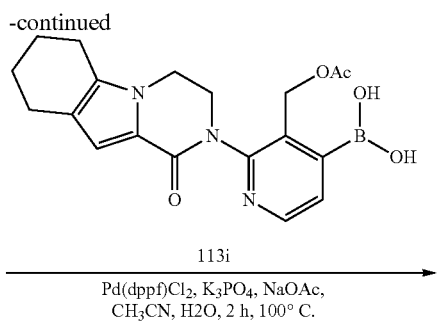
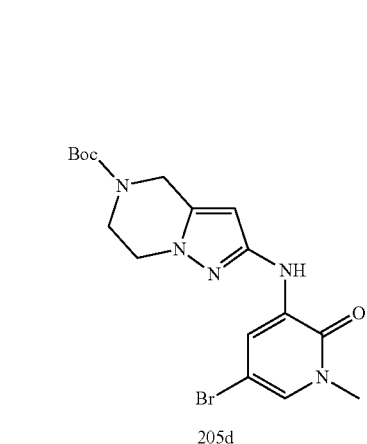

205d

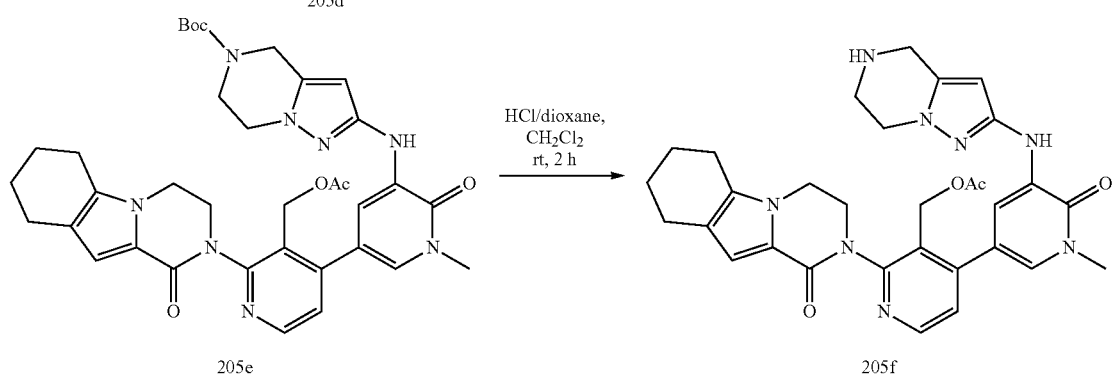

205e

205f

A 250-mL single-neck round-bottomed flask equipped with a magnetic stirrer was charged with 1-(2-bromoethyl)-5-(bromomethyl)-3-nitro-1H-pyrazole 125c (3.0 g, 9.64 mmol) in THF (35 mL) and aqueous ammonia (135 mL, 25-28%). The mixture was stirred at room temperature for 72 h under nitrogen. The reaction mixture was then concentrated under reduced pressure and the resulting residue was partitioned between ethyl acetate (100 mL) and water (100 mL). The aqueous layer was extracted with ethyl acetate (2×50 mL). The combined organic layer was washed with 10% potassium carbonate (2×100 mL), brine (200 mL), and dried over sodium sulfate. The drying agent was removed by filtration, and the filtrate was concentrated under reduced pressure to afford 205a as a yellow solid (1.23 g, 76%). MS: [M+H]$^+$ 169

Example 205b tert-Butyl 2-Nitro-6,7-dihydropyrazolo[1,5-a]pyrazine-5(4H)-carboxylate 205b To a solution of 205a (504 mg, 3.0 mmol) in THF (20 mL) was added (Boc)$_2$O (785 mg, 3.60 mmol) and DMAP (74 mg, 0.60 mmol). The reaction mixture was stirred at room temperature overnight. Then it was filtered and the filtrate was concentrated under reduced pressure. The resulting residue was purified by silica-gel column chromatography eluting with 100:1 dichloromethane/methanol to afford 205b as white solid (750 mg, 80%). MS-ESI: [M+H]$^+$ 269.3

Example 205c tert-Butyl 2-Amino-6,7-dihydropyrazolo[1,5-a]pyrazine-5(4H)-carboxylate 205c A 100-mL single-neck round-bottomed flask was purged with nitrogen and charged with 205b (0.75 g, 2.80 mmol), 10% palladium on carbon (50% wet, 280 mg), and methanol (30 mL). The mixture was evacuated, charged with hydrogen gas, and stirred at room temperature for 2 h. The hydrogen was then evacuated and nitrogen was charged into the flask. The catalyst was removed by filtration through a pad of CELITE® and the filtrate was concentrated under reduced pressure to afford 205c (524 mg, 79%). MS-ESI: [M+H]$^+$ 239.1

Example 205d tert-Butyl 2-(5-Bromo-1-methyl-2-oxo-1,2-dihydropyridin-3-ylamino)-6,7-dihydropyrazolo[1,5-a]pyrazine-5(4H)-carboxylate 205d A 50-mL single-neck round-bottomed flask equipped with a magnetic stirrer and a reflux condenser was charged with 205c (524 mg, 2.2 mmol), Pd$_2$(dba)$_3$ (201 mg, 0.22 mmol), XantPhos (254 mg, 0.44 mmol), cesium carbonate (1434 mg, 4.4 mmol), and 1,4-dioxane (20 mL). After three cycles of vacuum/argon flush, the mixture was heated at 100° C. for 4 h. After this time the reaction was cooled to room temperature. It was then filtered and the filtrate was evaporated in vacuo. The residue was purified by silica-gel column chromatography eluting with 50:1 dichloromethane/methanol to afford 205d (600 mg, 70%) as a yellow solid. MS-ESI: [M+H]$^+$ 424.2

Example 205e tert-Butyl 2-(5-(3-(Acetoxymethyl)-2-(1-oxo-3,4,6,7,8,9-hexahydropyrazino[1,2-a]indol-2(1H)-yl)pyridin-4-yl)-1-methyl-2-oxo-1,2-dihydropyridin-3-ylamino)-6,7-dihydropyrazolo[1,5-a]pyrazine-5(4H)-carboxylate 205e A sealed tube equipped with a magnetic stirrer was charged with 205d (213 mg, 0.50 mmol), 3-(acetoxymethyl)-2-(1-oxo-3,4,6,7,8,9-hexahydropyrazino[1,2-a]indol-2(1H)-yl)pyridin-4-ylboronic acid 113i (192 mg, 0.50 mmol), Pd(dppf)Cl$_2$ (41 mg, 0.050 mmol), sodium acetate (82 mg, 1.0 mmol), K$_3$PO$_4$ (212 mg, 1.0 mmol), acetonitrile (10 mL), and water (0.5 mL). After three cycles of vacuum/argon flush, the mixture was heated at 100° C. for 2 h. It was then filtered and the filtrate was evaporated in vacuo. The residue was purified by silica-gel column chromatography eluting with 25:1 dichloromethane/methanol to afford 205e (280 mg, 82%) as a yellow solid. MS-ESI: [M+H]$^+$ 683.3

Example 205f (4-(1-Methyl-6-oxo-5-(4,5,6,7-tetrahydropyrazolo[1,5-a]pyrazin-2-ylamino)-1,6-dihydropyridin-3-yl)-2-(1-oxo-3,4,6,7,8,9-hexahydropyrazino[1,2-a]indol-2(1H)-yl)pyridin-3-yl)methyl Acetate 205f A mixture of 205e (280 mg, 0.41 mmol), 4.0 M HCl/dioxane (4 mL), and dichloromethane (4 mL) was stirred at room temperature for 2 h. It was then concentrated under reduced pressure to afford 205f as a yellow solid (165 mg, 66%), which was used for the next step without further purification. MS-ESI: [M+H]$^+$ 583.3.

Example 205

2-[3-(hydroxymethyl)-4-[1-methyl-6-oxo-5-(4,5,6,7-tetrahydropyrazolo[1,5-a]pyrazin-2-ylamino)-3-pyridyl]-2-pyridyl]-3,4,6,7,8,9-hexahydropyrazino[1,2-a]indol-1-one 205

A mixture of 205f (165 mg, 0.28 mmol) and lithium hydroxide (67 mg, 2.80 mmol) in i-propanol/THF (1:1, 4 mL) and water (1 mL) was stirred at room temperature for 1 h. The mixture was evaporated in vacuo and diluted with water (4 mL). It was then extracted with ethyl acetate (10 mL×2). The combined ethyl acetate extract was concentrated under reduced pressure and the residue was purified by reverse-phase prep-HPLC to afford 205 (70 mg, 46%) as a white solid. MS-ESI: [M+H]$^+$ 541.2. $^1$H NMR (500 MHz, CDCl$_3$) δ 8.48 (d, J=5.0 Hz, 1H), 7.96 (d, J=2.0 Hz, 1H), 7.72 (d, J=2.0 Hz, 1H), 7.43 (s, 1H), 7.35 (d, J=5.5 Hz, 1H), 6.90 (s, 1H), 5.70 (s, 1H), 5.01 (s, 1H), 4.64-4.61 (m, 1H), 4.50 (s, 1H), 4.34 (s, 1H), 4.16-3.99 (m, 6H), 3.89-3.87 (m, 1H), 3.71 (s, 3H), 3.30 (t, J=5.5 Hz, 2H), 2.63-2.57 (m, 4H), 1.92-1.89 (m, 2H), 1.80-1.78 (m, 3H).

Example 206a tert-Butyl 3-Iodoazetidine-1-carboxylate 206a

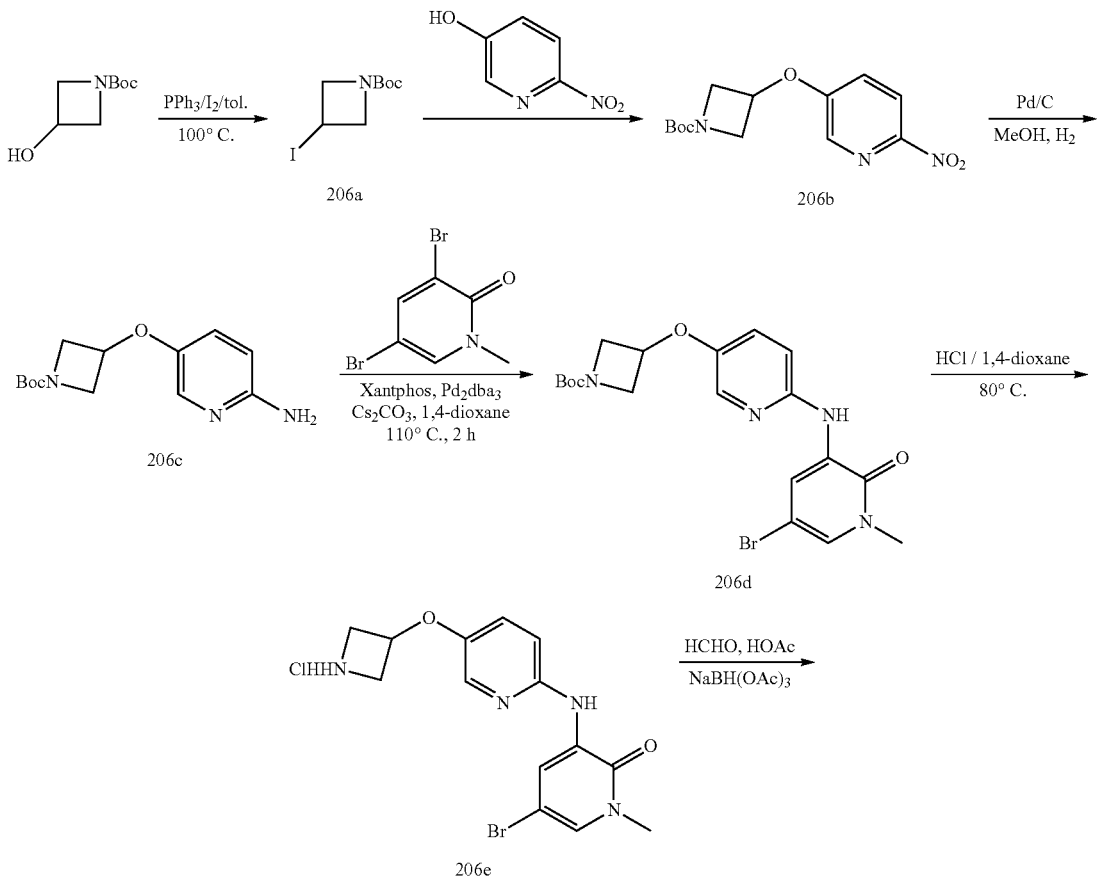

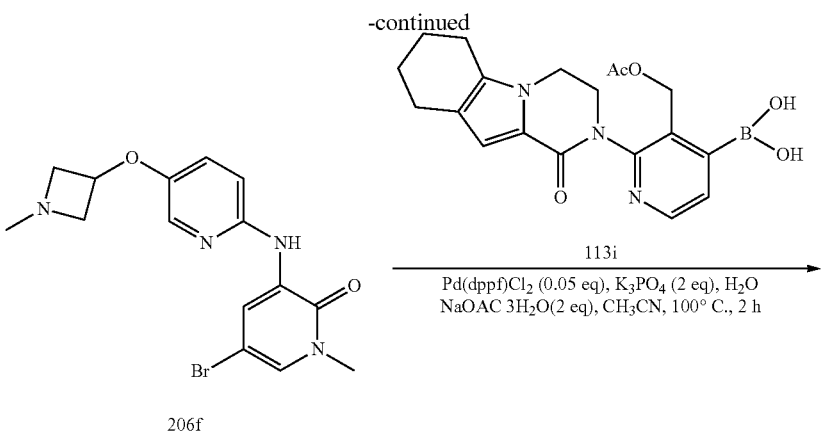

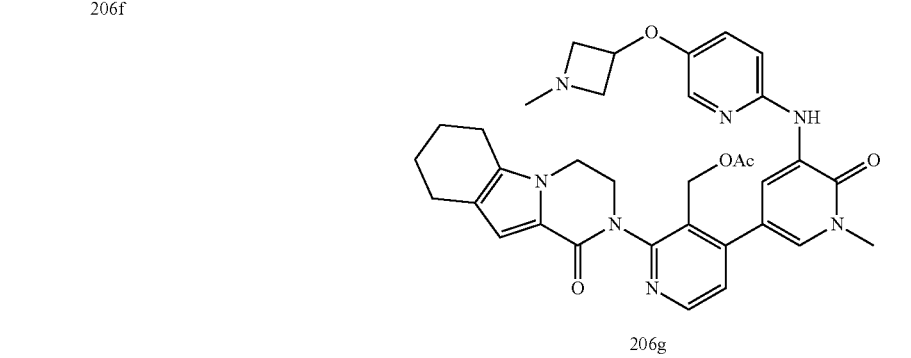

A solution of tert-butyl 3-hydroxyazetidine-1-carboxylate (3.5 g, 0.020 mol) in toluene (200 mL) was treated with imidazole (4.08 g, 0.060 mol), triphenylphosphine (0.60 g, 0.040 mol), and iodine (7.62 g, 0.030 mol). The mixture was heated at 100° C. for 1 h. It was then cooled to room temperature and poured into saturated $NaHCO_3$ solution (30 mL). Excess triphenylphosphine was destroyed by addition of iodine until iodine coloration persisted in organic layer. The mixture was washed with 5% $Na_2SO_3$ solution, dried over $Na_2SO_4$, and evaporated in vacuo. The residue was purified by silica-gel column chromatography to afford 206a (5.31 g, 93%). MS-ESI: $[M+H]^+$ 284.

Example 206b tert-Butyl 3-(6-Nitropyridin-3-yloxy)azetidine-1-carboxylate 206b A mixture of 206a (2.24 g, 7.9 mmol), 6-nitropyridin-3-ol (1.0 g, 7.2 mmol), and $Cs_2CO_3$ (2.6 g, 7.9 mmol) in DMF (8 mL) was heated at 125° C. in a sealed tube overnight. The solid was filtered and washed with ethyl acetate (2×20 mL). The combined filtrate was evaporated in vacuo and the residue was purified on reverse-phase Combiflash to afford 206b (1.25 g, 59%). MS-ESI: $[M+H]^+$ 296.

Example 206c tert-Butyl 3-(6-Aminopyridin-3-yloxy)azetidine-1-carboxylate 206c A 100-mL Parr hydrogenation bottle was purged with nitrogen and charged with 206b (1.07 g, 3.6 mmol), 10% palladium on carbon (50% wet, 0.30 g), and methanol (60 mL). The bottle was evacuated, charged with hydrogen gas to a pressure of 25 psi, and shaken for 2 h on a Parr hydrogenation apparatus. The hydrogen was then evacuated and nitrogen charged to the bottle. The catalyst was removed by filtration through a pad of CELITE® and the filtrate was concentrated under reduced pressure to afford 206c (0.95 g, 99%). MS-ESI: $[M+H]^+$ 266.

Example 206d tert-Butyl 3-(6-(5-Bromo-1-methyl-2-oxo-1,2-dihydropyridin-3-ylamino)pyridin-3-yloxy)azetidine-1-carboxylate 206d A 100-mL round-bottomed flask equipped with a reflux condenser was charged with 206c (950 mg, 3.6 mmol), Xant-Phos (125 mg, 0.29 mmol), $Pd_2dba_3$ (260 mg, 0.29 mmol), 3,5-dibromo-1-methylpyridin-2(1H)-one (1.03 g, 3.9 mmol), $Cs_2CO_3$ (1.8 g, 7.2 mmol), and 1,4-dioxane (20 mL). The system was evacuated and refilled with $N_2$. It was then heated at reflux for 2 h. After the completion of the reaction, the mixture was filtered off and washed with methanol (100 mL). The combined filtrate was evaporated in vacuo and the residue was purified on reverse-phase Combiflash to afford 206d (1.46 g, 90%). MS-ESI: $[M+H]^+$ 451.

Example 206e 3-(5-(Azetidin-3-yloxy)pyridin-2-ylamino)-5-bromo-1-methylpyridin-2(1H)-one Hydrochloride 206e A mixture of 206d (1.46 g, 3.2 mmol) and HCl/1,4-dioxane (3.2 mL, 4M, 12.8 mmol) in methanol (20 mL) was heated at 80° C. for 1 h. The mixture was then concentrated under reduced pressure to afford 206e (1.24 g, 99%). MS-ESI: [M+H]⁺ 351.

Example 206f

5-Bromo-1-methyl-3-(5-(1-methylazetidin-3-yloxy) pyridin-2-ylamino)pyridine-2(1H)-one 206f A mixture of 206e (1.24 g, 3.2 mmol), 37% aqueous formaldehyde solution (15 mL,), acetic acid (1 mL), and NaBH(OAc)₃ (1.36 g, 6.4 mmol) in methanol (10 mL) was stirred at room temperature for 4 h. The solvent was evaporated in vacuo and the residue was extracted with ethyl acetate (3×20 mL). The combined extract was dried over sodium sulfate and concentrated under reduced pressure. The residue was purified on reverse-phase Combiflash to afford 206f (940 mg, 80%). MS-ESI: [M+H]⁺ 365.

Example 206g (4-(1-Methyl-5-(5-(1-methylazetidin-3-yloxy)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 206g A 100-mL round-bottomed flask equipped with a reflux condenser was charged with 206f (108 mg, 0.30 mmol), 3-(acetoxymethyl)-2-(1-oxo-3,4,6,7,8,9-hexahydropyrazino[1,2-a]indol-2(1H)-yl)pyridin-4-ylboronic acid 113i (115 mg, 0.30 mmol), Pd(dppf)Cl₂ (15 mg, 0.015 mmol), K₃PO₄ (135 mg, 0.60 mmol), sodium acetate trihydrate (90 mg, 0.60 mmol) in acetonitrile (10 mL) and water (0.5 mL). The system was evacuated and refilled with N₂. The reaction mixture was heated at 100° C. for 2 h. It was then cooled to room temperature and filtered. The filtrate was concentrated under reduced pressure and the resulting residue was purified by silica-gel column chromatography eluting with 25:1 dichloromethane/methanol to afford 206g (90 mg, 52%) as a yellow brown solid. MS-ESI: [M+H]⁺ 624.2.

Example 206

2-[3-(hydroxymethyl)-4-[1-methyl-5-[[5-(1-methylazetidin-3-yl)oxy-2-pyridyl]amino]-6-oxo-3-pyridyl]-2-pyridyl]-3,4,6,7,8,9-hexahydropyrazino[1,2-a]indol-1-one 206

A mixture of 206g (93.6 mg, 0.15 mmol) and lithium hydroxide (65 mg, 1.5 mmol) in THF/i-propanol (5:3, 8 mL) and water (2 mL) was stirred at 30° C. for 1 h. The mixture was evaporated in vacuo and diluted with water (3 mL). It was then extracted with ethyl acetate (2×10 mL). The combined ethyl acetate extract was concentrated under reduced pressure and the residue was purified by reverse-phase prep-HPLC to afford 206 (35 mg, 42%) as white solid. MS-ESI: [M+H]⁺ 582.3. ¹H NMR (500 MHz, CHCl₃) δ 8.62 (d, J=1.5 Hz, 1H), 8.51 (d, J=5.0 Hz, 1H), 7.86 (d, J=2.0 Hz, 1H), 7.84 (s, 1H), 7.76 (d, J=3.0 Hz, 1H), 7.37 (d, J=5.0 Hz, 1H), 7.12-7.10 (m, 1H), 6.90 (s, 1H), 6.81-6.80 (m, 1H), 5.07-5.04 (m, 1H), 4.77 (t, J=5.5 Hz, 1H), 4.64-4.62 (m, 1H), 4.52-4.50 (m, 1H), 4.33-4.30 (m, 1H), 4.16-4.10 (m, 2H), 3.97-3.88 (m, 3H), 3.72 (s, 3H), 3.25-3.24 (m, 2H), 2.63-2.57 (m, 4H), 2.51 (s, 3H), 1.93-1.91 (m, 2H), 1.80-1.79 (m, 2H).

Example 207a (2-{4,4-Dimethyl-9-oxo-1,10-diazatricyclo[6.4.0.0²,⁶]dodeca-2(6),7-dien-10-yl}-4-[1-methyl-5-({5-[(1-methylazetidin-3-yl)oxy]pyridin-2-yl}amino)-6-oxopyridin-3-yl]pyridin-3-yl)methyl Acetate 207a

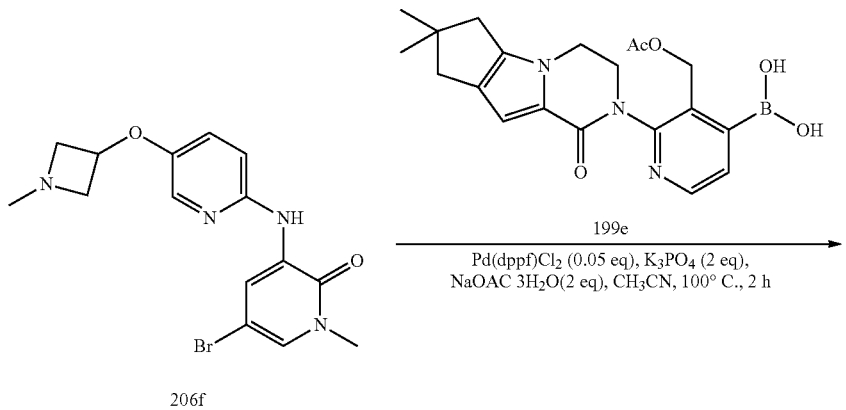

206f

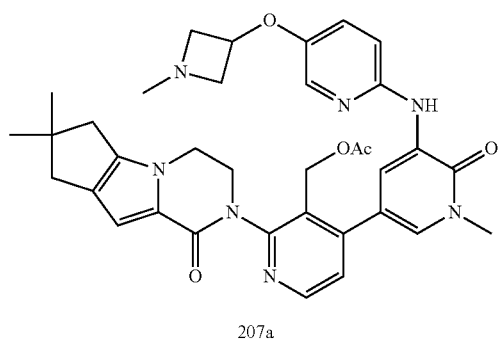

207a

A 50-mL single-neck round-bottomed flask equipped with a reflux condenser was charged with 5-bromo-1-methyl-3-(5-(1-methylazetidin-3-yloxy)pyridin-2-ylamino)-pyridin-2(1H)-one 206f (108 mg, 0.40 mmol), {3-[(acetyloxy)methyl]-2-{4,4-dimethyl-9-oxo-1,10-diaza-tricyclo[6.4.0.0$^{2,6}$] dodeca-2(6),7-dien-10-yl}pyridin-4-yl}boronic acid 199e (240 mg, 0.60 mmol), Pd(dppf)Cl$_2$ (20 mg, 0.02 mmol), K$_3$PO$_4$ (180 mg, 0.80 mmol), sodium acetate trihydrate (120 mg, 0.80 mmol), water (0.5 mL), and acetonitrile (10 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 10:1 dichloromethane/methanol to afford 207a (100 mg, 45%) as a yellow brown solid. LCMS-ESI: [M+H]$^+$ 638.4.

Example 207

3-[3-(hydroxymethyl)-4-[1-methyl-5-[[5-(1-methylazetidin-3-yl)oxy-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 207

A mixture of 207a (90 mg, 0.15 mmol) and lithium hydroxide (65 mg, 1.5 mmol) in THF/i-propanol(5:3, 8 mL) and water (2 mL) was stirred at 30° C. for 1 h. The mixture was evaporated under reduced pressure and diluted with water (4 mL). It was then extracted with ethyl acetate (2×20 mL). The combined ethyl acetate extract was concentrated under reduced pressure and the residue was purified by reverse-phase prep-HPLC to afford 207 (30 mg, 38%) as white solid. LCMS: [M+H]$^+$ 596.3. $^1$H NMR (500 MHz, CDCl$_3$) δ 8.61 (d, J=2.0 Hz, 1H), 8.51 (d, J=5.0 Hz, 1H), 7.86-7.83 (m, 2H), 7.77 (d, J=3.0 Hz, 1H), 7.37 (d, J=5.0 Hz, 1H), 7.12-7.10 (m, 1H), 6.85 (s, 1H), 6.81 (d, J=3.5 Hz, 1H), 5.07-5.04 (m, 1H), 4.74-4.64 (m, 2H), 4.52-4.51 (m, 1H), 4.34-4.32 (m, 1H), 4.17-4.16 (m, 2H), 3.88-3.87 (m, 3H), 3.72 (s, 3H), 3.17-3.16 (m, 2H), 2.58 (d, J=5.5 Hz, 2H), 2.52 (s, 2H), 2.45 (s, 3H), 1.28 (s, 6H).

Example 208a

5-Ethyl-2-nitro-4,5,6,7-tetrahydropyrazolo[1,5-a]pyrazine 208a

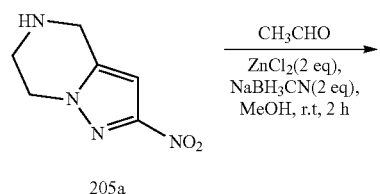

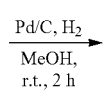

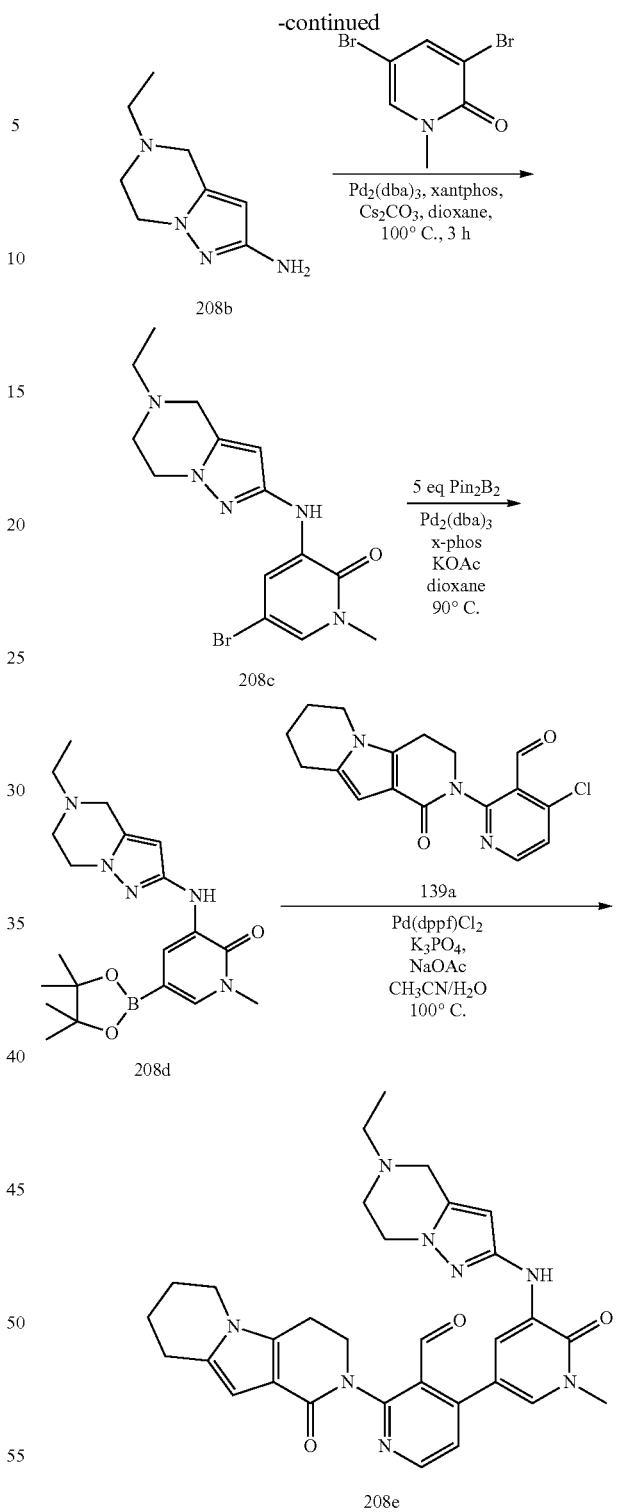

A 150-mL single-neck round-bottomed flask equipped with a magnetic stirrer was charged with methanol (60 mL), 2-nitro-4,5,6,7-tetrahydropyrazolo[1,5-a]pyrazine 205a (1.5 g, 8.9 mmol), ZnCl$_2$ (2.43 g, 17.8 mmol), acetaldehyde (784 mg, 17.8 mmol), and NaBH$_3$CN (1.12 g, 17.8 mmol). The mixture was stirred at room temperature for 2 h and concentrated under reduced pressure. The residue was purified with silica-gel column chromatography eluting with 40:1 petroleum ether/ethyl acetate to afford 208a (1.4 g, 81%) as a yellow oil. MS-ESI: [M+H]$^+$ 197

Example 208b

5-Ethyl-4,5,6,7-tetrahydropyrazolo[1,5-a]pyrazin-2-amine 208b

A 50-mL single-neck round-bottomed flask was purged with nitrogen and charged with 208a (1.4 g, 7.1 mmol), 10% palladium on carbon (50% wet, 208 mg), methanol (30 mL), and hydrogen gas. The mixture was stirred at room temperature under hydrogen atmosphere for 2 h. The catalyst was removed by filtration through a pad of CELITE® and the filtrate was concentrated under reduced pressure to afford 208b (1.0 g, 84%) as yellow oil. MS-ESI: [M+H]$^+$ 167

Example 208c

5-Bromo-3-(5-ethyl-4,5,6,7-tetrahydropyrazolo[1,5-a]pyrazin-2-ylamino)-1-methylpyridin-2(1H)-one 208c A 100-mL single-neck round-bottomed flask equipped with a magnetic stirrer and a reflux condenser was charged with 208b (1.0 g, 6.0 mmol), 3,5-dibromo-1-methylpyridin-2(1H)-one (1.6 g, 6.0 mmol), Pd$_2$(dba)$_3$ (274 mg, 0.30 mmol), XantPhos (347 mg, 0.60 mmol), cesium carbonate (3.9 g, 12.0 mmol), and 1,4-dioxane (50 mL). After three cycles of vacuum/argon flush, the mixture was stirred at 100° C. for 3 h. It was then filtered and the filtrate was evaporated in vacuo. The residue was purified by silica-gel column chromatography eluting with 40:1 dichloromethane/methanol to afford 208c (630 mg, 29%) as a yellow solid. MS-ESI: [M+H]$^+$ 352

Example 208d 3-(5-Ethyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 208d A 100-mL single-neck round-bottomed flask equipped with a magnetic stirrer and a reflux condenser was charged with 1,4-dioxane (20 mL), 208c (350 mg. 0.99 mmol), bis(pinacolato)diboron (1.31 g, 4.99 mmol), Pd$_2$(dba)$_3$ (45 mg, 0.050 mmol), X-phos (58 mg, 0.10 mmol), and potassium acetate (291 mg, 2.97 mmol). After bubbling nitrogen through the mixture for 30 minutes, it was heated at 90° C. for 3 h. Then it was filtered and the filtrate was evaporated in vacuo. The residue was washed with petroleum ether to afford 208d (120 mg, 30%) as a brown solid. MS-ESI: [M+H]$^+$ 400.2

Example 208e 4-(5-(5-Ethyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydro-pyrido[3,4-b]indolizin-2(1H)-yl)nicotinaldehyde 208e A 50-mL single-neck round-bottomed flask equipped with a magnetic stirrer and a reflux condenser was charged with 208d (120 mg, 0.30 mmol), 4-chloro-2-(1-oxo-3,4,6,7,8,9-hexahydropyrido-[3,4-b]indolizin-2(1H)-yl)nicotinaldehyde 139a (99 mg, 0.30 mmol), PdCl$_2$(dppf) (13 mg, 0.015 mmol), K$_3$PO$_4$ (127 mg, 0.60 mmol), sodium acetate (49 mg, 0.60 mmol), acetonitrile (10 mL), and water (0.5 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 30:1 dichloromethane/methanol to afford the 208e (95 mg, 56%) as a yellow solid. MS-ESI: [M+H]$^+$ 567.2.

Example 208

2-[4-[5-[(5-ethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrido[3,4-b]indolizin-1-one 208

To a mixture of 208e (95 mg, 0.16 mmol) at 0° C. in methanol (10 mL) was added sodium borohydride (19 mg, 0.50 mmol). The reaction mixture was stirred for 30 minutes and quenched with water (2.0 mL). It was then concentrated under reduced pressure and the residue was purified by reverse-phase prep-HPLC to afford 208 (8 mg, 9%) as white solid. MS-ESI: [M+H]$^+$ 569.3. $^1$H NMR (500 MHz, CDCl$_3$) δ 8.46 (d, J=5.0 Hz, 1H), 7.92 (d, J=2.0 Hz, 1H, 7.70 (d, J=2.0 Hz, 1H), 7.40 (s, 1H), 7.30 (d, J=5.0 Hz, 1H), 6.30 (s, 1H), 5.71 (s, 1H), 4.93-4.96 (m, 1H), 4.63-4.61 (m, 1H), 4.42-4.26 (m, 2H), 4.09 (s, 2H), 3.94-3.81 (m, 3H), 3.69-3.68 (m, overlap, 5H), 3.06-2.90 (m, 4H), 2.81 (d, J=3.0 Hz, 2H), 2.66 (d, J=3.5 Hz, 2H), 2.04-2.00 (m, 2H), 1.88-1.85 (m, 2H), 1.20 (t, J=7.5 Hz, 3H).

Example 209a 1-(2-Nitro-6,7-dihydropyrazolo[1,5-a]pyrazin-5(4H)-yl)ethanone 209a

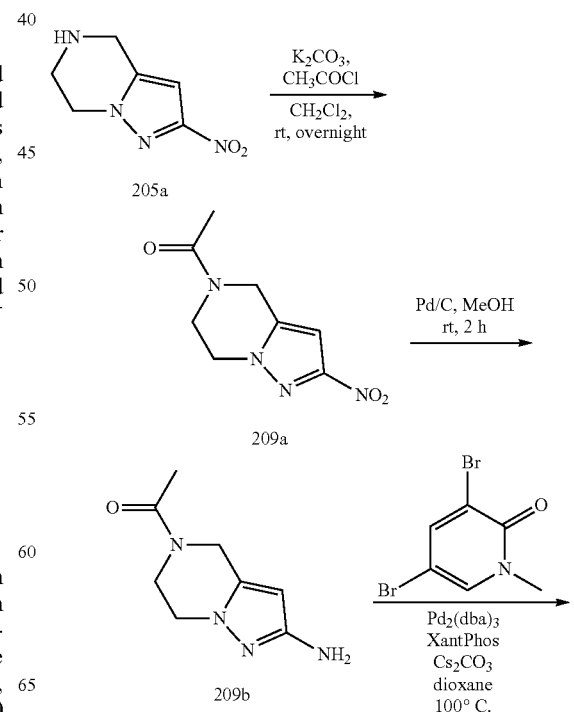

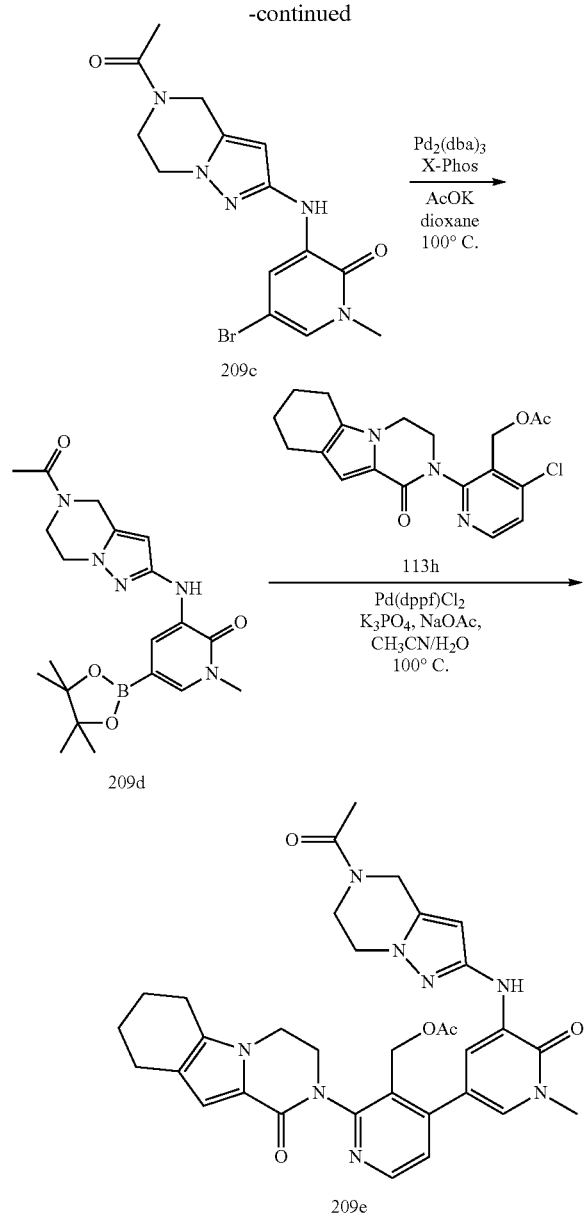

To a solution of 2-nitro-4,5,6,7-tetrahydropyrazolo[1,5-a]pyrazine 205a (672 mg, 4.0 mmol) in dichloromethane (20 mL) was added acetyl chloride (936 mg, 12.0 mmol) and $K_2CO_3$ (1104 mg, 8.0 mmol). The mixture was stirred overnight. It was then filtered and the filtrate was concentrated under reduced pressure. The resulting residue was purified by silica-gel column chromatography eluting with 100:1 dichloromethane/methanol to afford 209a as white solid (500 mg, 60%). MS: [M+H]$^+$ 211.2

Example 209b 1-(2-Amino-6,7-dihydropyrazolo[1,5-a]pyrazin-5(4H)-yl)ethanone 209b A 50-mL single-neck round-bottomed flask was purged with nitrogen and charged with 209a (492 mg, 2.34 mmol), 10% palladium on carbon (50% wet, 234 mg), and methanol (20 mL). The mixture was evacuated, charged with hydrogen gas, and stirred at room temperature for 2 h. The hydrogen was then evacuated and nitrogen was charged into the flask. The catalyst was removed by filtration through a pad of CELITE® and the filtrate was concentrated under reduced pressure to afford 209b (380 mg, 80%). MS: [M+H]$^+$ 181.1

Example 209c 3-(5-Acetyl-4,5,6,7-tetrahydropyrazolo[1,5-a]pyrazin-2-ylamino)-5-bromo-1-methylpyridin-2(1H)-one 209c A 50-mL single-neck round-bottomed flask equipped with a magnetic stirrer and a reflux condenser was charged with 3,5-dibromo-1-methylpyridin-2(1H)-one (481 mg, 1.8 mmol), 209b (270 mg, 1.5 mmol), 1,4-dioxane (20 mL), $Pd_2(dba)_3$ (137 mg, 0.15 mmol), XantPhos (173 mg, 0.30 mmol), and cesium carbonate (978 mg, 3.0 mmol). After three cycles of vacuum/argon flush, the mixture was heated at 100° C. for 6 h. After this time the reaction was cooled to room temperature. It was then filtered and the filtrate was evaporated in vacuo. The residue was purified by silica-gel column chromatography eluting with 50:1 dichloromethane/methanol to afford 209c (540 mg, 89%) as a yellow solid. MS: [M+H]$^+$368.0

Example 209d 3-(5-Acetyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 209d A 50-mL single-neck round-bottomed flask equipped with a magnetic stirrer and a reflux condenser was charged with 209c (365 mg, 1.0 mmol), Pin$_2$B$_2$ (1.26 g, 5.0 mmol), Pd$_2$(dba)$_3$ (91 mg, 0.10 mmol), X-phos (92 mg, 0.20 mmol), AcOK (294 mg, 3.0 mmol), and dioxane (10 mL). After three cycles of vacuum/argon flush, the mixture was heated at 60° C. for 16 h. It was then cooled to room temperature and filtered. The filtrate was concentrated under reduced pressure and the residue was purified by silica-gel column chromatography eluting with 50:1 methylene chloride/methanol to afford 209d as a brown solid (330 mg, 80%). MS: [M+H]$^+$ 414.2

Example 209e (4-(5-(5-Acetyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 209e A sealed tube equipped with a magnetic stirrer was charged with 209d (185 mg, 0.50 mmol), (4-chloro-2-(1-oxo-3,4,6,7,8,9-hexahydropyrazino-[1,2-a]indol-2(1H)-yl)pyridine-3-yl)methyl acetate 113h (192 mg, 0.50 mmol), Pd(dppf)Cl$_2$ (41 mg, 0.050 mmol), sodium acetate (82 mg, 1.0 mmol,), $K_3PO_4$ (212 mg, 1.0 mmol), water (0.5 mL), and acetonitrile (10 mL). After three cycles of vacuum/argon flush, the mixture was heated at 100° C. for 2 h. It was then filtered and the filtrate was evaporated in vacuo. The residue was purified by silica-gel column chromatography eluting with 25:1 dichloromethane/methanol to afford 209e (150 mg, 48%) as a yellow solid. MS-ESI: [M+H]$^+$ 625.4

Example 209

2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydro-pyrazino[1,2-a]indol-1-one 209

A mixture of 209e (150 mg, 0.24 mmol) and lithium hydroxide (58 mg, 2.4 mmol) in i-propanol/THF (1:1, 4 mL) and water (1 mL) was stirred at room temperature for 1 h. The mixture was evaporated in vacuo and diluted with water (4 mL). It was then extracted with ethyl acetate (2×10 mL). The combined ethyl acetate extract was concentrated under reduced pressure and the residue was purified by reverse-phase prep-HPLC to afford 209 (75 mg, 53%) as a white solid. MS-ESI: [M+H]⁺ 583.3. ¹H NMR (500 MHz, T=80° C., DMSO-d₆) δ 8.44 (d, J=8.5 Hz, 1H), 7.93-7.90 (m, 2H), 7.34 (d, J=4.5 Hz, 1H), 7.29 (d, J=8.5 Hz, 1H), 6.56 (s, 1H), 5.98 (s, 1H), 4.72-4.63 (m, 3H), 4.45-4.43 (m, 2H), 4.16-4.10 (m, 3H), 3.99-3.86 (m, overlap, 5H), 3.58 (s, 3H), 2.62-2.57 (m, 2H), 2.49-2.47 (m, 2H), 2.08 (s, 3H), 1.83-1.77 (m, 2H), 1.72-1.68 (m, 2H).

Example 210a

4-Chloro-2-{4,4-dimethyl-9-oxo-1,10-diazatricyclo-[6.4.0.0²,⁶]dodeca-2(6),7-dien-10-yl}pyridine-3-carboxylic Acid 210a

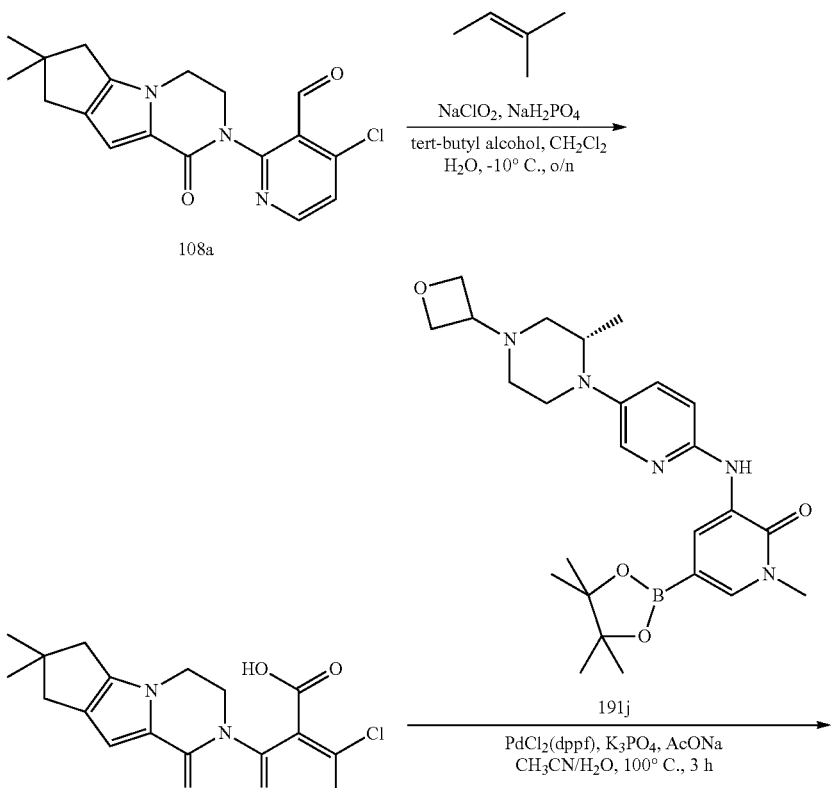

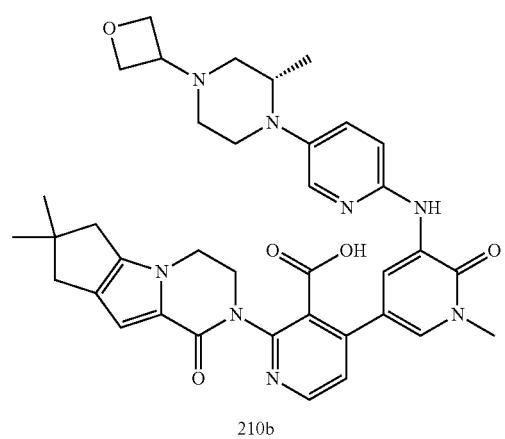

To a mixture of 4-chloro-2-{4,4-dimethyl-9-oxo-1,10-diazatricyclo[6.4.0.0$^{2,6}$]dodeca-2(6),7-dien-10-yl}pyridine-3-carbaldehyde 108a (500 mg, 1.46 mmol), tert-butyl alcohol (20 mL), and dichloromethane (5 mL) was added 2-methyl-2-butene (3066 mg, 43.8 mmol). An aqueous solution (8 mL) of NaClO$_2$ (263 mg, 2.92 mmol) and NaH$_2$PO$_4$.2 water (683 mg, 4.38 mmol) was added dropwise at −10° C. and the reaction mixture was stirred at −10° C. for overnight. It was concentrated under reduced pressure and the residue was extracted with ethyl acetate (4×20 mL). The combined organic extract was dried over MgSO$_4$ and concentrated. The residue was purified with reverse-phase prep-HPLC to afford 210a (315 mg, 60%) as a pale yellow solid. MS-ESI: [M+H]$^+$ 360.1

Example 210b

2-{4,4-Dimethyl-9-oxo-1,10-diazatricyclo[6.4.0.0$^{2,6}$]dodeca-2(6),7-dien-10-yl}-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridine-3-carboxylic Acid 210b A 25-mL round-bottomed flask equipped with a reflux condenser was charged with 210a (400 mg, 1.1 mmol), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (536 mg, 1.1 mmol), PdCl$_2$(dppf) (81 mg, 0.11 mmol), K$_3$PO$_4$ (466 mg, 2.2 mmol), sodium acetate (216 mg, 2.2 mmol), acetonitrile (10 mL), and water (0.2 mL). After three cycles of vacuum/argon flush, the mixture was heated at 100° C. for 3 h. It was then filtered and the filtrate was evaporated in vacuo. The residue was purified by silica-gel column chromatography eluting with 1:3 petroleum/ethyl acetate to afford 210b as a yellow solid (306 mg, 41%). MS-ESI: [M+H]$^+$ 679.3

Example 210

2-(7,7-dimethyl-4-oxo-1,2,6,8-tetrahydrocyclopenta[3,4]pyrrolo[3,5-b]pyrazin-3-yl)-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide 210

A 25-mL round-bottomed flask was charged with 210b (300 mg, 0.44 mmol), triethylamine (1 mL), DMAP (5 mg, 0.040 mmol), HATU (250 mg, 0.66 mmol), and DMF (10 mL). The mixture was stirred at room temperature for 0.5 h. Then 37% aqueous ammonia (15 mL) was added slowly and the reaction was stirred at room temperature for another 2.5 h. The mixture was treated with 20 mL water and extracted with dichloromethane (3×20 mL). The combined organic extract was concentrated under reduced pressure and residue was purified with reserve-phase prep-HPLC to afford 210 (98 mg, 33%) as yellow solid. MS-ESI: [M+H]$^+$ 678.3. $^1$H NMR (500 MHz, DMSO) δ 8.71 (d, J=2.0 Hz, 1H), 8.55 (d, J=2.5 Hz, 1H), 8.41 (s, 1H), 7.84 (d, J=3.0 Hz, 1H), 7.61 (s, 1H), 7.49 (s, 1H), 7.45-7.42 (m, 2H), 7.38-7.36 (m, 1H), 7.24-7.22 (m, 1H), 6.49 (s, 1H), 4.57-4.54 (m, 2H), 4.48-4.47 (m, 1H), 4.43-4.40 (m, 1H), 4.12-4.11 (m, 2H), 4.04-4.00 (m, 2H), 3.67-3.66 (m, 1H), 3.57 (s, 3H), 3.42-3.37 (m, 1H), 3.10-3.08 (m, 1H), 2.97-2.92 (m, 1H), 2.55-2.53 (m, 3H), 2.41 (s, 2H), 2.36-2.29 (m, 2H), 2.21-2.18 (m, 1H), 1.21 (s, 6H), 0.93 (d, J=6.0 Hz, 3H)

Example 211

2-(7,7-dimethyl-4-oxo-1,2,6,8-tetrahydrocyclopenta[3,4]pyrrolo[3,5-b]pyrazin-3-yl)-N-methyl-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide 211

A round-bottomed flask was charged with 2-{4,4-dimethyl-9-oxo-1,10-diazatricyclo[6.4.0.0$^{2,6}$]dodeca-2(6),7-dien-10-yl}-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridine-3-carboxylic acid 210b (300 mg, 0.44 mmol), triethylamine (1 mL), DMAP (5 mg, 0.040 mmol), HATU (250 mg, 0.66 mmol), and DMF (10 mL). The mixture was stirred at room temperature for 0.5 h. Then CH$_3$NH$_2$ (27 mg, 0.88 mmol) was added slowly and the reaction was stirred at room temperature for another 2.5 h. The mixture was treated with water (20 mL) and extracted with dichloromethane (20 mL×3). The combined organic extract was concentrated under reduced pressure and the residue was purified with reserve-phase prep-HPLC to afford 211 (106 mg, 35%) as yellow solid. MS-ESI: [M+H]$^+$ 692.5. $^1$H NMR (500 MHz, DMSO-d$_6$) δ 8.71 (d, J=2.5 Hz, 1H), 8.55 (d, J=5.0 Hz, 1H), 8.42 (s, 1H), 8.11-8.08 (m, 1H), 7.86 (d, J=2.5 Hz, 1H), 7.44-7.41 (m, 2H), 7.38-7.35 (m, 1H), 7.24-7.22 (m, 1H), 6.48 (s, 1H), 4.58-4.56 (m, 2H), 4.48-4.46 (m, 1H), 4.43-4.41 (m, 1H), 4.08-4.07 (m, 2H), 3.97-3.94 (m, 2H), 3.66-3.65 (m, 1H), 3.58 (s, 3H), 3.41-3.39 (m, 1H), 3.10-3.08 (m, 1H), 2.97-2.93 (m, 1H), 2.56 (s, 2H), 2.53-2.48 (m, overlap, 4H), 2.37-2.36 (m, 2H), 2.35-2.31 (m, 2H), 2.29-2.19 (m, 1H), 1.21 (s, 6H), 0.93 (d, J=6.0 Hz, 3H).

Example 212a

{4-[5-({5-Acetyl-4H,6H,7H-pyrazolo[1,5-a]pyrazin-2-yl}amino)-1-methyl-6-oxopyridin-3-yl]-2-{4,4-dimethyl-9-oxo-1,10-diazatricyclo[6.4.0.0$^{2,6}$]-dodeca-2(6),7-dien-10-yl}pyridin-3-yl}methyl Acetate 212a

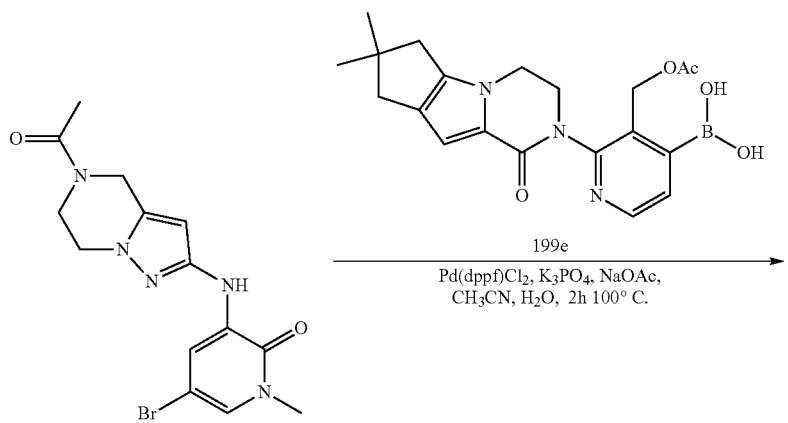

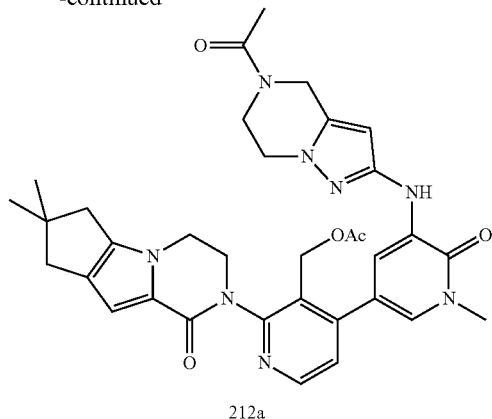

212a

A 50-mL round-bottomed flask equipped with a reflux condenser was charged with 3-(5-acetyl-4,5,6,7-tetrahydropyrazolo[1,5-a]pyrazin-2-ylamino)-5-bromo-1-methylpyridin-2(1H)-one 209c (185 mg, 0.50 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (200 mg, 0.50 mmol), Pd(dppf)Cl$_2$ (41 mg, 0.050 mmol), sodium acetate (82 mg, 1.0 mmol), K$_3$PO$_4$ (212 mg, 1.0 mmol), water (0.5 mL), and acetonitrile (10 mL). After three cycles of vacuum/argon flush, the mixture was heated at 100° C. for 2 h. It was then filtered and the filtrate was evaporated in vacuo. The residue was purified by silica-gel column chromatography eluting with 25:1 dichloromethane/methanol to afford 212a (180 mg, 56%) as a yellow solid. MS-ESI: [M+H]$^+$ 639.3

Example 212

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 212

A mixture of 212a (180 mg, 0.28 mmol) and lithium hydroxide (67 mg, 2.8 mmol) in i-propanol/THF (1:1, 4 mL) and water (1 mL) was stirred at 30° C. for 1 h. The mixture was evaporated in vacuo and diluted with water (4 mL). It was then extracted with ethyl acetate (2×10 mL). The combined ethyl acetate extract was concentrated under reduced pressure and the residue was purified by reverse-phase prep-HPLC to afford 212 (70 mg, 42%) as a white solid. MS-ESI: [M+H]$^+$ 597.3. $^1$H NMR (500 MHz, T=80° C., DMSO-d$_6$) δ 8.47 (d, J=8.0 Hz, 1H), 7.95 (d, J=4.0 Hz, 1H), 7.92 (s, 1H), 7.37 (d, J=3.5 Hz, 1H), 7.31 (d, J=8.5 Hz, 1H), 6.57 (s, 1H), 6.00 (s, 1H), 4.66 (bs, 2H), 4.47 (s, 2H), 4.20-4.18 (m, 3H), 4.00-3.99 (m, 3H), 3.92-3.88 (m, 3H), 3.61 (s, 3H), 2.59 (s, 2H), 2.46 (s, 2H), 2.11 (s, 3H), 1.25 (s, 6H).

Example 213a

5-Bromo-1-methyl-3-(2-methylpyrimidin-4-ylamino)pyridin-2(1H)-one 213a

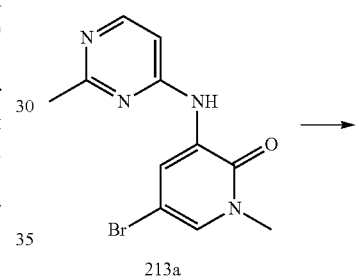

213a

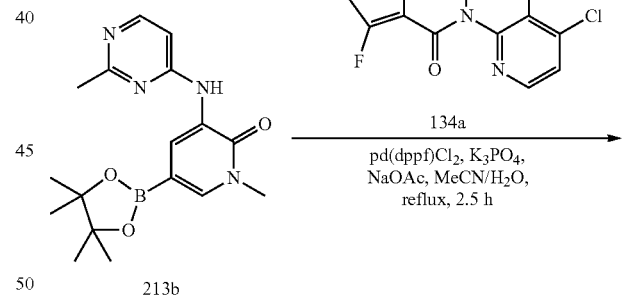

213b

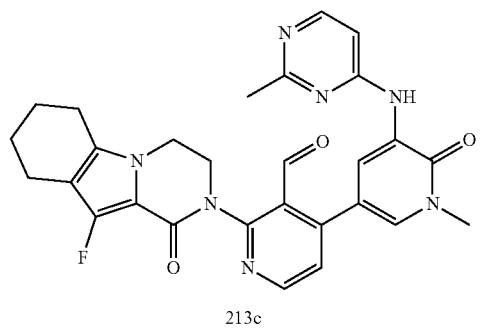

213c

Following the procedures described in Example 196, reaction of 2-methylpyrimidin-4-amine (2.0 g, 18.3 mmol) and 3,5-dibromo-1-methylpyridin-2(1H)-one (9.6 g, 36 mmol)

afforded 213a as a yellow solid (2.3 g, 43.4%). MS: [M+H]+ 295. ¹H NMR (500 MHz, DMSO-d₆) δ 9.20 (s, 1H), 8.78 (s, 1H), 8.26 (d, J=4.5 Hz, 1H), 7.68 (s, 1H), 7.18 (d, J=4.5 Hz, 1H), 3.59 (s, 3H), 2.52 (s, 3H).

Example 213b

1-Methyl-3-(2-methylpyrimidin-4-ylamino)-5-(4,4,5,5-tetramethyl-1,3,2-dioxaborolan-2-yl)pyridin-2(1H)-one 213b A 100-mL single-neck round-bottomed flask equipped with a magnetic stirrer and a reflux condenser was charged with bis(pinacolato)diboron (689 mg, 2.61 mmol), 1,4-dioxane (30 mL), 213a (307 mg, 1.04 mmol), Pd₂(dba)₃ (47 mg, 0.050 mmol), X-phos (48 mg, 0.10 mmol), and potassium acetate (305 mg, 3.12 mmol). The mixture was heated at 65° C. for 6 h. It was then filtered and the filtrate was evaporated in vacuo to afford 213b (300 mg, 84%) as a brown solid. MS: [M+H]+ 342.2

Example 213c 2-(10-Fluoro-1-oxo-3,4,6,7,8,9-hexahydropyrazino[1,2-a]indol-2(1H)-yl)-4-(1-methyl-5-(2-methylpyrimidin-4-ylamino)-6-oxo-1,6-dihydropyridin-3-yl)nicotinaldehyde 213c A 100-mL single-neck round-bottomed flask equipped with a magnetic stirrer and a reflux condenser was charged with 4-chloro-2-(10-fluoro-1-oxo-3,4,6,7,8,9-hexahydropyrazino[1,2-a]indol-2(1H)-yl)nicotinaldehyde 134c (150 mg, 0.43 mmol), 213b (147 mg 0.43 mmol), Pd(dppf)Cl₂ (35 mg, 0.043 mmol), sodium acetate (71 mg, 0.86 mmol), K₃PO₄ (182 mg, 0.86 mmol), water (0.5 mL), and acetonitrile (15 mL). After three cycles of vacuum/argon flush, the mixture was heated at 100° C. for 2.5 h. After cooling to room temperature the reaction was filtered. The filtrate was concentrated under reduced pressure and the resulting residue was purified by silica-gel column chromatography eluting with 40:1 dichloromethane/methanol to afford 213c as a yellow solid (130 mg, 57%). MS-ESI: [M+H]+ 528.2.

Example 213

10-fluoro-2-[3-(hydroxymethyl)-4-[1-methyl-5-[(2-methylpyrimidin-4-yl)amino]-6-oxo-3-pyridyl]-2-pyridyl]-3,4,6,7,8,9-hexahydropyrazino[1,2-a]indol-1-one 213

To a solution of 213c (120 mg, 0.23 mmol) at 0° C. in methanol (10 mL) was added sodium borohydride (26 mg, 0.69 mmol). The reaction mixture was stirred for 20 minutes and quenched with water (10 mL). It was then extracted with dichloromethane (3×20 mL) and the combined organic layer was concentrated under reduced pressure. The residue was purified by reverse-phase prep-HPLC to afford 213 (62 mg, 44%) as a white solid. MS-ESI: [M+H]+ 530.3. ¹H NMR (500 MHz, DMSO-d₆) δ 9.11 (s, 1H), 8.93 (d, J=2.5 Hz, 1H), 8.50 (d, J=5.0 Hz, 1H), 8.21 (d, J=6.0 Hz, 1H), 7.69 (d, J=2.5 Hz, 1H), 7.37 (d, J=5.0 Hz, 1H), 7.13 (d, J=5.5 Hz, 1H), 4.96 (t, J=5.5 Hz, 1H), 4.57-4.45 (m, 2H), 4.23-4.18 (m, 2H), 4.08-4.05 (m, 1H), 3.90-3.87 (m, 1H), 3.62 (s, 3H), 2.64-2.56 (m, 2H), 2.45 (s, 3H), 2.43-2.42 (m, 2H), 1.78-1.76 (m, 2H), 1.72-1.66 (m, 2H).

Example 214a

3-Bromo-5-iodopyridin-2-ol 214a

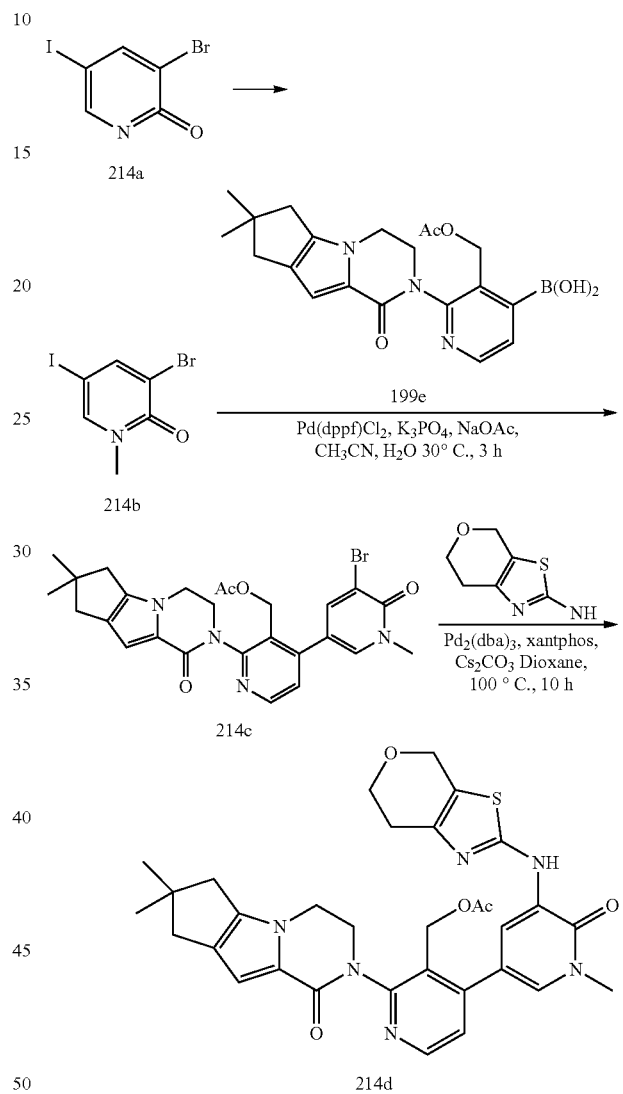

A 100-mL single-neck round-bottomed flask equipped with a magnetic stirrer was charged with acetonitrile (50 mL), trifluoroacetic acid (10 mL), 3-bromopyridin-2-ol (4.0 g, 11.56 mmol) and N-iodosuccinimide (5.2 g, 11.56 mmol). The mixture was stirred at room temperature for 15 h. The mixture was diluted with water (100 mL) and resulting white solid was collected by filtration to afford 214a (6.6 g, 96%) as a white solid. MS-ESI: [M+H]+ 300

Example 214b

3-Bromo-5-iodo-1-methylpyridin-2(1H)-one 214b

A 100-mL single-neck round-bottomed flask equipped with a magnetic stirrer was charged with DMF (50 mL), 214a (6.0 g, 20.0 mmol), iodomethane (4.26 g, 30.0 mmol), and K$_2$CO$_3$ (5.52 g, 40.0 mmol). The mixture was stirred at room temperature for 2 h and diluted with water (200 mL). The resulting white solid was collected by filtration to afford 214b (5.97 g, 95%) as a white solid. MS-ESI: [M+H]$^+$ 314

Example 214c

[4-(5-Bromo-1-methyl-6-oxo-1,6-dihydropyridin-3-yl)-2-{4,4-dimethyl-9-oxo-1,10-diazatricyclo [6.4.0.0$^{2,6}$]dodeca-2(6),7-dien-10-yl}pyridin-3-yl] methyl Acetate 214c A 100-mL single-neck round-bottomed flask equipped with a magnetic stirrer was charged with 214b (1.57 g, 5.0 mmol), {3-[(acetyloxy)methyl]-2-{4,4-dimethyl-9-oxo-1,10-diazatricyclo[6.4.0.0$^{2,6}$]-dodeca-2(6),7-dien-10-yl}pyridin-4-yl}boronic acid 199e (1.98 g, 5.0 mmol), PdCl$_2$ (dppf) (205 mg, 0.25 mmol), K$_3$PO$_4$ (2.12 g, 10.0 mmol), Sodium acetate (820 mg, 10.0 mmol), acetonitrile (45 mL), and water (1 mL). The system was evacuated and refilled with N$_2$. The reaction mixture was stirred at 30° C. for 3 h. It was then filtered and the filtrate was concentrated under reduced pressure. The resulting residue was purified by silica-gel column chromatography eluting with 30:1 dichloromethane/methanol to afford 214c (580 mg, 22%) as a white solid. MS-ESI: [M+H]$^+$ 539.2. $^1$H NMR (500 MHz, CDCl$_3$) δ 8.49 (d, J=5.0 Hz, 1H), 7.84 (d, J=2.5 Hz, 1H), 7.45 (d, J=2.0 Hz, 1H), 7.09 (d, J=5.0 Hz, 1H), 6.79 (s, 1H), 5.15 (s, 2H), 4.55-4.51 (m, 1H), 4.27-4.25 (m, 1H), 4.15-4.13 (m, 1H), 4.06-4.04 (m, 1H), 3.68 (s, 3H), 2.58-2.56 (m, 2H), 2.51 (s, 2H), 1.86 (s, 3H), 1.28 (s, 6H).

Example 214d (2-{4,4-Dimethyl-9-oxo-1,10-diazatricyclo[6.4.0. 0$^{2,6}$]dodeca-2(6),7-dien-10-yl}-4-[1-methyl-6-oxo-5-({4H,6H,7H-pyrano[4,3-d][1,3]thiazol-2-yl}amino)-1,6-dihydro-pyridin-3-yl]pyridin-3-yl)methyl Acetate 214d A 50-mL single-neck round-bottomed flask equipped with a magnetic stirrer and a reflux condenser was charged with 1,4-dioxane (10 mL), 214c (150 mg, 0.28 mmol), Pd$_2$(dba)$_3$ (27 mg, 0.030 mmol), XantPhos (35 mg, 0.060 mmol), and cesium carbonate (183 mg, 0.56 mmol). After three cycles of vacuum/argon flash, the mixture was heated at 100° C. for 10 h. After this time the reaction was cooled to room temperature. It was then filtered and the filtrate was evaporated in vacuo. The residue was purified by silica-gel column chromatography eluting with 50:1 dichloromethane/methanol to afford 214d (89 mg, 52%) as a yellow solid. MS-ESI: [M+H]$^+$ 615.2

Example 214

3-[4-[5-(6,7-dihydro-4H-pyrano[4,3-d]thiazol-2-ylamino)-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 214

A mixture of 214d (89 mg, 0.14 mmol), lithium hydroxide (35 mg, 1.45 mmol), and water/THF/i-propanol (3 mL/5 mL/5 mL) was stirred at 30° C. for 2 h. The reaction mixture was then concentrated under reduced pressure and the residue was extracted with dichloromethane (2×10 mL). The combined dichloromethane extract was concentrated under reduced pressure. The residue was purified with reverse-phase prep-HPLC to afford 214 (45 mg, 50%) as a yellow solid. MS-ESI: [M+H]$^+$ 573.2. $^1$H NMR (500 MHz, DMSO-d$_6$) δ 10.01 (s, 1H), 8.67 (d, J=2.5 Hz, 1H), 8.50 (d, J=5.0 Hz, 1H), 8.59 (d, J=2.5 Hz, 1H), 7.34 (d, J=5.0 Hz, 1H), 6.56 (s, 1H), 4.96-4.94 (m, 1H), 4.61 (s, 2H), 4.46-4.43 (m, 2H), 4.22-4.17 (m, 3H), 3.89-3.87 (m, 3H), 3.61 (s, 3H), 2.62-2.57 (m, 4H), 2.43 (s, 2H), 1.22 (s, 6H).

Example 215a

3-{4,4-Dimethyl-9-oxo-1,10-diazatricyclo[6.4.0.0$^{2,6}$] dodeca-2(6),7-dien-10-yl}-5-{1-methyl-5-[(2-methylpyrimidin-4-yl)amino]-6-oxo-1,6-dihydropyridin-3-yl}pyridine-4-carbaldehyde 215a

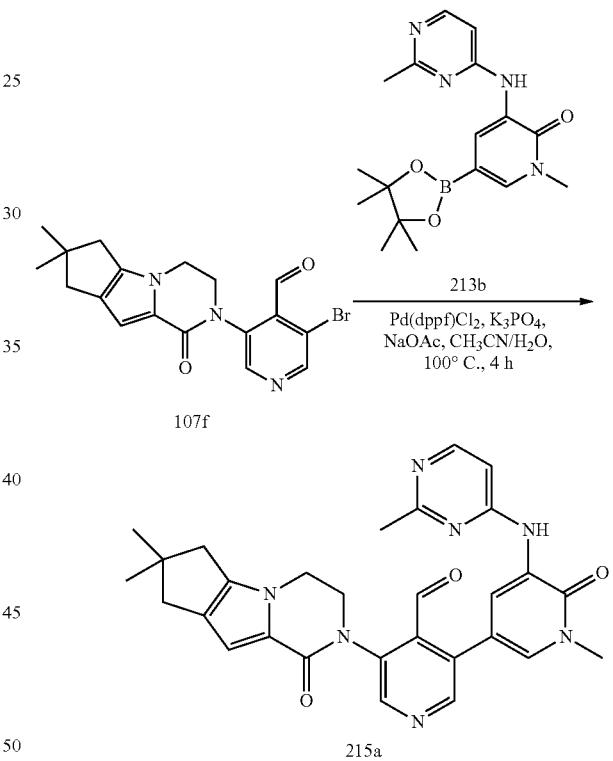

A sealed tube was charged with 3-bromo-5-{4,4-dimethyl-9-oxo-1,10-diazatricyclo-[6.4.0.0$^{2,6}$]dodeca-2(6),7-dien-10-yl}-pyridine-4-carbaldehyde 107f (210 mg, 0.54 mmol), 1-methyl-3-(pyrimidin-4-ylamino)-5-(4,4,5,5-tetramethyl-1,3,2-dioxaborolan-2-yl)pyridin-2-one 213b (177 mg, 0.54 mmol), PdCl$_2$(dppf) (42 mg, 0.050 mmol), K$_3$PO$_4$ (210 mg, 1.0 mmol), and sodium acetate (85 mg, 1.0 mmol), acetonitrile (8 mL), and water (0.5 mL). After three cycles of vacuum/argon flush, the mixture was heated at 100° C. for 4 h. It was then filtered and the filtrate was evaporated in vacuo. The residue was purified by silica-gel column chromatography eluting with 20:1 dichloromethane/methanol to afford 215a (150 mg, 53%). MS-ESI: [M+H]$^+$ 524.2.

Example 215

3-[4-(hydroxymethyl)-5-[1-methyl-5-[(2-methylpyrimidin-4-yl)amino]-6-oxo-3-pyridyl]-3-pyridyl]-7,7-dimethyl-1,2,6,8-tetrahydrocyclopenta[3,4]pyrrolo[3,5-b]pyrazin-4-one 215

A mixture of 215a (150 mg, 0.28 mmol) and NaBH₄ (20 mg, 0.50 mmol) in methanol (5 mL) was stirred at 25° C. for 0.2 h. The mixture was quenched by water (5 mL) and evaporated in vacuo. The residue was extracted with ethyl acetate (3×10 mL). The combined ethyl acetate extract was concentrated under reduced pressure and the residue was purified with reverse-phase prep-HPLC to afford 215 (80 mg, 53%). MS-ESI: [M+H]⁺ 526.3. ¹H NMR (500 MHz, DMSO-d₆) δ 9.09 (s, 1H), 8.89 (s, 1H), 8.56 (s, 1H), 8.53 (s, 1H), 8.20 (d, J=4.0 Hz, 1H), 7.61 (s, 1H), 7.13 (d, J=6.0 Hz, 1H), 6.52 (s, 1H), 5.19-5.18 (m, 1H), 4.47-4.46 (m, 2H), 4.23-4.20 (m, 3H), 3.95-3.93 (m, 1H), 3.62 (s, 3H), 2.57 (s, 2H), 2.42 (s, 3H), 2.41 (s, 2H), 1.21 (s, 6H).

Example 216a

1-Methyl-3-(5-methyl-4,5,6,7-tetrahydrothiazolo[5,4-c]pyridin-2-ylamino)-5-(4,4,5,5-tetramethyl-1,3,2-dioxaborolan-2-yl)pyridin-2(1H)-one 216a

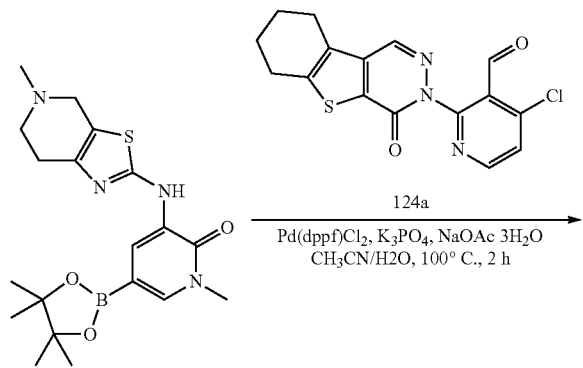

5-Bromo-1-methyl-3-(5-methyl-4,5,6,7-tetrahydrothiazolo[5,4-c]pyridin-2-ylamino)pyridin-2(1H)-one 203b (997 mg, 2.8 mmol) was dissolved in dioxane (50 mL), followed by addition of bis(pinacolato)diboron (3.0 g, 12.0 mmol), Pd₂(dba)₃ (128 mg, 0.14 mmol), X-phos (134 mg, 0.28 mmol), and potassium acetate (823 mg, 8.4 mmol). After three cycles of vacuum/argon flush, the mixture was heated at 65° C. for 2 h. The mixture was cooled to room temperature and filtered. The filtrate was concentrated under pressure and the residual was washed with petroleum ether (2×10 mL) to afford 216a as a yellow solid (968 mg, 86%), which was used in the next step without further purification. MS-ESI: [M+H]⁺ 403.2

Example 216b

4-[1-Methyl-5-({5-methyl-4H,6H,7H-[1,3]thiazolo[5,4-c]pyridin-2-yl}amino)-6-oxopyridin-3-yl]-2-{6-oxo-8-thia-4,5-diazatricyclo[7.4.0.0²,⁷]trideca-1(9),2(7),3-trien-5-yl}pyridine-3-carbaldehyde 216b A round-bottomed flask equipped with a magnetic stirrer and a reflux condenser was charged with 4-chloro-2-{6-oxo-8-thia-4,5-diazatricyclo[7.4.0.0²,⁷]trideca-1(9),2(7),3-trien-5-yl}pyridine-3-carbaldehyde 124a (138 mg, 0.40 mmol), 216a (240 mg, 0.60 mmol), PdCl₂(dppf) (20 mg, 0.020 mmol), K₃PO₄ (180 mg, 0.80 mmol), sodium acetate trihydrate (120 mg, 0.80 mmol), water (6 drops), and acetonitrile (15 mL). After three cycles of vacuum/argon flush, the mixture was heated at 100° C. for 2 h. Then, it was cooled to room temperature and filtered. The filtrate was evaporated under reduced pressure and the residue was purified by silica-gel column chromatography eluting with 25:1 dichloromethane/methanol to afford 216b as a yellow solid (100 mg, 45%). MS-ESI: [M+H]⁺ 586.2.

Example 216

3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-6,7,8,9-tetrahydrobenzothiopheno[2,3-d]pyridazin-4-one 216

To a solution of 216b (100 mg, 0.15 mmol) in methanol (6 mL) was added NaBH₄ (18 mg, 0.45 mmol). The reaction mixture was stirred at 30° C. for 1 h and quenched with brine (10 mL). It was then evaporated under reduced pressure. The residue was extracted with dichloromethane (2×20 mL) and the combined organic layer was concentrated under reduced pressure. The resulting residue was purified by reverse-phase prep-HPLC to afford 216 as a white solid (40 mg, 40%). MS-ESI: [M+H]⁺ 588.3. ¹H NMR (500 MHz, CDCl₃) δ 8.68 (d, J=5.0 Hz, 1H), 8.43 (d, J=2.0 Hz, 1H), 8.31 (s, 1H), 8.29 (s, 1H), 7.79 (d, J=2.5 Hz, 1H), 7.55 (d, J=5.0 Hz, 1H), 4.43-4.39 (m, 3H), 3.73 (s, 3H), 3.57-3.55 (m, 2H), 3.00-2.98 (m, 2H), 2.88-2.86 (m, 2H), 2.82-2.80 (m, 4H), 2.50 (s, 3H), 2.03-1.95 (m, 4H).

Example 217a (4-(5-Bromo-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 217a

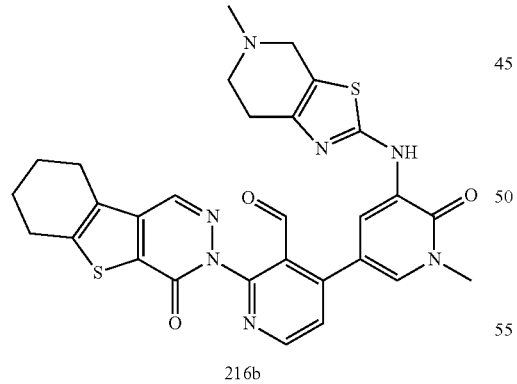

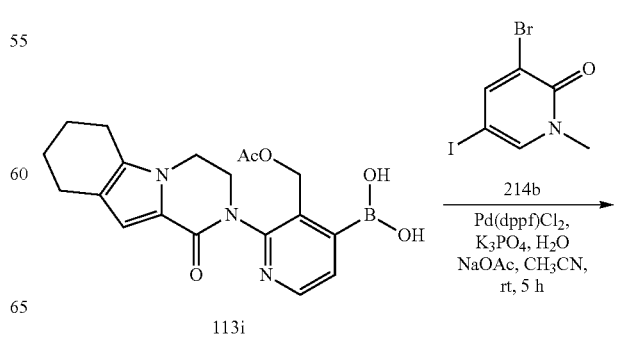

405

-continued

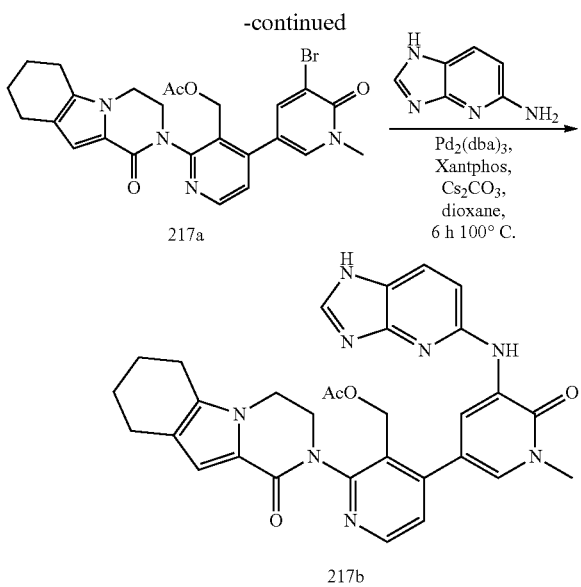

A sealed tube equipped with a magnetic stirrer was charged with 3-(acetoxymethyl)-2-(1-oxo-3,4,6,7,8,9-hexahydropyrazino[1,2-a]indol-2(1H)-yl)pyridin-4-ylboronic acid 113i (766 mg, 2.0 mmol), 3-bromo-5-iodo-1-methylpyridin-2 (1H)-one 214b (626 mg, 2.0 mmol), Pd(dppf)Cl$_2$ (164 mg, 0.20 mmol), sodium acetate (328 mg, 4.0 mmol), K$_3$PO$_4$ (848 mg, 4.0 mmol), acetonitrile (10 mL), and water (0.5 mL). After three cycles of vacuum/argon flush, the mixture was stirred at room temperature for 5 h. It was then filtered and the filtrate was evaporated in vacuo. The residue was purified by silica-gel column chromatography eluting with 50:1 dichloromethane/methanol to afford 217a (700 mg, 67%) as a yellow solid. MS-ESI: [M+H]$^+$ 525.2

Example 217b (4-(5-(1H-Imidazo[4,5-b]pyridin-5-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 217b A 25-mL single-neck round-bottomed flask equipped with a magnetic stirrer and reflux condenser was charged with 217a (158 mg, 0.30 mmol), 1H-imidazo[4,5-b]pyridin-5-amine (80 mg, 0.60 mmol), Pd$_2$(dba)$_3$ (27 mg, 0.030 mmol), XantPhos (35 mg, 0.061 mmol), cesium carbonate (200 mg, 0.60 mmol), and 1,4-dioxane (5 mL). After three cycles of vacuum/argon flush, the mixture was stirred at 100° C. for 6 h. After this time the reaction was cooled to room temperature. It was then filtered and the filtrate was evaporated in vacuo. The residue was purified by silica-gel column chromatography eluting with 30:1 dichloromethane/methanol to afford 217b (40 mg, 23%) as a yellow solid. MS-ESI: [M+H]$^+$ 579.4

Example 217

2-[3-(hydroxymethyl)-4-[5-(1H-imidazo[4,5-b]pyridin-5-ylamino)-1-methyl-6-oxo-3-pyridyl]-2-pyridyl]-3,4,6,7,8,9-hexahydropyrazino[1,2-a]indol-1-one 217

A mixture of 217b (40 mg, 0.070 mmol) and lithium hydroxide (26 mg, 0.70 mmol) in i-propanol/THF (1:1, 4 mL)

406 and water (1 mL) was stirred at room temperature for 1 h. The mixture was evaporated in vacuo and the residue was diluted with water and ethyl acetate. The water phase was separated and extracted with ethyl acetate (2×10 mL). The combined ethyl acetate extract was concentrated under reduced pressure and the residue was purified by reverse-phase prep-HPLC to afford 217 (15 mg, 40%) as a white solid. MS-ESI: [M+H]$^+$ 537.3. $^1$H NMR (500 MHz, DMSO-d$_6$) δ 12.62 (s, 1H), 8.91-8.64 (m, 2H), 8.52 (d, J=4.5 Hz, 1H), 8.19-8.06 (m, 1H), 7.89-7.79 (m, 1H), 7.57-7.53 (m, 1H), 7.43-7.40 (m, 1H), 7.22 (d, J=8.5 Hz, 1H), 6.59 (s, 1H), 5.06-4.96 (m, 1H), 4.5-4.40 (m, 2H), 4.26-4.11 (m, 3H), 3.88-3.85 (m, 1H), 3.62 (s, 3H), 2.62-2.54 (m, 2H), 2.50-2.48 (m, 2H), 1.81-1.79 (m, 2H), 1.71-1.67 (m, 2H).

Example 218a

5-Bromo-3-(1,5-dimethyl-1H-pyrazol-3-ylamino)-1-methylpyridin-2(1H)-one 218a

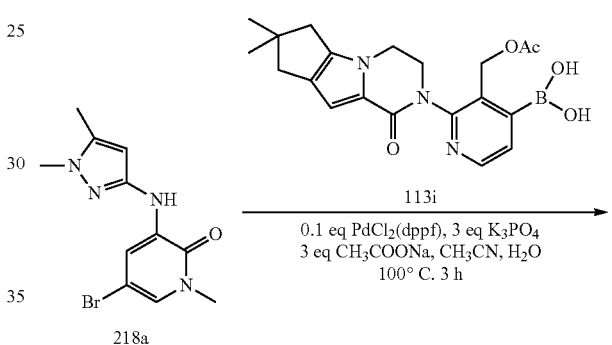

A solution of 5-bromo-1-methyl-3-(5-methyl-1H-pyrazol-3-ylamino)pyridin-2(1H)-one (2.8 g, 9.9 mmol) in anhydrous DMF (10 mL) was treated with 60% dispersion of NaH in mineral oil (0.51 g, 13 mmol) while stirring under nitrogen. After effervescence the reaction was stirred for an additional 30 minutes. At this time the reaction was treated with iodomethane (0.98 g, 7.0 mmol) with continued stirring under nitrogen for 2 hours. Water (50 mL) was added slowly and the mixture was filtered. The filtrate was extracted with ethyl acetate (3×30 mL). The combined extract was concentrated under reduced pressure and the residue was purified by flush column chromatography eluting with 3:1 petroleum ether/ethyl acetate to afford 218a (0.70 g, 24%). MS: [M+H]$^+$ 297.

Example 218b (4-{5-[(1,5-Dimethyl-1H-pyrazol-3-yl)amino]-1-methyl-6-oxo-1,6-dihydro-pyridin-3-yl}-2-{4,4-dimethyl-9-oxo-1,10-diazatricyclo[6.4.0.0$^{2,6}$]dodeca-2(6),7-dien-10-yl}pyridin-3-yl)methyl Acetate 218b A 50-mL round-bottomed flask equipped with a reflux condenser was charged with 218a (130 mg, 0.44 mmol), (3-(acetoxymethyl)-2-(7,7-dimethyl-1-oxo-3,4,7,8-tetrahydro-1H-cyclo-penta[4,5]pyrrolo[1,2-a]pyrazin-2(6H)-yl)pyridin-4-yl)boronic acid 199e (175 mg, 0.44 mmol), PdCl$_2$(dppf) (36 mg, 0.044 mmol), K$_3$PO$_4$ (343 mg, 1.32 mmol), sodium acetate (108 mg, 1.32 mmol), acetonitrile (10 mL), and water (0.5 mL). After three cycles of vacuum/argon flush, the mixture was heated at 100° C. for 3 h. It was then filtered and the filtrate was evaporated in vacuo. The residue was purified by silica-gel column chromatography eluting with 1:20 methanol/dichloromethane to afford 218b as a red solid (103 mg, 42%). MS-ESI: [M+H]$^+$ 570.2

Example 218

3-[4-[5-[(1,5-dimethylpyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 218

A mixture of 218b (103 mg, 0.17 mmol), lithium hydroxide (42 mg, 1.75 mmol), THF (3 mL), i-propanol (2 mL), and water (1 mL) was stirred at room temperature for 0.5 h. The reaction mixture was concentrated under reduced pressure and diluted with water (4 mL). It was then extracted with dichloromethane (10 mL×2) and the combined dichloromethane extract was concentrated under reduced pressure. The residue was purified with reverse-phase prep-HPLC to afford 218 (29 mg, 48%) as white solid. MS-ESI: [M+H]$^+$ 528.4. $^1$H NMR (500 MHz, DMSO-d$_6$) δ 8.48 (d, J=5.0 Hz, 1H), 8.04 (s, 1H), 8.02 (d, J=2.5 Hz, 1H), 7.38 (d, J=2.0 Hz, 1H), 7.32 (d, J=5.0 Hz, 1H), 6.55 (s, 1H), 5.89 (s, 1H), 4.97 (s, 1H), 4.48-4.39 (m, 2H), 4.24-4.16 (m, 3H), 3.86-3.84 (m, 1H), 3.58 (s, 3H), 3.57 (s, 3H), 2.62-2.56 (m, 2H), 2.42 (s, 2H), 2.16 (s, 3H), 1.22 (s, 6H).

Example 219a 3-(3-Aminophenylamino)-5-bromo-1-methylpyrazin-2(1H)-one 219a

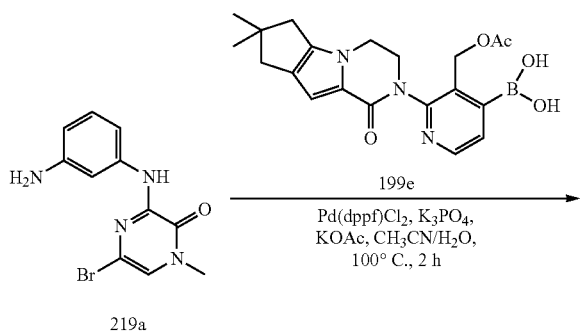

To a solution of 3,5-dibromo-1-methylpyrazin-2(1H)-one (536 mg, 2.0 mmol) and benzene-1,3-diamine (324 mg, 3.0 mmol) in isopropanol (18 mL) was added triethylamine (2.8 mL). The reaction mixture was stirred at 80° C. overnight. Then the mixture was evaporated under reduced pressure to afford 219a (480 mg, 81%) as a white solid. MS-ESI: [M+H]$^+$ 295.0

Example 219b (4-{6-[(3-Aminophenyl)amino]-4-methyl-5-oxo-4,5-dihydropyrazin-2-yl}-2-{4,4-dimethyl-9-oxo-1,10-diazatricyclo[6.4.0.0$^{2,6}$]dodeca-2(6),7-dien-10-yl}pyridin-3-yl)methyl Acetate 219b

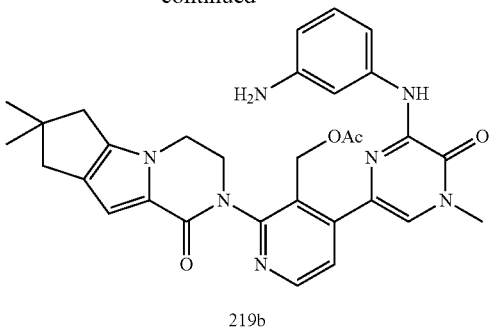

A 50-mL single-neck round-bottomed flask equipped with a magnetic stirrer and a reflux condenser was charged with 219a (480 mg, 1.62 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (1.61 g, 4.05 mmol), Pd(dppf)Cl$_2$ (134 mg, 0.162 mmol), potassium acetate (318 mg, 3.24 mmol), K$_3$PO$_4$ (706 mg, 3.24 mmol), acetonitrile (20 mL), and water (8 drops). After three cycles of vacuum/argon flush, the mixture was heated at 100° C. for 2 h. It was then filtered and the filtrate was evaporated in vacuo. The residue was purified by silica-gel column chromatography eluting with 20:1 ethyl acetate/methanol to afford 219b (354 mg, 38%) as a yellow solid. MS-ESI: [M+H]$^+$ 568.3

Example 219

3-[4-[6-(3-aminoanilino)-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one 219

A mixture of 219b (283.5 mg, 0.50 mmol) and lithium hydroxide monohydrate (630 mg, 15.0 mmol) in i-propanol/THF (1:1, 8 mL) and water (2 mL) was stirred at 35° C. for 0.5 h. The mixture was evaporated in vacuo and the residue was diluted with water (3 mL). It was then extracted with dichloromethane (3×20 mL). The combined dichloromethane extract was concentrated under reduced pressure and the residue was purified by reverse-phase prep-HPLC to afford 219 (170 mg, 79%) as a pale yellow solid. MS-ESI: [M+H]$^+$ 526.4. $^1$H NMR (500 MHz, DMSO-d$_6$) δ 8.85 (s, 1H), 8.47 (d, J=5.5 Hz, 1H), 7.63 (s, 1H), 7.56 (s, 1H), 7.51 (d, J=5.0 Hz, 1H), 6.92-6.91 (m, 2H), 6.57 (s, 1H), 6.24-6.22 (m, 1H), 5.13 (s, 2H), 4.84-4.75 (m, 2H), 4.49-4.46 (m, 1H), 4.30-4.26 (m, 1H), 4.20-4.19 (m, 2H), 3.95-3.92 (m, 1H), 3.56 (s, 3H), 2.62-2.54 (m, 2H), 2.43 (s, 2H), 1.23 (s, 6H).

Example 220a (S)-2-Chloro-4-(1-methyl-5-(5-(2-methyl-4-(oxetan-3-yl)piperazin-1-yl)pyridin-2-ylamino)-6-oxo-1,6-dihydropyridin-3-yl)nicotinaldehyde 220a

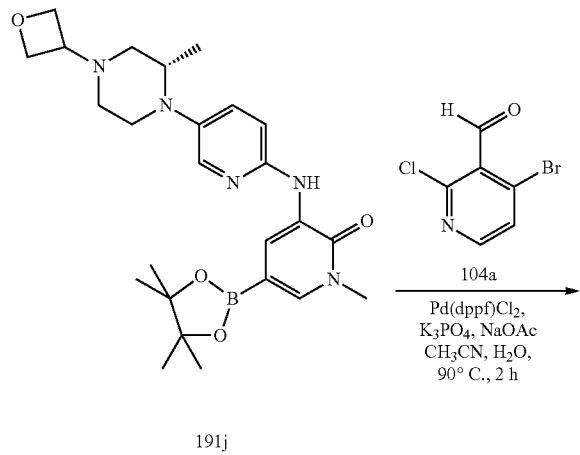

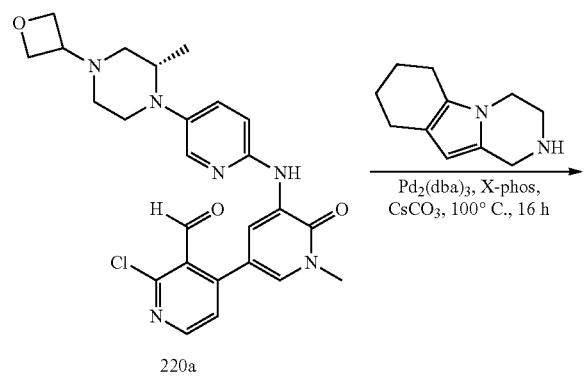

A 100-mL single-neck round-bottomed flask equipped with a magnetic stirrer and a reflux condenser was charged with (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (1.5 g, 1.0 eq., 3.11 mmol), 4-bromo-2-chloronicotinaldehyde 104a (1.02 g, 1.5 eq., 4.67 mmol), PdCl$_2$(dppf) (130 mg, 0.05 eq., 0.16 mmol), K$_3$PO$_4$ (1.32 g, 2 eq., 6.22 mmol), sodium acetate (510 mg, 2.0 eq., 6.22 mmol), acetonitrile (35 mL), and water (1.0 mL). After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 50:1 dichloromethane/ethanol to afford the 220a (1.1 g, 71%) as yellow solid. MS-ESI: [M+H]$^+$ 495.3.

Example 220b (S)-2-(3,4,6,7,8,9-Hexahydropyrazino[1,2-a]indol-2(1H)-yl)-4-(1-methyl-5-(5-(2-methyl-4-(oxetan-3-yl)piperazin-1-yl)pyridin-2-ylamino)-6-oxo-1,6-dihydropyridin-3-yl)nicotinaldehyde 220b A 50-mL single-neck round-bottomed flask equipped with a magnetic stirrer and a reflux condenser was charged with 220a (300 mg, 1.0 eq., 0.61 mmol), 1,2,3,4,6,7,8,9-octahydropyrazino[1,2-a]indole (128 mg, 1.2 eq., 0.73 mmol), Pd$_2$(dba)$_3$ (55 mg, 0.1 eq., 0.060 mmol), X-Phos (30 mg, 0.1 eq., 0.060 mmol), Cs$_2$CO$_3$ (390 mg, 2.0 eq., 1.22 mmol), and dioxane (15.0 mL). After three cycles of vacuum/argon flush, the mixture was heated at 100° C. for 16 h. It was then cooled to room temperature and filtered. The filtrate was concentrated under reduced pressure and the resulting residue was purified by silica-gel column chromatography eluting with 40:1 dichloromethane/EtOH to afford 220b (100 mg, 26%) as yellow solid. MS-ESI: [M+H]$^+$ 635.3.

Example 220

5-[2-(3,4,6,7,8,9-hexahydro-1H-pyrazino[1,2-a]indol-2-yl)-3-(hydroxymethyl)-4-pyridyl]-1-methyl-3-[[5-[(2S)-2-methyl-4-(oxetan-3-yl)piperazin-1-yl]-2-pyridyl]amino]pyridin-2-one 220

A 50-mL single-neck round-bottomed flask was charged with 220b (100 mg, 1.0 eq., 0.15 mmol), NaBH$_4$ (30 mg, 5.0 eq., 0.75 mmol), methanol (5 mL), and dichloromethane (5 mL). The mixture was stirred at 0° C. for 10 min and quenched with water (5 mL). It was then filtered and the filtrate was concentrated under reduced pressure. The residue was purified by reverse-phase prep-HPLC to afford the title compound (10 mg, 10%). MS-ESI: [M+H]$^+$ 637.5. $^1$H NMR (500 MHz, DMSO-d$_6$) δ 8.61 (d, J=2.0 Hz, 1H), 8.44 (s, 1H), 8.24 (d, J=5.0 Hz, 1H), 7.82 (d, J=3.0 Hz, 1H), 7.53 (d, J=2.0 Hz, 1H), 7.39-7.36 (m, 1H), 7.24 (d, J=9.0 Hz, 1H), 6.99 (d, J=5.0 Hz, 1H), 5.55 (s, 1H), 5.36-5.35 (m, 1H), 4.57-4.54 (m, 2H), 4.48-4.40 (m, 6H), 3.92-3.90 (m, 2H), 3.79-3.67 (m, 3H), 3.59 (s, 3H), 3.40-3.37 (m, 2H), 3.09-3.07 (m, 1H), 2.95-2.92 (m, 1H), 2.55-2.51 (m, 2H), 2.38-2.30 (m, 4H), 2.17-2.16 (m, 1H), 1.75-1.74 (m, 2H), 1.68-1.65 (m, 2H), 0.92 (d, J=6.5 Hz, 3H).

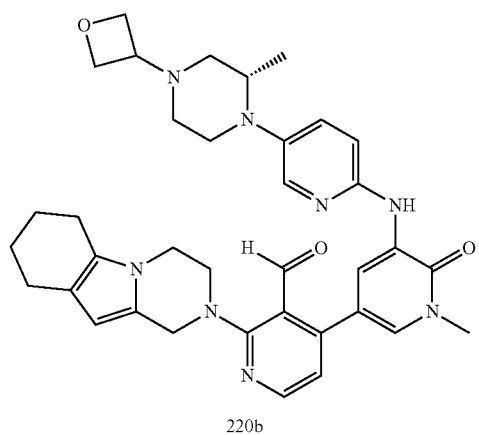

Example 221a

3-[(6-aminopyridin-2-yl)amino]-5-bromo-1-methyl-1,2-dihydropyridin-2-one 221a

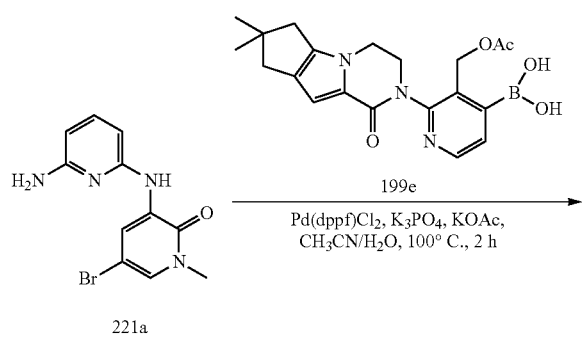

A 50-mL single-neck round-bottomed flask equipped with a magnetic stirrer and a reflux condenser was charged with 1,4-dioxane (20 mL), 3,5-dibromo-1-methylpyridin-2(1H)-one (1.06 g, 4.0 mmol), pyridine-2,6-diamine (872 mg, 8.0 mmol), $Pd_2(dba)_3$ (732 mg, 0.80 mmol), XantPhos (462.4 mg, 0.80 mmol), and cesium carbonate (2.6 g, 8.0 mmol). After three cycles of vacuum/argon flush, the mixture was heated at 110° C. for 1 h. After this time the reaction was cooled to room temperature. It was then filtered and the filtrate was evaporated in vacuo. The residue was purified by silica-gel column chromatography eluting with 20:1 ethyl acetate/methanol to afford 221a (570 mg, 48%) as a white solid. MS-ESI: $[M+H]^+$ 295.0

Example 221b (4-{5-[(6-Aminopyridin-2-yl)amino]-1-methyl-6-oxo-1,6-dihydropyridin-3-yl}-2-{4,4-dimethyl-9-oxo-1,10-diazatricyclo[6.4.0.0$^{2,6}$]dodeca-2(6),7-dien-10-yl}pyridin-3-yl)methyl Acetate 221b A 25-mL single-neck round-bottomed flask equipped with a magnetic stirrer and a reflux condenser was charged with 221a (354 mg, 1.2 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (1.20 g, 3.0 mmol), $Pd(dppf)Cl_2$ (99 mg, 0.12 mmol), potassium acetate (235 mg, 2.4 mmol), $K_3PO_4$ (532 mg, 2.4 mmol), acetonitrile (12 mL), and water (10 drops). After three cycles of vacuum/argon flush, the mixture was heated at 100° C. for 2 h. It was then filtered and the filtrate was evaporated in vacuo. The residue was purified by silica-gel column chromatography eluting with 30:1 ethyl acetate/methanol to afford 221b (210 mg, 31%) as a yellow solid. MS-ESI: $[M+H]^+$ 568.3

Example 221

3-[4-[5-[(6-amino-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 221

A mixture of 221b (181 mg, 0.32 mmol) and lithium hydroxide monohydrate (148 mg, 3.2 mmol) in i-propanol/THF (1:1, 6 mL) and water (1.5 mL) was stirred at 35° C. for 0.5 h. The mixture was concentrated under reduced pressure and the residue was purified by reverse-phase prep-HPLC to afford 221 (82 mg, 49%) as a pale yellow solid. MS-ESI: $[M+H]^+$ 526.3. $^1H$ NMR (500 MHz, DMSO-$d_6$) δ 8.84 (d, J=2.0 Hz, 1H), 8.46 (d, J=5.0 Hz, 1H), 8.11 (s, 1H), 7.54 (d, J=2.0 Hz, 1H), 7.38 (d, J=5.0 Hz, 1H), 7.23 (d, J=8.0 Hz, 1H), 6.57 (s, 1H), 6.36 (d, J=7.5 Hz, 1H), 5.91 (d, J=8.0 Hz, 1H), 5.79 (bs, 2H), 5.07 (t, J=5.0 Hz, 1H), 4.58-4.47 (m, 2H), 4.27-4.20 (m, 3H), 3.90 (d, J=10.5 Hz, 1H), 3.60 (s, 3H), 2.62-2.57 (m, 2H), 2.43 (s, 2H), 1.22 (s, 6H).

Example 222a

N-(5-Chloro-2-methoxypyridin-3-yl)-2-methylpyrimidin-4-amine 222a

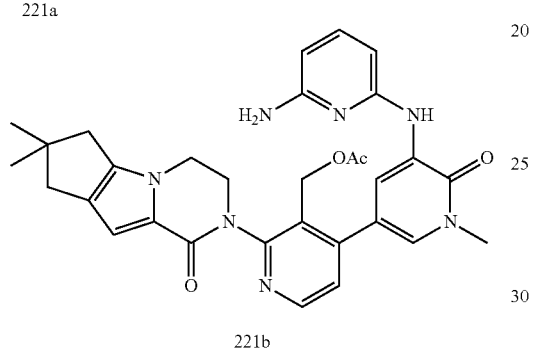

A 100-mL single-neck round-bottomed flask equipped with a magnetic stirrer and a reflux condenser was charged with 1,4-dioxane (30 mL), 3-bromo-5-chloro-2-methoxypyridine (865 mg, 3.9 mmol), 2-methylpyrimidin-4-amine (327 mg, 3.0 mmol), $Pd_2(dba)_3$ (275 mg, 0.30 mmol), XantPhos (173.4 mg, 0.30 mmol), and cesium carbonate (1.96 g, 6.0 mmol). After three cycles of vacuum/argon flush, the mixture was heated at 100° C. for 5 h. After this time the reaction was cooled to room temperature. It was then filtered and the filtrate was evaporated in vacuo. The residue was purified by silica-gel column chromatography eluting with 5:1 ethyl acetate/petroleum ether to afford 222a (555 mg, 74%) as a white solid. MS-ESI: $[M+H]^+$ 251.0

Example 222b (2-{4,4-Dimethyl-9-oxo-1,10-diazatricyclo[6.4.0. $0^{2,6}$]dodeca-2(6),7-dien-10-yl}-4-{6-methoxy-5-[(2-methylpyrimidin-4-yl)amino]pyridin-3-yl}pyridin-3-yl)methyl Acetate 222b A sealed tube equipped with a magnetic stirrer was charged with 222a (550 mg, 2.2 mmol), (3-(acetoxymethyl)-2-(7,7-dimethyl-1-oxo-3,4,7,8-tetrahydro-1H-cyclopenta[4,5]pyrrolo-[1,2-a]pyrazin-2(6H)-yl)pyridin-4-yl)boronic acid 199e (2.18 g, 5.5 mmol), $Pd_2(dba)_3$ (201 mg, 0.22 mmol), tricyclohexylphospine (84 mg, 0.30 mmol), $Cs_2CO_3$ (1.43 g, 4.4 mmol), dioxane (12 mL), and water (1 mL). After three cycles of vacuum/argon flush, the mixture was heated at 110° C. for 4 h. It was then filtered and the filtrate was evaporated in vacuo. The residue was purified by silica-gel column chromatography eluting with 30:1 ethyl acetate/methanol to afford 222b (310 mg, 25%) as a yellow solid. MS-ESI: $[M+H]^+$ 568.6

Example 222c

10-[3-(Hydroxymethyl)-4-{6-methoxy-5-[(2-methylpyrimidin-4-yl)amino]pyridin-3-yl}pyridin-2-yl]-4,4-dimethyl-1,10-diazatricyclo[6.4.0.0$^{2,6}$]dodeca-2 (6),7-dien-9-one 222c A mixture 222b (283.5 mg, 0.50 mmol) and lithium hydroxide monohydrate (630 mg, 15.0 mmol) in i-propanol/THF (1:1, 10 mL) and water (2.5 mL) was stirred at 35° C. for 0.5 h. The mixture was evaporated in vacuo and the residue was diluted with water (3 mL). It was then extracted with dichloromethane (3×20 mL). The combined organic extract was concentrated under reduced pressure to afford 222c (240 mg, 92%) as a white solid. MS-ESI: $[M+H]^+$ 526.2

Example 222

3-[3-(hydroxymethyl)-4-[5-[(2-methylpyrimidin-4-yl)amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one 222

To a solution of 222c (226 mg, 0.43 mmol) in dioxane (8 mL) was added concentrated HCl (1.1 mL). The reaction was stirred at 100° C. for 1 h. Then the mixture was adjusted to pH 7.0 by introducing saturated aqueous $NaHCO_3$. It was extracted with dichloromethane (3×20 mL) and the combined extract was evaporated under reduced pressure. The resulting residue was purified by reverse-phase prep-HPLC to afford 222 (30 mg, 14%) as a white solid. MS-ESI: $[M+H]^+$ 512.3. $^1H$ NMR (500 MHz, DMSO-$d_6$) δ 12.24 (s, 1H), 9.10 (s, 1H), 8.96 (d, J=2.0 Hz, 1H), 8.50 (d, J=5.0 Hz, 1H), 8.22 (d, J=6.5 Hz, 1H), 7.50 (d, J=2.0 Hz, 1H), 7.40 (d, J=5.0 Hz, 1H), 7.13 (d, J=6.0 Hz, 1H), 6.57 (s, 1H), 5.08-5.06 (m, 1H), 4.50-4.42 (m, 2H), 4.25-4.19 (m, 3H), 3.87-3.85 (m, 1H), 2.62-2.53 (m, 2H), 2.45 (s, 3H), 2.43 (s, 2H), 1.23 (s, 3H), 1.22 (s, 3H)

Example 223a 2-(10-Fluoro-1-oxo-3,4,6,7,8,9-hexahydropyrazino [1,2-a]indol-2(1H)-yl)-4-(1-methyl-5-(5-methyl-4,5,6,7-tetrahydrothiazolo[5,4-c]pyridin-2-ylamino)-6-oxo-1,6-dihydropyridin-3-yl)nicotinaldehyde 223a

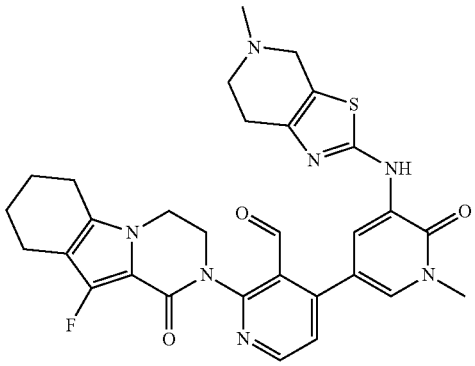

A 50-mL round-bottomed flush equipped with a reflux condenser was charged with 1-methyl-3-(5-methyl-4,5,6,7-tetrahydrothiazolo[5,4-c]pyridin-2-ylamino)-5-(4,4,5,5-tetra-methyl-1,3,2-dioxaborolan-2-yl)pyridin-2(1H)-one 216a (200 mg, 0.50 mmol), 4-chloro-2-(10-fluoro-1-oxo-3,4,6,7,8,9-hexahydropyrazino[1,2-a]indol-2(1H)-yl)nicotinaldehyde 134c (174 mg, 0.50 mmol), $K_3PO_4$ (212 mg, 1.0 mmol), sodium acetate (82 mg, 1.0 mmol), 1,1'-bis(diphenylphosphino)ferrocenedichloropalladium(II) (21 mg, 0.025 mmol), and acetonitrile/water (15/1 mL). After bubbling nitrogen through the mixture for 30 minutes, it was heated at 100° C. for 1 h under $N_2$ protection. Analysis of reaction mixture by LCMS showed complete conversion to the desired product. The reaction mixture was cooled to room temperature and filtered. The filtrate was concentrated under reduced pressure. The residue was diluted with dichloromethane (50 mL) and water (50 mL). The aqueous layer was extracted with dichloromethane (3×20 mL). The combined organic layer was dried over $Na_2SO_4$, filtered, and concentrated under reduced pressure. The dark residue was purified by silica-gel column chromatography eluting with dichloromethane/methanol (70/1 to 30/1) to afford 223a (167 mg, 57%) as yellow solid. MS-ESI: $[M+H]^+$ 588.1

Example 223

10-fluoro-2-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-3,4,6,7,8,9-hexahydropyrazino[1,2-a]indol-1-one 223

Compound 223a (160 mg, 0.27 mmol) was dissolved in methanol (30 mL), followed by addition of $NaBH_4$ (31 mg, 082 mmol) at 0° C. The reaction mixture was stirred for 30 min and then quenched with water (10 mL). It was concentrated under reduced pressure and the residue was extracted with dichloromethane (3×30 mL). The combined organic phase was concentrated under reduced pressure and the residual was purified by reverse-phase prep-HPLC to afford 223 (56 mg, 35%) as a white solid. MS-ESI: $[M+H]^+$ 590.2. $^1H$ NMR (500 MHz, DMSO-$d_6$): δ 9.92 (s, 1H), 8.64 (d, J=2.5 Hz, 1H), 8.48 (d, J=5.5 Hz, 1H), 7.56 (d, J=2.0 Hz, 1H), 7.34 (d, J=5.0 Hz, 1H), 4.93 (t, J=5.5 Hz, 1H), 4.46-4.41 (m, 2H), 4.19-4.17 (m, 2H), 4.08-4.03 (m, 1H), 3.88-3.85 (m, 1H), 3.60 (s, 3H), 3.42 (s, 2H), 2.63-2.58 (m, 6H), 2.41 (s, 3H), 2.34 (s, 2H), 1.78-1.76 (m, 2H), 1.68-1.66 (m, 2H).

Example 224a (S)-tert-Butyl 4-(6-(6-Chloro-2-methyl-3-oxo-2,3-dihydropyridazin-4-ylamino)pyridin-3-yl)-3-methylpiperazine-1-carboxylate 224a

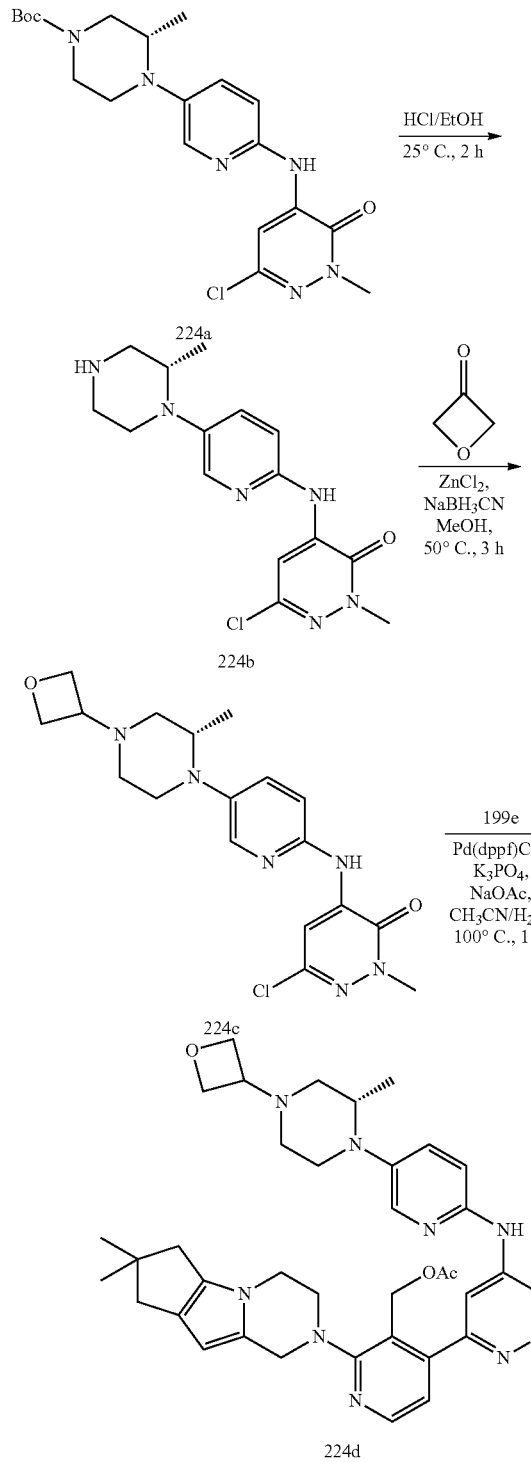

A 250-mL single-neck round-bottomed flask equipped with a magnetic stirrer and a reflux condenser was charged with (S)-tert-butyl 4-(6-aminopyridin-3-yl)-3-methylpiperazine-1-carboxylate 191f (2.5 g, 8.5 mmol), 4-bromo-6-chloro-2-methylpyridazin-3(2H)-one (2.2 g, 10.0 mmol), XantPhos (240 mg, 0.40 mmol), tris(dibenzylideneacetone)dipalladium(0) (360 mg, 0.40 mmol), $Cs_2CO_3$ (5.5 g, 17 mmol), and 1,4-dioxane (100 mL). After three cycles of vacuum/argon flush, the mixture was heated at 100° C. for 2.5 h. It was then cooled to room temperature and filtered. The filtrate was concentrated under reduced pressure and the resulting residue was purified by silica-gel column chromatography eluting with dichloromethane/methanol (40:1 to 30:1) to afford 224a as a pale yellow solid (3.2 g, 86%). MS-ESI: [M+H]$^+$ 435.1.

Example 224b (S)-6-Chloro-2-methyl-4-(5-(2-methylpiperazin-1-yl)pyridin-2-ylamino)pyridazin-3(2H)-one 224b A mixture of 224a (3.0 g, 6.9 mmol) and 4.0M HCl/ethanol (20 mL) was stirred at room temperature for 2 h. The mixture was then concentrated under reduced pressure to afford crude 224b as a yellow solid (2.5 g, 98%), which was used for the next step without further purification. MS-ESI: [M+H]$^+$ 335.1.

Example 224c (S)-6-Chloro-2-methyl-4-(5-(2-methyl-4-(oxetan-3-yl)piperazin-1-yl)pyridin-2-ylamino)pyridazin-3(2H)-one 224c A mixture of 224b (2.3 g, 6.8 mmol), oxetan-3-one (1.4 g, 20.0 mmol), NaBH$_3$CN (620 mg, 10 mmol), and zinc chloride (1.36 g, 10 mmol) in methanol (20 mL) was stirred at 50° C. for 3 hours. The mixture was added to water (40 mL) and concentrated under reduced pressure. The residue was extracted with dichloromethane three times. The combined organic layer was dried and concentrated under reduced pressure. The residue was purified by silica-gel column chromatography eluting with 50:1 dichloromethane/methanol to afford 224c (2.0 g, 75%). MS-ESI: [M+H]$^+$ 391.2.

Example 224d (2-{4,4-Dimethyl-9-oxo-1,10-diazatricyclo[6.4.0.0$^{2,6}$]dodeca-2(6),7-dien-10-yl}-4-[1-methyl-5-({5-[(2S)-2-methyl-4-(oxetan-3-yl)piperazin-1-yl]pyridin-2-yl}amino)-6-oxo-1,6-dihydropyridazin-3-yl]pyridin-3-yl)methyl Acetate 224d A sealed tube equipped with a magnetic stirrer was charged with 224c (200 mg, 0.50 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (240 mg, 0.60 mmol), Pd(dppf)Cl$_2$ (18 mg, 0.025 mmol), sodium acetate (74 mg, 0.90 mmol), K$_3$PO$_4$ (191 mg, 0.90 mmol), and acetonitrile/water (6:1, 3.5 mL). After three cycles of vacuum/argon flush, the mixture was heated at 100° C. for 1 h. It was then cooled to room temperature and filtered. The filtrate was evaporated under reduced pressure and the residue was purified by silica-gel column chromatography eluting with 25:1 dichloromethane/methanol to afford 224d (180 mg, 51%) as a brown solid. MS-ESI: [M+H]$^+$ 708.3.

Example 224

3-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one 224

A mixture of 224d (180 mg, 0.25 mmol) and lithium hydroxide (72 mg, 3.0 mmol) in i-propanol/THF (5/3 mL) and water (2 mL) was stirred at 35° C. for 0.2 h. The mixture was evaporated under reduced pressure and the residue was extracted with ethyl acetate (10 mL×2). The combined ethyl acetate extract was concentrated under reduced pressure and the residue was purified by reverse phase Combiflush eluting with 0.3% $NH_4HCO_3$ in water/acetonitrile to afford 224 (54 mg, 33%) as a white solid. MS-ESI: [M+H]$^+$ 666.3. $^1$H NMR (500 MHz, DMSO-$d_6$) δ 9.29 (s, 1H), 8.52 (d, J=4.0 Hz, 1H), 8.43 (s, 1H), 7.91 (s, 1H), 7.43-7.42 (m, 2H), 7.40-7.39 (m, 1H), 6.55 (s, 1H), 4.77-4.75 (m, 1H), 4.57-4.55 (m, 3H), 4.48-4.47 (m, 1H), 4.43-4.41 (m, 2H), 4.28-4.26 (m, 1H), 4.19-4.18 (m, 2H), 3.88-3.86 (m, 2H), 3.77 (s, 3H), 3.38-3.37 (m, 1H), 3.21-3.19 (m, 1H), 2.98-2.96 (m, 1H), 2.64-2.62 (m, 1H), 2.58-2.56 (m, 1H), 2.42-2.41 (m, 3H), 2.26-2.25 (m, 1H), 2.11-2.09 (m, 1H), 1.21 (s, 6H), 0.98 (d, J=5.5 Hz, 3H).

Example 225a

6-Chloro-2-methyl-4-(2-methylpyrimidin-4-ylamino)pyridazin-3(2H)-one 225a

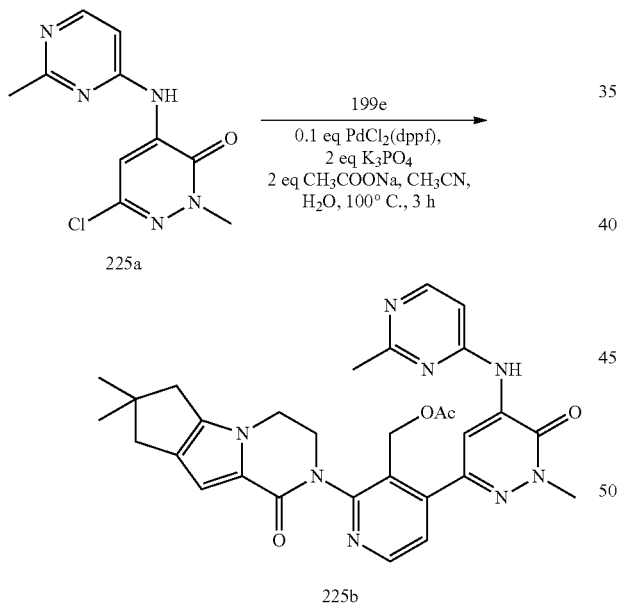

A 100-mL single-neck round-bottomed flask equipped with a reflux condenser was charged with 2-methylpyrimidin-4-amine (330 mg, 3.03 mmol), 4-bromo-6-chloro-2-methylpyridazin-3(2H)-one (675 mg, 3.03 mmol), Pd$_2$(dba)$_3$ (274 mg, 0.30 mmol), XantPhos (143 mg, 0.30 mmol), Cs$_2$CO$_3$ (2960 mg, 9.09 mmol), and dioxane (40 mL). After three cycles of vacuum/argon flush, the mixture was heated at 100° C. for overnight. It was then filtered and the filtrate was evaporated in vacuo. The residue was purified by silica-gel column chromatography eluting with 1:20 methanol/dichloromethane to afford 225a as a yellow solid (560 mg, 73%). MS-ESI: [M+H]$^+$ 252.1

Example 225b (2-{4,4-Dimethyl-9-oxo-1,10-diazatricyclo[6.4.0.0$^{2,6}$]dodeca-2(6),7-dien-10-yl}-4-{1-methyl-5-[(2-methylpyrimidin-4-yl)amino]-6-oxo-1,6-dihydropyridazin-3-yl}pyridin-3-yl)methyl Acetate 225b A round-bottomed flask equipped with a reflux condenser was charged with 225a (200 mg, 0.80 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (318 mg, 0.80 mmol), PdCl$_2$(dppf) (65.3 mg, 0.080 mmol), K$_3$PO$_4$ (624 mg, 2.4 mmol), sodium acetate (200 mg, 2.4 mmol), acetonitrile (10 mL), and water (0.5 mL). After three cycles of vacuum/argon flush, the mixture was heated at 100° C. for 3 h. It was then filtered and the filtrate was evaporated in vacuo. The residue was purified by silica-gel column chromatography eluting with 1:20 methanol/dichloromethane to afford 225b as a red solid (150 mg, 47%). MS-ESI: [M+H]$^+$ 569.3

Example 225

3-[3-(hydroxymethyl)-4-[1-methyl-5-[(2-methylpyrimidin-4-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one 225

A mixture of 225b (120 mg, 0.21 mmol), lithium hydroxide (59 mg, 2.11 mmol), THF (6 mL), i-propanol (4 mL), and water (2 mL) was stirred at room temperature for 0.5 h. The mixture was concentrated under reduced pressure and diluted with water (3 mL). It was then extracted with dichloromethane (2×10 mL). The combined dichloromethane extract was concentrated under reduced pressure and the residue was purified with reverse-phase prep-HPLC to afford 225 as a white solid (29 mg, 48%). MS-ESI: [M+H]$^+$ 527.3. $^1$H NMR (500 MHz, DMSO-$d_6$) δ 9.82 (s, 1H), 8.88 (s, 1H), 8.54 (d, J=5.0 Hz, 1H), 8.37 (d, J=6.0 Hz, 1H), 7.44 (d, J=4.5 Hz, 1H), 7.34 (d, J=3.5 Hz, 1H), 6.56 (d, J=4.0 Hz, 1H), 4.87 (t, J=1.5 Hz, 1H), 4.67 (d, J=11.5 Hz, 1H), 4.42 (d, J=12.5 Hz, 1H), 4.29-4.25 (m, 1H), 4.20 (bs, 2H), 3.93 (d, J=9.5 Hz, 1H), 3.81 (s, 3H), 2.62-2.58 (m, 2H), 2.50-2.49 (m, underneath solvent peak, 2H), 2.40 (s, 3H), 1.22 (s, 6H).

Example 226a

6-Chloro-2-methyl-4-({5-[(morpholin-4-yl)carbonyl]pyridin-2-yl}amino)-2,3-dihydropyridazin-3-one 226a

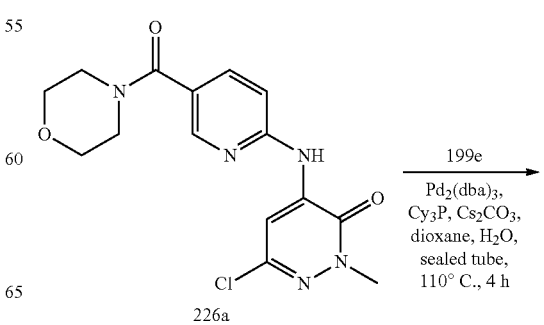

419

-continued

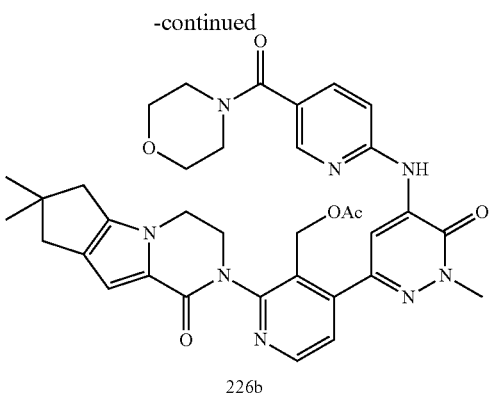

226b

A 100-mL single-neck round-bottomed flask equipped with a magnetic stirrer and a reflux condenser was charged with 1,4-dioxane (40 mL), (6-aminopyridin-3-yl)(morpholino)methanone 111a (2.07 g, 10.0 mmol), 4-bromo-6-chloro-2-methylpyridazin-3(2H)-one (3.35 g, 15.0 mmol), $Pd_2(dba)_3$ (915 mg, 1.0 mmol), XantPhos (578 mg, 1.0 mmol), and cesium carbonate (6.52 g, 20 mmol). After three cycles of vacuum/argon flush, the mixture was heated at 100° C. for 8 h. It was then cooled to room temperature and filtered. The solid was washed with dichloromethane (2×20 mL). The combined filtrate was dried over anhydrous $Na_2SO_4$ and concentrated under reduced pressure to afford 226a (2.45 g, 51%) as a yellow solid. MS: $[M+H]^+$ 350.1

Example 226b (2-{4,4-Dimethyl-9-oxo-1,10-diazatricyclo[6.4.0.$0^{2,6}$]dodeca-2(6),7-dien-10-yl}-4-[1-methyl-5-({5-[(morpholin-4-yl)carbonyl]pyridin-2-yl}amino)-6-oxo-1,6-dihydro-pyridazin-3-yl]pyridin-3-yl)methyl Acetate 226b A sealed tube equipped with a magnetic stirrer was charged with 226a (279 mg, 0.80 mmol), (2-{4,4-dimethyl-9-oxo-1,10-diazatricyclo[6.4.0.$0^{2,6}$]dodeca-2(6),7-dien-10-yl}-4-(tetramethyl-1,3,2-dioxaborolan-2-yl)pyridin-3-yl)methyl acetate 199e (1.53 g, 3.2 mmol), $Pd_2(dba)_3$ (73.2 mg, 0.080 mmol), tricyclohexyl-phosphine (44.6 mg, 0.16 mmol), cesium carbonate (521.6 mg, 1.6 mmol), 1,4-dioxane (10 mL), and water (8 drops). After three cycles of vacuum/argon flush, the mixture was stirred at 110° C. for 4 h. It was then filtered and the filtrate was evaporated in vacuo. The residue was purified by silica-gel column chromatography eluting with 40:1 ethyl acetate/methanol to afford 226b as a yellow solid (120 mg, 23%). MS-ESI: $[M+H]^+$ 667.3

Example 226

3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one 226

A mixture of 226b (120 mg, 0.18 mmol) and lithium hydroxide monohydrate (227 mg, 5.4 mmol) in i-propanol/THF/water (3 mL/3 mL/2 mL) was stirred at 35° C. for 0.5 h. The mixture was evaporated in vacuo and the residue was extracted with dichloromethane (3×10 mL). The combined dichloromethane extract was concentrated under reduced pressure and the residue was purified by reverse-phase prep-HPLC to afford 226 as a white solid (53 mg, 47%). MS-ESI: $[M+H]^+$ 625.3. $^1H$ NMR (500 MHz, DMSO-$d_6$) δ 9.75 (s, 1H), 8.64 (s, 1H), 8.54 (d, J=5.0 Hz, 1H), 8.36 (d, J=2.5 Hz, 1H), 7.79-7.77 (m, 1H), 7.59 (d, J=8.5 Hz, 1H), 7.43 (d, J=5.0 Hz, 1H), 6.56 (s, 1H), 4.82 (s, 1H), 4.60-4.57 (m, 1H), 4.40-4.37 (m, 1H), 4.27-4.25 (m, 1H), 4.20-4.17 (m, 2H), 3.91-3.88 (m, 1H), 3.80 (s, 3H), 3.60-3.45 (m, overlap, 8H), 2.62-2.56 (m, 2H), 2.42 (s, 2H), 1.22 (s, 6H).

Example 227a

{4-[1-Methyl-5-({5-[(morpholin-4-yl)carbonyl]pyridin-2-yl}amino)-6-oxo-1,6-dihydropyridazin-3-yl]-2-{1-oxo-1H,2H,3H,4H,6H,7H,8H,9H-pyrazino[1,2-a]indol-2-yl}pyridin-3-yl}methyl Acetate 227a

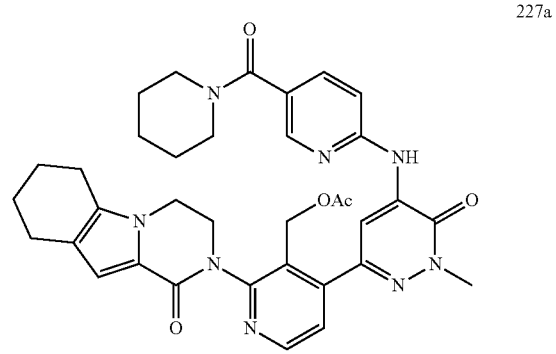 [SMILES: CC(=O)OCc1c(-c2cc(Nc3ccc(C(=O)N4CCCCC4)cn3)c(=O)n(C)n2)ccnc1N1CCn2c(cc3c2CCCC3)C1=O]

227a

A sealed tube equipped with a magnetic stirrer was charged with 6-chloro-2-methyl-4-({5-[(morpholin-4-yl)carbonyl]pyridin-2-yl}amino)-2,3-dihydropyridazin-3-one 226a (244 mg, 0.70 mmol), 3-(acetoxymethyl)-2-(1-oxo-3,4,6,7,8,9-hexahydropyrazino[1,2-a]indol-2(1H)-yl)pyridin-4-ylboronic acid 113i (558 mg, 1.5 mmol), $Pd_2(dba)_3$ (64 mg, 0.070 mmol), tricyclohexylphospine (39 mg, 0.14 mmol), cesium carbonate (456 mg, 1.4 mmol), 1,4-dioxane (7 mL), and water (6 drops). After three cycles of vacuum/argon flush, the mixture was stirred at 110° C. for 4 h. It was then filtered and the filtrate was evaporated in vacuo. The residue was purified by silica-gel column chromatography eluting with 40:1 ethyl acetate/methanol to afford 227a as a yellow solid (290 mg, 63%). MS-ESI: $[M+H]^+$ 653.3

Example 227

2-[3-(hydroxymethyl)-4-[1-methyl-5-[[5-(morpholine-4-carbonyl)-2-pyridyl]amino]-6-oxo-pyridazin-3-yl]-2-pyridyl]-3,4,6,7,8,9-hexahydropyrazino[1,2-a]indol-1-one 227

A mixture of 227a (131 mg, 0.20 mmol) and lithium hydroxide.1 water (120 mg, 2.0 mmol) in i-propanol/THF/water (4 mL/4 mL/2 mL) was stirred at 35° C. for 0.5 h. The mixture was evaporated in vacuo and the residue was extracted with dichloromethane (3×10 mL). The combined dichloromethane extract was concentrated under reduced pressure and the residue was purified by reverse-phase prep-HPLC to afford 227 as a white solid (75 mg, 62%). MS-ESI: $[M+H]^+$ 611.2. $^1H$ NMR (500 MHz, DMSO-$d_6$) δ 9.75 (s, 1H), 8.64 (s, 1H), 8.54 (d, J=5.0 Hz, 1H), 8.36 (d, J=2.0 Hz, 1H), 7.79-7.77 (m, 1H), 7.59 (d, J=8.5 Hz, 1H), 7.43 (d, J=5.0 Hz, 1H), 6.58 (s, 1H), 4.82 (s, 1H), 4.60-4.57 (m, 1H), 4.38-

4.36 (m, 1H), 4.29-4.19 (m, 2H), 4.10-4.05 (m, 1H), 3.93-3.90 (m, 1H), 3.80 (s, 3H), 3.60-3.50 (m, overlap, 8H), 2.66-2.54 (m, 2H), 2.48-2.46 (m, 2H), 1.81-1.66 (m, 4H).

Example 228a (S)-(4-(1-Methyl-5-(5-(2-methyl-4-(oxetan-3-yl)piperazin-1-yl)pyrazin-2-yl-amino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 228a

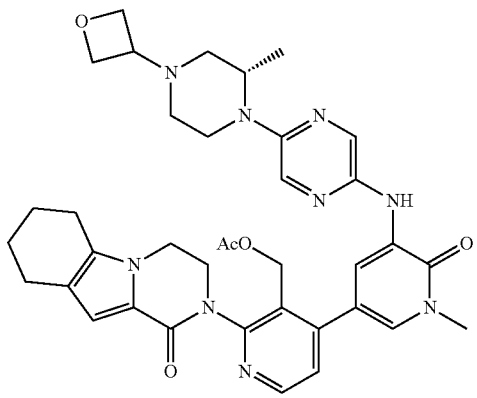

A 100-mL single-neck round-bottomed flask equipped with a magnetic stirrer and a reflux condenser was charged with (S)-5-bromo-1-methyl-3-(5-(2-methyl-4-(oxetan-3-yl)piperazin-1-yl)pyrazin-2-ylamino)pyridin-2(1H)-one (90 mg, 0.21 mmol) 191i, 3-(acetoxymethyl)-2-(1-oxo-3,4,6,7,8,9-hexahydropyrazino[1,2-a]indol-2(1H)-yl)pyridin-4-ylboronic acid 113i (80.4 mg, 0.21 mmol), Pd(dppf)Cl$_2$ (17.2 mg, 0.021 mmol), K$_3$PO$_4$ (89 mg, 0.42 mmol), sodium acetate (57.1 mg, 0.42 mmol), water (0.5 mL), and acetonitrile (30 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with dichloromethane/methanol (50:1 to 30:1) to afford 228a as brown solid (60 mg, 42%). MS-ESI: [M+H]$^+$ 694.3.

Example 228

2-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-3,4,6,7,8,9-hexahydropyrazino[1,2-a]indol-1-one 228

A mixture of 228a (50 mg, 0.070 mmol) and lithium hydroxide (43 mg, 1.8 mmol) in i-propanol/THF (1:1, 4 mL) and water (1 mL) was stirred at 35° C. for 30 mins. The reaction mixture was concentrated under reduced pressure and the residue was purified by reverse-phase prep-HPLC to afford 228 (10 mg, 21%). MS-ESI: [M+H]$^+$ 652.3. $^1$H NMR (500 MHz, DMSO-d$_6$) δ 8.61 (s, 1H), 8.48 (d, J=4.5 Hz, 1H), 8.39 (s, 1H), 8.34 (s, 1H), 7.84 (s, 1H), 7.48 (s, 1H), 7.34 (d, J=5.0 Hz, 1H), 6.58 (bs, 1H), 4.94 (bs, 1H), 4.56-4.55 (m, 2H), 4.49-4.47 (m, 1H), 4.42-4.36 (m, overlap, 4H) 4.25-4.17 (m, 2H), 4.13-4.10 (m, 1H), 3.86-3.76 (m, 2H), 3.60 (s, 3H), 3.39-3.37 (m, 1H), 3.01-2.96 (m, 1H), 2.78-2.76 (m, 1H), 2.62-2.57 (m, overlap, 3H), 2.50-2.47 (m, 2H), 2.10-2.07 (m, 1H), 1.94-1.90 (m, 1H), 1.80-1.78 (m, 2H), 1.70-1.69 (m, 2H), 1.12 (d, J=6.5 Hz, 3H).

Example 229a

2-Ethylpyrimidin-4-amine 229a

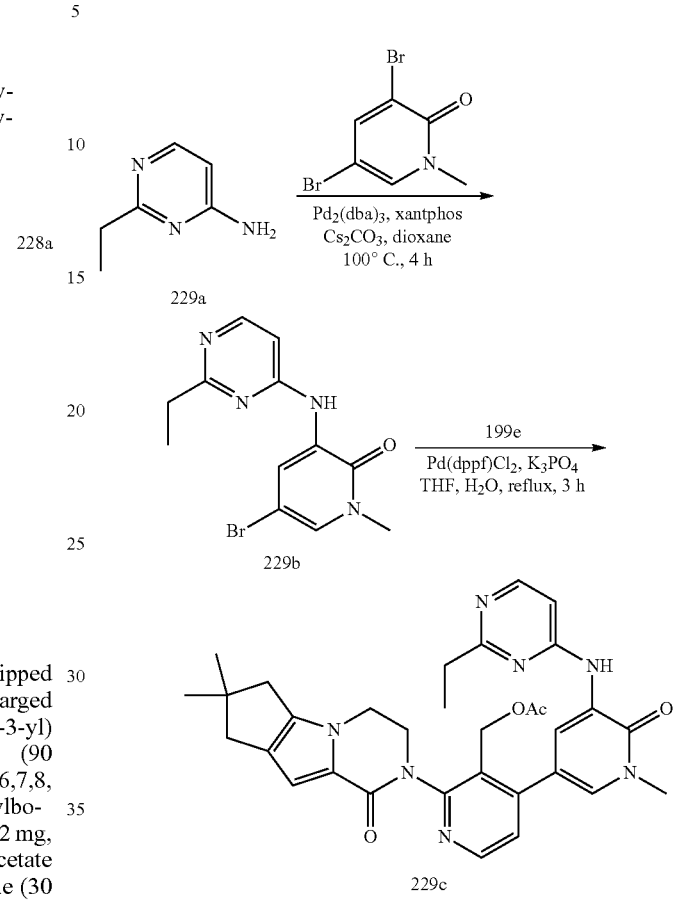

A 100-mL single-neck round-bottomed flask equipped with a magnetic stirrer and a reflux condenser was charged with 2-chloropyrimidin-4-amine (2.60 g, 20.0 mmol), triethylborane (20.0 mL, 1.0 M in THF, 20.0 mmol), Pd(dppf)Cl$_2$ (816 mg, 1.0 mmol), K$_3$PO$_4$ (13.0 g, 40.0 mmol), water (2 mL), and tetrahydrofuran (50 mL). After three cycles of vacuum/argon flush, the mixture was heated at reflux for 14 h. It was then cooled to room temperature and filtered. The filtrate was concentrated under reduced pressure and the resulting residue was purified by silica-gel column chromatography eluting with 40:1 dichloromethane/methanol to afford 229a as yellow solid (600 mg, 24%). MS-ESI: [M+H]$^+$ 124.3

Example 229b

5-Bromo-3-(2-ethylpyrimidin-4-ylamino)-1-methylpyridin-2(1H)-one 229b

A 100-mL single-neck round-bottomed flask equipped with a magnetic stirrer and a reflux condenser was charged with 229a (246 mg, 2.0 mmol), 3,5-dibromo-1-methylpyridin-2(1H)-one (534 mg, 2.0 mmol), Pd$_2$(dba)$_3$ (182 mg, 0.20 mmol), XantPhos (231 mg, 0.40 mmol), Cs$_2$CO$_3$ (1.30 g, 4.0 mmol), and 1,4-dioxane (20 mL). After three cycles of vacuum/argon flush, the mixture was heated at 100° C. for 4 h. It was then cooled to room temperature and filtered. The filtrate was concentrated under reduced pressure and the resulting residue was purified by silica-gel column chromatography eluting with 40:1 dichloromethane/methanol to afford 229b as off-white solid (308 mg, 50%). MS-ESI: [M+H]+ 309.1

Example 229c (2'-(7,7-Dimethyl-1-oxo-3,4,7,8-tetrahydro-1H-cyclopenta-[4,5]pyrrolo[1,2-a]pyrazin-2(6H)-yl)-5-((2-ethylpyrimidin-4-yl)amino)-1-methyl-6-oxo-1,6-dihydro-[3,4'-bipyridin]-3'-yl)methyl Acetate 229c A 100-mL round-bottomed flask equipped with a reflux condenser was charged with 229b (277 mg, 0.90 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (358 mg, 0.90 mmol), Pd(dppf)Cl$_2$ (74 mg, 0.090 mmol), K$_3$PO$_4$ (381 mg, 1.80 mmol), water (2 mL), and tetrahydrofuran (20 mL). After three cycles of vacuum/argon flush, the mixture was heated at reflux for 3 h. It was then cooled to room temperature and filtered. The filtrate was concentrated under reduced pressure and the resulting residue was purified by silica-gel column chromatography eluting with 60:1 dichloromethane/methanol to afford 229c as white solid (291 mg, 50%). MS-ESI: [M+H]+ 582.4

Example 229

3-[4-[5-[(2-ethylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 229

To a solution of 229c (291 mg, 0.45 mmol) in tetrahydrofuran (10 mL) and water (2 mL) was added lithium hydroxide (48 mg, 2.0 mmol). The reaction mixture was stirred at 25° C. for 1 h and concentrated under reduced pressure. The residue was purified by reverse-phase prep-HPLC to afford 229 (165 mg, 61%) as yellow solid. MS-ESI: [M+H]+ 540.3. $^1$H NMR (500 MHz, DMSO-d$_6$) δ 9.12 (s, 1H), 8.96 (d, J=2.5 Hz, 1H), 8.50 (d, J=5.0 Hz, 1H), 8.25 (d, J=5.5 Hz, 1H), 7.72 (d, J=2.5 Hz, 1H), 7.38 (d, J=5.5 Hz, 1H), 7.15 (d, J=6.0 Hz, 1H), 6.56 (s, 1H), 5.00 (t, J=5.5 Hz, 1H), 4.55-4.44 (m, 2H), 4.26-4.19 (m, overlap, 3H), 3.88-3.86 (m, 1H), 3.62 (s, 3H), 2.74 (q, J=7.5 Hz, 2H), 2.59-2.54 (m, 2H), 2.43 (s, 2H), 1.22-1.20 (m, overlap, 9H).

Example 230a (S)-tert-Butyl 4-(5-Bromopyrazin-2-yl)-3-methylpiperazine-1-carboxylate 230a

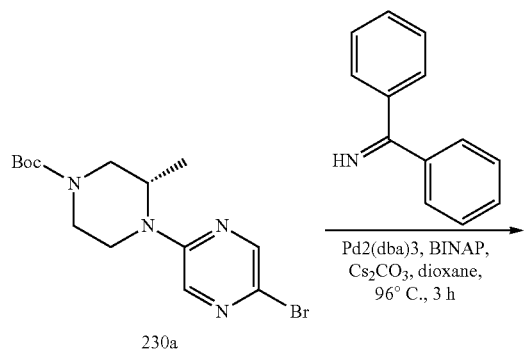

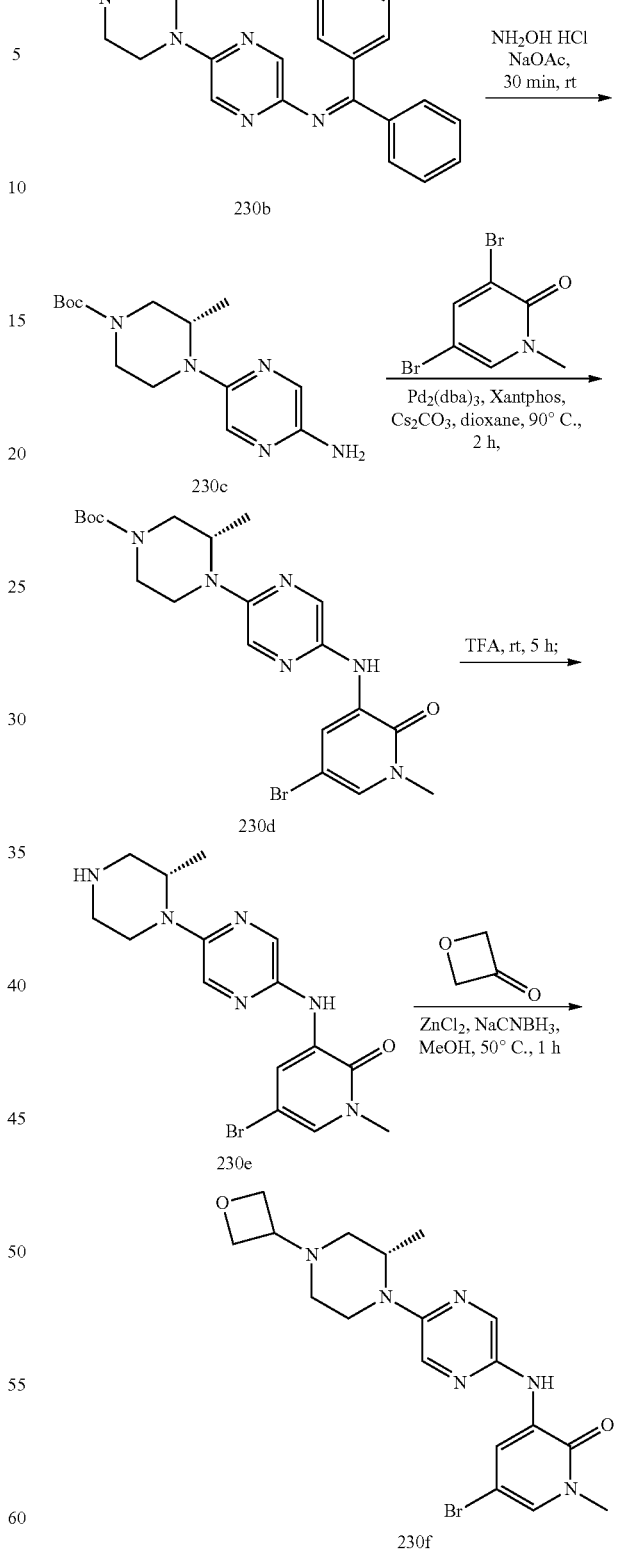

A mixture of (S)-tert-butyl 3-methylpiperazine-1-carboxylate (6.0 g, 30 mmol) and 2,5-dibromopyrazine (14.1 g, 60 mmol) was stirred at 80° C. for 15 h. It was then cooled to room temperature and purified by silica-gel column chromatography eluting with petroleum ether/ethyl acetate (10:1 to 2:1) to afford 230a as a yellow solid (1.14 g, 19%). MS: [M+H]⁺ 359.1.

Example 230b (S)-tert-Butyl 4-(5-(Diphenylmethyleneamino) pyrazin-2-yl)-3-methylpiperazine-1-carboxylate 230b A 100-mL single-neck round-bottomed flask equipped with a magnetic stirrer and a reflux condenser was charged with 230a (2.6 g, 7.3 mmol), diphenylmethanimine (1.3 g, 7.3 mmol), Pd₂(dba)₃ (669 mg, 0.73 mmol), (R)-(+)-2,2'-bis (diphenylphosphino)-1,1'-binaphthyl (968 mg, 1.46 mmol), Cs₂CO₃ (4.7 g, 14.6 mmol), and 1,4-dioxane (40 mL). After three cycles of vacuum/argon flush, the mixture was heated at 96° C. for 3 hrs. It was then cooled to room temperature and filtered. The filtrate was concentrated under reduced pressure and the resulting residue was purified by silica-gel column chromatography eluting with petroleum ether/ethyl acetate (10:1 to 3:1) to afford 230b as red oil (3.3 g, 75%). MS: [M+H]⁺ 458.3.

Example 230c (S)-tert-Butyl 4-(5-Aminopyrazin-2-yl)-3-methylpiperazine-1-carboxylate 230c To a solution of 230b (3.3 g, 7.2 mmol) in methanol (25 mL) were added sodium acetate (708 mg, 8.6 mmol) and hydroxylamine hydrochloride (907 mg, 8.6 mmol). The reaction mixture was stirred for 0.5 h. It was then concentrated in vacuo. The residue was purified by silica-gel column chromatography eluting with dichloromethane/methanol (50:1 to 30:1) to afford 230c as yellow oil (1.35 g, 64%). MS: [M+H]⁺ 294.3.

Example 230d (S)-tert-Butyl 4-(5-(5-Bromo-1-methyl-2-oxo-1,2-dihydropyridin-3-ylamino)pyrazin-2-yl)-3-methylpiperazine-1-carboxylate 230d A 250-mL single-neck round-bottomed flask equipped with a magnetic stirrer and a reflux condenser was charged with 230c (1.25 g, 4.3 mmol), 3,5-dibromo-1-methylpyridin-2(1H)-one (3.4 g, 12.9 mmol), Pd₂(dba)₃ (394 mg, 0.43 mmol), Xantphos (497 mg, 0.86 mmol), Cs₂CO₃ (4.7 g, 14.6 mmol), and 1,4-dioxane (80 mL). After three cycles of vacuum/argon flush, the mixture was heated at 90° C. for 2 hrs. It was then cooled to room temperature and filtered. The filtrate was concentrated under reduced pressure and the resulting residue was purified by silica-gel column chromatography eluting with dichloromethane/methanol (50:1 to 30:1) to afford 230d (1.9 g, 72%). MS: [M+H]⁺ 481.2.

Example 230e (S)-5-Bromo-1-methyl-3-(5-(2-methylpiperazin-1-yl)pyrazin-2-ylamino)pyridin-2(1H)-one 230e A mixture of 230d (1.9 g, 3.97 mmol) and trifluoroacetic acid (4 mL) was stirred at room temperature for 1 h. It was then concentrated under reduced pressure to afford crude 230e (1.45 g, 97%), which was used in the next step without further purification. MS: [M+H]⁺ 381.2.

Example 230f (S)-5-Bromo-1-methyl-3-(5-(2-methyl-4-(oxetan-3-yl)piperazin-1-yl)pyrazin-2-ylamino)pyridin-2(1H)-one 230f A mixture of 230e (2.0 g, 5.3 mmol), oxetan-3-one (763 mg, 10.6 mmol), NaBH₃CN (835 mg, 13.3 mmol), and zinc chloride (1.8 g, 13.3 mmol) in methanol (60 mL) was stirred at 50° C. for 30 min. The mixture was concentrated under reduced pressure. To the residue was added water and the resulting mixture was extracted with dichloromethane three times. The combined organic layer was then concentrated under reduced pressure and the resulting residue was purified by silica-gel column chromatography eluting with dichloromethane/methanol (50:1 to 20:1) to afford 230f as a yellow oil (1.6 g, 70%). MS: [M+H]⁺ 437.2.

Example 230g

5-[4-Chloro-3-(hydroxymethyl)pyridin-2-yl]-8-thia-4,5-diazatricyclo[7.4.0.0²,⁷]trideca-1(9),2(7),3-trien-6-one 230g

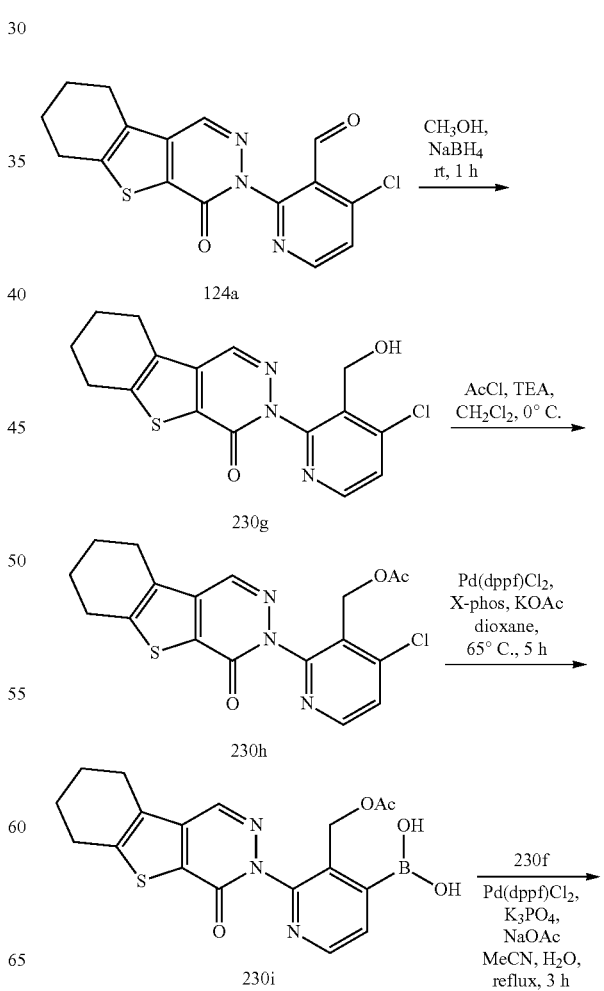

427

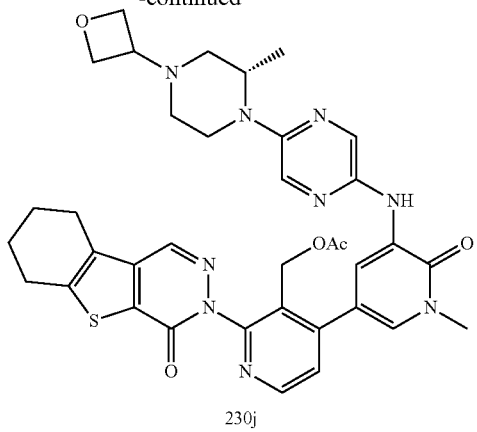

230j

A mixture of 4-chloro-2-{6-oxo-8-thia-4,5-diazatricyclo [7.4.0.0²,⁷]trideca-1(9),2(7),3-trine-5-yl}pyridine-3-carbaldehyde 124a (797 mg, 2.31 mmol), NaBH₄ (263 mg, 6.92 mmol), and CH₃OH (50 mL) was stirred at room temperature for 1 h. Then the reaction mixture was quenched with water (30 mL) and concentrated under reduced pressure. The residue was extracted with dichloromethane (2×30 mL) and the combined dichloromethane extract was concentrated under reduced pressure. The residue was purified by silica-gel chromatography eluting with 5:1 to afford 230g (649 mg, 81%) as a yellow solid. MS-ESI: [M+H]⁺ 348.1

Example 230h (4-Chloro-2-{6-oxo-8-thia-4,5-diazatricyclo[7.4.0. 0²,⁷]trideca-1(9),2(7),3-trien-5-yl}pyridin-3-yl)methyl Acetate 230h A round-bottomed flask was charged with 230g (597 mg, 1.72 mmol), dichloromethane (50 mL), and triethylamine (5 mL). The solution was stirred at 0° C. for 0.5 h and acetyl chloride (135 mg, 1.72 mmol) was added slowly. The mixture was stirred at 0° C. for another 2.5 h. It was then concentrated under reduced pressure. The residue was purified by silica-gel column chromatography eluting with 9:1 petroleum ether/ethyl acetate to afford 230h (602 mg, 90%) as a yellow solid. MS-ESI: [M+H]⁺ 390.1

Example 230i 4-(Dihydroxyboranyl)-2-{6-oxo-8-thia-4,5-diazatricyclo-[7.4.0.0²,⁷]trideca-1(9),2(7),3-trien-5-yl}pyridin-3-yl]methyl acetate 230i A 100-mL single-neck round-bottomed flask equipped with a magnetic stirrer and a reflux condenser was charged with 230h (595 mg, 1.53 mmol), Pin₂B₂ (1.94 g, 7.65 mmol), PdCl₂(dppf) (65 mg, 0.080 mmol), X-Phos (73 mg, 0.15 mmol), potassium acetate (304 mg, 3.1 mmol), and dioxane (50 mL). After three cycles of vacuum/argon flush, the mixture was heated at 65° C. for 5 h. It was then cooled to room temperature and filtered. The filtrate was concentrated under reduced pressure and the resulting residue was washed with petroleum ether to afford 230i (409 mg, 67%) as a yellow solid. MS-ESI: [M+H]⁺ 400.1

428

Example 230j

{4-[1-Methyl-5-({5-[(2S)-2-methyl-4-(oxetan-3-yl) piperazin-1-yl]pyrazin-2-yl}amino)-6-oxo-1,6-dihydropyridin-3-yl]-2-{6-oxo-8-thia-4,5-diazatricyclo [7.4.0.0²,⁷]trideca-1(9),2(7),3-trien-5-yl}pyridin-3-yl}methyl Acetate 230j A 100-mL single-neck round-bottomed flask equipped with a magnetic stirrer and a reflux condenser was charged with 230f (100 mg, 0.23 mmol), 230i (140 mg, 0.35 mmol), Pd(dppf)Cl₂ (19 mg, 0.023 mmol), sodium acetate (63 mg, 0.46 mmol), K₃PO₄ (98 mg, 0.46 mmol), water (0.5 mL), and acetonitrile (20 mL). After three cycles of vacuum/argon flush, the mixture was heated at 90° C. for 3 h. After cooling to room temperature the reaction was filtered. The filtrate was concentrated under reduced pressure and the resulting residue was purified by silica-gel column chromatography eluting with dichloromethane/methanol (50:1 to 30:1) to afford 230j as a yellow solid (90 mg, 55%). MS-ESI: [M+H]⁺ 710.2.

Example 230

3-[3-(hydroxymethyl)-4-[1-methyl-5-[[5-[(2S)-2-methyl-4-(oxetan-3-yl)piperazin-1-yl]pyrazin-2-yl] amino]-6-oxo-3-pyridyl]-2-pyridyl]-6,7,8,9-tetrahydrobenzothiopheno[2,3-d]pyridazin-4-one 230

A mixture of 230j (80 mg, 0.11 mmol) and lithium hydroxide (27 mg, 1.1 mmol) in i-propanol/THF (1:1, 10 mL) and water (2 mL) was stirred at 35° C. for 0.5 h. It was then cooled to room temperature and filtered. The filtrate was concentrated under reduced pressure and the resulting residue was purified by reverse-phase prep-HPLC to afford 230 (34 mg, 45%). MS-ESI: [M+H]⁺ 668.2. ¹H NMR (500 MHz, DMSO-d₆) δ 8.64 (s, 1H), 8.56 (d, J=6.0 Hz, 1H), 8.46 (s, 1H), 8.40 (d, J=2.5 Hz, 1H), 8.34 (d, J=1.5 Hz, 1H), 7.85 (s, 1H), 7.53 (d, J=6.0 Hz, 1H), 7.49 (d, J=2.5 Hz, 1H), 4.84 (bs, 1H), 4.58-4.54 (m, 2H), 4.50-4.47 (m, 1H), 4.43-4.36 (m, overlap, 4H), 3.78-3.75 (m, 1H), 3.59 (s, 3H), 3.39-3.35 (m, 1H), 3.02-3.0 (m, 1H), 2.98-2.95 (m, 2H), 2.90-2.82 (m, 2H), 2.78-2.76 (m, 1H), 2.60-2.56 (m, 1H), 2.10-2.09 (m, 1H), 1.95-1.88 (m, overlap, 5H), 1.10 (d, J=8.0 Hz, 3H).

Example 231a 2-(4-Chloro-3-(hydroxymethyl)pyridin-2-yl)-10-fluoro-3,4,6,7,8,9-hexahydropyrazino[1,2-a]indol-1 (2H)-one 231a

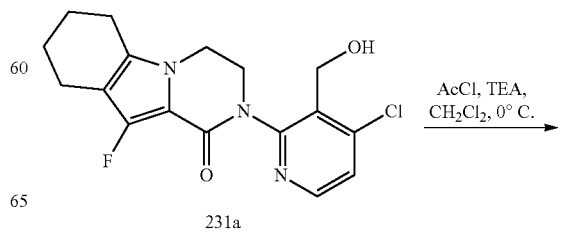

231a

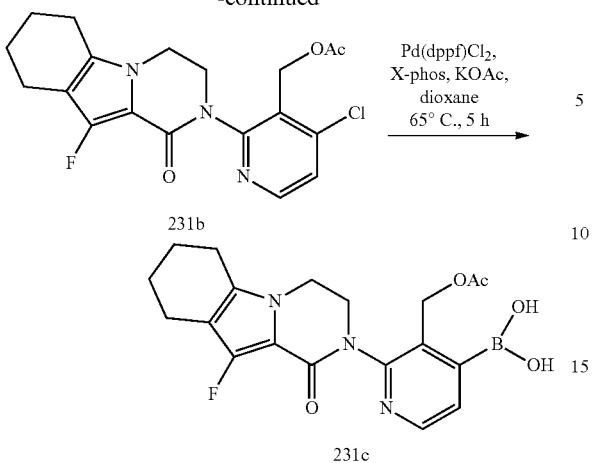

A mixture of 4-chloro-2-(10-fluoro-1-oxo-3,4,6,7,8,9-hexahydropyrazino[1,2-a]indol-2(1H)-yl)nicotinaldehyde 134c (800 mg, 2.31 mmol), NaBH₄ (263 mg, 6.92 mmol), and methanol (50 mL) was stirred at 0° C. for 1 h. Then the reaction mixture was quenched with water (30 mL) and concentrated under reduced pressure. The residue was extracted with dichloromethane (2×30 mL) and the combined dichloromethane extract was concentrated under reduced pressure. The residue was purified by silica-gel chromatography eluting with 5:1 petroleum ether/ethyl acetate to afford 231a (650 mg, 81%) as a yellow solid. MS-ESI: [M+H]⁺ 340.1

Example 231b (4-Chloro-2-(10-fluoro-1-oxo-3,4,6,7,8,9-hexahydropyrazino[1,2-a]indol-2(1H)-yl)pyridin-3-yl)methyl Acetate 231b A round-bottomed flask was charged with 231a (600 mg, 1.72 mmol), dichloromethane (50 mL), and triethylamine (5 mL). The solution was stirred at 0° C. for 0.5 h and acetyl chloride (135 mg, 1.72 mmol) was added slowly. The mixture was stirred at 0° C. for another 2.5 h. It was then evaporated under reduced pressure. The residue was purified by silica-gel column chromatography eluting with 9:1 petroleum ether/ethyl acetate to afford 231b (605 mg, 90%) as a yellow solid. MS-ESI: [M+H]⁺ 392.1

Example 231c 3-(Acetoxymethyl)-2-(10-fluoro-1-oxo-3,4,6,7,8,9-hexahydropyrazino[1,2-a]indol-2(1H)-yl)pyridin-4-ylboronic Acid 231c A 100-mL single-neck round-bottomed flask equipped with a magnetic stirrer and a reflux condenser was charged with 231b (600 mg, 1.53 mmol), Pin₂B₂ (1.94 g, 7.65 mmol), PdCl₂(dppf) (65 mg, 0.080 mmol), X-Phos (73 mg, 0.15 mmol), potassium acetate (304 mg, 3.1 mmol), and dioxane (30 mL). After three cycles of vacuum/argon flush, the mixture was heated at 65° C. for 5 h. It was then cooled to room temperature and filtered. The filtrate was concentrated under reduced pressure and the resulting residue was washed with petroleum ether to afford 231c (412 mg, 67%) as yellow solid. MS-ESI: [M+H]⁺ 402.1

Example 231d (S)-(2-(10-Fluoro-1-oxo-3,4,6,7,8,9-hexahydropyrazino[1,2-a]indol-2(1H)-yl)-4-(1-methyl-5-(5-(2-methyl-4-(oxetan-3-yl)piperazin-1-yl)pyridin-2-ylamino)-6-oxo-1,6-dihydropyridazin-3-yl)pyridin-3-yl)methyl Acetate 231d

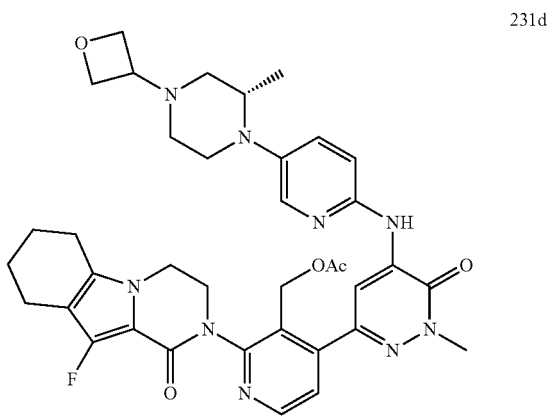 [SMILES: CC(=O)OCc1c(-c2cc(Nc3ccc(N4CCN(C5COC5)C[C@@H]4C)cn3)c(=O)n(C)n2)ccnc1N1CCn2c3c(c(F)c2C1=O)CCCC3]

A round-bottomed flask equipped with a reflux condenser was charged with 231c (200 mg, 0.50 mmol), (S)-6-chloro-2-methyl-4-(5-(2-methyl-4-(oxetan-3-yl)piperazin-1-yl)pyridin-2-ylamino)pyridazin-3(2H)-one 224c (195 mg, 0.50 mmol), PdCl₂(dppf) (24 mg, 0.030 mmol), K₃PO₄ (212 mg, 1.0 mmol), sodium acetate (98 mg, 1.0 mmol), acetonitrile (30 mL), and water (3 mL). After three cycles of vacuum/argon flush, the mixture was heated at 100° C. for 2 h. It was then cooled to room temperature and filtered. The filtrate was evaporated under reduced pressure. The residue was purified with silica-gel column chromatography eluting with 1:3 petroleum/ethyl acetate to afford 231d as a yellow solid (213 mg, 60%). MS-ESI: [M+H]⁺ 712.3

Example 231

10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-3,4,6,7,8,9-hexahydropyrazino[1,2-a]indol-1-one 231

A mixture of 231d (150 mg, 0.21 mmol) and lithium hydroxide (51 mg, 2.1 mmol) in i-propanol/THF (1:1, 10 mL) and water (3 mL) was stirred at room temperature for 1 h. The mixture was evaporated under reduced pressure and the residue was extracted with ethyl acetate (2×10 mL). The combined ethyl acetate extract was concentrated under reduced pressure and the residue was purified with reverse-phase prep-HPLC to afford 231 (83 mg, 59%) as a yellow solid. MS-ESI: [M+H]⁺ 670.3. ¹H NMR (500 MHz, DMSO-d₆) δ 9.29 (s, 1H), 8.53 (d, J=5.5 Hz, 1H), 8.42 (s, 1H), 7.91 (s, 1H), 7.43-7.40 (m, 3H), 4.76 (bs, 1H), 4.60-4.54 (m, 3H), 4.49-4.46 (m, 1H), 4.43-4.37 (m, 2H), 4.21-4.56 (m, 2H), 4.07-4.03 (m, 1H), 3.89-3.83 (m, 2H), 3.78 (s, 3H), 3.41-3.37 (m, 1H), 3.22-3.19 (m, 1H), 3.00-2.93 (m, 1H), 2.65-2.60 (m, 2H), 2.55-2.54 (m, 1H), 2.43-2.39 (m, 3H), 2.27-2.24 (m, 1H), 2.12-2.07 (m, 1H), 1.76-1.66 (m, 4H), 0.97 (d, J=9.0 Hz, 3H).

Example 232a

2-Nitro-5-(1,2,3,6-tetrahydropyridin-4-yl)pyridine 232a

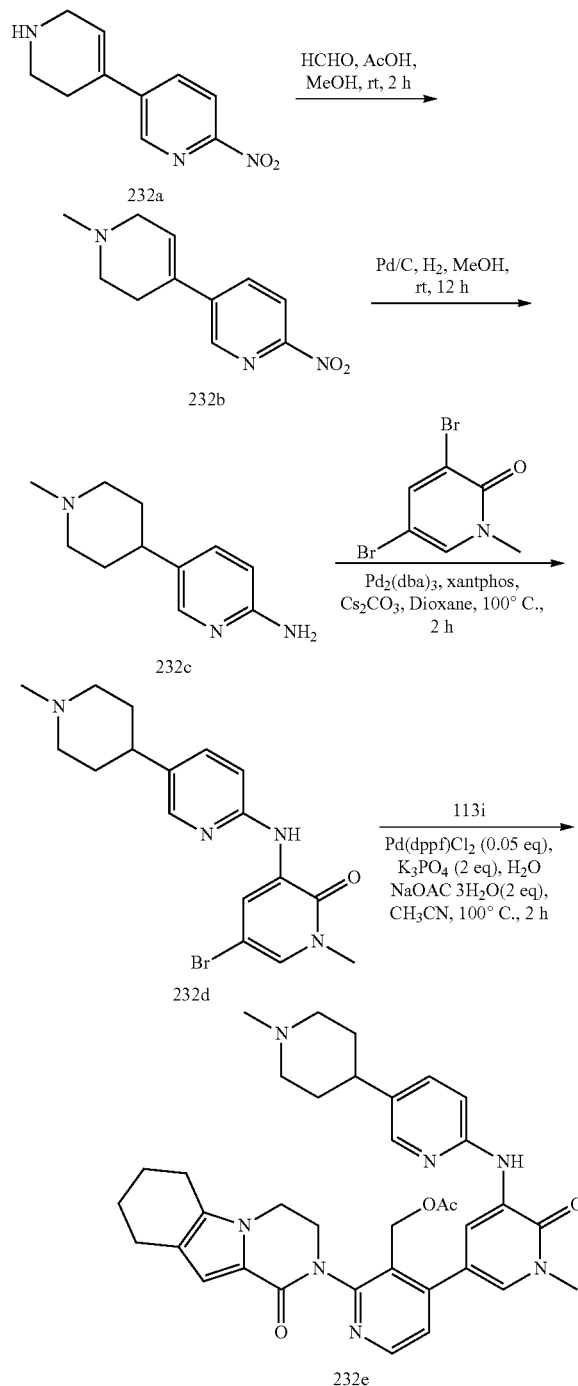

A mixture of tert-butyl 4-(6-nitropyridin-3-yl)-5,6-dihydropyridine-1(2H)-carboxylate 200a (2.0 g, 6.6 mmol) in HCl/dioxane (20 mL, 4M) was stirred at room temperature for 2 hours. It was then evaporated under reduced pressure. The residue was washed with ethyl acetate (3×7 mL) to afford 232a as a yellow solid (1.0 g, 74%). MS-ESI: [M+H]$^+$ 206.

Example 232b 5-(1-Methyl-1,2,3,6-tetrahydropyridin-4-yl)-2-nitropyridine 232b To a solution of 232a (1.2 g, 5.8 mmol) in CH$_3$OH (25 mL) was added HCHO (1 mL, 35 mmol) and acetic acid (1 mL), followed by the addition of NaBHCN$_3$ (1.0 g, 12 mmol). The mixture was stirred at room temperature for 2 h. It was then evaporated under reduced pressure and the residue was purified by reverse-phase Combiflush eluting with 0.3% NH$_4$HCO$_3$ in water/acetonitrile to afford 232b as a yellow solid (1.0 g, 78%). MS-ESI: [M+H]$^+$ 220.

Example 232c 5-(1-Methylpiperidin-4-yl)pyridin-2-amine 232c

A 250-mL single-neck round-bottomed flask was purged with nitrogen and charged with 232b (2.0 g, 9.0 mmol), 10% palladium on carbon (50% wet, 200 mg), and methanol (40 mL). The flask was evacuated, charged with hydrogen gas, and stirred under hydrogen at room temperature for 12 h. The hydrogen was then evacuated and nitrogen was charged to the flask. The catalyst was removed by filtration through a pad of CELITE® and the filtrate was concentrated under reduced pressure to afford 232c (1.6 g, 92.5%), which was used directly in the next step without further purification. MS-ESI: [M+H]$^+$ 192

Example 232d

5-Bromo-1-methyl-3-(5-(1-methylpiperidin-4-yl)pyridin-2-ylamino)pyridine-2(1H)-one 232d A 100-mL single-neck round-bottomed flask equipped with a magnetic stirrer and a reflux condenser was charged with 232c (1.5 g, 7.9 mmol), 3,5-dibromo-1-methylpyridin-2(1H)-one (2.0 g, 7.9 mmol), cesium carbonate (5.0 g, 16 mmol), and 1,4-dioxane (50 mL). After bubbling nitrogen through the resulting suspension for 30 minutes, XantPhos (455 mg, 0.79 mmol) and tris(dibenzylideneacetone)dipalladium(0) (718 mg, 0.79 mmol) were added. The system was subject to three cycles of vacuum/argon flush and heated at 100° C. for 2 h. After this time the reaction was cooled to room temperature and filtered. The filtrate was partitioned between ethyl acetate (100 mL) and water (100 mL). The aqueous layer was separated and extracted with ethyl acetate (3×50 mL). The combined organic layer was washed with brine (3×20 mL) and dried over sodium sulfate. The drying agent was removed by filtration and the filtrate was concentrated under reduced pressure. The residue was purified by silica-gel column chromatography eluting with 1:3 ethyl acetate/petroleum ether to afford 232d as a brown solid (1.5 g, 50%). MS-ESI: [M+H]$^+$ 377.

Example 232e (4-(1-Ethyl-5-(5-(1-methylpiperidin-4-yl)pyridin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 232e A round-bottomed flask equipped with a reflux condenser was charged with 232d (160 mg, 0.40 mmol), 3-(acetoxymethyl)-2-(1-oxo-3,4,6,7,8,9-hexahydropyrazino[1,2-a]indol-2(1H)-yl)pyridin-4-ylboronic acid 113i (191 mg, 0.50 mmol), Pd(dppf)Cl₂ (20 mg, 0.024 mmol), K₃PO₄ (180 mg, 0.80 mmol), sodium acetate trihydrate (120 mg, 0.80 mmol), water (0.5 mL), and acetonitrile (10 mL). After three cycles of vacuum/argon flush, the mixture was heated at 100° C. for 2 h. It was then filtered and the filtrate was evaporated in vacuo. The residue was purified by silica-gel column chromatography eluting with 25:1 dichloromethane/CH₃OH to afford 232e as a yellow solid (180 mg, 55%). MS-ESI: [M+H]⁺ 636.3

Example 232

2-[3-(hydroxymethyl)-4-[1-methyl-5-[[5-(1-methyl-4-piperidyl)-2-pyridyl]amino]-6-oxo-3-pyridyl]-2-pyridyl]-3,4,6,7,8,9-hexahydropyrazino[1,2-a]indol-1-one A mixture of 232e (180 mg, 0.30 mmol) and lithium hydroxide (130 mg, 3.0 mmol) in THF/i-propanol (6:3, 9 mL) and water (3 mL) was stirred at 30° C. for 1 h. The mixture was evaporated under reduced pressure and the residue was extracted with ethyl acetate (2×20 mL). The combined ethyl acetate extract was concentrated under reduced pressure and the residue was purified by reverse-phase prep-HPLC to 232 (55 mg, 35%) as white solid. MS-ESI: [M+H]⁺ 594.3. ¹H NMR (500 MHz, CDCl₃) δ 8.72 (d, J=3.0 Hz, 1H), 8.51 (d, J=6.0 Hz, 1H), 8.11 (d, J=3.0 Hz, 1H), 7.88 (d, J=2.0 Hz, 1H), 7.44-7.36 (m, 2H), 6.90 (s, 1H), 6.80-6.78 (m, 1H), 5.08-5.04 (m, 1H), 4.64-4.50 (m, 2H), 4.34-4.29 (m, 1H), 4.16-4.10 (m, 2H), 3.91-3.87 (m, 1H), 3.72 (s, 3H), 3.03-3.00 (m, 2H), 2.62-2.56 (m, 4H), 2.46-2.42 (m, 1H), 2.36 (s, 1H) 2.13-2.07 (m, 2H), 1.92-1.82 (m, overlap, 8H).

Example 233a tert-Butyl 2-(5-Bromo-1-methyl-2-oxo-1,2-dihydro-pyridin-3-ylamino)-6,7-dihydrothiazolo[5,4-c]pyridine-5(4H)-carboxylate 233a

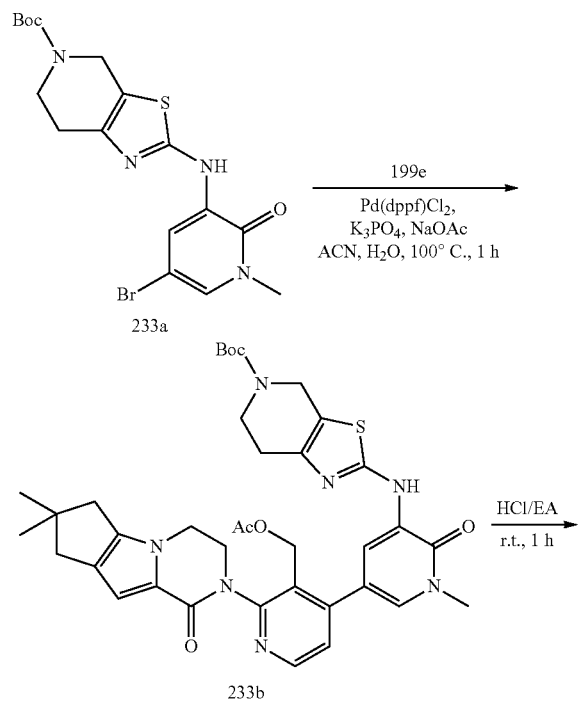

A 100-mL round-bottomed flask equipped with a reflux condenser was charged with tert-butyl 2-amino-6,7-dihydrothiazolo[5,4-c]pyridine-5(4H)-carboxylate (600 mg, 2.35 mmol), 3,5-dibromo-1-methylpyridin-2(1H)-one (942 mg, 3.53 mmol), Pd₂(dba)₃ (214 mg, 0.235 mmol), Xantphos (270.5 mg, 0.47 mmol), Cs₂CO₃ (1.53 g, 4.7 mmol), and dioxane (30 mL). After bubbling nitrogen through the mixture for 30 minutes, it was heated at 110° C. under N₂ protection for 12 h. Analysis of reaction mixture by LCMS showed complete conversion to the desired product. The mixture was cooled to room temperature and filtered. The filtrate was concentrated under reduced pressure and the residue was washed with acetonitrile to afford 233a (600 mg, 54%) as yellow solid. MS-ESI: [M+H]⁺ 441.1

Example 233b tert-Butyl 2-[(5-{3-[(Acetoxy)methyl]-2-{4,4-dimethyl-9-oxo-1,10-diazatricyclo[6.4.0.0²,⁶]dodeca-2(6),7-dien-10-yl}pyridin-4-yl}-1-methyl-2-oxo-1,2-dihydropyridin-3-yl)amino]-4H,5H,6H,7H-[1,3]thiazolo[5,4-c]pyridine-5-carboxylate 233b A 50-mL round-bottomed flask equipped with a reflux condenser was charged with 233a (300 mg, 0.68 mmol), (3-(acetoxymethyl)-2-(7,7-dimethyl-1-oxo-3,4,7,8-tetrahydro-1H-cyclopenta[4,5]pyrrolo-[1,2-a]pyrazin-2(6H)-yl)pyridin-4-yl)boronic acid 199e (1.8 g, 2.72 mmol), Pd(dppf)Cl₂ (27.7 mg, 0.034 mmol), K₃PO₄ (288.3 mg, 1.36 mmol), sodium acetate (111.5 mg, 1.36 mmol), water (10 drops), and acetonitrile (10 mL). After bubbling nitrogen through the mixture for 30 minutes, it was heated at 100° C. under N₂ protection for 1 h. Analysis of reaction mixture by LCMS showed complete conversion to the desired product. The mixture was filtered and the filtrate was concentrated under reduced pressure and the residue was purified by silica-gel column chromatography eluting with 100:1 dichloromethane/methanol to afford 233b (220 mg, 45%) as a yellow solid. MS-ESI: [M+H]⁺ 714.3

Example 233c (2-{4,4-Dimethyl-9-oxo-1,10-diazatricyclo[6.4.0.0²,⁶]dodeca-2(6),7-dien-10-yl}-4-[1-methyl-6-oxo-5-({4H,5H,6H,7H-[1,3]thiazolo[5,4-c]pyridin-2-yl}amino)-1,6-dihy-dropyridin-3-yl]pyridin-3-yl)methyl Acetate 233c To a solution of 233b (220 mg, 0.308 mmol) in ethyl acetate (5 mL) was added a solution of HCl in ethyl acetate (0.123 mL, 2.5M, 0.308 mmol). The mixture was stirred at room temperature for 1 h. It was then concentrated under reduced pressure to afford 233c (180 mg, crude), which was used directly for next step without further purification. MS-ESI: [M+H]+ 614.3

Example 233

3-[3-(hydroxymethyl)-4-[1-methyl-6-oxo-5-(4,5,6,7-tetrahydrothiazolo[5,4-c]pyridin-2-ylamino)-3-pyridyl]-2-pyridyl]-7,7-dimethyl-1,2,6,8-tetrahydrocyclopenta[3,4]pyrrolo[3,5-b]pyrazin-4-one 233

To a solution of 233c (180 mg, 0.29 mmol) in THF (3 mL) and propan-2-ol (3 mL) was added water (1 mL) and lithium hydroxide (14.0 mg, 0.58 mmol). The reaction mixture was stirred at room temperature for 1 h. It was then concentrated under reduced pressure and the resulting residue was purified by reverse-phase prep-HPLC to afford 233 (28.6 mg, 17%) as white solid. MS-ESI: [M+H]+ 572.3. $^1$H NMR (500 MHz, DMSO-$d_6$) δ 9.85 (s, 1H), 8.63 (d, J=2.5 Hz, 1H), 8.48 (d, J=6.5 Hz, 1H), 7.57 (d, J=2.5 Hz, 1H), 7.32 (d, J=6.0 Hz, 1H), 6.55 (s, 1H), 4.95-4.92 (m, 1H), 4.47-4.37 (m, 2H), 4.25-4.18 (m, 3H), 3.86-3.84 (m, 1H), 3.71 (s, 2H), 3.59 (s, 3H), 2.92-2.90 (m, 2H), 2.62-2.56 (m, 2H), 2.50-2.39 (m, 5H), 1.21 (s, 6H).

Example 235a (2-{4,4-Dimethyl-9-oxo-1,10-diazatricyclo[6.4.0.0$^{2,6}$]dodeca-2(6),7-dien-10-yl}-4-[1-methyl-5-({5-[(2S)-2-methyl-4-(oxetan-3-yl)piperazin-1-yl]pyrazin-2-yl}amino)-6-oxo-1,6-dihydropyridin-3-yl]pyridin-3-yl)methyl Acetate 235a

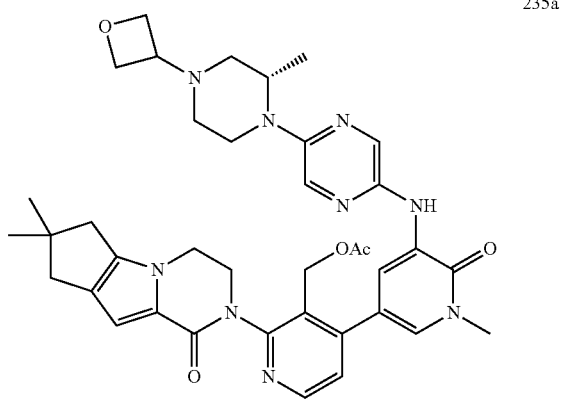

A 50-mL single-neck round-bottomed flask equipped with a magnetic stirrer and a reflux condenser was charged with (S)-5-bromo-1-methyl-3-(5-(2-methyl-4-(oxetan-3-yl)piperazin-1-yl)pyrazin-2-ylamino)pyridin-2(1H)-one 230f (200 mg, 0.46 mmol), {3-[(acetoxy)methyl]-2-{4,4-dimethyl-9-oxo-1,10-diazatricyclo[6.4.0.0$^{2,6}$]-dodeca-2(6),7-dien-10-yl}pyridin-4-yl}boronic acid 199e (366 mg, 0.92 mmol), Pd(dppf)Cl$_2$ (38 mg, 0.046 mmol), sodium acetate (126 mg, 0.92 mmol), K$_3$PO$_4$ (196 mg, 0.92 mmol), water (0.5 mL), and acetonitrile (10 mL). After three cycles of vacuum/argon flush, the mixture was heated at 65° C. for 3 hrs. After cooling to room temperature the reaction was filtered. The filtrate was concentrated under reduced pressure and the resulting residue was purified by silica-gel column chromatography eluting with dichloromethane/methanol (50:1 to 30:1) to afford 235a as brown solid (100 mg, 31%). MS-ESI: [M+H]+ 708.5.

Example 235

3-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 235

A mixture of 235a (90.0 mg, 0.13 mmol) and lithium hydroxide (36.4 mg, 3.25 mmol) in i-propanol/THF (1:1, 5 mL) and water (1 mL) was stirred at 35° C. for 0.5 h. It was then cooled to room temperature and filtered. The filtrate was concentrated under reduced pressure and the resulting residue was purified by reverse-phase prep-HPLC to afford 235 (18.2 mg, 22%). MS-ESI: [M+H]+ 666.3. $^1$H NMR (500 MHz, DMSO-$d_6$) δ 8.61 (s, 1H), 8.48 (d, J=4.5 Hz, 1H), 8.39 (d, J=1.5 Hz, 1H), 8.34 (s, 1H), 7.83 (s, 1H), 7.47 (d, J=2.0 Hz, 1H), 7.33 (d, J=5.0 Hz, 1H), 6.56 (s, 1H), 4.96 (bs, 1H), 4.57-4.55 (m, 2H), 4.49-4.47 (m, 1H), 4.42-4.37 (m, overlap, 4H), 4.22-4.18 (m, overlap, 3H), 3.84-3.76 (m, 2H), 3.60 (s, 3H), 3.39-3.37 (m, 1H), 3.02-2.81 (m, 1H), 2.78-2.76 (m, 1H), 2.62-2.56 (m, 3H), 2.43-2.41 (m, 2H), 2.10-2.07 (m, 1H), 1.92-1.90 (m, 1H), 1.22 (s, 6H), 1.12 (d, J=6.0 Hz, 3H).

Example 236a (2-{4,4-Dimethyl-9-oxo-1,10-diazatricyclo[6.4.0.0$^{2,6}$]dodeca-2(6),7-dien-10-yl}-4-(1-methyl-5-{[5-(1-methylpiperidin-4-yl)pyridin-2-yl]amino}-6-oxopyridin-3-yl)pyridin-3-yl)methyl Acetate 236a

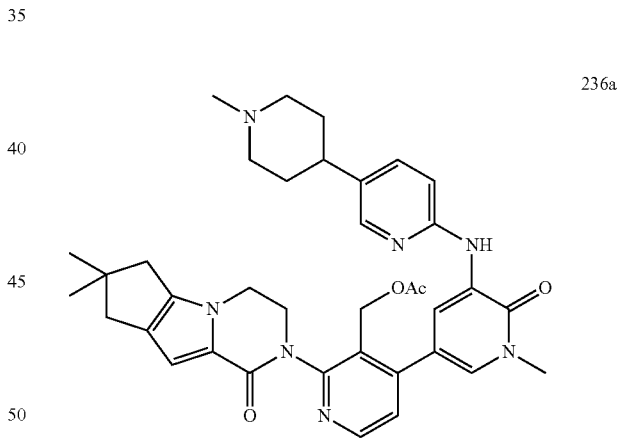

A 50-mL round-bottomed flask equipped with a reflux condenser was charged with 5-bromo-1-methyl-3-(5-(1-methylpiperidin-4-yl)pyridin-2-ylamino)pyridin-2(1H)-one 232d (160 mg, 0.40 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (240 mg, 0.60 mmol), Pd(dppf)Cl$_2$ (20 mg, 0.020 mmol), K$_3$PO$_4$ (180 mg, 0.80 mmol), sodium acetate trihydrate (120 mg, 0.80 mmol), water (0.5 mL), and acetonitrile (10 mL). After three cycles of vacuum/argon flush, the mixture was heated at 100° C. for 2 h. It was then filtered and the filtrate was evaporated under reduced pressure. The residue was purified on silica-gel column chromatography eluting with 25:1 dichloromethane/methanol to afford 236a as a yellow solid (150 mg, 38%). MS-ESI: [M+H]+ 650.3

Example 236

3-[3-(hydroxymethyl)-4-[1-methyl-5-[[5-(1-methyl-4-piperidyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 236

A mixture of 236a (150 mg, 0.25 mmol) and lithium hydroxide (105 mg, 2.5 mmol) in THF/i-propanol (6:3, 9 mL) and water (3 mL) was stirred at 30° C. for 1 h. The mixture was evaporated in vacuo and the residue was extracted with ethyl acetate (2×20 mL). The combined ethyl acetate extract was concentrated under reduced pressure and the residue was purified by reverse-phase prep-HPLC to afford 236 (40 mg, 30%) as light green solid. MS-ESI: [M+H]$^+$ 608.3. $^1$H NMR (500 MHz, CDCl$_3$) δ 8.73 (s, 1H), 8.52 (d, J=4.0 Hz, 1H), 8.13 (s, 1H), 7.90-7.88 (m, 2H), 7.45-7.37 (m, 2H), 6.86-6.80 (m, 2H), 5.11 (bs, 1H), 4.67-4.65 (m, 1H), 4.53-4.51 (m, 1H), 4.35-4.33 (m, 1H), 4.18 (bs, 2H), 3.90-3.89 (m, 1H), 3.73 (s, 3H), 3.24-3.22 (m, 2H), 2.59-2.50 (m, overlap, 8H), 2.36-2.32 (m, 2H), 2.01-1.87 (m, 4H), 1.29 (s, 6H).

Example 237a

2-{10-Fluoro-1-oxo-1H,2H,3H,4H,6H,7H,8H,9H-pyrido[3,4-b]indolizin-2-yl}-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridine-3-carbaldehyde 237a

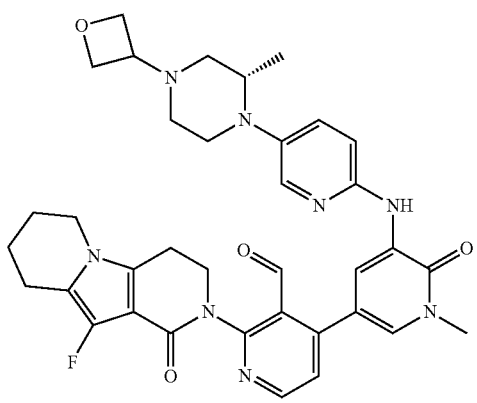

A 50-mL single-neck round-bottomed flask equipped with a magnetic stirrer and a reflux condenser was charged with 4-chloro-2-(10-fluoro-1-oxo-3,4,6,7,8,9-hexahydropyrido[3,4-b]indolizin-2(1H)-yl)nicotinaldehyde 134c (70 mg, 0.20 mmol), 1-methyl-3-({5-[(2S)-2-methyl-4-(oxetan-3-yl)piperazin-1-yl]pyridin-2-yl}amino)-5-(tetramethyl-1,3,2-dioxaborolan-2-yl)-1,2-dihydropyridin-2-one 191j (192 mg, 0.40 mmol), Pd(dppf)Cl$_2$ (33 mg, 0.040 mmol), potassium acetate (39 mg, 0.40 mmol), K$_3$PO$_4$ (87 mg, 0.40 mmol), acetonitrile (7 mL), and water (6 drops). After three cycles of vacuum/argon flush, the mixture was heated at 95° C. for 2 h. It was then filtered and the filtrate was evaporated under reduced pressure. The residue was purified by silica-gel column chromatography eluting with 50:1 ethyl acetate/methanol to afford 237a (286 mg, purity: 46%, yield: 98%) as a solid. MS-ESI: [M+H]$^+$ 667.3

Example 237

10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-3,4,6,7,8,9-hexahydropyrido[3,4-b]indolizin-1-one 237

To a solution of 237a (131 mg, 0.197 mmol) in methanol (7 mL) was added sodium borohydride (59.8 mg, 1.57 mmol) at 0° C. The reaction was stirred at 0-25° C. for 1.5 h. It was then quenched with water (1.5 mL). The mixture was evaporated under reduced pressure and the residue was extracted with dichloromethane (3×30 mL). The combined dichloromethane extract was concentrated under reduced pressure and the residue was purified by reverse-phase prep-HPLC to afford 237 (36 mg, 28%) as a white solid. MS-ESI: [M+H]$^+$ 669.3. $^1$H NMR (500 MHz, CDCl$_3$) δ 8.66 (d, J=1.5 Hz, 1H), 8.51 (d, J=5.0 Hz, 1H), 7.99 (s, 1H), 7.85 (s, 1H), 7.83 (d, J=2.0 Hz, 1H), 7.36-7.32 (m, 2H), 6.84 (d, J=9.0 Hz, 1H), 4.90-4.86 (m, 1H), 4.73-4.65 (m, 5H), 4.39-4.30 (m, 2H), 3.90-3.77 (m, 3H), 3.72 (s, 3H), 3.56-3.48 (m, 2H), 3.10-3.09 (m, 2H), 2.98-2.92 (m, 2H), 2.79-2.75 (m, 2H), 2.59-2.57 (m, 1H), 2.50-2.49 (m, 2H), 2.22-2.21 (s, 1H), 2.04-1.99 (m, 2H), 1.88-1.84 (m, 2H), 1.01 (d, J=6.0 Hz, 3H).

Example 238a (E)-Methyl 3-((tert-Butylsulfinylimino)methyl)-5,6,7,8-tetrahydroindolizine-2-carboxylate 238a

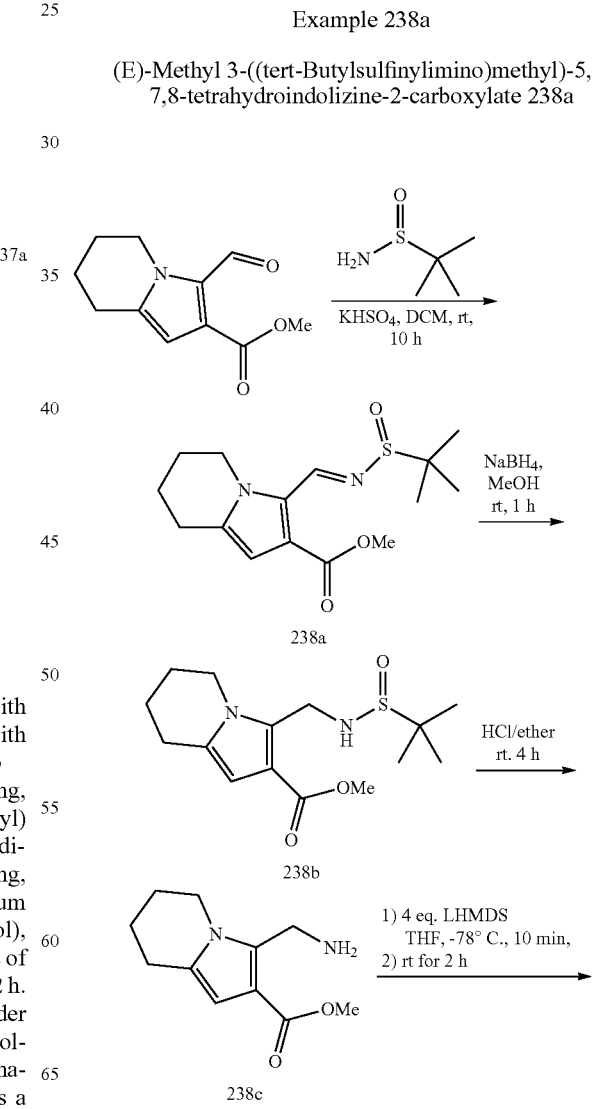

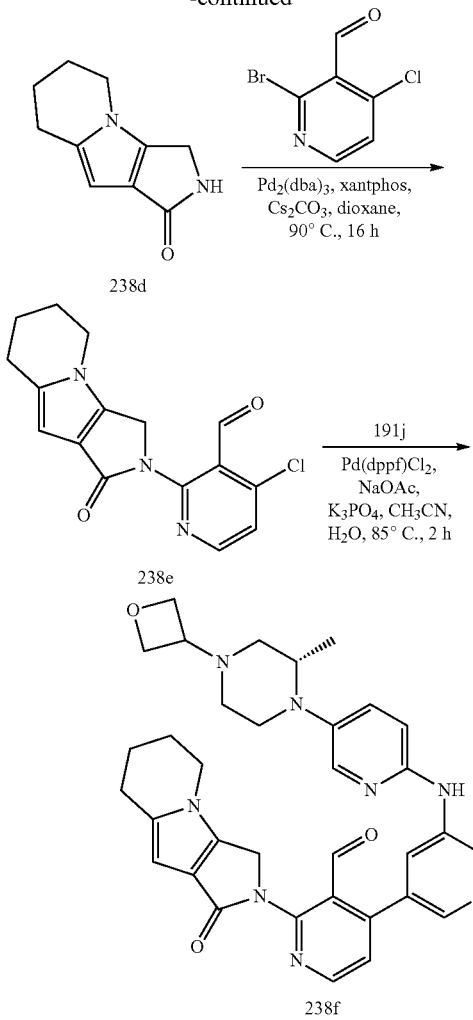

A 500-mL single-neck round-bottomed flask equipped with a magnetic stirrer was charged with methyl 3-formyl-5,6,7,8-tetrahydroindolizine-2-carboxylate (10.0 g, 48.3 mmol, 1.0 eq.), 2-methylpropane-2-sulfinamide (11.7 g, 96.6 mmol, 2.0 eq.), KHSO$_4$ (32.8 g, 241.5 mmol, 5 eq.), and dichloromethane (250 mL). The mixture was stirred at room temperature for 10 h. It was then filtered and filtrate was concentrated under reduced pressure. The resulting residue was purified by silica-gel column chromatography eluting with 1:3 ethyl acetate/petroleum ether to afford 238a (12.4 g, 83%) as a yellow solid. MS: [M+H]$^+$ 311.3.

Example 238b

Methyl 3-((1,1-Dimethylethylsulfinamido)methyl)-5,6,7,8-tetrahydroindolizine-2-carboxylate 238b A 250-mL single-neck round-bottomed flask equipped with a magnetic stirrer was charged with 238a (4.0 g, 12.8 mmol, 1.0 eq.), NaBH$_4$ (2.9 g, 76.9 mmol, 6.0 eq.), and methanol (100 mL). The reaction mixture was stirred at room temperature for 1 h. After this time water (50 mL) was added to the reaction and the resulting mixture was concentrated under reduced pressure. The residue was extracted with dichloromethane (3×50 mL). The combined organic layer was evaporated under reduced pressure to afford 238b (3.9 g, 96%), which was directly used in next step without further purification. MS: [M-C$_4$H$_{10}$NOS]$^+$ 192.3.

Example 238c

Methyl 3-(Aminomethyl)-5,6,7,8-tetrahydroindolizine-2-carboxylate 238c

A 100-mL single-neck round-bottomed flask equipped with a magnetic stirrer was charged with 238b (3.5 g, 11.2 mmol), saturated HCl/diethyl ether solution (15 mL), and dichloromethane (15 mL). The mixture was stirred at room temperature for 4 h. After the reaction was completed, saturated aqueous NaHCO$_3$ solution (50 mL) was added to the reaction mixture and the mixture was extracted with dichloromethane (3×50 mL). The combined organic layer was evaporated under reduced pressure to afford 238c (2.2 g, 94%), which was directly used in the next step without further purification. MS: [M-NH$_2$]$^+$ 192.1. $^1$H NMR (500 MHz, MeOD) δ 6.28 (s, 1H), 4.38 (s, 2H), 4.03 (t, J=6.5 Hz, 2H), 3.84 (s, 3H), 2.78 (t, J=6.5 Hz, 2H), 2.06-2.02 (m, 2H), 1.87-1.82 (m, 2H).

Example 238d 2,3,5,6,7,8-Hexahydropyrrolo[3,4-b]indolizin-1-one 238d

A 100-mL single-neck round-bottomed flask equipped with a magnetic stirrer was charged with 238c (1.3 g, 6.25 mmol, 1.0 eq.) and THF (20 mL). At −78° C., to the solution was added lithium hexamethyldisilazane/THF (18.7 mL, 18.7 mmol, 3.0 eq.). It was then stirred at room temperature for 2 hrs. After the reaction was completed, saturated aqueous NH$_4$Cl solution (30 mL) was added and the mixture was concentrated under reduced pressure. The residue was extracted with dichloromethane (3×50 mL) and the combined organic layer was evaporated under reduced pressure. The resulting residue was purified by silica-gel column chromatography eluting with 60:1 dichloromethane/methanol to afford 238d (585 mg, 53%) as a yellow solid. MS: [M+H]$^+$ 177.3. $^1$H NMR (500 MHz, DMSO-d$_6$) δ 7.38 (s, 1H), 5.82 (s, 1H), 4.13 (s, 2H), 3.86 (t, J=6.5 Hz, 2H), 2.73 (t, J=6.5 Hz, 2H), 191-1.88 (m, 2H), 1.75-1.73 (m, 2H).

Example 238e

4-Chloro-2-(1-oxo-5,6,7,8-tetrahydro-1H-pyrrolo[3,4-b]indolizin-2(3H)-yl)nicotinaldehyde 238e A 100-mL single-neck round-bottomed flask equipped with a magnetic stirrer and a reflux condenser was charged with 238d (400 mg, 2.27 mmol), 2-bromo-4-chloronicotinaldehyde (1.50 g, 6.90 mmol, 3.0 eq.), Pd$_2$(dba)$_3$ (208 mg, 0.227 mmol, 0.1 eq.), xantphos (131 mg, 0.227 mmol, 0.1 eq.), Cs$_2$CO$_3$ (1.50 g, 4.54 mmol, 2.0 eq.), and dioxane (30 mL). After bubbling nitrogen through the resulting mixture for 30 minutes, the reaction mixture was stirred at 90° C. for 16 h. After the reaction was complete, the mixture was cooled to room temperature and filtered. The filtrate was concentrated under reduced pressure and the residual was purified by silica-gel column chromatography eluting with 1:3 ethyl acetate/petroleum ether to afford 238e (300 mg, 42%) as a light yellow solid. MS-ESI: [M+H]$^+$ 316.1.

Example 238f

S)-4-(1-methyl-5-(5-(2-methyl-4-(oxetan-3-yl)piperazin-1-yl)pyridin-2-yl-amino)-6-oxo-1,6-dihydropyridin-3-yl)-2-(1-oxo-5,6,7,8-tetrahydro-1H-pyrrolo[3,4-b]indolizin-2(3H)-yl)nicotinaldehyde 238f A 50-mL single-neck round-bottomed flask equipped with a magnetic stirrer and a reflux condenser was charged with 238e (150 mg, 0.48 mmol, 1.0 eq.), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (459 mg, 0.95 mmol, 2.0 eq.), Pd(dppf)Cl$_2$ (39 mg, 0.048 mmol, 0.1 eq.), sodium acetate (78 mg, 0.95 mmol, 2.0 eq.), K$_3$PO$_4$ (202 mg, 0.95 mmol, 2.0 eq.), acetonitrile (10 mL), and water (1 mL). After three cycles of vacuum/argon flush, the mixture was heated at 85° C. for 2 h. It was then cooled to room temperature and filtered. The filtrate was concentrated under reduced pressure and the resulting residue was purified by silica-gel column chromatography eluting with 40:1 dichloromethane/ethanol to afford 238f (90 mg, 30%) as a yellow solid. MS-ESI: [M+H]$^+$ 635.3.

Example 238

2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-5,6,7,8-tetrahydro-1H-pyrrolo[3,4-b]indolizin-3-one 238

A 25-mL single-neck round-bottomed flask equipped with a magnetic stirrer was charged with 238f (90 mg, 1.0 eq., 0.14 mmol), NaBH$_4$ (23 mg, 5 eq., 0.60 mmol), and methanol (5 mL). The resulting mixture was stirred at room temperature for 20 minutes and quenched with water. It was then concentrated under reduced pressure and the residue was purified by reverse-phase prep-HPLC to afford 238 (60 mg, 66%) as a white solid. MS-ESI: [M+H]$^+$ 637.3. $^1$H NMR (500 MHz, CDCl$_3$) δ 8.69 (d, J=1.5 Hz, 1H), 8.47 (d, J=5.0 Hz, 1H), 7.99 (d, J=2.5 Hz, 1H), 7.93 (d, J=2.0 Hz, 1H), 7.86 (s, 1H), 7.36-7.31 (m, 2H), 6.83 (d, J=9.0 Hz, 1H), 6.15 (s, 1H), 5.71 (t, J=6.5 Hz, 1H), 4.96 (s, 2H), 4.72-4.63 (m, 4H), 4.52-4.51 (m, 2H), 3.97-3.95 (m, 2H), 3.75 (s, 3H), 3.55-3.53 (m, 1H), 3.48-3.46 (m, 1H), 3.10-3.08 (m, 2H), 2.91-2.89 (m, 2H), 2.58-2.56 (m, 1H), 2.49-2.48 (m, 2H), 2.23-2.19 (m, 1H), 2.08-2.02 (m, 2H), 1.93-1.89 (m, 2H), 1.00 (d, J=6.0 Hz, 3H).

Example 239a tert-Butyl 3-(6-(5-Bromo-1-methyl-2-oxo-1,2-dihydropyridin-3-ylamino)pyridine-3-yl)azetidine-1-carboxylate 239a

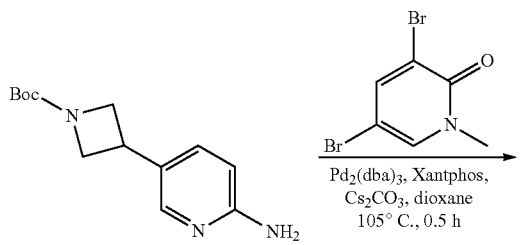

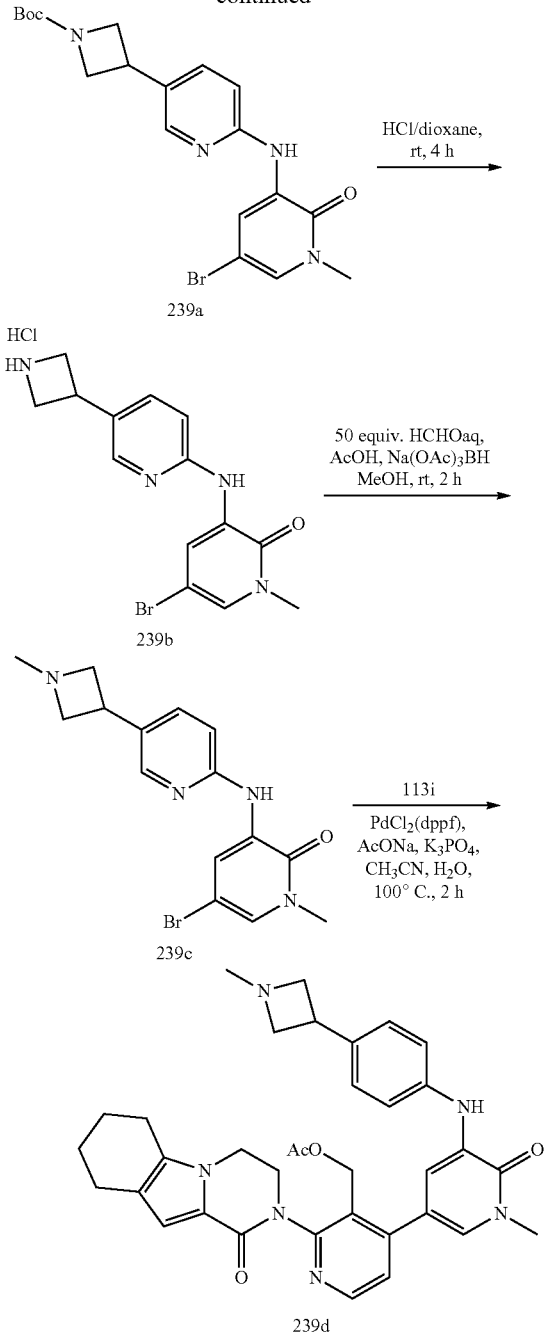

A 100-mL single-neck round-bottomed flask equipped with a magnetic stirrer and a reflux condenser was charged with 1,4-dioxane (50 mL), tert-butyl 3-(6-aminopyridin-3-yl)azetidine-1-carboxylate (1.8 g, 7.2 mmol), 3,5-dibromo-1-methylpyridin-2(1H)-one (1.9 g, 7.2 mmol), and cesium carbonate (4.7 g, 14.4 mmol). After bubbling nitrogen through the resulting suspension for 30 minutes, XantPhos (418 mg, 0.72 mmol) and tris(dibenzylideneacetone)dipalladium(0) (661 mg, 0.72 mmol) were added. The reaction mixture was subjected to three cycles of vacuum/argon flush and heated at 105° C. for 0.5 h. After this time the reaction was cooled to room temperature and filtered. The filtrate was partitioned between ethyl acetate (120 mL) and water (60 mL). The aqueous layer was separated and extracted with ethyl acetate (3×80 mL). The combined organic layer was washed with brine (30 mL) and dried over sodium sulfate. The drying agent was removed by filtration and the filtrate was concentrated under reduced pressure. The residue was purified by silica-gel column chromatography eluting with 1:4 ethyl acetate/petroleum ether to afford the 239a as a yellow solid (3.06 g, 98%). MS-ESI: [M+H]+ 435.

Example 239b 3-(5-(Azetidin-3-yl)pyridin-2-ylamino)-5-bromo-1-methylpyridin-2(1H)-one 239b Compound 239a (1.0 g, 2.3 mmol) was suspended in 4M HCl/dioxane (10 mL). The reaction mixture was stirred at room temperature for 4 h. It was then concentrated under reduced pressure. The residue was basified with aqueous NaOH and the resulting mixture was extracted with dichloromethane. The combined organic layer was washed with brine and concentrated under reduced pressure to afford 239b as a yellow solid (650 mg, 84%). MS-ESI: [M+H]+ 335.

Example 239c

5-Bromo-1-methyl-3-(5-(1-methylazetidin-3-yl)pyridin-2-ylamino)pyridine-2(1H)-one 239c A mixture of 239b (469 mg, 1.4 mmol), 37% aqueous formaldehyde (4.0 g, 50 mmol), NaBH$_3$CN (261 mg, 4.2 mmol), and 1M zinc chloride in ethoxyethane (4 mL, 4.2 mmol) in methanol (40 mL) was stirred at room temperature for 2 hours. The mixture was added to water (20 mL) and concentrated under reduced pressure. The residue was extracted with dichloromethane (3×50 mL). The combined organic layer was concentrated under reduced pressure and the residue was purified by silica-gel column chromatography eluting with 10:1 methylene chloride/methanol to afford 239c as a yellow solid (300 mg, 83%). MS-ESI: [M+H]+ 349.

Example 239d (4-(1-Methyl-5-(4-(1-methylazetidin-3-yl)phenylamino)-6-oxo-1,6-dihydro-pyridin-3-yl)-2-(1-oxo-3,4,6,7,8,9-hexahydropyrazino[1,2-a]indol-2(1H)-yl)pyridin-3-yl)methyl Acetate 239d A 50-mL round-bottomed flask equipped with a magnetic stirrer and a reflux condenser was charged with 239c (106 mg, 0.30 mmol), 3-(acetoxymethyl)-2-(1-oxo-3,4,6,7,8,9-hexahydropyrazino[1,2-a]indol-2(1H)-yl)pyridin-4-ylboronic acid 113i (115 mg, 0.30 mmol), Pd(dppf)Cl$_2$ (25 mg, 0.030 mmol), K$_3$PO$_4$ (127 mg, 0.60 mmol), sodium acetate (49 mg, 0.60 mmol), water (1 mL) and acetonitrile (10 mL). After three cycles of vacuum/argon flush, the mixture was heated under reflux for 2 h. It was then cooled to room temperature and filtered. The filtrate was concentrated under reduced pressure and the resulting residue was purified by silica-gel column chromatography eluting with 15:1 dichloromethane/methanol to afford 239d as white solid (100 mg, 49%). MS-ESI: [M+H]+ 607.3

Example 239

2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrazino[1,2-a]indol-1-one 239

To a solution of 239d (100 mg, 0.16 mmol) in propan-2-ol (2 mL), tetrahydrofuran (2 mL), and water (1 mL) was added lithium hydroxide (38 mg, 1.60 mmol). The mixture was stirred at 30° C. for 2 h. It was then evaporated under reduced pressure and the residue was purified by reverse-phase prep-HPLC to afford 239 (22.5 mg, 26%) as a white solid. MS-ESI: [M+H]+ 566.4. $^1$H NMR (500 MHz, CDCl$_3$) δ 8.75 (d, J=1.5 Hz, 1H), 8.52 (d, J=5.0 Hz, 1H), 8.17 (d, J=2.0 Hz, 1H), 7.91-7.89 (m, 2H), 7.59 (d, J=8.5 Hz, 1H), 7.38 (d, J=5.0 Hz, 1H), 6.91 (s, 1H), 6.84 (d, J=8.5 Hz, 1H), 5.09-5.06 (m, 1H), 4.66-4.64 (m, 1H), 4.54-4.50 (m, 1H), 4.36-4.33 (m, 1H), 4.18-4.11 (m, 2H), 3.92-3.88 (m, 1H), 3.75-3.72 (m, overlap, 5H), 3.63-3.58 (m, 1H), 3.16-3.14 (m, 2H), 2.64-2.58 (m, 4H), 2.40 (s, 3H), 1.93-1.90 (m, 2H), 1.84-1.79 (m, 2H).

Example 240a (2-{4,4-Dimethyl-9-oxo-1,10-diazatricyclo[6.4.0.0$^{2,6}$]dodeca-2(6),7-dien-10-yl}-4-(1-methyl-5-{[5-(1-methylazetidin-3-yl)pyridin-2-yl]amino}-6-oxopyridin-3-yl)pyridin-3-yl)methyl Acetate 240

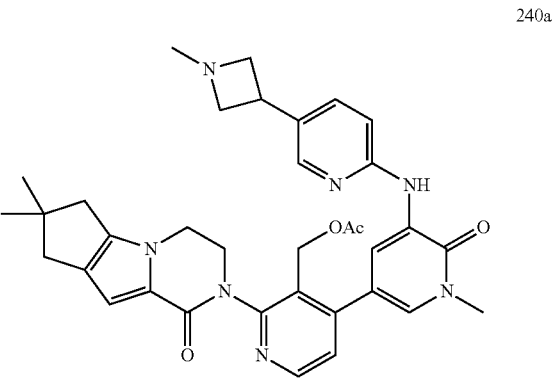

A 50-mL round-bottomed flask equipped with a magnetic stirrer and a reflux condenser was charged with 5-bromo-1-methyl-3-(5-(1-methylazetidin-3-yl)pyridin-2-ylamino)-pyridin-2(1H)-one 239c (106 mg, 0.30 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (119 mg, 0.30 mmol), Pd(dppf)Cl$_2$ (25 mg, 0.031 mmol), K$_3$PO$_4$ (127 mg, 0.60 mmol), sodium acetate (49 mg, 0.60 mmol), water (0.5 mL), and acetonitrile (10 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 15:1 dichloromethane/methanol to afford 240a as white solid (80 mg, 48%). MS-ESI: [M+H]+ 622.7

Example 240

3-[3-(hydroxymethyl)-4-[1-methyl-5-[[5-(1-methylazetidin-3-yl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 240

To a solution of 240a (80 mg, 0.130 mmol) in propan-2-ol (2 mL), tetrahydrofuran (2 mL), and water (1 mL) was added lithium hydroxide (38 mg, 1.60 mmol). The mixture was stirred at 30° C. for 1 h. The reaction was evaporated under reduced pressure and the residue was purified by reverse-phase prep-HPLC to afford 240 24.3 mg, 33%) as a white solid. MS-ESI: [M+H]⁺ 580.4. ¹H NMR (500 MHz, CDCl₃) δ 8.76 (d, J=2.0 Hz, 1H), 8.52 (d, J=5.0 Hz, 1H), 8.17 (d, J=2.0 Hz, 1H), 7.92-7.90 (m, 2H), 7.59 (dd, J=1.5, 8.5 Hz, 1H), 7.38 (d, J=5.0 Hz, 1H), 6.87 (s, 1H), 6.84 (d, J=8.5 Hz, 1H), 5.09-5.06 (m, 1H), 4.68-4.66 (m, 1H), 4.56-4.54 (m, 1H), 4.37-4.35 (m, 1H), 4.19-4.17 (m, 2H), 3.90-3.88 (m, 1H), 3.75-3.72 (m, overlap, 5H), 3.64-3.62 (m, 1H), 3.19-3.16 (m, 2H), 2.60 (d, J=5.0 Hz, 2H), 2.54 (s, 2H), 2.42 (s, 3H), 1.30 (s, 6H).

Example 241a

2-{10-Fluoro-1-oxo-1H,2H,3H,4H,6H,7H,8H,9H-pyrido[3,4-b]indolizin-2-yl}-4-[1-methyl-5-({5-methyl-4H,5H,6H,7H-pyrazolo[1,5-a]pyrazin-2-yl}amino)-6-oxo-1,6-dihydropyridin-3-yl]pyridine-3-carbaldehyde 241a

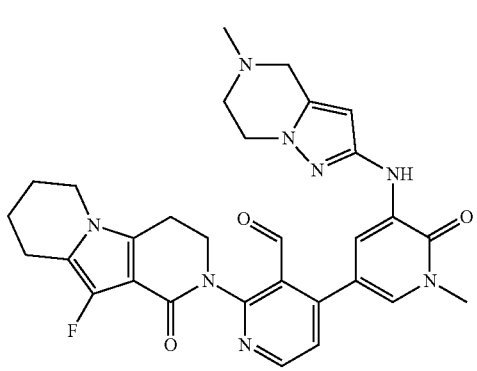

A 25-mL single-neck round-bottomed flask equipped with a magnetic stirrer and a reflux condenser was charged with 4-chloro-2-(10-fluoro-1-oxo-3,4,6,7,8,9-hexahydropyrido[3,4-b]indolizin-2(1H)-yl)nicotinaldehyde 134c (59.6 mg, 0.17 mmol), 1-methyl-3-({5-methyl-4H,5H,6H,7H-pyrazolo[1,5-a]pyrazin-2-yl}amino)-5-(tetramethyl-1,3,2-dioxaborolan-2-yl)-1,2-dihydropyridin-2-one 135a (261.8 mg, 0.68 mmol), Pd(dppf)Cl₂ (25.0 mg, 0.030 mmol), Na₂CO₃ (54.1 mg, 0.51 mmol), DMF (6 mL), and water (0.75 mL). After three cycles of vacuum/argon flush, the mixture was heated at 70° C. for 1 h. It was then filtered and the filtrate was evaporated under reduced pressure. The residue was purified by silica-gel column chromatography eluting with 50:1 dichloromethane/methanol to afford 241a (100 mg, purity: 54%, yield: 56%) as a yellow solid. MS-ESI: [M+H]⁺ 571.3

Example 241

10-fluoro-2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-3,4,6,7,8,9-hexahydropyrido[3,4-b]indolizin-1-one 241

To the solution of 241a (54.0 mg, 0.095 mmol) in methanol (5 mL) was added sodium borohydride (28.9 mg, 0.76 mmol) at 0° C. The reaction was stirred at 0-25° C. for 1.5 h. It was then quenched with water (5 mL). The mixture was evaporated under reduced pressure and the residue was extracted with dichloromethane (3×30 mL). The combined dichloromethane extract was concentrated under reduced pressure and the residue was purified by reverse-phase prep-HPLC to afford 241 (8.0 mg, 15%) as a white solid. MS-ESI: [M+H]⁺ 573.3. ¹H NMR (500 MHz, DMSO-d₆) δ 8.47 (d, J=5.0 Hz, 1H), 8.21 (s, 1H), 8.06 (d, J=2.0 Hz, 1H), 7.40 (d, J=2.0 Hz, 1H), 7.31 (d, J=5.0 Hz, 1H), 5.88 (s, 1H), 4.87-4.85 (m, 1H), 4.44-4.35 (m, 2H), 4.13-4.08 (m, 1H), 3.92-3.89 (m, 3H), 3.79-3.76 (m, 2H), 3.58 (s, 3H), 3.49 (s, 2H), 2.99-2.94 (m, 2H), 2.79-2.77 (m, 2H), 2.66-2.64 (m, 2H), 2.35 (s, 3H), 1.90-1.78 (m, 2H), 1.75-1.73 (m, 2H).

Example 242a 3-(1,5-Dimethyl-1H-pyrazol-3-ylamino)-1-methyl-5-(4,4,5,5-tetramethyl-1,3,2-dioxaborolan-2-yl)pyridin-2(1H)-one 242a

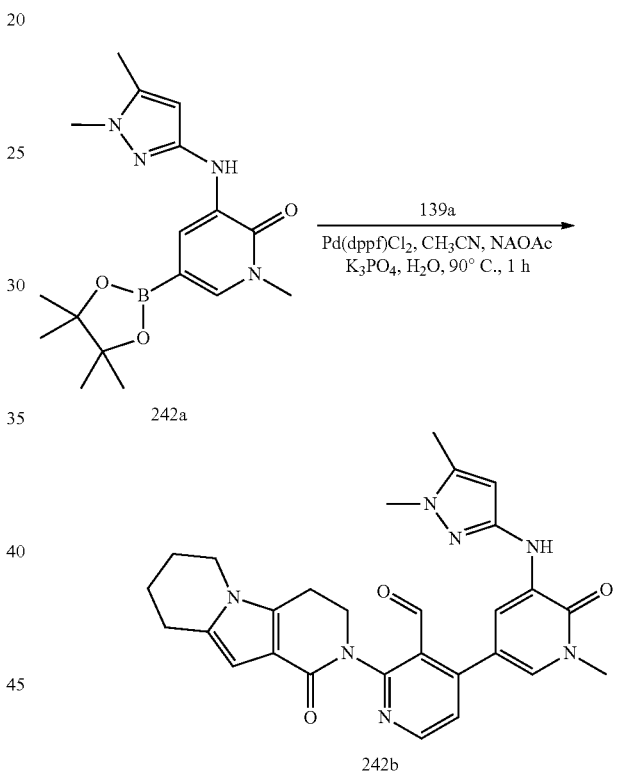

A 100-mL single-neck round-bottomed flask equipped with a magnetic stirrer and a reflux condenser was charged with 5-bromo-3-(1,5-dimethyl-1H-pyrazol-3-ylamino)-1-methylpyridin-2(1H)-one 218a (800 mg, 2.69 mmol, 1.0 eq.), 4,4,4',4',5,5,5',5'-octamethyl-2,2'-bi(1,3,2-dioxaborolane) (1.70 g, 6.73 mmol, 2.5 eq.), Pd₂(dba)₃ (123 mg, 0.13 mmol, 0.05 eq.), X-Phos (128 mg, 0.27 mmol, 0.1 eq.), potassium acetate (528 mg, 5.38 mmol, 2.0 eq.), and dioxane (50 mL). After three cycles of vacuum/argon flush, the mixture was heated at 70° C. for 2 h. It was then cooled to room temperature and filtered. The filtrate was concentrated under reduced pressure and the resulting residue was purified by silica-gel column chromatography eluting with 1:70 methanol/dichloromethane to afford 242a (740 mg, 79%) as a green solid. MS-ESI: [M+H]⁺ 345.3

Example 242b 4-(5-(1,5-Dimethyl-1H-pyrazol-3-ylamino)-1-methyl-6-oxo-1,6-dihydropyridin-3-yl)-2-(1-oxo-3,4,6,7,8,9-hexahydropyrido[3,4-b]indolizin-2(1H)-yl)nicotinaldehyde 242b A-100 mL single-neck round-bottomed flask equipped with a magnetic stirrer and a reflux condenser was charged with 242a (282 mg, 0.82 mmol, 1.5 eq.), 4-chloro-2-(1-oxo-3,4,6,7,8,9-hexahydropyrido[3,4-b]indolizin-2(1H)-yl)nicotinaldehyde 139a (180 mg, 0.55 mmol, 1.0 eq.), Pd(dppf)Cl$_2$ (45 mg, 0.055 mmol, 0.1 eq.), sodium acetate (90 mg, 1.25 mmol, 2.0 eq.), K$_3$PO$_4$ (232 mg, 1.25 mmol, 2.0 eq.), acetonitrile (20 mL), and water (1 mL). After three cycles of vacuum/argon flush, the mixture was heated at 90° C. for 1 h. It was then cooled to room temperature and filtered. The filtrate was concentrated under reduced pressure and the resulting residue was purified by silica-gel column chromatography eluting with 50:1 dichloromethane/methanol to afford 242b (150 mg, 48%) as a yellow solid. MS-ESI: [M+H]$^+$ 512.3.

Example 242

2-[4-[5-[(1,5-dimethylpyrazol-3-yl)amino]-1-methyl-6-oxo-3-pyridyl]-3-(hydroxymethyl)-2-pyridyl]-3,4,6,7,8,9-hexahydropyrido[3,4-b]indolizin-1-one 242

A 50-mL single-neck round-bottomed flask equipped with a magnetic stirrer was charged with 242b (150 mg, 0.29 mmol, 1.0 eq.), NaBH$_4$ (55 mg, 1.46 mmol, 5.0 eq.), and methanol (10 mL). The resulting mixture was stirred at room temperature for 20 min. It was then filtered and the filtrate was concentrated under reduced pressure. The residue was purified by reverse-phase prep-HPLC to afford 242 (100 mg, 66%) as a white solid. MS-ESI: [M+H]$^+$ 514.3. $^1$H NMR (500 MHz, DMSO-d$_6$) δ 8.47 (d, J=5.5 Hz, 1H), 8.04-8.03 (m, 2H), 7.42 (d, J=2.0 Hz, 1H), 7.30 (d, J=5.0 Hz, 1H), 6.05 (s, 1H), 5.90 (s, 1H), 4.87-4.85 (m, 1H), 4.43-4.35 (m, 2H), 4.18-4.12 (m, 1H), 3.98-3.93 (m, 1H), 3.84-3.78 (m, 2H), 3.59 (s, 3H), 3.58 (s, 3H), 3.06-2.92 (m, 2H), 2.75-2.68 (m, 2H), 2.18 (s, 3H), 1.94-1.92 (m, 2H), 1.79-1.73 (m, 2H).

Example 243a tert-Butyl 4-(Methylsulfonyloxy)piperidine-1-carboxylate 243a

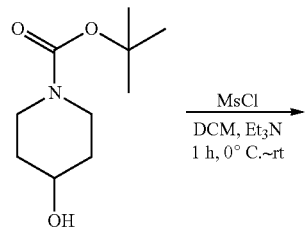

449
-continued

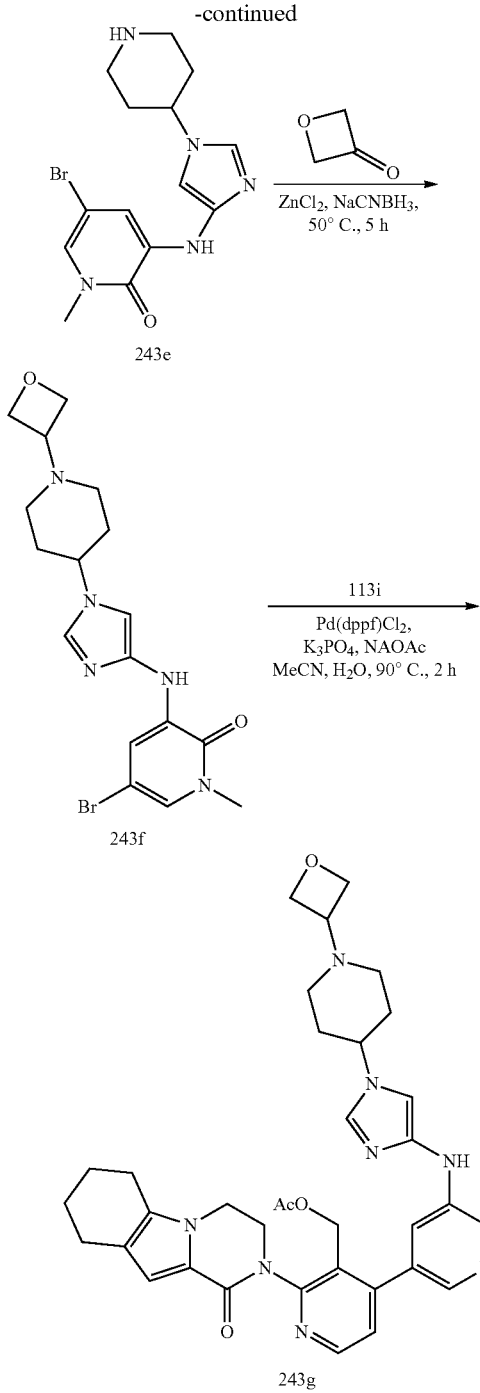

To a solution of tert-butyl 4-hydroxypiperidine-1-carboxylate (14.0 g, 70.0 mmol) at 0° C. in triethylamine (9.9 g, 98 mmol) and dichloromethane (100 mL) was added dropwise methanesulfonyl chloride (11.2 g, 98.0 mmol). The reaction was brought to ambient temperature and stirred for 1 h. Then the reaction mixture was quenched with water (50 mL). The aqueous layer was separated and extracted with ethyl acetate (2×50 mL). The combined organic layer was washed with brine (50 mL), and dried over sodium sulfate. The drying agent was removed by filtration and the filtrate was concentrated under reduced pressure to afford 243a, which was used in the next step without further purification (19.5 g, 100%). MS-ESI: [M-t-Bu]$^+$ 224.1

450

Example 243b tert-Butyl 4-(4-Nitro-1H-imidazol-1-yl)piperidine-1-carboxylate 243b A 250-mL single-neck round-bottomed flask equipped with a magnetic stirrer and a reflux condenser was charged with 243a (7.0 g, 25.1 mmol), DMF (120 mL), 4-nitro-1H-imidazole (2.80 g, 25.1 mmol), and K$_2$CO$_3$ (6.9 g, 50.2 mmol). The mixture was heated at 120° C. for overnight. After this time the reaction was cooled to room temperature and filtered. The filtrate was evaporated in vacuo. The residue was purified by silica-gel column chromatography eluting with 2:2:1 ethyl acetate/petroleum ether/dichloromethane to afford 243b (2.4 g, 32.4%) as a yellow solid. MS-ESI: [M+H]$^+$ 297.3

Example 243c tert-Butyl 4-(4-Amino-1H-imidazol-1-yl)piperidine-1-carboxylate 243c A 100-mL single-neck round-bottomed flask was purged with nitrogen and charged with 243b (2.3 g, 7.8 mmol), 10% palladium on carbon (10% wet, 230 mg), and ethanol (40 mL). The mixture was evacuated, charged with hydrogen gas, and stirred at room temperature for 3 h. The hydrogen was then evacuated and nitrogen was charged into the flask. The catalyst was removed by filtration through a pad of CELITE® and the filtrate was concentrated under reduced pressure to afford 243c (2.0 g, 95%). MS-ESI: [M+H]$^+$ 267.2.

Example 243d tert-Butyl 4-(4-(5-Bromo-1-methyl-2-oxo-1,2-dihydropyridin-3-ylamino)-1H-imidazol-1-yl)piperidine-1-carboxylate 243d A 250-mL single-neck round-bottomed flask equipped with a magnetic stirrer and a reflux condenser was charged with 243c (2.3 g, 8.6 mmol), 3,5-dibromo-1-methylpyridin-2(1H)-one (2.3 g, 8.6 mmol), tris-(dibenzylideneacetone)dipalladium(0) (789 mg, 0.86 mmol), XantPhos (994 mg, 1.72 mmol), Cs$_2$CO$_3$ (5.6 g, 17.2 mmol), and 1,4-dioxane (80 mL). After three cycles of vacuum/argon flush, the mixture was heated at 95° C. for 4 hrs. It was then cooled to room temperature and filtered. The filtrate was concentrated under reduced pressure and the resulting residue was purified by silica-gel column chromatography eluting with dichloromethane/methanol (50:1 to 20:1) to afford 243d as yellow oil solid (2.3 g, 59%). MS-ESI: [M+H]$^+$ 452.3.

Example 243e

5-Bromo-1-methyl-3-(1-(piperidin-4-yl)-1H-imidazol-4-ylamino)pyridin-2(1H)-one 243e A mixture of 243d (2.2 g, 4.88 mmol) and trifluoroacetic acid (20 mL) was stirred at room temperature for 1 h. It was then concentrated under reduced pressure to afford crude 243e (1.5 g, 88%), which was used in the next step without further purification. MS-ESI: [M+H]$^+$ 352.2

Example 243f

5-Bromo-1-methyl-3-(1-(1-(oxetan-3-yl)piperidin-4-yl)-1H-imidazol-4-ylamino)pyridin-2(1H)-one 243f A 250-mL single-neck round-bottomed flask equipped with a magnetic stirrer and a reflux condenser was charged

451 with 243e (2.2 g, 6.3 mmol), NaBH₃CN (995 mg, 15.8 mmol), oxetan-3-one (907 mg, 12.6 mmol), zinc chloride (2.1 g, 15.8 mmol), and methanol (60 mL). The reaction mixture was stirred at 50° C. for 5 hrs and concentrated under reduced pressure. To the residue was added water and the resulting mixture was extracted with dichloromethane three times. The combined organic layer was then concentrated under reduced pressure and the resulting residue was purified by silica-gel column chromatography eluting with 1% triethylamine in methanol. The fractions containing the desired product were concentrated under reduced pressure. Dichloromethane was added to the residue and the resulting suspension was filtered. The filtrate was concentrated under reduced pressure afford 243f as a yellow solid (800 mg, 62%). MS-ESI: [M+H]⁺ 408.2

Example 243g (4-(1-Methyl-5-(1-(1-(oxetan-3-yl)piperidin-4-yl)-1H-imidazol-4-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 243g A 50-mL single-neck round-bottomed flask equipped with a magnetic stirrer and a reflux condenser was charged with 243f (300 mg, 0.74 mmol), 3-(acetoxymethyl)-2-(1-oxo-3,4,6,7,8,9-hexahydropyrazino[1,2-a]indol-2(1H)-yl)pyridin-4-ylboronic acid 113i (567 mg, 1.48 mmol), Pd(dppf)Cl₂ (60.5 mg, 0.074 mmol), K₃PO₄ (314 mg, 1.48 mmol), sodium acetate (201 mg, 1.48 mmol), water (0.5 mL), and acetonitrile (10 mL). After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 1:1 dichloromethane/methanol containing 0.5% triethylamine to afford 243g as yellow solid (100 mg, 20%). MS-ESI: [M+H]⁺ 667.4.

Example 243

2-[3-(hydroxymethyl)-4-[1-methyl-5-[[1-[1-(oxetan-3-yl)-4-piperidyl]imidazol-4-yl]amino]-6-oxo-3-pyridyl]-2-pyridyl]-3,4,6,7,8,9-hexahydropyrazino[1,2-a]indol-1-one 243

A mixture of 243g (80 mg, 0.12 mmol) and lithium hydroxide (100 mg, 2.4 mmol) in i-propanol/THF/water (2:2:1, 8 mL) was stirred at 35° C. for 30 mins. The reaction mixture was then concentrated under reduced pressure. To the residue was added water and the resulting mixture was extracted with dichloromethane three times. The combined organic layer was concentrated under reduced pressure and the resulting residue was purified by reverse-phase prep-HPLC to afford 243 (28.0 mg, 30%). MS-ESI: [M+H]⁺ 625.4. ¹H NMR (500 MHz, DMSO-d₆) δ 8.48 (d, J=6.5 Hz, 1H), 7.54 (d, J=1.5 Hz, 1H), 7.53 (s, 1H), 7.45 (d, J=3.0 Hz, 1H), 7.35-7.34 (m, 2H), 7.11 (d, J=1.0 Hz, 1H), 6.58 (s, 1H), 5.14 (bs, 1H), 4.54 (t, J=7.5 Hz, 2H), 4.43-4.40 (m, 4H), 4.23-4.11 (m, 3H), 3.99-3.96 (m, 1H), 3.91-3.84 (m, 1H), 3.59 (s, 3H), 3.43-3.39 (m, 1H), 2.77-2.76 (m, 2H), 2.62-2.57 (m, 2H), 2.47-2.46 (m, 2H), 1.94-1.89 (m, 6H), 1.79-1.78 (m, 2H), 1.69-1.66 (m, 2H).

452

Example 244a 2-(4-Chloro-3-(hydroxymethyl)pyridin-2-yl)-3,4,6,7,8,9-hexahydropyrido[3,4-b]indolizin-1(2H)-one 244a

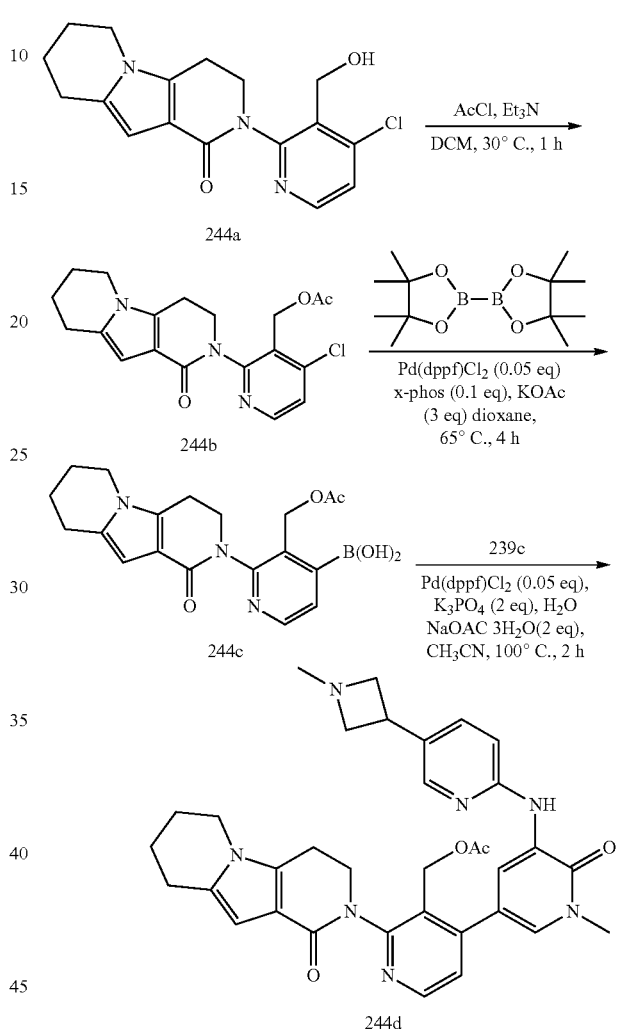

To a solution of 4-chloro-2-(1-oxo-3,4,6,7,8,9-hexahydropyrido[3,4-b]indolizin-2(1H)-yl)nicotinaldehyde 139a (1.0 g, 3.0 mmol) in methanol (30 mL) was added sodium borohydride (380 mg, 9.0 mmol) at 30° C. The reaction mixture was stirred for another 1 h and quenched with water (10 mL). It was then concentrated under reduced pressure and the residue was extracted with dichloromethane (3×20 mL). The combined organic extract was dried over anhydrous Na₂SO₄, filtered, and evaporated under reduced pressure to afford 244a as a yellow solid (920 mg, 92%). MS-ESI: [M+H]⁺ 332.3

Example 244b (4-Chloro-2-(1-oxo-3,4,6,7,8,9-hexahydropyrido[3,4-b]indolizin-2(1H)-yl)pyridin-3-yl)methyl acetate 244b To a mixture of 244a (900 mg, 2.7 mmol) and triethylamine (810 mg, 8.1 mmol) in dichloromethane (30 mL) was added acetyl chloride (630 mg, 8.1 mmol) dropwise. The reaction mixture was stirred at 30° C. for 1 h. It was then concentrated under reduced pressure and the residue was purified by silica-gel column chromatography eluting with dichloromethane to afford 244b as white solid (900 mg, 90%). MS-ESI: [M+H]$^+$ 374.2

Example 244c 3-(Acetoxymethyl)-2-(1-oxo-3,4,6,7,8,9-hexahydro-pyrido[3,4-b]indolizin-2(1H)-yl)pyridin-4-ylboronic Acid 244c A 100-mL single-neck round-bottomed flask equipped with a magnetic stirrer and a reflux condenser was charged with 244b (900 mg, 2.4 mmol), Pin$_2$B$_2$ (3.05 g, 12 mmol), Pd(dppf)Cl$_2$ (98 mg, 0.12 mmol), X-phos (114 mg, 0.24 mmol), potassium acetate (720 mg, 7.2 mmol), and dioxane (20 mL). After three cycles of vacuum/argon flush, the mixture was heated at 65° C. for 4 h. It was then cooled to room temperature and filtered. The filtrate was concentrated under reduced pressure and the resulting residue was washed with 5:1 petroleum ether/ethyl acetate (10 mL) to afford 244c as a yellow solid (1.0 g, purity: 60%). MS-ESI: [M+H]$^+$ 384.1.

Example 244d (4-(1-Methyl-5-(5-(1-methylazetidin-3-yl)pyridin-2-ylamino)-6-oxo-1,6-dihydropyridin-3-yl)-2-(1-oxo-3,4,6,7,8,9-hexahydropyrido[3,4-b]indolizin-2(1H)-yl)pyridin-3-yl)methyl Acetate 244d A 50-mL round-bottomed flask equipped with a reflux condenser was charged with 5-bromo-1-methyl-3-(5-(1-methylazetidin-3-yl)pyridin-2-ylamino)pyridin-2(1H)-one 239c (140 mg, 0.40 mmol), 244c (230 mg, 0.60 mmol), Pd(dppf)Cl$_2$ (20 mg, 0.020 mmol), K$_3$PO$_4$ (180 mg, 0.80 mmol), sodium acetate.3 water (120 mg, 0.80 mmol), water (0.5 mL), and acetonitrile (10 mL). After three cycles of vacuum/argon flush, the mixture was heated at 100° C. for 2 h. It was then filtered and the filtrate was evaporated under reduced pressure. The residue was purified on silica-gel column chromatography eluting with 25:1 dichloromethane/methanol to afford 244d as a yellow solid (90 mg, 43%). MS-ESI: [M+H]$^+$ 608.3

Example 244

2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrido[3,4-b]indolizin-1-one 244

A mixture of 244d (90 mg, 0.15 mmol) and lithium hydroxide (60 mg, 1.5 mmol) in THF/i-propanol (5:3, 8 mL) and water (2 mL) was stirred at 30° C. for 1 h. The mixture was evaporated in vacuo and the residue was diluted with water (3 mL). It was then extracted with ethyl acetate (20 mL×2). The combined ethyl acetate extract was concentrated under reduced pressure and the residue was purified by reverse-phase prep-HPLC to afford 244 (25 mg, 30%) as white solid. MS-ESI: [M+H]$^+$ 566.4. $^1$H NMR (500 MHz, CDCl$_3$) δ 8.74 (d, J=2.5 Hz, 1H), 8.51 (d, J=5.5 Hz, 1H), 8.16 (d, J=2.0 Hz, 1H), 7.91 (s, 1H), 7.87 (d, J=2.0 Hz, 1H), 7.59-7.57 (m, 1H), 7.35 (d, J=5.0 Hz, 1H), 6.85-6.83 (m, 1H), 6.33 (s, 1H), 5.04-5.01 (m, 1H), 4.67-4.65 (m, 1H), 4.44-4.39 (m, 1H), 4.33-4.29 (m, 1H), 3.95-3.91 (m, 1H), 3.86-3.83 (m, 2H), 3.76-3.74 (m, 1H), 3.73 (s, 3H), 3.62-3.59 (m, 1H), 3.16-3.13 (m, 2H), 3.02-2.95 (m, 2H), 2.84-2.83 (m, 2H), 2.39 (s, 3H), 2.05-2.02 (m, 2H), 1.90-1.87 (m, 2H).

Example 245a

4-Chloro-2-(1-oxo-6,7,8,9-tetrahydropyrido[3,4-b]indolizin-2(1H)-yl)nicotinaldehyde 245a

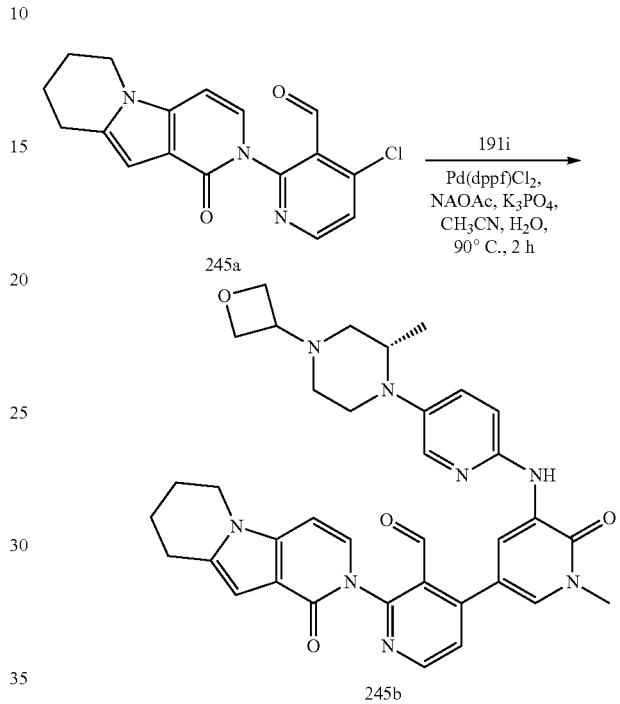

A 100-mL single-neck round-bottomed flask equipped with a magnetic stirrer and a reflux condenser was charged with 6,7,8,9-tetrahydropyrido[3,4-b]indolizin-1(2H)-one 112d (1.48 g, 7.9 mmol, 1.0 eq.), 2-bromo-4-chloronicotinaldehyde (3.48 g, 15.8 mmol, 2.0 eq.), CuI (1.50 g, 7.9 mmol, 1.0 eq.), 4,7-dimethoxy-1,10-phenanthroline (2.13 g, 7.9 mmol, 1.0 eq.), K$_2$CO$_3$ (2.18 g, 15.8 mmol, 2.0 eq.) and dioxane (50 mL). The reaction mixture was stirred at 100° C. for 24 h. After the reaction was completed, the mixture was filtered and the filtrate was concentrated under reduced pressure. The residue was purified by silica-gel column chromatography eluting with 1:2 ethyl acetate/petroleum ether to afford 245a (550 mg, 21%) as a slight yellow solid. MS-ESI: [M+H]$^+$ 328.1.

Example 245b

4-Fluoro-2-(1-methyl-5-(5-(4-(oxetan-3-yl)piperazin-1-yl)pyridin-2-ylamino)-6-oxo-1,6-dihydropyridin-3-yl)-6-(1-oxo-5,6,7,8-tetrahydro-1H-pyrrolo[3,4-b]indolizin-2(3H)-yl)benzaldehyde 245b A 50-mL single-neck round-bottomed flask equipped with a reflux condenser was charged with 245a (140 mg, 0.42 mmol, 1.0 eq.), (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191i (308 mg, 0.63 mmol, 1.5 eq.), Pd(dppf)Cl$_2$ (35 mg, 0.042 mmol, 0.1 eq.), sodium acetate (70 mg, 0.84 mmol, 2.0 eq.), K$_3$PO$_4$ (175 mg, 0.84 mmol, 2.0 eq.), acetonitrile (20 mL), and water (1 mL).

After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 40:1 dichloromethane/methanol to afford 245b (100 mg, 36%) as a yellow solid. MS-ESI: [M+H]$^+$ 647.4.

Example 245

(S)-2-(3-(Hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-6,7,8,9-tetrahydropyrido[3,4-b]indolizin-1(2H)-one 245

A 50-mL single-neck round-bottomed flask equipped with a magnetic stirrer was charged with 245b (100 mg, 0.15 mmol, 1.0 eq.), NaBH$_4$ (29 mg, 0.77 mmol, 5.0 eq.), and methanol (10 mL). The resulting mixture was stirred at room temperature for 20 min. It was then filtered and the filtrate was concentrated under reduced pressure. The residue was purified by reverse-phase prep-HPLC to afford 245 (80 mg, 79%) as a white solid. MS-ESI: [M+H]$^+$ 649.3. $^1$H NMR (500 MHz, DMSO-d$_6$) δ 8.69-8.68 (m, 1H), 8.57 (d, J=5.0 Hz, 1H), 8.46 (s, 1H), 7.85 (d, J=3.0 Hz, 1H), 7.55 (d, J=2.5 Hz, 1H), 7.52 (d, J=5.0 Hz, 1H), 7.39-7.36 (m, 1H), 7.26-7.24 (m, 2H), 6.69 (d, J=7.5 Hz, 1H), 6.31 (s, 1H), 4.97 (bs, 1H), 4.58-4.54 (m, 2H), 4.49-4.41 (m, 1H), 4.34-4.27 (m, 2H), 4.09-4.06 (m, 2H), 3.69-3.68 (m, 1H), 3.61 (s, 3H), 3.41-3.39 (m, 1H), 3.12-3.19 (m, 1H), 2.97-2.93 (m, 1H), 2.87 (t, J=6.0 Hz, 2H), 2.56-2.54 (m, 1H), 2.37-2.30 (m, 2H), 2.21-2.16 (m, 1H), 2.03-1.98 (m, 2H), 1.85-1.82 (m, 2H), 0.94 (d, J=5.5 Hz, 3H).

Example 246a 4-(5-(1,5-Dimethyl-1H-pyrazol-3-ylamino)-1-methyl-6-oxo-1,6-dihydropyridin-3-yl)-2-(1-oxo-6,7,8,9-tetrahydropyrido[3,4-b]indolizin-2(1H)-yl)nicotinaldehyde 246a

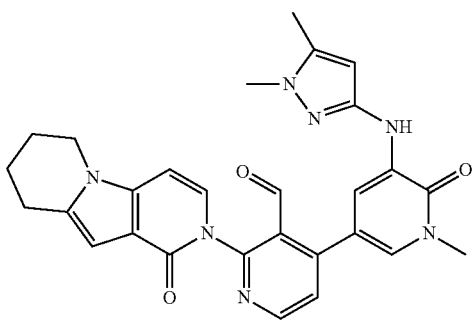

246a

A 50-mL single-neck round-bottomed flask equipped with a magnetic stirrer and a reflux condenser was charged with 4-chloro-2-(1-oxo-6,7,8,9-tetrahydropyrido[3,4-b]indolizin-2(1H)-yl)nicotinaldehyde 245a (130 mg, 0.39 mmol, 1.0 eq.), 3-(1,5-dimethyl-1H-pyrazol-3-ylamino)-1-methyl-5-(4,4,5,5-tetramethyl-1,3,2-dioxaborolan-2-yl)pyridin-2(1H)-one 218a (600 mg, 1.75 mmol, 4.0 eq.), Pd(dppf)Cl$_2$ (32 mg, 0.040 mmol, 0.1 eq.), sodium acetate (64 mg, 0.78 mmol, 2.0 eq.), K$_3$PO$_4$ (165 mg, 0.78 mmol, 2.0 eq.), acetonitrile (15 mL), and water (1 mL). After three cycles of vacuum/argon flush, the mixture was heated at 90° C. for 2 h. It was then cooled to room temperature and filtered. The filtrate was concentrated under reduced pressure and the resulting residue was purified by silica-gel column chromatography eluting with 50:1 dichloromethane/ethanol to afford 246a (38 mg, 19%) as a yellow solid. MS-ESI: [M+H]$^+$ 510.3.

Example 246

2-[4-[5-[(1,5-dimethylpyrazol-3-yl)amino]-1-methyl-6-oxo-3-pyridyl]-3-(hydroxymethyl)-2-pyridyl]-6,7,8,9-tetrahydropyrido[3,4-b]indolizin-1-one 246

A 25-mL single-neck round-bottomed flask equipped with a magnetic stirrer was charged with 246a (38 mg, 0.074 mmol, 1.0 eq.), NaBH$_4$ (29 mg, 0.37 mmol, 5.0 eq.), and methanol (5 mL). The resulting mixture was stirred at room temperature for 20 min. It was then filtered and the filtrate was concentrated. The residue was purified by reverse-phase prep-HPLC to afford the title compound (18 mg, 48%) as a white solid. MS-ESI: [M+H]$^+$ 512.3. $^1$H NMR (500 MHz, CDCl$_3$) δ 8.58 (d, J=5.0 Hz, 1H), 7.98 (d, J=2.5 Hz, 1H), 7.78 (d, J=2.5 Hz, 1H), 7.52 (d, J=5.0 Hz, 1H), 7.37 (s, 1H), 7.17 (d, J=7.0 Hz, 1H), 6.58-6.57 (m, 2H), 5.74 (s, 1H), 5.41-5.39 (m, 1H), 4.42-4.32 (m, 2H), 4.08 (t, J=6.5 Hz, 2H), 3.72 (s, 3H), 3.70 (s, 3H), 2.98 (t, J=6.5 Hz, 2H), 2.25 (s, 3H), 2.13-2.09 (m, 2H), 1.97-1.92 (m, 2H).

Example 247a

{4-[5-({5-Acetyl-4H,5H,6H,7H-pyrazolo[1,5-a]pyrazin-2-yl}amino)-1-methyl-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridin-3-yl}methyl Acetate 247a

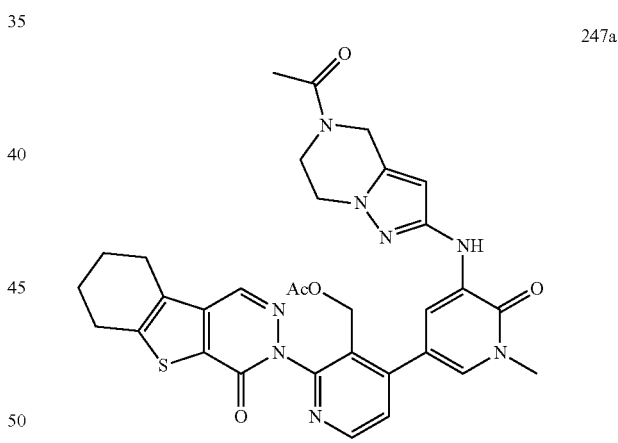

247a

A 25-mL single-neck round-bottomed flask equipped with a magnetic stirrer and a reflux condenser was charged with 3-(5-acetyl-4,5,6,7-tetrahydropyrazolo[1,5-a]pyrazin-2-ylamino)-5-bromo-1-methylpyridin-2(1H)-one 209c (183 mg, 0.50 mmol), {3-[(acetoxy)methyl]-2-{6-oxo-8-thia-4,5-diazatricyclo[7.4.0.0$^{2,7}$]trideca-1(9),2(7),3-trien-5-yl}pyridin-4-yl}boronic acid 230i (200 mg, 0.50 mmol), Pd(dppf)Cl$_2$ (37 mg, 0.05 mmol), K$_3$PO$_4$ (212 mg, 1.0 mmol), sodium acetate (82 mg, 1.0 mmol), water (0.5 mL), and acetonitrile (5 mL). After three cycles of vacuum/argon flush, the mixture was heated at 90° C. for 1 h. It was then cooled to room temperature and filtered. The filtrate was concentrated under reduced pressure and the resulting residue was purified by silica-gel column chromatography eluting with dichloromethane/methanol (50:1 to 20:1) to afford 247a as yellow solid (100 mg, 31%). MS-ESI: [M+H]$^+$ 641.2.

Example 247

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-6,7,8,9-tetrahydrobenzothiopheno[2,3-d]pyridazin-4-one 247

A mixture of {4-[5-({5-acetyl-4H,5H,6H,7H-pyrazolo[1,5-a]pyrazin-2-yl}amino)-1-methyl-6-oxo-1,6-dihydropyridin-3-yl]-2-{6-oxo-8-thia-4,5-diazatricyclo[7.4.0.0$^{2,7}$]trideca-1(9),2(7),3-trien-5-yl}pyridin-3-yl}methyl acetate 247a (100 mg, 0.16 mmol) and lithium hydroxide (96 mg, 4.0 mmol) in i-propanol/THF/water (2:2:1, 10 mL) was stirred at 35° C. for 30 min. The mixture was concentrated under reduced pressure. To the residue was added water (5 mL) and the resulting mixture was extracted with dichloromethane three times. The combined organic layer was then concentrated under reduced pressure and the resulting residue was purified by reverse-phase prep-HPLC to afford 247 (51 mg, 53%). MS-ESI: [M+H]$^+$ 599.3. $^1$H NMR (500 MHz, DMSO-d$_6$, T=80° C.) δ 8.54-8.51 (m, 1H), 8.38 (d, J=3.0 Hz, 1H), 7.93-7.91 (m, 2H), 7.48 (d, J=8.5 Hz, 1H), 7.35 (d, J=3.0 Hz, 1H), 6.00 (s, 1H), 4.64-4.62 (m, 2H), 4.39 (s, 2H), 3.98-3.95 (m, 2H), 3.89-3.86 (m, 2H), 3.58 (s, 3H), 2.95-2.93 (m, 2H), 2.87-2.84 (m, 2H), 2.08 (s, 3H), 1.89-1.87 (m, 4H).

Example 248a (R)-(6-Aminopyridin-3-yl)(3-methylmorpholino)methanone 248a

To a solution of (R)-3-methylmorpholine (2.02 g, 20 mmol) in ethanol (25 mL) was added 1-ethyl-3-(3-dimethylaminopropyl)carbodiimide (EDCI) (3.33 g, 17.4 mmol), hydroxybenzotriazole (HOBt) (2.35 g, 17.4 mmol), and 6-aminonicotinic acid (2.0 g, 14.5 mmol). After stirring for 18 h at room temperature, the reaction suspension was filtered and the filtrate was concentrated under reduced pressure. The residue was purified by silica-gel column chromatography eluting with 3:1 ethyl acetate/petroleum ether to afford 248a as white solid (1.6 g, 36%). MS-ESI: [M+H]$^+$ 222.3.

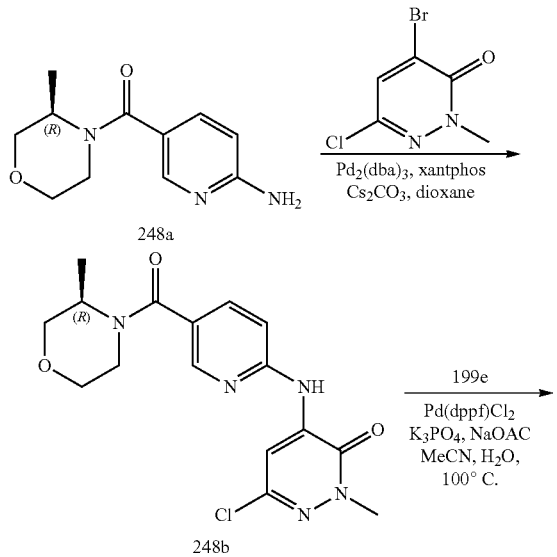

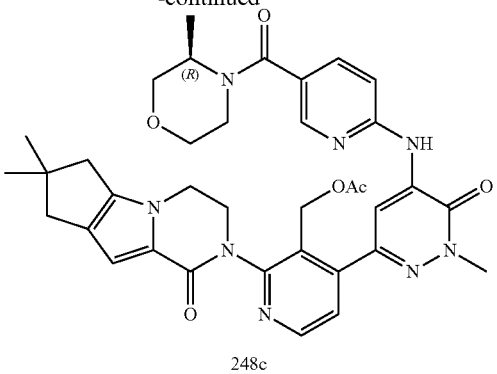

248c

Example 248b

6-Chloro-2-methyl-4-[(5-{[(3R)-3-methylmorpholin-4-yl]carbonyl}pyridin-2-yl)amino]-2,3-dihydropyridazin-3-one 248b A 100-mL single-neck round-bottomed flask equipped with a magnetic stirrer and a reflux condenser was charged with 1,4-dioxane (50 mL), 248a (330 mg, 1.5 mmol), 4-bromo-6-chloro-2-methylpyridazin-3(2H)-one (446 mg, 2.0 mmol), cesium carbonate (978 mg, 3.0 mmol), Xantphos (88 mg, 0.15 mmol), and tris(dibenzylideneacetone)dipalladium(0) (68 mg, 0.075 mmol). The system was subjected to three cycles of vacuum/argon flush and heated at reflux for 4 h. It was then cooled to room temperature and filtered. The solid was washed with dichloromethane (3×30 mL) and the combined filtrate was concentrated under reduced pressure. The residue was purified by silica-gel column chromatography eluting with petroleum ether/ethyl acetate (2:1 to 1:2) to afford 248b (430 mg, 79%) as yellow solid. MS-ESI: [M+H]$^+$ 364.3

Example 248c (2-{4,4-Dimethyl-9-oxo-1,10-diazatricyclo[6.4.0.0$^{2,6}$]dodeca-2(6),7-dien-10-yl}-4-{1-methyl-5-[(5-{[(3R)-3-methylmorpholin-4-yl]carbonyl}pyridin-2-yl)amino]-6-oxo-1,6-dihydropyridazin-3-yl}pyridin-3-yl)methyl Acetate 248c A 100-mL single-neck round-bottomed flask equipped with a magnetic stirrer and a reflux condenser was charged with 248b (364 mg, 1.0 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (596 mg, 1.5 mmol), K$_3$PO$_4$ (424 mg, 2.0 mmol), 1,1'-bis(diphenylphosphino)ferrocenedichloropalladium(II) (73 mg, 0.10 mmol), sodium acetate (164 mg, 2.0 mmol), acetonitrile (10 mL), and water (0.5 mL). After three cycles of vacuum/argon flush, the reaction mixture was heated at 100° C. for 2.5 h. Analysis of the reaction mixture by LCMS showed complete conversion to the desired product. The reaction mixture was cooled to room temperature and filtered. The filtrate was concentrated under reduced pressure. The residue was diluted with dichloromethane (50 mL) and water (50 mL). The aqueous layer was separated and extracted with dichloromethane (3×20 mL). The combined organic layer was dried over Na$_2$SO$_4$ and filtered. The filtrate was concentrated under reduced pressure and the dark residue was purified by silica-gel column chromatography eluting with dichloromethane/methanol (80:1 to 50:1) to afford 248c (250 mg, 37%) as yellow oil. MS-ESI: [M+H]+ 681.3

Example 248

3-[3-(hydroxymethyl)-4-[1-methyl-5-[[5-[(3R)-3-methylmorpholine-4-carbonyl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one 248

To a solution of 248c (250 mg, 0.37 mmol) in THF/i-propanol/water (2.5/2/0.5 mL) was added lithium hydroxide (86 mg, 3.6 mmol) at room temperature. After the reaction was stirred for 3 h, LCMS indicated the reaction was complete. Then the mixture was poured into water (20 mL) and extracted with dichloromethane (3×20 mL). The combined organic layer was washed with brine (30 mL), dried over Na$_2$SO$_4$, filtered. The filtrate was concentrated under reduced pressure. The residue solid was purified by reverse-phase prep-HPLC to afford 248 (110 mg, 48%) as a white solid. MS-ESI: [M+H]+ 639.3. $^1$H NMR (500 MHz, MeOD) δ 8.85 (s, 1H), 8.58 (d, J=5.0 Hz, 1H), 8.44 (d, J=2.0 Hz, 1H), 7.79 (dd, J=2.5, 8.5 Hz, 1H), 7.57 (d, J=5.0 Hz, 1H), 7.32 (d, J=8.5 Hz, 1H), 6.74 (s, 1H), 4.85-4.83 (m, 1H), 4.66-4.64 (m, 1H), 4.42-4.27 (m, 4H), 4.02-3.88 (m, over lap, 6H), 3.74-3.67 (m, 2H), 3.56-3.46 (m, 2H), 2.67-2.59 (m, 2H), 2.51 (s, 2H), 1.39 (d, J=6.5 Hz, 3H), 1.28 (s, 6H).

Example 249a (R)-5-Bromo-1-methyl-3-(5-(3-methylmorpholine-4-carbonyl)pyridin-2-ylamino)pyridin-2(1H)-one 249a

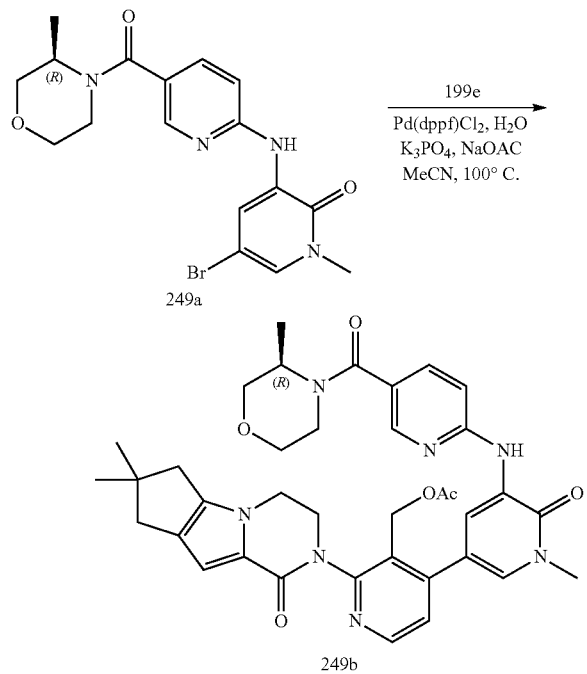

A 100-mL single-neck round-bottomed flask equipped with a magnetic stirrer and a reflux condenser was charged with 1,4-dioxane (15 mL), (R)-(6-aminopyridin-3-yl)(3-methylmorpholino)methanone 248a (332 mg, 1.5 mmol), 3,5-dibromo-1-methylpyridin-2(1H)-one (480 mg, 1.8 mmol), and cesium carbonate (978 mg, 3.0 mmol). After bubbling nitrogen through the suspension for 3 minutes, Xantphos (87 mg, 0.15 mmol) and tris(dibenzylideneacetone)dipalladium (0) (69 mg, 0.075 mmol) were added. The system was subjected to three cycles of vacuum/argon flush and heated at reflux for 2.5 h. It was then cooled to room temperature and filtered. The solid was washed with dichloromethane (2×50 mL) and the combined filtrate was concentrated under reduced pressure. The residue was purified by silica-gel column chromatography eluting with petroleum ether/ethyl acetate (2:1 to 1:2) to afford 249a (430 mg, 70%) as a yellow solid. MS-ESI: [M+H]+ 407.3

Example 249b (2-{4,4-Dimethyl-9-oxo-1,10-diazatricyclo[6.4.0.0$^{2,6}$]dodeca-2(6),7-dien-10-yl}-4-{1-methyl-5-[(5-{[(3R)-3-methylmorpholin-4-yl]carbonyl}pyridin-2-yl)amino]-6-oxo-1,6-dihydropyridin-3-yl]pyridin-3-yl)methyl Acetate 249b A 25-mL single-neck round-bottomed flask equipped with a magnetic stirrer and a reflux condenser was charged with 249a (407 mg, 1.0 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (800 mg, 2.0 mmol), K$_3$PO$_4$ (424 mg, 2.0 mmol), 1,1'-bis(diphenylphosphino)ferrocenedichloropalladium(II) (73 mg, 0.1 mmol), sodium acetate (164 mg, 2.0 mmol), acetonitrile (8 mL), and water (0.2 mL). After three cycles of vacuum/argon flush, the mixture was heated at 100° C. for 1.5 h. Analysis of the reaction mixture by LCMS showed complete conversion to the desired product. The reaction mixture was cooled to room temperature and concentrated under reduced pressure. The residue was diluted with dichloromethane (20 mL) and water (20 mL). The aqueous layer was separated and extracted with dichloromethane (20 mL×3). The combined organic layer was dried over Na$_2$SO$_4$ and filtered. The filtrate was concentrated under reduced pressure. The dark residue was purified by silica-gel column chromatography eluting with 60:1 dichloromethane/methanol to afford 249b (200 mg, 29%) as yellow solid. MS-ESI: [M+H]+ 680.1

Example 249

3-[3-(hydroxymethyl)-4-[1-methyl-5-[[5-[(3R)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 249

To a solution of 249b (204 mg, 0.30 mmol) in THF/i-propanol/water (3/3/0.5 mL) was added lithium hydroxide (72 mg, 3 mmol) at room temperature. After the reaction was stirred for 3 h, LCMS indicated the reaction was complete. The mixture was concentrated under reduced pressure and the residue was diluted with water (10 mL). It was then extracted with dichloromethane (3×10 mL). The combined organic layer was washed with brine (30 mL), dried over Na$_2$SO$_4$ and filtered. The filtrate was concentrated under reduced pressure. The residue was purified by reverse-phase prep-HPLC (A: 1% NH$_4$HCO$_3$ in water, B: acetonitrile) to afford 249 (85 mg, 44%) as a white solid. MS-ESI: [M+H]+ 638.3. $^1$H NMR (500 MHz, MeOD) δ 8.93 (d, J=2.0 Hz, 1H), 8.52 (d, J=5.0 Hz, 1H), 8.33 (d, J=2.0 Hz, 1H), 7.69 (dd, J=2.0, 6.5 Hz, 1H), 7.61 (d, J=2.0 Hz, 1H), 7.48 (d, J=5.0 Hz, 1H), 7.13 (d, J=8.5 Hz, 1H), 6.74 (s, 1H), 4.70 (d, J=12.0 Hz, 1H), 4.58 (d, J=12.0 Hz, 1H), 4.40-4.27 (m, 4H), 3.99-3.89 (m, 3H), 3.74 (S, 3H), 3.55-3.46 (m, overlap, 4H), 2.67-2.59 (m, 2H), 2.51 (s, 2H), 1.39 (d, J=6.5 Hz, 3H), 1.28 (s, 6H).

Example 250a 1-(5-(Hydroxymethyl)-3-nitro-1H-pyrazol-1-yl)propan-2-ol 250a

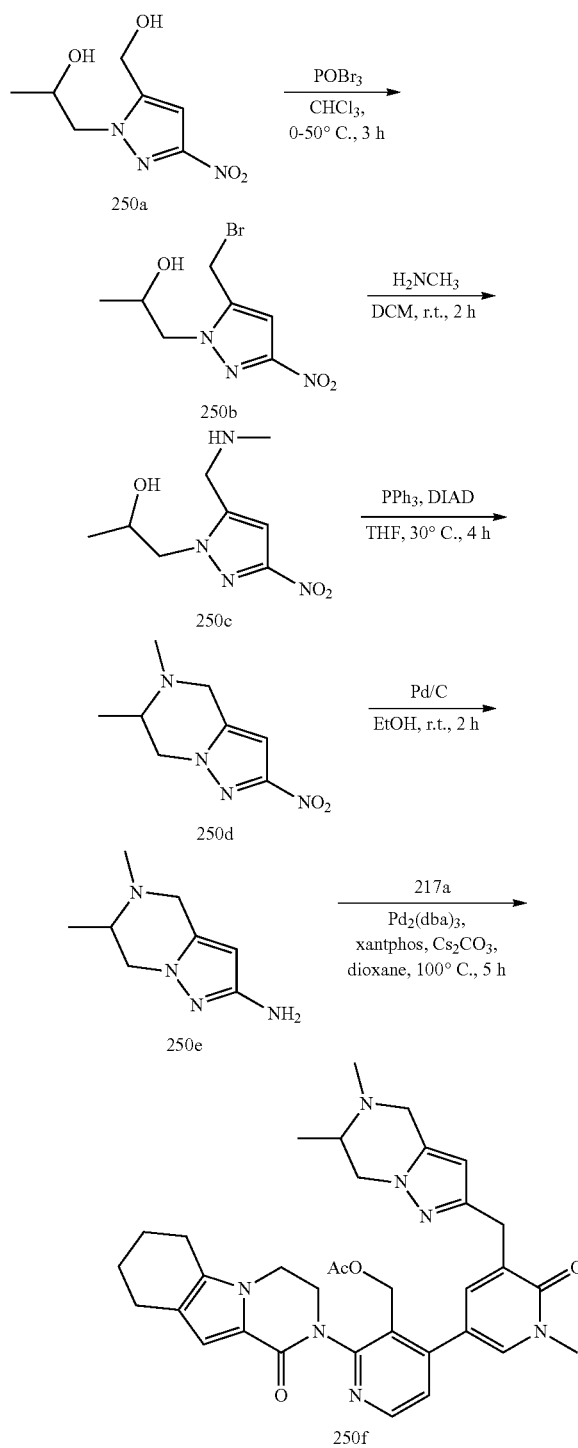

A 100-mL single-neck round-bottomed flask equipped with a magnetic stirrer was charged with (3-nitro-1H-pyrazol-5-yl)methanol (0.57 g, 4.0 mmol), Cs$_2$CO$_3$ (261 mg, 0.8 mmol), and 2-methyloxirane (20 mL). The mixture was stirred at 30° C. for 2 days. The mixture was cooled to room temperature and diluted with dichloromethane (100 mL). The resulting mixture was filtered and the filtrate was concentrated under reduced pressure. The residue was purified by silica-gel column chromatography eluting with 30:1 dichloromethane/methanol to afford 250a (0.40 g, 50%) as a white solid. MS-ESI: [M+H]$^+$ 202.3

Example 250b 1-(5-(Bromomethyl)-3-nitro-1H-pyrazol-1-yl)propan-2-ol 250b

To a mixture of 250a (4.0 g, 20.0 mmol) in chloroform (100 mL) cooled at 0° C. was added the solution of POBr$_3$ (22.9 g, 80 mmol) in chloroform (20 mL) over 30 minutes while maintaining the internal temperature below 5° C. The reaction mixture was warmed to 50° C. and stirred at this temperature for 3 h. It was then cooled to 0° C. and quenched with water. The organic layer was separated and evaporated under reduced pressure. The residue was purified by silica-gel column chromatography eluting with 30:1 dichloromethane/methanol to afford 250b (3.3 g, 62%) as yellow solid. MS-ESI: [M+H]$^+$ 264.1

Example 250c 1-(5-((Methylamino)methyl)-3-nitro-1H-pyrazol-1-yl)propan-2-ol 250c To a solution of 250b (3.0 g, 11.4 mmol) in dichloromethane (30 mL) was added the solution of CH$_3$NH$_2$ (3.0 g, 34.2 mmol, 35% in water). This reaction mixture was stirred at room temperature for 1 h. Then the organic layer was separated, dried over Na$_2$SO$_4$, and filtered. The filtrate was concentrated under reduced pressure to afford 250c (1.9 g, 78%) as yellow solid. MS-ESI: [M+H]$^+$ 215.3

Example 250d 5,6-Dimethyl-2-nitro-4,5,6,7-tetrahydropyrazolo[1,5-a]pyrazine 250d To a mixture of 250c (1.129 g, 5.27 mmol) and triphenylphosphine (4.14 g, 15.8 mmol) in anhydrous THF (40 mL) cooled at 0° C. was added the solution of di-isopropyl azodicarboxylate (DIAD) (3.19 g, 15.8 mmol) in THF (15 mL) over a period of 30 minutes while maintaining the internal temperature below 5° C. The reaction mixture was warmed to 30° C. and stirred at this temperature for 5 h. The mixture was then quenched with water (50 mL) and concentrated under reduced pressure. The residue was extracted with dichloromethane (3×80 mL). The combined organic layer was dried over Na$_2$SO$_4$ and filtered. The filtrate was concentrated under reduced pressure. The residue was purified by silica-gel column chromatography eluting with dichloromethane/methanol (80:1 to 30:1) to afford 250d (0.83 g, 80%) as yellow solid. MS-ESI: [M+H]$^+$ 197.2

Example 250e 5,6-Dimethyl-4,5,6,7-tetrahydropyrazolo[1,5-a]pyrazin-2-amine 250e A solution of 250d (550 mg, 2.8 mmol) in methanol (20 mL) was added Raney Ni (about 600 mg). The reaction was charged with hydrogen gas (via balloon) and stirred for 2 h at room temperature. It was then filtered through a plug of CELITE® and the filtrate was concentrated under reduced pressure to afford 250e as a yellow solid (400 mg, 86%), which was used directly in the next step without further purification. MS-ESI: [M+H]$^+$ 167.3

Example 250f (4-(5-(5,6-Dimethyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 250f A 50-mL round-bottomed flask equipped with a magnetic stirrer and a reflux condenser was charged with (4-(5-bromo-1-methyl-6-oxo-1,6-di-hydropyridin-3-yl)-2-(1-oxo-3,4,6,7,8,9-hexahydropyrazino[1,2-a]indol-2(1H)-yl)pyridin-3-yl)methyl acetate 217a (525 mg, 1.0 mmol), 250e (166 mg, 1.0 mmol), cesium carbonate (652 mg, 2.0 mmol), and 1,4-dioxane (10 mL). After bubbling nitrogen through the suspension for 30 minutes, xantphos (116 mg, 0.20 mmol) and tris(dibenzylideneacetone)dipalladium(0) (92 mg, 0.10 mmol) were added. The system was subjected to three cycles of vacuum/argon flush and heated at reflux for 5 h. It was then cooled to room temperature and filtered. The solid was washed with dichloromethane (2×30 mL) and the combined filtrate was concentrated under reduced pressure. The residue was purified by silica-gel column chromatography eluting with dichloromethane/methanol (80:1 to 30:1) to afford 250f (80 mg, 13%) as yellow solid. MS-ESI: [M+H]$^+$ 611.4

Example 250

2-[4-[5-[(5,6-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one 250

To a solution of 250f (75 mg, 0.123 mmol) in THF/i-propanol/water (4/2/2 mL) was added lithium hydroxide (15 mg, 0.62 mmol). The mixture was stirred at 30° C. for 1 h. After the reaction was complete, the mixture was evaporated under reduced pressure and the residue was purified by reverse-phase prep-HPLC to afford 250 as a white solid (40 mg, 57%). MS-ESI: [M+H]$^+$ 569.3. $^1$H NMR (500 MHz, CDCl$_3$) δ 8.49 (d, J=5.0 Hz, 1H), 7.96 (bs, 1H), 7.73 (d, J=2.0 Hz, 1H), 7.43 (s, 1H), 7.36 (d, J=5.0 Hz, 1H), 6.91 (s, 1H), 5.71 (s, 1H), 5.03 (t, J=3.5 Hz, 1H), 4.65-4.62 (m, 1H), 4.52-4.50 (m, 1H), 4.35-4.33 (m, 1H), 4.17-4.05 (m, 3H), 3.91-3.88 (m, 2H), 3.73-3.71 (m, 1H), 3.71 (s, 3H), 3.55-3.52 (m, 1H), 2.90-2.87 (m, 1H), 2.64-2.58 (m, 4H), 2.43 (s, 3H), 1.93-1.90 (m, 2H), 1.81-1.80 (m, 2H), 1.24 (d, J=6.5 Hz, 3H).

Example 252a

5-Bromo-3-(1-ethyl-5-methyl-1H-pyrazol-3-ylamino)-1-methylpyridin-2(1H)-one 252a

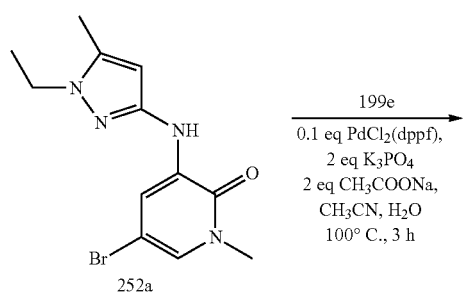

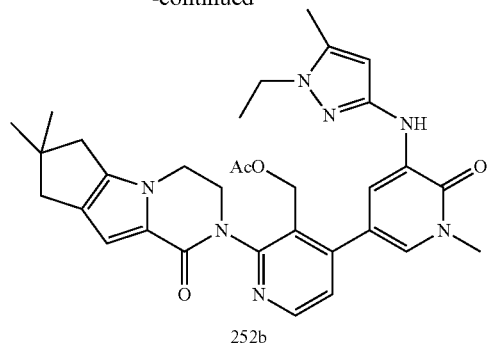

A 100-mL round-bottomed flask was charged with 5-bromo-1-methyl-3-(5-methyl-1H-pyrazol-3-ylamino)pyridin-2(1H)-one 115a (800 mg, 2.83 mmol), bromoethane (216 mg, 1.98 mmol), K$_2$CO$_3$ (780 mg, 5.66 mmol), and DMF (20 mL). The mixture was heated at 85° C. overnight. It was then filtered and the filtrate was evaporated in vacuo. The residue was purified by silica-gel column chromatography eluting with 1:20 methanol/dichloromethane to afford 252a as a red solid (298 mg, 37%). MS-ESI: [M+H]$^+$ 311.0. $^1$H NMR (500 MHz, DMSO-d$_6$) δ 8.28 (s, 1H), 7.99 (d, J=2.5 Hz, 1H), 7.35 (d, J=2.5 Hz, 1H), 5.85 (s, 1H), 3.98-3.94 (m, 2H), 3.48 (s, 3H), 2.19 (s, 3H), 1.27 (t, J=7.0 Hz, 3H).

Example 252b (2-{4,4-Dimethyl-9-oxo-1,10-diazatricyclo[6.4.0.0$^{2,6}$]dodeca-2(6),7-dien-10-yl}-4-{5-[(1-ethyl-5-methyl-1H-pyrazol-3-yl)amino]-1-methyl-6-oxo-1,6-dihydropyridin-3-yl}pyridin-3-yl)methyl Acetate 252b A round-bottomed flask equipped with a reflux condenser was charged with 252a (200 mg, 0.64 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (309 mg, 0.64 mmol), PdCl$_2$(dppf) (52.5 mg, 0.060 mmol), K$_3$PO$_4$ (333 mg, 1.29 mmol), sodium acetate (105 mg, 1.29 mmol), acetonitrile (10 mL), and water (0.5 mL). After three cycles of vacuum/argon flush, the mixture was heated at 100° C. for 3 h. It was then filtered and the filtrate was evaporated in vacuo. The residue was purified by silica-gel column chromatography eluting with 1:20 methanol/dichloromethane to afford 252b as a yellow solid (120 mg, 27.6%). MS-ESI: [M+H]$^+$ 584.3

Example 252

3-[4-[5-[(1-ethyl-5-methyl-pyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 252

A mixture of 252b (120 mg, 0.21 mmol) and lithium hydroxide (23 mg, 0.82 mmol) in THF (6 mL), i-propanol (4 mL), and water (2 mL) was stirred at room temperature for 0.5 h. It was then concentrated under reduced pressure and the residue was diluted with water (5 mL). The resulting mixture was extracted with dichloromethane (2×10 mL). The combined dichloromethane extract was concentrated under reduced pressure. The residue was purified with reverse-phase prep-HPLC to afford 252 (52 mg, 47%) as a white solid. MS-ESI: [M+H]$^+$ 542.3. $^1$H NMR (500 MHz, DMSO-d$_6$) δ 9.06 (d, J=5.5 Hz, 1H), 8.09 (s, 1H), 8.07 (s, 1H), 7.41

(s, 1H), 7.33 (d, J=5.0 Hz, 1H), 6.56 (s, 1H), 5.88 (s, 1H), 4.97 (t, J=4.5 Hz, 1H), 4.50-4.41 (m, 2H), 4.24-4.19 (m, 3H), 3.93-3.85 (m, 3H), 3.59 (s, 3H), 2.62-2.57 (m, 2H), 2.43 (s, 2H), 2.19 (s, 3H), 1.27-1.23 (m, overlap, 9H).

Example 253a

4-Bromo-6-chloro-2-((2-(trimethylsilyl)ethoxy)methyl)pyridazin-3(2H)-one 253a

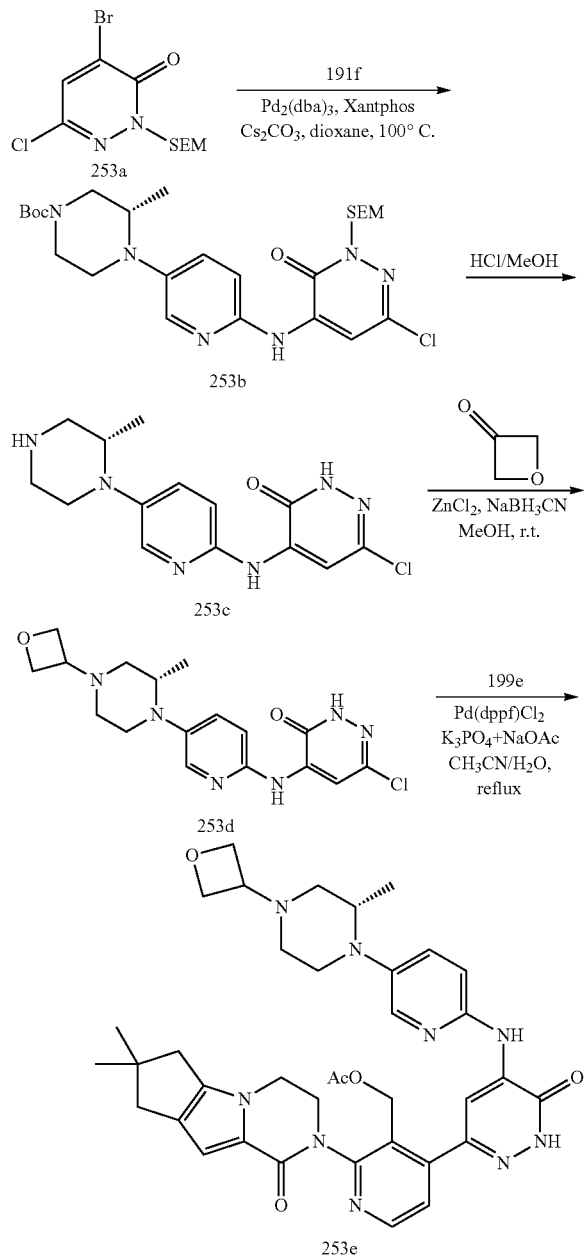

A 500-mL single-neck round-bottomed flask equipped with a magnetic stirrer was purged with nitrogen and charged with anhydrous DMF (150 mL) and 4-bromo-6-chloro-pyridazin-3(2H)-one (10.0 g, 47.8 mmol). The reaction mixture was cooled to 0° C. and sodium hydride was added. The reaction was stirred at 0° C. for 20 min. After this time, 2-(trimethylsilyl)ethoxymethyl chloride (11.9 g, 71.6 mmol) was added and the cooling bath was removed, and the reaction was stirred at room temperature for 3 h. The reaction was then quenched with saturated aqueous sodium bicarbonate (30 mL). The mixture was extracted with ethyl acetate (2×300 mL). The extracts were dried over sodium sulfate, filtered and concentrated under reduced pressure. The resulting residue was purified by flash chromatography to afford 253a in a 56% yield (9.00 g) as a yellow oil: $^1$H NMR (300 MHz, CDCl$_3$) δ 8.02 (s, 1H), 5.42 (s, 2H), 3.79 (t, 2H, J=5.4 Hz), 0.96 (t, 2H, J=5.4 Hz), 0.01 (s, 9H).

Example 253b (S)-tert-Butyl 4-(6-(6-Chloro-3-oxo-2-((2-(trimethylsilyl)ethoxy)-methyl)-2,3-dihydropyridazin-4-ylamino)pyridin-3-yl)-3-methylpiperazine-1-carboxylate 253b A 50-mL round-bottomed flask equipped with a reflux condenser was charged with (S)-tert-butyl 4-(6-aminopyridin-3-yl)-3-methylpiperazine-1-carboxylate 191f (580 mg, 2.0 mmol), 253a (1.36 g, 4.0 mmol), Pd$_2$(dba)$_3$ (180 mg, 0.20 mmol), Xantphos (230 mg, 0.40 mmol), Cs$_2$CO$_3$ (1.3 g, 4.0 mmol), and dioxane (20 mL). After three cycles of vacuum/argon flush, the mixture was heated at 100° C. for 2 h. It was then cooled to room temperature and filtered. The filtrate was evaporated under reduced pressure and the resulting residue was purified by silica-gel column chromatography eluting with 4:1 petroleum ether/ethyl acetate to afford 253b (1.0 g, 91%) as yellow solid. MS-ESI: [M+H]$^+$ 551.2

Example 253c (S)-6-Chloro-4-(5-(2-methylpiperazin-1-yl)pyridin-2-ylamino)pyridazin-3(2H)-one 253c A 50-mL round-bottomed flask was charged with 253b (551 mg, 1.0 mmol), concentrated HCl (2 mL), and methanol (10 mL). The mixture was stirred at room temperature overnight. It was then concentrated under reduced pressure to afford 253c, which was used directly in the next step without further purification. MS-ESI: [M+H]$^+$ 321.1

Example 253d (S)-6-Chloro-4-(5-(2-methyl-4-(oxetan-3-yl)piperazin-1-yl)pyridin-2-ylamino)pyridazin-3(2H)-one 253d A 50-mL round-bottomed flask equipped with a magnetic stirrer was charged with 253c (321 mg, 1.0 mmol), 3-oxetanone (142 mg, 2.0 mmol), NaBH$_3$CN (125 mg, 2.0 mmol), ZnCl$_2$ (272 mg, 2.0 mmol), and methanol (10 mL). The mixture was stirred at room temperature overnight and concentrated under reduced pressure. Water (20 mL) was added to the residue and the resulting mixture was extracted with dichloromethane (3×20 mL). The combined organic layer was concentrated under reduced pressure and the residue was purified by silica-gel column chromatography eluting with ethyl acetate to afford 253d (210 mg, 56%) as yellow solid. MS-ESI: [M+H]$^+$ 377.3.

Example 253e (2-{4,4-Dimethyl-9-oxo-1,10-diazatricyclo[6.4.0. 0$^{2,6}$]dodeca-2(6),7-dien-10-yl}-4-[5-({5-[(2S)-2-methyl-4-(oxetan-3-yl)piperazin-1-yl]pyridin-2-yl}amino)-6-oxo-1,6-dihydropyridazin-3-yl]pyridin-3-yl)methyl Acetate 253e A 25-mL single-neck round-bottomed flask equipped with a magnetic stirrer and a reflux condenser was charged with 253d (172 mg, 0.46 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (0.91 g, 2.29 mmol), Pd(dppf)Cl$_2$ (36 mg, 0.050 mmol), K$_3$PO$_4$ (195 mg, 0.92 mmol), sodium acetate (75 mg, 0.050 mmol), water (0.5 mL), and acetonitrile (10 mL). After three cycles of vacuum/argon flush, the mixture was heated at 90° C. for 2 h. It was then cooled to room temperature and filtered. The filtrate was evaporated under reduced pressure and the resulting residue was purified by silica-gel column chromatography eluting with 20:1 ethyl acetate/methanol to afford the 253e (100 mg, 31%) as brown solid. MS-ESI: [M+H]$^+$ 694.3.

Example 253

3-[3-(hydroxymethyl)-4-[5-[[5-[(2S)-2-methyl-4-(oxetan-3-yl)piperazin-1-yl]-2-pyridyl]amino]-6-oxo-1H-pyridazin-3-yl]-2-pyridyl]-7,7-dimethyl-1,2,6,8-tetrahydrocyclopenta[3,4]pyrrolo[3,5-b]pyrazin-4-one 253

A 25-mL single-neck round-bottomed flask equipped with a magnetic stirrer was charged with 253e (92 mg, 0.13 mmol), lithium hydroxide (16 mg, 0.65 mmol), THF (2 mL), i-propanol (2 mL), and water (0.5 mL). The mixture was stirred at room temperature for 1 h. It was then concentrated under reduced pressure. Water (10 mL) was added to the residue and the resulting mixture was extracted with dichloromethane (3×20 mL). The combined organic layer was concentrated under reduced pressure and the residue was purified by reverse-phase prep-HPLC to afford 253 (22 mg, 26%) as white solid. MS-ESI: [M+H]$^+$ 652.2. $^1$H NMR (500 MHz, CDCl$_3$) δ 10.83 (s, 1H), 8.61 (s, 1H), 8.58 (d, J=5.0 Hz, 1H), 8.12 (s, 1H), 8.05 (d, J=2.5 Hz, 1H), 7.45 (d, J=5.0 Hz, 1H), 7.32 (dd, J=3.0 Hz, 5.5 Hz, 1H), 7.00 (d, J=3.5 Hz, 1H), 6.84 (s, 1H), 4.74-4.68 (m, 3H), 4.65-4.58 (m, 3H), 4.26-4.14 (m, 2H), 3.99-3.96 (m, 1H), 3.71-3.69 (m, 1H), 3.55-3.53 (m, 1H), 3.18-3.14 (m, 2H), 2.64-2.59 (m, 3H), 2.53-2.47 (m, 4H), 2.40-2.33 (m, 2H), 1.29 (s, 6H), 1.09 (d, J=7.0 Hz, 3H).

Example 254a

4-[5-({5-Acetyl-4H,5H,6H,7H-pyrazolo[1,5-a]pyrazin-2-yl}amino)-1-methyl-6-oxo-1,6-dihydropyridin-3-yl]-2-{4,4-dimethyl-9-oxo-7-thia-10-azatricyclo[6.4.0.0$^{2,6}$]dodeca-1(8),2(6)-dien-10-yl}pyridine-3-carbaldehyde 254a

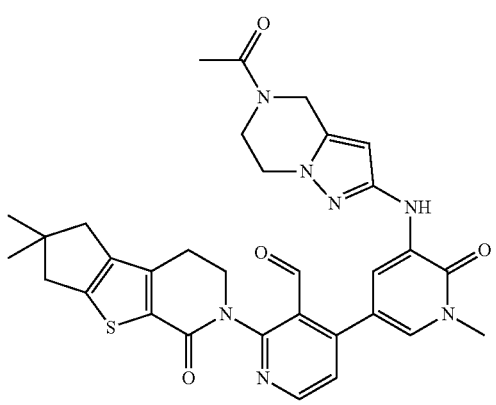

A 50-mL single-neck round-bottomed flask equipped with a magnetic stirrer and a reflux condenser was charged with 3-(5-acetyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 209d (344 mg, 0.83 mmol), 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (202 mg, 0.56 mmol), Pd(dppf)Cl$_2$ (20 mg, 0.028 mmol), K$_3$PO$_4$ (235 mg, 1.11 mmol), sodium acetate (91 mg, 1.11 mmol), water (0.5 mL), and acetonitrile (10 mL). After three cycles of vacuum/argon flush, the mixture was heated at 100° C. for 1 h. Analysis of the reaction mixture by LCMS showed complete conversion to the desired product. The mixture was cooled down to room temperature and filtered. The filtrate was concentrated under reduced pressure to afford 254a (400 mg, crude), which was directly used in next step without further purification. MS-ESI: [M+H]$^+$ 612.3

Example 254

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]thieno[1,3-c]pyridin-4-one 254

To a solution of 254a (98 mg, 0.16 mmol) in methanol and dichloromethane was added NaBH$_4$ (13 mg, 0.33 mmol). The reaction mixture was stirred at room temperature for 1 h. Analysis of the reaction mixture by LCMS showed complete conversion to the desired product. The mixture was quenched with aqueous NH$_4$Cl solution (5 mL) and concentrated under reduced pressure. The residue was extracted with dichloromethane (3×10 mL). The combined extract was concentrated under reduced pressure and the residue was purified by reverse-phase prep-HPLC to afford 254 (53 mg, 54%) as white solid. MS-ESI: [M+H]$^+$ 613.9. $^1$H NMR (500 MHz, DMSO-d$_6$, T=80° C.) δ 8.45 (d, J=8.5 Hz, 1H), 7.93-7.92 (m, 2H), 7.33 (d, J=3.5 Hz, 1H), 7.30 (d, J=8.5 Hz, 1H), 5.97 (s, 1H), 4.67-4.63 (m, 3H), 4.46-4.45 (m, 2H), 3.97-3.93 (m, 2H), 3.89-3.86 (m, 3H), 3.56 (s, 3H), 2.97-2.91 (m, 2H), 2.53-2.55 (m, 2H), 2.49-2.46 (m, 2H), 2.08 (s, 3H), 1.21 (s, 6H).

Example 255a 4-(5-(5-Acetyl-4,5,6,7-tetrahydropyrazolo[1,5-a]pyrazin-2-ylamino)-1-methyl-6-oxo-1,6-dihydropyridin-3-yl)-2-(10-fluoro-1-oxo-3,4,6,7,8,9-hexahydropyrazino[1,2-a]indol-2(1H)-yl)nicotinaldehyde 255a

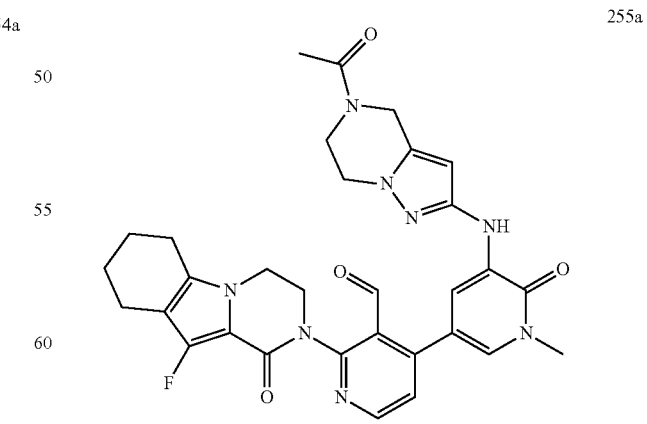

Following the procedure described in Example 246, and starting with 4-chloro-2-(10-fluoro-1-oxo-3,4,6,7,8,9-hexahydropyrazino[1,2-a]indol-2(1H)-yl)nicotinaldehyde 134c (200 mg, 0.575 mmol) and 3-(5-acetyl-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 209d (356 mg, 0.863 mmol), 255a was obtained as a red oil (320 mg, 93%). MS-ESI: [M+H]+ 599.3

Example 255

2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-10-fluoro-3,4,6,7,8,9-hexahydropyrazino[1,2-a]indol-1-one 255

Following the procedure described in Example 254, and starting with 255a (200 mg, 0.334 mmol), 255 was obtained as a white solid (55.5 mg, 28%). MS-ESI: [M+H]+ 601.3. $^1$H NMR (500 MHz, DMSO-$d_6$, T=80° C.) δ 8.45 (d, J=8.0 Hz, 1H), 7.93 (d, J=3.5 Hz, 2H), 7.33 (d, J=4.0 Hz, 1H), 7.30 (d, J=8.5 Hz, 1H), 5.97 (s, 1H), 4.70-4.63 (m, 3H), 4.46 (d, J=8.5 Hz, 2H), 4.10-3.86 (m, overlap, 8H), 3.58 (s, 3H), 2.57-2.55 (m, 2H), 2.43-2.39 (m, 2H), 2.08 (s, 3H), 1.79-1.67 (m, 4H).

Example 256a (S)-(6-Aminopyridin-3-yl)(3-methylmorpholino)methanone 256a

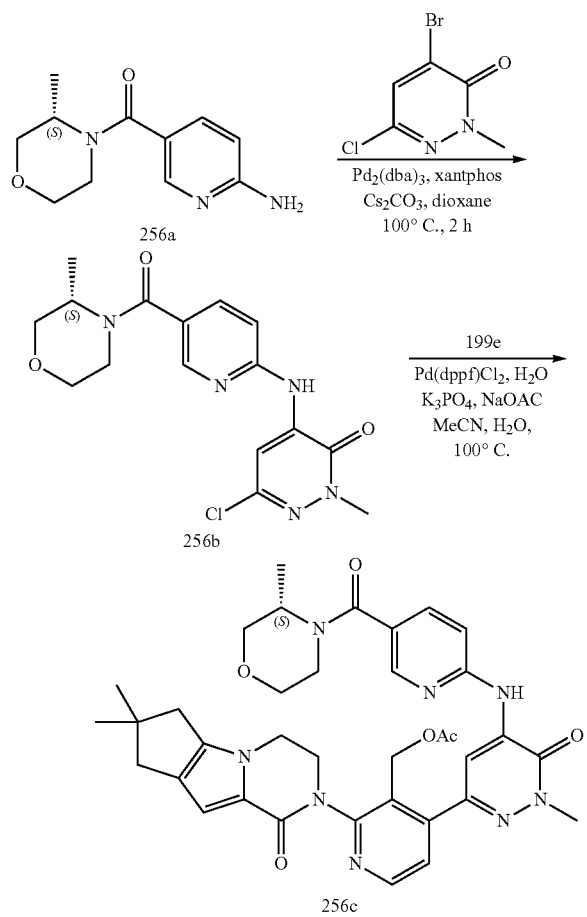

To a solution of (S)-3-methylmorpholine (1.5 g, 15.0 mmol) in ethanol (20 mL) was added EDCI (3.33 g, 17.4 mmol), HOBt (2.35 g, 17.4 mmol), and 6-aminonicotinic acid (2.07 g, 15.0 mmol) at room temperature. After stirring for 18 h, the resulting suspension was filtered. The solid was purified by silica-gel column chromatography eluting with 2:1 petroleum ether/ethyl acetate to straight ethyl acetate to afford 256a (1.0 g, 30%) as white solid. MS-ESI: 222.3 (M+H)+.

Example 256b (S)-5-Bromo-1-methyl-3-(5-(3-methylmorpholine-4-carbonyl pyridine-2-ylamino)pyridin-2(1H)-one 256b A 50-mL single-neck round-bottomed flask equipped with a magnetic stirrer and a reflux condenser was charged with 1,4-dioxane (10 ml), 256a (111 mg, 0.50 mmol), 4-bromo-6-chloro-2-methylpyridazin-3(2H)-one (134 mg, 0.60 mmol), cesium carbonate (326 mg, 1.0 mmol), Xantphos (29 mg, 0.05 mmol), and tris(dibenzylideneacetone)dipalladium(0) (23 mg, 0.025 mmol). The system was subjected to three cycles of vacuum/argon flush and heated at 100° C. for 5 h. It was then cooled to room temperature and filtered. The solid was washed with dichloromethane (3×30 mL) and the combined filtrate was concentrated under reduced pressure. The residue was purified by silica-gel column chromatography eluting with petroleum ether/ethyl acetate (2:1 to 1:2) to afford 256b (140 mg, 77%) as a yellow solid. MS-ESI: [M+H]+ 364.3

Example 256c (2-{4,4-Dimethyl-9-oxo-1,10-diazatricyclo[6.4.0.0$^{2,6}$]dodeca-2(6),7-dien-10-yl}-4-{1-methyl-5-[(5-{[(3S)-3-methylmorpholin-4-yl]carbonyl}pyridin-2-yl)amino]-6-oxo-1,6-dihydropyridazin-3-yl}pyridin-3-yl)methyl Acetate 256c A 25-mL single-neck round-bottomed flask equipped with a magnetic stirrer and a reflux condenser was charged with 256b (140 mg, 0.38 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (159 mg, 0.40 mmol), K$_3$PO$_4$ (85 mg, 0.40 mmol), sodium acetate (33 mg, 0.40 mmol), 1,1'-bis(diphenylphosphino) ferrocenedichloropalladium(II) (15 mg, 0.020 mmol), acetonitrile (10 mL), and water (0.5 mL). The system was subjected to three cycles of vacuum/argon flush and heated at 100° C. for 2.5 h. Analysis of the reaction mixture by LCMS showed complete conversion to the desired product. The reaction mixture was cooled to room temperature and diluted with dichloromethane (30 mL) and water (30 mL). The aqueous layer was separated and extracted with dichloromethane (3×20 mL). The combined organic layer was dried over Na$_2$SO$_4$ and filtered. The filtrate was concentrated under reduced pressure. The dark residue was purified by silica-gel column chromatography eluting with 60:1 dichloromethane:/methanol to afford 256c (90 mg, 35%) as yellow solid. MS-ESI: [M+H]+ 681.3

Example 256

3-[3-(hydroxymethyl)-4-[1-methyl-5-[[5-[(3S)-3-methylmorpholine-4-carbonyl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one 256

To a solution of 256c (90 mg, 0.13 mmol) in THF/i-propanol/water (2.0/1/0.5 ml) was added lithium hydroxide (31 mg, 1.3 mmol) at room temperature. After the reaction was stirred for 3 h, LCMS indicated the reaction was complete. Then the mixture was poured into water (15 mL) and extracted with dichloromethane (3×10 mL). The combined organic layer was washed with brine (30 mL), dried over Na₂SO₄, and filtered. The filtrate was concentrated under reduced pressure and the residue was purified by reverse-phase prep-HPLC to afford 256 (40 mg, 48%) as white solid. MS-ESI: [M+H]⁺ 639.3. ¹H NMR (500 MHz, MeOD) δ 8.86 (s, 1H), 8.58 (d, J=5.0 Hz, 1H), 8.44 (d, J=2.0 Hz, 1H), 7.79 (dd, J=2.0, 6.5 Hz, 1H), 7.57 (d, J=5.0 Hz, 1H), 7.32 (d, J=8.5 Hz, 1H), 6.74 (s, 1H), 4.85-4.82 (m, 1H), 4.66-4.64 (m, 1H), 4.42-4.27 (m, 4H), 4.02-3.88 (m, overlap, 6H), 3.74-3.67 (m, 2H), 3.56-3.46 (m, 2H), 2.67-2.59 (m, 2H), 2.51 (s, 2H), 1.39 (d, J=7.0 Hz, 3H), 1.28 (s, 6H).

Example 257

(S)-5-Bromo-1-methyl-3-(5-(3-methylmorpholine-4-carbonyl)pyridine-2-ylamino)pyridin-2(1H)-one 257a

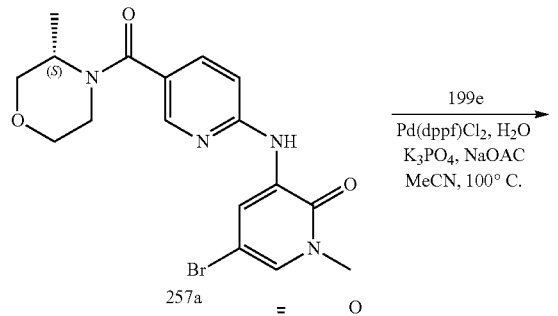

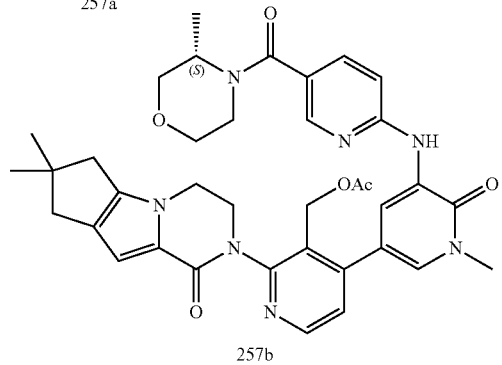

A 50-mL single-neck round-bottomed flask equipped with a magnetic stirrer and a reflux condenser was charged with (S)-(6-aminopyridin-3-yl)(3-methylmorpholino)methanone (222 mg, 1.0 mmol), 3,5-dibromo-1-methylpyridin-2(1H)-one (320 mg, 1.2 mmol), cesium carbonate (652 mg, 2 mmol), and 1,4-dioxane (10 mL). After bubbling nitrogen through the suspension for 10 minutes, Xantphos (58 mg, 0.10 mmol) and tris(dibenzylideneacetone)dipalladium(0) (46 mg, 0.050 mmol) were added. The system was subject to three cycles of vacuum/argon flush and heated at reflux for 2.5 h. It was then cooled to room temperature and filtered. The solid was washed with dichloromethane (2×30 mL) and the combined filtrate was concentrated under reduced pressure. The residue was purified by silica-gel column chromatography eluting with petroleum ether/ethyl acetate (2:1 to 1:2) to afford 257a (280 mg, 69%) as a yellow solid. MS-ESI: [M+H]⁺ 407.3

Example 257b (2-{4,4-Dimethyl-9-oxo-1,10-diazatricyclo[6.4.0. 0²,⁶]dodeca-2(6),7-dien-10-yl}-4-{1-methyl-5-[(5-{[(3S)-3-methylmorpholin-4-yl]carbonyl}pyridin-2-yl)amino]-6-oxo-1,6-dihydropyridin-3-yl}pyridin-3-yl)methyl Acetate 257b A 25-mL single-neck round-bottomed flask equipped with a magnetic stirrer and a reflux condenser was charged with 257a (203 mg, 0.50 mmol), {3-[(acetoxy)methyl]-2-{4,4-dimethyl-9-oxo-1,10-diazatricyclo[6.4.0.0²,⁶]dodeca-2(6), 7-dien-10-yl}pyridin-4-yl}boronic acid 199e (640 mg, 1.6 mmol), K₃PO₄ (212 mg, 1.0 mmol), 1,1'-bis(diphenylphosphino)ferrocenedichloropalladium(II) (18 mg, 0.025 mmol), sodium acetate (82 mg, 1.0 mmol), acetonitrile (10 mL), and water (0.2 mL). After three cycles of vacuum/argon flush, the mixture was heated at 100° C. for 2.5 h. Analysis of the reaction mixture by LCMS showed complete conversion to the desired product. The reaction mixture was cooled to room temperature and concentrated under reduced pressure. The residue was diluted with dichloromethane (20 mL) and water (20 mL). The aqueous layer was separated and extracted with dichloromethane (3×20 mL). The combined organic layer was dried over Na₂SO₄ and filtered. The filtrate was concentrated under reduced pressure. The dark residue was purified by silica-gel column chromatography eluting with 60:1 dichloromethane/methanol to afford 257b (160 mg, 47%) as black solid. MS-ESI: [M+H]⁺ 680.1

Example 257

3-[3-(hydroxymethyl)-4-[1-methyl-5-[[5-[(3S)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 257

To a solution of 257b (157 mg, 0.23 mmol) in THF/i-propanol/water (2/2/0.5 mL) was added lithium hydroxide (55 mg, 2.3 mmol) at room temperature. After the reaction was stirred for 3 h, LCMS indicated the reaction was completed. The mixture was poured into water (15 mL) and extracted with dichloromethane (3×15 mL). The combined organic layer was washed with brine (30 mL), dried over Na₂SO₄ and filtered. The filtrate was concentrated under reduced pressure. The residue solid was purified by reverse-phase prep-HPLC (A: 1‰ NH₄HCO₃ in water; B: acetonitrile) to afford 257 (52 mg, 35%) as yellow solid. MS-ESI: [M+H]⁺ 668.3. ¹H NMR (500 MHz, MeOD) δ 8.94 (d, J=2.0 Hz, 1H), 8.53 (d, J=5.0 Hz, 1H), 8.33 (d, J=2.0 Hz, 1H), 7.69 (dd, J=2.0, 6.5 Hz, 1H), 7.61 (d, J=2.0 Hz, 1H), 7.48 (d, J=5.0 Hz, 1H), 7.13 (d, J=8.5 Hz, 1H), 6.74 (s, 1H), 4.70 (d, J=12.0 Hz, 1H), 4.58 (d, J=12.0 Hz, 1H), 4.41-4.27 (m, 4H), 3.99-3.89 (m, 3H), 3.74-3.66 (m, overlap, 5H), 3.55-3.46 (m, 2H), 2.67-2.59 (m, 2H), 2.51 (s, 2H), 1.39 (d, J=6.5 Hz, 3H), 1.28 (s, 6H).

Example 258a

6-Chloro-2-methyl-4-({5-[(morpholin-4-yl)carbonyl]pyridin-2-yl}amino)-2,3-dihydropyridazin-3-one 258a

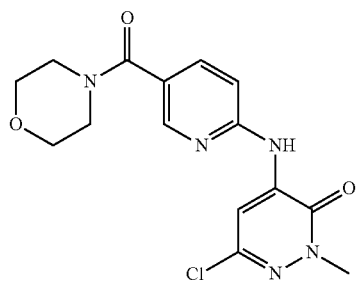 [SMILES: Cn1nc(Cl)cc(Nc2ccc(C(=O)N3CCOCC3)cn2)c1=O]

A 100-mL single-neck round-bottomed flask equipped with a magnetic stirrer and a reflux condenser was charged with 1,4-dioxane (40 mL), (6-aminopyridin-3-yl)(morpholino)-methanone (2.07 g, 10.0 mmol), 4-bromo-6-chloro-2-methylpyridazin-3(2H)-one 111a (3.35 g, 15.0 mmol), Pd₂(dba)₃ (915 mg, 1.0 mmol), XantPhos (578 mg, 1.0 mmol), and cesium carbonate (6.52 g, 20 mmol). After three cycles of vacuum/argon flush, the mixture was heated at 100° C. for 8 h. It was then cooled to room temperature and filtered. The solid was washed with dichloromethane (2×20 mL). The combined filtrate was dried over anhydrous Na₂SO₄ and concentrated under reduced pressure to afford 258a (2.45 g, 51%) as a yellow solid. MS: [M+H]⁺ 350.1

Example 258b

1-Methyl-5-(5-(morpholine-4-carbonyl)pyridin-2-ylamino)-6-oxo-1,6-dihydropyridazin-3-ylboronic Acid 258b

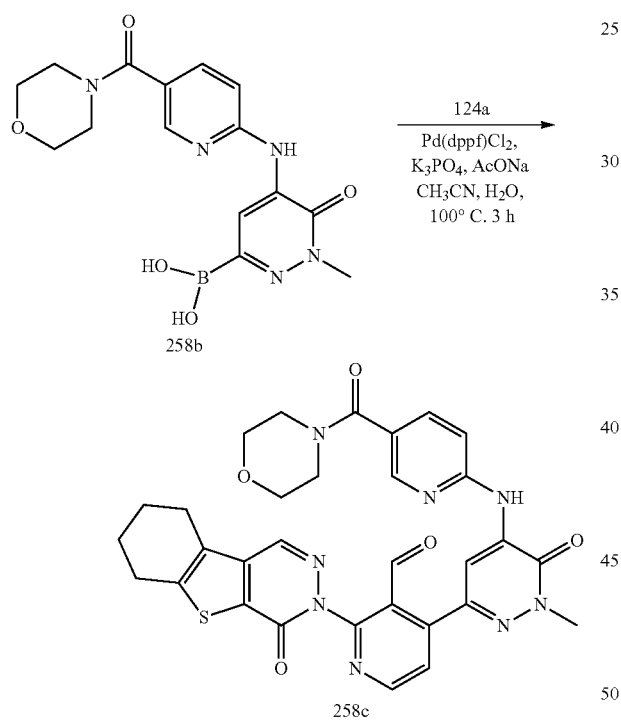

A 250-mL single-neck round-bottomed flask equipped with a magnetic stirrer and a reflux condenser was charged with 258a (2.0 g, 5.73 mmol, 1.0 eq.), 4,4,4',4',5,5,5',5'-octamethyl-2,2'-bi(1,3,2-dioxaborolane) (7.56 g, 28.6 mmol, 5.0 eq.), Pd(dppf)Cl₂ (465 mg, 0.57 mmol, 0.1 eq.), X-Phos (461 mg, 1.14 mmol, 0.2 eq.), potassium acetate (1.11 g, 11.4 mmol, 2.0 eq.), and dioxane (50 mL). After three cycles of vacuum/argon flush, the mixture was heated at 50° C. for 6 h. It was then cooled to room temperature and filtered. The filtrate was concentrated under reduced pressure and the resulting residue was washed with 1:3 ethyl acetate/petroleum ether to afford 258b (1.70 g, 83%) as a yellow solid, which was used in the next step without further purification. MS: [M+H]⁺ 360.1

Example 258c

4-Chloro-2-{6-oxo-8-thia-4,5-diazatricyclo[7.4.0.0²,⁷]trideca-1(9),2(7),3-trien-5-yl}pyridine-3-carbaldehyde 258c A 100-mL round-bottomed flask equipped with a reflux condenser was charged with 4-chloro-2-{6-oxo-8-thia-4,5-diazatricyclo[7.4.0.0²,⁷]trideca-1(9),2(7),3-trien-5-yl}pyridine-3-carbaldehyde 124a (100 mg, 0.29 mmol), 258b (128 mg, 0.36 mmol), PdCl₂(dppf) (24 mg, 0.031 mmol), K₃PO₄ (123 mg, 0.58 mmol), sodium acetate (57 mg, 0.58 mmol), acetonitrile (30 mL), and water (3 mL). After three cycles of vacuum/argon flush, the mixture was stirred at 100° C. for 3 h. It was then filtered and the filtrate was evaporated in vacuo. The residue was purified with silica-gel column chromatography eluting with 1:3 petroleum/ethyl acetate to afford 258c as a yellow solid (45 mg, 25%). MS-ESI: [M+H]⁺ 625.2

Example 258

3-[3-(hydroxymethyl)-4-[1-methyl-5-[[5-(morpholine-4-carbonyl)-2-pyridyl]amino]-6-oxo-pyridazin-3-yl]-2-pyridyl]-6,7,8,9-tetrahydrobenzothiopheno[2,3-d]pyridazin-4-one 258

A mixture of 258c (45 mg, 0.071 mmol), NaBH₄ (8 mg, 0.21 mmol), and methanol (7 mL) was stirred at room temperature for 2 h. Then the reaction mixture was quenched with water (5 mL) and concentrated under reduced pressure. The residue was extracted with dichloromethane (2×10 mL) and the combined dichloromethane extract was concentrated under reduced pressure. The residue was purified by reverse-phase prep-HPLC to afford 258 (24 mg, 53%) as a yellow solid. MS-ESI: [M+H]⁺ 627.2. ¹H NMR (500 MHz, DMSO-d₆) δ 9.80 (s, 1H), 8.68 (s, 1H), 8.65 (d, J=4.5 Hz, 1H), 8.50 (s, 1H), 8.39 (d, J=2.0 Hz, 1H), 7.80-7.78 (m, 1H), 7.67 (d, J=5.0 Hz, 1H), 7.60 (d, J=8.5 Hz, 1H), 4.85 (t, J=5.5 Hz, 1H), 4.52-4.35 (m, 2H), 3.82 (s, 3H), 3.60-3.49 (m, 8H), 2.95-2.93 (m, 2H), 2.89-2.84 (m, 2H), 1.94-1.83 (m, 4H).

Example 259a

2-{4,4-Dimethyl-9-oxo-7-thia-10-azatricyclo[6.4.0.0²,⁶]dodeca-1(8),2(6)-dien-10-yl}-4-[1-methyl-5-({5-[(morpholin-4-yl)carbonyl]pyridin-2-yl}amino)-6-oxopyridazin-3-yl]pyridine-3-carbaldehyde 259a

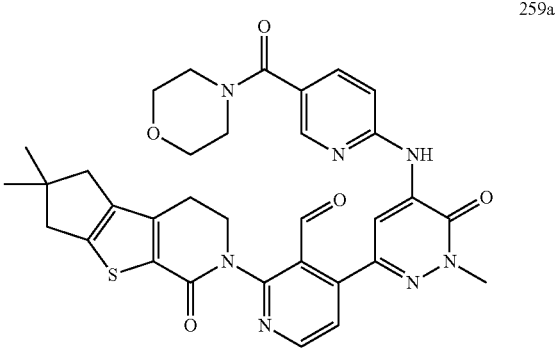

A round-bottomed flask equipped with a reflux condenser was charged with 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (144 mg, 0.40 mmol), 1-methyl-5-(5-(morpholine-4-carbonyl)pyridin-2-ylamino)-6-oxo-1,6-dihydropyridazin-3-ylboronic acid 258a (215 mg, 0.60 mmol), PdCl$_2$(dppf) (16 mg, 0.020 mmol), K$_3$PO$_4$ trihydrate (207 mg, 0.80 mmol), sodium acetate (66 mg, 0.80 mmol), acetonitrile (15 mL), and water (1.5 mL). After three cycles of vacuum/argon flush, the mixture was stirred at 100° C. for 2 h. It was then filtered and the filtrate was evaporated in vacuo. The residue was purified with silica-gel column chromatography eluting with 25:1 dichloromethane/methanol to afford 259a as a yellow solid (80 mg, 30%). MS-ESI: [M+H]$^+$ 640.3.

Example 259

3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]thieno[1,3-c]pyridin-4-one 259

A mixture of 259a (80 mg, 0.12 mmol), NaBH$_4$ (14 mg, 0.36 mmol), and methanol (5 mL) was stirred at room temperature for 1 h. It was then quenched with brine (5 mL) and evaporated under reduced pressure. The residue was extracted with dichloromethane (2×10 mL) and the combined dichloromethane extract was concentrated under reduced pressure. The resulting residue was purified by reverse-phase prep-HPLC to afford 259 as a white solid (38 mg, 49%). MS-ESI: [M+H]$^+$ 642.8. $^1$H NMR (500 MHz, CDCl$_3$) δ 8.78 (s, 1H), 8.61 (d, J=5.0 Hz, 1H), 8.44 (d, J=2.5 Hz, 2H), 7.80-7.77 (m, 1H), 7.45 (d, J=5.0 Hz, 1H), 7.06-7.04 (m, 1H), 4.65-4.59 (m, 2H), 4.42 (s, 1H), 4.30-4.27 (m, 1H), 3.95 (s, 3H), 3.90-3.87 (m, 1H), 3.76-3.68 (m, 8H), 3.04-2.92 (m, 2H), 2.82-2.80 (m, 2H), 2.59-2.54 (m, 2H), 1.30 (s, 6H).

Example 260a (2-{4,4-Dimethyl-9-oxo-1,10-diazatricyclo[6.4.0.0$^{2,6}$]dodeca-2(6),7-dien-10-yl}-4-{1-methyl-5-[(5-methyl-1H-pyrazol-3-yl)amino]-6-oxo-1,6-dihydropyridin-3-yl}pyridin-3-yl)methyl Acetate 260a

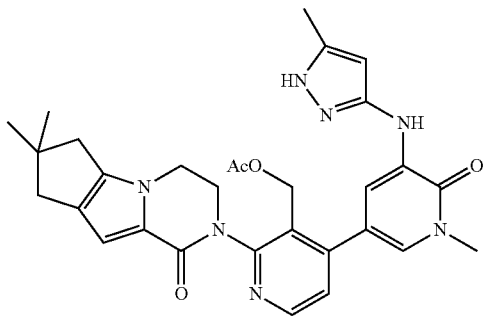

A round-bottomed flask equipped with a reflux condenser was charged with 5-bromo-1-methyl-3-(5-methyl-1H-pyrazol-3-ylamino)pyridin-2(1H)-one 218a (201 mg, 0.71 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (282 mg, 0.71 mmol), Pd(dppf)Cl$_2$ (51 mg, 0.07 mmol), K$_3$PO$_4$ (301 mg, 1.42 mmol), sodium acetate (116 mg, 1.42 mmol), acetonitrile (10 mL), and water (0.2 mL). After three cycles of vacuum/argon flush, the mixture was heated at 100° C. for 3 h. It was then filtered and the filtrate was evaporated under reduced pressure. The residue was purified by silica-gel column chromatography eluting with 1:20 methanol/dichloromethane to afford 260a as a red solid (150 mg, 38%). MS-ESI: [M+H]$^+$ 556.3

Example 260

3-[3-(hydroxymethyl)-4-[1-methyl-5-[(5-methyl-1H-pyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 260

A mixture of 260a (150 mg, 0.27 mmol) and lithium hydroxide (13 mg, 0.54 mmol) in THF (6 mL), i-propanol (4 mL), and water (2 mL) was stirred at room temperature for 0.5 h. The mixture was concentrated under reduced pressure and the residue was diluted with water (5 mL). It was then extracted with dichloromethane (2×10 mL) and the combined dichloromethane extract was concentrated under reduced pressure. The residue was purified with reverse-phase prep-HPLC to afford 260 (28 mg, 20%) as a white solid. MS-ESI: [M+H]$^+$ 514.3. $^1$H NMR (500 MHz, DMSO-d$_6$) δ 11.76 (s, 1H), 8.47 (d, J=5.0 Hz, 1H), 8.07-8.05 (m, 2H), 7.38-7.31 (m, 2H), 6.55 (s, 1H), 5.88 (s, 1H), 4.95-4.93 (m, 1H), 4.48-4.39 (m, 2H), 4.22-4.18 (m, 3H), 3.83 (d, J=5.5 Hz, 1H), 3.58 (s, 3H), 2.64-2.56 (m, 2H), 2.36-2.34 (m, 2H), 2.16 (s, 3H), 1.22 (s, 6H).

Example 261a

4-{5-[(1,5-Dimethyl-1H-pyrazol-3-yl)amino]-1-methyl-6-oxo-1,6-dihydro pyridin-3-yl}-2-{10-fluoro-1-oxo-1H,2H,3H,4H,6H,7H,8H,9H-pyrido[3,4-b]indolizin-2-yl}pyridine-3-carbaldehyde 261a

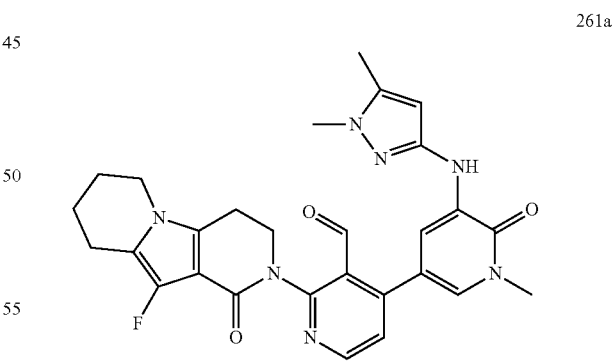

A 25-mL single-neck round-bottomed flask equipped with a magnetic stirrer and a reflux condenser was charged with 4-chloro-2-(10-fluoro-1-oxo-3,4,6,7,8,9-hexahydropyrido[3,4-b]indolizin-2(1H)-yl)nicotinaldehyde 134c (97 mg, 0.28 mmol), 3-[(1,5-dimethyl-1H-pyrazol-3-yl)amino]-1-methyl-5-(tetramethyl-1,3,2-dioxaborolan-2-yl)-1,2-dihydropyridin-2-one 218a (192.6 mg, 0.56 mmol), Pd$_2$(dba)$_3$ (54.9 mg, 0.060 mmol), tri(cyclohexyl)phosphine (50.2 mg, 0.18 mmol), Cs$_2$CO$_3$ (182.6 mg, 0.56 mmol), dioxane (8 mL), and water (0.25 mL). After three cycles of vacuum/argon flush, the mixture was stirred at 110° C. for 2 h. It was then filtered and the filtrate was evaporated in vacuo. The residue was purified by silica-gel column chromatography eluting with 35:1 ethyl acetate/methanol to afford 261a (90 mg, 61%) as a black solid. MS-ESI: [M+H]$^+$ 530.2

Example 261

2-[4-[5-[(1,5-dimethylpyrazol-3-yl)amino]-1-methyl-6-oxo-3-pyridyl]-3-(hydroxymethyl)-2-pyridyl]-10-fluoro-3,4,6,7,8,9-hexahydropyrido[3,4-b]indolizin-1-one 261

To a solution of 261a (90.0 mg, 0.17 mmol) in methanol (5 mL) was added sodium borohydride (64.6 mg, 1.7 mmol) at room temperature. The reaction was stirred for 0.5 h. It was then quenched with water (2 mL) and evaporated in vacuo. The residue was extracted with dichloromethane (3×10 mL). The combined dichloromethane extract was concentrated under reduced pressure and the residue was purified by reverse-phase prep-HPLC to afford 261 (47.0 mg, 52%) as a white solid. MS-ESI: [M+H]$^+$ 532.3. $^1$H NMR (500 MHz, DMSO-d$_6$) δ 8.47 (d, J=5.0 Hz, 1H), 8.05 (s, 1H), 8.03 (d, J=2.5 Hz, 1H), 7.39 (d, J=2.5 Hz, 1H), 7.31 (d, J=5.0 Hz, 1H), 5.89 (s, 1H), 4.87-4.85 (m, 1H), 4.45-4.36 (m, 2H), 4.11-4.09 (m, 1H), 3.93-3.91 (m, 1H), 3.79-3.76 (m, 2H), 3.59 (s, 3H), 3.58 (s, 3H), 3.00-2.94 (m, 2H), 2.66-2.63 (m, 2H), 2.18 (s, 3H), 1.90-1.88 (m, 2H), 1.78-1.73 (m, 2H)

Example 262a

5-Bromo-1-methyl-3-(5-methyloxazol-2-ylamino) pyridin-2(1H)-one 262a

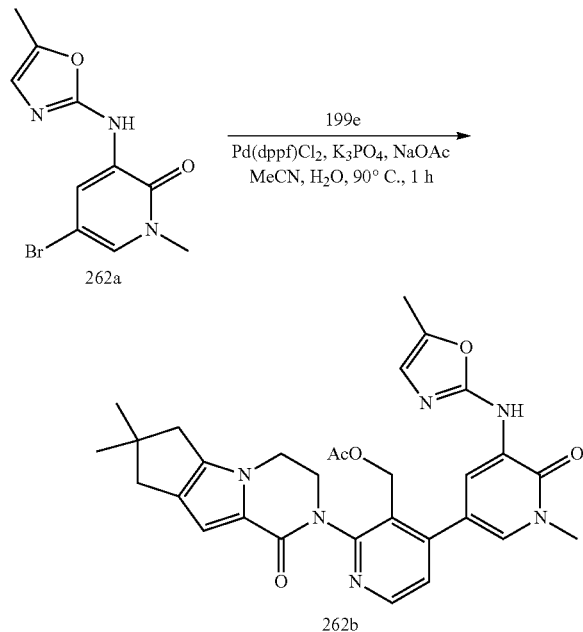

A 100-mL single-neck round-bottomed flask equipped with a magnetic stirrer and a reflux condenser was charged with 5-methyloxazol-2-amine (276 mg, 2.82 mmol), 3,5-dibromo-1-methylpyridin-2(1H)-one (753 mg, 2.82 mmol), tris-(dibenzylideneacetone)dipalladium(0) (256 mg, 0.28 mmol), XantPhos (324 mg, 0.56 mmol), Cs$_2$CO$_3$ (1.8 g, 5.64 mmol), and 1,4-dioxane (30 mL). After three cycles of vacuum/argon flush, the mixture was heated at 92° C. for 3 hrs. It was then cooled to room temperature and filtered. The filtrate was concentrated under reduced pressure and the resulting residue was purified by silica-gel column chromatography eluting with 100:1 dichloromethane/methanol to afford 262a as white solid (702 mg, 88%). MS-ESI: [M+H]$^+$ 284.1.

Example 262b (2-{4,4-Dimethyl-9-oxo-1,10-diazatricyclo[6.4.0. 0$^{2,6}$]dodeca-2(6),7-dien-10-yl}-4-{1-methyl-5-[(5-methyl-1,3-oxazol-2-yl)amino]-6-oxo-1,6-dihydropyridin-3-yl}pyridin-3-yl)methyl Acetate 262b A 50-mL single-neck round-bottomed flask equipped with a magnetic stirrer and a reflux condenser was charged with 262a (150 mg, 0.53 mmol), {3-[(acetyloxy)methyl]-2-{4,4-dimethyl-9-oxo-1,10-diazatricyclo[6.4.0.0$^{2,6}$]dodeca-2(6), 7-dien-10-yl}pyridin-4-yl}boronic acid 199e (421 mg, 1.06 mmol), Pd(dppf)Cl$_2$ (37 mg, 0.050 mmol), K$_3$PO$_4$ (225 mg, 1.06 mmol), sodium acetate (87 mg, 1.06 mmol), water (0.5 mL), and acetonitrile (10 mL). After three cycles of vacuum/argon flush, the mixture was heated at 90° C. for 1 h. It was then cooled to room temperature and filtered. The filtrate was concentrated under reduced pressure and the resulting residue was purified by silica-gel column chromatography eluting with dichloromethane/methanol (50:1 to 30:1) to afford 262b as yellow solid (100 mg, 34%). MS-ESI: [M+H]$^+$ 556.9.

Example 262

3-[3-(hydroxymethyl)-4-[1-methyl-5-[(5-methyloxazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 262

A mixture of 262b (100 mg, 0.18 mmol) and lithium hydroxide (108 mg, 4.5 mmol) in i-propanol/THF/water (4/4/2 mL) was stirred at 35° C. for 30 min. The mixture was concentrated under reduced pressure. To the residue was added water (5 mL) and the resulting mixture was extracted with dichloromethane three times. The combined organic layer was concentrated under reduced pressure and the resulting residue was purified by reverse-phase prep-HPLC to afford 262 as white solid (21.0 mg, 23%). MS-ESI: [M+H]$^+$ 515.3. $^1$H NMR (500 MHz, DMSO-d$_6$) δ 9.19 (s, 1H), 8.49 (d, J=5.0 Hz, 1H), 8.30 (s, 1H), 7.60 (d, J=1.0 Hz, 1H), 7.32 (d, J=4.5 Hz, 1H), 6.62 (s, 1H), 6.56 (s, 1H), 4.96-4.94 (m, 1H), 4.45-4.36 (m, 2H), 4.24-4.14 (m, 3H), 3.84 (d, J=10.5 Hz, 1H), 3.59 (s, 3H), 2.62-2.56 (m, 2H), 2.44-2.42 (m, 2H), 2.22 (s, 3H), 1.22 (s, 6H).

Example 263a

6-Chloro-2-methyl-4-(pyrimidin-4-ylamino)pyridazin-3(2H)-one 263a

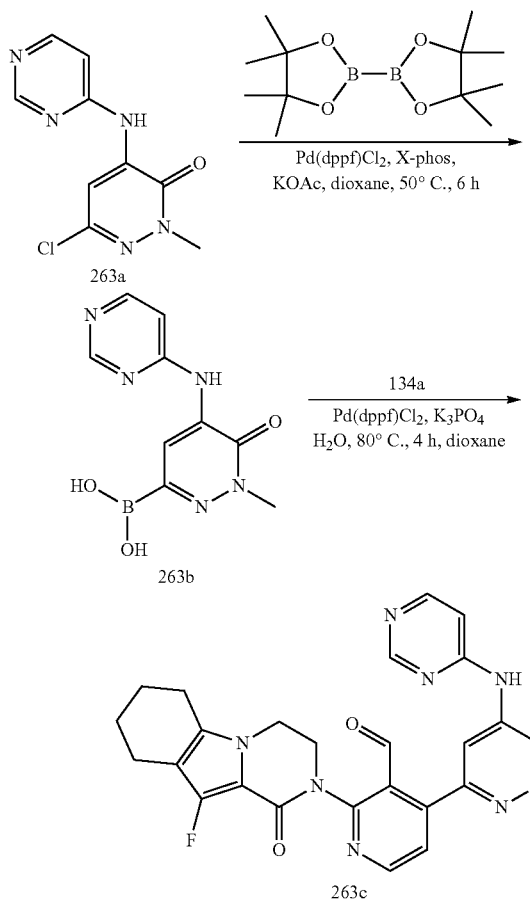

A 250-mL single-neck round-bottomed flask equipped with a magnetic stirrer and a reflux condenser was charged with 1,4-dioxane (150 mL), pyrimidin-4-amine (1.7 g, 18.0 mmol), 4-bromo-6-chloro-2-methylpyridazin-3(2H)-one (4.0 g, 18.0 mmol), and cesium carbonate (11.74 g, 36.0 mmol). After bubbling nitrogen through the suspension for 30 minutes, Xantphos (1.04 g, 1.8 mmol) and tris(dibenzylideneacetone)dipalladium(0) (823 mg, 0.9 mmol) were added. The system was subjected to three cycles of vacuum/argon flush and heated at reflux for 15 h. It was then cooled to room temperature and filtered. The solid was washed with dichloromethane (2×50 mL). The combined filtrate was concentrated and the residue was washed with acetonitrile (5 mL) to afford 263a (2.99 g, 70%) as a yellow solid. MS: [M+H]$^+$ 238

Example 263b

1-methyl-6-oxo-5-(pyrimidin-4-ylamino)-1,6-dihydropyridazin-3-yl-boronic acid 263b A 100-mL single-neck round-bottomed flask equipped with a magnetic stirrer and a reflux condenser was charged with 263a (500 mg, 2.11 mmol), 4,4,4',4',5,5,5',5'-octamethyl-2,2'-bi(1,3,2-dioxaborolane) (2.68 g, 10.6 mmol), Pd(dppf)Cl$_2$ (170 mg, 0.20 mmol), X-phos (170 mg, 0.40 mmol), potassium acetate (410 mg, 4.21 mmol), and dioxane (30 mL). The system was subjected to 3 cycles of vacuum/argon flush and stirred at 50° C. for 6 h. LCMS indicated that 263a was totally converted to 263b.

Example 263c

2-(10-Fluoro-1-oxo-3,4,6,7,8,9-hexahydropyrazino[1,2-a]indol-2(1H)-yl)-4-(1-methyl-6-oxo-5-(pyrimidin-4-ylamino)-1,6-dihydropyridazin-3-yl)nicotinaldehyde 263c To the mixture of 263b at room temperature was added 4-chloro-2-(10-fluoro-1-oxo-3,4,6,7,8,9-hexahydropyrazino[1,2-a]indol-2(1H)-yl)nicotinaldehyde 134c (300 mg, 0.90 mmol), Pd(dppf)Cl$_2$ (170 mg, 0.20 mmol), K$_3$PO$_4$ (103 mg, 0.40 mmol), and water (2 mL). The system was subjected to 3 cycles of vacuum/argon flush again and stirred at 80° C. for 4 h. The reaction mixture was then cooled to room temperature, diluted with water (30 mL), and filtered. The filtrate was extracted with dichloromethane (2×30 mL). The combined dichloromethane extract was concentrated under reduced pressure and the residue was purified by silica-gel column chromatography eluting with dichloromethane/methanol (40:1 to 20:1) to afford 263c as a yellow solid (210 mg, 45%). MS-ESI: [M+H]$^+$ 515.3

Example 263

10-fluoro-2-[3-(hydroxymethyl)-4-[1-methyl-6-oxo-5-(pyrimidin-4-ylamino)pyridazin-3-yl]-2-pyridyl]-3,4,6,7,8,9-hexahydropyrazino[1,2-a]indol-1-one 263

A 100-mL single-neck round-bottomed flask equipped with a magnetic stirrer was charged with 263c (100 mg, 0.19 mmol), NaBH$_4$ (30 mg, 0.78 mmol), and methanol (20 mL). The mixture was stirred at room temperature for 0.5 h. It was then diluted with water (30 mL) and concentrated under reduced pressure. The residue was extracted with dichloromethane (2×30 mL) and the combined dichloromethane extract was dried and concentrated under reduced pressure. The residue was purified with reverse-phase prep-HPLC to afford 263 as a white solid (67 mg, 68%). MS-ESI: [M+H]$^+$ 517.3. $^1$H NMR (500 MHz, DMSO-d$_6$) δ 9.93 (s, 1H), 8.81 (s, 1H), 8.67 (s, 1H), 8.55 (d, J=4.5 Hz, 1H), 8.49 (d, J=5.5 Hz, 1H), 7.56 (dd, J=1.0, 6.0 Hz, 1H), 7.43 (d, J=5.0 Hz, 1H), 4.83 (t, J=5.5 Hz, 1H), 4.62-4.58 (m, 1H), 4.39-4.36 (m, 1H), 4.25-4.19 (m, 2H), 4.06-4.04 (m, 1H), 3.92-3.90 (m, 1H), 3.81 (s, 3H), 2.64-2.54 (m, 2H), 2.43-2.41 (m 2H), 1.78-1.76 (m, 2H), 1.69-1.67 (m, 2H).

Example 264a

2-(4-Aminopyrimidin-2-yl)propan-2-ol 264a

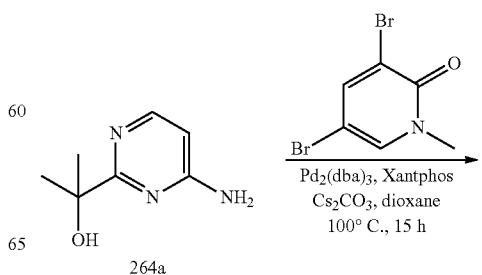

481

-continued

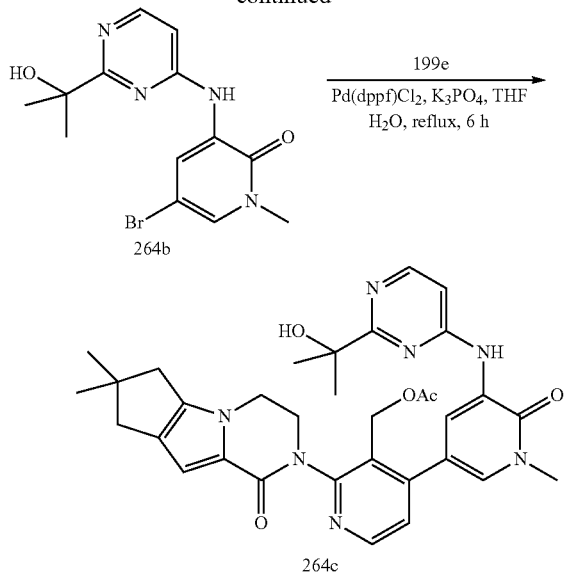

To a solution of ethyl 4-aminopyrimidine-2-carboxylate (840 mg, 5.0 mmol) in anhydrous tetrahydrofuran (50 mL) cooled at −20° C. was added a solution of methylmagnesium bromide in THF (8.5 mL, 25.0 mmol, 3.0 M) over a period of 5 minutes. The reaction mixture was stirred at 0° C. for another 2 h. It was then quenched with saturated NH$_4$Cl (20 mL) and concentrated under reduced pressure. The residue was extracted with ethyl acetate (5×40 mL). The combined organic layer was dried over anhydrous Mg$_2$SO$_4$, filtered, and evaporated under reduced pressure. The residue was purified by reverse-phase Combiflash to afford 264a as yellow solid (240 mg, 32%) MS-ESI: [M+H]$^+$ 154.1

Example 264b

5-Bromo-3-(2-(2-hydroxypropan-2-yl)pyrimidin-4-ylamino)-1-methylpyridin-2(1H)-one 264b A 100-mL single-neck round-bottomed flask equipped with a magnetic stirrer and a reflux condenser was charged with 264a (300 mg, 2.0 mmol), 3,5-dibromo-1-methylpyridin-2(1H)-one (800 mg, 3.0 mmol), Pd$_2$(dba)$_3$ (182 mg, 0.20 mmol), XantPhos (231 mg, 0.40 mmol), Cs$_2$CO$_3$ (1.30 g, 4.0 mmol), and 1,4-dioxane (20 mL). After three cycles of vacuum/argon flush, the mixture was heated at 100° C. for 15 h. It was then cooled to room temperature and filtered. The filtrate was concentrated under reduced pressure. The resulting residue was purified by silica-gel column chromatography eluting with 40:1 dichloromethane/methanol (40:1) and further purified by reverse-phase Combiflash to afford 264b as white solid (200 mg, 30%). MS-ESI: [M+H]$^+$ 339.0

Example 264c (2-{4,4-Dimethyl-9-oxo-1,10-diazatricyclo[6.4.0. 0$^{2,6}$]dodeca-2(6),7-dien-10-yl}-4-(5-{[2-(2-hydroxypropan-2-yl)pyrimidin-4-yl]amino}-1-methyl-6-oxo-1,6-dihydro-pyridin-3-yl)pyridin-3-yl)methyl Acetate 264c A 50-mL round-bottomed flask equipped with a reflux condenser was charged with 264b (170 mg, 0.50 mmol), (3-(acetoxymethyl)-2-(7,7-dimethyl-1-oxo-3,4,7,8-tetrahydro-1H-cyclopenta[4,5]pyrrolo[1,2-a]pyrazin-2(6H)-yl)pyridin-4-yl)boronic acid 199e (200 mg, 0.50 mmol), Pd(dppf)Cl$_2$ (40 mg, 0.050 mmol), K$_3$PO$_4$ (212 mg, 1.0 mmol), water (0.5 mL), and tetrahydrofuran (10 mL). After three cycles of vacuum/argon flush, the mixture was heated at reflux for 6 h. It was then cooled to room temperature and filtered. The filtrate was concentrated under reduced pressure and the resulting residue was purified by silica-gel column chromatography eluting with 40:1 dichloromethane/methanol to afford 264c as brown solid (200 mg, 54%). MS-ESI: [M+H]$^+$ 612.3

Example 264

3-[3-(hydroxymethyl)-4-[5-[[2-(1-hydroxy-1-methyl-ethyl)pyrimidin-4-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 264

To a solution of 264c (170 mg, 0.27 mmol) in tetrahydrofuran (10 mL) and water (2 mL) was added lithium hydroxide (64 mg, 3.0 mmol). The reaction mixture was stirred at 35° C. for 2 h. It was then concentrated under reduced pressure and the residue was purified by reverse-phase prep-HPLC to afford 264 (86 mg, 46%) as yellow solid. MS-ESI: [M+H]$^+$ 570.1. $^1$H NMR (500 MHz, DMSO-d$_6$) δ 9.27 (s, 1H), 8.94 (d, J=2.0 Hz, 1H), 8.50 (d, J=5.0 Hz, 1H), 8.33 (d, J=6.0 Hz, 1H), 7.76 (d, J=2.5 Hz, 1H), 7.41 (d, J=5.0 Hz, 1H), 7.22 (d, J=5.5 Hz, 1H), 6.56 (s, 1H), 5.14 (t, J=5.0 Hz, 1H), 4.89 (s, 1H), 4.48-4.42 (m, 2H), 4.23-4.19 (m, overlap, 3H), 3.85-3.84 (m, 1H), 3.62 (s, 3H), 2.67-2.56 (m, 2H), 2.42 (s, 2H), 1.42 (s, 3H), 1.40 (s, 3H), 1.21 (s, overlap, 6H).

Example 265a 1-(2-Nitro-6,7-dihydropyrazolo[1,5-a]pyrazin-5(4H)-yl)propan-1-one 265a

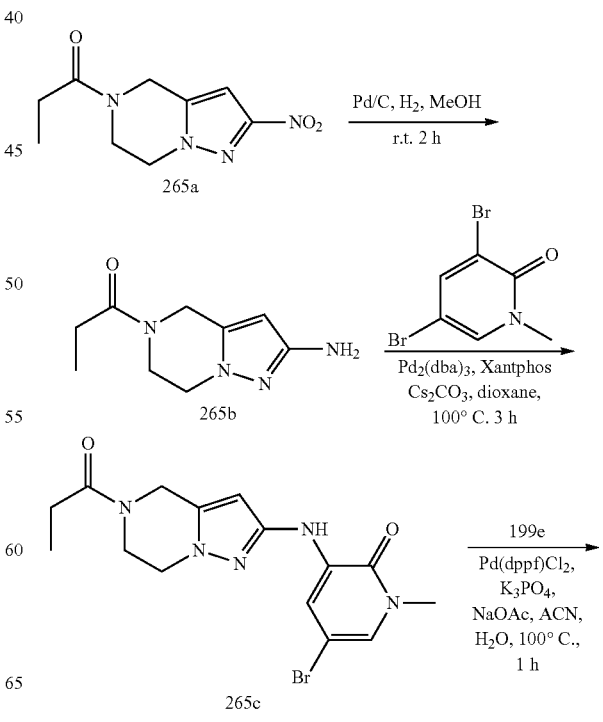

Example 265d (2-{4,4-Dimethyl-9-oxo-1,10-diazatricyclo[6.4.0.0²,⁶]dodeca-2(6),7-dien-10-yl}-4-[1-methyl-6-oxo-5-({5-propanoyl-4H,5H,6H,7H-pyrazolo[1,5-a]pyrazin-2-yl}amino)-1,6-dihydropyridin-3-yl]pyridin-3-yl)methyl Acetate 265d

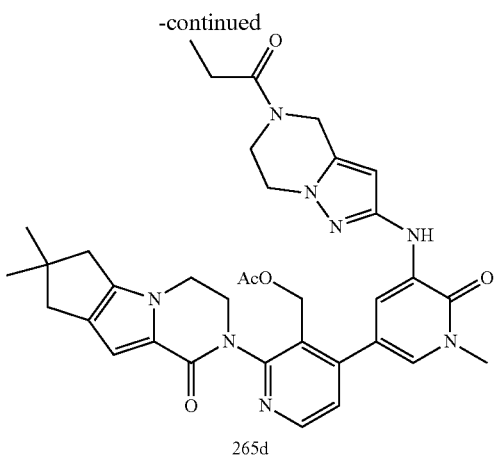

265d

To a solution of 2-nitro-4,5,6,7-tetrahydropyrazolo[1,5-a]pyrazine 209a (200 mg, 1.19 mmol) in dichloromethane (8 mL) was added Et₃N (240 mg, 2.38 mmol). After stirring for 5 minutes, a solution of propionyl chloride (121 mg, 1.31 mmol) in dichloromethane (2 mL) was added and the reaction mixture was stirred at room temperature for 1 h. Analysis of the reaction mixture by LCMS showed complete conversion to the desired product. The mixture was washed with water and brine, dried over Na₂SO₄, and filtered. The filtrate was concentrated under reduced pressure to afford 265a (260 mg, 98%) as white solid, which was used in the next step without further purification. MS-ESI: [M+H]⁺ 225.0

Example 265b 1-(2-Amino-6,7-dihydropyrazolo[1,5-a]pyrazin-5(4H)-yl)propan-1-one 265b To a solution of 265a (260 mg, 1.16 mmol) in methanol (10 mL) was added 10% Pd/C (26 mg). The system was evacuated and then refilled with H₂. After stirring for 2 h, analysis of the reaction mixture by LCMS showed complete conversion to the desired product. The mixture was filtered, and the filtrate was concentrated under reduced pressure to afford 265b as a yellow solid (225 mg, 99%). MS-ESI: [M+H]⁺ 195.1

Example 265c

5-Bromo-1-methyl-3-(5-propionyl-4,5,6,7-tetrahydropyrazolo[1,5-a]pyrazin-2-ylamino)pyridin-2(1H)-one 265c A 50-mL single-neck round-bottomed flask equipped with a magnetic stirrer and a reflux condenser was charged with 265b (200 mg, 1.03 mmol), 3,5-dibromo-1-methylpyridin-2(1H)-one (414 mg, 1.55 mmol), Pd₂(dba)₃ (47 mg, 0.052 mmol), Xantphos (60 mg, 0.103 mmol), Cs₂CO₃ (671.6 mg, 2.06 mmol), and dioxane (20 mL). After three cycles of vacuum/argon flush, the reaction mixture was heated at 100° C. for 3 h. Analysis of the reaction mixture by LCMS showed complete conversion to the desired product. The reaction mixture was cooled to room temperature and filtered. The filtrate was concentrated under reduced pressure and the residue was purified by silica-gel column chromatography eluting with 80:1 dichloromethane/methanol to afford 265c (280 mg, 72%) as white solid. MS-ESI: [M+H]⁺ 380.2

Example 265d (2-{4,4-Dimethyl-9-oxo-1,10-diazatricyclo[6.4.0.0²,⁶]dodeca-2(6),7-dien-10-yl}-4-[1-methyl-6-oxo-5-({5-propanoyl-4H,5H,6H,7H-pyrazolo[1,5-a]pyrazin-2-yl}amino)-1,6-dihydropyridin-3-yl]pyridin-3-yl)methyl Acetate 265d A 50-mL single-neck round-bottomed flask equipped with a magnetic stirrer and a reflux condenser was charged with 265c (200 mg, 0.53 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (834 mg, 2.10 mmol), Pd(dppf)Cl₂ (19 mg, 0.0263 mmol), K₃PO₄ (223 mg, 1.052 mmol), sodium acetate (86 mg, 1.052 mmol), acetonitrile (10 mL), and water (5 drops). After three cycles of vacuum/argon flush, the reaction mixture was heated at 100° C. for 3 h. Analysis of the reaction mixture by LCMS showed complete conversion to the desired product. The reaction mixture was cooled down to room temperature and filtered. The filtrate was concentrated under reduced pressure and the residue was purified by silica-gel column chromatography eluting with 60:1 dichloromethane/methanol to afford 265d (100 mg, 29%) as yellow oil. MS-ESI: [M+H]⁺ 653.3

Example 265

3-[3-(hydroxymethyl)-4-[1-methyl-6-oxo-5-[(5-propanoyl-6,7-dihydro-4H-pyrazolo[1,5-a]pyrazin-2-yl)amino]-3-pyridyl]-2-pyridyl]-7,7-dimethyl-1,2,6,8-tetrahydrocyclopenta[3,4]pyrrolo[3,5-b]pyrazin-4-one 265

To a solution of 265d (100 mg, 0.153 mmol) in THF (3 mL), i-propanol (3 mL), and water (5 mL) was added lithium hydroxide (37 mg, 1.53 mmol). The reaction mixture was stirred at room temperature for 1 h. Analysis of the reaction mixture by LCMS showed complete conversion to the desired product. The mixture was concentrated under reduced pressure and the residue was purified by reverse-phase prep-HPLC to afford 265 (50 mg, 54%) as white solid. MS-ESI: [M+H]⁺ 611.3. ¹H NMR (500 MHz, DMSO-d₆, T=80° C.) δ 8.45 (d, J=8.5 Hz, 1H), 7.93-7.90 (m, 2H), 7.35 (d, J=3.5 Hz, 1H), 7.29 (d, J=8.5 Hz, 1H), 6.55 (s, 1H), 5.98 (s, 1H), 4.74-4.71 (m, 1H), 4.65 (s, 2H), 4.46-4.44 (m, 2H), 4.18-4.16 (m, 2H), 3.97-3.87 (m, overlap, 5H), 3.58 (s, 3H), 2.57-2.56 (m, 2H), 2.49-2.37 (m, 4H), 1.22 (s, 6H), 1.03 (t, J=12.0 Hz, 3H).

Example 266a 5-bromo-1-methyl-3-((5-(oxetan-3-yl)-1H-pyrazol-3-yl)amino)pyridin-2(1H)-one 266a

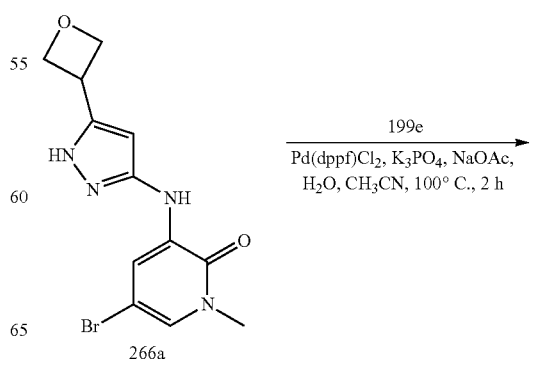

266a

-continued

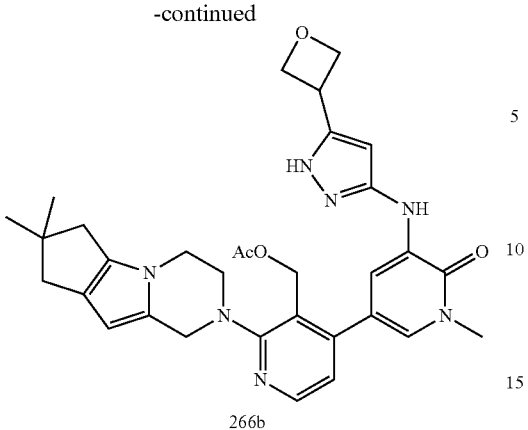

266b

Following the reaction scheme of FIG. 26, 266a was prepared.

Example 266b (2'-(7,7-dimethyl-1-oxo-3,4,7,8-tetrahydro-1H-cyclopenta[4,5]pyrrolo[1,2-a]pyrazin-2(6H)-yl)-1-methyl-5-(5-(oxetan-3-yl)-1H-pyrazol-3-yl)amino)-6-oxo-1,6-dihydro-[3,4'-bipyridin]-3'-yl)methyl acetate 266b A 25-mL single-neck round-bottomed flask equipped with a magnetic stirrer and a reflux condenser was charged with 266a (33 mg, 0.10 mmol), {3-[(acetyloxy)methyl]-2-{4,4-dimethyl-9-oxo-1,10-diazatricyclo[6.4.0.0$^{2,6}$]dodeca-2(6), 7-dien-10-yl}pyridin-4-yl}boronic acid 199e (60 mg, 0.15 mmol), Pd(dppf)Cl$_2$ (7 mg, 0.010 mmol), K$_3$PO$_4$ (42 mg, 0.20 mmol), sodium acetate (16 mg, 0.20 mmol), acetonitrile (6 mL), water (0.1 mL). After three cycles of vacuum/argon flush, the mixture was heated at reflux for 2 h. It was then cooled to room temperature and filtered. The filtrate was concentrated under reduced pressure and the resulting residue was purified by silica-gel column chromatography eluting with 30:1 dichloromethane/methanol to afford 266b as a white solid (17 mg, 28%). MS-ESI: [M+H]$^+$ 598.4

Example 266

3-[3-(hydroxymethyl)-4-[1-methyl-5-[[5-(oxetan-3-yl)-1H-pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 266

A mixture of 266b (15 mg, 0.025 mmol) and lithium hydroxide (6 mg, 0.25 mmol) in i-propanol/THF (1:1, 4 mL) and water (1 mL) was stirred at 30° C. for 1 h. The mixture was evaporated under reduced pressure and the residue was diluted with water (5 mL). It was then extracted with ethyl acetate (2×10 mL). The combined ethyl acetate extract was concentrated under reduced pressure and the residue was purified by reverse-phase prep-HPLC to afford 266 (4.5 mg, 33%) as a white solid. MS-ESI: [M+H]$^+$ 556.3. $^1$H NMR (500 MHz, CDCl$_3$) δ 8.49 (d, J=5.0 Hz, 1H), 7.98 (s, 1H), 7.68 (s, 1H), 7.58 (s, 1H), 7.33 (d, J=5.0 Hz, 1H), 6.86 (s, 1H), 6.09 (s, 1H), 5.07-5.04 (m, 2H), 4.79-4.76 (m, 2H), 4.68-4.66 (m, 1H), 4.54-4.51 (m, 1H), 4.37-4.34 (m, 1H), 4.28-4.25 (m, 1H), 4.18 (d, J=5.5 Hz, 2H), 3.89-3.87 (m, 1H), 3.73 (s, 3H), 2.59-2.57 (m, 2H), 2.54-2.52 (m, 3H), 1.29 (s, 6H).

Example 267a

5-Bromo-1-methyl-3-(5-methyl-1,3,4-thiadiazol-2-ylamino)pyridin-2(1H)-one 267a

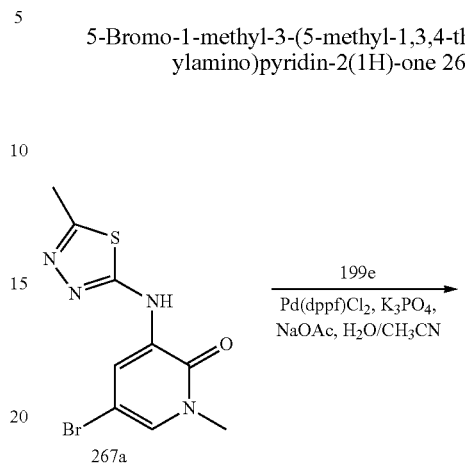

267a

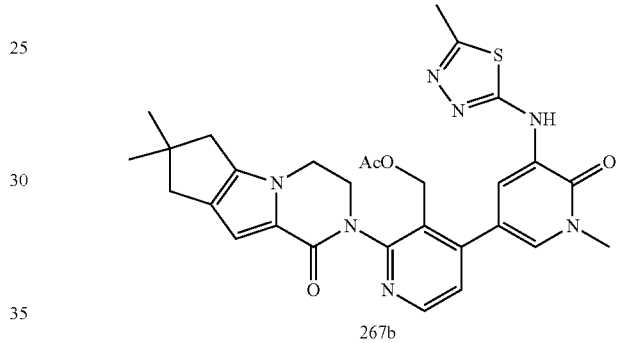

267b

A 100-mL single-neck round-bottomed flask equipped with a magnetic stirrer and a reflux condenser was charged with 5-methyl-1,3,4-thiadiazol-2-amine (1.15 g, 10.0 mmol), 3,5-dibromo-1-methylpyridin-2(1H)-one (4.00 g, 15.0 mmol), Pd$_2$(dba)$_3$ (916 mg, 1.0 mmol), Xantphos (1.16 g, 2.0 mmol), Cs$_2$CO$_3$ (6.52 g, 20.0 mmol), and dioxane (50 mL). After three cycles of vacuum/argon flush, the mixture was heated at 100° C. for 3 h. It was then cooled to room temperature and filtered. The filtrate was evaporated under reduced pressure and the resulting residue was purified by silica-gel column chromatography eluting with 20:1 dichloromethane/methanol to afford 267a (2.2 g, 73%) as white solid. MS-ESI: [M+H]$^+$ 301.2

Example 267b (2-{4,4-Dimethyl-9-oxo-1,10-diazatricyclo[6.4.0.0$^{2,6}$]dodeca-2(6),7-dien-10-yl}-4-{1-methyl-5-[(5-methyl-1,3,4-thiadiazol-2-yl)amino]-6-oxo-1,6-dihydropyridin-3-yl}pyridin-3-yl)methyl Acetate 267b A 50-mL round-bottomed flask equipped with a reflux condenser was charged with 267a (150 mg, 0.50 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (640 mg, 1.5 mmol), PdCl$_2$(dppf) (37 mg, 0.050 mmol), K$_3$PO$_4$ (212 mg, 1.0 mmol), sodium acetate (82 mg, 1.0 mmol), acetonitrile (10 mL), and water (0.2 mL). After three cycles of vacuum/argon flush, the mixture was heated at 90° C. for 2 h. It was then cooled to room temperature and filtered. The filtrate was evaporated under reduced pressure and the resulting residue was purified by silica-gel column chromatography eluting with 50:1 dichloromethane/methanol to afford 267b (80 mg, 28%) as yellow solid. MS-ESI: [M+H]+ 574.2

Example 267

3-[3-(hydroxymethyl)-4-[1-methyl-5-[(5-methyl-1,3,4-thiadiazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 267

A 25-mL round-bottomed flask equipped with a magnetic stirrer was charged 267b (80 mg, 0.14 mmol), lithium hydroxide (17 mg, 0.70 mmol), THF (2 mL), i-propanol (2 mL), and water (0.5 mL). The mixture was stirred at room temperature for 1 h and concentrated under reduced pressure. The residue was diluted with water (5 mL) extracted with dichloromethane (10 mL×3) and the combined organic layer was concentrated under reduced pressure. The residue was purified by reverse-phase prep-HPLC to afford 267 (32 mg, 43%) as white solid. MS-ESI: [M+H]+ 532.3. $^1$H NMR (500 MHz, DMSO-d$_6$) δ 10.19 (s, 1H), 8.57 (d, J=3.0 Hz, 1H), 8.49 (d, J=6.0 Hz, 1H), 7.63 (d, J=3.0 Hz, 1H), 7.32 (d, J=6.0 Hz, 1H), 6.56 (s, 1H), 4.92 (t, J=6.5 Hz, 1H), 4.45-4.37 (m, 2H), 4.22-4.17 (m, 3H), 3.85-3.80 (m, 1H), 3.60 (s, 3H), 2.58-2.56 (m, 2H), 2.52 (s, 3H), 2.42 (s, 2H), 1.17 (s, 6H).

Example 268a

1-Methyl-4-nitro-1H-imidazole 268a

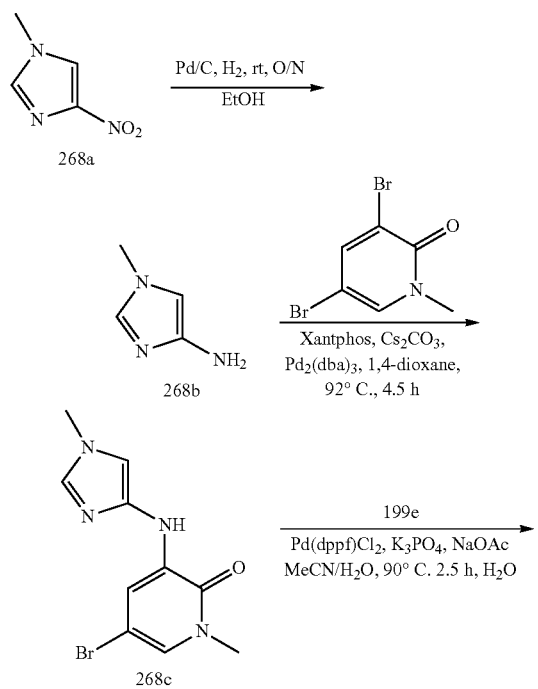

To a mixture of 4-nitro-1H-imidazole (2.0 g, 17.7 mmol) and K$_2$CO$_3$ (3.67 g, 26.5 mmol) in acetonitrile (20 mL) was added iodomethane (1.3 mL, 3.0 g, 21.2 mmol) dropwise while stirring at room temperature. The resulting mixture was stirred at 60° C. overnight. It was then evaporated under reduced pressure and the residue was diluted with water (20 mL). The mixture was extracted with dichloromethane (2×20 mL). The combined extract was concentrated under reduced pressure and the residue was purified by silica-gel column chromatography eluting with 100:1 dichloromethane/methanol to afford 268a as a yellow solid (1.8 g, 82%). MS-ESI: [M+H]+ 128.1. $^1$H NMR (500 MHz, DMSO-d$_6$) δ 8.37 (s, 1H), 7.82 (s, 1H), 3.76 (s, 3H).

Example 268b

1-Methyl-1H-imidazol-4-amine 268b

A 100-mL round-bottomed flask was charged with 268a (1.6 g, 12.6 mmol), 10% palladium on carbon (50% wet, 160 mg), and ethanol (15 mL). The flask was evacuated, charged with hydrogen gas, and stirred at room temperature overnight. The catalyst was removed by filtration through a pad of CELITE® and the filtrate was concentrated under reduced pressure to afford 268b (1.2 g, 98%) as a yellow solid. MS-ESI: [M+H]+ 98.2

Example 268c

5-Bromo-1-methyl-3-(1-methyl-1H-imidazol-4-ylamino)pyridin-2(1H)-one 268c

A 100-mL single-neck round-bottomed flask equipped with a magnetic stirrer and a reflux condenser was charged with 1,4-dioxane (50 mL), 268b (1.1 g, 11.3 mmol), 3,5-dibromo-1-methylpyridin-2(1H)-one (3.0 g, 11.3 mmol), Pd$_2$(dba)$_3$ (1.0 g, 1.13 mmol), XantPhos (1.3 g, 2.26 mmol), and cesium carbonate (7.3 g, 22.6 mmol). After three cycles of vacuum/argon flush, the mixture was heated at 92° C. for 4.5 hrs. It was then cooled to room temperature and filtered. The filtrate was concentrated under reduced pressure and the resulting residue was purified by silica-gel column chromatography eluting with dichloromethane/methanol (100:1 to 50:1) to afford 268c (2.4 g, 76%) as yellow solid. MS-ESI: [M+H]+ 283.1

Example 268d (2-{4,4-Dimethyl-9-oxo-1,10-diazatricyclo[6.4.0.0$^{2,6}$]dodeca-2(6),7-dien-10-yl}-4-{1-methyl-5-[(1-methyl-1H-imidazol-4-yl)amino]-6-oxo-1,6-dihydropyridin-3-yl}pyridin-3-yl)methyl Acetate 268d -continued

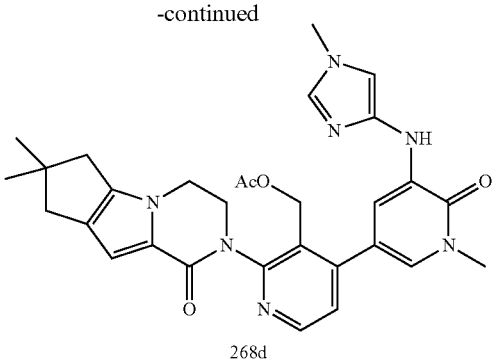

A 50-mL round-bottomed flask equipped with a reflux condenser was charged with 268c (150 mg, 0.53 mmol), {3-[(acetyloxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (80.4 mg, 0.21 mmol), Pd(dppf)Cl₂ (17.2 mg, 0.021 mmol), K₃PO₄ (89 mg, 0.42 mmol), sodium acetate (57.1 mg, 0.42 mmol), water (0.2 mL), and acetonitrile (10 mL). After three cycles of vacuum/argon flush, the mixture was heated at 90° C. for 2.5 hrs. It was then cooled to room temperature and filtered. The filtrate was concentrated under reduced pressure and the resulting residue was purified by silica-gel column chromatography eluting with dichloromethane/methanol (30:1 to 20:1) to afford 268d (110 mg, 37.2%) as brown solid. MS-ESI: [M+H]+ 556.4.

Example 268

3-[3-(hydroxymethyl)-4-[1-methyl-5-[(1-methylimidazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 268

A mixture of 268d (100 mg, 0.18 mmol) and lithium hydroxide (189 mg, 4.5 mmol) in i-propanol/THF (1:1, 4.0 mL) and water (1.0 mL) was stirred at 35° C. for 30 min. The mixture was concentrated under reduced pressure. To the residue was added water (5 mL) and the resulting mixture was extracted with dichloromethane (3×10 mL). The combined organic layer was concentrated under reduced pressure and the resulting residue was purified by reverse-phase prep-HPLC to afford 268 (19.8 mg, 22%) as a yellow solid. MS-ESI: [M+H]⁺ 514.3. ¹H NMR (500 MHz, DMSO-d₆) δ 8.47 (d, J=5.5 Hz, 1H), 7.57 (s, 1H), 7.44 (d, J=2.5 Hz, 1H), 7.39 (s, 1H), 7.36 (d, J=2.5 Hz, 1H), 7.34 (d, J=5.0 Hz, 1H), 6.95 (s, 1H), 6.56 (s, 1H), 5.12-5.10 (m, 1H), 4.44-4.41 (m, 2H), 4.22-4.18 (m, 3H), 3.84-3.82 (m, 1H), 3.60 (s, 3H), 3.59 (s, 3H), 2.59-2.56 (m, 2H), 2.44-2.42 (m, 2H), 1.22 (s, 6H).

Example 269a

2-{4,4-Dimethyl-9-oxo-1,10-diazatricyclo[6.4.0.0²,⁶]dodeca-2(6),7-dien-10-yl}-4-[1-methyl-5-({5-[(morpholin-4-yl)carbonyl]pyridin-2-yl}amino)-6-oxo-1,6-dihydropyridin-3-yl]pyridine-3-carbaldehyde 269a

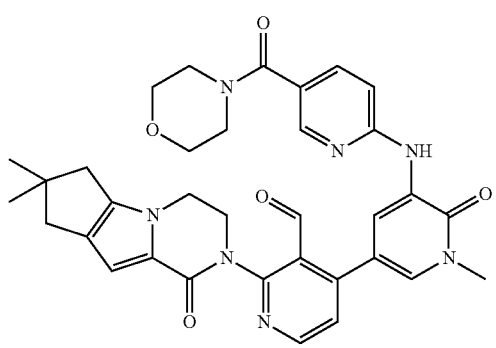

A 50-mL single-neck round-bottomed flask equipped with a magnetic stirrer and a reflux condenser was charged with 4-chloro-2-{4,4-dimethyl-9-oxo-1,10-diazatricyclo[6.4.0.0²,⁶]dodeca-2(6),7-dien-10-yl}pyridine-3-carbaldehyde 108a (100 mg, 0.29 mmol), 1-methyl-3-(5-(morpholine-4-carbonyl)pyridin-2-ylamino)-5-(4,4,5,5-tetramethyl-1,3,2-di-oxaborolan-2-yl)pyridin-2(1H)-one 111c (192 mg, 0.44 mmol), Pd(dppf)Cl₂ (12 mg, 0.015 mmol), K₃PO₄ (123 mg, 0.58 mmol), sodium acetate (47 mg, 0.58 mmol), acetonitrile (10 mL), and water (5 drops). After three cycles of vacuum/N₂ flush, the mixture was heated at 100° C. for 1 h. Analysis of the reaction mixture by LCMS showed complete conversion to the desired product. It was cooled to room temperature, and filtered. The filtrate was concentrated under reduced pressure and the residue was purified by silica-gel column chromatography (dichloromethane/methanol 40:1) to afford 269a (150 mg, 83%) as a brown solid. MS-ESI: [M+H]⁺ 621.8

Example 269

3-[3-(hydroxymethyl)-4-[1-methyl-5-[[5-(morpholine-4-carbonyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 269

To a solution of 269a (150 mg, 0.24 mmol) in dichloromethane (5 mL) and methanol (5 mL) was added NaBH₄ (18.2 mg, 0.482 mmol). After stirring at room temperature for 1 h, the mixture was quenched with aqueous NH₄Cl (10 mL) and concentrated under reduced pressure. The residue was extracted with dichloromethane (3×20 m). The combined extract was washed with brine, dried over Na₂SO4, concentrated under reduced pressure, and purified by reverse-phase prep-HPLC to afford 269 (114 mg, 76%) as a white solid. MS-ESI: [M+H]⁺ 624.3. ¹H NMR (500 MHz, DMSO-d₆) δ 9.00 (s, 1H), 8.79 (d, J=2.0 Hz, 1H), 8.50 (d, J=4.5 Hz, 1H), 8.26 (d, J=1.5 Hz, 1H), 7.67 (dd, J=2.0, 9.0 Hz, 1H), 7.61 (d, J=1.5 Hz, 1H), 7.38-7.36 (m, 2H), 6.56 (s, 1H), 5.00 (s, 1H), 4.47-4.40 (m, 2H), 4.25-4.19 (m, 3H), 3.86-3.84 (m, 1H), 3.62-3.60 (overlap, m, 4H), 3.51 (s, 3H), 3.52-3.50 (m, 4H), 2.59-2.57 (m, 2H), 2.43 (s, 2H), 1.22 (s, 6H).

Example 270a

Ethyl N-[(Pyrazin-2-yl)carbamothioyl]carbamate 270a

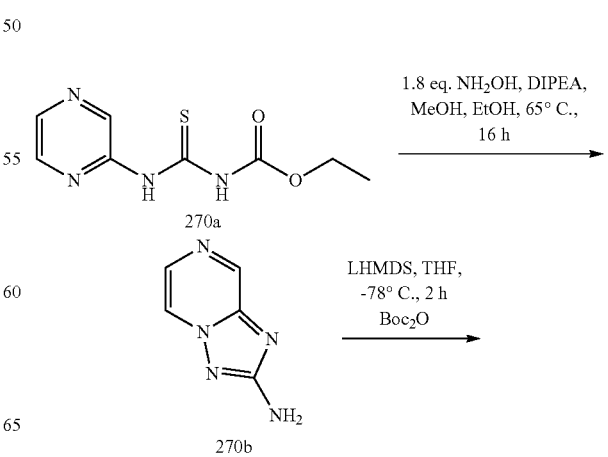

-continued

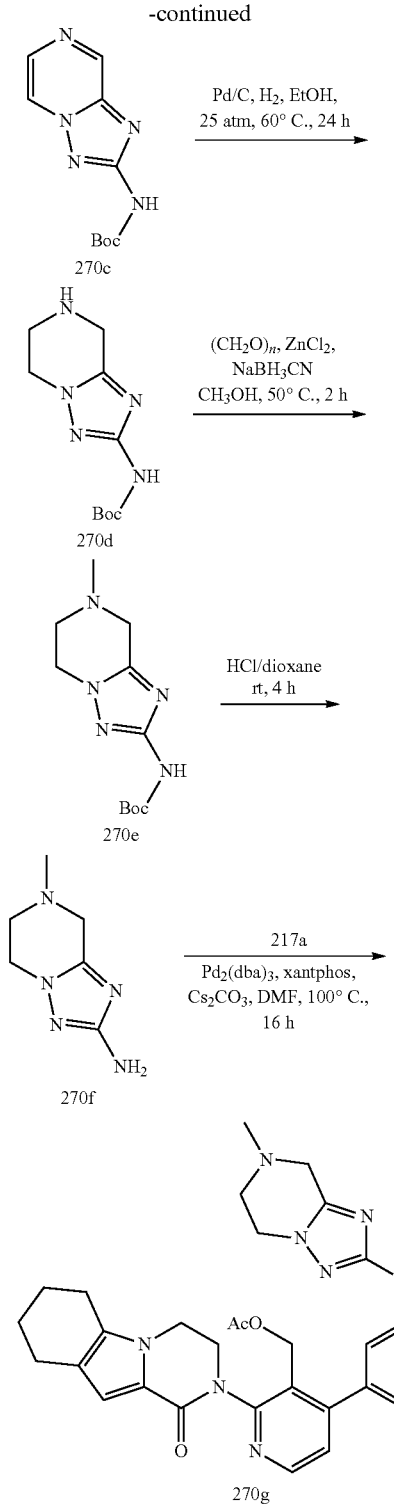

washed with ethyl acetate (3×20 mL) to afford 270a (14.0 g, 77%) as a white solid. MS-ESI: [M+H]⁺ 227.3

Example 270b

[1,2,4]Triazolo[1,5-a]pyrazin-2-amine 270b

A 250-mL single-neck round-bottomed flask equipped with a magnetic stirrer and a reflux condenser was charged with 270a (6.00 g, 26.43 mmol, 1.0 eq.), hydroxylamine hydrochloride (3.32 g, 47.52 mmol, 1.8 eq.), DIPEA (12 mL), ethanol (40 mL), and methanol (40 mL). The reaction mixture was stirred at 65° C. for 16 hours. After the reaction was complete, it was cooled to room temperature and concentrated to a volume of around 20 mL under reduced pressure. The resulting suspension was collected by filtration and the solid was washed with 60:1 dichloromethane/ethanol (50 mL) to afford 270b (3.3 g, 92%) as a white solid. MS-ESI: [M+H]⁺ 136.3. ¹H NMR (500 MHz, DMSO-$d_6$) δ 8.84 (d, J=1.0 Hz, 1H), 8.70 (dd, J=1.0, 4.0 Hz, 1H), 7.98 (d, J=5.0 Hz, 1H), 6.47 (s, 2H).

Example 270c tert-Butyl[1,2,4]Triazolo[1,5-a]pyrazin-2-ylcarbamate 270c

A 250-mL single-neck round-bottomed flask equipped with a magnetic stirrer was charged with 270b (2.00 g, 14.8 mmol, 1.0 eq.), Boc₂O (3.87 g, 17.77 mmol, 1.2 eq.), and anhydrous THF (60 mL). The system was evacuated and refilled with N₂. The reaction mixture was cooled to −78° C., followed by the addition of LHMDS (37.0 mL, 37.0 mmol, 2.5 eq., 1.0M in THF). After the reaction was stirred at −78° C. for 2 hours, it was quenched with saturated aqueous NH₄Cl solution (30 mL). The mixture was concentrated under reduced pressure and the residue extracted with dichloromethane (3×50 mL). The combined organic layer was dried over sodium sulfate, filtered, and concentrated under reduced pressure. The resulting residue was purified by silica-gel column chromatography eluting with 1:4 ethyl acetate/petroleum ether to afford 270c (1.87 g, 53%) as a white solid. MS-ESI: [M-t-Bu]⁺ 180.0. ¹H NMR (500 MHz, DMSO-$d_6$) δ 10.31 (s, 1H), 8.94 (s, 1H), 8.72 (d, J=3.5 Hz, 1H), 7.95 (d, J=4.0 Hz, 1H), 1.25 (s, 9H).

Example 270d tert-Butyl 5,6,7,8-Tetrahydro-[1,2,4]triazolo[1,5-a]pyrazin-2-ylcarbamate 270d A 100-mL round-bottomed flask was purged with nitrogen and charged with 270c (1.0 g, 4.25 mmol), 20% palladium on carbon (10% wet, 200 mg), and ethanol (40 mL). It was then evacuated, charged with hydrogen gas (25 atm), and stirred at 60° C. for 24 h. The hydrogen was evacuated and nitrogen was charged into the flask. The catalyst was removed by filtration through a pad of CELITE® and the filtrate was concentrated under reduced pressure to afford 270d (700 mg, 68%). MS-ESI: [M-t-Bu]⁺ 184.0

Example 270e tert-Butyl 7-Methyl-5,6,7,8-tetrahydro-[1,2,4]triazolo[1,5-a]pyrazin-2-yl-carbamate 270e Following the procedure in Example 191i, and starting with 270d (500 mg, 2.1 mmol, 1.0 eq.), paraformaldehyde A 250-mL single-neck round-bottomed flask equipped with a magnetic stirrer was charged with pyrazin-2-amine (7.6 g, 80.0 mmol, 1.0 eq.), O-ethyl carbonisothiocyanatidate (12.5 g, 95.4 mmol, 1.2 eq.), and dioxane (150 mL). The reaction mixture was stirred at room temperature for 24 hours. After the reaction was complete, it was concentrated to a volume of around 20 mL under reduced pressure and the resulting suspension was filtered. The solid was collected and (630 mg, 21.0 mmol, 10.0 eq.), ZnCl2/diethyl ether (2.1 mL, 2.1 mmol, 1.0 M), NaBH3CN (390 mg, 6.3 mmol, 3.0 eq.), and methanol (20 mL) afforded 270e as a yellow solid (500 mg, 94%). MS-ESI: [M-tBu]+ 198.0.

Example 270f

7-Methyl-5,6,7,8-tetrahydro-[1,2,4]triazolo[1,5-a]pyrazin-2-amine 270f

Following the procedure in Example 131e, and starting with 270e (500 mg, 1.97 mmol) Boc deprotection with acid afforded 270f as a yellow solid (200 mg, 66%). MS-ESI: [M+H]+ 154.1.

Example 270g (4-(1-Methyl-5-(7-methyl-5,6,7,8-tetrahydro-[1,2,4]triazolo[1,5-a]pyrazin-2-ylamino)-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 270g A 50-mL single-neck round-bottomed flask equipped with a magnetic stirrer and a reflux condenser was charged with 270f (100 mg, 0.65 mmol, 1.7 eq.), (4-(5-bromo-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 217a (200 mg, 0.38 mmol, 1.0 eq.), DMF (10 mL), and cesium carbonate (499 mg, 1.52 mmol, 4.0 eq.). After bubbling nitrogen through the resulting solution for 10 minutes, Xantphos (44 mg, 0.076 mmol, 0.20 eq.) and tris(dibenzylideneacetone)dipalladium(0) (35 mg, 0.038 mmol, 0.10 eq.) were added. The reaction mixture was subjected to three cycles of vacuum/argon flush and heated at 100° C. for 16 h. After this time the reaction was cooled to room temperature and filtered. The filtrate was partitioned between ethyl acetate (50 mL) and water (10 mL). The aqueous layer was separated and extracted with ethyl acetate (3×20 mL). The combined organic layer was concentrated under reduced pressure. The residue was purified on silica-gel column chromatography eluting with 50:1 dichloromethane/methanol to afford 270g (90 mg, 41%). MS-ESI: [M+H]+ 598.3.

Example 270

2-[3-(hydroxymethyl)-4-[1-methyl-5-[(7-methyl-6,8-dihydro-5H-[1,2,4]triazolo[1,5-a]pyrazin-2-yl)amino]-6-oxo-3-pyridyl]-2-pyridyl]-3,4,6,7,8,9-hexahydropyrazino[1,2-a]indol-1-one 270

Following the procedure for Example 241, and starting with 270g (90 mg, 0.15 mmol), afforded 270 as a white solid (47 mg, 56%). MS-ESI: [M+H]+ 556.3. 1H NMR (500 MHz, DMSO-$d_6$) δ 8.50 (d, J=5.0 Hz, 1H), 8.03 (d, J=2.5 Hz, 1H), 7.83 (s, 1H), 7.50 (d, J=2.5 Hz, 1H), 7.33 (d, J=5.5 Hz, 1H), 6.58 (s, 1H), 4.93 (t, J=5.5 Hz, 1H), 4.44-4.38 (m, 2H), 4.24-4.02 (m, 5H), 3.88-3.85 (m, 1H), 3.61-3.59 (m, overlap, 5H), 2.87 (t, J=5.5 Hz, 2H), 2.64-2.58 (m, 2H), 2.49-2.46 (m, 2H), 2.40 (s, 3H), 1.80-1.69 (m, 4H).

Example 271a (S)-tert-Butyl 4-(6-(5-Chloro-2-methoxypyridin-3-ylamino)pyridin-3-yl)-3-methylpiperazine-1-carboxylate 271a

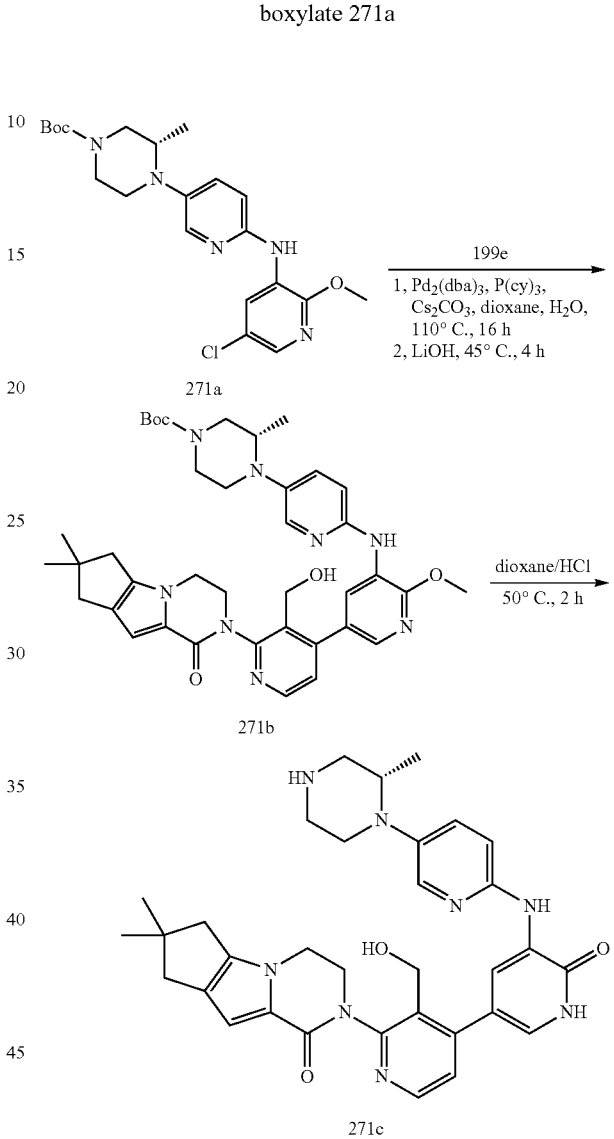

A 100-mL single-neck round-bottomed flask equipped with a magnetic stirrer and a reflux condenser was charged with 1,4-dioxane (40 mL), (S)-tert-butyl 4-(6-amino pyridin-3-yl)-3-methylpiperazine-1-carboxylate 101h (2.04 g, 7.0 mmol), 3-bromo-5-chloro-2-methoxypyridine (2.8 g, 12.6 mmol), Pd2(dba)3 (640 mg, 0.70 mmol), XantPhos (404.6 mg, 0.70 mmol), and cesium carbonate (4.56 g, 14.0 mmol). After three cycles of vacuum/argon flush, the mixture was heated at 100° C. for 4 h. After this time the reaction was cooled to room temperature. It was then filtered and the filtrate was evaporated under reduced pressure. The residue was purified by silica-gel column chromatography eluting with 1:3 ethyl acetate/petroleum ether to afford 271a (1.7 g, 57%) as a yellow solid. MS-ESI: [M+H]+ 434.2

Example 271b tert-Butyl (3S)-4-(6-{[5-(2-{4,4-Dimethyl-9-oxo-1,10-diazatricyclo[6.4.0.0²,⁶]dodeca-2(6),7-dien-10-yl}-3-(hydroxymethyl)pyridin-4-yl)-2-methoxypyridin-3-yl]amino}pyridin-3-yl)-3-methylpiperazine-1-carboxylate 271b A 100-mL single-neck round-bottomed flask equipped with a magnetic stirrer and a reflux condenser was charged with 271a (650 mg, 1.50 mmol), {3-[(acetyloxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (1.79 g, 4.5 mmol), Pd₂(dba)₃ (137.2 mg, 0.15 mmol), P(cy)₃ (167.4 mg, 0.60 mmol), Cs₂CO₃ (978 mg, 3.0 mmol), dioxane (20 mL), and water (0.5 mL). After three cycles of vacuum/argon flush, the mixture was heated at 110° C. for 16 h. After this time the reaction was cooled to room temperature. Lithium hydroxide monohydrate (1.89 g, 45 mmol) and water (2.0 mL) were added. The resulting mixture was stirred at 45° C. for 4 h. It was then filtered and the filtrate was evaporated under reduced pressure. The residue was purified by silica-gel column chromatography eluting with 3:1 ethyl acetate/petroleum ether to afford 271b (290 mg, 27%) as a yellow solid. MS-ESI: [M+H]⁺ 709.3

Example 271c

10-[3-(Hydroxymethyl)-4-[5-({5-[(2S)-2-methylpiperazin-1-yl]pyridin-2-yl}amino)-6-oxo-1,6-dihydropyridin-3-yl]pyridin-2-yl]-4,4-dimethyl-1,10-diazatricyclo[6.4.0.0²,⁶]dodeca-2(6),7-dien-9-one 271c A solution of 271b (286.6 mg, 0.40 mmol) in dioxane/HCl (30 mL) was stirred at 50° C. for 2 h. It was evaporated under reduced pressure to afford 271c (450 mg, crude) as a black solid. MS-ESI: [M+H]⁺ 595.3

Example 271

3-[3-(hydroxymethyl)-4-[5-[[5-[(2S)-2-methyl-4-(oxetan-3-yl)piperazin-1-yl]-2-pyridyl]amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one 271

To a solution of 271c (450 mg, 0.75 mmol) in methanol (10 mL) was added oxetan-3-one (162 mg, 2.25 mmol), NaBH₃CN (141.8 mg, 2.25 mmol), and ZnCl₂ (306 mg, 2.25 mmol). The reaction was stirred at room temperature for 3 h. The mixture was evaporated under reduced pressure and the residue was diluted with water (5 mL). It was then extracted with dichloromethane (3×10 mL) and the combined dichloromethane extract was concentrated under reduced pressure. The residue was purified by reverse-phase prep-HPLC to afford 271 (23.0 mg, 8.8%, over two steps) as a yellow solid. MS-ESI: [M+H]⁺ 651.3. ¹H NMR (500 MHz, CDCl₃) δ 9.76 (s, 1H), 8.74 (d, J=2.0 Hz, 1H), 8.53 (d, J=5.0 Hz, 1H), 7.99 (d, J=3.0 Hz, 1H), 7.84 (s, 1H), 7.73 (s, 1H), 7.41 (d, J=4.5 Hz, 1H), 7.35 (dd, J=2.5 Hz, 8.5 Hz, 1H), 6.87 (s, 1H), 6.85 (d, J=9.0 Hz, 1H), 5.16-5.13 (m, 1H), 4.72-4.69 (m, 5H), 4.54-4.53 (m, 1H), 4.36-4.35 (m, 1H), 4.19-4.17 (m, 2H), 3.89-3.87 (m, 1H), 3.56-3.49 (m, 2H), 3.11-3.09 (m, 2H), 2.60-2.48 (m, overlap, 7H), 2.24-2.21 (m, 1H), 1.29 (s, 6H), 1.02 (d, J=6.0 Hz, 3H)

Example 272a

5-Bromo-1-methyl-3-(5-(1-(oxetan-3-yl)azetidin-3-yl)pyridin-2-ylamino)pyridine-2(1H)-one 272a

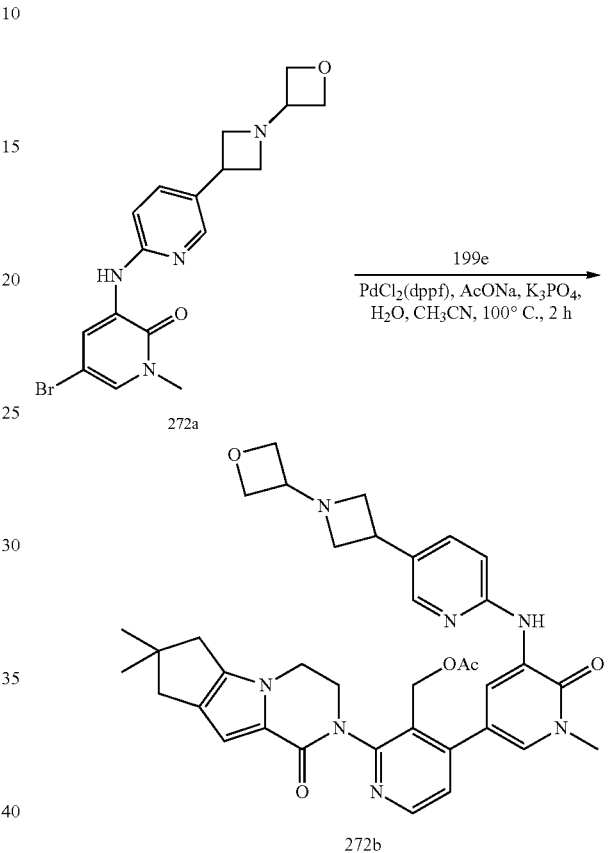

A mixture of 3-(5-(azetidin-3-yl)pyridin-2-ylamino)-5-bromo-1-methylpyridin-2(1H)-one 239b (140 mg, 0.42 mmol), oxetan-3-one (91 mg, 1.26 mmol), NaBH₃CN (78 mg, 1.26 mmol), and zinc chloride (171 mg, 1.26 mmol) in methanol (10 mL) was stirred at 50° C. for 2 hours. The mixture was concentrated under reduced pressure and water (5 mL) was added to the residue. It was then extracted with dichloromethane (3×10 mL). The combined organic layer was concentrated under reduced pressure. The residue was purified by column chromatography eluting with 50:1 dichloromethane/methanol to afford 272a (145 mg, 85%). MS-ESI: [M+H]⁺ 390.8

Example 272b (2-{4,4-Dimethyl-9-oxo-1,10-diazatricyclo[6.4.0.0²,⁶]dodeca-2(6),7-dien-10-yl}-4-[1-methyl-5-({5-[1-(oxetan-3-yl)azetidin-3-yl]pyridin-2-yl}amino)-6-oxopyridin-3-yl]pyridin-3-yl)methyl Acetate 272b A 25-ml round-bottomed flask equipped with a reflux condenser was charged with 272a (140 mg, 0.35 mmol), {3-[(acetoxy)methyl]-2-{4,4-dimethyl-9-oxo-1,10-diaza-tricyclo[6.4.0.0²,⁶]dodeca-2(6),7-dien-10-yl}pyridin-4- yl}boronic acid 199e (140 mg, 0.35 mmol), Pd(dppf)Cl₂ (28 mg, 0.035 mmol), sodium acetate (58 mg, 0.70 mmol,), K₃PO₄ (148 mg, 0.70 mmol), water (6 drops), and acetonitrile (6 mL). After three cycles of vacuum/argon flush, the mixture was heated at 100° C. for 2 h. It was then filtered and the filtrate was evaporated under reduced pressure. The residue was purified by silica-gel column chromatography eluting with 25:1 dichloromethane/methanol to afford 272b (114 mg, 46%) as a brown solid. MS-ESI: [M+H]⁺ 664.4

Example 272

3-[3-(hydroxymethyl)-4-[1-methyl-5-[[5-[1-(oxetan-3-yl)azetidin-3-yl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one 272

A mixture of 272b (114 mg, 0.17 mmol) and lithium hydroxide (41 mg, 1.7 mmol) in i-propanol/THF (1:1, 4 mL) and water (1 mL) was stirred at 30° C. for 1 h. The mixture was evaporated in vacuo and the residue was diluted with water (5 mL). It was then extracted with ethyl acetate (3×10 mL). The combined ethyl acetate extract was concentrated under reduced pressure and the residue was purified by reverse-phase prep-HPLC to afford 272 (52 mg, 50%) as a white solid. MS-ESI: [M+H]⁺ 622.3. ¹H NMR (500 MHz, CDCl₃) δ 8.77 (d, J=2.0 Hz, 1H), 8.52 (d, J=5.0 Hz, 1H), 8.19 (d, J=1.5 Hz, 1H), 7.94 (s, 1H), 7.90 (d, J=2.0 Hz, 1H), 7.61 (dd, J=2.0, 8.5 Hz, 1H), 7.38 (d, J=5.0 Hz, 1H), 6.86-6.84 (m, 2H), 5.12-5.09 (m, 1H), 4.77-4.74 (m, 2H), 4.69-4.66 (m, 1H), 4.61-4.59 (m, 2H), 4.54 (bs, 1H), 4.36-4.32 (m, 1H), 4.19-4.17 (m, 2H), 3.90-3.83 (m, 2H), 3.80-3.77 (m, 2H), 3.74 (s, 3H), 3.71-3.68 (m, 1H), 3.30-3.27 (m, 2H), 2.60-2.59 (m, 2H), 2.54 (s, 2H), 1.30 (s, 6H).

Example 273a

[4-(5-Bromo-1-methyl-6-oxo-1,6-dihydropyridin-3-yl)-2-{4,4-dimethyl-9-oxo-1,10-diazatricyclo[6.4.0.0²,⁶]dodeca-2(6),7-dien-10-yl}pyridin-3-yl]methyl acetate 273a

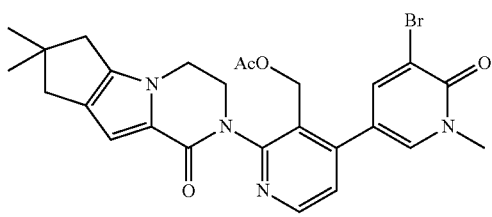

A 100-mL single-neck round-bottomed flask equipped with a magnetic stirrer was charged with 3-bromo-5-iodo-1-methylpyridin-2(1H)-one 214b (1.57 g, 5.0 mmol), {3-[(acetyloxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (1.98 g, 5.0 mmol), PdCl₂(dppf) (205 mg, 0.25 mmol), K₃PO₄ (2.12 g, 10.0 mmol), sodium acetate (820 mg, 10.0 mmol), acetonitrile (45 mL), and water (1 mL). The system was evacuated and refilled with N₂. The reaction mixture was stirred at 30° C. for 3 h. It was then filtered and the filtrate was concentrated under reduced pressure. The resulting residue was purified by silica-gel column chromatography eluting with 30:1 dichloromethane/methanol to afford 273a (580 mg, 22%) as a white solid. MS-ESI: [M+H]⁺ 539.2. ¹H NMR (500 MHz, CDCl₃) δ 8.49 (d, J=5.0 Hz, 1H), 7.84 (d, J=2.5 Hz, 1H), 7.45 (d, J=2.0 Hz, 1H), 7.09 (d, J=5.0 Hz, 1H), 6.79 (s, 1H), 5.15 (s, 2H), 4.55-4.51 (m, 1H), 4.27-4.25 (m, 1H), 4.15-4.13 (m, 1H), 4.06-4.04 (m, 1H), 3.68 (s, 3H), 2.58-2.56 (m, 2H), 2.51 (s, 2H), 1.86 (s, 3H), 1.28 (s, 6H).

Example 273b (2'-(7,7-dimethyl-1-oxo-3,4,7,8-tetrahydro-1H-cyclopenta[4,5]pyrrolo[1,2-a]pyrazin-2(6H)-yl)-1-methyl-6-oxo-5-(pyridin-2-ylamino)-1,6-dihydro-[3,4'-bipyridin]-3'-yl)methyl acetate 273b

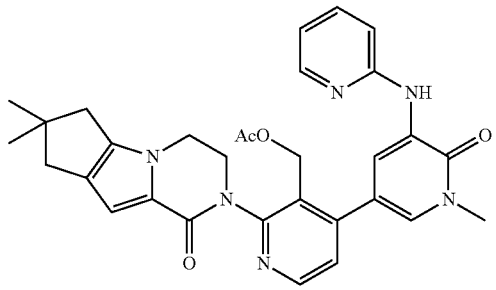

Into a 1-dram vial was added 273a (40 mg, 0.074 mmol), 2-aminopyridine, (1.2 equiv), cesium carbonate (1.5 equiv), Xantphos (10 mol %) and tris(dibenzylideneacetone)dipalladium(0) (5 mol %) in dry 1,4-dioxane (0.2 M). The reaction was then stirred at 80° C. for 3 hours. After cooling to room temperature, the reaction was then diluted with dichloromethane (3 mL) and washed with water (2×3 mL). The organic layer was dried over magnesium sulfate, filtered and concentrated in vacuo. The crude product 273b was then carried on to the subsequent step without purification.

Example 273

3-[3-(hydroxymethyl)-4-[1-methyl-6-oxo-5-(2-pyridylamino)-3-pyridyl]-2-pyridyl]-7,7-dimethyl-1,2,6,8-tetrahydrocyclopenta[3,4]pyrrolo[3,5-b]pyrazin-4-one 273

Into a 1 dram vial was added 273b (1 equiv) in a 4:1 mixture of THF and water (1 mL). Lithium hydroxide (1.5 equiv) was then added to the mixture and the reaction was stirred at room temperature for 16 hours. The reaction was then diluted with dichloromethane (3 mL) and washed with water (2×3 mL). The organic layer was collected, dried over magnesium sulfate, filtered, and concentrated in vacuo. The crude material was purified by reverse-phase chromatography to give 273. ¹H NMR (400 MHz, DMSO-d6) δ 8.73 (d, J=2.4 Hz, 1H), 8.62 (s, 1H), 8.49 (d, J=5.0 Hz, 1H), 8.17 (dd, J=5.1, 1.9 Hz, 1H), 7.62-7.56 (m, 1H), 7.54 (d, J=2.5 Hz, 1H), 7.35 (d, J=5.1 Hz, 1H), 7.30 (d, J=8.5 Hz, 1H), 6.80 (dd, J=7.0, 5.1 Hz, 1H), 6.56 (s, 1H), 4.96-4.93 (m, 1H), 4.48-4.39 (m, 2H), 4.24-4.17

(m, 2H), 3.89-3.84 (m, 1H), 3.61 (s, 3H), 2.58 (d, J=8.0 Hz, 2H), 2.43 (s, 3H), 1.22 (s, 6H).

Example 274

3-[3-(hydroxymethyl)-4-[1-methyl-5-[(5-methylpyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 274

Following the procedures of Example 273, and substituting 2-amino-5-methylpyrazine for 2-aminopyridine, 274 was prepared. $^1$H NMR (400 MHz, DMSO-d6) δ 8.98 (s, 1H), 8.68-8.58 (m, 2H), 8.49 (d, J=5.1 Hz, 1H), 8.04 (s, 1H), 7.58 (d, J=2.4 Hz, 1H), 7.34 (d, J=5.1 Hz, 1H), 6.56 (s, 1H), 5.75 (s, 1H), 4.93 (t, J=5.2 Hz, 1H), 4.47-4.37 (m, 2H), 4.25-4.16 (m, 2H), 3.88-3.82 (m, 1H), 3.62 (s, 3H), 2.57 (d, J=8.0 Hz, 2H), 2.43 (s, 2H), 2.34 (s, 3H), 1.22 (s, 6H).

Example 275

3-[4-[5-[(5-fluoro-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 275

Following the procedures of Example 273, and substituting 2-amino-5-fluoropyridine for 2-aminopyridine, 275 was prepared. $^1$H NMR (400 MHz, DMSO-d6) δ 8.79 (s, 1H), 8.65 (d, J=2.4 Hz, 1H), 8.49 (d, J=5.1 Hz, 1H), 8.14 (d, J=3.1 Hz, 1H), 7.58 (td, J=8.7, 3.1 Hz, 1H), 7.54 (d, J=2.4 Hz, 1H), 7.40 (dd, J=9.2, 3.9 Hz, 1H), 7.35 (d, J=5.0 Hz, 1H), 6.56 (s, 1H), 4.98-4.91 (m, 1H), 4.46-4.38 (m, 2H), 4.23-4.16 (m, 2H), 3.88-3.82 (m, 1H), 3.61 (s, 3H), 2.61-2.51 (m, 2H), 2.43 (s, 2H), 1.22 (s, 6H).

Example 276

6-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyridine-3-carbonitrile 276

Following the procedures of Example 273, and substituting 2-amino-5-cyanopyridine for 2-aminopyridine, 276 was prepared. $^1$H NMR (400 MHz, DMSO-d6) δ 9.38 (s, 1H), 8.73 (d, J=2.2 Hz, 1H), 8.58 (d, J=2.4 Hz, 1H), 8.49 (d, J=5.0 Hz, 1H), 7.94 (dd, J=9.0, 2.4 Hz, 1H), 7.68 (d, J=2.4 Hz, 1H), 7.44 (d, J=8.9 Hz, 1H), 7.36 (d, J=5.2 Hz, 1H), 6.56 (s, 1H), 5.75 (s, 1H), 4.97 (t, J=5.3 Hz, 1H), 4.46-4.38 (m, 2H), 4.21 (s, 3H), 3.84 (s, 1H), 3.62 (s, 3H), 2.58 (d, J=8.1 Hz, 2H), 2.45 (s, 2H), 1.22 (s, 6H).

Example 277

3-[3-(hydroxymethyl)-4-[5-[(5-methoxy-2-pyridyl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 277

Following the procedures of Example 273, and substituting 2-amino-5-methoxypyridine for 2-aminopyridine, 277 was prepared. $^1$H NMR (400 MHz, DMSO-d6) δ 8.61 (d, J=2.4 Hz, 1H), 8.51-8.47 (m, 2H), 7.91 (d, J=2.4 Hz, 1H), 7.48 (d, J=2.4 Hz, 1H), 7.34 (d, J=5.0 Hz, 1H), 7.33-7.29 (m, 2H), 6.56 (s, 1H), 4.94 (t, J=5.3 Hz, 1H), 4.47-4.38 (m, 2H), 4.24-4.16 (m, 2H), 3.87-3.83 (m, 1H), 3.75 (s, 3H), 3.60 (s, 3H), 2.58 (d, J=7.9 Hz, 2H), 2.43 (s, 2H), 1.22 (s, 6H).

Example 278

3-[4-[5-[(5-cyclopropyl-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 278

Following the procedures of Example 273, and substituting 2-amino-5-cyclopropylpyridine for 2-aminopyridine, 278 was prepared. $^1$H NMR (400 MHz, DMSO-d6) δ 8.67 (d, J=2.4 Hz, 1H), 8.53-8.45 (m, 2H), 8.01 (d, J=2.5 Hz, 1H), 7.50 (d, J=2.4 Hz, 1H), 7.34 (d, J=5.0 Hz, 1H), 7.28 (dd, J=8.6, 2.5 Hz, 1H), 7.21 (d, J=8.6 Hz, 1H), 6.56 (s, 1H), 4.96-4.92 (m, 1H), 4.47-4.41 (m, 2H), 4.24-4.16 (m, 2H), 3.89-3.85 (m, 1H), 3.60 (s, 3H), 2.58 (d, J=7.9 Hz, 2H), 2.44 (s, 2H), 1.86-1.77 (m, 1H), 1.22 (s, 6H), 0.93 (t, J=8.0 Hz, 1H), 0.90-0.85 (m, 1H), 0.67-0.58 (m, 2H).

Example 279

3-[3-(hydroxymethyl)-4-[1-methyl-6-oxo-5-[[5-(trifluoromethyl)-2-pyridyl]amino]-3-pyridyl]-2-pyridyl]-7,7-dimethyl-1,2,6,8-tetrahydrocyclopenta[3,4]pyrrolo[3,5-b]pyrazin-4-one 279

Following the procedures of Example 273, and substituting 2-amino-5-trifluoromethylpyridine for 2-aminopyridine, 279 was prepared. $^1$H NMR (400 MHz, DMSO-d6) δ 9.23 (s, 1H), 8.80 (d, J=2.4 Hz, 1H), 8.54-8.46 (m, 2H), 7.88 (dd, J=8.7, 2.6 Hz, 1H), 7.66 (d, J=2.3 Hz, 1H), 7.48 (d, J=8.8 Hz, 1H), 7.37 (d, J=5.1 Hz, 1H), 6.56 (s, 1H), 4.97 (t, J=5.1 Hz, 1H), 4.50-4.40 (m, 2H), 4.26-4.16 (m, 2H), 3.90-3.81 (m, 1H), 3.62 (s, 3H), 2.58 (d, J=8.2 Hz, 2H), 2.43 (s, 2H), 1.22 (s, 6H).

Example 280

3-[3-(hydroxymethyl)-4-[1-methyl-5-[[1-methyl-5-(morpholine-4-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 280

Following the procedures of Example 273, and substituting (3-amino-1-methyl-1H-pyrazol-5-yl)(morpholino)methanone for 2-aminopyridine, 280 was prepared. $^1$H NMR (400 MHz, DMSO-d6) δ 8.48 (d, J=5.0 Hz, 1H), 8.27 (s, 1H), 8.05 (d, J=2.4 Hz, 1H), 7.43 (d, J=2.4 Hz, 1H), 7.33 (d, J=5.1 Hz, 1H), 6.55 (s, 1H), 6.30 (s, 2H), 4.99-4.91 (m, 1H), 4.48-4.39 (m, 2H), 4.23-4.15 (m, 7H), 3.89-3.82 (m, 2H), 3.72 (s, 3H), 3.59 (s, 3H), 3.27 (s, 2H), 2.58 (d, J=7.5 Hz, 2H), 2.43 (s, 2H), 1.22 (s, 6H).

Example 281

3-[3-(hydroxymethyl)-4-[1-methyl-5-[(5-methyl-2-pyridyl)amino]-6-oxo-3-pyridyl]-2-pyridyl]-7,7-dimethyl-1,2,6,8-tetrahydrocyclopenta[3,4]pyrrolo[3,5-b]pyrazin-4-one 281

Following the procedures of Example 273, and substituting 2-amino-5-methylpyridine for 2-aminopyridine, 281 was prepared. $^1$H NMR (400 MHz, DMSO-d6) δ 8.67 (d, J=2.4 Hz, 1H), 8.48 (d, J=5.4 Hz, 2H), 8.01 (d, J=2.3 Hz, 1H), 7.51 (d, J=2.4 Hz, 1H), 7.44 (dd, J=8.5, 2.4 Hz, 1H), 7.34 (d, J=5.1 Hz, 1H), 7.21 (d, J=8.5 Hz, 1H), 6.56 (s, 1H), 5.75 (s, 1H), 4.93 (t, J=5.4 Hz, 1H), 4.46-4.36 (m, 2H), 4.26-4.16 (m, 2H), 3.86-3.80 (m, 1H), 3.60 (s, 3H), 2.58 (d, J=7.8 Hz, 2H), 2.43 (s, 2H), 2.17 (s, 3H), 1.22 (s, 6H).

Example 282a

3,3-Dimethylcyclopentanone 282a

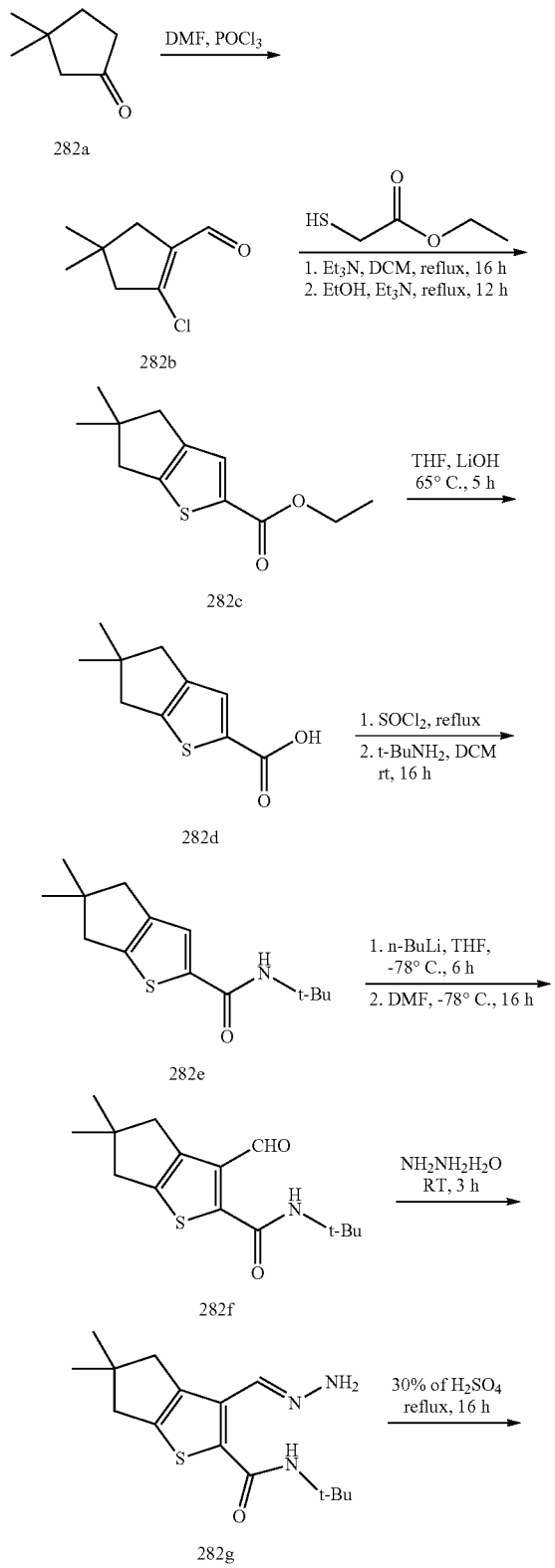

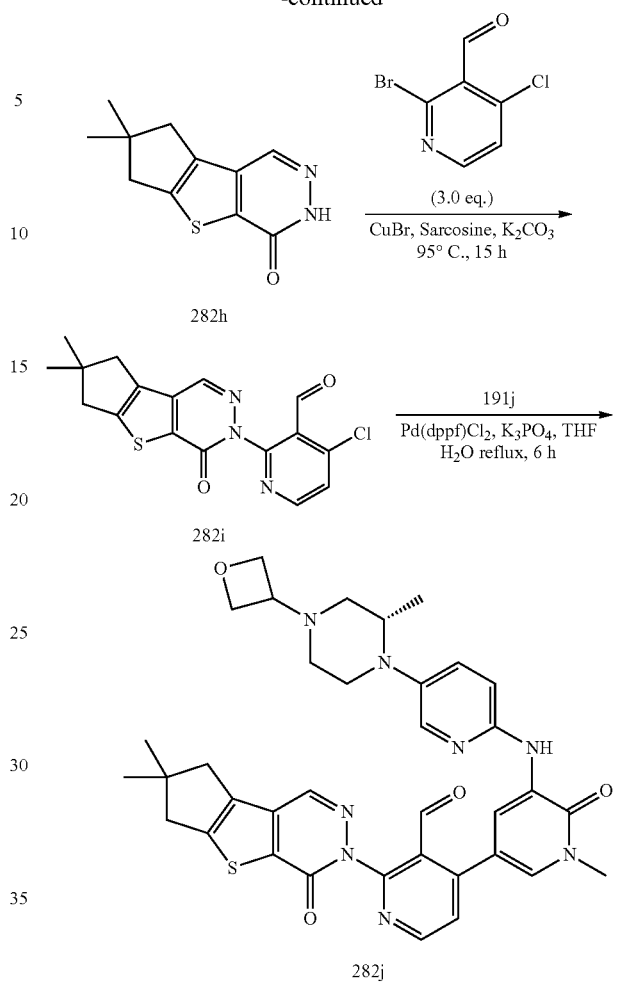

To a suspension of CuI (81.0 g, 420 mmol) in anhydrous ethyl ether (500 mL) cooled to 0° C. was added the solution of methyllithium in ethyl ether (430 mL, 860 mmol, 2.0M) over a period of 30 minutes. The mixture was stirred at 0° C. for 2 h. To the above mixture was added 3-methylcyclopent-2-enone (33.6 g, 350 mmol) dropwise over a period of 1 h at 0° C. The resulting mixture was stirred at 0° C. for another 2 h. It was then quenched with saturated $NH_4Cl$ (300 mL) and filtered. The filtrate was extracted with ethyl ether (2×200 mL). The combined organic layer was dried over anhydrous $Mg_2SO_4$ and filtered. The filtrate was evaporated under reduced pressure to afford 282a as a colorless oil (28 g, 71%). $^1H$ NMR (500 MHz, DMSO-$d_6$) δ 2.31 (t, J=8.0 Hz, 2H), 2.05 (s, 2H), 1.79 (t, J=8.0 Hz, 2H), 1.12 (s, 6H).

Example 282b

2-Chloro-4,4-dimethylcyclopent-1-enecarbaldehyde 282b

To a solution of DMF (18.3 g, 250 mmol) in dichloromethane (300 mL) cooled to 0° C. was added $POCl_3$ (40.5 g, 250 mmol) over a period of 10 minutes. The mixture was stirred at 20° C. for 1 h. To the above mixture was added 282a (28.0 g, 250 mmol) dropwise over a period of 20 minutes. The resulting mixture was heated at reflux for 20 h. The reaction mixture was cooled to room temperature and poured into a solution of sodium acetate (60 g) in ice-water (400 g). The mixture was extracted with dichloromethane (2×300 mL). The combined organic layer was washed with water (2×200 mL), dried over anhydrous $Mg_2SO_4$ and filtered. The filtrate was evaporated under reduced pressure to afford 282b as a colorless oil (33.0 g, crude). $^1$H NMR (500 MHz, DMSO-$d_6$) δ 9.99 (s, 1H), 2.62 (d, J=2.0 Hz, 2H), 2.38 (d, J=2.0 Hz, 2H), 1.15 (s, 6H).

Example 282c

Ethyl 5,5-Dimethyl-5,6-dihydro-4H-cyclopenta[b]thiophene-2-carboxylate 282c

To a solution of 282b (33.0 g, crude) in dichloromethane (400 mL) and triethylamine (60 g, 600 mmol) was added ethyl 2-mercaptoacetate (19.2 g, 160 mmol). The reaction mixture was heated at reflux for 6 h. It was then concentrated under reduced pressure. The residue was dissolved in ethanol (400 mL) and triethylamine (60 g, 600 mmol). The mixture was heated at reflux for 12 h. It was concentrated again under reduced pressure and the residue was purified by silica-gel column chromatography eluting with 40:1 petroleum ether/ethyl acetate to afford 282c as yellow solid (18.0 g, 32%, over two steps). MS-ESI: $[M+H]^+$ 225.3. $^1$H NMR (500 MHz, DMSO-$d_6$) δ 7.49 (s, 1H), 4.32 (q, J=7.0 Hz, 2H), 2.72 (s, 2H), 2.56 (s, 2H), 1.35 (t, J=7.0 Hz, 3H), 1.22 (s, 6H).

Example 282d 5,5-Dimethyl-5,6-dihydro-4H-cyclopenta[b]thiophene-2-carboxylic acid 282d To the solution of 282c (16.0 g, 71.0 mmol) in propan-2-ol (200 mL), tetrahydrofuran (200 mL), and water (200 mL) was added lithium hydroxide (6.82 g, 284 mmol). The reaction mixture was heated at 65° C. for 5 h. The organic solvents were removed under reduced pressure. The pH of the residue was adjusted to 1.0 with hydrochloride acid (12M). The precipitate was collected by filtration and dried in vacuo to afford 282d (12.0 g, 86%) as white solid. MS-ESI: $[M+H]^+$ 196.9

Example 282e

N-tert-Butyl-5,5-dimethyl-5,6-dihydro-4H-cyclopenta[b]thiophene-2-carboxamide 282e A suspension of 282d (12.0 g, 61.0 mmol) in $SOCl_2$ (80 mL) was heated at 65° C. for 2 h. The reaction mixture was concentrated under reduced pressure. The residue was diluted with dichloromethane (20 mL), which was added to the solution of 2-methylpropan-2-amine (4.45 g, 61.0 mmol) and triethylamine (18.0 g, 180 mmol) in dichloromethane (180 mL). The resulting mixture was stirred for 16 h and diluted with dichloromethane (200 mL). It was washed with water (3×50 mL), dried over anhydrous $Mg_2SO_4$, filtered, and evaporated under reduced pressure to afford 282e (15.0 g, 97%) as yellow solid. MS-ESI: $[M+H]^+$ 252.0

Example 282f

N-tert-Butyl-3-formyl-5,5-dimethyl-5,6-dihydro-4H-cyclopenta[b]thiophene-2-carboxamide 282f To a solution of 282e (1.5 g, 6.0 mmol) in anhydrous THF (60 mL) cooled at −70° C. was added the solution of n-butyl lithium (10.0 mL, 25 mmol, 2.5 Min hexane) over a period of 5 minutes. It was stirred at −70° C. for 6 h. DMF (1.3 g, 18.0 mmol) was added over a period of 5 minutes and the result mixture was stirred at room temperature for overnight. It was then quenched with saturated $NH_4Cl$ (40 mL) and concentrated under reduced pressure. The residue was extracted with ethyl acetate (2×30 mL). The combined organic layer was dried over anhydrous $Mg_2SO_4$ and filtered. The filtrate was evaporated under reduced pressure to afford 282f as yellow solid (1.34 g, 80%). MS-ESI: $[M+H]^+$ 280.3

Example 282g

N-tert-Butyl-3-(hydrazonomethyl)-5,5-dimethyl-5,6-dihydro-4H-cyclopenta[b]thiophene-2-carboxamide 282g To a solution of 85% aqueous hydrazine (10 mL) in THF (180 mL) was added 282f (5.6 g, 20.0 mmol) in anhydrous THF (20 mL) over a period of 5 minutes. It was stirred at 20° C. for 3 h. The reaction mixture was concentrated under reduced pressure to afford 282g as black solid (6.0 g, yield: 95%, purity: 95%). MS-ESI: $[M+H]^+$ 294.0

Example 282h 4,4-Dimethyl-7-thia-10,11-diazatricyclo[6.4.0.0$^{2,6}$]dodeca-1(8),2(6),11-trien-9-one 282h A solution of 282g (3.8 g, 13.0 mmol) in 30% $H_2SO_4$ (100 mL) was heated at reflux for 16 h. The reaction mixture was cooled to room temperature and extracted with dichloromethane (3×200 mL). The combined organic layer was concentrated under reduced pressure and the residue was purified by silica-gel column chromatography eluting with 100:1 dichloromethane/methanol to afford 282h as yellow solid (1.72 g, 60%). MS-ESI: $[M+H]^+$ 221.0

Example 282i

4-Chloro-2-{4,4-dimethyl-9-oxo-7-thia-10,11-diazatricyclo[6.4.0.0$^{2,6}$]dodeca-1(8),2(6),11-trien-10-yl}pyridine-3-carbaldehyde 282i Following the procedures as described in Example 108a, and starting with 282h (330 mg, 1.5 mmol) and 2-bromo-4-chloronicotinaldehyde (950 mg, 4.5 mmol), 282i was obtained as a yellow solid (260 mg, 48%). MS-ESI: $[M+H]^+$ 359.9

Example 282j

2-{4,4-Dimethyl-9-oxo-7-thia-10,11-diazatricyclo[6.4.0.0$^{2,6}$]dodeca-1(8),2(6),11-trien-10-yl}-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridine-3-carbaldehyde 282j Following the procedure for preparation in Example 191k, and starting with 282i (216 mg, 0.60 mmol), and (S)-1-methyl-3-(5-(2-methyl-4-(oxetan-3-yl)piperazin-1-yl)pyridin-2-ylamino)-5-(4,4,5,5-tetramethyl-1,3,2-dioxaborolan-2-yl)pyridin-2(1H)-one 191j (482 mg, 0.90 mmol), 282j was obtained as a yellow solid (407 mg, 48%). MS-ESI: $[M+H]^+$ 678.8

Example 282

3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,7-dimethyl-6,8-dihydrocyclopenta[3,4]thieno[1,3-d]pyridazin-4-one 282

Following the procedures in Example 191, and starting with 282j (370 mg, 0.55 mmol), 282 was obtained as a yellow solid (64 mg, 17%). MS-ESI: [M+H]$^+$ 681.3. $^1$H NMR (500 MHz, DMSO-d$_6$) δ 8.63 (d, J=2.0 Hz, 1H), 8.56 (d, J=5.0 Hz, 1H), 8.46-8.45 (m, 2H), 7.85 (d, J=3.0 Hz, 1H), 7.53 (d, J=5.0 Hz, 1H), 7.47 (d, J=2.5 Hz, 1H), 7.36 (dd, J=3.0, 9.0 Hz, 1H), 7.24 (d, J=9.0 Hz, 1H), 4.85 (t, J=5.0 Hz, 1H), 4.57-4.54 (m, 2H), 4.47 (t, J=6.0 Hz, 1H), 4.4-4.37 (m, 3H), 3.68-3.67 (m, 1H), 3.60 (s, 3H), 3.40-3.38 (m, 1H), 3.11-3.08 (m, 1H), 2.96-2.90 (m, 3H), 2.81-2.79 (m, 2H), 2.56-2.53 (m, 1H), 2.33-2.32 (m, 2H), 2.19-2.16 (m, 1H), 1.28 (s, 3H), 1.27 (s, 3H), 0.93 (d, J=6.0 Hz, 3H).

Example 283a

5-Bromo-1-methyl-3-(5-methylisoxazol-3-ylamino)pyridin-2(1H)-one 283a

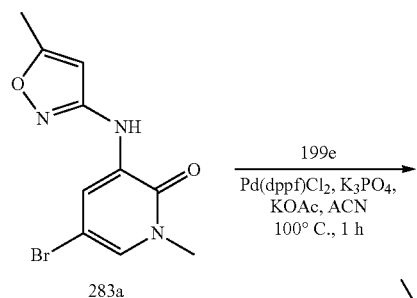

A 100-mL single-neck round-bottomed flask equipped with a magnetic stirrer and a reflux condenser was charged with 5-methylisoxazol-3-amine (1.0 g, 10.2 mmol), 3,5-dibromo-1-methylpyridin-2(1H)-one (4.09 g, 15.3 mmol), Pd$_2$(dba)$_3$ (467 mg, 0.51 mmol), Xantphos (598 mg, 1.02 mmol), Cs$_2$CO$_3$ (6.65 g, 20.4 mmol), and dioxane (50 mL). After three cycles of vacuum/argon flush, the reaction mixture was heated at 100° C. for 3 h. Analysis of the reaction mixture by LCMS showed complete conversion to the desired product. It was filtered when the mixture was still hot. The filtrate was cooled down to room temperature and the resulting precipitation was collected by filtration to afford 283a (1.6 g, 55%) as a yellow solid. MS-ESI: [M+H]$^+$ 284.1

Example 283b (2-{4,4-Dimethyl-9-oxo-1,10-diazatricyclo[6.4.0.0$^{2,6}$]dodeca-2(6),7-dien-10-yl}-4-{1-methyl-5-[(5-methyl-1,2-oxazol-3-yl)amino]-6-oxo-1,6-dihydropyridin-3-yl}pyridin-3-yl)methyl Acetate 283b A 50-mL round-bottomed flask equipped with a magnetic stirrer and a reflux condenser was charged with 283a (150 mg,

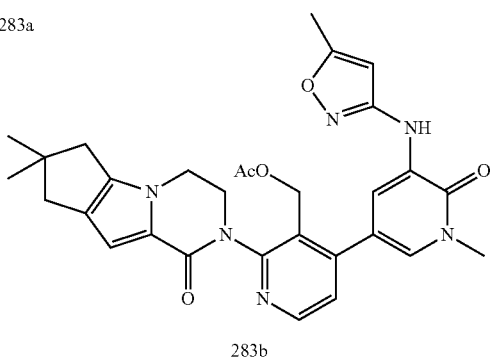

0.53 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (834 mg, 2.1 mmol), Pd(dppf)Cl$_2$ (21 mg, 0.026 mmol), K$_3$PO$_4$ (224 mg, 0.053 mmol), sodium acetate (87 mg, 1.1 mmol), acetonitrile (10 mL), and water (5 drops). After three cycles of vacuum/N$_2$ flush, the mixture was heated at 100° C. for 1 h. Then it was cooled to room temperature and filtered. The filtrate was concentrated under reduced pressure and the residue was washed with acetonitrile to afford the 283b (100 mg, 34%) as white solid. MS-ESI: [M+H]$^+$ 557.3

Example 283

3-[3-(hydroxymethyl)-4-[1-methyl-5-[(5-methylisoxazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 283

To a solution of 283b (90 mg, 0.162 mmol) in THF (5 mL), i-propanol (5 mL), and water (5 mL) was added lithium hydroxide (3.8 mg, 1.62 mmol). The reaction mixture was stirred at room temperature for 1 h and concentrated under reduced pressure. The residue was extracted with dichloromethane (20 mL×3). The combined organic layer was washed with brine, dried over Na$_2$SO$_4$, filtered, and concentrated under reduced pressure. The residue was purified by reverse-phase prep-HPLC to afford 283 (65 mg, 78%) as white solid. MS-ESI: [M+H]$^+$ 514.9. $^1$H NMR (500 MHz, DMSO-d$_6$) δ 8.98 (s, 1H), 8.49 (d, J=5.0 Hz, 1H), 8.02 (d, J=2.0 Hz, 1H), 7.56 (d, J=2.5 Hz, 1H), 7.32 (d, J=5.0 Hz, 1H), 6.57 (s, 1H), 6.25 (s, 1H), 4.93 (t, J=5.0 Hz, 1H), 4.48-4.38 (m, 2H), 4.25-4.19 (m, 3H), 3.87-3.85 (m, 1H), 3.60 (s, 3H), 2.62-2.54 (m, 2H), 2.43 (s, 2H), 2.31 (s, 3H), 1.22 (s, 6H).

Example 284a 2-(10-Fluoro-1-oxo-3,4,6,7,8,9-hexahydropyrazino[1,2-a]indol-2(1H)-yl)-4-(1-methyl-5-(5-(oxetan-3-yl)-4,5,6,7-tetrahydropyrazolo[1,5-a]pyrazin-2-ylamino)-6-oxo-1,6-dihydropyridin-3-yl)nicotinaldehyde 284a

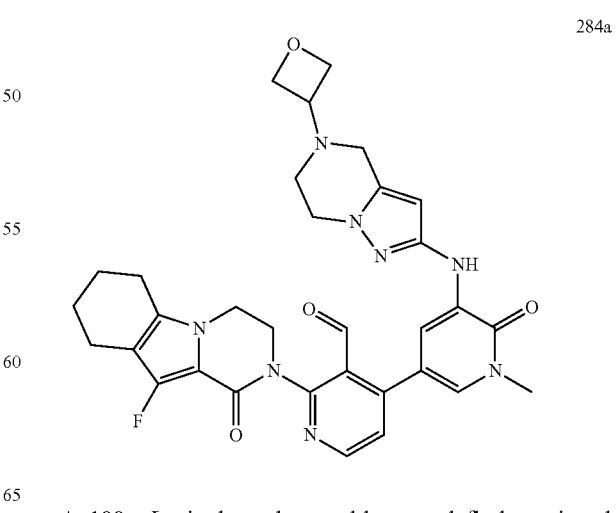

A 100-mL single-neck round-bottomed flask equipped with a magnetic stirrer and reflux condenser was charged with 1-methyl-3-(5-(oxetan-3-yl)-4,5,6,7-tetrahydropyrazolo[1,5-a]pyrazin-2-ylamino)-5-(4,4,5,5-tetramethyl-1,3,2-dioxaborolan-2-yl)pyridin-2(1H)-one 163a (354 mg, 0.83 mmol), 4-chloro-2-(10-fluoro-1-oxo-3,4,6,7,8,9-hexahydropyrazino[1,2-a]indol-2(1H)-yl)nicotinaldehyde 134c (289 mg, 0.83 mmol), PdCl$_2$(dppf) (68 mg, 0.08 mmol), K$_3$PO$_4$ (352 mg, 1.66 mmol), sodium acetate (136 mg, 1.66 mmol), acetonitrile (50 mL), and water (3 mL). The system was evacuated and refilled with N$_2$. The reaction mixture was heated at 100° C. for 2 h. It was then cooled to room temperature and filtered. The filtrate was concentrated under reduced pressure and the resulting residue was purified by silica-gel column chromatography eluting with 30:1 dichloromethane/methanol to afford 284a (305 mg, 60%) as a brown solid. MS-ESI: [M+H]$^+$: 613.6.

Example 284

10-fluoro-2-[3-(hydroxymethyl)-4-[1-methyl-5-[[5-(oxetan-3-yl)-6,7-dihydro-4H-pyrazolo[1,5-a]pyrazin-2-yl]amino]-6-oxo-3-pyridyl]-2-pyridyl]-3,4,6,7,8,9-hexahydropyrido[3,4-b]indolizin-1-one 284

To a suspension of 284a (250 mg, 0.41 mmol) in methanol (20 mL) was added sodium borohydride (47 mg, 1.23 mmol) at 0° C. The mixture was stirred for 30 minutes. It was then quenched with water (2 mL) and concentrated under reduced pressure. The residue was purified by reverse-phase prep-HPLC to afford 284 (20 mg, 6.6%). MS-ESI: [M+H]$^+$ 615.6. $^1$H NMR (500 MHz, CDCl$_3$) δ 8.46 (d, J=5.0 Hz, 1H), 7.94 (d, J=3.0 Hz, 1H), 7.66 (d, J=2.0 Hz, 1H), 7.43 (s, 1H), 7.34 (d, J=5.0 Hz, 1H), 5.75 (s, 1H), 4.95 (t, J=6.5 Hz, 1H), 4.76-4.74 (m, 2H), 4.69-4.65-4.67 (m, 3H), 4.46-4.44 (m, 1H), 4.35-4.33 (m, 1H), 4.10-4.08 (m, 4H), 3.38-3.35 (m, 2H), 3.69 (s, 3H), 3.58-3.56 (m, 2H), 2.84-2.82 (m, 2H), 2.58-2.53 (m, 4H), 1.89-1.84 (m, 2H), 1.77-1.76 (m, 2H).

Example 285a

4-Nitro-1-(oxetan-3-yl)-1H-imidazole 285a

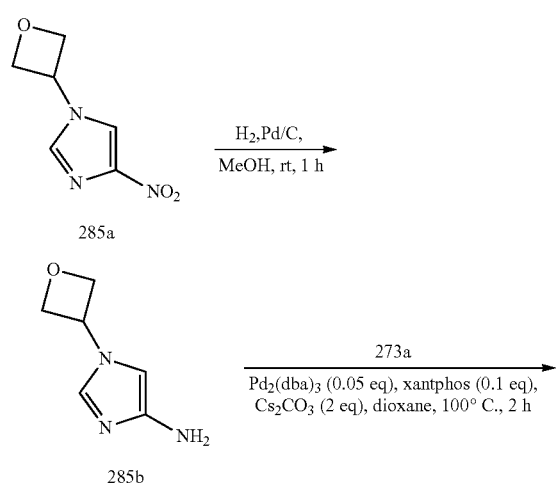

A sealed tube was charged with 4-nitro-1H-imidazole (500 mg, 4.42 mmol), 3-iodooxetane (920 mg, 5.0 mmol), Cs$_2$CO$_3$ (2.90 g, 8.84 mmol), and dioxane (12 mL). The sealed tube was heated at 120° C. for 16 h. It was then cooled to room temperature and filtered. The filtrate was evaporated under reduced pressure. The residue was purified by silica-gel column chromatography eluting with 30:1 dichloromethane/methanol to afford 285a as a white solid (250 mg, 33%). MS-ESI: [M+H]$^+$ 170.2.

Example 285b 1-(Oxetan-3-yl)-1H-imidazol-4-amine 285b

A 25-mL single-neck round-bottomed flask was purged with nitrogen and charged with 285a (100 mg, 0.6 mmol), 10% palladium on carbon (10% wet, 10 mg) and methanol (10 mL). The flask was evacuated, charged with hydrogen gas (via balloon), and stirred for 1 h at room temperature. The hydrogen was then evacuated and nitrogen was charged to the flask. The catalyst was removed by filtration through a pad of CELITE® and the filtrate was concentrated under reduced pressure to afford 285b (70 mg, 85%). MS-ESI: [M+H]$^+$ 140.3.

Example 285c (2-{4,4-Dimethyl-9-oxo-1,10-diazatricyclo[6.4.0.0$^{2,6}$]dodeca-2(6),7-dien-10-yl}-4-(1-methyl-5-{[1-(oxetan-3-yl)-1H-imidazol-4-yl]amino}-6-oxo-1,6-dihydropyridin-3-yl)pyridin-3-yl)methyl Acetate 285c

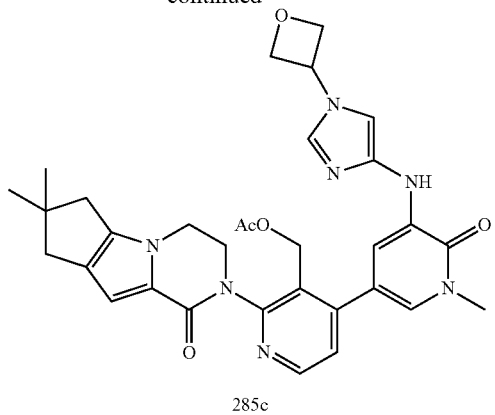

A 25-mL round-bottomed flask equipped with a magnetic stirrer and a reflux condenser was charged with 285b (40 mg, 0.28 mmol), [4-(5-bromo-1-methyl-6-oxo-1,6-dihydropyridin-3-yl)-2-{4,4-dimethyl-9-oxo-1,10-diazatri-cyclo[6.4.0.0$^{2,6}$]dodeca-2(6),7-dien-10-yl}pyridin-3-yl]methyl acetate 273a (150 mg, 0.28 mmol), Pd$_2$(dba)$_3$ (15 mg, 0.015 mmol), XantPhos (18 mg, 0.03 mmol), cesium carbonate (200 mg, 0.6 mmol), and 1,4-dioxane (6 mL). After three cycles of vacuum/argon flush, the mixture was heated at 100° C. for 2 h. It was then cooled to room temperature and filtered. The filtrate was concentrated under reduced pressure and the residue was purified by silica-gel column chromatography eluting with 25:1 dichloromethane/methanol to afford 285c as a yellow solid (80 mg, 47%). MS-ESI: [M+H]$^+$ 598.3.

Example 285

3-[3-(hydroxymethyl)-4-[1-methyl-5-[[1-(oxetan-3-yl)imidazol-4-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 285

A mixture of 285c (80 mg, 0.13 mmol) and lithium hydroxide.water (55 mg, 1.3 mmol) in i-propanol/THF (3:2, 5 mL) and water (2 mL) was stirred at 30° C. for 1 h. The mixture was evaporated under reduced pressure and water (5 mL) was added to the residue. It was then extracted with dichloromethane (3×10 mL). The combined dichloromethane extract was concentrated under reduced pressure and the residue was purified by reverse-phase prep-HPLC to afford 285 (36 mg, 50%) as a white solid. MS-ESI: [M+H]$^+$ 556.3. $^1$H NMR (500 MHz, CDCl$_3$) δ 8.48 (d, J=5.0 Hz, 1H), 7.53 (d, J=2.0 Hz, 1H), 7.47-7.45 (m, 2H), 7.35-7.34 (m, 2H), 7.28 (s, 1H), 6.88 (s, 1H), 5.27-5.19 (m, 2H), 5.10-5.07 (m, 2H), 4.94-4.91 (m, 2H), 4.69-4.65 (m, 1H), 4.52-4.44 (m, 2H), 4.17-4.16 (m, 2H), 3.87-3.84 (m, 1H), 3.72 (s, 3H), 2.59-2.58 (m, 2H), 2.53 (s, 2H), 1.29 (s, 6H).

Example 286a (2-{4,4-Dimethyl-9-oxo-1,10-diazatricyclo[6.4.0.0$^{2,6}$]dodeca-2(6),7-dien-10-yl}-4-{1-methyl-5-[(1,2-oxazol-3-yl)amino]-6-oxo-1,6-dihydropyridin-3-yl}pyridin-3-yl)methyl Acetate 286a

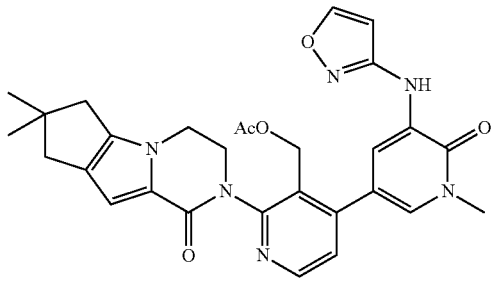

A 25-mL round-bottomed flask equipped with a reflux condenser was charged with [4-(5-bromo-1-methyl-6-oxo-1,6-dihydropyridin-3-yl)-2-{4,4-dimethyl-9-oxo-1,10-diazatricy-clo[6.4.0.0$^{2,6}$]dodeca-2(6),7-dien-10-yl}pyridin-3-yl]methyl acetate 273a (161 g, 0.30 mmol), isoxazol-3-amine (25 mg, 0.30 mmol), cesium carbonate (196 mg, 0.60 mmol), and 1,4-dioxane (10 mL). After bubbling nitrogen through the suspension for 10 minutes, tris(dibenzylideneacetone)dipalladium(0) (14.0 mg, 0.015 mmol) and xantphos (17 mg, 0.030 mmol) were added. The system was subjected to three cycles of vacuum/argon flush and heated at reflux for 5 h. It was then cooled to room temperature and filtered. The solid was washed with dichloromethane (2×10 mL). The combined organic filtrate was concentrated under reduced pressure. The residue was purified by silica-gel column chromatography eluting with dichloromethane/methanol (80/1 to 30/1) to afford 286a (96 mg, 59%) as yellow solid. MS-ESI: [M+H]$^+$ 542.8.

Example 286

3-[3-(hydroxymethyl)-4-[5-(isoxazol-3-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one 286

To a solution of 286a (96 mg, 0.18 mmol) in THF/i-propanol/water (5/3/2 mL) was added lithium hydroxide (21 mg, 0.88 mmol). The mixture was stirred at room temperature for 1 h. After the reaction was complete, the mixture was evaporated under pressure and the residue was purified by reverse-phase prep-HPLC to afford 286 as a white solid (75 mg, 85%). MS-ESI: [M+H]$^+$ 501.3. $^1$H NMR (500 MHz, CDCl$_3$) δ 8.49 (d, J=6.5 Hz, 1H), 8.19 (d, J=2.5 Hz, 1H), 8.10 (d, J=2.5 Hz, 1H), 8.97 (d, J=3.0 Hz, 1H), 7.71 (s, 1H), 7.37 (d, J=6.5 Hz, 1H), 6.85 (s, 1H), 6.18 (d, J=2.5 Hz, 1H), 5.12-5.11 (m, 1H), 4.66-4.64 (m, 1H), 4.52-4.51 (m, 1H), 4.29-4.27 (m, 1H), 4.18-4.16 (m, 2H), 3.87-3.86 (m, 1H), 3.73 (s, 3H), 2.59-2.57 (m, 2H), 2.53-2.51 (m, 2H), 1.28 (s, 6H).

Example 287a

N-Methoxy-N-methyl-3-nitro-1H-pyrazole-5-carboxamide 287a

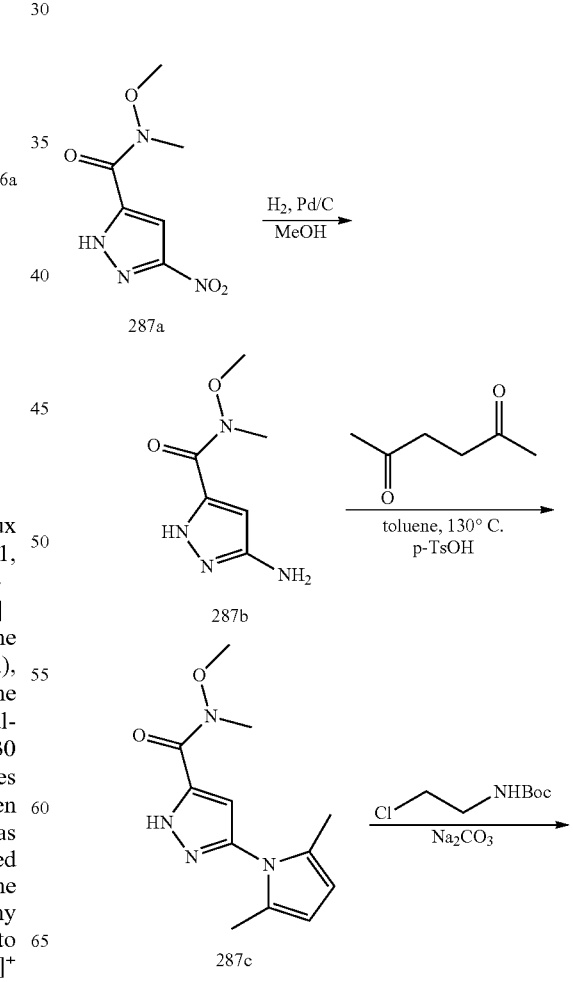

511
-continued

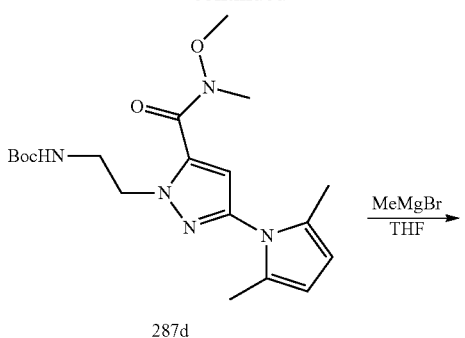
287d

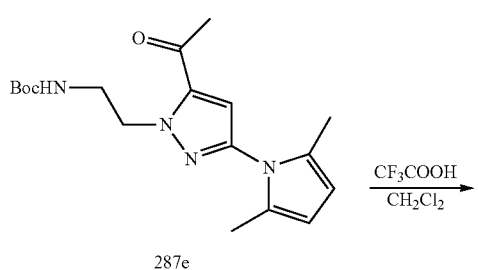
287e

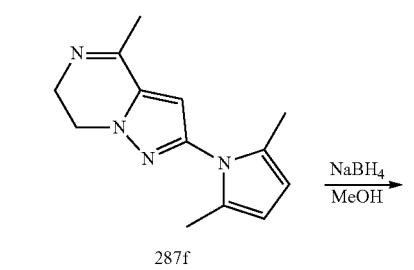
287f

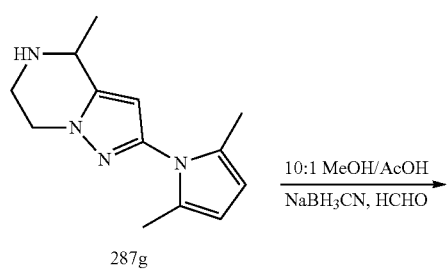
287g

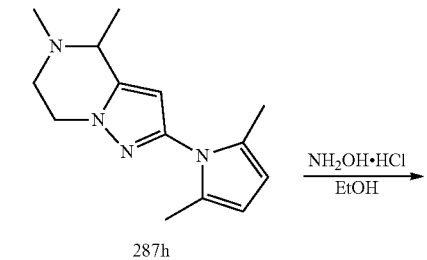
287h

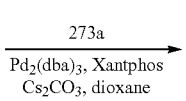
287i

512
-continued

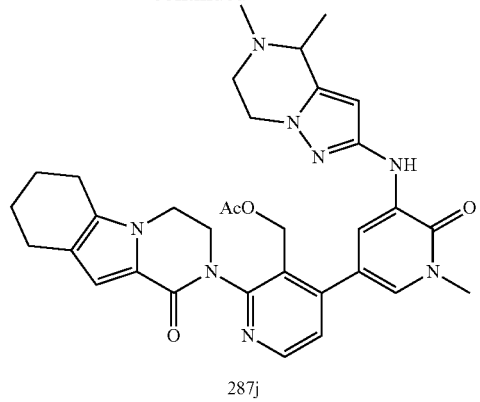
287j

A 500-mL single-neck round-bottomed flask equipped with a magnetic stirrer was charged with 3-nitro-1H-pyrazole-5-carboxylic acid (15.7 g, 1.0 eq., 100 mmol), N,O-dimethylhydroxylamine hydrochloride (19.5 g, 2.0 eq., 200 mmol), HATU (76.0 g, 2.0 eq., 200 mmol), triethylamine (40.4 g, 4.0 eq., 400 mmol), and dichloromethane (300 mL). The reaction mixture was stirred at room temperature for overnight. The solvent was removed under reduced pressure. The resulting residue was purified by silica-gel column chromatography eluting with 100:1 dichloromethane/methanol to afford 287a (16.0 g, 80%) as white solid. MS-ESI: [M+H]+ 201.1

Example 287b

3-Amino-N-methoxy-N-methyl-1H-pyrazole-5-carboxamide 287b

A 250-mL single-neck round-bottomed flask was purged with nitrogen and charged with 287a (16.0 g, 1.0 eq., 80.0 mmol), 10% palladium on carbon (50% wet, 800 mg), and methanol (100 mL). The mixture was evacuated, charged with hydrogen gas, and stirred under hydrogen atmosphere at room temperature overnight. The hydrogen was then evacuated and nitrogen was charged into the flask. The catalyst was removed by filtration through a pad of CELITE®. The filtrate was concentrated under reduced pressure to afford 287b (11.0 g, 81%) as white solid. MS-ESI: [M+H]+ 171.1

Example 287c 3-(2,5-Dimethyl-1H-pyrrol-1-yl)-N-methoxy-N-methyl-1H-pyrazole-5-carboxamide 287c A 250-mL round-bottomed flask equipped with a magnetic stirrer and a Dean-Stark trap was charged with 287b (11.0 g, 1.0 eq., 64.7 mmol), hexane-2,5-dione (11.1 g, 1.5 eq., 97.2 mmol), p-toluenesulfonic acid monohydrate (558 mg, 0.05 eq., 3.24 mmol), and toluene (100 mL). The reaction mixture was refluxed overnight. The resulting mixture was cooled to room temperature and concentrated under reduced pressure. The resulting residue was purified by silica-gel column chromatography eluting with 1:2 petroleum ether/ethyl acetate to afford 287c (10.4 g, 65%) as white solid. MS-ESI: [M+H]+ 249.0

Example 287d tert-Butyl 2-(3-(2,5-Dimethyl-1H-pyrrol-1-yl)-5-(methoxy(methyl)carbamoyl)-1H-pyrazol-1-yl)ethyl-carbamate 287d A 250-mL round-bottomed flask equipped with a magnetic stirrer was charged with 287c (10.4 g, 1.0 eq., 41.9 mmol), tert-butyl 2-chloroethylcarbamate (37.7 g, 5.0 eq., 210.0 mmol), $Na_2CO_3$ (22.3 g, 5.0 eq., 210.0 mmol), and DMF (100 mL). The reaction mixture was stirred at 110° C. overnight. After cooling to room temperature, the resulting mixture was poured into water (200 mL) and extracted with ethyl acetate (3×100 mL). The combined organic layer was concentrated under reduced pressure. The resulting residue was purified by silica-gel column chromatography eluting with ethyl acetate to afford 287d (10.8 g, 66%) as yellow oil. MS-ESI: $[M+H]^+$ 392.0

Example 287e tert-Butyl 2-(5-Acetyl-3-(2,5-dimethyl-1H-pyrrol-1-yl)-1H-pyrazol-1-yl)ethylcarbamate 287e A 250-mL round-bottomed flask equipped with a magnetic stirrer was charged with 287d (7.82 g, 1.0 eq., 20.0 mmol) and THF (100 mL) under $N_2$ protection. A solution of MeMgBr (3.0 M in ether) (17 mL, 2.5 eq., 50.0 mmol) was added at −78° C. The mixture was stirred at room temperature for 3 h and quenched with saturated $NH_4Cl$ solution. It was then concentrated under reduced pressure and the residue was extracted with ethyl acetate (3×50 mL). The combined organic layer was evaporated under reduced pressure. The residue was purified by silica-gel column chromatography eluting with 4:1 petroleum ether/ethyl acetate to afford 287e as colorless oil (5.40 g, 78%). MS-ESI: $[M+H]^+$ 347.0. $^1H$ NMR (500 MHz, $CDCl_3$) δ 6.57 (s, 1H), 5.91 (s, 2H), 4.93 (bs, 1H), 4.71 (t, J=5.5 Hz, 2H), 3.62 (t, J=5.5 Hz, 2H), 2.57 (s, 3H), 2.16 (s, 6H), 1.28 (s, 9H).

Example 287f 2-(2,5-Dimethyl-1H-pyrrol-1-yl)-4-methyl-6,7-dihydropyrazolo[1,5-a]pyrazine 287f A 100-mL single-neck round-bottomed flask equipped with a magnetic stirrer was charged with 287e (5.40 g, 1.0 eq., 15.6 mmol), $CF_3COOH$ (10 mL), and dichloromethane (50 mL). The mixture was stirred at room temperature for 1 h and concentrated under reduced pressure to afford crude 287f, which was used in the next step without further purification. MS-ESI: $[M+H]^+$ 229.1

Example 287g 2-(2,5-Dimethyl-1H-pyrrol-1-yl)-4-methyl-4,5,6,7-tetrahydropyrazolo[1,5-a]pyrazine 287g A 100-mL single-neck round-bottomed flask equipped with a magnetic stirrer was charged with 287f (3.56 g, 1.0 eq., 15.6 mmol), $NaBH_4$ (2.96 g, 5.0 eq., 78.0 mmol), and methanol (50 mL). The mixture was stirred at room temperature for 1 h and concentrated under reduced pressure. The residue was partitioned between water (50 mL) and dichloromethane (50 mL). The water phase was extracted with dichloromethane (3×50 mL). The combined organic layer was concentrated under reduced pressure. The residue was purified by silica-gel column chromatography eluting with 10:1 dichloromethane/methanol to afford 287g as a colorless oil (1.54 g, 43% over two steps). MS-ESI: $[M+H]^+$ 231.3. $^1H$ NMR (500 MHz, $CDCl_3$) δ 5.91 (s, 1H), 5.86 (s, 2H), 4.17-4.11 (m, 3H), 3.51-3.48 (m, 1H), 3.36-3.31 (m, 1H), 2.13 (s, 6H), 1.50 (d, J=6.5 Hz, 3H).

Example 287h 2-(2,5-Dimethyl-1H-pyrrol-1-yl)-4,5-dimethyl-4,5,6,7-tetrahydropyrazolo[1,5-a]pyrazine 287h A 100-mL single-neck round-bottomed flask equipped with a magnetic stirrer was charged with 287g (1.54 g, 1.0 eq., 6.70 mmol), formaldehyde (37% in water) (1.09 g, 2.0 eq., 13.4 mmol), $NaBH_3CN$ (2.11 g, 5.0 eq., 33.5 mmol), HOAc (3 mL), and methanol (30 mL). The mixture was stirred at room temperature for 1 h and concentrated under reduced pressure. The residue was partitioned between water (50 mL) and dichloromethane (50 mL). The water phase was extracted with dichloromethane (3×50 mL). The combined organic layer was concentrated under reduced pressure to afford crude 287h, which was used in the next step without further purification. MS-ESI: $[M+H]^+$ 245.0

Example 287i 4,5-Dimethyl-4,5,6,7-tetrahydropyrazolo[1,5-a]pyrazin-2-amine 287i A 100-mL single-neck round-bottomed flask equipped with a reflux condenser was charged with 287h (1.63 g, 1.0 eq., 6.70 mmol), $NH_2OH·HCl$ (2.33 g, 5.0 eq., 33.5 mmol), and ethanol (50 mL). The mixture was refluxed for 2 days. It was then cooled to room temperature and concentrated under reduced pressure. The residue was purified by reverse-phase prep-HPLC to afford 287i as a yellow solid (211 mg, 19%). MS-ESI: $[M+H]^+$ 167.1. $^1H$ NMR (500 MHz, $CDCl_3$) δ 5.36 (s, 1H), 4.04-4.00 (m, 1H), 3.94-3.92 (m, 1H), 3.61 (bs, 2H), 3.30 (q, J=6.5 Hz, 1H), 3.10-3.08 (m, 1H), 2.81-2.75 (m, 1H), 2.43 (s, 3H), 1.38 (d, J=6.5 Hz, 3H).

Example 287j (4-(5-(4,5-Dimethyl-4,5,6,7-tetrahydropyrazolo[1,5-a]pyrazin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 287j A 25-mL round-bottomed flask equipped with a magnetic stirrer and a reflux condenser was charged with 287i (20 mg, 1.0 eq., 0.12 mmol), (4-(5-bromo-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 273a (127 mg, 2.0 eq., 0.24 mmol), $Pd_2(dba)_3$ (9.0 mg, 0.1 eq., 0.010 mmol), Xantphos (11 mg, 0.2 eq., 0.020 mmol), $Cs_2CO_3$ (78 mg, 2.0 eq., 0.24 mmol), and dioxane (5 mL). After three cycles of vacuum/$N_2$ flush, the mixture was stirred at 100° C. for 2 h. It was then cooled to room temperature and filtered. The filtrate was concentrated under reduced pressure. The resulting residue was purified by silica-gel column chromatography eluting with 20:1 dichloromethane/methanol to afford 287j as a brown solid (60 mg, 82%). MS-ESI: $[M+H]^+$ 610.9

Example 287

2-[4-[5-[(4,5-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydro-pyrazino[1,2-a]indol-1-one 287

A 25-mL single-neck round-bottomed flask equipped with a magnetic stirrer was charged with 287j (60 mg, 1.0 eq., 0.098 mmol), lithium hydroxide (12 mg, 5.0 eq., 0.49 mmol), i-propanol/THF (4/4 mL), and water (1 mL). The mixture was stirred at room temperature for 1 h and concentrated under reduced pressure. The residue was purified by reverse-phase prep-HPLC to afford 287 as a yellow solid (24 mg, 43%). MS-ESI: [M+H]$^+$ 568.9. $^1$H NMR (500 MHz, CDCl$_3$) δ 8.49 (d, J=5.0 Hz, 1H), 7.99 (s, 1H), 7.72 (d, J=2.0 Hz, 1H), 7.44 (s, 1H), 7.36 (d, J=5.0 Hz, 1H), 6.91 (s, 1H), 5.74 (s, 1H), 5.04-5.02 (m, 1H), 4.64-4.62 (m, 1H), 4.56-4.54 (m, 1H), 4.39-4.37 (m, 1H), 4.17-3.92 (m, 4H), 3.86-3.84 (m, 1H), 3.72 (s, 3H), 3.45-3.37 (m, 1H), 3.17-3.14 (m, 1H), 2.89-2.81 (m, 1H), 2.64-2.58 (m, 4H), 2.48 (s, 3H), 1.93-1.89 (m, 2H), 1.81-1.80 (m, 2H), 1.46 (d, J=6.5 Hz, 3H).

Example 288a

1-Methyl-3-(5-methylisoxazol-3-ylamino)-5-(4,4,5,5-tetramethyl-1,3,2-dioxaborolan-2-yl)pyridin-2(1H)-one 288a

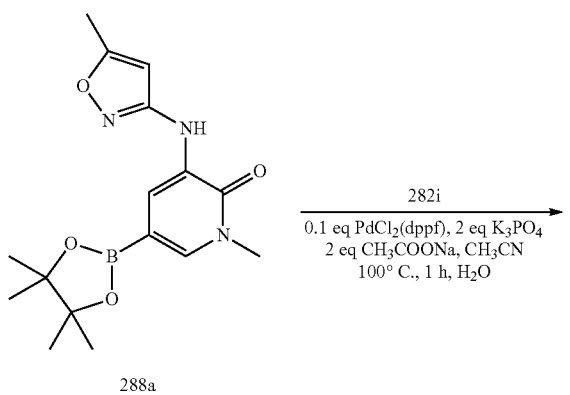

A 50-mL round bottomed flask equipped with a magnetic stirrer and a reflux condenser was charged with 5-bromo-1-methyl-3-(5-methylisoxazol-3-ylamino)pyridin-2(1H)-one 283a (330 mg, 1.16 mmol), Pin$_2$B$_2$ (442 mg, 1.74 mmol), Pd$_2$(dba)$_3$ (53 mg, 0.058 mmol), X-Phos (55 mg, 0.116 mmol), potassium acetate (227 mg, 2.32 mmol), and dioxane in (20 mL). After three cycles of vacuum/N$_2$ flush, the mixture was heated at 70° C. for 2 h. Analysis of the reaction mixture by LCMS showed complete conversion to the desired product. It was cooled to room temperature and filtered. The filtrate was concentrated under reduced pressure and the residue was washed with petroleum ether to afford 288a (300 mg, 78%) as yellow solid. MS-ESI: [M+H]$^+$ 332.3

Example 288b

2-{4,4-Dimethyl-9-oxo-7-thia-10,11-diazatricyclo[6.4.0.0$^{2,6}$]dodeca-1(8),2(6),11-trien-10-yl}-4-{1-methyl-5-[(5-methyl-1,2-oxazol-3-yl)amino]-6-oxo-1,6-dihydro-pyridin-3-yl}pyridine-3-carbaldehyde 288b A 50-mL round-bottomed flask equipped with a magnetic stirrer was charged with 4-chloro-2-{4,4-dimethyl-9-oxo-7-thia-10,11-diazatricyclo[6.4.0.0$^{2,6}$]dodeca-1(8),2(6),11-trien-10-yl}pyridine-3-carbaldehyde 282i (72 mg, 0.20 mmol), 288a (102 mg, 0.30 mmol), PdCl$_2$(dppf) (16 mg, 0.020 mmol), K$_3$PO$_4$ (85 mg, 0.40 mmol), sodium acetate (33 mg, 0.40 mmol), acetonitrile (10 mL), and water (0.5 mL). After bubbling nitrogen into the mixture for 10 minutes, a reflux condenser was attached to the flask and the mixture was heated at 100° C. for 1 h. It was then cooled to room temperature and filtered. The filtrate was concentrated under reduced pressure to afford 288b, which was used in the next step without further purification. MS-ESI: [M+H]$^+$ 529.3.

Example 288

3-[3-(hydroxymethyl)-4-[1-methyl-5-[(5-methylisoxazol-3-yl)amino]-6-oxo-3-pyridyl]-2-pyridyl]-7,7-dimethyl-6,8-dihydrocyclopenta[3,4]thieno[1,3-d]pyridazin-4-one 288

A mixture of 288a (82 mg, 0.16 mmol) and NaBH$_4$ (18.1 mg, 0.48 mmol) in methanol (10 mL) was stirred at room temperature for 30 min. The mixture was quenched with water (5 mL) and evaporated under reduced pressure. The residue was extracted with dichloromethane (3×10 mL). The combined extract was concentrated under reduced pressure and the residue was purified by reverse-phase prep-HPLC to afford 288 (54 mg, two steps: 34%) as white solid. MS-ESI: [M+H]$^+$ 531.3. $^1$H NMR (500 MHz, DMSO-d$_6$) δ 9.0 (s, 1H), 8.57 (d, J=5.0 Hz, 1H), 8.46 (s, 1H), 8.00 (d, J=1.5 Hz, 1H), 7.57 (d, J=2.0 Hz, 1H), 7.51 (d, J=5.0 Hz, 1H), 6.25 (s, 1H), 4.86 (bs, 1H), 4.39 (d, J=8.5 Hz, 2H), 3.60 (s, 3H), 2.91 (s, 2H), 2.81 (s, 2H), 2.31 (s, 3H), 1.28 (s, 6H).

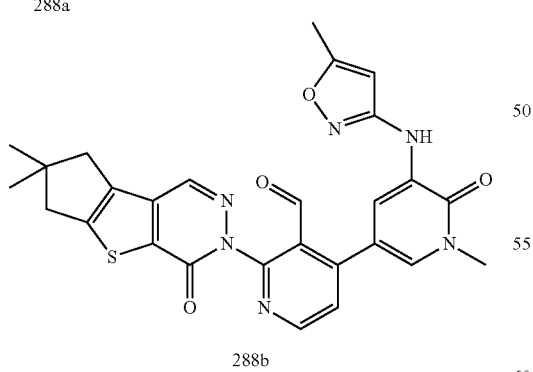

Example 289a tert-Butyl 3-Amino-1H-pyrazole-1-carboxylate 289a

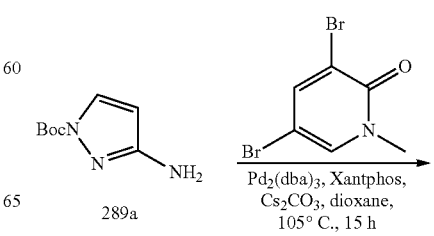

-continued

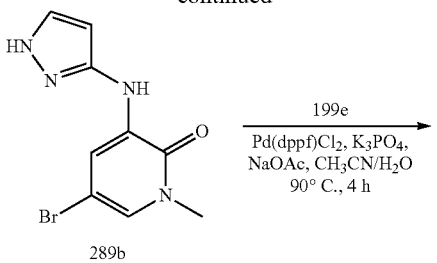

289b

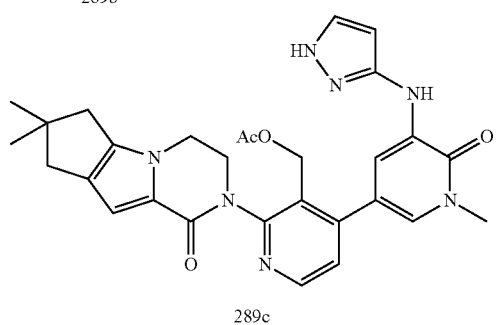

289c

To a mixture of 3-cyclopropyl-1H-pyrazol-5-amine (3.0 g, 36 mmol) and triethylamine (7.6 g, 75 mmol) in 1,4-dioxane (35 mL) was added (Boc)$_2$O (7.8 g, 36 mmol). The reaction mixture was stirred at 25° C. for 2 h. It was then concentrated under reduced pressure. The residue was purified by silica-gel column eluting with 3:1 petroleum ether/ethyl acetate to afford 289a as a white solid (3.4 g, 52%). MS-ESI: [M+H]$^+$ 184.1.

Example 289b 3-(1H-Pyrazol-3-ylamino)-5-bromo-1-methylpyridin-2(1H)-one 289b

A 250-mL single-neck round-bottomed flask equipped with a magnetic stirrer and a reflux condenser was charged with 289a (2.2 g, 12 mmol), XantPhos (0.69 g, 1.2 mmol), Pd$_2$(dba)$_3$ (1.1 g, 1.2 mmol), 3,5-dibromo-1-methylpyridin-2(1H)-one (6.4 g, 24 mmol), Cs$_2$CO$_3$ (15.6 g, 48 mmol), and 1,4-dioxane (50 mL). After bubbling nitrogen through the resulting mixture for 10 minutes, it was heated at 105° C. for 15 h. The mixture was cooled to room temperature and filtered. The filtrate was concentrated under reduced pressure and the residue the mixture was washed with methanol (8 mL) to afford 289b as a pale yellow solid (1.2 g, 37%). MS-ESI: [M+H]$^+$ 269.1.

Example 289c (2-{4,4-Dimethyl-9-oxo-1,10-diazatricyclo[6.4.0. 0$^{2,6}$]dodeca-2(6),7-dien-10-yl}-4-{1-methyl-6-oxo-5-[(1H-pyrazol-3-yl)amino]-1,6-dihydropyridin-3-yl}pyridin-3-yl)methyl Acetate 289c A 50-mL round-bottomed flask equipped with a magnetic stirrer and a reflux condenser was charged with 289b (200 mg, 0.74 mmol), (2-{4,4-dimethyl-9-oxo-1,10-diazatricyclo[6.4.0.0$^{2,6}$]dodeca-{3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (360 mg, 0.90 mmol), PdCl$_2$(dppf) (41 mg, 0.050 mmol), K$_3$PO$_4$ (320 mg, 1.5 mmol), sodium acetate (123 mg, 1.5 mmol), acetonitrile (10 mL), and water (0.2 mL). The system was evacuated and then refilled with N$_2$. Then it was heated at 90° C. for 4 h. The mixture was cooled to room temperature and filtered. The filtrate was concentrated under reduced pressure and the residue was purified by silica-gel column chromatography eluting with 10:1 dichloromethane/methanol to afford 289c as a pale yellow solid (150 mg, 38%). MS-ESI: [M+H]$^+$ 542.3.

Example 289

3-[3-(hydroxymethyl)-4-[1-methyl-6-oxo-5-(1H-pyrazol-3-ylamino)-3-pyridyl]-2-pyridyl]-7,7-dimethyl-1,2,6,8-tetrahydrocyclopenta[3,4]pyrrolo[3,5-b]pyrazin-4-one 289

A mixture of 289c (150 mg, 0.28 mmol) and lithium hydroxide hydrate (236 mg, 5.6 mmol) in THF (4 mL), i-propanol (4 mL) and water (2 mL) was stirred at 40° C. for 0.5 h. The mixture was evaporated under reduced pressure and diluted with water (10 mL). It was then extracted with ethyl acetate (3×15 mL). The combined extract was concentrated under reduced pressure and the residue was purified by reverse-phase prep-HPLC to afford 289 as a pale yellow solid (25 mg, 18%). MS-ESI: [M+H]$^+$ 499.9. $^1$H NMR (500 MHz, DMSO-d$_6$) δ 12.07 (s, 1H), 8.47 (d, J=5.0 Hz, 1H), 8.17 (s, 1H), 8.08 (s, 1H), 7.55-7.54 (m, 1H), 7.40-7.39 (m, 1H), 7.32 (d, J=5.0 Hz, 1H), 6.55 (s, 1H), 6.12 (s, 1H), 4.94-4.92 (m, 1H), 4.48-4.47 (m, 1H), 4.41-4.39 (m, 1H), 4.23-4.17 (m, 3H), 3.84-3.82 (m, 1H), 3.59 (s, 3H), 2.58-2.56 (m, 2H), 2.50-2.42 (m, 2H), 1.22 (s, 6H).

Example 290a

5-Bromo-1-methyl-3-(1-methyl-1H-pyrazol-3-ylamino)pyridin-2(1H)-one 290a

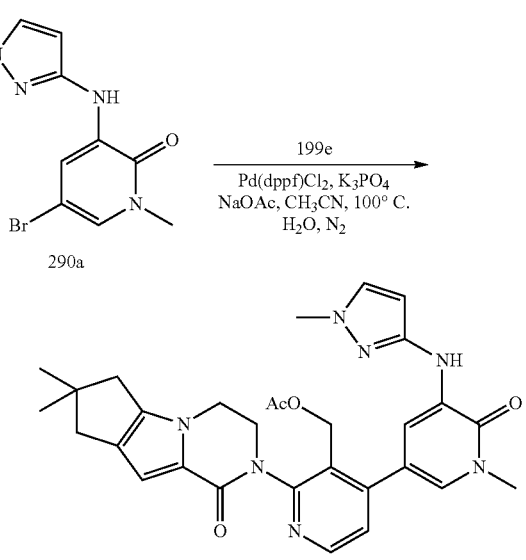

A 250-mL single-neck round-bottomed flask equipped with a magnetic stirrer and a reflux condenser was charged with 1,4-dioxane (100 mL), 1-methyl-1H-pyrazol-3-amine (970 mg, 10.0 mmol), 3,5-dibromo-1-methylpyridin-2-(1H)-one (2.9 g, 11 mmol), and cesium carbonate (6.5 g, 20.0 mmol). After bubbling nitrogen through the suspension for 10 minutes, tris(dibenzylideneacetone)dipalladium(0) (457 mg, 0.50 mmol) and Xantphos (587 mg, 1.0 mmol) were added. The system was subjected to three cycles of vacuum/argon flush and heated at reflux for 2 h. It was then cooled to room temperature and filtered. The solid was washed with dichloromethane (2×50 mL) and the combined organic filtrate was concentrated. The residue was purified by silica-gel column chromatography eluting with 30:1 dichloromethane/methanol to afford 290a as a yellow solid (900 mg, 32%). MS-ESI: [M+H]+ 283.1

Example 290b (2-{4,4-Dimethyl-9-oxo-1,10-diazatricyclo[6.4.0.0²,⁶]dodeca-2(6),7-dien-10-yl}-4-{1-methyl-5-[(1-methyl-1H-pyrazol-3-yl)amino]-6-oxo-1,6-dihydropyridin-3-yl}pyridin-3-yl)methyl Acetate 290b A 50-mL single-neck round-bottomed flask equipped with a magnetic stirrer and a reflux condenser was charged with {3-[(acetyloxy)methyl]-2-{4,4-dimethyl-9-oxo-1,10-diazatri-cyclo[6.4.0.0²,⁶]dodeca-2(6),7-dien-10-yl}pyridin-4-yl}boronic acid 199e (595 mg, 1.5 mmol), 290a (282 mg, 1.0 mmol), K₃PO₄ (424 mg, 2.0 mmol), sodium acetate (164 mg, 2.0 mmol), 1,1'-bis(diphenylphosphino)ferrocenedichloropalladium(II) (82 mg, 0.1 mmol), and acetonitrile/water (15/1 mL). After three cycles of vacuum/N₂ flush, the mixture was heated at 100° C. for 1.5 h. The mixture was cooled to room temperature and concentrated under reduced pressure. The residue was partitioned between dichloromethane (30 mL) and water (30 mL). The aqueous layer was extracted with dichloromethane (3×20 mL). The combined organic layer was dried over Na₂SO₄, filtered, and concentrated under reduced pressure. The dark residue was purified by silica-gel column chromatography eluting with dichloromethane/methanol (80/1 to 50/1) to 290b (300 mg, 54%) as yellow solid. MS-ESI: [M+H]+ 556.1

Example 290

3-[3-(hydroxymethyl)-4-[1-methyl-5-[(1-methylpyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 290

To a solution of 290b (139 mg, 0.25 mmol) in THF (5 mL), propan-2-ol (5 mL), and water (2 mL) was added lithium hydroxide (60 mg, 2.5 mmol). The reaction mixture was stirred at room temperature for 2.5 h. It was then concentrated under reduced pressure. The residue was partitioned between dichloromethane (20 mL) and water (10 mL). The aqueous layer was extracted with dichloromethane (3×10 mL). The combined extract was washed with brine, dried over Na₂SO₄, filtered, and concentrated under reduced pressure. The residue was purified by reverse-phase prep-HPLC to afford 290 (30 mg, 23%) as white solid. MS-ESI: [M+H]+ 514.3. ¹H NMR (500 MHz, DMSO-d₆) δ 8.47 (d, J=5.0 Hz, 1H), 8.16 (s, 1H), 8.03 (d, J=2.5 Hz, 1H), 7.48 (d, J=2.0 Hz, 1H), 7.39 (d, J=1.5 Hz, 1H), 7.33 (d, J=5.0 Hz, 1H), 6.55 (s, 1H), 6.07 (d, J=2.0 Hz, 1H), 4.97 (t, J=5.0 Hz, 1H), 4.47-4.40 (m, 2H), 4.24-4.18 (m, 3H), 3.85-3.83 (m, 1H), 3.70 (s, 3H), 3.58 (s, 3H), 2.58-2.56 (m, 2H), 2.42 (s, 2H), 1.22 (s, 6H).

Example 291a (4-{1-Methyl-5-[(5-methyl-1,2-oxazol-3-yl)amino]-6-oxo-1,6-dihydropyridin-3-yl}-2-{6-oxo-8-thia-4,5-diazatricyclo[7.4.0.0²,⁷]trideca-1(9),2(7),3-trien-5-yl}pyridin-3-yl)methyl Acetate 291a

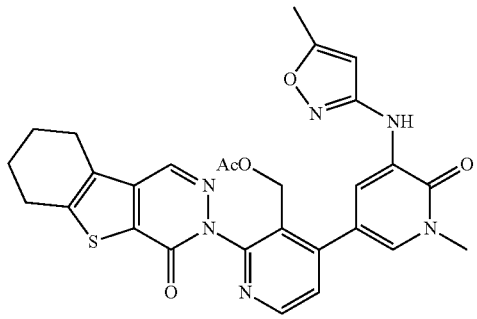

291a

A 50-mL round-bottomed flask equipped with a reflux condenser was charged with (2-{6-oxo-8-thia-4,5-diazatricyclo[7.4.0.0²,⁷]trideca-1(9),2(7),3-trien-5-yl}-4-(tetramethyl-1,3,2-dioxaborolan-2-yl)pyridin-3-yl)methyl acetate 230i (150 mg, 0.31 mmol), 5-bromo-1-methyl-3-(5-methylisoxazol-3-ylamino)pyridine-2(1H)-one 283a (88 mg, 0.31 mmol), PdCl₂(dppf) (24 mg, 0.031 mmol), K₃PO₄ (131 mg, 0.62 mmol), sodium acetate (61 mg, 0.62 mmol), water (0.2 mL), and acetonitrile (10 mL). The system was subjected to three cycles of vacuum/argon flush and stirred at 100° C. for 3 h. The reaction mixture was cooled to room temperature and filtered. The filtrate was concentrated under reduced pressure. The residue was partitioned between dichloromethane (20 mL) and water (10 mL). The organic layer was separated and the water layer was extracted with dichloromethane (2×20 mL). The combined organic layer was dried over Na₂SO₄, filtered, and concentrated under reduced pressure. The dark residue was purified by silica-gel column chromatography eluting with 30:1 dichloromethane/methanol to afford 291a (104 mg, 60%) as a yellow solid. MS-ESI: [M+H]+ 559.1

Example 291

3-[3-(hydroxymethyl)-4-[1-methyl-5-[(5-methylisoxazol-3-yl)amino]-6-oxo-3-pyridyl]-2-pyridyl]-6,7,8,9-tetrahydrobenzothiopheno[2,3-d]pyridazin-4-one 291

To a solution of 291a (100 mg, 0.18 mmol) in THF/i-propanol/water (10/5/5 mL) was added lithium hydroxide (43 mg, 1.8 mmol) at room temperature. After being stirred for 1 h, MS indicated the reaction was complete. Then the mixture was concentrated under reduced pressure and the residue was partitioned between water (10 mL) and dichloromethane (15 mL). The water phase was extracted with dichloromethane (3×10 mL). The combined organic layer was washed with brine (30 mL), dried over Na₂SO₄, filtered, and concentrated under reduced pressure. The residue was purified by reverse-phase prep-HPLC to afford 291 (56 mg, 60%) as white solid. MS-ESI: [M+H]+ 517.2. ¹H NMR (500 MHz, DMSO-d₆) δ 9.02 (s, 1H), 8.58 (d, J=5.0 Hz, 1H), 8.48 (s, 1H), 8.00 (d, J=2.0 Hz, 1H), 7.58 (d, J=2.0 Hz, 1H), 7.52 (d, J=5.0 Hz, 1H), 6.25 (s, 1H), 4.87-4.85 (m, 1H), 4.42-4.36 (m, 2H), 3.61 (s, 3H), 2.98-2.85 (m, 4H), 2.32 (s, 3H), 1.92-1.86 (m, 4H).

Example 292a

4-{5-[(1,5-Dimethyl-1H-pyrazol-3-yl)amino]-1-methyl-6-oxo-1,6-dihydro-pyridin-3-yl}-2-{4,4-dimethyl-9-oxo-7-thia-10,11-diazatricyclo[6.4.0.0²,⁶]dodeca-1(8),(6),11-trien-10-yl}pyridine-3-carbaldehyde 292a

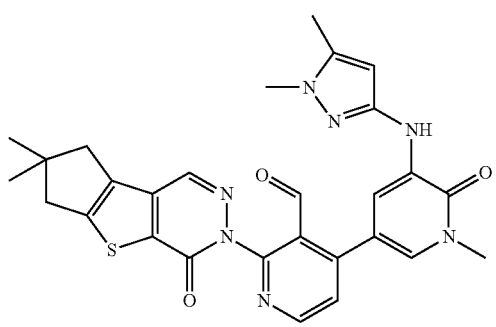

A 100-mL single-neck round-bottomed flask equipped with a magnetic stirrer and a reflux condenser was charged with 3-(1,5-dimethyl-1H-pyrazol-3-ylamino)-1-methyl-5-(4,4,5,5-tetramethyl-1,3,2-dioxaborolan-2-yl)pyridin-2(1H)-one 242a (344 mg, 1.0 mmol), 4-chloro-2-{4,4-dimethyl-9-oxo-7-thia-10,11-diazatricyclo[6.4.0.0²,⁶]dodeca-1(8),2(6),11-trien-10-yl}pyridine-3-carbaldehyde 282i (538.5 mg, 1.5 mmol), Pd₂(dba)₃ (91.5 mg, 0.10 mmol), tricyclohexylphospine (112 mg, 0.40 mmol), cesium carbonate (652 mg, 2.0 mmol), 1,4-dioxane (20 mL), and water (0.5 mL). After three cycles of vacuum/argon flush, the mixture was heated at 75° C. for 2 h. It was then filtered and the filtrate was evaporated under reduced pressure. The residue was washed with petroleum ether to afford 292a (300 mg, crude) as a black solid. MS-ESI: [M+H]⁺ 542.2

Example 292

3-[4-[5-[(1,5-dimethylpyrazol-3-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one 292

To a solution of 292a (162.6 mg, 0.30 mmol) in methanol (6 mL) was added sodium borohydride (114 mg, 3.0 mmol) at 0° C. The reaction was stirred at 25° C. for 0.5 h. It was then quenched with water (10 mL). The resulting mixture was evaporated under reduced pressure and the residue was extracted with dichloromethane (3×20 mL). The combined dichloromethane extract was concentrated under reduced pressure and the residue was purified by reverse-phase prep-HPLC to afford 292 (35 mg, 22%) as a yellow solid. MS-ESI: [M+H]⁺ 543.8. ¹H NMR (500 MHz, DMSO-d₆) δ 8.57 (d, J=5.0 Hz, 1H), 8.47 (s, 1H), 8.08 (s, 1H), 8.02 (d, J=1.5 Hz, 1H), 7.52 (d, J=5.0 Hz, 1H), 7.40 (d, J=1.5 Hz, 1H), 5.90 (s, 1H), 4.88 (s, 1H), 4.40 (d, J=5.0 Hz, 2H), 3.59 (s, 3H), 3.58 (s, 3H), 2.92 (d, J=4.5 Hz, 2H), 2.81 (s, 2H), 2.18 (s, 3H), 1.29 (s, 3H), 1.28 (s, 6H).

Example 293a

1-Methyl-4-nitro-1H-1,2,3-triazole 293a

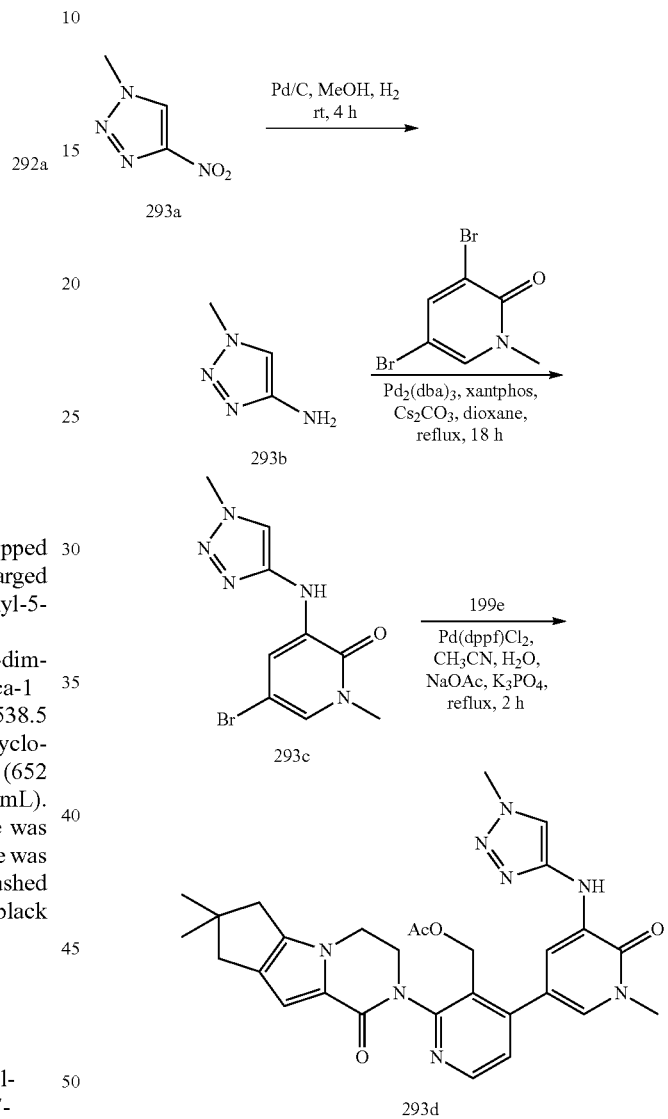

To a 100-mL single-neck round-bottomed containing 4-nitro-2H-1,2,3-triazole (2.0 g, 17.5 mmol) and THF (10 mL) at 0° C. was added NaH (1.7 g, 35.0 mmol, 2.0 eq.). The mixture was stirred at 0° C. for 15 min. A solution of iodomethane (3.68 g, 26.3 mmol, 1.5 eq.) in acetone (40 mL) was added and the resulting reaction mixture was stirred at room temperature for 2 h. After this time, the reaction was quenched by water (20 mL) at 0° C. and concentrated under reduced pressure. The residue was diluted with dichloromethane (100 mL). It was then washed with brine, dried over anhydrous Na₂SO₄, and concentrated under reduced pressure. The residue was purified by silica-gel column chromatography eluting with 6:1 petroleum ether/ethyl acetate to afford 293a (800 mg, 35%) as a light yellow solid and the regioisomer 1-methyl-5-nitro-1H-1,2,3-triazole (1.34 g, 60%) as a white solid. $^1$H NMR (500 MHz, CDCl$_3$) δ 8.34 (s, 1H), 4.26 (s, 3H).

Example 293b

1-Methyl-1H-1,2,3-triazol-4-amine 293b

Following the procedure in Example 130b, and starting with 293a (800 mg, 6.25 mmol) and 10% palladium on carbon (50% wet, 160 mg) afforded 293b as a yellow solid (600 mg, 98%). $^1$H NMR (500 MHz, CDCl$_3$) δ 6.91 (s, 1H), 3.97 (s, 3H), 3.65 (brs, 2H).

Example 293c

5-Bromo-1-methyl-3-(1-methyl-1H-1,2,3-triazol-4-ylamino)pyridin-2(1H)-one 293c

Following the procedure in Example 130c, and starting with 293b (500 mg, 5.10 mmol, 1.0 eq.) and 3,5-dibromo-1-methylpyridin-2(1H)-one (2.04 g, 7.65 mmol, 1.5 eq.) afforded 293c as a yellow solid (760 mg, 52%). MS-ESI: [M+H]$^+$ 283.9.

Example 293d (2-{4,4-Dimethyl-9-oxo-1,10-diazatricyclo[6.4.0. 0$^{2,6}$]dodeca-2(6),7-dien-10-yl}-4-{1-methyl-5-[(1-methyl-1H-1,2,3-triazol-4-yl)amino]-6-oxo-1,6-dihydropyridin-3-yl}pyridin-3-yl)methyl Acetate 293d Following the procedure in Example 283b, and starting with 293c (150 mg, 0.53 mmol, 1.0 eq.) and {3-[(acetoxy) methyl]-2-{4,4-dimethyl-9-oxo-1,10-diazatricyclo[6.4.0. 0$^{2,6}$]dodeca-2(6),7-dien-10-yl}pyridin-4-yl}boronic acid 199e (629 mg, 1.59 mmol, 3.0 eq.) afforded 293d as a yellow solid (110 mg, 37%). MS-ESI: [M+H]$^+$ 557.4.

Example 293

3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 293

Following the procedure in Example 283, and starting with 293d (110 mg, 0.20 mmol) afforded 293 as a pale yellow solid (78 mg, 75%). MS-ESI: [M+H]$^+$ 514.9. $^1$H NMR (500 MHz, CDCl$_3$) δ 8.49 (d, J=4.5 Hz, 1H), 7.78 (s, 1H), 7.73 (s, 1H), 7.60 (s, 1H), 7.42 (s, 1H), 7.33 (d, J=4.0 Hz, 1H), 6.87 (s, 1H), 5.25 (brs, 1H), 4.65-4.38 (m, 3H), 4.21-4.20 (m, 2H), 4.08 (s, 3H), 3.89-3.85 (m, 1H), 3.73 (s, 3H), 2.59 (s, 2H), 2.54 (s, 2H), 1.29 (s, 6H).

Example 294

3-[4-[5-[(5-tert-butylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 294

Following the procedures in Example 273, and substituting 5-(tert-butyl)isoxazol-3-amine for 2-aminopyridine, 294 was prepared (5.1 mg, 16% yield). $^1$H NMR (400 MHz, DMSO-d$_6$) δ 8.93 (s, 1H), 8.48 (d, J=5.0 Hz, 1H), 8.04 (d, J=2.3 Hz, 1H), 7.56 (d, J=2.3 Hz, 1H), 7.32 (d, J=5.0 Hz, 1H), 6.56 (s, 1H), 6.22 (s, 1H), 4.90 (t, J=5.3 Hz, 1H), 4.51-4.36 (m, 2H), 4.26-4.16 (m, 3H), 3.85 (d, J=10.7 Hz, 1H), 3.60 (s, 3H), 2.58 (d, J=7.7 Hz, 2H), 2.43 (s, 2H), 1.27 (s, 9H), 1.22 (s, 6H). ES-MS m/z 557.4 [M+1].

Example 295a

5-Ethylisoxazol-3-amine 295a

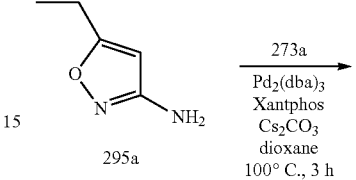

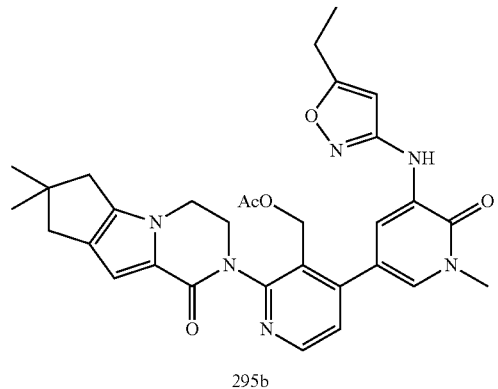

To a solution of 3-oxopentanenitrile (1.0 g, 10.3 mmol) in water (20 mL) was added NaOH (535.6 mg, 13.4 mmol). After stirring for 5 minutes, hydroxylamine hydrochloride (787.4 mg, 11.33 mmol) was added and mixture was heated at 40° C. for 12 h. At this point, conc. HCl (3 mL) was added and the reaction mixture was heated at 50° C. for 2 h. Analysis of the reaction mixture by LCMS showed complete conversion to the desired product. It was then cooled to room temperature and adjusted the pH to 10 with aqueous NaOH (30%). The mixture was extracted with ethyl acetate (3×50 mL). The combined organic layer was washed with brine, dried over Na$_2$SO$_4$, and concentrated under reduced pressure. The residue was purified by silica-gel column chromatography eluting with 2:1 petroleum ether/ethyl acetate to afford 295a as a yellow solid (300 mg, 25%). MS-ESI: [M+H]$^+$ 113.3. $^1$H NMR (500 MHz, DMSO-d$_6$) 5.55 (s, 1H), 5.40 (s, 2H), 2.56-2.52 (m, 2H), 1.13 (t, J=7.5 Hz, 3H).

Example 295b (2-{4,4-Dimethyl-9-oxo-1,10-diazatricyclo[6.4.0. 0$^{2,6}$]dodeca-2(6),7-dien-10-yl}-4-{5-[(5-ethyl-1,2-oxazol-3-yl)amino]-1-methyl-6-oxo-1,6-dihydropyridin-3-yl}pyridin-3-yl)methyl Acetate 295b A 25-mL single-neck round-bottomed flask equipped with a magnetic stirrer and a reflux condenser was charged with 295a (24.8 mg, 0.222 mmol), [4-(5-bromo-1-methyl-6-oxo-1,6-dihydropyridin-3-yl)-2-{4,4-dimethyl-9-oxo-1,10-diazatri-cyclo[6.4.0.0$^{2,6}$]dodeca-2(6),7-dien-10-yl}pyridin-3-yl]methyl acetate 273a (100 mg, 0.185 mmol), Pd$_2$(dba)$_3$ (8.5 mg, 0.0093 mmol), Xantphos (10.7 mg, 0.019 mmol), Cs$_2$CO$_3$ (120.6 mg, 0.37 mmol), and dioxane (10 mL). The system was subjected to three cycles of vacuum/nitrogen flush and heated at 100° C. under N₂ protection for 3 h. Analysis of the reaction mixture by LCMS showed complete conversion to the desired product. It was cooled to room temperature and filtered. The filtrate was concentrated under reduced pressure. The residue was washed with acetonitrile (0.5 mL) to afford 295b as white solid (52 mg, 49.5%), which was used in the next step without further purification. MS-ESI: [M+H]⁺ 570.8

Example 295

3-[4-[5-[(5-ethylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 295

To a solution of 295b (42 mg, 0.0736 mmol) in THF (4 mL), i-propanol (4 mL), and water (4 mL) was added lithium hydroxide (17.7 mg, 0.736 mmol). The reaction mixture was stirred at room temperature for 1 h and concentrated under reduced pressure. The residue was diluted with water (5 mL) and extracted with dichloromethane (3×20 mL). The combined extract was dried over Na₂SO₄, filtered, and concentrated under reduced pressure. The residue was purified by reverse-phase prep-HPLC to afford 295 (22 mg, 57%) as a white solid. MS-ESI: [M+H]⁺ 528.8. ¹H NMR (500 MHz, DMSO-d₆) δ 8.99 (s, 1H), 8.49 (d, J=5.5 Hz, 1H), 8.03 (d, J=2.0 Hz, 1H), 7.56 (d, J=2.0 Hz, 1H), 7.33 (d, J=5.0 Hz, 1H), 6.57 (s, 1H), 6.25 (s, 1H), 4.94-4.92 (m, 1H), 4.48-4.38 (m, 2H), 4.26-4.19 (m, 3H), 3.87-3.85 (m, 1H), 3.61 (s, 3H), 2.68-2.66 (m, 2H), 2.62-2.59 (m, 2H), 2.43 (s, 2H), 1.22 (s, 6H), 1.19 (t, J=7.5 Hz, 3H).

Example 296a (3-Nitro-1H-pyrazol-5-yl)methanol 296a

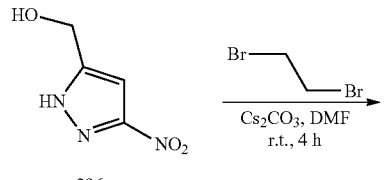

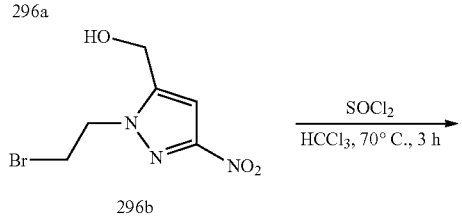

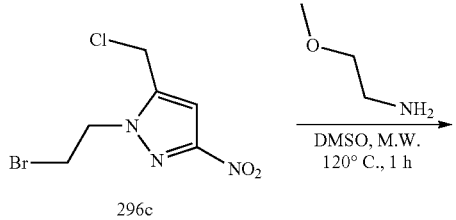

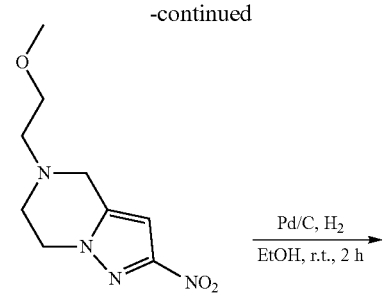

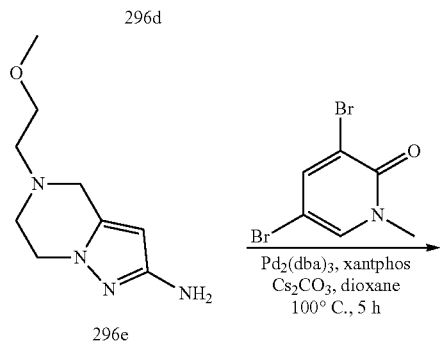

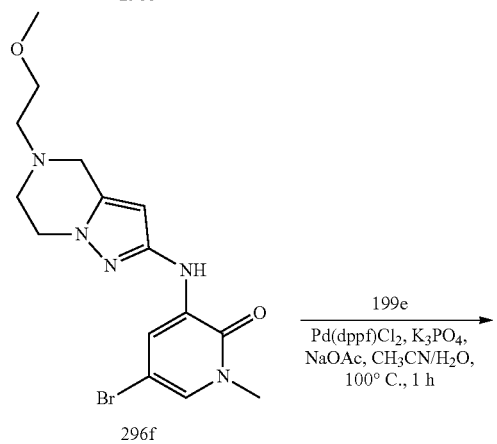

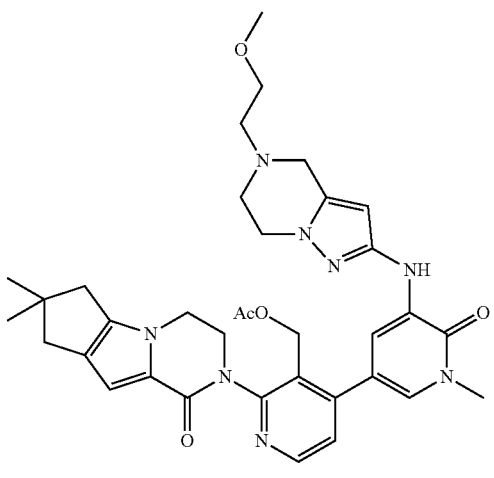

A 100-mL three-neck round-bottomed flask equipped with a nitrogen inlet was purged with nitrogen and charged with 3-nitropyrazole-5-carboxylic acid (0.56 g, 3.56 mmol) and THF (8 mL). The system was cooled to −5° C. using an ice/acetone bath. Borane-THF complex solution (1.0M, 11 mL, 11.0 mmol) was added at a rate that maintained the internal reaction temperature below 5° C. After the addition was complete the cooling bath was removed and the reaction was stirred at 60° C. for 3 h. After this time the reaction was cooled to −5° C. using an ice/acetone bath, water (2 mL) and 4N hydrochloric acid (2 mL) was added. The reaction mixture was stirred at 70° C. for 1 h in order to destroy the borane-pyrazole complex. It was cooled to room temperature and concentrated under reduced pressure to a volume of approximately 1 mL. Ethyl acetate (20 mL) and water (10 mL) were added and the mixture was stirred for 15 min. The aqueous layer was separated and extracted with ethyl acetate (4×10 mL). The combined organic layer was washed with saturated aqueous sodium bicarbonate (2×10 mL), brine (10 mL), and dried over sodium sulfate. The drying agent was removed by filtration and the filtrate was concentrated under reduced pressure to afford 296a (345 mg, 68%) as a light yellow solid. MS-ESI: [M+H]$^+$ 144

Example 296b (1-(2-Bromoethyl)-3-nitro-1H-pyrazol-5-yl)methanol 296b

A mixture of 296a (345 mg, 2.41 mmol), and cesium carbonate (965 mg, 2.96 mmol) in DMF (5 mL) was cooled to 0° C. using an ice/acetone bath and dibromoethane (4.48 g, 24.1 mmol) was added portion-wise (no exotherm). The reaction was stirred at 0° C. for 1 h and room temperature for 4 h. After this time ethyl acetate (20 mL) and water (15 mL) were added. The aqueous layer was separated and extracted with ethyl acetate (2×10 mL). The combined organic layer was washed with water (10 mL), brine (10 mL), and dried over sodium sulfate. The drying agent was removed by filtration. The filtrate was concentrated under reduced pressure to afford the crude product, which was purified by silica-gel column chromatography eluting with 6:1 petroleum ether/ethyl acetate to afford 296b (300 mg, 50%). MS-ESI: [M+H]$^+$ 250

Example 296c 1-(2-Bromoethyl)-5-(chloromethyl)-3-nitro-1H-pyrazole 296c

A 50-mL three-necked round-bottomed flask equipped with a nitrogen inlet and a reflux condenser was purged with nitrogen and charged with 296b (438 mg, 1.76 mmol) and chloroform (10 mL). The reaction was cooled to −5° C. using an ice/acetone bath and SOCl$_2$ (628 mg, 5.28 mmol) was added portion-wise. The cooling bath was removed and the reaction was stirred at 70° C. for 3 h. After this time, the solvent was removed under reduced pressure. ethyl acetate was added to the residue and the resulting solution was cooled to −5° C. Saturated aqueous sodium bicarbonate (3 mL) was added until a pH of 8.5 was reached. The mixture was partitioned between ethyl acetate and water. The combined organic layer was washed with saturated aqueous sodium carbonate (2×5 mL), brine (10 mL), and dried over sodium sulfate. The drying agent was removed by filtration. The filtrate was concentrated under reduced pressure to afford 296c (284 mg, 60%).

Example 296d 5-(2-Methoxyethyl)-2-nitro-4,5,6,7-tetrahydropyrazolo[1,5-a]pyrazine 296d A microwave vial equipped with a magnetic stirrer was charged with 296c (2.67 g, 10.0 mmol), 2-methoxyethanamine (2.25 g, 30.0 mmol), and DMSO (14 mL). The reaction mixture was heated at 120° C. under microwave irradiation for 1.0 h. It was cooled to room temperature and diluted with ethyl acetate (40 mL). The mixture was washed with water (3×15 mL). The organic layer was dried and filtered. The filtrate was concentrated under pressure and the residual was purified by silica-gel column chromatography eluting with 30:1 dichloromethane/methanol to afford 296d (1.7 g, 75%) as a yellow solid. MS-ESI: [M+H]$^+$ 227.0

Example 296e 5-(2-Methoxyethyl)-4,5,6,7-tetrahydropyrazolo[1,5-a]pyrazin-2-amine 296e To a solution of 296d (1.7 g, 7.5 mmol) in ethanol (50 mL) was added Pd/C (10%, 800 mg). The reaction was charged with hydrogen gas (via balloon) and stirred at room temperature for 2 h. After reaction was complete, the mixture was filtered through a plug of CELITE®. The filtrate was concentrated reduced pressure to afford 296e as a yellow solid (1.2 g, 82%), which was used directly without further purification. MS-ESI: [M+H]$^+$ 197.3

Example 296f

5-Bromo-3-(5-(2-methoxyethyl)-4,5,6,7-tetrahydropyrazolo[1,5-a]pyrazin-2-ylamino)-1-methylpyridin-2(1H)-one 296f A 100-mL single-neck round-bottomed flask equipped with a magnetic stirrer and a reflux condenser was charged with 1,4-dioxane (40 mL), 296e (588 mg, 3.0 mmol), 3,5-dibromo-1-methylpyridin-2(1H)-one (800 mg, 3.0 mmol), and cesium carbonate (1.96 g, 6.0 mmol). After bubbling nitrogen through the suspension for 20 minutes, xantphos (173 mg, 0.30 mmol) and tris(dibenzylideneacetone)dipalladium(0) (137 mg, 0.15 mmol) were added. The system was subjected to three cycles of vacuum/argon flush and heated at reflux for 5 h. It was then cooled to room temperature and filtered. The solid was washed with dichloromethane (2×15 mL). The combined filtrate was concentrated under reduced pressure. The residue solid was purified by silica-gel column chromatography eluting with dichloromethane/methanol (80/1 to 30/1) to afford 296f (745 mg, 65%) as yellow solid. MS-ESI: [M+H]$^+$ 382.9

Example 296g (2-{4,4-Dimethyl-9-oxo-1,10-diazatricyclo[6.4.0.0$^{2,6}$]dodeca-2(6),7-dien-10-yl}-4-(5-{[5-(2-methoxyethyl)-4H,5H,6H,7H-pyrazolo[1,5-a]pyrazin-2-yl]amino}-1-methyl-6-oxo-1,6-dihydropyridin-3-yl)pyridin-3-yl)methyl Acetate 296g A 25-mL round-bottomed flask equipped with a reflux condenser was charged with {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (198 mg, 0.50 mmol), 296f (190 mg, 0.50 mmol), K$_3$PO$_4$ (212 mg, 1.0 mmol), sodium acetate (82 mg, 1.0 mmol), Pd(dppf)Cl$_2$ (21 mg, 0.025 mmol), acetonitrile (8 mL), and water (0.5 mL). The system was subjected to three cycles of vacuum/nitrogen flush and heated at 100° C. under N$_2$ protection for 1 h. Analysis of the reaction mixture by LCMS showed complete conversion to the desired product. The reaction mixture was cooled to room temperature and filtered. The filtrate was concentrated under reduced pressure. The residue was partitioned between dichloromethane (20 mL) and water (10 mL). The water layer was extracted with dichloromethane (2×20 mL). The combined organic extract was dried over $Na_2SO_4$, filtered, and concentrated under reduced pressure. The dark residue was purified by silica-gel column chromatography eluting with dichloromethane/methanol (80/1 to 30/1) to afford 296g (163 mg, 50%) as a yellow solid. MS-ESI: $[M+H]^+$ 654.9

Example 296

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 296

To a solution of 296g (160 mg, 0.245 mmol) in THF/i-propanol/water (8/5/3 mL) was added lithium hydroxide (29 mg, 1.22 mmol). The mixture was stirred at room temperature for 1 h and evaporated under pressure. The residue was purified by reverse-phase prep-HPLC to afford 296 as a white solid (117 mg, 78%). MS-ESI: $[M+H]^+$ 613.3. $^1$H NMR (500 MHz, $CDCl_3$) δ 8.48 (d, J=5.0 Hz, 1H), 7.93 (d, J=2.0 Hz, 1H), 7.73 (d, J=2.5 Hz, 1H), 7.41 (s, 1H), 7.35 (d, J=5.0 Hz, 1H), 6.86 (s, 1H), 5.71 (s, 1H), 5.05 (t, J=7.0 Hz, 1H), 4.66-4.65 (m, 1H), 4.52-4.50 (m, 1H), 4.36-4.34 (m, 1H), 4.17-4.05 (m, 2H), 4.10-4.08 (m, 2H), 3.88-3.87 (m, 1H), 3.75-3.73 (m, 2H), 3.71 (s, 3H), 3.61-3.59 (m, 2H), 2.40 (s, 3H), 3.04-3.03 (m, 2H), 2.80 (t, J=5.5 Hz, 2H), 2.59-2.57 (m, 2H), 2.54-2.53 (m, 2H), 1.29 (s, 6H).

Example 297a

6-Chloro-2-methyl-4-(5-methyl-4,5,6,7-tetrahydropyrazolo[1,5-a]pyrazin-2-ylamino)pyridazin-3(2H)-one 297a

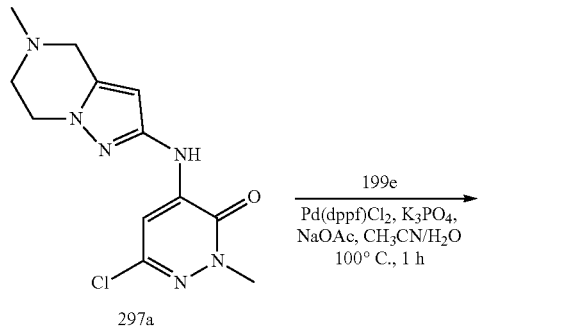

A 100-mL single-neck round-bottomed flask equipped with a magnetic stirrer and a reflux condenser was charged with 1,4-dioxane (30 mL), 5-methyl-4,5,6,7-tetrahydropyrazolo[1,5-a]pyrazin-2-amine 113e (1.70 g, 11.2 mmol), 4-bromo-6-chloro-2-methylpyridazin-3(2H)-one (2.68 g, 12.0 mmol), and cesium carbonate (7.30 g, 22.4 mmol). After bubbling nitrogen through the suspension for 30 minutes, Xantphos (0.59 g, 1.02 mmol) and tris(dibenzylideneacetone)dipalladium(0) (467 mg, 0.51 mmol) were added. The system was subjected to three cycles of vacuum/argon flash and heated at 90° C. for 2 h. It was then cooled to room temperature and filtered. The filtrate was evaporated in vacuo. The residue was purified by silica-gel column chromatography eluting with 30:1 dichloromethane/methanol to afford 297a (1.9 g, 60%) as a brown solid. LCMS: $[M+H]^+$ 295.1

Example 297b (2-{4,4-Dimethyl-9-oxo-1,10-diazatricyclo[6.4.0.0$^{2,6}$]dodeca-2(6),7-dien-10-yl}-4-[1-methyl-5-({5-methyl-4H,5H,6H,7H-pyrazolo[1,5-a]pyrazin-2-yl}amino)-6-oxo-1,6-dihydropyridazin-3-yl]pyridin-3-yl)methyl Acetate 297b A 25-mL round-bottomed flask equipped with a magnetic stirrer and a reflux condenser was charged with 297a (195 mg, 0.66 mmol), (2-{4,4-dimethyl-9-oxo-1,10-diazatricyclo[6.4.0.0$^{2,6}$]dodeca-2(6),7-dien-10-yl}-4-(tetramethyl-1,3,2-dioxaborolan-2-yl)pyridin-3-yl)methyl acetate 199e (315 mg, 0.66 mmol), $PdCl_2$(dppf) (40 mg, 0.050 mmol), $K_3PO_4$ (250 mg, 1.2 mmol), sodium acetate (100 mg, 1.20 mmol), acetonitrile (8 mL), and water (1 mL). The system was evacuated and then refilled with $N_2$. It was then heated at 100° C. for 1 h. The mixture was cooled to room temperature and filtered. The filtrate was concentrated under reduced pressure and the residue was purified by silica-gel column chromatography eluting with 20:1 dichloromethane/methanol to afford 297b as a yellow solid (150 mg, 38%). MS-ESI: $[M+H]^+$ 612.3.

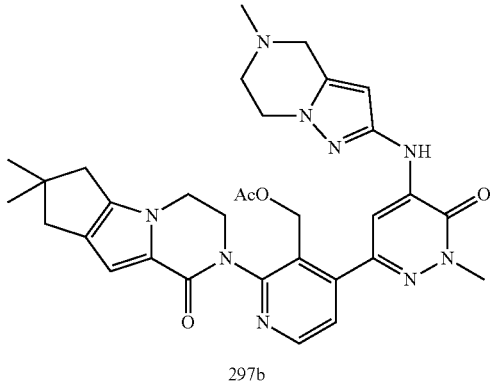

Example 297

3-[3-(hydroxymethyl)-4-[1-methyl-5-[(5-methyl-6,7-dihydro-4H-pyrazolo[1,5-a]pyrazin-2-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one 297

A mixture of 297b (150 mg, 0.24 mmol) and lithium hydroxide hydrate (96 mg, 2.4 mmol) in THF (8 mL), i-propanol (8 mL), and water (2 mL) was stirred at 40° C. for 0.5 h. The mixture was evaporated under reduced pressure and the residue was partitioned between dichloromethane (15 mL) and water (10 mL). The combined extract was concentrated under reduced pressure and the residue was purified by reverse-phase prep-HPLC to afford 297 as a pale yellow solid (98 mg, 70%). MS-ESI: $[M+H]^+$ 570.3. $^1$H NMR (500 MHz, DMSO-$d_6$) δ 9.30 (s, 1H), 8.52 (d, J=4.5 Hz, 1H), 7.90 (s, 1H), 7.38 (d, J=5.0 Hz, 1H), 6.55 (s, 1H), 5.99 (s, 1H), 4.74-4.73 (m, 1H), 4.60-4.58 (m, 1H), 4.40-4.37 (m, 1H), 4.26-4.24 (m, 1H), 4.19-4.18 (m, 2H), 3.96-3.95 (m, 2H), 3.89-3.87 (m, 1H), 3.75 (s, 3H), 3.53-3.52 (m, 2H), 2.80-2.78 (m, 2H), 2.57-2.55 (m, 2H), 2.52-2.50 (m, 2H), 2.35 (s, 3H), 1.22 (s, 6H).

Example 298a (4-{5-[(5-Cyanopyrazin-2-yl)amino]-1-methyl-6-oxo-1,6-dihydropyridin-3-yl}-2-{4,4-dimethyl-9-oxo-1,10-diazatricyclo[6.4.0.0²,⁶]dodeca-2(6),7-dien-10-yl}pyridin-3-yl)methyl a\Acetate 298a

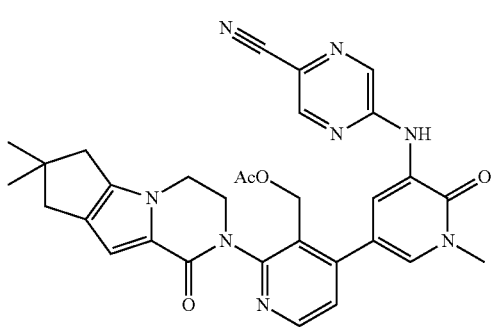

298a

A 50-mL round-bottomed flask equipped with a reflux condenser was charged with [4-(5-bromo-1-methyl-6-oxo-1,6-dihydropyridin-3-yl)-2-{4,4-dimethyl-9-oxo-1,10-diaza-tricy-clo[6.4.0.0²,⁶]dodeca-2(6),7-dien-10-yl}pyridin-3-yl] methyl acetate 273a (269 mg, 0.50 mmol), 5-aminopyrazine-2-carbonitrile (60 mg, 0.50 mmol), XantPhos (29 mg, 0.050 mmol), Pd₂(dba)₃ (45 mg, 0.050 mmol), Cs₂CO₃ (326 mg, 1.0 mmol), and 1,4-dioxane (10 mL). The reaction mixture was heated at 100° C. under microwave irradiation for 1 h after three times atmosphere/argon flush. The mixture was filtered off and the solid was washed with methanol (50 mL). The combined filtrate was evaporated under reduced pressure and the residue was purified with silica-gel column chromatography eluting with 50:1 dichloromethane/methanol to afford 298a (200 mg, 69%) as yellow solid. MS-ESI: [M+H]⁺ 579.3

Example 298

5-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyrazine-2-carbonitrile 298

A mixture of 298a (200 mg, 0.35 mmol) and lithium hydroxide (84 mg, 3.5 mmol) in i-propanol/THF (5 mL/5 mL) and water (2 mL) was stirred at room temperature for 2 h. The mixture was evaporated under reduced pressure and the residue was partitioned between ethyl acetate (20 mL) and water (10 mL). The combined extract was concentrated under reduced pressure and the residue was purified by reverse-phase prep-HPLC to afford 298 (40 mg, 21%) as yellow solid. MS-ESI: [M+H]⁺ 537.3. ¹H NMR (500 MHz, DMSO-d₆) δ 9.96 (s, 1H), 8.77 (s, 1H), 8.701 (d, J=2.5 Hz, 1H), 8.67 (s, 1H), 8.50 (d, J=5.0 Hz, 1H), 7.76 (d, J=2.0 Hz, 1H), 7.35 (d, J=5.0 Hz, 1H), 6.56 (s, 1H), 5.00 (t, J=5.0 Hz, 1H), 4.42-4.39 (m, 2H), 4.24-4.19 (m, 3H), 3.84 (m, 1H), 3.63 (s, 3H), 2.57 (m, 2H), 2.42 (s, 2H), 1.23 (s, 6H)

Example 299a

5-Phenylisoxazol-3-amine 299a

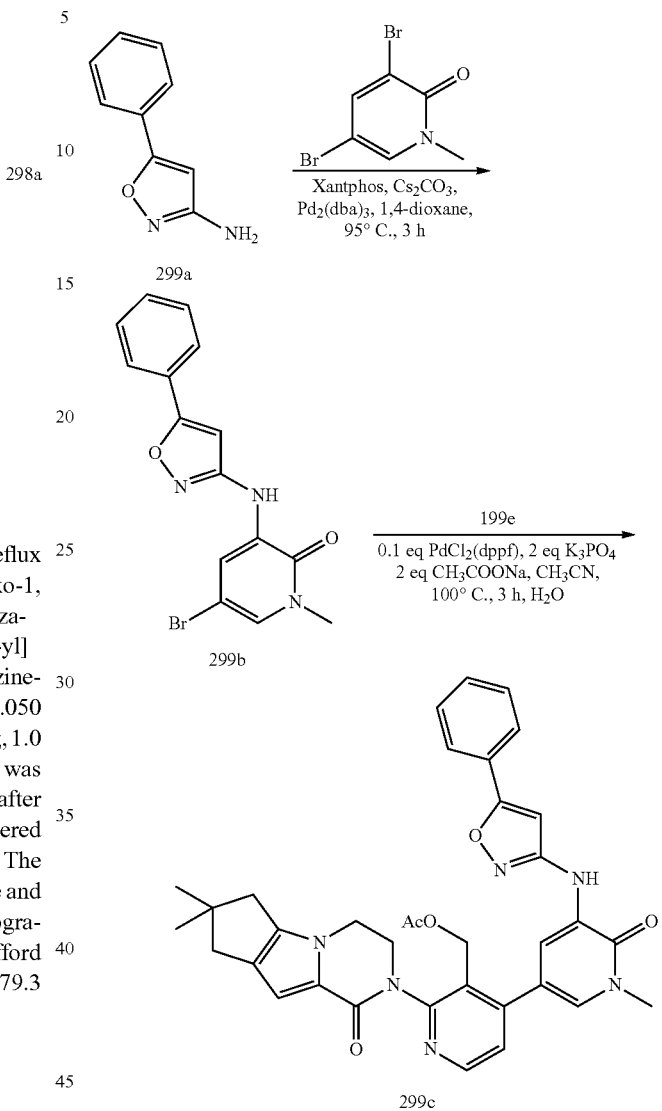

To a stirred solution of 3-oxo-3-phenylpropanenitrile (1.5 g, 10.3 mmol) and NaOH (452 mg, 11.3 mmol) in water (10 mL)/EtOH (10 mL) was added hydroxylamine hydrochloride (785 mg, 11.3 mmol). The mixture was stirred at 80° C. for overnight. At this point, conc. HCl (1.3 mL, 15.5 mmol) was added and the resulting mixture was heated at 80° C. for 2 h. It was then basified to pH 10 and extracted with ethyl acetate. The combined extract was concentrated under reduced pressure and the residue was purified by silica-gel column chromatography eluting with ethyl acetate/petroleum ether (1:50 to 1:10) to afford 299a as a yellow solid (1.1 g, 68%). MS-ESI: [M+H]⁺ 161.3.

Example 299b

5-Bromo-1-methyl-3-(5-phenylisoxazol-3-ylamino)pyridin-2(1H)-one 299b

A 100-mL single-neck round-bottomed flask equipped with a magnetic stirrer and a reflux condenser was charged with 1,4-dioxane (40 mL), 299a (640 mg, 4.0 mmol), 3,5-dibromo-1-methylpyridin-2(1H)-one (1.1 g, 4.0 mmol), Pd₂(dba)₃ (366.8 mg, 0.40 mmol), XantPhos (462.4 mg, 0.80 mmol), and cesium carbonate (2.6 g, 8.0 mmol). After three cycles of vacuum/argon flush, the mixture was heated at 92° C. for 3 hrs. It was then cooled to room temperature and filtered. The filtrate was concentrated under reduced pressure and the resulting residue was washed with acetonitrile to afford 299b (1.7 g, 87%). MS-ESI: [M+H]+ 346.0.

Example 299c (2-{4,4-Dimethyl-9-oxo-1,10-diazatricyclo[6.4.0. 0²,⁶]dodeca-2(6),7-dien-10-yl}-4-{1-methyl-6-oxo-5-[(5-phenyl-1,2-oxazol-3-yl)amino]-1,6-dihydropy-ridin-pyridin-3-yl}pyridin-3-yl)methyl Acetate 299c A 50-mL round-bottomed flask equipped with a magnetic stirrer and a reflux condenser was charged with 299b (138 mg, 0.40 mmol), {3-[(acetoxy)methyl]-2-{4,4-dimethyl-9-oxo-1,10-diaza-tricyclo[6.4.0.0²,⁶]dodeca-2(6),7-dien-10-yl}pyridin-4-yl}boronic acid 199e (158.8 mg, 0.40 mmol), Pd(dppf)Cl₂ (32.7 mg, 0.040 mmol), K₃PO₄ (169.6 mg, 0.80 mmol), sodium acetate (108.8 mg, 0.80 mmol), water (0.5 mL), and acetonitrile (10 mL). After three cycles of vacuum/argon flush, the mixture was heated at 100° C. for 3 hrs. It was then cooled to room temperature and filtered. The filtrate was concentrated under reduced pressure and the resulting residue was purified by silica-gel column chromatography eluting with 50:1 dichloromethane/methanol to afford 299c as a brown solid (120 mg, 49%). MS-ESI: [M+H]+ 618.8.

Example 299

3-[3-(hydroxymethyl)-4-[1-methyl-6-oxo-5-[(5-phenylisoxazol-3-yl)amino]-3-pyridyl]-2-pyridyl]-7,7-dimethyl-1,2,6,8-tetrahydrocyclopenta[3,4]pyrrolo[3,5-b]pyrazin-4-one 299

A mixture of 299c (100 mg, 0.16 mmol) and lithium hydroxide (96 mg, 4.0 mmol) in i-propanol/THF (1:1, 4 mL) and water (1 mL) was stirred at 40° C. for 30 mins. The reaction mixture was concentrated under reduced pressure and diluted with water (5 mL). The resulting mixture was extracted with dichloromethane for three times. The combined organic layer was concentrated under reduced pressure and the resulting residue was purified by reverse-phase prep-HPLC to afford 299 as a white solid (35 mg, 31%). MS-ESI: [M+H]+ 576.8. ¹H NMR (500 MHz, DMSO-d₆) δ 9.17 (s, 1H), 8.51 (d, J=5.5 Hz, 1H), 8.11 (d, J=2.5 Hz, 1H), 7.79-7.77 (m, 2H), 7.60 (d, J=2.0 Hz, 1H), 7.55-7.49 (m, 3H), 7.35 (d, J=4.5 Hz, 1H), 6.91 (s, 1H), 6.57 (s, 1H), 4.96-4.93 (m, 1H), 4.50-4.40 (m, 2H), 4.26-4.19 (m, 3H), 3.88-3.85 (m, 1H), 3.63 (s, 3H), 2.62-2.59 (m, 2H), 2.44-2.42 (m, 2H), 1.23 (s, 6H).

Example 300a 5-(1-Methoxypropan-2-yl)-2-nitro-4,5,6,7-tetrahydropyrazolo[1,5-a]pyrazine 300a

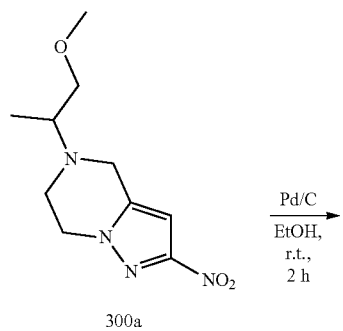

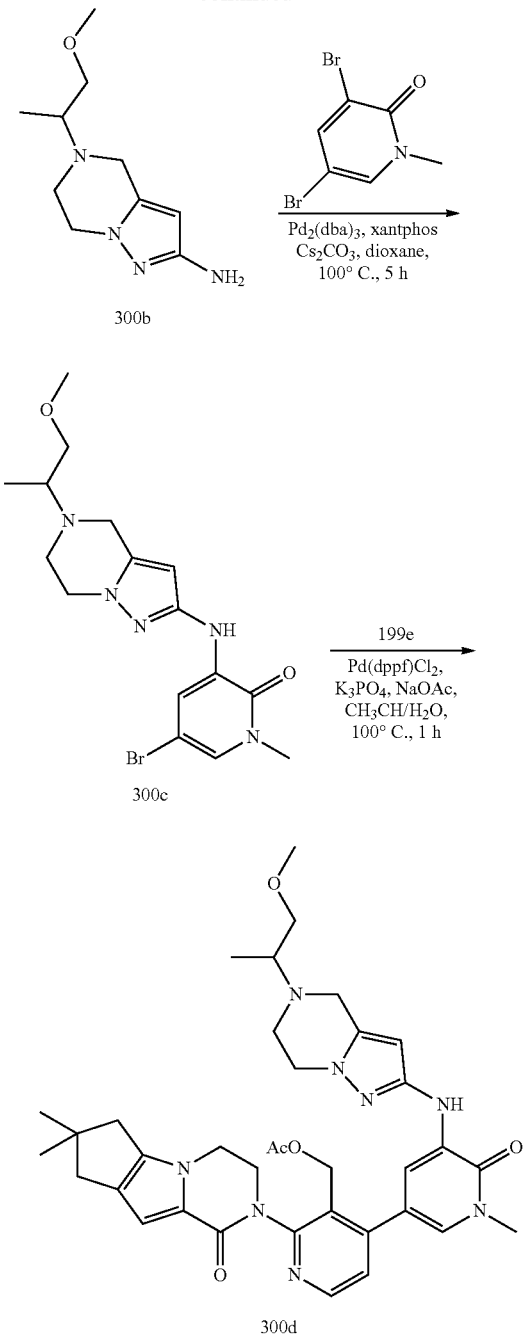

A microwave vial equipped with a magnetic stirrer was charged with 1-(2-bromoethyl)-5-(chloromethyl)-3-nitro-1H-pyrazole 296c (1.0 g, 3.7 mmol), 1-methoxypropan-2-amine (1.0 g, 11.2 mmol), and DMSO (6 mL). The mixture was heated at 120° C. under microwave irradiation for 1.0 h. It was the cooled to room temperature and diluted with water (30 mL). The resulting mixture was extracted with ethyl acetate (3×20 mL). The combined organic layer was dried and concentrated under reduced pressure. The residue was purified by silica-gel column chromatography eluting with petroleum ether/ethyl acetate (60/1 to 1/1) to afford 300a (600 mg, 68%) as a yellow solid. MS-ESI: [M+H]+ 241.0

Example 300b 5-(1-Methoxypropan-2-yl)-4,5,6,7-tetrahydropyrazolo[1,5-a]pyrazin-2-amine 300b A solution of 300a (600 mg, 2.5 mmol) in EtOH (40 mL) was added Pd/C (10%, 60 mg). The reaction mixture was charged with hydrogen gas (via balloon) and stirred at room temperature for 2 h. After reaction was complete, the mixture was filtered through a plug of CELITE®. The filtrate was concentrated reduced pressure to afford 300b as a yellow solid (467 mg, 89%), which was used without further purification. MS-ESI: [M+H]+ 211.1

Example 300c

5-Bromo-3-(5-(1-methoxypropan-2-yl)-4,5,6,7-tetrahydropyrazolo[1,5-a]-pyrazin-2-ylamino)-1-methylpyridin-2(1H)-one 300c A 100-mL single-neck round-bottomed flask equipped with a magnetic stirrer and a reflux condenser was charged with 1,4-dioxane (40 mL), 300b (400 mg, 1.9 mmol), 3,5-dibromo-1-methylpyridin-2(1H)-one (H-001) (508 mg, 1.9 mmol), and cesium carbonate (1.24 g, 3.8 mmol). After bubbling nitrogen through the suspension for 20 minutes, xantphos (109 mg, 0.19 mmol) and Pd$_2$(dba)$_3$ (87 mg, 0.095 mmol) were added. The system was subjected to three cycles of vacuum/argon flush and heated at reflux for 5 h. It was then cooled to room temperature and filtered. The solid was washed with dichloromethane (2×30 mL). The combined filtrate was concentrated under reduced pressure. The residue was purified by silica-gel column chromatography eluting with dichloromethane/methanol (80/1 to 30/1) to afford 300c (436 mg, 58%) as yellow solid. MS-ESI: [M+H]+ 396.0

Example 300d (2-{4,4-Dimethyl-9-oxo-1,10-diazatricyclo[6.4.0.0$^{2,6}$]dodeca-2(6),7-dien-10-yl}-4-(5-{[5-(1-methoxypropan-2-yl)-4H,5H,6H,7H-pyrazolo[1,5-a]pyrazin-2-yl]amino}-1-methyl-6-oxo-1,6-dihydropyridin-3-yl)pyridin-3-yl)methyl Acetate 300d A 50-mL round bottomed flask equipped with a reflux condenser was charged with {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (238 mg, 0.60 mmol), 300c (240 mg, 0.80 mmol), K$_3$PO$_4$ (254 mg, 1.2 mmol), sodium acetate (98 mg, 1.6 mmol), Pd(dppf)Cl$_2$ (22 mg, 0.030 mmol), and acetonitrile/water (12/0.5 mL). The system was subjected to three cycles of vacuum/nitrogen flush and heated at 100° C. under N$_2$ protection for 1 h. Analysis of the reaction mixture by LCMS showed complete conversion to the desired product. The reaction mixture was cooled to room temperature and filtered. The filtrate was concentrated under reduced pressure. The residue was partitioned between dichloromethane (30 mL) and water (30 mL). The water layer was extracted with dichloromethane (2×30 mL). The combined organic extract was dried over Na$_2$SO$_4$, filtered, and concentrated under reduced pressure. The dark residue was purified by silica-gel column chromatography eluting with dichloromethane/methanol (80/1 to 30/1) to afford 300d (200 mg, 50%) as yellow solid. MS-ESI: [M+H]+ 669.4

Example 300

(R)-2-(3'-(hydroxymethyl)-5-((5-(1-methoxypropan-2-yl)-4,5,6,7-tetrahydropyrazolo[1,5-a]pyrazin-2-yl)amino)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one 300

To a solution of 300d (200 mg, 0.30 mmol) in THF/i-propanol/water (6/3/3 mL) was added lithium hydroxide (36 mg, 1.5 mmol). The mixture was stirred at 30° C. for 1 h and concentrated under reduced pressure. The residue was partition between ethyl acetate (15 mL) and (10 mL). The water phase was extracted with ethyl acetate (3×10 mL). The combined organic layer was dried, filtered, and concentrated under reduced pressure. Prep-HPLC and chiral resolution afforded the two enantiomers: 300 (35 mg, 18.6%) as white solid; and 303 (28 mg, 15%) as white solid. MS-ESI: [M+H]+ 627.4. $^1$H NMR (500 MHz, CDCl$_3$) δ 8.49 (d, J=5.0 Hz, 1H), 7.92 (d, J=2.5 Hz, 1H), 7.73 (d, J=2.0 Hz, 1H), 7.41 (s, 1H), 7.35 (d, J=5.0 Hz, 1H), 6.85 (s, 1H), 5.72 (s, 1H), 5.05-5.03 (m, 1H), 4.67-4.45 (m, 1H), 4.52-4.50 (m, 1H), 4.35-4.31 (m, 1H), 4.18-4.16 (m, 2H), 4.09-4.07 (m, 2H), 3.87-3.85 (m, 3H), 3.71 (s, 3H), 3.56-3.52 (m, 1H), 3.45-3.43 (m, 1H), 3.38 (s, 3H), 3.11-3.08 (m, 3H), 2.60-2.58 (m, 2H), 2.53 (s, 2H), 1.29 (s, 6H), 1.17 (d, J=6.0 Hz, 3H).

Example 301a 6-(Trifluoromethyl)pyridazin-3-amine 301a

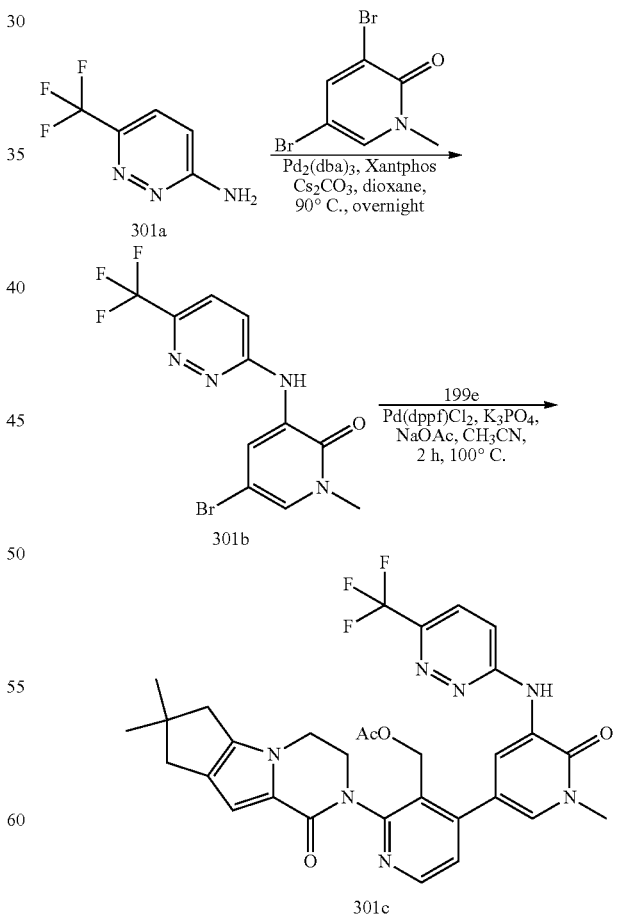

A mixture of 3-chloro-6-trifluoromethylpyridazine (1.6 g, 8.80 mmol) and ammonium hydroxide (9 mL) in THF (3 mL)

was heated at 100° C. in a microwave reactor for 1 h. After this period, the reaction mixture was evaporated and the residue was extracted with dichloromethane. The combined extract was dried over with MgSO$_4$, filtered, and evaporated under reduce pressure to afford 301a (1.3 g, 93%) as a white solid. MS-ESI: [M+H]$^+$ 164.1

Example 301b

5-Bromo-1-methyl-3-(6-(trifluoromethyl)pyridazin-3-ylamino)pyridin-2(1H)-one 301b A 100-mL single-neck round-bottomed flask equipped with a magnetic stirrer and a reflux condenser was charged with 301a (750 mg, 4.6 mmol), XantPhos (532 mg, 0.92 mmol), Pd$_2$dba$_3$ (421 mg, 0.46 mmol), 2-bromo-4-chloronicotinaldehyde (H-001) (1.84 g, 6.9 mmol), Cs$_2$CO$_3$ (3.0 g, 9.2 mmol), and 1,4-dioxane (50 mL). The system was subjected to three cycles of vacuum/argon flush and heated at 90° C. for overnight. After the completion of the reaction, the mixture was filtered and the solid was washed with methanol (30 mL). The combined filtrate was evaporated under reduced pressure and the residue was purified by silica-gel column chromatography eluting with 20:1 dichloromethane/methanol to afford 301b (1.38 g, 89%) as a yellow solid. MS-ESI: [M+H]$^+$ 350.8

Example 301c (2-{4,4-Dimethyl-9-oxo-1,10-diazatricyclo[6.4.0. 0$^{2,6}$]dodeca-2(6),7-dien-10-yl}-4-(1-methyl-6-oxo-5-{[6-(trifluoromethyl)pyridazin-3-yl]amino}-1,6-dihydropyridin-3-yl)pyridin-3-yl)methyl Acetate 301c A 100-mL single-neck round-bottomed flask equipped with a magnetic stirrer and a reflux condenser was charged with 301b (300 mg, 0.86 mmol), (2-{4,4-dimethyl-9-oxo-1,10-diazatricyclo[6.4.0.0$^{2,6}$]dodeca-2(6),7-dien-10-yl}-4-(tetramethyl-1,3,2-dioxaborolan-2-yl)pyridin-3-yl)methyl acetate 199e (824 mg, 1.72 mmol), CH$_3$COONa (140 mg, 1.72 mmol), PdCl$_2$(dppf) (70 mg, 0.086 mmol), K$_3$PO$_4$ (360 mg, 1.72 mmol), acetonitrile (20 mL), and water (0.5 mL). After bubbling nitrogen through the resulting mixture for 20 minutes, it was heated at 100° C. under nitrogen atmosphere for 2 h. The mixture was cooled to room temperature and filtered. The filtrate was evaporated under reduced pressure and the residue was purified by silica-gel column chromatography eluting with 50:1 dichloromethane/methanol to afford 301c as white solid (125 mg, 23%). MS-ESI: [M+H]$^+$ 622.3

Example 301

3-[3-(hydroxymethyl)-4-[1-methyl-6-oxo-5-[[6-(trifluoromethyl)pyridazin-3-yl]amino]-3-pyridyl]-2-pyridyl]-7,7-dimethyl-1,2,6,8-tetrahydrocyclopenta[3,4]pyrrolo[3,5-b]pyrazin-4-one 301

A mixture of 301c (90 mg, 0.14 mmol) and lithium hydroxide (24 mg, 0.56 mmol) in i-propanol/THF/water (6 mL/4 mL/2 mL) was stirred at room temperature for 0.5 h. The mixture was evaporated under reduced pressure and the residue was portioned between dichloromethane (20 mL) and water (10 mL). The combined dichloromethane extract was concentrated under reduced pressure and the residue was purified by reverse-phase prep-HPLC to afford 301c as a white solid (39 mg, 48%). MS-ESI: [M+H]$^+$ 580.3. $^1$H NMR (500 MHz, DMSO-d$_6$) δ 9.57 (s, 1H), 8.87 (d, J=2.5 Hz, 1H), 8.51 (d, J=5.0 Hz, 1H), 7.96 (d, J=9.0 Hz, 1H), 7.88 (d, J=9.0 Hz, 1H), 7.74 (d, J=2.0 Hz, 1H), 7.38 (d, J=5.0 Hz, 1H), 6.58 (s, 1H), 4.98-4.97 (m, 1H), 4.48-4.40 (m, 2H), 4.27-4.20 (m, 3H), 3.88-3.86 (m, 1H), 3.65 (s, 3H), 2.62-2.53 (m, 2H), 2.42-2.41 (m, 2H), 1.2 (s, 6H).

Example 302a

N-Methyl(1-methyl-3-nitro-1H-pyrazol-5-yl)methanamine 302a

To a stirred solution of MeNH$_2$ (30% wt in water) (2.5 g, 20 mmol) in acetone (10 mL) at 0° C. (ice bath) was added K$_2$CO$_3$ (415 mg, 3 mmol), followed by the dropwise addition of a solution of 5-(bromomethyl)-1-methyl-3-nitro-1H-pyrazole (220 mg, 1 mmol) in acetone (5 mL). The reaction mixture was then warmed to room temperature and stirred for 3 h. The solvent was removed and the residue was extracted with methylene chloride (3×15 mL), dried over Na$_2$SO$_4$ and concentrated to afford 302a as a yellow oil (170 mg, 99%), which was used in the next step without additional purification. LCMS: (M+H)$^+$ 171

Example 302b

N-Methyl-N-((1-methyl-3-nitro-1H-pyrazol-5-yl)methyl)oxetan-3-amine 302b

To a mixture of 302a (170 mg, 1 mmol) in methanol (4 mL), ZnCl$_2$ (1 mmol/L in diethyl ether) (2 mL, 2 mmol) and oxetan-3-one (150 mg, 2 mmol) were added at room temperature under nitrogen protection, followed by the addition of NaBH$_3$CN (130 mg, 2 mmol). The reaction mixture was warmed to 50° C. and stirred for 3 h. The mixture was then cooled to room temperature and the solvent was removed. The residue was purified on flush column eluting with 50:1 methylene chloride/methanol to afford 302b as a yellow solid (180 mg, 80%, two steps). LCMS: (M+H)$^+$ 227. $^1$H NMR (500 MHz, DMSO) δ 6.99 (s, 1H), 4.52 (t, J=6.5, 2H), 4.42 (t, J=6, 2H), 3.98 (s, 3H), 3.63 (m, 1H), 3.50 (s, 2H), 2.03 (s, 3H).

Example 302c

1-Methyl-5-((methyl(oxetan-3-yl)amino)methyl)-1H-pyrazol-3-amine 302c

To a solution of 302b (1.8 g, 7.96 mmol) in ethanol (20 mL) and water (20 mL), NH$_4$Cl (3.3 g, 63.6 mmol) and iron powder (1.80 g, 31.8 mmol) were added. The reaction mixture was heated at 70° C. for 2 h. After that, the mixture was cooled to room temperature and filtered. The filtrate was evaporated and the residue was extracted with methylene chloride (3×30 mL), dried Na$_2$SO$_4$, and concentrated to afford the crude product, which was purified on flash column eluting with 50:1 methylene chloride/methanol containing 0.5% triethylamine to afford 302c as a yellow oil (1.3 g, 83%). LCMS: (M+H)$^+$ 197

Example 302d

5-Bromo-1-methyl-3-(1-methyl-5-((methyl(oxetan-3-yl)amino)methyl)-1H-pyrazol-3-ylamino)pyridin-2(1H)-one 302d

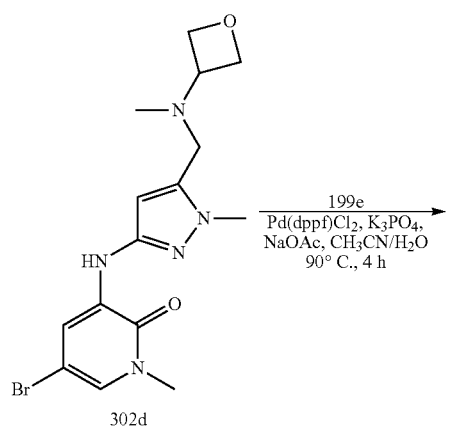

Following the procedure in Example 292c, and starting with 302c and 3,5-dibromo-1-methylpyridin-2(1H)-one afforded 302d in 63% yield. LCMS: $(M+H)^+$ 383. $^1H$ NMR (500 MHz, DMSO) δ 8.35 (s, 1H), 7.99 (d, J=2.5, 1H), 7.36 (d, J=2.5, 1H), 5.99 (s, 1H), 4.50 (t, J=7, 2H), 4.40 (t, J=6.5, 2H), 3.77 (s, 3H), 3.57 (m, 1H), 3.49 (s, 3H), 3.35 (s, 2H), 2.01 (s, 3H).

Example 302e (2-{4,4-Dimethyl-9-oxo-1,10-diazatricyclo[6.4.0.02,6]dodeca-2(6),7-dien-10-yl}-4-{1-methyl-5-[(1-methyl-5-{[methyl(oxetan-3-yl)amino]methyl}-1H-pyrazol-3-yl)amino]-6-oxo-1,6-dihydropyridin-3-yl}pyridin-3-yl)methyl Acetate 302e A 25-mL round-bottomed flask equipped with a magnetic stirrer and a reflux condenser was charged with 302d (200 mg, 0.52 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (210 mg, 0.53 mmol), PdCl$_2$(dppf) (37 mg, 0.050 mmol), K$_3$PO$_4$ (250 mg, 1.2 mmol), sodium acetate (100 mg, 1.20 mmol), acetonitrile (8 mL), and water (0.5 mL). The system was evacuated and then refilled with N$_2$. The mixture was heated at 100° C. for 1 h. It was then cooled to room temperature and filtered. The filtrate was concentrated under reduced pressure and the residue was purified by silica-gel column chromatography eluting with 20:1 dichloromethane/methanol to afford 302e as a yellow solid (150 mg, 44%). MS-ESI: $[M+H]^+$ 655.3.

Example 302

3-[3-(hydroxymethyl)-4-[1-methyl-5-[[1-methyl-5-[[methyl(oxetan-3-yl)amino]methyl]pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 302

A mixture of 302e (150 mg, 0.23 mmol) and lithium hydroxide hydrate (90 mg, 2.3 mmol) in THF (8 mL), i-propanol (8 mL), and water (2 mL) was stirred at 40° C. for 0.5 h. The mixture was concentrated under reduced pressure. The residue was partitioned between water (10 mL) and dichloromethane (3×15 mL). The combined organic extract was concentrated under reduced pressure and the residue was purified by reverse-phase prep-HPLC to afford 302 as a pale yellow solid (105 mg, 75%). MS-ESI: $[M+H]^+$ 612.8. $^1H$ NMR (500 MHz, DMSO-d$_6$) δ 8.48 (d, J=5.0 Hz, 1H), 8.14 (s, 1H), 8.05 (d, J=2.5 Hz, 1H), 7.40 (d, J=2.0 Hz, 1H), 7.33 (d, J=5.0 Hz, 1H), 6.55 (s, 1H), 6.01 (s, 1H), 4.99-4.97 (m, 1H), 4.50-4.46 (m, 3H), 4.40-4.38 (m, 3H), 4.25-4.18 (m, 3H), 3.85-3.84 (m, 1H), 3.72 (s, 3H), 3.59 (s, 3H), 3.58-3.54 (m, 1H), 2.58-2.56 (m, 2H), 2.52-2.50 (m, 2H), 2.43-2.42 (m, 2H), 2.00 (s, 3H), 1.22 (s, 6H).

Example 303

(S)-10-[3-(hydroxymethyl)-4-[5-({5-[(2R)-1-methoxypropan-2-yl]-4H,5H,6H,7H-pyrazolo[1,5-a]pyrazin-2-yl}amino)-1-methyl-6-oxo-1,6-dihydropyridin-3-yl]pyridin-2-yl]-4,4-dimethyl-1,10-diazatricyclo[6.4.0.0$^{2,6}$]dodeca-2(6),7-dien-9-one 303

Following Example 300, single enantiomer 303 was obtained (28 mg, 15%) as a white solid. MS-ESI: $[M+H]^+$ 627.4. $^1H$ NMR (500 MHz, CDCl$_3$) δ 8.49 (d, J=5.0 Hz, 1H), 7.92 (d, J=2.5 Hz, 1H), 7.73 (d, J=2.0 Hz, 1H), 7.41 (s, 1H), 7.35 (d, J=5.0 Hz, 1H), 6.85 (s, 1H), 5.72 (s, 1H), 5.05-5.03 (m, 1H), 4.67-4.45 (m, 1H), 4.52-4.50 (m, 1H), 4.35-4.31 (m, 1H), 4.18-4.16 (m, 2H), 4.09-4.07 (m, 2H), 3.87-3.85 (m, 3H), 3.71 (s, 3H), 3.56-3.52 (m, 1H), 3.45-3.43 (m, 1H), 3.38 (s, 3H), 3.11-3.08 (m, 3H), 2.60-2.58 (m, 2H), 2.53 (s, 2H), 1.29 (s, 6H), 1.17 (d, J=6.0 Hz, 3H).

Example 304a 5-(2-Methoxyethyl)-2-nitro-4,5,6,7-tetrahydropyrazolo[1,5-a]pyrazine 304a

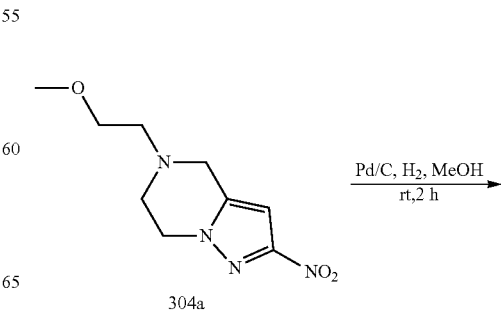

-continued

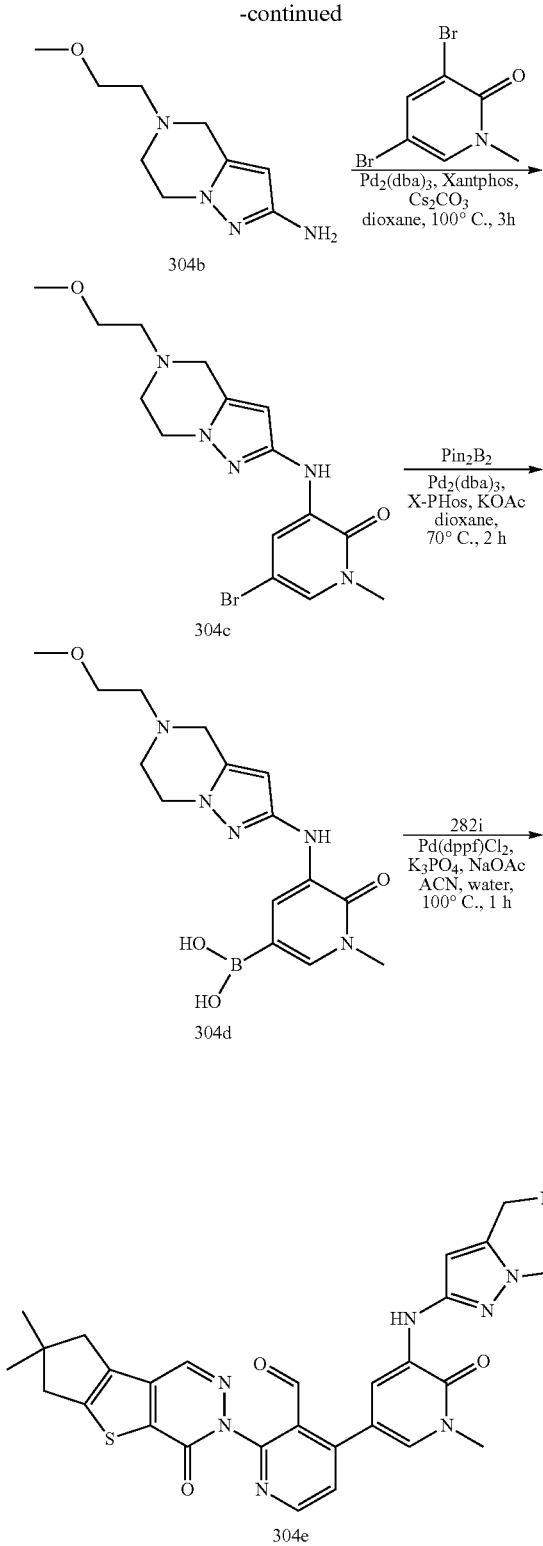

To a solution of 2-nitro-4,5,6,7-tetrahydropyrazolo[1,5-a]pyrazine (190 mg, 1.13 mmol) 125i in acetonitrile (10 mL) was added $K_2CO_3$ (311.9 mg, 2.26 mmol) and 1-bromo-2-methoxyethane (188.3 mg, 1.36 mmol). The reaction mixture was heated at 80° C. for 17 h under microwave irradiation. Analysis of reaction mixture by LCMS showed complete conversion to the desired product. The mixture was cooled to room temperature and filtered. The filtrate was concentrated under reduced pressure to afford 304a as a white solid (230 mg, 90%), which was used in the next step without further purification. MS-ESI: $[M+H]^+$ 227.0

Example 304b 5-(2-Methoxyethyl)-4,5,6,7-tetrahydropyrazolo[1,5-a]pyrazin-2-amine 304b To a solution of 304a (286 mg, 1.26 mmol) in methanol (10 mL) was added Pd/C (28.6 mg). The system was evacuated and then refilled with $H_2$. After stirring at room temperature for 2 h, the mixture was filtered off. The filtrate was concentrated under reduced pressure to afford 304b as a yellow solid (240 mg, 97%), which was used in the next step without further purification. MS-ESI: $[M+H]^+$ 197.0

Example 304c

5-Bromo-3-(5-(2-methoxyethyl)-4,5,6,7-tetrahydropyrazolo[1,5-a]pyrazin-2-ylamino)-1-methylpyridin-2(1H)-one 304c A 100-mL round-bottomed flask equipped with a magnetic stirrer and a reflux condenser was charged with 304b (230 mg, 1.17 mmol), 3,5-dibromo-1-methylpyridin-2(1H)-one (468.4 mg, 1.76 mmol), $Pd_2(dba)_3$ (53.5 mg, 0.0585 mmol), Xantphos (67.6 mg, 0.117 mmol), $Cs_2CO_3$ (762.8 mg, 2.34 mmol), and dioxane (20 mL). After three cycles of vacuum/$N_2$ flush, the mixture was heated at 100° C. for 3 h. Analysis of the reaction mixture by LCMS showed complete conversion to the desired product. It was cooled to room temperature and filtered. The filtrate was concentrated under reduced pressure. The residue was purified by silica-gel column chromatography eluting with 40:1 dichloromethane/methanol to afford 304c as a dark solid (380 mg, 85%). MS-ESI: $[M+H]^+$ 382.2

Example 304d 3-(5-(2-Methoxyethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 304d A 50-mL single-neck round-bottomed flask equipped with a magnetic stirrer and a reflux condenser was charged with 304c (330 mg, 0.86 mmol), $Pin_2B_2$ (329 mg, 1.30 mmol), $Pd_2(dba)_3$ (40 mg, 0.043 mmol), X-phos (41 mg, 0.086 mmol), potassium acetate (169 mg, 1.726 mmol), and dioxane (10 mL). After three cycles of vacuum/$N_2$ flush, the mixture was heated at 70° C. for 2 h. Analysis of reaction mixture by LCMS showed complete conversion to the desired product. It was cooled to room temperature and filtered. The filtrate was concentrated under reduced pressure. The residue was washed with petroleum ether to afford 304d as a dark oil (240 mg, 80%), which was used in the next step without further purification. MS-ESI: $[M+H]^+$ 348.3

Example 304e

2-{4,4-Dimethyl-9-oxo-7-thia-10,11-diazatricyclo[6.4.0.0$^{2,6}$]dodeca-1(8),2(6),11-trien-10-yl}-4-(5-{[5-(2-methoxyethyl)-4H,5H,6H,7H-pyrazolo[1,5-a]pyrazin-2-yl]amino}-1-methyl-6-oxo-1,6-dihydropyridin-3-yl)pyridine-3-carbaldehyde 304e A 50-mL round-bottomed flask equipped with a reflux condenser was charged with 4-chloro-2-{4,4-dimethyl-9- oxo-7-thia-10,11-diazatricyclo[6.4.0.0$^{2,6}$]dodeca-1(8),2(6),11-trien-10-yl}pyridine-3-carbaldehyde 282i (60 mg, 0.167 mmol), 304d (143.4 mg, 0.334 mmol), Pd(dppf)Cl$_2$ (6.8 mg, 0.0084 mol), K$_3$PO$_4$ (70.8 mg, 0.334 mmol), sodium acetate (27.4 mg, 0.334 mmol), acetonitrile (10 mL), and water (3 drops). The system was subjected to three cycles of vacuum/nitrogen flush and heated at 100° C. for 1 h under N$_2$ protection. Analysis of reaction mixture by LCMS showed complete conversion to the desired product. It was cooled to room temperature and filtered. The filtrate was concentrated under reduced pressure. The residue was purified by silica-gel column chromatography eluting with 40:1 dichloromethane/methanol to afford 304e (80 mg, 77%) as white solid. MS-ESI: [M+H]$^+$ 626.8

Example 304

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-6,8-dihydrocyclopenta[3,4]thieno[1,3-d]pyridazin-4-one 304

To a solution of 304e (80 mg, 0.128 mmol) in dichloromethane (4 mL) and methanol (4 mL) was added NaBH$_4$ (9.7 mg, 0.256 mmol). The reaction mixture was stirred at room temperature for 1 h. It was quenched with aqueous NH$_4$Cl (10 mL) and concentrated under reduced pressure and the residue was extracted with dichloromethane (3×20 mL). The combined extract was dried over Na$_2$SO$_4$ and concentrated under reduced pressure. The residue was purified by reverse-phase prep-HPLC to afford 304 (23.5 mg, 29%) as white solid. MS-ESI: [M+H]$^+$ 628.8. $^1$H NMR (500 MHz, DMSO-d$_6$) δ 8.57 (d, J=4.5 Hz, 1H), 8.46 (s, 1H), 8.23 (s, 1H), 8.05 (d, J=2.0 Hz, 1H), 7.52 (d, J=5.5 Hz, 1H), 7.40 (d, J=2.5 Hz, 1H), 5.89 (s, 1H), 4.87 (s, 1H), 4.39 (s, 2H), 3.92-3.90 (m, 2H), 3.61 (s, 2H), 3.59 (s, 3H), 3.50 (t, J=5.5 Hz, 2H), 3.26 (s, 3H), 2.92-2.89 (m, 4H), 2.81 (s, 2H), 2.68-2.66 (m, 2H), 1.29 (s, 3H), 1.28 (s, 3H).

Example 305a

6-Chloro-4-(5-(2-methoxyethyl)-4,5,6,7-tetrahydropyrazolo[1,5-a]pyrazin-2-ylamino)-2-methylpyridazin-3(2H)-one 305a

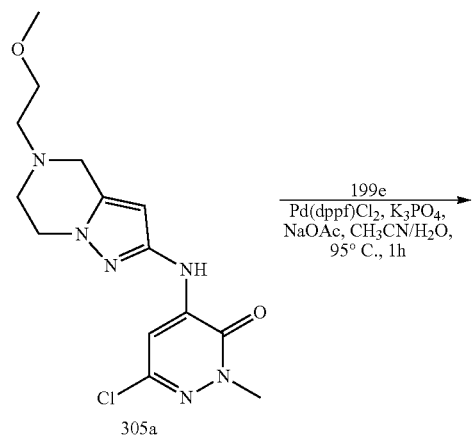

Example 305b (2-{4,4-Dimethyl-9-oxo-1,10-diazatricyclo[6.4.0.0$^{2,6}$]dodeca-2(6),7-dien-10-yl}-4-(5-{[5-(2-methoxyethyl)-4H,5H,6H,7H-pyrazolo[1,5-a]pyrazin-2-yl]amino}-1-methyl-6-oxo-1,6-dihydropyridazin-3-yl)pyridin-3-yl)methyl Acetate 305b

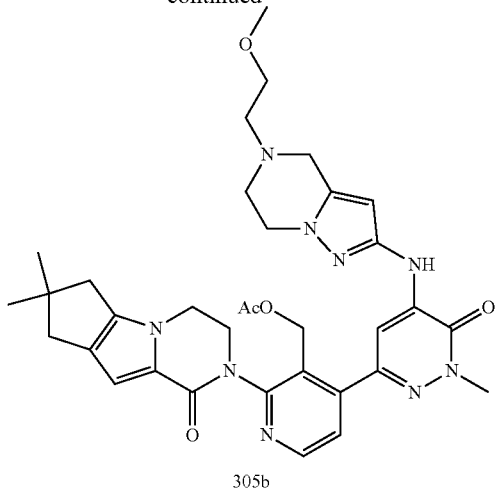

A 100-mL round-bottomed flask equipped with a reflux condenser was charged with 5-(2-methoxyethyl)-4,5,6,7-tetrahydropyrazolo[1,5-a]pyrazin-2-amine 304b (392 mg, 2.0 mmol), 3,5-dibromo-1-methylpyridin-2(1H)-one (446 mg, 2.0 mmol), cesium carbonate (1.30 g, 4.0 mmol), and 1,4-dioxane (40 mL). After bubbling nitrogen through the suspension for 10 minutes, xantphos (115 mg, 0.20 mmol) and tris(dibenzylideneacetone)dipalladium(0) (92 mg, 0.10 mmol) were added. The system was subjected to three cycles of vacuum/argon flush and heated at 100° C. for 5 h. It was then cooled to room temperature and filtered. The solid was washed with dichloromethane (2×15 mL). The combined filtrate was concentrated under reduced pressure. The residue was purified by silica-gel column chromatography eluting with dichloromethane/methanol (80/1 to 30/1) to afford 305a (412 mg, 61%) as a yellow solid. MS-ESI: [M+H]$^+$ 338.9

A 25-mL round-bottomed flask equipped with a reflux condenser was charged with 305a (200 mg, 0.60 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (238 mg, 0.60 mmol), K$_3$PO$_4$ (254 mg, 1.2 mmol), sodium acetate (98 mg, 1.2 mmol) and Pd(dppf)Cl$_2$ (22 mg, 0.030 mmol), and acetonitrile/water (8/0.5 mL). The system was subjected to three cycles of vacuum/nitrogen flush and heated at 100° C. under N$_2$ protection for 1 h. Analysis of the reaction mixture by LCMS showed complete conversion to the desired product. The reaction mixture was cooled to room temperature and filtered. The filtrate was concentrated under reduced pressure. The residue was partitioned between dichloromethane (30 mL) and water (20 mL). The water layer was extracted with dichloromethane (2×30 mL). The combined organic extract was dried over Na$_2$SO$_4$, filtered, and concentrated under reduced pressure. The dark residue was purified by silica-gel column chromatography eluting with dichloromethane/methanol (80/1 to 30/1) to afford 305b (169 mg, 43%) as a yellow solid. MS-ESI: [M+H]$^+$ 655.9

Example 305

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-pyridazin-3-yl]-2-pyridyl]-7,7-dimethyl-1,2,6,8-tetrahydrocyclopenta[3,4]pyrrolo[3,5-b]pyrazin-4-one 305

To a solution of 305b (160 mg, 0.24 mmol) in THF/i-propanol/water (6/4/3 mL) was added lithium hydroxide (29 mg, 1.2 mmol). The mixture was stirred at room temperature for 1 h and concentrated under reduced pressure. The residue was partitioned between water (15 mL) and ethyl acetate (20 mL). The water phase was extracted with ethyl acetate (3×20 mL). The combined organic layer was dried and concentrated under pressure. The residue was purified by reverse-phase prep-HPLC to afford 305 as a white solid (88 mg, 60%). MS-ESI: [M+H]$^+$ 614.3. $^1$H NMR (500 MHz, CDCl$_3$) δ 8.56 (d, J=5.0 Hz, 1H), 7.99 (s, 1H), 7.87 (s, 1H), 7.44 (d, J=5.0 Hz, 1H), 6.84 (s, 1H), 5.96 (s, 1H), 4.59-4.57 (m, 3H), 4.49-4.47 (m, 1H), 4.17-4.12 (m, 4H), 3.92-3.90 (m, 4H, overlap), 3.77-3.75 (m, 2H), 3.61-3.60 (m, 2H), 3.41 (s, 3H), 3.05-3.03 (m, 2H), 2.81-2.79 (m, 2H), 2.60-2.58 (m, 2H), 2.52-2.50 (m, 2H), 1.28 (s, 6H).

Example 306a (2-{4,4-Dimethyl-9-oxo-1,10-diazatricyclo[6.4.0.0$^{2,6}$]dodeca-2(6),7-dien-10-yl}-4-{5-[(6-methoxypyridazin-3-yl)amino]-1-methyl-6-oxo-1,6-dihydropyridin-3-yl}pyridin-3-yl)methyl Acetate 306a

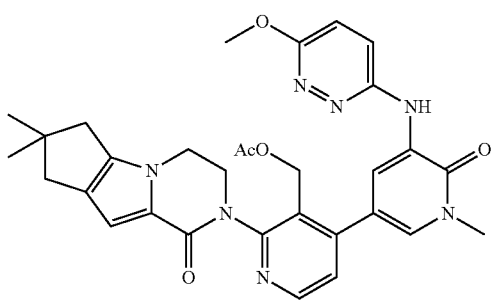

A 25-mL single-neck round-bottomed flask equipped with a magnetic stirrer and a reflux condenser was charged with 6-methoxypyridazin-3-amine (65 mg, 0.52 mmol), XantPhos (29 mg, 0.050 mmol), Pd$_2$dba$_3$ (45 mg, 0.050 mmol), [4-(5-bromo-1-methyl-6-oxo-1,6-dihydropyridin-3-yl)-2-{4,4-dimethyl-9-oxo-1,10-diazatricy-clo[6.4.0.0$^{2,6}$]dodeca-2(6),7-dien-10-yl}pyridin-3-yl]methyl acetate 273a (281 mg, 0.52 mmol), Cs$_2$CO$_3$ (326 mg, 1.0 mmol), and 1,4-dioxane (10 mL). After bubbling nitrogen through the resulting mixture for 20 minutes, it was heated at reflux for 2 h. After the completion of the reaction, the mixture was evaporated under reduced pressure and the residue was partitioned between ethyl acetate (20 mL) and water (10 mL). The ethyl acetate was concentrated under reduced pressure and the residue was purified by silica-gel column chromatography eluting with 20:1 dichloromethane/methanol to afford 306a (180 mg, 60%). MS-ESI: [M+H]$^+$ 584.3.

Example 306

3-[3-(hydroxymethyl)-4-[5-[(6-methoxypyridazin-3-yl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 306

A mixture of 306a (180 mg, 0.32 mmol) and lithium hydroxide monohydrate (84 mg, 2.0 mmol) in THF (5 mL), i-propanol (5 mL), and water (1.5 mL) was stirred at 40° C. for 0.5 h. The mixture was evaporated under reduced pressure and the residue was partitioned between ethyl acetate (20 mL) and water (10 mL). The ethyl acetate was concentrated under reduced pressure and the residue was purified by reverse-phase prep-HPLC to afford 306 (80 mg, 49%). MS-ESI: [M+H]$^+$ 542.3. $^1$H NMR (500 MHz, DMSO-d$_6$) δ 8.86 (s, 1H), 8.76 (d, J=2.5 Hz, 1H), 8.51 (d, J=5.0 Hz, 1H), 7.73 (d, J=10.0 Hz, 1H), 7.56 (d, J=2.5 Hz, 1H), 7.35 (d, J=5.0 Hz, 1H), 7.11-7.10 (m, 1H), 6.56 (s, 1H), 4.94-4.93 (m, 1H), 4.48-4.45 (m, 1H), 4.40-4.38 (m, 1H), 4.25-4.18 (m, 3H), 3.91 (s, 3H), 3.86-3.84 (m, 1H), 3.62 (s, 3H), 2.58-2.56 (m, 2H), 2.50-2.49 (m, 2H), 1.21 (s, 6H).

Example 307a 1,3-Dimethyl-5-nitro-1H-indazole 307a

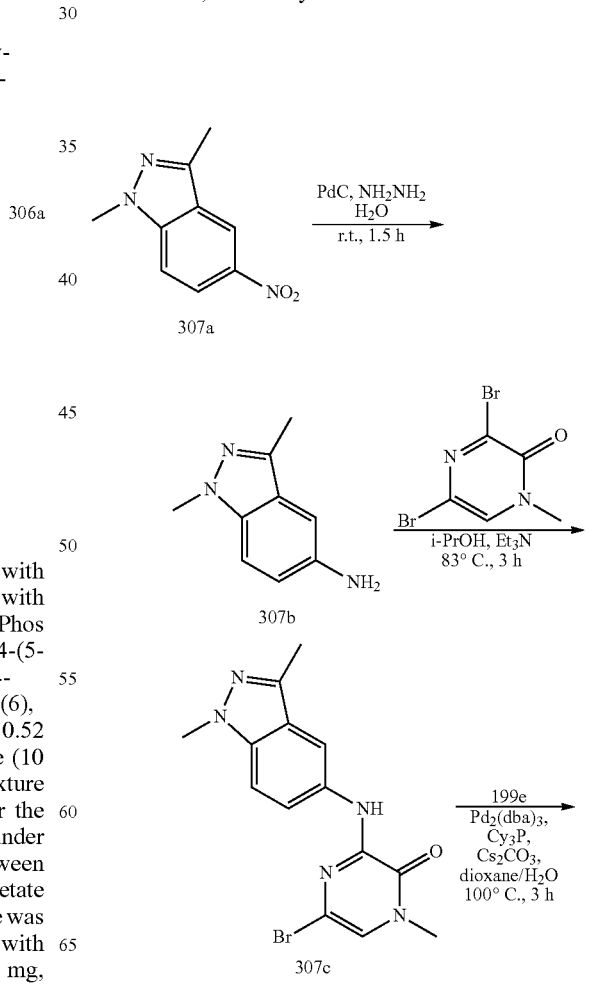

-continued

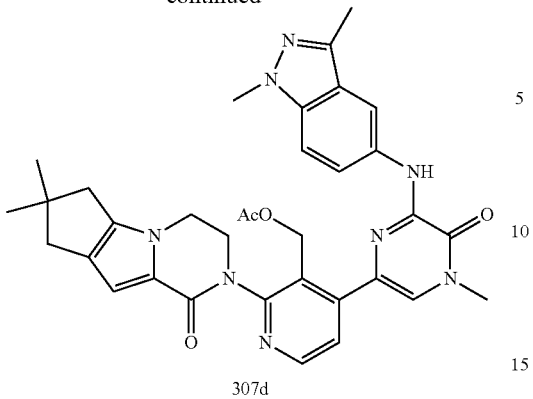

307d

To a solution of 1-(2-chloro-5-nitrophenyl)ethanone (500 mg, 2.5 mmol) in anhydrous ethanol (15 mL) was added 1,1-dimethylhydrazine hydrochloride (3.38 g, 35.0 mmol) under nitrogen protection. The mixture was heated at reflux for 10 h and evaporated under reduced pressure to afford crude 307a (3.0 g), which was used in the next step without further purification. MS-ESI: [M+H]$^+$ 192.2

Example 307b 1,3-Dimethyl-1H-indazol-5-amine 307b

To a solution of 307a (crude, 2.5 mmol) in ethanol (95%, 30 mL) was added NH$_2$NH$_2$.water (1.25 g, 25.0 mmol), Pd/C (100 mg) under nitrogen protection. The mixture was stirred at 50° C. for 1.5 h. It was then cooled to room temperature and filtered through a pad of CELITE®. The filtrate was concentrated under reduced pressure and the residue was recrystallized from anhydrous ethanol (5 mL) to afford 307b as white solid (340 mg, 84% over two steps). MS-ESI: [M+H]$^+$ 162.3

Example 307c

5-Bromo-3-(1,3-dimethyl-1H-indazol-5-ylamino-1-methylpyrazin-2(1H)-one 307c

To a solution of 307b (280 mg, 1.74 mmol) in i-propanol (7 mL) was added triethylamine (352 mg, 3.48 mmol) and 3,5-dibromo-1-methylpyrazin-2(1H)-one (H-005) (700 mg, 2.61 mmol). After being stirred at reflux for 6 h, the mixture was cooled to room temperature. The precipitate was filtered, washed with i-propanol (2×2 mL), and dried at 60° C. under reduced pressure to afford 307c as a brown solid (560 mg, 92%). MS-ESI: [M+H]$^+$ 347.8.

Example 307d (4-{6-[(1,3-Dimethyl-1H-indazol-5-yl)amino]-4-methyl-5-oxo-4,5-dihydro-pyrazin-2-yl}-2-{4,4-dimethyl-9-oxo-1,10-diazatricyclo[6.4.0.0$^{2,6}$]dodeca-2(6),7-dien-10-yl}pyridin-3-yl)methyl Acetate 307d A 50-mL single-neck round-bottomed flask equipped with a magnetic stirrer and a reflux condenser was charged with 307c (300 mg, 0.86 mmol), 1,4-dioxane (20 mL), water (1 mL), [4-(dihydroxyboranyl)-2-{4,4-dimethyl-9-oxo-1,10-diazatricyclo[6.4.0.0$^{2,6}$]dodeca-2(6),7-dien-10-yl}pyridin-3-yl]methyl acetate 199e (512 mg, 1.28 mmol), and cesium carbonate (560 mg, 1.72 mmol). After bubbling nitrogen through the suspension for 10 minutes, Cy$_3$P (96 mg, 0.34 mmol) and Pd$_2$(dba)$_3$ (79 mg, 0.086 mmol) were added. The system was subjected to three cycles of vacuum/argon flush and heated at reflux for 3 h. It was then cooled to room temperature and filtered. The solid was washed with dichloromethane (3×20 mL). The combined filtrate was concentrated under reduced pressure and the residue was purified by silica-gel column chromatography eluting with 100:1 dichloromethane/methanol to afford 307d (230 mg, 43%) as a yellow solid. MS-ESI: [M+H]$^+$ 620.9

Example 307

3-[4-[6-[(1,3-dimethylindazol-5-yl)amino]-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one 307

A mixture of 307d (230 mg, 0.37 mmol), lithium hydroxide (89 mg, 3.7 mmol) in i-propanol/THF (1:1, 10 mL) and water (2 mL) was stirred at room temperature for 1 h. It was filtered and the filtrate was concentrated under reduced pressure. The resulting residue was purified by reverse-phase prep-HPLC to afford 307 (41 mg, 19%) as a white solid. MS-ESI: [M+H]$^+$ 578.4. $^1$H NMR (500 MHz, CDCl$_3$) δ 8.58 (d, J=2.0 Hz, 1H), 8.56 (d, J=5.0 Hz, 1H), 8.37 (s, 1H), 8.11 (s, 1H), 7.88 (d, J=5.0 Hz, 1H), 7.51 (dd, J=2.0, 9.0 Hz, 1H), 7.33 (d, J=9.0 Hz, 1H), 6.86 (s, 1H), 5.17-5.14 (m, 1H), 4.75-4.73 (m, 1H), 4.55-4.52 (m, 1H), 4.48-4.43 (m, 1H), 4.20-4.16 (m, 2H), 4.02 (s, 3H), 3.92-3.70 (m, 1H), 3.70 (s, 3H), 2.60 (d, J=7.0 Hz, 2H), 2.57 (s, 3H), 2.54 (s, 2H), 1.30 (s, 6H).

Example 308a

2-{4,4-Dimethyl-9-oxo-7-thia-10-azatricyclo[6.4.0.0$^{2,6}$]dodeca-1(8),2(6)-dien-10-yl}-4-(5-{[5-(2-methoxyethyl)-4H,5H,6H,7H-pyrazolo[1,5-a]pyrazin-2-yl]amino}-1-methyl-6-oxo-1,6-dihydropyridin-3-yl)pyridine-3-carbaldehyde 308a

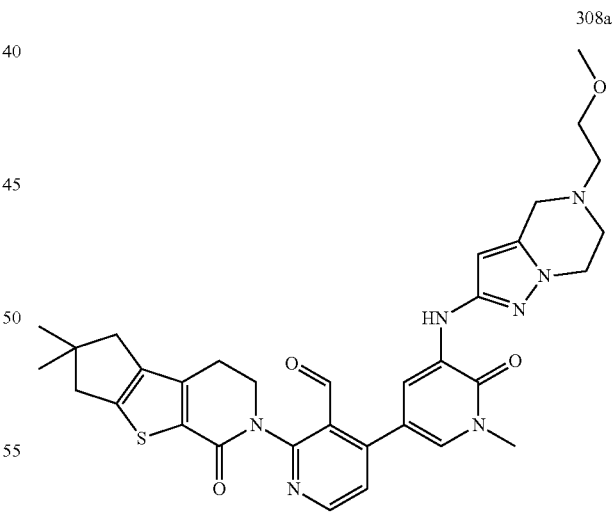

308a

Following the procedure in Example 304, and starting with 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (250 mg, 0.693 mmol) and 3-(5-(2-methoxyethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 304d (595 mg, 0.1.386 mmol), 308a was obtained as a yellow solid (250 mg, 57%). MS-ESI: [M+H]$^+$ 628.3

Example 308

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]thieno[1,3-c]pyridin-4-one 308

Following the procedures in Example 304, and starting with 308a (230 mg, 0.366 mmol) and NaBH$_4$ (27.7 mg, 0.732 mmol), 308 was obtained as a white solid (53.2 mg, 23%). MS-ESI: [M+H]$^+$ 629.8. $^1$H NMR (500 MHz, DMSO-d$_6$) δ 8.49 (d, J=5.0 Hz, 1H), 8.19 (s, 1H), 8.04 (d, J=2.0 Hz, 1H), 7.37 (d, J=2.5 Hz, 1H), 7.34 (d, J=5.0 Hz, 1H), 5.89 (s, 1H), 4.95-4.93 (m, 1H), 4.47-4.39 (m, 2H), 4.20-4.14 (m, 1H), 3.92-3.91 (m, 2H), 3.84-3.80 (m, 1H), 3.61 (s, 2H), 3.58 (s, 3H), 3.51-3.49 (m, 2H), 3.25 (s, 3H), 3.06-3.00 (m, 1H), 2.91-2.87 (m, 3H), 2.77 (s, 2H), 2.68-2.53 (m, 4H), 1.19 (s, 3H), 1.18 (s, 3H).

Example 309a 5-(3-Methoxypropyl)-2-nitro-4,5,6,7-tetrahydropyrazolo[1,5-a]pyrazine 309a

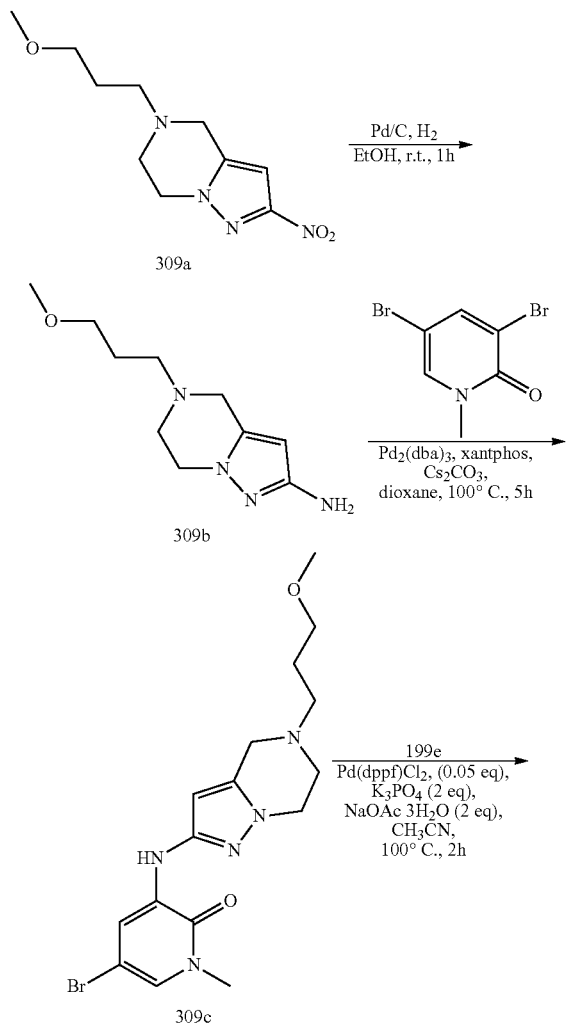

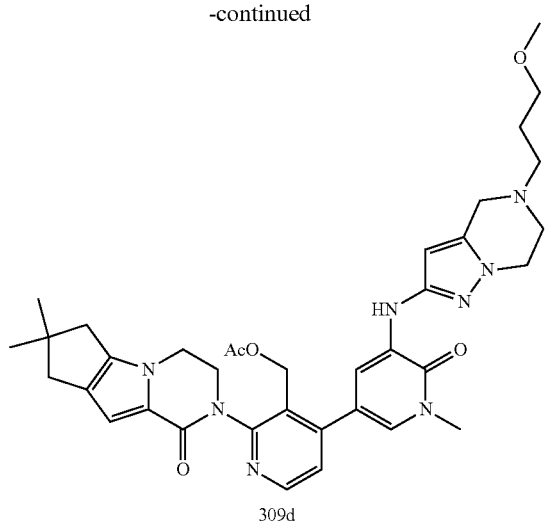

A microwave vial equipped with a magnetic stirrer was charged with 1-(2-bromoethyl)-5-(chloromethyl)-3-nitro-1H-pyrazole 296c (600 mg, 2.2 mmol), 3-methoxypropan-1-amine (595 mg, 6.6 mmol), and DMSO (6 mL). It was heated at 120° C. under microwave irradiation for 0.5 h. The mixture was then cooled to room temperature and diluted with ethyl acetate (30 mL). The resulting mixture was washed with water (3×10 ml). The organic layer was dried and filtered. The filtrate was concentrated under pressure and the residue was purified by silica-gel column chromatography eluting with 30:1 dichloromethane/methanol to afford 309a (350 mg, 66%) as a yellow solid. MS-ESI: [M+H]$^+$ 241.1

Example 309b 5-(3-Methoxypropyl)-4,5,6,7-tetrahydropyrazolo[1,5-a]pyrazin-2-amine 309b A solution of 309a (300 mg, 1.25 mmol) in ethanol (20 mL) was added Pd/C (10%, 30 mg). The reaction was charged with hydrogen gas (via balloon) and stirred at room temperature for 1 h. After the reaction was complete, the mixture was filtered through a plug of CELITE®. The filtrate was concentrated under reduced pressure to afford 309b as a yellow solid (250 mg, 92%), which was used without further purification in the next step. MS-ESI: [M+H]$^+$ 211.3

Example 309c

5-Bromo-3-(5-(3-methoxypropyl)-4,5,6,7-tetrahydropyrazolo[1,5-a]pyrazin-2-yl-amino)-1-methylpyridin-2(1H)-one 309c A 100-mL single-neck round-bottomed flask equipped with a magnetic stirrer and a reflux condenser was charged with 3,5-dibromo-1-methylpyridin-2(1H)-one (320 mg, 1.2 mmol), 309b (250 mg, 1.2 mmol), tris(dibenzylideneacetone)dipalladium(0) (55 mg, 0.060 mmol), xantphos (70 mg, 0.12 mmol), cesium carbonate (782 mg, 2.4 mmol), and 1,4-dioxane (20 mL). The system was subjected to three cycles of vacuum/argon flush and heated at 100° C. for 5 h. It was then cooled to room temperature and filtered. The solid was washed with dichloromethane (2×10 mL). The combined filtrate was concentrated under reduced pressure. The residue was purified by silica-gel column chromatography eluting

Example 309d (2-{4,4-Dimethyl-9-oxo-1,10-diazatricyclo[6.4.0.
0²,⁶]dodeca-2(6),7-dien-10-yl}-4-(5-{[5-(3-methoxypropyl)-4H,5H,6H,7H-pyrazolo[1,5-a]pyrazin-2-yl]
amino}-1-methyl-6-oxo-1,6-dihydropyridin-3-yl)
pyridin-3-yl)methyl Acetate 309d A 25-mL round-bottomed flask equipped with a reflux condenser was charged with 309c (120 mg, 0.30 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (240 mg, 0.60 mmol), K₃PO₄ (127 mg, 0.60 mmol), sodium acetate monohydrate (82 mg, 0.60 mmol), Pd(dppf)Cl₂ (12 mg, 0.015 mmol), and acetonitrile/water (8/0.5 mL). The system was subjected to three cycles of vacuum/nitrogen flush and heated at 100° C. under N₂ protection for 2 h. Analysis of the reaction mixture by LCMS showed complete conversion to the desired product. The reaction mixture was cooled to room temperature and concentrated under reduced pressure. The residue was partitioned between dichloromethane (20 mL) and water (10 mL). The water layer was extracted with dichloromethane (2×10 mL). The combined organic extract was dried over Na₂SO₄, filtered, and concentrated under reduced pressure. The dark residue was purified by silica-gel column chromatography eluting with dichloromethane/methanol (80:1 to 30:1) to afford 309d (150 mg, 74%) as yellow solid. MS-ESI: [M+H]⁺ 668.9

Example 309

3-[3-(hydroxymethyl)-4-[5-[[5-(3-methoxypropyl)-6,
7-dihydro-4H-pyrazolo[1,5-a]pyrazin-2-yl]amino]-1-
methyl-6-oxo-3-pyridyl]-2-pyridyl]-7,7-dimethyl-1,
2,6,8-tetrahydrocyclopenta[3,4]pyrrolo[3,5-b]
pyrazin-4-one 309

To a solution of 309d (120 mg, 0.18 mmol) in THF/i-propanol/water (5/3/3 mL) was added lithium hydroxide monohydrate (76 mg, 1.8 mmol). The mixture was stirred at 30° C. for 1 h. After the reaction was complete, the mixture was filtered and the solvent was evaporated under reduced pressure. The residue was purified by reverse-phase prep-HPLC to afford 309 as a white solid (85 mg, 76%). MS-ESI: [M+H]⁺ 627.3. ¹H NMR (500 MHz, CDCl₃) δ 8.48 (d, J=5.0 Hz, 1H), 7.95 (d, J=2.0 Hz, 1H), 7.72 (d, J=2.0 Hz, 1H), 7.42 (s, 1H), 7.35 (d, J=5.0 Hz, 1H), 6.86 (s, 1H), 5.71 (s, 1H), 5.05 (t, J=6.0 Hz, 1H), 4.66-4.64 (m, 1H), 4.52-4.50 (m, 1H), 4.36-4.32 (m, 1H), 4.17-4.16 (m, 2H), 4.08-4.06 (m, 2H), 3.88-3.85 (m, 1H), 3.71 (s, 3H), 3.65-3.64 (m, 2H), 3.48 (t, J=6.0 Hz, 2H), 3.36 (s, 3H), 2.93 (t, J=6.0 Hz, 2H), 2.65-2.62 (m, 2H), 2.59-2.58 (m, 2H), 2.53 (s, 2H), 1.87-1.83 (m, 2H), 1.29 (s, 6H).

Example 310a (2-{4,4-Dimethyl-9-oxo-1,10-diazatricyclo[6.4.0.
0²,⁶]dodeca-2(6),7-dien-10-yl}-4-{1-methyl-5-[(5-
methyl-1,2-thiazol-3-yl)amino]-6-oxo-1,6-dihydro-
pyridin-3-yl}pyridin-3-yl)methyl Acetate 310a

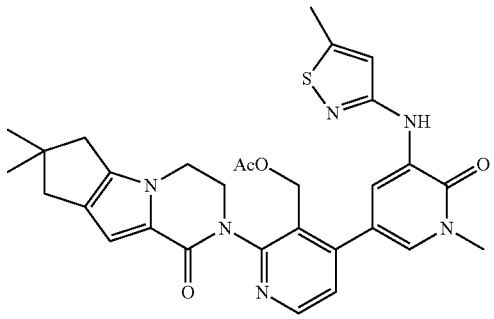

A 25-mL sealed tube was charged with [4-(5-bromo-1-methyl-6-oxo-1,6-dihydropyridin-3-yl)-2-{4,4-dimethyl-9-oxo-1,10-diazatricyclo[6.4.0.0²,⁶]dodeca-2(6),7-dien-10-yl}pyridin-3-yl]methyl acetate 273a (150 mg, 0.28 mmol), 5-methylisothiazol-3-amine hydrochloride (55 mg, 0.33 mmol), Cs₂CO₃ (183 mg, 0.56 mmol), Pd₂(dba)₃ (27 mg, 0.030 mmol), XantPhos (35 mg, 0.060 mmol), and dioxane (10 mL). After three cycles of vacuum/argon flush, the mixture was heated at 110° C. under microwave irradiation for 0.5 hour. It was the cooled to room temperature and evaporated under reduced pressure. The residue was purified by silica-gel column eluting with 20:1 methylene chloride/methanol to afford 310a as a yellow solid (50 mg, 31%). MS-ESI: [M+H]⁺ 573.2.

Example 310

3-[3-(hydroxymethyl)-4-[1-methyl-5-[(5-methyl-
isothiazol-3-yl)amino]-6-oxo-3-pyridyl]-2-pyridyl]-
7,7-dimethyl-1,2,6,8-tetrahydrocyclopenta[3,4]pyr-
rolo[3,5-b]pyrazin-4-one 310

To a solution of 310a (50 mg, 0.090 mmol) in THF/i-propanol/water (4 mL/4 mL/1 mL) was added lithium hydroxide (21 mg, 0.90 mmol). The reaction mixture was stirred at room temperature for 0.5 h and concentrated under reduced pressure. The residue was diluted with water (10 mL) and extracted with ethyl acetate (3×20 mL). The combined organic layer was dried with Na₂SO₄ and concentrated under reduced pressure to afford a yellow solid, which was purified by reverse-phase prep-HPLC to afford 310 as a yellow solid (20 mg, 43%). MS-ESI: [M+H]⁺ 530.8. ¹H NMR (500 MHz, CDCl₃) δ 8.61 (d, J=2.0 Hz, 1H), 8.49 (d, J=5.5 Hz, 1H), 8.05 (s, 1H), 7.93 (d, J=2.0 Hz, 1H), 7.37 (d, J=5.0 Hz, 1H), 6.84 (s, 1H), 6.51 (s, 1H), 5.09-5.06 (m, 1H), 4.66-4.47 (m, 2H), 4.28-4.27 (m, 1H), 4.17-4.12 (m, 2H), 3.89-3.82 (m, 1H), 3.71 (s, 3H), 2.57 (d, J=6.0 Hz, 2H), 2.52-2.50 (m, overlap, 5H), 1.27 (s, 6H).

Example 311a (4-{5-[(5-Cyclopropyl-1,2-oxazol-3-yl)amino]-1-methyl-6-oxo-1,6-dihydro-pyridin-3-yl}-2-{4,4-dimethyl-9-oxo-1,10-diazatricyclo[6.4.0.0$^{2,6}$]dodeca-2(6),7-dien-10-yl}pyridin-3-yl)methyl Acetate 311a

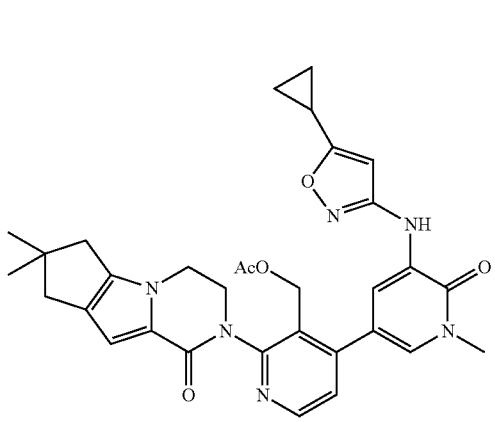

A 25-mL single-neck round-bottomed flask equipped with a magnetic stirrer and a reflux condenser was charged with 5-cyclopropylisoxazol-3-amine (80 mg, 0.65 mmol), XantPhos (29 mg, 0.050 mmol), Pd$_2$dba$_3$ (45 mg, 0.050 mmol), [4-(5-bromo-1-methyl-6-oxo-1,6-dihydropyridin-3-yl)-2-{4,4-dimethyl-9-oxo-1,10-diazatricy-clo[6.4.0.0$^{2,6}$]dodeca-2(6),7-dien-10-yl}pyridin-3-yl]methyl acetate 273a (350 mg, 0.65 mmol), Cs$_2$CO$_3$ (390 mg, 1.2 mmol), and 1,4-dioxane (10 mL). After bubbling nitrogen through the resulting mixture for 10 minutes, it was heated at reflux for 2 h. The mixture was then evaporated under reduced pressure and the residue was partitioned between ethyl acetate (20 mL) and water (10 mL). The organic layer was concentrated under reduced pressure and the resulting residue was purified by silica-gel column chromatography eluting with 20:1 dichloromethane/methanol to afford 311a (120 mg, 32%) as a brown solid. MS-ESI: [M+H]$^+$ 583.2.

Example 311

3-[4-[5-[(5-cyclopropylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 311

A mixture of 311a (120 mg, 0.20 mmol) and lithium hydroxide monohydrate (80 mg, 2.0 mmol) in THF (5 mL), i-propanol (5 mL) and water (1.5 mL) was stirred at 40° C. for 0.5 h. The mixture was evaporated under reduced pressure and the residue was diluted with water (5 mL). It was then extracted with ethyl acetate (2×10 mL). The combined extract was concentrated under reduced pressure and the residue was purified by reverse-phase prep-HPLC to afford 311 (65 mg, 58%) as pale yellow solid. MS-ESI: [M+H]$^+$ 541.3. $^1$H NMR (500 MHz, DMSO-d$_6$) δ 8.92 (s, 1H), 8.48 (d, J=5.0 Hz, 1H), 7.99 (d, J=2.0 Hz, 1H), 7.55 (d, J=2.0 Hz, 1H), 7.31 (d, J=5.0 Hz, 1H), 6.56 (s, 1H), 6.19 (s, 1H), 4.92-4.90 (m, 1H), 4.45-4.44 (m, 1H), 4.40-4.39 (m, 1H), 4.24-4.18 (m, 3H), 3.86-3.83 (m, 1H), 3.59 (s, 3H), 2.58-2.56 (m, 2H), 2.44-243 (m, 2H), 2.07-2.04 (m, 1H), 1.22 (s, 6H) 1.03-0.99 (m, 2H), 0.84-0.81 (m, 2H).

Example 312a

5-Bromo-1-methyl-3-(5-methyl-1-(oxetan-3-yl)-1H-pyrazol-3-ylamino)pyridin-2(1H)-one 312a

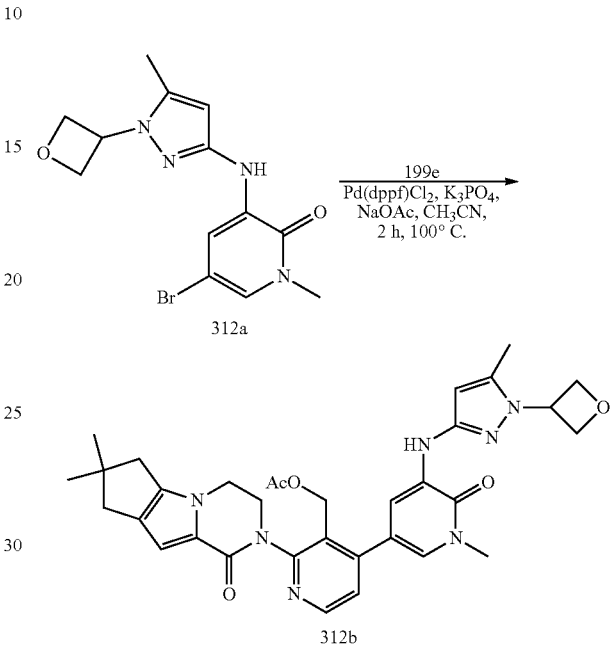

A mixture of 5-bromo-1-methyl-3-(5-methyl-1H-pyrazol-3-ylamino)pyridin-2(1H)-one 115a (200 mg, 0.71 mmol), 3-iodooxetane (647 mg, 3.53 mmol), Cs$_2$CO$_3$ (1150 mg, 3.53 mmol), and acetonitrile (5 mL) was heated at 80° C. in a sealed tube overnight. The mixture was then cooled to room temperature and filtered. The filtrate was concentrated under reduced pressure and the residue was purified by silica-gel column chromatography eluting with 20:1 dichloromethane/methanol to afford the 312a as a yellow solid (120 mg, 50%). MS-ESI: [M+H]$^+$ 339.1

Example 312b (2-{4,4-Dimethyl-9-oxo-1,10-diazatricyclo[6.4.0.0$^{2,6}$]dodeca-2(6),7-dien-10-yl}-4-(1-methyl-5-{[5-methyl-1-(oxetan-3-yl)-1H-pyrazol-3-yl]amino}-6-oxo-1,6-dihydropyridin-3-yl)pyridin-3-yl)methyl Acetate 312b A 50-mL single-neck round-bottomed flask equipped with a magnetic stirrer and a reflux condenser was charged with 312a (170 mg, 0.50 mmol), (2-{4,4-dimethyl-9-oxo-1,{3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (200 mg, 0.50 mmol), CH$_3$COONa (82 mg, 1.00 mmol), PdCl$_2$(dppf) (41 mg, 0.050 mmol), K$_3$PO$_4$ (212 mg, 1.00 mmol), acetonitrile (10 mL), and water (0.5 mL). After bubbling nitrogen through the resulting mixture for 20 minutes, it was heated at 100° C. under nitrogen atmosphere for 2 h. The mixture was cooled to room temperature and filtered. The filtrate was evaporated under reduced pressure and the residue was purified by silica-gel column chro-

Example 312

3-[3-(hydroxymethyl)-4-[1-methyl-5-[[5-methyl-1-(oxetan-3-yl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 312

A mixture of 312b (90 mg, 0.15 mmol) and lithium hydroxide (14 mg, 0.60 mmol) in i-propanol/THF/water (6/4/2 mL) was stirred at room temperature for 0.5 h. The mixture was concentrated under reduced pressure. The residue was partitioned between water (10 mL) and dichloromethane (3×20 mL). The combined dichloromethane extract was concentrated under reduced pressure and the residue was purified by reverse-phase prep-HPLC to afford 312 as a white solid (54 mg, 64%). MS-ESI: [M+H]$^+$ 569.9. $^1$H NMR (500 MHz, DMSO-d$_6$) δ 8.47 (d, J=5.0 Hz, 1H), 8.24 (d, J=2.0 Hz, 1H), 8.23 (s, 1H), 7.48 (d, J=1.5 Hz, 1H), 7.36 (d, J=5.0 Hz, 1H), 6.55 (s, 1H), 5.95 (s, 1H), 5.46-5.42 (m, 1H), 4.99-4.91 (m, 3H), 4.81-4.78 (m, 2H), 4.52-4.41 (m, 2H), 4.24-4.18 (m, 3H), 3.87-3.84 (m, 1H), 3.60 (s, 3H), 2.61-2.56 (m, 2H), 2.43 (s, 2H), 2.15 (s, 3H), 1.22 (s, 3H), 1.19 (s, 3H).

Example 313a

Ethyl 2-(5-(Hydroxymethyl)-3-nitro-1H-pyrazol-1-yl)acetate 313a

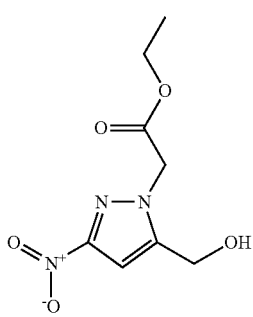

A 100-mL single-neck round-bottomed flask equipped with a magnetic stirrer was charged with acetonitrile (30 mL), (3-nitro-1H-pyrazol-5-yl)methanol (1.43 g, 10.0 mmol), Cs$_2$CO$_3$ (490 mg, 1.5 mmol), and ethyl 2-bromoacetate (2.00 g, 12 mmol). The mixture was stirred at 40° C. for 5 h. It was then cooled to room temperature and filtered. The filtrate was concentrated under reduced pressure and the residue was purified by silica-gel column chromatography eluting with 30:1 dichloromethane/methanol to afford 313a (1.65 g, 72%) as a yellow solid. MS-ESI: [M+H]$^+$ 229.9

Example 313b

Ethyl 2-(5-(Chloromethyl)-3-nitro-1H-pyrazol-1-yl)acetate 313b

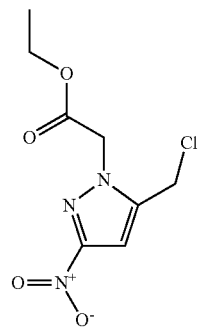 [SMILES: CCOC(=O)Cn1nc([N+](=O)[O-])cc1CCl]

To a mixture of 313a (1.50 g, 6.55 mmol) in CHCl$_3$ (60 mL) cooled at 0° C. was slowly added SOCl$_2$ (2.34 g, 19.6 mmol) while maintaining the internal temperature below 5° C. This reaction mixture was warmed to 50° C. and stirred at this temperature for 3 h. It was then cooled to 0° C. and quenched with water. The organic layer was separated and evaporated under reduced pressure. The residue was purified by silica-gel column chromatography eluting with 30:1 dichloromethane/methanol to afford 313b (1.1 g, 68%) as a yellow solid. MS-ESI: [M+H]$^+$ 247.9

Example 313c

5-Methyl-2-nitro-4,5-dihydropyrazolo[1,5-a]pyrazin-6(7H)-one 313c

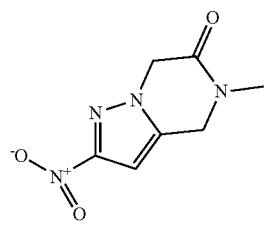

To a solution of 313b (1.0 g, 4.0 mmol) in dichloromethane (30 mL) was added a solution of CH$_3$NH$_2$ (1.07 g, 12.0 mmol, 35% in methanol). This reaction mixture was stirred at room temperature for 3 h and diluted with water (30 mL). The organic layer was separated, dried over Na$_2$SO$_4$, and concentrated under reduced pressure. The residual was purified by silica-gel column chromatography eluting with 30:1 dichloromethane/methanol to afford 313c (450 mg, 57%) as a yellow solid. MS-ESI: [M+H]$^+$ 196.9

(Top of page, continuation:) matography eluting with 50:1 dichloromethane/methanol to afford 312b as white solid (172 mg, 56%). MS-ESI: [M+H]$^+$ 612.4

Example 313d

2-Amino-5-methyl-4,5-dihydropyrazolo[1,5-a]pyrazin-6(7H)-one 313d

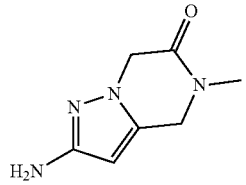

A solution of 313c (450 mg, 2.3 mmol) in ethanol (30 mL) was added Pd/C (10%, 400 mg). The reaction was charged with hydrogen gas (via balloon) and stirred at room temperature for 2 h. After reaction was complete, the mixture was filtered through a plug of CELITE® and the filtrate was concentrated under reduced pressure to afford 313d as a yellow solid (320 mg, 84%), which was used without further purification in the next step. MS-ESI: [M+H]$^+$ 167.1

Example 313e 2-(5-Bromo-1-methyl-2-oxo-1,2-dihydropyridin-3-ylamino)-5-methyl-4,5-dihydropyrazolo[1,5-a]pyrazin-6(7H)-one 313e A 100-mL round-bottomed flask equipped with a magnetic stirrer and a reflux condenser was charged with 313d (300 mg, 1.8 mmol), 3,5-dibromo-1-methylpyridin-2(1H)-one (482 mg, 1.8 mmol), cesium carbonate (1.17 g, 3.6 mmol), and 1,4-dioxane (20 mL). After bubbling nitrogen through the suspension for 10 minutes, xantphos (104 mg, 0.18 mmol) and tris(dibenzylideneacetone)dipalladium(0) (82 mg, 0.090 mmol) were added. The system was subjected to three cycles of vacuum/argon flush and heated at reflux for 5 h. It was then cooled to room temperature and filtered. The solid was washed with dichloromethane (2×30 m). The combined filtrate was concentrated under reduced pressure. The residue was purified by silica-gel column chromatography eluting with dichloromethane/methanol (80/1 to 30/1) to afford 313e (390 mg, 61%) as a yellow solid.

Example 313f (2-{4,4-Dimethyl-9-oxo-1,10-diazatricyclo[6.4.0.0$^{2,6}$]dodeca-2(6),7-dien-10-yl}-4-[1-methyl-5-({5-methyl-6-oxo-4H,5H,6H,7H-pyrazolo[1,5-a]pyrazin-2-yl}amino)-6-oxo-1,6-dihydropyridin-3-yl]pyridin-3-yl)methyl Acetate 313f

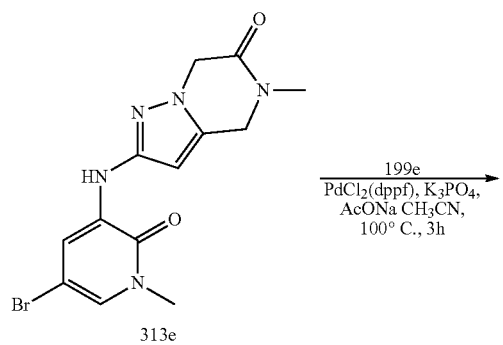

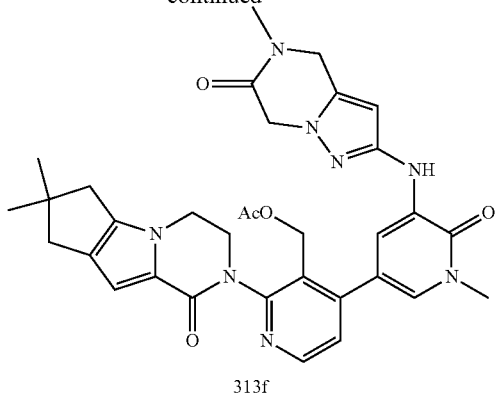

A 25-mL single-neck round-bottomed flask equipped with a magnetic stirrer and a reflux condenser was charged with 313e (150 mg, 0.43 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (170 mg, 0.43 mmol), K$_3$PO$_4$ (183 mg, 0.86 mmol), sodium acetate (71 mg, 0.86 mmol), Pd(dppf)Cl$_2$ (35 mg, 0.043 mmol), acetonitrile (10 mL), and water (0.5 mL). The system was subjected to three cycles of vacuum/nitrogen flush and heated at 100° C. for 3 h. After this time the reaction was cooled to room temperature and filtered. The filtrate was concentrated under reduced pressure. The residue was purified by silica-gel column chromatography eluting with 30:1 dichloromethane/methanol to afford 313f (131 mg, 49%) as a yellow solid. MS-ESI: [M+H]$^+$ 625.3.

Example 313

3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one 313

A mixture of 313f (130 mg, 0.21 mmol) and lithium hydroxide (10 mg, 0.42 mmol) in i-propanol/THF (1:1, 7 mL) and water (2 mL) was stirred at 0° C. for 0.5 h. The mixture was concentrated under reduced pressure. The residue was partitioned between water (10 mL) and ethyl acetate (3×10 mL). The combined ethyl acetate extract was concentrated under reduced pressure and the residue was purified with reverse-phase prep-HPLC to afford 313 (60 mg, 49%) as a white solid. MS-ESI: [M+H]$^+$ 582.8. $^1$H NMR (500 MHz, DMSO-d$_6$) δ 8.48 (d, J=5.0 Hz, 1H), 8.37 (s, 1H), 8.10 (d, J=2.0 Hz, 1H), 7.43 (d, J=2.5 Hz, 1H), 7.33 (d, J=5.0 Hz, 1H), 6.57 (s, 1H), 6.07 (s, 1H), 4.95 (bs, 1H), 4.62-4.54 (m, 4H), 4.46-4.42 (m, 2H), 4.24-4.19 (m, 3H), 3.89-3.82 (m, 1H), 3.60 (s, 3H), 2.99 (s, 3H), 2.60-2.57 (m, 2H), 2.45-2.44 (m, 2H), 1.23 (s, 6H).

Example 314a 1-(6-Nitropyridin-3-yl)azetidin-3-ol 314a

A 100-mL single-neck round-bottomed flask equipped with a magnetic stirrer and a reflux condenser was charged with acetonitrile (50 mL), 5-fluoro-2-nitropyridine (1.2 g, 7.9 mmol), K$_2$CO$_3$ (2.1 g, 15.8 mmol), and azetidin-3-ol hydrochloride (1.3 g, 11.9 mmol). The mixture was heated at 60° C. for 1 h. After this time the reaction was cooled to room temperature. It was then filtered and the filtrate was evaporated under reduced pressure. The residue was purified by silica-gel column chromatography eluting with dichloromethane/methanol (50:1 to 20:1) to afford 314a (1.1 g, 73%) as a yellow solid. MS-ESI: [M+H]+ 196.0.

Example 314b 1-(6-Aminopyridin-3-yl)azetidin-3-ol 314b

A 100-mL single-neck round-bottomed flask was purged with nitrogen and charged with 314a (1.0 g, 5.1 mmol), 10% palladium on carbon (10% wet, 100 mg), and ethanol (40 mL). The mixture was evacuated, charged with hydrogen gas, and stirred at room temperature for 5 h. The hydrogen was then evacuated and nitrogen was charged into the flask. The catalyst was removed by filtration through a pad of CELITE® and the filtrate was concentrated under reduced pressure to afford 314b as a yellow solid (792 mg, 85%). MS-ESI: [M+H]+ 166.1.

Example 314c

5-Bromo-3-(5-(3-hydroxyazetidin-1-yl)pyridin-2-ylamino)-1-methylpyridin-2(1H)-one 314c A 100-mL single-neck round-bottomed flask equipped with a magnetic stirrer and a reflux condenser was charged with 314b (792 mg, 4.8 mmol), 3,5-dibromo-1-methylpyridin-2(1H)-one (1.9 g, 7.2 mmol), tris-(dibenzylideneacetone)dipalladium(0) (440 mg, 0.48 mmol), XantPhos (555 mg, 0.96 mmol), Cs$_2$CO$_3$ (3.1 g, 9.6 mmol), and 1,4-dioxane (40 mL). After three cycles of vacuum/argon flush, the mixture was heated at 90° C. for 3.0 hrs. It was then cooled to room temperature and filtered. The filtrate was concentrated under reduced pressure and the resulting residue was purified by silica-gel column chromatography eluting with dichloromethane/methanol (50:1 to 20:1) to afford 314c as a yellow solid (1.5 g, 89%). MS-ESI: [M+H]+ 351.1

Example 314d (2-{4,4-Dimethyl-9-oxo-1,10-diazatricyclo[6.4.0. 0$^{2,6}$]dodeca-2(6),7-dien-10-yl}-4-(5-{[5-(3-hydroxyazetidin-1-yl)pyridin-2-yl]amino}-1-methyl-6-oxo-1,6-dihydropyridin-3-yl)pyridin-3-yl)methyl Acetate 314d

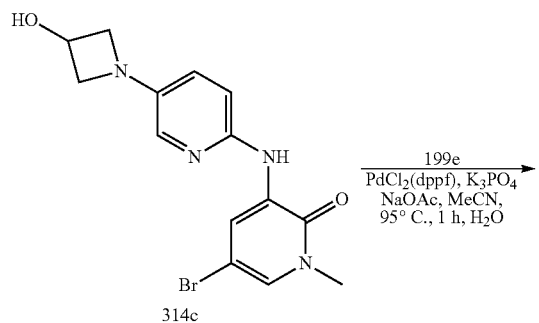

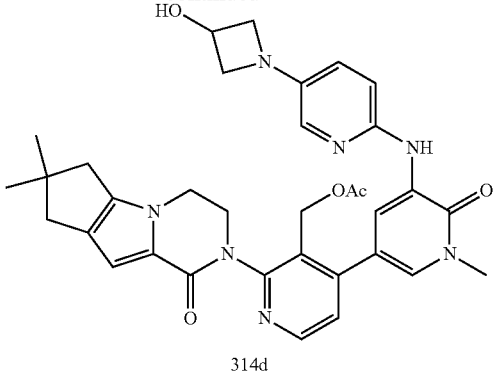

A 50-mL round-bottomed flask equipped with a reflux condenser was charged with 314c (176 mg, 0.50 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (198 mg, 0.50 mmol), Pd(dppf)Cl$_2$ (41 mg, 0.050 mmol), K$_3$PO$_4$ (212.0 mg, 1.0 mmol), sodium acetate (82.0 mg, 1.0 mmol), water (0.5 mL), and acetonitrile (10 mL). After three cycles of vacuum/argon flush, the mixture was heated at 95° C. for 1 hour. It was then cooled to room temperature and filtered. The filtrate was concentrated under reduced pressure and the resulting residue was purified by silica-gel column chromatography eluting with 30:1 dichloromethane/methanol to afford crude 314d as a brown solid, which was used in the next step without further purification. MS-ESI: [M+H]+ 623.8.

Example 314

3-[4-[5-[[5-(3-hydroxyazetidin-1-yl)-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 314

A mixture of 314d (crude product 311.5 mg, 0.50 mmol) and lithium hydroxide hydrate (300 mg, 12.5 mmol) in i-propanol/THF/water (2:2:1, 10 mL) was stirred at room temperature for 30 min. The mixture was concentrated under reduced pressure. The residue was partitioned between water (10 mL) and dichloromethane (3×10 mL). The combined extract was concentrated under reduced pressure and the residue was purified by reverse-phase prep-HPLC to afford 314 (46 mg, two step: 16%) as yellow solid. MS-ESI: [M+H]+ 581.9. $^1$H NMR (500 MHz, DMSO-d$_6$) δ 8.54 (d, J=2.5 Hz, 1H), 8.47 (d, J=5.0 Hz, 1H), 7.78 (d, J=2.5 Hz, 1H), 7.70 (s, 1H), 7.54 (d, J=2.5 Hz, 1H), 7.35 (d, J=5.0 Hz, 1H), 6.83-6.81 (m, 2H), 6.75 (d, J=8.5 Hz, 1H), 5.04-5.02 (m, 1H), 4.77-4.75 (m, 1H), 4.64-4.62 (m, 1H), 4.50-4.48 (m, 1H), 4.34-4.32 (m, 1H), 4.17-4.14 (m, 4H), 3.86-3.83 (m, 1H), 3.70 (s, 3H), 3.64-3.62 (m, 2H), 2.57-2.56 (m, 2H), 2.51 (s, 2H), 2.31-2.30 (m, 1H), 1.27 (s, 6H).

Example 315

3-[3-(hydroxymethyl)-4-[1-methyl-5-[[1-methyl-5-(pyrrolidine-1-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one 315

Following the procedures of Example 273, and substituting (3-amino-1-methyl-1H-pyrazol-5-yl)(pyrrolidin-1-yl)methanone for 2-aminopyridine, 315 was prepared. 27.3 mg, 60% yield. $^1$H NMR (400 MHz, DMSO-d$_6$) δ 8.48 (d, J=5.1 Hz, 1H), 8.23 (s, 1H), 8.05 (d, J=2.4 Hz, 1H), 7.43 (d, J=2.4

Hz, 1H), 7.34 (d, J=5.1 Hz, 1H), 6.55 (s, 1H), 6.46 (s, 1H), 4.95 (t, J=5.2 Hz, 1H), 4.42-4.47 (m, 1H), 4.17-4.21 (m, 3H), 3.79 (s, 2H), 3.59 (s, 3H), 3.48 (dt, J=11.1, 6.6 Hz, 3H), 3.27 (s, 2H), 2.57 (d, J=7.5 Hz, 2H), 2.43 (s, 2H), 1.90-1.84 (m, 3H), 1.22 (s, 6H). ES-MS m/z 611.4 [M+1].

Example 316

3-[3-(hydroxymethyl)-4-[5-[[5-(methoxymethyl)-1-methyl-pyrazol-3-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 316

Following the procedures of Example 273, and substituting 5-(methoxymethyl)-1-methyl-1H-pyrazol-3-amine for 2-aminopyridine, 316 was prepared. 43.2 mg, 84% yield. $^1$H NMR (400 MHz, DMSO-d6) δ 8.47 (d, J=5.0 Hz, 1H), 8.15 (s, 1H), 8.04 (d, J=2.4 Hz, 1H), 7.39 (d, J=2.1 Hz, 1H), 7.33 (d, J=5.0 Hz, 1H), 6.55 (s, 1H), 6.11 (s, 1H), 4.96-4.90 (m, 1H), 4.38-4.46 (m, 1H), 4.38 (s, 2H), 4.19 (d, J=9.8 Hz, 2H), 3.82-3.96 (m, 1H), 3.65 (s, 3H), 3.58 (s, 3H), 3.27 (s, 2H), 2.57 (d, J=7.5 Hz, 2H), 2.43 (s, 2H), 1.22 (s, 6H). ES-MS m/z 558.3 [M+1].

Example 317a

5-Methyl-2-(1-methyl-2-oxo-5-(4,4,5,5-tetramethyl-1,3,2-dioxaborolan-2-yl)-1,2-dihydropyridin-3-ylamino)-4,5-dihydropyrazolo[1,5-a]pyrazin-6(7H)-one 317a

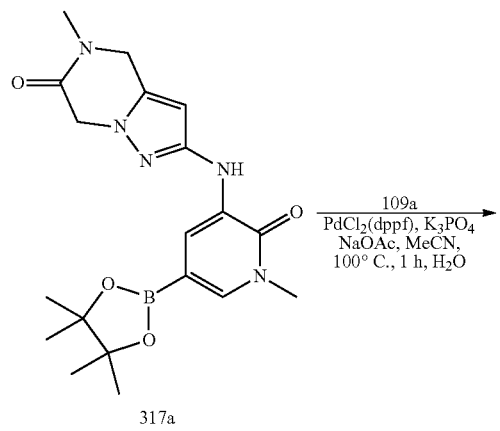

A 50-mL single-neck round-bottomed flask equipped with a magnetic stirrer and a reflux condenser was charged with 2-(5-bromo-1-methyl-2-oxo-1,2-dihydropyridin-3-ylamino)-5-methyl-4,5-dihydropyrazolo[1,5-a]pyrazin-6(7H)-one 313e (270 mg, 1.0 eq., 0.68 mmol), Pin$_2$B$_2$ (863.6 mg, 5.0 eq., 3.4 mmol), Pd$_2$(dba)$_3$ (62.4 mg, 0.1 eq., 0.068 mmol), X-Phos (64.8 mg, 0.2 eq., 0.14 mmol), potassium acetate (200 mg, 3.0 eq., 2.04 mmol), and dioxane (15 mL). After three cycles of vacuum/argon flush, the mixture was heated at 65° C. for 3 h. It was then cooled to room temperature and filtered. The filtrate was concentrated under reduced pressure to afford crude 317a, which was used in the next step without further purification. MS-ESI: [M+H]$^+$ 399.9.

Example 317b

2-{4,4-Dimethyl-9-oxo-7-thia-10-azatricyclo[6.4.0.0$^{2,6}$]dodeca-1(8),2(6)-dien-10-yl}-4-[1-methyl-5-({5-methyl-6-oxo-4H,5H,6H,7H-pyrazolo[1,5-a]pyrazin-2-yl}amino)-6-oxo-1,6-dihydropyridin-3-yl]pyridine-3-carbaldehyde 317b A 50-mL single-neck round-bottomed flask equipped with a magnetic stirrer and a reflux condenser was charged with 317a (100 mg, 0.28 mmol), 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (112 mg, 0.28 mmol), Pd(dppf)Cl$_2$ (22.9 mg, 0.028 mmol), K$_3$PO$_4$ (118.7 mg, 0.56 mmol), sodium acetate (45.9 mg, 0.56 mmol), water (0.5 mL), and acetonitrile (10 mL). After three cycles of vacuum/argon flush, the mixture was heated at reflux for 1 hour. It was then cooled to room temperature and filtered. The filtrate was concentrated under reduced pressure and the resulting residue was purified by silica-gel column chromatography eluting with dichloromethane/methanol (50:1 to 30:1) to afford 317b as a yellow solid (60 mg, 36%). MS-ESI: [M+H]$^+$ 597.8.

Example 317

3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]thieno[1,3-c]pyridin-4-one 317

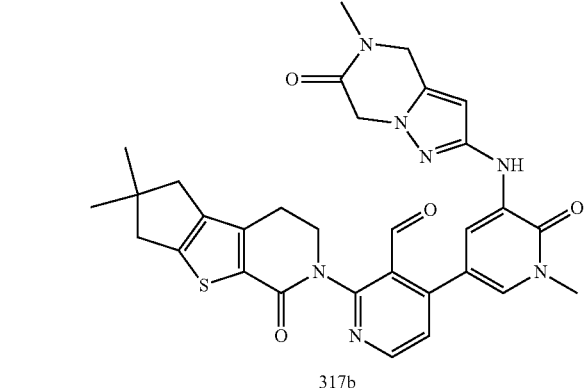

A mixture of 317b (60 mg, 0.10 mmol) and NaBH$_4$ (11.3 mg, 0.30 mmol) in methanol (5 mL) was stirred at room temperature for 30 min. The mixture was quenched with water (15 mL) and concentrated under reduced pressure. The residue was extracted with dichloromethane (3×10 mL). The combined extract was concentrated under reduced pressure and the residue was purified by reverse-phase prep-HPLC to afford 317 (15 mg, 25%) as a yellow solid. MS-ESI: [M+H]+ 599.8. $^1$H NMR (500 MHz, CDCl$_3$) δ 8.50 (d, J=5.0 Hz, 1H), 8.0 (d, J=2.0 Hz, 1H), 7.69 (d, J=2.5 Hz, 1H), 7.50 (s, 1H), 7.34 (d, J=5.0 Hz, 1H), 5.86 (s, 1H), 4.82-4.66 (m, 4H), 4.56 (s, 2H), 4.42-4.33 (m, 2H), 3.83-3.81 (m, 1H), 3.70 (s, 3H), 3.15 (s, 3H), 2.98-2.94 (m, 2H), 2.80 (s, 2H), 2.57-2.52 (m, 2H), 1.28 (s, 6H).

Example 318a

{4-[5-({4,5-Dimethyl-4H,5H,6H,7H-pyrazolo[1,5-a]pyrazin-2-yl}amino)-1-methyl-6-oxo-1,6-dihydropyridin-3-yl]-2-{4,4-dimethyl-9-oxo-1,10-diazatricyclo[6.4.0.0$^{2,6}$]dodeca-2(6),7-dien-10-yl}pyridin-3-yl}methyl Acetate 318a

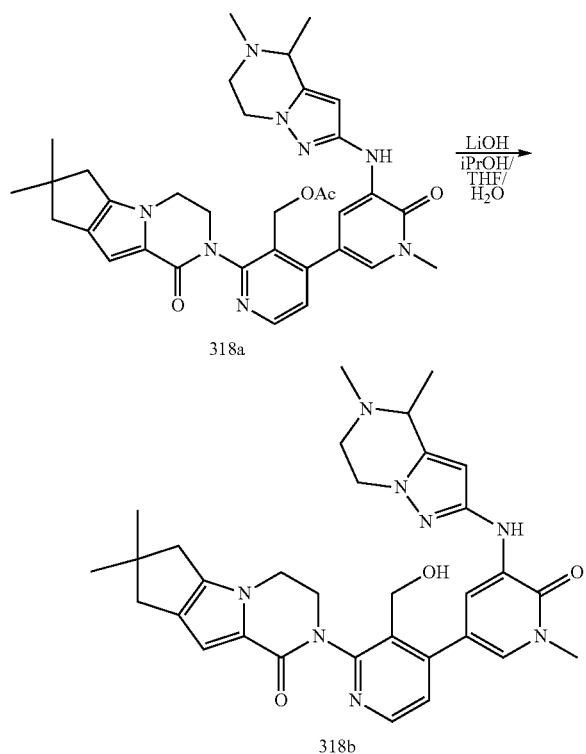

318a

318b

A 50-mL round-bottomed flask equipped with a reflux condenser was charged with 4,5-dimethyl-4,5,6,7-tetrahydropyrazolo[1,5-a]pyrazin-2-amine 287i (123 mg, 1.0 eq., 0.74 mmol), [4-(5-bromo-1-methyl-6-oxo-1,6-dihydropyridin-3-yl)-2-{4,4-dimethyl-9-oxo-1,10-diazatricyclo[6.4.0.0$^{2,6}$]dodeca-2(6),7-dien-10-yl}pyridin-3-yl]methyl acetate 273a (400 mg, 1.0 eq., 0.74 mmol), Pd$_2$(dba)$_3$ (68 mg, 0.1 eq., 0.074 mmol), Xantphos (86 mg, 0.2 eq., 0.148 mmol), Cs$_2$CO$_3$ (487 mg, 2.0 eq., 1.48 mmol), and dioxane (15 mL). After three cycles of vacuum/N$_2$ flush, the mixture was stirred at 100° C. for 2 hr. The mixture was cooled to room temperature and filtered. The filtrate was concentrated under reduced pressure. The resulting residue was purified by silica-gel column chromatography eluting with 20:1 ethyl acetate/methanol to afford 318a as a brown solid (221 mg, 48%). MS-ESI: [M+H]$^+$ 624.9

Example 318b

10-{4-[5-({4,5-Dimethyl-4H,5H,6H,7H-pyrazolo[1,5-a]pyrazin-2-yl}amino)-1-methyl-6-oxo-1,6-dihydropyridin-3-yl]-3-(hydroxymethyl)pyridin-2-yl}-4,4-dimethyl-1,10-diazatricyclo[6.4.0.0$^{2,6}$]dodeca-2(6),7-dien-9-one 318b A 25-mL single-neck round-bottomed flask equipped with a magnetic stirrer was charged with 318a (200 mg, 1.0 eq., 0.32 mmol), lithium hydroxide (38 mg, 5.0 eq., 1.60 mmol), i-propanol/THF (8/8 mL), and water (2 mL). The mixture was stirred at room temperature for 1 h and concentrated under reduced pressure. The residue was added partitioned between water and dichloromethane. The combined organic layer was concentrated under reduced pressure. The residue was purified by reverse-phase prep-HPLC to afford racemic mixture 318b as a yellow solid (91 mg, 43%).

Example 318

(R)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one 318

Chiral HPLC (column: OZ—H, 100% methanol (0.1% ethyl acetate)) resolution of 318b separated enantiomers 318 and 319. 318: MS-ESI: [M+H]$^+$ 582.8. $^1$H NMR (500 MHz, CDCl$_3$) δ 8.49 (d, J=5.0 Hz, 1H), 7.99 (s, 1H), 7.72 (d, J=2.5 Hz, 1H), 7.44 (s, 1H), 7.36 (d, J=5.0 Hz, 1H), 6.86 (s, 1H), 5.74 (s, 1H), 5.04 (t, J=6.5 Hz, 1H), 4.66-4.64 (m, 1H), 4.52-4.48 (m, 1H), 4.36-4.34 (m, 1H), 4.18-4.05 (m, overlap, 4H), 3.88-3.86 (m, 1H), 3.72 (s, 3H), 3.43-3.41 (m, 1H), 3.17-3.15 (m, 1H), 2.87-2.85 (m, 1H), 2.60-2.59 (m, 2H), 2.53 (s, 2H), 2.48 (s, 3H), 1.46 (d, J=6.5 Hz, 3H), 1.29 (s, 6H).

Example 319

(S)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one 319

Chiral HPLC (column: OZ—H, 100% methanol (0.1% ethyl acetate)) resolution of racemic 318b separated enantiomers 318 and 319. 319: MS-ESI: [M+H]$^+$ 582.8. $^1$H NMR (500 MHz, CDCl$_3$) δ 8.49 (d, J=5.0 Hz, 1H), 7.99 (s, 1H), 7.72 (d, J=2.5 Hz, 1H), 7.44 (s, 1H), 7.36 (d, J=5.0 Hz, 1H), 6.86 (s, 1H), 5.74 (s, 1H), 5.04 (t, J=6.5 Hz, 1H), 4.67-4.65 (m, 1H), 4.52-4.48 (m, 1H), 4.36-4.34 (m, 1H), 4.18-4.05 (m, overlap, 4H), 3.88-3.86 (m, 1H), 3.72 (s, 3H), 3.43-3.41 (m, 1H), 3.17-3.15 (m, 1H), 2.87-2.85 (m, 1H), 2.60-2.59 (m, 2H), 2.53 (s, 2H), 2.48 (s, 3H), 1.46 (d, J=6.5 Hz, 3H), 1.30 (s, 6H).

Example 320a (6-Aminopyridin-3-yl)((3R,5S)-3,5-dimethylmorpholino)methanone 320a

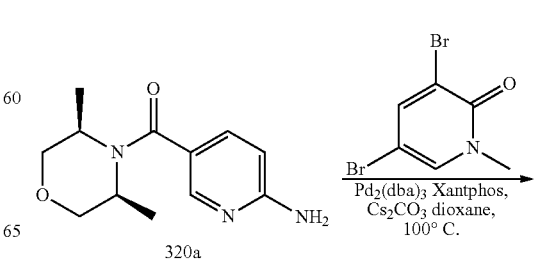

320a

-continued

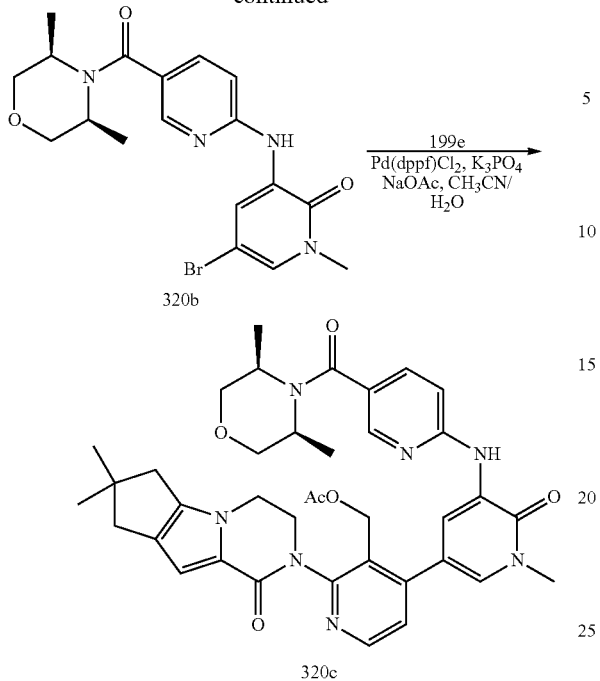

To a solution of (3S,5R)-3,5-dimethylmorpholine (1.15 g, 10 mmol) in DMF (15 mL) was added HATU (3.8 g, 10 mmol), DIPEA (2.6 g, 20 mmol), and 6-aminonicotinic acid (1.38 g, 10 mmol) at room temperature. The reaction mixture was stirred for 18 h. It was then filtered and the filtrate was purified with Combiflash (A: 1‰NH$_4$HCO$_3$/water, B: in acetonitrile) to afford 320a (650 mg, 27%) as a yellow solid. MS-ESI: [M+H]$^+$ 236.1.

Example 320b

5-Bromo-3-(5-((3R,5S)-3,5-dimethylmorpholine-4-carbonyl)pyridin-2-ylamino)-1-methylpyridin-2 (1H)-one 320b A 50-mL round-bottomed flask equipped with a magnetic stirrer and a reflux condenser was charged with 320a (160 mg, 1.0 eq., 0.68 mmol), 3,5-dibromo-1-methylpyridin-2(1H)-one (273 mg, 1.5 eq., 1.02 mmol), Pd$_2$(dba)$_3$ (64 mg, 0.1 eq., 0.070 mmol), Xantphos (79 mg, 0.2 eq., 0.14 mmol), Cs$_2$CO$_3$ (444 mg, 2.0 eq., 1.36 mmol), and dioxane (20 mL). After three cycles of vacuum/nitrogen flush, the mixture was heated at 100° C. for 2 h. It was then cooled to room temperature and filtered. The filtrate was evaporated under reduced pressure and the resulting residue was purified by silica-gel column chromatography eluting with ethyl acetate to afford 320b (190 mg, 66%) as a yellow solid. MS-ESI: [M+H]$^+$ 420.8.

Example 320c (2-{4,4-Dimethyl-9-oxo-1,10-diazatricyclo[6.4.0. 0$^{2,6}$]dodeca-2(6),7-dien-10-yl}-4-{5-[(5-{[(3R,5S)-3,5-dimethylmorpholin-4-yl]carbonyl}pyridin-2-yl) amino]-1-methyl-6-oxo-1,6-dihydropyridin-3-yl}pyridin-3-yl)methyl Acetate 320c A 50-mL single-neck round-bottomed flask equipped with a magnetic stirrer and a reflux condenser was charged with 320b (150 mg, 1.0 eq., 0.36 mmol), {3-[(acetoxy)methyl]-2-{4,4-dimethyl-9-oxo-1,10-diazatricyclo[6.4.0.0$^{2,6}$]dodeca-2 (6),7-dien-10-yl}pyridin-4-yl}boronic acid 199e (286 mg, 2.0 eq., 0.72 mmol), PdCl$_2$(dppf) (29 mg, 0.10 eq., 0.040 mmol), K$_3$PO$_4$ (153 mg, 2.0 eq., 0.72 mmol), sodium acetate (59 mg, 2.0 eq., 0.72 mmol), acetonitrile (10 mL), and water (0.2 mL). After three cycles of vacuum/nitrogen flush, the mixture was heated at 90° C. for 2 h. It was then cooled to room temperature and filtered. The filtrate was evaporated under reduced pressure and the resulting residue was purified by silica-gel column chromatography eluting with 50:1 dichloromethane/methanol to afford 320c (161 mg, 64%) as brown solid. MS-ESI: [M+H]$^+$ 693.8

Example 320

3-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b] pyrazin-4-one 320

A 25-mL single-neck round-bottomed flask equipped with a magnetic stirrer was charged with 320b (145 mg, 1.0 eq., 0.21 mmol), lithium hydroxide (26 mg, 5.0 eq., 1.05 mmol), THF (4.0 mL), i-propanol (4.0 mL), and water (1.0 mL). The mixture was stirred at room temperature for 1 h and filtered. The filtrate was concentrated under reduced pressure. The resulting residue was diluted with water (10 mL) and extracted with dichloromethane (3×15 mL). The combined organic layer was concentrated under reduced pressure. The residue was purified by reverse-phase prep-HPLC to afford 320 (35 mg, 26%) as white solid. MS-ESI: [M+H]$^+$ 651.9

Example 321a

6-Chloro-4-(5-((3R,5S)-3,5-dimethylmorpholine-4-carbonyl)pyridin-2-ylamino)-2-methylpyridazin-3 (2H)-one 321a

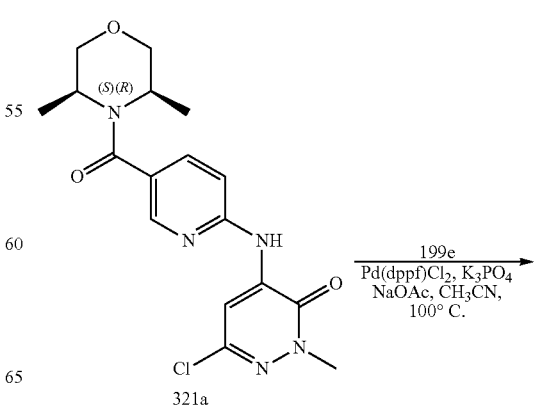

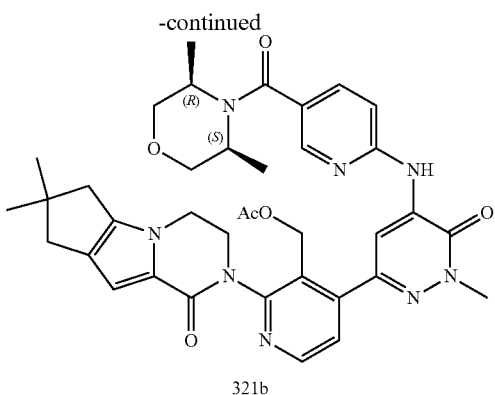

321b

A 25-mL round-bottomed flask equipped with a magnetic stirrer and a reflux condenser was charged with (6-aminopyridin-3-yl)((3R,5S)-3,5-dimethylmorpholino)methanone 320a (235 mg, 1.0 mmol), 4-bromo-6-chloro-2-methylpyridazin-3(2H)-one (232 mg, 1.05 mmol), cesium carbonate (652 mg, 2.0 mmol), and 1,4-dioxane (6.0 mL). After bubbling nitrogen through the suspension for 10 minutes, Xantphos (116 mg, 0.20 mmol) and tris(dibenzylideneacetone)dipalladium(0) (70 mg, 0.10 mmol) were added. The system was subjected to three cycles of vacuum/nitrogen flush and heated at reflux for 2.5 h. It was then cooled to room temperature and filtered. The solid was washed with dichloromethane (3×10 ml). The combined organic layer was concentrated under reduced pressure. The residue was purified by silica-gel column chromatography eluting with petroleum ether/ethyl acetate (2:1 to 1:10) to afford 321a (140 mg, 37%) as a yellow solid. MS-ESI: [M+H]+ 378.3

Example 321b (2-{4,4-Dimethyl-9-oxo-1,10-diazatricyclo[6.4.0. 0²,⁶]dodeca-2(6),7-dien-10-yl}-4-{5-[(5-{[(3R,5S)-3,5-dimethylmorpholin-4-yl]carbonyl}pyridin-2-yl) amino]-1-methyl-6-oxo-1,6-dihydropyridazin-3-yl}pyridin-3-yl)methyl Acetate 321b A 50-mL round-bottomed flask equipped with a reflux condenser was charged with 321a (140 mg, 0.37 mmol), (2-{4,4-dimethyl-9-oxo-1,10-diazatricyclo[6.4.0.0²,⁶] dodeca-2(6),7-dien-10-yl}-4-(4,4,5,5-tetramethyl-1,3,2-dioxaborolan-2-yl)pyridin-3-yl)methyl acetate 199e (355 mg, 0.74 mmol), K₃PO₄ (157 mg, 0.74 mmol), sodium acetate (61 mg, 0.74 mmol), 1,1'-bis(diphenylphosphino) ferrocenedichloropalladium(II) (36 mg, 0.040 mmol), acetonitrile (10 mL), and water (0.2 mL). The system was subjected to three cycles of vacuum/nitrogen flush and heated at 100° C. under N₂ protection for 1.5 h. Analysis of reaction mixture by LCMS showed complete conversion to the desired product. The reaction mixture was cooled to room temperature and concentrated under reduced pressure. The residue was partitioned between dichloromethane (30 mL) and water (30 mL). The aqueous layer was separated and extracted with dichloromethane (3×20 mL). The combined organic layer was dried over Na₂SO₄, filtered, and concentrated under reduced pressure. The dark residue was purified by gel-silica column chromatography eluting with 60:1 dichloromethane/methanol to afford 320b (105 mg, 41%) as a black solid. MS-ESI: [M+H]+ 695.3

Example 321

3-[4-[5-[[5-[(3S,5R)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1,2,6,8-tetrahydrocyclopenta[3,4]pyrrolo[3,5-b]pyrazin-4-one 321

To a solution of 321b (105 mg, 0.15 mmol) in THF/i-propanol/water (2/1/0.5 mL) was added lithium hydroxide (36 mg, 1.5 mmol) at room temperature. After the reaction was stirred for 3 h, LCMS indicated the reaction was complete. Then the mixture was poured into water (25 mL) and extracted with dichloromethane (3×20 mL). The combined organic layer was washed with brine (30 mL), dried over Na₂SO₄, filtered, and concentrated under reduced pressure. The residue was purified by reverse-phase prep-HPLC (A: 1‰NH₄HCO₃/water, B: acetonitrile) to afford 321 (100 mg, 95%) as a white solid. MS-ESI: [M+H]+ 652.8. ¹H NMR (500 MHz, DMSO-d₆) δ 9.69 (s, 1H), 8.63 (s, 1H), 8.53 (d, J=5.0 Hz, 1H), 8.31 (d, J=1.5 Hz, 1H), 7.77-7.75 (m, 1H), 7.58 (d, J=8.5 Hz, 1H), 7.41 (d, J=5.0 Hz, 1H), 6.56 (s, 1H), 4.78 (t, J=5.5 Hz, 1H), 4.60-4.57 (m, 1H), 4.41-4.37 (m, 1H), 4.30-4.25 (m, 1H), 4.19 (d, J=3.5 Hz, 2H), 4.01-4.00 (m, 2H), 3.92-3.88 (m, 1H), 3.82 (s, 3H), 3.65-3.61 (m, 2H), 3.56-3.53 (m, 2H), 2.61-2.58 (m, 2H), 2.42 (s, 2H), 1.25 (d, J=6.0 Hz, 6H), 1.21 (s, 6H)

Example 322a (4-(5-(5-((3R,5S)-3,5-Dimethylmorpholine-4-carbonyl)pyridin-2-ylamino)-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl Acetate 322a

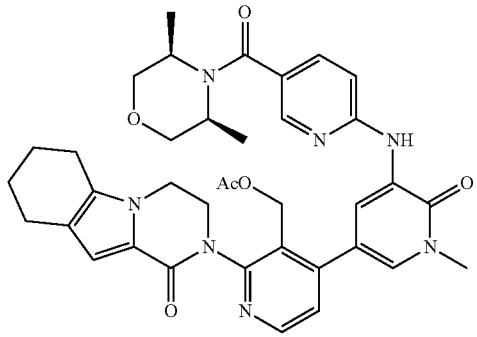

322a

A 25-mL round-bottomed flask equipped with a magnetic stirrer and a reflux condenser was charged with (6-aminopyridin-3-yl)((3R,5S)-3,5-dimethylmorpholino)methanone 320a (120 mg, 0.50 mmol), (4-(5-bromo-1-methyl-6-oxo-1,6-dihydropyridin-3-yl)-2-(1-oxo-3,4,6,7,8,9-hexahydropyrazino[1,2-a]indol-2(1H)-yl)pyridin-3-yl)methyl acetate 217a (262 mg, 0.50 mmol), cesium carbonate (326 mg, 1.0 mmol), and 1,4-dioxane (6 mL). After bubbling nitrogen through the suspension for 10 minutes, Xantphos (58 mg, 0.10 mmol) and tris(dibenzylideneacetone)dipalladium(0) (45 mg, 0.050 mmol) were added. The system was subjected to three cycles of vacuum/nitrogen flush and heated at reflux for 2.5 h. It was then cooled to room temperature and filtered. The solid was washed with dichloromethane (3×10 mL). The combined filtrate was concentrated under reduced pressure. The residue was purified by silica-gel column chromatography eluting with dichloromethane/methanol (80/1 to 50/1) to afford 322a (200 mg, 59%) as a yellow solid. MS-ESI: [M+H]+ 680.3

Example 322

2-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one 322

To a solution of 322a (136 mg, 0.20 mmol) in THF/i-propanol/water (4/2/1 mL) was added lithium hydroxide (48 mg, 2.0 mmol) at room temperature. After the reaction was stirred for 2 h, LCMS indicated the reaction was complete. Then the mixture was poured into water (15 mL) and extracted with dichloromethane (3×15 mL). The combined organic layer was washed with brine (30 mL), dried over $Na_2SO_4$, filtered, and concentrated under reduced pressure. The residue was purified by reverse-phase prep-HPLC (A: 1‰$NH_4HCO_3$/water, B: acetonitrile) to afford 322 (50 mg, 40%) as a white solid. MS-ESI: [M+H]+ 638.3. $^1$HNMR (500 MHz, DMSO-$d_6$) δ 8.94 (s, 1H), 8.77 (d, J=5.5 Hz, 1H), 8.48 (d, J=5.0 Hz, 1H), 8.20 (d, J=2.0 Hz, 1H), 7.64-7.62 (m, 1H), 7.59 (d, J=2.5 Hz, 1H), 7.37-7.35 (m, 2H), 6.57 (s, 1H), 4.95 (t, J=4.5 Hz, 1H), 4.47-4.38 (m, 2H), 4.23-3.99 (m, 5H), 3.88-3.87 (m, 1H), 3.65-3.61 (m, overlap, 5H), 3.56-3.53 (m, 2H), 2.66-2.56 (m, 2H), 2.47-2.44 (m, 2H), 1.80-1.79 (m, 2H), 1.70-1.66 (m, 2H), 1.25 (d, J=6.0 Hz, 6H)

Example 323a 5-(3-Methoxyazetidin-1-yl)-2-nitropyridine 323a

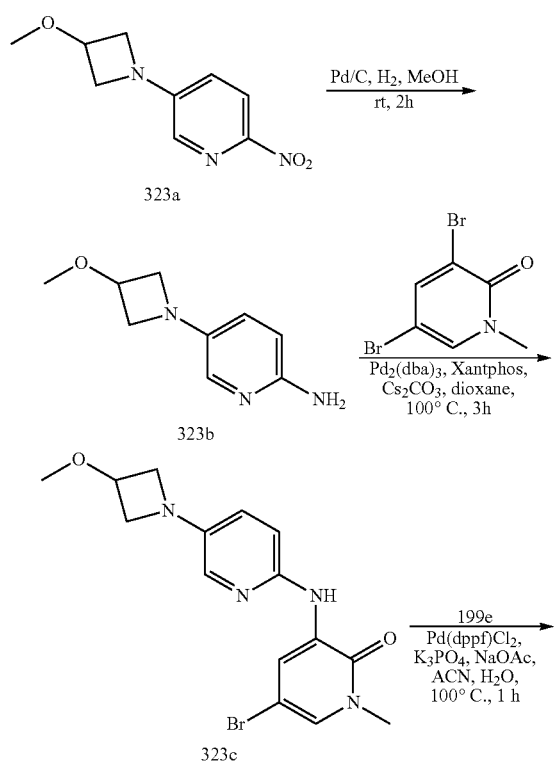

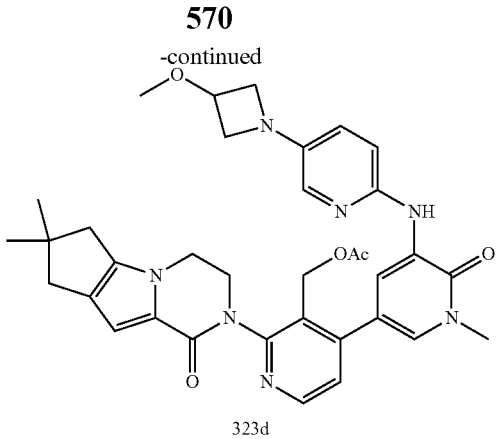

A 100-mL round bottomed flask was equipped with a reflux condenser was charged with 3-methoxyazetidine hydrochloride (1.0 g, 8.09 mmol), 5-bromo-2-nitropyridine (1.97 g, 9.71 mmol), $Pd_2(dba)_3$ (370.1 mg, 0.404 mmol), Xantphos (467.6 mg, 0.809 mmol), $Cs_2CO_3$ (7.9 g, 24.3 mmol), and dioxane (50 mL). After bubbling nitrogen through the reaction mixture for 20 minutes, it was heated at 100° C. under $N_2$ protection for 3 h. Analysis of the reaction mixture by LCMS showed complete conversion to the desired product. It was cooled to room temperature and filtered. The filtrate was concentrated under reduced pressure and the residue was purified by silica-gel column chromatography eluting with 50:1 dichloromethane/methanol to afford 323a as a yellow solid (1.63 g, 96%). MS-ESI: [M+H]+ 210.2

Example 323b 5-(3-Methoxyazetidin-1-yl)pyridin-2-amine 323b

To a solution of 323a (1.5 g, 7.17 mmol) in methanol (150 mL) was added 10% Pd/C (150 mg). The system was evacuated and then refilled with $H_2$. After stirring at room temperature for 2 h, the mixture was filtered. The filtrate was concentrated under reduced pressure to afford 323b as a yellow oil (1.2 g, 93%), which was used in next step without further purification. MS-ESI: [M+H]+ 180.1

Example 323c

5-Bromo-3-(5-(3-methoxyazetidin-1-yl)pyridin-2-ylamino)-1-methylpyridin-2(1H)-one 323c A 100-mL round bottomed flask was equipped with a reflux condenser was charged with 323b (1.2 g, 6.7 mmol), 3,5-dibromo-1-methylpyridin-2(1H)-one (2.14 g, 8.04 mmol), $Pd_2(dba)_3$ (306.5 mg, 0.335 mmol), Xantphos (387.3 mg, 0.67 mmol), $Cs_2CO_3$ (4.37 g, 13.4 mmol), and dioxane (50 mL). After bubbling nitrogen through the reaction mixture for 20 minutes, it was heated at 100° C. under $N_2$ protection for 3 h. Analysis of the reaction mixture by LCMS showed complete conversion to the desired product. It was cooled to room temperature and filtered. The filtrate was concentrated under reduced pressure. The residue was washed with petroleum ether to afford 323c as a brown solid (1.16 g, 47%), which was used in next step without further purification. MS-ESI: [M+H]+ 364.8.

Example 323d (2-{4,4-Dimethyl-9-oxo-1,10-diazatricyclo[6.4.0.0²,⁶]dodeca-2(6),7-dien-10-yl}-4-(5-{[5-(3-methoxyazetidin-1-yl)pyridin-2-yl]amino}-1-methyl-6-oxo-1,6-dihydropyridin-3-yl)pyridin-3-yl)methyl Acetate 323d A 50-mL round bottomed flask was equipped with a reflux condenser was charged with 323c (150 mg, 0.411 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (326.5 mg, 0.822 mmol), Pd(dppf)Cl₂ (16.8 mg, 0.0205 mmol), K₃PO₄ (174.3 mg, 0.822 mmol), sodium acetate (67.5 mg, 0.822 mmol), acetonitrile (10 mL), and water (5 drops). After bubbling nitrogen through the reaction mixture for 20 minutes, it was heated 100° C. under N₂ protection for 1 h. Analysis of the reaction mixture by LCMS showed complete conversion to the desired product. It was cooled to room temperature and filtered. The filtrate was concentrated under reduced pressure. The residue was purified by silica-gel column chromatography eluting with 40:1 dichloromethane/methanol to afford 323d as a yellow oil (180 mg, 68.7%). MS-ESI: [M+H]⁺ 637.8

Example 323

3-[3-(hydroxymethyl)-4-[5-[[5-(3-methoxyazetidin-1-yl)-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 323

To a solution of 323d (160 mg, 0.251 mmol) in THF (5 mL), i-propanol (5 mL), and water (5 mL) was added lithium hydroxide (95 mg, 2.51 mmol). The reaction mixture was stirred at room temperature for 1 h. Analysis of the reaction mixture by LCMS showed complete conversion to the desired product. It was then concentrated under reduced pressure and the residue was diluted with water (10 mL). The resulting mixture was extracted with dichloromethane (3×15 mL). The combined organic layer was dried over Na₂SO₄, filtered, and concentrated under reduced pressure. The residue was purified by reverse-phase prep-HPLC to afford 323 (33.8 mg, 23%) as a white solid. MS-ESI: [M+H]⁺ 595.8. ¹H NMR (500 MHz, DMSO-d₆) δ 8.55 (d, J=2.0 Hz, 1H), 8.49 (d, J=5.0 Hz, 1H), 8.31 (s, 1H), 7.48 (d, J=3.5 Hz, 1H), 7.45 (d, J=2.0 Hz, 1H), 7.34 (d, J=5.0 Hz, 1H), 7.21 (d, J=8.5 Hz, 1H), 6.91 (dd, J=2.5, 8.5 Hz, 1H), 6.56 (s, 1H), 4.96-4.94 (m, 1H), 4.47-4.39 (m, 2H), 4.31-4.19 (m, 4H), 4.03-4.00 (m, 2H), 3.85-3.83 (m, 1H), 3.60 (s, 3H), 3.55-3.53 (m, 2H), 3.23 (s, 3H), 2.62-2.54 (m, 2H), 2.44-2.42 (m, 2H), 1.22 (s, 6H).

Example 324a (6-Aminopyridin-3-yl)((3S,5S)-3,5-dimethylmorpholino)methanone 324a

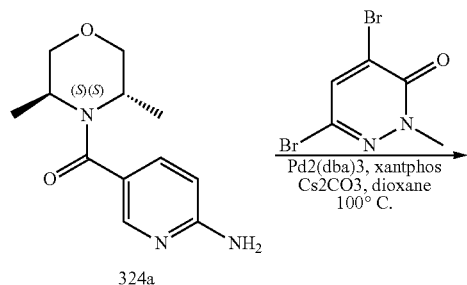

324a

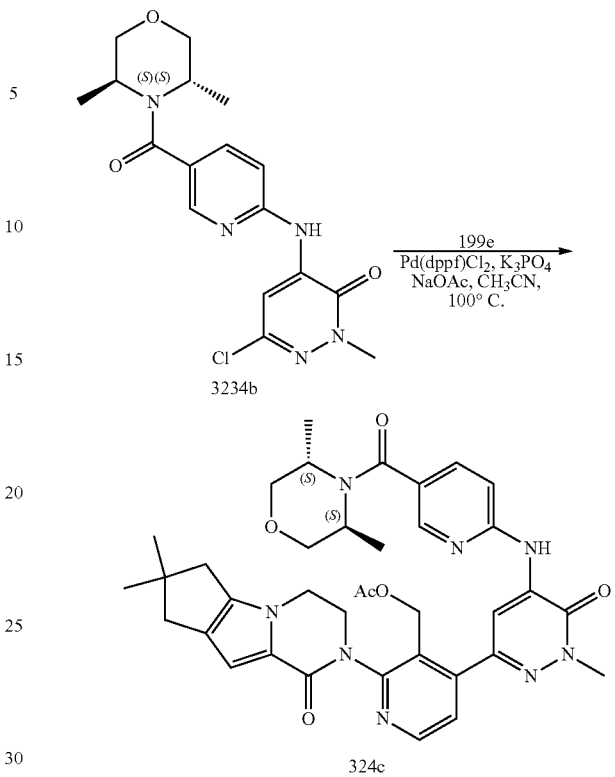

To a solution of (3S,5S)-3,5-dimethylmorpholine (115 mg, 1.0 mmol) in DMF (2 mL) was added HATU (380 mg, 1.0 mmol), DIPEA (260 mg, 2.0 mmol), and 6-aminonicotinic acid (138 mg, 1.0 mmol) at room temperature. After stirring for 18 h, the reaction mixture was filtered and purified with Combiflash (A: 1‰NH₄HCO₃/water, B: acetonitrile) to afford 324a (80 mg, 34%) as a yellow solid. MS (ESI): 236.1 (M+H).

Example 324b

6-Chloro-4-(5-((3S,5S)-3,5-dimethylmorpholine-4-carbonyl)pyridine-2-ylamino)-2-methylpyridazin-3(2H)-one 324b A 100-mL single-neck round-bottomed flask equipped with a magnetic stirrer and a reflux condenser was charged with 1,4-dioxane (8 mL), cesium carbonate (221 mg, 0.68 mmol), 324a (80 mg, 0.34 mmol), and 4-bromo-6-chloro-2-methylpyridazin-3(2H)-one (80 mg, 0.36 mmol). After bubbling nitrogen through the suspension for 5 minutes, Xantphos (40 mg, 0.068 mmol) and tris(dibenzylideneacetone)dipalladium(0) (24 mg, 0.034 mmol) were added. The system was subjected to three cycles of vacuum/nitrogen flush and heated at reflux for 2.5 h. It was then cooled to room temperature and filtered. The solid was washed with dichloromethane (3×10 mL). The combined filtrate was concentrated under reduced pressure. The residue was purified by silica-gel column chromatography eluting with petroleum ether/ethyl acetate (2/1 to 100% ethyl acetate) to afford 324b (40 mg, 31%) as a yellow solid. MS-ESI: [M+H]⁺ 378.3

573

Example 324c (2-{4,4-Dimethyl-9-oxo-1,10-diazatricyclo[6.4.0. 0$^{2,6}$]dodeca-2(6),7-dien-10-yl}-4-{5-[(5-{[(3S,5S)-3, 5-dimethylmorpholin-4-yl]carbonyl}pyridin-2-yl) amino]-1-methyl-6-oxo-1,6-dihydropyridazin-3-yl}pyridin-3-yl)methyl Acetate 324c A 50-mL round-bottomed flask equipped with a reflux condenser was charged with 324b (40 mg, 0.11 mmol), (2-{4, 4-dimethyl-9-oxo-1,10-diazatricyclo[6.4.0.0$^{2,6}$]dodeca-2 (6),7-dien-10-yl}-4-(4,4,5,5-tetramethyl-1,3,2-dioxaborolan-2-yl)pyridin-3-yl)methyl acetate 199e (105 mg, 0.22 mmol), K$_3$PO$_4$ (47 mg, 0.22 mmol), sodium acetate (18 mg, 0.22 mmol), 1,1'-bis(diphenylphosphino)ferrocenedichloropalladium(II) (20 mg, 0.022 mmol), acetonitrile (10 mL), and water (6 drops). The system was subjected to three cycles of vacuum/nitrogen flush and heated at 100° C. under N$_2$ protection for 1.5 h. LCMS analysis showed complete conversion to the desired product. The reaction mixture was cooled to room temperature and filtered. The filtrate was concentrated under reduced pressure. The residue was diluted with dichloromethane (50 mL) and water (50 mL). The aqueous layer was separated and extracted with dichloromethane (3×20 mL). The combined extract was dried over Na$_2$SO$_4$, filtered, and concentrated under reduced pressure. The dark residue was purified by silica-gel column chromatography eluting with 60:1 dichloromethane/methanol to afford 324c (40 mg, 52%) as a black solid. MS-ESI: [M+H]$^+$ 695.3

Example 324

3-[4-[5-[[5-[(3S,5S)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1, 2,6,8-tetrahydrocyclopenta[3,4]pyrrolo[3,5-b] pyrazin-4-one 324

To a solution of 324c (40 mg, 0.057 mmol) in THF/i-propanol/water (1/1/0.5 ml) was added lithium hydroxide (14 mg, 0.57 mmol) at room temperature. After the reaction was stirred for 3 h, LCMS indicated the reaction was complete. Then the mixture was poured into water (20 mL) and extracted with dichloromethane (3×15 mL). The combined organic layer was washed with brine (30 mL), dried over Na$_2$SO$_4$, filtered, and concentrated under reduced pressure. The residue solid was purified by reverse-phase prep-HPLC (A: 1‰NH$_4$HCO$_3$/water, B: acetonitrile) to afford 324 (10 mg, 27.7%) as a white solid. MS-ESI: [M+H]+ 653.3. $^1$H NMR (500 MHz, DMSO-d$_6$) δ 9.69 (s, 1H), 8.63 (s, 1H), 8.53 (d, J=5.0, 1H), 8.31 (d, J=1.5 Hz, 1H), 7.77-7.75 (m, 1H), 7.58 (d, J=8.5 Hz, 1H), 7.41 (d, J=5.0 Hz, 1H), 6.56 (s, 1H), 4.78 (t, J=5.5 Hz, 1H), 4.60-4.57 (m, 1H), 4.41-4.37 (m, 1H), 4.30-4.25 (m, 1H), 4.19 (d, J=3.5 Hz, 2H), 4.01 (s, 2H), 3.92-3.88 (m, 1H), 3.82 (s, 3H), 3.65-3.61 (m, 2H), 3.56-3.53 (m, 2H), 2.57 (d, J=6.5 Hz, 2H), 2.42 (s, 2H), 1.25 (d, J=6.0 Hz, 6H), 1.21 (s, 6H)

574

Example 325a

3-Amino-5-bromo-1-methylpyridin-2(1H)-one 325a

-continued

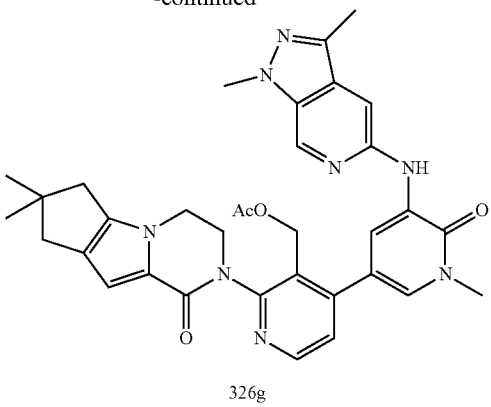

326g

To a solution of 5-bromo-3-(diphenylmethyleneamino)-1-methylpyridin-2(1H)-one (3.82 g, 10.4 mmol) in ethyl acetate (10 mL) was added 4 MHCl/dioxane (7.8 mL, 31.3 mmol). The reaction mixture was stirred for 0.5 h and concentrated under reduced pressure. The residue was washed with tert-butyl methyl ether and filtered. The solid was dissolved in ethyl acetate (10 mL) and water (10 mL). The pH of the resulting mixture was adjusted to between 7 and 8 by adding $K_2CO_3$ gradually. The water phase was separated and extracted with dichloromethane for three times. The combined organic layer was concentrated under reduced pressure to afford 325a as a yellow solid (1.1 g, 52%). MS-ESI: [M+H]$^+$ 202.9.

Example 325b 1-(2-Bromo-5-fluoropyridin-4-yl)ethanol 325b

To a 250-mL 3-neck flask was added a THF solution (20 mL) of 2-bromo-5-fluoropyridine (8.80 g, 50 mmol). At −78° C., to the solution was added LDA (25.0 mL, 50 mmol, 2.5 M in THF) dropwise. After stirring for 5 min, diisopropylamine (7.0 mL, 50 mmol) was added dropwise via a syringe and the mixture was stirred at −78° C. for 4 h. A THF solution of acetaldehyde (11 mL, 55 mmol, 5M in THF) was added dropwise via a syringe. The contents were removed from the cold bath and stirred with warming to room temperature overnight. The mixture was diluted with water (150 mL) and vigorously stirred for 5 min. The contents were concentrated under reduced pressure and the residue was extracted with ethyl ether (3×150 mL). The combined organic layer was dried over $MgSO_4$, filtered, and concentrated under reduced pressure to afford yellow oil, which was purified by silica-gel column chromatography eluting with petroleum ether/ethyl acetate (10:1 to 5:1) to afford 325b (8.0 g, 72.7%) as a yellow solid. MS-ESI: [M+H]$^+$ 220.1. $^1$H NMR (500 MHz, CDCl$_3$) δ 8.15 (d, J=1.5 Hz, 1H), 7.68 (d, J=5.5 Hz, 1H), 5.17 (d, J=6.5 Hz, 1H), 2.18-2.16 (m, 1H), 1.52 (d, J=6.5 Hz, 3H).

Example 325c 1-(2-Bromo-5-fluoropyridin-4-yl)ethanone 325c

A mixture of 325b (7.5 g, 34.2 mmol) and 2-iodoxybenzoic acid (38.4 g, 137 mmol) in ethyl acetate (200 mL) was stirred at 85° C. for 20 hrs. The reaction mixture was filtered and the filtrate was concentrated under reduced pressure. The resulting residue was purified by silica-gel column chromatography eluting with petroleum ether/ethyl acetate (20:1 to 10:1) to afford 325c (6.8 g, 92%) as a yellow oil. MS-ESI: [M+H]+ 217.9.

Example 325d

5-Bromo-3-methyl-1H-pyrazolo[3,4-c]pyridine 325d

To a 250-mL round-bottomed flask equipped with a reflux condenser was added dry ethylene glycol (30 mL) and 325c (4.3 g, 20 mmol). Then hydrazine hydrate (5.0 mL, 4.8 g, 81.6 mmol) was added dropwise via a syringe. The mixture was heated at 165° C. for 3.5 h. The resulting orange-tan mixture was cooled to room temperature and the contents were poured onto a stirring mixture of 100 mL ice/water (1:1), whereupon precipitation occurred. After stirring for 10 min, the off-white precipitate was collected, which was dried in vacuo to afford 325d as an off-white solid (3.1 g, 74%). MS-ESI: [M+H]+ 211.9.

Example 325e

5-Bromo-1,3-dimethyl-1H-pyrazolo[3,4-c]pyridine 325e and 5-Bromo-2,3-dimethyl-2H-pyrazolo[3,4-c]pyridine 326a A mixture of 325d (3.0 g, 14.2 mmol), CH$_3$I (2.40 g, 17.0 mmol), and $K_2CO_3$ (2.9 g, 21.3 mmol) in acetonitrile (60 mL) was stirred at 30° C. for 1 h. The reaction mixture was filtered and the filtrate was concentrated under reduced pressure. The resulting residue was purified by silica-gel column chromatography eluting with 8:1 petroleum ether/ethyl acetate to afford 325e (920 mg, 29.0%) as a white solid, and eluting with 2:1 petroleum ether/ethyl acetate to afford 326a (390 mg, 12.0%) as a gray solid. MS-ESI: [M+H]$^+$ 226.1.

Example 325f

5-Bromo-3-(1,3-dimethyl-1H-pyrazolo[3,4-c]pyridin-5-ylamino)-1-methylpyridin-2(1H)-one 325f A sealed tube was charged with 325e (202 mg, 1.0 mmol), 325a (337.5 mg, 1.5 mmol), Pd$_2$(dba)$_3$ (91.7 mg, 0.10 mmol), BINAP (124.6 mg, 0.20 mmol), cesium carbonate (650 mg, 2.0 mmol), and 1,4-dioxane (10 mL). After three cycles of vacuum/nitrogen flush, the sealed tube was heated at 100° C. for 2 hrs. It was then cooled to room temperature and filtered. The filtrate was concentrated under reduced pressure. The resulting residue was purified by silica-gel column chromatography eluting with petroleum ether/ethyl acetate (5:1 to 2:1) to afford 325f (140 mg, 40%) as a yellow solid. MS-ESI: [M+H]$^+$ 348.2.

Example 325g

{4-[5-({1,3-Dimethyl-1H-pyrazolo[3,4-c]pyridin-5-yl}amino)-1-methyl-6-oxo-1,6-dihydropyridin-3-yl]-2-{4,4-dimethyl-9-oxo-1,10-diazatricyclo[6.4.0.0$^{2,6}$]dodeca-2(6),7-dien-10-yl}pyridin-3-yl}methyl Acetate 325g A 100-mL round-bottomed flask equipped with a magnetic stirrer and a reflux condenser was charged with 325f (120 mg, 0.35 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (417 mg, 1.05 mmol), Pd(dppf)Cl$_2$ (29 mg, 0.035 mmol), $K_3PO_4$ (148.0 mg, 0.70 mmol), sodium acetate (57.4 mg, 0.70 mmol), water (0.5 mL), and acetonitrile (15 mL). After three cycles of vacuum/nitrogen flush, the mixture was heated at reflux for 1 hr. It was then cooled to room temperature and filtered. The filtrate was concentrated under reduced pressure and the resulting residue was purified by silica-gel column chromatography eluting with 30:1 dichloromethane/methanol to afford 325g as a yellow solid (70 mg, 33%). MS-ESI: [M+H]+ 620.8.

Example 325

3-[4-[5-[(1,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 325

A mixture of 325g (60 mg, 0.10 mmol) and lithium hydroxide (60 mg, 2.5 mmol) in i-propanol/THF (1:1, 4 mL) and water (1 mL) was stirred at 35° C. for 30 min. To the reaction mixture was added water (10 mL) and the resulting mixture was concentrated under reduced pressure. The residue was extracted with dichloromethane three times. The combined organic layer was concentrated under reduced pressure and the resulting residue was purified by reverse-phase prep-HPLC to afford 325 as a yellow solid (20 mg, 31%). MS-ESI: [M+H]+ 578.8. ¹H NMR (500 MHz, DMSO) δ 8.80 (s, 1H), 8.49 (d, J=5.0 Hz, 1H), 8.36 (d, J=2.0 Hz, 1H), 8.29 (s, 1H), 7.55 (s, 1H), 7.49 (d, J=2.0 Hz, 1H), 7.37 (d, J=5.0 Hz, 1H), 6.56 (s, 1H), 5.06-5.05 (m, 1H), 4.51-4.43 (m, 2H), 4.25-4.19 (m, 3H), 4.00 (s, 3H), 3.86-3.84 (m, 1H), 3.63 (s, 3H), 2.62-2.59 (m, 2H), 2.44-2.43 (m, overlap, 5H), 1.22 (s, 6H).

Example 326b

5-Bromo-3-(2,3-dimethyl-2H-pyrazolo[3,4-c]pyridin-5-ylamino)-1-methylpyridin-2(1H)-one 326b

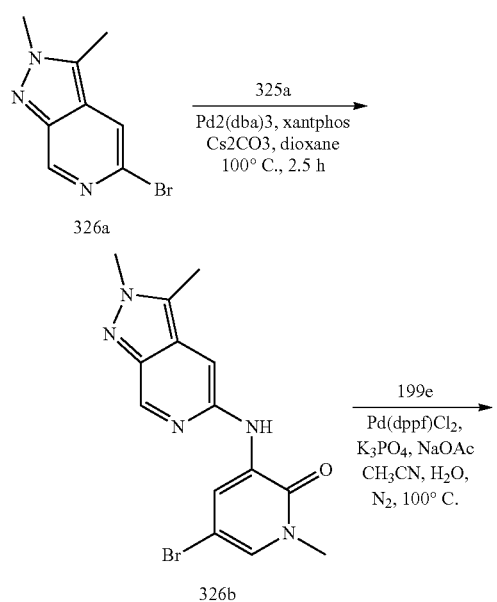

-continued

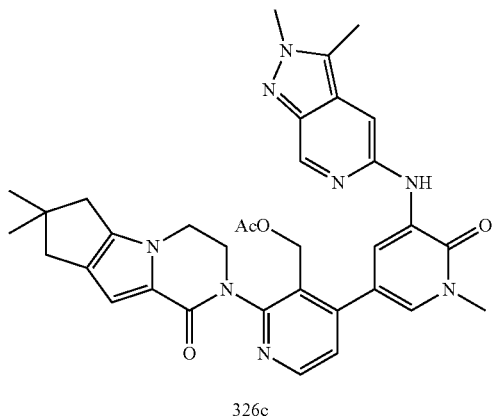

326c

A 100-mL round-bottomed flask equipped with a magnetic stirrer and a reflux condenser was charged with 5-bromo-2,3-dimethyl-2H-pyrazolo[3,4-c]pyridine 326a from Example 325 (452 mg, 2.0 mmol), 3-amino-5-bromo-1-methylpyridin-2(1H)-one 325a (400 mg, 2.0 mmol), cesium carbonate (1.3 g, 4.0 mmol), and 1,4-dioxane (10 mL). After bubbling nitrogen through the suspension for 5 minutes, BINAP (124 mg, 0.2 mmol) and tris(dibenzylideneacetone)dipalladium (0) (140 mg, 0.2 mmol) were added. The system was subjected to three cycles of vacuum/nitrogen flush and heated at reflux for 2.5 h. It was then cooled to room temperature and filtered. The solid was washed with dichloromethane (3×10 mL). The combined filtrate was concentrated under reduced pressure. The residue was purified by silica-gel column chromatography eluting with petroleum ether/ethyl acetate (2/1 to 100% ethyl acetate) to afford 326b (160 mg, 23%) as a yellow solid. MS-ESI: [M+H]⁺ 348.3

Example 326c

{4-[5-({2,3-Dimethyl-2H-pyrazolo[3,4-c]pyridin-5-yl}amino)-1-methyl-6-oxo-1,6-dihydropyridin-3-yl]-2-{4,4-dimethyl-9-oxo-1,10-diazatricyclo[6.4.0.0²,⁶]dodeca-2(6),7-dien-10-yl}pyridin-3-yl}methyl Acetate 326c A 50-mL round-bottomed flask equipped with a reflux condenser was charged with 326b (160 mg, 0.46 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (300 mg, 0.69 mmol), K₃PO₄ (195 mg, 0.92 mmol), sodium acetate (75 mg, 0.92 mmol), 1,1'-bis(diphenylphosphino) ferrocenedichloropalladium(II) (42 mg, 0.046 mmol), acetonitrile (10 mL), and water (6 drops). The system was subjected to three cycles of vacuum/nitrogen flush and heated at 100° C. under N₂ protection for 1.5 h. LCMS Analysis showed complete conversion to the desired product. The reaction mixture was cooled to room temperature and filtered. The filtrate was concentrated under reduced pressure. The residue was diluted with dichloromethane (50 mL) and water (50 mL). The aqueous layer was separated and extracted with dichloromethane (3×20 mL). The combined extract was dried over $Na_2SO_4$, filtered, and concentrated under reduced pressure. The dark residue was purified by gel-silica column chromatography eluting with 60:1 dichloromethane/methanol to afford 326c (130 mg, 45%) as a black solid. MS-ESI: $[M+H]^+$ 621.3

Example 326

3-[4-[5-[(2,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 326

To a solution of 326c (130 mg, 0.21 mmol) in THF/i-propanol/water (4/2/1 mL) was added lithium hydroxide (50 mg, 2.0 mmol) at room temperature. After the reaction was stirred for 3 h, LCMS indicated the reaction was complete. Then the mixture was poured into water (30 mL) and extracted with dichloromethane (3×30 mL). The combined organic layer was washed with brine (30 mL), dried over $Na_2SO_4$, filtered, and concentrated under reduced pressure. The residue solid was purified by reverse-phase prep-HPLC (A: 1‰$NH_4HCO_3$/water, B: acetonitrile) to afford 326 (60 mg, 50%) as a white solid. MS-ESI: [M+H]+ 579.3. $^1$H NMR (500 MHz, DMSO-$d_6$) δ 8.86 (s, 1H), 8.48 (d, J=5.0 Hz, 1H), 8.06 (d, J=1.5 Hz, 1H), 7.99 (s, 1H), 7.47 (d, J=2.0 Hz, 1H), 7.41 (s, 1H), 7.38 (d, J=5.0 Hz, 1H), 6.57 (s, 1H), 5.13 (t, J=5.0 Hz, 1H), 4.50-4.46 (m, 2H), 4.24-4.19 (m, 3H), 4.09 (s, 3H), 3.86-3.85 (m, 1H), 3.62 (s, 3H), 2.62-2.53 (m, overlap, 5H), 2.43 (s, 2H), 1.22 (s, 6H)

Example 327a 5-(2-Methoxyethyl)-2-nitro-4,5,6,7-tetrahydropyrazolo[1,5-a]pyrazine 327a

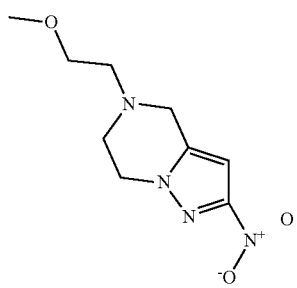

To a solution of 2-nitro-4,5,6,7-tetrahydropyrazolo[1,5-a]pyrazine (190 mg, 1.13 mmol) 209a in acetonitrile (10 mL) was added $K_2CO_3$ (311.9 mg, 2.26 mmol) and 1-bromo-2-methoxyethane (188.3 mg, 1.36 mmol). The reaction mixture was heated at 80° C. for 17 h under microwave irradiation. Analysis of the reaction mixture by LCMS showed complete conversion to the desired product. The mixture was cooled to room temperature and filtered. The filtrate was concentrated under reduced pressure to afford 327a as a white solid (230 mg, 90%), which was used in the next step without further purification. MS-ESI: $[M+H]^+$ 227.0

Example 327b 5-(2-Methoxyethyl)-4,5,6,7-tetrahydropyrazolo[1,5-a]pyrazin-2-amine 327b

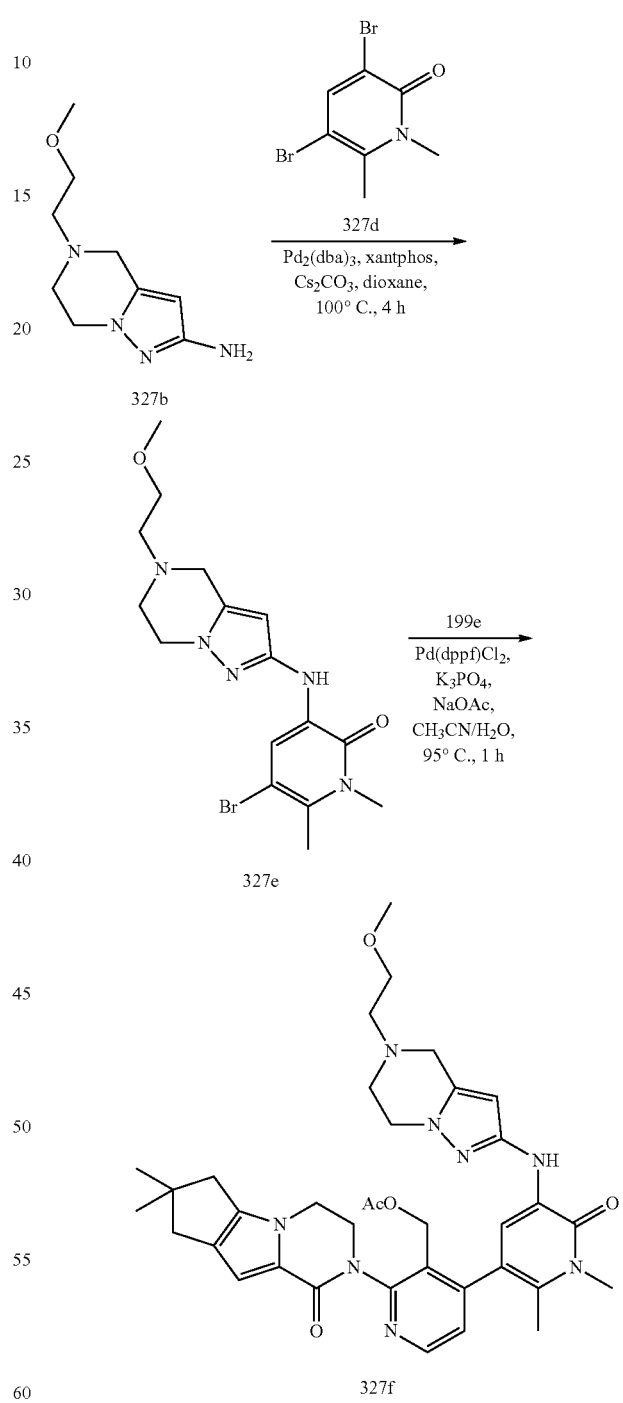

To a solution of 327a (286 mg, 1.26 mmol) in methanol (10 mL) was added Pd/C (28.6 mg). The system was evacuated and then refilled with $H_2$. After stirring at room temperature for 2 h, the mixture was filtered. The filtrate was concentrated under reduced pressure to afford 327b as a yellow solid (240 mg, 97%), which was used in the next step without further purification. MS-ESI: [M+H]$^+$ 197.0

Example 327c

3,5-Dibromo-6-methylpyridin-2(1H)-one 327c

6-Methyl-pyridin-2-ol (10.9 g, 0.10 mol) was suspended in anhydrous dichloromethane (300 mL) and stirred at ambient temperature. Under cooling with an ice/water cooling bath, N-bromosuccinimide (NBS) (11.4 g, 0.20 mol) was added slowly portion-wise over a time interval of 5 minutes. The suspension was stirred at reflux for 2 hours. Thereafter, the suspension was filtered. The filter cake was thoroughly washed with methanol and dried in vacuo to afford 327c as a white solid (22.7 g, 85%). MS-ESI: [M+H]$^+$ 266.

Example 327d

3,5-Dibromo-1,6-dimethylpyridin-2(1H)-one 327d

A 100-mL single-neck round-bottomed flask equipped with a magnetic stirrer was charged with DMF (50 mL), 327c (10.0 g, 37.5 mmol), CH$_3$I (5.3 g, 37.5 mmol), and K$_2$CO$_3$ (7.8 g, 56.2 mmol). The mixture was stirred at room temperature for 5 h. Water (100 mL) was added and the resulting white solid was collected to afford 327d (8.2 g, 78%) as a white solid. MS-ESI: [M+H]$^+$ 280.

Example 327e

5-Bromo-3-(5-(2-methoxyethyl)-4,5,6,7-tetrahydropyrazolo[1,5-a]pyrazin-2-ylamino)-1,6-dimethylpyridin-2(1H)-one 327e A 100-mL round-bottomed flask equipped with a reflux condenser was charged with 327b (392 mg, 2.0 mmol), 327d (562 mg, 2.0 mmol), cesium carbonate (1.30 g, 4.0 mmol), and 1,4-dioxane (20 mL). After bubbling nitrogen through the suspension for 10 minutes, xantphos (115 mg, 0.20 mmol) and tris(dibenzylideneacetone)dipalladium(0) (92 mg, 0.10 mmol) were added. The system was subjected to three cycles of vacuum/nitrogen flush and heated at reflux for 5 h. It was then cooled to room temperature and filtered. The solid was washed with dichloromethane (2×15 mL). The combined filtrate was concentrated under reduced pressure. The residue was purified by silica-gel column chromatography eluting with dichloromethane/methanol (80:1 to 30:1) to afford 327e (490 mg, 62%) as a yellow solid. MS-ESI: [M+H]$^+$ 396.2

Example 327f

(2-{4,4-Dimethyl-9-oxo-1,10-diazatricyclo[6.4.0.0$^{2,6}$]dodeca-2(6),7-dien-10-yl}-4-(5-{[5-(2-methoxyethyl)-4H,5H,6H,7H-pyrazolo[1,5-a]pyrazin-2-yl]amino}-1,2-dimethyl-6-oxo-1,6-dihydropyridin-3-yl)pyridin-3-yl)methyl Acetate 327f A 25-mL single-neck round-bottomed flask equipped with a magnetic stirrer and a reflux condenser was charged with 327e (158 mg, 0.40 mmol), {3-[(acetyloxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (159 mg, 0.40 mmol), K$_3$PO$_4$ (170 mg, 0.80 mmol), sodium acetate (66 mg, 0.80 mmol), Pd(dppf)Cl$_2$ (15 mg, 0.020 mmol), and acetonitrile/water (7/0.5 mL). After three cycles of vacuum/N$_2$ flush, the mixture was heated at 95° C. for 1 h. LCMS analysis showed complete conversion to the desired product. The reaction mixture was cooled to room temperature, and diluted with dichloromethane (50 mL) and water (30 mL). The water layer was extracted with dichloromethane (2×30 mL). The combined organic extract was dried over Na$_2$SO$_4$, filtered, and concentrated under reduced pressure. The dark residue was purified by silica-gel column chromatography eluting with dichloromethane/methanol (80:1 to 30:1) to afford 327f (120 mg, 45%) as a yellow solid. MS-ESI: [M+H]$^+$ 668.8

Example 327

3-[3-(hydroxymethyl)-4-[5-[[5-(2-methoxyethyl)-6,7-dihydro-4H-pyrazolo[1,5-a]pyrazin-2-yl]amino]-1,2-dimethyl-6-oxo-3-pyridyl]-2-pyridyl]-7,7-dimethyl-1,2,6,8-tetrahydrocyclopenta[3,4]pyrrolo[3,5-b]pyrazin-4-one 327

To a solution of 327f (120 mg, 0.18 mmol) in THF/i-propanol/water (6/4/3 mL) was added lithium hydroxide (22 mg, 0.90 mmol). The mixture was stirred at room temperature for 1 h. The mixture was concentrated under reduced pressure and the residue was diluted with water (15 mL). It was then extracted with ethyl acetate (3×20 mL). The combined organic layer was dried over sodium sulfate and concentrated under pressure. The residue was purified by reverse-phase prep-HPLC to afford 327 as a white solid (55 mg, 49%). MS-ESI: [M+H]$^+$ 626.9. $^1$H NMR (500 MHz, CDCl$_3$) δ 8.49 (d, J=5.0 Hz, 1H), 7.49 (s, 1H), 7.32 (s, 1H), 7.15 (d, J=4.5 Hz, 1H), 6.82 (s, 1H), 5.61 (bs, 1H), 4.53-4.45 (m, 3H), 4.26-4.16 (m, 3H), 4.03-3.97 (m, 3H), 3.71-3.69 (m, 5H, overlap), 3.58 (t, J=5.5 Hz, 2H), 3.39 (s, 3H), 2.98 (t, J=5.0 Hz, 2H), 2.77 (t, J=5.0 Hz, 2H), 2.60-2.57 (m, 2H), 2.53 (s, 2H), 2.17 (s, 3H), 1.29 (s, 6H).

Example 328a

3-(5-(2-Methoxyethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 328a

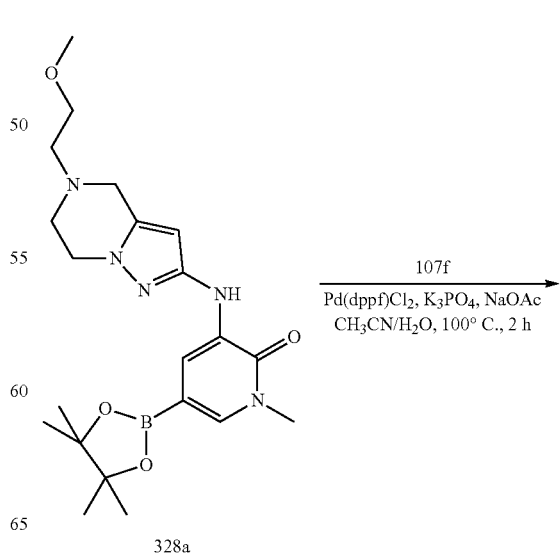

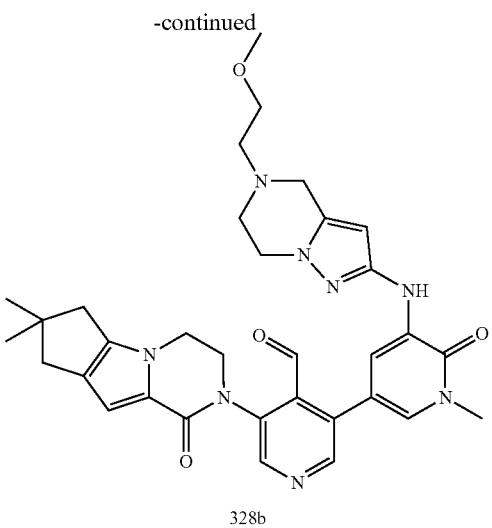

328b

A 50-mL single-neck round-bottomed flask equipped with a magnetic stirrer and a reflux condenser was charged with 5-bromo-3-(5-(2-methoxyethyl)-4,5,6,7-tetrahydropyrazolo[1,5-a]pyrazin-2-ylamino)-1-methylpyridin-2(1H)-one 296f (330 mg, 0.86 mmol), Pin$_2$B$_2$ (329 mg, 1.30 mmol), Pd$_2$(dba)$_3$ (40 mg, 0.043 mmol), X-phos (41 mg, 0.086 mmol), potassium acetate (169 mg, 1.726 mmol), and dioxane (10 mL). After three cycles of vacuum/N$_2$ flush, the mixture was heated at 70° C. for 2 h. Analysis of the reaction mixture by LCMS showed complete conversion to the desired product. It was cooled to room temperature and filtered. The filtrate was concentrated under reduced pressure. The residue was washed with petroleum ether to afford 328a as a dark oil (240 mg, 80%), which was used in the next step without further purification. MS-ESI: [M+H]$^+$ 348.3

Example 328b

3-{4,4-Dimethyl-9-oxo-1,10-diazatricyclo[6.4.0.0$^{2,6}$]dodeca-2(6),7-dien-10-yl}-5-(5-{[5-(2-methoxyethyl)-4H,5H,6H,7H-pyrazolo[1,5-a]pyrazin-2-yl]amino}-1-methyl-6-oxo-1,6-dihydropyridin-3-yl)pyridine-4-carbaldehyde 328b A sealed tube equipped with a magnetic stirrer was charged with 3-bromo-5-{4,4-dimethyl-9-oxo-1,10-diazatricyclo[6.4.0.0$^{2,6}$]dodeca-2(6),7-dien-10-yl}pyri-dine-4-carbaldehyde 107f (100 mg, 0.26 mmol), 328a (110 mg, 0.26 mmol), Pd(dppf)Cl$_2$ (10 mg, 0.026 mmol), sodium acetate (50 mg, 0.50 mmol), K$_3$PO$_4$ (100 mg, 0.50 mmol), and acetonitrile/water (5 mL/1 mL). After three cycles of vacuum/nitrogen flush, the mixture was heated at 100° C. for 2 h. It was then filtered and the filtrate was evaporated under reduced pressure. The residue was purified by silica-gel column chromatography eluting with 10:1 dichloromethane/methanol to afford 328b (50 mg, 32%) as a brown solid. MS-ESI: [M+H]$^+$ 611.3.

Example 328

3-[4-(hydroxymethyl)-5-[5-[[5-(2-methoxyethyl)-6,7-dihydro-4H-pyrazolo[1,5-a]pyrazin-2-yl]amino]-1-methyl-6-oxo-3-pyridyl]-3-pyridyl]-7,7-dimethyl-1,2,6,8-tetrahydrocyclopenta[3,4]pyrrolo[3,5-b]pyrazin-4-one 328

A mixture of 328b (50 mg, 0.08 mmol) and NaBH$_4$ (8.0 mg, 0.20 mmol) in methanol (4 mL) was stirred at 25° C. for 0.5 h. The reaction mixture was quenched with water (10 mL) and evaporated under reduced pressure. The residue was added extracted with dichloromethane (2×10 mL). The combined extract was concentrated under reduced pressure and the residue was purified by reverse-phase prep-HPLC to afford 328 (13 mg, 25%) as a pale yellow solid. MS-ESI: [M+H]$^+$ 613.3. $^1$H NMR (500 MHz, CDCl$_3$) δ 8.62 (s, 1H), 8.48 (s, 1H), 7.92 (d, J=2.0 Hz, 1H), 7.38 (s, 1H), 7.31 (d, J=2.0 Hz, 1H), 6.82 (s, 1H), 5.67 (s, 1H), 4.64-4.62 (m, 1H), 4.57-4.55 (m, 1H), 4.38-4.34 (m, 1H), 4.22-4.17 (m, 3H), 4.05-4.02 (m, 2H), 3.99-3.96 (m, 1H), 3.71-3.70 (m, 2H), 3.69 (s, 3H), 3.57 (t, J=5.0 Hz, 2H), 3.37 (s, 3H), 2.99 (t, J=5.0 Hz, 2H), 2.77 (t, J=5.0 Hz, 2H), 2.56 (s, 2H), 2.51 (s, 2H), 1.27 (s, 6H).

Example 329a

2-Chloro-4-{4,4-dimethyl-9-oxo-1,10-diazatricyclo[6.4.0.0$^{2,6}$]dodeca-2(6),7-dien-10-yl}pyridine-3-carbaldehyde 329a

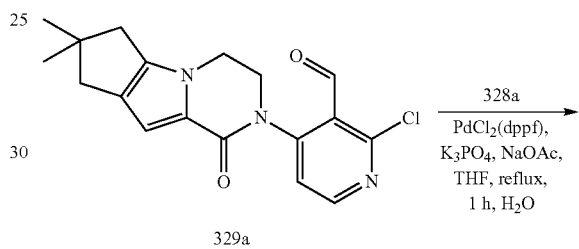

329a

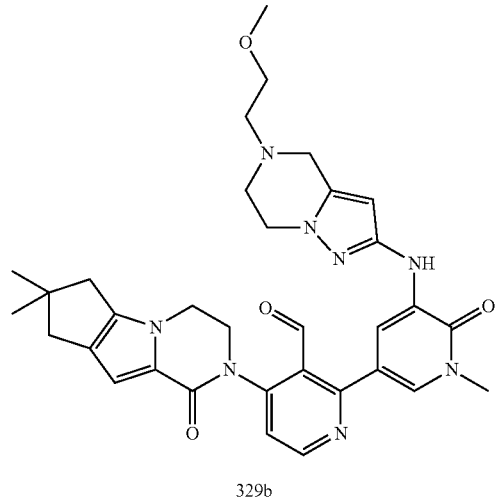

329b

A 100-mL round-bottomed flask equipped with a reflux condenser was charged with 4,4-dimethyl-1,10-diazatricyclo[6.4.0.0$^{2,6}$]dodeca-2(6),7-dien-9-one 107e (612 mg, 3.0 mmol), 4-bromo-2-chloronicotinaldehyde (2.0 g, 9.0 mmol), Pd$_2$(dba)$_3$ (275 mg, 0.30 mmol), XantPhos (347 mg, 0.60 mmol), cesium carbonate (1.95 g, 6.0 mmol), and 1,4-dioxane (30 mL). After three cycles of vacuum/nitrogen flush, the mixture was heated at 97° C. overnight. It was then cooled to room temperature and filtered. The filtrate was concentrated under reduced pressure and the resulting residue was purified by silica-gel column chromatography eluting with 1:2 ethyl acetate/petroleum ether to afford 329a as a yellow solid (660 mg, 65%). MS-ESI: [M+H]+ 344.1.

Example 329b

4-{4,4-Dimethyl-9-oxo-1,10-diazatricyclo[6.4.0.0$^{2,6}$]dodeca-2(6),7-dien-10-yl}-2-(5-{[5-(2-methoxyethyl)-4H,5H,6H,7H-pyrazolo[1,5-a]pyrazin-2-yl]amino}-1-methyl-6-oxo-1,6-dihydropyridin-3-yl)pyridine-3-carbaldehyde 329b A 100-mL single-neck round-bottomed flask equipped with a magnetic stirrer and a reflux condenser was charged with 329a (100 mg, 0.30 mmol), 3-(5-(2-methoxyethyl)-4,5,6,7-tetrahydropyrazolo[1,5-a]pyrazin-2-ylamino)-1-methyl-5-(4,4,5,5-tetramethyl-1,3,2-dioxaborolan-2-yl)pyridin-2(1H)-one 328a (257 mg, 0.60 mmol), Pd(dppf)Cl$_2$ (25 mg, 0.030 mmol), K$_3$PO$_4$ (127 mg, 0.60 mmol), sodium acetate (49 mg, 0.60 mmol), water (0.50 mL), and THF (10 mL). After three cycles of vacuum/nitrogen flush, the mixture was heated at reflux for 1 h. It was then cooled to room temperature and filtered. The filtrate was concentrated under reduced pressure and the resulting residue was purified by silica-gel column chromatography eluting with 30:1 dichloromethane/methanol to afford 329b as a brown solid (60 mg, 34%). MS-ESI: [M+H]+ 611.3.

Example 329

3-[3-(hydroxymethyl)-2-[5-[[5-(2-methoxyethyl)-6,7-dihydro-4H-pyrazolo[1,5-a]pyrazin-2-yl]amino]-1-methyl-6-oxo-3-pyridyl]-4-pyridyl]-7,7-dimethyl-1,2,6,8-tetrahydrocyclopenta[3,4]pyrrolo[3,5-b]pyrazin-4-one 329

A mixture of 329b (50 mg, 0.080 mmol) and NaBH$_4$ (9.1 mg, 0.24 mmol) in methanol (5 mL) was stirred at room temperature for 10 min. The mixture was quenched with water (10 mL) and evaporated under reduced pressure. The residue was extracted with dichloromethane (3×10 m). The combined extract was concentrated under reduced pressure and the residue was purified by reverse-phase prep-HPLC to afford 329 (15 mg, 30%) as a yellow solid. MS-ESI: [M+H]$^+$ 613.3. $^1$H NMR (500 MHz, CDCl$_3$) δ 8.66 (d, J=4.5 Hz, 1H), 8.13 (s, 1H), 7.63 (s, 1H), 7.35 (s, 1H), 7.12 (d, J=5.0 Hz, 1H), 6.83 (s, 1H), 5.71 (s, 1H), 4.67-4.63 (m, 1H), 4.49-4.43 (m, 1H), 4.24-4.23 (m, 2H), 4.19-4.17 (m, 1H), 4.06-4.04 (m, 2H), 4.01-3.97 (m, 1H), 3.74-3.71 (m, 2H), 3.70 (s, 3H), 3.59-3.55 (m, 2H), 3.38 (s, 3H), 3.00 (t, J=5.0 Hz, 2H), 2.77 (t, J=5.0 Hz, 2H), 2.56 (s, 2H), 2.51 (s, 2H), 1.27 (s, 6H).

Example 330a

10-[4-Chloro-3-(hydroxymethyl)pyridin-2-yl]-4,4-dimethyl-7-thia-10-azatricyclo[6.4.0.0$^{2,6}$]dodeca-1(8),2(6)-dien-9-one 330a

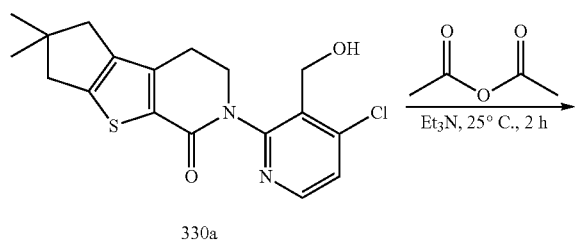

330a

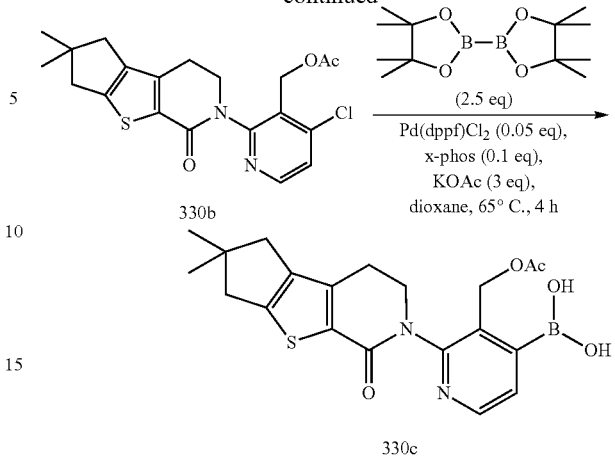

330b

330c

A mixture of 4-chloro-2-{4,4-dimethyl-9-oxo-7-thia-10-azatricyclo[6.4.0.0$^{2,6}$]dodeca-1(8),2(6)-dien-10-yl}pyridine-3-carbaldehyde 109a (1.2 g, 3.3 mmol), NaBH$_4$ (228 mg, 6.0 mmol), and methanol (10 mL) was stirred at 0° C. for 0.5 h. Then the reaction mixture was quenched with water (10 mL) and concentrated under reduced pressure. The residue was extracted with dichloromethane (2×15 mL). The combined dichloromethane extract was concentrated under reduced pressure to afford 330a as a pale yellow solid (1.0 g, 84%). MS-ESI: [M+H]$^+$ 362.9

Example 330b (4-Chloro-2-{4,4-dimethyl-9-oxo-7-thia-10-azatricyclo[6.4.0.0$^{2,6}$]dodeca-1(8),2(6)-dien-10-yl}pyridin-3-yl)methyl Acetate 330b A mixture of 330a (1.0 g, 2.76 mmol), triethylamine (610 mg, 6.0 mmol), and acetic anhydride (5 mL) was stirred at 25° C. for 2 h. Then the reaction mixture was quenched with water (10 mL) and the pH was adjusted to around 8 with NaHCO$_3$ (aq.). The mixture was extracted with dichloromethane (2×15 mL). The combined dichloromethane extract was concentrated under reduced pressure and the residue was purified by silica-gel column chromatography eluting with 1:1 ethyl acetate/petroleum ether to afford 330b as a pale yellow solid (1.0 g, 90%). MS-ESI: [M+H]$^+$ 405.2

Example 330c (2-{4,4-Dimethyl-9-oxo-7-thia-10-azatricyclo[6.4.0.0$^{2,6}$]dodeca-1(8),2(6)-dien-10-yl}-4-(4,4,5,5-tetramethyl-1,3,2-dioxaborolan-2-yl)pyridin-3-yl)methyl Acetate 330c A 50-mL round-bottomed flask equipped with a magnetic stirrer and a reflux condenser was charged with 330b (1.0 g, 2.47 mmol), 4,4,4',4',5,5,5',5'-octamethyl-2,2'-bi(1,3,2-dioxaborolane) (1.87 g, 7.40 mmol), Pd(dppf)Cl$_2$ (100 mg, 0.13 mmol), X-phos (125 mg, 0.25 mmol), potassium acetate (500 mg, 5.0 mmol) and 1,4-dioxane (10 mL). After three cycles of vacuum/nitrogen flush, the mixture was heated at 65° C. for 4 h. It was then filtered and the filtrate was evaporated under reduced pressure to afford 330c (1.0 g, 98%) as a brown oil without further purification. MS-ESI: [M+H]$^+$ 415.2.

Example 330d (3-Nitro-1H-pyrazol-5-yl)methanol 330d

A mixture of 3-nitro-1H-pyrazole-5-carboxylic acid (4.71 g, 30 mmol), BH$_3$/THF (75 mL, 1 mol/L, 75 mmol) was stirred at 60° C. for 2 h. The mixture was cooled to room temperature and 4M HCl (19 mL, 75 mmol) was added. It was stirred at 70° C. for 2 h. After cooling to room temperature, the mixture was concentrated under reduced pressure. The residue was partitioned between ethyl acetate and brine (100:100 mL). The aqueous phase was extract with ethyl acetate (4×50 mL). The combined organic layer was dried on Na$_2$SO$_4$ and evaporated under reduced pressure. The residue was purified by silica-gel column chromatography eluting with petroleum ether/ethyl acetate (5:1 to 1:1) to afford 330d (3.5 g, 79%) as a white solid. MS-ESI: [M+H]$^+$ 144.2

Example 330e 1-(5-(Hydroxymethyl)-3-nitro-1H-pyrazol-1-yl)-2-methylpropan-2-ol 330e A sealed tube was charged with 330d (2.145 g, 15 mmol), Cs$_2$CO$_3$ (978 mg, 3.0 mmol), and 2,2-dimethyloxirane (15 mL). The mixture was stirred at 70° C. for 3 h. After cooling to room temperature, the mixture was concentrated under reduced pressure. The residue was purified by silica-gel column chromatography eluting with petroleum ether/ethyl acetate (5:1 to 1:1) to afford 330e (1.2 g, 38%) as a white solid. MS-ESI: [M+H]$^+$ 216.2

Example 330f 6,6-Dimethyl-2-nitro-6,7-dihydro-4H-pyrazolo[5,1-c][1,4]oxazine 330f To a solution of 330e (1.1 g, 5.1 mmol) in DMF (10 mL), was added NaH (60 percent dispersion in mineral oil, 246 mg, 6.14 mmol) at 0° C. The resulting suspension was stirred for 30 min, followed by the addition of p-toluenesulfonyl chloride (1169 mg, 6.14 mmol). The mixture was stirred at 60° C. overnight. After cooling to room temperature, saturated ammonium chloride solution was added and the mixture was extracted with dichloromethane. The combined organic layer was washed with brine, dried over Na$_2$SO$_4$, and evaporated under reduced pressure. The residue was purified by silica-gel column chromatography eluting with petroleum ether/ethyl acetate gradient (9:1 to 2:1) to afford 330f (228 mg, 22%). MS-ESI: [M+H]$^+$ 198.3

Example 330g 6,6-Dimethyl-6,7-dihydro-4H-pyrazolo[5,1-c][1,4]oxazin-2-amine 330g A 50-mL single-neck round-bottomed flask was purged with nitrogen and charged with 330f (0.21 g, 1.25 mmol), 10% palladium on carbon (50% wet, 125 mg), and methanol (10 mL). The mixture was evacuated, charged with hydrogen gas, and stirred at room temperature for 2 h. The hydrogen was then evacuated and nitrogen was charged into the flask. The catalyst was removed by filtration through a pad of CELITE® and the filtrate was concentrated under reduced pressure to afford 330g (167 mg, 93%). MS-ESI: [M+H]$^+$ 168.1

Example 330h

6-Chloro-4-(6,6-dimethyl-6,7-dihydro-4H-pyrazolo[5,1-c][1,4]oxazin-2-ylamino)-2-methylpyridazin-3(2H)-one 330h

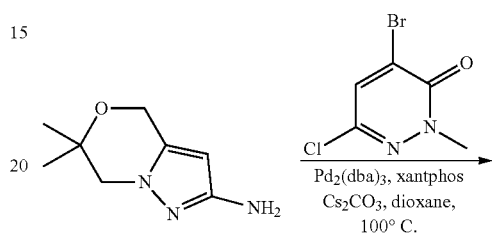

A 50-mL single-neck round-bottomed flask equipped with a magnetic stirrer and a reflux condenser was charged with 330g (250 mg, 1.5 mmol), 4-bromo-6-chloro-2-methylpyridazin-3(2H)-one (669 mg, 3.0 mmol), Pd$_2$(dba)$_3$ (137 mg, 0.15 mmol), Xantphos (173 mg, 0.30 mmol), Cs$_2$CO$_3$ (978 mg, 3.0 mmol), and 1,4-dioxane (20 mL). After three cycles of vacuum/argon flush, the mixture was heated at 100° C. for 3 h. It was then cooled to room temperature and filtered. The filtrate was concentrated under reduced pressure and washed with ethyl acetate to afford 330h as a yellow solid (209 mg, 45%). MS-ESI: [M+H]$^+$ 310.1

Example 330i

{4-[5-({6,6-Dimethyl-4H,6H,7H-pyrazolo[3,2-c][1,4]oxazin-2-yl}amino)-1-methyl-6-oxo-1,6-dihydropyridazin-3-yl]-2-{4,4-dimethyl-9-oxo-7-thia-10-azatricyclo[6.4.0.0²,⁶]dodeca-1(8),2(6)-dien-10-yl}pyridin-3-yl}methyl Acetate 330i A 100-mL single-neck round-bottomed flask equipped with a magnetic stirrer and reflux condenser was charged with 330h (133 mg, 0.43 mmol), 330c (178 mg, 0.43 mmol), sodium acetate (71 mg, 0.86 mmol), $K_3PO_4$ (182 mg, 0.86 mmol), Pd(dppf)Cl$_2$ (35 mg, 0.043 mmol), acetonitrile (15 mL), and water (0.5 mL). After bubbling nitrogen through the resulting mixture for 20 minutes, the reaction mixture was heated at 95° C. for 3 h. After this time the reaction was cooled to room temperature and filtered. The filtrate was concentrated under reduced pressure. The residue was purified with silica-gel column chromatography eluting with 30:1 dichloromethane/methanol to afford 330i as a yellow solid (69 mg, 25%). MS-ESI: [M+H]$^+$ 644.3.

Example 330

3-[4-[5-[(6,6-dimethyl-4,7-dihydropyrazolo[5,1-c][1,4]oxazin-2-yl)amino]-1-methyl-6-oxo-pyridazin-3-yl]-3-(hydroxymethyl)-2-pyridyl]-7,7-dimethyl-1,2,6,8-tetrahydrocyclopenta[3,4]thieno[1,3-c]pyridin-4-one 330

A mixture of 330i (69 mg, 0.11 mmol) and lithium hydroxide (10 mg, 0.42 mmol) in i-propanol/THF (1:1, 3.5 mL) and water (1 mL) was stirred at room temperature for 1 h. The mixture was then concentrated under reduced pressure and the residue was diluted with water (10 mL). It was extracted with ethyl acetate (2×10 mL). The combined ethyl acetate extract was concentrated under reduced pressure and the residue was purified with reverse-phase prep-HPLC to afford 330 (30 mg, 47%). MS-ESI: [M+H]$^+$ 602.5. $^1$H NMR (500 MHz, CDCl$_3$) δ 8.56 (d, J=5.0 Hz, 1H), 8.00 (s, 1H), 7.90 (s, 1H), 7.43 (d, J=5.0 Hz, 1H), 5.94 (s, 1H), 4.82 (s, 2H), 4.60-4.58 (m, 2H), 4.38-4.36 (m, 2H), 3.89 (s, 3H), 3.89-3.87 (m, 3H), 3.02-2.93 (m, 2H), 2.79-2.75 (m, 2H), 2.59-2.54 (m, 2H), 1.37 (s, 6H), 1.28 (s, 6H).

Example 331a

5-Bromo-1-methyl-3-(3-methylisothiazol-5-ylamino)pyrazin-2(1H)-one 331a

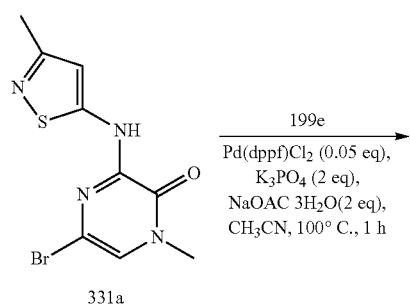

A sealed tube equipped with a magnetic stirrer was charged with 3-methylisothiazol-5-amine (170 mg, 1.5 mmol), 3,5-dibromo-1-methylpyrazin-2(1H)-one (400 mg, 1.5 mmol), Pd(OAc)$_2$ (84 mg, 0.375 mmol), BINAP (116 mg, 0.188 mmol), K$_2$CO$_3$ (450 mg, 4.5 mmol), and 1,4-dioxane (4 mL). After three cycles of vacuum/nitrogen flush, the mixture was heated at 120° C. in a sealed tube for 18 h. It was then cooled to room temperature and filtered. The filtrate was evaporated under reduced pressure. The residue was purified by silica-gel column chromatography eluting with dichloromethane/methanol (100:1 to 25:1) to afford 331a (220 mg, 50%) as a yellow solid. MS-ESI: [M+H]$^+$ 301.0.

Example 331b (2-{4,4-Dimethyl-9-oxo-1,10-diazatricyclo[6.4.0.0²,⁶]dodeca-2(6),7-dien-10-yl}-4-{4-methyl-6-[(3-methyl-1,2-thiazol-5-yl)amino]-5-oxo-4,5-dihydropyrazin-2-yl}pyridin-3-yl)methyl Acetate 331b

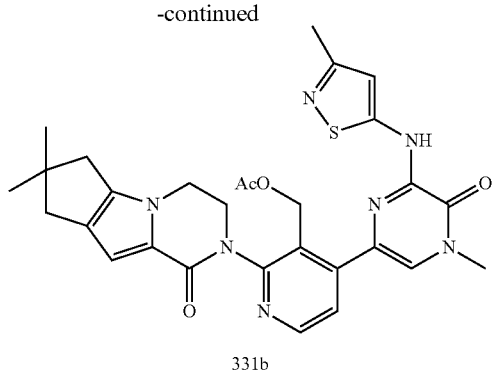

A 50-mL round-bottomed flask equipped with a reflux condenser was charged with 331a (150 mg, 0.50 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (400 mg, 1.0 mmol), Pd(dppf)Cl$_2$ (25 mg, 0.025 mmol), K$_3$PO$_4$ (220 mg, 1.0 mmol), sodium acetate trihydrate (136 mg, 1.0 mmol), acetonitrile (10 mL), and water (0.5 mL). The system was evacuated and refilled with N$_2$. The reaction mixture was heated at 100° C. for 1 h. It was then cooled to room temperature and filtered. The filtrate was concentrated under reduced pressure and the resulting residue was purified by silica-gel column chromatography eluting with dichloromethane/methanol (100/1 to 25/1) to afford 331b (200 mg, 70%) as a yellow solid. MS-ESI: [M+H]$^+$ 574.2.

Example 331

3-[3-(hydroxymethyl)-4-[4-methyl-6-[(3-methylisothiazol-5-yl)amino]-5-oxo-pyrazin-2-yl]-2-pyridyl]-7,7-dimethyl-1,2,6,8-tetrahydrocyclopenta[3,4]pyrrolo[3,5-b]pyrazin-4-one 331

A mixture of 331b (120 mg, 0.21 mmol) and lithium hydroxide monohydrate (88 mg, 2.1 mmol) in THF/i-propanol (4:2, 6 mL) and water (2 mL) was stirred at 30° C. for 1 h. The mixture was evaporated under reduced pressure and diluted with water (10 mL). It was then extracted with ethyl acetate (2×15 mL). The combined ethyl acetate extract was concentrated under reduced pressure and the residue was purified by reverse-phase prep-HPLC to afford 331 (50 mg, 45%) as a white solid. MS-ESI: [M+H]+ 532.2. ¹H NMR (500 MHz, CHCL₃) δ 9.13 (s, 1H), 8.61 (d, J=5 Hz, 1H), 8.37 (s, 1H), 7.99 (d, J=5.0 Hz, 1H), 6.87 (s, 1H), 6.74 (s, 1H), 5.32-5.39 (m, 1H), 4.77-4.75 (m, 1H), 4.58-4.56 (m, 1H), 4.32-4.37 (m, 1H), 4.21-4.18 (m, 2H), 3.96-3.94 (m, 1H), 3.72 (s, 3H), 2.61-2.58 (m, 2H), 2.54 (s, 2H), 2.48 (s, 3H), 1.30 (s, 6H).

Example 332a

5-Bromo-3-(5-ethyl-1,3,4-thiadiazol-2-ylamino)-1-methylpyridin-2(1H)-one 332a

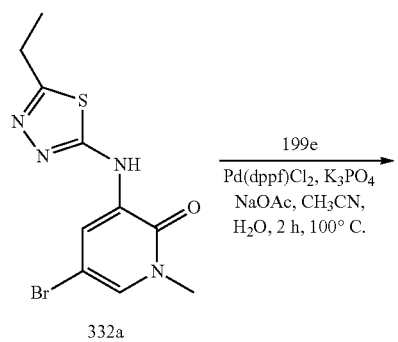

A 100-mL single-neck round-bottomed flask equipped with a magnetic stirrer and a reflux condenser was charged with 5-ethyl-1,3,4-thiadiazol-2-amine (500 mg, 3.88 mmol), 3,5-dibromo-1-methylpyridin-2(1H)-one (1.55 g, 5.81 mmol), Pd₂(dba)₃ (357 mg, 0.39 mmol), XantPhos (451 mg, 0.78 mmol), Cs₂CO₃ (2.5 g, 7.67 mmol), and 1,4-dioxane (40 mL). The system was subjected to three cycles of vacuum/nitrogen flush and heated at 100° C. for 2 h. The mixture was cooled to 90° C. and filtered. The filtrate was cooled in an ice-water bath and then filtered again to afford 332a (574 mg, 47%) as a white solid. MS-ESI: [M+H]+ 315.1

Example 332b (2-{4,4-Dimethyl-9-oxo-1,10-diazatricyclo[6.4.0.0²,⁶]dodeca-2(6),7-dien-10-yl}-4-{5-[(5-ethyl-1,3,4-thiadiazol-2-yl)amino]-1-methyl-6-oxo-1,6-dihydropyridin-3-yl}pyridin-3-yl)methyl Acetate 332b A 100-mL round-bottomed flask equipped with a reflux condenser was charged with 332a (200 mg, 0.63 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (754 mg, 1.89 mmol), PdCl₂(dppf) (51 mg, 0.063 mmol), K₃PO₄ (267 mg, 1.26 mmol), CH₃COONa (103 mg, 1.26 mmol), acetonitrile (15 mL), and water (0.5 mL). After bubbling nitrogen through the resulting mixture for 20 minutes, it was heated at 100° C. under a nitrogen atmosphere for 2 h. The resulting mixture was cooled to room temperature and filtered. The filtrate was evaporated under reduced pressure and the residue was purified by silica-gel column chromatography eluting with 50:1 dichloromethane/methanol to afford 332b as a brown solid (178 mg, 48%). MS-ESI: [M+H]+ 588.2

Example 332

3-[4-[5-[(5-ethyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 332

A mixture of 332b (158 mg, 0.27 mmol) and lithium hydroxide (19 mg, 0.81 mmol) in i-propanol/THF/water (9 mL/6 mL/6 mL) was stirred at room temperature for 0.5 h. The mixture was evaporated under reduced pressure and the residue was extracted with dichloromethane (3×20 mL). The combined dichloromethane extract was concentrated under reduced pressure and the residue was purified by reverse-phase prep-HPLC to afford 332 as a white solid (80 mg, 54%). MS-ESI: [M+H]+ 546.2. ¹H NMR (500 MHz, DMSO-d₆) δ 10.20 (s, 1H), 8.60 (d, J=2.0 Hz, 1H), 8.49 (d, J=5.0 Hz, 1H), 7.63 (d, J=2.5 Hz, 1H), 7.33 (d, J=5.0 Hz, 1H), 6.57 (s, 1H), 4.92 (t, J=4.5 Hz, 1H), 4.49-4.39 (m, 2H), 4.25-4.19 (m, 3H), 3.87-3.85 (m, 1H), 3.61 (s, 3H), 2.92-2.88 (m, 2H), 2.58-2.53 (m, 2H), 2.43 (s, 2H), 1.27-1.22 (m, overlap, 9H).

Example 333a (2-{4,4-Dimethyl-9-oxo-7-thia-10-azatricyclo[6.4.0.0²,⁶]dodeca-1(8),2(6)-dien-10-yl}-4-{1-methyl-5-[(1-methyl-1H-1,2,3-triazol-4-yl)amino]-6-oxo-1,6-dihydropyridin-3-yl}pyridin-3-yl)methyl Acetate 333a

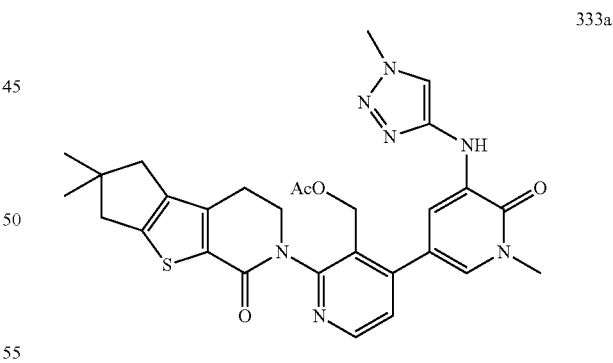

A 50-mL round-bottomed flask equipped with a magnetic stirrer and a reflux condenser was charged with (2-{4,4-dimethyl-9-oxo-7-thia-10-azatricyclo[6.4.0.0²,⁶]dodeca-1(8),2(6)-dien-10-yl}-4-(4,4,5,5-tetramethyl-1,3,2-dioxaborolan-2-yl)pyridin-3-yl)methyl acetate 330c (180 mg, 0.37 mmol), 5-bromo-1-methyl-3-(1-methyl-1H-1,2,3-triazol-4-ylamino)pyridin-2(1H)-one 292c (125 mg, 0.43 mmol), Pd(dppf)Cl₂ (20 mg, 0.025 mmol), potassium acetate (80 mg, 0.80 mmol), K₃PO₄ (165 mg, 0.80 mmol), and acetonitrile/water (10 mL/1 mL). After three cycles of vacuum/nitrogen flush, the mixture was heated at 100° C. for 1 h. It was then filtered and the filtrate was evaporated under reduced pres-

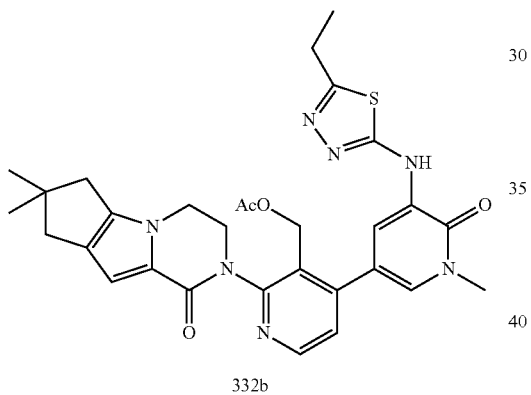

sure. The residue was purified by silica-gel column chromatography eluting with 20:1 dichloromethane/methanol to afford 333a (150 mg, 71%) as a brown solid. MS-ESI: [M+H]+ 574.1

Example 333

3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]thieno[1,3-c]pyridin-4-one 333

A mixture of 333a (150 mg, 0.26 mmol) and lithium hydroxide hydrate (84 mg, 2.0 mmol) in THF (5 mL), i-propanol (5 mL) and water (1.5 mL) was stirred at 40° C. for 0.5 h. The mixture was evaporated under reduced pressure and diluted with water (10 mL). It was then extracted with dichloromethane (2×10 mL). The combined organic layer was concentrated under reduced pressure and the residue was purified by reverse-phase prep-HPLC to afford 333 (52 mg, 38%) as a pale yellow solid. MS-ESI: [M+H]+ 532.3. $^1$H NMR (500 MHz, DMSO-d$_6$) δ 8.48-8.47 (m, 1H), 8.28 (s, 1H), 7.78-7.77 (m, 2H), 7.42 (d, J=2.5 Hz, 1H), 7.34-7.33 (m, 1H), 4.97-4.95 (t, J=5.0 Hz, 1H), 4.43-4.41 (m, 2H), 4.17-4.16 (m, 1H), 3.99 (s, 3H), 3.94-3.92 (m, 1H), 3.59 (s, 3H), 3.04-3.02 (m, 1H), 2.90-2.89 (m, 1H), 2.77-2.75 (m, 2H), 2.56-2.54 (m, 2H), 1.23 (s, 3H), 1.22 (s, 3H).

Example 334

3-[4-[5-[(5-cyclopropyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 334

Following the procedures of Example 273, and substituting 5-cyclopropyl-1,3,4-thiadiazol-2-amine for 2-amino pyridine gave 334 (8.7 mg, 22% yield). $^1$H NMR (400 MHz, DMSO-d6) δ 8.48 (d, J=5.1 Hz, 1H), 8.20 (s, 1H), 8.10 (d, J=2.4 Hz, 1H), 7.53 (d, J=2.4 Hz, 1H), 7.44 (d, J=5.1 Hz, 1H), 6.53 (s, 1H), 4.95 (t, J=5.2 Hz, 1H), 4.55-4.49 (m, 1H), 4.27-4.23 (m, 3H), 3.78 (s, 2H), 3.51 (s, 3H), 3.48 (dt, J=12.3, 5.2 Hz, 3H), 3.24 (s, 2H), 2.50 (d, J=7.2 Hz, 2H), 2.33 (s, 2H), 1.85-1.82 (m, 3H), 1.23 (s, 6H). ES-MS m/z 531.3 [M+1].

Example 335a

5-Bromo-3-(6,6-dimethyl-6,7-dihydro-4H-pyrazolo[5,1-c][1,4]oxazin-2-ylamino)-1-methylpyridin-2(1H)-one 335a

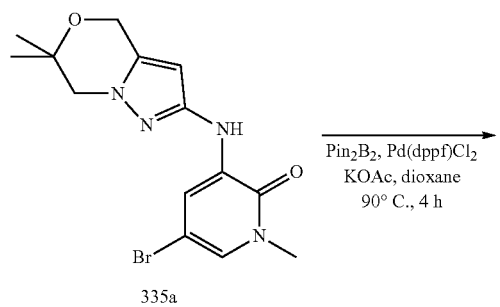

A 100-mL round-bottomed flask equipped with a reflux condenser was charged with 1,4-dioxane (10 mL), 6,6-dimethyl-6,7-dihydro-4H-pyrazolo[5,1-c][1,4]oxazin-2-amine 330g (167 mg, 1.0 mmol), 3,5-dibromo-1-methylpyridin-2 (1H)-one (320 mg, 1.2 mmol), Pd$_2$(dba)$_3$ (91 mg, 0.10 mmol), XantPhos (116 mg, 0.20 mmol), and cesium carbonate (652 mg, 2.0 mmol). After three cycles of vacuum/argon flush, the mixture was heated at 100° C. for 3 h. It was then filtered and the filtrate was evaporated under reduced pressure. The residue was purified by silica-gel column chromatography eluting with 100:1 dichloromethane/methanol to afford 335a (210 mg, 60%) as a yellow solid. MS-ESI: [M+H]+ 352.9

Example 335b 3-(6,6-Dimethyl-6,7-dihydro-4H-pyrazolo[5,1-c][1,4]oxazin-2-ylamino)-1-methyl-5-(4,4,5,5-tetramethyl-1,3,2-dioxaborolan-2-yl)pyridin-2(1H)-one 335b To a mixture of 335a (160 mg, 0.45 mmol) and 4,4,4',4',5,5,5',5'-octamethyl-2,2'-bi(1,3,2-dioxaborolane) (572 g, 2.25 mmol) in dioxane (20 mL) was added PdCl$_2$(dppf) (36.8 mg, 0.045 mmol) and potassium acetate (88.2 mg, 0.90 mmol). After three cycles of vacuum/nitrogen flush, the mixture was stirred at 90° C. for 4 h under nitrogen atmosphere. It was then filtered and the filtrate was evaporated under reduced pressure to afford 335b, which was used in the next step without further purification. MS-ESI: [M+H]+ 401.3.

Example 335c

4-[5-({6,6-Dimethyl-4H,6H,7H-pyrazolo[3,2-c][1,4]oxazin-2-yl}amino)-1-methyl-6-oxo-1,6-dihydropyridin-3-yl]-2-{4,4-dimethyl-9-oxo-7-thia-10,11-diazatricyclo[6.4.0.0$^{2,6}$]dodeca-1(8),2(6),11-trien-10-yl}pyridine-3-carb aldehyde 335c A 50-mL single-neck round-bottomed flask equipped with a magnetic stirrer and a reflux condenser was charged with

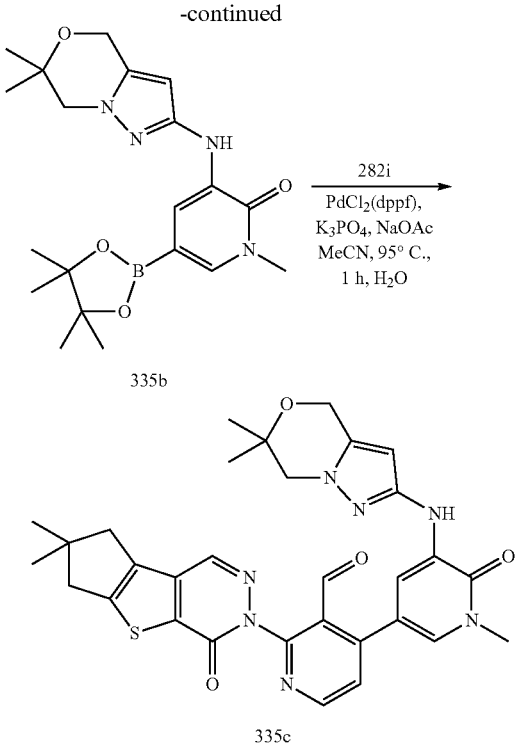

335b (240 mg, 0.60 mmol), 4-chloro-2-{4,4-dimethyl-9-oxo-7-thia-10,11-diazatricyclo[6.4.0.0²,⁶]dodeca-1(8),2(6),11-trien-10-yl}pyridine-3-carbaldehyde 282i (107.7 mg, 0.30 mmol), Pd(dppf)Cl$_2$ (24.5 mg, 0.030 mmol), K$_3$PO$_4$ (127.2 mg, 0.60 mmol), sodium acetate (49.2 mg, 0.60 mmol), water (0.5 mL), and acetonitrile (10 mL). After three cycles of vacuum/nitrogen flush, the mixture was heated at 95° C. for 1 h. It was then cooled to room temperature and filtered. The filtrate was concentrated under reduced pressure and the resulting residue was purified by silica-gel column chromatography eluting with 30:1 dichloromethane/methanol to afford 335c as a brown solid (60 mg, 22%, two steps). MS-ESI: [M+H]⁺ 598.2.

Example 335

3-[4-[5-[(6,6-dimethyl-4,7-dihydropyrazolo[5,1-c][1,4]oxazin-2-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one 335

A mixture of 335c (50 mg, 0.080 mmol) and NaBH$_4$ (9.1 mg, 0.24 mmol) in methanol (5 mL) was stirred at room temperature for 10 min. The mixture was quenched with water (10 mL) and evaporated under reduced pressure. The residue was extracted with dichloromethane (3×10 mL). The combined extract was concentrated under reduced pressure and the residue was purified by reverse-phase prep-HPLC to afford 335 (15 mg, 30%) as a yellow solid. MS-ESI: [M+H]⁺ 600.2. ¹H NMR (500 MHz, DMSO-d$_6$) δ 8.56 (d, J=5.0 Hz, 1H), 8.46 (s, 1H), 8.31 (s, 1H), 8.07 (d, J=2.0 Hz, 1H), 7.52 (d, J=5.0 Hz, 1H), 7.40 (d, J=2.5 Hz, 1H), 5.94 (s, 1H), 4.85-4.83 (m, 1H), 4.72 (s, 2H), 4.38-4.37 (m, 2H), 3.79-3.78 (m, 2H), 3.3 (s, 3H), 2.92-2.91 (m, 2H), 2.81 (s, 2H), 1.28 (s, 6H), 1.25 (s, 6H).

Example 336a 5-(Methoxymethyl)-1-methyl-3-nitro-1H-pyrazole 336a

A 250-mL single-neck round-bottomed flask equipped with a magnetic stirrer and a reflux condenser was charged with 5-(bromomethyl)-1-methyl-3-nitro-1H-pyrazole (8.8 g, 40 mmol), sodium methoxide (4.3 g, 80 mmol), and methanol (50 mL). The reaction mixture was heated at reflux for 2 h. After this time the reaction was cooled to room temperature and concentrated under reduced pressure. The residue was partitioned between ethyl acetate (60 mL) and water (60 mL). The aqueous layer was separated and extracted with ethyl acetate (2×50 mL). The combined organic layer was washed with brine (50 mL) and dried over sodium sulfate. The drying agent was removed by filtration and the filtrate was concentrated under reduced pressure to afford 336a as a yellow oil (6.1 g, 90%). MS-ESI: [M+H]⁺ 172.

Example 336b 5-(Methoxymethyl)-1-methyl-1H-pyrazol-3-amine 336b

A 250-mL single-neck round-bottomed flask equipped with a magnetic stirrer was charged with 336a (4.0 g, 23 mmol), Pd/C (1.0 g), and ethanol (100 mL). The mixture was hydrogenated at room temperature for 15 h. It was then filtered and the filtrate was concentrated under reduced pressure to afford 336b as a yellow oil (3.3 g, 99%), which was used in the next step without further purification. MS-ESI: [M+H]⁺ 142.

Example 336c

5-Bromo-3-(5-(methoxymethyl)-1-methyl-1H-pyrazol-3-ylamino)-1-methylpyridin-2(1H)-one 336c

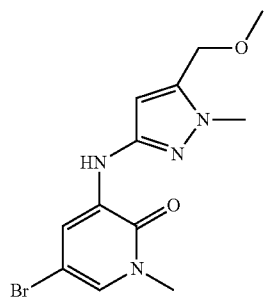 [SMILES: COCc1cc(Nc2cc(Br)cn(C)c2=O)nn1C]

Following the procedure in Example 335a, and starting with 335b (1.7 g, 12 mmol) and 3,5-dibromo-1-methylpyridin-2(1H)-one (3.2 g, 12 mmol) afforded 336c as a yellow solid (2.8 g, 71%). MS-ESI: [M+H]⁺ 327. ¹H NMR (500 MHz, CDCl$_3$) δ 7.86 (d, J=2.5 Hz, 1H), 7.38 (s, 1H), 6.88 (d, J=2.5 Hz, 1H), 5.86 (s, 1H), 4.41 (s, 2H), 3.82 (s, 3H), 3.58 (s, 3H), 3.36 (s, 3H).

Example 336d 3-(5-(Methoxymethyl)-1-methyl-1H-pyrazol-3-ylamino)-1-methyl-5-(4,4,5,5-tetramethyl-1,3,2-dioxaborolan-2-yl)pyridin-2(1H)-one 336d A 100-mL single-neck round-bottomed flask equipped with a magnetic stirrer and a reflux condenser was charged with 336c (600 mg, 1.83 mmol), 4,4,4',4',5,5,5',5'-octamethyl-2,2'-bi(1,3,2-dioxaborolane) (1.39 g, 5.49 mmol), Pd$_2$(dba)$_3$ (183 mg, 0.20 mmol), X-phos (190 mg, 0.40 mmol), potassium acetate (392 mg, 4.0 mmol), and 1,4-dioxane (30 mL). After three cycles of vacuum/nitrogen flush, the mixture was heated at 85° C. for 3 h. It was then cooled to room temperature and filtered. The filtrate was concentrated under reduced pressure to afford crude 336d as a black oil (400 mg, 75%), which was used in the next step without purification. MS-ESI: [M+H]⁺ 293.1

Example 336e 4-(5-(5-(Methoxymethyl)-1-methyl-1H-pyrazol-3-ylamino)-1-methyl-6-oxo-1,6-dihydropyridin-3-yl)-2-(1-oxo-3,4,6,7,8,9-hexahydropyrido[3,4-b]indolizin-2(1H)-yl)nicotinaldehyde 336e

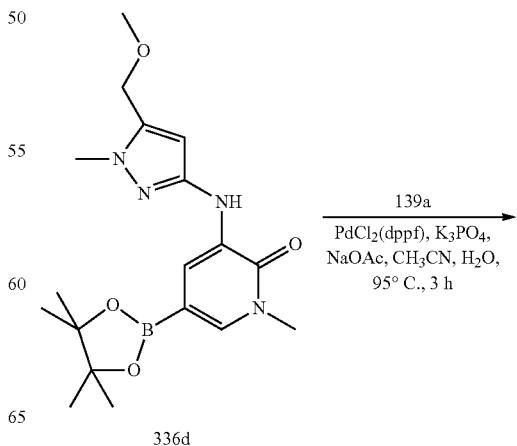

Example 336

2-[3-(hydroxymethyl)-4-[5-[[5-(methoxymethyl)-1-methyl-pyrazol-3-yl]amino]-1-methyl-6-oxo-3-pyridyl]-2-pyridyl]-3,4,6,7,8,9-hexahydropyrido[3,4-b]indolizin-1-one 336

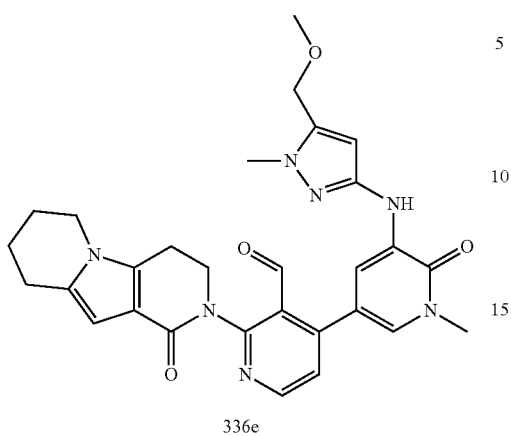

336e

A 50-mL round-bottomed flask equipped with a reflux condenser was charged with 336d (368 mg, 0.98 mmol), 4-chloro-2-(1-oxo-3,4,6,7,8,9-hexahydropyrido[3,4-b]indolizin-2(1H)-yl)nicotinaldehyde 139a (270 mg, 0.82 mmol), PdCl₂(dppf) (60 mg, 0.082 mmol), K₃PO₄ (348 mg, 1.64 mmol)), sodium acetate (135 mg, 1.65 mmol), acetonitrile (15 mL), and water (0.5 mL). The system was subjected to three cycles of vacuum/nitrogen flush and heated at 95° C. for 3 h. It was then cooled to room temperature and filtered. The filtrate was concentrated under reduced pressure and the residue was purified by silica-gel column chromatography eluting with 20:1 ethyl acetate/methanol to afford 336e (100 mg, 22%). MS-ESI: [M+H]⁺ 542.2

To a solution of 336e (100 mg, 0.18 mmol) in methanol (10 mL) was added NaBH₄ (41 mg, 1.08 mmol). The mixture was stirred at room temperature for 1 h and LCMS showed the starting material had disappeared. The reaction was quenched with 1.0 M HCl solution (10 mL) and evaporated under reduced pressure until most of methanol was distilled. The residue was extracted with dichloromethane (3×15 mL). The combined organic layer was dried with Na₂SO₄ and evaporated under reduced pressure. The residue was purified by reverse-phase prep-HPLC to afford 336 as a white solid (41 mg, 41%). MS-ESI: [M+H]⁺ 544.2. ¹H NMR (500 MHz, CDCl₃) δ 8.49 (d, J=5.0 Hz, 1H), 7.96 (d, J=2.5 Hz, 1H), 7.73 (d, J=2.5 Hz, 1H), 7.41 (s, 1H), 7.33 (d, J=5.0 Hz, 1H), 6.33 (s, 1H), 5.95 (s, 1H), 4.99-4.96 (m, 1H), 4.67-4.64 (m, 1H), 4.42-4.41 (m, 3H), 4.36-4.26 (m, 1H), 3.98-3.91 (m, 1H), 3.88-3.82 (m, 2H), 3.79 (s, 3H), 3.71 (s, 3H), 3.37 (s, 3H), 3.06-2.91 (m, 2H), 2.87-2.79 (m, 2H), 2.08-2.01 (m, 2H), 1.91-1.86 (m, 2H).

Example 337a 1,2-Dimethyl-4-nitro-1H-imidazole 337a

To a mixture of 2-methyl-4-nitro-1H-imidazole (10.0 g, 78.7 mmol) and K₂CO₃ (21.7 g, 160 mmol) in DMF (80 mL) was added CH₃I (13.4 g, 94 mmol) dropwise while stirring at room temperature. The mixture was stirred for 2 h. Water (200 mL) was then added to the mixture. The resulting suspension was filtered, washed with water, and dried in vacuo to afford 337a as a white solid (5.0 g, 45%). MS-ESI: [M+H]⁺ 142.1.

Example 337b tert-Butyl 1,2-Dimethyl-1H-imidazol-4-ylcarbamate 337b

A 100-mL single-neck round-bottomed flask was purged with nitrogen and charged with 337a (2.0 g, 14.1 mmol), 10% palladium on carbon (50% wet, 400 mg), (Boc)₂O (9.22 g, 43.3 mmol), triethylamine (2.85 g, 28.2 mmol), and ethanol (20 mL). The mixture was evacuated, charged with hydrogen gas, and stirred at room temperature for 5 h. The hydrogen was then evacuated and nitrogen was charged into the flask. The catalyst was removed by filtration through a pad of CELITE® and the filtrate was concentrated under reduced pressure. The residue was purified by silica-gel column chromatography eluting with 40:1 dichloromethane/methanol to afford 337b (1.2 g, 40%) as a brown solid. MS-ESI: [M+H]$^+$ 212.1

Example 337c 1,2-Dimethyl-1H-imidazol-4-amine Hydrochloride 337c

To a solution of 337b (1.2 g, 5.68 mmol) in dichloromethane (5.0 mL) was added 3M HCl in dioxane (5.0 mL). This mixture was stirred at room temperature for 4 h and concentrated under reduced pressure. The crude product was washed by ethyl acetate to afford 337c (450 mg, 55%) as a pale yellow solid, which was used in the next step without further purification. MS-ESI: [M+H]$^+$ 112.2

Example 337d

5-Bromo-3-(1,2-dimethyl-1H-imidazol-4-ylamino)-1-methylpyridin-2(1H)-one 337d

A 100-mL single-neck round-bottomed flask equipped with a magnetic stirrer and a reflux condenser was charged with 337c (400 mg, 3.60 mmol), 3,5-dibromo-1-methylpyridin-2(1H)-one (960 mg, 3.60 mmol), XantPhos (240 mg, 0.40 mmol), tris(dibenzylideneacetone)dipalladium(0) (360 mg, 0.40 mmol), Cs$_2$CO$_3$ (4.69 g, 14.4 mmol), and 1,4-dioxane (20 mL). After three cycles of vacuum/nitrogen flush, the mixture was heated at 90° C. for 2.5 h. It was then cooled to room temperature and filtered. The filtrate was concentrated under reduced pressure and the resulting residue was purified by silica-gel column chromatography eluting with dichloromethane/methanol (30:1 to 20:1) to afford 337d as a pale yellow solid (350 mg, 33%). MS-ESI: [M+H]$^+$ 297.1.

Example 337e (4-{5-[(1,2-Dimethyl-1H-imidazol-4-yl)amino]-1-methyl-6-oxo-1,6-dihydropyridin-3-yl}-2-{4,4-dimethyl-9-oxo-1,10-diazatricyclo[6.4.0.0,2,6]-dodeca-2(6),7-dien-10-yl}pyridin-3-yl)methyl Acetate 337e A 50-mL single-neck round-bottomed flask equipped with a magnetic stirrer and a reflux condenser was charged with 337d (20 mg, 0.67 mmol), {3-[(acetoxy)methyl]-2-{4,4-dimethyl-9-oxo-1,10-diazatricyclo[6.4.0.0$^{2,6}$]dodeca-2(6),7-dien-10-yl}pyridin-4-yl}boronic acid 199e (270 mg, 0.67 mmol), Pd(dppf)Cl$_2$ (42 mg, 0.050 mmol), sodium acetate (82 mg, 1.0 mmol), K$_3$PO$_4$ trihydrate (266 mg, 1.0 mmol), water (6 drops), and acetonitrile (6 mL). After three cycles of vacuum/nitrogen flush, the mixture was heated at 95° C. for 2 h. It was then filtered and the filtrate was evaporated under reduced pressure. The residue was purified by silica-gel column chromatography eluting with 25:1 dichloromethane/methanol to afford 337e (200 mg, 50%) as a brown solid. LCMS-ESI: [M+H]$^+$ 570.3

Example 337

3-[4-[5-[(1,2-dimethylimidazol-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one 337

A mixture of 337e (100 mg, 0.19 mmol) and lithium hydroxide (34 mg, 1.4 mmol) in i-propanol/THF (1:1, 4 mL) and water (1 mL) was stirred at 40° C. for 0.5 h. The mixture was evaporated under reduced pressure and the residue was diluted with water (10 mL). It was then extracted with ethyl acetate (2×10 mL). The combined ethyl acetate extract was concentrated under reduced pressure and the residue was purified by reverse-phase prep-HPLC to afford 337 (35 mg, 40%) as a white solid. LCMS-ESI: [M+H]$^+$ 528.3. $^1$H NMR (500 MHz, CDCl$_3$) δ 8.45 (d, J=5.0 Hz, 1H), 7.36 (s, 1H), 7.28-7.27 (m, 2H), 7.25 (d, J=5.0 Hz, 1H), 6.84 (s, 1H), 6.79 (s, 1H), 4.62-4.40 (m, 3H), 4.15-4.14 (m, 2H), 3.84-3.81 (m, 1H), 3.67 (s, 3H), 3.52 (s, 3H), 2.57-2.56 (m, 2H), 2.51 (s, 2H), 2.32 (s, 3H), 1.27 (s, 6H).

Example 338a 3-(2-Nitro-6,7-dihydropyrazolo[1,5-a]pyrazin-5(4H)-yl)propanenitrile 338a

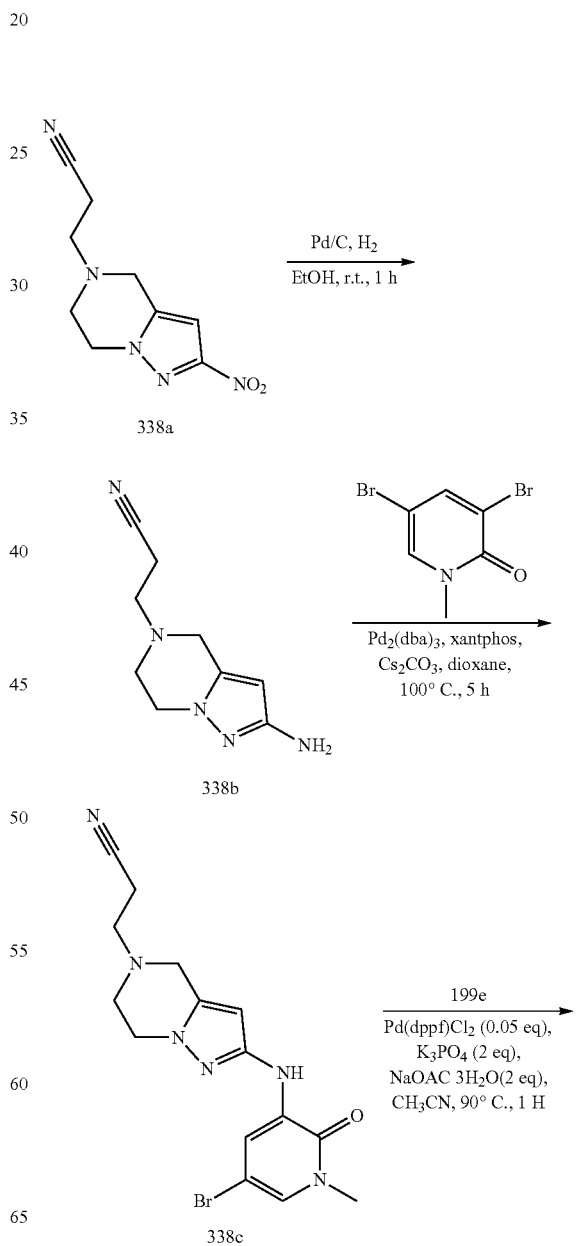

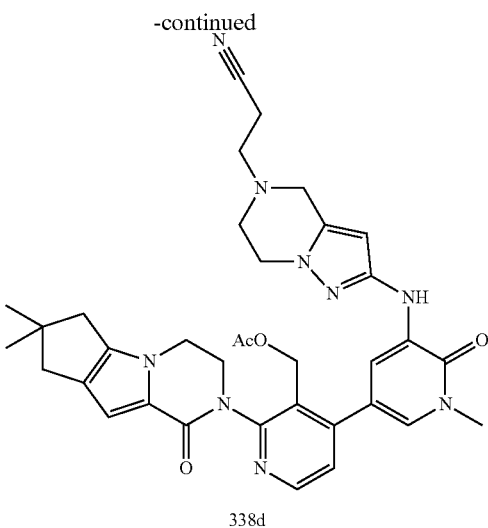

338d

Following the procedure of Example 296d, and starting with 1-(2-bromoethyl)-5-(chloromethyl)-3-nitro-1H-pyrazole 296d (268 mg, 1.00 mmol) and 3-aminopropanenitrile (210 mg, 3.00 mmol) afforded 338a as a white solid (180 mg, 81%). MS-ESI: [M+H]$^+$ 222.1

Example 338b 3-(2-Amino-6,7-dihydropyrazolo[1,5-a]pyrazin-5 (4H)-yl)propanenitrile 338b Following the procedure of Example 296e, and starting with 338a (180 mg, 0.81 mmol) afforded 338b as a yellow solid (120 mg, 77%). MS-ESI: [M+H]$^+$ 192.2

Example 338c 3-(2-(5-Bromo-1-methyl-2-oxo-1,2-dihydropyridin-3-ylamino)-6,7-dihydropyrazolo[1,5-a]pyrazin-5 (4H)-yl)propanenitrile 338c Following the procedure of Example 309c, and starting with 338b (120 mg, 0.63 mmol) and 3,5-dibromo-1-methylpyridin-2(1H)-one (169 mg, 0.63 mmol) afforded 338c as a yellow solid (150 mg, 63%). MS-ESI: [M+H]$^+$ 377.2

Example 338d

[4-(5-{[5-(2-Cyanoethyl)-4H,5H,6H,7H-pyrazolo[1,5-a]pyrazin-2-yl]amino}-1-methyl-6-oxo-1,6-dihydropyridin-3-yl)-2-{4,4-dimethyl-9-oxo-1,10-diazatricyclo[6.4.0.0$^{2,6}$]dodeca-2(6),7-dien-10-yl}pyridin-3-yl]methyl Acetate 338d Following the procedure of Example 309d, and starting with 338c (150 mg, 0.45 mmol) and {3-[(acetoxy)methyl]-2-{4,4-dimethyl-9-oxo-1,10-diazatricyclo[6.4.0.0$^{2,6}$]dodeca-2 (6),7-dien-10-yl}pyridin-4-yl}boronic acid 199e (358 mg, 0.90 mmol) afforded 338d as a yellow solid (150 mg, 52%). MS-ESI: [M+H]$^+$ 650.3

Example 338

3-[2-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]-6,7-dihydro-4H-pyrazolo[1,5-a]pyrazin-5-yl]propanenitrile 338

Following the procedure of Example 309, and starting with 338e (150 mg, 0.23 mmol) afforded 338 as a white solid (55 mg, 40%). MS-ESI: [M+H]$^+$ 608.3. $^1$H NMR (500 MHz, CDCl$_3$) δ 8.49 (d, J=5.0 Hz, 1H), 7.96 (d, J=2.5 Hz, 1H), 7.71 (d, J=2.0 Hz, 1H), 7.42 (s, 1H), 7.35 (d, J=5.0 Hz, 1H), 6.85 (s, 1H), 5.74 (s, 1H), 5.05 (t, J=6.5 Hz, 1H), 4.66-4.64 (m, 1H), 4.52-4.50 (m, 1H), 4.36-4.34 (m, 1H), 4.17-4.16 (m, 2H), 4.09-4.07 (m, 2H), 3.88-3.84 (m, 1H), 3.75 (s, 2H), 3.71 (s, 3H), 3.05-3.03 (m, 2H), 2.93-2.90 (m, 2H), 2.63-2.58 (m, 4H), 2.53 (s, 2H), 1.29 (s, 6H).

Example 339a tert-Butyl 4-(6-Nitropyridin-3-yl)piperazine-1-carboxylate 339a

To a solution of 5-bromo-2-nitropyridin (30.0 g, 148 mmol) in DMSO (1 L) were added K$_2$CO$_3$ (40.0 g, 296 mmol) and tert-butyl piperazine-1-carboxylate (28.0 g, 148 mmol). The mixture was stirred at 65° C. overnight. After cooling down, it was poured into water (2 L). The solid precipitated was collected and dried in vacuo. It was then further purified by silica-gel column chromatography eluting with 20:1 petroleum ether/ethyl acetate and then with dichloromethane to afford 339a as a yellow solid (17.0 g, 37%). MS-ESI: [M+H]$^+$ 309.

Example 339b tert-Butyl 4-(6-Aminopyridin-3-yl)piperazine-1-carboxylate 339b

A 500-mL round-bottomed flask was purged with nitrogen and charged with 339a (3.1 g, 10 mmol), 10% palladium on carbon (50% wet, 1.0 g), and ethanol (100 mL). It was evacuated, charged with hydrogen gas via a balloon, and stirred at room temperature for 16 h. The hydrogen was then evacuated and nitrogen was charged into the flask. The catalyst was removed by filtration through a pad of CELITE® and the filtrate was concentrated under reduced pressure to afford 339b (2.7 g, 97%). MS-ESI: [M+H]$^+$ 279

Example 339c tert-Butyl 4-(6-(5-Bromo-1-methyl-2-oxo-1,2-dihydropyridin-3-ylamino)pyridine-3-yl)piperazine-1-carboxylate 339c A 100-mL single-neck round-bottomed flask equipped with a magnetic stirrer and a reflux condenser was charged with 339b (1.3 g, 4.7 mmol), 3,5-dibromo-1-methylpyridin-2(1H)-one (1.24 g, 4.7 mmol), cesium carbonate (3.8 g, 12 mmol), and 1,4-dioxane (50 mL). After bubbling nitrogen through the resulting mixture for 30 minutes, XantPhos (272 mg, 0.47 mmol) and tris(dibenzylideneacetone)dipalladium (0) (430 mg, 0.47 mmol) were added. The system was subjected to three cycles of argon/vacuum flush and heated at reflux for 3 h. After this time the reaction was cooled to room temperature and filtered. The filtrate was partitioned between ethyl acetate (100 mL) and water (100 mL). The aqueous layer was separated and extracted with ethyl acetate (2×50 mL). The combined organic layer was washed with brine (50 mL) and dried over sodium sulfate. The drying agent was removed by filtration and the filtrate was concentrated under reduced pressure. The residue was purified by silica-gel column chromatography eluting with 50:1 dichloromethane/methanol to afford 339c (1.3 g, 59%). MS-ESI: [M+H]$^+$ 464.

Example 339d tert-Butyl 4-{6-[(5-{3-[(Acetoxy)methyl]-2-{4,4-dimethyl-9-oxo-1,10-diazatricyclo[6.4.0.0$^{2,6}$]dodeca-2(6),7-dien-10-yl}pyridin-4-yl}-1-methyl-2-oxo-1,2-dihydropyridin-3-yl)amino]pyridin-3-yl}piperazine-1-carboxylate 339d

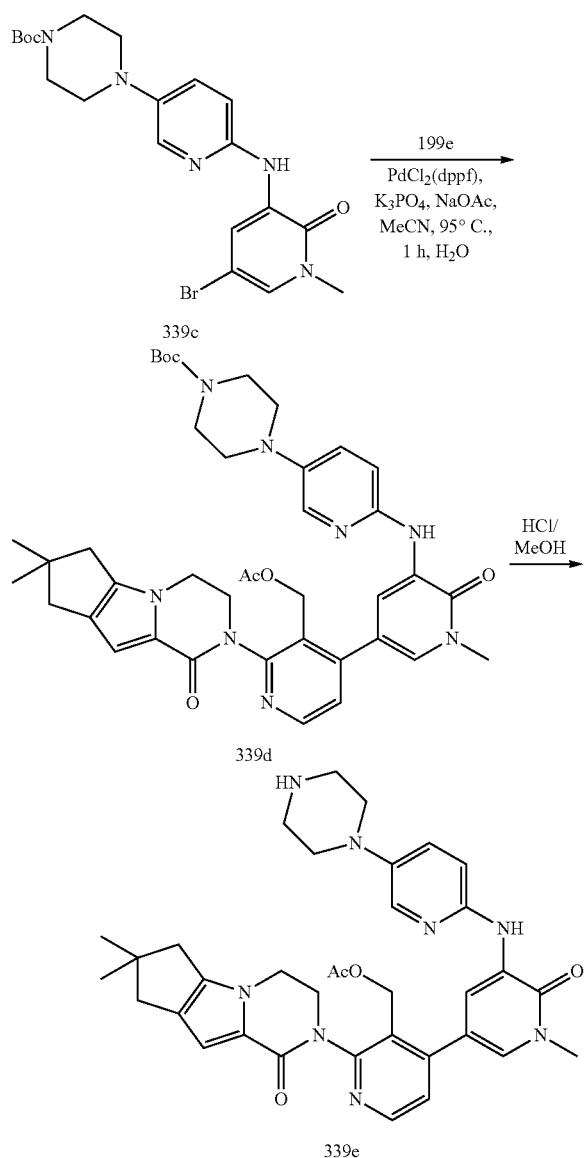

A 50-mL single-neck round-bottomed flask equipped with a magnetic stirrer and a reflux condenser was charged with (2-{4,4-dimethyl-9-oxo-1,10-diazatricyclo[6.4.0.0$^{2,6}$]dodeca-2(6),7-dien-10-yl}-4-(4,4,5,5-tetramethyl-1,3,2-dioxaborolan-2-yl)pyridin-3-yl)methyl acetate 199e (287.4 mg, 0.60 mmol), 339c (145 mg, 0.30 mmol), Pd(dppf)Cl$_2$ (24.5 mg, 0.030 mmol), K$_3$PO$_4$ (127.2 mg, 0.60 mmol), sodium acetate (49.2 mg, 0.60 mmol), water (0.50 mL), and acetonitrile (10 mL). After three cycles of vacuum/nitrogen flush, the mixture was heated at 95° C. for 1 h. It was then cooled to room temperature and filtered. The filtrate was concentrated under reduced pressure and the resulting residue was purified by silica-gel column chromatography eluting with ethyl acetate to afford 339d as a yellow solid (140 mg, 61%). MS-ESI: [M+H]$^+$ 737.3.

Example 339e (2-{4,4-Dimethyl-9-oxo-1,10-diazatricyclo[6.4.0.0$^{2,6}$]dodeca-2(6),7-dien-10-yl}-4-(1-methyl-6-oxo-5-{[5-(piperazin-1-yl)pyridin-2-yl]amino}-1,6-dihydropyridin-3-yl)pyridin-3-yl)methyl Acetate 339e A mixture of 339d (130 mg, 0.18 mmol) and HCl/methanol (4.0 mL) was stirred at room temperature for 4 h. It was then concentrated under reduced pressure to afford crude 339e (100 mg, 87%), which was used in the next step without further purification. MS-ESI: [M+H]$^+$ 637.3.

Example 339

3-[3-(hydroxymethyl)-4-[5-[[5-[4-(2-methoxyethyl)piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 339

A mixture of 339e (100 mg, 0.18 mmol), 1-bromo-2-methoxyethane (24.8 mg, 0.18 mmol), and K$_2$CO$_3$ (49.7 mg, 0.36 mmol) in acetonitrile (5.0 mL) in a sealed was stirred at 85° C. overnight. The mixture was cooled to room temperature and filtered. The filtrate was concentrated under reduced pressure. To the residue was added water and the resulting mixture was extracted with dichloromethane three times. The combined organic layer was concentrated under reduced pressure and the resulting residue was purified by reverse-phase prep-HPLC to afford 339 as a yellow solid (31.1 mg, 30%). MS-ESI: [M+H]$^+$ 653.3. $^1$H NMR (500 MHz, DMSO) δ 8.61 (d, J=2.0 Hz, 1H), 8.49 (d, J=5.0 Hz, 1H), 8.40 (s, 1H), 7.84 (d, J=3.0 Hz, 1H), 7.46 (d, J=2.0 Hz, 1H), 7.38-7.34 (m, 2H), 7.23 (d, J=9.5 Hz, 1H), 6.57 (s, 1H), 4.97-4.95 (m, 1H), 4.45-4.40 (m, 2H), 4.23-4.19 (m, 3H), 3.85-3.83 (m, 1H), 3.60 (s, 3H), 3.47-3.44 (m, 2H), 3.24 (s, 3H), 3.04-3.02 (m, 4H), 2.59-2.53 (m, overlap, 8H), 2.43 (s, 2H), 1.23 (s, 6H).

Example 340a (3S)-tert-Butyl 3-Methyl-4-(6-nitropyridin-3-yl)piperazine-1-carboxylate 340a Following the procedure of Example 323a, and starting with (3S)-tert-butyl 3-methylpiperazine-1-carboxylate (10.0 g, 50 mmol) and 5-bromo-2-nitropyridine (10.5 g, 50 mmol) afforded 340a as a yellow solid (8.05 g, 50%). MS-ESI: [M+H]$^+$ 323

Example 340b

(3S)-tert-Butyl 4-(6-Aminopyridin-3-yl)-3-methylpiperazine-1-carboxylate 340b Following the procedure of Example 323b, and starting with 340a (5.8 g, 18 mmol) afforded 340b as a brown solid (4.9 g, 93%). MS-ESI: [M+H]+ 293

Example 340c

(3S)-tert-Butyl 4-(6-(5-Bromo-1-methyl-2-oxo-1,2-dihydropyridin-3-ylamino)pyridine-3-yl)-3-methylpiperazine-1-carboxylate 340c Following the procedures of Example 323c, and starting with 340b (4.0 g, 13.7 mmol) and 3,5-dibromo-1-methylpyridin-2(1H)-one (5.5 g, 20.6 mmol) afforded 340c as a yellow solid (5.4 g, 83%). MS-ESI: [M+H]+ 478

Example 340d

(3S)-5-Bromo-1-methyl-3-(5-(2-methylpiperazin-1-yl)pyridin-2-ylamino)pyridine-2(1H)-one 340d Following the procedure of Example 271c, and starting with 340c (3.1 g, 6.5 mmol) afforded 340d as a yellow solid (2.3 g, 94%). MS-ESI: [M+H]+ 378.

Example 340e

(S)-5-Bromo-3-(5-(4-(2-methoxyethyl)-2-methylpiperazin-1-yl)pyridin-2-ylamino)-1-methylpyridin-2(1H)-one 340e

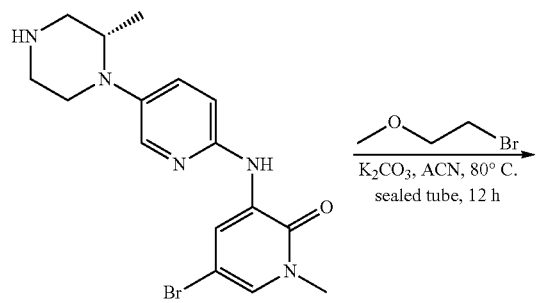

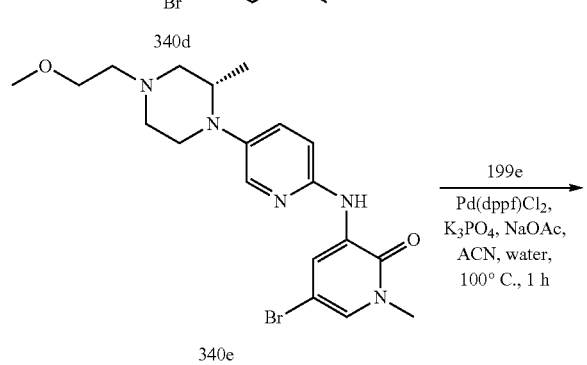

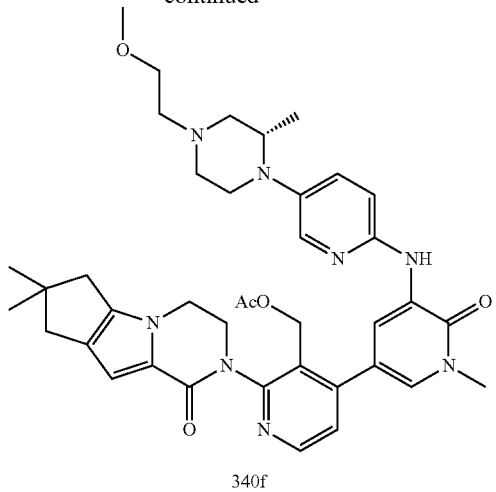

340f

A mixture of 340d (500 mg, 1.32 mmol), 1-bromo-2-methoxyethane (239.1 mg, 1.72 mmol), K₂CO₃ (364 mg, 2.64 mmol), and acetonitrile (6 mL) in a sealed tube was heated at 80° C. for 12 h. Analysis of the reaction mixture by LCMS showed complete conversion to the desired product. It was cooled to room temperature and filtered. The filtrate was concentrated under reduced pressure. The residue was dissolved in water (20 mL) and ethyl acetate (30 mL). The water phase was extracted with ethyl acetate (3×30 mL). The combined organic layer was washed with brine, dried over Na₂SO₄, concentrated under reduced pressure to afford crude 340e as a dark oil (600 mg), which was used in the next step without further purification. MS-ESI: [M+H]+ 436.1

Example 340f

(2-{4,4-Dimethyl-9-oxo-1,10-diazatricyclo[6.4.0.0²,⁶]dodeca-2(6),7-dien-10-yl}-4-[5-({5-[(2S)-4-(2-methoxyethyl)-2-methylpiperazin-1-yl]pyridin-2-yl}amino)-1-methyl-6-oxo-1,6-dihydropyridin-3-yl]pyridin-3-yl)methyl Acetate 340f A 50-mL round bottomed flask equipped with a reflux condenser was charged with 340e (180 mg, 0.412 mmol), {3-[(acetoxy)methyl]-2-{4,4-dimethyl-9-oxo-1,10-diazatricyclo[6.4.0.0²,⁶]dodeca-2(6),7-dien-10-yl}pyridin-4-yl}boronic acid 199e (327.3 mg, 0.824 mmol), Pd(dppf)Cl₂ (16.8 mg, 0.0206 mmol), K₃PO₄ (174.7 mg, 0.824 mmol), sodium acetate (67.6 mg, 0.824 mmol), acetonitrile (10 mL), and water (3 drops). The system was subjected to three cycles of vacuum/nitrogen flush and heated at 100° C. under N₂ protection for 1 h. Analysis of the reaction mixture by LCMS showed complete conversion to the desired product. It was then cooled to room temperature and filtered. The filtrate was concentrated under reduced pressure. The residue was purified by silica-gel column chromatography eluting with 20:1 dichloromethane/methanol to afford 340f as a yellow oil (190 mg, 65%). MS-ESI: [M+H]+ 709.4

Example 340

3-[3-(hydroxymethyl)-4-[5-[[5-[(2S)-4-(2-methoxyethyl)-2-methyl-piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one 340

To a solution of 340f (170 mg, 0.24 mmol) in THF (6 mL), i-propanol (6 mL), and water (6 mL) was added lithium hydroxide (57.6 mg, 2.4 mmol). After stirring at room temperature for 1 h, The reaction mixture was concentrated under reduced pressure. The residue was dissolved in dichloromethane (20 mL) and water (10 mL). The water phase was extracted with dichloromethane (3×20 mL). The combined organic layer was washed with brine, dried over $Na_2SO_4$, concentrated under reduced pressure, and purified by reverse-phase prep-HPLC to afford 340 (48.5 mg, 30%) as a white solid. MS-ESI: [M+H]$^+$ 667.3. $^1$H NMR (500 MHz, DMSO-$d_6$) δ 8.62 (d, J=2.5 Hz, 1H), 8.49 (d, J=5.0 Hz, 1H), 8.42 (s, 1H), 7.82 (d, J=2.5 Hz, 1H), 7.47 (d, J=2.5 Hz, 1H), 7.37-7.34 (m, 2H), 7.24 (d, J=9.0 Hz, 1H), 6.56 (s, 1H), 4.97-4.95 (m, 1H), 4.47-4.41 (m, 2H), 4.25-4.19 (m, 3H), 3.85-3.83 (m, 1H), 3.63-3.62 (m, 1H), 3.61 (s, 3H), 3.47-3.45 (m, 2H), 3.25 (s, 3H), 3.06-3.04 (m, 1H), 2.93-2.89 (m, 1H), 2.70-2.68 (m, 1H), 2.62-2.32 (m, overlap, 9H), 1.22 (s, 6H), 0.91 (d, J=6.5 Hz, 3H).

Example 901

Biochemical Btk Assay

A generalized procedure for a standard biochemical Btk Kinase Assay that can be used to test Formula I compounds is as follows. A master mix minus Btk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 μM Promega PTK Biotinylated peptide substrate 2, and 0.01% BSA. A master mix plus Btk enzyme is prepared containing 1× Cell Signaling kinase buffer, 0.5 μM PTK Biotinylated peptide substrate 2, 0.01% BSA, and 100 ng/well (0.06 mU/well) Btk enzyme. Btk enzyme is prepared as follows: full length human wild-type Btk (accession number NM-000061) with a C-terminal V5 and 6×His tag was subcloned into pFastBac vector for making baculovirus carrying this epitope-tagged Btk. Generation of baculovirus is done based on Invitrogen's instructions detailed in its published protocol "Bac-to-Bac Baculovirus Expression Systems" (Cat. Nos. 10359-016 and 10608-016). Passage 3 virus is used to infect Sf9 cells to overexpress the recombinant Btk protein. The Btk protein is then purified to homogeneity using Ni-NTA column. The purity of the final protein preparation is greater than 95% based on the sensitive Sypro-Ruby staining A solution of 200 μM ATP is prepared in water and adjusted to pH7.4 with 1N NaOH. A quantity of 1.25 μL of compounds in 5% DMSO is transferred to a 96-well ½ area Costar polystyrene plate. Compounds are tested singly and with an 11-point dose-responsive curve (starting concentration is 10 μM; 1:2 dilution). A quantity of 18.75 μL of master mix minus enzyme (as a negative control) and master mix plus enzyme is transferred to appropriate wells in 96-well ½ area costar polystyrene plate. 5 μL of 200 μM ATP is added to that mixture in the 96-well ½ area Costar polystyrene plate for final ATP concentration of 40 μM. The reaction is allowed to incubate for 1 hour at room temperature. The reaction is stopped with Perkin Elmer 1× detection buffer containing 30 mM EDTA, 20 nM SA-APC, and 1 nM PT66 Ab. The plate is read using time-resolved fluorescence with a Perkin Elmer Envision using excitation filter 330 nm, emission filter 665 nm, and 2$^{nd}$ emission filter 615 nm. IC$_{50}$ values are subsequently calculated. Alternatively, the Lanthascreen assay can be used to evaluate Btk activity through quantification of its phosphorylated peptide product. The FRET (Fluorescence Resonance Energy Transfer) that occurs between the fluorescein on the peptide product and the terbium on the detection antibody decreases with the addition of inhibitors of Btk that reduce the phosphorylation of the peptide. In a final reaction volume of 25 uL, Btk (h) (0.1 ng/25 ul reaction) is incubated with 50 mM Hepes pH 7.5, 10 mM $MgCl_2$, 2 mM $MnCl_2$, 2 mM DTT, 0.2 mM NaVO4, 0.01% BSA, and 0.4 uM fluorescein poly-GAT. The reaction is initiated by the addition of ATP to 25 uM (Km of ATP). After incubation for 60 minutes at room temperature, the reaction is stopped by the addition of a final concentration of 2 nM Tb-PY20 detection antibody in 60 mM EDTA for 30 minutes at room temperature. Detection is determined on a Perkin Elmer Envision with 340 nM excitation and emission at 495 nm and 520 nm. Exemplary Btk inhibition IC50 values are in Tables 1, 2, and 3.

Example 902

Ramos Cell Btk Assay

Another generalized procedure for a standard cellular Btk Kinase Assay that can be used to test Formula I compounds is as follows. Ramos cells are incubated at a density of 0.5×10$^7$ cells/ml in the presence of test compound for 1 hr at 37° C. Cells are then stimulated by incubating with 10 μg/ml anti-human IgM F(ab)$_2$ for 5 minutes at 37° C. Cells are pelleted, lysed, and a protein assay is performed on the cleared lysate. Equal protein amounts of each sample are subject to SDS-PAGE and western blotting with either anti-phosphoBtk (Tyr223) antibody (Cell Signaling Technology #3531; Epitomics, cat. #2207-1) or phosphoBtk(Tyr551) antibody (BD Transduction Labs #558034) to assess Btk autophosphorylation or an anti-Btk antibody (BD Transduction Labs #611116) to control for total amounts of Btk in each lysate.

Example 903

B-Cell Proliferation Assay

A generalized procedure for a standard cellular B-cell proliferation assay that can be used to test Formula I compounds is as follows. B-cells are purified from spleens of 8-16 week old Balb/c mice using a B-cell isolation kit (Miltenyi Biotech, Cat #130-090-862). Testing compounds are diluted in 0.25% DMSO and incubated with 2.5×10$^5$ purified mouse splenic B-cells for 30 min prior to addition of 10 μg/ml of an anti-mouse IgM antibody (Southern Biotechnology Associates Cat #1022-01) in a final volume of 100 μl. Following 24 hr incubation, 1 μCi$^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

Example 904

T Cell Proliferation Assay

A generalized procedure for a standard T cell proliferation assay that can be used to test Formula I compounds is as follows. T cells are purified from spleens of 8-16 week old Balb/c mice using a Pan T cell isolation kit (Miltenyi Biotech, Cat #130-090-861). Testing compounds are diluted in 0.25% DMSO and incubated with 2.5×10$^5$ purified mouse splenic T cells in a final volume of 100 μl in flat clear bottom plates precoated for 90 min at 37° C. with 10 μg/ml each of anti-CD3 (BD #553057) and anti-CD28 (BD #553294) antibodies. Following 24 hr incubation, 1 μCi$^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 905

CD86 Inhibition Assay

A generalized procedure for a standard assay for the inhibition of B cell activity that can be used to test Formula I compounds is as follows. Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 24 hr at 37° C., 5% $CO_2$. Following the 24 hr incubation, cells are transferred to conical bottom clear 96-well plates and pelleted by centrifugation at 1200×g×min. Cells are preblocked by CD16/CD32 (BD Pharmingen #553142), followed by triple staining with CD19-FITC (BD Pharmingen #553785), CD86-PE (BD Pharmingen #553692), and 7AAD (BD Pharmingen #51-68981E). Cells are sorted on a BD FACSCalibur and gated on the CD19$^+$/7AAD$^-$ population. The levels of CD86 surface expression on the gated population is measured versus test compound concentration.

Example 906

B-ALL Cell Survival Assay

The following is a procedure for a standard B-ALL (acute lymphoblastic leukemia) cell survival study using an XTT readout to measure the number of viable cells. This assay can be used to test Formula I compounds for their ability to inhibit the survival of B-ALL cells in culture. One human B-cell acute lymphoblastic leukemia line that can be used is SUP-B15, a human Pre-B-cell ALL line that is available from the ATCC.

SUP-B15 pre-B-ALL cells are plated in multiple 96-well microtiter plates in 100 µl of Iscove's media+20% FBS at a concentration of $5 \times 10^5$ cells/ml. Test compounds are then added with a final conc. of 0.4% DMSO. Cells are incubated at 37° C. with 5% $CO_2$ for up to 3 days. After 3 days cells are split 1:3 into fresh 96-well plates containing the test compound and allowed to grow up to an additional 3 days. After each 24 h period, 50 ul of an XTT solution is added to one of the replicate 96-well plates and absorbance readings are taken at 2, 4 and 20 hours following manufacturer's directions. The reading taken with an OD for DMSO only treated cells within the linear range of the assay (0.5-1.5) is then taken and the percentage of viable cells in the compound treated wells are measured versus the DMSO only treated cells.

Example 907

CD69 Whole Blood Assay

Human blood is obtained from healthy volunteers, with the following restrictions: 1 week drug-free, non-smokers. Blood (approximately 20 mls to test 8 compounds) is collected by venipuncture into Vacutainer® (Becton, Dickinson and Co.) tubes with sodium heparin.

Solutions of Formula I compounds at 10 mM in DMSO are diluted 1:10 in 100% DMSO, then are diluted by three-fold serial dilutions in 100% DMSO for a ten point dose-response curve. The compounds are further diluted 1:10 in PBS and then an aliquot of 5.5 µl of each compound is added in duplicate to a 2 ml 96-well plate; 5.5 µl of 10% DMSO in PBS is added as control and no-stimulus wells. Human whole blood—HWB (100 µl) is added to each well. After mixing the plates are incubated at 37° C., 5% $CO_2$, 100% humidity for 30 minutes. Goat F(ab')$_2$ anti-human IgM (10 µl of a 500 µg/ml solution, 50 µg/ml final) is added to each well (except the no-stimulus wells) with mixing and the plates are incubated for an additional 20 hours. At the end of the 20 hour incubation, samples are incubated with fluorescent labeled antibodies for 30 minutes, at 37° C., 5% $CO_2$, 100% humidity. Include induced control, unstained and single stains for compensation adjustments and initial voltage settings. Samples are then lysed with PharM Lyse™ (BD Biosciences Pharmingen) according to the manufacturer's instructions. Samples are then transferred to a 96 well plate suitable to be run on the BD Biosciences HTS 96 well system on the LSRII machine. Data acquired and Mean Fluorescence Intensity values were obtained using BD Biosciences DIVA Software. Results are initially analyzed by FACS analysis software (Flow Jo). The inhibitory concentrations (IC50, IC70, IC90, etc.) for test compounds is defined as the concentration which decreases by, for example 50%, the percent positive of CD69 cells that are also CD20 positive stimulated by anti-IgM (average of 8 control wells, after subtraction of the average of 8 wells for the no-stimulus background). The IC70 values are calculated by Prism version 5, using a nonlinear regression curve fit and are shown in Tables 1 and 2.

Example 908

In Vitro Cell Proliferation Assay

Efficacy of Formula I compounds are measured by a cell proliferation assay employing the following protocol (Mendoza et al (2002) Cancer Res. 62:5485-5488). The CellTiter-Glo® Luminescent Cell Viability Assay, including reagents and protocol are commercially available (Promega Corp., Madison, Wis., Technical Bulletin TB288). The assay assesses the ability of compounds to enter cells and inhibit cell proliferation. The assay principle is based on the determination of the number of viable cells present by quantitating the ATP present in a homogenous assay where addition of the Cell-Titer Glo reagent results in cell lysis and generation of a luminescent signal through the luciferase reaction. The luminescent signal is proportional to the amount of ATP present.

A panel of B-cell lymphoma cell lines (BJAB, SUDHL-4, TMD8, OCI-Ly10, OCI-Ly3, WSU-DLCL2) are plated into 384-well plate in normal growth medium, and serially diluted BTK inhibitors or DMSO alone were added to each well. Cell viability is assessed after 96 hour incubation by CellTiter-Glo® (Promega). Data may be presented as Relative cell viability in BTK inhibitor-treated cells relative to DMSO-treated control cells. Data points are the mean of 4 replicates at each dose level. Error bars represent SD from the mean.

Procedure: Day 1—Seed Cell Plates (384-well black, clear bottom, microclear, TC plates with lid from Falcon #353962), Harvest cells, Seed cells at 1000 cells per 54 µl per well into 384 well Cell Plates for 3 days assay. Cell Culture Medium: RPMI or DMEM high glucose, 10% Fetal Bovine Serum, 2 mM L-Glutamine, P/S. Incubate O/N at 37° C., 5% CO2.

Day 2—Add Drug to Cells, Compound Dilution, DMSO Plates (serial 1:2 for 9 points), Add 20 µA compounds at 10 mM in the 2nd column of 96 well plate. Perform serial 1:2 across the plate (10 μl+20 μl 100% DMSO) for a total of 9 points using Precision. Media Plates 96-well conical bottom polypropylene plates from Nunc (cat. #249946) (1:50 dilution) Add 147 μl of Media into all wells. Transfer 3 μl of DMSO+compound from each well in the DMSO Plate to each corresponding well on Media Plate using Rapidplate.

Drug Addition to Cells, Cell Plate (1:10 dilution), Add 6 μl of media+compound directly to cells (54 μl of media on the cells already). Incubate 3 days at 37 C, 5% CO2 in an incubator that will not be opened often.

Day 5—Develop Plates, Thaw Cell Titer Glo Buffer at room temperature. Remove Cell Plates from 37° C. and equilibrate to room temperature. for about 30 minutes. Add Cell Titer Glo Buffer to Cell Titer Glo Substrate (bottle to bottle). Add 30 μl Cell Titer Glo Reagent (Promega cat. #G7572) to each well of cells. Place on plate shaker for about 30 minutes. Read luminescence on Analyst HT Plate Reader (half second per well).

Cell viability assays and combination assays: Cells were seeded at 1000-2000 cells/well in 384-well plates for 16 h. On day two, nine serial 1:2 compound dilutions are made in DMSO in a 96 well plate. The compounds are further diluted into growth media using a Rapidplate robot (Zymark Corp., Hopkinton, Mass.). The diluted compounds are then added to quadruplicate wells in 384-well cell plates and incubated at 37° C. and 5% CO2. After 4 days, relative numbers of viable cells are measured by luminescence using Cell-Titer Glo (Promega) according to the manufacturer's instructions and read on a Wallac Multilabel Reader (PerkinElmer, Foster City). EC50 values are calculated using Prism® 4.0 software (GraphPad, San Diego). Formula I compounds and chemotherapeutic agents are added simultaneously or separated by 4 hours (one before the other) in all assays.

An additional exemplary in vitro cell proliferation assay includes the following steps:

1. An aliquot of 100 μl of cell culture containing about 10$^4$ cells in medium is deposited in each well of a 384-well, opaque-walled plate.

2. Control wells are prepared containing medium and without cells.

3. The compound is added to the experimental wells and incubated for 3-5 days.

4. The plates are equilibrated to room temperature for approximately 30 minutes.

5. A volume of CellTiter-Glo Reagent equal to the volume of cell culture medium present in each well is added.

6. The contents are mixed for 2 minutes on an orbital shaker to induce cell lysis.

7. The plate is incubated at room temperature for 10 minutes to stabilize the luminescence signal.

8. Luminescence is recorded and reported in graphs as RLU=relative luminescence units.

Although the foregoing invention has been described in some detail by way of illustration and example for purposes of clarity of understanding, the descriptions and examples should not be construed as limiting the scope of the invention. Accordingly, all suitable modifications and equivalents may be considered to fall within the scope of the invention as defined by the claims that follow. The disclosures of all patent and scientific literature cited herein are expressly incorporated in their entirety by reference.

We claim:

1. A compound selected from Formula I:

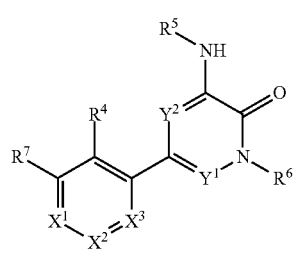

I or stereoisomers, tautomers, or pharmaceutically acceptable salts thereof, wherein:

$X^1$ is $CR^1$ or N;

$X^2$ is $CR^2$ or N;

$X^3$ is $CR^3$ or N;

where one or two of $X^1$, $X^2$, and $X^3$ are N;

$R^1$, $R^2$ and $R^3$ are independently selected from H, F, Cl, —NH$_2$, —NHCH$_3$, —N(CH$_3$)$_2$, —OH, —OCH$_3$, —OCH$_2$CH$_3$, —OCH$_2$CH$_2$OH, and C$_1$-C$_3$ alkyl;

$R^4$ is selected from H, F, Cl, CN, —CH$_2$OH, —CH(CH$_3$)OH, —C(CH$_3$)$_2$OH, —CH(CF$_3$)OH, —CH$_2$F, —CHF$_2$, —CH$_2$CHF$_2$, —CF$_3$, —C(O)NH$_2$, —C(O)NHCH$_3$, —C(O)N(CH$_3$)$_2$, —NH$_2$, —NHCH$_3$, —N(CH$_3$)$_2$, —NHC(O)CH$_3$, —OH, —OCH$_3$, —OCH$_2$CH$_3$, —OCH$_2$CH$_2$OH, cyclopropyl, cyclopropylmethyl, 1-hydroxycyclopropyl, imidazolyl, pyrazolyl, 3-hydroxy-oxetan-3-yl, oxetan-3-yl, and azetidin-1-yl;

$R^5$ is optionally substituted C$_6$-C$_{20}$ aryl, C$_3$-C$_{12}$ carbocyclyl, C$_2$-C$_{20}$ heterocyclyl, C$_1$-C$_{20}$ heteroaryl, —(C$_6$-C$_{20}$ aryl)-(C$_2$-C$_{20}$ heterocyclyl), —(C$_1$-C$_{20}$ heteroaryl)-(C$_2$-C$_{20}$ heterocyclyl), —(C$_1$-C$_{20}$ heteroaryl)-(C$_2$-C$_{20}$ heterocyclyl)-(C$_2$-C$_{20}$ heterocyclyl), —(C$_1$-C$_{20}$ heteroaryl)-(C$_2$-C$_{20}$ heterocyclyl)-(C$_1$-C$_6$ alkyl), —(C$_1$-C$_{20}$ heteroaryl)-(C$_1$-C$_6$ alkyl), —(C$_2$-C$_{20}$ heterocyclyl)-(C$_1$-C$_6$ alkyl), —(C$_2$-C$_{20}$ heterocyclyl)-(C$_3$-C$_{12}$ carbocyclyl), —(C$_1$-C$_{20}$ heteroaryl)-(C$_3$-C$_{12}$ carbocyclyl), or —(C$_1$-C$_{20}$ heteroaryl)-C(=O)—(C$_2$-C$_{20}$ heterocyclyl);

$R^6$ is H, —CH$_3$, —CH$_2$CH$_3$, —CH$_2$CH$_2$OH, —CHF$_2$, —NH$_2$, or —OH;

$R^7$ is selected from the structures:

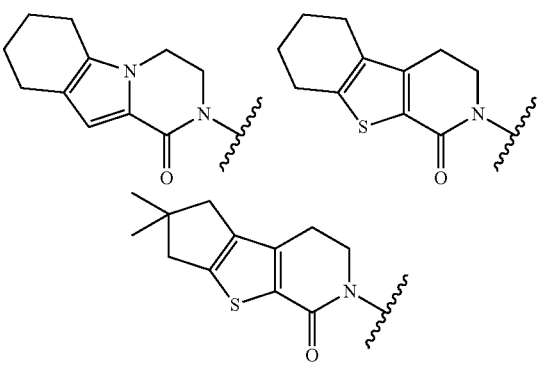

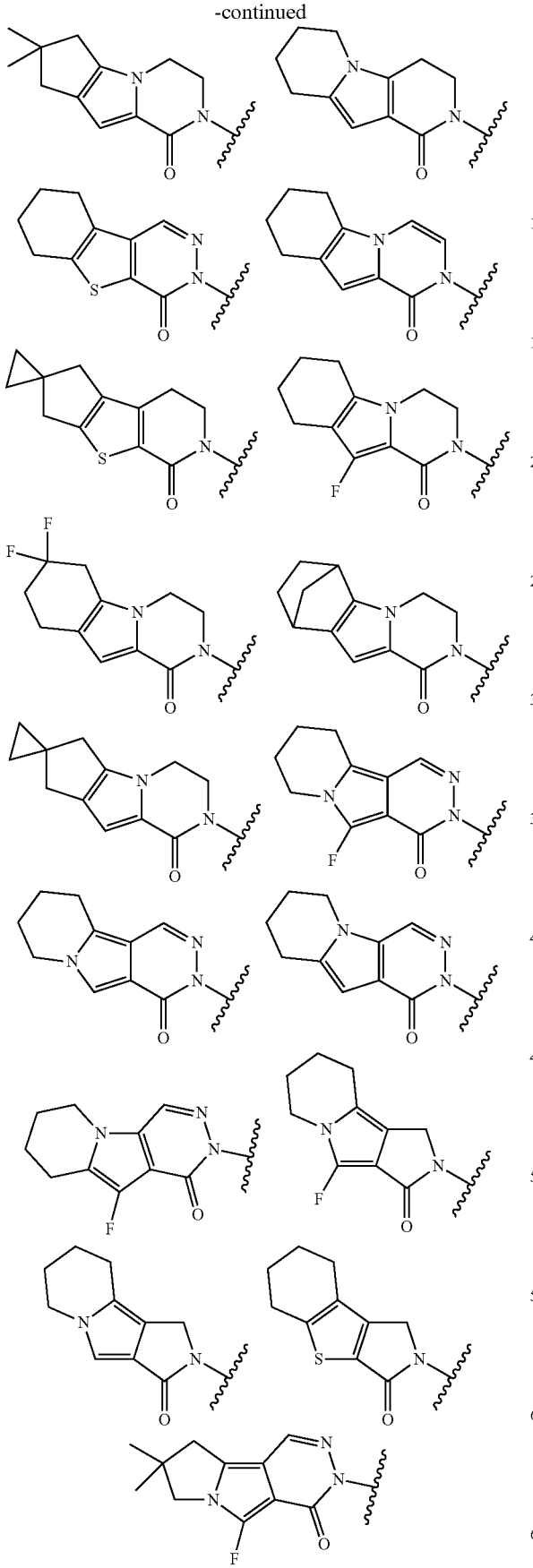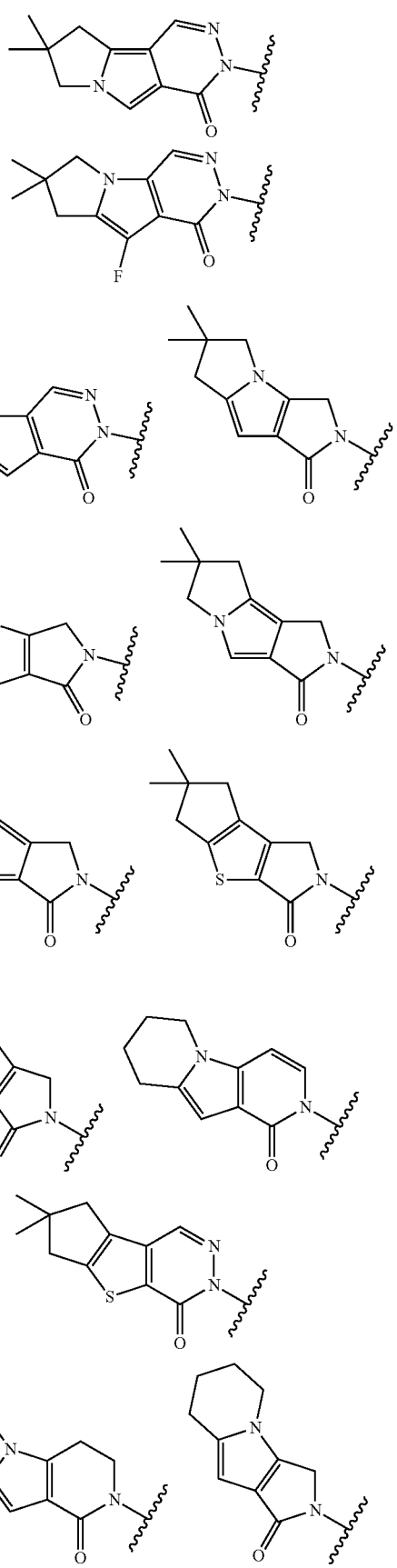

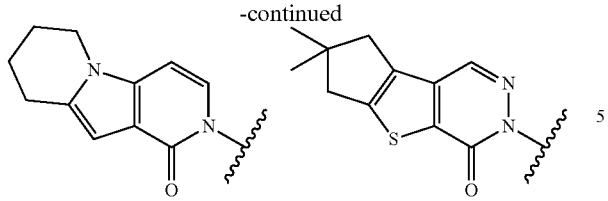

where the wavy line indicates the site of attachment; and $Y^1$ and $Y^2$ are independently selected from CH and N, where $Y^1$ and $Y^2$ are not each N;

where alkyl, carbocyclyl, heterocyclyl, aryl, and heteroaryl are optionally substituted with one or more groups independently selected from F, Cl, Br, I, —CN, —CH$_3$, —CH$_2$CH$_3$, —CH(CH$_3$)$_2$, —CH$_2$CH(CH$_3$)$_2$, —CH$_2$OH, —CH$_2$OCH$_3$, —CH$_2$CH$_2$OH, —C(CH$_3$)$_2$OH, —CH(OH)CH(CH$_3$)$_2$, —C(CH$_3$)$_2$CH$_2$OH, —CH$_2$CH$_2$SO$_2$CH$_3$, —CH$_2$OP(O)(OH)$_2$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —CO$_2$H, —COCH$_3$, —CO$_2$CH$_3$, —CO$_2$C(CH$_3$)$_3$, —COCH(OH)CH$_3$, —CONH$_2$, —CONHCH$_3$, —CON(CH$_3$)$_2$, —C(CH$_3$)$_2$CONH$_2$, —NH$_2$, —NHCH$_3$, —N(CH$_3$)$_2$, —NHCOCH$_3$, —N(CH$_3$)COCH$_3$, —NHS(O)$_2$CH$_3$, —N(CH$_3$)C(CH$_3$)$_2$CONH$_2$, —N(CH$_3$)CH$_2$CH$_2$S(O)$_2$CH$_3$, —NO$_2$, =O, —OH, —OCH$_3$, —OCH$_2$CH$_3$, —OCH$_2$CH$_2$OCH$_3$, —OCH$_2$CH$_2$OH, —OCH$_2$CH$_2$N(CH$_3$)$_2$, —OP(O)(OH)$_2$, —S(O)$_2$N(CH$_3$)$_2$, —SCH$_3$, —S(O)$_2$CH$_3$, —S(O)$_3$H, cyclopropyl, oxetanyl, azetidinyl, 1-methylazetidin-3-yl)oxy, N-methyl-N-oxetan-3-ylamino, azetidin-1-ylmethyl, and morpholino.

2. The compound of claim 1 wherein $X^1$ is N.
3. The compound of claim 1 wherein $X^2$ is N.
4. The compound of claim 1 wherein $X^3$ is N.
5. The compound of claim 1 wherein $X^1$ and $X^3$ are N, $X^1$ and $X^2$ are N, or $X^2$ and $X^3$ are N.
6. The compound of claim 1 wherein $R^5$ is optionally substituted $C_1$-$C_{20}$ heteroaryl selected from pyrazolyl, pyridinyl, pyrimidinyl, 5-methyl-4,5,6,7-tetrahydropyrazolo[1,5-a]pyrazin-2-yl, 5-acetyl-4,5,6,7-tetrahydropyrazolo[1,5-a]pyrazin-2-yl, 6,7-dihydro-4H-pyrazolo[5,1-c][1,4]oxazin-2-yl, and 1-methyl-5-(5-(4-methylpiperazin-1-yl)pyridin-2-yl.
7. The compound of claim 1 wherein $R^5$ is —($C_1$-$C_{20}$ heteroaryl)-($C_2$-$C_{20}$ heterocyclyl) where heteroaryl is optionally substituted pyridinyl and heterocyclyl is optionally substituted piperazinyl.
8. The compound of claim 1 wherein $R^5$ is phenyl, optionally substituted with one or more groups selected from F, Cl, —CH$_3$, —S(O)$_2$CH$_3$, cyclopropyl, azetidinyl, oxetanyl, and morpholino.
9. The compound of claim 1 wherein $R^5$ is selected from the structures:

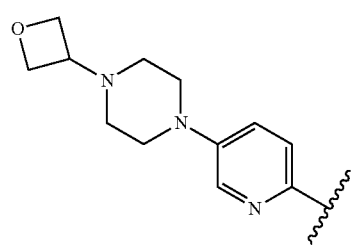

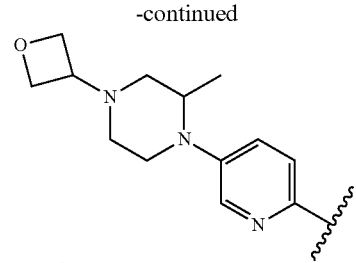

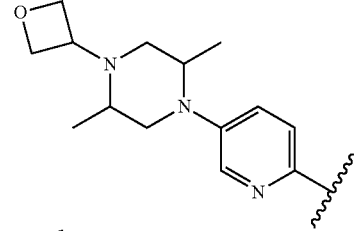

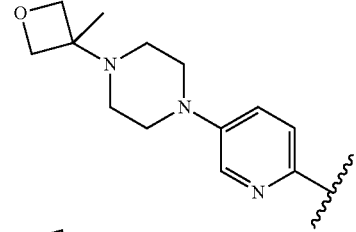

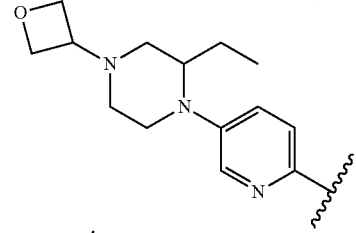

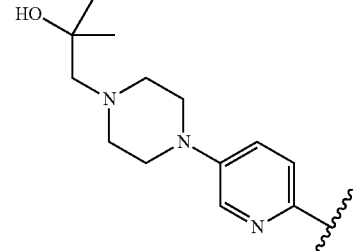

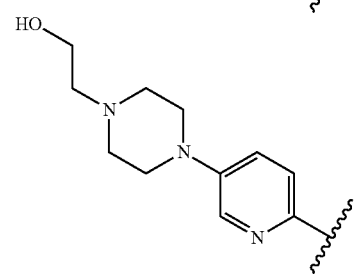

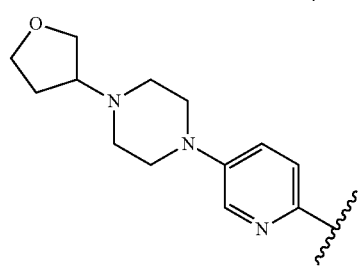

617
-continued
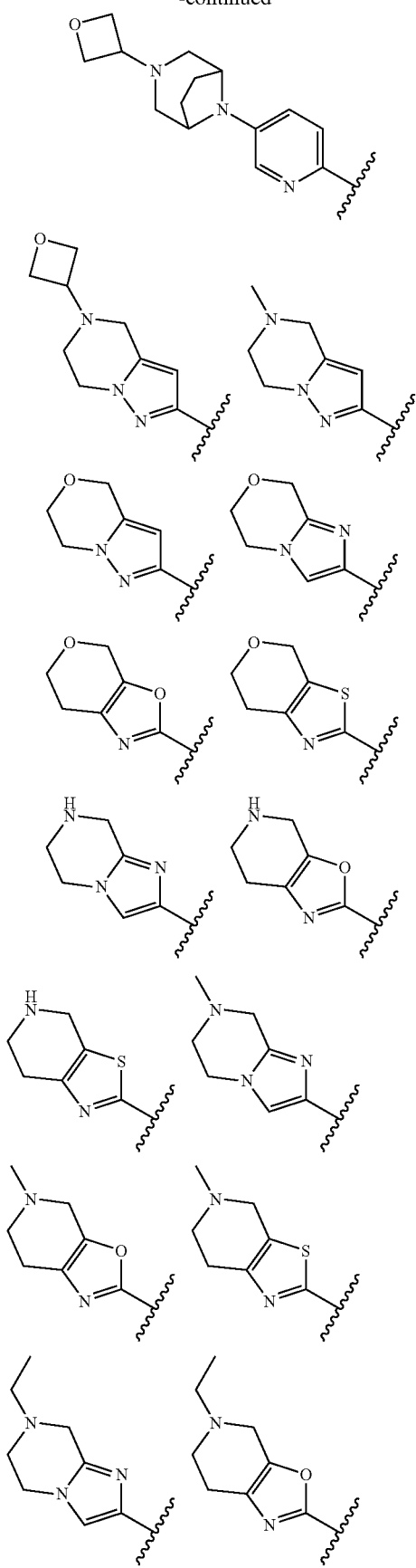
618
-continued
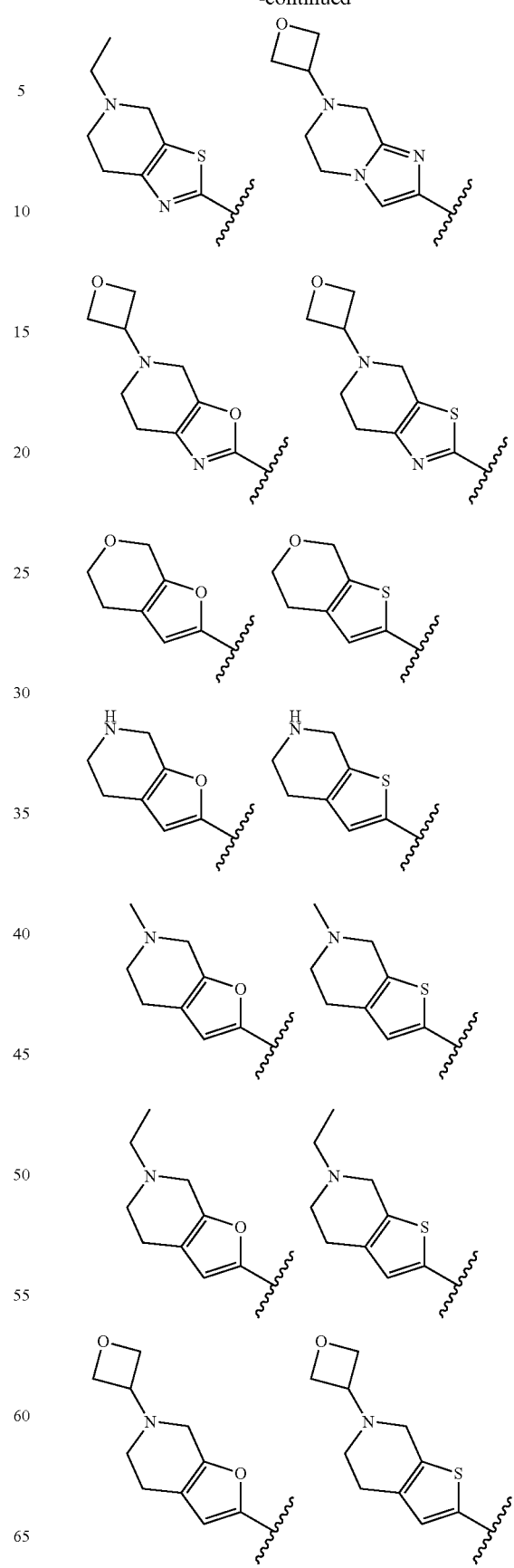

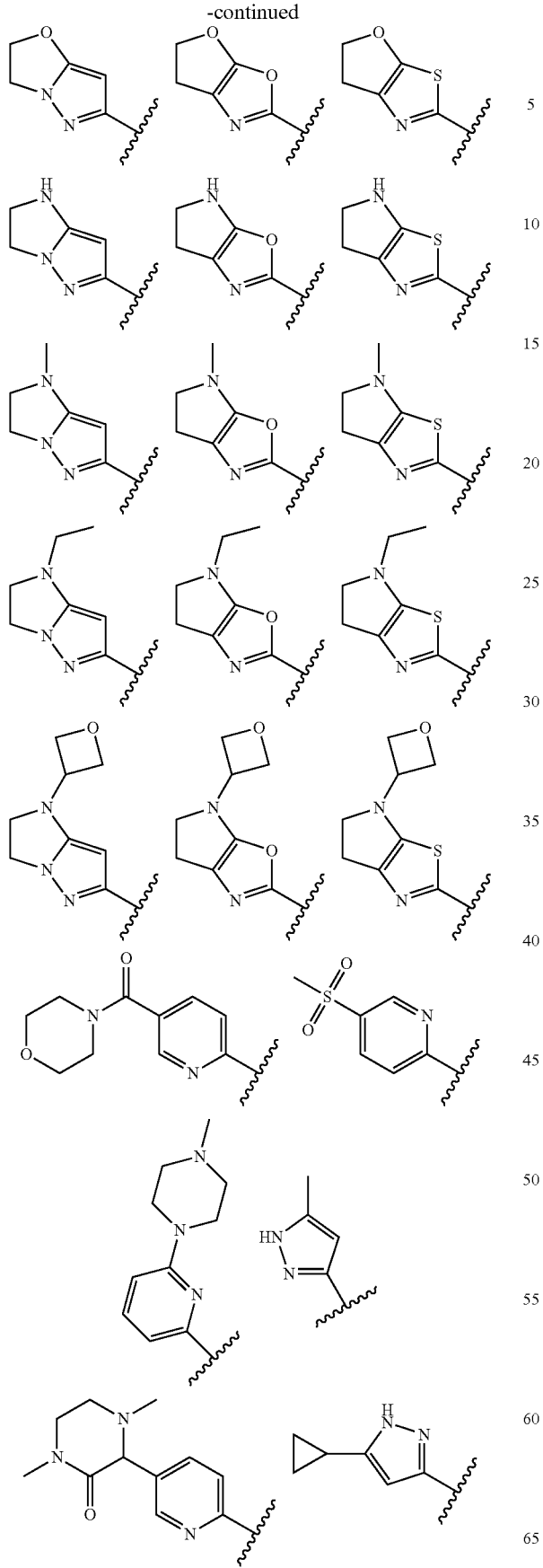
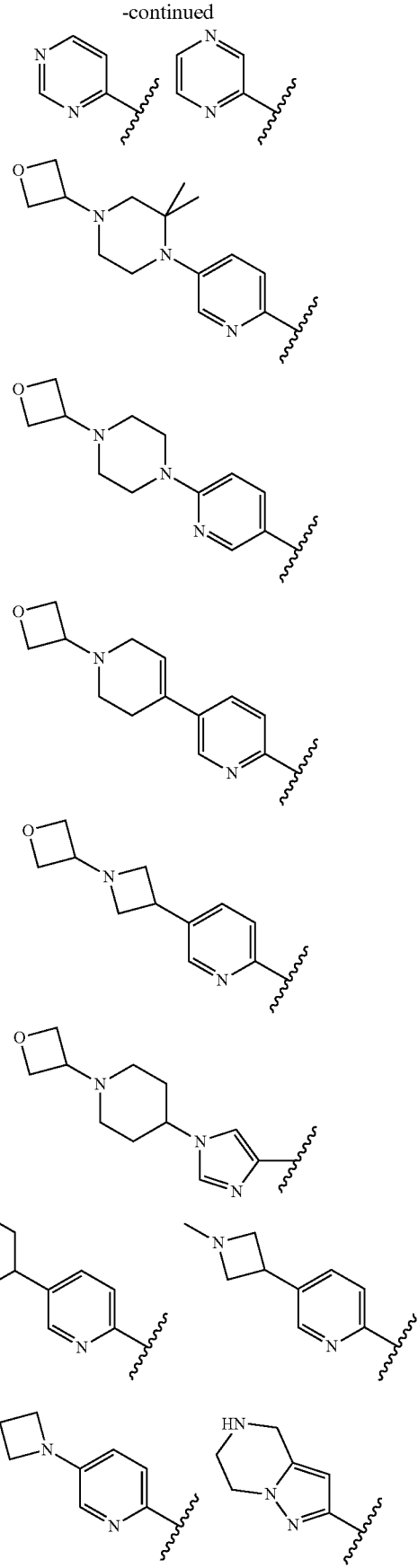

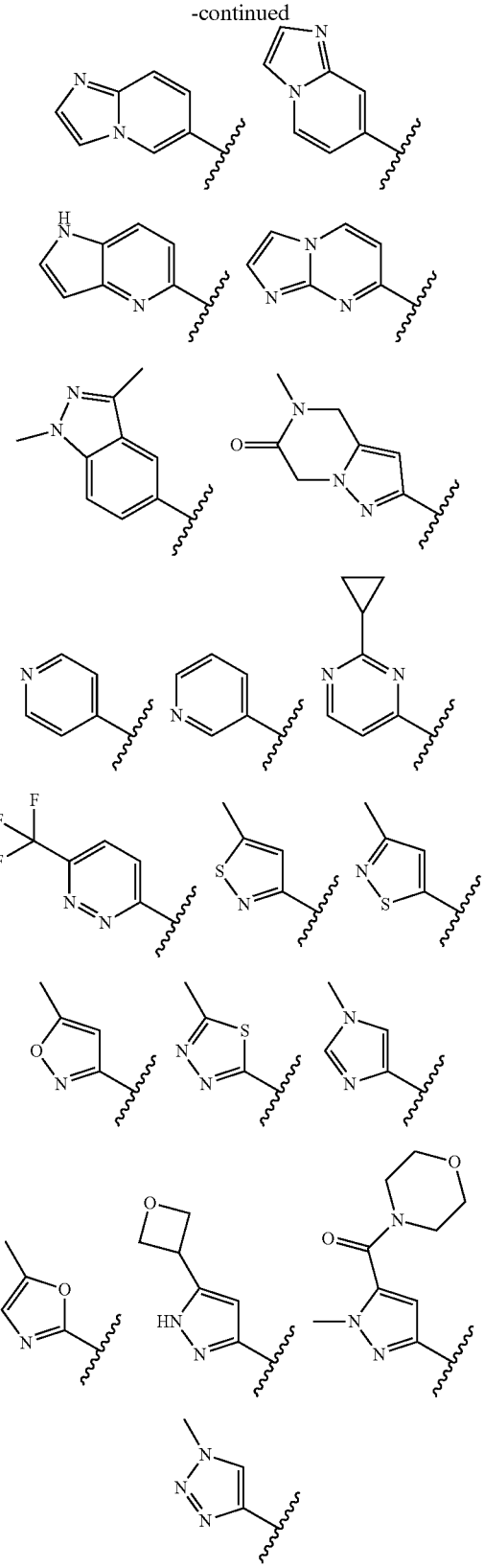

where the wavy line indicates the site of attachment.

10. The compound of claim 1 wherein $R^5$ is:

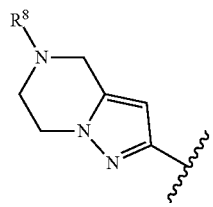

where $R^8$ is selected from H, —CH$_3$, —CH$_2$OCH$_3$, —CH$_2$CH$_3$, —CH(CH$_3$)$_2$, —CH$_2$CH$_2$OH, —CH$_2$CH$_2$OCH$_3$, —CH$_2$F, —CHF$_2$, —CF$_3$, —CH$_2$CF$_3$, —CH$_2$CHF$_2$, —CH(CH$_3$)CN, —C(CH$_3$)$_2$CN, —CH$_2$CN, —C(O)CH$_3$, —C(O)CH$_2$CH$_3$, —C(O)CH(CH$_3$)$_2$, —NH$_2$, —NHCH$_3$, —N(CH$_3$)$_2$, —OH, —OCH$_3$, —OCH$_2$CH$_3$, —OCH$_2$CH$_2$OH, cyclopropyl, and oxetanyl.

11. The compound of claim 1 wherein $R^6$ is CH$_3$.
12. The compound of claim 1 wherein $Y^1$ is CH and $Y^2$ is N.
13. The compound of claim 1 wherein $Y^1$ is N and $Y^2$ is CH.
14. The compound of claim 1 wherein $Y^1$ and $Y^2$ are each CH.
15. The compound of claim 1 wherein $Y^1$ and $Y^2$ are each CH, and $R^6$ is CH$_3$.
16. The compound of claim 1 selected from
2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-3,4,6,7,8,9-hexahydro-2H-pyrazino[1,2-a]indol-1-one;
2-{4-Hydroxymethyl-1'-methyl-5'-[5-(4-methyl-piperazin-1-yl)-pyridin-2-ylamino]-6'-oxo-1',6'-dihydro[3,3]bipyridinyl-5-yl}-3,4,6,7,8,9-hexahydro-2H-pyrazino[1,2-a]indol-1-one;
2-(3-(Hydroxymethyl)-4-(1-methyl-5-(5-(4-(oxetan-3-yl)piperazin-1-yl)pyridin-2-ylamino)-6-oxo-1,6-dihydropyridin-3-yl)pyridin-2-yl)-3,4,6,7,8,9-hexahydropyrazino[1,2-a]indol-1(2H)-one;
2-(3-(Hydroxymethyl)-2-(1-methyl-5-(5-(4-(oxetan-3-yl)piperazin-1-yl)pyridin-2-ylamino)-6-oxo-1,6-dihydropyridin-3-yl)pyridin-4-yl)-3,4,6,7,8,9-hexahydropyrazino[1,2-a]indol-1(2H)-one;
2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-3,4,5,6,7,8-hexahydro-2H-benzo[4,5]thieno[2,3-c]pyridin-1-one;
6-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-2,2-dimethyl-2,3,5,6-tetrahydro-1H,4H-8-thia-6-aza-cyclopenta[a]inden-7-one;
2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-7,7-dimethyl-3,4,7,8-tetrahydro-2H,6H-cyclopenta[4,5]pyrrolo[1,2-a]pyrazin-1-one;
2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one;
6-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-2,2-dimethyl-2,3,5,6-tetrahydro-1H,4H-8-thia-6-aza-cyclopenta[a]inden-7-one;
2-{3'-Hydroxymethyl-1-methyl-5-[6-(4-methyl-piperazin-1-yl)-pyridin-2-ylamino]-6-oxo-1,6-dihydro-[3, 4']bipyridinyl-2'-yl}-3,4,6,7,8,9-hexahydro-2H-pyrazino[1,2-a]indol-1-one;

2-{3'-Hydroxymethyl-1-methyl-5-[5-(morpholine-4-carbonyl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-2,3,5,6,7,8-hexahydro-4H-2,4-b-diaza-fluoren-1-one;

2-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one;

2-(4-{6-[4-((R)-1,4-Dimethyl-3-oxo-piperazin-2-yl)-phenylamino]-4-methyl-5-oxo-4,5-dihydro-pyrazin-2-yl}-3-hydroxymethyl-pyridin-2-yl)-3,4,6,7,8,9-hexahydro-2H-pyrazino[1,2-a]indol-1-one;

2-[3'-Hydroxymethyl-1-methyl-5-(5-methyl-1H-pyrazol-3-ylamino)-6-oxo-1,6-dihydro-[3,4']bipyridinyl-2'-yl]-3,4,6,7,8,9-hexahydro-2H-pyrazino[1,2-a]indol-1-one;

3-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-6,7,8,9-tetrahydro-3H-benzo[4,5]thieno[2,3-d]pyridazin-4-one;

2-[3'-Hydroxymethyl-5-(5-methanesulfonyl-pyridin-2-ylamino)-1-methyl-6-oxo-1,6-dihydro-[3,4']bipyridinyl-2'-yl]-3,4,6,7,8,9-hexahydro-2H-pyrazino[1,2-a]indol-1-one;

2-[5-(5-Cyclopropyl-1H-pyrazol-3-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one;

2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-(3'-Hydroxymethyl-5-{5-[4-(2-hydroxy-2-methyl-propyl)-piperazin-1-yl]-pyridin-2-ylamino}-1-methyl-6-oxo-1,6-dihydro-[3,4']bipyridinyl-2'-yl)-3,4,6,7,8,9-hexahydro-2H-pyrazino[1,2-a]indol-1-one;

2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-6,7,8,9-tetrahydro-2H-pyrazino[1,2-a]indol-1-one;

2-[5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one;

2-(5-{5-[4-(2-Hydroxy-ethyl)-piperazin-1-yl]-pyridin-2-ylamino}-3'-hydroxymethyl-1-methyl-6-oxo-1,6-dihydro-[3,4']bipyridinyl-2'-yl)-3,4,6,7,8,9-hexahydro-2H-pyrazino[1,2-a]indol-1-one;

3-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-6,7,8,9-tetrahydro-3H-benzo[4,5]thieno[2,3-d]pyridazin-4-one;

2-[3'-Hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one;

2-{4-Hydroxymethyl-1'-methyl-5'-[5-(4-oxetan-3-yl-piperazin-1-yl)-pyridin-2-ylamino]-6'-oxo-1',6'-dihydro-[3,3']bipyridinyl-5-yl}-6,7,8,9-tetrahydro-2H-pyrazino[1,2-a]indol-1-one;

2-[3'-Hydroxymethyl-1-methyl-6-oxo-5-(5-piperazin-1-yl-pyridin-2-ylamino)-1,6-dihydro-[3,4']bipyridinyl-2'-yl]-3,4,6,7,8,9-hexahydro-2H-pyrazino[1,2-a]indol-1-one;

2-[5-(5-Cyclopropyl-4,5,6,7-tetrahydro-pyrazolo[1,5-a]pyrazin-2-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one;

2-[5-(6,7-Dihydro-4H-pyrazolo[5,1-c][1,4]oxazin-2-ylamino)-3'-hydroxymethyl-1-methyl-6-oxo-1,6-dihydro-[3,4']bipyridinyl-2'-yl]-3,4,6,7,8,9-hexahydro-2H-pyrazino[1,2-a]indol-1-one;

2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one;

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-3,4,6,7,8,9-hexahydro-2H-pyrazino[1,2-a]indol-1-one;

2-{4-[5-(6,7-Dihydro-4H-pyrazolo[5,1-c][1,4]oxazin-2-ylamino)-1-methyl-6-oxo-1,6-dihydro-pyridazin-3-yl]-3-hydroxymethyl-pyridin-2-yl}-3,4,6,7,8,9-hexahydro-2H-pyrazino[1,2-a]indol-1-one;

2-{3-Hydroxymethyl-4-[1-methyl-5-(5-methyl-4,5,6,7-tetrahydro-pyrazolo[1,5-a]pyrazin-2-ylamino)-6-oxo-1,6-dihydro-pyridazin-3-yl]-pyridin-2-yl}-3,4,6,7,8,9-hexahydro-2H-pyrazino[1,2-a]indol-1-one;

10-Fluoro-2-{3'-hydroxymethyl-1-methyl-5-[5-(4-oxetan-3-yl-piperazin-1-yl)-pyridin-2-ylamino]-6-oxo-1,6-dihydro[3,4']bipyridinyl-2'-yl}-3,4,6,7,8,9-hexahydro-2H-pyrazino[1,2-a]indol-1-one;

10-Fluoro-2-[3'-hydroxymethyl-1-methyl-5-(5-methyl-4,5,6,7-tetrahydro-pyrazolo[1,5-a]pyrazin-2-ylamino)-6-oxo-1,6-dihydro[3,4']bipyridinyl-2'-yl]-3,4,6,7,8,9-hexahydro-2H-pyrazino[1,2-a]indol-1-one;

10-Fluoro-2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-[4-Hydroxymethyl-1'-methyl-5'-(5-methyl-4,5,6,7-tetrahydro-pyrazolo[1,5-a]pyrazin-2-ylamino)-6'-oxo-1',6'-dihydro[3,3']bipyridinyl-5-yl]-3,4,6,7,8,9-hexahydro-2H-pyrazino[1,2-a]indol-1-one;

2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-2,3,5,6,7,8-hexahydro-4H-2,4b-diaza-fluoren-1-one;

7,7-Difluoro-2-{3'-hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-[3'-Hydroxymethyl-1-methyl-5-(5-methyl-4,5,6,7-tetrahydro-pyrazolo[1,5-a]pyrazin-2-ylamino)-6-oxo-1,6-dihydro[3,4']bipyridinyl-2'-yl]-7,7-dimethyl-3,4,7,8-tetrahydro-2H,6H-cyclopenta[4,5]pyrrolo[1,2-a]pyrazin-1-one;

2-[3'-Hydroxymethyl-1-methyl-6-oxo-5-(pyrimidin-4-ylamino)-1,6-dihydro-[3,4']bipyridinyl-2'-yl]-3,4,6,7,8,9-hexahydro-2H-pyrazino[1,2-a]indol-1-one;

6-[3'-Hydroxymethyl-1-methyl-6-oxo-5-(pyrimidin-4-ylamino)-1,6-dihydro-[3,4']bipyridinyl-2'-yl]-2,2-dimethyl-2,3,5,6-tetrahydro-1H,4H-8-thia-6-aza-cyclopenta[a]inden-7-one;

2-[3'-Hydroxymethyl-1-methyl-6-oxo-5-(pyrimidin-4-ylamino)-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one;

6-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,2-dimethyl-2,3,5,6-tetrahydro-1H,4H-8-thia-6-aza-cyclopenta[a]inden-7-one;

10-Fluoro-2-[3'-hydroxymethyl-1-methyl-6-oxo-5-(pyrimidin-4-ylamino)-1,6-dihydro-[3,4']bipyridinyl-2'-yl]-3,4,6,7,8,9-hexahydro-2H-pyrazino[1,2-a]indol-1-one;

2-[3'-Hydroxymethyl-1-methyl-5-(5-methyl-4,5,6,7-tetrahydro-pyrazolo[1,5-a]pyrazin-2-ylamino)-6-oxo-1,6-dihydro[3,4']bipyridinyl-2'-yl]-2,3,5,6,7,8-hexahydro-4H-2,4b-diaza-fluoren-1-one;

2-{3'-(3-Hydroxy-oxetan-3-yl)-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-{3'-Hydroxymethyl-1-methyl-5-[5-((S)-2-methyl-4-oxetan-3-yl-piperazin-1-yl)-pyridin-2-ylamino]-6-oxo-1,6-dihydro-[3,4']bipyridinyl-2'-yl}-2,3,5,6,7,8-hexahydro-4H-2,4b-diaza-fluoren-1-one;

2-[4-Hydroxymethyl-1'-methyl-5'-(5-methyl-4,5,6,7-tetrahydro-pyrazolo[1,5-a]pyrazin-2-ylamino)-6'-oxo-1',6'-dihydro[3,3']bipyridinyl-5-yl]-7,7-dimethyl-3,4,7,8-tetrahydro-2H,6H-cyclopenta[4,5]pyrrolo[1,2-a]pyrazin-1-one;

2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-2H-pyrazino[1,2-a]indol-1-one;

2-{3'-Hydroxymethyl-1-methyl-5-[5-((1S,5R)-3-oxetan-3-yl-3,8-diaza-bicyclo[3.2.1]oct-8-yl)-pyridin-2-ylamino]-6-oxo-1,6-dihydro-[3,4']bipyridinyl-2'-yl}-3,4,6,7,8,9-hexahydro-2H-pyrazino[1,2-a]indol-1-one;

2-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one;

3-{3'-Hydroxymethyl-1-methyl-5-[5-((R)-2-methyl-4-oxetan-3-yl-piperazin-1-yl)-pyridin-2-ylamino]-6-oxo-1,6-dihydro-[3,4']bipyridinyl-2'-yl}-6,7,8,9-tetrahydro-3H-benzo[4,5]thieno[2,3-d]pyridazin-4-one;

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-2,3,5,6,7,8-hexahydro-4H-2,4b-diaza-fluoren-1-one;

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-10-fluoro-3,4,6,7,8,9-hexahydro-2H-pyrazino[1,2-a]indol-1-one;

2-{5'-[5-((2S,5R)-2,5-Dimethyl-4-oxetan-3-yl-piperazin-1-yl)-pyridin-2-ylamino]-4-hydroxymethyl-1'-methyl-6'-oxo-1',6'-dihydro[3,3']bipyridinyl-5-yl}-3,4,6,7,8,9-hexahydro-2H-pyrazino[1,2-a]indol-1-one;

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one;

3-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one;

2-{5-[5-((2S,5R)-2,5-Dimethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one;

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-2,3,5,6,7,8-hexahydro-4H-2,4b-diaza-fluoren-1-one;

2-[3'-Hydroxymethyl-1-methyl-6-oxo-5-(pyrazin-2-ylamino)-1,6-dihydro-[3,4']bipyridinyl-2'-yl]-3,4,6,7,8,9-hexahydro-2H-pyrazino[1,2-a]indol-1-one;

2-[3'-Hydroxymethyl-1-methyl-5-(5-oxetan-3-yl-4,5,6,7-tetrahydro-pyrazolo[1,5-a]pyrazin-2-ylamino)-6-oxo-1,6-dihydro[3,4']bipyridinyl-2'-yl]-7,7-dimethyl-3,4,7,8-tetrahydro-2H,6H-cyclopenta[4,5]pyrrolo[1,2-a]pyrazin-1-one;

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-7,7-dimethyl-3,4,7,8-tetrahydro-2H,6H-cyclopenta[4,5]pyrrolo[1,2-a]pyrazin-1-one;

2-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-2H-pyrazino[1,2-a]indol-1-one;

10-Fluoro-2-[3'-hydroxymethyl-1-methyl-5-(5-oxetan-3-yl-4,5,6,7-tetrahydro-pyrazolo[1,5-a]pyrazin-2-ylamino)-6-oxo-1,6-dihydro-[3,4']bipyridinyl-2'-yl]-3,4,6,7,8,9-hexahydro-2H-pyrazino[1,2-a]indol-1-one;

2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one;

2-[5-(6,7-Dihydro-4H-pyrazolo[5,1-c][1,4]oxazin-2-ylamino)-3'-hydroxymethyl-1-methyl-6-oxo-1,6-dihydro-[3,4']bipyridinyl-2'-yl]-7,7-dimethyl-3,4,7,8-tetrahydro-2H,6H-cyclopenta[4,5]pyrrolo[1,2-a]pyrazin-1-one;

2-{3'-Hydroxymethyl-1-methyl-5-[5-(4-oxetan-3-yl-piperazin-1-yl)-pyridin-2-ylamino]-6-oxo-1,6-dihydro-[3,4']bipyridinyl-2'-yl}-3,4,5,6,7,8-hexahydro-2H-benzo[4,5]thieno[2,3-c]pyridin-1-one;

2-(3-(hydroxymethyl)-4-(1-methyl-5-(5-methyl-4,5,6,7-tetrahydropyrazolo[1,5-a]pyrazin-2-ylamino)-6-oxo-1,6-dihydropyridin-3-yl)pyridin-2-yl)-3,4,6,7,8,9-hexahydro-6,9-methanopyrazino[1,2-a]indol-1(2H)-one;

(1S,11R)-6-[3-(Hydroxymethyl)-4-[1-methyl-5-({5-[(2S)-2-methyl-4-(oxetan-3-yl)piperazin-1-yl]pyridin-2-yl}amino)-6-oxo-1,6-dihydropyridin-3-yl]pyridin-2-yl]-3,6-diazatetracyclo[9.2.1.0$^{2,10}$0.0$^{3,8}$]tetradeca-2(10), 8-dien-7-one;

2-(4-(5-(1,2,4-triazin-3-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one;

2-[5-(2,6-Dimethyl-pyrimidin-4-ylamino)-3'-hydroxymethyl-1-methyl-6-oxo-1,6-dihydro-[3,4']bipyridinyl-2'-7,7-dimethyl-3,4,7,8-tetrahydro-2H,6H-cyclopenta[4,5]pyrrolo[1,2-a]pyrazin-1-one;

(1R,11S)-6-[3-(Hydroxymethyl)-4-[1-methyl-5-({5-[(2S)-2-methyl-4-(oxetan-3-yl)piperazin-1-yl]pyridin- 2-yl} amino)-6-oxo-1,6-dihydropyridin-3-yl]pyridin-2-yl]-3,6-diazatetracyclo[9.2.1.0$^{2,10}$.0$^{3,8}$]tetradeca-2(10),8-dien-7-one;

3-{5-[5-((S)-2-Ethyl-4-oxetan-3-yl-piperazin-1-yl)-pyridin-2-ylamino]-3'-hydroxymethyl-1-methyl-6-oxo-1,6-dihydro-[3,4']bipyridinyl-2'-yl}-6,7,8,9-tetrahydro-3H-benzo[4,5]thieno[2,3-d]pyridazin-4-one;

(S)-2-(3-(hydroxymethyl)-4-(1-methyl-5-(5-(2-methyl-4-(oxetan-3-yl)piperazin-1-yl)pyridin-2-ylamino)-6-oxo-1,6-dihydropyridin-3-yl)pyridin-2-yl)-6,7,8,9-tetrahydropyrazino[1,2-a]indol-1(2H)-one;

2-(4-(5-(5-ethyl-4,5,6,7-tetrahydropyrazolo[1,5-a]pyrazin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one;

3-[3'-Hydroxymethyl-1-methyl-6-oxo-5-(pyridin-2-ylamino)-1,6-dihydro-[3,4']bipyridinyl-2'-yl]-6,7,8,9-tetrahydro-3H-benzo[4,5]thieno[2,3-d]pyridazin-4-one;

2-[3'-Hydroxymethyl-1-methyl-5-(2-methyl-pyrimidin-4-ylamino)-6-oxo-1,6-dihydro-[3,4]bipyridinyl-2'-yl]-7,7-dimethyl-3,4,7,8-tetrahydro-2H,6H-cyclopenta[4,5]pyrrolo[1,2-a]pyrazin-1-one;

2-[3'-Hydroxymethyl-1-methyl-5-(6-methyl-pyrimidin-4-ylamino)-6-oxo-1,6-dihydro-[3,4]bipyridinyl-2'-yl]-7,7-dimethyl-3,4,7,8-tetrahydro-2H,6H-cyclopenta[4,5]pyrrolo[1,2-a]pyrazin-1-one;

3-[3'-Hydroxymethyl-1-methyl-5-(5-methyl-4,5,6,7-tetrahydro-pyrazolo[1,5-a]pyrazin-2-ylamino)-6-oxo-1,6-dihydro-[3,4']bipyridinyl-2'-yl]-6,7,8,9-tetrahydro-3H-benzo[4,5]thieno[2,3-d]pyridazin-4-one;

3-[3'-Hydroxymethyl-1-methyl-6-oxo-5-(pyrimidin-4-ylamino)-1,6-dihydro-[3,4']bipyridinyl-2'-yl]-6,7,8,9-tetrahydro-3H-benzo[4,5]thieno[2,3-d]pyridazin-4-one;

10-fluoro-2-(3-(hydroxymethyl)-4-(1-methyl-6-oxo-5-(pyridin-2-ylamino)-1,6-dihydropyridin-3-yl)pyridin-2-yl)-3,4,6,7,8,9-hexahydropyrazino[1,2-a]indol-1(2H)-one;

6-[3'-Hydroxymethyl-1-methyl-6-oxo-5-(pyrazin-2-ylamino)-1,6-dihydro-[3,4]bipyridinyl-2'-yl]-2,2-dimethyl-2,3,5,6-tetrahydro-1H,4H-8-thia-6-aza-cyclopenta[a]inden-7-one;

2-{3-Hydroxymethyl-4-[6-(imidazo[1,2-a]pyridin-7-ylamino)-4-methyl-5-oxo-4,5-dihydro-pyrazin-2-yl]-pyridin-2-yl}-7,7-dimethyl-3,4,7,8-tetrahydro-2H,6H-cyclopenta[4,5]pyrrolo[1,2-a]pyrazin-1-one;

10-fluoro-2-(3-(hydroxymethyl)-4-(4-methyl-5-oxo-6-(pyridin-3-ylamino)-4,5-dihydropyrazin-2-yl)pyridin-2-yl)-3,4,6,7,8,9-hexahydropyrazino[1,2-a]indol-1(2H)-one;

2-(4-(5-(5-(2,2-dimethyl-4-(oxetan-3-yl)piperazin-1-yl)pyridin-2-ylamino)-1-methyl-6-oxo-1,6-dihydropyridin-3-yl)-3-(hydroxymethyl)pyridin-2-yl)-3,4,6,7,8,9-hexahydropyrazino[1,2-a]indol-1(2H)-one;

2-[3'-Hydroxymethyl-1-methyl-6-oxo-5-(pyrazin-2-ylamino)-1,6-dihydro-[3,4]bipyridinyl-2'-yl]-7,7-dimethyl-3,4,7,8-tetrahydro-2H,6H-cyclopenta[4,5]pyrrolo[1,2-a]pyrazin-1-one; and 2-(3-(hydroxymethyl)-4-(1-methyl-5-(5-(4-(oxetan-3-yl)piperazin-1-yl)pyrazin-2-ylamino)-6-oxo-1,6-dihydropyridin-3-yl)pyridin-2-yl)-3,4,6,7,8,9-hexahydropyrazino[1,2-a]indol-1(2H)-one.

17. The compound of claim 1 selected from

2-[4-[5-[[5-[2,2-dimethyl-4-(oxetan-3-yl)piperazin-1-yl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one;

3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydrobenzothiopheno[2,3-d]pyridazin-4-one;

3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one;

2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydropyridazino[4,5-b]indolizin-1-one;

3-[3-(hydroxymethyl)-4-[1-methyl-6-oxo-5-(pyrazin-2-ylamino)-3-pyridyl]-2-pyridyl]-6,7,8,9-tetrahydrobenzothiopheno[2,3-d]pyridazin-4-one;

2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyrazino[1,2-a]indol-1-one;

3-[4-[5-[(2-cyclopropylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

2-[3-(hydroxymethyl)-4-[4-methyl-6-[[6-[4-(oxetan-3-yl)piperazin-1-yl]-3-pyridyl]amino]-5-oxo-pyrazin-2-yl]-2-pyridyl]-3,4,6,7,8,9-hexahydropyrazino[1,2-a]indol-1-one;

3-[3-(hydroxymethyl)-4-[1-methyl-5-[[5-[4-(oxetan-3-yl)piperazin-1-yl]-2-pyridyl]amino]-6-oxo-3-pyridyl]-2-pyridyl]-7,8,9,10-tetrahydropyridazino[4,5-a]indolizin-4-one;

3-[3-(hydroxymethyl)-4-[5-(imidazo[1,2-a]pyrimidin-7-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

2-[3-(hydroxymethyl)-4-[1-methyl-5-[[5-[1-(oxetan-3-yl)-3,6-dihydro-2H-pyridin-4-yl]-2-pyridyl]amino]-6-oxo-3-pyridyl]-2-pyridyl]-3,4,6,7,8,9-hexahydropyrazino[1,2-a]indol-1-one;

3-[3-(hydroxymethyl)-4-[6-(imidazo[1,2-a]pyridin-6-ylamino)-4-methyl-5-oxo-pyrazin-2-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-7,8,9,10-tetrahydropyridazino[4,5-a]indolizin-4-one;

3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-6,7,8,9-tetrahydropyridazino[4,5-b]indolizin-1-one;

2-[3-(hydroxymethyl)-4-[1-methyl-6-oxo-5-(4,5,6,7-tetrahydropyrazolo[1,5-a]pyrazin-2-ylamino)-3-pyridyl]-2-pyridyl]-3,4,6,7,8,9-hexahydropyrazino[1,2-a]indol-1-one;

2-[3-(hydroxymethyl)-4-[1-methyl-5-[[5-(1-methylazetidin-3-yl)oxy-2-pyridyl]amino]-6-oxo-3-pyridyl]-2-pyridyl]-3,4,6,7,8,9-hexahydropyrazino[1,2-a]indol-1-one;

3-[3-(hydroxymethyl)-4-[1-methyl-5-[[5-(1-methylazetidin-3-yl)oxy-2-pyridyl]amino]-6-oxo-3-pyridyl]-2-pyridyl]-7,7-dimethyl-1,2,6,8-tetrahydrocyclopenta[3,4-b]pyrrolo[3,5-b]pyrazin-4-one;

2-[4-[5-[(5-ethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrido[3,4-b]indolizin-1-one 2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one;

2-(7,7-dimethyl-4-oxo-1,2,6,8-tetrahydrocyclopenta[3,4]pyrrolo[3,5-b]pyrazin-3-yl)-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide;

2-(7,7-dimethyl-4-oxo-1,2,6,8-tetrahydrocyclopenta[3,4]pyrrolo[3,5-b]pyrazin-3-yl)-N-methyl-4-[1-methyl-5-[[5-[(2S)-2-methyl-4-(oxetan-3-yl)piperazin-1-yl]-2-pyridyl]amino]-6-oxo-3-pyridyl]pyridine-3-carboxamide;

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-5-[(2-methylpyrimidin-4-yl)amino]-6-oxo-3-pyridyl]-2-pyridyl]-3,4,6,7,8,9-hexahydropyrazino[1,2-a]indol-1-one;

3-[4-[5-(6,7-dihydro-4H-pyrano[4,3-d]thiazol-2-ylamino)-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-(hydroxymethyl)-5-[1-methyl-5-[(2-methylpyrimidin-4-yl)amino]-6-oxo-3-pyridyl]-3-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-6,7,8,9-tetrahydrobenzothiopheno[2,3-d]pyridazin-4-one;

2-[3-(hydroxymethyl)-4-[5-(1H-imidazo[4,5-b]pyridin-5-ylamino)-1-methyl-6-oxo-3-pyridyl]-2-pyridyl]-3,4,6,7,8,9-hexahydropyrazino[1,2-a]indol-1-one;

3-[4-[5-[(1,5-dimethylpyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[6-(3-aminoanilino)-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one;

5-[2-(3,4,6,7,8,9-hexahydro-1H-pyrazino[1,2-a]indol-2-yl)-3-(hydroxymethyl)-4-pyridyl]-1-methyl-3-[[5-[(2S)-2-methyl-4-(oxetan-3-yl)piperazin-1-yl]-2-pyridyl]amino]pyridin-2-one;

3-[4-[5-[(6-amino-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[(2-methylpyrimidin-4-yl)amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-5-[(5-methyl-6,7-dihydro-4H-thiazolo[5,4-c]pyridin-2-yl)amino]-6-oxo-3-pyridyl]-2-pyridyl]-3,4,6,7,8,9-hexahydropyrazino[1,2-a]indol-1-one;

3-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(2-methylpyrimidin-4-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

2-[3-(hydroxymethyl)-4-[1-methyl-5-[[5-(morpholine-4-carbonyl)-2-pyridyl]amino]-6-oxo-pyridazin-3-yl]-2-pyridyl]-3,4,6,7,8,9-hexahydropyrazino[1,2-a]indol-1-one;

2-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-3,4,6,7,8,9-hexahydropyrazino[1,2-a]indol-1-one;

3-[4-[5-[(2-ethylpyrimidin-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-6,7,8,9-tetrahydrobenzothiopheno[2,3-d]pyridazin-4-one;

10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-pyridazin-3-yl]-2-pyridyl]-3,4,6,7,8,9-hexahydropyrazino[1,2-a]indol-1-one;

2-[3-(hydroxymethyl)-4-[1-methyl-5-[[5-(1-methyl-4-piperidyl)-2-pyridyl]amino]-6-oxo-3-pyridyl]-2-pyridyl]-3,4,6,7,8,9-hexahydropyrazino[1,2-a]indol-1-one;

3-[3-(hydroxymethyl)-4-[1-methyl-6-oxo-5-(4,5,6,7-tetrahydrothiazolo[5,4-c]pyridin-2-ylamino)-3-pyridyl]-2-pyridyl]-7,7-dimethyl-1,2,6,8-tetrahydrocyclopenta[3,4]pyrrolo[3,5-b]pyrazin-4-one;

2-[4-[5-[(5-acetyl-6,7-dihydro-4H-thiazolo[5,4-c]pyridin-2-yl)amino]-1-methyl-6-oxo-3-pyridyl]-3-(hydroxymethyl)-2-pyridyl]-10-fluoro-3,4,6,7,8,9-hexahydropyrazino[1,2-a]indol-1-one;

3-[3-(hydroxymethyl)-4-[1-methyl-5-[[5-[(2S)-2-methyl-4-(oxetan-3-yl)piperazin-1-yl]pyrazin-2-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-(1-methyl-4-piperidyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-3,4,6,7,8,9-hexahydropyrido[3,4-b]indolizin-1-one;

2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-5,6,7,8-tetrahydro-1H-pyrrolo[3,4-b]indolizin-3-one;

2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrazino[1,2-a]indol-1-one;

3-[3-(hydroxymethyl)-4-[1-methyl-5-[[5-(1-methylazetidin-3-yl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-5-[(5-methyl-6,7-dihydro-4H-pyrazolo[1,5-a]pyrazin-2-yl)amino]-6-oxo-3-pyridyl]-2-pyridyl]-3,4,6,7,8,9-hexahydropyrido[3,4-b]indolizin-1-one;

2-[4-[5-[(1,5-dimethylpyrazol-3-yl)amino]-1-methyl-6-oxo-3-pyridyl]-3-(hydroxymethyl)-2-pyridyl]-3,4,6,7,8,9-hexahydropyrido[3,4-b]indolizin-1-one;

2-[3-(hydroxymethyl)-4-[1-methyl-5-[[1-[1-(oxetan-3-yl)-4-piperidyl]imidazol-4-yl]amino]-6-oxo-3-pyridyl]-2-pyridyl]-3,4,6,7,8,9-hexahydropyrazino[1,2-a]indol-1-one;

2-[3-(hydroxymethyl)-4-[1-methyl-5-[[5-(1-methylazetidin-3-yl)-2-pyridyl]amino]-6-oxo-3-pyridyl]-2-pyridyl]-3,4,6,7,8,9-hexahydropyrido[3,4-b]indolizin-1-one 2-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-6,7,8,9-tetrahydropyrido[3,4-b]indolizin-1-one;

2-[4-[5-[(1,5-dimethylpyrazol-3-yl)amino]-1-methyl-6-oxo-3-pyridyl]-3-(hydroxymethyl)-2-pyridyl]-6,7,8,9-tetrahydropyrido[3,4-b]indolizin-1-one;

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-6,7,8,9-tetrahydrobenzothiopheno[2,3-d]pyridazin-4-one;

3-[3-(hydroxymethyl)-4-[1-methyl-5-[[5-[(3R)-3-methylmorpholine-4-carbonyl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-[(3R)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

2-[4-[5-[(5,6-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one;

3-[4-[5-[(1-ethyl-5-methyl-pyrazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[[5-[(2S)-2-methyl-4-(oxetan-3-yl)piperazin-1-yl]-2-pyridyl]amino]-6-oxo-1H-pyridazin-3-yl]-2-pyridyl]-7,7-dimethyl-1,2,6,8-tetrahydrocyclopenta[3,4]pyrrolo[3,5-b]pyrazin-4-one;

3-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-7,7-dimethyl-1,2,6,8-tetrahydrocyclopenta[3,4]thieno[1,3-c]pyridin-4-one;

2-[4-[5-[(5-acetyl-6,7-dihydro-4H-pyrazolo[1,5-a]pyrazin-2-yl)amino]-1-methyl-6-oxo-3-pyridyl]-3-(hydroxymethyl)-2-pyridyl]-10-fluoro-3,4,6,7,8,9-hexahydropyrazino[1,2-a]indol-1-one;

3-[3-(hydroxymethyl)-4-[1-methyl-5-[[5-[(3S)-3-methylmorpholine-4-carbonyl]-2-pyridyl]amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-[(3S)-3-methylmorpholine-4-carbonyl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-(morpholine-4-carbonyl)-2-pyridyl]amino]-6-oxo-pyridazin-3-yl]-2-pyridyl]-6,7,8,9-tetrahydrobenzothiopheno[2,3-d]pyridazin-4-one;

3-[3-(hydroxymethyl)-4-[1-methyl-5-[[5-(morpholine-4-carbonyl)-2-pyridyl]amino]-6-oxo-pyridazin-3-yl]-2-pyridyl]-7,7-dimethyl-1,2,6,8-tetrahydrocyclopenta[3,4]thieno[1,3-c]pyridin-4-one;

3-[3-(hydroxymethyl)-4-[1-methyl-5-[(5-methyl-1H-pyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

2-[4-[5-[(1,5-dimethylpyrazol-3-yl)amino]-1-methyl-6-oxo-3-pyridyl]-3-(hydroxymethyl)-2-pyridyl]-10-fluoro-3,4,6,7,8,9-hexahydropyrido[3,4-b]indolizin-1-one;

3-[3-(hydroxymethyl)-4-[1-methyl-5-[(5-methyloxazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-6-oxo-5-(pyrimidin-4-ylamino)pyridazin-3-yl]-2-pyridyl]-3,4,6,7,8,9-hexahydropyrazino[1,2-a]indol-1-one;

3-[3-(hydroxymethyl)-4-[5-[[2-(1-hydroxy-1-methylethyl)pyrimidin-4-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-6-oxo-5-[(5-propanoyl-6,7-dihydro-4H-pyrazolo[1,5-a]pyrazin-2-yl)amino]-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-(oxetan-3-yl)-1H-pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-1,3,4-thiadiazol-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(1-methylimidazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-(morpholine-4-carbonyl)-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

2-[3-(hydroxymethyl)-4-[1-methyl-5-[(7-methyl-6,8-dihydro-5H-[1,2,4]triazolo[1,5-a]pyrazin-2-yl)amino]-6-oxo-3-pyridyl]-2-pyridyl]-3,4,6,7,8,9-hexahydropyrazino[1,2-a]indol-1-one;

3-[3-(hydroxymethyl)-4-[5-[[5-[(2S)-2-methyl-4-(oxetan-3-yl)piperazin-1-yl]-2-pyridyl]amino]-6-oxo-1H-pyridin-3-yl]-2-pyridyl]-7,7-dimethyl-1,2,6,8-tetrahydrocyclopenta[3,4]pyrrolo[3,5-b]pyrazin-4-one;

3-[3-(hydroxyethyl)-4-[1-methyl-5-[[5-[1-(oxetan-3-yl)azetidin-3-yl]-2-pyridyl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-6-oxo-5-(2-pyridylamino)-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methylpyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[(5-fluoro-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

6-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyridine-3-carbonitrile;

3-[3-(hydroxymethyl)-4-[5-[(5-methoxy-2-pyridyl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[(5-cyclopropyl-2-pyridyl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-6-oxo-5-[[5-(trifluoromethyl)-2-pyridyl]amino]-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[1-methyl-5-(morpholine-4-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-2-pyridyl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-[(2S)-2-methyl-4-(oxetan-3-yl)piperazin-1-yl]-2-pyridyl]amino]-6-oxo-3-pyridyl]-2-pyridyl]-7,7-dimethyl-6,8-dihydrocyclopenta[3,4]thieno[1,3-d]pyridazin-4-one;

3-[3-(hydroxymethyl)-4-[1-methyl-5-[(5-methylisoxazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

10-fluoro-2-[3-(hydroxymethyl)-4-[1-methyl-5-[[5-(oxetan-3-yl)-6,7-dihydro-4H-pyrazolo[1,5-a]pyrazin-2-yl]amino]-6-oxo-3-pyridyl]-2-pyridyl]-3,4,6,7,8,9-hexahydropyrido[3,4-b]indolizin-1-one;

3-[3-(hydroxymethyl)-4-[1-methyl-5-[[1-(oxetan-3-yl)imidazol-4-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-(isoxazol-3-ylamino)-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

2-[4-[5-[(4,5-dimethyl-6,7-dihydro-4H-pyrazolo[1,5-a]pyrazin-2-yl)amino]-1-methyl-6-oxo-3-pyridyl]-3-(hydroxymethyl)-2-pyridyl]-3,4,6,7,8,9-hexahydropyrazino[1,2-a]indol-1-one;

3-[3-(hydroxymethyl)-4-[1-methyl-5-[(5-methylisoxazol-3-yl)amino]-6-oxo-3-pyridyl]-2-pyridyl]-7,7-dimethyl-6,8-dihydrocyclopenta[3,4]thieno[1,3-d]pyridazin-4-one;

3-[3-(hydroxymethyl)-4-[1-methyl-6-oxo-5-(1H-pyrazol-3-ylamino)-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(1-methylpyrazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methylisoxazol-3-yl)amino]-6-oxo-3-pyridyl]-2-pyridyl]-6,7,8,9-tetrahydrobenzothiopheno[2,3-d]pyridazin-4-one;

3-[4-[5-[(1,5-dimethylpyrazol-3-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one;

3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[(5-tert-butylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[5-[(5-ethylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-6,7-dihydro-4H-pyrazolo[1,5-a]pyrazin-2-yl)amino]-6-oxo-pyridazin-3-yl]-2-pyridyl]-7,7-dimethyl-1,2,6,8-tetrahydrocyclopenta[3,4]pyrrolo[3,5-b]pyrazin-4-one;

5-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]pyrazine-2-carbonitrile;

3-[3-(hydroxymethyl)-4-[1-methyl-6-oxo-5-[(5-phenylisoxazol-3-yl)amino]-3-pyridyl]-2-pyridyl]-7,7-dimethyl-1,2,6,8-tetrahydrocyclopenta[3,4]pyrrolo[3,5-b]pyrazin-4-one;

(R)-2-(3'-(hydroxymethyl)-5-((5-(1-methoxypropan-2-yl)-4,5,6,7-tetrahydropyrazolo[1,5-a]pyrazin-2-yl)amino)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one;

3-[3-(hydroxymethyl)-4-[1-methyl-6-oxo-5-[[6-(trifluoromethyl)pyridazin-3-yl]amino]-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[1-methyl-5-[[methyl(oxetan-3-yl)amino]methyl]pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

(S)-2-(3'-(hydroxymethyl)-5-((5-(1-methoxypropan-2-yl)-4,5,6,7-tetrahydropyrazolo[1,5-a]pyrazin-2-yl)amino)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one;

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-6,8-dihydrocyclopenta[3,4]thieno[1,3-d]pyridazin-4-one;

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-pyridazin-3-yl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[(6-methoxypyridazin-3-yl)amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[6-[(1,3-dimethylindazol-5-yl)amino]-4-methyl-5-oxo-pyrazin-2-yl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[[5-(2-methoxyethyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]thieno[1,3-c]pyridin-4-one;

3-[3-(hydroxymethyl)-4-[5-[[5-(3-methoxypropyl)-6,7-dihydro-4H-pyrazolo[1,5-a]pyrazin-2-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methylisothiazol-3-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[(5-cyclopropylisoxazol-3-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[5-methyl-1-(oxetan-3-yl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[[5-(3-hydroxyazetidin-1-yl)-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[[1-methyl-5-(pyrrolidine-1-carbonyl)pyrazol-3-yl]amino]-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[[5-(methoxymethyl)-1-methyl-pyrazol-3-yl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(5-methyl-6-oxo-4,7-dihydropyrazolo[1,5-a]pyrazin-2-yl)amino]-6-oxo-3-pyridyl]-2-pyridyl]-7,7-dimethyl-1,2,6,8-tetrahydrocyclopenta[3,4]thieno[1,3-c]pyridin-4-one;

(R)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one;

(S)-2-(5-((4,5-dimethyl-4,5,6,7-tetrahydropyrazolo[1,5-a]pyrazin-2-yl)amino)-3'-(hydroxymethyl)-1-methyl-6-oxo-1,6-dihydro-[3,4'-bipyridin]-2'-yl)-7,7-dimethyl-2,3,4,6,7,8-hexahydro-1H-cyclopenta[4,5]pyrrolo[1,2-a]pyrazin-1-one;

3-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[5-[[5-[(3S,5R)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1,2,6,8-tetrahydrocyclopenta[3,4]pyrrolo[3,5-b]pyrazin-4-one;

2-[4-[5-[[5-[(3S,5R)-3,5-dimethylmorpholine-4-carbonyl]-2-pyridyl]amino]-1-methyl-6-oxo-3-pyridyl]-3-(hydroxymethyl)-2-pyridyl]-3,4,6,7,8,9-hexahydropyrazino[1,2-a]indol-1-one;

3-[3-(hydroxymethyl)-4-[5-[[5-(3-methoxyazetidin-1-yl)-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one;

3-[4-[5-[[5-[(3S,5S)-3,5-dimethylmorpholine-4-carbonyl]-2-pyridyl]amino]-1-methyl-6-oxo-pyridazin-3-yl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[5-[(1,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[5-[(2,3-dimethylpyrazolo[3,4-c]pyridin-5-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[5-[[5-(2-methoxyethyl)-6,7-dihydro-4H-pyrazolo[1,5-a]pyrazin-2-yl]amino]-1,2-dimethyl-6-oxo-3-pyridyl]-2-pyridyl]-7,7-dimethyl-1,2,6,8-tetrahydrocyclopenta[3,4]pyrrolo[3,5-b]pyrazin-4-one;

3-[4-(hydroxymethyl)-5-[[5-(2-methoxyethyl)-6,7-dihydro-4H-pyrazolo[1,5-a]pyrazin-2-yl]amino]-1-methyl-6-oxo-3-pyridyl]-3-pyridyl]-7,7-dimethyl-1,2,6,8-tetrahydrocyclopenta[3,4]pyrrolo[3,5-b]pyrazin-4-one;

3-[3-(hydroxymethyl)-2-[5-[[5-(2-methoxyethyl)-6,7-dihydro-4H-pyrazolo[1,5-a]pyrazin-2-yl]amino]-1-methyl-6-oxo-3-pyridyl]-4-pyridyl]-7,7-dimethyl-1,2,6,8-tetrahydrocyclopenta[3,4]pyrrolo[3,5-b]pyrazin-4-one;

3-[4-[5-[(6,6-dimethyl-4,7-dihydropyrazolo[5,1-c][1,4]oxazin-2-yl)amino]-1-methyl-6-oxo-pyridazin-3-yl]-3-(hydroxymethyl)-2-pyridyl]-7,7-dimethyl-1,2,6,8-tetrahydrocyclopenta[3,4]thieno[1,3-c]pyridin-4-one;

3-[3-(hydroxymethyl)-4-[4-methyl-6-[(3-methylisothiazol-5-yl)amino]-5-oxo-pyrazin-2-yl]-2-pyridyl]-7,7-dimethyl-1,2,6,8-tetrahydrocyclopenta[3,4]pyrrolo[3,5-b]pyrazin-4-one;

3-[4-[5-[(5-ethyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[3-(hydroxymethyl)-4-[1-methyl-5-[(1-methyltriazol-4-yl)amino]-6-oxo-3-pyridyl]-2-pyridyl]-7,7-dimethyl-1,2,6,8-tetrahydrocyclopenta[3,4]thieno[1,3-c]pyridin-4-one;

3-[4-[5-[(5-cyclopropyl-1,3,4-thiadiazol-2-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[4-[5-[(6,6-dimethyl-4,7-dihydropyrazolo[5,1-c][1,4]oxazin-2-yl)amino]-1-methyl-6-oxo-3-pyridyl]-3-(hydroxymethyl)-2-pyridyl]-7,7-dimethyl-6,8-dihydrocyclopenta[3,4]thieno[1,3-d]pyridazin-4-one;

2-[3-(hydroxymethyl)-4-[5-[[5-(methoxymethyl)-1-methyl-pyrazol-3-yl]amino]-1-methyl-6-oxo-3-pyridyl]-2-pyridyl]-3,4,6,7,8,9-hexahydropyrido[3,4-b]indolizin-1-one;

3-[4-[5-[(1,2-dimethylimidazol-4-yl)amino]-1-methyl-6-oxo-3-pyridyl]-3-(hydroxymethyl)-2-pyridyl]-7,7-dimethyl-1,2,6,8-tetrahydrocyclopenta[3,4]pyrrolo[3,5-b]pyrazin-4-one;

3-[2-[[5-[2-(7,7-dimethyl-4-oxo-1,2,6,8-tetrahydrocyclopenta[3,4]pyrrolo[3,5-b]pyrazin-3-yl)-3-(hydroxymethyl)-4-pyridyl]-1-methyl-2-oxo-3-pyridyl]amino]-6,7-dihydro-4H-pyrazolo[1,5-a]pyrazin-5-yl]propanenitrile;

3-[3-(hydroxymethyl)-4-[5-[[5-[4-(2-methoxyethyl)piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one; and 3-[3-(hydroxymethyl)-4-[5-[[5-[(2S)-4-(2-methoxyethyl)-2-methyl-piperazin-1-yl]-2-pyridyl]amino]-1-methyl-6-oxo-3-pyridyl]-2-pyridyl]-7,7-dimethyl-1,2,6,8-tetrahydrocyclopenta[3,4]pyrrolo[3,5-b]pyrazin-4-one.

18. A pharmaceutical composition comprised of a compound of claim 1 and a pharmaceutically acceptable carrier, glidant, diluent, or excipient.

19. The pharmaceutical composition according to claim 18, further comprising a therapeutic agent.

20. A process for making a pharmaceutical composition which comprises combining a compound of claim 1 with a pharmaceutically acceptable carrier.

21. A kit for treating a condition mediated by Bruton's tyrosine kinase, comprising:
  a) a pharmaceutical composition of claim 18; and
  b) instructions for use.

* * * * *

(12) SUPPLEMENTAL EXAMINATION CERTIFICATE

United States Patent  
Crawford et al.

(10) Number: US 8,716,274 F1  
(45) Certificate Issued: Oct. 8, 2014

Control No.: 96/000,074  
Primary Examiner: Dwayne C. Jones

Filing Date: Sep. 2, 2014

No substantial new question of patentability is raised in the request for supplemental examination. See the Reasons for Substantial New Question of Patentability Determination in the file of this proceeding.

(56) Items of Information

U.S. PATENT DOCUMENTS

| | | |
|---|---|---|
| US 2012/0010191 | 01/2012 | Barbosa et al. |